United States Patent
Ray et al.

(10) Patent No.: US 9,873,709 B2
(45) Date of Patent: Jan. 23, 2018

(54) TRIAZOLOPYRIDINE COMPOUNDS, COMPOSITIONS AND METHODS OF USE THEREOF

(71) Applicant: Genentech, Inc., South San Francisco, CA (US)

(72) Inventors: Nicholas C. Ray, Harlow Essex (GB); Yun-Xing Cheng, Beijing (CN); Christine Edwards, Harlow Essex (GB); Simon C. Goodacre, Harlow Essex (GB); Wei Li, Beijing (CN); Snahel Patel, Foster City, CA (US); Matthew W. Cartwright, Harlow Essex (GB); Mohammed Sajad, Harlow Essex (GB); Po-wai Yuen, Ann Arbor, MI (US); Mark E. Zak, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/499,662

(22) Filed: Apr. 27, 2017

(65) Prior Publication Data

US 2017/0226132 A1    Aug. 10, 2017

Related U.S. Application Data

(63) Continuation of application No. 15/061,760, filed on Mar. 4, 2016, now abandoned, which is a continuation of application No. PCT/CN2014/085276, filed on Aug. 27, 2014.

(60) Provisional application No. 61/874,038, filed on Sep. 5, 2013.

(51) Int. Cl.
*C07D 519/00* (2006.01)
*C07D 471/04* (2006.01)

(52) U.S. Cl.
CPC ......... *C07D 519/00* (2013.01); *C07D 471/04* (2013.01)

(58) Field of Classification Search
None
See application file for complete search history.

(56) References Cited

U.S. PATENT DOCUMENTS

2010/0331359 A1    12/2010    Menet

FOREIGN PATENT DOCUMENTS

| WO | 2003/031445 | | 4/2003 |
|----|----|----|----|
| WO | 2008/065198 | A1 | 6/2008 |
| WO | 2009/155551 | A1 | 12/2009 |
| WO | 2009/155565 | A1 | 12/2009 |
| WO | 2010/010184 | | 1/2010 |
| WO | 2010/010186 | A1 | 1/2010 |
| WO | 2010/010188 | | 1/2010 |
| WO | 2010/141796 | | 12/2010 |
| WO | 2013/118986 | A1 | 8/2013 |

OTHER PUBLICATIONS

PCT ISR for PCT/CN2014/085276, dated Dec. 3, 2014.
PCT Written Opinion of the ISA for PCT/CN2014/085276, dated Dec. 3, 2014.
Siu Michael et al., "2-Amino-[1,2,4]triazolo[1,5-a]pyridines as JAK2 inhibitors" Bioorganic & Medicinal Chemistry Letters 23(17):5014-5021 (Jun. 15, 2013).

*Primary Examiner* — Brian J Davis
(74) *Attorney, Agent, or Firm* — Tamara A. Kale

(57) ABSTRACT

Compounds of Formula 0, Formula I and Formula II and methods of use as Janus kinase inhibitors are described herein.

14 Claims, No Drawings

TRIAZOLOPYRIDINE COMPOUNDS, COMPOSITIONS AND METHODS OF USE THEREOF

CROSS-REFERENCE TO RELATED APPLICATION

This application is a continuation of U.S. application Ser. No. 15/061,760, filed Mar. 4, 2016, which is a continuation of International Application No. PCT/CN2014/085276, filed Aug. 27, 2014, which claims the benefit of priority to U.S. Provisional Application Ser. No. 61/874,038, filed Sep. 5, 2013, each of which is incorporated herein by reference in its entirety.

FIELD OF THE INVENTION

The field of the invention pertains to compounds of Formulas 0, I and II, and subformulas thereof, that are inhibitors of a Janus kinase, such as JAK1, as well as compositions containing these compounds, and methods of use including, but not limited to, diagnosis or treatment of patients suffering from a condition responsive to the inhibition of a JAK kinase.

BACKGROUND OF INVENTION

Cytokine pathways mediate a broad range of biological functions, including many aspects of inflammation and immunity. Janus kinases (JAK), including JAK1, JAK2, JAK3 and TYK2, are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, J. Biol. Chem. 282: 20059-63). JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence. Exemplary therapeutic benefits of the inhibition of JAK enzymes are discussed, for example, in International Application No. WO 2013/014567.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFNgamma), and IL-2 and IL-6 cytokine receptor complexes (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). JAK1 knockout mice die perinatally due to defects in LIF receptor signaling (Kisseleva et al., 2002, Gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4 and IL-6 pathways. A humanized monoclonal antibody targeting the IL-6 pathway (Tocilizumab) was recently approved by the European Commission for the treatment of moderate-to-severe rheumatoid arthritis (Scheinecker et al., 2009, Nat. Rev. Drug Discov. 8:273-274).

CD4 T cells play an important role in asthma pathogenesis through the production of TH2 cytokines within the lung, including IL-4, IL-9 and IL-13 (Cohn et al., 2004, Annu. Rev. Immunol. 22:789-815). IL-4 and IL-13 induce increased mucus production, recruitment of eosinophils to the lung, and increased production of IgE (Kasaian et al., 2008, Biochem. Pharmacol. 76(2): 147-155). IL-9 leads to mast cell activation, which exacerbates the asthma symptoms (Kearley et al., 2011, Am. J. Resp. Crit. Care Med., 183(7): 865-875). The IL-4Ra chain activates JAK1 and binds to either IL-4 or IL-13 when combined with the common gamma chain or the IL-13R$\alpha$1 chain respectively (Pernis et al., 2002, J. Clin. Invest. 109(10):1279-1283). The common gamma chain can also combine with IL-9R$\alpha$ to bind to IL-9, and IL-9R$\alpha$ activates JAK1 as well (Demoulin et al., 1996, Mol. Cell Biol. 16(9):4710-4716). While the common gamma chain activates JAK3, it has been shown that JAK1 is dominant over JAK3, and inhibition of JAK1 is sufficient to inactivate signaling through the common gamma chain despite JAK3 activity (Haan et al., 2011, Chem. Biol. 18(3):314-323). Inhibition of IL-4, IL-13 and IL-9 signaling by blocking the JAK/STAT signaling pathway can alleviate asthmatic symptoms in pre-clinical lung inflammation models (Mathew et al., 2001, J. Exp. Med. 193(9): 1087-1096; Kudlacz et. al., 2008, Eur. J. Pharmacol. 582(1-3): 154-161).

Biochemical and genetic studies have shown an association between JAK2 and single-chain (e.g., EPO), IL-3 and interferon gamma cytokine receptor families (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). Consistent with this, JAK2 knockout mice die of anemia (O'Shea et al., 2002, Cell, 109 (suppl.): S121-S131). Kinase activating mutations in JAK2 (e.g., JAK2 V617F) are associated with myeloproliferative disorders in humans.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, Gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and IL-23 cytokines (Ustekinumab) was recently approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

There exists a need in the art for additional or alternative treatments of conditions mediated by JAK kinases, such as those described above.

SUMMARY OF INVENTION

One aspect of the invention includes a compound of Formula 0:

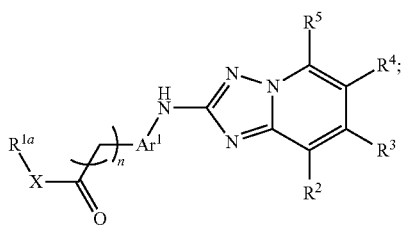

0 stereoisomers and salts thereof, wherein $Ar^1$, $R^{1a}$, $R^2$-$R^5$, X and n are defined herein.

One other aspect of the invention includes a compound of Formula I:

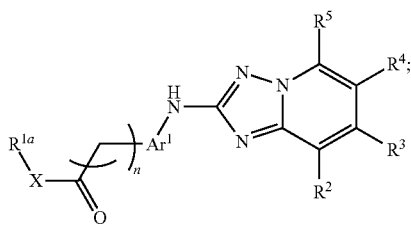

I stereoisomers and salts thereof, wherein $Ar^1$, $R^{1a}$, $R^2$-$R^5$, X and n are defined herein.

Another aspect of the present invention includes a compound of Formula II:

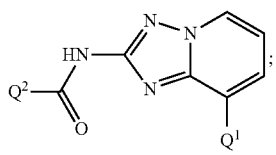

II and stereoisomers and salts thereof, wherein $Q^1$ and $Q^2$ are defined herein.

Also provided herein are compounds of Formulas Ia, Ib, Ic, Id, Ie, If, and Ig, as described below.

Another aspect includes a pharmaceutical composition that comprises a compound of Formula 0, I, Ia, Ib, Ic, Id, Ie, If, Ig or II, or a compound of any of Examples 1-1 to 1-303, 2-1 to 2-486 or 3-1, and a pharmaceutically acceptable carrier, diluent or excipient.

Another aspect includes use of a compound of Formula 0, I, Ia, Ib, Ic, Id, Ie, If, Ig or II, or a compound of any of Examples 1-1 to 1-303, 2-1 to 2-486 or 3-1, for use in therapy, such as the treatment of an inflammatory disease or cancer.

Another aspect includes a method of preventing, treating or lessening the severity of a disease or condition responsive to the inhibition of a Janus kinase, such as JAK1 kinase, in a patient. The method can comprise administering to the patient a therapeutically effective amount of a compound of Formula 0, I, Ia, Ib, Ic, Id, Ie, If, Ig or II, or a compound of any of Examples 1-1 to 1-303, 2-1 to 2-486 or 3-1.

Another aspect includes the use of a compound of Formula 0, I, Ia, Ib, Ic, Id, Ie, If, Ig or II, or a compound of any of Examples 1-1 to 1-303, 2-1 to 2-486 or 3-1, in the manufacture of a medicament for the treatment of a disease responsive to the inhibition of a Janus kinase, such as JAK1 kinase.

Another aspect includes a kit for treating a disease or disorder responsive to the inhibition of a Janus kinase, such as JAK1 kinase. The kit can comprise a first pharmaceutical composition comprising a compound of Formula 0, I, Ia, Ib, Ic, Id, Ie, If, Ig or II, or a compound of any of Examples 1-1 to 1-303, 2-1 to 2-486 or 3-1, and instructions for use.

DETAILED DESCRIPTION OF THE INVENTION

Definitions

"Halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical, wherein the alkyl radical may be optionally substituted. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2CH(CH_3)_2$), 3,3-dimethyl-2-butyl (—CH($CH_3$)C($CH_3$)$_3$, 1-heptyl and 1-octyl. In some embodiments, substituents for "optionally substituted alkyls" include one to four instances of F, Cl, Br, I, OH, SH, CN, $NH_2$, $NHCH_3$, $N(CH_3)_2$, $NO_2$, $N_3$, C(O)$CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

The term "alkenyl" refers to linear or branched-chain monovalent hydrocarbon radical with at least one site of unsaturation, i.e., a carbon-carbon double bond, wherein the alkenyl radical may be optionally substituted, and includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH═CH$_2$), prop-1-enyl (—CH═CHCH$_3$), prop-2-enyl (—CH$_2$CH═CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl. In some embodiments, substituents for "optionally substituted alkenyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list.

The term "alkynyl" refers to a linear or branched monovalent hydrocarbon radical with at least one site of unsaturation, i.e., a carbon-carbon, triple bond, wherein the alkynyl radical may be optionally substituted. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_6$ or $C_2$-$C_3$. Examples include, but are not limited to, ethynyl (—CCH), prop-1-ynyl CH$_3$), prop-2-ynyl (propargyl , —CH$_2$CCH), but-1-ynyl, but-2-ynyl and but-3-ynyl. In some embodiments, substituents for "optionally substituted alkynyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list.

"Alkylene" refers to a saturated, branched or straight chain hydrocarbon group having two monovalent radical centers derived by the removal of two hydrogen atoms from the same or two different carbon atoms of a parent alkane. In one example, the divalent alkylene group is one to eighteen carbon atoms ($C_1$-$C_{18}$). In other examples, the divalent alkylene group is $C_0$-$C_6$, $C_0$-$C_5$, $C_0$-$C_3$, $C_1$-$C_{12}$, $C_1$-$C_{10}$, $C_1$-$C_6$, $C_1$-$C_5$, $C_1$-$C_4$, or $C_1$-$C_3$. The group $C_0$ alkylene refers to a bond. Example alkylene groups include methylene (—CH$_2$—), 1,1-ethyl (—CH(CH$_3$)—), (1,2-ethyl (—CH$_2$CH$_2$—), 1,1-propyl (—CH(CH$_2$CH$_3$)—), 2,2-propyl (-C(CH$_3$)$_2$—), 1,2-propyl (—CH(CH$_3$)CH$_2$—), 1,3-propyl (—CH$_2$CH$_2$CH$_2$—), 1,1-dimethyleth-1,2-yl (—C(CH$_3$)$_2$CH$_2$—), 1,4-butyl (—CH$_2$CH$_2$CH$_2$CH$_2$—), and the like.

"Alkenylene" refers to an unsaturated, branched or straight chain hydrocarbon group having two monovalent radical centers derived by the removal of two hydrogen atoms from the same or two different carbon atoms of a parent alkene. In one example, the alkenylene group is two to eighteen carbon atoms ($C_2$-$C_{18}$). In other examples, the alkenylene group is $C_2$-$C_{12}$, $C_2$-$C_{10}$, $C_2$-$C_8$, $C_2$-$C_6$ or $C_2$-$C_3$. An exemplary alkenylene group is 1,2-ethylene (—CH═CH—).

"Alkynylene" refers to an unsaturated, branched or straight chain hydrocarbon group having two monovalent radical centers derived by the removal of two hydrogen atoms from the same or two different carbon atoms of a parent alkyne. In one example, the alkynylene radical is two to eighteen carbon atoms ($C_2$-$C_{18}$). In other examples, the alkynylene radical is $C_2$-$C_{12}$, $C_2$-$C_{10}$, $C_2$-$C_8$, $C_2$-$C_6$ or $C_2$-$C_3$. Example alkynylene radicals include: acetylene (—CC—), propargyl (—CH$_2$CC—), and 4-pentynyl (—CH$_2$CH$_2$CH$_2$CC—).

The term "heteroalkyl" refers to a straight or branched chain monovalent hydrocarbon radical, consisting of the stated number of carbon atoms, or, if none are stated, up to 18 carbon atoms, and from one to five heteroatoms selected from the group consisting of O, N, Si and S, and wherein the nitrogen and sulfur atoms can optionally be oxidized and the nitrogen heteroatom can optionally be quaternized. In some embodiments, the heteroatom is selected from O, N and S, wherein the nitrogen and sulfur atoms can optionally be oxidized and the nitrogen heteroatom can optionally be quaternized. The heteroatom(s) can be placed at any interior position of the heteroalkyl group, including the position at which the alkyl group is attached to the remainder of the molecule (e.g., —O—CH$_2$—CH$_3$). Examples include —CH$_2$—CH$_2$-O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —S(O)—CH$_3$, —CH$_2$—CH$_2$—S(O)$_2$—CH$_3$, —Si(CH$_3$)$_3$ and —CH$_2$—CH═N—OCH$_3$. Up to two heteroatoms can be consecutive, such as, for example, —CH$_2$—NH—OCH$_3$ and —CH$_2$—O—Si(CH$_3$)$_3$. Heteroalkyl groups can be optionally substituted. In some embodiments, substituents for "optionally substituted heteroalkyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list.

"Amidine" means the group -C(NH)-NHR in which R is hydrogen, alkyl, cycloalkyl, aryl or heterocyclyl, wherein the alkyl, cycloalkyl, aryl and heterocyclyl groups are as defined herein. A particular amidine is the group —NH—C(NH)—NH$_2$.

"Amino" means primary (i.e., —NH$_2$), secondary (i.e., —NRH) and tertiary (i.e., —NRR) amines, that are optionally substituted, in which R is alkyl, cycloalkyl, aryl, or heterocyclyl, wherein the alkyl, cycloalkyl, aryl and heterocyclyl groups are as defined herein. Particular secondary and tertiary amines are alkylamine, dialkylamine, arylamine, diarylamine, aralkylamine and diaralkylamine, wherein the alkyl and aryl portions can be optionally substituted. Particular secondary and tertiary amines are methylamine, ethylamine, propylamine, isopropylamine, phenyl amine, benzylamine, dimethylamine, diethylamine, dipropylamine and diisopropylamine.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl. Substituted phenyl or substituted aryl means a phenyl group or aryl group substituted with one, two, three, four or five sub stituents, for example, 1-2, 1-3 or 1-4 substituents, such as chosen from groups specified herein (see "optionally substituted" definition), such as F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane. In some embodiments, substituents for "optionally substituted cycloalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonyl amino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list.

"Guanidine" or "guanidinyl" means the group —NH—C(NH)—NHR in which R is hydrogen, alkyl, cycloalkyl, aryl or heterocyclyl, wherein the alkyl, cycloalkyl, aryl and heterocyclyl groups are as defined herein. A particular guanidine is the group —NH—C(NH)—$NH_2$.

"Heterocyclic group", "heterocyclic", "heterocycle", "heterocyclyl", or "heterocyclo" are used interchangeably and refer to any mono-, bi-, tricyclic or spiro, saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles, e.g., 5-6 membered heteroaryl. In another example, heterocyclyl includes 3-11 membered heterocycloyalkyls, such as 4-11 membered heterocycloalkyls. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[Nlt_4]^+Cl^-$, $[NR_4]^+OH^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1] heptanyl, 6-azabicyclo[3.1.1]heptanyl, 3-azabicyclo[3.1.1] heptanyl, 3-azabicyclo[4.1.0]heptanyl, azabicyclo[2.2.2] hexanyl, 2-azabicyclo[3.2.1]octanyl, 8-azabicyclo[3.2.1] octanyl, 2-azabicyclo[2.2.2]octanyl, 8-azabicyclo[2.2.2] octanyl, 7-oxabicyclo[2.2.1]heptane, azaspiro[3.5]nonanyl, azaspiro[2.5]octanyl, azaspiro[4.5]decanyl, 1-azaspiro[4.5] decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonyl amino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list.

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) 13$^{th}$ ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b] pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

"Heteroarylene" refers to a heteroaryl having two monovalent radical centers derived by the removal of two hydrogen atoms from two different atoms of a parent heteroaryl group.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to a linear or branched monovalent radical represented by the formula —OR in which R is alkyl, as defined herein. Alkoxy groups include methoxy, ethoxy, propoxy, isopropoxy, mono-, di- and tri-fluoromethoxy and cyclopropoxy.

"Acyl" means a carbonyl containing substituent represented by the formula —C(O)—R in which R is hydrogen, alkyl, cycloalkyl, aryl or heterocyclyl, wherein the alkyl, cycloalkyl, aryl and heterocyclyl are as defined herein. Acyl groups include alkanoyl (e.g., acetyl), aroyl (e.g., benzoyl), and heteroaroyl (e.g., pyridinoyl).

"Optionally substituted" unless otherwise specified means that a group may be unsubstituted or substituted by one or more (e.g., 0, 1, 2, 3, 4, or 5 or more, or any range derivable therein) of the sub stituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

Optional substituents for alkyl radicals, alone or as part of another substituent (e.g., alkoxy), as well as alkylenyl, alkenyl, alkynyl, heteroalkyl, heterocycloalkyl, and cycloalkyl, also each alone or as part of another substituent, can be a variety of groups, such as those described herein, as well as selected from the group consisting of halogen; oxo; CN; NO; $N_3$; —OR'; perfluoro-$C_1$-$C_4$ alkoxy; unsubstituted $C_3$-$C_7$ cycloalkyl; $C_3$-$C_7$ cycloalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl (e.g., phenyl); $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; —SR'; —SiR'R"R'"; —OC(O)R'; —C(O)R'; —CO$_2$R'; —CONR'R"; —OC(O)NR'R"; —NR"C(O)R'; —NR'"C(O)NR'R"; —NR"C(O)$_2$R'; —S(O)$_2$R'; —S(O)$_2$NR'R"; —NR'S(O)$_2$R"; —NR'"S(O)$_2$NR'R"; amidinyl; guanidinyl; —(CH$_2$)$_{1-4}$—OR'; —(CH$_2$)$_{1-4}$—NR'R"; —(CH$_2$)$_{1-4}$—SR'; —(CH$_2$)$_{1-4}$—SiR'R"R'"; —(CH$_2$)$_{1-4}$—OC(O)R'; —(CH$_2$)$_{1-4}$—C(O)R'; —(CH$_2$)$_{1-4}$—CO$_2$R'; and —(CH$_2$)$_{1-4}$CONR'R", or combinations thereof, in a number ranging from zero to (2m'+1), where m' is the total number of carbon atoms in such radical. R', R" and R'" each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R". When R' and R" are attached to the same nitrogen atom, they can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R". For example, —NR'R" is meant to include 1-pyrrolidinyl and 4-morpholinyl.

Similarly, optional substituents for the aryl and heteroaryl groups are varied. In some embodiments, substituents for aryl and heteroaryl groups are selected from the group consisting of halogen; CN; NO; $N_3$; —OR'; perfluoro-$C_1$-$C_4$ alkoxy; unsubstituted $C_3$-$C_7$ cycloalkyl; $C_3$-$C_7$ cycloalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl (e.g., phenyl); $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; —NR'R"; —SR'; —SiR'R"R'"; —OC(O)R'; —C(O)R'; —CO$_2$R'; —CONR'R"; —OC(O)NR'R"; —NR"C(O)R'; —NR'"C(O)NR'R"; —NR"C(O)$_2$R'; —S(O)$_2$R'; —S(O)$_2$NR'R"; —NR'S(O)$_2$R"; —NR'"S(O)$_2$NR'R"; amidinyl; guanidinyl; —(CH$_2$)$_{1-4}$—OR'; —(CH$_2$)$_{1-4}$—NR'R"; —(CH$_2$)$_{1-4}$—SR'; —(CH$_2$)$_{1-4}$—SiR'R"R'"; —(CH$_2$)$_{1-4}$—OC(O)R'; —(CH$_2$)$_{1-4}$—C(O)R'; —(CH$_2$)$_{1-4}$—CO$_2$R'; and —(CH$_2$)$_{1-4}$CONR'R", or combinations thereof, in a number ranging from zero to (2m'+1), where m' is the total number of carbon atoms in such radical. R', R" and R'" each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R". When R' and R" are attached to the same nitrogen atom, they can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R". For example, —NR'R" is meant to include 1-pyrrolidinyl and 4-morpholinyl.

The term "oxo" refers to =O or (=O)$_2$.

As used herein a wavy line "〰" that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment.

In certain embodiments, divalent groups are described generically without specific bonding configurations. It is understood that the generic description is meant to include both bonding configurations, unless specified otherwise. For example, in the group $R^1$—$R^2$—$R^3$, if the group $R^2$ is described as —CH$_2$C(O)—, then it is understood that this group can be bonded both as $R^1$—CH$_2$C(O)—$R^3$, and as $R^1$—C(O)CH$_2$—$R^3$, unless specified otherwise.

The phrase "pharmaceutically acceptable" refers to molecular entities and compositions that do not produce an adverse, allergic or other untoward reaction when administered to an animal, such as, for example, a human, as appropriate.

Compounds of the present invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A "sterile" formulation is aseptic or free from all living microorganisms and their spores.

"Stereoisomers" refer to compounds that have identical chemical constitution, but differ with regard to the arrangement of the atoms or groups in space. Stereoisomers include diastereomers, enantiomers, conformers and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the present invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the present invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyloxycarbonyl) and Cbz (Carbobenzyloxy). Further examples of these groups are found in T. W. Greene and P. G. M. Wuts, "Protecting Groups in Organic Synthesis, $3^{rd}$ ed., John Wiley & Sons, Inc., 1999. The term "protected amino" refers to an amino group substituted with one of the above amino-protecting groups.

"Carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, $3^{rd}$ ed., John Wiley & Sons, Inc., 1999. The term "protected carboxy" refers to a carboxy group substituted with one of the above carboxy-protecting groups.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silyl ethers (e.g., TBS, TBDPS) groups. Further examples of these groups are found in T. W. Greene and P. G. M. Wuts, "Protecting Groups in Organic Synthesis, $3^{rd}$ ed., John Wiley & Sons, Inc., 1999. The term "protected hydroxy" refers to a hydroxy group substituted with one of the above hydroxy-protecting groups.

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of Formula 0, I, Ia, Ib, Ic, Id, Ie, If, Ig or II, or a compound of any of Examples 1-1 to 1-303, 2-1 to 2-486 or 3-1, to a patient, the patient is typically in need thereof.

The term "Janus kinase" refers to JAK1, JAK2, JAK3 and TYK2 protein kinases. In some embodiments, a Janus kinase may be further defined as one of JAK1, JAK2, JAK3 or TYK2. In any embodiment, any one of JAK1, JAK2, JAK3 and TYK2 may be specifically excluded as a Janus kinase. In some embodiments, a Janus kinase is JAK1. In some embodiments, a Janus kinase is a combination of JAK1 and JAK2.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., JAK1 activity) compared to normal.

In some embodiments, a compound of Formula 0, I, Ia, Ib, Ic, Id, Ie, If, Ig or II, or a compound of any of Examples 1-1 to 1-303, 2-1 to 2-486 or 3-1, is selective for inhibition of JAK1 over JAK3 and TYK2. In some embodiments, a compound of Formula 0, I, Ia, Ib, Ic, Id, Ie, If, Ig or II, or a compound of any of Examples 1-1 to 1-249, 2-1 to 2-481 or 3-1, is selective for inhibition of JAK1 over JAK2, JAK3, or TYK2, or any combination of JAK2, JAK3, or TYK2. In some embodiments, a compound of Formula 0, I, Ia, Ib, Ic, Id, Ie, If, Ig or II, or a compound of any of Examples 1-1 to 1-303, 2-1 to 2-486 or 3-1, is selective for inhibition of JAK1 and JAK2 over JAK3 and TYK2. In some embodiments, a compound of Formula 0, I, Ia, Ib, Ic, Id, Ie, If, Ig or II, or a compound of any of Examples 1-1 to 1-303, 2-1 to 2-486 or 3-1, is selective for inhibition of JAK1 over JAK3. By "selective for inhibition" it is meant that the compound is at least a 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, better inhibitor of a particular Janus kinase (e.g., JAK1) activity compared to another particular Janus kinase (e.g., JAK1) activity, or is at least a 2-, 3-, 4-, 5-, 10-, 25-, 50-, 100-, 250-, or 500-fold better inhibitor of a particular Janus kinase (e.g., JAK1) activity compared to another particular Janus kinase (e.g., JAK1) activity.

"Therapeutically effective amount" means an amount of a compound of the present invention, such as a compound of Formula 0, I, Ia, Ib, Ic, Id, Ie, If, Ig or II, or a compound of any of Examples 1-1 to 1-303, 2-1 to 2-486 or 3-1, that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., asthma). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, such as a compound of Formula 0, I, Ia, Ib, Ic, Id, Ie, If, Ig or II, or a compound of any of Examples 1-1 to 1-303, 2-1 to 2-486 or 3-1, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound of the present invention, such as a compound of Formula 0, I, Ia, Ib, Ic, Id, Ie, If, Ig or II, or a compound of any of Examples 1-1 to 1-303, 2-1 to 2-486 or 3-1, encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Non-limiting examples of autoimmune diseases include rheumatoid arthritis, lupus and multiple sclerosis. "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, contact dermatitis, chronic obstructive pulmonary disease and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

"Package insert" is used to refer to instructions customarily included in commercial packages of therapeutic products that contain information about the indications, usage, dosage, administration, contraindications or warnings concerning the use of such therapeutic products.

The terms "compound(s) of this invention," and "compound(s) of the present invention" and the like, unless otherwise indicated, include compounds of Formula 0, I, Ia, Ib, Ic, Id, Ie, If, Ig or II, or a compound of any of Examples 1-1 to 1-303, 2-1 to 2-486 or 3-1, and stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

Unless otherwise stated, structures depicted herein are also meant to include compounds that differ only in the presence of one or more isotopically enriched atoms. Exemplary isotopes that can be incorporated into compounds of the present invention, such as a compound of Formula 0, I, Ia, Ib, Ic, Id, Ie, If, Ig or II, or a compound of any of Examples 1-1 to 1-249, 2-1 to 2-481 or 3-1, include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^3H$ and $^{14}C$) can be useful in compound or substrate tissue distribution assays. Tritiated (i.e., $^3H$) and carbon-14 (i.e., $^{14}C$) isotopes can be useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements). In some embodiments, in compounds of Formula 0, I, Ia, Ib, Ic, Id, Ie, If, Ig or II, or a compound of any of Examples 1-1 to 1-303, 2-1 to 2-486 or 3-1, one or more hydrogen atoms are replaced by $^2H$ or $^3H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

Inhibitors of Janus Kinases

One aspect of the invention provides compounds of Formula 0:

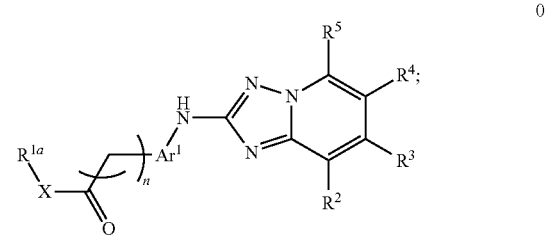

and stereoisomers and salts thereof, wherein:

$Ar^1$ is phenylene or 3-11 membered heteroarylene (e.g., 5-11, e.g., 5-6, membered heteroaryl containing 1 to 4 heteroatoms selected from O, N and S), wherein $Ar^1$ is optionally substituted;

X is —O— or —N($R^{1b}$)—($CR^{x1}R^{y1}$)$_p$—, wherein $R^{x1}$ and $R^{y1}$ are each independently hydrogen or $C_1$-$C_6$ alkyl and p is 0 to 6, and wherein the —N($R^{1b}$)— portion of —N($R^{1b}$)—($CR^{x1}R^{y1}$)$_p$— is bound to the carbonyl carbon of Formula 0;

$R^{1a}$ is hydrogen, $C_1$-$C_6$ alkyl, $C_3$-$C_8$ cycloalkyl, phenyl, or 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) and $R^{1a}$ is optionally substituted by $R^9$;

$R^{1b}$ is hydrogen, $C_1$-$C_6$ alkyl, or $C_3$-$C_8$ cycloalkyl, and wherein one or more alkylene units of said alkyl group is optionally substituted by —O— and wherein any alkyl or cycloalkyl group is optionally substituted by OH, or when p is 0 and X is —N($R^{1b}$)—, $R^{1a}$ and $R^{1b}$ may be joined together with the nitrogen atom to which $R^{1a}$ and $R^{1b}$ is attached to form a 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) optionally substituted by $R^9$;

$R^2$ is a 3-11 membered heterocyclyl containing at least 1 nitrogen, selected from groups (a)-(e) and (h)-(j), or a $C_5$-$C_8$ cycloalkenyl ring (f), or a —O—$(CR^xR^y)_q$—$Ar^2$ group (g) where $R^x$ and $R^y$ are independently hydrogen or $C_1$-$C_6$ alkyl, q is 0 to 3 and $Ar^2$ is optionally substituted $C_6$-$C_{10}$ aryl or optionally substituted (e.g., by oxo or ($C_1$-$C_6$ alkyl)phenyl) 5-11 membered heteroaryl (e.g., 5-6 membered heteroaryl containing 1 to 4 heteroatoms selected from O, N and S or 5-11 membered heterocycloalkyl containing 1 to 4 heteroatoms selected from O, N and S):

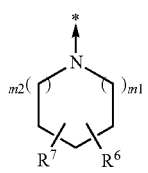
(a)

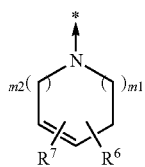
(b)

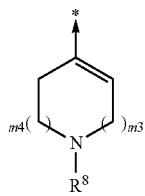
(c)

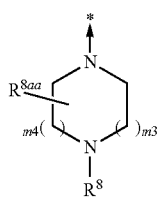
(d)

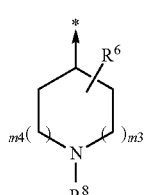
(e)

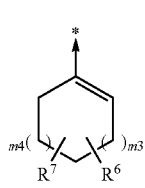
(f)

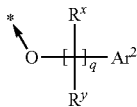
(g)

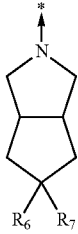
(h)

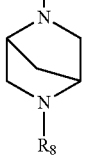
(i)

(j)

;

$R^3$, $R^4$ and $R^5$ are each independently selected from the group consisting of hydrogen, $CH_3$, $CH_2CH_3$, $OCH_3$, $CF_3$, F and Cl;

$R^6$ and $R^7$ are independently selected from the group consisting of hydrogen, halogen, OH, CN, phenyl, $C_1$-$C_6$ alkyl, ($C_0$-$C_6$ alkylene)$C_3$-$C_8$ cycloalkyl, ($C_0$-$C_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), ($C_0$-$C_6$ alkylene)C(O)$NR^aR^b$, ($C_0$-$C_6$ alkylene)$NR^aC(O)(C_1$-$C_6$ alkyl), ($C_0$-$C_6$ alkylene)$NR^a$(O)(phenyl), ($C_0$-$C_6$ alkylene)C(O)$R^{8a}$, ($C_0$-$C_6$ alkylene)C(O)$OR^{8a}$, $C_1$-$C_6$ alkoxy, —O—($C_3$-$C_6$ cycloalkyl), —O—($C_0$-$C_6$ alkylene)C(O)$NR^aR^b$, —C=N—O—($C_1$-$C_6$ alkyl), —O—($C_1$-$C_6$ alkyl)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), ($C_0$-$C_6$ alkylene)$NR^aSO_2(C_1$-$C_6$ alkyl), ($C_0$-$C_6$ alkylene)$NR^aSO_2$(phenyl), and —O—(3-11 membered heterocyclyl) (e.g., 5-6 membered heteroaryl containing 1 to 4 heteroatoms selected from O, N and S or 4-11 membered heterocycloalkyl containing 1 to 4 heteroatoms selected from O, N and S); wherein said alkyl, alkylene, alkoxy, cycloalkyl, phenyl and heterocyclyl are each independently optionally substituted (e.g., by halogen, CN, oxo, OH, $C_1$-$C_6$ alkyl, —O($C_1$-$C_6$ alkylene)-O—($C_1$-$C_6$ alkylene), CONR$^a$R$^b$, $CHF_2$, $CH_2F$, $CF_3$, —S—($C_1$-$C_6$ alkyl), $C_1$-$C_6$ alkoxy, or $NR^aR^b$);

or $R_6$ and $R_7$ together form an optionally substituted (e.g., $C_1$-$C_6$ alkyl, CN or oxo) phenyl or optionally substituted (e.g., $C_1$-$C_6$ alkyl, CN or oxo) 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S);

R$^8$ is H, C$_1$-C$_6$ alkyl, (C$_0$-C$_6$ alkylene)phenyl, (C$_0$-C$_6$ alkylene)C$_3$-C$_8$ cycloalkyl, (C$_0$-C$_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), C(O)NR$^a$R$^b$, SO$_2$NR$^a$R$^b$, (C$_1$-C$_6$ alkylene)C(O)OR$^{8a}$ or C(O)R$^{8a}$, wherein said alkyl, alkylene, heterocyclyl and phenyl are each independently optionally substituted (e.g., C$_1$-C$_6$ alkyl, C$_1$-C$_6$ alkoxy or CN);

R$^{8a}$ is H, NR$^a$R$^b$, C$_1$-C$_6$ alkyl, (C$_0$-C$_6$ alkylene)C$_3$-C$_8$ cycloalkyl, (C$_0$-C$_6$ alkylene)phenyl, or (C$_0$-C$_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), wherein said alkyl, alkylene, cycloalkyl, phenyl and heterocyclyl are each independently optionally substituted (e.g., by halogen, OH, CN, NR$^a$R$^b$, C$_1$-C$_6$ alkyl, C$_1$-C$_6$ alkoxy, or oxo);

R$^{8aa}$ is H, C$_1$-C$_6$ alkyl optionally substituted by OH, or C(O)NR$^a$R$^b$; or or R$^8$ and R$^{8aa}$ together form an optionally substituted (e.g., by oxo) 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S);

R$^9$, independently at each occurrence, is OH, halogen, C$_1$-C$_6$ alkyl, (C$_0$-C$_6$ alkylene)C$_3$-C$_8$ cycloalkyl, (C$_0$-C$_6$ alkylene)phenyl, (C$_0$-C$_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), (C$_0$-C$_6$ alkylene)C(O)NR$^a$R$^b$, (C$_0$-C$_6$ alkylene)NR$^a$R$^b$, or C(O)(C$_1$-C$_6$ alkyl), wherein said alkyl, alkylene, cycloalkyl, phenyl and heterocyclyl are each independently optionally substituted (e.g., by OH, CN, halogen, NR$^a$R$^b$, 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), or C$_1$-C$_6$ alkyl optionally substituted by halogen);

R$^a$ and R$^b$, independently at each occurrence, are selected from the group consisting of hydrogen, C$_1$-C$_6$ alkyl optionally substituted by halogen or CN, (C$_0$-C$_6$ alkylene)C$_3$-C$_8$ cycloalkyl, or (C$_0$-C$_6$ alkylene)phenyl, and wherein one or more alkylene units of any alkyl group is independently optionally substituted by —O—, or alternatively R$^a$ and R$^b$ may be joined together with the nitrogen atom to which they are attached to form an optionally substituted (e.g., by CN or C$_1$-C$_6$ alkyl) 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S);

m$^1$, m$^2$, m$^3$ and m$^4$ are each independently 0, 1 or 2; and n is 0 or 1.

In some embodiments, a compound of Formula 0 is further defined as a compound of Formula I:

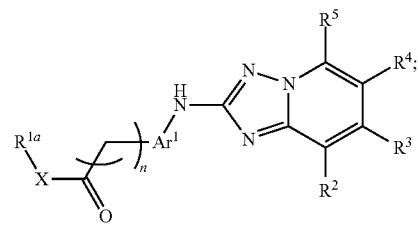

and stereoisomers and salts thereof, wherein:

Ar$^1$ is phenylene or 3-11 membered heteroarylene (e.g., 5-6 membered heteroaryl containing 1 to 4 heteroatoms selected from O, N and S), wherein Ar$^1$ is optionally substituted;

X is —O— or —N(R$^{1b}$)—(CR$^{x1}$R$^{y1}$)$_p$—, wherein R$^{x1}$ and R$^{y1}$ are each independently hydrogen or C$_1$-C$_6$ alkyl and p is 0 to 6, and wherein the —N(R$^{1b}$)— portion of —N(R$^{1b}$)—(CR$^{x1}$R$^{y1}$)$_p$— is bound to the carbonyl carbon of Formula I, as in:

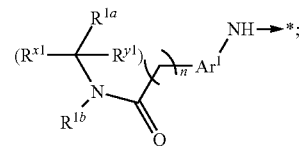

R$^{1a}$ is hydrogen, C$_1$-C$_6$ alkyl, C$_3$-C$_8$ cycloalkyl, phenyl, or 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) and R$^{1a}$ is optionally substituted by R$^9$;

R$^{1b}$ is hydrogen, C$_1$-C$_6$ alkyl, or C$_3$-C$_8$ cycloalkyl, and wherein one or more alkylene units of said alkyl group is optionally substituted by —O— and wherein any alkyl or cycloalkyl group is optionally substituted by OH, or when p is 0 and X is —N(R$^{1b}$)—, R$^{1a}$ and R$^{1b}$ may be joined together with the nitrogen atom to which R$^{1a}$ and R$^{1b}$ is attached to form a 3-11 membered heterocyclyl (e.g., 5-6 membered heteroaryl containing 1 to 4 heteroatoms selected from O, N and S; a 4-11 membered heterocycloalkyl containing 1 to 4 heteroatoms selected from O, N and S; or the 3-11 membered heterocyclyl contains at least one nitrogen) optionally substituted by R$^9$;

R$^2$ is a 3-11 membered heterocyclyl (e.g., 5-6 membered heteroaryl or 4-11 membered heterocycloalkyl) containing at least 1 nitrogen, selected from groups (a)-(e), or a C$_5$-C$_8$ cycloalkenyl ring (f), or a —O—(CR$^x$R$^y$)$_q$—Ar$^2$ group (g) where R$^x$ and R$^y$ are independently hydrogen or C$_1$-C$_6$ alkyl, q is 0 to 3 and Ar$^2$ is optionally substituted C$_6$-C$_{10}$ aryl or optionally substituted 5-11 membered heteroaryl (e.g., 5-6 membered heteroaryl containing 1 to 4 heteroatoms selected from O, N and S:

(a)

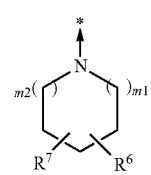

-continued

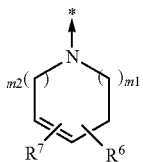

(b)

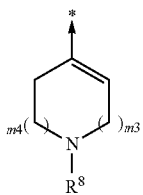

(c)

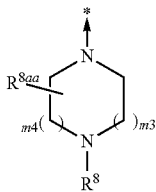

(d)

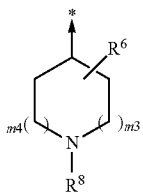

(e)

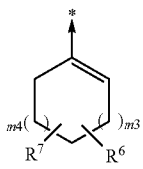

(f)

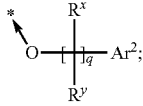

(g)

$R^3$, $R^4$ and $R^5$ are each independently selected from the group consisting of hydrogen, $CH_3$, $CH_2CH_3$, $OCH_3$, $CF_3$, F and Cl; for example, $R^3$-$R^5$ may each be hydrogen;

$R^6$ and $R^7$ are independently selected from the group consisting of hydrogen, halogen, OH, CN, phenyl, $C_1$-$C_6$ alkyl, ($C_0$-$C_6$ alkylene)$C_3$-$C_8$ cycloalkyl, ($C_0$-$C_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), ($C_0$-$C_6$ alkylene)C(O)NR$^a$R$^b$, ($C_0$-$C_6$ alkylene)NR$^a$C(O)($C_1$-$C_6$ alkyl), ($C_0$-$C_6$ alkylene)C(O)R$^{8a}$, ($C_0$-$C_6$ alkylene)C(O)OR$^{8a}$, $C_1$-$C_6$ alkoxy, —O—($C_3$-$C_6$ cycloalkyl), —O—($C_0$-$C_6$ alkylene)C(O)NR$^a$R$^b$, and —O—(3-11 membered heterocyclyl) (e.g., 5-6 membered heteroaryl containing 1 to 4 heteroatoms selected from O, N and S or 4-11 membered heterocycloalkyl containing 1 to 4 heteroatoms selected from O, N and S); wherein said alkyl, alkylene, alkoxy, cycloalkyl, phenyl and heterocyclyl are each independently optionally substituted, or $R_6$ and $R_7$ together form an optionally substituted phenyl or optionally substituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S);

$R^8$ is $C_1$-$C_6$ alkyl, ($C_0$-$C_6$ alkylene)phenyl, C(O)NR$^a$R$^b$, SO$_2$NR$^a$R$^b$, C(O)OR$^{8a}$ or C(O)R$^{8a}$, wherein said alkyl, alkylene and phenyl are each independently optionally substituted;

$R^{8a}$ is $C_1$-$C_6$ alkyl, ($C_0$-$C_6$ alkylene)$C_3$-$C_8$ cycloalkyl, ($C_0$-$C_6$ alkylene)phenyl, or ($C_0$-$C_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), wherein said alkyl, alkylene, cycloalkyl, phenyl and heterocyclyl are each independently optionally substituted;

$R^{8aa}$ is H; or or $R^8$ and $R^{8aa}$ together form an optionally substituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S);

$R^9$, independently at each occurrence, is OH, halogen, $C_1$-$C_6$ alkyl, ($C_0$-$C_6$ alkylene)$C_3$-$C_8$ cycloalkyl, ($C_0$-$C_6$ alkylene)phenyl, ($C_0$-$C_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), ($C_0$-$C_6$ alkylene)C(O)NR$^a$R$^b$, ($C_0$-$C_6$ alkylene)N-R$^a$R$^b$, or C(O)($C_1$-$C_6$ alkyl), wherein said alkyl, alkylene, cycloalkyl, phenyl and heterocyclyl are each independently optionally substituted;

$R^a$ and $R^b$ are independently at each occurrence selected from the group consisting of hydrogen, $C_1$-$C_6$ alkyl, ($C_0$-$C_6$ alkylene)$C_3$-$C_8$ cycloalkyl, or ($C_0$-$C_6$ alkylene)phenyl, and wherein one or more alkylene units of any alkyl group is independently optionally substituted by —O—, or alternatively $R^a$ and $R^b$ may be joined together with the nitrogen atom to which they are attached to form an optionally substituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S);

$m^1$, $m^2$, $m^3$ and $m^4$ are each independently 0, 1 or 2; and n is 0 or 1.

In some embodiments, a compound of Formula 0 is further defined as a compound of Formula Ia:

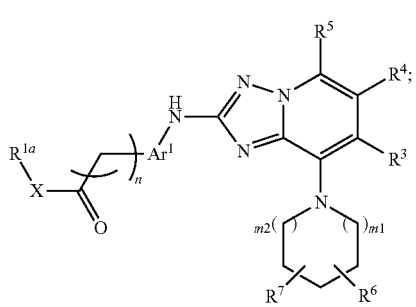

Ia wherein Ar$^1$, X, R$^{1a}$, R$^3$-R$^7$, m$^1$, m$^2$ and n are as defined herein.

In some embodiments, in a compound of the present invention, such as a compound of Formula 0, I or Ia, m$^1$ is 1 and m$^2$ is 1, or m$^1$ is 2 and m$^2$ is 1.

In some embodiments of a compound of the present invention, such as a compound of Formula 0, I, Ia, Ib or If, $R^6$ and $R^7$ are attached to the ring at the same carbon atom. In some embodiments of a compound of the present invention, such as a compound of Formula 0, I, Ia, Ib or If, $R^6$ is $C_1$-$C_6$ alkyl or $C_1$-$C_6$-alkoxy, and $R^7$ is optionally substituted phenyl, such as phenyl substituted by halogen, CN, $C_1$-$C_6$ alkyl or $C_1$-$C_6$ alkoxy. In some embodiments in a compound of the present invention, such as a compound of Formula 0, I, Ia, Ib or If, $R^6$ is $C_1$-$C_6$ alkyl, $C_3$-$C_6$ cycloalkyl or optionally substituted phenyl, such as phenyl substituted by halogen, CN, $C_1$-$C_6$ alkyl or $C_1$-$C_6$ alkoxy, and $R^7$ is OH, $(C_0$-$C_6$ alkylene)$C(O)NR^aR^b$, $(C_0$-$C_6$ alkylene)CN or —O—$(C_0$-$C_6$ alkyl)CN. In some embodiments in a compound of the present invention, such as a compound of Formula 0, I, Ia, Ib or If, $R^6$ is hydrogen and $R^7$ is selected from $(C_0$-$C_6$ alkylene)$C(O)NR^aR^b$, $(C_0$-$C_6$ alkylene)CN, $C_1$-$C_6$-alkoxy, —O—$(C_3$-$C_6$ cycloalkyl), —O—$(C_0$-$C_6$ alkylene)$C(O)NR^aR^b$, and —O—$(C_1$-$C_6$ alkylene)CN. In some embodiments in a compound of the present invention, such as a compound of Formula 0, I, Ia, Ib or If, $R^6$ and $R^7$ together form a 3-11 membered heterocycloalkyl (such as a heterocycloalkyl containing at least one nitrogen) optionally substituted by oxo.

In some embodiments of compounds of the present invention, such as a compound of Formula 0, I or Ia, the moiety shown below,

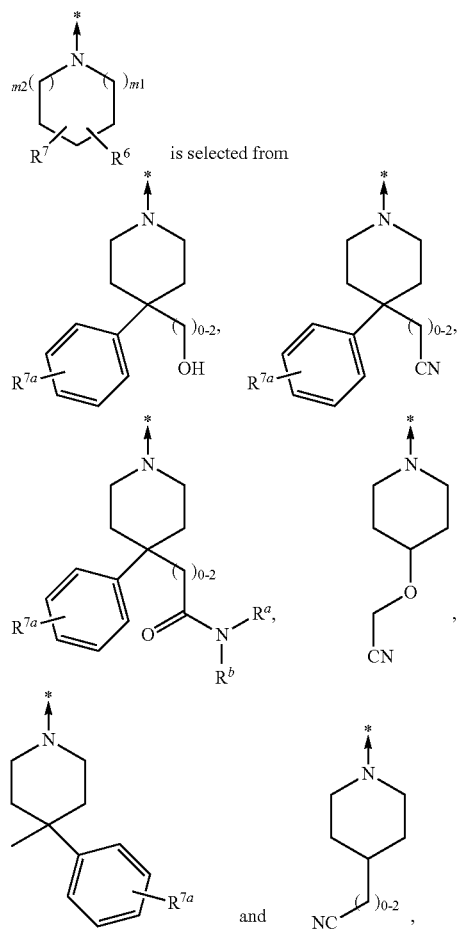

wherein $R^{7a}$ is selected from hydrogen, halogen, OH, $C_1$-$C_6$ alkyl, $C_1$-$C_6$ alkoxy, $C_1$-$C_6$ haloalkyl and CN.

In some embodiments, a compound of Formula 0 is further defined as a compound of Formula Ib:

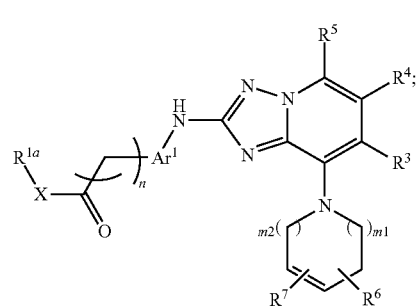

wherein $Ar^1$, X, $R^{1a}$, $m^1$, $m^2$ and n are as defined herein.

In some embodiments of a compound of the present invention, such as a compound of Formula 0, I or Ib, $m^1$ is 1 and $m^2$ is 2, or $m^1$ is 2 and $m^2$ is 1, or $m^1$ is 1 and $m^2$ is 1.

In some embodiments of a compound of the present invention, such as a compound of Formula 0, I, Ia, Ib or If, $R^6$ is H and $R^7$ and is substituted phenyl.

In some embodiments of a compound of the present invention, such as a compound of Formula 0, I or Ib, the moiety shown below,

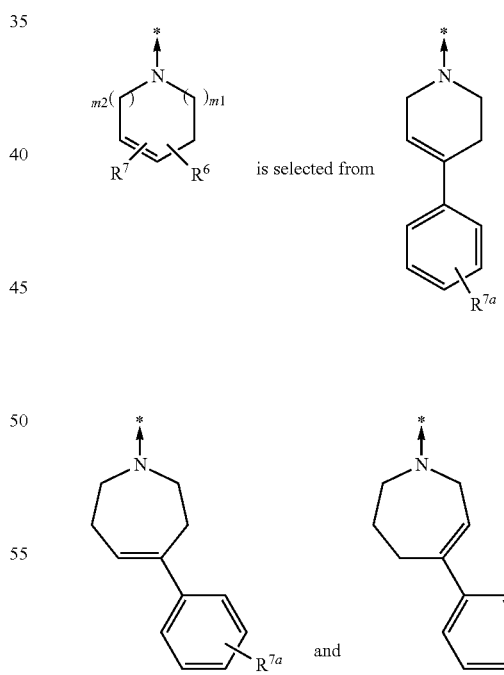

wherein $R^{7a}$ is selected from hydrogen, halogen, $C_1$-$C_6$ alkyl, $C_1$-$C_6$ haloalkyl and CN.

In some embodiments, a compound of Formula 0 is further defined as a compound of Formula Ic:

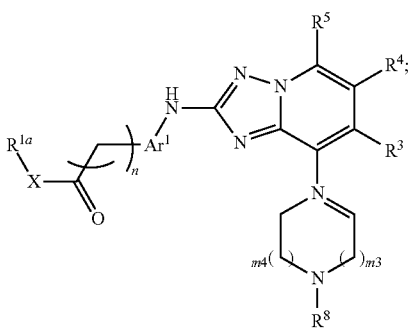

Ic wherein $Ar^1$, X, $R^{1a}$, $R^3$-$R^5$, $R^8$, $m^3$, $m^4$ and n are as defined herein.

In some embodiments of a compound of the present invention, such as a compound of Formula 0, I or Ic, $m^3$ is 1 and $m^4$ is 1, or $m^3$ is 1 and $m^4$ is 2, or $m^3$ is 1 and $m^4$ is 0.

In some embodiments of a compound of the present invention, such as a compound of Formula 0, I, Ic, Id or Ie, the following moiety, shown below,

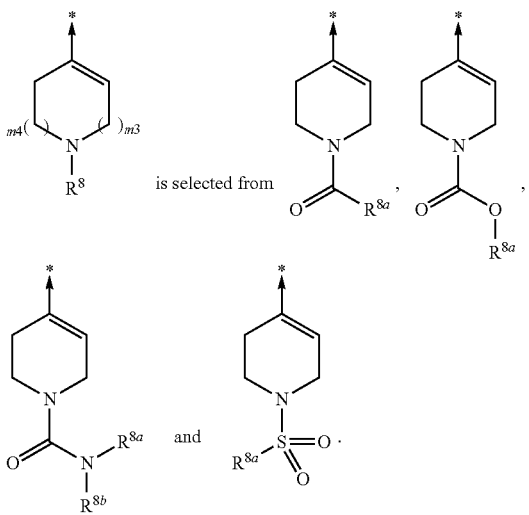

In some embodiments, a compound of Formula 0 is further defined as a compound of Formula Id:

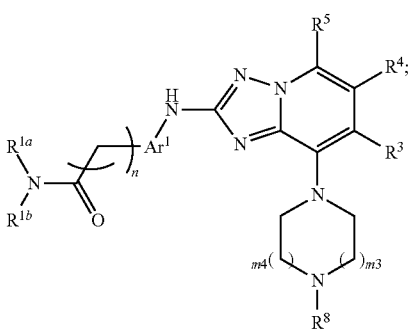

Id wherein $Ar^1$, $R^{1a}$, $R^{1b}$, $R^3$-$R^5$, $R^8$, $m^3$, $m^4$ and n are defined herein.

In some embodiments of a compound of the present invention, such as a compound of Formula 0, I or Id, $m^3$ is 1 and $m^4$ is 1, $m^3$ is 1 and $m^4$ is 1, or $m^3$ is 1 and $m^4$ is 2.

In some embodiments of a compound of the present invention, such as a compound of Formula 0, I, Ic, Id, or Ie, $R^8$ is substituted phenyl, such as mono- or disubstituted phenyl, $C(O)NR^aR^b$ or $C(O)R^{8a}$.

In some embodiments, a compound of Formula 0 is further defined as a compound of Formula Ie:

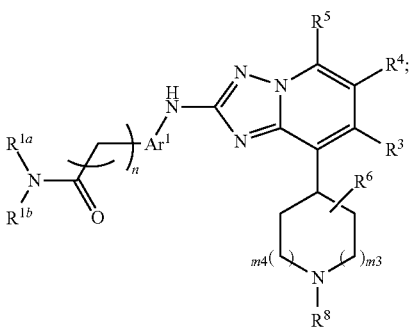

Ie wherein $Ar^1$, $R^{1a}$, $R^{1b}$, $R^3$-$R^6$, $R^8$, $m^3$, $m^4$ and n are as defined herein.

In some embodiments of a compound of the present invention, such as a compound of Formula 0, I or Ie, $m^3$ is 0 and $m^4$ is 1 or $m^3$ is 1 and $m^4$ is 1.

In some embodiments of a compound of the present invention, such as a compound of Formula 0, I, Ia, Ib, Ie or If, $R^6$ is hydrogen.

In some embodiments of a compound of the present invention, such as a compound of Formula 0, I, Id, Ie or If, $R^8$ is $C(O)NR^aR^b$.

In some embodiments, a compound of Formula 0, is further defined as a compound of Formula If:

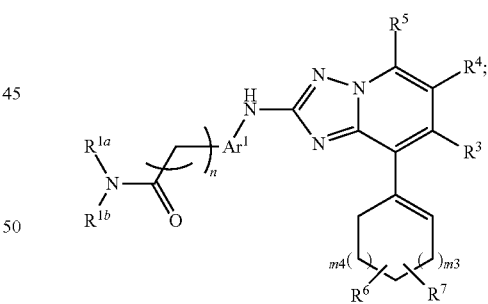

If wherein $Ar^1$, $R^{1a}$, $R^{1b}$, $R^3$-$R^7$, $m^3$, $m^4$ and n are as defined herein.

In some embodiments of a compound of the present invention, such as a compound of Formula 0, I or If, $m^3$ is 1 and $m^4$ is 1.

In some embodiments of a compound of the present invention, such as a compound of Formula 0, I, Ia, Ib, or If, $R^7$ is OH or $C_1$-$C_6$-alkoxy.

In some embodiments of compounds of the present invention, such as a compound of Formula 0, I, Ia, Ib, or If, one or both of $R^6$ and $R^7$ is located at the para position of the ring. In some embodiments of compounds of the present invention, such as a compound of Formula 0, I, Ia, Ib, or If, $R^6$ and $R^7$ are attached to different ring atoms. In some embodiments of compounds of the present invention, such as a compound of Formula 0, I, Ia, Ib, or If, $R^6$ and $R^7$ are both attached to the same ring atom.

In some embodiments, a compound of Formula 0 is further defined as a compound of Formula Ig:

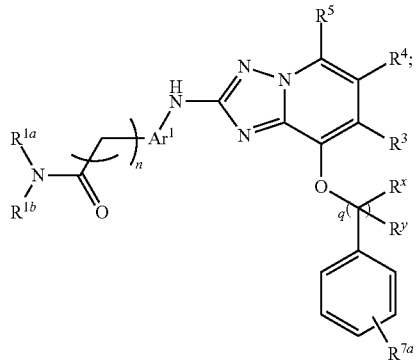

wherein $Ar^1$, $R^{1a}$, $R^{1b}$, $R^3$-$R^5$, $R^{7a}$ and n are as defined herein, $R^{7a}$ is selected from hydrogen, OH, halogen, $C_1$-$C_6$ alkyl, $C_1$-$C_6$ alkoxy, $C_1$-$C_6$ haloalkyl and CN, and q is either 0 or 1, and when q is 1, then $R^x$ and $R^y$ are hydrogen.

In some embodiments of a compound of the present invention, such as a compound of Formula 0, I, Ia, Ib, Ic, Id, Ie, If, or Ig, $Ar^1$ is unsubstituted phenylene or unsubstituted 3-11 membered heteroarylene. In some embodiments of a compound of the present invention, such as a compound of Formula 0, I, Ia, Ib, Ic, Id, Ie, If, or Ig, $Ar^1$ is optionally substituted phenylene or optionally substituted pyrazolylene. In some embodiments of a compound of the present invention, such as a compound of Formula 0, I, Ia, Ib, Ic, Id, Ie, If, or Ig, $Ar^1$ is unsubstituted phenylene or unsubstituted pyrazolylene. In some embodiments of a compound of the present invention, such as a compound of Formula 0, I, Ia, Ib, Ic, Id, Ie, If, or Ig, $Ar^1$ is unsubstituted phenylene and n is 0. In some embodiments of a compound of the present invention, such as a compound of Formula 0, I, Ia, Ib, Ic, Id, Ie, If, or Ig, $Ar^1$ is unsubstituted pyrazolylene and n is 1. In some embodiments of a compound of the present invention, such as a compound of Formula 0, I, Ia, Ib, Ic, Id, Ie, If, or Ig, $Ar^1$, such as phenyl, is not substituted by halogen, methyl, methoxy, ethoxy, isopropoxy, OH, $CF_3$, or —$OCH_2C(O)N(CH_3)_2$. In some embodiments, $Ar^1$ is not unsubstituted or substituted pyridyl.

In some embodiments of a compound of the present invention, such as a compound of Formula 0, I, Ia, Ib or Ic, the moiety

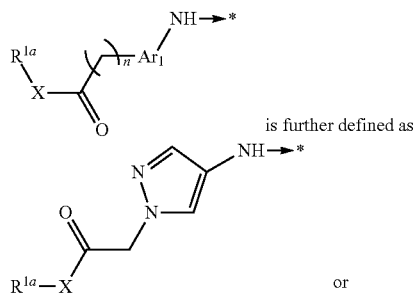

is further defined as

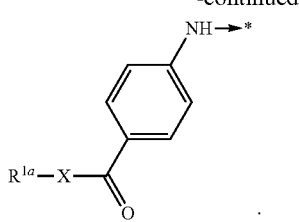

In some embodiments of a compound of the present invention, such as a compound of Formula 0, I, Ia, Ib, or Ic, —X—$R^{1a}$ is $C_1$-$C_6$ alkoxy or —O-3-11 membered heterocycloalkyl (such as heterocycloalkyl containing at least one nitrogen). For example, —X—$R^{1a}$ may be —$OCH_3$, —$OC_2H_5$, or

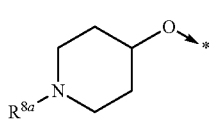

wherein $R^{8a}$ is $C_1$-$C_6$ alkyl.

In some embodiments of a compound of the present invention, such as a compound of Formula 0, I, Ia, Ib, or Ic, —X—$R^{1a}$ is —$N(R^{1b})$—$(CR^{x1}R^{y1})_p$—$R^{1a}$. In some embodiments of a compound of the present invention, such as a compound of Formula 0, I, Ia, Ib, or Ic, $R^{1b}$ is $C_1$-$C_6$ alkyl optionally substituted by $C_1$-$C_6$ alkoxy, p is 0-3, $R^{x1}$ and $R^{y1}$ are each independently hydrogen or $C_1$-$C_6$ alkyl, $R^{1a}$ is $C_1$-$C_6$ alkyl and $R^9$ is $NR^aR^b$. In other embodiments of a compound of the present invention, such as a compound of Formula 0, I, Ia, Ib, or Ic, $R^{1b}$ is $C_1$-$C_6$ alkyl optionally substituted by $C_1$-$C_6$ alkoxy, p is 0-3, $R^{x1}$ and $R^{y1}$ are each independently hydrogen or $C_1$-$C_6$ alkyl, and $R^{1a}$ is 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) optionally substituted by $R^9$. In yet other embodiments of a compound of the present invention, such as a compound of Formula 0, I, Ia, Ib, or Ic, p is 0 and $R^{1a}$ and $R^{1b}$ are joined to form a 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) optionally substituted by W In some embodiments of a compound of the present invention, such as a compound of Formula 0, I, Ia, Ib, or Ic, —X—$R^{1a}$ is —$N(R^{1b})$—$(CR^{x1}R^{y1})_p$—$R^{1a}$ and is selected from

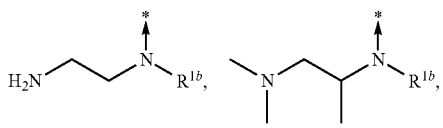

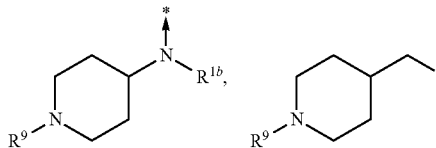

-continued
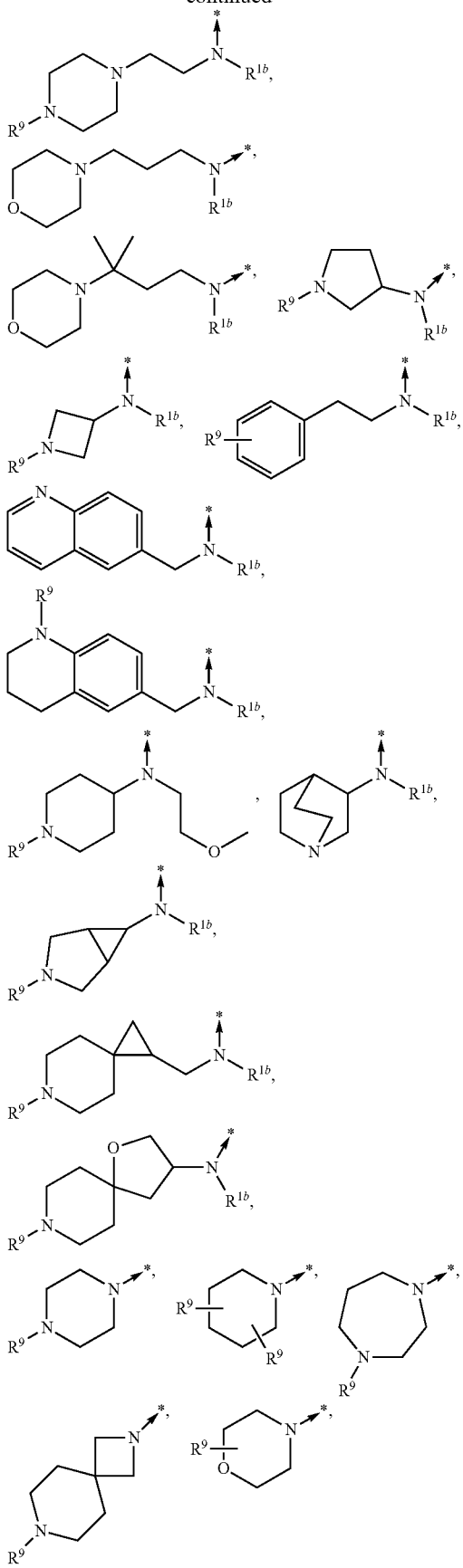
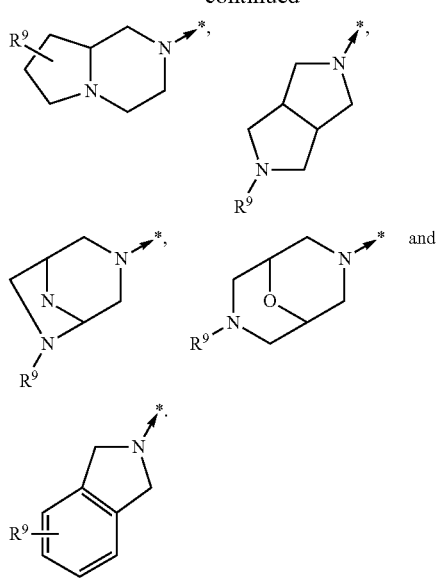
In some embodiments of a compound of the present invention, such as a compound of Formula 0, I, Ia, Ib, or Ic —X—$R^{1a}$ is —N($R^{1b}$)—($CR^{x1}R^{y1}$)$_p$—$R^{1a}$ and is selected from -continued

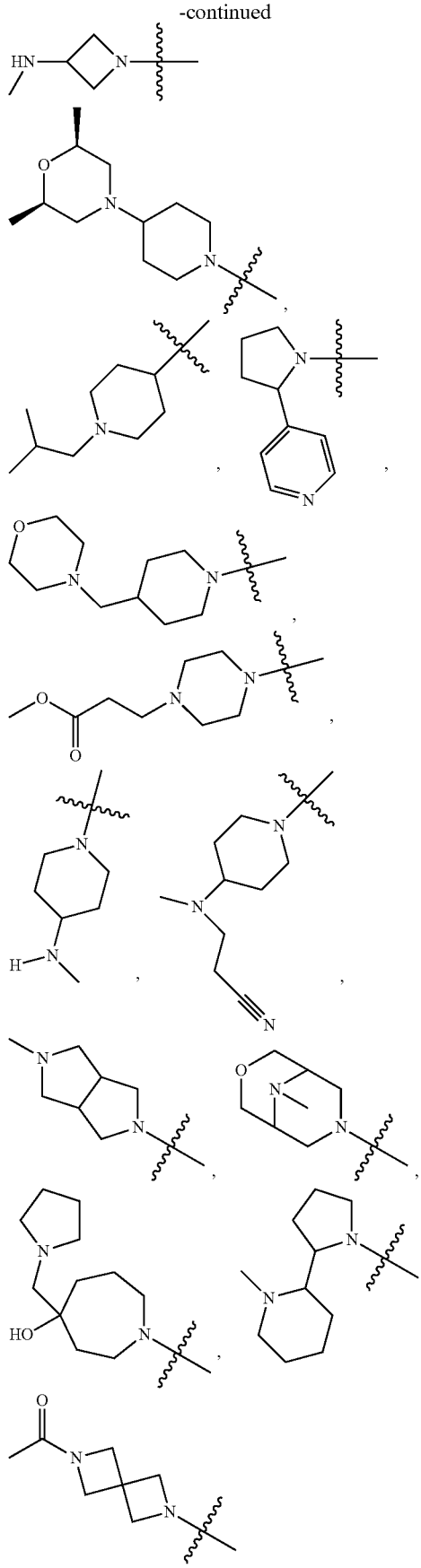

-continued

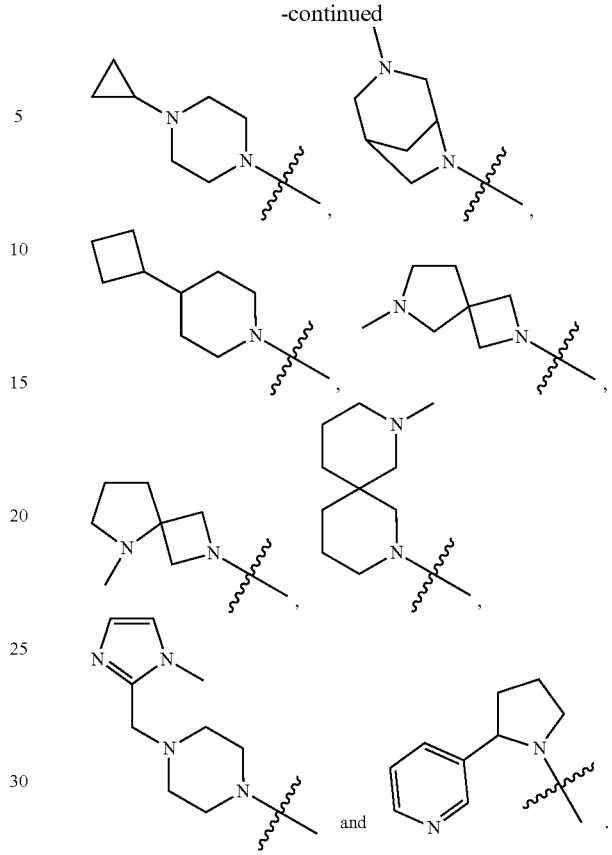

In some embodiments of a compound of the present invention, such as a compound of Formula 0, I, Ia, Ib, Ic, Id, Ie, If, or Ig, $R^9$ is optionally substituted $C_1$-$C_6$ alkyl or optionally substituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S). For example, in some embodiments of compounds of the present invention, such as a compound of Formula 0, I, Ia, Ib, Ic, Id, Ie, or Ig, the optional substituents of optionally substituted $C_1$-$C_6$ alkyl of $R^9$ or optionally substituted 3-11 membered heterocyclyl of $R^9$ are selected from OH; CN; $NR^aR^b$; $C_1$-$C_6$ alkyl; $C_3$-$C_8$ cycloalkyl; $C_1$-$C_6$ alkoxy; phenyl; 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) optionally substituted by $C_1$-$C_6$ alkyl or $NR^aR^b$; $C(O)C_1$-$C_6$ alkyl; and C(O)-3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) optionally substituted by $C_1$-$C_6$ alkyl.

In some embodiments of a compound of the present invention, such as a compound of Formula 0, I, Ia, Ib, Ic, Id, Ie, If, or Ig, the group —X—$R^{1a}$ is a group selected from:

(i) A group

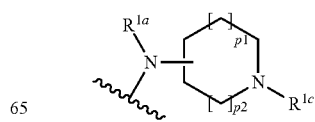

wherein R$^{1b}$ and R$^{1c}$ are independently hydrogen, C$_1$-C$_6$ alkyl or C$_3$-C$_6$ cycloalkyl and p1 and p2 are independently 0, 1 or 2;

(ii) A group

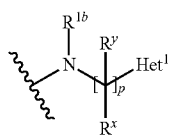

wherein R$^{1b}$ is hydrogen, C$_1$-C$_6$ alkyl or C$_3$-C$_6$ cycloalkyl; p is 0-6, such as 1-3; R$^x$ and R$^y$ are independently hydrogen or C$_1$-C$_6$ alkyl; Het$^1$ is a 5-, 6- or 7-membered heterocycloalkyl ring or a 6-membered heteroaryl ring. Exemplary structures include

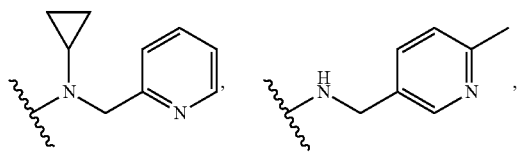

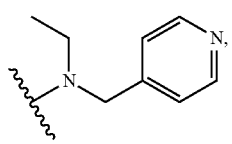

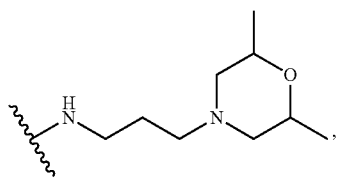

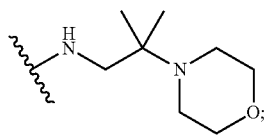

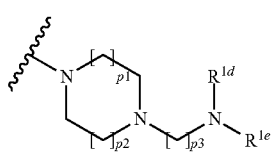

(iii) A group

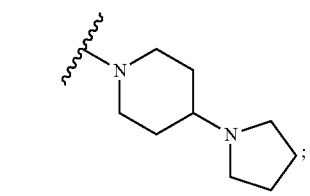

wherein R$^{1d}$ and R$^{1e}$ are independently hydrogen, C$_1$-C$_6$ alkyl or C$_3$-C$_6$ cycloalkyl, or R$^{1d}$ and R$^{1e}$ are joined in a ring optionally containing a further heteroatom selected from O, N and S, such as one further N or one further O, and p1, p2 and p3 are independently 0, 1 or 2. An exemplary group is

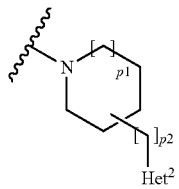

(iv) A group

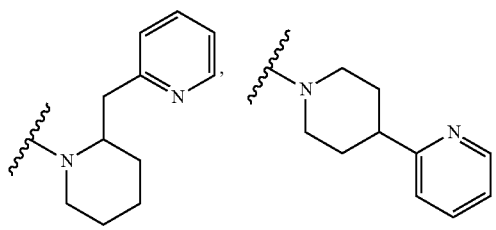

wherein p1 and p2 are independently 0, 1 or 2; Het$^2$ is a 3-11 (e.g., 4-7) membered heterocycloalkyl ring or 3-11 (e.g., 5-6) membered heteroaryl ring. Exemplary structures include

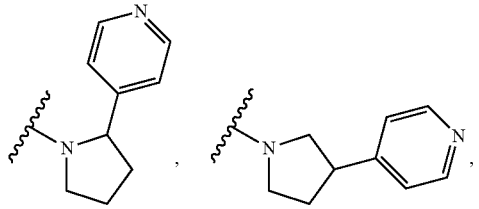

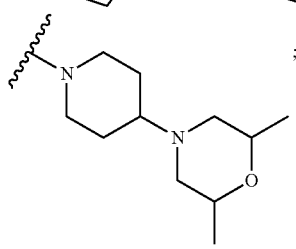

(v) A group

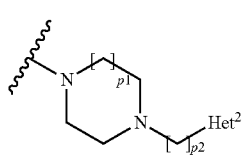

wherein p1 and p2 are independently 0, 1 or 2; Het$^2$ is a 3-11 (e.g., 4-7) membered heterocycloalkyl or 3-11 (e.g., 5-6) membered heteroaryl ring;

(vi) A bridged bicyclic group such as

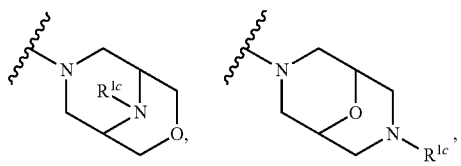

and $R^{1c}$ is hydrogen, $C_1$-$C_6$ alkyl or $C_3$-$C_6$ cycloalkyl; or

wherein p is 0, 1 or 2, $R^{1d}$ and $R^{1e}$ are independently hydrogen, $C_1$-$C_6$ alkyl or $C_3$-$C_6$ cycloalkyl, or $R^{1d}$ and $R^{1e}$ are joined in a ring optionally containing a further heteroatom selected from O, N and S, such as one further N or one further O;

(vii) A bridged bicyclic group such as

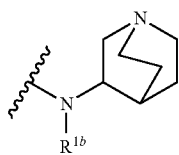

wherein $R^{1b}$ is hydrogen, $C_1$-$C_6$ alkyl or $C_3$-$C_6$ cycloalkyl;

(viii) A spirocyclic group comprising two 4-, 5- or 6-membered rings optionally containing further 1-4 heteroatoms, selected from O, N and S, such as N or O, such as

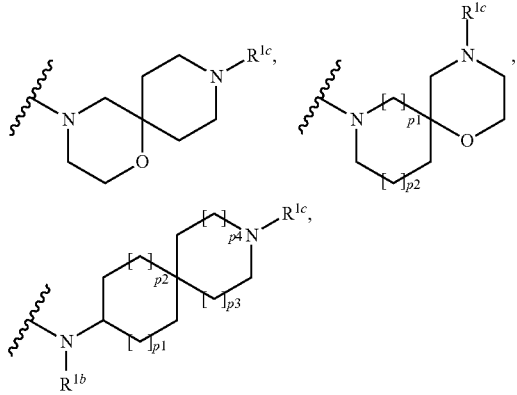

-continued

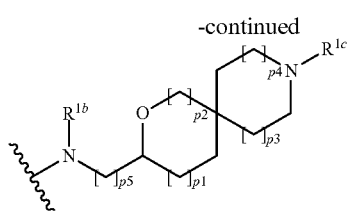

wherein p1, p2, p3, p4 and p5 are independently selected from 0, 1 and 2, $R^{1b}$ is hydrogen, $C_1$-$C_6$ alkyl or $C_3$-$C_6$ cycloalkyl, and $R^{1c}$ is hydrogen, $C_1$-$C_6$ alkyl or $C_3$-$C_6$ cycloalkyl. An exemplary group is

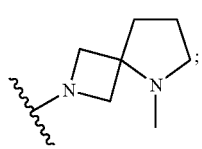 [SMILES: *N1CC2(CCCN2C)C1]

(ix) A group

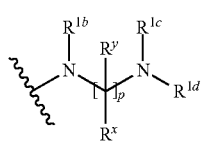

wherein $R^{1b}$, $R^{1c}$ and $R^{1d}$ are independently hydrogen, $C_1$-$C_6$ alkyl or $C_3$-$C_6$ cycloalkyl; p is 0-6, such as 1-3; $R^x$ and $R^y$ are independently hydrogen, $C_1$-$C_6$ alkyl, or $C_3$-$C_6$ cycloalkyl; or (x) A bicyclic group

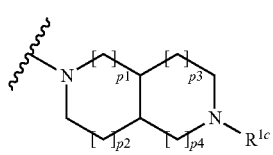

wherein p1, p2, p3 and p4 are independently selected from 0, 1 and 2 and $R^{1c}$ is hydrogen, $C_1$-$C_6$ alkyl or $C_3$-$C_6$ cycloalkyl. An exemplary group is

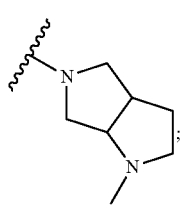 [SMILES: *N1CC2CCN(C)C2C1]

(xi) A bicyclic group

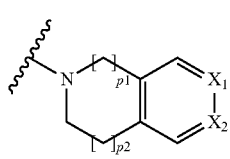

wherein p1 and p2 are independently 0, 1 or 2 and one of $X^1$ and $X^2$ is nitrogen and the other is CH;

(xii) A bicyclic group

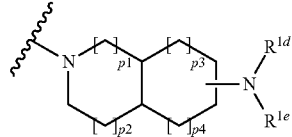

wherein p1, p2, p3 and p4 are independently selected from 0, 1 and 2 and $R^{1d}$ and $R^{1e}$ are independently hydrogen, $C_1$-$C_6$ alkyl or $C_3$-$C_6$ cycloalkyl or $R^{1d}$ and $R^{1e}$ are joined in a ring optionally containing a further 1-3 heteroatoms, such as O, N or S, such as a further N atom or a further O atom;

(xiii) A bicyclic group

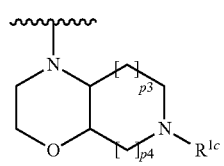

wherein p3 and p4 are independently 0, 1 or 2 and $R^{1c}$ is hydrogen, $C_1$-$C_6$ alkyl or $C_3$-$C_6$ cycloalkyl: or (xiv) A bicyclic group

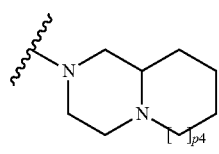

wherein p4 is 0 or 1.

In some embodiments the group —X—$R^{1a}$ is a group selected from:

(i) A group

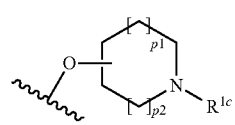

wherein $R^{1c}$ is hydrogen, $C_1$-$C_6$ alkyl or $C_3$-$C_6$ cycloalkyl and p1 and p2 are independently 0, 1 or 2. An exemplary group is

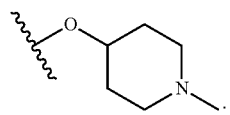 [SMILES: *OC1CCN(C)CC1]

In some embodiments of a compound of the present invention, such as a compound of Formula 0, I, Ia, Ib, Ic, Id, Ie, If, or Ig, $R^{1a}$ is selected from the following:

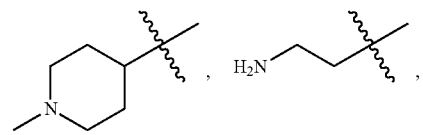

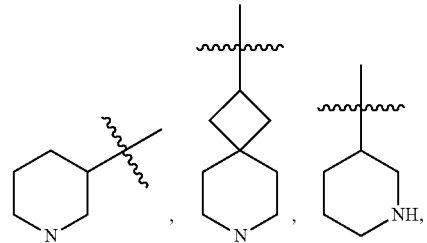

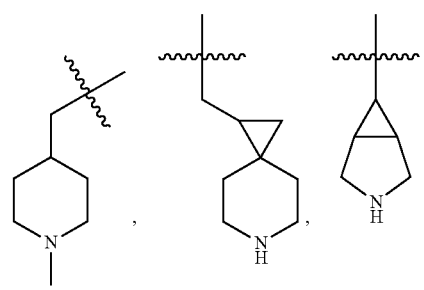

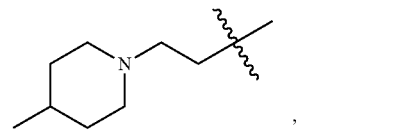

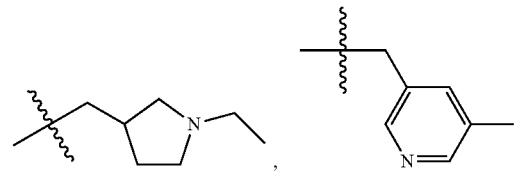

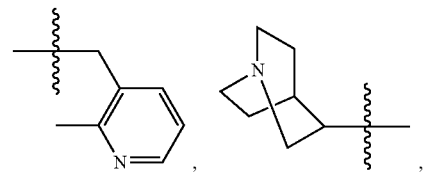

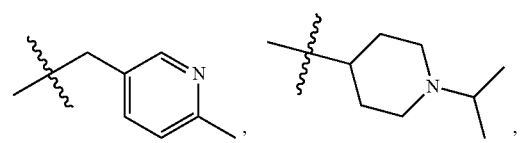

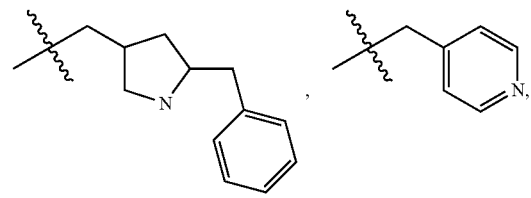

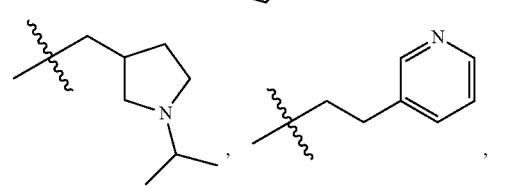

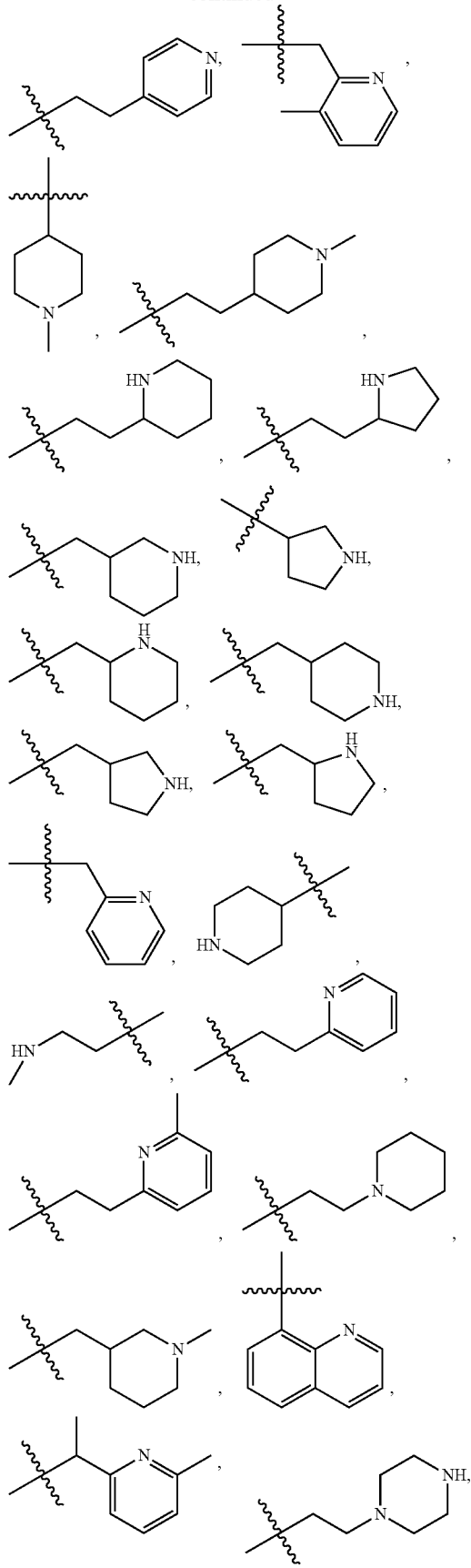
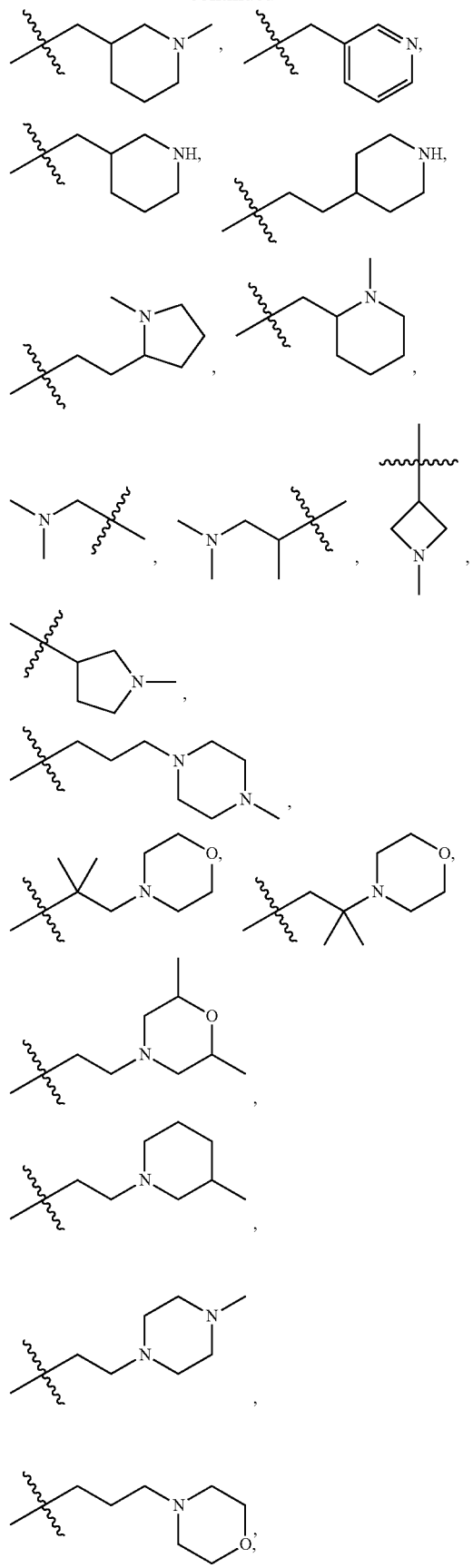

-continued

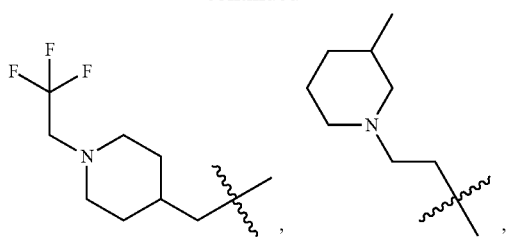
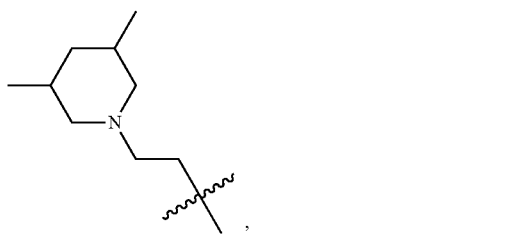
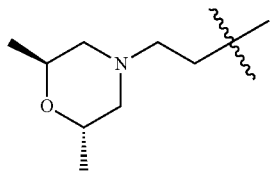
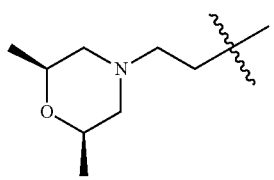
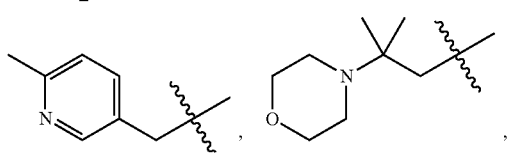
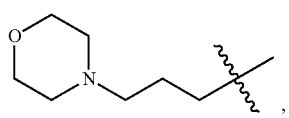
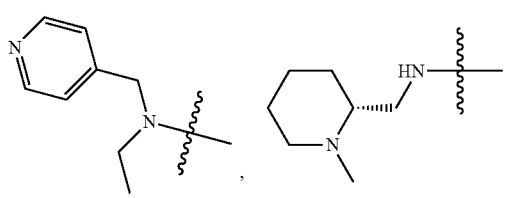
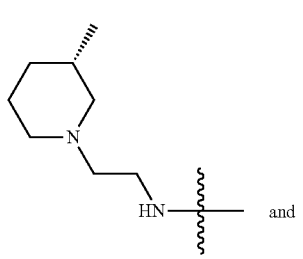

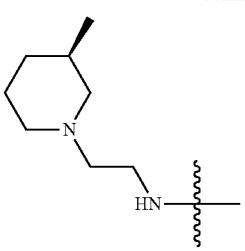 [SMILES: *NCCN1CCC[C@@H](C)C1]

-continued

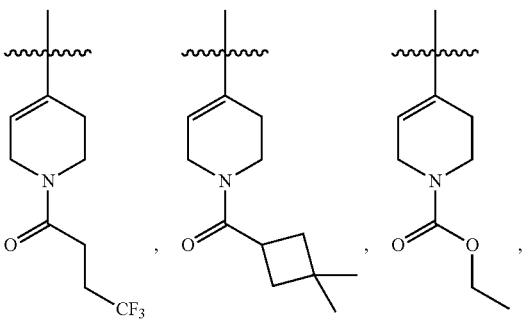

and stereoisomers thereof.

In some embodiments of a compound of the present invention, such as a compound of Formula 0, I, Ia, Ib, Ic, Id, Ie, If, or Ig, $R^{1a}$ is selected from the moieties shown in Table I or Table II, or stereoisomers thereof In some embodiments of a compound of the present invention, such as a compound of Formula 0, I, Ia, Ib, Ic, Id, Ie, If, or Ig, $R^{1a}$ is not hydrogen.

In some embodiments of a compound of the present invention, such as a compound of Formula 0, I, Ia, Ib, Ic, Id, Ie, If, or Ig, $R^2$ is selected from the following:

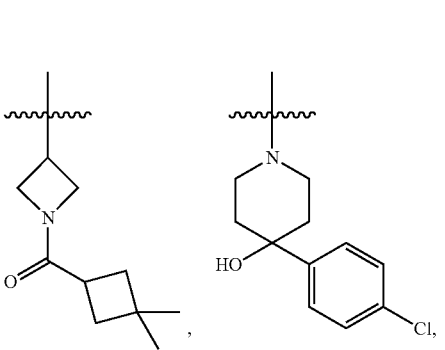
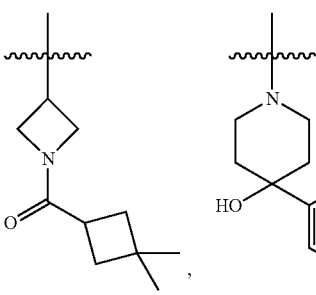
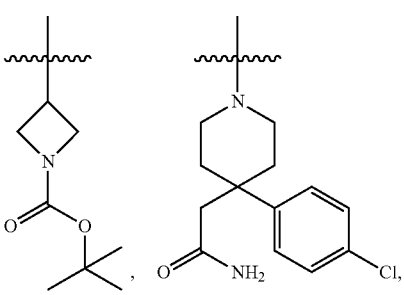

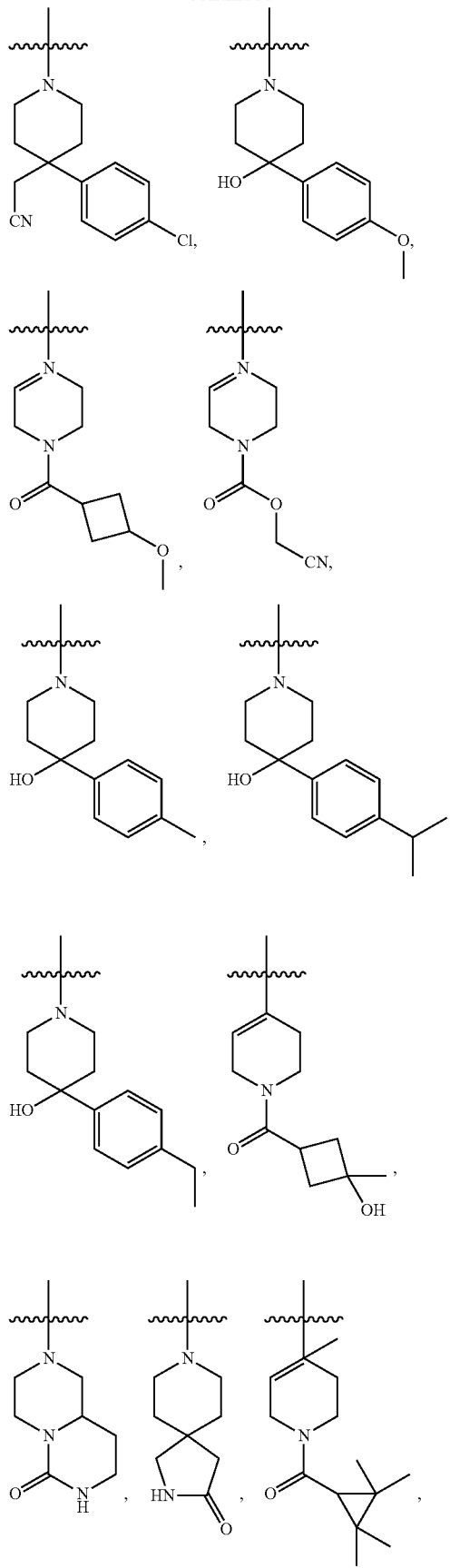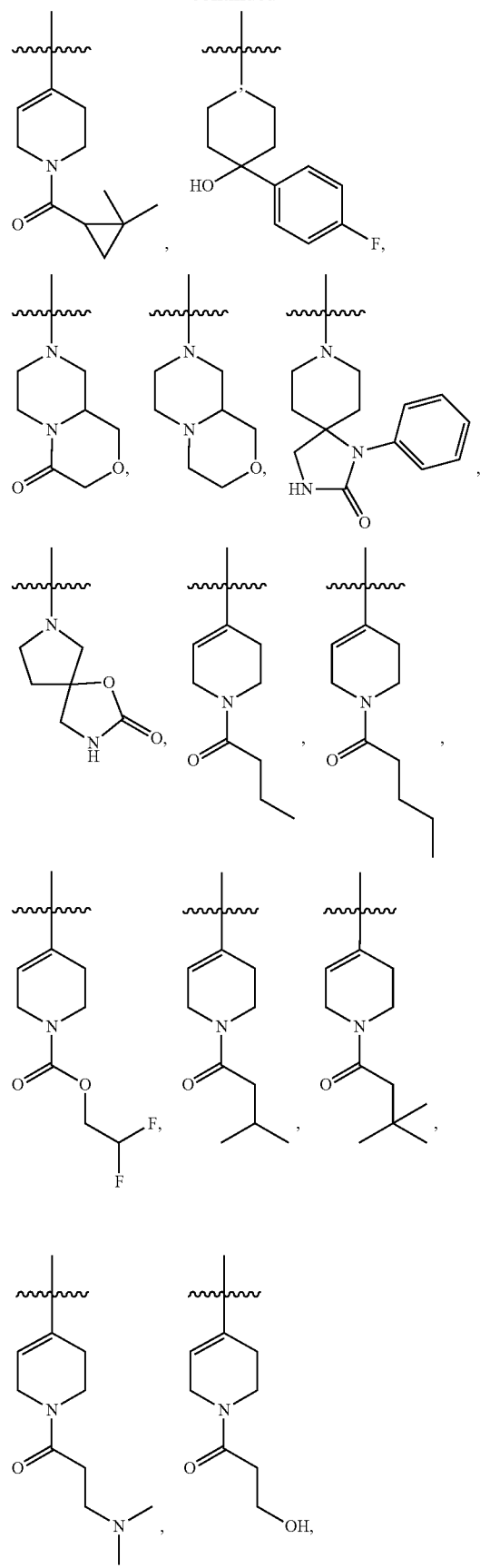

-continued
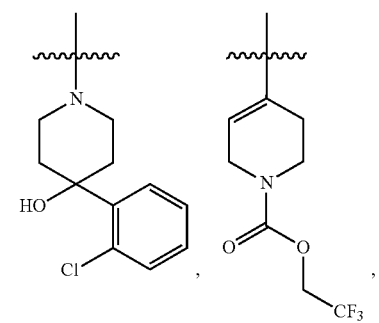
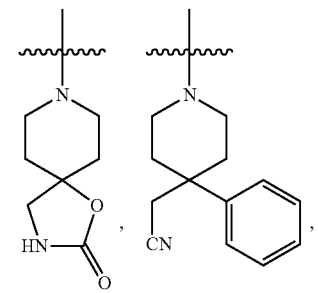
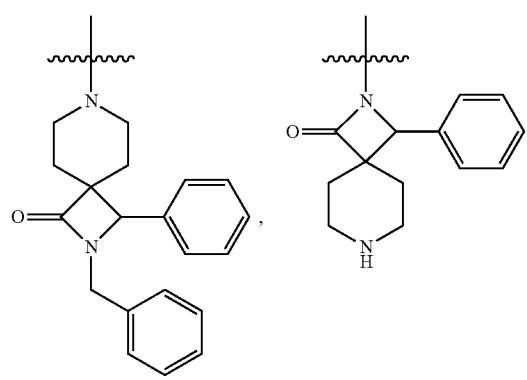
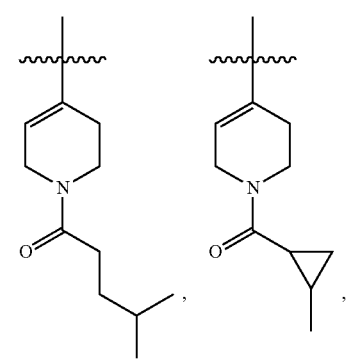
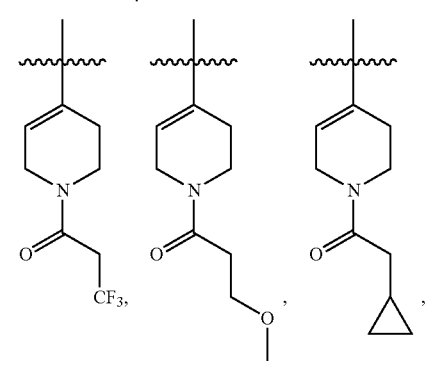
-continued
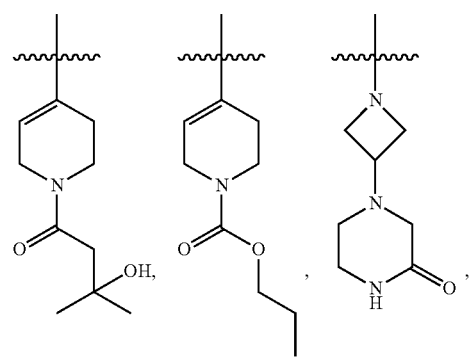
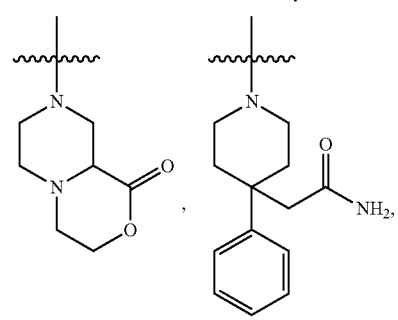
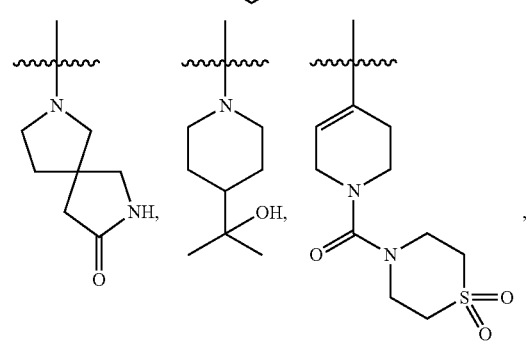
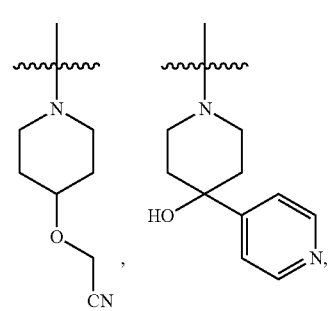
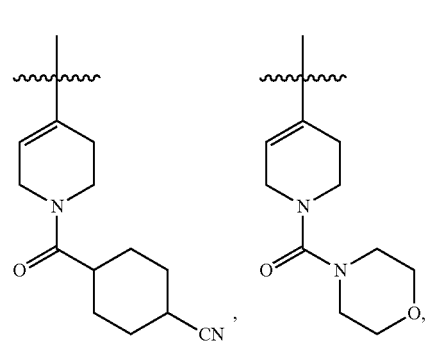

-continued
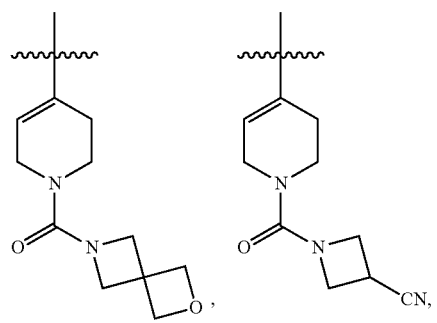
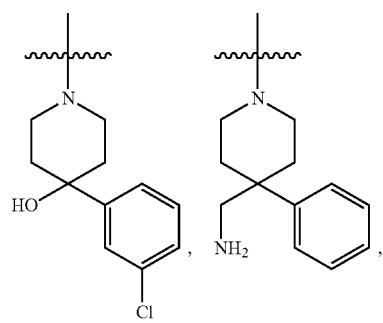
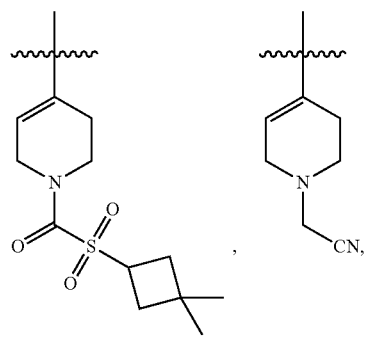
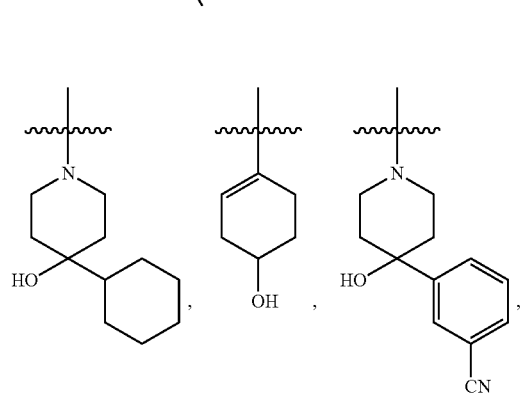
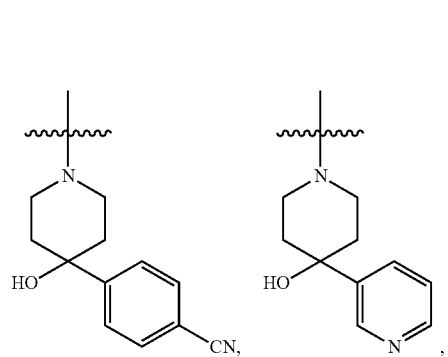
-continued
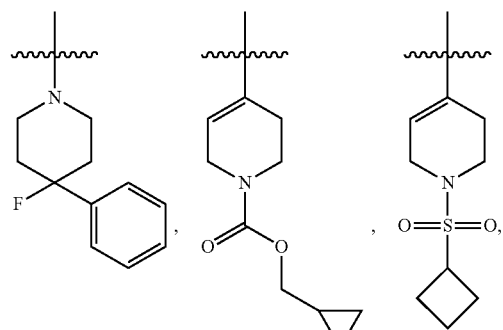
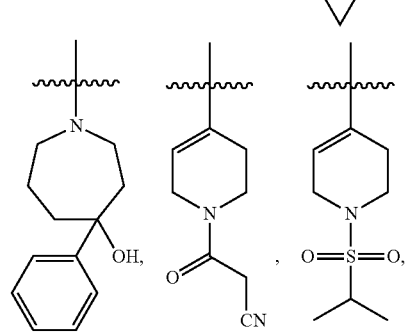
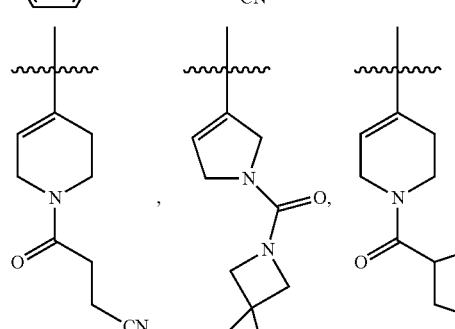
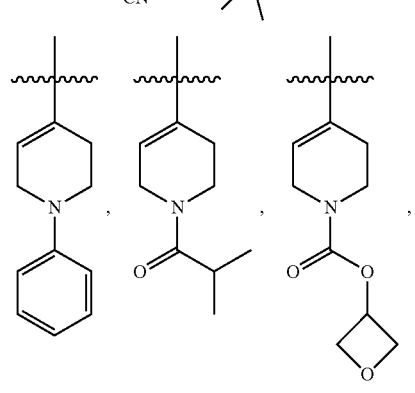
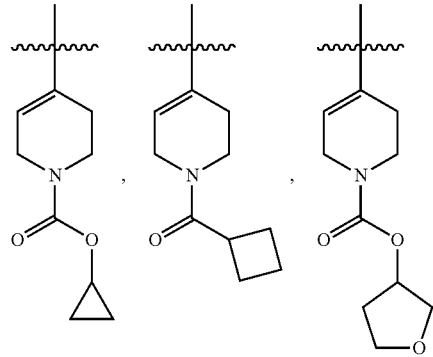

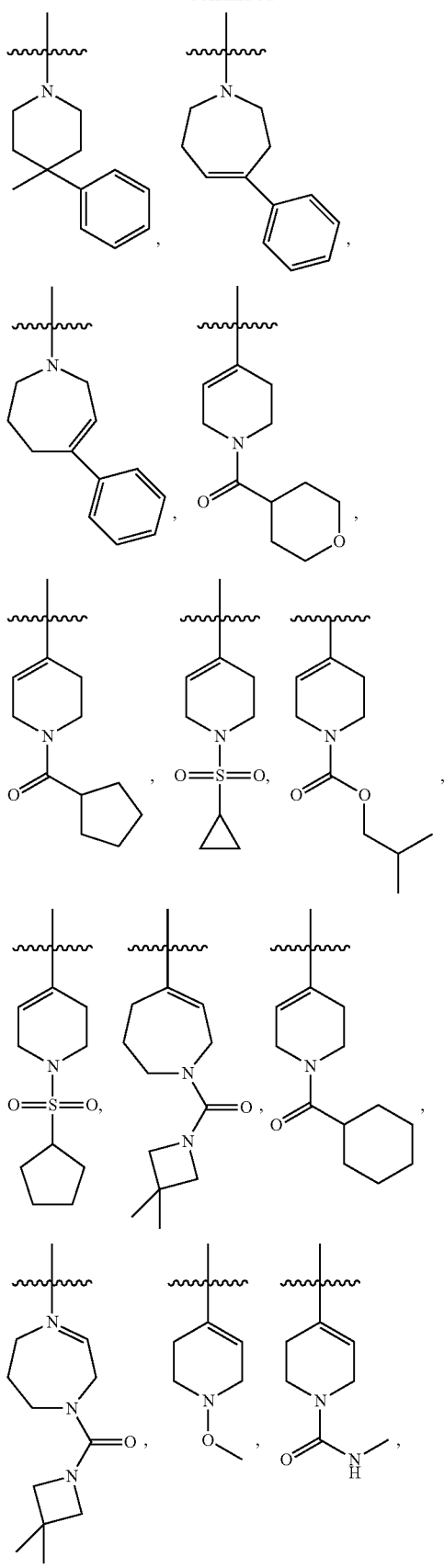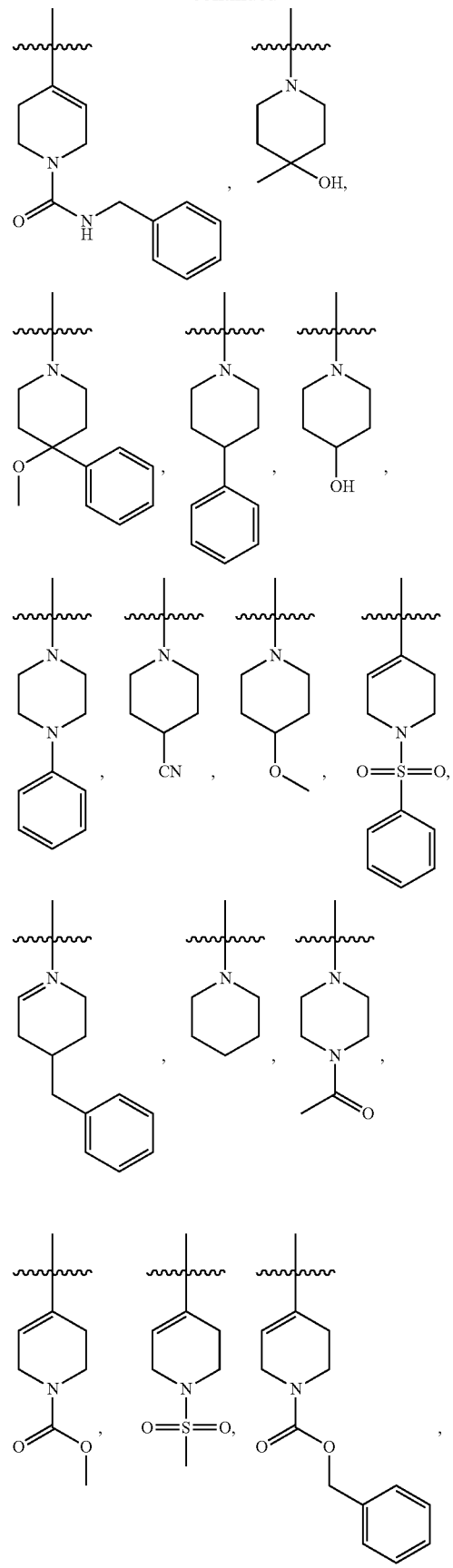

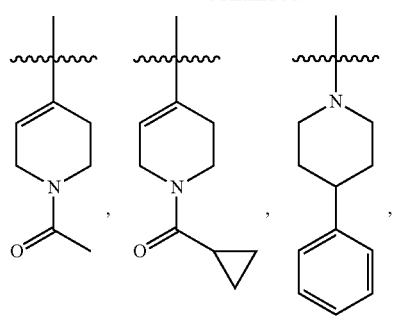
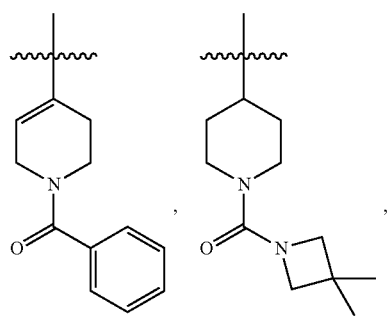
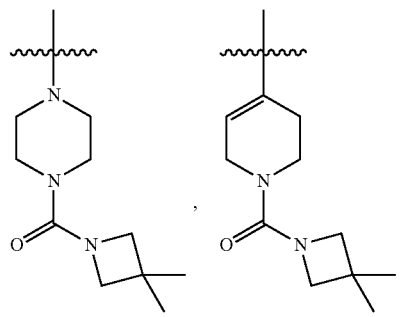
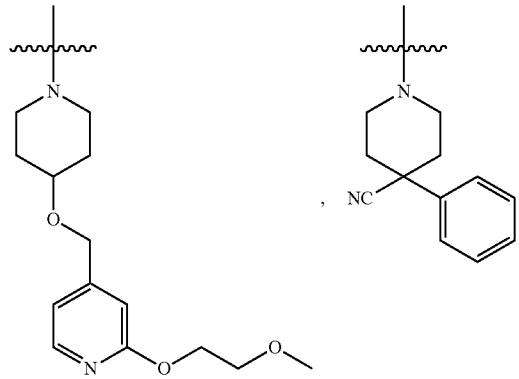
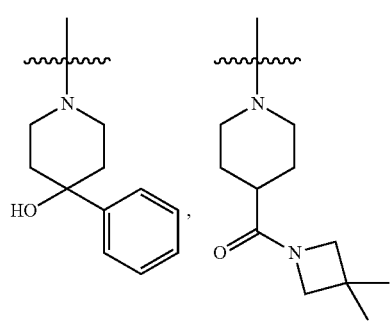
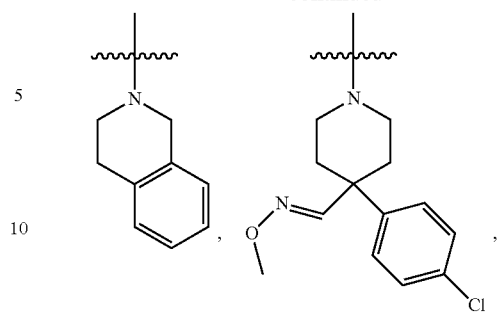
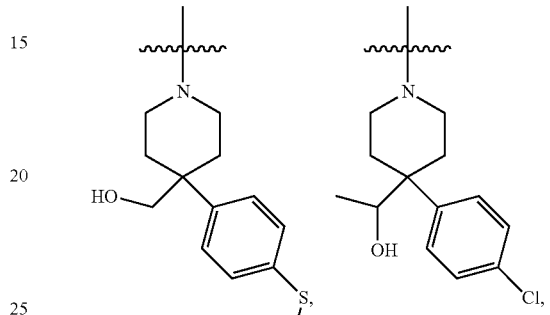
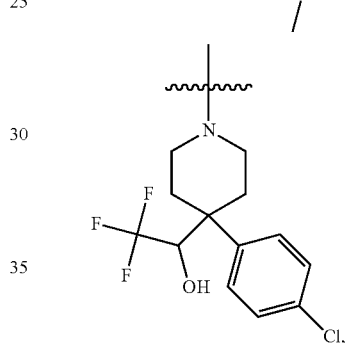
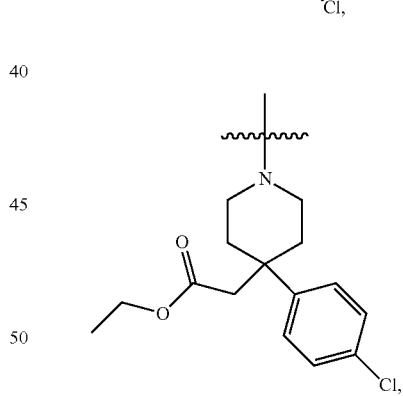
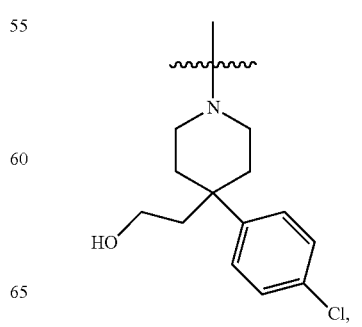

-continued
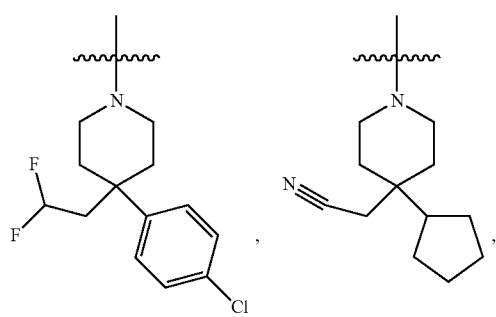
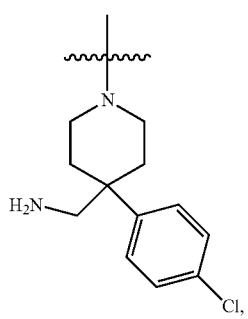
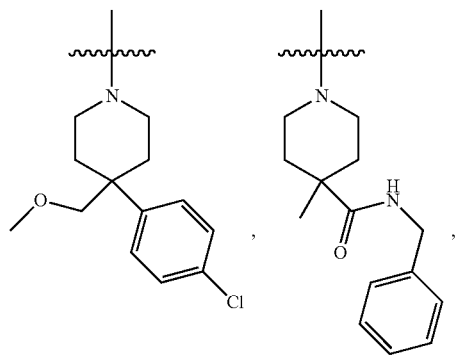
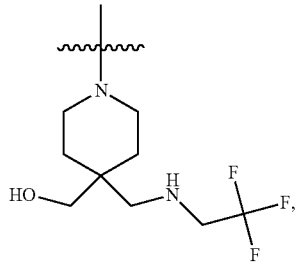
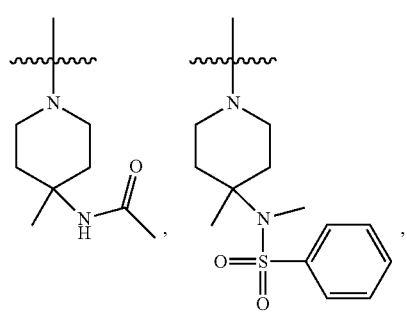
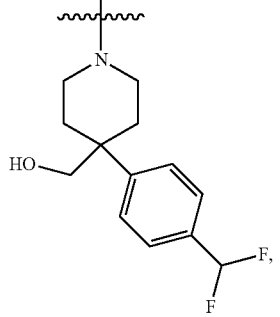
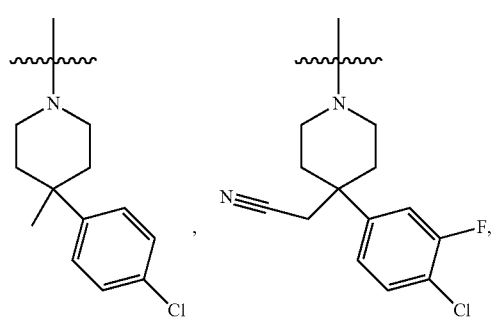
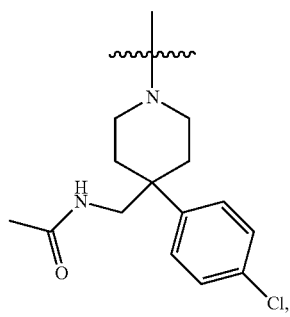
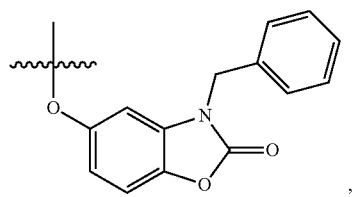
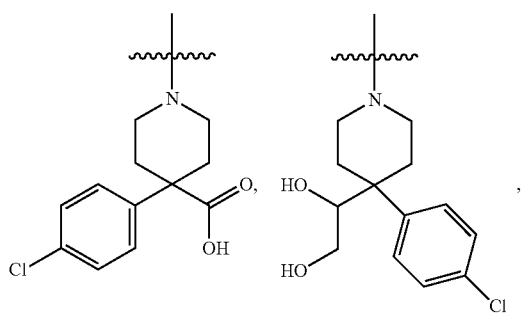

-continued

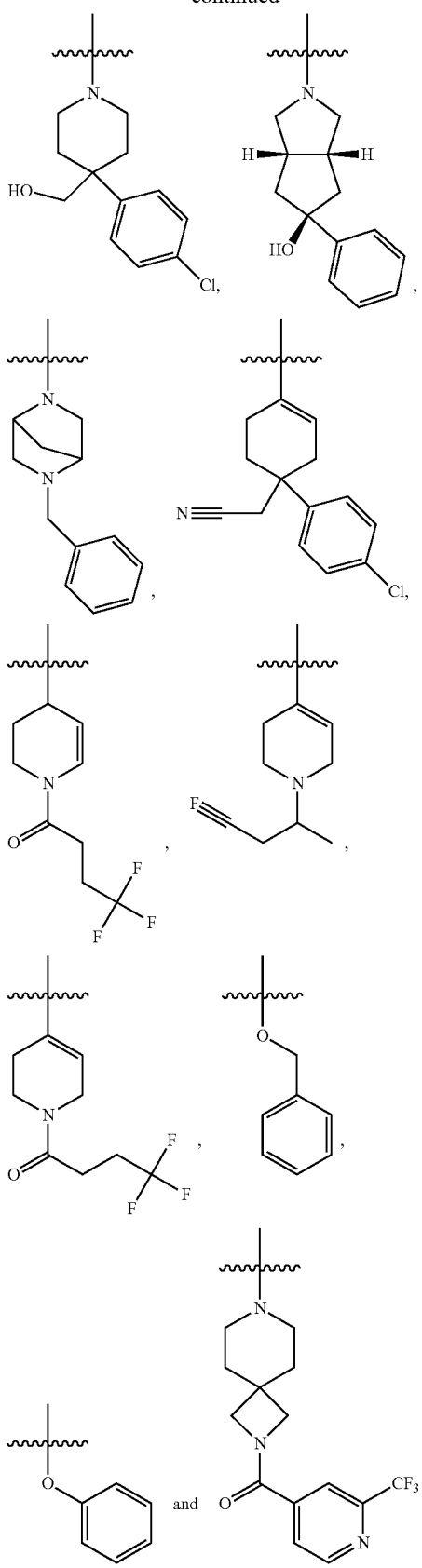

and stereoisomers thereof.

In some embodiments of a compound of the present invention, such as a compound of Formula 0, I, Ia, Ib, Ic, Id, Ie, If, or Ig, $R^{1b}$ is hydrogen or $CH_3$.

In some embodiments of a compound of the present invention, such as a compound of Formula 0, I, Ia, Ib, Ic, Id, Ie, If, or Ig, p is 0, 1, 2 or 3. In some embodiments of a compound of Formula 0, I, Ia, Ib, Ic, Id, Ie, If, or Ig, p is 0, 1 or 2.

In some embodiments of a compound of the present invention, such as a compound of Formula 0, I, Ia, Ib, Ic, Id, Ie, If, or Ig, $R^3$, $R^4$ and $R^5$ are each independently selected from the group consisting of hydrogen, $CH_3$, $CH_2CH_3$, $OCH_3$, $CF_3$, F and Cl. In some embodiments of a compound of the present invention, such as a compound of Formula 0, I, Ia, Ib, Ic, Id, Ie, If, or Ig, $R^3$, $R^4$ and $R^5$ are each independently selected from the group consisting of hydrogen, $CH_3$, $CH_2CH_3$, $CF_3$, F and Cl. In some embodiments of a compound of the present invention, such as a compound of Formula 0, I, Ia, Ib, Ic, Id, Ie, If, or Ig, $R^3$ is hydrogen. In some embodiments of a compound of the present invention, such as a compound of Formula 0, I, Ia, Ib, Ic, Id, Ie, If, or Ig, $R^4$ is hydrogen. In some embodiments of a compound of the present invention, such as a compound of Formula 0, I, Ia, Ib, Ic, Id, Ie, If, or Ig, $R^5$ is hydrogen. In some embodiments of a compound of the present invention, such as a compound of Formula 0, I, Ia, Ib, Ic, Id, Ie, If, or Ig, $R^3$, $R^4$ and $R^5$ are each independently hydrogen. In some embodiments of a compound of the present invention, such as a compound of Formula 0, I, Ia, Ib, Ic, Id, Ie, If, or Ig, none of $R^3$, $R^4$ and $R^5$ are $OCH_3$.

In some embodiments of a compound of the present invention such as a compound of Formula 0, I, Ia, Ib, Ic, Id, Ie, If, or Ig, X is not O.

Another aspect of the invention provides compounds of Formula II:

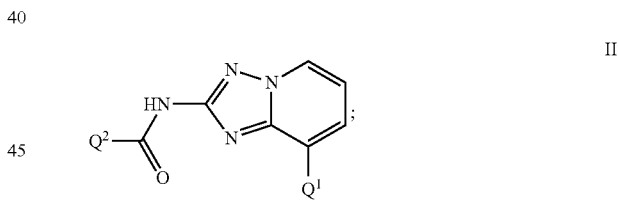

and stereoisomers and salts thereof, wherein:

$Q^1$ is a 3-11 membered heterocyclyl (e.g., 5-6 membered heteroaryl or 4-11 membered heterocycloalkyl) containing at least 1 nitrogen, selected from groups (a)-(e), or a $C_5$-$C_8$ cycloalkenyl ring (f), or a —O—$(CR^xR^y)_q$—$Ar^2$ group (g) where $R^x$ and $R^y$ are independently hydrogen or $C_1$-$C_6$ alkyl, q is 0 to 3 and $Ar^2$ is optionally substituted $C_6$-$C_{10}$ aryl or optionally substituted 5-11 membered heteroaryl:

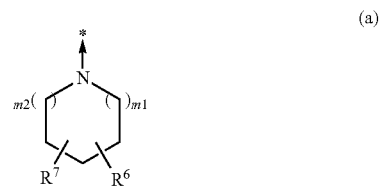

(a)

-continued

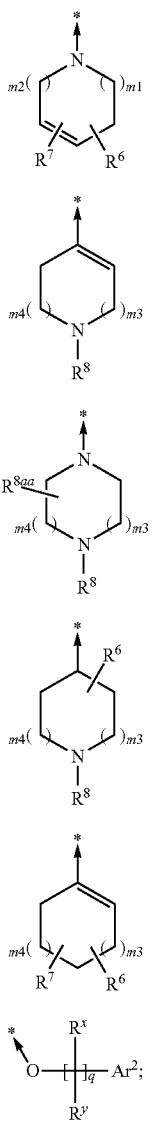

R⁶ and R⁷ are independently selected from the group consisting of hydrogen, halogen, OH, CN, phenyl, $C_1$-$C_6$ alkyl, ($C_0$-$C_6$ alkylene)$C_3$-$C_8$ cycloalkyl, ($C_0$-$C_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), ($C_0$-$C_6$ alkylene)C(O)NR$^a$R$^b$, ($C_0$-$C_6$ alkylene)NR$^a$C(O)($C_1$-$C_6$ alkyl), ($C_0$-$C_6$ alkylene)C(O)R$^{8a}$, ($C_0$-$C_6$ alkylene)C(O)OR$^{8a}$, $C_1$-$C_6$ alkoxy, —O—($C_3$-$C_6$ cycloalkyl), —O—($C_0$-$C_6$ alkylene)C(O)NR$^a$R$^b$, and —O—(3-11 membered heterocyclyl) (e.g., 5-6 membered heteroaryl containing 1 to 4 heteroatoms selected from O, N and S or 4-11 membered heterocycloalkyl containing 1 to 4 heteroatoms selected from O, N and S); wherein said alkyl, alkylene, alkoxy, cycloalkyl, phenyl and heterocyclyl are each independently optionally substituted, or R₆ and R₇ together form an optionally substituted phenyl or optionally substituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S);

$R^8$ is $C_1$-$C_6$ alkyl, ($C_0$-$C_6$ alkylene)phenyl, C(O)NR$^a$R$^b$, SO$_2$NR$^a$R$^b$, C(O)OR$^{8a}$ or C(O)R$^{8a}$, wherein said alkyl, alkylene and phenyl are each independently optionally substituted;

$R^{8a}$ is $C_1$-$C_6$ alkyl, ($C_0$-$C_6$ alkylene)$C_3$-$C_8$ cycloalkyl, ($C_0$-$C_6$ alkylene)phenyl, or ($C_0$-$C_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), wherein said alkyl, alkylene, cycloalkyl, phenyl and heterocyclyl are each independently optionally substituted;

$R^{8aa}$ is H; or or $R^8$ and $R^{8aa}$ together form an optionally substituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S);

$R^9$, independently at each occurrence, is OH, halogen, $C_1$-$C_6$ alkyl, ($C_0$-$C_6$ alkylene)$C_3$-$C_8$ cycloalkyl, ($C_0$-$C_6$ alkylene)phenyl, ($C_0$-$C_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), ($C_0$-$C_6$ alkylene)C(O)NR$^a$R$^b$, ($C_0$-$C_6$ alkylene)NR$^a$R$^b$, or C(O)($C_1$-$C_6$ alkyl), wherein said alkyl, cycloalkyl, phenyl and heterocyclyl are each independently optionally substituted;

R$^a$ and R$^b$ are independently at each occurrence hydrogen, $C_1$-$C_6$ alkyl, ($C_0$-$C_6$ alkylene)$C_3$-$C_8$ cycloalkyl, or ($C_0$-$C_6$ alkylene)phenyl, and wherein one or more alkylene units of any alkyl group is independently optionally substituted by —O—, or alternatively R$^a$ and R$^b$ may be joined together with the nitrogen atom to which they are attached to form an optionally substituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S);

$m^1$, $m^2$, $m^3$ and $m^4$ are each independently 0, 1 or 2; and $Q^2$ is $C_3$-$C_8$ cycloalkyl optionally substituted with $C_1$-$C_6$ alkyl, $C_1$-$C_6$ haloalkyl, $C_1$-$C_6$ heteroalkyl, F, Cl, Br, I, OH, SH, NH$_2$, CN or N$_3$.

In certain embodiments, $Q^1$ is ring (a). In certain embodiments, $Q^1$ is ring (b). In certain embodiments, $Q^1$ is ring (c). In certain embodiments, $Q^1$ is ring (d). In certain embodiments, $Q^1$ is ring (e). In certain embodiments, $Q^1$ is ring (f). In certain embodiments, $Q^1$ is ring (g). In certain embodiments, $Q^1$ is a $C_3$-$C_8$ cyclopropyl ring optionally substituted with one or more substituents selected from $C_1$-$C_6$ alkyl, $C_1$-$C_6$ haloalkyl, $C_1$-$C_6$ heteroalkyl, F, Cl, Br, I, OH, CN, OCF$_3$ and N$_3$. In certain embodiments, $Q^2$ is a cyclopropyl group. In certain embodiments, $Q^2$ is a cyclobutanyl group. In certain embodiments, $Q^2$ is a cyclopentyl group. In certain embodiments, $Q^2$ is a cyclohexyl group. In certain embodiments, $Q^2$ is a cycloheptyl group. In certain embodiments, $Q^2$ is a cyclooctyl group. In certain embodiments, $Q^1$ is ring (a) and $Q^2$ is an unsubstituted $C_3$-$C_8$ cycloalkyl group. In certain embodiments, $Q^1$ is ring (a) and $Q^2$ is an unsubstituted cyclopropyl group.

In some embodiments of a compound of the present invention, such as a compound of Formula 0, I, Ia, Ib, or If, R⁶ and R⁷ are attached to the ring at the same carbon atom. In some embodiments of a compound of the present invention, such as a compound of Formula 0, I, Ia, Ib, or If, R⁶ and $R^7$ are independently selected from the group consisting of hydrogen; halogen; OH; CN; phenyl; phenyl substituted by halogen, CN, $C_1$-$C_6$ alkyl or $C_1$-$C_6$ alkoxy; $C_1$-$C_6$ alkyl; $C_1$-$C_6$ alkyl substituted by OH or CN; ($C_0$-$C_6$ alkylene)$C_3$-$C_8$ cycloalkyl; ($C_0$-$C_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), such as piperidinyl; ($C_0$-$C_6$ alkylene)C(O)NR$^a$R$^b$; ($C_0$-$C_6$ alkylene)NR$^a$C(O)($C_1$-$C_6$ alkyl); ($C_0$-$C_6$ alkylene)C(O)R$^{8a}$; ($C_0$-$C_6$ alkylene)C(O)OR$^{8a}$; $C_1$-$C_6$ alkoxy; $C_1$-$C_6$ alkoxy substituted by CN; —O—($C_3$-$C_6$ cycloalkyl), —O—($C_0$-$C_6$ alkylene)C(O)NR$^a$R$^b$, and —O—(3-11 membered heterocyclyl) (e.g., 5-6 membered heteroaryl containing 1 to 4 heteroatoms selected from O, N and S or 4-11 membered heterocycloalkyl containing 1 to 4 heteroatoms selected from O, N and S).

In some embodiments of a compound of the present invention, such as a compound of Formula 0, I, Ia, Ib, or If, $R^6$ is $C_1$-$C_6$ alkyl or $C_1$-$C_6$-alkoxy, and $R^7$ is optionally substituted phenyl, such as phenyl substituted by halogen, CN, $C_1$-$C_6$ alkyl or $C_1$-$C_6$ alkoxy. In some embodiments in a compound of the present invention, such as a compound of Formula 0, I, Ia, Ib, or If, $R^6$ is $C_1$-$C_6$ alkyl, $C_3$-$C_6$ cycloalkyl or optionally substituted phenyl, such as phenyl substituted by halogen, CN, $C_1$-$C_6$ alkyl or $C_1$-$C_6$ alkoxy, and $R^7$ is OH, ($C_0$-$C_6$ alkylene)C(O)NR$^a$R$^b$, ($C_0$-$C_6$ alkylene)CN or —O—($C_0$-$C_6$ alkyl)CN. In some embodiments in a compound of the present invention, such as a compound of Formula 0, I, Ia, Ib, or If, $R^6$ is hydrogen and $R^7$ is selected from ($C_0$-$C_6$ alkylene)C(O)NR$^a$R$^b$, ($C_0$-$C_6$ alkylene)CN, $C_1$-$C_6$-alkoxy, —O—($C_3$-$C_6$ cycloalkyl), —O—($C_0$-$C_6$ alkylene)C(O)NR$^a$R$^b$, and —O—($C_1$-$C_6$ alkylene)CN. In some embodiments in a compound of the present invention, such as a compound of Formula 0, I, Ia, Ib, or If, $R^6$ and $R^7$ together form a 3-11 membered heterocycloalkyl, such as containing 1-4 heteroatoms selected from O, N and S, optionally substituted by oxo.

In some embodiments of a compound of the present invention, such as a compound of Formula 0, I, Ia, Ib, or If, optional substituents of $R^6$ and $R^7$, or $R^6$ taken together with $R^7$, are selected from the group consisting of halogen, CN, OH, oxo, $C_1$-$C_6$ alkyl, $C_1$-$C_6$ alkoxy, and $C_1$-$C_6$ alkoxy-$C_1$-$C_6$ alkyl-$C_1$-$C_6$ alkoxy.

In some embodiments of compounds of the present invention, such as a compound of Formula 0, I, Ic, Id, or Ie, $R^8$ is selected from the $R^8$ examples of Table II. In some embodiments of compounds of the present invention, such as a compound of Formula 0, I, Ic, Id or Ie, $R^8$ is selected from the group consisting of $C_1$-$C_6$ alkyl optionally substituted with halogen, CN, $C_1$-$C_6$ alkoxy, or OH; ($C_0$-$C_6$ alkylene)phenyl, such as ($C_0$-$C_1$ alkylene)phenyl, where the alkylene is unsubstituted, where the phenyl may be optionally substituted with halogen, CN, oxo or OH; C(O)NR$^a$R$^b$, wherein R$^a$ and R$^b$ are each independently hydrogen or $C_1$-$C_6$ alkyl optionally substituted by halogen, OH or CN, or R$^a$ and R$^b$ together form a 3-11 membered heterocycloalkyl group, such as containing 1-4 heteroatoms selected from O, N and S, optionally substituted with $C_1$-$C_6$ alkyl, oxo, CN or OH; SO$_2$NR$^a$R$^b$, wherein R$^a$ and R$^b$ are each independently hydrogen or $C_1$-$C_6$ alkyl optionally substituted by halogen, OH or CN, or R$^a$ and R$^b$ together form a 3-11 membered heterocycloalkyl group, such as containing 1-4 heteroatoms selected from O, N and S, optionally substituted by $C_1$-$C_6$ alkyl, halogen, oxo, CN or OH; C(O)OR$^{8a}$ or C(O)R$^{8a}$, wherein R$^{8a}$ is $C_1$-$C_6$ alkyl optionally substituted by halogen, $C_1$-$C_6$ alkoxy, oxo, CN or OH, or R$^{8a}$ is a $C_3$-$C_8$ cycloalkyl group optionally substituted by $C_1$-$C_6$ alkyl, or R$^{8a}$ is a 3-11 membered heterocycloyalkyl, such as containing 1-4 heteroatoms selected from O, N and S, optionally substituted by $C_1$-$C_6$ alkyl, halogen, oxo, CN or OH.

In some embodiments of a compound of the present invention, such as a compound of Formula 0, I, Ic, Id or Ie, optional substituents of $R^8$ are selected from the group consisting of halogen, oxo, CN, OH, $C_1$-$C_6$ alkyl, NH$_2$, NH($C_1$-$C_6$ alkyl), and N($C_1$-$C_6$ alkyl)$_2$.

In some embodiments of a compound of the present invention, such as a compound of Formula 0, I, Ic, Id or Ie, $R^8$ and $R^{8aa}$ together form a 3-11 membered heterocyclyl (e.g., a 5-6 membered heteroaryl containing 1-4 heteroatoms selected from O, N and S or 4-11 membered heterocycloalkyl containing 1-4 heteroatoms selected from O, N and S) optionally substituted by halogen, oxo, CN, OH, $C_1$-$C_6$ alkyl or $C_1$-$C_6$ alkoxy.

In some embodiments of a compound of the present invention, such as a compound of Formula 0, I, Ia, Ib, Ic, Id, Ie, If, Ig or II, $R^6$, $R^7$ and $R^8$ are each independently selected from C(O)NR$^a$R$^b$, C(O)R$^{8a}$, and C(O)OR$^{8a}$. In some embodiments, R$^a$R$^b$ are independently selected from hydrogen, $C_1$-$C_6$ alkyl, or ($C_1$-$C_6$ alkylene)phenyl, or R$^a$ and R$^b$ are taken together to form a 3-11 membered heterocyclyl (e.g., a 5-6 membered heteroaryl containing 1-4 heteroatoms selected from O, N and S or 4-11 membered heterocycloalkyl containing 1-4 heteroatoms selected from O, N and S) optionally substituted by halogen, $C_1$-$C_6$ alkyl, oxo, OH, CN, NH$_2$, NHCH$_3$, or N(CH$_3$)$_2$. In some embodiments, R$^{8a}$ is selected from $C_1$-$C_6$ alkyl optionally substituted by halogen, CN, OH, NH$_2$, NHCH$_3$, or N(CH$_3$)$_2$; $C_3$-$C_8$ cycloalkyl optionally substituted by $C_1$-$C_6$ alkyl or $C_1$-$C_6$ alkoxy; 3-11 membered heterocyclyl (e.g., a 5-6 membered heteroaryl containing 1-4 heteroatoms selected from O, N and S or 4-11 membered heterocycloalkyl containing 1-4 heteroatoms selected from O, N and S) optionally substituted by halogen, CN, OH, oxo, NH$_2$, NHCH$_3$, N(CH$_3$)$_2$, or $C_1$-$C_6$ alkyl.

In some embodiments of a compound of the present invention, such as a compound of Formula 0, I, Ia, Ib, Ic, Id, Ie, If or Ig, $R^9$, independently at each occurrence, is OH; halogen; $C_1$-$C_6$ alkyl optionally substituted with halogen, OH, CN, $C_1$-$C_6$ alkoxy, 5-6 membered heteroaryl (e.g., containing 1-4 heteroatoms selected from O, N and S), 3-11 membered heterocycloalkyl (e.g., containing 1-4 heteroatoms selected from O, N and S), NH$_2$, NHCH$_3$, or N(CH$_3$)$_2$; NH$_2$, NHCH$_3$, or N(CH$_3$)$_2$; ($C_0$-$C_6$ alkylene)$C_3$-$C_8$ cycloalkyl wherein the cycloalkyl is optionally substituted by halogen, $C_1$-$C_6$ alkyl, CN, OH, oxo or NR$^a$R$^b$; ($C_0$-$C_6$ alkylene)phenyl wherein the phenyl is optionally substituted by halogen, CN, OH, $C_1$-$C_6$ alkyl, or NR$^a$R$^b$; ($C_0$-$C_6$ alkylene)3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S), wherein the heterocyclyl is optionally substituted by halogen, CN, OH, oxo, $C_1$-$C_6$ alkyl, C(O)$C_1$-$C_6$ alkyl, NRaR$^b$ or 5-6 membered heteroaryl optionally substituted by $C_1$-$C_6$ alkyl; ($C_0$-$C_6$ alkylene)C(O)NR$^a$R$^b$; ($C_0$-$C_6$ alkylene)NR$^a$R$^b$; or C(O)($C_1$-$C_6$ alkyl); wherein unless otherwise specified, R$^a$ and R$^b$ are independently at each occurrence hydrogen, $C_1$-$C_6$ alkyl, ($C_0$-$C_6$ alkylene)$C_3$-$C_8$ cycloalkyl, or ($C_0$-$C_6$ alkylene)phenyl, and wherein one or more alkylene units of any alkyl group is independently optionally substituted by —O—, or alternatively R$^a$ and R$^b$ may be joined together with the nitrogen atom to which they are attached to form an optionally substituted 3-11 membered heterocyclyl, e.g., 5-6 membered heteroaryl containing 1 to 4 heteroatoms selected from O, N and S or 4-11 membered heterocycloalkyl containing 1 to 4 heteroatoms selected from O, N and S, and wherein said optional substituents of said 3-11 membered heterocyclyl group are selected from CN, halogen, OH, C(O)CH$_3$, 5-6 membered heteroaryl optionally substituted by C$_1$-C$_6$ alkyl or halogen, and C$_1$-C$_6$ alkyl optionally substituted by halogen, OH, CN, oxo, or C$_1$-C$_6$ alkoxy. In some embodiments, R$^a$ and R$^b$ are selected from NH$_2$, NHCH, and N(CH$_3$)$_2$.

In some embodiments of a compound of the present invention, such as a compound of Formula 0, I, Ia, Ib, Ic, Id, Ie, If or Ig, an optional substituent of R$^9$ is selected from the group consisting of halogen, CN, OH, C$_1$-C$_6$ alkyl, C$_1$-C$_6$ alkoxy, or NR$^a$R$^b$, wherein R$^a$ and R$^b$ are independently selected from the group consisting of NH$_2$, NHCH$_3$, and N(CH$_3$)$_2$, or R$^a$ and R$^b$ may be joined together with the nitrogen atom to which they are attached to form an optionally substituted 3-11 membered heterocyclyl, e.g., 5-6 membered heteroaryl containing 1 to 4 heteroatoms selected from O, N and S or 4-11 membered heterocycloalkyl containing 1 to 4 heteroatoms selected from O, N and S, and wherein said optional substituents of said 3-11 membered heterocyclyl group are selected from CN, halogen, OH, C(O)(C$_1$-C$_6$ alkyl) (e.g., C(O)CH$_3$), 5-6 membered heteroaryl optionally substituted with C$_1$-C$_6$ alkyl or halogen, and C$_1$-C$_6$ alkyl optionally substituted by halogen, OH, CN, oxo, OH or C$_1$-C$_6$ alkoxy.

In some embodiments of a compound of the present invention, such as a compound of Formula 0, I, Ia, Ib, Ic, Id, Ie, If, Ig or II, R$^a$ and R$^b$, independently at each occurrence, are selected from the group consisting of NH$_2$, NHCH$_3$, and N(CH$_3$)$_2$, or R$^a$ and R$^b$ may be joined together with the nitrogen atom to which they are attached to form an optionally substituted 3-11 membered heterocyclyl, e.g., 5-6 membered heteroaryl containing 1 to 4 heteroatoms selected from O, N and S or 4-11 membered heterocycloalkyl containing 1 to 4 heteroatoms selected from O, N and S, and wherein said optional substituents of said 3-11 membered heterocyclyl group are selected from CN, halogen, OH, C(O)(C$_1$-C$_6$ alkyl) (e.g., C(O)CH$_3$), 5-6 membered heteroaryl containing 1 to 4 heteroatoms selected from O, N and S optionally substituted with halogen, OH, CN or C$_1$-C$_6$ alkyl, and C$_1$-C$_6$ alkyl optionally substituted by halogen, OH, CN, oxo, OH or C$_1$-C$_6$ alkoxy.

In some embodiments of a compound of the present invention, such as a compound of Formula 0, I, Ia, Ib, Ic, Id, Ie, If, or Ig, n is 0. In some embodiments of a compound of the present invention, such as a compound of Formula 0, I, Ia, Ib, Ic, Id, Ie, If, or Ig, n is 0 and p is 0. In some embodiments of a compound of the present invention, such as a compound of Formula 0, I, Ia, Ib, Ic, Id, Ie, If, or Ig, n is 0 and p is 0-6. In some embodiments of a compound of the present invention, such as a compound of Formula 0, I, Ia, Ib, Ic, Id, Ie, If, or Ig, n is 0 and p is 1-6. In some embodiments, of a compound of the present invention, such as a compound of Formula 0, I, Ia, Ib, Ic, Id, Ie, If, or Ig, n is 1 and p is 0. In some embodiments of a compound of the present invention, such as a compound of Formula 0, I, Ia, Ib, Ic, Id, Ie, If, or Ig, n is 1 and p is 0-6. In some embodiments of a compound of the present invention, such as a compound of Formula 0, I, Ia, Ib, Ic, Id, Ie, If, or Ig, n is 1 and p is 1-6.

In some embodiments of a compound of the present invention, such as a compound of Formula 0, I or II, Ar$^2$ is unsubstituted phenyl. In some embodiments in a compound of the present invention, such as a compound of Formula 0, I or II, Ar$^2$ is unsubstituted phenyl, q is 0 or 1, and R$^x$ and R$^y$ are each independently hydrogen.

In some embodiments, a compound of Formula 0 or I excludes a compound of Formula Ia. In some embodiments, a compound of Formula 0 or I excludes a compound of Formula Ib. In some embodiments, a compound of Formula 0 or I excludes a compound of Formula Ic. In some embodiments, a compound of Formula 0 or I excludes a compound of Formula Id. In some embodiments, a compound of Formula 0 or I excludes a compound of Formula Ie. In some embodiments, a compound of Formula 0 or I excludes a compound of Formula If. In some embodiments, a compound of Formula 0 or I excludes a compound of Formula Ig. In some embodiments, a compound of Formula 0 or I excludes two or more compounds of Formula Ia, Ib, Ic, Id, Ie, If or Ig.

In any compound of the present invention, including a compound of Formula 0 or I, Ia, Ib, Ic, Id, Ie, If, or Ig, any substituent indicated as "optionally substituted", such as portions of R$^2$, R$^6$, R$^7$, R$^6$ together with R$^7$, R$^8$, R$^{8a}$, R$^8$ together with R$^{8aa}$, or R$^9$, may be optionally substituted by, e.g., halogen; oxo; CN; NO; N$_3$; —OR; perfluoro-C$_1$-C$_4$ alkoxy; unsubstituted C$_3$-C$_7$ cycloalkyl; C$_3$-C$_7$ cycloalkyl substituted by halogen, CN, OH, unsubstituted C$_1$-C$_6$ alkyl, unsubstituted C$_1$-C$_6$ alkoxy, oxo or NR'R''; unsubstituted C$_6$-C$_{10}$ aryl (e.g., phenyl); C$_6$-C$_{10}$ aryl substituted by halogen, CN, OH, unsubstituted C$_1$-C$_6$ alkyl, unsubstituted C$_1$-C$_6$ alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, CN, OH, unsubstituted C$_1$-C$_6$ alkyl, unsubstituted C$_1$-C$_6$ alkoxy, oxo or NR'R''; -NR'R''; —SR'; —SiR'R''R'''; —OC(O)R'; —C(O)R'; —CO$_2$R'; —CONR'R''; —OC(O)NR'R''; —NR''C(O)R'; —NR'''C(O)NR'R''; —NR''C(O)$_2$R'; —S(O)$_2$R'; —S(O)$_2$NR'R''; —NR'S(O)$_2$R''; —NR'''S(O)$_2$NR'R''; amidinyl; guanidinyl; —(CH$_2$)$_{1-4}$—OR'; —(CH$_2$)$_{1-4}$—NR'R''; —(CH$_2$)$_{1-4}$—SR'; —(CH$_2$)$_{1-4}$—SiR'R''R'''; —(CH$_2$)$_{1-4}$—OC(O)R'; —(CH$_2$)$_{1-4}$—C(O)R'; —(CH$_2$)$_{1-4}$—CO$_2$R'; and —(CH$_2$)$_{1-4}$CONR'R'', or combinations thereof, in a number ranging from zero to (2m'+1), where m' is the total number of carbon atoms in such radical. R', R'' and R''' each independently refer to groups including, for example, hydrogen; unsubstituted C$_1$-C$_6$ alkyl; C$_1$-C$_6$ alkyl substituted by halogen, CN, OH, unsubstituted C$_1$-C$_6$ alkyl, unsubstituted C$_1$-C$_6$ alkoxy, oxo or NR'R''; unsubstituted C$_1$-C$_6$ heteroalkyl; C$_1$-C$_6$ heteroalkyl substituted by halogen, CN, OH, unsubstituted C$_1$-C$_6$ alkyl, unsubstituted C$_1$-C$_6$ alkoxy, oxo or NR'R''; unsubstituted C$_6$-C$_{10}$ aryl; C$_6$-C$_{10}$ aryl substituted by halogen, CN, OH, unsubstituted C$_1$-C$_6$ alkyl, unsubstituted C$_1$-C$_6$ alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, CN, OH, unsubstituted C$_1$-C$_6$ alkyl, unsubstituted C$_1$-C$_6$ alkoxy, oxo or NR'R''. When R' and R'' are attached to the same nitrogen atom, they can be combined with the nitrogen atom to form a 3-, 4-, 5-, 6-, or 7-membered ring wherein a ring atom is optionally substituted with N, O or S and wherein the ring is optionally substituted with halogen, CN, OH, unsubstituted $C_1$-$C_6$ alkyl, unsubstituted $C_1$-$C_6$ alkoxy, oxo or NR'R".

Also provided is a compound selected from Examples 1-1 to 1-303, 2-1 to 2-486 and 3-1, or any combination thereof.

See Table A. Although specific salts may be shown in Table A, it is to be understood that other salts are contemplated, as described herein. Should there be any discrepancy between an Example's structure in Table A and an Example of Table I or II, Table A's structure prevails.

TABLE A

Exemplary Compounds of the Present Invention

| Ex. | Structure | Name |
|---|---|---|
| 1-1 | 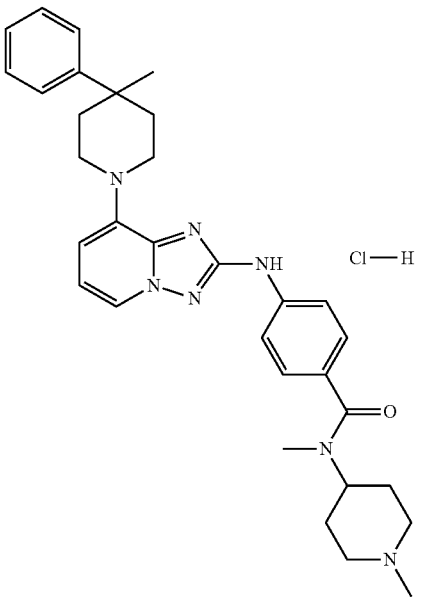 | N-methyl-4-[[8-(4-methyl-4-phenyl-1-piperidyl)-[1,2,4]triazolo[1,5-a]pyridin-2-yl]amino]-N-(1-methyl-4-piperidyl)benzamide; hydrochloride |
| 1-2 | 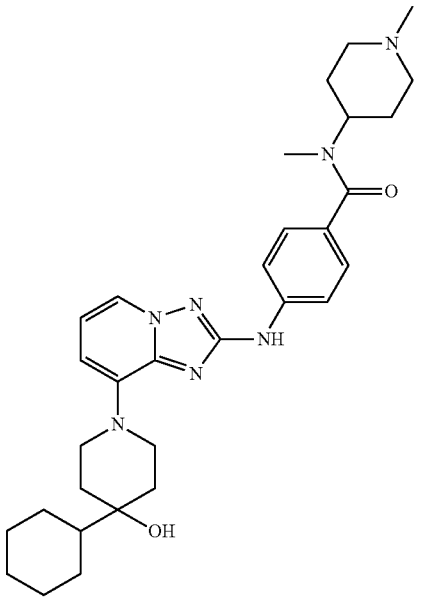 [SMILES: CN1CCC(N(C)C(=O)c2ccc(Nc3nc4c(N5CCC(O)(C6CCCCC6)CC5)cccn4n3)cc2)CC1] | 4-[[8-(4-cyclohexyl-4-hydroxy-1-piperidyl)-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 1-3 | 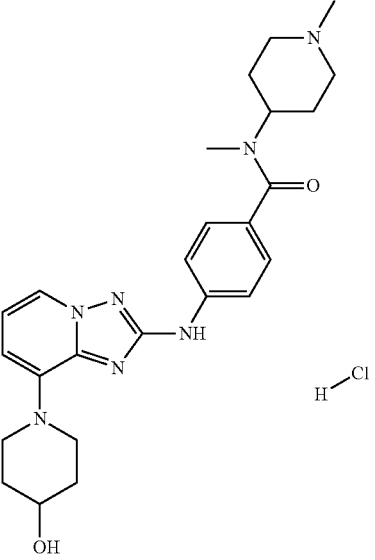 [SMILES: CN1CCC(N(C)C(=O)c2ccc(Nc3nc4c(N5CCC(O)CC5)cccn4n3)cc2)CC1 ; Cl] | 4-[[8-(4-hydroxy-1-piperidyl)-[1,2,4]triazolo[1,5-a]pyridin-2-yl]amino]-N-methyl-N-(1-methyl-4-piperidyl)benzamide; hydrochloride |
| 1-4 | 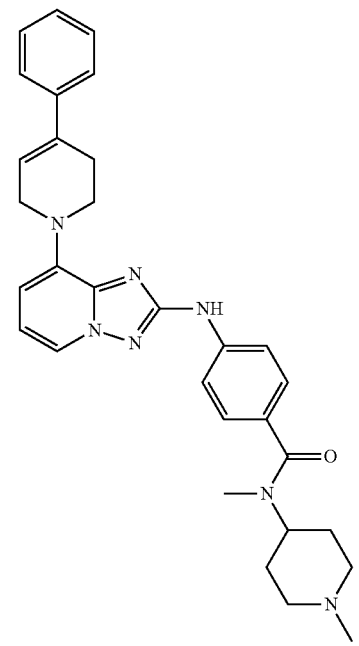 [SMILES: CN1CCC(N(C)C(=O)c2ccc(Nc3nc4c(N5CC=C(c6ccccc6)CC5)cccn4n3)cc2)CC1] | N-methyl-N-(1-methyl-4-piperidyl)-4-[[8-(4-phenyl-3,6-dihydro-2H-pyridin-1-yl)-[1,2,4]triazolo[1,5-a]pyridin-2-yl]amino]benzamide |

TABLE A-continued
Exemplary Compounds of the Present Invention
| Ex. | Structure | Name |
|---|---|---|
| 1-5 | 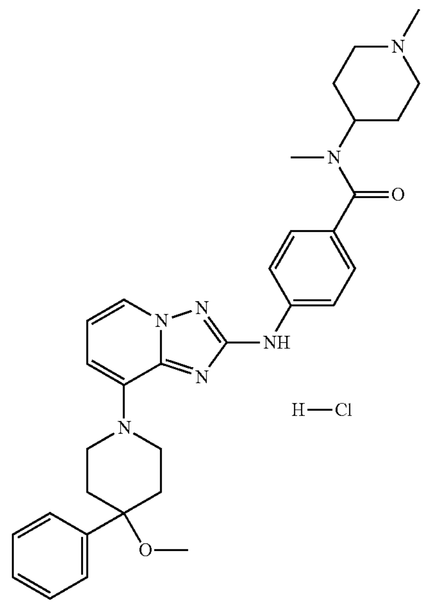 [SMILES: COC1(c2ccccc2)CCN(c2cccn3nc(Nc4ccc(C(=O)N(C)C5CCN(C)CC5)cc4)nc23)CC1 ; Cl] | 4-[[8-(4-methoxy-4-phenyl-1-piperidyl)-[1,2,4]triazolo[1,5-a]pyridin-2-yl]amino]-N-methyl-N-(1-methyl-4-piperidyl)benzamide; hydrochloride |
| 1-6 | 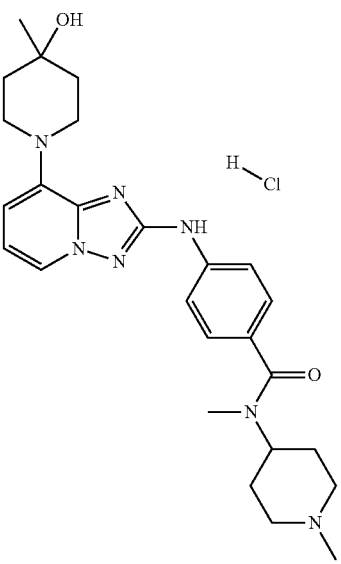 [SMILES: CN1CCC(N(C)C(=O)c2ccc(Nc3nc4c(N5CCC(C)(O)CC5)cccn4n3)cc2)CC1 ; Cl] | 4-[[8-(4-hydroxy-4-methyl-1-piperidyl)-[1,2,4]triazolo[1,5-a]pyridin-2-yl]amino]-N-methyl-N-(1-methyl-4-piperidyl)benzamide; hydrochloride |

TABLE A-continued
Exemplary Compounds of the Present Invention
| Ex. | Structure | Name |
|---|---|---|
| 1-7 | 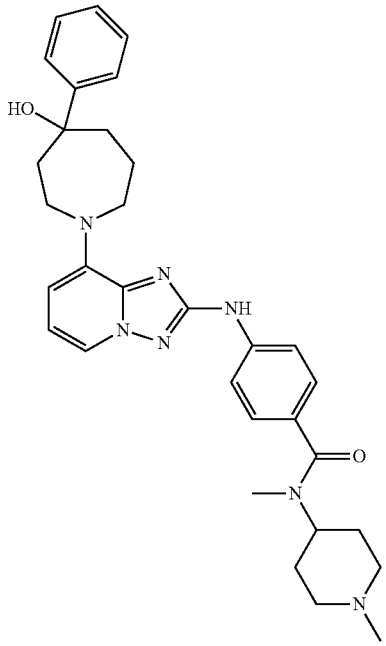 [SMILES: CN1CCC(N(C)C(=O)c2ccc(Nc3nc4c(N5CCCC(O)(c6ccccc6)CC5)cccn4n3)cc2)CC1] | 4-[[8-(4-hydroxy-4-phenyl-azepan-1-yl)-[1,2,4]triazolo[1,5-a]pyridin-2-yl]amino]-N-methyl-N-(1-methyl-4-piperidyl)benzamide |
| 1-8 | 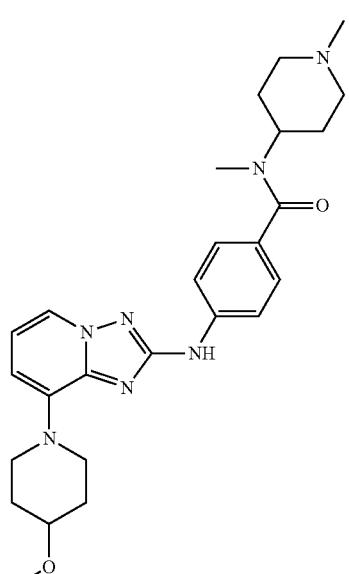 | 4-[[8-(4-methoxy-1-piperidyl)-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 1-9 | 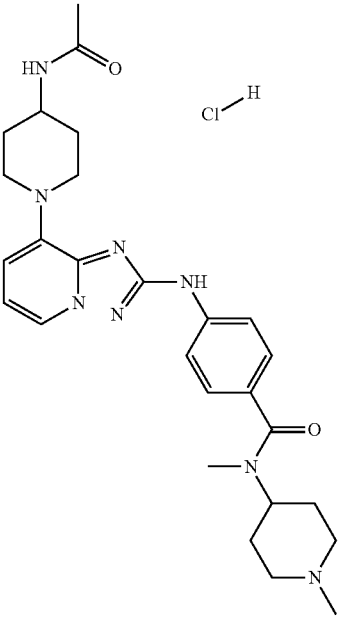 [SMILES: CC(=O)NC1CCN(c2ccc[nH]/c2=N\C(=N)Nc2ccc(C(=O)N(C)C3CCN(C)CC3)cc2)CC1 ; Cl] | 4-[[8-(4-acetamido-1-piperidyl)-[1,2,4]triazolo[1,5-a]pyridin-2-yl]amino]-N-methyl-N-(1-methyl-4-piperidyl)benzamide; hydrochloride |
| 1-10 | 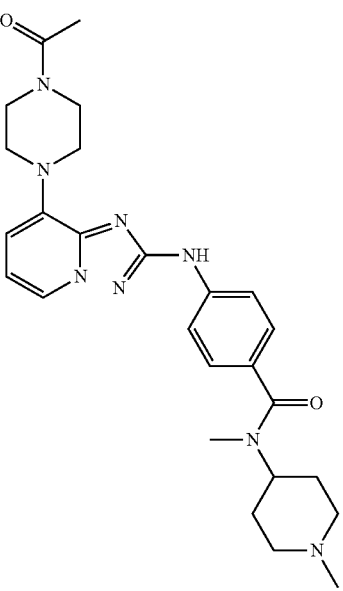 [SMILES: CC(=O)N1CCN(c2ccc[nH]/c2=N\C(=N)Nc2ccc(C(=O)N(C)C3CCN(C)CC3)cc2)CC1] | 4-[[8-(4-acetylpiperazin-1-yl)-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 1-11 | 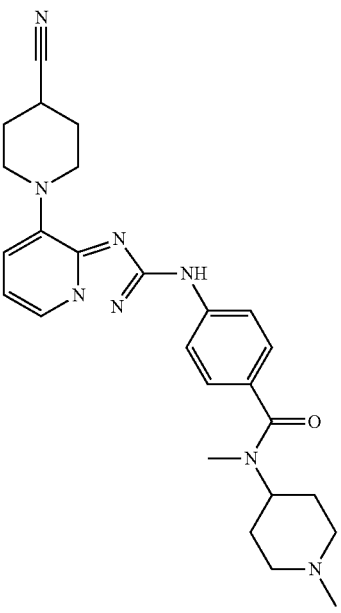 [SMILES: CN1CCC(N(C)C(=O)c2ccc(NC(=N)/N=c3\[nH]cccc3N3CCC(C#N)CC3)cc2)CC1] | 4-[[8-(4-cyano-1-piperidyl)-[1,2,4]triazolo[1,5-a]pyridin-2-yl]amino]-N-methyl-N-(1-methyl-4-piperidyl)benzamide |
| 1-12 | 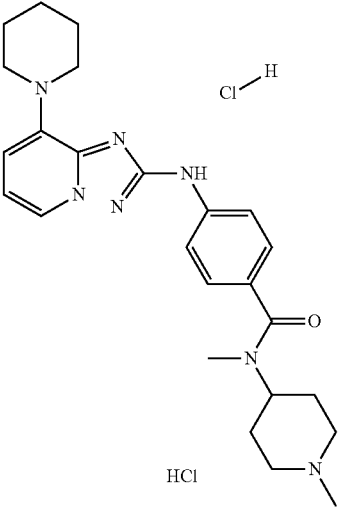 [SMILES: CN1CCC(N(C)C(=O)c2ccc(NC(=N)/N=c3\[nH]cccc3N3CCCCC3)cc2)CC1 ; Cl ; Cl] | N-methyl-N-(1-methyl-4-piperidyl)-4-[[8-(1-piperidyl)-[1,2,4]triazolo[1,5-a]pyridin-2-yl]amino]benzamide; dihydrochloride |
| 1-13 | 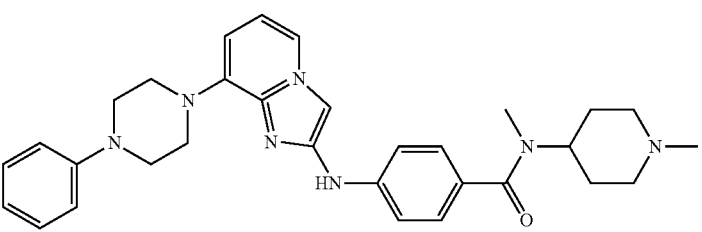 | N-methyl-N-(1-methyl-4-piperidyl)-4-[[8-(4-phenylpiperazin-1-yl)-[1,2,4]triazolo[1,5-a]pyridin-2-yl]amino]benzamide |

TABLE A-continued
Exemplary Compounds of the Present Invention
| Ex. | Structure | Name |
|---|---|---|
| 1-14 | 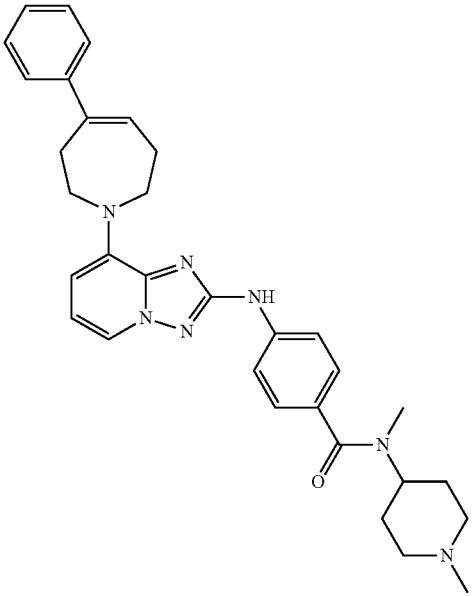 [SMILES: CN1CCC(N(C)C(=O)c2ccc(Nc3nc4c(N5CCC=C(c6ccccc6)CC5)cccn4n3)cc2)CC1] | N-methyl-N-(1-methyl-4-piperidyl)-4-[[8-(4-phenyl-2,3,6,7-tetrahydroazepin-1-yl)-[1,2,4]triazolo[1,5-a]pyridin-2-yl]amino]benzamide |
| 1-15 | 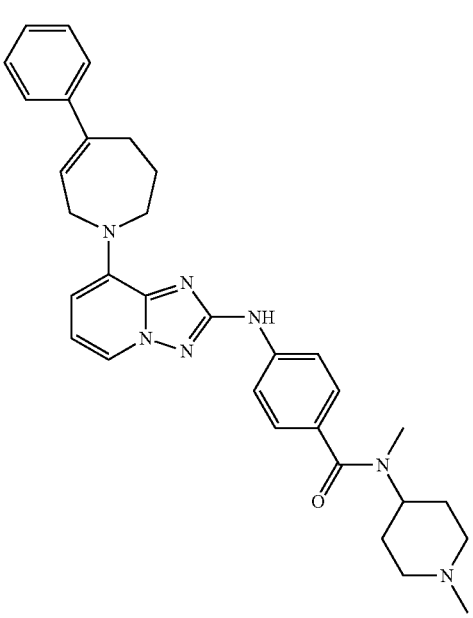 [SMILES: CN1CCC(N(C)C(=O)c2ccc(Nc3nc4c(N5CC=C(c6ccccc6)CCC5)cccn4n3)cc2)CC1] | N-methyl-N-(1-methyl-4-piperidyl)-4-[[8-(5-phenyl-2,3,4,7-tetrahydroazepin-1-yl)-[1,2,4]triazolo[1,5-a]pyridin-2-yl]amino]benzamide |

TABLE A-continued

Exemplary Compounds of the Present Invention

| Ex. | Structure | Name |
|---|---|---|
| 1-16 | 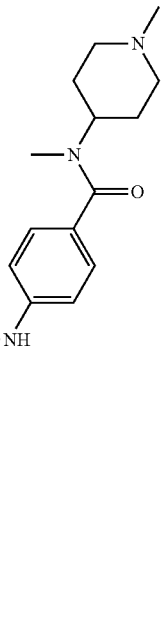 | 4-[[8-(4-fluoro-4-phenyl-1-piperidyl)-[1,2,4]triazolo[1,5-a]pyridin-2-yl]amino]-N-methyl-N-(1-methyl-4-piperidyl)benzamide |
| 1-17 | 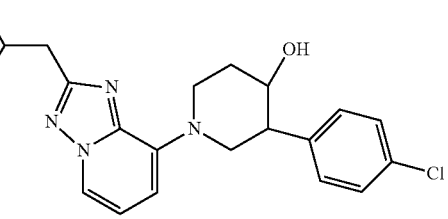 | 4-[[8-[4-(4-chlorophenyl)-4-hydroxy-1-piperidyl]-[1,2,4]triazolo[1,5-a]pyridin-2-yl]amino]-N-methyl-N-(1-methyl-4-piperidyl)benzamide |
| 1-18 | 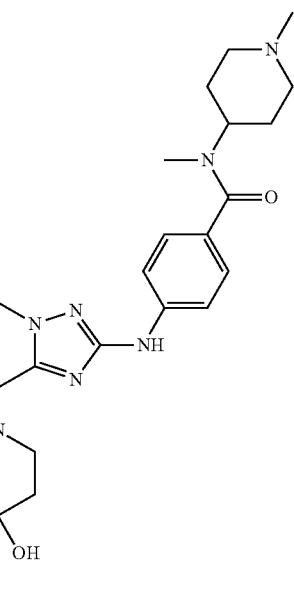 | 4-[[8-[4-(3-chlorophenyl)-4-hydroxy-1-piperidyl]-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 1-19 | 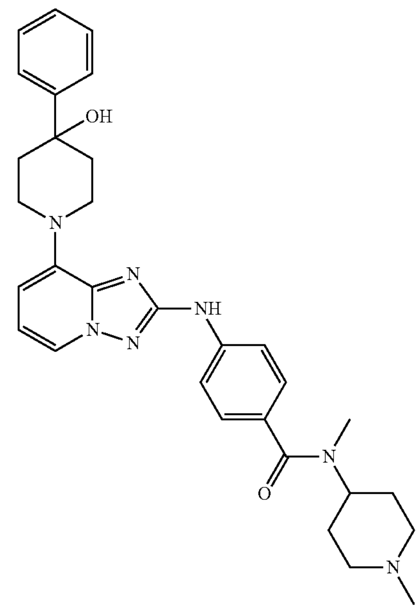 [SMILES: CN1CCC(N(C)C(=O)c2ccc(Nc3nc4c(N5CCC(O)(c6ccccc6)CC5)cccn4n3)cc2)CC1] | 4-[[8-[4-hydroxy-4-(3-pyridyl)-1-piperidyl]-[1,2,4]triazolo[1,5-a]pyridin-2-yl]amino]-N-methyl-N-(1-methyl-4-piperidyl)benzamide |
| 1-20 | 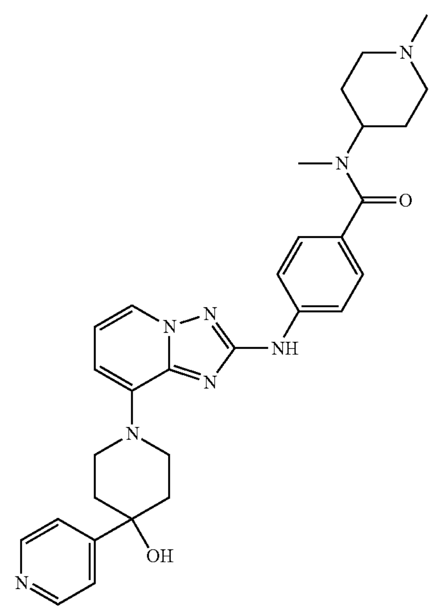 [SMILES: CN1CCC(N(C)C(=O)c2ccc(Nc3nc4c(N5CCC(O)(c6ccncc6)CC5)cccn4n3)cc2)CC1] | 4-[[8-[4-hydroxy-4-(4-pyridyl)-1-piperidyl]-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 1-21 | 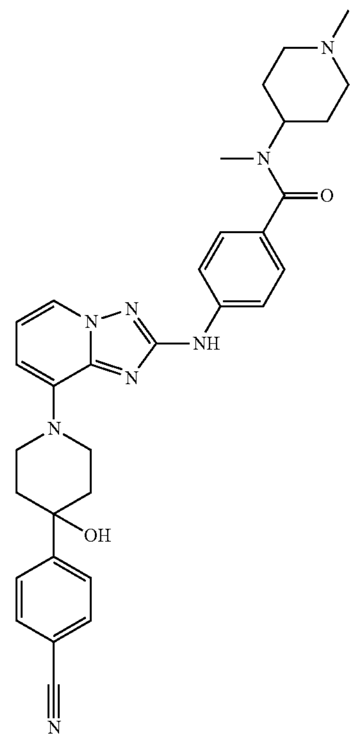 [SMILES: CN1CCC(N(C)C(=O)c2ccc(Nc3nc4c(N5CCC(O)(c6ccc(C#N)cc6)CC5)cccn4n3)cc2)CC1] | 4-[[8-[4-(4-cyanophenyl)-4-hydroxy-1-piperidyl]-[1,2,4]triazolo[1,5-a]pyridin-2-yl]amino]-N-methyl-N-(1-methyl-4-piperidyl)benzamide |
| 1-22 | 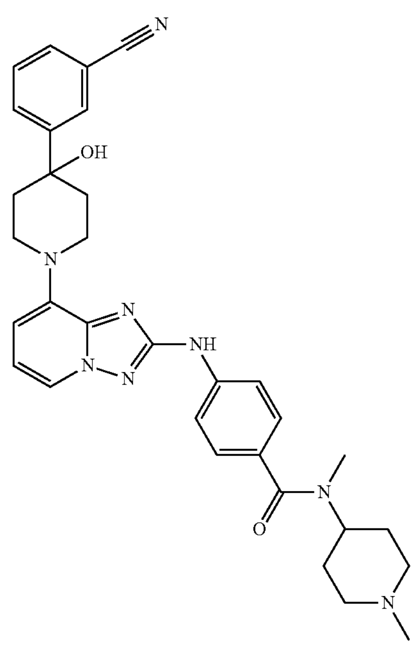 [SMILES: CN1CCC(N(C)C(=O)c2ccc(Nc3nc4c(N5CCC(O)(c6cccc(C#N)c6)CC5)cccn4n3)cc2)CC1] | 4-[[8-[4-(3-cyanophenyl)-4-hydroxy-1-piperidyl]-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 1-23 | 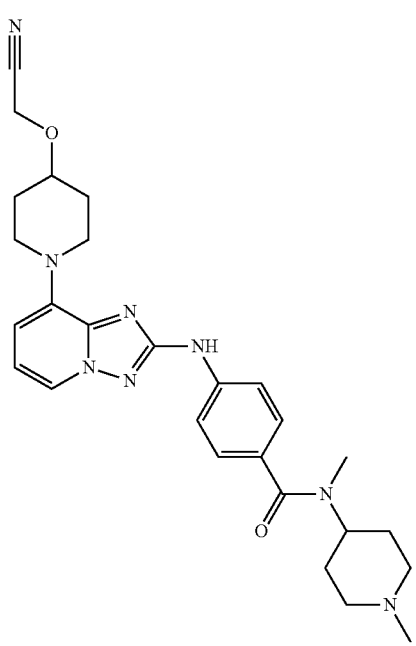 [SMILES: CN1CCC(N(C)C(=O)c2ccc(Nc3nc4c(N5CCC(OCC#N)CC5)cccn4n3)cc2)CC1] | 4-[[8-[4-(cyanomethoxy)-1-piperidyl]-[1,2,4]triazolo[1,5-a]pyridin-2-yl]amino]-N-methyl-N-(1-methyl-4-piperidyl)benzamide |
| 1-24 | 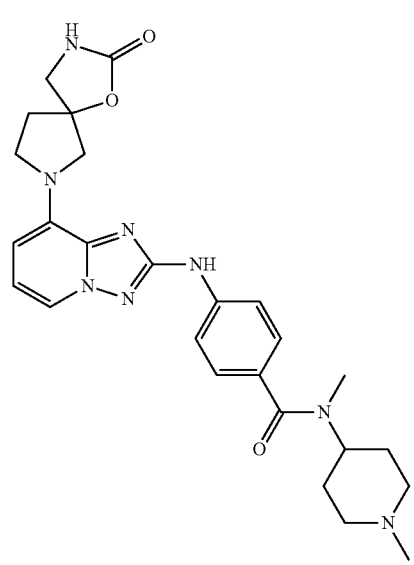 [SMILES: CN1CCC(N(C)C(=O)c2ccc(Nc3nc4c(N5CCC6(CNC(=O)O6)C5)cccn4n3)cc2)CC1] | N-methyl-N-(1-methyl-4-piperidyl)-4-[[8-(2-oxo-1-oxa-3,7-diazaspiro[4.4]nonan-7-yl)-[1,2,4]triazolo[1,5-a]pyridin-2-yl]amino]benzamide |

TABLE A-continued

Exemplary Compounds of the Present Invention

| Ex. | Structure | Name |
|---|---|---|
| 1-25 | 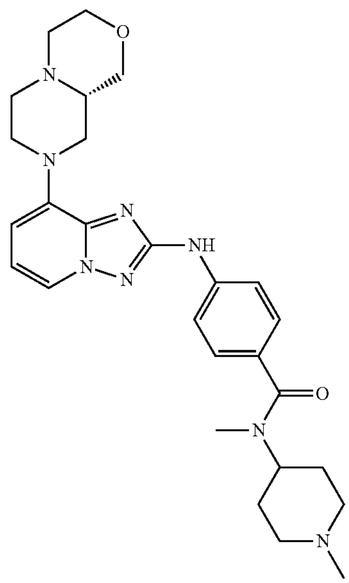 [SMILES: CN1CCC(N(C)C(=O)c2ccc(Nc3nc4c(N5CCN6CCOC[C@@H]6C5)cccn4n3)cc2)CC1] | 4-[[8-[(9aS)-3,4,6,7,9,9a-hexahydro-1H-pyrazino[2,1-c][1,4]oxazin-8-yl]-[1,2,4]triazolo[1,5-a]pyridin-2-yl]amino]-N-methyl-N-(1-methyl-4-piperidyl)benzamide |
| 1-26 | 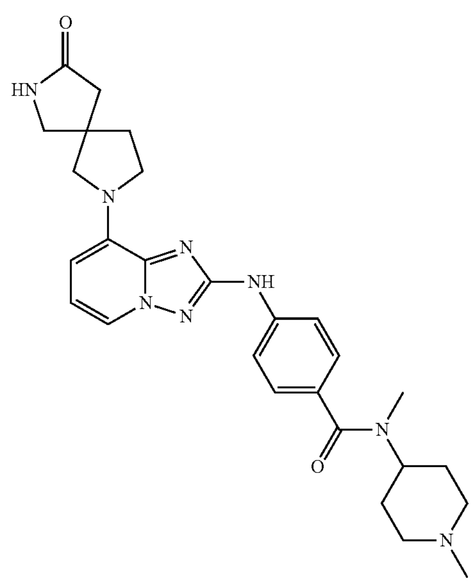 [SMILES: CN1CCC(N(C)C(=O)c2ccc(Nc3nc4c(N5CCC6(CNC(=O)C6)C5)cccn4n3)cc2)CC1] | N-methyl-N-(1-methyl-4-piperidyl)-4-[[8-(8-oxo-2,7-diazaspiro[4.4]nonan-2-yl)-[1,2,4]triazolo[1,5-a]pyridin-2-yl]amino]benzamide |

TABLE A-continued
Exemplary Compounds of the Present Invention
| Ex. | Structure | Name |
|---|---|---|
| 1-27 | 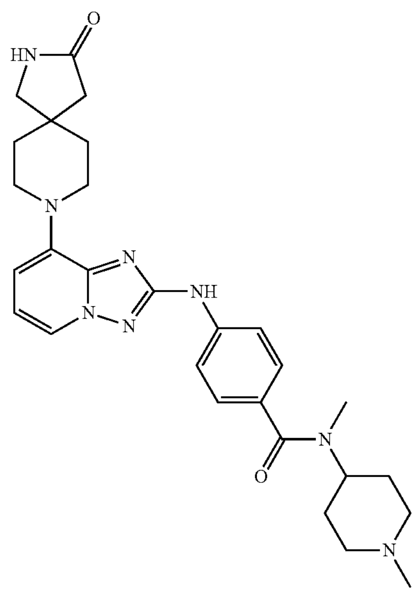 [SMILES: CN1CCC(N(C)C(=O)c2ccc(Nc3nc4c(N5CCC6(CC5)CNC(=O)O6)cccn4n3)cc2)CC1] | N-methyl-N-(1-methyl-4-piperidyl)-4-[[8-(3-oxo-2,8-diazaspiro[4.5]decan-8-yl)-[1,2,4]triazolo[1,5-a]pyridin-2-yl]amino]benzamide |
| 1-28 | 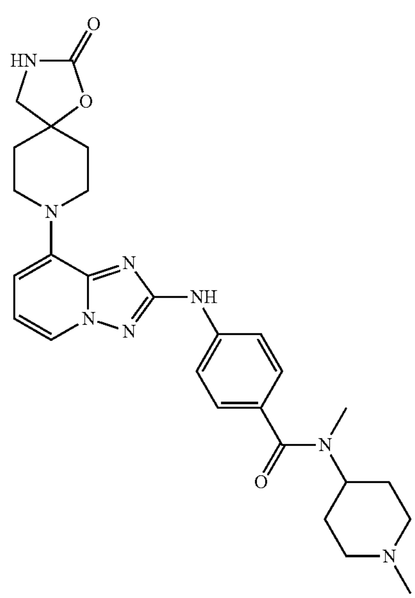 | N-methyl-N-(1-methyl-4-piperidyl)-4-[[8-(2-oxo-1-oxa-3,8-diazaspiro[4.5]decan-8-yl)-[1,2,4]triazolo[1,5-a]pyridin-2-yl]amino]benzamide |

TABLE A-continued
Exemplary Compounds of the Present Invention
| Ex. | Structure | Name |
|---|---|---|
| 1-29 | 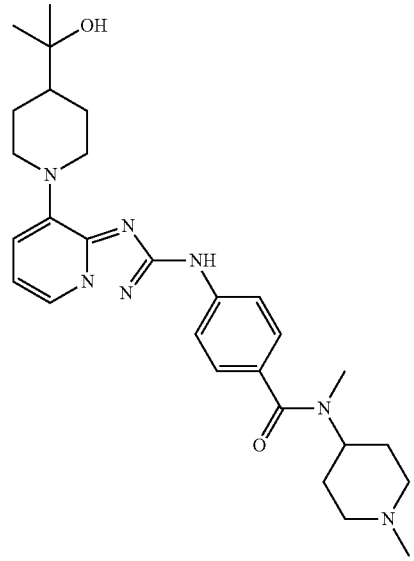 [SMILES: CN1CCC(N(C)C(=O)c2ccc(NC(=N)/N=c3\[nH]cccc3N3CCC(C(C)(C)O)CC3)cc2)CC1] | 4-[[8-[4-(1-hydroxy-1-methyl-ethyl)-1-piperidyl]-[1,2,4]triazolo[1,5-a]pyridin-2-yl]amino]-N-methyl-N-(1-methyl-4-piperidyl)benzamide |
| 1-30 | 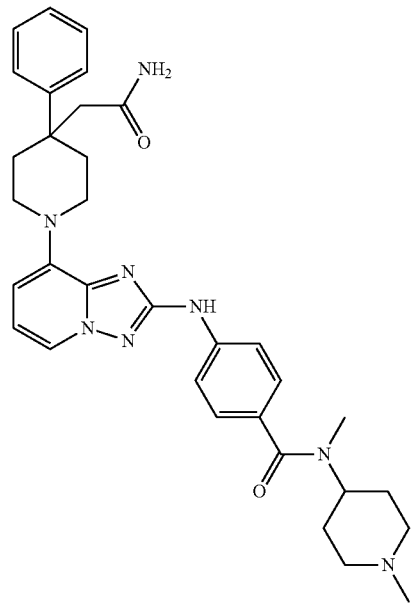 [SMILES: CN1CCC(N(C)C(=O)c2ccc(Nc3nc4c(N5CCC(CC(N)=O)(c6ccccc6)CC5)cccn4n3)cc2)CC1] | 4-[[8-[4-(2-amino-2-oxo-ethyl)-4-phenyl-1-piperidyl]-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 1-31 | 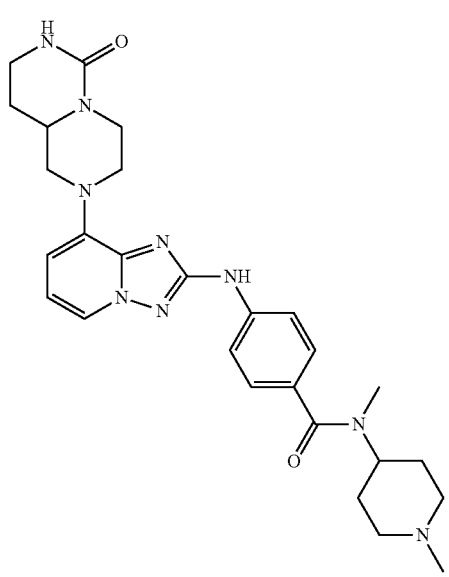 [SMILES: CN1CCC(N(C)C(=O)c2ccc(Nc3nc4c(N5CCN6C(=O)NCCC6C5)cccn4n3)cc2)CC1] | N-methyl-N-(1-methyl-4-piperidyl)-4-[[8-(6-oxo-3,4,7,8,9,9a-hexahydro-1H-pyrazino[1,2-c]pyrimidin-2-yl)-[1,2,4]triazolo[1,5-a]pyridin-2-yl]amino]benzamide |
| 1-32 | 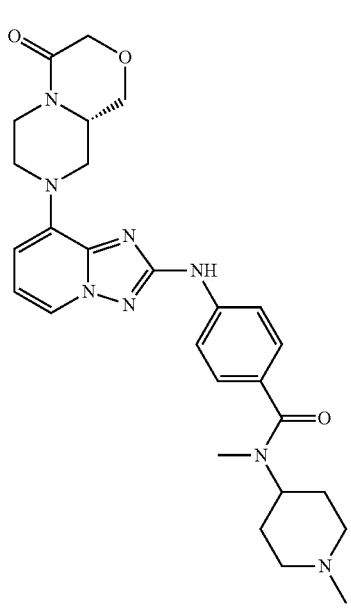 [SMILES: CN1CCC(N(C)C(=O)c2ccc(Nc3nc4c(N5CCN6C(=O)COC[C@@H]6C5)cccn4n3)cc2)CC1] | 4-[[8-[(9aS)-4-oxo-6,7,9,9a-tetrahydro-1H-pyrazino[2,1-c][1,4]oxazin-8-yl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 1-33 | 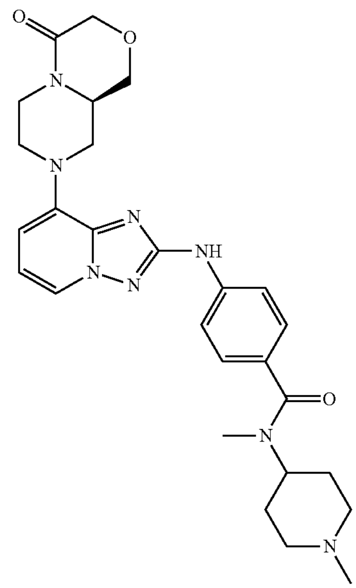 [SMILES: CN1CCC(N(C)C(=O)c2ccc(Nc3nc4c(N5CCN6C(=O)COC[C@H]6C5)cccn4n3)cc2)CC1] | 4-[[8-[(9aR)-4-oxo-6,7,9,9a-tetrahydro-1H-pyrazino[2,1-c][1,4]oxazin-8-yl]-[1,2,4]triazolo[1,5-a]pyridin-2-yl]amino]-N-methyl-N-(1-methyl-4-piperidyl)benzamide |
| 1-34 | 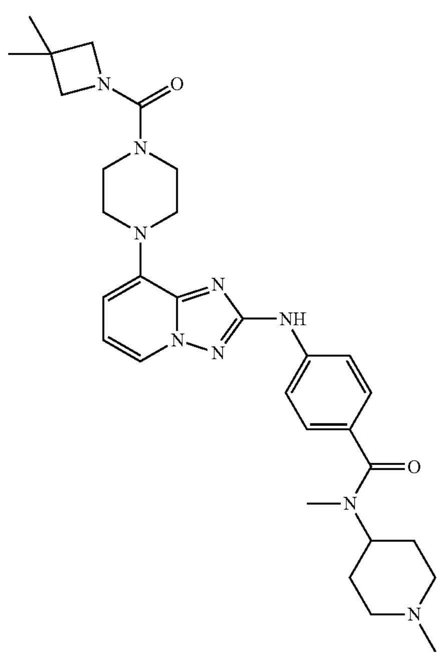 | 4-[[8-[4-(3,3-dimethylazetidine-1-carbonyl)piperazin-1-yl]-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 1-35 | 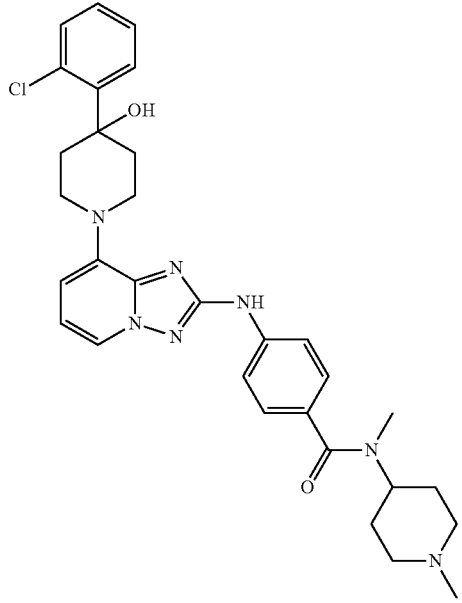 [SMILES: CN1CCC(N(C)C(=O)c2ccc(Nc3nc4c(N5CCC(O)(c6ccccc6Cl)CC5)cccn4n3)cc2)CC1] | 4-[[8-[4-(2-chlorophenyl)-4-hydroxy-1-piperidyl]-[1,2,4]triazolo[1,5-a]pyridin-2-yl]amino]-N-methyl-N-(1-methyl-4-piperidyl)benzamide |
| 1-36 | 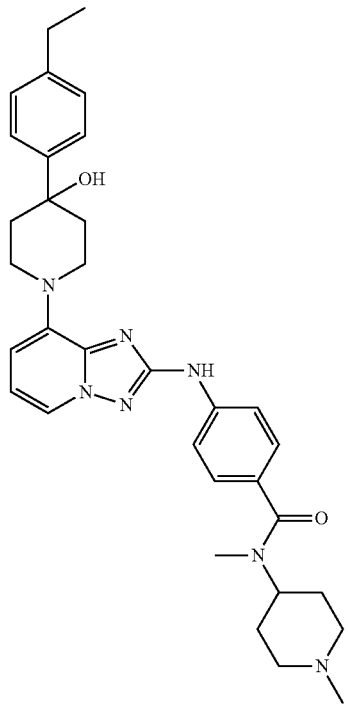 [SMILES: CCc1ccc(C2(O)CCN(c3cccn4nc(Nc5ccc(C(=O)N(C)C6CCN(C)CC6)cc5)nc34)CC2)cc1] | 4-[[8-[4-(4-ethylphenyl)-4-hydroxy-1-piperidyl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 1-37 | 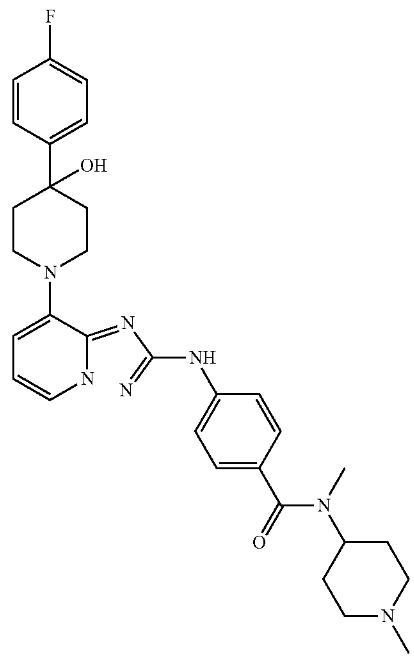 [SMILES: CN1CCC(N(C)C(=O)c2ccc(NC(=N)/N=c3\[nH]cccc3N3CCC(O)(c4ccc(F)cc4)CC3)cc2)CC1] | 4-[[8-[4-(4-fluorophenyl)-4-hydroxy-1-piperidyl]-[1,2,4]triazolo[1,5-a]pyridin-2-yl]amino]-N-methyl-N-(1-methyl-4-piperidyl)benzamide |
| 1-38 | 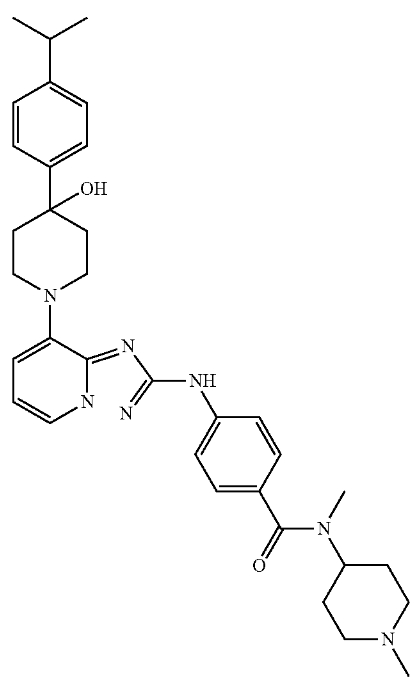 [SMILES: CC(C)c1ccc(C2(O)CCN(c3ccc[nH]/c3=N\C(=N)Nc3ccc(C(=O)N(C)C4CCN(C)CC4)cc3)CC2)cc1] | 4-[[8-[4-hydroxy-4-(4-isopropylphenyl)-1-piperidyl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 1-39 | 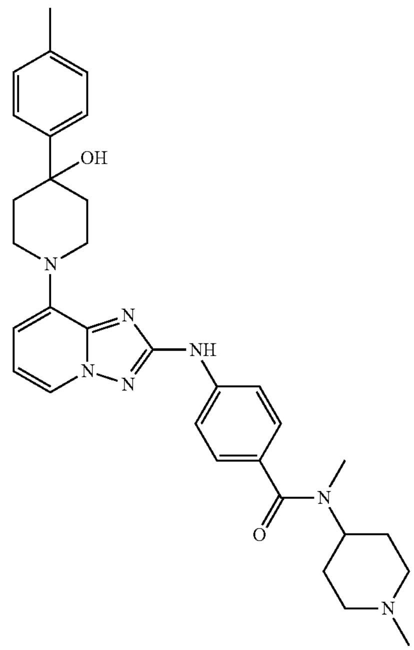 [SMILES: Cc1ccc(C2(O)CCN(c3cccn4nc(Nc5ccc(C(=O)N(C)C6CCN(C)CC6)cc5)nc34)CC2)cc1] | 4-[[8-[4-hydroxy-4-(p-tolyl)-1-piperidyl]-[1,2,4]triazolo[1,5-a]pyridin-2-yl]amino]-N-methyl-N-(1-methyl-4-piperidyl)benzamide |
| 1-40 | 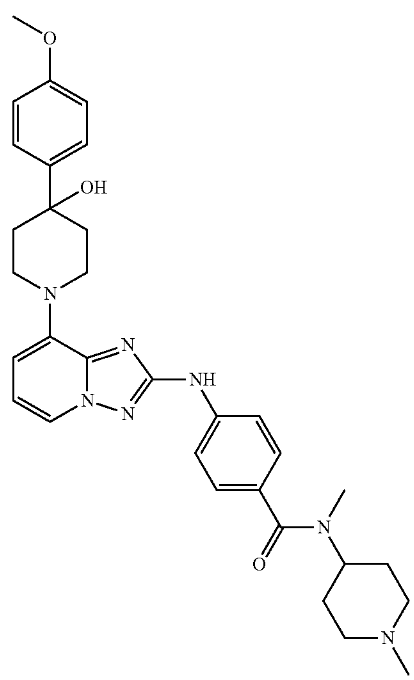 [SMILES: COc1ccc(C2(O)CCN(c3cccn4nc(Nc5ccc(C(=O)N(C)C6CCN(C)CC6)cc5)nc34)CC2)cc1] | 4-[[8-[4-hydroxy-4-(4-methoxyphenyl)-1-piperidyl]-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 1-41 | 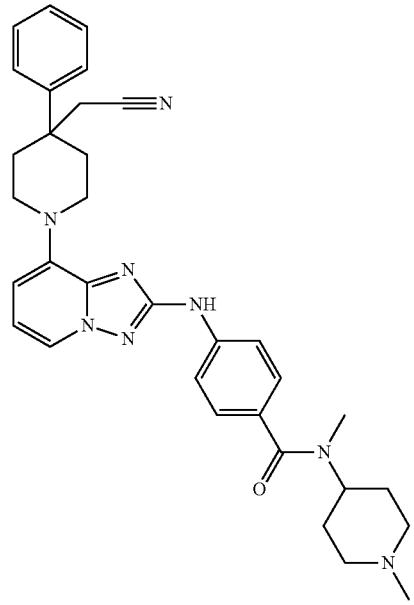 [SMILES: CN1CCC(N(C)C(=O)c2ccc(Nc3nc4c(N5CCC(CC#N)(c6ccccc6)CC5)cccn4n3)cc2)CC1] | 4-[[8-[4-(cyanomethyl)-4-phenyl-1-piperidyl]-[1,2,4]triazolo[1,5-a]pyridin-2-yl]amino]-N-methyl-N-(1-methyl-4-piperidyl)benzamide |
| 1-42 | 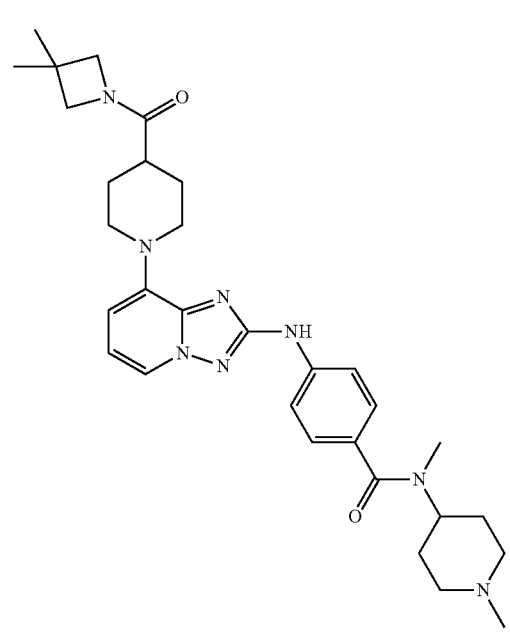 | 4-[[8-[4-(3,3-dimethylazetidine-1-carbonyl)-1-piperidyl]-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 1-43 | 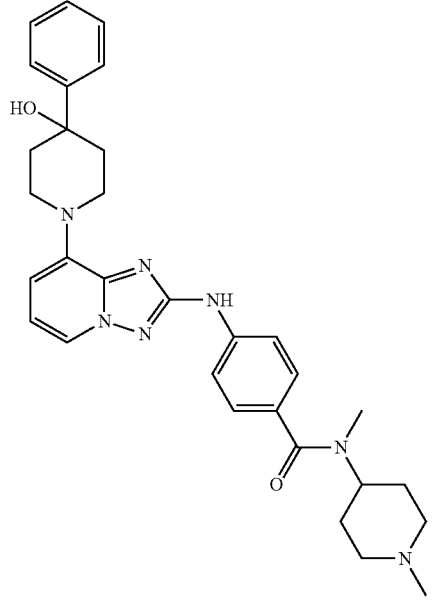 [SMILES: CN1CCC(N(C)C(=O)c2ccc(Nc3nc4c(N5CCC(O)(c6ccccc6)CC5)cccn4n3)cc2)CC1] | 4-[[8-(4-hydroxy-4-phenyl-1-piperidyl)-[1,2,4]triazolo[1,5-a]pyridin-2-yl]amino]-N-methyl-N-(1-methyl-4-piperidyl)benzamide |
| 1-44 | 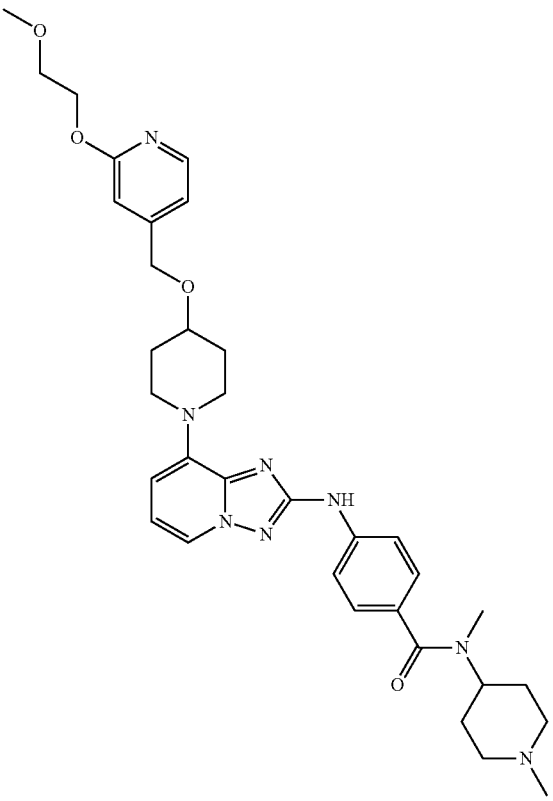 | 4-[[8-[4-[[2-(2-methoxyethoxy)-4-pyridyl]methoxy]-1-piperidyl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 1-45 | 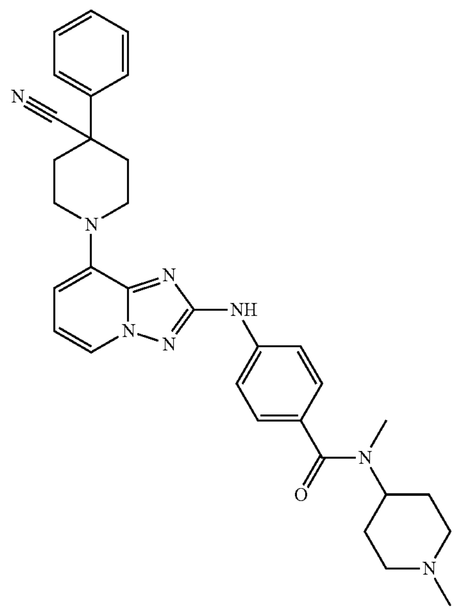 [SMILES: CN1CCC(N(C)C(=O)c2ccc(Nc3nc4c(N5CCC(C#N)(c6ccccc6)CC5)cccn4n3)cc2)CC1] | 4-[[8-(4-cyano-4-phenyl-1-piperidyl)-[1,2,4]triazolo[1,5-a]pyridin-2-yl]amino]-N-methyl-N-(1-methyl-4-piperidyl)benzamide |
| 1-46 | 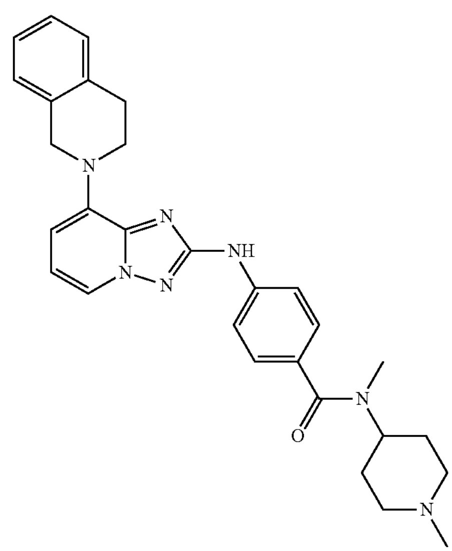 [SMILES: CN1CCC(N(C)C(=O)c2ccc(Nc3nc4c(N5CCc6ccccc6C5)cccn4n3)cc2)CC1] | 4-[[8-(3,4-dihydro-1H-isoquinolin-2-yl)-[1,2,4]triazolo[1,5-a]pyridin-2-yl]amino]-N-methyl-N-(1-methyl-4-piperidyl)benzamide |
| 1-47 | 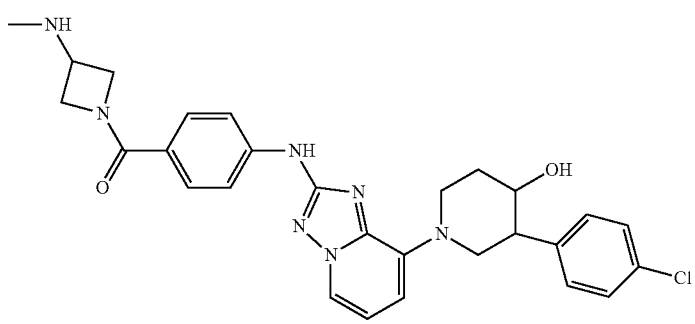 [SMILES: CNC1CN(C(=O)c2ccc(Nc3nc4c(N5CCC(O)C(c6ccc(Cl)cc6)C5)cccn4n3)cc2)C1] | [4-[[8-[4-(4-chlorophenyl)-4-hydroxy-1-piperidyl]-[1,2,4]triazolo[1,5-a]pyridin-2-yl]amino]phenyl]-[3-(methylamino)azetidin-1-yl]methanone |

TABLE A-continued

Exemplary Compounds of the Present Invention

| Ex. | Structure | Name |
|---|---|---|
| 1-48 | 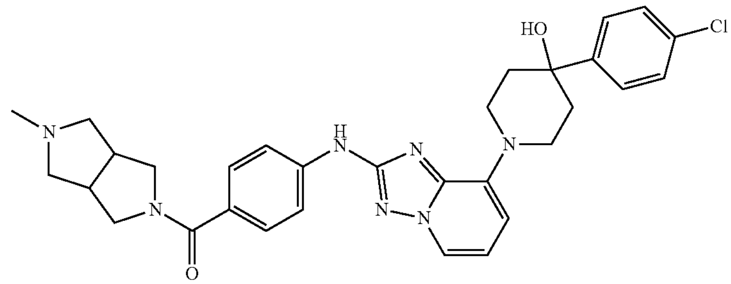 [SMILES: CN1CC2CN(C(=O)c3ccc(Nc4nc5c(N6CCC(O)(c7ccc(Cl)cc7)CC6)cccn5n4)cc3)CC2C1] | [4-[[8-[4-(4-chlorophenyl)-4-hydroxy-1-piperidyl]-[1,2,4]triazolo[1,5-a]pyridin-2-yl]amino]phenyl]-(2-methyl-1,3,3a,4,6,6a-hexahydropyrrolo[3,4-c]pyrrol-5-yl)methanone |
| 1-49 | 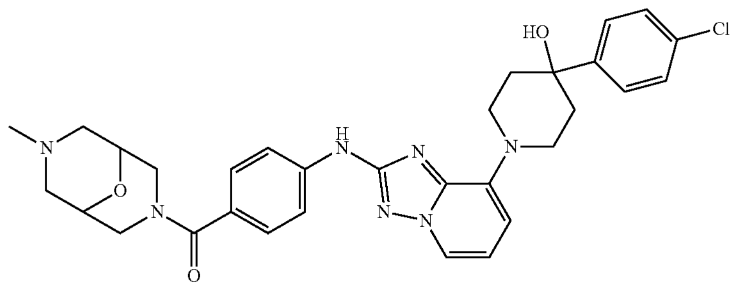 [SMILES: CN1CC2CN(C(=O)c3ccc(Nc4nc5c(N6CCC(O)(c7ccc(Cl)cc7)CC6)cccn5n4)cc3)CC(C1)O2] | [4-[[8-[4-(4-chlorophenyl)-4-hydroxy-1-piperidyl]-[1,2,4]triazolo[1,5-a]pyridin-2-yl]amino]phenyl]-(7-methyl-9-oxa-3,7-diazabicyclo[3.3.1]nonan-3-yl)methanone |
| 1-50 | 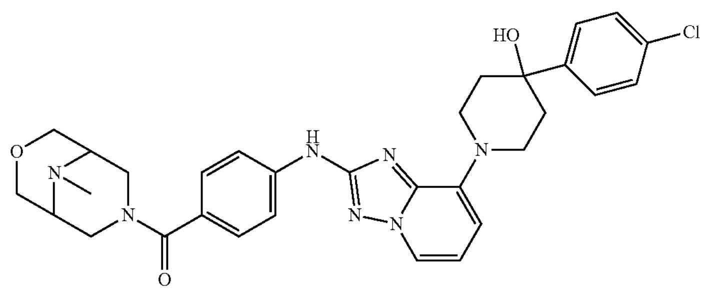 [SMILES: CN1C2COCC1CN(C(=O)c1ccc(Nc3nc4c(N5CCC(O)(c6ccc(Cl)cc6)CC5)cccn4n3)cc1)C2] | [4-[[8-[4-(4-chlorophenyl)-4-hydroxy-1-piperidyl]-[1,2,4]triazolo[1,5-a]pyridin-2-yl]amino]phenyl]-(9-methyl-3-oxa-7,9-diazabicyclo[3.3.1]nonan-7-yl)methanone |
| 1-51 | 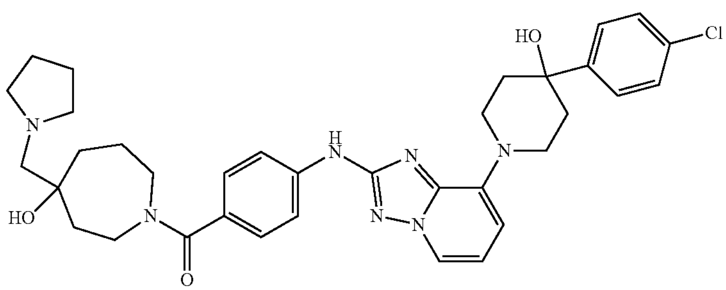 [SMILES: O=C(c1ccc(Nc2nc3c(N4CCC(O)(c5ccc(Cl)cc5)CC4)cccn3n2)cc1)N1CCCC(O)(CN2CCCC2)CC1] | [4-[[8-[4-(4-chlorophenyl)-4-hydroxy-1-piperidyl]-[1,2,4]triazolo[1,5-a]pyridin-2-yl]amino]phenyl]-[4-hydroxy-4-(pyrrolidin-1-ylmethyl)azepan-1-yl]methanone |
| 1-52 | 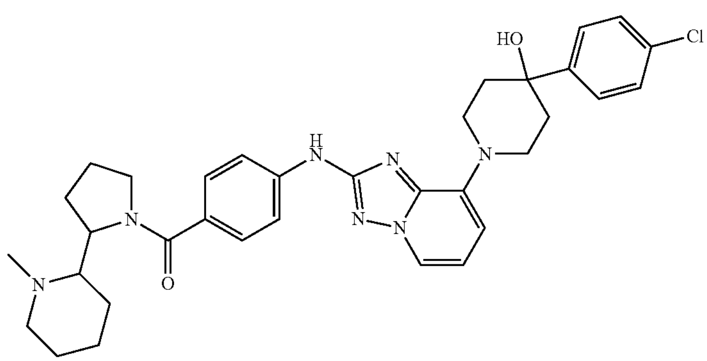 [SMILES: CN1CCCCC1C1CCCN1C(=O)c1ccc(Nc2nc3c(N4CCC(O)(c5ccc(Cl)cc5)CC4)cccn3n2)cc1] | [4-[[8-[4-(4-chlorophenyl)-4-hydroxy-1-piperidyl]-[1,2,4]triazolo[1,5-a]pyridin-2-yl]amino]phenyl]-[2-(1-methyl-2-piperidyl)pyrrolidin-1-yl]methanone |

TABLE A-continued

Exemplary Compounds of the Present Invention

| Ex. | Structure | Name |
|---|---|---|
| 1-53 | 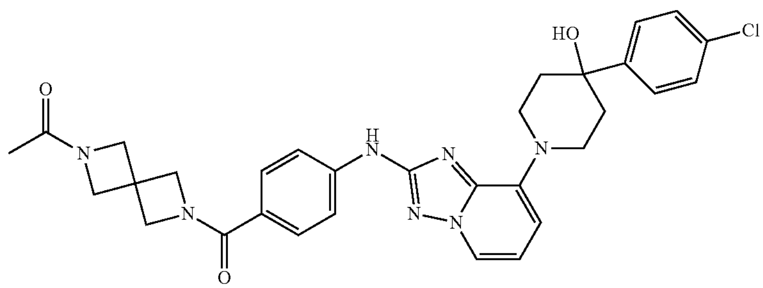 [SMILES: CC(=O)N1CC2(C1)CN(C(=O)c1ccc(Nc3nc4c(N5CCC(O)(c6ccc(Cl)cc6)CC5)cccn4n3)cc1)C2] | 1-[2-[4-[[8-[4-(4-chlorophenyl)-4-hydroxy-1-piperidyl]-[1,2,4]triazolo[1,5-a]pyridin-2-yl]amino]benzoyl]-2,6-diazaspiro[3.3]heptan-6-yl]ethanone |
| 1-54 | 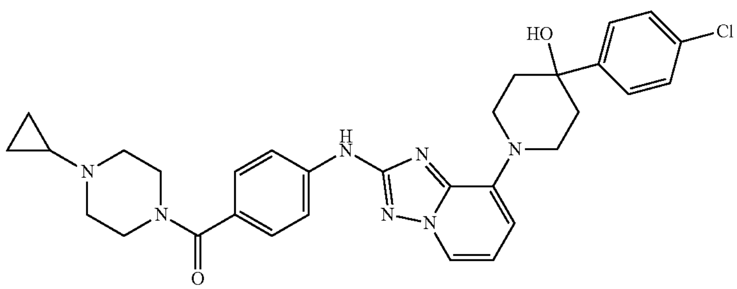 [SMILES: O=C(c1ccc(Nc2nc3c(N4CCC(O)(c5ccc(Cl)cc5)CC4)cccn3n2)cc1)N1CCN(C2CC2)CC1] | [4-[[8-[4-(4-chlorophenyl)-4-hydroxy-1-piperidyl]-[1,2,4]triazolo[1,5-a]pyridin-2-yl]amino]phenyl]-(4-cyclopropylpiperazin-1-yl)methanone |
| 1-55 | 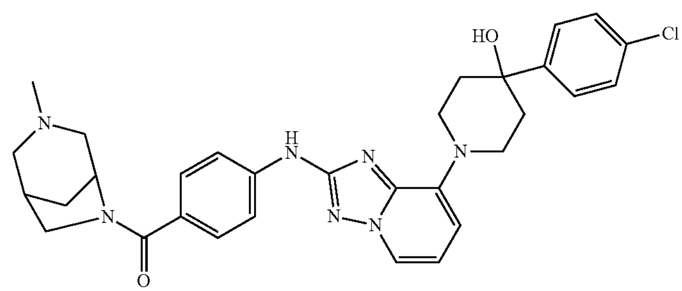 [SMILES: CN1CC2CC(C1)N(C(=O)c1ccc(Nc3nc4c(N5CCC(O)(c6ccc(Cl)cc6)CC5)cccn4n3)cc1)C2] | [4-[[8-[4-(4-chlorophenyl)-4-hydroxy-1-piperidyl]-[1,2,4]triazolo[1,5-a]pyridin-2-yl]amino]phenyl]-(3-methyl-3,6-diazabicyclo[3.2.1]octan-6-yl)methanone |
| 1-56 | 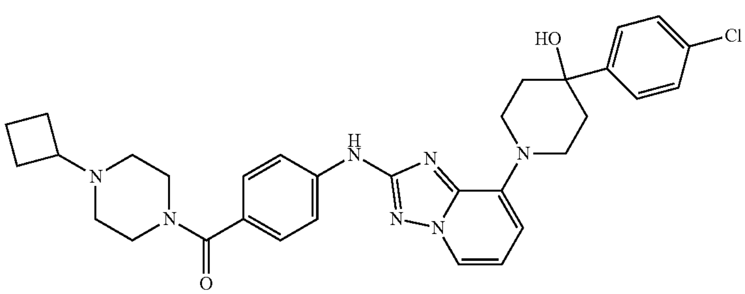 [SMILES: O=C(c1ccc(Nc2nc3c(N4CCC(O)(c5ccc(Cl)cc5)CC4)cccn3n2)cc1)N1CCN(C2CCC2)CC1] | [4-[[8-[4-(4-chlorophenyl)-4-hydroxy-1-piperidyl]-[1,2,4]triazolo[1,5-a]pyridin-2-yl]amino]phenyl]-(4-cyclobutylpiperazin-1-yl)methanone |
| 1-57 | 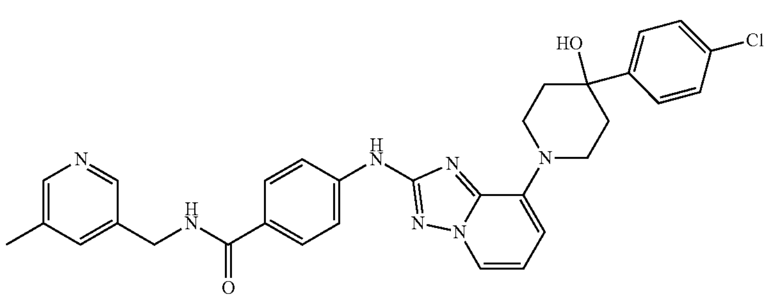 | 4-[[8-[4-(4-chlorophenyl)-4-hydroxy-1-piperidyl]-[1,2,4]triazolo[1,5-a]pyridin-2-yl]amino]-N-[(5-methyl-3-pyridyl)methyl]benzamide |

TABLE A-continued

Exemplary Compounds of the Present Invention

| Ex. | Structure | Name |
|---|---|---|
| 1-58 | 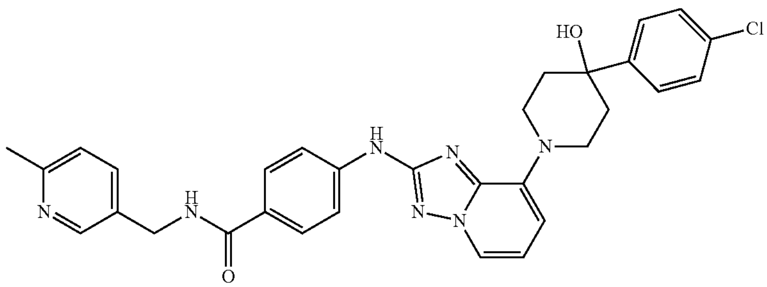 [SMILES: Cc1ccc(CNC(=O)c2ccc(Nc3nc4c(N5CCC(O)(c6ccc(Cl)cc6)CC5)cccn4n3)cc2)cn1] | 4-[[8-[4-(4-chlorophenyl)-4-hydroxy-1-piperidyl]-[1,2,4]triazolo[1,5-a]pyridin-2-yl]amino]-N-[(6-methyl-3-pyridyl)methyl]benzamide |
| 1-59 | 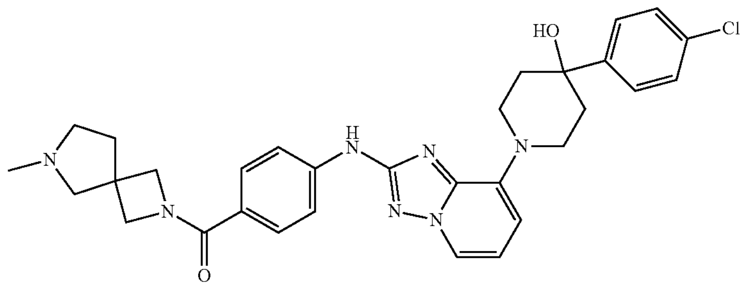 [SMILES: CN1CCC2(C1)CN(C(=O)c1ccc(Nc3nc4c(N5CCC(O)(c6ccc(Cl)cc6)CC5)cccn4n3)cc1)C2] | [4-[[8-[4-(4-chlorophenyl)-4-hydroxy-1-piperidyl]-[1,2,4]triazolo[1,5-a]pyridin-2-yl]amino]phenyl]-(7-methyl-2,7-diazaspiro[3.4]octan-2-yl)methanone |
| 1-60 | 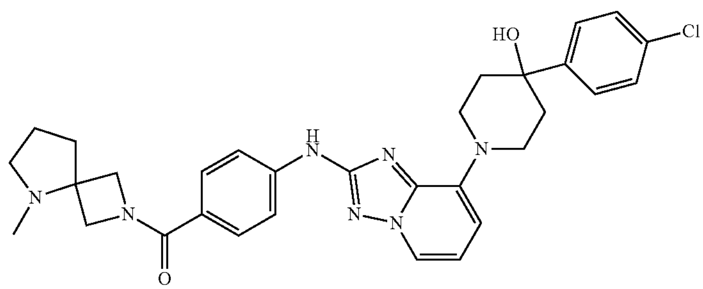 [SMILES: CN1CCCC12CN(C(=O)c1ccc(Nc3nc4c(N5CCC(O)(c6ccc(Cl)cc6)CC5)cccn4n3)cc1)C2] | [4-[[8-[4-(4-chlorophenyl)-4-hydroxy-1-piperidyl]-[1,2,4]triazolo[1,5-a]pyridin-2-yl]amino]phenyl]-(5-methyl-2,5-diazaspiro[3.4]octan-2-yl)methanone |
| 1-61 | 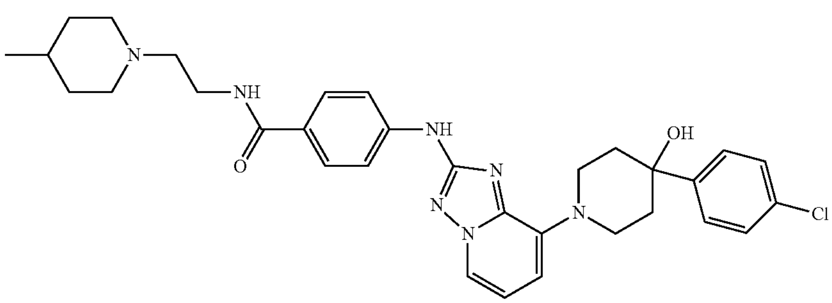 | 4-[[8-[4-(4-chlorophenyl)-4-hydroxy-1-piperidyl]-[1,2,4]triazolo[1,5-a]pyridin-2-yl]amino]-N-[2-(4-methyl-1-piperidyl)ethyl]benzamide |
| 1-62 | 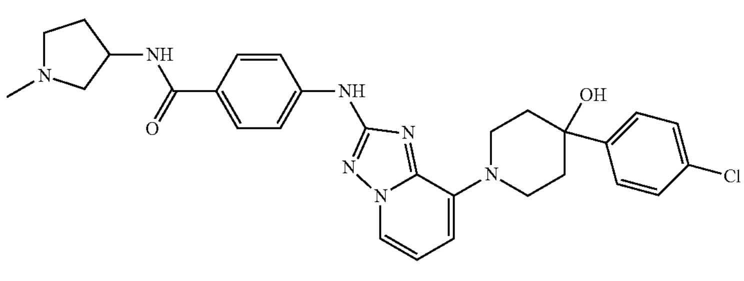 [SMILES: CN1CCC(NC(=O)c2ccc(Nc3nc4c(N5CCC(O)(c6ccc(Cl)cc6)CC5)cccn4n3)cc2)C1] | 4-[[8-[4-(4-chlorophenyl)-4-hydroxy-1-piperidyl]-[1,2,4]triazolo[1,5-a]pyridin-2-yl]amino]-N-(1-methylpyrrolidin-3-yl)benzamide |

TABLE A-continued

Exemplary Compounds of the Present Invention

| Ex. | Structure | Name |
|---|---|---|
| 1-63 | 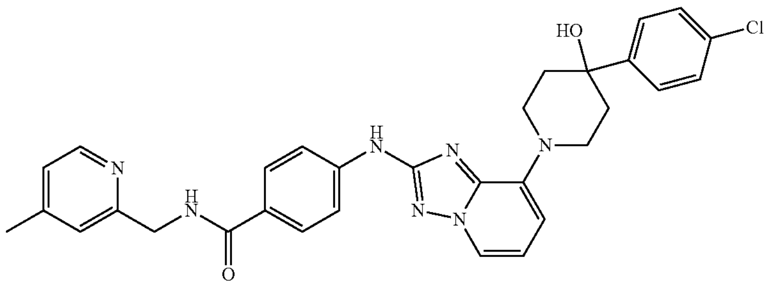 [SMILES: Cc1ccnc(CNC(=O)c2ccc(Nc3nc4c(N5CCC(O)(c6ccc(Cl)cc6)CC5)cccn4n3)cc2)c1] | 4-[[8-[4-(4-chlorophenyl)-4-hydroxy-1-piperidyl]-[1,2,4]triazolo[1,5-a]pyridin-2-yl]amino]-N-[(4-methyl-2-pyridyl)methyl]benzamide |
| 1-64 | 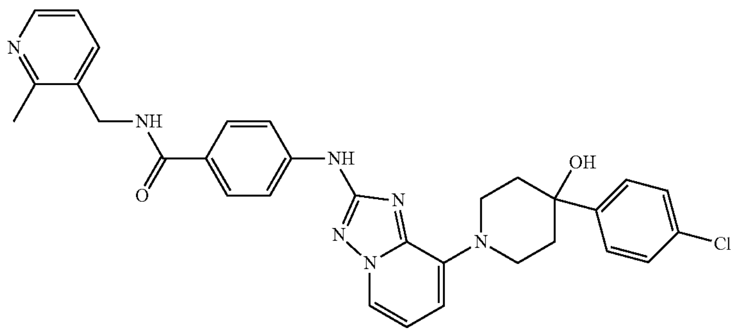 [SMILES: Cc1ncccc1CNC(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[(2-methyl-3-pyridyl)methyl]benzamide |
| 1-65 | 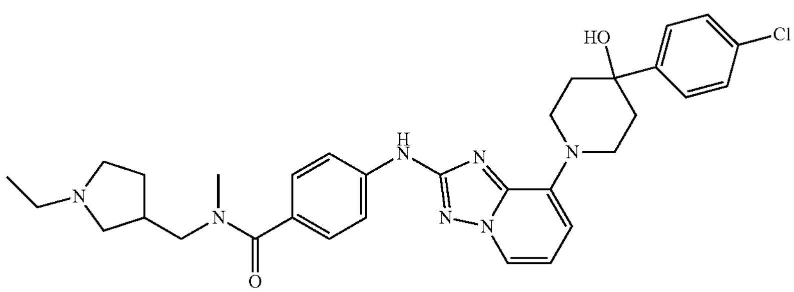 [SMILES: CCN1CCC(CN(C)C(=O)c2ccc(Nc3nc4c(N5CCC(O)(c6ccc(Cl)cc6)CC5)cccn4n3)cc2)C1] | 4-[[8-[4-(4-chlorophenyl)-4-hydroxy-1-piperidyl]-[1,2,4]triazolo[1,5-a]pyridin-2-yl]amino]-N-[(1-ethylpyrrolidin-3-yl)methyl]-N-methyl-benzamide |
| 1-66 | 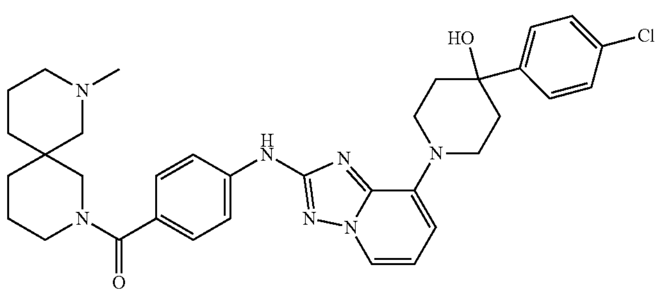 [SMILES: CN1CCCC2(CCCN(C(=O)c3ccc(Nc4nc5c(N6CCC(O)(c7ccc(Cl)cc7)CC6)cccn5n4)cc3)C2)C1] | [4-[[8-[4-(4-chlorophenyl)-4-hydroxy-1-piperidyl]-[1,2,4]triazolo[1,5-a]pyridin-2-yl]amino]phenyl]-(8-methyl-2,8-diazaspiro[5.5]undecan-2-yl)methanone |
| 1-67 | 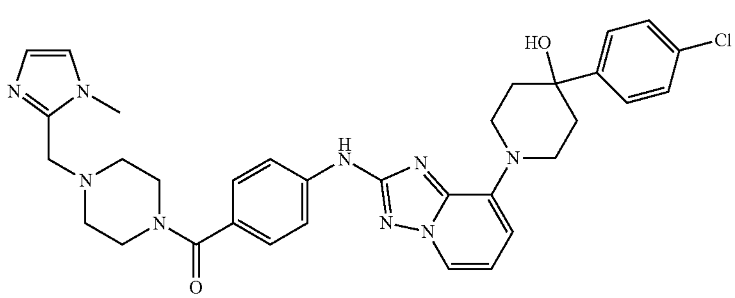 [SMILES: Cn1ccnc1CN1CCN(C(=O)c2ccc(Nc3nc4c(N5CCC(O)(c6ccc(Cl)cc6)CC5)cccn4n3)cc2)CC1] | [4-[[8-[4-(4-chlorophenyl)-4-hydroxy-1-piperidyl]-[1,2,4]triazolo[1,5-a]pyridin-2-yl]amino]phenyl]-[4-[(1-methylimidazol-2-yl)methyl]piperazin-1-yl]methanone |

TABLE A-continued

Exemplary Compounds of the Present Invention

| Ex. | Structure | Name |
|---|---|---|
| 1-68 | 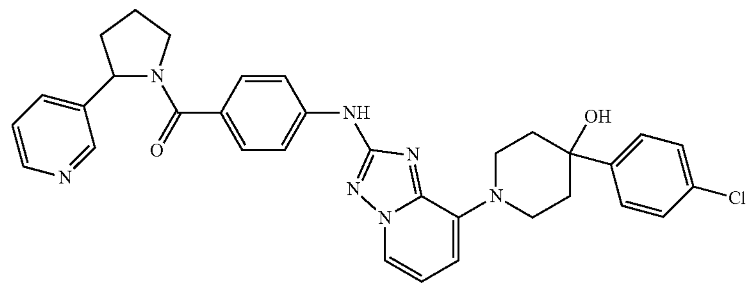 [SMILES: O=C(c1ccc(Nc2nc3c(N4CCC(O)(c5ccc(Cl)cc5)CC4)cccn3n2)cc1)N1CCCC1c1cccnc1] | [4-[[8-[4-(4-chlorophenyl)-4-hydroxy-1-piperidyl]-[1,2,4]triazolo[1,5-a]pyridin-2-yl]amino]phenyl]-[2-(3-pyridyl)pyrrolidin-1-yl]methanone |
| 1-69 | 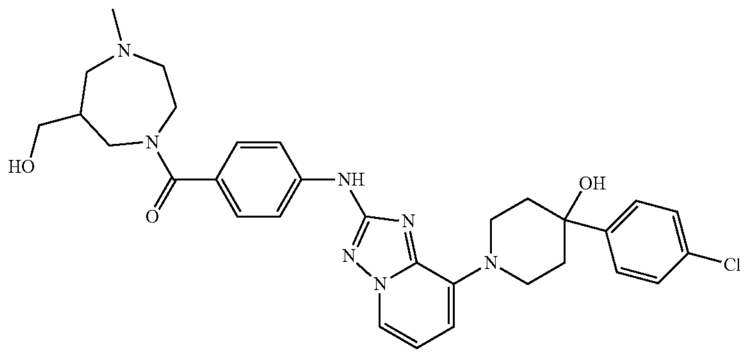 [SMILES: CN1CCN(C(=O)c2ccc(Nc3nc4c(N5CCC(O)(c6ccc(Cl)cc6)CC5)cccn4n3)cc2)CC(CO)C1] | [4-[[8-[4-(4-chlorophenyl)-4-hydroxy-1-piperidyl]-[1,2,4]triazolo[1,5-a]pyridin-2-yl]amino]phenyl]-[6-(hydroxymethyl)-4-methyl-1,4-diazepan-1-yl]methanone |
| 1-70 | 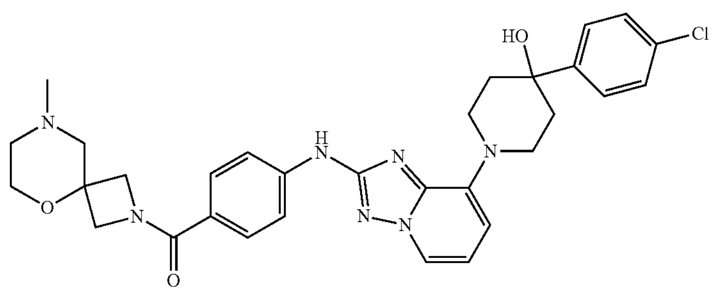 [SMILES: CN1CCOC2(C1)CN(C(=O)c1ccc(Nc3nc4c(N5CCC(O)(c6ccc(Cl)cc6)CC5)cccn4n3)cc1)C2] | [4-[[8-[4-(4-chlorophenyl)-4-hydroxy-1-piperidyl]-[1,2,4]triazolo[1,5-a]pyridin-2-yl]amino]phenyl]-(8-methyl-5-oxa-2,8-diazaspiro[3.5]nonan-2-yl)methanone |
| 1-71 | 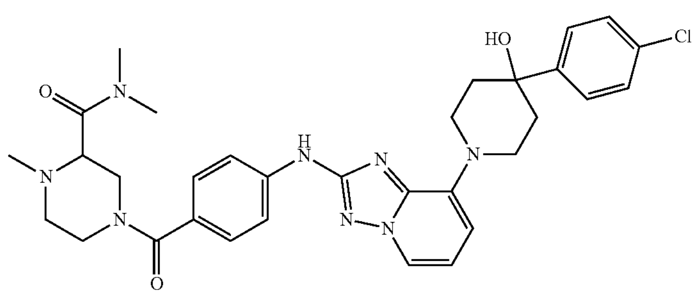 [SMILES: CN(C)C(=O)C1CN(C(=O)c2ccc(Nc3nc4c(N5CCC(O)(c6ccc(Cl)cc6)CC5)cccn4n3)cc2)CCN1C] | 4-[4-[[8-[4-(4-chlorophenyl)-4-hydroxy-1-piperidyl]-[1,2,4]triazolo[1,5-a]pyridin-2-yl]amino]benzoyl]-N,N,1-trimethyl-piperazine-2-carboxamide |
| 1-72 | 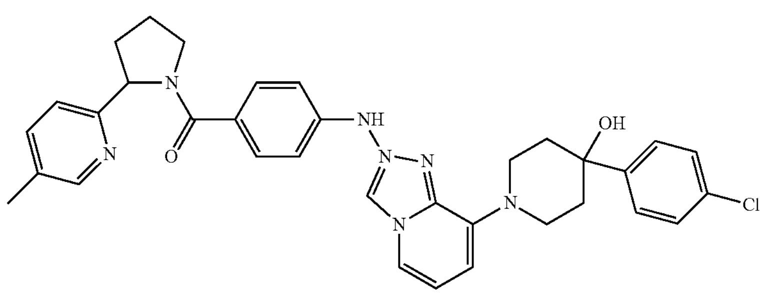 | [4-[[8-[4-(4-chlorophenyl)-4-hydroxy-1-piperidyl]-[1,2,4]triazolo[1,5-a]pyridin-2-yl]amino]phenyl]-[2-(5-methyl-2-pyridyl)pyrrolidin-1-yl]methanone |

TABLE A-continued

Exemplary Compounds of the Present Invention

| Ex. | Structure | Name |
|---|---|---|
| 1-73 | 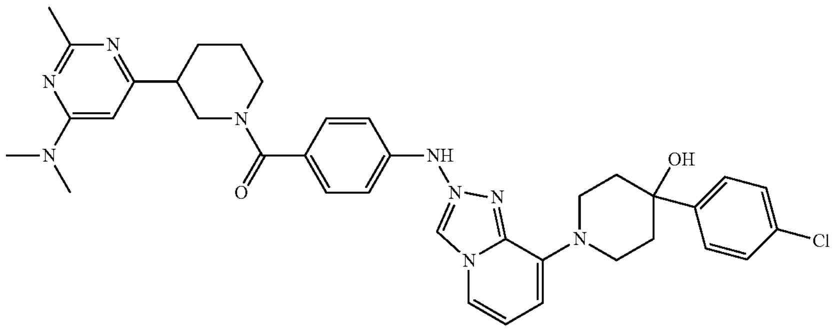 | [4-[[8-[4-(4-chlorophenyl)-4-hydroxy-1-piperidyl]-[1,2,4]triazolo[1,5-a]pyridin-2-yl]amino]phenyl]-[3-[6-(dimethylamino)-2-methyl-pyrimidin-4-yl]-1-piperidyl]methanone |
| 1-74 | 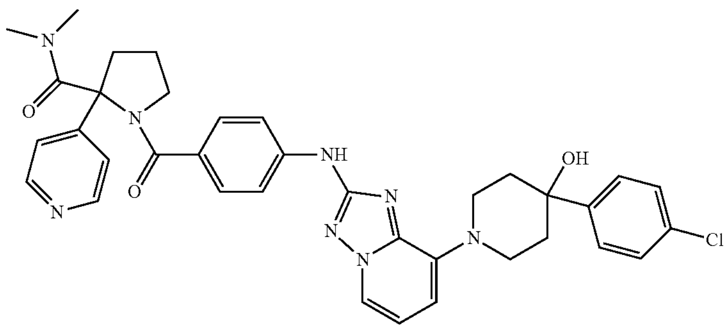 [SMILES: CN(C)C(=O)C1(c2ccncc2)CCCN1C(=O)c1ccc(Nc2nc3c(N4CCC(O)(c5ccc(Cl)cc5)CC4)cccn3n2)cc1] | 1-[4-[[8-[4-(4-chlorophenyl)-4-hydroxy-1-piperidyl]-[1,2,4]triazolo[1,5-a]-pyridin-2-yl]amino]benzoyl]-N,N-dimethyl-2-(4-pyridyl)pyrrolidine-2-carboxamide |
| 1-75 | 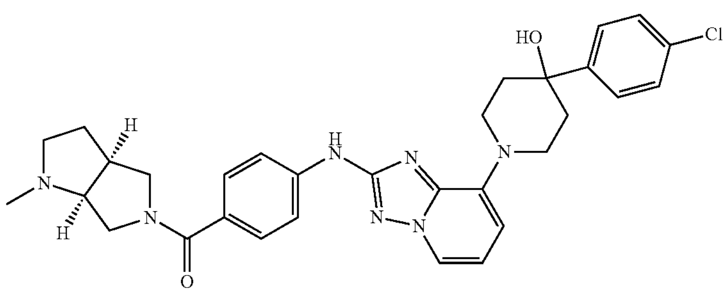 [SMILES: CN1CC[C@H]2CN(C(=O)c3ccc(Nc4nc5c(N6CCC(O)(c7ccc(Cl)cc7)CC6)cccn5n4)cc3)C[C@H]21] | [(3aS,6aS)-1-methyl-2,3,3a,4,6,6a-hexahydropyrrolo[3,4-b]pyrrol-5-yl]-[4[[8-[4-(4-chlorophenyl)-4-hydroxy-1-piperidyl]-[1,2,4]triazolo[1,5-a]pyridin-2-yl]amino]phenyl]methanone |
| 1-76 | 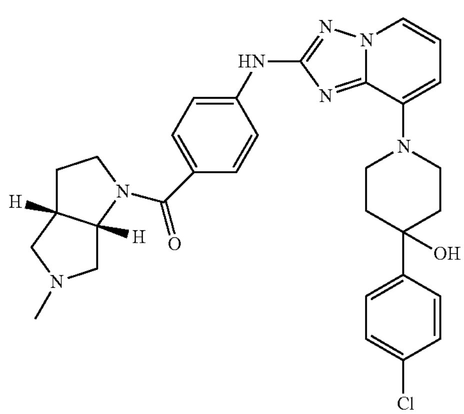 [SMILES: CN1C[C@@H]2CCN(C(=O)c3ccc(Nc4nc5c(N6CCC(O)(c7ccc(Cl)cc7)CC6)cccn5n4)cc3)[C@@H]2C1] | [(3aS,6aS)-5-methyl-2,3,3a,4,6,6a-hexahydropyrrolo[2,3-c]pyrrol-1-yl]-[4-[[8-[4-(4-chlorophenyl)-4-hydroxy-1-piperidyl]-[1,2,4]triazolo[1,5-a]pyridin-2-yl]amino]phenyl]methanone |

TABLE A-continued

Exemplary Compounds of the Present Invention

| Ex. | Structure | Name |
|---|---|---|
| 1-77 | 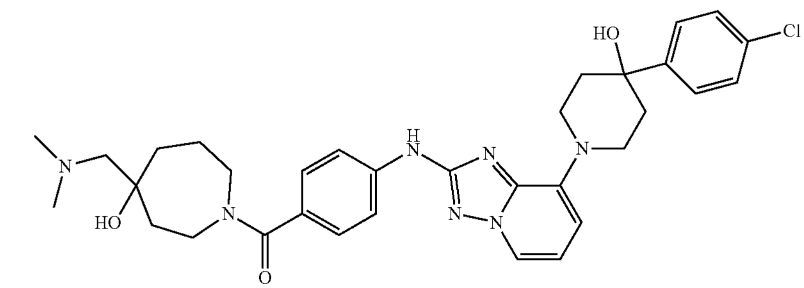 [SMILES: CN(C)CC1(O)CCCN(C(=O)c2ccc(Nc3nc4c(N5CCC(O)(c6ccc(Cl)cc6)CC5)cccn4n3)cc2)CC1] | [4-[[8-[4-(4-chlorophenyl)-4-hydroxy-1-piperidyl]-[1,2,4]triazolo[1,5-a]pyridin-2-yl]amino]phenyl]-[4-[(dimethylamino)methyl]-4-hydroxy-azepan-1-yl]methanone |
| 1-78 | 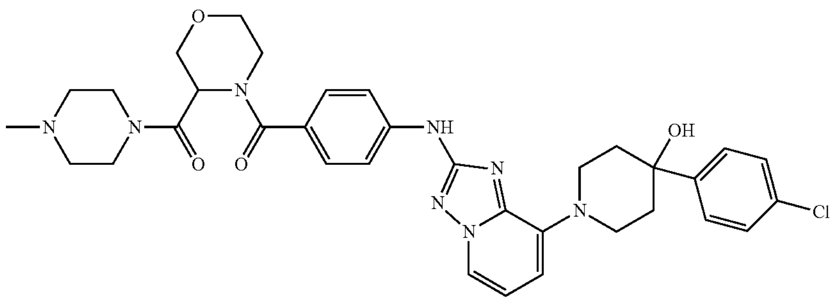 [SMILES: CN1CCN(C(=O)C2COCCN2C(=O)c2ccc(Nc3nc4c(N5CCC(O)(c6ccc(Cl)cc6)CC5)cccn4n3)cc2)CC1] | [4-[[8-[4-(4-chlorophenyl)-4-hydroxy-1-piperidyl]-[1,2,4]triazolo[1,5-a]pyridin-2-yl]amino]phenyl]-[3-(4-methylpiperazine-1-carbonyl)morpholin-4-yl]methanone |
| 1-79 | 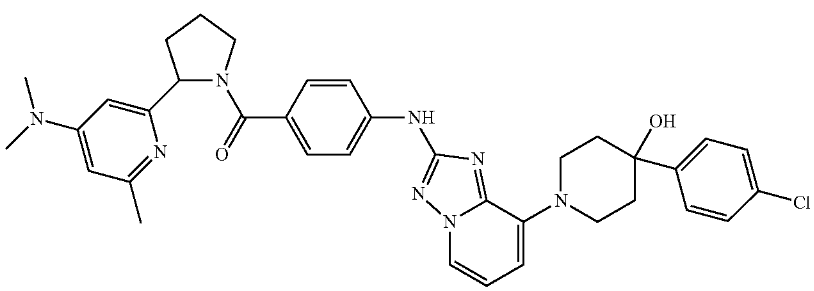 [SMILES: Cc1cc(N(C)C)cc(C2CCCN2C(=O)c2ccc(Nc3nc4c(N5CCC(O)(c6ccc(Cl)cc6)CC5)cccn4n3)cc2)n1] | [4-[[8-[4-(4-chlorophenyl)-4-hydroxy-1-piperidyl]-[1,2,4]triazolo[1,5-a]pyridin-2-yl]amino]phenyl]-[2-[4-(dimethylamino)-6-methyl-2-pyridyl]pyrrolidin-1-yl]methanone |
| 1-80 | 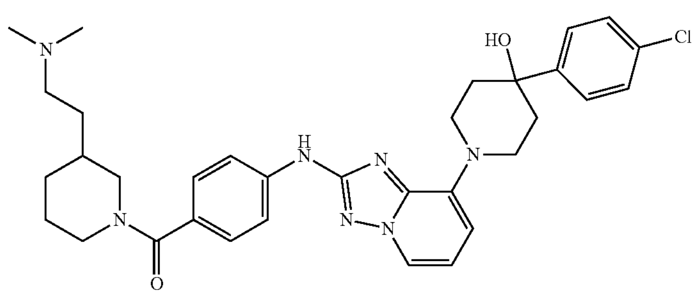 [SMILES: CN(C)CCC1CCCN(C(=O)c2ccc(Nc3nc4c(N5CCC(O)(c6ccc(Cl)cc6)CC5)cccn4n3)cc2)C1] | [4[[8-[4-(4-chlorophenyl)-4-hydroxy-1-piperidyl]-[1,2,4]triazolo[1,5-a]pyridin-2-yl]amino]phenyl]-[3-[2-(dimethylamino)ethyl]-1-piperidyl]methanone |
| 1-81 | 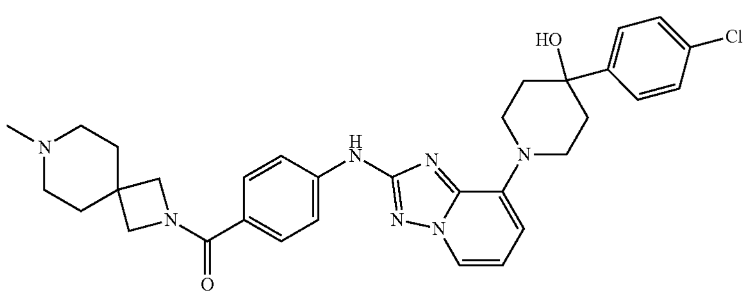 [SMILES: CN1CCC2(CC1)CN(C(=O)c1ccc(Nc3nc4c(N5CCC(O)(c6ccc(Cl)cc6)CC5)cccn4n3)cc1)C2] | [4-[[8-[4-(4-chlorophenyl)-4-hydroxy-1-piperidyl]-[1,2,4]triazolo[1,5-a]pyridin-2-yl]amino]phenyl]-(7-methyl-2,7-diazaspiro[3.5]nonan-2-yl)methanone |

TABLE A-continued

Exemplary Compounds of the Present Invention

| Ex. | Structure | Name |
|---|---|---|
| 1-82 | 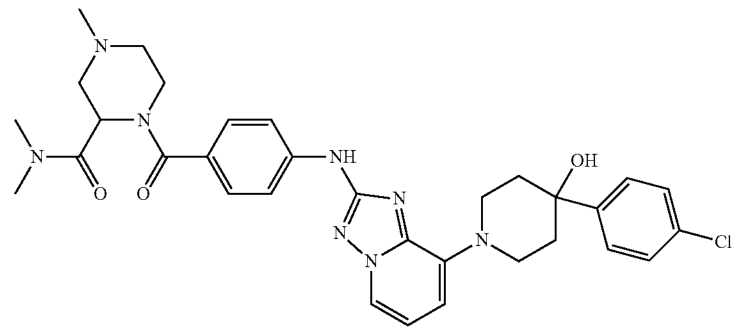 [SMILES: CN1CCN(C(=O)c2ccc(Nc3nc4c(N5CCC(O)(c6ccc(Cl)cc6)CC5)cccn4n3)cc2)C(C(=O)N(C)C)C1] | 1-[4-[[8-[4-(4-chlorophenyl)-4-hydroxy-1-piperidyl]-[1,2,4]triazolo[1,5-a]pyridin-2-yl]amino]benzoyl]-N,N,4-trimethyl-piperazine-2-carboxamide |
| 1-83 | 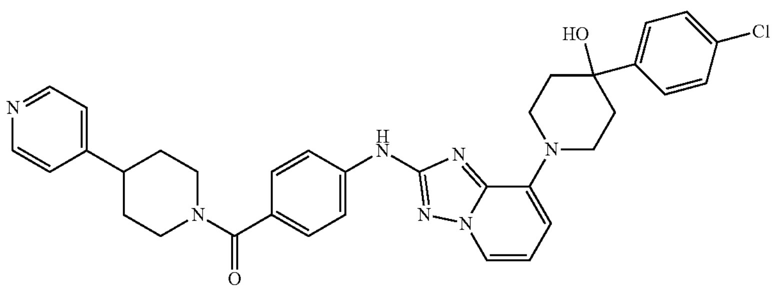 [SMILES: O=C(c1ccc(Nc2nc3c(N4CCC(O)(c5ccc(Cl)cc5)CC4)cccn3n2)cc1)N1CCC(c2ccncc2)CC1] | [4-[[8-[4-(4-chlorophenyl)-4-hydroxy-1-piperidyl]-[1,2,4]triazolo[1,5-a]pyridin-2-yl]amino]phenyl]-[4-(4-pyridyl)-1-piperidyl]methanone |
| 1-84 | 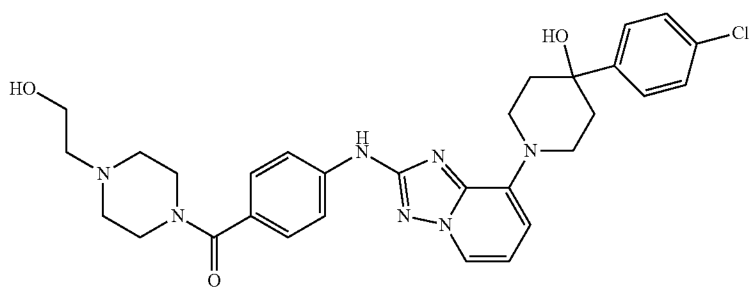 [SMILES: O=C(c1ccc(Nc2nc3c(N4CCC(O)(c5ccc(Cl)cc5)CC4)cccn3n2)cc1)N1CCN(CCO)CC1] | [4-[[8-[4-(4-chlorophenyl)-4-hydroxy-1-piperidyl]-[1,2,4]triazolo[1,5-a]pyridin-2-yl]amino]phenyl]-[4-(2-hydroxyethyl)piperazin-1-yl]methanone |
| 1-85 | 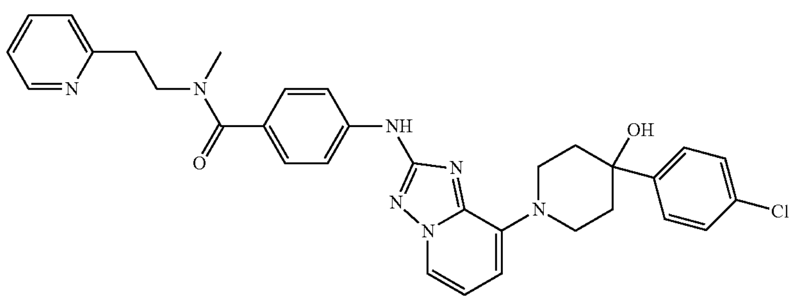 [SMILES: CN(CCc1ccccn1)C(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-methyl-N-[2-(2-pyridyl)ethyl]benzamide |
| 1-86 | 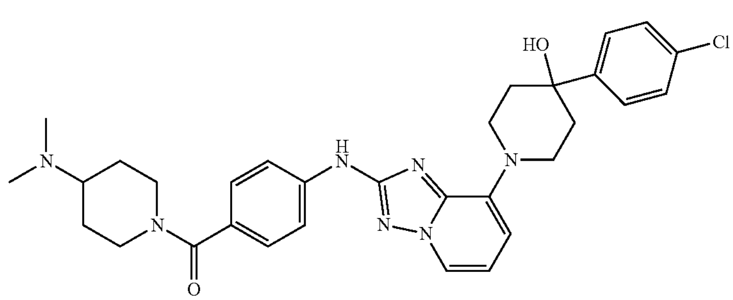 [SMILES: CN(C)C1CCN(C(=O)c2ccc(Nc3nc4c(N5CCC(O)(c6ccc(Cl)cc6)CC5)cccn4n3)cc2)CC1] | [4-[[8-[4-(4-chlorophenyl)-4-hydroxy-1-piperidyl]-[1,2,4]triazolo[1,5-a]pyridin-2-yl]amino]phenyl]-[4-(dimethylamino)-1-piperidyl]methanone |

TABLE A-continued

Exemplary Compounds of the Present Invention

| Ex. | Structure | Name |
|---|---|---|
| 1-87 | 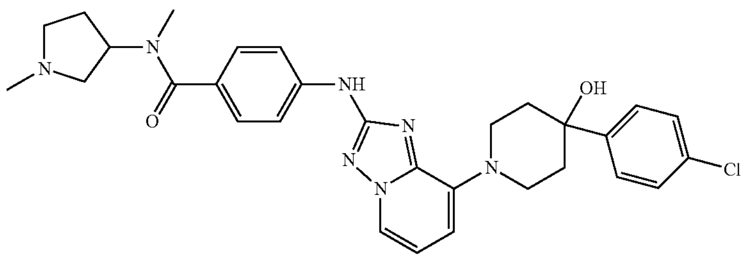 [SMILES: CN1CCC(N(C)C(=O)c2ccc(Nc3nc4c(N5CCC(O)(c6ccc(Cl)cc6)CC5)cccn4n3)cc2)C1] | 4-[[8-[4-(4-chlorophenyl)-4-hydroxy-1-piperidyl]-[1,2,4]triazolo[1,5-a]pyridin-2-yl]amino]-N-methyl-N-(1-methylpyrrolidin-3-yl)benzamide |
| 1-88 | 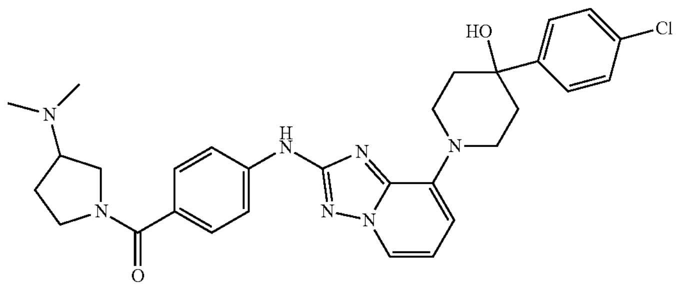 [SMILES: CN(C)C1CCN(C(=O)c2ccc(Nc3nc4c(N5CCC(O)(c6ccc(Cl)cc6)CC5)cccn4n3)cc2)C1] | [4-[[8-[4-(4-chlorophenyl)-4-hydroxy-1-piperidyl]-[1,2,4]triazolo[1,5-a]pyridin-2-yl]amino]phenyl]-[3-(dimethylamino)pyrrolidin-1-yl]methanone |
| 1-89 | 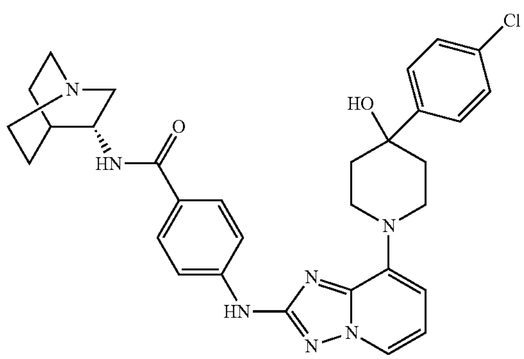 [SMILES: O=C(N[C@H]1CN2CCC1CC2)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[(3R)-quinuclidin-3-yl]benzamide |
| 1-90 | 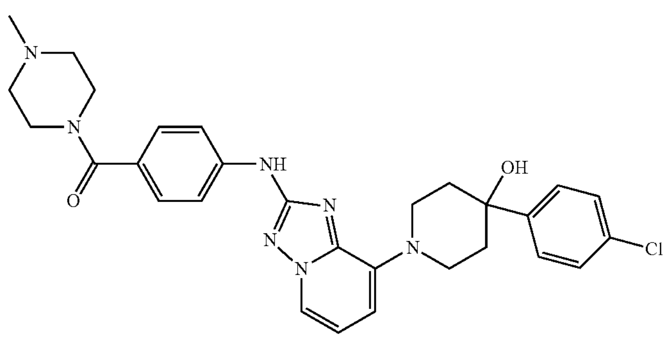 [SMILES: CN1CCN(C(=O)c2ccc(Nc3nc4c(N5CCC(O)(c6ccc(Cl)cc6)CC5)cccn4n3)cc2)CC1] | [4-[[8-[4-(4-chlorophenyl)-4-hydroxy-1-piperidyl]-[1,2,4]triazolo[1,5-a]pyridin-2-yl]amino]phenyl]-(4-methylpiperazin-1-yl)methanone |
| 1-91 | 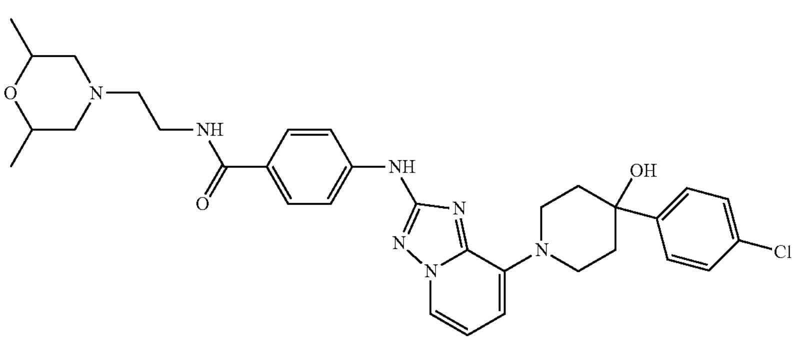 [SMILES: CC1CN(CCNC(=O)c2ccc(Nc3nc4c(N5CCC(O)(c6ccc(Cl)cc6)CC5)cccn4n3)cc2)CC(C)O1] | 4-[[8-[4-(4-chlorophenyl)-4-hydroxy-1-piperidyl]-[1,2,4]triazolo[1,5-a]pyridin-2-yl]amino]-N-[2-(2,6-dimethylmorpholin-4-yl)ethyl]benzamide |

TABLE A-continued

Exemplary Compounds of the Present Invention

| Ex. | Structure | Name |
|---|---|---|
| 1-92 | 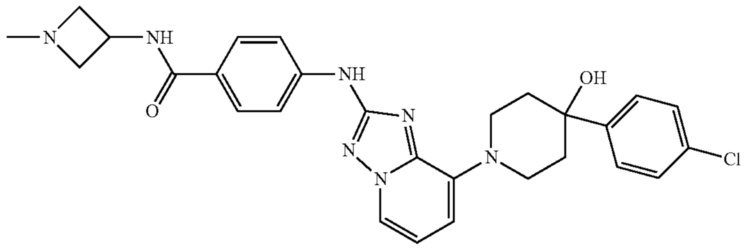 [SMILES: CN1CC(NC(=O)c2ccc(Nc3nc4c(N5CCC(O)(c6ccc(Cl)cc6)CC5)cccn4n3)cc2)C1] | 4-[[8-[4-(4-chlorophenyl)-4-hydroxy-1-piperidyl]-[1,2,4]triazolo[1,5-a]pyridin-2-yl]amino]-N-(1-methylazetidin-3-yl)benzamide |
| 1-93 | 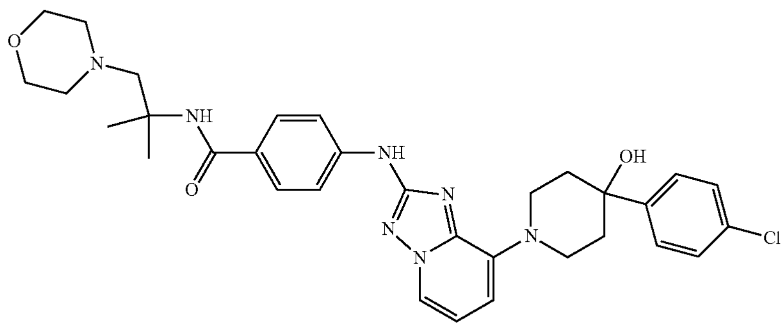 [SMILES: CC(C)(CN1CCOCC1)NC(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(1,1-dimethyl-2-morpholino-ethyl)benzamide |
| 1-94 | 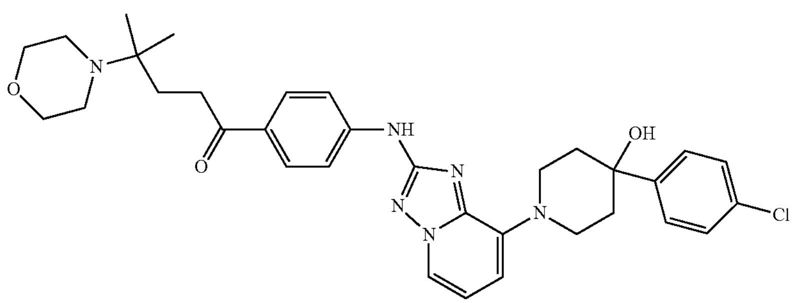 [SMILES: CC(C)(CCC(=O)c1ccc(Nc2nc3c(N4CCC(O)(c5ccc(Cl)cc5)CC4)cccn3n2)cc1)N1CCOCC1] | 4-[[8-[4-(4-chlorophenyl)-4-hydroxy-1-piperidyl]-[1,2,4]triazolo[1,5-a]pyridin-2-yl]amino]-N-(2-methyl-2-morpholino-propyl)benzamide |
| 1-95 | 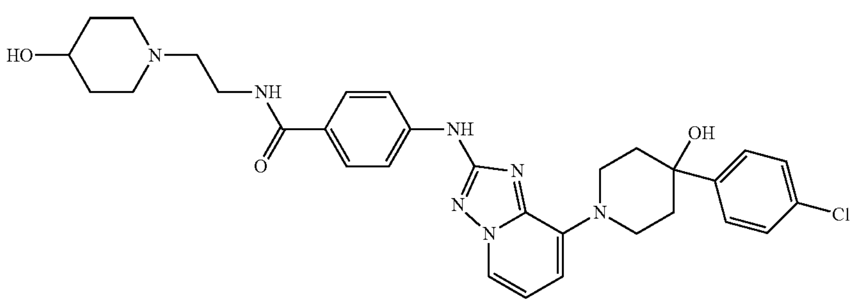 [SMILES: O=C(NCCN1CCC(O)CC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[2-(4-hydroxy-1-piperidyl)ethyl]benzamide |
| 1-96 | 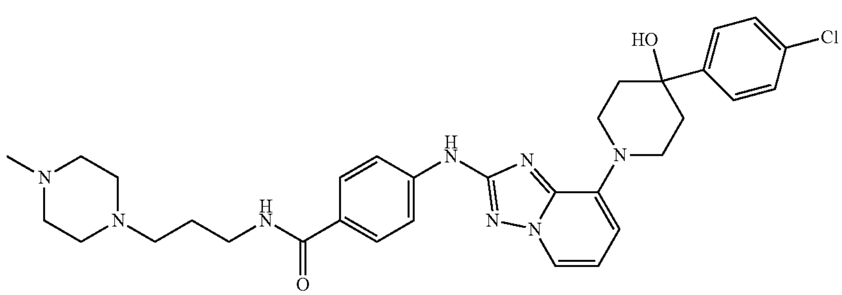 [SMILES: CN1CCN(CCCNC(=O)c2ccc(Nc3nc4c(N5CCC(O)(c6ccc(Cl)cc6)CC5)cccn4n3)cc2)CC1] | 4-[[8-[4-(4-chlorophenyl)-4-hydroxy-1-piperidyl]-[1,2,4]triazolo[1,5-a]pyridin-2-yl]amino]-N-[3-(4-methylpiperazin-1-yl)propyl]benzamide |

TABLE A-continued

Exemplary Compounds of the Present Invention

| Ex. | Structure | Name |
|---|---|---|
| 1-97 | 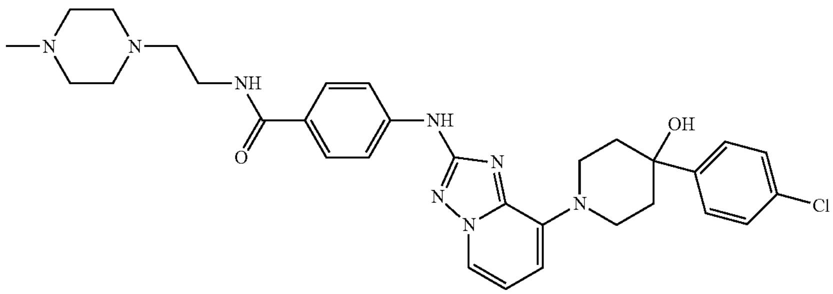 [SMILES: CN1CCN(CCNC(=O)c2ccc(Nc3nc4c(N5CCC(O)(c6ccc(Cl)cc6)CC5)cccn4n3)cc2)CC1] | 4-[[8-[4-(4-chlorophenyl)-4-hydroxy-1-piperidyl]-[1,2,4]triazolo[1,5-a]pyridin-2-yl]amino]-N-[2-(4-methylpiperazin-1-yl)ethyl]benzamide |
| 1-98 | 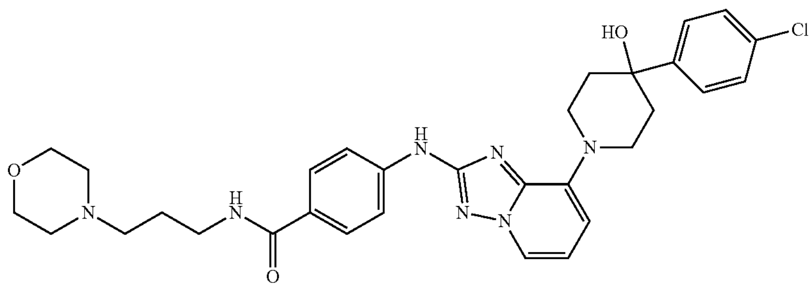 [SMILES: O=C(NCCCN1CCOCC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(3-morpholinopropyl)benzamide |
| 1-99 | 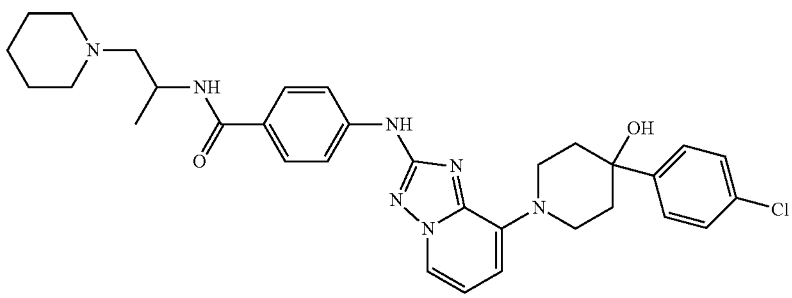 [SMILES: CC(CN1CCCCC1)NC(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[2-(3-methyl-1-piperidyl)ethyl]benzamide |
| 1-100 | 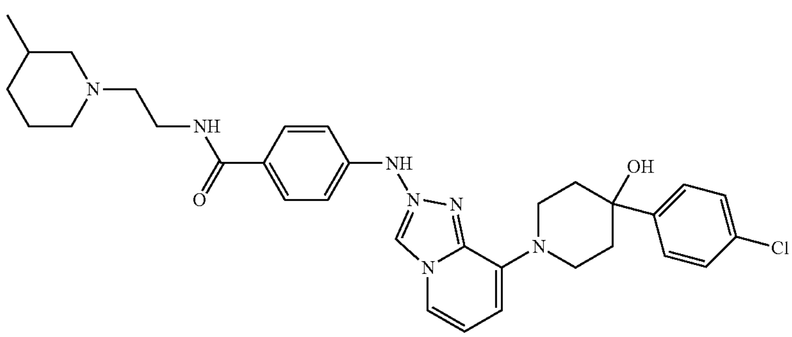 | 4-[[8-[4-(4-chlorophenyl)-4-hydroxy-1-piperidyl]-[1,2,4]triazolo[1,5-a]pyridin-2-yl]amino]-N-[2-(3-methyl-1-piperidyl)ethyl]benzamide |
| 1-101 | 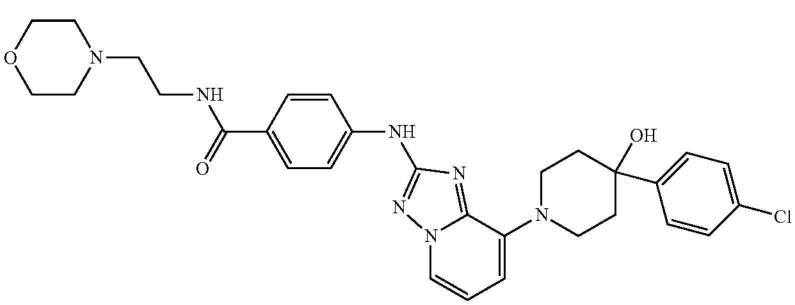 [SMILES: O=C(NCCN1CCOCC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(2-morpholinoethyl)benzamide |

TABLE A-continued

Exemplary Compounds of the Present Invention

| Ex. | Structure | Name |
|---|---|---|
| 1-102 | 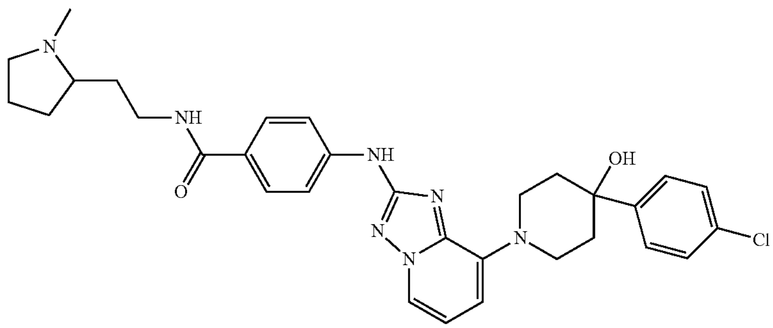 [SMILES: CN1CCCC1CCNC(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[2-(1-methylpyrrolidin-2-yl)ethyl]benzamide |
| 1-103 | 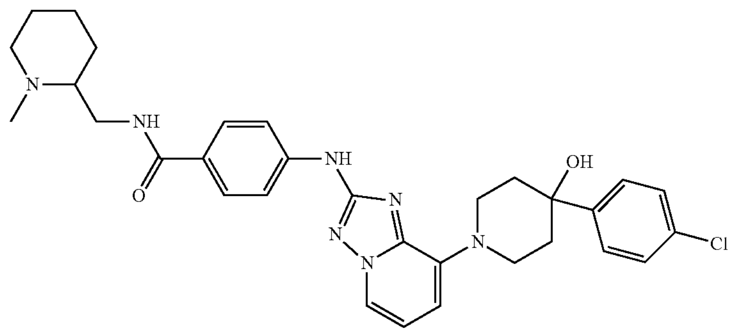 [SMILES: CN1CCCCC1CNC(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[(1-methyl-2-piperidyl)methyl]benzamide |
| 1-104 | 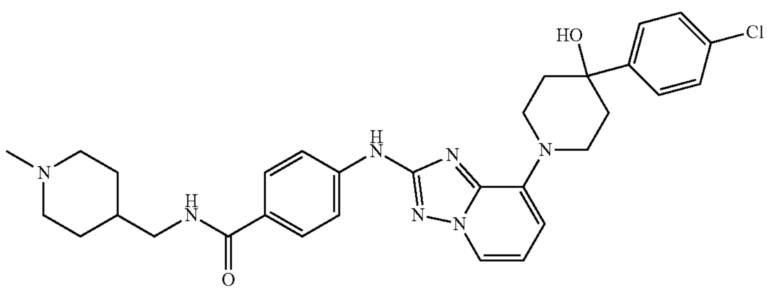 [SMILES: CN1CCC(CNC(=O)c2ccc(Nc3nc4c(N5CCC(O)(c6ccc(Cl)cc6)CC5)cccn4n3)cc2)CC1] | 4-[[8-[4-(4-chlorophenyl)-4-hydroxy-1-piperidyl]-[1,2,4]triazolo[1,5-a]pyridin-2-yl]amino]-N-[(1-methyl-4-piperidyl)methyl]benzamide |
| 1-105 | 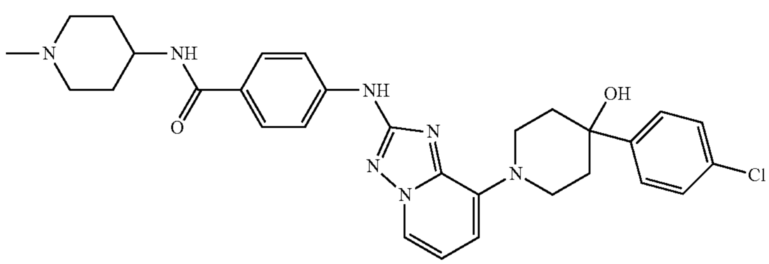 [SMILES: CN1CCC(NC(=O)c2ccc(Nc3nc4c(N5CCC(O)(c6ccc(Cl)cc6)CC5)cccn4n3)cc2)CC1] | 4-[[8-[4-(4-chlorophenyl)-4-hydroxy-1-piperidyl]-[1,2,4]triazolo[1,5-a]pyridin-2-yl]amino]-N-(1-methyl-4-piperidyl)benzamide |
| 1-106 | 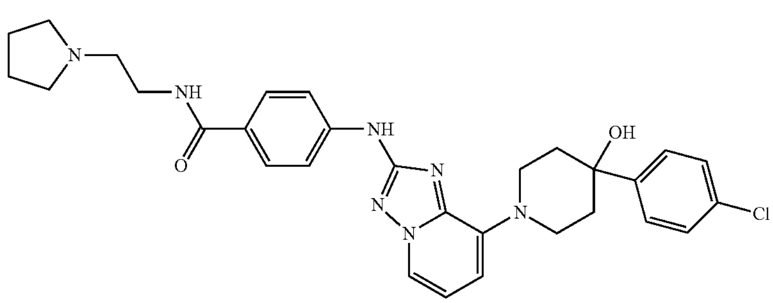 [SMILES: O=C(NCCN1CCCC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(2-pyrrolidin-1-ylethyl)benzamide |

TABLE A-continued

Exemplary Compounds of the Present Invention

| Ex. | Structure | Name |
|---|---|---|
| 1-107 | 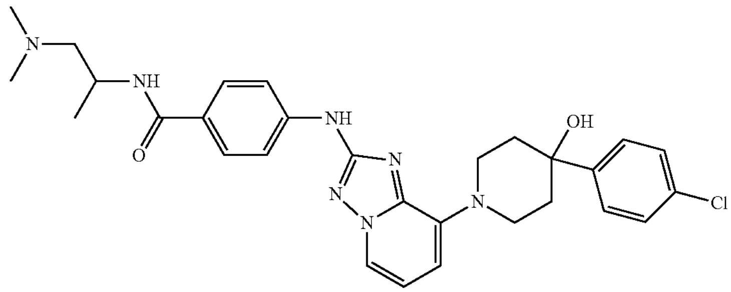 [SMILES: CC(CN(C)C)NC(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[2-(dimethylamino)-1-methyl-ethyl]benzamide |
| 1-108 | 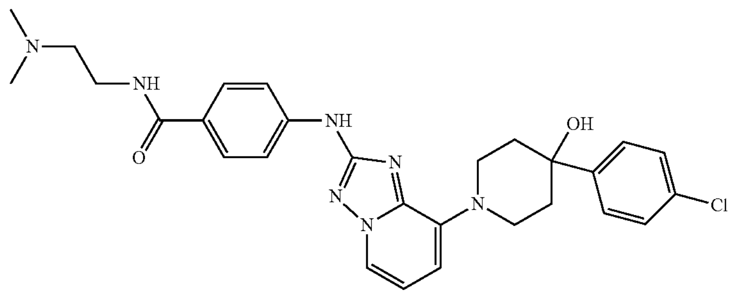 [SMILES: CN(C)CCNC(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[2-(dimethylamino)ethyl]benzamide |
| 1-109 | 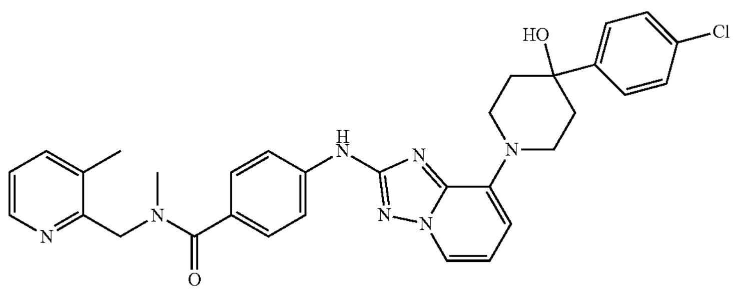 [SMILES: Cc1cccnc1CN(C)C(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-methyl-N-[(3-methyl-2-pyridyl)methyl]benzamide |
| 1-110 | 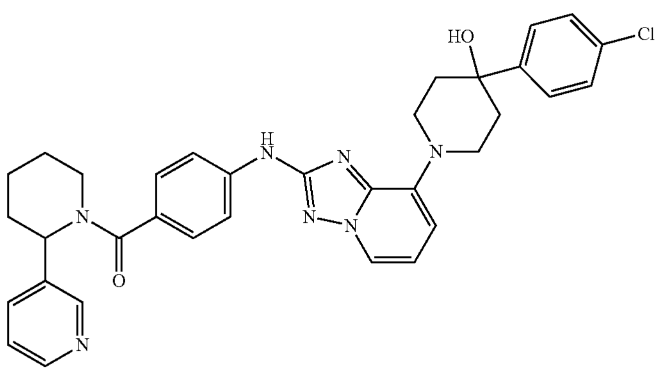 [SMILES: O=C(c1ccc(Nc2nc3c(N4CCC(O)(c5ccc(Cl)cc5)CC4)cccn3n2)cc1)N1CCCCC1c1cccnc1] | [4-[[8-[4-(4-chlorophenyl)-4-hydroxy-1-piperidyl]-[1,2,4]triazolo[1,5-a]pyridin-2-yl]amino]phenyl]-[2-(3-pyridyl)-1-piperidyl]methanone |
| 1-111 | 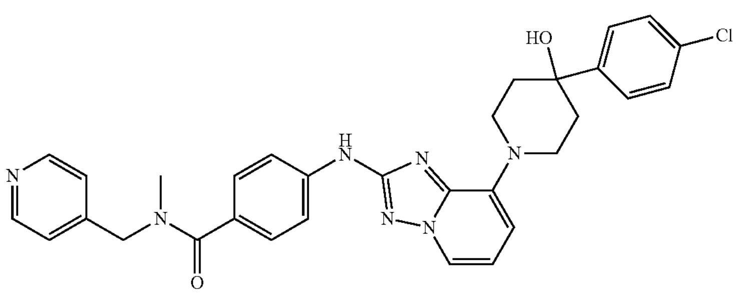 [SMILES: CN(Cc1ccncc1)C(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-methyl-N-(4-pyridylmethyl)benzamide |

TABLE A-continued

Exemplary Compounds of the Present Invention

| Ex. | Structure | Name |
|---|---|---|
| 1-112 | 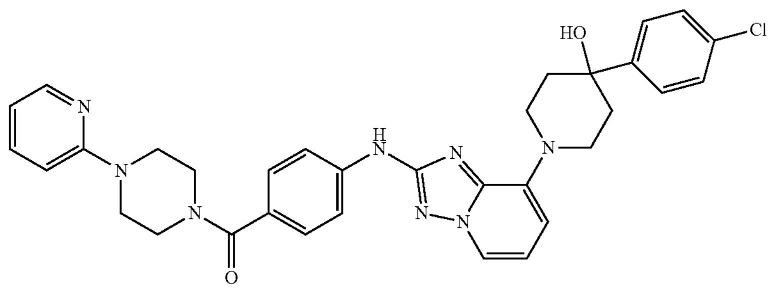 [SMILES: O=C(c1ccc(Nc2nc3c(N4CCC(O)(c5ccc(Cl)cc5)CC4)cccn3n2)cc1)N1CCN(c2ccccn2)CC1] | [4-[[8-[4-(4-chlorophenyl)-4-hydroxy-1-piperidyl]-[1,2,4]triazolo[1,5-a]pyridin-2-yl]amino]phenyl]-[4-(2-pyridyl)piperazin-1-yl]methanone |
| 1-113 | 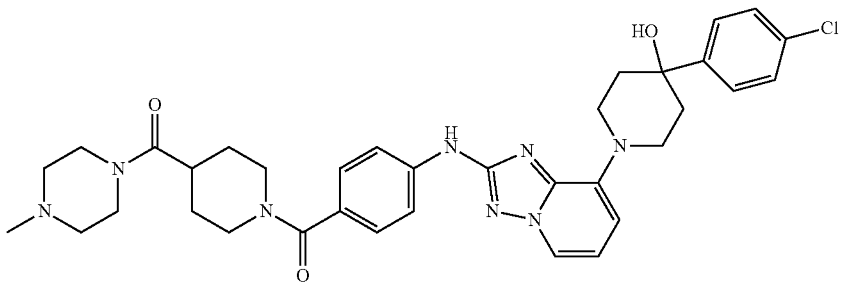 [SMILES: CN1CCN(C(=O)C2CCN(C(=O)c3ccc(Nc4nc5c(N6CCC(O)(c7ccc(Cl)cc7)CC6)cccn5n4)cc3)CC2)CC1] | [4-[[8-[4-(4-chlorophenyl)-4-hydroxy-1-piperidyl]-[1,2,4]triazolo[1,5-a]pyridin-2-yl]amino]phenyl]-[4-(4-methylpiperazine-1-carbonyl)-1-piperidyl]methanone |
| 1-114 | 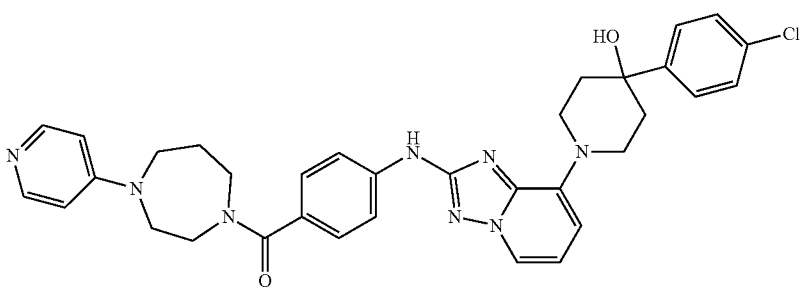 [SMILES: O=C(c1ccc(Nc2nc3c(N4CCC(O)(c5ccc(Cl)cc5)CC4)cccn3n2)cc1)N1CCCN(c2ccncc2)CC1] | [4-[[8-[4-(4-chlorophenyl)-4-hydroxy-1-piperidyl]-[1,2,4]triazolo[1,5-a]pyridin-2-yl]amino]phenyl]-[4-(4-pyridyl)-1,4-diazepan-1-yl]methanone |
| 1-115 | 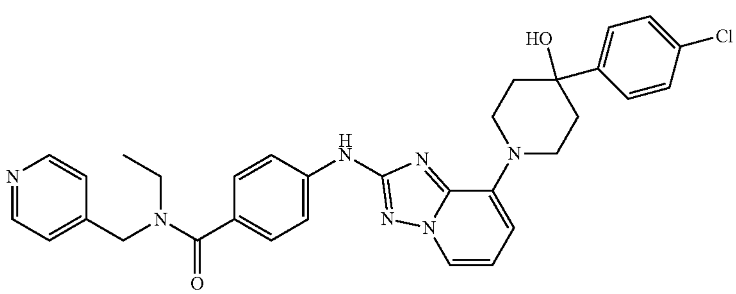 [SMILES: CCN(Cc1ccncc1)C(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-ethyl-N-(4-pyridylmethyl)benzamide |
| 1-116 | 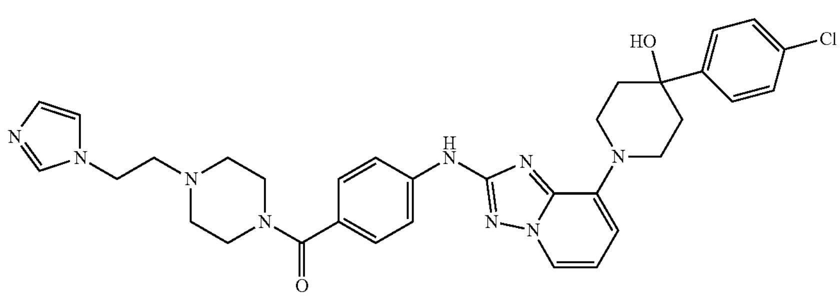 [SMILES: O=C(c1ccc(Nc2nc3c(N4CCC(O)(c5ccc(Cl)cc5)CC4)cccn3n2)cc1)N1CCN(CCn2ccnc2)CC1] | [4-[[8-[4-(4-chlorophenyl)-4-hydroxy-1-piperidyl]-[1,2,4]triazolo[1,5-a]pyridin-2-yl]amino]phenyl]-[4-(2-imidazol-1-ylethyl)piperazin-1-yl]methanone |

TABLE A-continued

Exemplary Compounds of the Present Invention

| Ex. | Structure | Name |
|---|---|---|
| 1-117 | 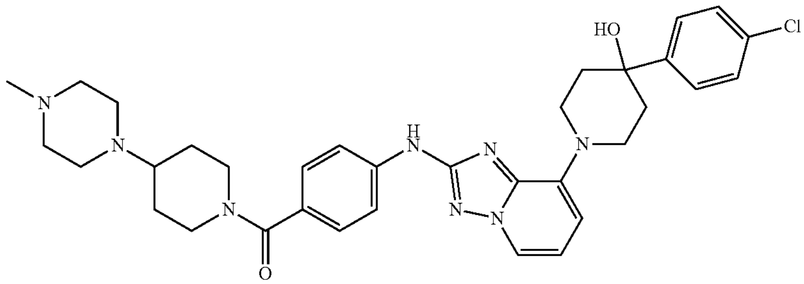 [SMILES: CN1CCN(C2CCN(C(=O)c3ccc(Nc4nc5c(N6CCC(O)(c7ccc(Cl)cc7)CC6)cccn5n4)cc3)CC2)CC1] | [4-[[8-[4-(4-chlorophenyl)-4-hydroxy-1-piperidyl]-[1,2,4]triazolo[1,5-a]pyridin-2-yl]amino]phenyl]-[4-(4-methylpiperazin-1-yl)-1-piperidyl]methanone |
| 1-118 | 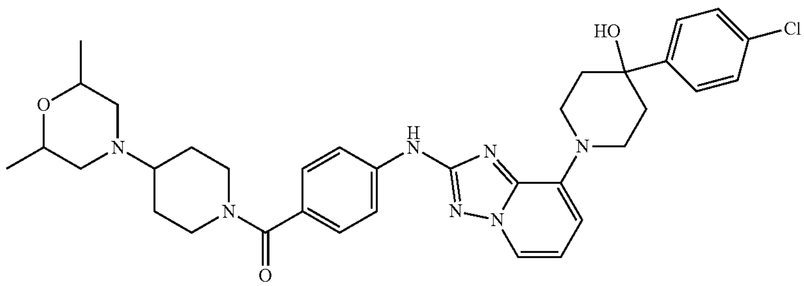 [SMILES: CC1CN(C2CCN(C(=O)c3ccc(Nc4nc5c(N6CCC(O)(c7ccc(Cl)cc7)CC6)cccn5n4)cc3)CC2)CC(C)O1] | [4-[[8-[4-(4-chlorophenyl)-4-hydroxy-1-piperidyl]-[1,2,4]triazolo[1,5-a]pyridin-2-yl]amino]phenyl]-[4-(2,6-dimethylmorpholin-4-yl)-1-piperidyl]methanone |
| 1-119 | 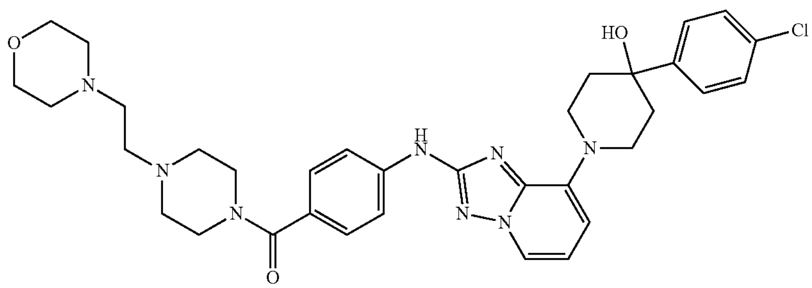 [SMILES: O=C(c1ccc(Nc2nc3c(N4CCC(O)(c5ccc(Cl)cc5)CC4)cccn3n2)cc1)N1CCN(CCN2CCOCC2)CC1] | [4-[[8-[4-(4-chlorophenyl)-4-hydroxy-1-piperidyl]-[1,2,4]triazolo[1,5-a]pyridin-2-yl]amino]phenyl]-[4-(2-morpholinoethyl)piperazin-1-yl]methanone |
| 1-120 | 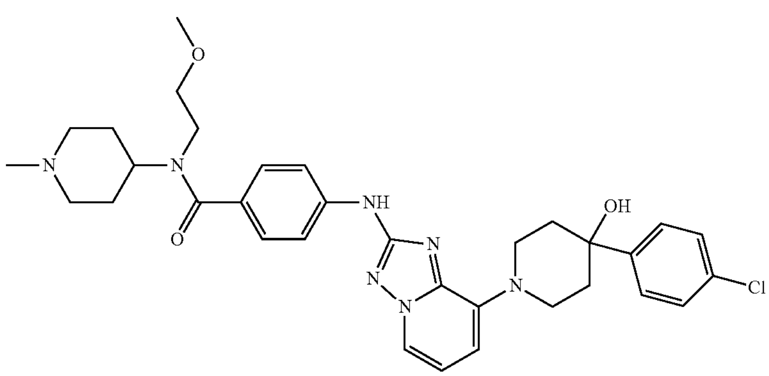 [SMILES: COCCN(C(=O)c1ccc(Nc2nc3c(N4CCC(O)(c5ccc(Cl)cc5)CC4)cccn3n2)cc1)C1CCN(C)CC1] | 4-[[8-[4-(4-chlorophenyl)-4-hydroxy-1-piperidyl]-[1,2,4]triazolo[1,5-a]pyridin-2-yl]amino]-N-(2-methoxyethyl)-N-(1-methyl-4-piperidyl)benzamide |
| 1-121 | 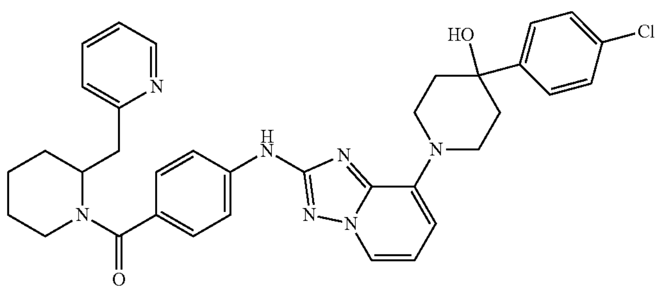 [SMILES: O=C(c1ccc(Nc2nc3c(N4CCC(O)(c5ccc(Cl)cc5)CC4)cccn3n2)cc1)N1CCCCC1Cc1ccccn1] | [4-[[8-[4-(4-chlorophenyl)-4-hydroxy-1-piperidyl]-[1,2,4]triazolo[1,5-a]pyridin-2-yl]amino]phenyl]-[2-(2-pyridylmethyl)-1-piperidyl]methanone |

TABLE A-continued

Exemplary Compounds of the Present Invention

| Ex. | Structure | Name |
|---|---|---|
| 1-122 | 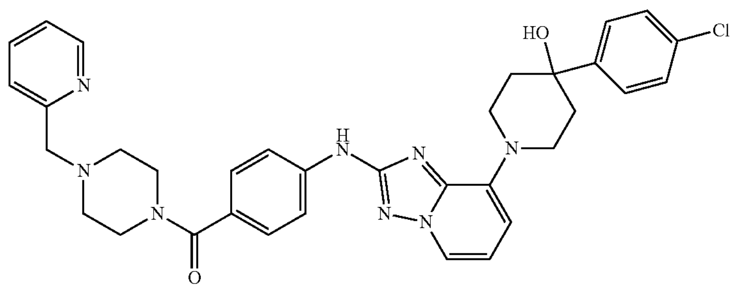 [SMILES: O=C(c1ccc(Nc2nc3c(N4CCC(O)(c5ccc(Cl)cc5)CC4)cccn3n2)cc1)N1CCN(Cc2ccccn2)CC1] | [4-[[8-[4-(4-chlorophenyl)-4-hydroxy-1-piperidyl]-[1,2,4]triazolo[1,5-a]pyridin-2-yl]amino]phenyl]-[4-(2-pyridylmethyl)piperazin-1-yl]methanone |
| 1-123 | 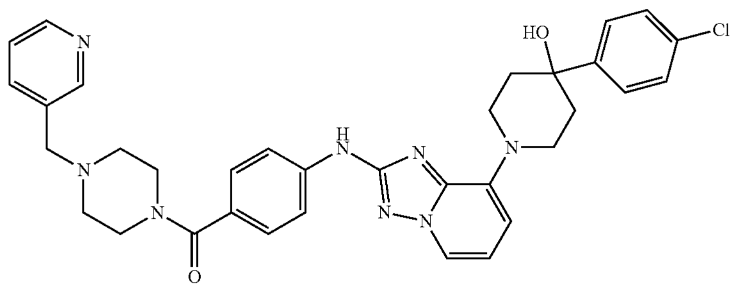 | [4-[[8-[4-(4-chlorophenyl)-4-hydroxy-1-piperidyl]-[1,2,4]triazolo[1,5-a]pyridin-2-yl]amino]phenyl]-[4-(3-pyridylmethyl)piperazin-1-yl]methanone |
| 1-124 | 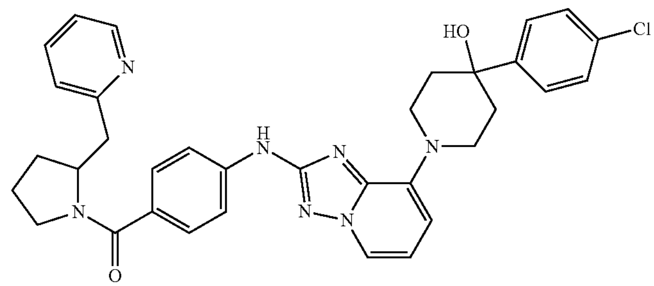 [SMILES: O=C(c1ccc(Nc2nc3c(N4CCC(O)(c5ccc(Cl)cc5)CC4)cccn3n2)cc1)N1CCCC1Cc1ccccn1] | [4-[[8-[4-(4-chlorophenyl)-4-hydroxy-1-piperidyl]-[1,2,4]triazolo[1,5-a]pyridin-2-yl]amino]phenyl]-[2-(2-pyridylmethyl)pyrrolidin-1-yl]methanone |
| 1-125 | 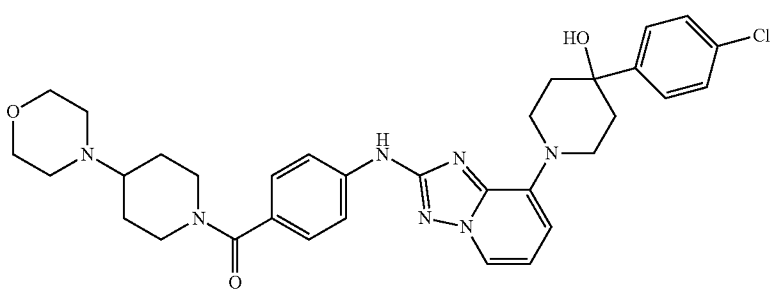 [SMILES: O=C(c1ccc(Nc2nc3c(N4CCC(O)(c5ccc(Cl)cc5)CC4)cccn3n2)cc1)N1CCC(N2CCOCC2)CC1] | [4-[[8-[4-(4-chlorophenyl)-4-hydroxy-1-piperidyl]-[1,2,4]triazolo[1,5-a]pyridin-2-yl]amino]phenyl]-(4-morpholino-1-piperidyl)methanone |
| 1-126 | 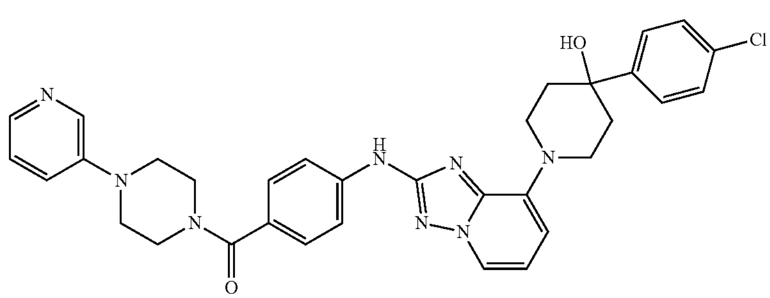 [SMILES: O=C(c1ccc(Nc2nc3c(N4CCC(O)(c5ccc(Cl)cc5)CC4)cccn3n2)cc1)N1CCN(c2cccnc2)CC1] | [4-[[8-[4-(4-chlorophenyl)-4-hydroxy-1-piperidyl]-[1,2,4]triazolo[1,5-a]pyridin-2-yl]amino]phenyl]-[4-(3-pyridyl)piperazin-1-yl]methanone |

US 9,873,709 B2

TABLE A-continued

Exemplary Compounds of the Present Invention

| Ex. | Structure | Name |
|---|---|---|
| 1-127 | 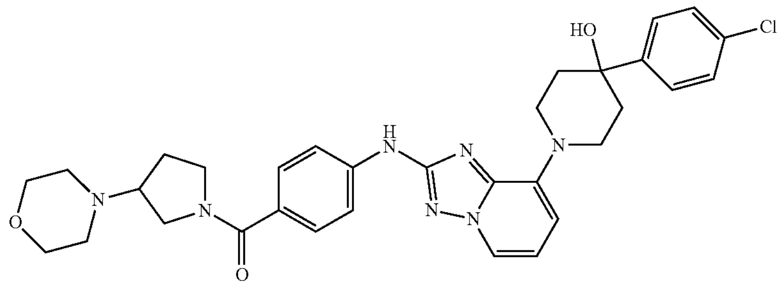 [SMILES: O=C(c1ccc(Nc2nc3c(N4CCC(O)(c5ccc(Cl)cc5)CC4)cccn3n2)cc1)N1CCC(N2CCOCC2)C1] | [4-[[8-[4-(4-chlorophenyl)-4-hydroxy-1-piperidyl]-[1,2,4]triazolo[1,5-a]pyridin-2-yl]amino]phenyl]-(3-morpholinopyrrolidin-1-yl)methanone |
| 1-128 | 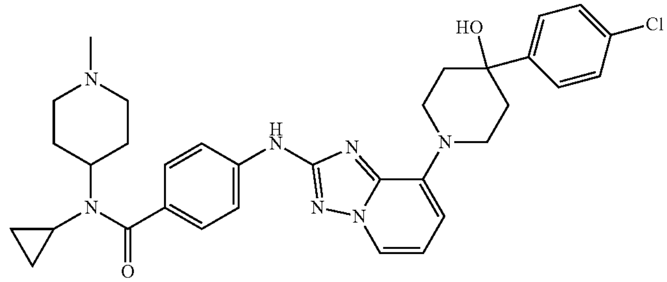 [SMILES: CN1CCC(N(C(=O)c2ccc(Nc3nc4c(N5CCC(O)(c6ccc(Cl)cc6)CC5)cccn4n3)cc2)C2CC2)CC1] | 4-[[8-[4-(4-chlorophenyl)-4-hydroxy-1-piperidyl]-[1,2,4]triazolo[1,5-a]pyridin-2-yl]amino]-N-cyclopropyl-N-(1-methyl-4-piperidyl)benzamide |
| 1-129 | 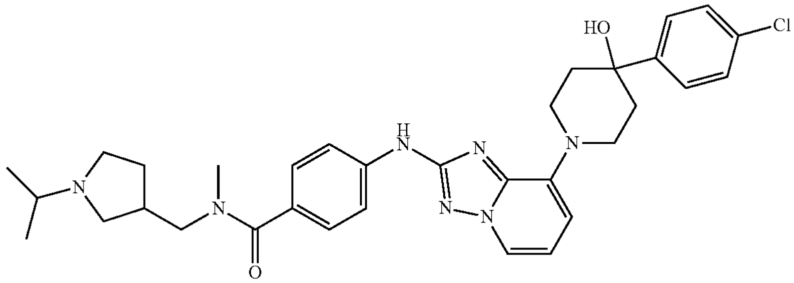 [SMILES: CC(C)N1CCC(CN(C)C(=O)c2ccc(Nc3nc4c(N5CCC(O)(c6ccc(Cl)cc6)CC5)cccn4n3)cc2)C1] | 4-[[8-[4-(4-chlorophenyl)-4-hydroxy-1-piperidyl]-[1,2,4]triazolo[1,5-a]pyridin-2-yl]amino]-N-[(1-isopropylpyrrolidin-3-yl)methyl]-N-methyl-benzamide |
| 1-130 | 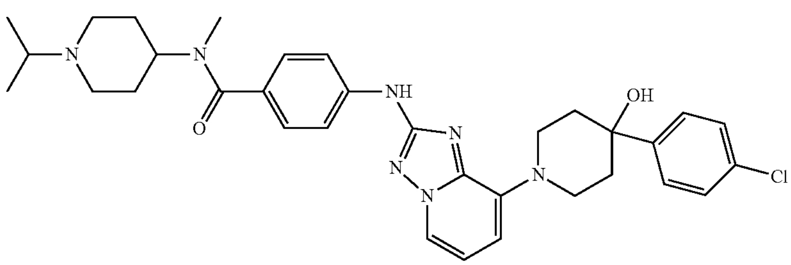 [SMILES: CC(C)N1CCC(N(C)C(=O)c2ccc(Nc3nc4c(N5CCC(O)(c6ccc(Cl)cc6)CC5)cccn4n3)cc2)CC1] | 4-[[8-[4-(4-chlorophenyl)-4-hydroxy-1-piperidyl]-[1,2,4]triazolo[1,5-a]pyridin-2-yl]amino]-N-(1-isopropyl-4-piperidyl)-N-methyl-benzamide |
| 1-131 | 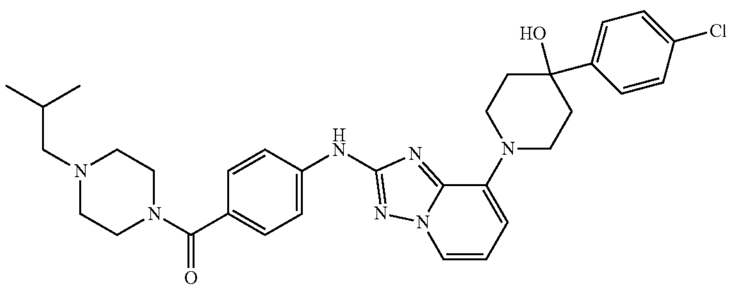 [SMILES: CC(C)CN1CCN(C(=O)c2ccc(Nc3nc4c(N5CCC(O)(c6ccc(Cl)cc6)CC5)cccn4n3)cc2)CC1] | [4-[[8-[4-(4-chlorophenyl)-4-hydroxy-1-piperidyl]-[1,2,4]triazolo[1,5-a]pyridin-2-yl]amino]phenyl]-(4-isobutylpiperazin-1-yl)methanone |

TABLE A-continued

Exemplary Compounds of the Present Invention

| Ex. | Structure | Name |
|---|---|---|
| 1-132 | 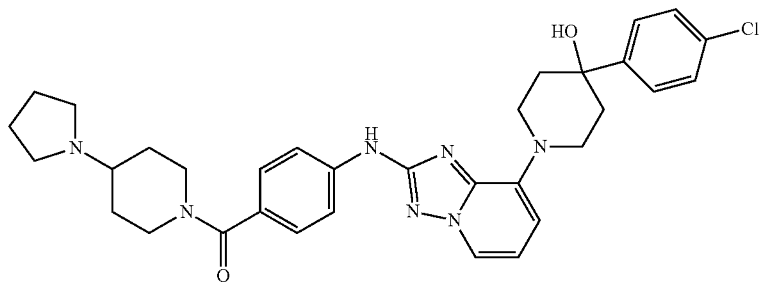 [SMILES: O=C(c1ccc(Nc2nc3c(N4CCC(O)(c5ccc(Cl)cc5)CC4)cccn3n2)cc1)N1CCC(N2CCCC2)CC1] | [4-[[8-[4-(4-chlorophenyl)-4-hydroxy-1-piperidyl]-[1,2,4]triazolo[1,5-a]pyridin-2-yl]amino]phenyl]-(4-pyrrolidin-1-yl-1-piperidyl)methanone |
| 1-133 | 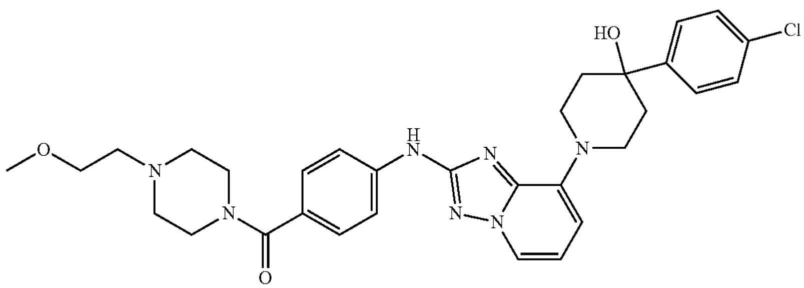 [SMILES: COCCN1CCN(C(=O)c2ccc(Nc3nc4c(N5CCC(O)(c6ccc(Cl)cc6)CC5)cccn4n3)cc2)CC1] | [4-[[8-[4-(4-chlorophenyl)-4-hydroxy-1-piperidyl]-[1,2,4]triazolo[1,5-a]pyridin-2-yl]amino]phenyl]-[4-(2-methoxyethyl)piperazin-1-yl]methanone |
| 1-134 | 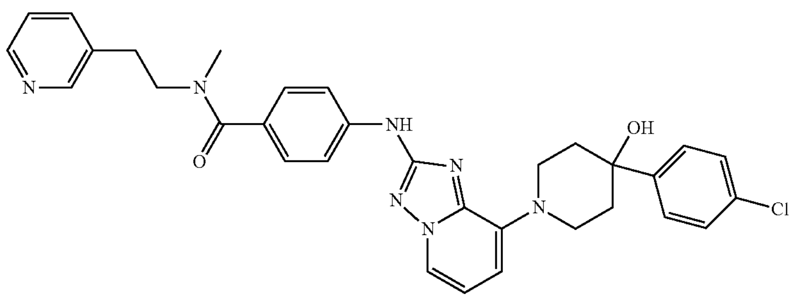 [SMILES: CN(CCc1cccnc1)C(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-methyl-N-[2-(3-pyridyl)ethyl]benzamide |
| 1-135 | 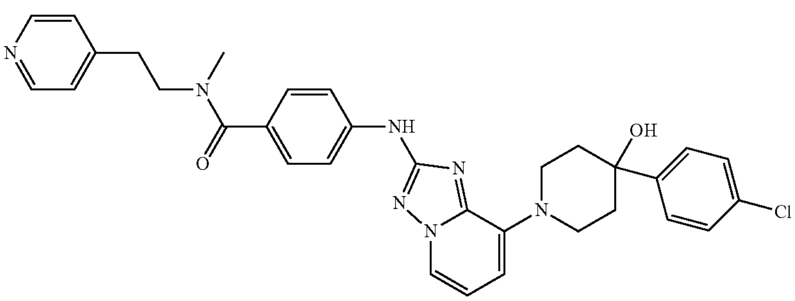 [SMILES: CN(CCc1ccncc1)C(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-methyl-N-[2-(4-pyridyl)ethyl]benzamide |
| 1-136 | 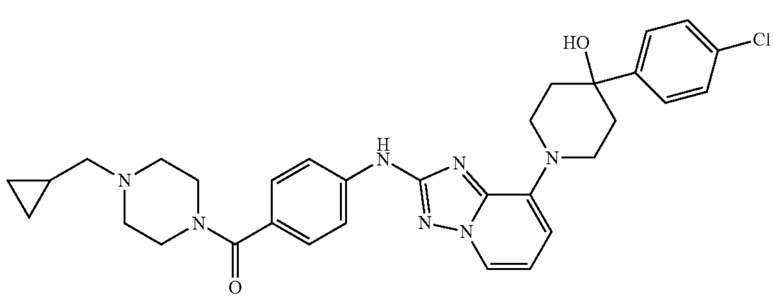 [SMILES: O=C(c1ccc(Nc2nc3c(N4CCC(O)(c5ccc(Cl)cc5)CC4)cccn3n2)cc1)N1CCN(CC2CC2)CC1] | [4-[[8-[4-(4-chlorophenyl)-4-hydroxy-1-piperidyl]-[1,2,4]triazolo[1,5-a]pyridin-2-yl]amino]phenyl]-[4-(cyclopropylmethyl)piperazin-1-yl]methanone |

TABLE A-continued

Exemplary Compounds of the Present Invention

| Ex. | Structure | Name |
|---|---|---|
| 1-137 | 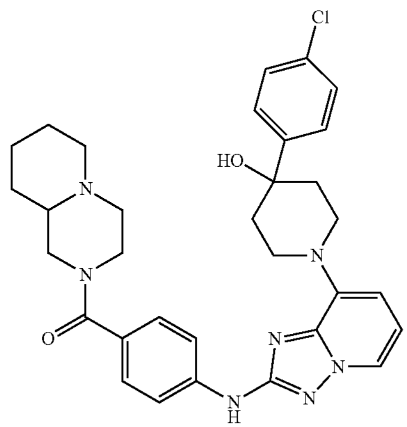 [SMILES: O=C(c1ccc(Nc2nc3c(N4CCC(O)(c5ccc(Cl)cc5)CC4)cccn3n2)cc1)N1CCN2CCCCC2C1] | 1,3,4,6,7,8,9,9a-octahydropyrido[1,2-a]pyrazin-2-yl-[4-[[8-[4-(4-chlorophenyl)-4-hydroxy-1-piperidyl]-[1,2,4]triazolo[1,5-a]pyridin-2-yl]amino]phenyl]methanone |
| 1-138 | 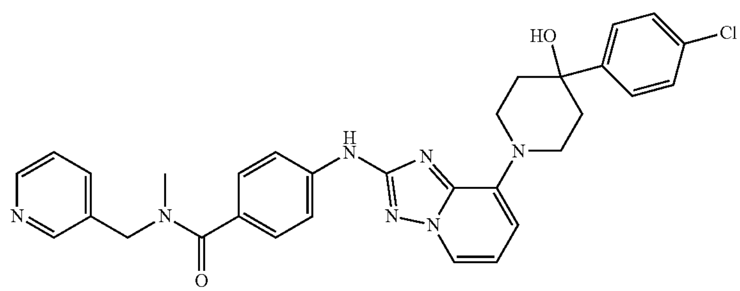 [SMILES: CN(Cc1cccnc1)C(=O)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-methyl-N-(3-pyridylmethyl)benzamide |
| 1-139 | 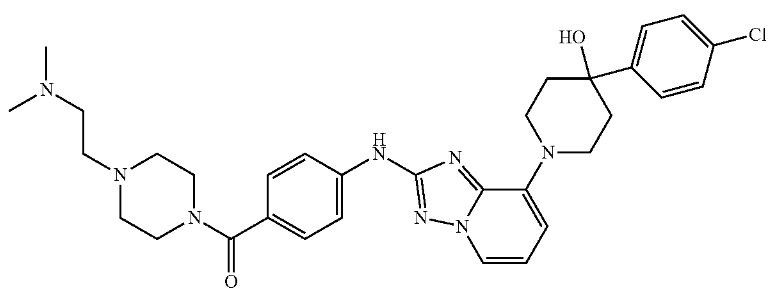 [SMILES: CN(C)CCN1CCN(C(=O)c2ccc(Nc3nc4c(N5CCC(O)(c6ccc(Cl)cc6)CC5)cccn4n3)cc2)CC1] | [4-[[8-[4-(4-chlorophenyl)-4-hydroxy-1-piperidyl]-[1,2,4]triazolo[1,5-a]pyridin-2-yl]amino]phenyl]-[4-[2-(dimethylamino)ethyl]piperazin-1-yl]methanone |
| 1-140 | 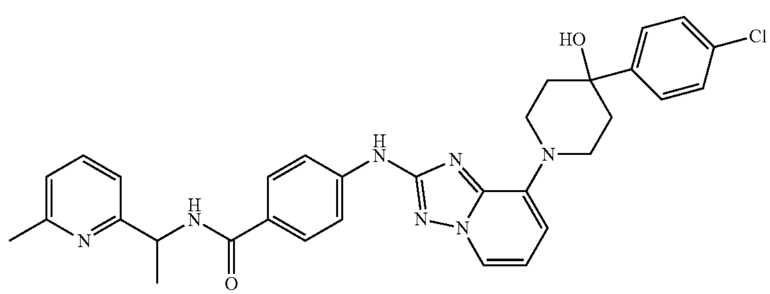 [SMILES: Cc1cccc(C(C)NC(=O)c2ccc(Nc3nc4c(N5CCC(O)(c6ccc(Cl)cc6)CC5)cccn4n3)cc2)n1] | 4-[[8-[4-(4-chlorophenyl)-4-hydroxy-1-piperidyl]-[1,2,4]triazolo[1,5-a]pyridin-2-yl]amino]-N-[1-(6-methyl-2-pyridyl)ethyl]benzamide |

TABLE A-continued

Exemplary Compounds of the Present Invention

| Ex. | Structure | Name |
|---|---|---|
| 1-141 | 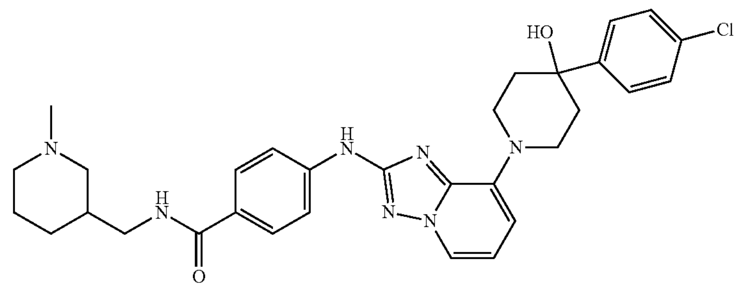 [SMILES: CN1CCCC(CNC(=O)c2ccc(Nc3nc4c(N5CCC(O)(c6ccc(Cl)cc6)CC5)cccn4n3)cc2)C1] | 4-[[8-[4-(4-chlorophenyl)-4-hydroxy-1-piperidyl]-[1,2,4]triazolo[1,5-a]pyridin-2-yl]amino]-N-[(1-methyl-3-piperidyl)methyl]benzamide |
| 1-142 | 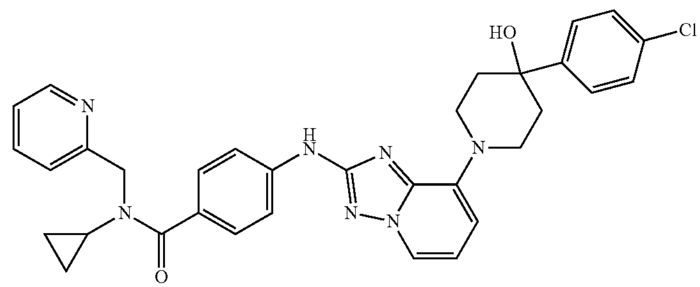 [SMILES: O=C(c1ccc(Nc2nc3c(N4CCC(O)(c5ccc(Cl)cc5)CC4)cccn3n2)cc1)N(Cc1ccccn1)C1CC1] | 4-[[8-[4-(4-chlorophenyl)-4-hydroxy-1-piperidyl]-[1,2,4]triazolo[1,5-a]pyridin-2-yl]amino]-N-cyclopropyl-N-(2-pyridylmethyl)benzamide |
| 1-143 | 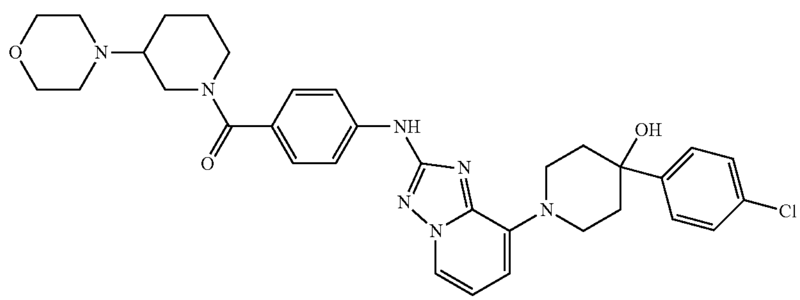 [SMILES: O=C(c1ccc(Nc2nc3c(N4CCC(O)(c5ccc(Cl)cc5)CC4)cccn3n2)cc1)N1CCCC(N2CCOCC2)C1] | [4-[[8-[4-(4-chlorophenyl)-4-hydroxy-1-piperidyl]-[1,2,4]triazolo[1,5-a]pyridin-2-yl]amino]phenyl]-(3-morpholino-1-piperidyl)methanone |
| 1-144 | 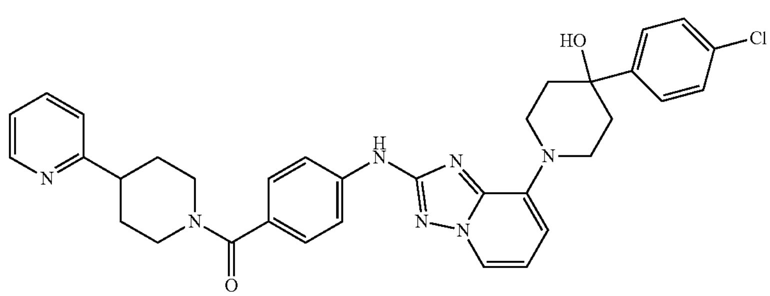 [SMILES: O=C(c1ccc(Nc2nc3c(N4CCC(O)(c5ccc(Cl)cc5)CC4)cccn3n2)cc1)N1CCC(c2ccccn2)CC1] | [4-[[8-[4-(4-chlorophenyl)-4-hydroxy-1-piperidyl]-[1,2,4]triazolo[1,5-a]pyridin-2-yl]amino]phenyl]-[4-(2-pyridyl)-1-piperidyl]methanone |
| 1-145 | 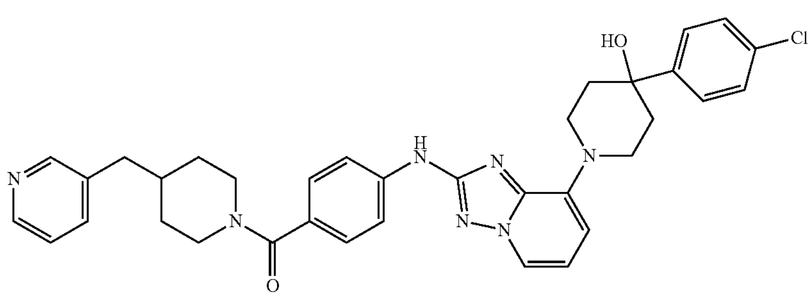 [SMILES: O=C(c1ccc(Nc2nc3c(N4CCC(O)(c5ccc(Cl)cc5)CC4)cccn3n2)cc1)N1CCC(Cc2cccnc2)CC1] | [4-[[8-[4-(4-chlorophenyl)-4-hydroxy-1-piperidyl]-[1,2,4]triazolo[1,5-a]pyridin-2-yl]amino]phenyl]-[4-(3-pyridylmethyl)-1-piperidyl]methanone |

TABLE A-continued

Exemplary Compounds of the Present Invention

| Ex. | Structure | Name |
|---|---|---|
| 1-146 | 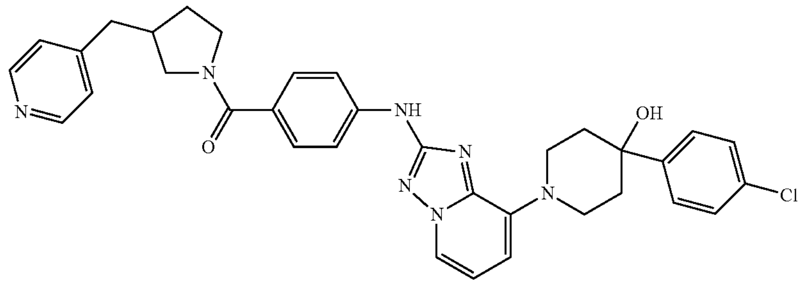 [SMILES: O=C(c1ccc(Nc2nc3c(N4CCC(O)(c5ccc(Cl)cc5)CC4)cccn3n2)cc1)N1CCC(Cc2ccncc2)C1] | [4-[[8-[4-(4-chlorophenyl)-4-hydroxy-1-piperidyl]-[1,2,4]triazolo[1,5-a]pyridin-2-yl]amino]phenyl]-[3-(4-pyridylmethyl)pyrrolidin-1-yl]methanone |
| 1-147 | 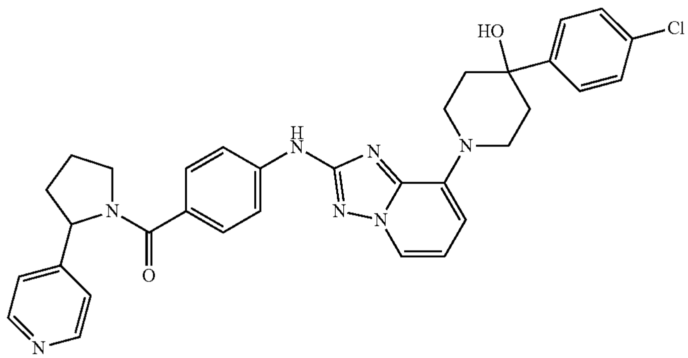 [SMILES: O=C(c1ccc(Nc2nc3c(N4CCC(O)(c5ccc(Cl)cc5)CC4)cccn3n2)cc1)N1CCCC1c1ccncc1] | [4-[[8-[4-(4-chlorophenyl)-4-hydroxy-1-piperidyl]-[1,2,4]triazolo[1,5-a]pyridin-2-yl]amino]phenyl]-[2-(4-pyridyl)pyrrolidin-1-yl]methanone |
| 1-148 | 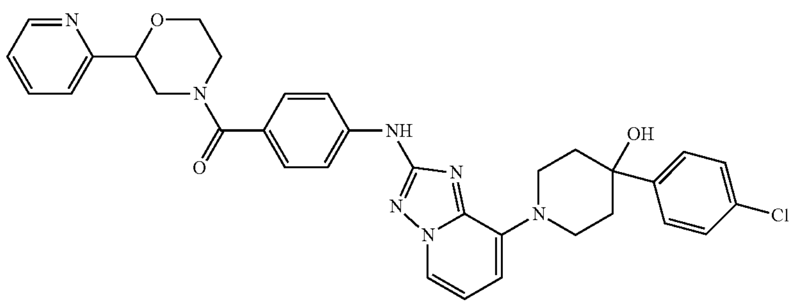 [SMILES: O=C(c1ccc(Nc2nc3c(N4CCC(O)(c5ccc(Cl)cc5)CC4)cccn3n2)cc1)N1CCOC(c2ccccn2)C1] | [4-[[8-[4-(4-chlorophenyl)-4-hydroxy-1-piperidyl]-[1,2,4]triazolo[1,5-a]pyridin-2-yl]amino]phenyl]-[2-(2-pyridyl)morpholin-4-yl]methanone |
| 1-149 | 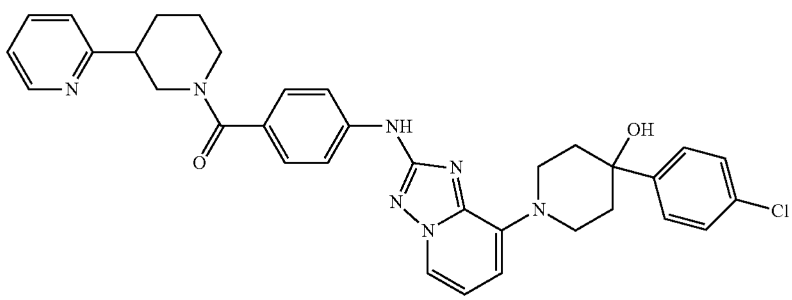 [SMILES: O=C(c1ccc(Nc2nc3c(N4CCC(O)(c5ccc(Cl)cc5)CC4)cccn3n2)cc1)N1CCCC(c2ccccn2)C1] | [4-[[8-[4-(4-chlorophenyl)-4-hydroxy-1-piperidyl]-[1,2,4]triazolo[1,5-a]pyridin-2-yl]amino]phenyl]-[3-(2-pyridyl)-1-piperidyl]methanone |
| 1-150 | 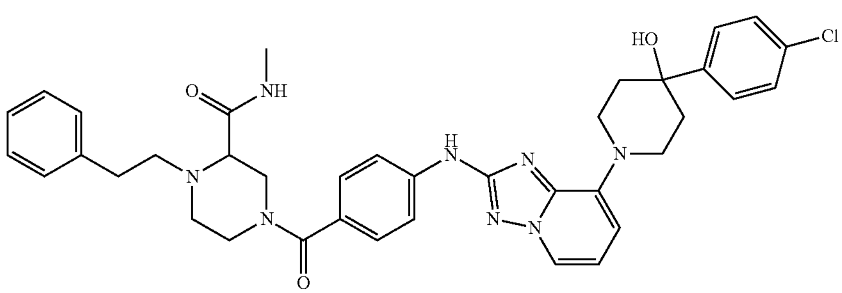 [SMILES: CNC(=O)C1CN(C(=O)c2ccc(Nc3nc4c(N5CCC(O)(c6ccc(Cl)cc6)CC5)cccn4n3)cc2)CCN1CCc1ccccc1] | 4-[[8-[4-(4-chlorophenyl)-4-hydroxy-1-piperidyl]-[1,2,4]triazolo[1,5-a]pyridin-2-yl]amino]benzoyl]-N-methyl-1-(2-phenylethyl)piperazine-2-carboxamide |

TABLE A-continued

Exemplary Compounds of the Present Invention

| Ex. | Structure | Name |
|---|---|---|
| 1-151 | 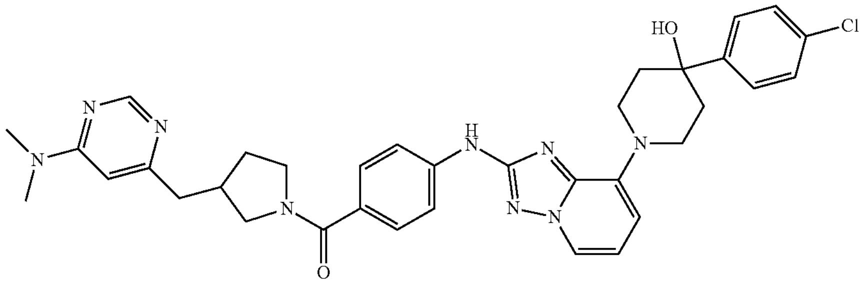 [SMILES: CN(C)c1cc(CC2CCN(C(=O)c3ccc(Nc4nc5c(N6CCC(O)(c7ccc(Cl)cc7)CC6)cccn5n4)cc3)C2)ncn1] | [4-[[8-[4-(4-chlorophenyl)-4-hydroxy-1-piperidyl]-[1,2,4]triazolo[1,5-a]pyridin-2-yl]amino]phenyl]-[3-[[6-(dimethylamino)pyrimidin-4-yl]methyl]pyrrolidin-1-yl]methanone |
| 1-152 | 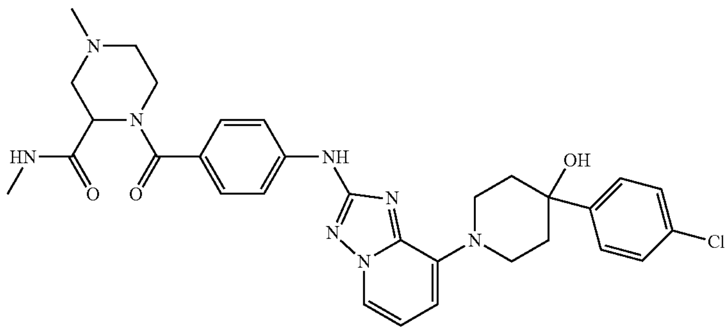 [SMILES: CNC(=O)C1CN(C)CCN1C(=O)c1ccc(Nc2nc3c(N4CCC(O)(c5ccc(Cl)cc5)CC4)cccn3n2)cc1] | 1-[4-[[8-[4-(4-chlorophenyl)-4-hydroxy-1-piperidyl]-[1,2,4]triazolo[1,5-a]pyridin-2-yl]amino]benzoyl]-N,4-dimethyl-piperazine-2-carboxamide |
| 1-153 | 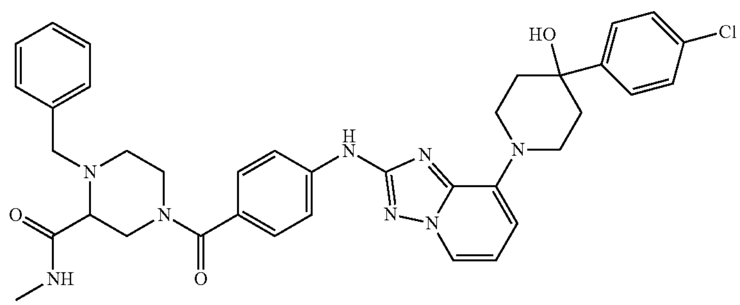 [SMILES: CNC(=O)C1CN(C(=O)c2ccc(Nc3nc4c(N5CCC(O)(c6ccc(Cl)cc6)CC5)cccn4n3)cc2)CCN1Cc1ccccc1] | 1-benzyl-4-[4-[[8-[4-(4-chlorophenyl)-4-hydroxy-1-piperidyl]-[1,2,4]triazolo[1,5-a]pyridin-2-yl]amino]benzoyl]-N-methyl-piperazine-2-carboxamide |
| 1-154 | 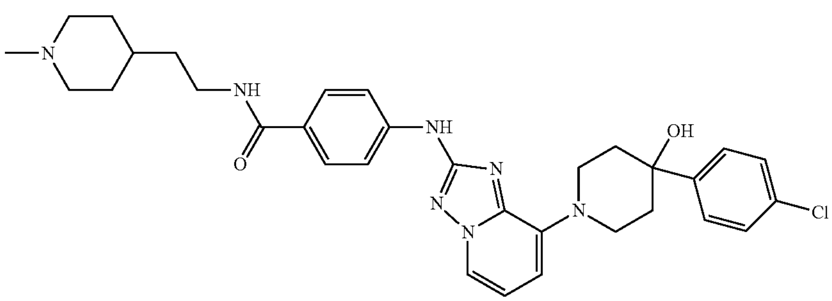 [SMILES: CN1CCC(CCNC(=O)c2ccc(Nc3nc4c(N5CCC(O)(c6ccc(Cl)cc6)CC5)cccn4n3)cc2)CC1] | 4-[[8-[4-(4-chlorophenyl)-4-hydroxy-1-piperidyl]-[1,2,4]triazolo[1,5-a]pyridin-2-yl]amino]-N-[2-(1-methyl-4-piperidyl)ethyl]benzamide |
| 1-155 | 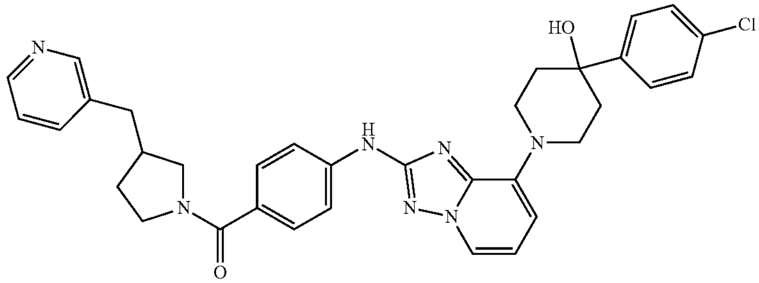 [SMILES: O=C(c1ccc(Nc2nc3c(N4CCC(O)(c5ccc(Cl)cc5)CC4)cccn3n2)cc1)N1CCC(Cc2cccnc2)C1] | [4-[[8-[4-(4-chlorophenyl)-4-hydroxy-1-piperidyl]-[1,2,4]triazolo[1,5-a]pyridin-2-yl]amino]phenyl]-[3-(3-pyridylmethyl)pyrrolidin-1-yl]methanone |

TABLE A-continued

Exemplary Compounds of the Present Invention

| Ex. | Structure | Name |
|---|---|---|
| 1-156 | 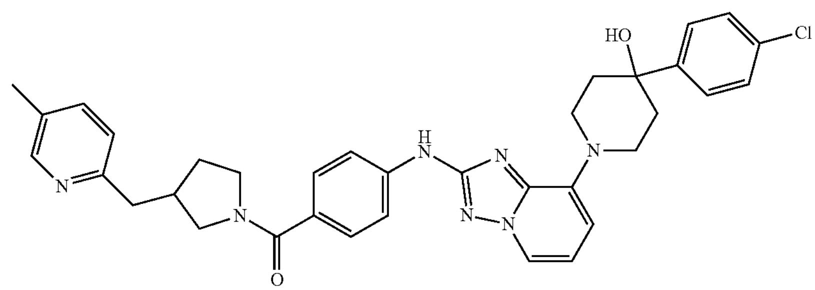 [SMILES: Cc1ccc(CC2CCN(C(=O)c3ccc(Nc4nc5c(N6CCC(O)(c7ccc(Cl)cc7)CC6)cccn5n4)cc3)C2)nc1] | [4-[[8-[4-(4-chlorophenyl)-4-hydroxy-1-piperidyl]-[1,2,4]triazolo[1,5-a]pyridin-2-yl]amino]phenyl]-[3-[(5-methyl-2-pyridyl)methyl]pyrrolidin-1-yl]methanone |
| 1-157 | 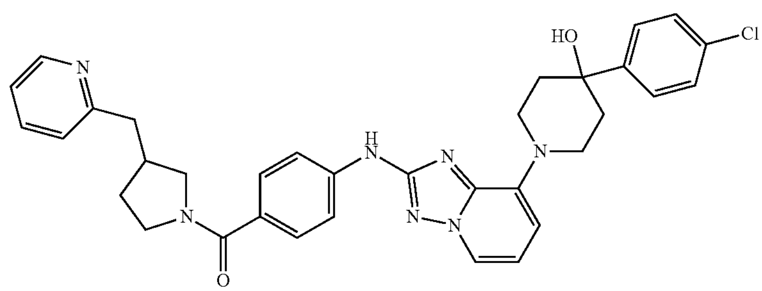 [SMILES: O=C(c1ccc(Nc2nc3c(N4CCC(O)(c5ccc(Cl)cc5)CC4)cccn3n2)cc1)N1CCC(Cc2ccccn2)C1] | [4-[[8-[4-(4-chlorophenyl)-4-hydroxy-1-piperidyl]-[1,2,4]triazolo[1,5-a]pyridin-2-yl]amino]phenyl]-[3-(2-pyridylmethyl)pyrrolidin-1-yl]methanone |
| 1-158 | 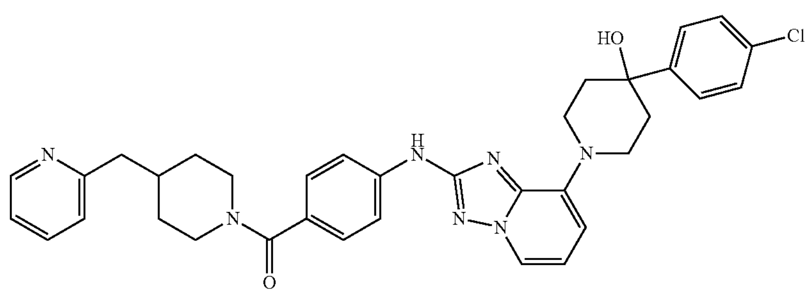 [SMILES: O=C(c1ccc(Nc2nc3c(N4CCC(O)(c5ccc(Cl)cc5)CC4)cccn3n2)cc1)N1CCC(Cc2ccccn2)CC1] | [4-[[8-[4-(4-chlorophenyl)-4-hydroxy-1-piperidyl]-[1,2,4]triazolo[1,5-a]pyridin-2-yl]amino]phenyl]-[4-(2-pyridylmethyl)-1-piperidyl]methanone |
| 1-159 | 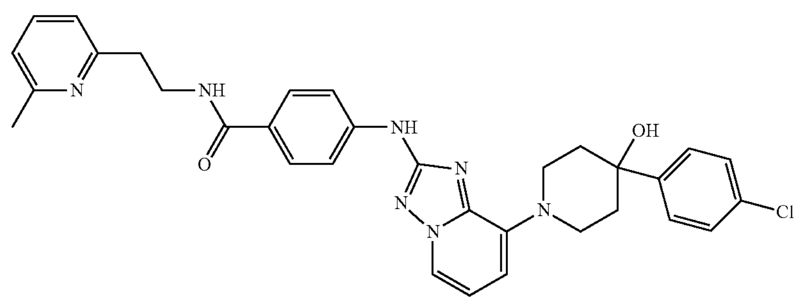 [SMILES: Cc1cccc(CCNC(=O)c2ccc(Nc3nc4c(N5CCC(O)(c6ccc(Cl)cc6)CC5)cccn4n3)cc2)n1] | 4-[[8-[4-(4-chlorophenyl)-4-hydroxy-1-piperidyl]-[1,2,4]triazolo[1,5-a]pyridin-2-yl]amino]-N-[2-(6-methyl-2-pyridyl)ethyl]benzamide |
| 1-160 | 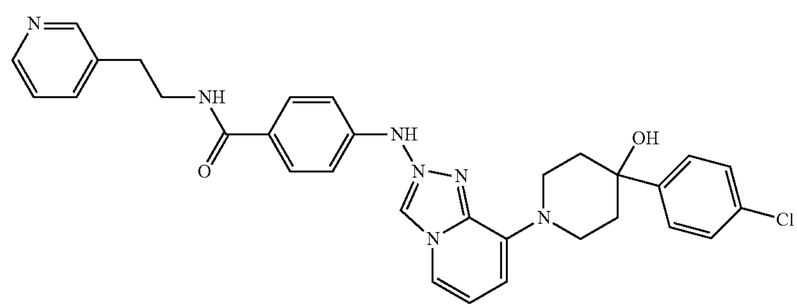 | 4-[[8-[4-(4-chlorophenyl)-4-hydroxy-1-piperidyl]-[1,2,4]triazolo[1,5-a]pyridin-2-yl]amino]-N-[2-(3-pyridyl)ethyl]benzamide |

TABLE A-continued

Exemplary Compounds of the Present Invention

| Ex. | Structure | Name |
|---|---|---|
| 1-161 | 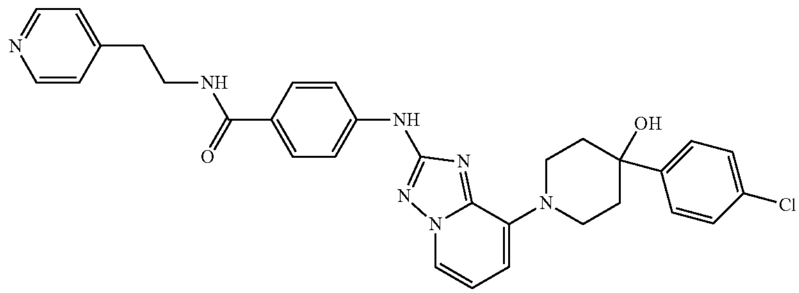 [SMILES: O=C(NCCc1ccncc1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[2-(4-pyridyl)ethyl]benzamide |
| 1-162 | 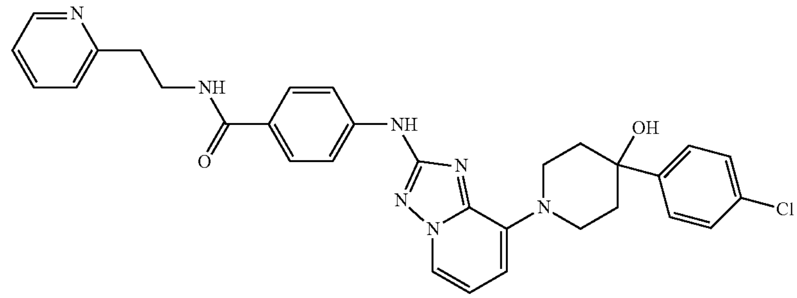 [SMILES: O=C(NCCc1ccccn1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[2-(2-pyridyl)ethyl]benzamide |
| 1-163 | 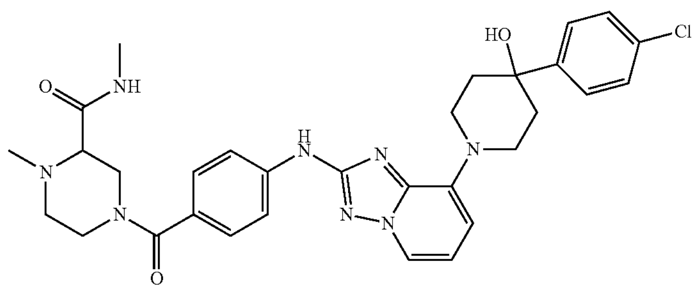 [SMILES: CNC(=O)C1CN(C(=O)c2ccc(Nc3nc4c(N5CCC(O)(c6ccc(Cl)cc6)CC5)cccn4n3)cc2)CCN1C] | 4-[4-[[8-[4-(4-chlorophenyl)-4-hydroxy-1-piperidyl]-[1,2,4]triazolo[1,5-a]pyridin-2-yl]amino]benzoyl]-N,1-dimethyl-piperazine-2-carboxamide |
| 1-164 | 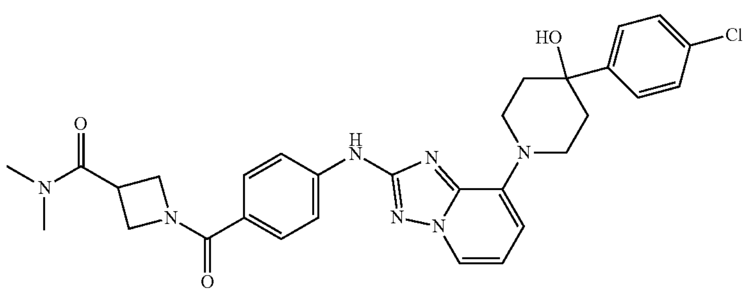 [SMILES: CN(C)C(=O)C1CN(C(=O)c2ccc(Nc3nc4c(N5CCC(O)(c6ccc(Cl)cc6)CC5)cccn4n3)cc2)C1] | 1-[4-[[8-[4-(4-chlorophenyl)-4-hydroxy-1-piperidyl]-[1,2,4]triazolo[1,5-a]pyridin-2-yl]amino]benzoyl]-N,N-dimethyl-azetidine-3-carboxamide |
| 1-165 | 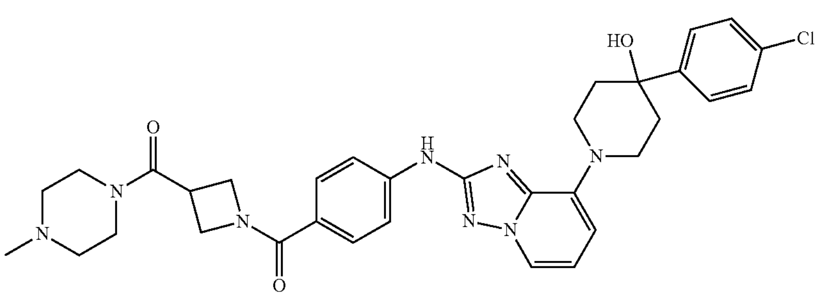 [SMILES: CN1CCN(C(=O)C2CN(C(=O)c3ccc(Nc4nc5c(N6CCC(O)(c7ccc(Cl)cc7)CC6)cccn5n4)cc3)C2)CC1] | [4-[[8-[4-(4-chlorophenyl)-4-hydroxy-1-piperidyl]-[1,2,4]triazolo[1,5-a]pyridin-2-yl]amino]phenyl]-[3-(4-methylpiperazine-1-carbonyl)azetidin-1-yl]methanone |

TABLE A-continued

Exemplary Compounds of the Present Invention

| Ex. | Structure | Name |
|---|---|---|
| 1-166 | 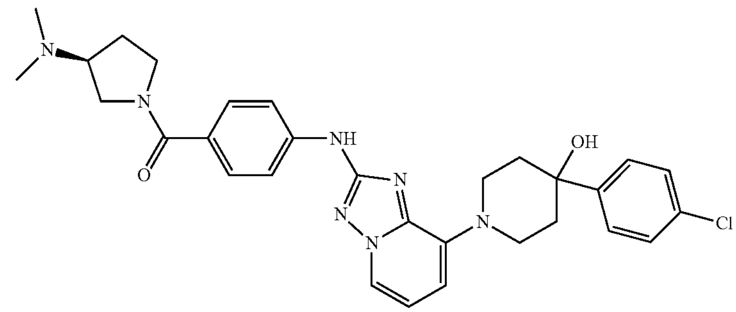 [SMILES: CN(C)[C@H]1CCN(C(=O)c2ccc(Nc3nc4c(N5CCC(O)(c6ccc(Cl)cc6)CC5)cccn4n3)cc2)C1] | [4-[[8-[4-(4-chlorophenyl)-4-hydroxy-1-piperidyl]-[1,2,4]triazolo[1,5-a]pyridin-2-yl]amino]phenyl]-[(3S)-3-(dimethylamino)pyrrolidin-1-yl]methanone |
| 1-167 | 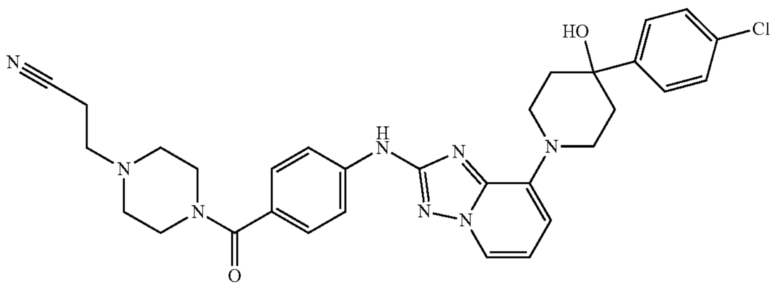 [SMILES: N#CCCN1CCN(C(=O)c2ccc(Nc3nc4c(N5CCC(O)(c6ccc(Cl)cc6)CC5)cccn4n3)cc2)CC1] | 3-[4-[4-[[8-[4-(4-chlorophenyl)-4-hydroxy-1-piperidyl]-[1,2,4]triazolo[1,5-a]pyridin-2-yl]amino]benzoyl]piperazin-1-yl]propanenitrile |
| 1-168 | 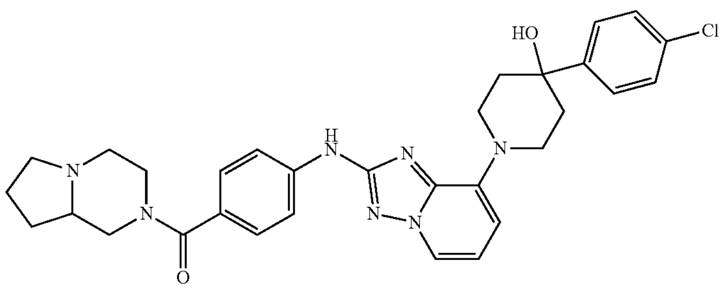 [SMILES: O=C(c1ccc(Nc2nc3c(N4CCC(O)(c5ccc(Cl)cc5)CC4)cccn3n2)cc1)N1CCN2CCCC2C1] | 3,4,6,7,8,8a-hexahydro-1H-pyrrolo[1,2-a]pyrazin-2-yl-[4-[[8-[4-(4-chlorophenyl)-4-hydroxy-1-piperidyl]-[1,2,4]triazolo[1,5-a]pyridin-2-yl]amino]phenyl]methanone |
| 1-169 | 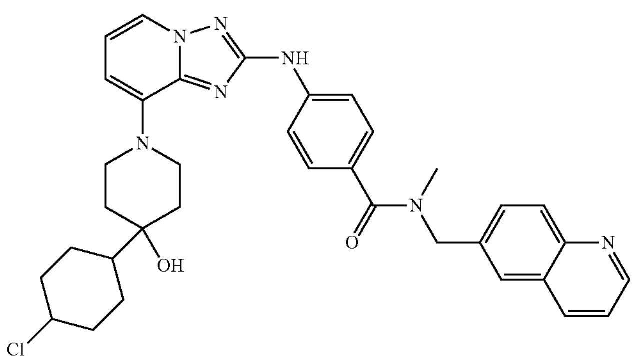 [SMILES: CN(Cc1ccc2ncccc2c1)C(=O)c1ccc(Nc2nc3c(N4CCC(O)(C5CCC(Cl)CC5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-methyl-N-(6-quinolylmethyl)benzamide |
| 1-170 | 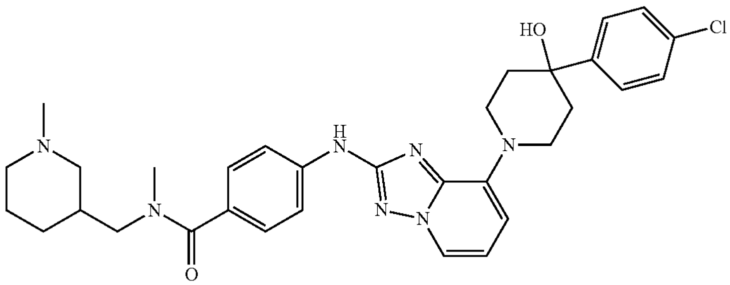 [SMILES: CN1CCCC(CN(C)C(=O)c2ccc(Nc3nc4c(N5CCC(O)(c6ccc(Cl)cc6)CC5)cccn4n3)cc2)C1] | 4-[[8-[4-(4-chlorophenyl)-4-hydroxy-1-piperidyl]-[1,2,4]triazolo[1,5-a]pyridin-2-yl]amino]-N-methyl-N-[(1-methyl-3-piperidyl)methyl]benzamide |

TABLE A-continued

Exemplary Compounds of the Present Invention

| Ex. | Structure | Name |
|---|---|---|
| 1-171 | 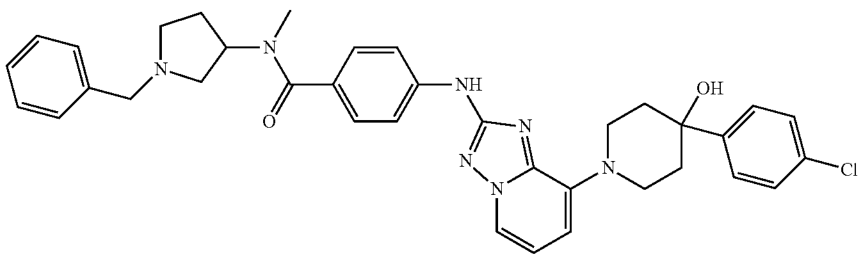 [SMILES: CN(C(=O)c1ccc(Nc2nc3c(N4CCC(O)(c5ccc(Cl)cc5)CC4)cccn3n2)cc1)C1CCN(Cc2ccccc2)C1] | N-(1-benzylpyrrolidin-3-yl)-4-[[8-[4-(4-chlorophenyl)-4-hydroxy-1-piperidyl]-[1,2,4]triazolo[1,5-a]pyridin-2-yl]amino]-N-methyl-benzamide |
| 1-172 | 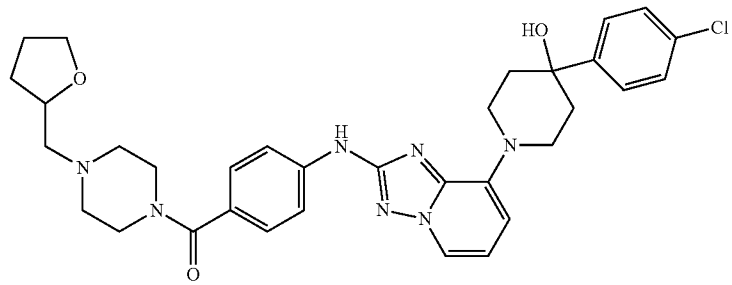 [SMILES: O=C(c1ccc(Nc2nc3c(N4CCC(O)(c5ccc(Cl)cc5)CC4)cccn3n2)cc1)N1CCN(CC2CCCO2)CC1] | [4-[[8-[4-(4-chlorophenyl)-4-hydroxy-1-piperidyl]-[1,2,4]triazolo[1,5-a]pyridin-2-yl]amino]phenyl]-[4-(tetrahydrofuran-2-ylmethyl)piperazin-1-yl]methanone |
| 1-173 | 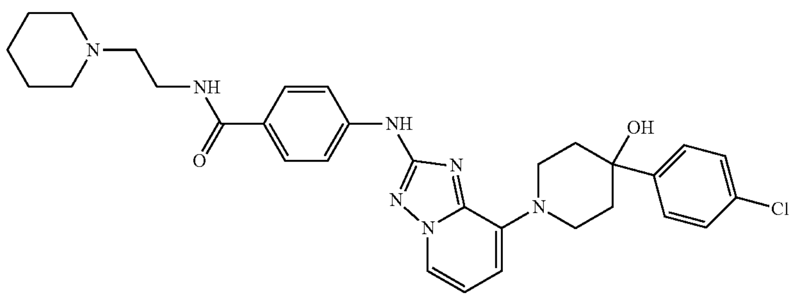 [SMILES: O=C(NCCN1CCCCC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[2-(1-piperidyl)ethyl]benzamide |
| 1-174 | 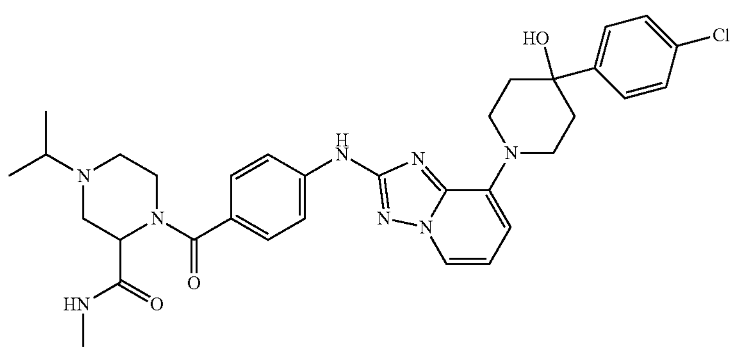 [SMILES: CNC(=O)C1CN(C(C)C)CCN1C(=O)c1ccc(Nc2nc3c(N4CCC(O)(c5ccc(Cl)cc5)CC4)cccn3n2)cc1] | 1-[4-[[8-[4-(4-chlorophenyl)-4-hydroxy-1-piperidyl]-[1,2,4]triazolo[1,5-a]pyridin-2-yl]amino]benzoyl]-4-isopropyl-N-methyl-piperazine-2-carboxamide |
| 1-175 | 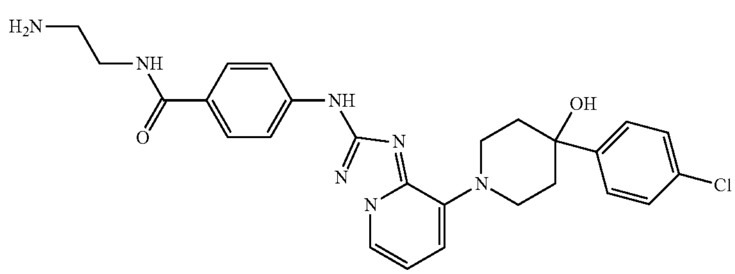 [SMILES: N=C(/N=c1\[nH]cccc1N1CCC(O)(c2ccc(Cl)cc2)CC1)Nc1ccc(C(=O)NCCN)cc1] | N-(2-aminoethyl)-4-[[8-[4-(4-chlorophenyl)-4-hydroxy-1-piperidyl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 1-176 | 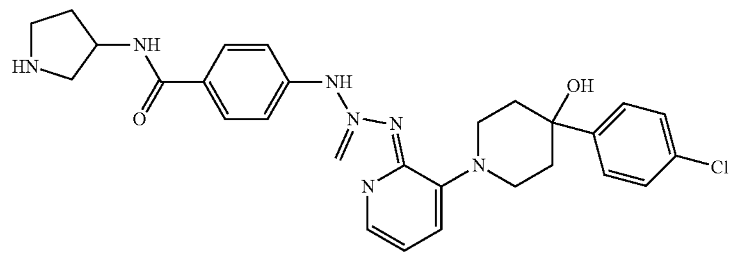 | 4-[[8-[4-(4-chlorophenyl)-4-hydroxy-1-piperidyl]-[1,2,4]triazolo[1,5-a]pyridin-2-yl]amino]-N-pyrrolidin-3-yl-benzamide |
| 1-177 | 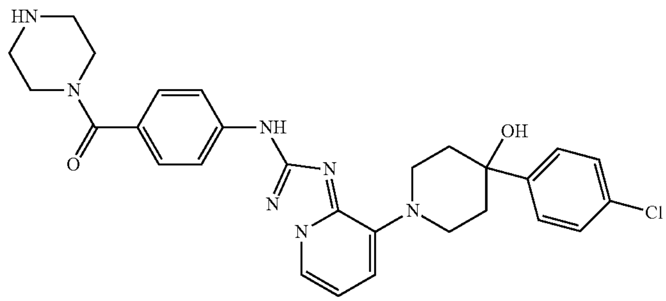 [SMILES: N=C(/N=c1\[nH]cccc1N1CCC(O)(c2ccc(Cl)cc2)CC1)Nc1ccc(C(=O)N2CCNCC2)cc1] | [4-[[8-[4-(4-chlorophenyl)-4-hydroxy-1-piperidyl]-[1,2,4]triazolo[1,5-a]pyridin-2-yl]amino]phenyl]-piperazin-1-yl-methanone |
| 1-178 | 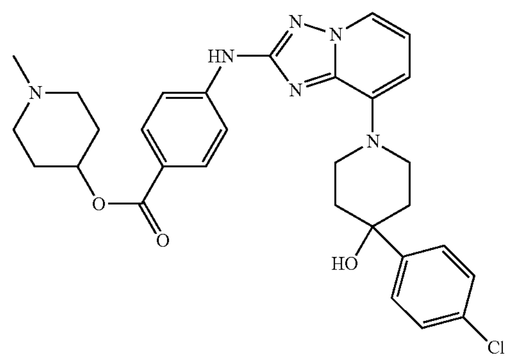 [SMILES: CN1CCC(OC(=O)c2ccc(Nc3nc4c(N5CCC(O)(c6ccc(Cl)cc6)CC5)cccn4n3)cc2)CC1] | (1-methyl-4-piperidyl) 4-[[8-[4-(4-chlorophenyl)-4-hydroxy-1-piperidyl]-[1,2,4]triazolo[1,5-a]pyridin-2-yl]amino]benzoate |
| 1-179 | 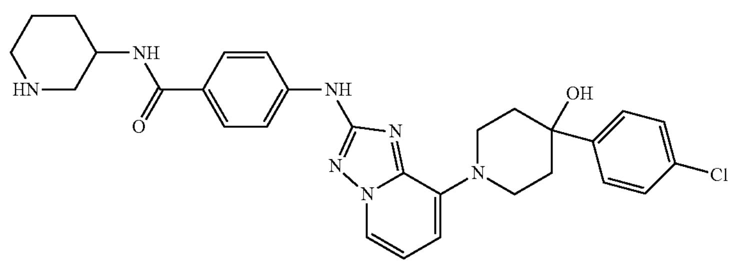 [SMILES: O=C(NC1CCCNC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(3-piperidyl)benzamide |
| 1-180 | 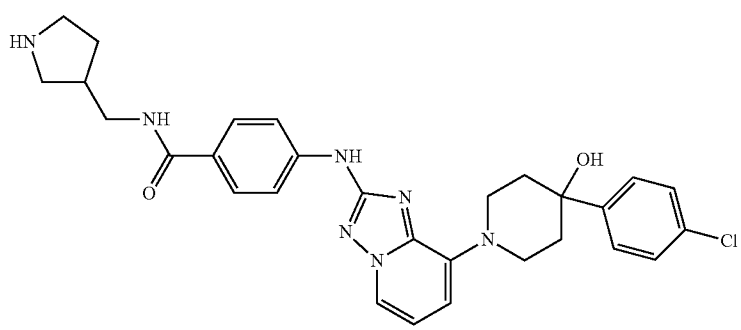 [SMILES: O=C(NCC1CCNC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(pyrrolidin-3-ylmethyl)benzamide |

TABLE A-continued

Exemplary Compounds of the Present Invention

| Ex. | Structure | Name |
|---|---|---|
| 1-181 | 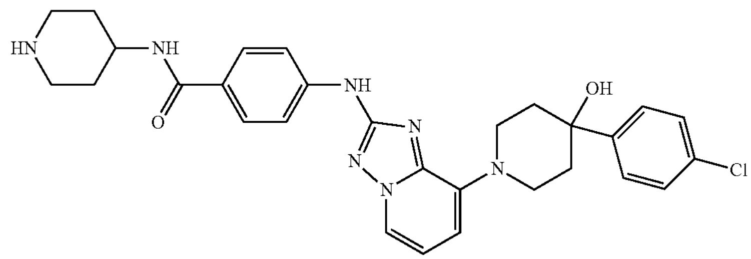 [SMILES: O=C(NC1CCNCC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(4-piperidyl)benzamide |
| 1-182 | 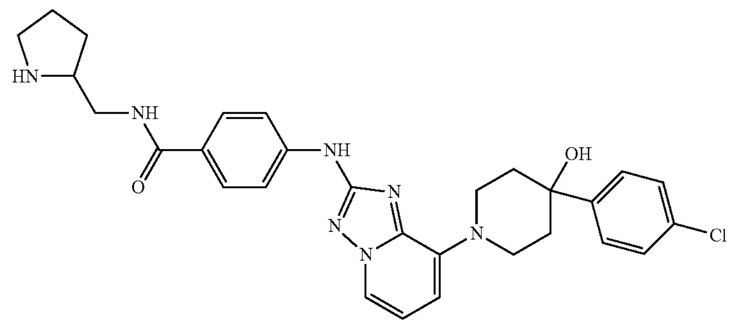 [SMILES: O=C(NCC1CCCN1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(pyrrolidin-2-ylmethyl)benzamide |
| 1-183 | 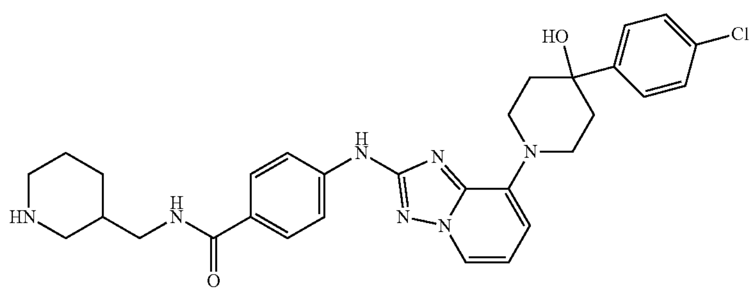 [SMILES: O=C(NCC1CCCNC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(3-piperidylmethyl)benzamide |
| 1-184 | 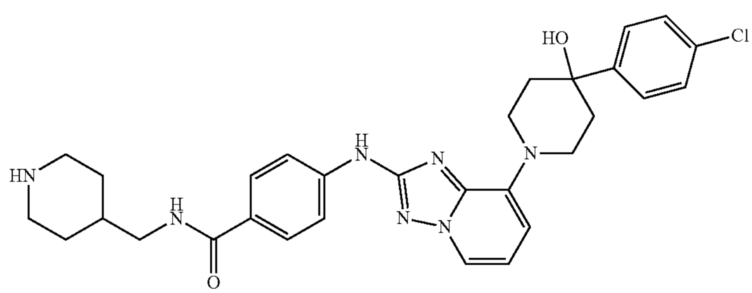 [SMILES: O=C(NCC1CCNCC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(4-piperidylmethyl) |
| 1-186 | 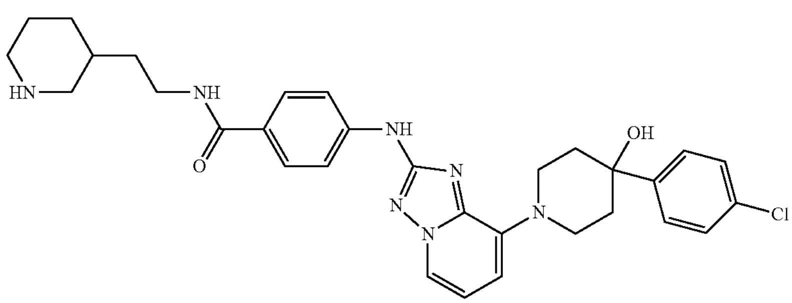 [SMILES: O=C(NCCC1CCCNC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[2-(3-piperidyl)ethyl]benzamide |

TABLE A-continued

Exemplary Compounds of the Present Invention

| Ex. | Structure | Name |
|---|---|---|
| 1-187 | 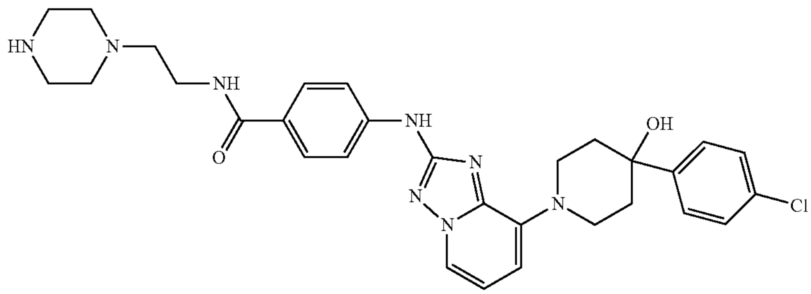 [SMILES: O=C(NCCN1CCNCC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(2-piperazin-1-yl)ethyl)benzamide |
| 1-188 | 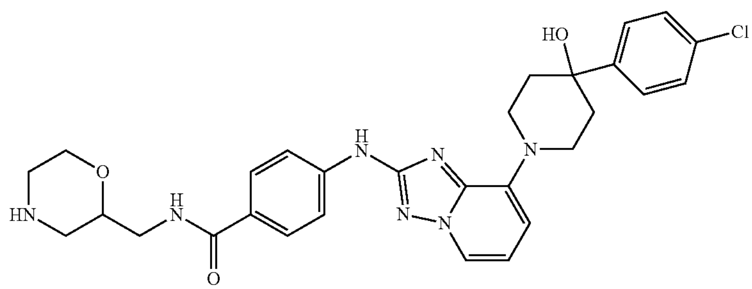 | 4-[[8-[4-(4-chlorophenyl)-4-hydroxy-1-piperidyl]-[1,2,4]triazolo[1,5-a]pyridin-2-yl]amino]-N-(morpholin-2-ylmethyl)benzamide |
| 1-189 | 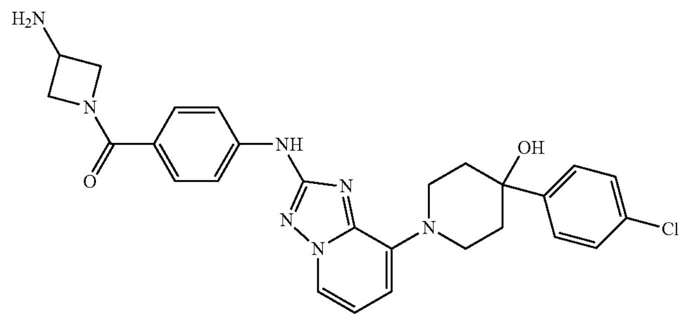 [SMILES: NC1CN(C(=O)c2ccc(Nc3nc4c(N5CCC(O)(c6ccc(Cl)cc6)CC5)cccn4n3)cc2)C1] | (3-aminoazetidin-1-yl)-[4-[[-[4-(4-chlorophenyl)-4-hydroxy-1-piperidyl]-[1,2,4]triazolo[1,5-a]pyridin-2-yl]amino]phenyl]methanone |
| 1-190 | 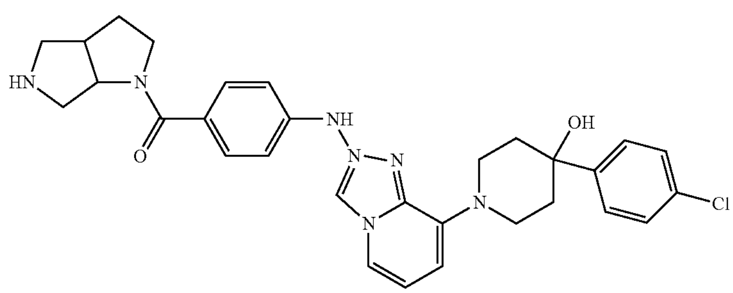 | 3,3a,4,5,6,6a-hexahydro-2H-pyrrolo[2,3-c]pyrrol-1-yl-[4-[[8-[4-(4-chlorophenyl)-4-hydroxy-1-piperidyl]-[1,2,4]triazolo[1,5-a]pyridin-2-yl]amino]phenyl]methanone |
| 1-191 | 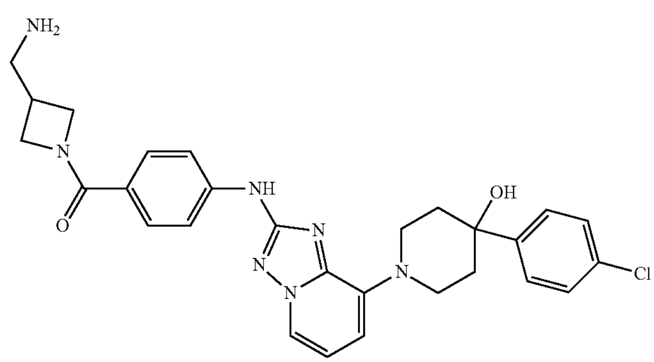 [SMILES: NCC1CN(C(=O)c2ccc(Nc3nc4c(N5CCC(O)(c6ccc(Cl)cc6)CC5)cccn4n3)cc2)C1] | [3-(aminomethyl)azetidin-1-yl]-[4-[[8-[4-(4-chlorophenyl)-4-hydroxy-1-piperidyl][1,2,4]triazolo[1,5-a]pyridin-2-yl]amino]phenyl]methanone |

TABLE A-continued

Exemplary Compounds of the Present Invention

| Ex. | Structure | Name |
|---|---|---|
| 1-192 | 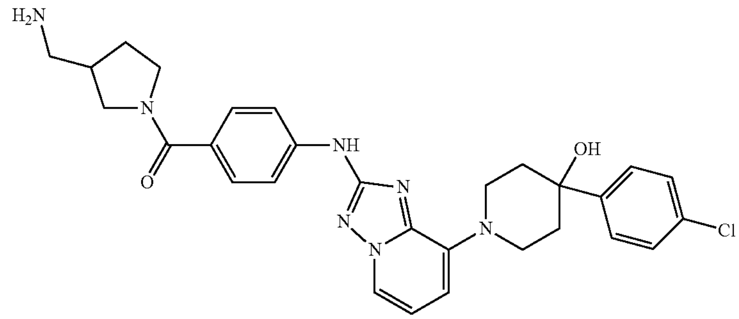 [SMILES: NCC1CCN(C(=O)c2ccc(Nc3nc4c(N5CCC(O)(c6ccc(Cl)cc6)CC5)cccn4n3)cc2)C1] | [3-(aminomethyl)pyrrolidin-1-yl]-[4-[[-[4-(4-chlorophenyl)-4-hydroxy-1-piperidyl]-[1,2,4]triazolo[1,5-a]pyridin-2-yl]amino]phenyl] methanone |
| 1-193 | 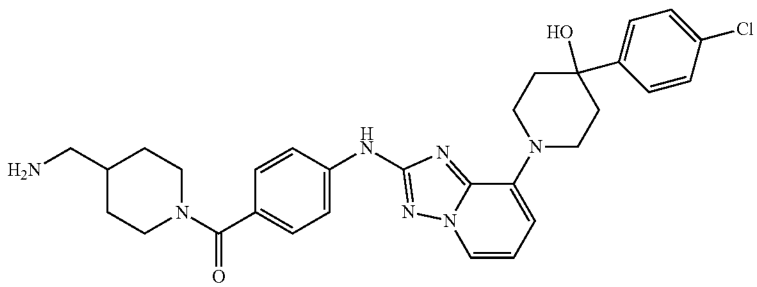 [SMILES: NCC1CCN(C(=O)c2ccc(Nc3nc4c(N5CCC(O)(c6ccc(Cl)cc6)CC5)cccn4n3)cc2)CC1] | [4-(aminomethyl)-1-piperidyl]-[4-[[8-[4-(4-chlorophenyl)-4-hydroxy-1-piperidyl]-[1,2,4]triazolo[1,5-a]pyridin-2-yl]amino]phenyl] methanone |
| 1-194 | 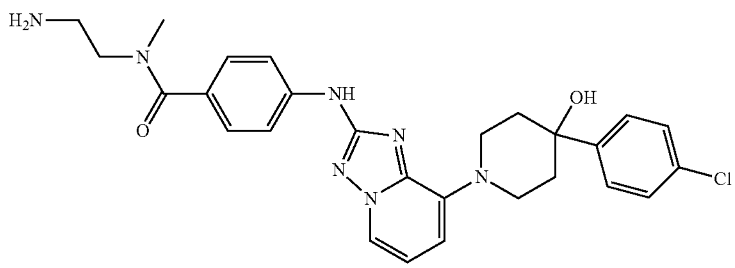 [SMILES: CN(CCN)C(=O)c1ccc(Nc2nc3c(N4CCC(O)(c5ccc(Cl)cc5)CC4)cccn3n2)cc1] | N-(2-aminoethyl)-4-[[8-[4-(4-chlorophenyl)-4-hydroxy-1-piperidyl]-[1,2,4]triazolo[1,5-a]pyridin-2-yl]amino]-N-methyl-benzamide |
| 1-195 | 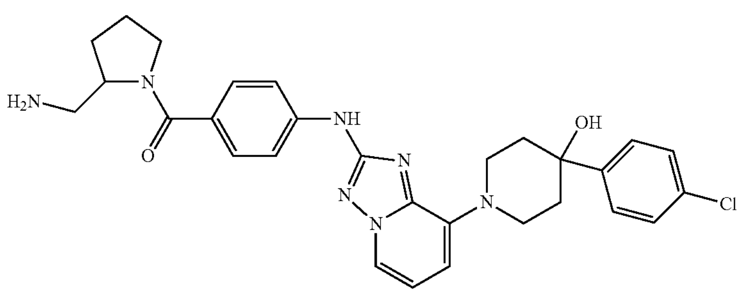 [SMILES: NCC1CCCN1C(=O)c1ccc(Nc2nc3c(N4CCC(O)(c5ccc(Cl)cc5)CC4)cccn3n2)cc1] | [2-(aminomethyl)pyrrolidin-1-yl]-[4-[[8-[4-(4-chlorophenyl)-4-hydroxy-1-piperidyl]-[1,2,4]triazolo[1,5-a]pyridin-2-yl]amino]phenyl] methanone |
| 1-196 | 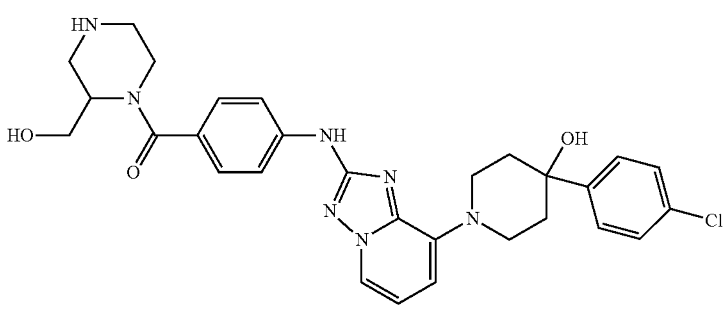 [SMILES: O=C(c1ccc(Nc2nc3c(N4CCC(O)(c5ccc(Cl)cc5)CC4)cccn3n2)cc1)N1CCNCC1CO] | [4-[[8-[4-(4-chlorophenyl)-4-hydroxy-1-piperidyl]-[1,2,4]triazolo[1,5-a]pyridin-2-yl]amino]phenyl]-[2-(hydroxymethyl)piperazin-1-yl]methanone |

TABLE A-continued

Exemplary Compounds of the Present Invention

| Ex. | Structure | Name |
|---|---|---|
| 1-197 | 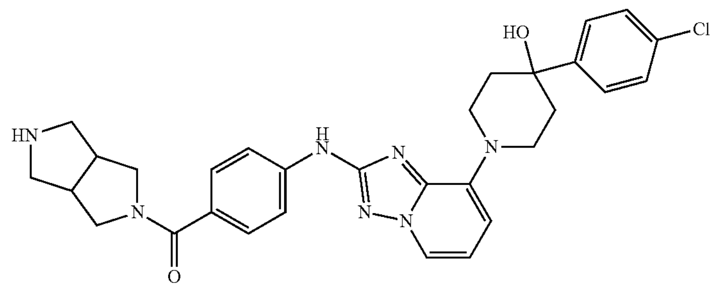 [SMILES: O=C(c1ccc(Nc2nc3c(N4CCC(O)(c5ccc(Cl)cc5)CC4)cccn3n2)cc1)N1CC2CNCC2C1] | 2,3,3a,4,6,6a-hexahydro-1H-pyrrolo[3,4-c]pyrrol-5-yl-[4-[[8-[4-(4-chlorophenyl)-4-hydroxy-1-piperidyl]-[1,2,4]triazolo[1,5-a]pyridin-2-yl]amino]phenyl]methanone |
| 1-198 | 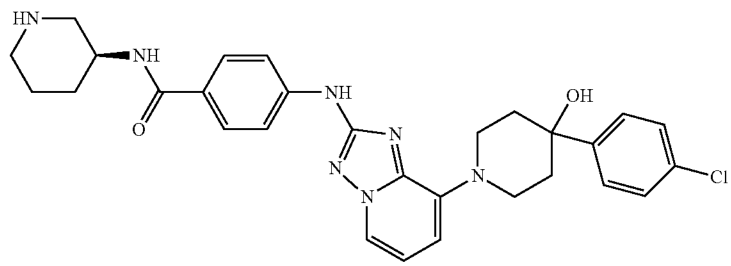 [SMILES: O=C(N[C@H]1CCCNC1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-[(3S)-3-piperidyl]benzamide |
| 1-199 | 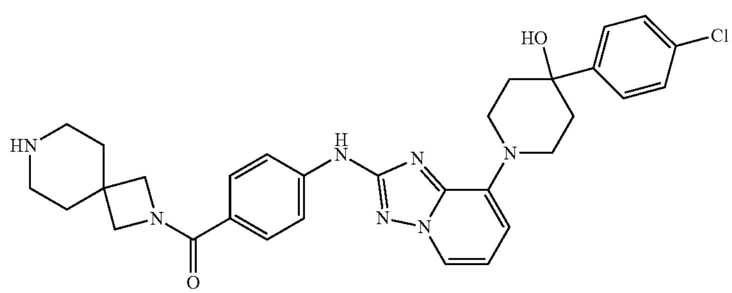 [SMILES: O=C(c1ccc(Nc2nc3c(N4CCC(O)(c5ccc(Cl)cc5)CC4)cccn3n2)cc1)N1CC2(CCNCC2)C1] | [4-[[8-[4-(4-chlorophenyl)-4-hydroxy-1-piperidyl]-[1,2,4]triazolo[1,5-a]pyridin-2-yl]amino]phenyl]-(2,7-diazaspiro[3.5]nonan-2-yl)methanone |
| 1-200 | 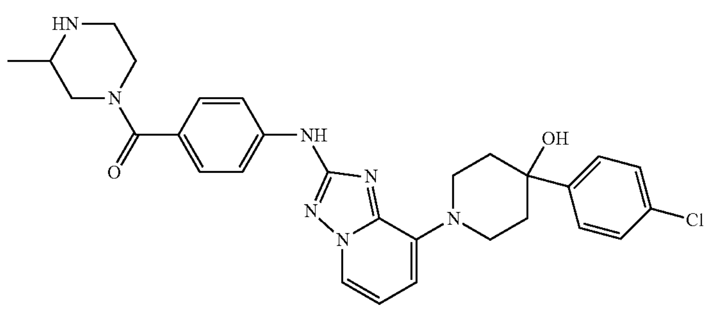 [SMILES: CC1CN(C(=O)c2ccc(Nc3nc4c(N5CCC(O)(c6ccc(Cl)cc6)CC5)cccn4n3)cc2)CCN1] | [4-[[8-[4-(4-chlorophenyl)-4-hydroxy-1-piperidyl]-[1,2,4]triazolo[1,5-a]pyridin-2-yl]amino]phenyl]-(3-methylpiperazin-1-yl)methanone |
| 1-201 | 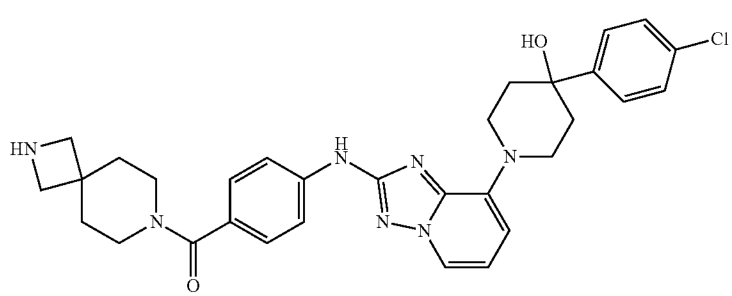 [SMILES: O=C(c1ccc(Nc2nc3c(N4CCC(O)(c5ccc(Cl)cc5)CC4)cccn3n2)cc1)N1CCC2(CC1)CNC2] | [4-[[8-[4-(4-chlorophenyl)-4-hydroxy-1-piperidyl]-[1,2,4]triazolo[1,5-a]pyridin-2-yl]amino]phenyl]-(2,7-diazaspiro[3.5]nonan-7-yl)methanone |

TABLE A-continued

Exemplary Compounds of the Present Invention

| Ex. | Structure | Name |
|---|---|---|
| 1-202 | 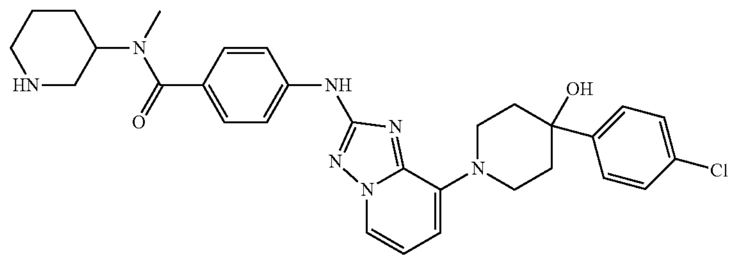 [SMILES: CN(C(=O)c1ccc(Nc2nc3c(N4CCC(O)(c5ccc(Cl)cc5)CC4)cccn3n2)cc1)C1CCCNC1] | 4-[[8-[4-(4-chlorophenyl)-4-hydroxy-1-piperidyl]-[1,2,4]triazolo[1,5-a]pyridin-2-yl]amino]-N-methyl-N-(3-piperidyl)benzamide |
| 1-203 | 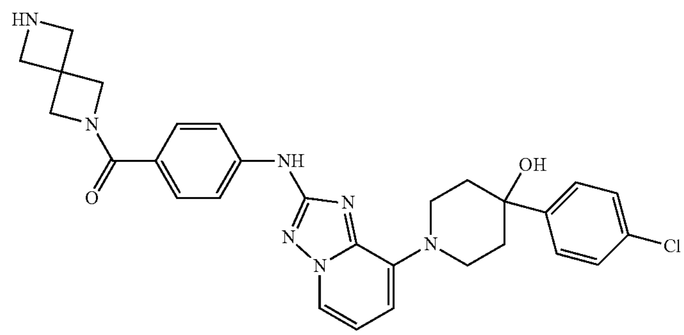 [SMILES: O=C(c1ccc(Nc2nc3c(N4CCC(O)(c5ccc(Cl)cc5)CC4)cccn3n2)cc1)N1CC2(CNC2)C1] | [4-[[8-[4-(4-chlorophenyl)-4-hydroxy-1-piperidyl]-[1,2,4]triazolo[1,5-a]pyridin-2-yl]amino]phenyl]-(2,6-diazaspiro[3.3]heptan-2-yl)methanone |
| 1-204 | 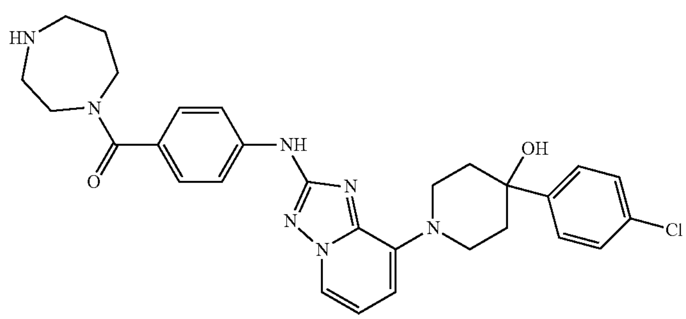 [SMILES: O=C(c1ccc(Nc2nc3c(N4CCC(O)(c5ccc(Cl)cc5)CC4)cccn3n2)cc1)N1CCCNCC1] | [4-[[8-[4-(4-chlorophenyl)-4-hydroxy-1-piperidyl]-[1,2,4]triazolo[1,5-a]pyridin-2-yl]amino]phenyl]-(1,4-diazepan-1-yl)methanone |
| 1-205 | 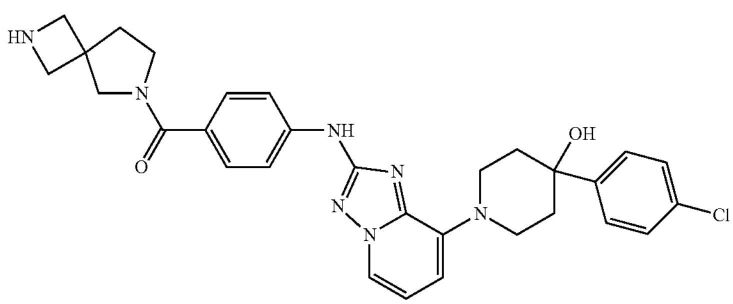 [SMILES: O=C(c1ccc(Nc2nc3c(N4CCC(O)(c5ccc(Cl)cc5)CC4)cccn3n2)cc1)N1CCC2(CNC2)C1] | [4-[[8-[4-(4-chlorophenyl)-4-hydroxy-1-piperidyl]-[1,2,4]triazolo[1,5-a]pyridin-2-yl]amino]phenyl]-(2,6-diazaspiro[3.4]octan-6-yl)methanone |
| 1-206 | 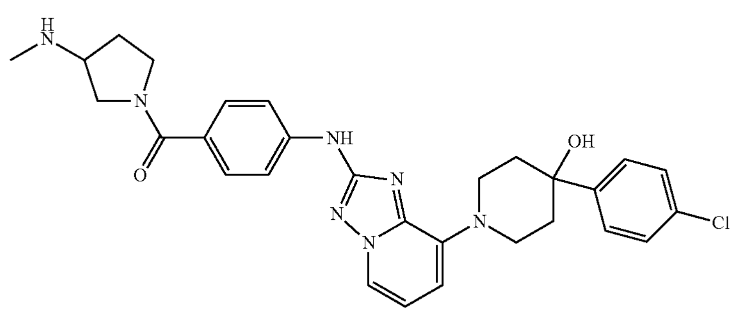 [SMILES: CNC1CCN(C(=O)c2ccc(Nc3nc4c(N5CCC(O)(c6ccc(Cl)cc6)CC5)cccn4n3)cc2)C1] | [4-[[8-[4-(4-chlorophenyl)-4-hydroxy-1-piperidyl]-[1,2,4]triazolo[1,5-a]pyridin-2-yl]amino]phenyl]-[3-(methylamino)pyrrolidin-1-yl]methanone |

TABLE A-continued

Exemplary Compounds of the Present Invention

| Ex. | Structure | Name |
|---|---|---|
| 1-207 | 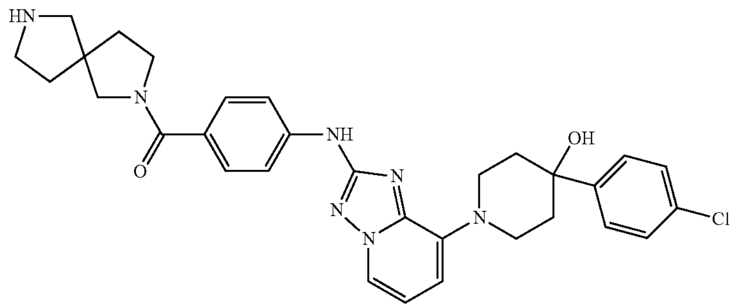 [SMILES: O=C(c1ccc(Nc2nc3c(N4CCC(O)(c5ccc(Cl)cc5)CC4)cccn3n2)cc1)N1CCC2(CCNC2)C1] | [4-[[8-[4-(4-chlorophenyl)-4-hydroxy-1-piperidyl]-[1,2,4]triazolo[1,5-a]pyridin-2-yl]amino]phenyl]-(2,7-diazaspiro[4.4]nonan-2-yl)methanone |
| 1-208 | 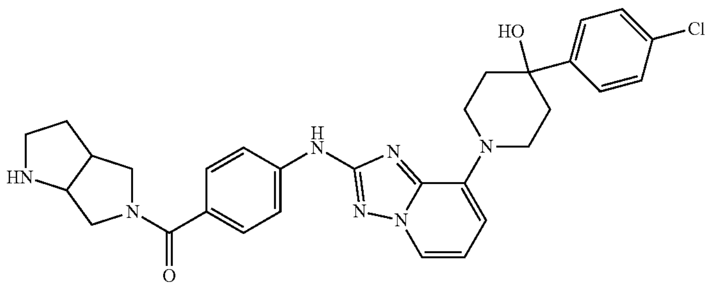 [SMILES: O=C(c1ccc(Nc2nc3c(N4CCC(O)(c5ccc(Cl)cc5)CC4)cccn3n2)cc1)N1CC2CCNC2C1] | [4-[[8-[4-(4-chlorophenyl)-4-hydroxy-1-piperidyl]-[1,2,4]triazolo[1,5-a]pyridin-2-yl]amino]phenyl]-(1,7-diazaspiro[4.4]nonan-7-yl)methanone |
| 1-209 | 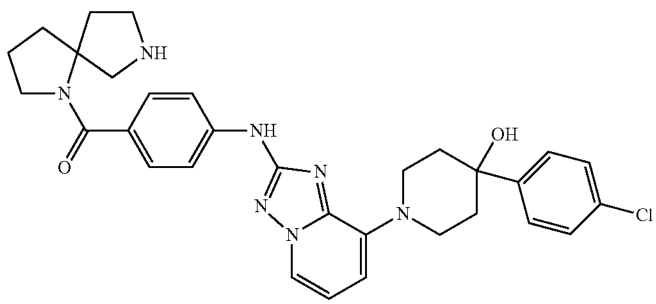 [SMILES: O=C(c1ccc(Nc2nc3c(N4CCC(O)(c5ccc(Cl)cc5)CC4)cccn3n2)cc1)N1CCCC12CCNC2] | [4-[[8-[4-(4-chlorophenyl)-4-hydroxy-1-piperidyl]-[1,2,4]triazolo[1,5-a]pyridin-2-yl]amino]phenyl]-(1,7-diazaspiro[4.4]nonan-1-yl)methanone |
| 1-210 | 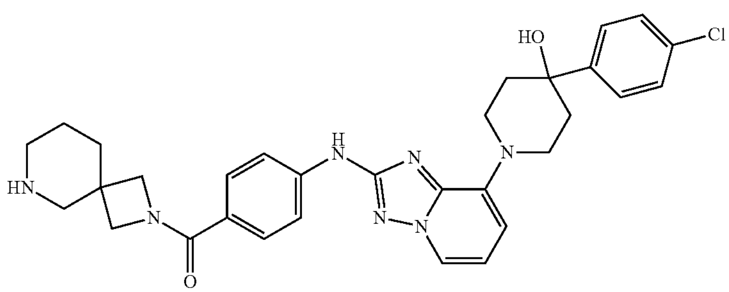 [SMILES: O=C(c1ccc(Nc2nc3c(N4CCC(O)(c5ccc(Cl)cc5)CC4)cccn3n2)cc1)N1CC2(CCCNC2)C1] | [4-[[8-[4-(4-chlorophenyl)-4-hydroxy-1-piperidyl]-[1,2,4]triazolo[1,5-a]pyridin-2-yl]amino]phenyl]-(2,8-diazaspiro[3.5]nonan-2-yl)methanone |
| 1-211 | 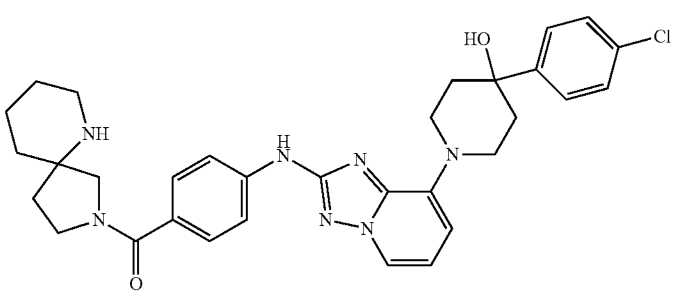 [SMILES: O=C(c1ccc(Nc2nc3c(N4CCC(O)(c5ccc(Cl)cc5)CC4)cccn3n2)cc1)N1CCC2(CCCCN2)C1] | [4-[[8-[4-(4-chlorophenyl)-4-hydroxy-1-piperidyl]-[1,2,4]triazolo[1,5-a]pyridin-2-yl]amino]phenyl]-(2,6-diazaspiro[4.5]decan-2-yl)methanone |

TABLE A-continued

Exemplary Compounds of the Present Invention

| Ex. | Structure | Name |
|---|---|---|
| 1-212 | 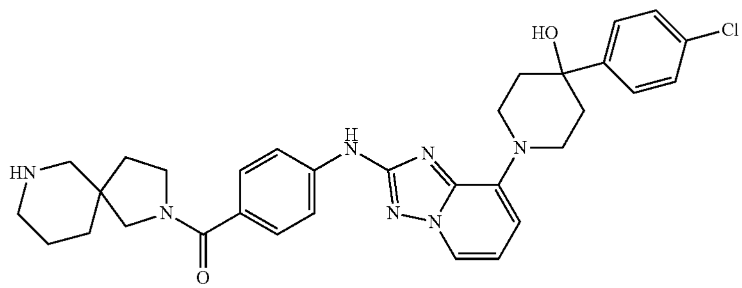 [SMILES: O=C(c1ccc(Nc2nc3c(N4CCC(O)(c5ccc(Cl)cc5)CC4)cccn3n2)cc1)N1CCC2(CCCNC2)C1] | [4-[[8-[4-(4-chlorophenyl)-4-hydroxy-1-piperidyl]-[1,2,4]triazolo[1,5-a]pyridin-2-yl]amino]phenyl]-(2,9-diazaspiro[4.5]decan-2-yl)methanone |
| 1-213 | 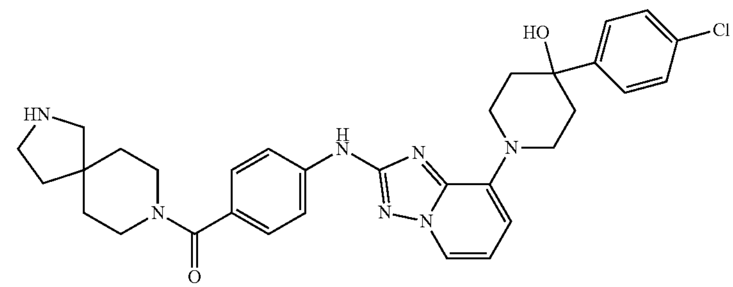 [SMILES: O=C(c1ccc(Nc2nc3c(N4CCC(O)(c5ccc(Cl)cc5)CC4)cccn3n2)cc1)N1CCC2(CCNC2)CC1] | [4-[[8-[4-(4-chlorophenyl)-4-hydroxy-1-piperidyl]-[1,2,4]triazolo[1,5-a]pyridin-2-yl]amino]phenyl]-(2,8-diazaspiro[4.5]decan-8-yl)methanone |
| 1-214 | 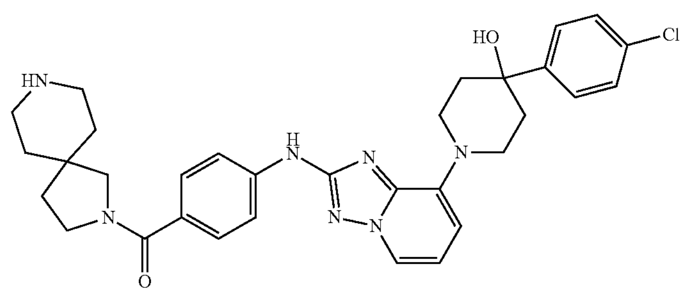 [SMILES: O=C(c1ccc(Nc2nc3c(N4CCC(O)(c5ccc(Cl)cc5)CC4)cccn3n2)cc1)N1CCC2(CCNCC2)C1] | [4-[[8-[4-(4-chlorophenyl)-4-hydroxy-1-piperidyl]-[1,2,4]triazolo[1,5-a]pyridin-2-yl]amino]phenyl]-(2,8-diazaspiro[4.5]decan-2-yl)methanone |
| 1-215 | 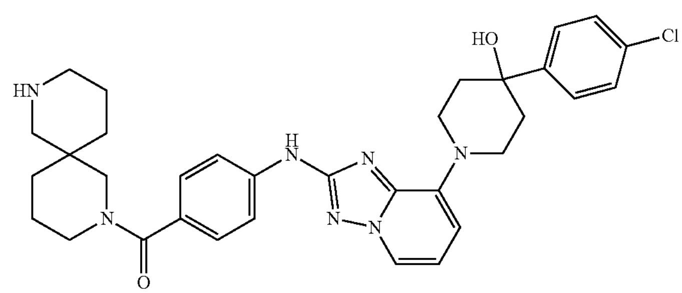 [SMILES: O=C(c1ccc(Nc2nc3c(N4CCC(O)(c5ccc(Cl)cc5)CC4)cccn3n2)cc1)N1CCCC2(CCCNC2)C1] | [4-[[8-[4-(4-chlorophenyl)-4-hydroxy-1-piperidyl]-[1,2,4]triazolo[1,5-a]pyridin-2-yl]amino]phenyl]-(2,8-diazaspiro[5.5]undecan-2-yl)methanone |
| 1-216 | 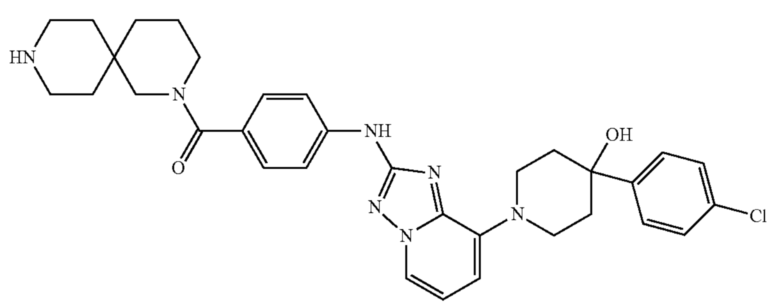 [SMILES: O=C(c1ccc(Nc2nc3c(N4CCC(O)(c5ccc(Cl)cc5)CC4)cccn3n2)cc1)N1CCCC2(CCNCC2)C1] | [4-[[8-[4-(4-chlorophenyl)-4-hydroxy-1-piperidyl]-[1,2,4]triazolo[1,5-a]pyridin-2-yl]amino]phenyl]-(2,9-diazaspiro[5.5]undecan-2-yl)methanone |

TABLE A-continued

Exemplary Compounds of the Present Invention

| Ex. | Structure | Name |
|---|---|---|
| 1-217 | 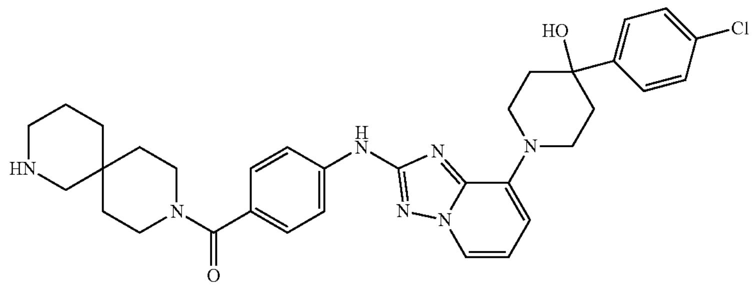 [SMILES: O=C(c1ccc(Nc2nc3c(N4CCC(O)(c5ccc(Cl)cc5)CC4)cccn3n2)cc1)N1CCC2(CCCNC2)CC1] | [4-[[8-[4-(4-chlorophenyl)-4-hydroxy-1-piperidyl]-[1,2,4]triazolo[1,5-a]pyridin-2-yl]amino]phenyl]-(2,9-diazaspiro[5.5]undecan-9-yl)methanone |
| 1-218 | 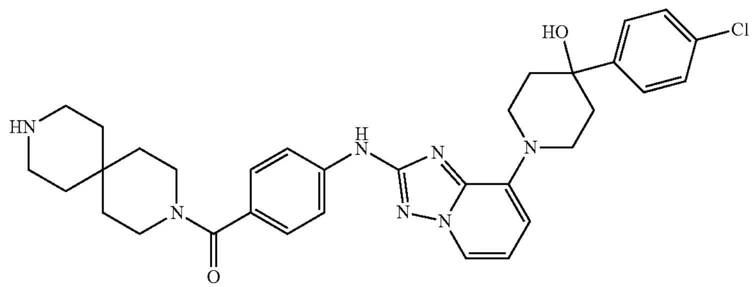 [SMILES: O=C(c1ccc(Nc2nc3c(N4CCC(O)(c5ccc(Cl)cc5)CC4)cccn3n2)cc1)N1CCC2(CCNCC2)CC1] | [4-[[8-[4-(4-chlorophenyl)-4-hydroxy-1-piperidyl]-[1,2,4]triazolo[1,5-a]pyridin-2-yl]amino]phenyl]-(3,9-diazaspiro[5.5]undecan-3-yl)methanone |
| 1-219 | 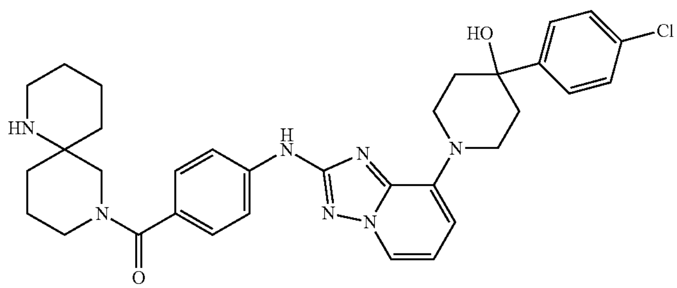 [SMILES: O=C(c1ccc(Nc2nc3c(N4CCC(O)(c5ccc(Cl)cc5)CC4)cccn3n2)cc1)N1CCCC2(CCCCN2)C1] | [4-[[8-[4-(4-chlorophenyl)-4-hydroxy-1-piperidyl]-[1,2,4]triazolo[1,5-a]pyridin-2-yl]amino]phenyl]-(1,8-diazaspiro[5.5]undecan-8-yl)methanone |
| 1-220 | 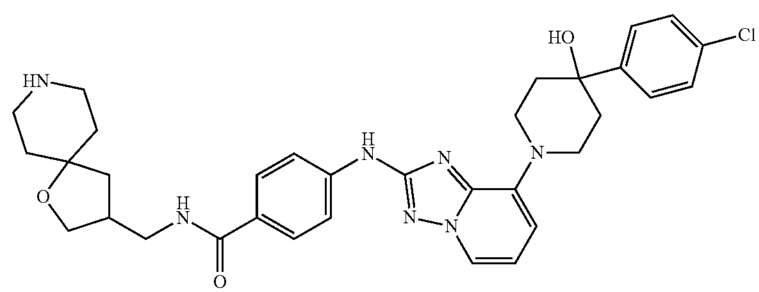 [SMILES: O=C(NCC1COC2(CCNCC2)C1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(1-oxa-8-azaspiro[4.5]decan-3-ylmethyl)benzamide |
| 1-221 | 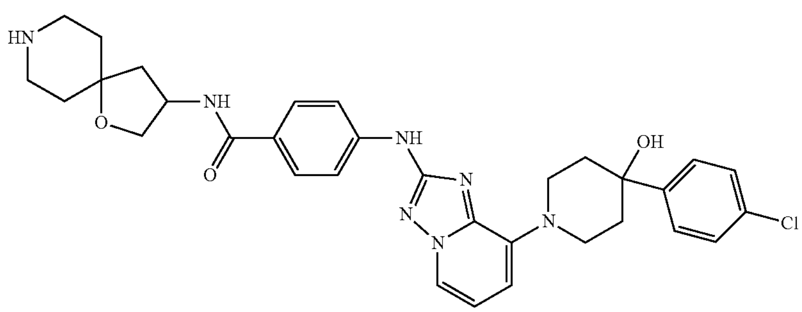 [SMILES: O=C(NC1COC2(CCNCC2)C1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(1-oxa-8-azaspiro[4.5]decan-3-yl)benzamide |

TABLE A-continued

Exemplary Compounds of the Present Invention

| Ex. | Structure | Name |
|---|---|---|
| 1-222 | 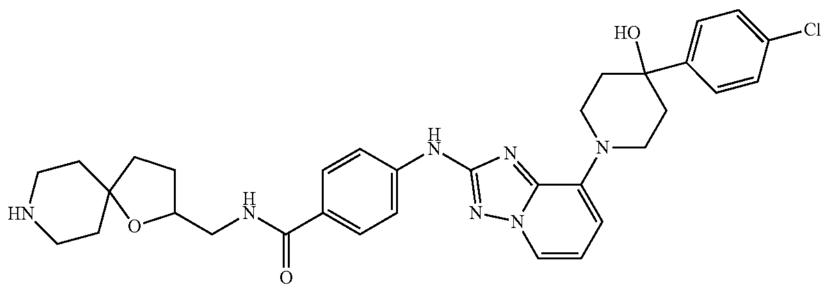 [SMILES: O=C(NCC1CCC2(CCNCC2)O1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(1-oxa-8-azaspiro[4.5]decan-2-ylmethyl)benzamide |
| 1-223 | 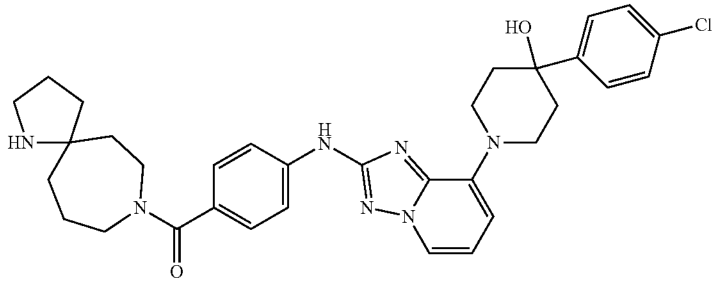 [SMILES: O=C(c1ccc(Nc2nc3c(N4CCC(O)(c5ccc(Cl)cc5)CC4)cccn3n2)cc1)N1CCCC2(CCCN2)CC1] | [4-[[8-[4-(4-chlorophenyl)-4-hydroxy-1-piperidyl]-[1,2,4]triazolo[1,5-a]pyridin-2-yl]amino]phenyl]-(1,9-diazaspiro[4.6]undecan-9-yl)methanone |
| 1-224 | 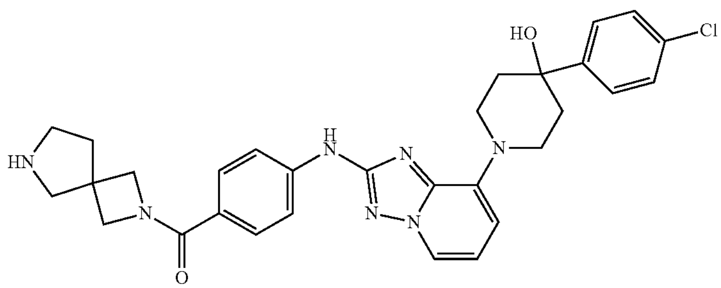 [SMILES: O=C(c1ccc(Nc2nc3c(N4CCC(O)(c5ccc(Cl)cc5)CC4)cccn3n2)cc1)N1CC2(CCNC2)C1] | [4-[[8-[4-(4-chlorophenyl)-4-hydroxy-1-piperidyl]-[1,2,4]triazolo[1,5-a]pyridin-2-yl]amino]phenyl]-(2,7-diazaspiro[3.4]octan-2-yl)methanone |
| 1-225 | 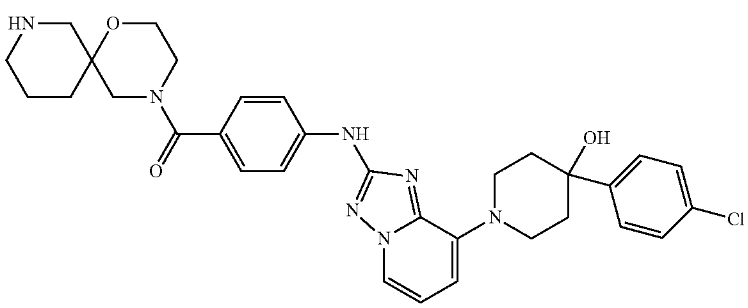 [SMILES: O=C(c1ccc(Nc2nc3c(N4CCC(O)(c5ccc(Cl)cc5)CC4)cccn3n2)cc1)N1CCOC2(CCCNC2)C1] | [4-[[8-[4-(4-chlorophenyl)-4-hydroxy-1-piperidyl]-[1,2,4]triazolo[1,5-a]pyridin-2-yl]amino]phenyl]-(1-oxa-4,8-diazaspiro[5.5]undecan-4-yl)methanone |
| 1-226 | 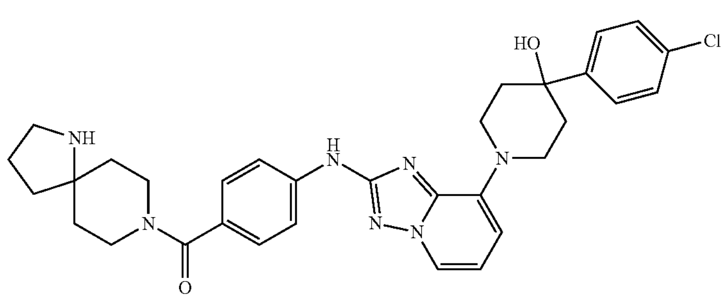 [SMILES: O=C(c1ccc(Nc2nc3c(N4CCC(O)(c5ccc(Cl)cc5)CC4)cccn3n2)cc1)N1CCC2(CCCN2)CC1] | [4-[[8-[4-(4-chlorophenyl)-4-hydroxy-1-piperidyl]-[1,2,4]triazolo[1,5-a]pyridin-2-yl]amino]phenyl]-(1,8-diazaspiro[4.5]decan-8-yl)methanone |

TABLE A-continued

Exemplary Compounds of the Present Invention

| Ex. | Structure | Name |
|---|---|---|
| 1-227 | 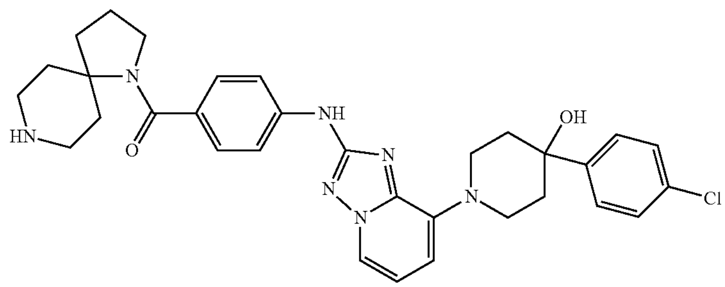 [SMILES: O=C(c1ccc(Nc2nc3c(N4CCC(O)(c5ccc(Cl)cc5)CC4)cccn3n2)cc1)N1CCCC12CCNCC2] | [4-[[8-[4-(4-chlorophenyl)-4-hydroxy-1-piperidyl]-[1,2,4]triazolo[1,5-a]pyridin-2-yl]amino]phenyl]-(1,8-diazaspiro[4.5]decan-1-yl)methanone |
| 1-228 | 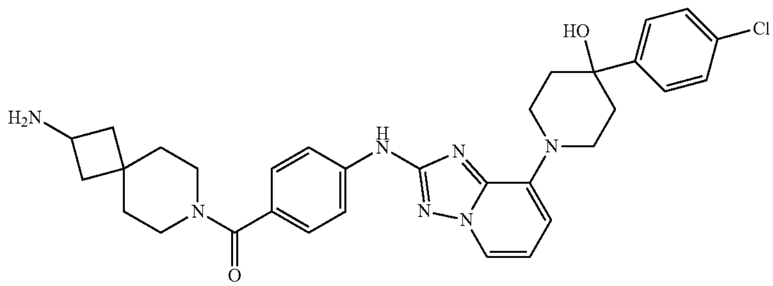 [SMILES: NC1CC2(CCN(C(=O)c3ccc(Nc4nc5c(N6CCC(O)(c7ccc(Cl)cc7)CC6)cccn5n4)cc3)CC2)C1] | (2-amino-7-azaspiro[3.5]nonan-7-yl)-[4-[[8-[4-(4-chlorophenyl)-4-hydroxy-1-piperidyl]-[1,2,4]triazolo[1,5-a]pyridin-2-yl]amino]phenyl]methanone |
| 1-229 | 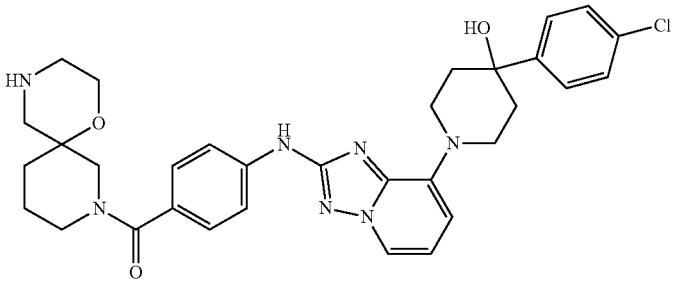 [SMILES: O=C(c1ccc(Nc2nc3c(N4CCC(O)(c5ccc(Cl)cc5)CC4)cccn3n2)cc1)N1CCCC2(CNCCO2)C1] | [4-[[8-[4-(4-chlorophenyl)-4-hydroxy-1-piperidyl]-[1,2,4]triazolo[1,5-a]pyridin-2-yl]amino]phenyl]-(1-oxa-4,8-diazaspiro[5.5]undecan-8-yl)methanone |
| 1-230 | 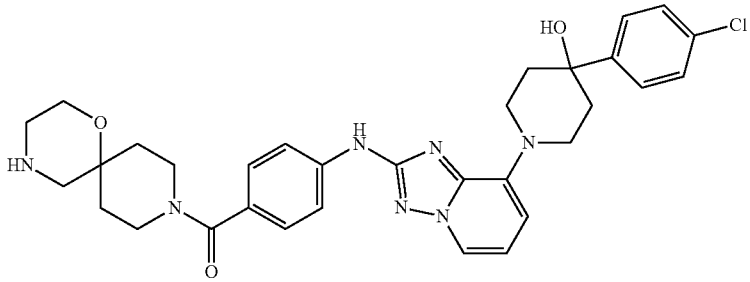 [SMILES: O=C(c1ccc(Nc2nc3c(N4CCC(O)(c5ccc(Cl)cc5)CC4)cccn3n2)cc1)N1CCC2(CC1)CNCCO2] | [4-[[8-[4-(4-chlorophenyl)-4-hydroxy-1-piperidyl]-[1,2,4]triazolo[1,5-a]pyridin-2-yl]amino]phenyl]-(1-oxa-4,9-diazaspiro[5.5]undecan-9-yl)methanone |
| 1-231 | 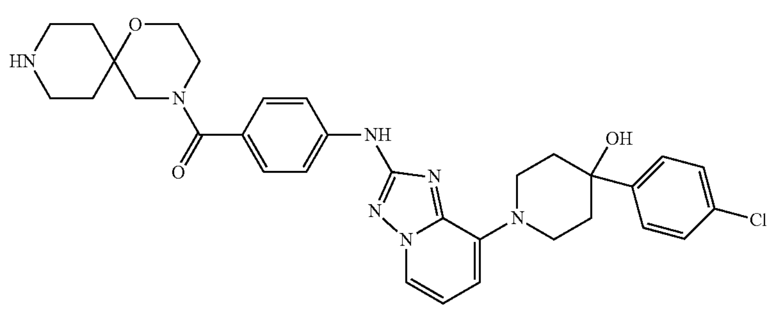 [SMILES: O=C(c1ccc(Nc2nc3c(N4CCC(O)(c5ccc(Cl)cc5)CC4)cccn3n2)cc1)N1CCOC2(CCNCC2)C1] | [4-[[8-[4-(4-chlorophenyl)-4-hydroxy-1-piperidyl]-[1,2,4]triazolo[1,5-a]pyridin-2-yl]amino]phenyl]-(1-oxa-4,9-diazaspiro[5.5]undecan-4-yl)methanone |

TABLE A-continued

Exemplary Compounds of the Present Invention

| Ex. | Structure | Name |
|---|---|---|
| 1-232 | 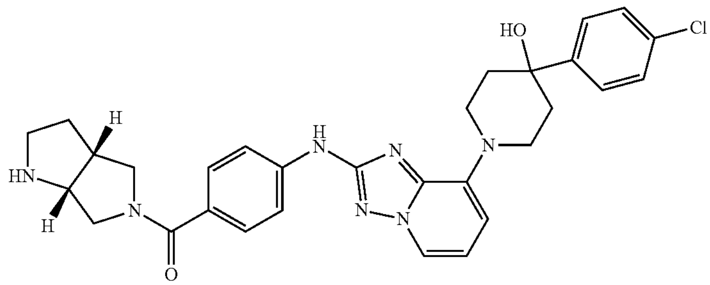 [SMILES: O=C(c1ccc(Nc2nc3c(N4CCC(O)(c5ccc(Cl)cc5)CC4)cccn3n2)cc1)N1C[C@H]2CCN[C@H]2C1] | [4-[[8-[4-(4-chlorophenyl)-4-hydroxy-1-piperidyl]-[1,2,4]triazolo[1,5-a]pyridin-2-yl]amino]phenyl]-[(1R,5R)-3,6-diazabicyclo[3.2.0]heptan-3-yl]methanone |
| 1-233 | 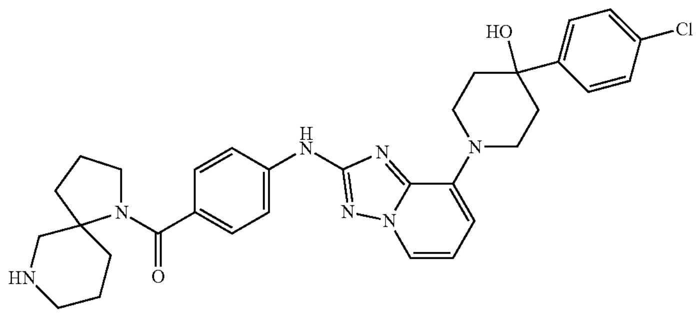 [SMILES: O=C(c1ccc(Nc2nc3c(N4CCC(O)(c5ccc(Cl)cc5)CC4)cccn3n2)cc1)N1CCCC12CCCNC2] | [4-[[8-[4-(4-chlorophenyl)-4-hydroxy-1-piperidyl]-[1,2,4]triazolo[1,5-a]pyridin-2-yl]amino]phenyl]-(1,9-diazaspiro[4.5]decan-1-yl)methanone |
| 1-234 | 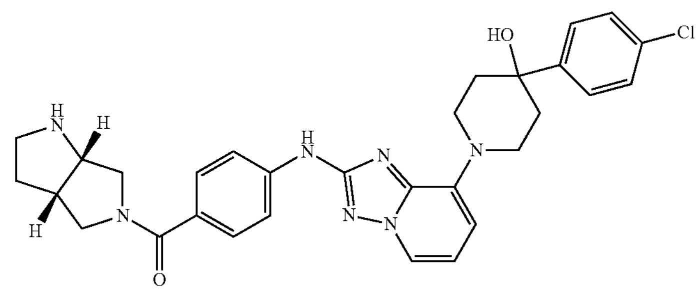 [SMILES: O=C(c1ccc(Nc2nc3c(N4CCC(O)(c5ccc(Cl)cc5)CC4)cccn3n2)cc1)N1C[C@@H]2CCN[C@@H]2C1] | [(3aS,6aS)-2,3,3a,4,6,6a-hexahydro-1H-pyrrolo[2,3-c]pyrrol-chlorophenyl)-4-hydroxy-1-piperidyl]-[1,2,4]triazolo[1,5-a]pyridin-2-yl]amino]phenyl] methanone |
| 1-235 | 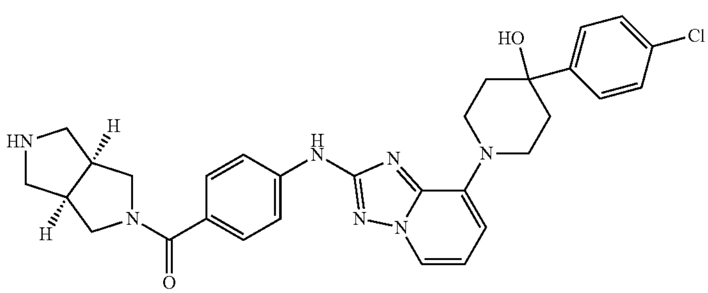 [SMILES: O=C(c1ccc(Nc2nc3c(N4CCC(O)(c5ccc(Cl)cc5)CC4)cccn3n2)cc1)N1C[C@H]2CNC[C@H]2C1] | [(3aR,6aS)-2,3,3a,4,6,6a-hexahydro-1H-pyrrolo[3,4-c]pyrrol-5-yl]-[4-[[8-[4-(4-chlorophenyl)-4-hydroxy-1-piperidyl]-[1,2,4]triazolo[1,5-a]pyridin-2-yl]amino]phenyl] methanone |
| 1-236 | 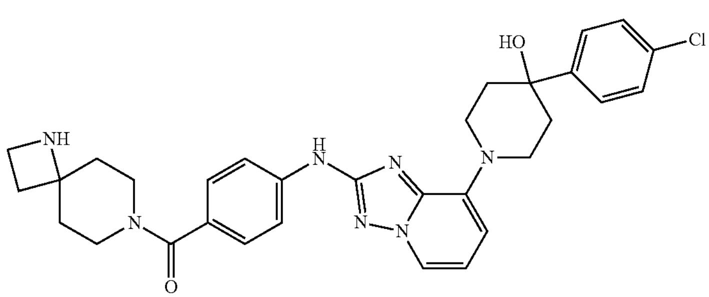 [SMILES: O=C(c1ccc(Nc2nc3c(N4CCC(O)(c5ccc(Cl)cc5)CC4)cccn3n2)cc1)N1CCC2(CCN2)CC1] | [4-[[8-[4-(4-chlorophenyl)-4-hydroxy-1-piperidyl]-[1,2,4]triazolo[1,5-a]pyridin-2-yl]amino]phenyl]-(1,7-diazaspiro[3.5]nonan-7-yl)methanone |

TABLE A-continued

Exemplary Compounds of the Present Invention

| Ex. | Structure | Name |
|---|---|---|
| 1-237 | 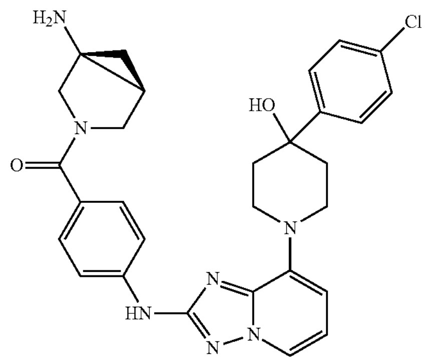 [SMILES: N[C@]12C[C@H]1CN(C(=O)c1ccc(Nc3nc4c(N5CCC(O)(c6ccc(Cl)cc6)CC5)cccn4n3)cc1)C2] | [(1S,5R)-5-amino-3-azabicyclo[3.1.0]hexan-3-yl]-[4-[[8-[4-(4-chlorophenyl)-4-hydroxy-1-piperidyl]-[1,2,4]triazolo[1,5-a]pyridin-2-yl]amino]phenyl]methanone |
| 1-238 | 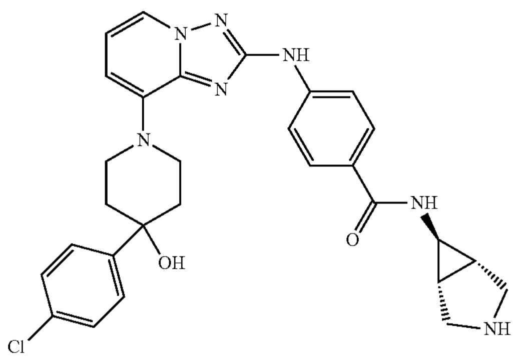 [SMILES: O=C(N[C@H]1[C@@H]2CNC[C@@H]21)c1ccc(Nc2nc3c(N4CCC(O)(c5ccc(Cl)cc5)CC4)cccn3n2)cc1] | N-[(1R,5S)-3-azabicyclo[3.1.0]hexan-6-yl]-4-[[8-[4-(4-chlorophenyl)-4-hydroxy-1-piperidyl]-[1,2,4]triazolo[1,5-a]pyridin-2-yl]amino]benzamide |
| 1-239 | 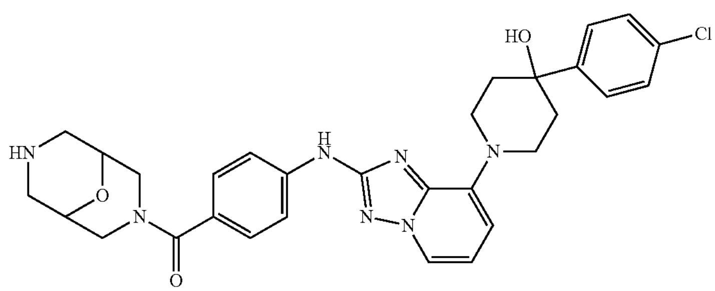 [SMILES: O=C(c1ccc(Nc2nc3c(N4CCC(O)(c5ccc(Cl)cc5)CC4)cccn3n2)cc1)N1CC2CNCC(C1)O2] | [4-[[8-[4-(4-chlorophenyl)-4-hydroxy-1-piperidyl]-[1,2,4]triazolo[1,5-a]pyridin-2-yl]amino]phenyl]-(9-oxa-3,7-diazabicyclo[3.3.1]nonan-3-yl)methanone |
| 1-240 | 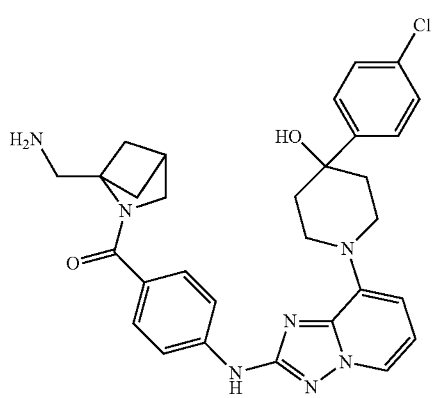 [SMILES: NCC12CC(CN1C(=O)c1ccc(Nc3nc4c(N5CCC(O)(c6ccc(Cl)cc6)CC5)cccn4n3)cc1)C2] | 4-(aminomethyl)-3-azabicyclo[2.1.1]hexan-3-yl]-[4-[[8-[4-(4-chlorophenyl)-4-hydroxy-1-piperidyl]-[1,2,4]triazolo[1,5-a]pyridin-2-yl]amino]phenyl]methanone |

TABLE A-continued

Exemplary Compounds of the Present Invention

| Ex. | Structure | Name |
|---|---|---|
| 1-241 | 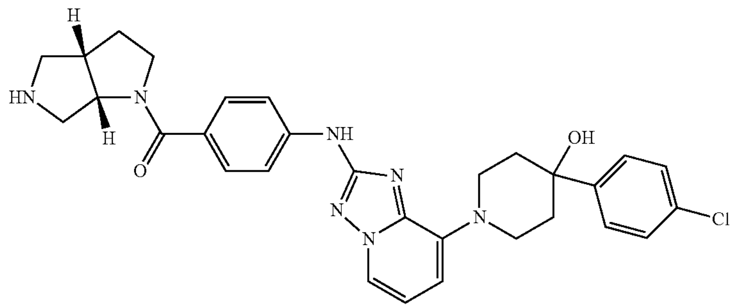 [SMILES: O=C(c1ccc(Nc2nc3c(N4CCC(O)(c5ccc(Cl)cc5)CC4)cccn3n2)cc1)N1CC[C@H]2CNC[C@H]21] | [(3aS,6aS)-3,3a,4,5,6,6a-hexahydro-2H-pyrrolo[2,3-c]pyrrol-1-yl]-[4-[[8-[4-(4-chlorophenyl)-4-hydroxy-1-piperidyl]-[1,2,4]triazolo[1,5-a]pyridin-2-yl]amino]phenyl]methanone |
| 1-242 | 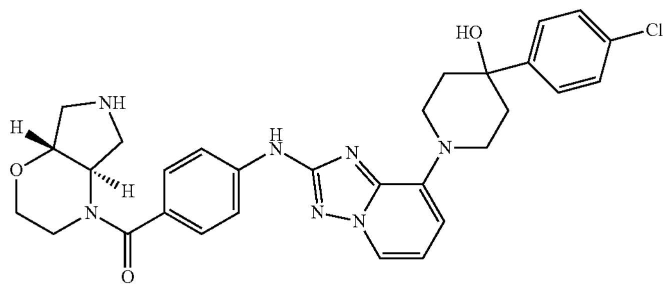 [SMILES: O=C(c1ccc(Nc2nc3c(N4CCC(O)(c5ccc(Cl)cc5)CC4)cccn3n2)cc1)N1CCO[C@@H]2CNC[C@H]21] | [(4aR,7aR)-3,4a,5,6,7,7a-hexahydro-2H-pyrrolo[3,4-b][1,4]oxazin-4-yl]-[4-[[8-[4-(4-chlorophenyl)-4-hydroxy-1-piperidyl]-[1,2,4]triazolo[1,5-a]pyridin-2-yl]amino]phenyl]methanone |
| 1-243 | 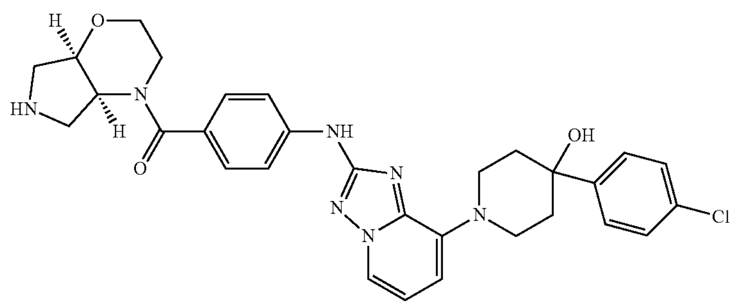 [SMILES: O=C(c1ccc(Nc2nc3c(N4CCC(O)(c5ccc(Cl)cc5)CC4)cccn3n2)cc1)N1CCO[C@@H]2CNC[C@@H]21] | [(4aS,7aR)-3,4a,5,6,7,7a-hexahydro-2H-pyrrolo[3,4-b][1,4]oxazin-4-yl]-[4-[[8-[4-(4-chlorophenyl)-4-hydroxy-1-piperidyl]-[1,2,4]triazolo[1,5-a]pyridin-2-yl]amino]phenyl]methanone |
| 1-244 | 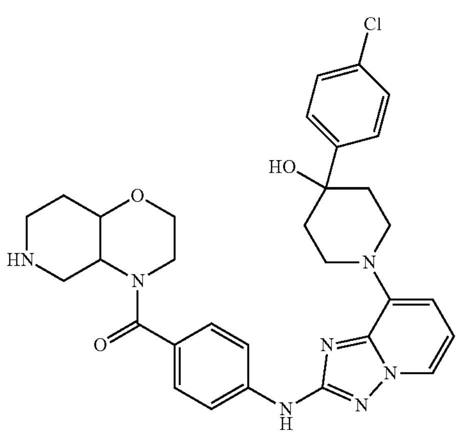 [SMILES: O=C(c1ccc(Nc2nc3c(N4CCC(O)(c5ccc(Cl)cc5)CC4)cccn3n2)cc1)N1CCOC2CCNCC21] | 2,3,4a,5,6,7,8,8a-octahydropyrido[4,3-b][1,4]oxazin-4-yl[4-[[8-[4-(4-chlorophenyl)-4-hydroxy-1-piperidyl]-[1,2,4]triazolo[1,5-a]pyridin-2-yl]amino]phenyl]methanone |

TABLE A-continued

Exemplary Compounds of the Present Invention

| Ex. | Structure | Name |
|---|---|---|
| 1-245 | 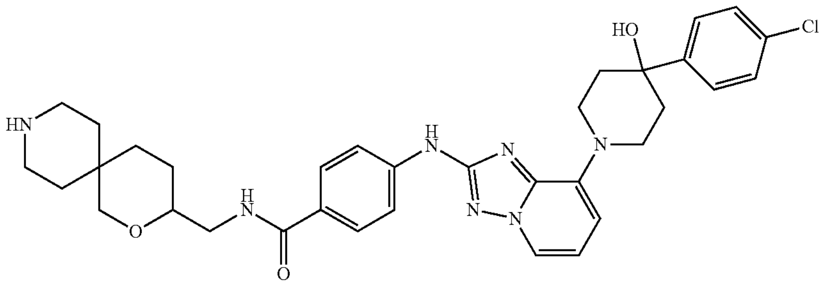 [SMILES: O=C(NCC1CCC2(CCNCC2)CO1)c1ccc(Nc2nc3c(N4CCC(O)(c5ccc(Cl)cc5)CC4)cccn3n2)cc1] | 4-[[8-[4-(4-chlorophenyl)-4-hydroxy-1-piperidyl]-[1,2,4]triazolo[1,5-a]pyridin-2-yl]amino]-N-(2-oxa-9-azaspiro[5.5]undecan-3-ylmethyl)benzamide |
| 1-246 | 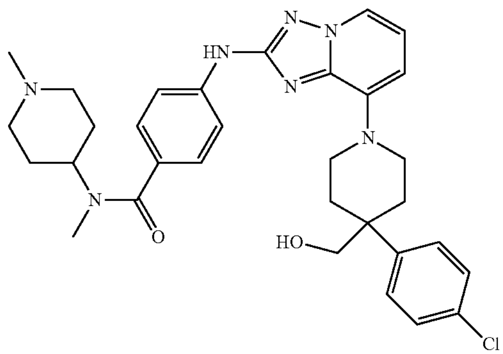 [SMILES: CN1CCC(N(C)C(=O)c2ccc(Nc3nc4c(N5CCC(CO)(c6ccc(Cl)cc6)CC5)cccn4n3)cc2)CC1] | 4-[[8-[4-(4-chlorophenyl)-4-(hydroxymethyl)-1-piperidyl]-[1,2,4]triazolo[1,5-a]pyridin-2-yl]amino]-N-methyl-N-(1-methyl-4-piperidyl)benzamide |
| 1-247 | 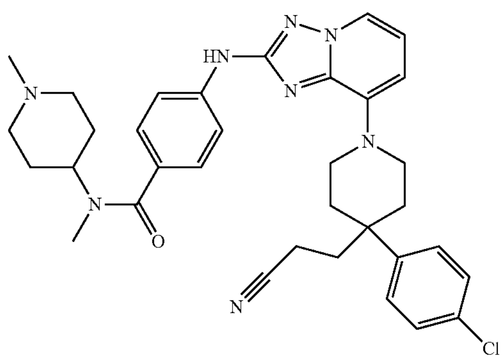 [SMILES: CN1CCC(N(C)C(=O)c2ccc(Nc3nc4c(N5CCC(CCC#N)(c6ccc(Cl)cc6)CC5)cccn4n3)cc2)CC1] | 4-[[8-[4-(4-chlorophenyl)-4-(2-cyanoethyl)-1-piperidyl]-[1,2,4]triazolo[1,5-a]pyridin-2-yl]amino]-N-methyl-N-(1-methyl-4-piperidyl)benzamide |
| 1-248 | 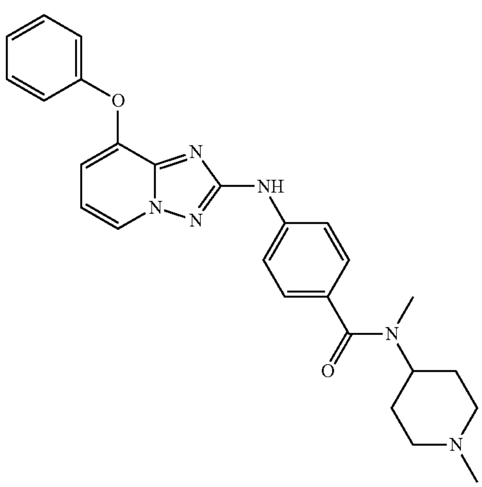 [SMILES: CN1CCC(N(C)C(=O)c2ccc(Nc3nc4c(Oc5ccccc5)cccn4n3)cc2)CC1] | N-methyl-N-(1-methyl-4-piperidyl)-4-[(8-phenoxy-[1,2,4]triazolo[1,5-a]pyridin-2-yl)amino]benzamide |

TABLE A-continued

Exemplary Compounds of the Present Invention

| Ex. | Structure | Name |
|---|---|---|
| 1-249 | 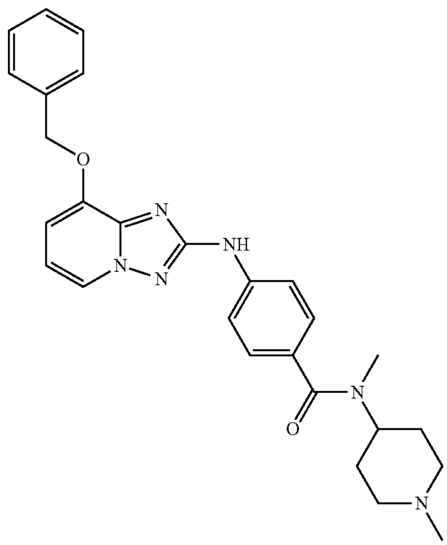 [SMILES: CN1CCC(N(C)C(=O)c2ccc(Nc3nc4c(OCc5ccccc5)cccn4n3)cc2)CC1] | 4-[(8-benzyloxy-[1,2,4]triazolo[1,5-a]pyridin-2-yl)amino]-N-methyl-N-(1-methyl-4-piperidyl)benzamide |
| 1-250 | 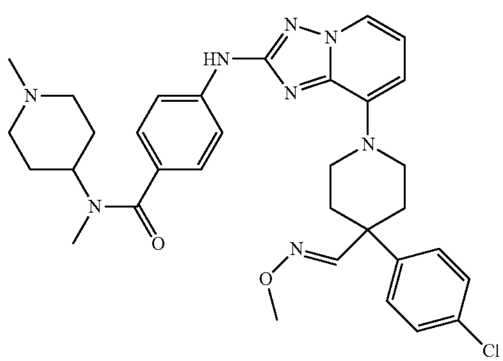 [SMILES: CO/N=C/C1(c2ccc(Cl)cc2)CCN(c2cccn3nc(Nc4ccc(C(=O)N(C)C5CCN(C)CC5)cc4)nc23)CC1] | 4-[[8-[4-(4-chlorophenyl)-4-[(E)-methoxyiminomethyl]-1-piperidyl]-[1,2,4]triazolo[1,5-a]pyridin-2-yl]amino]-N-methyl-N-(1-methyl-4-piperidyl)benzamide |
| 1-251 | 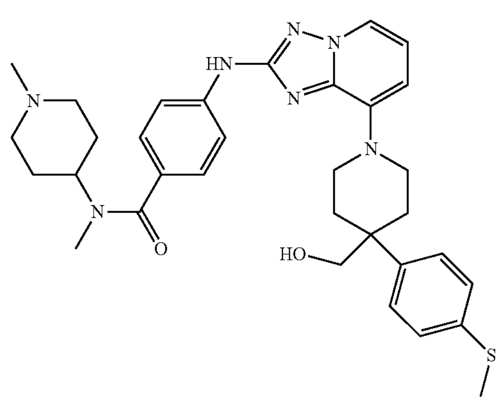 [SMILES: CSc1ccc(C2(CO)CCN(c3cccn4nc(Nc5ccc(C(=O)N(C)C6CCN(C)CC6)cc5)nc34)CC2)cc1] | 4-[[8-[4-(hydroxymethyl)-4-(4-methylsulfanylphenyl)-1-piperidyl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 1-252 | 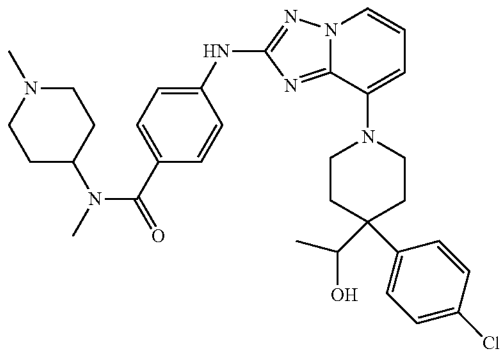 [SMILES: CC(O)C1(c2ccc(Cl)cc2)CCN(c2cccn3nc(Nc4ccc(C(=O)N(C)C5CCN(C)CC5)cc4)nc23)CC1] | 4-[[8-[4-(4-chlorophenyl)-4-(1-hydroxyethyl)-1-piperidyl]-[1,2,4]triazolo[1,5-a]pyridin-2-yl]amino]-N-methyl-N-(1-methyl-4-piperidyl)benzamide |
| 1-253 | 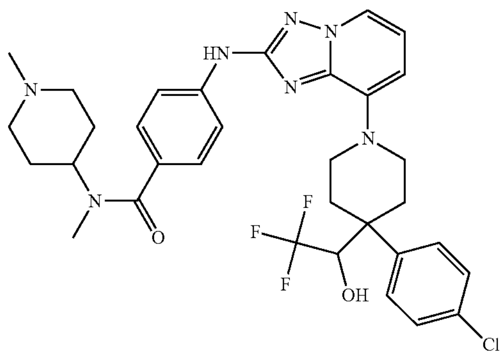 [SMILES: CN1CCC(N(C)C(=O)c2ccc(Nc3nc4c(N5CCC(c6ccc(Cl)cc6)(C(O)C(F)(F)F)CC5)cccn4n3)cc2)CC1] | 4-[[8-[4-(4-chlorophenyl)-4-(2,2,2-trifluoro-1-hydroxy-ethyl)-1-piperidyl]-[1,2,4]triazolo[1,5-a]pyridin-2-yl]amino]-N-methyl-N-(1-methyl-4-piperidyl)benzamide |
| 1-254 | 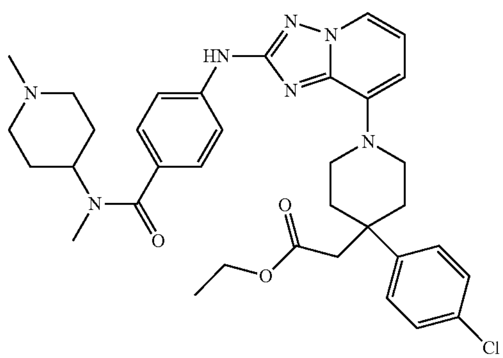 [SMILES: CCOC(=O)CC1(c2ccc(Cl)cc2)CCN(c2cccn3nc(Nc4ccc(C(=O)N(C)C5CCN(C)CC5)cc4)nc23)CC1] | ethyl 2-[4-(4-chlorophenyl)-1-[2-[4-[methyl-(1-methyl-4-piperidyl)carbamoyl]anilino]-[1,2,4]triazolo[1,5-a]pyridin-8-yl]-4-piperidyl]acetate |
| 1-255 | 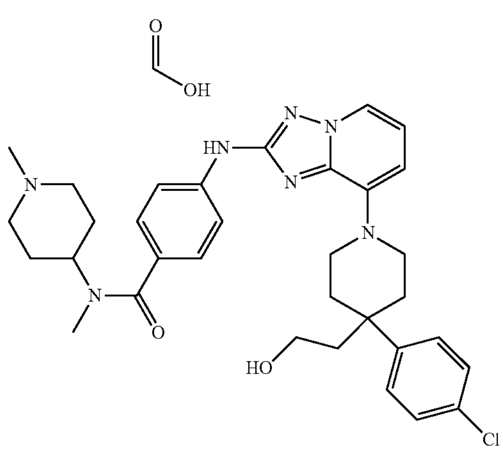 [SMILES: O=CO ; CN1CCC(N(C)C(=O)c2ccc(Nc3nc4c(N5CCC(CCO)(c6ccc(Cl)cc6)CC5)cccn4n3)cc2)CC1] | 4-[[8-[4-(4-chlorophenyl)-4-(2-hydroxyethyl)-1-piperidyl]-[1,2,4]triazolo[1,5-a]pyridin-2-yl]amino]-N-methyl-N-(1-methyl-4-piperidyl)benzamide; formic acid |

TABLE A-continued

Exemplary Compounds of the Present Invention

| Ex. | Structure | Name |
|---|---|---|
| 1-256 | 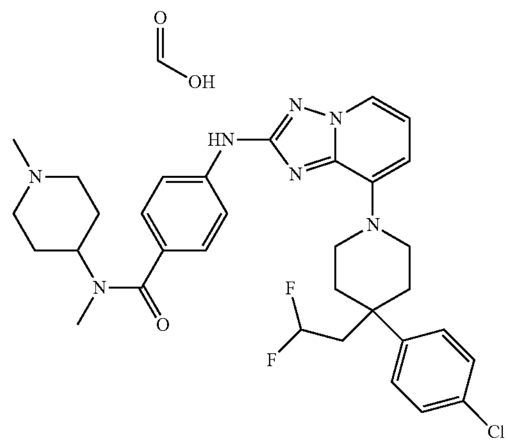 [SMILES: O=CO ; CN1CCC(N(C)C(=O)c2ccc(Nc3nc4c(N5CCC(CC(F)F)(c6ccc(Cl)cc6)CC5)cccn4n3)cc2)CC1] | 4-[[piperidyl]-8-[4-(4-chlorophenyl)-4-(2,2-difluoroethyl)-1-[1,2,4]triazolo[1,5-a]pyridin-2-yl]amino]-N-methyl-N-(1-methyl-4-piperidyl)benzamide; formic acid |
| 1-257 | 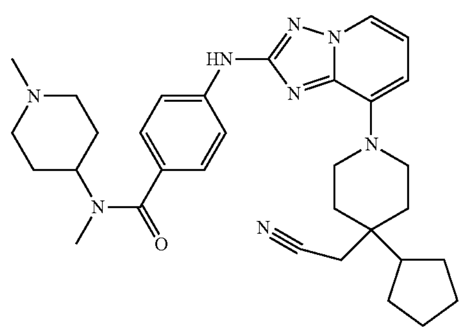 [SMILES: CN1CCC(N(C)C(=O)c2ccc(Nc3nc4c(N5CCC(CC#N)(C6CCCC6)CC5)cccn4n3)cc2)CC1] | 4-[[8-[4-(cyanomethyl)-4-cyclopentyl-1-piperidyl]-[1,2,4]triazolo[1,5-a]pyridin-2-yl]amino]-N-methyl-N-(1-methyl-4-piperidyl)benzamide |
| 1-258 | 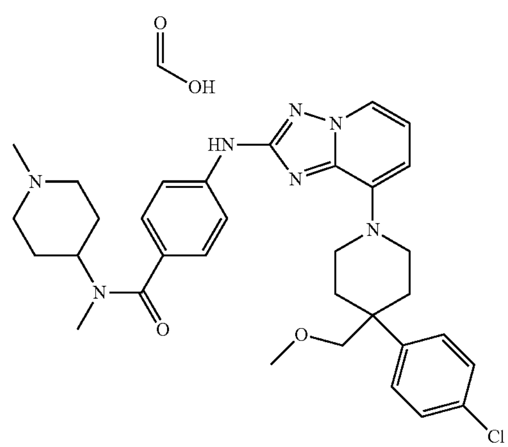 [SMILES: O=CO ; COCC1(c2ccc(Cl)cc2)CCN(c2cccn3nc(Nc4ccc(C(=O)N(C)C5CCN(C)CC5)cc4)nc23)CC1] | 4-[[8-[4-(4-chlorophenyl)-4-(methoxymethyl)-1-piperidyl]-[1,2,4]triazolo[1,5-a]pyridin-2-yl]amino]-N-methyl-N-(1-methyl-4-piperidyl)benzamide; formic acid |
| 1-259 | 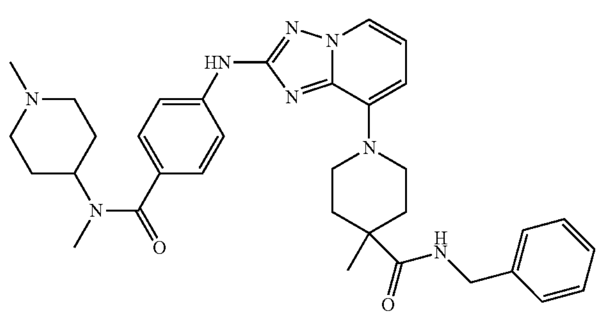 [SMILES: CN1CCC(N(C)C(=O)c2ccc(Nc3nc4c(N5CCC(C)(C(=O)NCc6ccccc6)CC5)cccn4n3)cc2)CC1] | N-benzyl-4-methyl-1-[2-[4-[methyl-(1-methyl-4-piperidyl)carbamoyl]anilino]-[1,2,4]triazolo[1,5-a]pyridin-8-yl]piperidine-4-carboxamide |

TABLE A-continued

Exemplary Compounds of the Present Invention

| Ex. | Structure | Name |
|---|---|---|
| 1-260 | 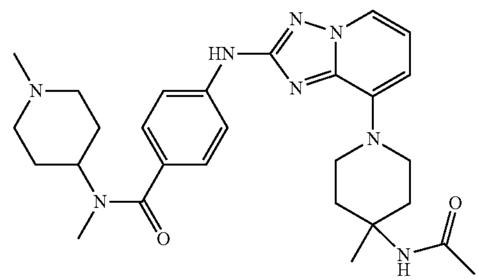 [SMILES: CC(=O)NC1(C)CCN(c2cccn3nc(Nc4ccc(C(=O)N(C)C5CCN(C)CC5)cc4)nc23)CC1] | 4-[[8-(4-acetamido-4-methyl-1-piperidyl)-[1,2,4]triazolo[1,5-a]pyridin-2-yl]amino]-N-methyl-N-(1-methyl-4-piperidyl)benzamide |
| 1-261 | 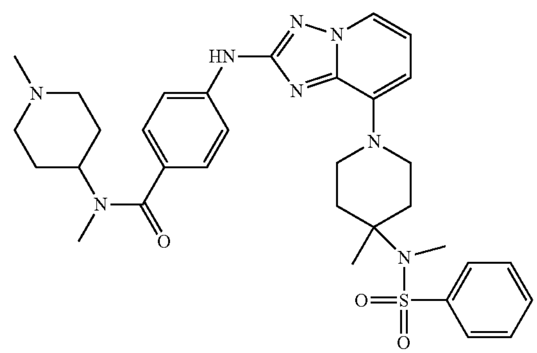 [SMILES: CN1CCC(N(C)C(=O)c2ccc(Nc3nc4c(N5CCC(C)(N(C)S(=O)(=O)c6ccccc6)CC5)cccn4n3)cc2)CC1] | 4-[[8-[4-[benzenesulfonyl(methyl)amino]-4-methyl-1-piperidyl]-[1,2,4]triazolo[1,5-a]pyridin-2-yl]amino]-N-methyl-N-(1-methyl-4-piperidyl)benzamide |
| 1-262 | 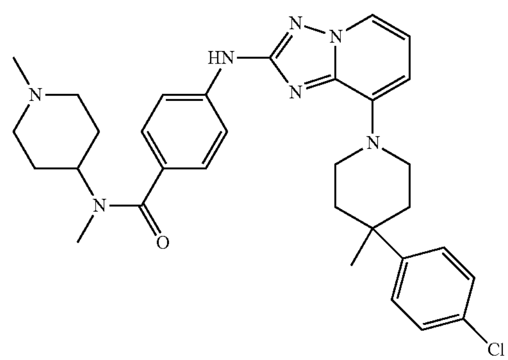 [SMILES: CN1CCC(N(C)C(=O)c2ccc(Nc3nc4c(N5CCC(C)(c6ccc(Cl)cc6)CC5)cccn4n3)cc2)CC1] | 4-[[8-[4-(4-chlorophenyl)-4-methyl-1-piperidyl]-[1,2,4]triazolo[1,5-a]pyridin-2-yl]amino]-N-methyl-N-(1-methyl-4-piperidyl)benzamide |
| 1-263 | 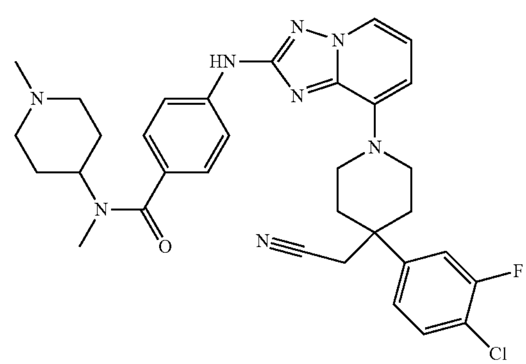 [SMILES: CN1CCC(N(C)C(=O)c2ccc(Nc3nc4c(N5CCC(CC#N)(c6ccc(Cl)c(F)c6)CC5)cccn4n3)cc2)CC1] | 4-[[8-[4-(4-chloro-3-fluoro-phenyl)-4-(cyanomethyl)-1-piperidyl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 1-264 | 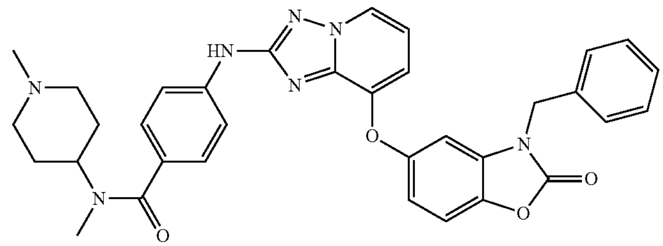 [SMILES: CN1CCC(N(C)C(=O)c2ccc(Nc3nc4c(Oc5ccc6oc(=O)n(Cc7ccccc7)c6c5)cccn4n3)cc2)CC1] | 4-[[8-[(3-benzyl-2-oxo-1,3-benzoxazol-5-yl)oxy]-[1,2,4]triazolo[1,5-a]pyridin-2-yl]amino]-N-methyl-N-(1-methyl-4-piperidyl)benzamide |
| 1-265 | 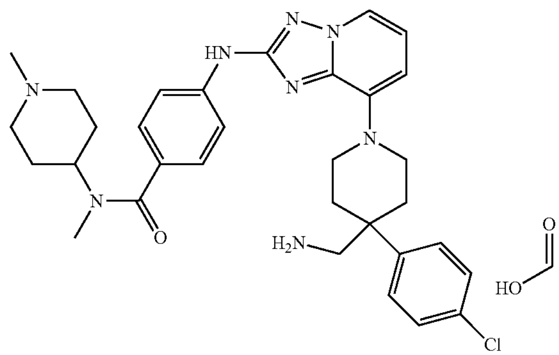 | 4-[[8-[4-(aminomethyl)-4-(4-chlorophenyl)-1-piperidyl]-[1,2,4]triazolo[1,5-a]pyridin-2-yl]amino]-N-methyl-N-(1-methyl-4-piperidyl)benzamide; formic acid |
| 1-266 | 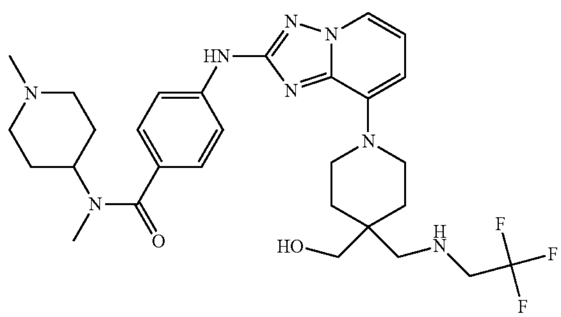 [SMILES: CN1CCC(N(C)C(=O)c2ccc(Nc3nc4c(N5CCC(CO)(CNCC(F)(F)F)CC5)cccn4n3)cc2)CC1] | 4-[[8-[4-(hydroxymethyl)-4-[(2,2,2-trifluoroethylamino)methyl]-1-piperidyl]-[1,2,4]triazolo[1,5-a]pyridin-2-yl]amino]-N-methyl-N-(1-methyl-4-piperidyl)benzamide |
| 1-267 | 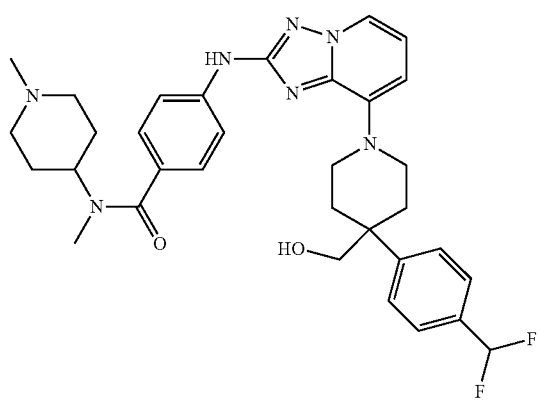 [SMILES: CN1CCC(N(C)C(=O)c2ccc(Nc3nc4c(N5CCC(CO)(c6ccc(C(F)F)cc6)CC5)cccn4n3)cc2)CC1] | 4-[[8-[4-[4-(difluoromethyl)phenyl]-4-(hydroxymethyl)-1-piperidyl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 1-268 | 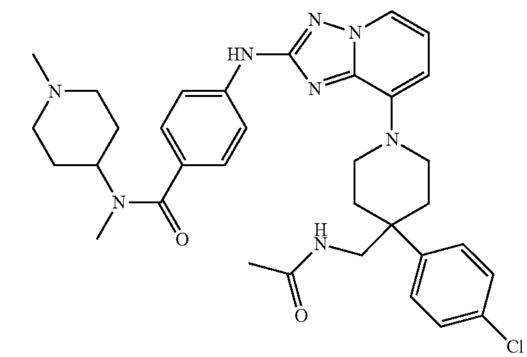 [SMILES: CC(=O)NCC1(c2ccc(Cl)cc2)CCN(c2cccn3nc(Nc4ccc(C(=O)N(C)C5CCN(C)CC5)cc4)nc23)CC1] | 4-[[8-[4-(acetamidomethyl)-4-(4-chlorophenyl)-1-piperidyl]-[1,2,4]triazolo[1,5-a]pyridin-2-yl]amino]-N-methyl-N-(1-methyl-4-piperidyl)benzamide |
| 1-269 | 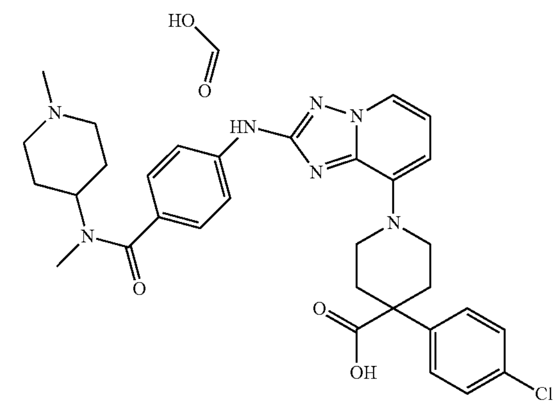 | 4-(4-chlorophenyl)-1-[2-[4-[methyl-(1-methyl-4-piperidyl)carbamoyl]anilino]-[1,2,4]triazolo[1,5-a]pyridin-8-yl]piperidine-4-carboxylic acid; formic acid |
| 1-270 | 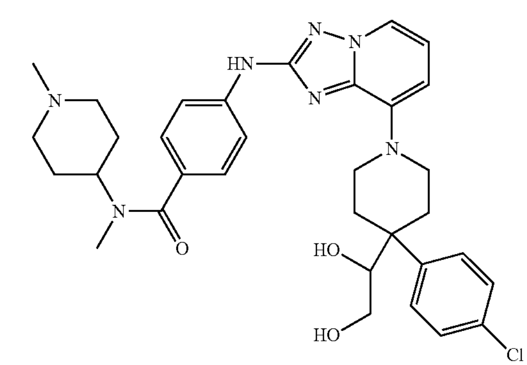 [SMILES: CN1CCC(N(C)C(=O)c2ccc(Nc3nc4c(N5CCC(c6ccc(Cl)cc6)(C(O)CO)CC5)cccn4n3)cc2)CC1] | 4-[[8-[4-(4-chlorophenyl)-4-(1,2-dihydroxyethyl)-1-piperidyl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 1-271 | 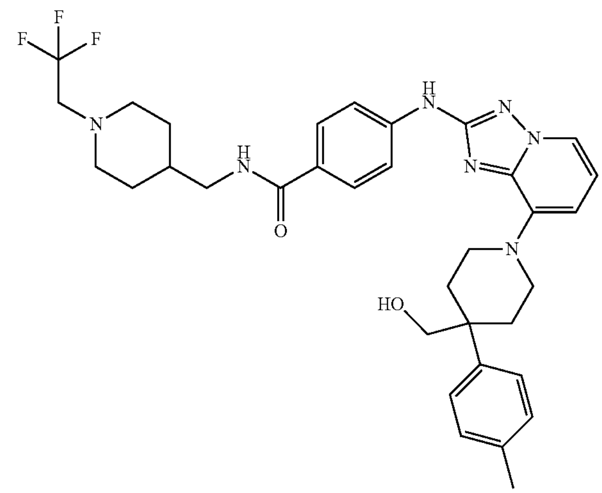 [SMILES: Cc1ccc(C2(CO)CCN(c3cccn4nc(Nc5ccc(C(=O)NCC6CCN(CC(F)(F)F)CC6)cc5)nc34)CC2)cc1] | 4-[[8-[4-(4-chlorophenyl)-4-(hydroxymethyl)-1-piperidyl]-[1,2,4]triazolo[1,5-a]pyridin-2-yl]amino]-N-[[1-(2,2,2-trifluoroethyl)-4-piperidyl]methyl]benzamide |
| 1-272 | 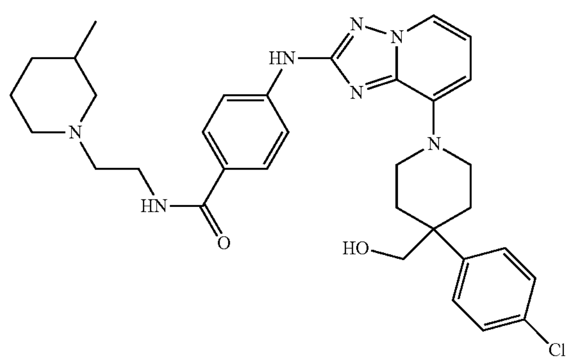 [SMILES: CC1CCCN(CCNC(=O)c2ccc(Nc3nc4c(N5CCC(CO)(c6ccc(Cl)cc6)CC5)cccn4n3)cc2)C1] | 4-[[8-[4-(4-chlorophenyl)-4-(hydroxymethyl)-1-piperidyl]-[1,2,4]triazolo[1,5-a]pyridin-2-yl]amino]-N-[2-(3-methyl-1-piperidyl)ethyl]benzamide |
| 1-273 | 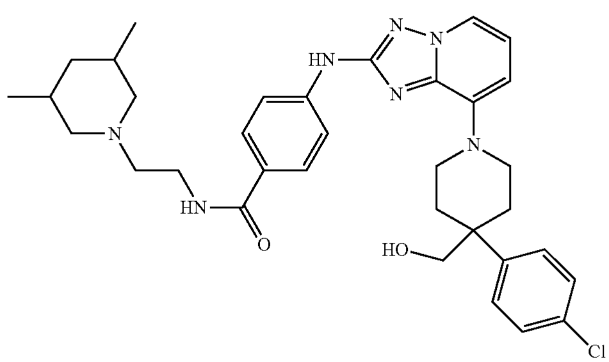 [SMILES: CC1CC(C)CN(CCNC(=O)c2ccc(Nc3nc4c(N5CCC(CO)(c6ccc(Cl)cc6)CC5)cccn4n3)cc2)C1] | 4-[[8-[4-(4-chlorophenyl)-4-(hydroxymethyl)-1-piperidyl]-[1,2,4]triazolo[1,5-a]pyridin-2-yl]amino]-N-[2-(3,5-dimethyl-1-piperidyl)ethyl]benzamide |

TABLE A-continued

Exemplary Compounds of the Present Invention

| Ex. | Structure | Name |
|---|---|---|
| 1-274 | 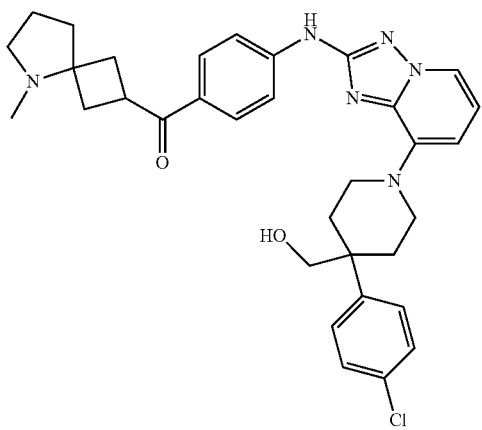 [SMILES: CN1CCCC12CC(C(=O)c1ccc(Nc3nc4c(N5CCC(CO)(c6ccc(Cl)cc6)CC5)cccn4n3)cc1)C2] | [4-[[8-[4-(4-chlorophenyl)-4-(hydroxymethyl)-1-piperidyl]-[1,2,4]triazolo[1,5-a]pyridin-2-yl]amino]phenyl]-(5-methyl-2,5-diazaspiro[3.4]octan-2-yl)methanone |
| 1-275 | 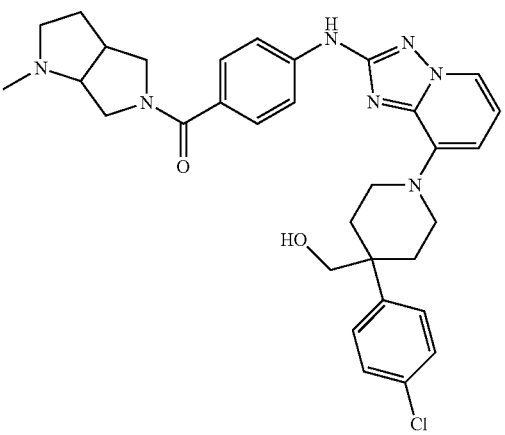 [SMILES: CN1CCC2CN(C(=O)c3ccc(Nc4nc5c(N6CCC(CO)(c7ccc(Cl)cc7)CC6)cccn5n4)cc3)CC21] | [4-[[8-[4-(4-chlorophenyl)-4-(hydroxymethyl)-1-piperidyl]-[1,2,4]triazolo[1,5-a]pyridin-2-yl]amino]phenyl]-(1-methyl-2,3,3a,4,6,6a-hexahydropyrrolo[2,3-c]pyrrol-5-yl)methanone |
| 1-276 | 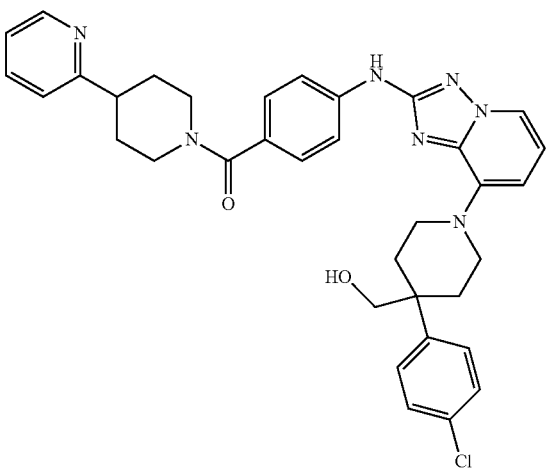 [SMILES: O=C(c1ccc(Nc2nc3c(N4CCC(CO)(c5ccc(Cl)cc5)CC4)cccn3n2)cc1)N1CCC(c2ccccn2)CC1] | [4-[[8-[4-(4-chlorophenyl)-4-(hydroxymethyl)-1-piperidyl]-[1,2,4]triazolo[1,5-a]pyridin-2-yl]amino]phenyl]-[4-(2-pyridyl)-1-piperidyl]methanone |

TABLE A-continued

Exemplary Compounds of the Present Invention

| Ex. | Structure | Name |
|---|---|---|
| 1-277 | 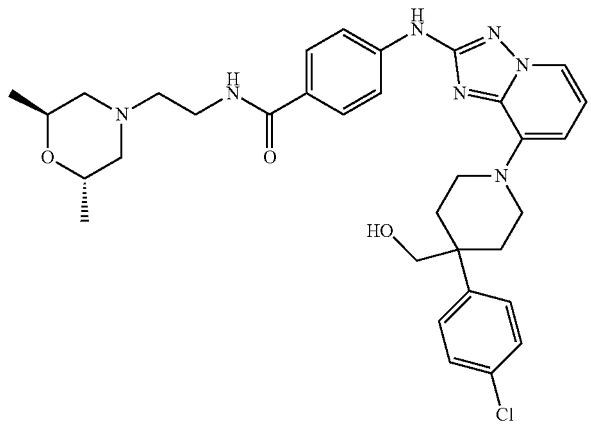 [SMILES: C[C@H]1CN(CCNC(=O)c2ccc(Nc3nc4c(N5CCC(CO)(c6ccc(Cl)cc6)CC5)cccn4n3)cc2)C[C@H](C)O1] | 4-[[8-[4-(4-chlorophenyl)-4-(hydroxymethyl)-1-piperidyl]-[1,2,4]triazolo[1,5-a]pyridin-2-yl]amino]-N-[2-[(2S,6S)-2,6-dimethylmorpholin-4-yl]ethyl]benzamide |
| 1-278 | 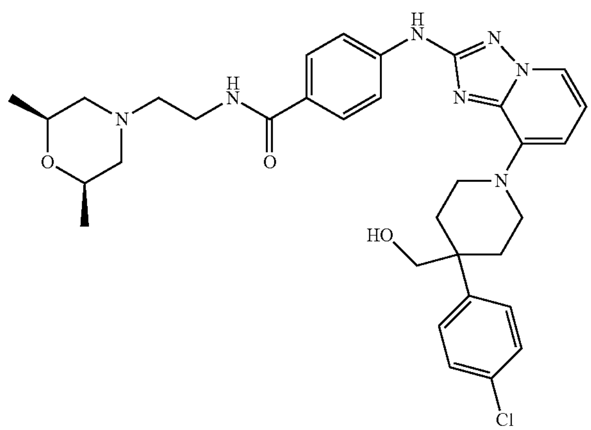 [SMILES: C[C@@H]1CN(CCNC(=O)c2ccc(Nc3nc4c(N5CCC(CO)(c6ccc(Cl)cc6)CC5)cccn4n3)cc2)C[C@H](C)O1] | 4-[[8-[4-(4-chlorophenyl)-4-(hydroxymethyl)-1-piperidyl]-[1,2,4]triazolo[1,5-a]pyridin-2-yl]amino]-N-[2-[(2R,6S)-2,6-dimethylmorpholin-4-yl]ethyl]benzamide |
| 1-279 | 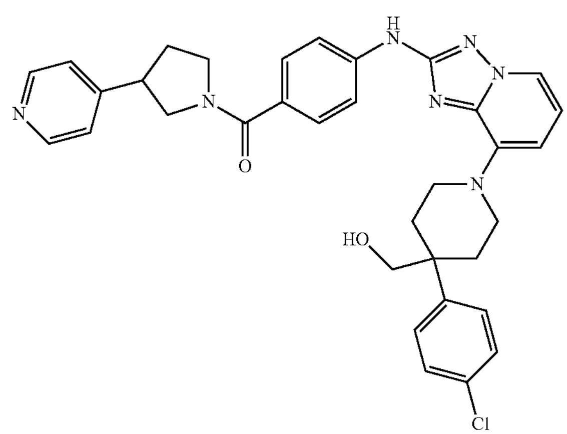 [SMILES: O=C(c1ccc(Nc2nc3c(N4CCC(CO)(c5ccc(Cl)cc5)CC4)cccn3n2)cc1)N1CCC(c2ccncc2)C1] | [4-[[8-[4-(4-chlorophenyl)-4-(hydroxymethyl)-1-piperidyl]-[1,2,4]triazolo[1,5-a]pyridin-2-yl]amino]phenyl]-[3-(4-pyridyl)pyrrolidin-1-yl]methanone |

TABLE A-continued

Exemplary Compounds of the Present Invention

| Ex. | Structure | Name |
|---|---|---|
| 1-280 | 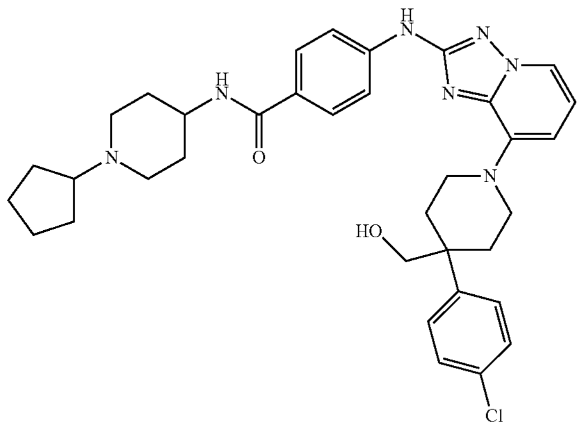 [SMILES: O=C(NC1CCN(C2CCCC2)CC1)c1ccc(Nc2nc3c(N4CCC(CO)(c5ccc(Cl)cc5)CC4)cccn3n2)cc1] | 4-[[8-[4-(4-chlorophenyl)-4-(hydroxymethyl)-1-piperidyl]-[1,2,4]triazolo[1,5-a]pyridin-2-yl]amino]-N-(1-cyclopentyl-4-piperidyl)benzamide |
| 1-281 | 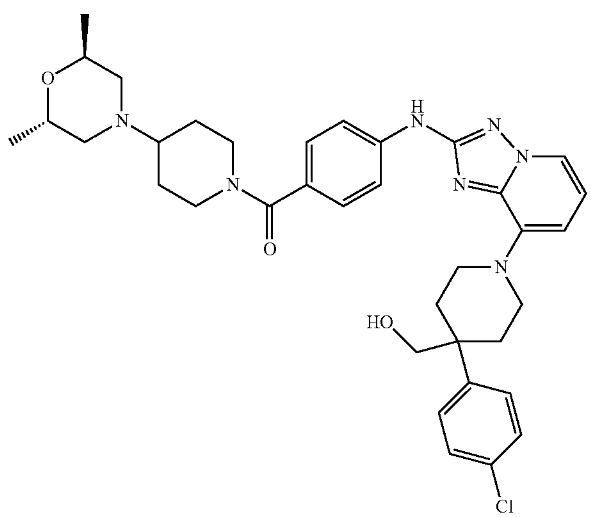 [SMILES: C[C@H]1CN(C2CCN(C(=O)c3ccc(Nc4nc5c(N6CCC(CO)(c7ccc(Cl)cc7)CC6)cccn5n4)cc3)CC2)C[C@H](C)O1] | [4-[[8-[4-(4-chlorophenyl)-4-(hydroxymethyl)-1-piperidyl]-[1,2,4]triazolo[1,5-a]pyridin-2-yl]amino]phenyl]-[4-[(2S,6S)-2,6-dimethylmorpholin-4-yl]-1-piperidyl]methanone |
| 1-282 | 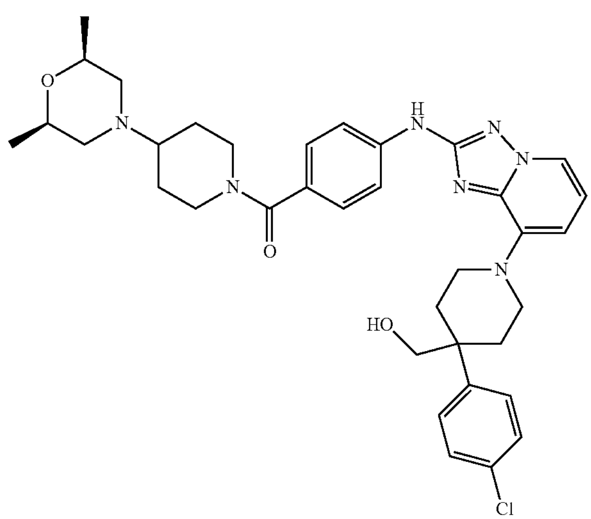 [SMILES: C[C@@H]1CN(C2CCN(C(=O)c3ccc(Nc4nc5c(N6CCC(CO)(c7ccc(Cl)cc7)CC6)cccn5n4)cc3)CC2)C[C@H](C)O1] | [4-[[8-[4-(4-chlorophenyl)-4-(hydroxymethyl)-1-piperidyl]-[1,2,4]triazolo[1,5-a]pyridin-2-yl]amino]phenyl]-[4-[(2R,6S)-2,6-dimethylmorpholin-4-yl]-1-piperidyl]methanone |

TABLE A-continued

Exemplary Compounds of the Present Invention

| Ex. | Structure | Name |
|---|---|---|
| 1-283 | 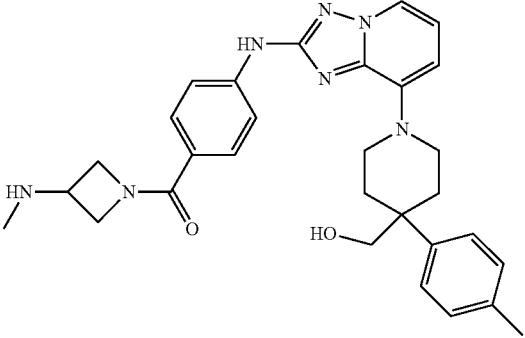 | [4-[[8-[4-(4-chlorophenyl)-4-(hydroxymethyl)-1-piperidyl]-[1,2,4]triazolo[1,5-a]pyridin-2-yl]amino]phenyl]-[3-(methylamino)azetidin-1-yl]methanone |
| 1-284 | 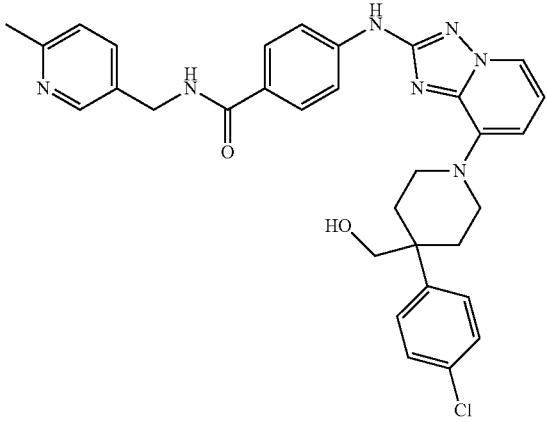 [SMILES: Cc1ccc(CNC(=O)c2ccc(Nc3nc4c(N5CCC(CO)(c6ccc(Cl)cc6)CC5)cccn4n3)cc2)cn1] | 4-[[8-[4-(4-chlorophenyl)-4-(hydroxymethyl)-1-piperidyl]-[1,2,4]triazolo[1,5-a]pyridin-2-yl]amino]-N-[(6-methyl-3-pyridyl)methyl]benzamide |
| 1-285 | 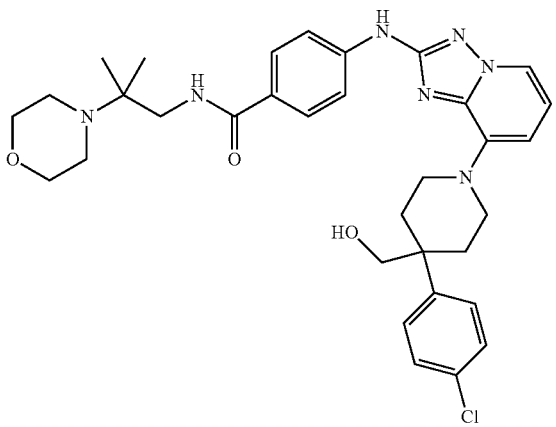 [SMILES: CC(C)(CNC(=O)c1ccc(Nc2nc3c(N4CCC(CO)(c5ccc(Cl)cc5)CC4)cccn3n2)cc1)N1CCOCC1] | 4-[[8-[4-(4-chlorophenyl)-4-(hydroxymethyl)-1-piperidyl]-[1,2,4]triazolo[1,5-a]pyridin-2-yl]amino]-N-(2-methyl-2-morpholino-propyl)benzamide |

TABLE A-continued

Exemplary Compounds of the Present Invention

| Ex. | Structure | Name |
|---|---|---|
| 1-286 | 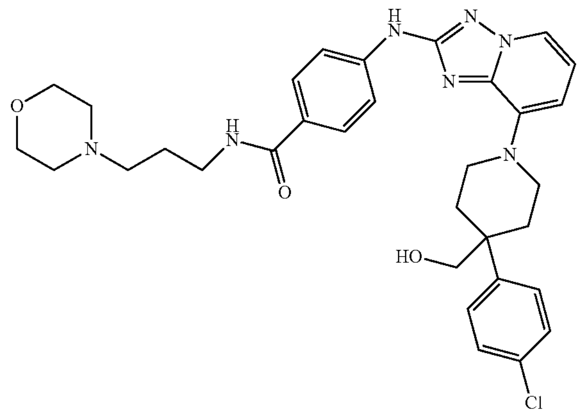 [SMILES: O=C(NCCCN1CCOCC1)c1ccc(Nc2nc3c(N4CCC(CO)(c5ccc(Cl)cc5)CC4)cccn3n2)cc1] | 4-[[8-[4-(4-chlorophenyl)-4-(hydroxymethyl)-1-piperidyl]-[1,2,4]triazolo[1,5-a]pyridin-2-yl]amino]-N-(3-morpholinopropyl)benzamide |
| 1-287 | 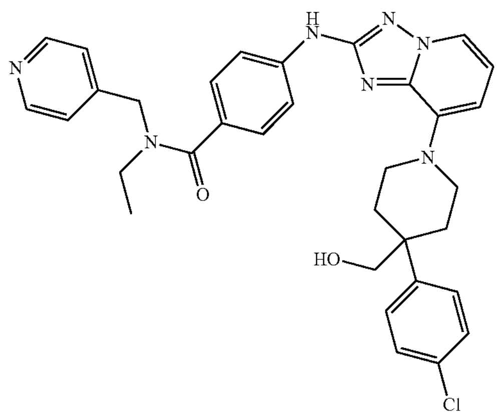 [SMILES: CCN(Cc1ccncc1)C(=O)c1ccc(Nc2nc3c(N4CCC(CO)(c5ccc(Cl)cc5)CC4)cccn3n2)cc1] | 4-[[8-[4-(4-chlorophenyl)-4-(hydroxymethyl)-1-piperidyl]-[1,2,4]triazolo[1,5-a]pyridin-2-yl]amino]-N-ethyl-N-(4-pyridylmethyl)benzamide |
| 1-288 | 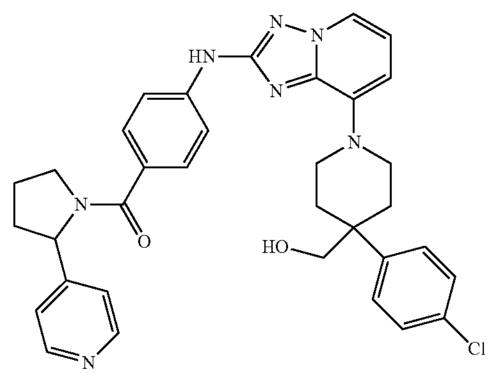 [SMILES: O=C(c1ccc(Nc2nc3c(N4CCC(CO)(c5ccc(Cl)cc5)CC4)cccn3n2)cc1)N1CCCC1c1ccncc1] | [4-[[8-[4-(4-chlorophenyl)-4-(hydroxymethyl)-1-piperidyl]-[1,2,4]triazolo[1,5-a]pyridin-2-yl]amino]phenyl]-[2-(4-pyridyl)pyrrolidin-1-yl]methanone |
| 1-289 | 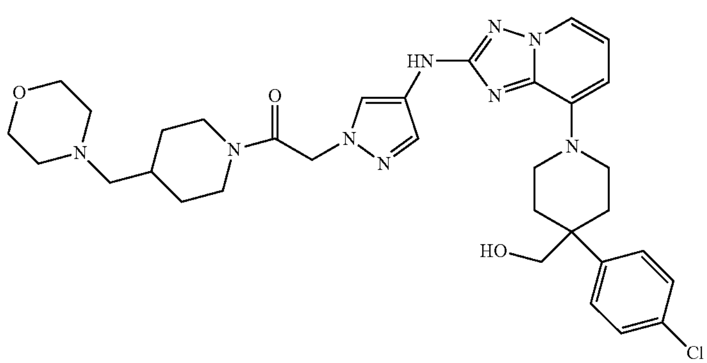 [SMILES: O=C(Cn1cc(Nc2nc3c(N4CCC(CO)(c5ccc(Cl)cc5)CC4)cccn3n2)cn1)N1CCC(CN2CCOCC2)CC1] | 2-[4-[[8-[4-(4-chlorophenyl)-4-(hydroxymethyl)-1-piperidyl]-[1,2,4]triazolo[1,5-a]pyridin-2-yl]amino]pyrazol-1-yl]-1-[4-(morpholinomethyl)-1-piperidyl]ethanone |

TABLE A-continued

Exemplary Compounds of the Present Invention

| Ex. | Structure | Name |
|---|---|---|
| 1-290 | 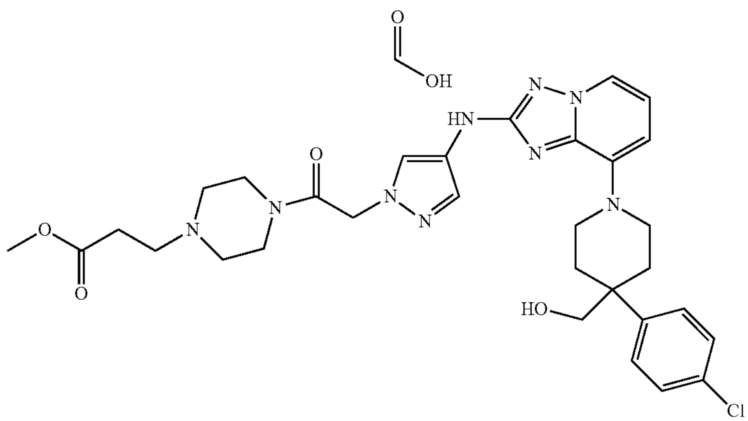 | formic acid; methyl 3-[4-[2-[4-[[8-[4-(4-chlorophenyl)-4-(hydroxymethyl)-1-piperidyl]-[1,2,4]triazolo[1,5-a]pyridin-2-yl]amino]pyrazol-1-yl]acetyl]piperazin-1-yl]propanoate |
| 1-291 | 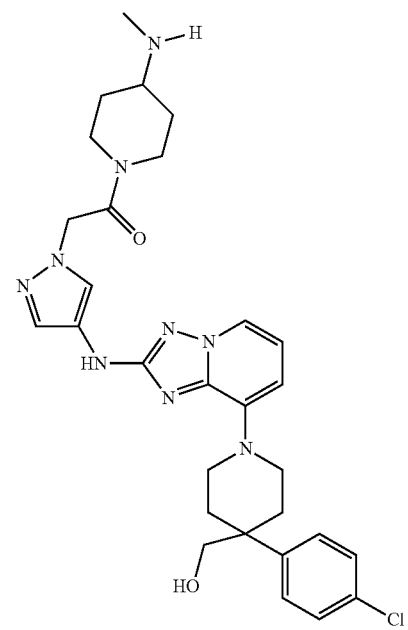 [SMILES: CNC1CCN(C(=O)Cn2cc(Nc3nc4c(N5CCC(CO)(c6ccc(Cl)cc6)CC5)cccn4n3)cn2)CC1] | 2-[4-[[8-[4-(4-chlorophenyl)-4-(hydroxymethyl)-1-piperidyl]-[1,2,4]triazolo[1,5-a]pyridin-2-yl]amino]pyrazol-1-yl]-1-[4-(methylamino)-1-piperidyl]ethanone |
| 1-292 | 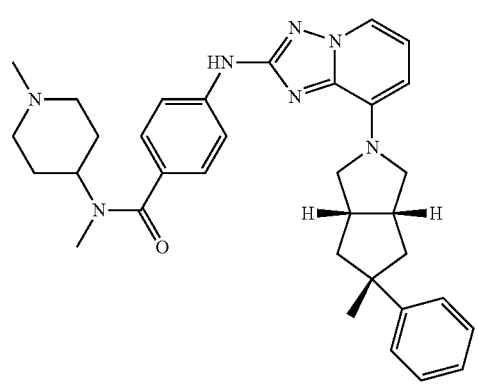 [SMILES: CN1CCC(N(C)C(=O)c2ccc(Nc3nc4c(N5C[C@@H]6C[C@](C)(c7ccccc7)C[C@@H]6C5)cccn4n3)cc2)CC1] | 4-[[8-[(3aR,6aS)-5-hydroxy-5-phenyl-1,3,3a,4,6,6a-hexahydrocyclopenta[c]pyrrol-2-yl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 1-293 | 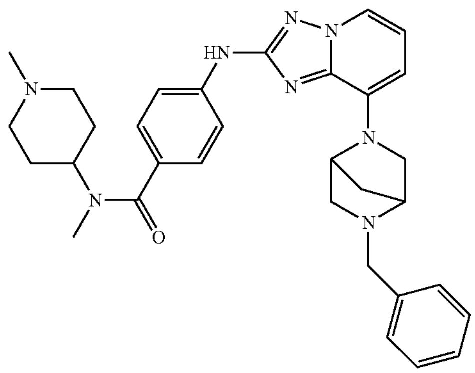 [SMILES: CN1CCC(N(C)C(=O)c2ccc(Nc3nc4c(N5CC6CC5CN6Cc5ccccc5)cccn4n3)cc2)CC1] | 4-[[8-(5-benzyl-2,5-diazabicyclo[2.2.1]heptan-2-yl)-[1,2,4]triazolo[1,5-a]pyridin-2-yl]amino]-N-methyl-N-(1-methyl-4-piperidyl)benzamide |
| 1-294 | 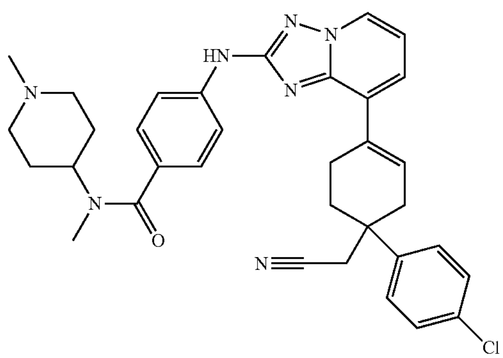 [SMILES: CN1CCC(N(C)C(=O)c2ccc(Nc3nc4c(C5=CCC(CC#N)(c6ccc(Cl)cc6)CC5)cccn4n3)cc2)CC1] | 4-[[8-[4-(4-chlorophenyl)-4-(cyanomethyl)cyclohexen-1-yl]-[1,2,4]triazolo[1,5-a]pyridin-2-yl]amino]-N-methyl-N-(1-methyl-4-piperidyl)benzamide |
| 1-295 | 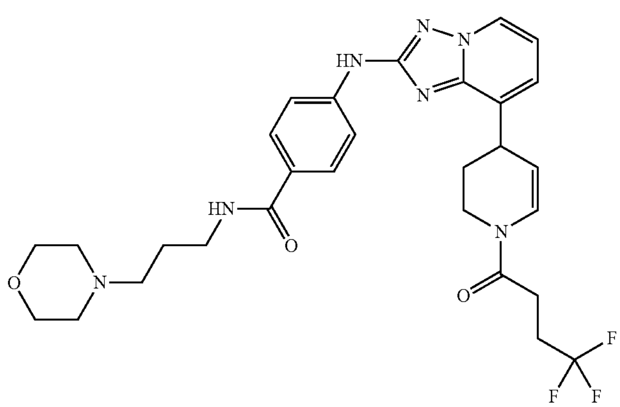 [SMILES: O=C(NCCCN1CCOCC1)c1ccc(Nc2nc3c(C4C=CN(C(=O)CCC(F)(F)F)CC4)cccn3n2)cc1] | N-(3-morpholinopropyl)-4-[[8-[1-(4,4,4-trifluorobutanoyl)-3,4-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 1-296 | 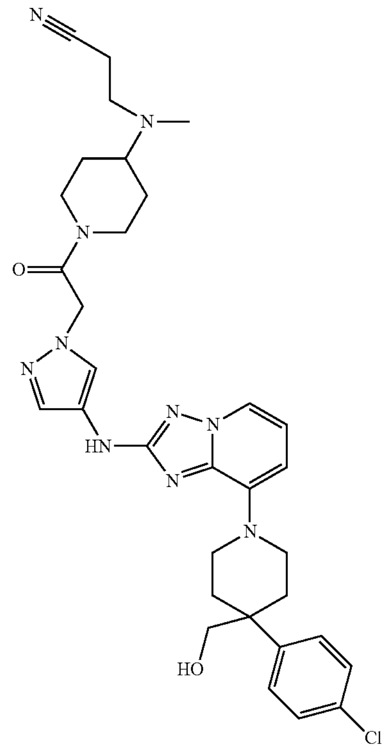 [SMILES: CN(CCC#N)C1CCN(C(=O)Cn2cc(Nc3nc4c(N5CCC(CO)(c6ccc(Cl)cc6)CC5)cccn4n3)cn2)CC1] | 3-[[1-[2-[4-[[8-[4-(4-chlorophenyl)-4-(hydroxymethyl)-1-piperidyl]-[1,2,4]triazolo[1,5-a]pyridin-2-yl]amino]pyrazol-1-yl]acetyl]-4-piperidyl]-methyl-amino]propanenitrile |
| 1-297 | 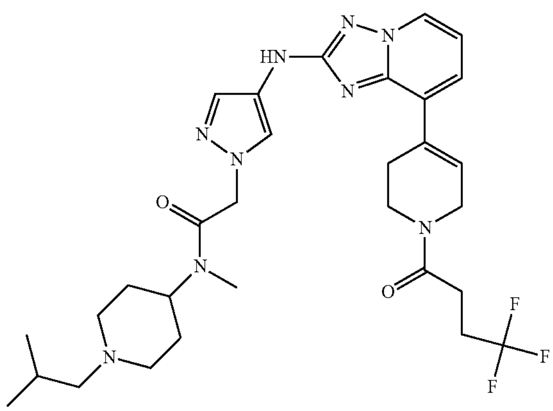 [SMILES: CC(C)CN1CCC(N(C)C(=O)Cn2cc(Nc3nc4c(C5=CCN(C(=O)CCC(F)(F)F)CC5)cccn4n3)cn2)CC1] | N-(1-isobutyl-4-piperidyl)-N-methyl-2-[4-[[8-[1-(4,4,4-trifluorobutanoyl)-3,6-dihydro-2H-pyridin-4-yl]-[1,2,4]triazolo[1,5-a]pyridin-2-yl]amino]pyrazol-1-yl]acetamide |
| 1-298 | 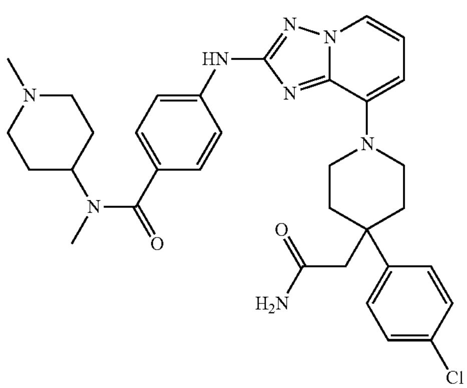 [SMILES: CN1CCC(N(C)C(=O)c2ccc(Nc3nc4c(N5CCC(CC(N)=O)(c6ccc(Cl)cc6)CC5)cccn4n3)cc2)CC1] | 4-[[8-[4-(2-amino-2-oxo-ethyl)-4-(4-chlorophenyl)-1-piperidyl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 1-299 | 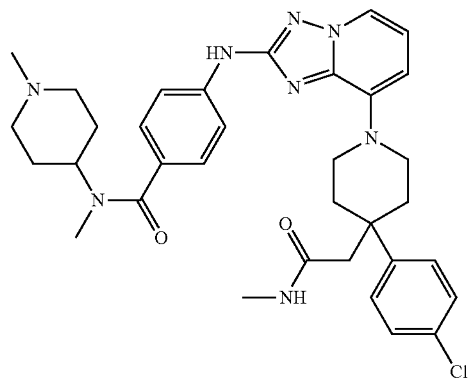 [SMILES: CNC(=O)CC1(c2ccc(Cl)cc2)CCN(c2cccn3nc(Nc4ccc(C(=O)N(C)C5CCN(C)CC5)cc4)nc23)CC1] | 4-[[8-[4-(4-chlorophenyl)-4-[2-(methylamino)-2-oxo-ethyl]-1-piperidyl]-[1,2,4]triazolo[1,5-a]pyridin-2-yl]amino]-N-methyl-N-(1-methyl-4-piperidyl)benzamide |
| 1-300 | 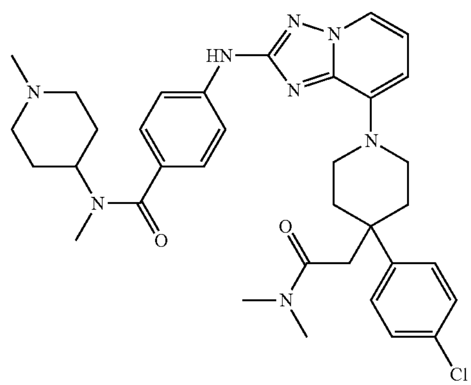 [SMILES: CN1CCC(N(C)C(=O)c2ccc(Nc3nc4c(N5CCC(CC(=O)N(C)C)(c6ccc(Cl)cc6)CC5)cccn4n3)cc2)CC1] | 4-[[8-[4-(4-chlorophenyl)-4-[2-(dimethylamino)-2-oxo-ethyl]-1-piperidyl]-[1,2,4]triazolo[1,5-a]pyridin-2-yl]amino]-N-methyl-N-(1-methyl-4-piperidyl)benzamide |
| 1-301 | 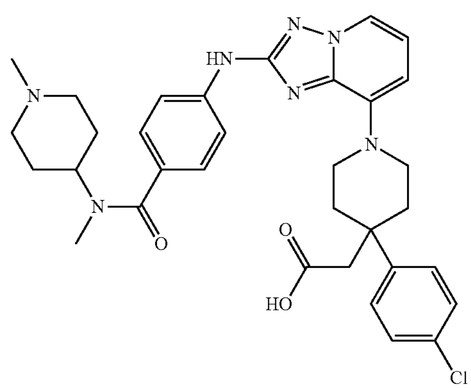 [SMILES: CN1CCC(N(C)C(=O)c2ccc(Nc3nc4c(N5CCC(CC(=O)O)(c6ccc(Cl)cc6)CC5)cccn4n3)cc2)CC1] | 2-[4-(4-chlorophenyl)-1-[2-[4-[methyl-(1-methyl-4-piperidyl)carbamoyl]anilino]-[1,2,4]triazolo[1,5-a]pyridin-8-yl]-4-piperidyl]acetic acid |
| 1-302 | 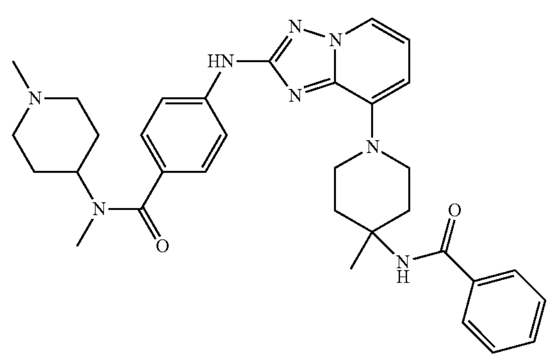 [SMILES: CN1CCC(N(C)C(=O)c2ccc(Nc3nc4c(N5CCC(C)(NC(=O)c6ccccc6)CC5)cccn4n3)cc2)CC1] | 4-[[8-(4-benzamido-4-methyl-1-piperidyl)-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 1-303 | 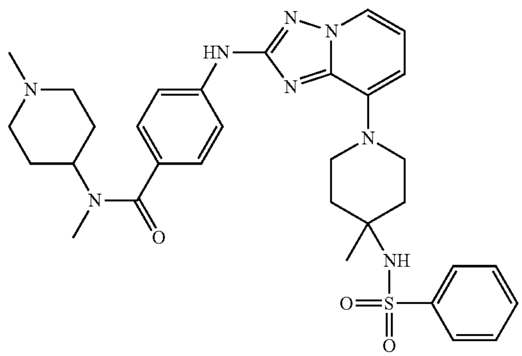 [SMILES: CN1CCC(N(C)C(=O)c2ccc(Nc3nc4c(N5CCC(C)(NS(=O)(=O)c6ccccc6)CC5)cccn4n3)cc2)CC1] | 4-[[8-[4-(benzenesulfonamido)-4-methyl-1-piperidyl]-[1,2,4]triazolo[1,5-a]pyridin-2-yl]amino]-N-methyl-N-(1-methyl-4-piperidyl)benzamide |
| 2-1 | 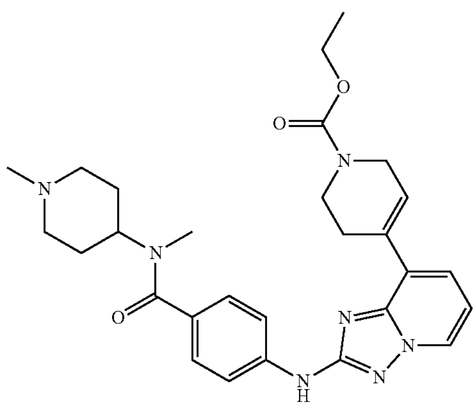 [SMILES: CCOC(=O)N1CC=C(c2cccn3nc(Nc4ccc(C(=O)N(C)C5CCN(C)CC5)cc4)nc23)CC1] | ethyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |
| 2-2 | 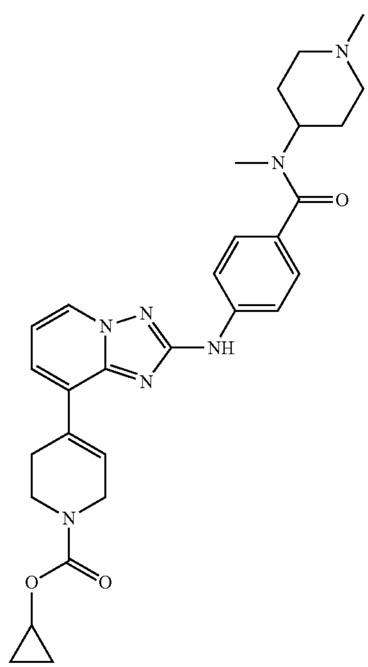 [SMILES: CN1CCC(N(C)C(=O)c2ccc(Nc3nc4c(C5=CCN(C(=O)OC6CC6)CC5)cccn4n3)cc2)CC1] | cyclopropyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-3 | 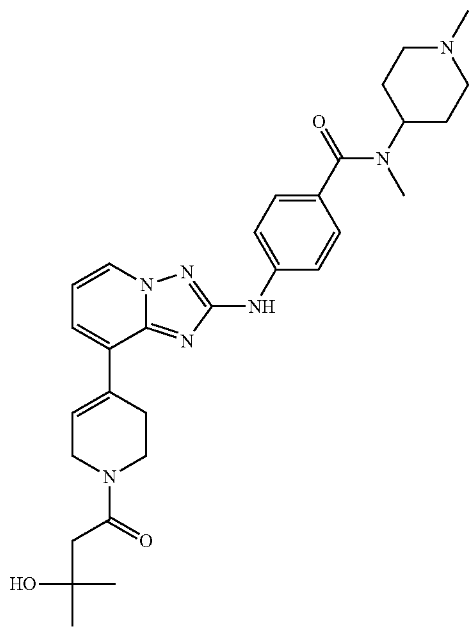 [SMILES: CN1CCC(N(C)C(=O)c2ccc(Nc3nc4c(C5=CCN(C(=O)CC(C)(C)O)CC5)cccn4n3)cc2)CC1] | 4-[[8-[1-(3-hydroxy-3-methyl-butanoyl)-3,6-dihydro-2H-pyridin-4-yl]-[1,2,4]triazolo[1,5-a]pyridin-2-yl]amino]-N-methyl-N-(1-methyl-4-piperidyl)benzamide |
| 2-4 | 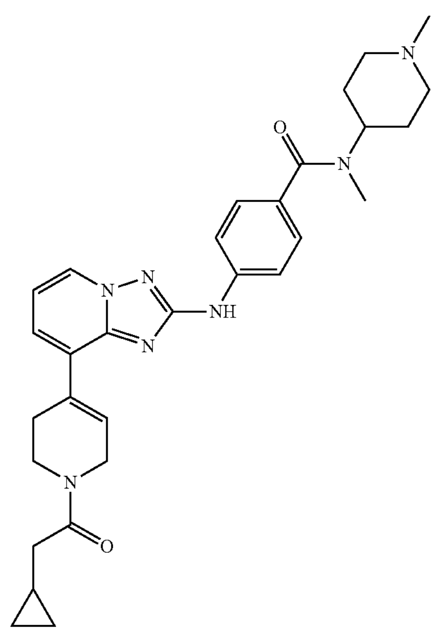 [SMILES: CN1CCC(N(C)C(=O)c2ccc(Nc3nc4c(C5=CCN(C(=O)CC6CC6)CC5)cccn4n3)cc2)CC1] | 4-[[8-[1-(2-cyclopropylacetyl)-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 2-5 | 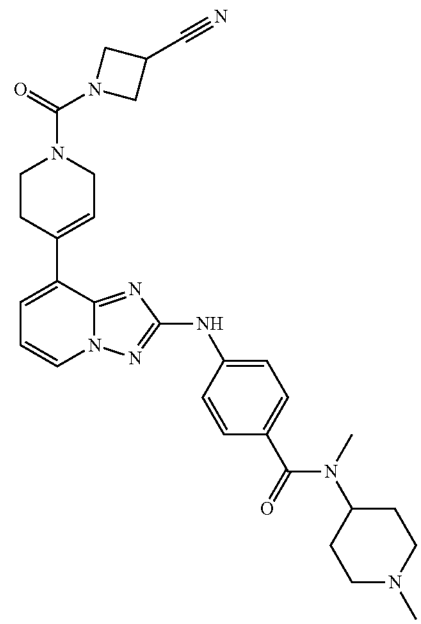 [SMILES: CN1CCC(N(C)C(=O)c2ccc(Nc3nc4c(C5=CCN(C(=O)N6CC(C#N)C6)CC5)cccn4n3)cc2)CC1] | 4-[[8-[1-(3-cyanoazetidine-1-carbonyl)-3,6-dihydro-2H-pyridin-4-yl]-[1,2,4]triazolo[1,5-a]pyridin-2-yl]amino]-N-methyl-N-(1-methyl-4-piperidyl)benzamide |
| 2-6 | 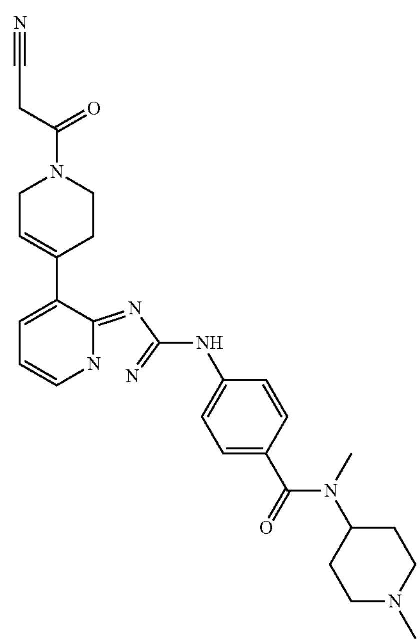 [SMILES: CN1CCC(N(C)C(=O)c2ccc(NC(=N)/N=c3\[nH]cccc3C3=CCN(C(=O)CC#N)CC3)cc2)CC1] | 4-[[8-[1-(2-cyanoacetyl)-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 2-7 | 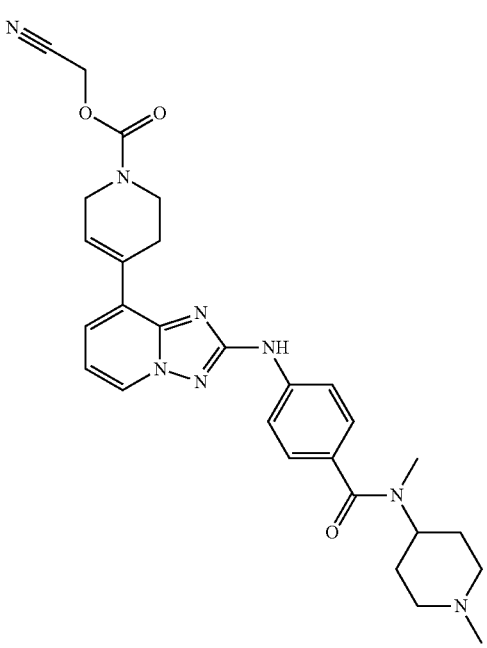 [SMILES: CN1CCC(N(C)C(=O)c2ccc(Nc3nc4c(C5=CCN(C(=O)OCC#N)CC5)cccn4n3)cc2)CC1] | cyanomethyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |
| 2-8 | 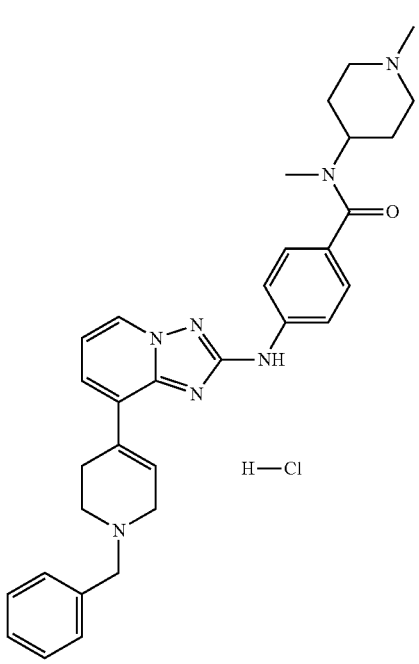 [SMILES: CN1CCC(N(C)C(=O)c2ccc(Nc3nc4c(C5=CCN(Cc6ccccc6)CC5)cccn4n3)cc2)CC1 ; Cl] | 4-[[8-(1-benzyl-3,6-dihydro-2H-pyridin-4-yl)-[1,2,4]triazolo[1,5-a]pyridin-2-yl]amino]-N-methyl-N-(1-methyl-4-piperidyl)benzamide; hydrochloride |

TABLE A-continued

Exemplary Compounds of the Present Invention

| Ex. | Structure | Name |
|---|---|---|
| 2-9 | 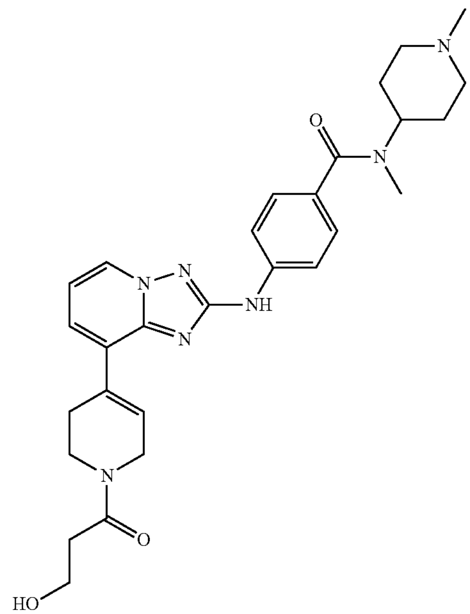 [SMILES: CN1CCC(N(C)C(=O)c2ccc(Nc3nc4c(C5=CCN(C(=O)CCO)CC5)cccn4n3)cc2)CC1] | 4-[[8-[1-(3-hydroxypropanoyl)-3,6-dihydro-2H-pyridin-4-yl]-[1,2,4]triazolo[1,5-a]pyridin-2-yl]amino]-N-methyl-N-(1-methyl-4-piperidyl)benzamide |
| 2-10 | 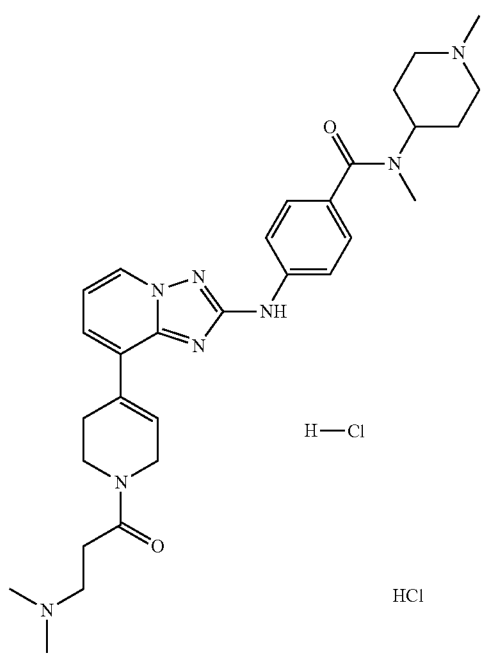 | 4-[[8-[1-[3-(dimethylamino)propanoyl]-3,6-dihydro-2H-pyridin-4-yl]-[1,2,4]triazolo[1,5-a]pyridin-2-yl]amino]-N-methyl-N-(1-methyl-4-piperidyl)benzamide; dihydrochloride |

TABLE A-continued

Exemplary Compounds of the Present Invention

| Ex. | Structure | Name |
|---|---|---|
| 2-11 | 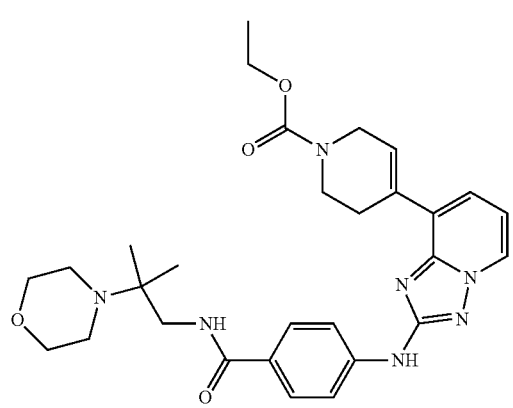 [SMILES: CCOC(=O)N1CC=C(c2cccn3nc(Nc4ccc(C(=O)NCC(C)(C)N5CCOCC5)cc4)nc23)CC1] | ethyl 4-[2-[4-[(2-methyl-2-morpholino-propyl)carbamoyl]anilino]-[1,2,4]triazolo[1,5-a]pyridin-8-yl]-3,6-dihydro-2H-pyridine-1-carboxylate |
| 2-12 | 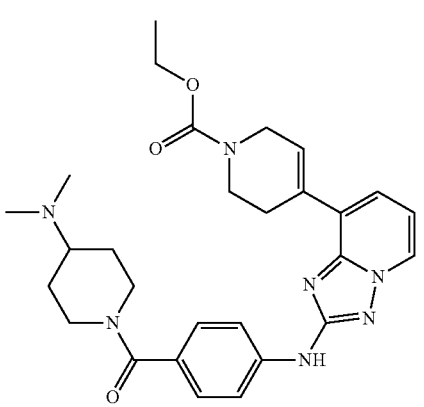 [SMILES: CCOC(=O)N1CC=C(c2cccn3nc(Nc4ccc(C(=O)N5CCC(N(C)C)CC5)cc4)nc23)CC1] | ethyl 4-[2-[4-[4-(dimethylamino)piperidine-1-carbonyl]anilino]-[1,2,4]triazolo[1,5-a]pyridin-8-yl]-3,6-dihydro-2H-pyridine-1-carboxylate |
| 2-13 | 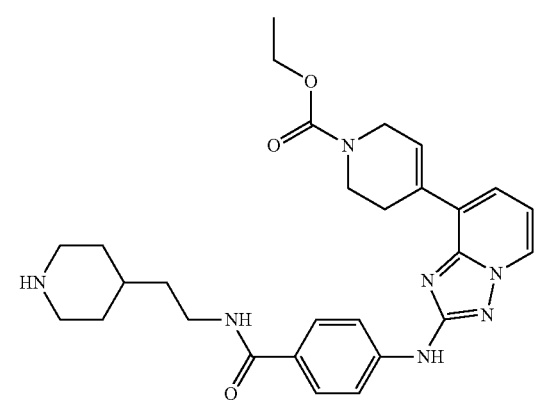 | ethyl 4-[2-[4-[2-(4-piperidyl)ethylcarbamoyl]anilino]-[1,2,4]triazolo[1,5-a]pyridin-8-yl]-3,6-dihydro-2H-pyridine-1-carboxylate |

US 9,873,709 B2

TABLE A-continued

Exemplary Compounds of the Present Invention

| Ex. | Structure | Name |
| --- | --- | --- |
| 2-14 | 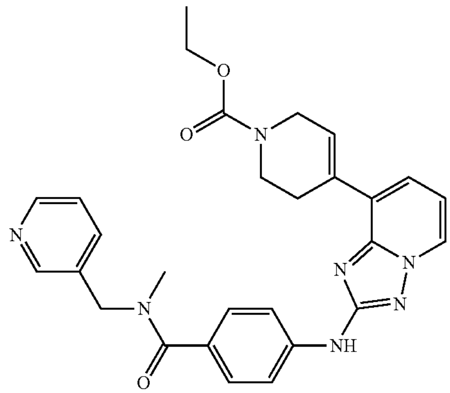 [SMILES: CCOC(=O)N1CC=C(c2cccn3nc(Nc4ccc(C(=O)N(C)Cc5cccnc5)cc4)nc23)CC1] | ethyl 4-[2-[4-[methyl(3-pyridylmethyl)carbamoyl]anilino]-[1,2,4]triazolo[1,5-a]pyridin-8-yl]-3,6-dihydro-2H-pyridine-1-carboxylate |
| 2-15 | 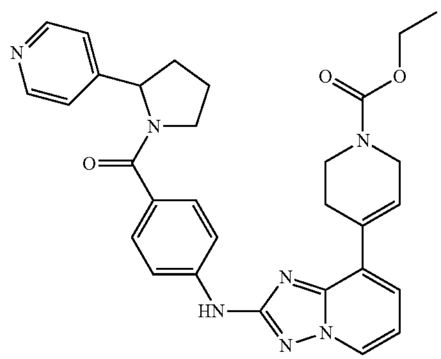 [SMILES: CCOC(=O)N1CC=C(c2cccn3nc(Nc4ccc(C(=O)N5CCCC5c5ccncc5)cc4)nc23)CC1] | ethyl 4-[2-[4-[2-(4-pyridyl)pyrrolidine-1-carbonyl]anilino]-[1,2,4]triazolo[1,5-a]pyridin-8-yl]-3,6-dihydro-2H-pyridine-1-carboxylate |
| 2-16 | 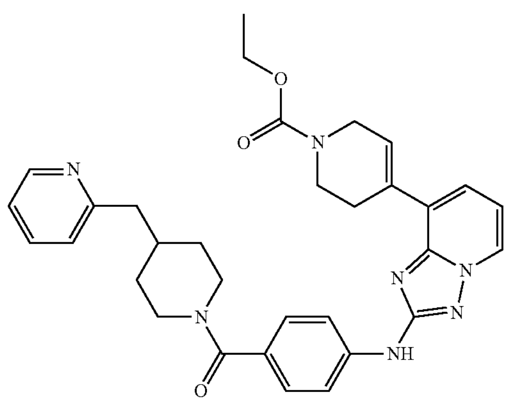 [SMILES: CCOC(=O)N1CC=C(c2cccn3nc(Nc4ccc(C(=O)N5CCC(Cc6ccccn6)CC5)cc4)nc23)CC1] | ethyl 4-[2-[4-[4-(2-pyridylmethyl)piperidine-1-carbonyl]anilino]-[1,2,4]triazolo[1,5-a]pyridin-8-yl]-3,6-dihydro-2H-pyridine-1-carboxylate |
| 2-17 | 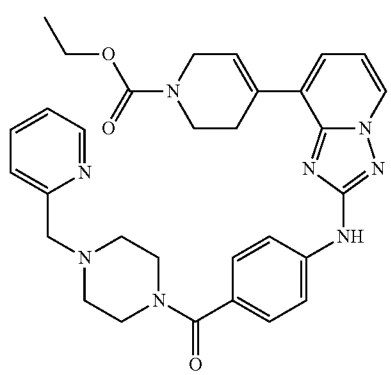 | ethyl 4-[2-[4-[4-(2-pyridylmethyl)piperazine-1-carbonyl]anilino]-[1,2,4]triazolo[1,5-a]pyridin-8-yl]-3,6-dihydro-2H-pyridine-1-carboxylate |

239

240

TABLE A-continued

Exemplary Compounds of the Present Invention

| Ex. | Structure | Name |
|---|---|---|
| 2-18 | 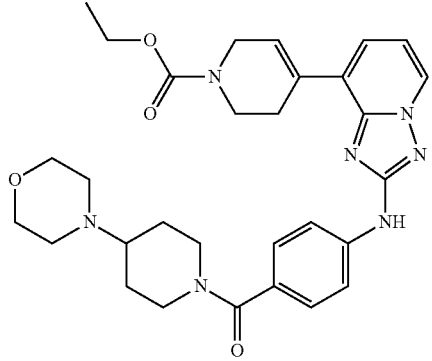 [SMILES: CCOC(=O)N1CC=C(c2cccn3nc(Nc4ccc(C(=O)N5CCC(N6CCOCC6)CC5)cc4)nc23)CC1] | ethyl 4-[2-[4-(4-morpholinopiperidine-1-carbonyl)anilino]-[1,2,4]triazolo[1,5-a]pyridin-8-yl]-3,6-dihydro-2H-pyridine-1-carboxylate |
| 2-19 | 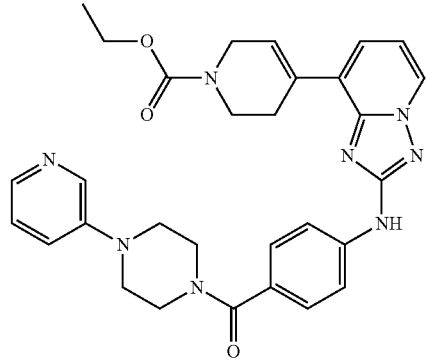 [SMILES: CCOC(=O)N1CC=C(c2cccn3nc(Nc4ccc(C(=O)N5CCN(c6cccnc6)CC5)cc4)nc23)CC1] | ethyl 4-[2-[4-[4-(3-pyridyl)piperazine-1-carbonyl]anilino]-[1,2,4]triazolo[1,5-a]pyridin-8-yl]-3,6-dihydro-2H-pyridine-1-carboxylate |
| 2-20 | 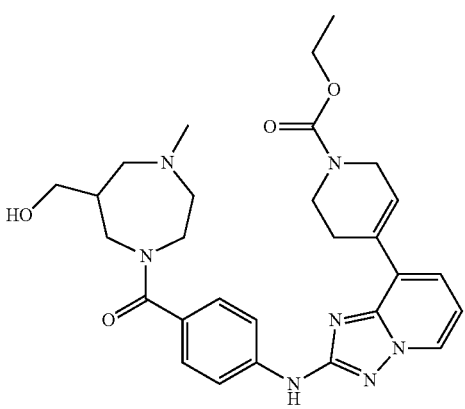 [SMILES: CCOC(=O)N1CC=C(c2cccn3nc(Nc4ccc(C(=O)N5CCN(C)CC(CO)C5)cc4)nc23)CC1] | ethyl 4-[2-[4-[6-(hydroxymethyl)-4-methyl-1,4-diazepane-1-carbonyl]anilino]-[1,2,4]triazolo[1,5-a]pyridin-8-yl]-3,6-dihydro-2H-pyridine-1-carboxylate |
| 2-21 | 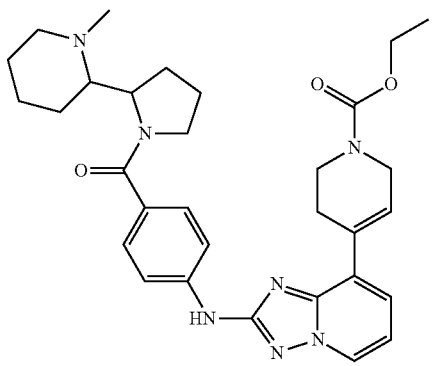 [SMILES: CCOC(=O)N1CC=C(c2cccn3nc(Nc4ccc(C(=O)N5CCCC5C5CCCCN5C)cc4)nc23)CC1] | ethyl 4-[2-[4-[2-(1-methyl-2-piperidyl)pyrrolidine-1-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-22 | 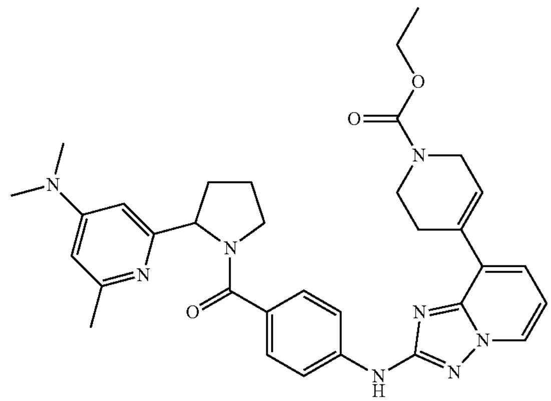 [SMILES: CCOC(=O)N1CC=C(c2cccn3nc(Nc4ccc(C(=O)N5CCCC5c5cc(N(C)C)cc(C)n5)cc4)nc23)CC1] | ethyl 4-[2-[4-[2-[4-(dimethylamino)-6-methyl-2-pyridyl]pyrrolidine-1-carbonyl]anilino]-[1,2,4]triazolo[1,5-a]pyridin-8-yl]-3,6-dihydro-2H-pyridine-1-carboxylate |
| 2-23 | 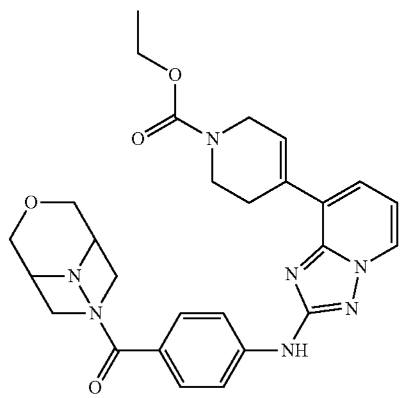 | ethyl 4-[2-[4-(9-methyl-3-oxa-7,9-diazabicyclo[3.3.1]nonane-7-carbonyl)anilino]-[1,2,4]triazolo[1,5-a]pyridin-8-yl]-3,6-dihydro-2H-pyridine-1-carboxylate |
| 2-24 | 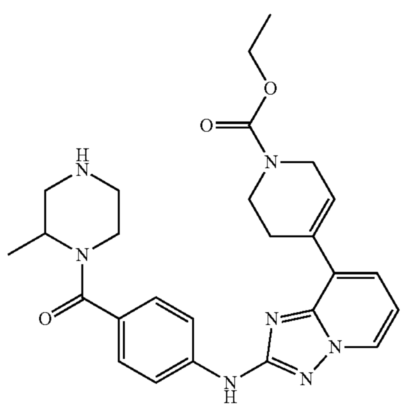 [SMILES: CCOC(=O)N1CC=C(c2cccn3nc(Nc4ccc(C(=O)N5CCNCC5C)cc4)nc23)CC1] | ethyl 4-[2-[4-(2-methylpiperazine-1-carbonyl)anilino]-[1,2,4]triazolo[1,5-a]pyridin-8-yl]-3,6-dihydro-2H-pyridine-1-carboxylate |
| 2-25 | 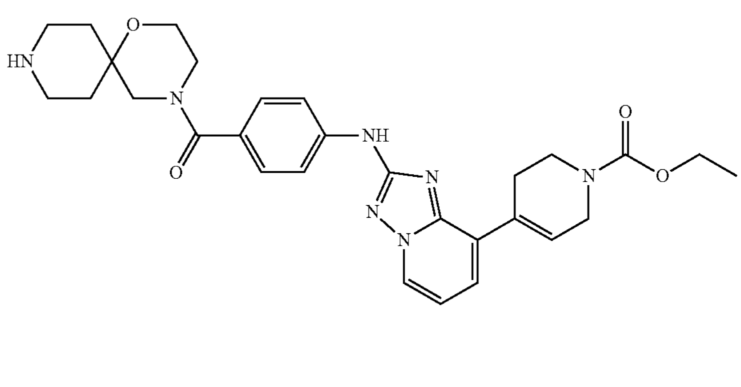 [SMILES: CCOC(=O)N1CC=C(c2cccn3nc(Nc4ccc(C(=O)N5CCOC6(CCNCC6)C5)cc4)nc23)CC1] | ethyl 4-[2-[4-(1-oxa-4,9-diazaspiro[5.5]undecane-4-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-26 | 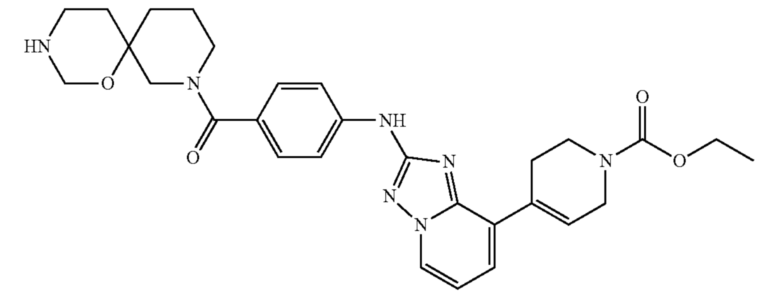 [SMILES: CCOC(=O)N1CC=C(c2cccn3nc(Nc4ccc(C(=O)N5CCCC6(CCNCO6)C5)cc4)nc23)CC1] | ethyl 4-[2-[4-(1-oxa-4,8-diazaspiro[5.5]undecane-8-carbonyl)anilino]-[1,2,4]triazolo[1,5-a]pyridin-8-yl]-3,6-dihydro-2H-pyridine-1-carboxylate |
| 2-27 | 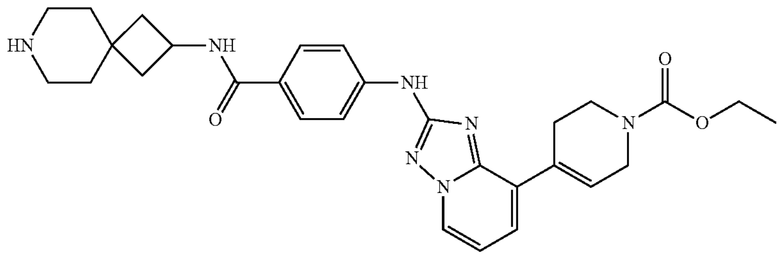 [SMILES: CCOC(=O)N1CC=C(c2cccn3nc(Nc4ccc(C(=O)NC5CC6(CCNCC6)C5)cc4)nc23)CC1] | ethyl 4-[2-[4-(7-azaspiro[3.5]nonan-2-ylcarbamoyl)anilino]-[1,2,4]triazolo[1,5-a]pyridin-8-yl]-3,6-dihydro-2H-pyridine-1-carboxylate |
| 2-28 | 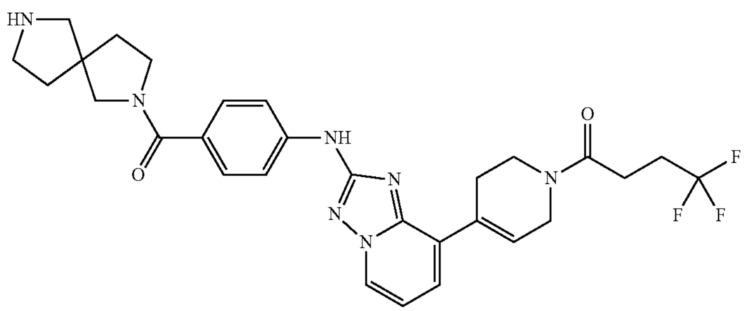 [SMILES: O=C(CCC(F)(F)F)N1CC=C(c2cccn3nc(Nc4ccc(C(=O)N5CCC6(CCNC6)C5)cc4)nc23)CC1] | 1-[4-[2-[4-(2,7-diazaspiro[4.4]nonane-2-carbonyl)anilino]-[1,2,4]triazolo[1,5-a]pyridin-8-yl]-3,6-dihydro-2H-pyridin-1-yl]-4,4,4-trifluoro-butan-1-one |
| 2-29 | 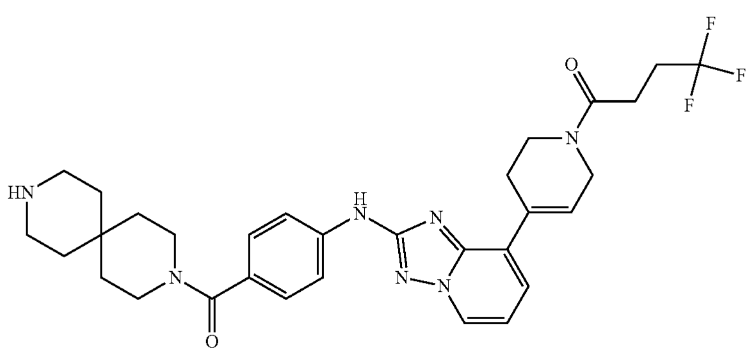 [SMILES: O=C(CCC(F)(F)F)N1CC=C(c2cccn3nc(Nc4ccc(C(=O)N5CCC6(CCNCC6)CC5)cc4)nc23)CC1] | 1-[4-[2-[4-(3,9-diazaspiro[5.5]undecane-3-carbonyl)anilino]-[1,2,4]triazolo[1,5-a]pyridin-8-yl]-3,6-dihydro-2H-pyridin-1-yl]-4,4,4-trifluoro-butan-1-one |
| 2-30 | 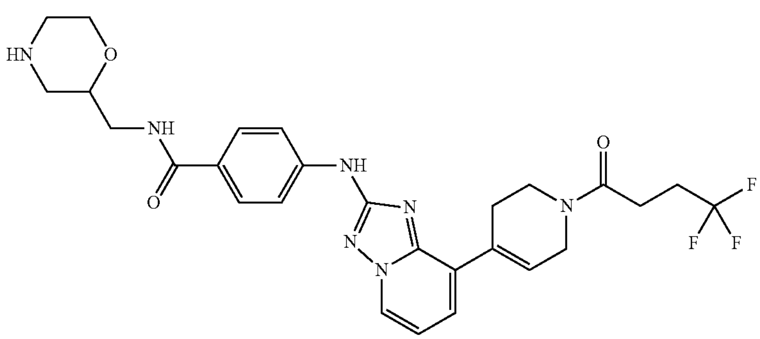 [SMILES: O=C(NCC1CNCCO1)c1ccc(Nc2nc3c(C4=CCN(C(=O)CCC(F)(F)F)CC4)cccn3n2)cc1] | N-(morpholin-2-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-31 | 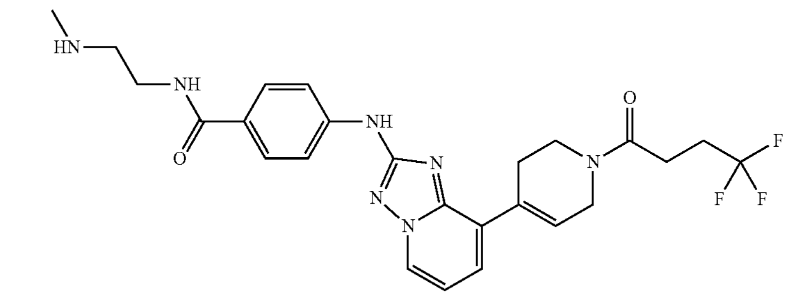 [SMILES: CNCCNC(=O)c1ccc(Nc2nc3c(C4=CCN(C(=O)CCC(F)(F)F)CC4)cccn3n2)cc1] | N-[2-(methylamino)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-32 | 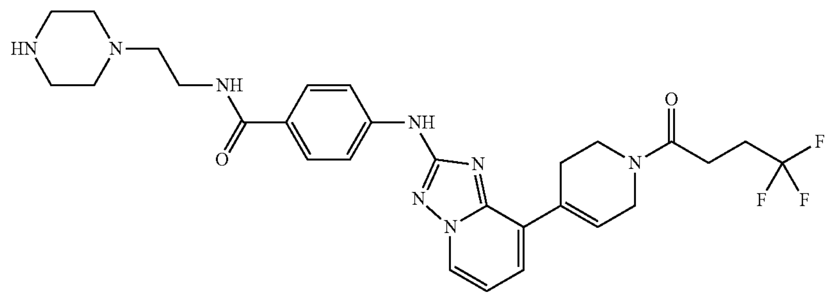 [SMILES: O=C(NCCN1CCNCC1)c1ccc(Nc2nc3c(C4=CCN(C(=O)CCC(F)(F)F)CC4)cccn3n2)cc1] | N-(2-piperazin-1-ylethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-33 | 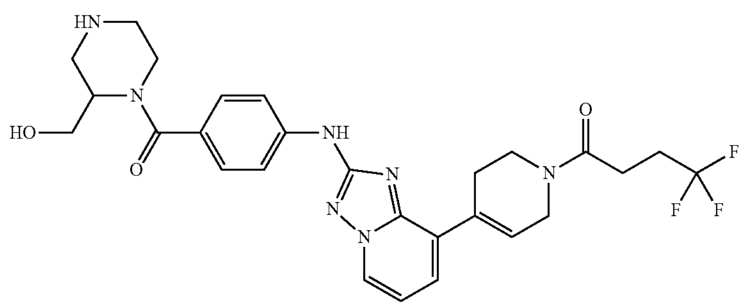 [SMILES: O=C(CCC(F)(F)F)N1CC=C(c2cccn3nc(Nc4ccc(C(=O)N5CCNCC5CO)cc4)nc23)CC1] | 4,4,4-trifluoro-1-[4-[2-[4-[2-(hydroxymethyl)piperazine-1-carbonyl]anilino]-[1,2,4]triazolo[1,5-a]pyridin-8-yl]-3,6-dihydro-2H-pyridin-1-yl]butan-1-one |
| 2-34 | 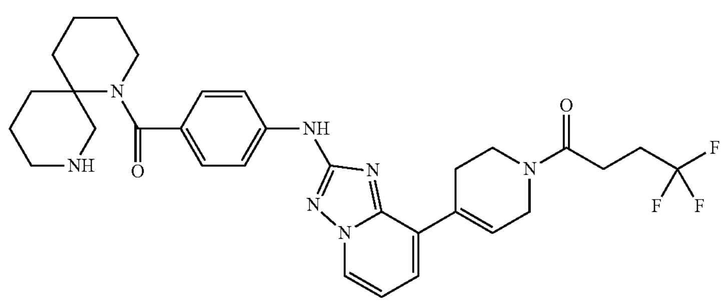 [SMILES: O=C(CCC(F)(F)F)N1CC=C(c2cccn3nc(Nc4ccc(C(=O)N5CCCCC56CCCNC6)cc4)nc23)CC1] | 1-[4-[2-[4-(1,8-diazaspiro[5.5]undecane-1-carbonyl)anilino]-[1,2,4]triazolo[1,5-a]pyridin-8-yl]-3,6-dihydro-2H-pyridin-1-yl]-4,4,4-trifluoro-butan-1-one |
| 2-35 | 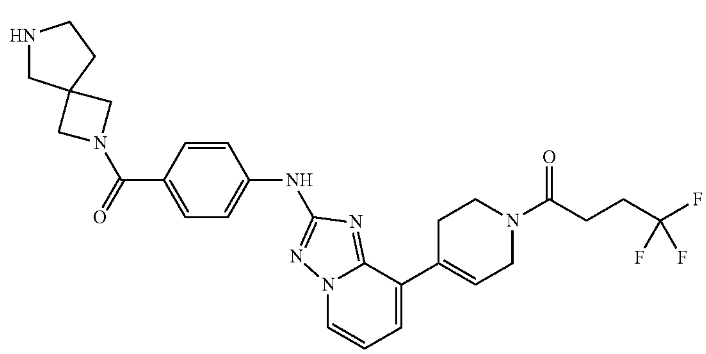 [SMILES: O=C(CCC(F)(F)F)N1CC=C(c2cccn3nc(Nc4ccc(C(=O)N5CC6(CCNC6)C5)cc4)nc23)CC1] | 1-[4-[2-[4-(2,7-diazaspiro[3.4]octane-2-carbonyl)anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-36 | 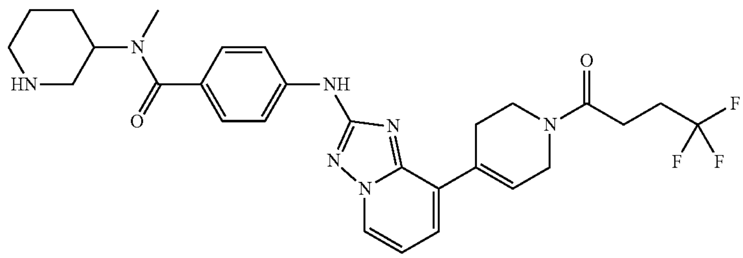 [SMILES: CN(C(=O)c1ccc(Nc2nc3c(C4=CCN(C(=O)CCC(F)(F)F)CC4)cccn3n2)cc1)C1CCCNC1] | N-methyl-N-(3-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-37 | 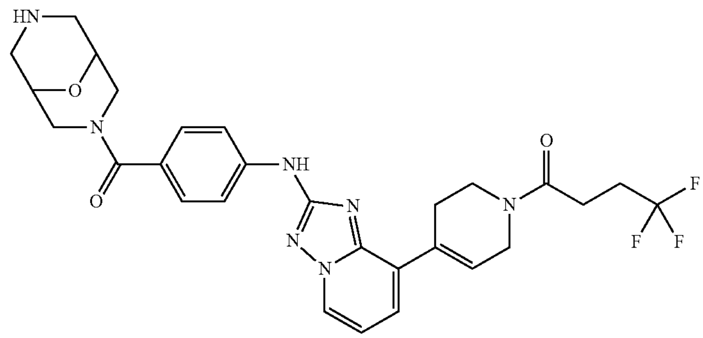 [SMILES: O=C(CCC(F)(F)F)N1CC=C(c2cccn3nc(Nc4ccc(C(=O)N5CC6CNCC(C5)O6)cc4)nc23)CC1] | 4,4,4-trifluoro-1-[4-[2-[4-(9-oxa-3,7-diazabicyclo[3.3.1]nonane-3-carbonyl)anilino]-[1,2,4]triazolo[1,5-a]pyridin-8-yl]-3,6-dihydro-2H-pyridin-1-yl]butan-1-one |
| 2-38 | 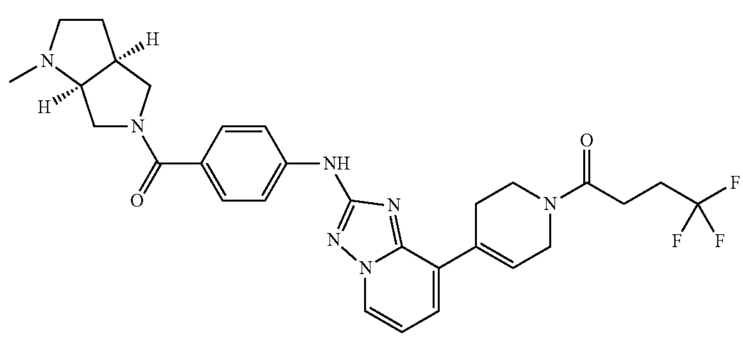 [SMILES: CN1CC[C@H]2CN(C(=O)c3ccc(Nc4nc5c(C6=CCN(C(=O)CCC(F)(F)F)CC6)cccn5n4)cc3)C[C@H]21] | 1-[4-[2-[4-[(3aS,6aS)-1-methyl-2,3,3a,4,6,6a-hexahydropyrrolo[3,4-b]pyrrole-5-carbonyl]anilino]-[1,2,4]triazolo[1,5-a]pyridin-8-yl]-3,6-dihydro-2H-pyridin-1-yl]-4,4,4-trifluoro-butan-1-one |
| 2-39 | 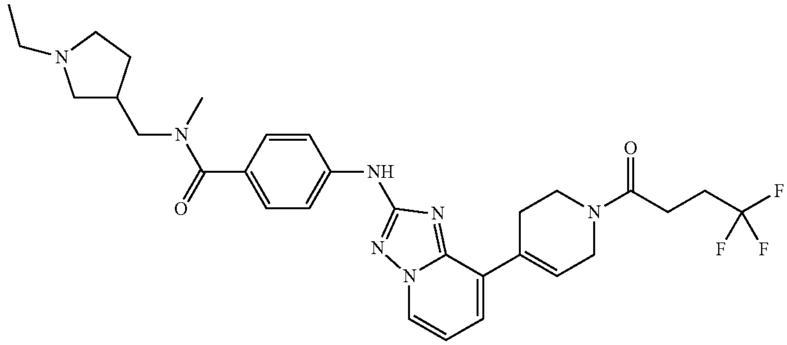 [SMILES: CCN1CCC(CN(C)C(=O)c2ccc(Nc3nc4c(C5=CCN(C(=O)CCC(F)(F)F)CC5)cccn4n3)cc2)C1] | N-[(1-ethylpyrrolidin-3-yl)methyl]-N-methyl-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-40 | 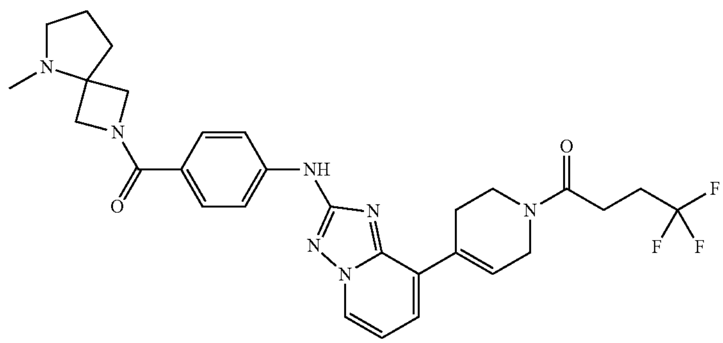 [SMILES: CN1CCCC12CN(C(=O)c1ccc(Nc3nc4c(C5=CCN(C(=O)CCC(F)(F)F)CC5)cccn4n3)cc1)C2] | 4,4,4-trifluoro-1-[4-[2-[4-[4-(5-methyl-2,5-diazaspiro[3.4]octane-2-carbonyl)anilino]-[1,2,4]triazolo[1,5-a]pyridin-8-yl]-3,6-dihydro-2H-pyridin-1-yl]butan-1-one |
| 2-41 | 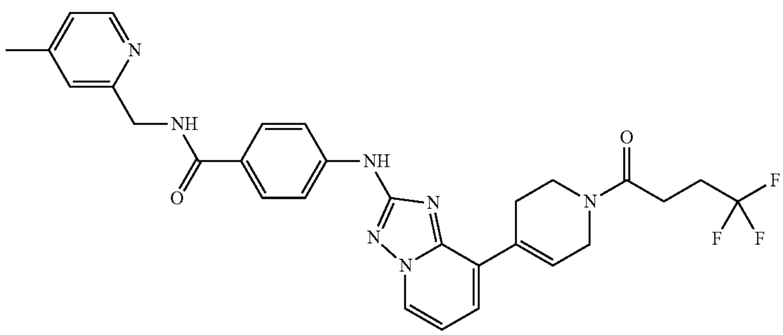 [SMILES: Cc1ccnc(CNC(=O)c2ccc(Nc3nc4c(C5=CCN(C(=O)CCC(F)(F)F)CC5)cccn4n3)cc2)c1] | N-[(4-methyl-2-pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-42 | 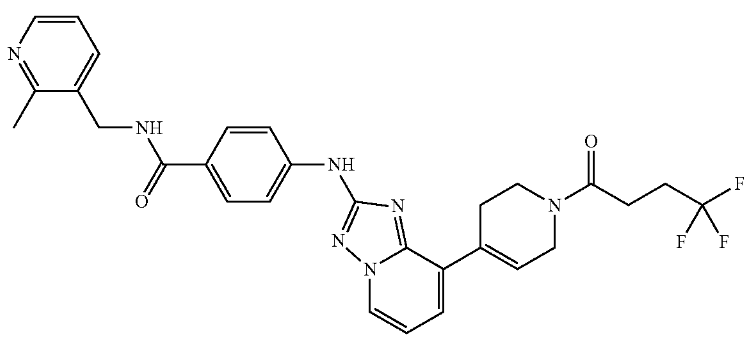 [SMILES: Cc1ncccc1CNC(=O)c1ccc(Nc2nc3c(C4=CCN(C(=O)CCC(F)(F)F)CC4)cccn3n2)cc1] | N-[(2-methyl-3-pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-43 | 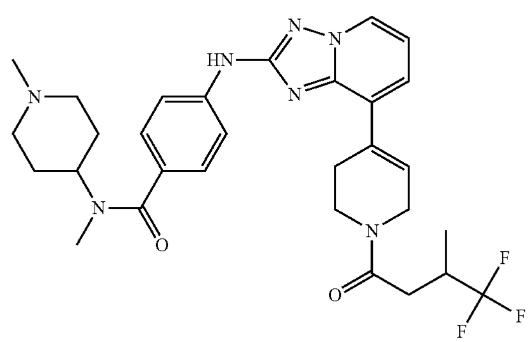 [SMILES: CC(CC(=O)N1CC=C(c2cccn3nc(Nc4ccc(C(=O)N(C)C5CCN(C)CC5)cc4)nc23)CC1)C(F)(F)F] | N-methyl-N-(1-methyl-4-piperidyl)-4-[[8-[1-(4,4,4-trifluoro-3-methyl-butanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-44 | 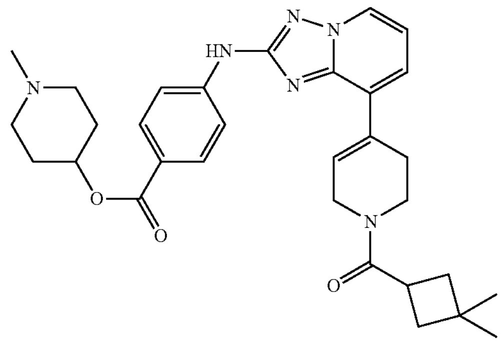 [SMILES: CN1CCC(OC(=O)c2ccc(Nc3nc4c(C5=CCN(C(=O)C6CC(C)(C)C6)CC5)cccn4n3)cc2)CC1] | (1-methyl-4-piperidyl) 4-[[8-[1-(3,3-dimethylcyclobutane carbonyl)-3,6-dihydro-2H-pyridin-4-yl]-[1,2,4]triazolo[1,5-a]pyridin-2-yl]amino]benzoate |
| 2-45 | 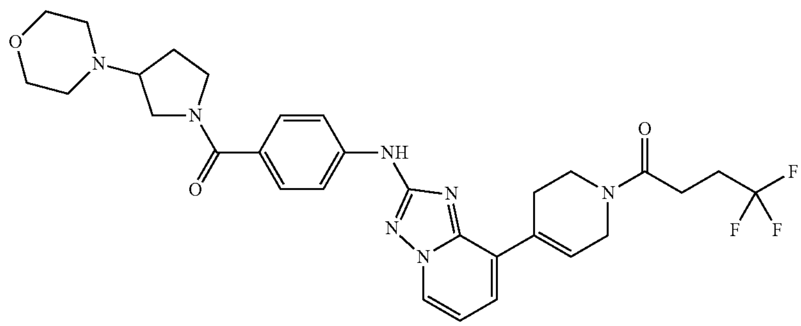 [SMILES: O=C(CCC(F)(F)F)N1CC=C(c2cccn3nc(Nc4ccc(C(=O)N5CCC(N6CCOCC6)C5)cc4)nc23)CC1] | 4,4,4-trifluoro-1-[4-[2-[4-(3-morpholinopyrrolidine-1-carbonyl)anilino]-[1,2,4]triazolo[1,5-a]pyridin-8-yl]-3,6-dihydro-2H-pyridin-1-yl]butan-1-one |
| 2-46 | 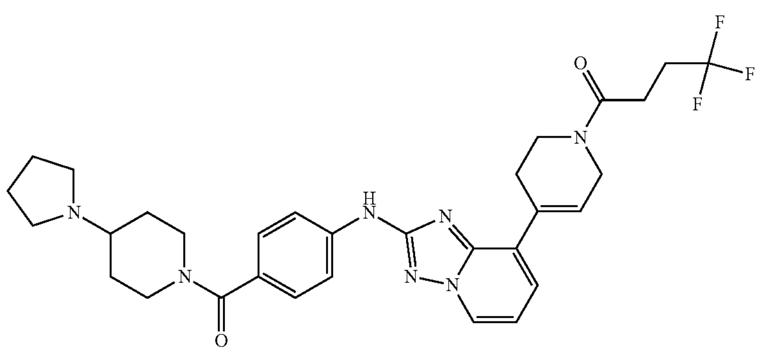 [SMILES: O=C(CCC(F)(F)F)N1CC=C(c2cccn3nc(Nc4ccc(C(=O)N5CCC(N6CCCC6)CC5)cc4)nc23)CC1] | 4,4,4-trifluoro-1-[4-[2-[4-(4-pyrrolidin-1-ylpiperidine-1-carbonyl)anilino]-[1,2,4]triazolo[1,5-a]pyridin-8-yl]-3,6-dihydro-2H-pyridin-1-yl]butan-1-one |
| 2-47 | 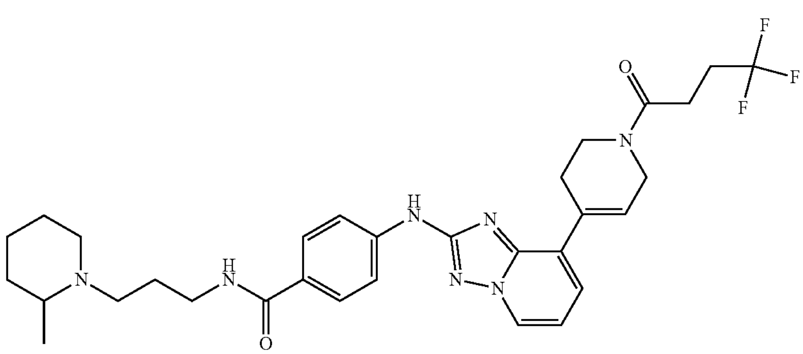 [SMILES: CC1CCCCN1CCCNC(=O)c1ccc(Nc2nc3c(C4=CCN(C(=O)CCC(F)(F)F)CC4)cccn3n2)cc1] | N-[3-(2-methyl-1-piperidyl)propyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-48 | 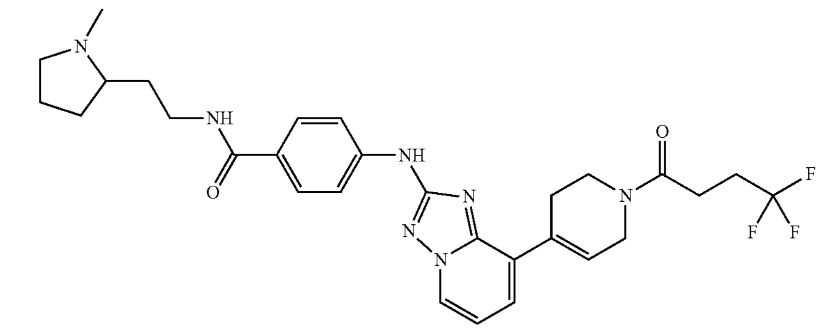 [SMILES: CN1CCCC1CCNC(=O)c1ccc(Nc2nc3c(C4=CCN(C(=O)CCC(F)(F)F)CC4)cccn3n2)cc1] | N-[2-(1-methylpyrrolidin-2-yl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-49 | 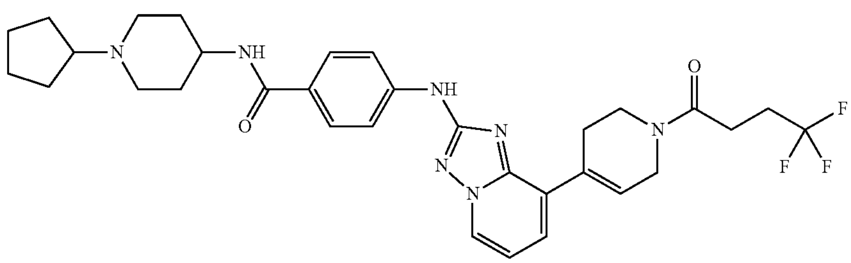 [SMILES: O=C(NC1CCN(C2CCCC2)CC1)c1ccc(Nc2nc3c(C4=CCN(C(=O)CCC(F)(F)F)CC4)cccn3n2)cc1] | N-(1-cyclopentyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-50 | 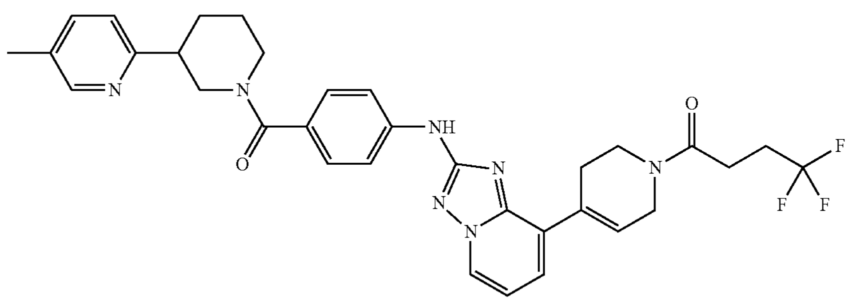 [SMILES: Cc1ccc(C2CCCN(C(=O)c3ccc(Nc4nc5c(C6=CCN(C(=O)CCC(F)(F)F)CC6)cccn5n4)cc3)C2)nc1] | 4,4,4-tri fluoro-1-[4-[2-[4-[3-(5-methyl-2-pyridyl)piperidine-1-carbonyl]anilino]-[1,2,4]triazolo[1,5-a]pyridin-8-yl]-3,6-dihydro-2H-pyridin-1-yl]butan-1-one |
| 2-51 | 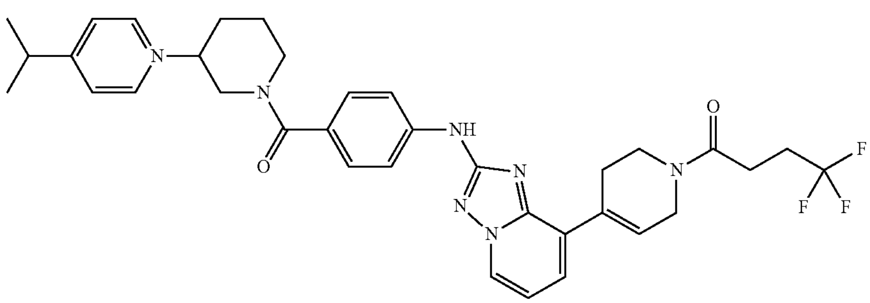 | 1-[4-[2-[4-[3-[5-(dimethylamino)-2-pyridyl]piperidine-1-carbonyl]anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-52 | 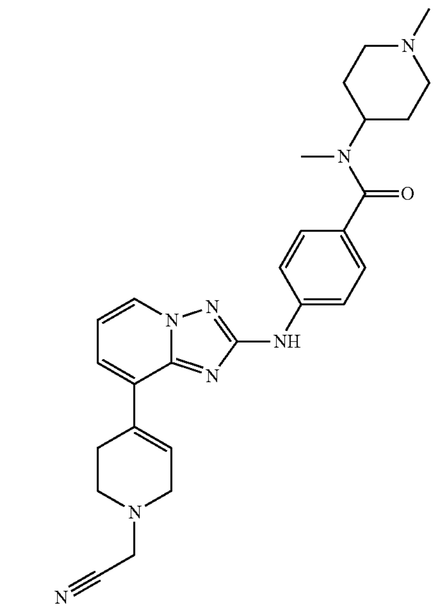 [SMILES: CN1CCC(N(C)C(=O)c2ccc(Nc3nc4c(C5=CCN(CC#N)CC5)cccn4n3)cc2)CC1] | 4-[[8-[1-(cyanomethyl)-3,6-dihydro-2H-pyridin-4-yl]-[1,2,4]triazolo[1,5-a]pyridin-2-yl]amino]-N-methyl-N-(1-methyl-4-piperidyl)benzamide |
| 2-53 | 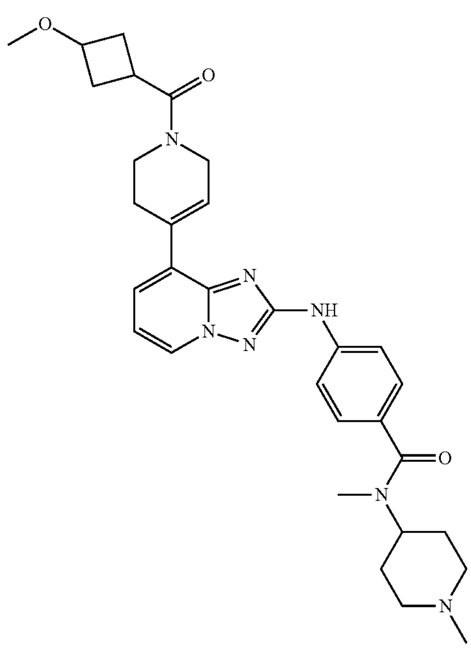 | 4-[[8-[1-(3-methoxycyclobutanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 2-54 | 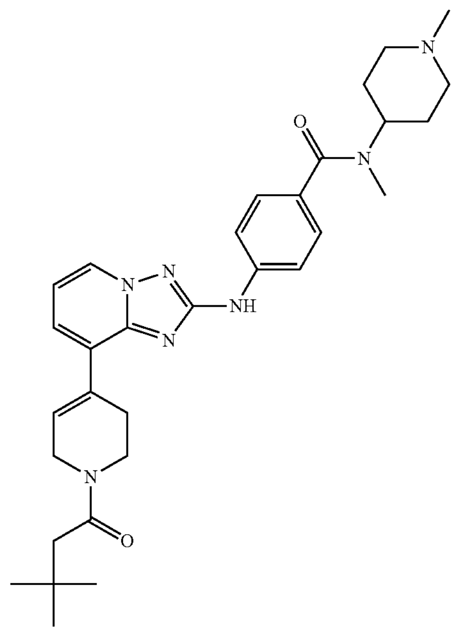 [SMILES: CN1CCC(N(C)C(=O)c2ccc(Nc3nc4c(C5=CCN(C(=O)CC(C)(C)C)CC5)cccn4n3)cc2)CC1] | 4-[[8-[1-(3,3-dimethylbutanoyl)-3,6-dihydro-2H-pyridin-4-yl]-[1,2,4]triazolo[1,5-a]pyridin-2-yl]amino]-N-methyl-N-(1-methyl-4-piperidyl)benzamide |
| 2-55 | 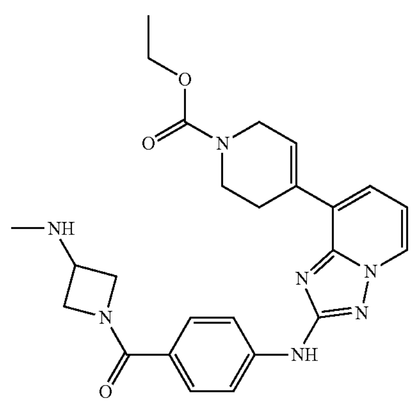 [SMILES: CCOC(=O)N1CC=C(c2cccn3nc(Nc4ccc(C(=O)N5CC(NC)C5)cc4)nc23)CC1] | ethyl 4-[2-[4-[3-(methylamino)azetidine-1-carbonyl]anilino]-[1,2,4]triazolo[1,5-a]pyridin-8-yl]-3,6-dihydro-2H-pyridine-1-carboxylate |
| 2-56 | 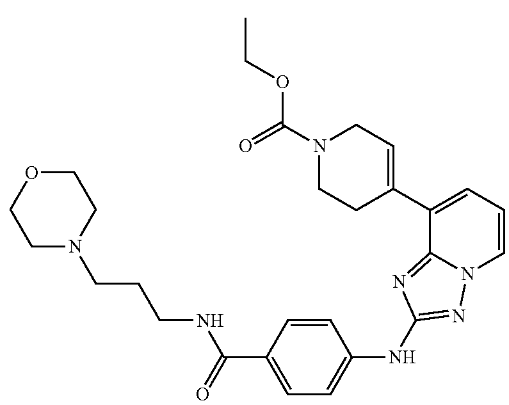 [SMILES: CCOC(=O)N1CC=C(c2cccn3nc(Nc4ccc(C(=O)NCCCN5CCOCC5)cc4)nc23)CC1] | ethyl 4-[2-[4-(3-morpholinopropyl carbamoyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-57 | 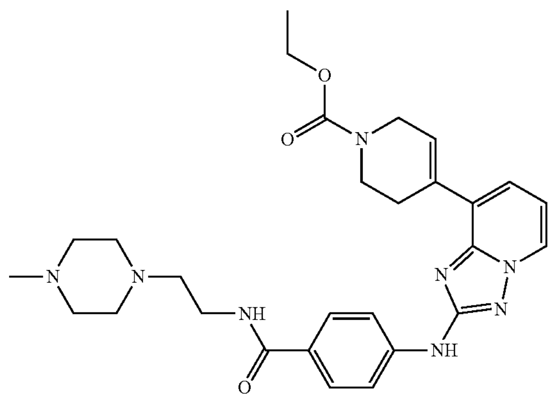 [SMILES: CCOC(=O)N1CC=C(c2cccn3nc(Nc4ccc(C(=O)NCCN5CCN(C)CC5)cc4)nc23)CC1] | ethyl 4-[2-[4-[2-(4-methylpiperazin-1-yl)ethylcarbamoyl]anilino]-[1,2,4]triazolo[1,5-a]pyridin-8-yl]-3,6-dihydro-2H-pyridine-1-carboxylate |
| 2-58 | 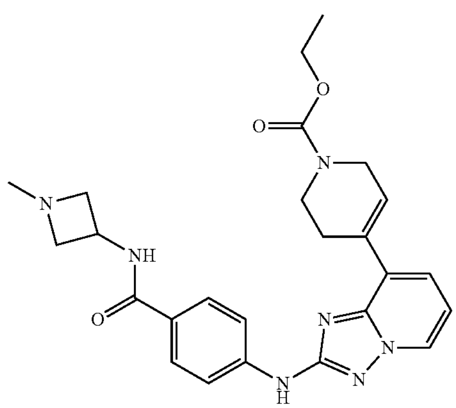 [SMILES: CCOC(=O)N1CC=C(c2cccn3nc(Nc4ccc(C(=O)NC5CN(C)C5)cc4)nc23)CC1] | ethyl 4-[2-[4-[(1-methylazetidin-3-yl)carbamoyl]anilino]-[1,2,4]triazolo[1,5-a]pyridin-8-yl]-3,6-dihydro-2H-pyridine-1-carboxylate |
| 2-59 | 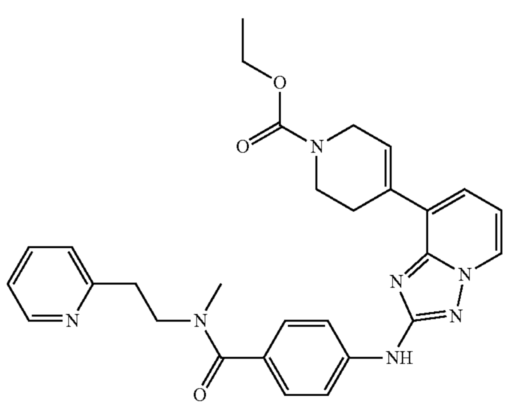 [SMILES: CCOC(=O)N1CC=C(c2cccn3nc(Nc4ccc(C(=O)N(C)CCc5ccccn5)cc4)nc23)CC1] | ethyl 4-[2-[4-[methyl-[2-(2-pyridyl)ethyl]carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-60 | 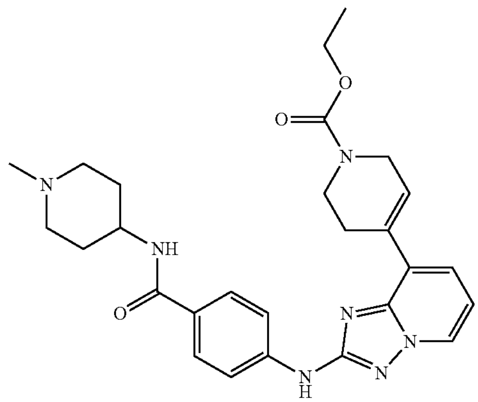 [SMILES: CCOC(=O)N1CC=C(c2cccn3nc(Nc4ccc(C(=O)NC5CCN(C)CC5)cc4)nc23)CC1] | ethyl 4-[2-[4-[(1-methyl-4-piperidyl)carbamoyl]anilino]-[1,2,4]triazolo[1,5-a]pyridin-8-yl]-3,6-dihydro-2H-pyridine-1-carboxylate |
| 2-61 | 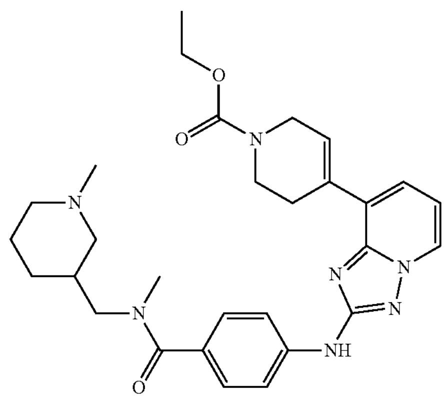 [SMILES: CCOC(=O)N1CC=C(c2cccn3nc(Nc4ccc(C(=O)N(C)CC5CCCN(C)C5)cc4)nc23)CC1] | ethyl 4-[2-[4-[methyl-[(1-methyl-3-piperidyl)methyl]carbamoyl]anilino]-[1,2,4]triazolo[1,5-a]pyridin-8-yl]-3,6-dihydro-2H-pyridine-1-carboxylate |
| 2-62 | 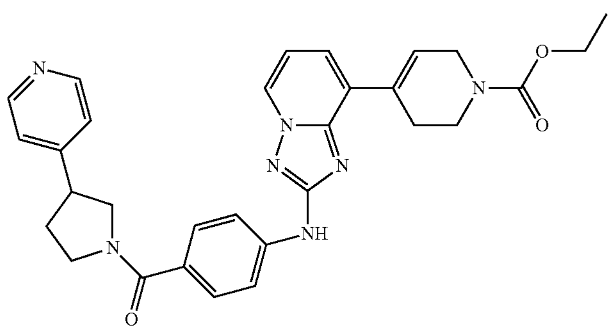 [SMILES: CCOC(=O)N1CC=C(c2cccn3nc(Nc4ccc(C(=O)N5CCC(c6ccncc6)C5)cc4)nc23)CC1] | ethyl 4-[2-[4-[3-(4-pyridyl)pyrrolidine-1-carbonyl]anilino]-[1,2,4]triazolo[1,5-a]pyridin-8-yl]-3,6-dihydro-2H-pyridine-1-carboxylate |
| 2-63 | 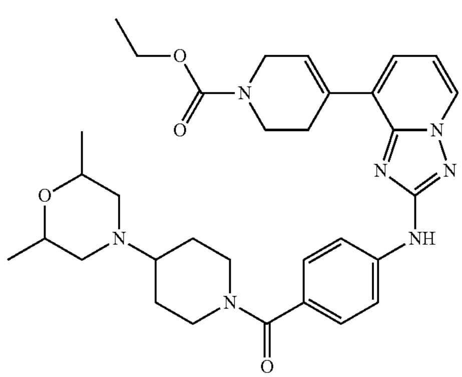 [SMILES: CCOC(=O)N1CC=C(c2cccn3nc(Nc4ccc(C(=O)N5CCC(N6CC(C)OC(C)C6)CC5)cc4)nc23)CC1] | ethyl 4-[2-[4-[4-(2,6-dimethylmorpholin-4-yl)piperidine-1-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-64 | 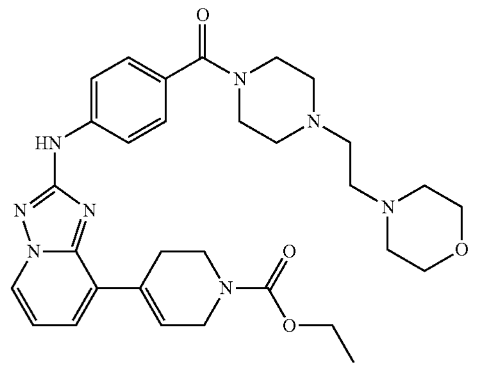 [SMILES: CCOC(=O)N1CC=C(c2cccn3nc(Nc4ccc(C(=O)N5CCN(CCN6CCOCC6)CC5)cc4)nc23)CC1] | ethyl 4-[2-[4-[4-(2-morpholinoethyl)piperazine-1-carbonyl]anilino]-[1,2,4]triazolo[1,5-a]pyridin-8-yl]-3,6-dihydro-2H-pyridine-1-carboxylate |
| 2-65 | 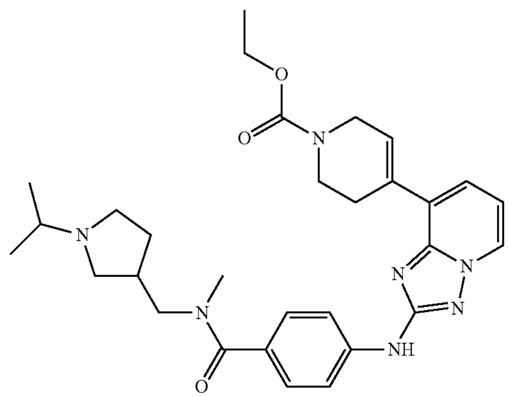 [SMILES: CCOC(=O)N1CC=C(c2cccn3nc(Nc4ccc(C(=O)N(C)CC5CCN(C(C)C)C5)cc4)nc23)CC1] | ethyl 4-[2-[4-[(1-isopropylpyrrolidin-3-yl)methyl-methyl-carbamoyl]anilino]-[1,2,4]triazolo[1,5-a]pyridin-8-yl]-3,6-dihydro-2H-pyridine-1-carboxylate |
| 2-66 | 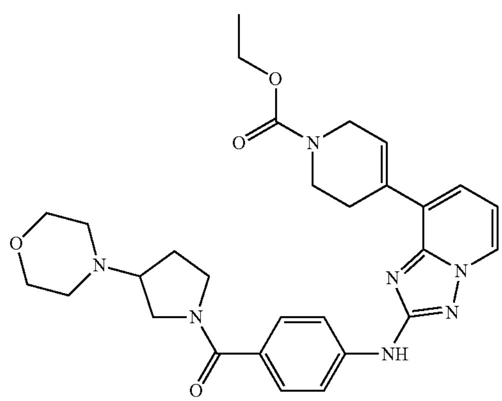 [SMILES: CCOC(=O)N1CC=C(c2cccn3nc(Nc4ccc(C(=O)N5CCC(N6CCOCC6)C5)cc4)nc23)CC1] | ethyl 4-[2-[4-(3-morpholinopyrrolidine-1-carbonyl)anilino]-[1,2,4]triazolo[1,5-a]pyridin-8-yl]-3,6-dihydro-2H-pyridine-1-carboxylate |
| 2-67 | 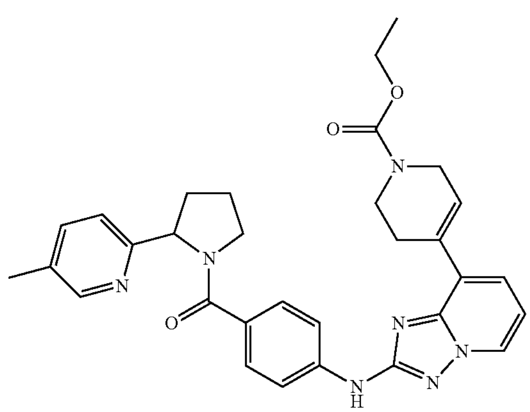 [SMILES: CCOC(=O)N1CC=C(c2cccn3nc(Nc4ccc(C(=O)N5CCCC5c5ccc(C)cn5)cc4)nc23)CC1] | ethyl 4-[2-[4-[2-(5-methyl-2-pyridyl)pyrrolidine-1-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-68 | 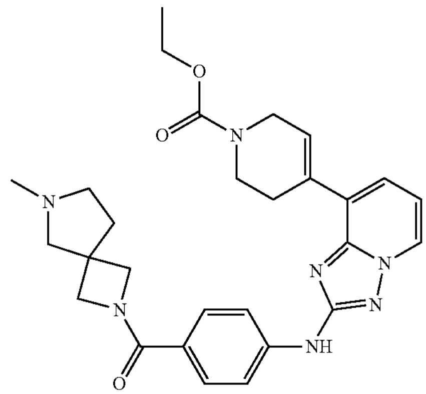 [SMILES: CCOC(=O)N1CC=C(c2cccn3nc(Nc4ccc(C(=O)N5CC6(CCN(C)C6)C5)cc4)nc23)CC1] | ethyl 4-[2-[4-(7-methyl-2,7-diazaspiro[3.4]octane-2-carbonyl)anilino]-[1,2,4]triazolo[1,5-a]pyridin-8-yl]-3,6-dihydro-2H-pyridine-1-carboxylate |
| 2-69 | 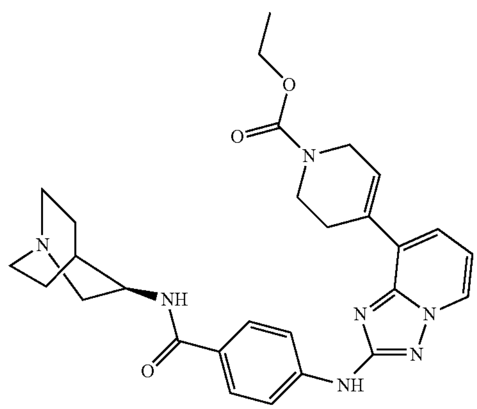 [SMILES: CCOC(=O)N1CC=C(c2cccn3nc(Nc4ccc(C(=O)N[C@H]5CN6CCC5CC6)cc4)nc23)CC1] | ethyl 4-[2-[4-[[(3R)-quinuclidin-3-yl]carbamoyl]anilino]-[1,2,4]triazolo[1,5-a]pyridin-8-yl]-3,6-dihydro-2H-pyridine-1-carboxylate |
| 2-70 | 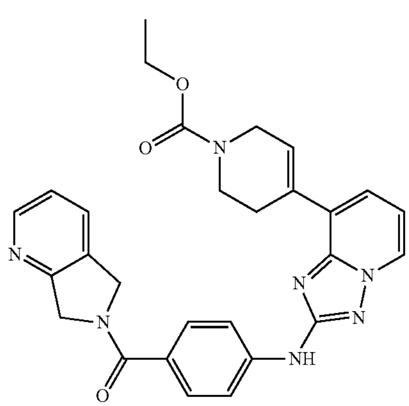 [SMILES: CCOC(=O)N1CC=C(c2cccn3nc(Nc4ccc(C(=O)N5Cc6cccnc6C5)cc4)nc23)CC1] | ethyl 4-[2-[4-(5,7-dihydropyrrolo[3,4-b]pyridine-6-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-71 | 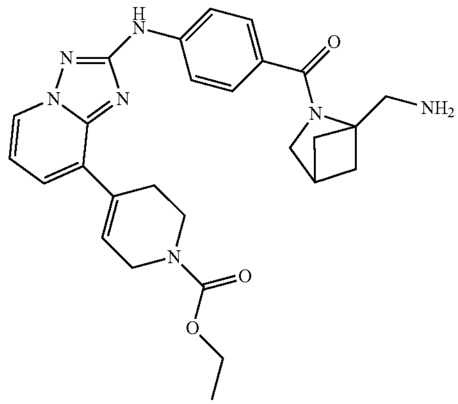 [SMILES: CCOC(=O)N1CC=C(c2cccn3nc(Nc4ccc(C(=O)N5CC6CC5(CN)C6)cc4)nc23)CC1] | ethyl 4-[2-[4-[4-(aminomethyl)-3-azabicyclo[2.1.1]hexane-3-carbonyl]anilino]-[1,2,4]triazolo[1,5-a]pyridin-8-yl]-3,6-dihydro-2H-pyridine-1-carboxylate |
| 2-72 | 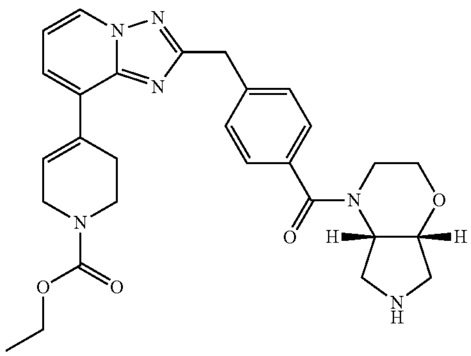 [SMILES: CCOC(=O)N1CC=C(c2cccn3nc(Cc4ccc(C(=O)N5CCO[C@@H]6CNC[C@@H]65)cc4)nc23)CC1] | ethyl 4-[2-[4-[(4aS,7aR)-3,4a,5,6,7,7a-hexahydro-2H-pyrrolo[3,4-b][1,4]oxazine-4-carbonyl]anilino]-[1,2,4]triazolo[1,5-a]pyridin-8-yl]-3,6-dihydro-2H-pyridine-1-carboxylate |
| 2-73 | 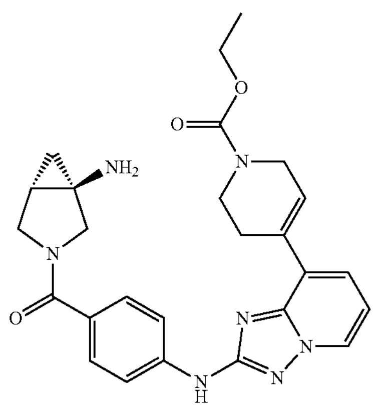 [SMILES: CCOC(=O)N1CC=C(c2cccn3nc(Nc4ccc(C(=O)N5C[C@@H]6C[C@]6(N)C5)cc4)nc23)CC1] | ethyl 4-[2-[4-[(1S,5R)-5-amino-3-azabicyclo[3.1.0]hexane-3-carbonyl]anilino]-[1,2,4]triazolo[1,5-a]pyridin-8-yl]-3,6-dihydro-2H-pyridine-1-carboxylate |
| 2-74 | 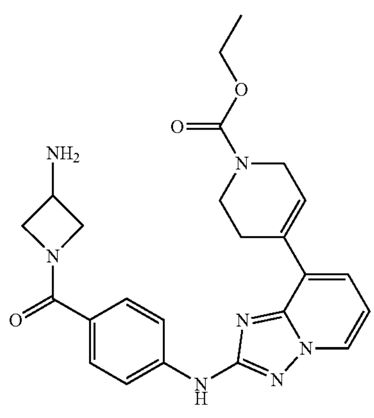 [SMILES: CCOC(=O)N1CC=C(c2cccn3nc(Nc4ccc(C(=O)N5CC(N)C5)cc4)nc23)CC1] | ethyl 4-[2-[4-(3-aminoazetidine-1-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-75 | 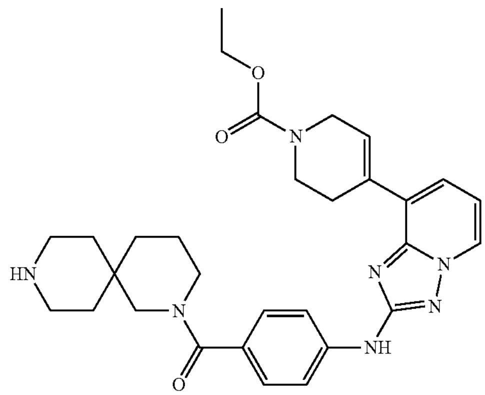 [SMILES: CCOC(=O)N1CC=C(c2cccn3nc(Nc4ccc(C(=O)N5CCCC6(CCNCC6)C5)cc4)nc23)CC1] | ethyl 4-[2-[4-(2,9-diazaspiro[5.5]undecane-2-carbonyl)anilino]-[1,2,4]triazolo[1,5-a]pyridin-8-yl]-3,6-dihydro-2H-pyridine-1-carboxylate |
| 2-76 | 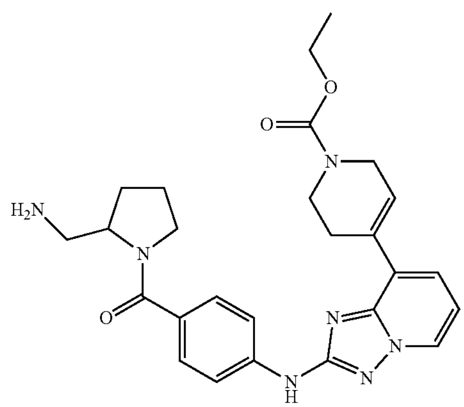 [SMILES: CCOC(=O)N1CC=C(c2cccn3nc(Nc4ccc(C(=O)N5CCCC5CN)cc4)nc23)CC1] | ethyl 4-[2-[4-[2-(aminomethyl)pyrrolidine-1-carbonyl]anilino]-[1,2,4]triazolo[1,5-a]pyridin-8-yl]-3,6-dihydro-2H-pyridine-1-carboxylate |
| 2-77 | 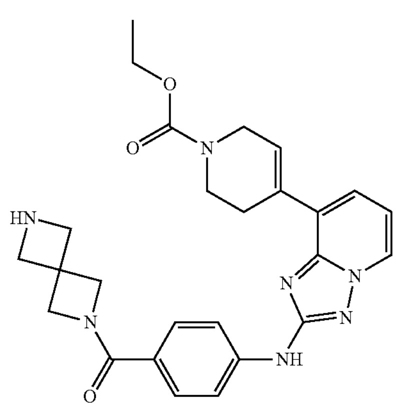 [SMILES: CCOC(=O)N1CC=C(c2cccn3nc(Nc4ccc(C(=O)N5CC6(CNC6)C5)cc4)nc23)CC1] | ethyl 4-[2-[4-(2,6-diazaspiro[3.3]heptane-2-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-78 | 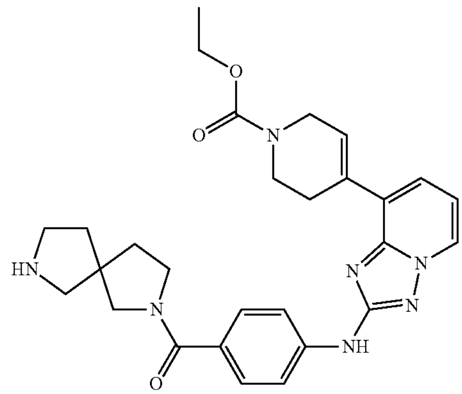 [SMILES: CCOC(=O)N1CC=C(c2cccn3nc(Nc4ccc(C(=O)N5CCC6(CCNC6)C5)cc4)nc23)CC1] | ethyl 4-[2-[4-(2,7-diazaspiro[4.4]nonane-2-carbonyl)anilino]-[1,2,4]triazolo[1,5-a]pyridin-8-yl]-3,6-dihydro-2H-pyridine-1-carboxylate |
| 2-79 | 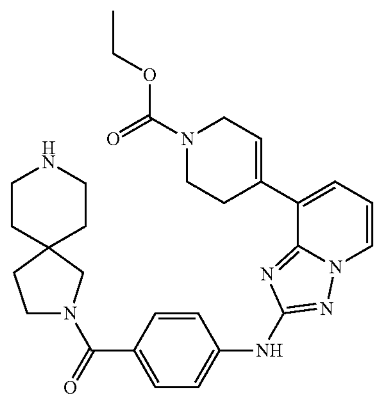 [SMILES: CCOC(=O)N1CC=C(c2cccn3nc(Nc4ccc(C(=O)N5CCC6(CCNCC6)C5)cc4)nc23)CC1] | ethyl 4-[2-[4-(2,8-diazaspiro[4.5]decane-2-carbonyl)anilino]-[1,2,4]triazolo[1,5-a]pyridin-8-yl]-3,6-dihydro-2H-pyridine-1-carboxylate |
| 2-80 | 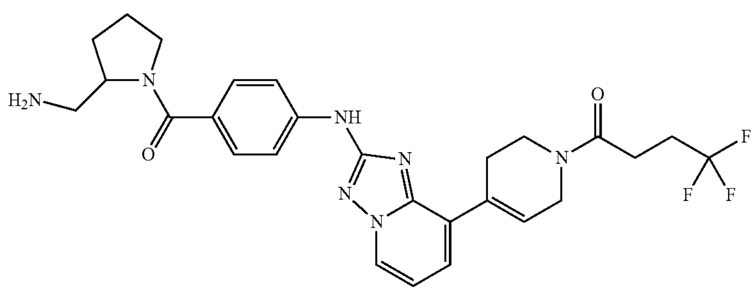 [SMILES: NCC1CCCN1C(=O)c1ccc(Nc2nc3c(C4=CCN(C(=O)CCC(F)(F)F)CC4)cccn3n2)cc1] | 1-[4-[2-[4-[2-(aminomethyl)pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-81 | 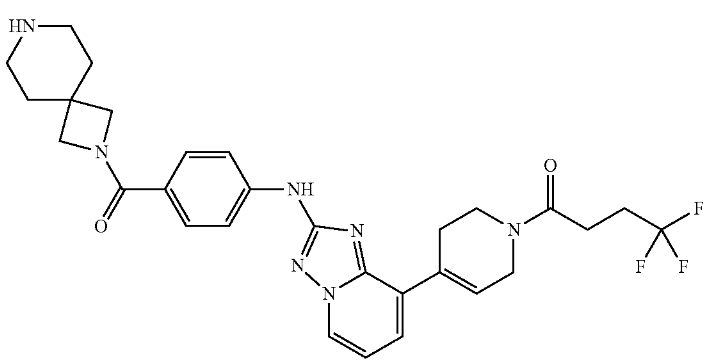 [SMILES: O=C(CCC(F)(F)F)N1CC=C(c2cccn3nc(Nc4ccc(C(=O)N5CC6(CCNCC6)C5)cc4)nc23)CC1] | 1-[4-[2-[4-(2,7-diazaspiro[3.5]nonane-2-carbonyl)anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-82 | 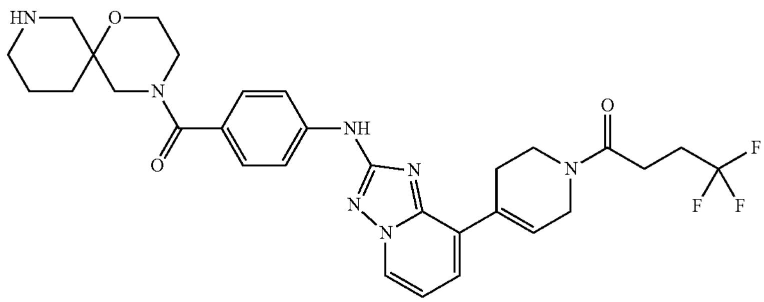 [SMILES: O=C(CCC(F)(F)F)N1CC=C(c2cccn3nc(Nc4ccc(C(=O)N5CCOC6(CCCNC6)C5)cc4)nc23)CC1] | 4,4,4-trifluoro-1-[4-[2-[4-(1-oxa-4,8-diazaspiro[5.5]undecane-4-carbonyl)anilino]-[1,2,4]triazolo[1,5-a]pyridin-8-yl]-3,6-dihydro-2H-pyridin-1-yl]butan-1-one |
| 2-83 | 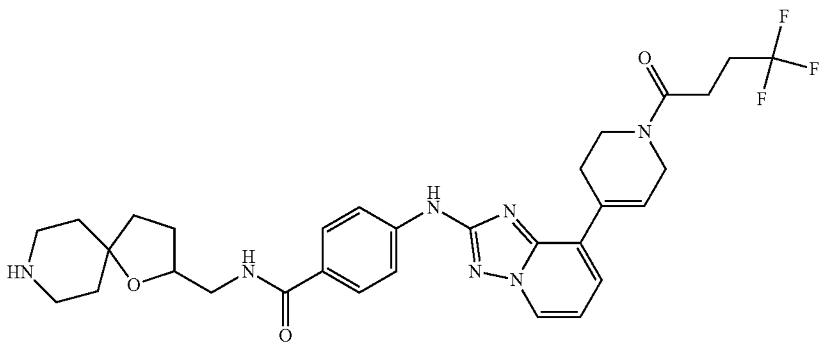 [SMILES: O=C(NCC1CCC2(CCNCC2)O1)c1ccc(Nc2nc3c(C4=CCN(C(=O)CCC(F)(F)F)CC4)cccn3n2)cc1] | N-(1-oxa-8-azaspiro[4.5]decan-2-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-84 | 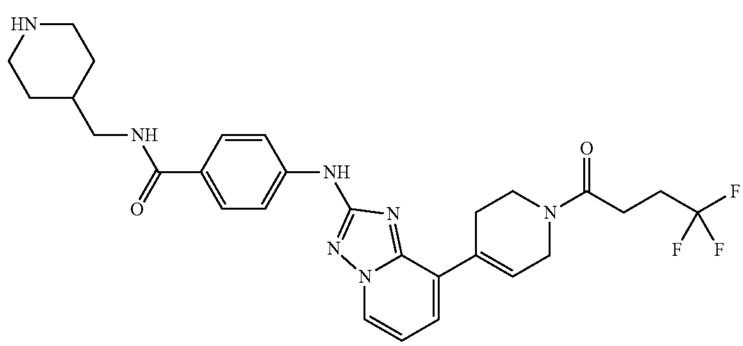 [SMILES: O=C(NCC1CCNCC1)c1ccc(Nc2nc3c(C4=CCN(C(=O)CCC(F)(F)F)CC4)cccn3n2)cc1] | N-(4-piperidylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-85 | 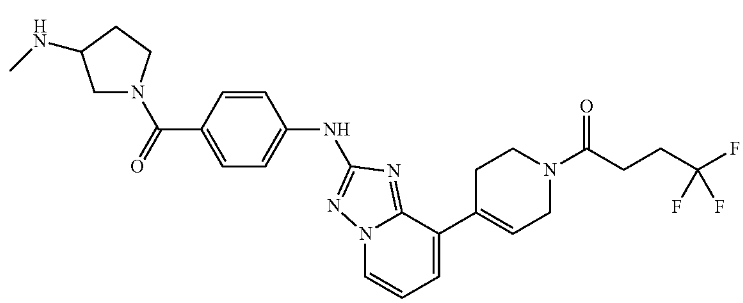 [SMILES: CNC1CCN(C(=O)c2ccc(Nc3nc4c(C5=CCN(C(=O)CCC(F)(F)F)CC5)cccn4n3)cc2)C1] | 4,4,4-trifluoro-1-[4-[2-[4-[3-(methylamino)pyrrolidine-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-86 | 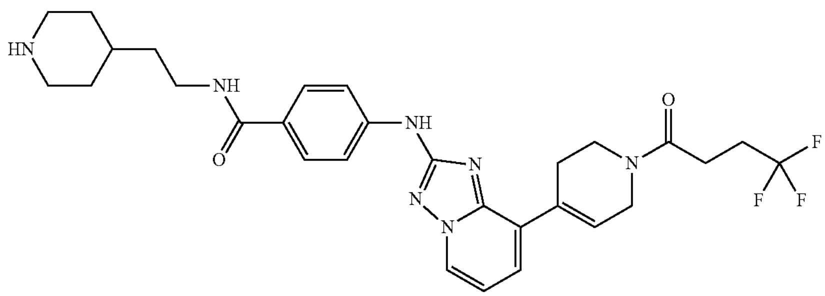 | N-[2-(4-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-87 | 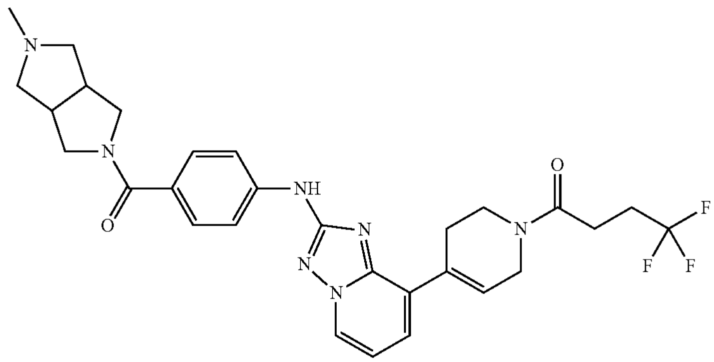 [SMILES: CN1CC2CN(C(=O)c3ccc(Nc4nc5c(C6=CCN(C(=O)CCC(F)(F)F)CC6)cccn5n4)cc3)CC2C1] | 4,4,4-trifluoro-1-[4-[2-[4-(2-methyl-1,3,3a,4,6,6a-hexahydropyrrolo[3,4-c]pyrrole-5-carbonyl)anilino]-[1,2,4]triazolo[1,5-a]pyridin-8-yl]-3,6-dihydro-2H-pyridin-1-yl]butan-1-one |
| 2-88 | 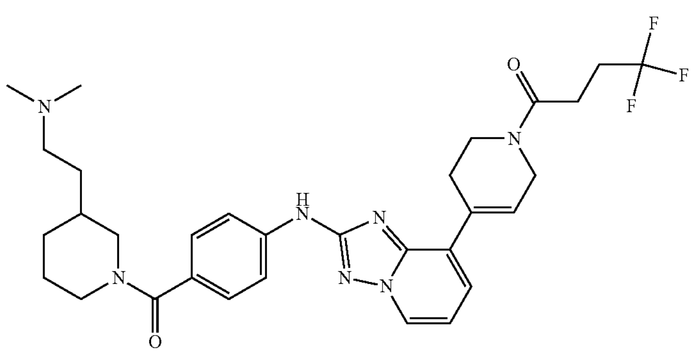 [SMILES: CN(C)CCC1CCCN(C(=O)c2ccc(Nc3nc4c(C5=CCN(C(=O)CCC(F)(F)F)CC5)cccn4n3)cc2)C1] | 1-[4-[2-[4-[3-[2-(dimethylamino)ethyl]piperidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-89 | 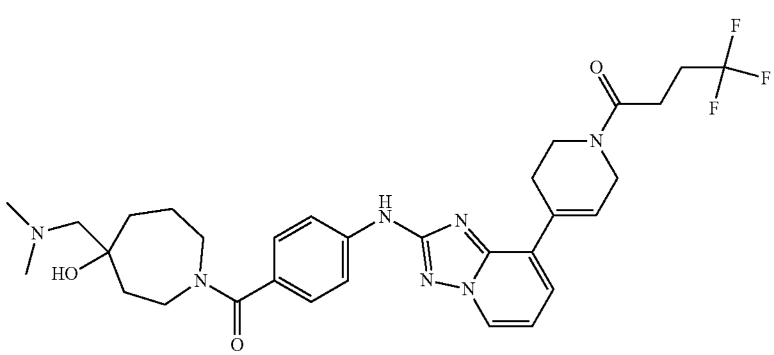 [SMILES: CN(C)CC1(O)CCCN(C(=O)c2ccc(Nc3nc4c(C5=CCN(C(=O)CCC(F)(F)F)CC5)cccn4n3)cc2)CC1] | 1-[4-[2-[4-[4-[(dimethylamino)methyl]-4-hydroxy-azepane-1-carbonyl]anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-90 | 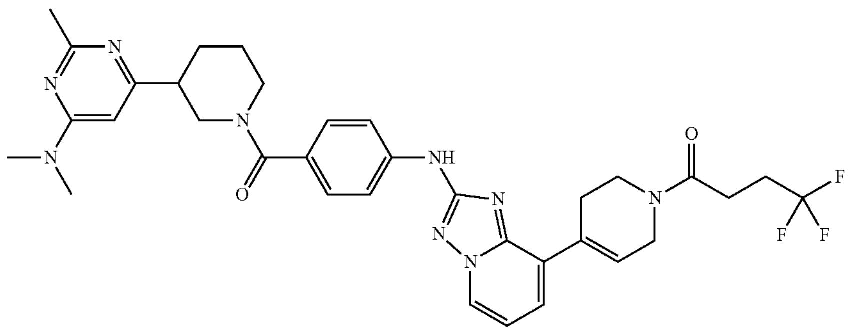 [SMILES: Cc1nc(C2CCCN(C(=O)c3ccc(Nc4nc5c(C6=CCN(C(=O)CCC(F)(F)F)CC6)cccn5n4)cc3)C2)cc(N(C)C)n1] | 1-[4-[2-[4-[3-[6-(dimethylamino)-2-methyl-pyrimidin-4-yl]piperidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-91 | 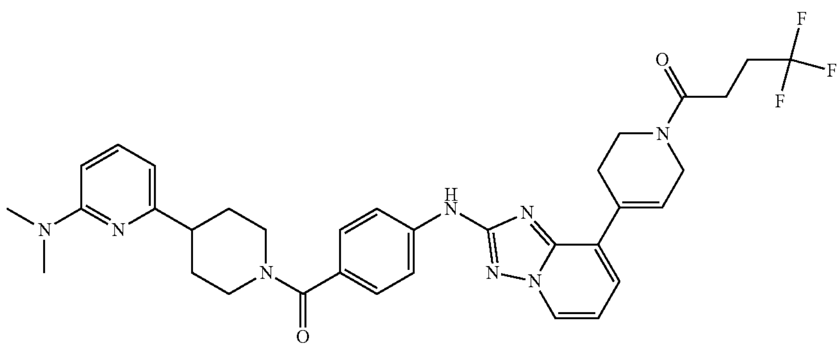 [SMILES: CN(C)c1cccc(C2CCN(C(=O)c3ccc(Nc4nc5c(C6=CCN(C(=O)CCC(F)(F)F)CC6)cccn5n4)cc3)CC2)n1] | 1-[4-[2-[4-[4-[6-(dimethylamino)-2-pyridyl]piperidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-92 | 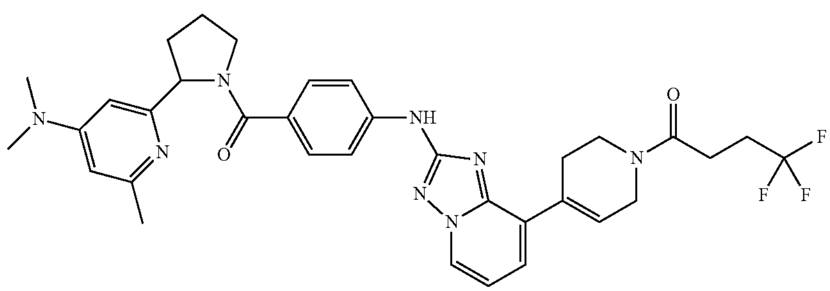 [SMILES: Cc1cc(N(C)C)cc(C2CCCN2C(=O)c2ccc(Nc3nc4c(C5=CCN(C(=O)CCC(F)(F)F)CC5)cccn4n3)cc2)n1] | 1-[4-[2-[4-[2-[4-(dimethylamino)-6-methyl-2-pyridyl]pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-93 | 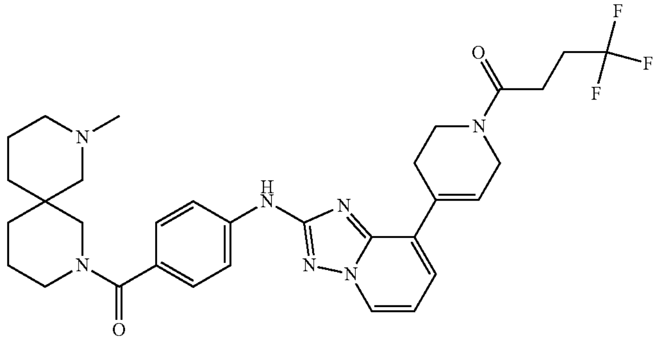 [SMILES: CN1CCCC2(CCCN(C(=O)c3ccc(Nc4nc5c(C6=CCN(C(=O)CCC(F)(F)F)CC6)cccn5n4)cc3)C2)C1] | 4,4,4-trifluoro-1-[4-[2-[4-(8-methyl-2,8-diazaspiro[5.5]undecane-2-carbonyl)anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-94 | 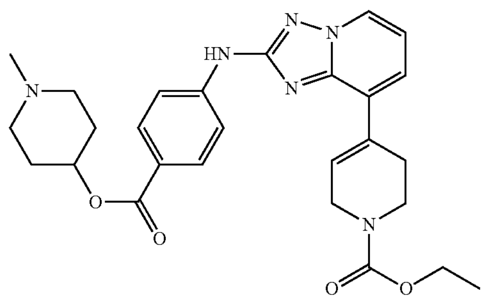 [SMILES: CCOC(=O)N1CC=C(c2cccn3nc(Nc4ccc(C(=O)OC5CCN(C)CC5)cc4)nc23)CC1] | ethyl 4-[2-[4-[(1-methyl-4-piperidyl)oxycarbonyl]anilino]-[1,2,4]triazolo[1,5-a]pyridin-8-yl]-3,6-dihydro-2H-pyridine-1-carboxylate |
| 2-95 | 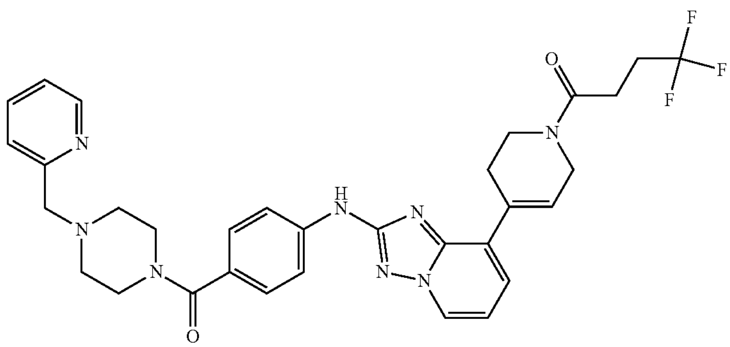 [SMILES: O=C(CCC(F)(F)F)N1CC=C(c2cccn3nc(Nc4ccc(C(=O)N5CCN(Cc6ccccn6)CC5)cc4)nc23)CC1] | 4,4,4-trifluoro-1-[4-[2-[4-[4-(2-pyridylmethyl)piperazine-1-carbonyl]anilino]-[1,2,4]triazolo[1,5-a]pyridin-8-yl]-3,6-dihydro-2H-pyridin-1-yl]butan-1-one |
| 2-96 | 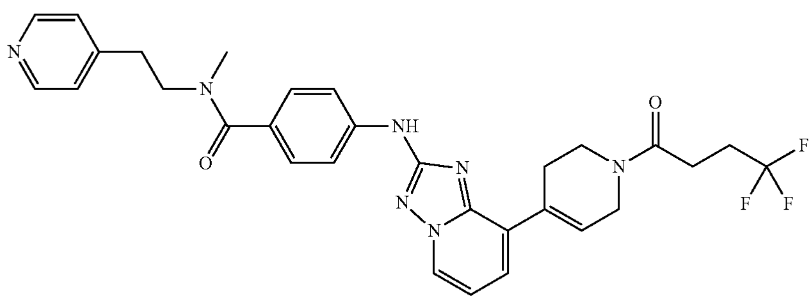 [SMILES: CN(CCc1ccncc1)C(=O)c1ccc(Nc2nc3c(C4=CCN(C(=O)CCC(F)(F)F)CC4)cccn3n2)cc1] | N-methyl-N-[2-(4-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-97 | 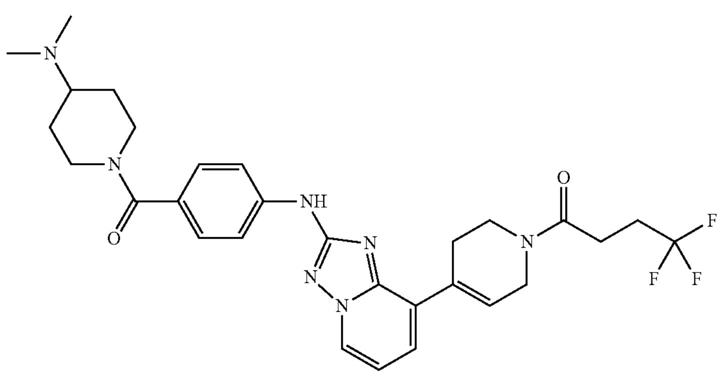 [SMILES: CN(C)C1CCN(C(=O)c2ccc(Nc3nc4c(C5=CCN(C(=O)CCC(F)(F)F)CC5)cccn4n3)cc2)CC1] | 1-[4-[2-[4-[4-(dimethylamino)piperidine-1-carbonyl]anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-98 | 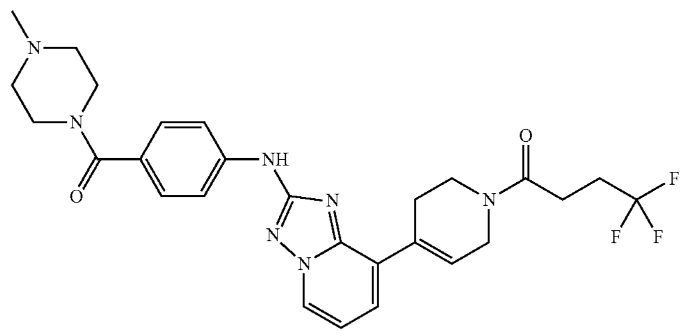 [SMILES: CN1CCN(C(=O)c2ccc(Nc3nc4c(C5=CCN(C(=O)CCC(F)(F)F)CC5)cccn4n3)cc2)CC1] | 4,4,4-trifluoro-1-[4-[2-[4-(4-methylpiperazine-1-carbonyl)anilino]-[1,2,4]triazolo[1,5-a]pyridin-8-yl]-3,6-dihydro-2H-pyridin-1-yl]butan-1-one |
| 2-99 | 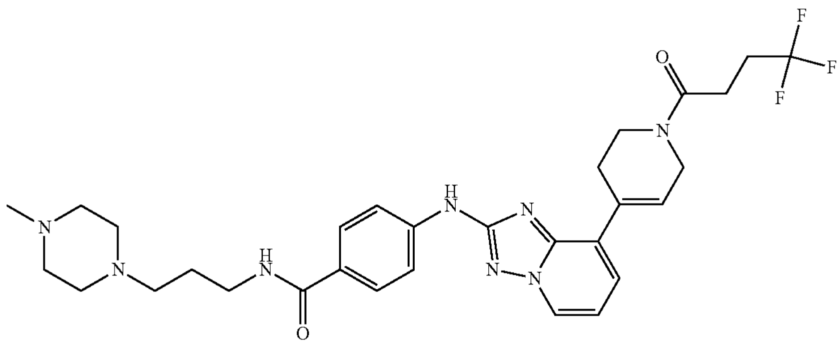 [SMILES: CN1CCN(CCCNC(=O)c2ccc(Nc3nc4c(C5=CCN(C(=O)CCC(F)(F)F)CC5)cccn4n3)cc2)CC1] | N-[3-(4-methylpiperazin-1-yl)propyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-100 | 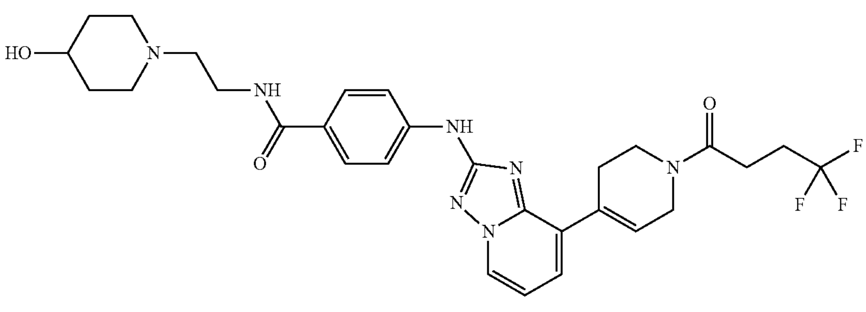 [SMILES: O=C(NCCN1CCC(O)CC1)c1ccc(Nc2nc3c(C4=CCN(C(=O)CCC(F)(F)F)CC4)cccn3n2)cc1] | N-[2-(4-hydroxy-1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-101 | 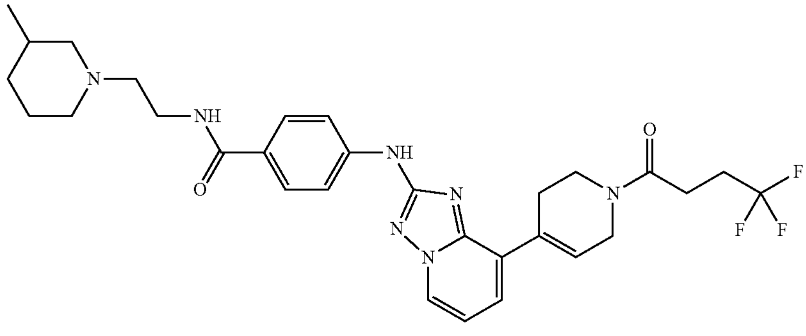 [SMILES: CC1CCCN(CCNC(=O)c2ccc(Nc3nc4c(C5=CCN(C(=O)CCC(F)(F)F)CC5)cccn4n3)cc2)C1] | N-[2-(3-methyl-1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-102 | 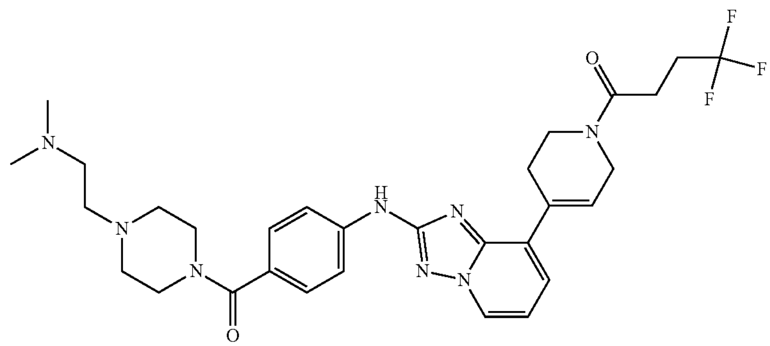 [SMILES: CN(C)CCN1CCN(C(=O)c2ccc(Nc3nc4c(C5=CCN(C(=O)CCC(F)(F)F)CC5)cccn4n3)cc2)CC1] | 1-[4-[2-[4-[4-[2-(dimethylamino)ethyl] piperazine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-103 | 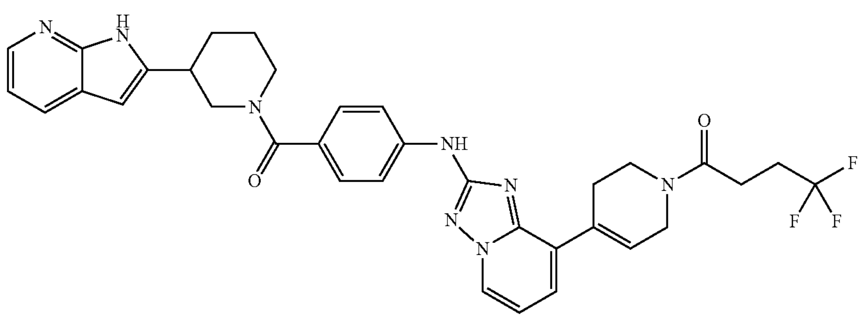 [SMILES: O=C(CCC(F)(F)F)N1CC=C(c2cccn3nc(Nc4ccc(C(=O)N5CCCC(c6cc7cccnc7[nH]6)C5)cc4)nc23)CC1] | 4,4,4-trifluoro-1-[4-[2-[4-[3-(1H-pyrrolo[2,3-b]pyridin-2-yl)piperidine-1-carbonyl]anilino]-[1,2,4]triazolo[1,5-a]pyridin-8-yl]-3,6-dihydro-2H-pyridin-1-yl]butan-1-one |
| 2-104 | 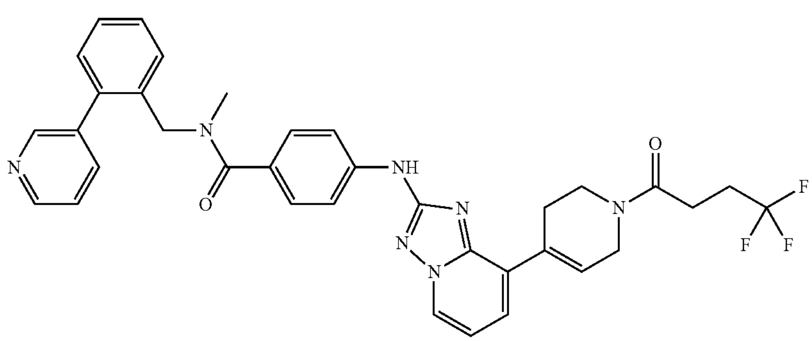 [SMILES: CN(Cc1ccccc1-c1cccnc1)C(=O)c1ccc(Nc2nc3c(C4=CCN(C(=O)CCC(F)(F)F)CC4)cccn3n2)cc1] | N-methyl-N-[[2-(3-pyridyl)phenyl]methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-105 | 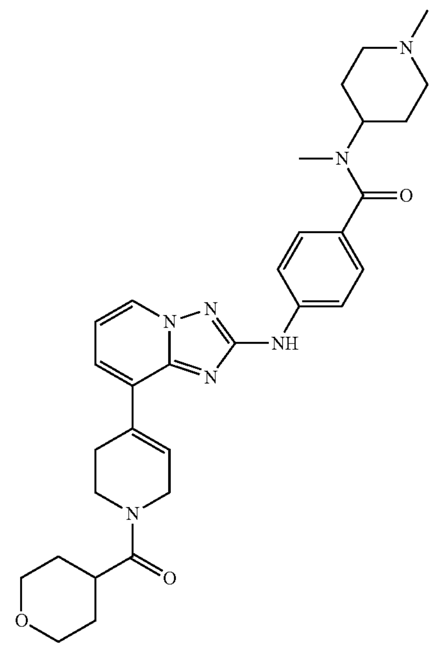 [SMILES: CN1CCC(N(C)C(=O)c2ccc(Nc3nc4c(C5=CCN(C(=O)C6CCOCC6)CC5)cccn4n3)cc2)CC1] | N-methyl-N-(1-methyl-4-piperidyl)-4-[[8-[1-(tetrahydropyran-4-carbonyl)-3,6-dihydro-2H-pyridin-4-yl]-[1,2,4]triazolo[1,5-a]pyridin-2-yl]amino]benzamide |
| 2-106 | 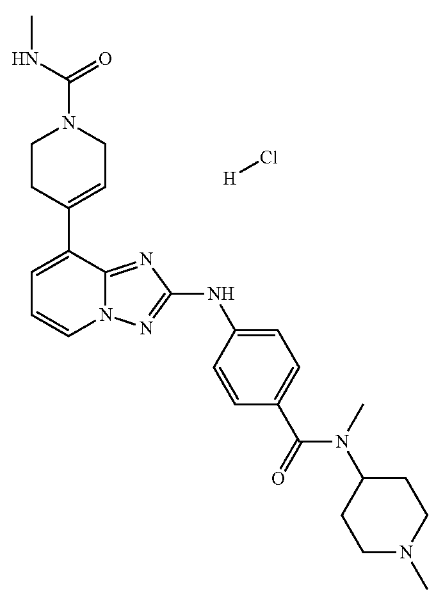 [SMILES: CNC(=O)N1CC=C(c2cccn3nc(Nc4ccc(C(=O)N(C)C5CCN(C)CC5)cc4)nc23)CC1 ; Cl] | N-methyl-4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxamide; hydrochloride |

TABLE A-continued
Exemplary Compounds of the Present Invention
| Ex. | Structure | Name |
|---|---|---|
| 2-107 | 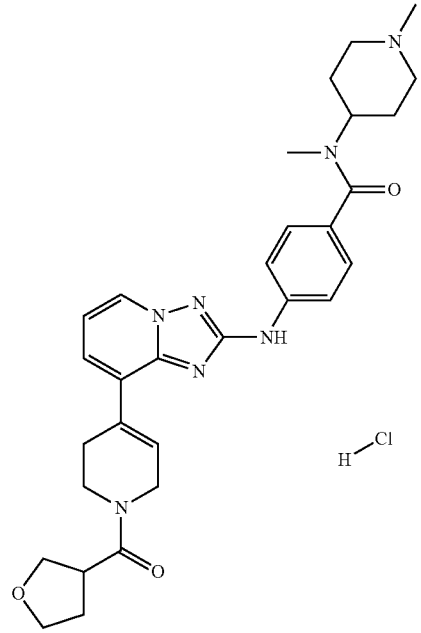 [SMILES: CN1CCC(N(C)C(=O)c2ccc(Nc3nc4c(C5=CCN(C(=O)C6CCOC6)CC5)cccn4n3)cc2)CC1 ; Cl] | N-methyl-N-(1-methyl-4-piperidyl)-4-[[8-[1-(tetrahydrofuran-3-carbonyl)-3,6-dihydro-2H-pyridin-4-yl]-[1,2,4]triazolo[1,5-a]pyridin-2-yl]amino]benzamide; hydrochloride |
| 2-108 | 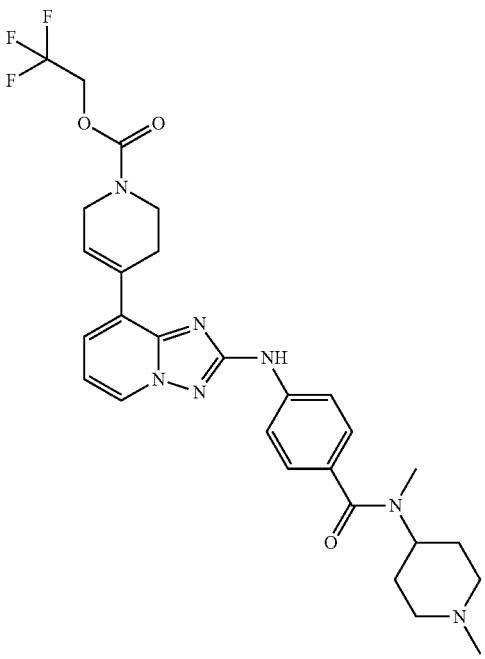 [SMILES: CN1CCC(N(C)C(=O)c2ccc(Nc3nc4c(C5=CCN(C(=O)OCC(F)(F)F)CC5)cccn4n3)cc2)CC1] | 2,2,2-trifluoroethyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-109 | 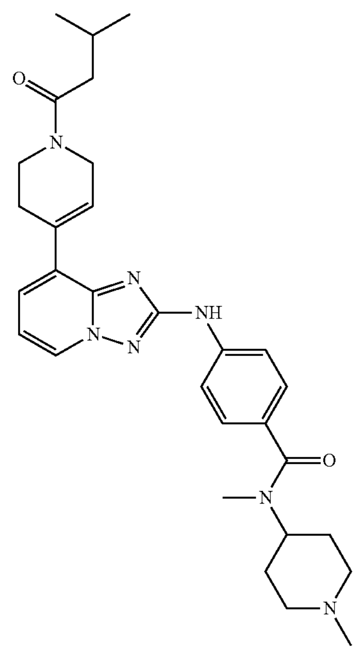 [SMILES: CC(C)CC(=O)N1CC=C(c2cccn3nc(Nc4ccc(C(=O)N(C)C5CCN(C)CC5)cc4)nc23)CC1] | N-methyl-4-[[8-[1-(3-methylbutanoyl)-3,6-dihydro-2H-pyridin-4-yl]-[1,2,4]triazolo[1,5-a]pyridin-2-yl]amino]-N-(1-methyl-4-piperidyl)benzamide |
| 2-110 | 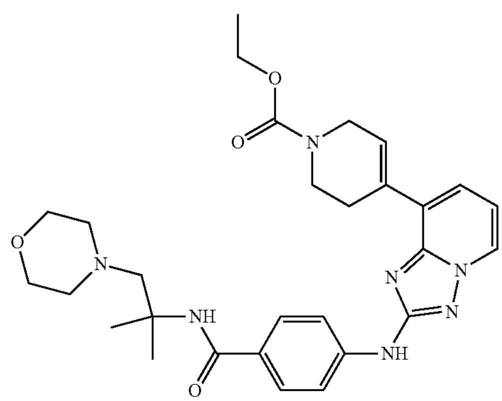 [SMILES: CCOC(=O)N1CC=C(c2cccn3nc(Nc4ccc(C(=O)NC(C)(C)CN5CCOCC5)cc4)nc23)CC1] | ethyl 4-[2-[4-[(1,1-dimethyl-2-morpholino-ethyl)carbamoyl]anilino]-[1,2,4]triazolo[1,5-a]pyridin-8-yl]-3,6-dihydro-2H-pyridine-1-carboxylate |
| 2-111 | 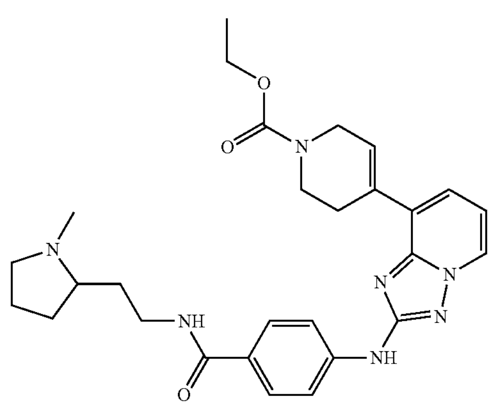 [SMILES: CCOC(=O)N1CC=C(c2cccn3nc(Nc4ccc(C(=O)NCCC5CCCN5C)cc4)nc23)CC1] | ethyl 4-[2-[4-[2-(1-methylpyrrolidin-2-yl)ethylcarbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-112 | 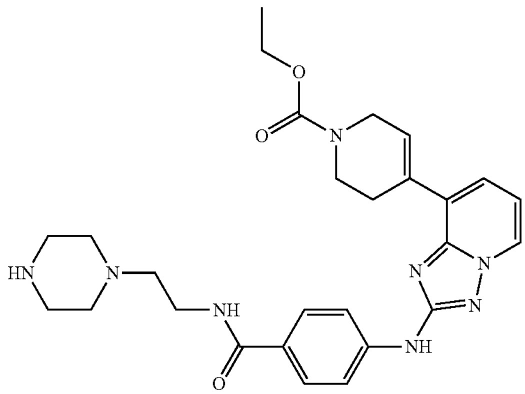 [SMILES: CCOC(=O)N1CC=C(c2cccn3nc(Nc4ccc(C(=O)NCCN5CCNCC5)cc4)nc23)CC1] | ethyl 4-[2-[4-(2-piperazin-1-ylethylcarbamoyl)anilino]-[1,2,4]triazolo[1,5-a]pyridin-8-yl]-3,6-dihydro-2H-pyridine-1-carboxylate |
| 2-113 | 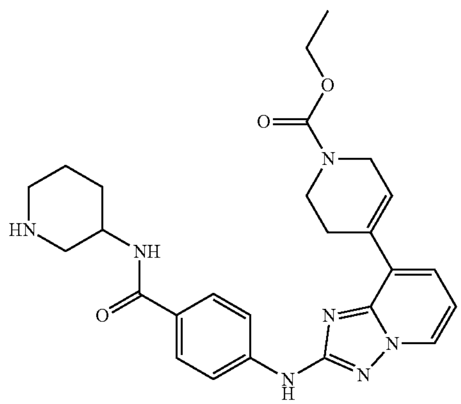 [SMILES: CCOC(=O)N1CC=C(c2cccn3nc(Nc4ccc(C(=O)NC5CCCNC5)cc4)nc23)CC1] | ethyl 4-[2-[4-(3-piperidylcarbamoyl)anilino]-[1,2,4]triazolo[1,5-a]pyridin-8-yl]-3,6-dihydro-2H-pyridine-1-carboxylate |
| 2-114 | 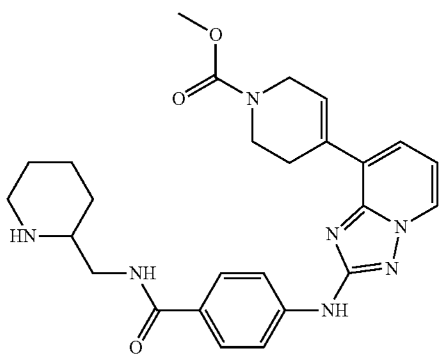 [SMILES: COC(=O)N1CC=C(c2cccn3nc(Nc4ccc(C(=O)NCC5CCCCN5)cc4)nc23)CC1] | ethyl 4-[2-[4-(2-piperidylmethylcarbamoyl)anilino]-[1,2,4]triazolo[1,5-a]pyridin-8-yl]-3,6-dihydro-2H-pyridine-1-carboxylate |
| 2-115 | 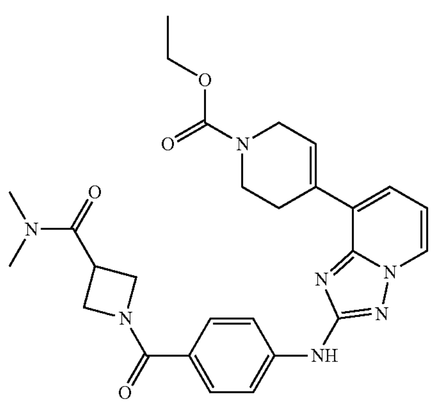 [SMILES: CCOC(=O)N1CC=C(c2cccn3nc(Nc4ccc(C(=O)N5CC(C(=O)N(C)C)C5)cc4)nc23)CC1] | ethyl 4-[2-[4-[3-(dimethylcarbamoyl)azetidine-1-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-116 | 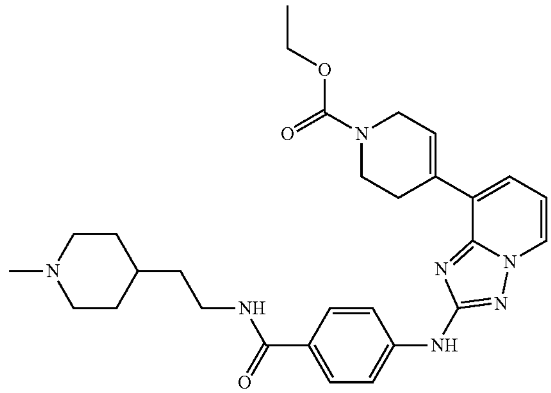 [SMILES: CCOC(=O)N1CC=C(c2cccn3nc(Nc4ccc(C(=O)NCCC5CCN(C)CC5)cc4)nc23)CC1] | ethyl 4-[2-[4-[2-(1-methyl-4-piperidyl)ethylcarbamoyl]anilino]-[1,2,4]triazolo[1,5-a]pyridin-8-yl]-3,6-dihydro-2H-pyridine-1-carboxylate |
| 2-117 | 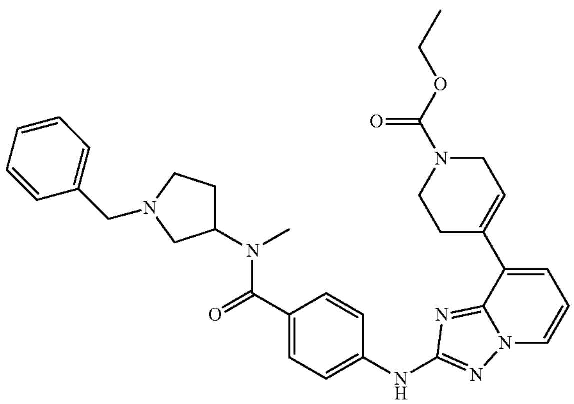 [SMILES: CCOC(=O)N1CC=C(c2cccn3nc(Nc4ccc(C(=O)N(C)C5CCN(Cc6ccccc6)C5)cc4)nc23)CC1] | ethyl 4-[2-[4-[(1-benzylpyrrolidin-3-yl)-methyl-carbamoyl]anilino]-[1,2,4]triazolo[1,5-a]pyridin-8-yl]-3,6-dihydro-2H-pyridine-1-carboxylate |
| 2-118 | 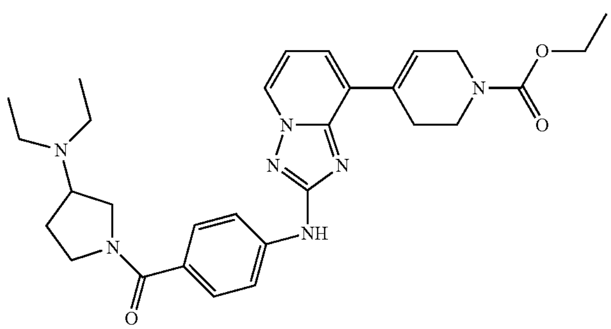 [SMILES: CCOC(=O)N1CC=C(c2cccn3nc(Nc4ccc(C(=O)N5CCC(N(CC)CC)C5)cc4)nc23)CC1] | ethyl 4-[2-[4-[3-(diethylamino)pyrrolidine-1-carbonyl]anilino]-[1,2,4]triazolo[1,5-a]pyridin-8-yl]-3,6-dihydro-2H-pyridine-1-carboxylate |
| 2-119 | 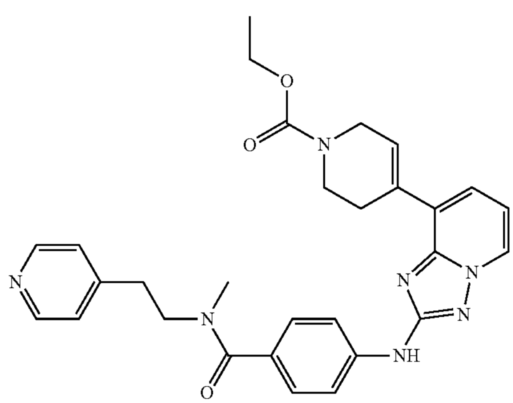 [SMILES: CCOC(=O)N1CC=C(c2cccn3nc(Nc4ccc(C(=O)N(C)CCc5ccncc5)cc4)nc23)CC1] | ethyl 4-[2-[4-[methyl-[2-(4-pyridyl)ethyl]carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-120 | 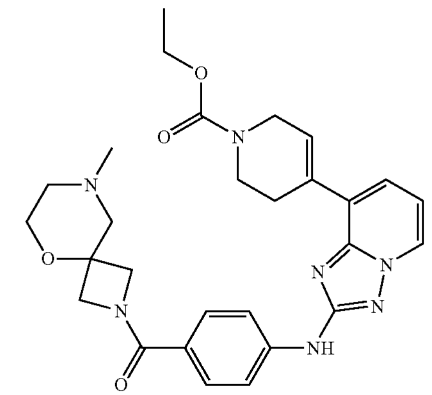 [SMILES: CCOC(=O)N1CC=C(c2cccn3nc(Nc4ccc(C(=O)N5CC6(CN(C)CCO6)C5)cc4)nc23)CC1] | ethyl 4-[2-[4-(8-methyl-5-oxa-2,8-diazaspiro[3.5]nonane-2-carbonyl)anilino]-[1,2,4]triazolo[1,5-a]pyridin-8-yl]-3,6-dihydro-2H-pyridine-1-carboxylate |
| 2-121 | 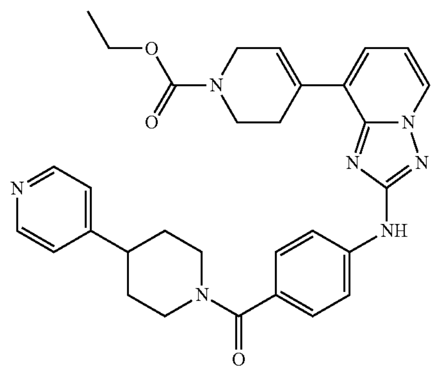 [SMILES: CCOC(=O)N1CC=C(c2cccn3nc(Nc4ccc(C(=O)N5CCC(c6ccncc6)CC5)cc4)nc23)CC1] | ethyl 4-[2-[4-[4-(4-pyridyl)piperidine-1-carbonyl]anilino]-[1,2,4]triazolo[1,5-a]pyridin-8-yl]-3,6-dihydro-2H-pyridine-1-carboxylate |
| 2-122 | 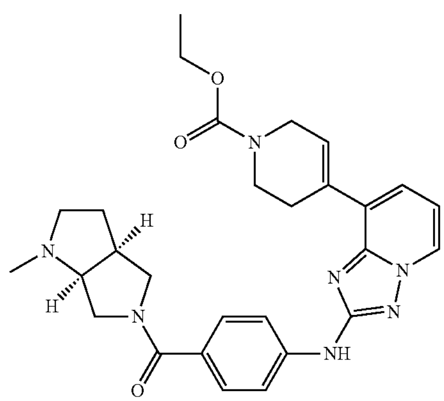 [SMILES: CCOC(=O)N1CC=C(c2cccn3nc(Nc4ccc(C(=O)N5C[C@@H]6CCN(C)[C@@H]6C5)cc4)nc23)CC1] | ethyl 4-[2-[4-[(3aS,6aS)-1-methyl-2,3,3a,4,6,6a-hexahydropyrrolo[3,4-b]pyrrole-5-carbonyl]anilino]-[1,2,4]triazolo[1,5-a]pyridin-8-yl]-3,6-dihydro-2H-pyridine-1-carboxylate |
| 2-123 | 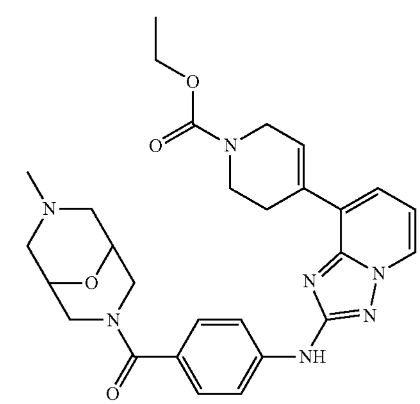 [SMILES: CCOC(=O)N1CC=C(c2cccn3nc(Nc4ccc(C(=O)N5CC6CN(C)CC(C5)O6)cc4)nc23)CC1] | ethyl 4-[2-[4-(7-methyl-9-oxa-3,7-diazabicyclo[3.3.1]nonane-3-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-124 | 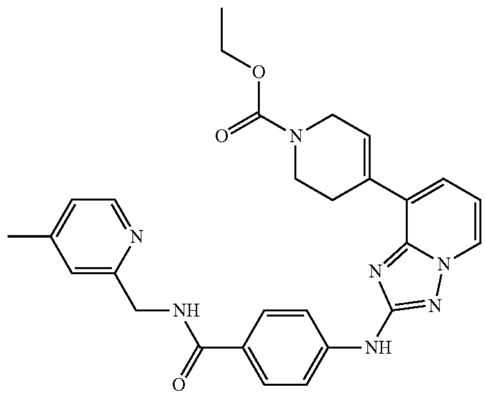 [SMILES: CCOC(=O)N1CC=C(c2cccn3nc(Nc4ccc(C(=O)NCc5cc(C)ccn5)cc4)nc23)CC1] | ethyl 4-[2-[4-[(4-methyl-2-pyridyl)methylcarbamoyl]anilino]-[1,2,4]triazolo[1,5-a]pyridin-8-yl]-3,6-dihydro-2H-pyridine-1-carboxylate |
| 2-125 | 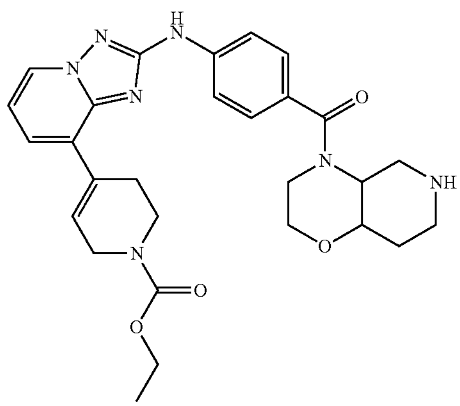 [SMILES: CCOC(=O)N1CC=C(c2cccn3nc(Nc4ccc(C(=O)N5CCOC6CCNCC65)cc4)nc23)CC1] | ethyl 4-[2-[4-(2,3,4a,5,6,7,8,8a-octahydropyrido[4,3-b][1,4]oxazine-4-carbonyl)anilino]-[1,2,4]triazolo[1,5-a]pyridin-8-yl]-3,6-dihydro-2H-pyridine-1-carboxylate |
| 2-126 | 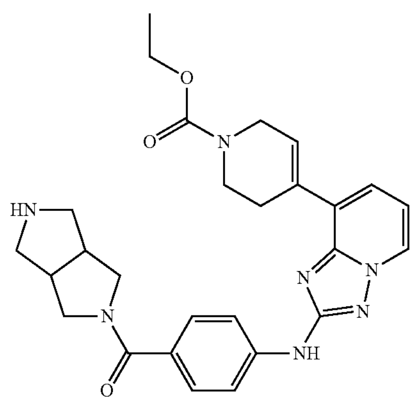 [SMILES: CCOC(=O)N1CC=C(c2cccn3nc(Nc4ccc(C(=O)N5CC6CNCC6C5)cc4)nc23)CC1] | ethyl 4-[2-[4-(2,3,3a,4,6,6a-hexahydro-1H-pyrrolo[3,4-c]pyrrole-5-carbonyl)anilino]-[1,2,4]triazolo[1,5-a]pyridin-8-yl]-3,6-dihydro-2H-pyridine-1-carboxylate |
| 2-127 | 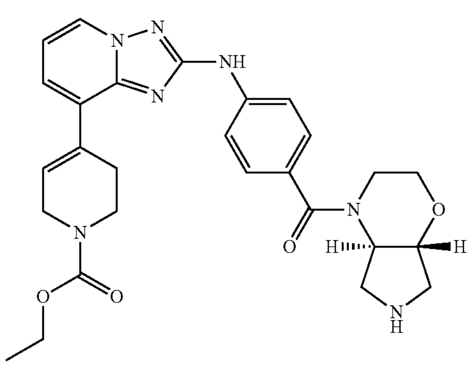 [SMILES: CCOC(=O)N1CC=C(c2cccn3nc(Nc4ccc(C(=O)N5CCO[C@@H]6CNC[C@H]65)cc4)nc23)CC1] | ethyl 4-[2-[4-[(4aR,7aR)-3,4a,5,6,7,7a-hexahydro-2H-pyrrolo[3,4-b][,4]oxazine-4-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-128 | 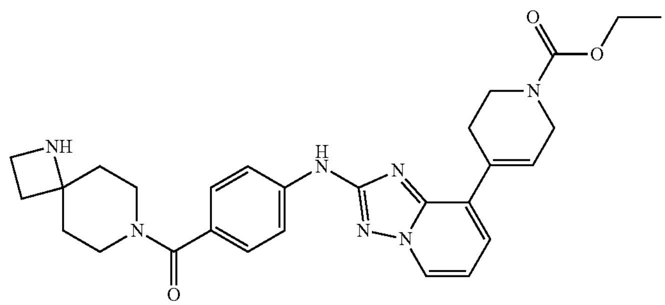 [SMILES: CCOC(=O)N1CC=C(c2cccn3nc(Nc4ccc(C(=O)N5CCC6(CCN6)CC5)cc4)nc23)CC1] | ethyl 4-[2-[4-(1,7-diazaspiro[3.5]nonane-7-carbonyl)anilino]-[1,2,4]triazolo[1,5-a]pyridin-8-yl]-3,6-dihydro-2H-pyridine-1-carboxylate |
| 2-129 | 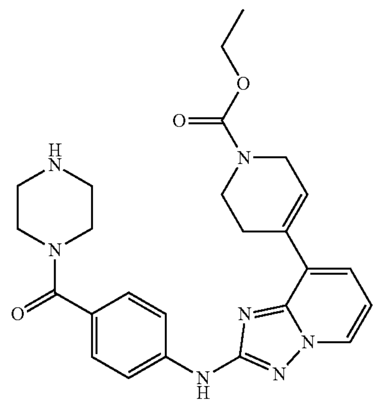 [SMILES: CCOC(=O)N1CC=C(c2cccn3nc(Nc4ccc(C(=O)N5CCNCC5)cc4)nc23)CC1] | ethyl 4-[2-[4-(piperazine-1-carbonyl)anilino]-[1,2,4]triazolo[1,5-a]pyridin-8-yl]-3,6-dihydro-2H-pyridine-1-carboxylate |
| 2-130 | 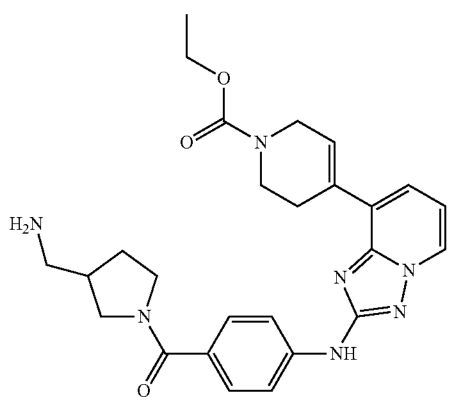 [SMILES: CCOC(=O)N1CC=C(c2cccn3nc(Nc4ccc(C(=O)N5CCC(CN)C5)cc4)nc23)CC1] | ethyl 4-[2-[4-[3-(aminomethyl)pyrrolidine-1-carbonyl]anilino]-[1,2,4]triazolo[1,5-a]pyridin-8-yl]-3,6-dihydro-2H-pyridine-1-carboxylate |
| 2-131 | 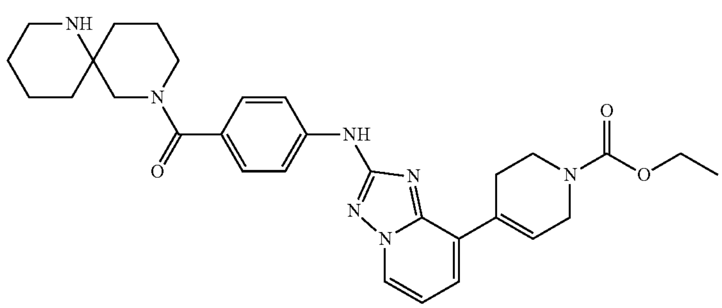 [SMILES: CCOC(=O)N1CC=C(c2cccn3nc(Nc4ccc(C(=O)N5CCCC6(CCCCN6)C5)cc4)nc23)CC1] | ethyl 4-[2-[4-(1,8-diazaspiro[5.5]undecane-8-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-132 | 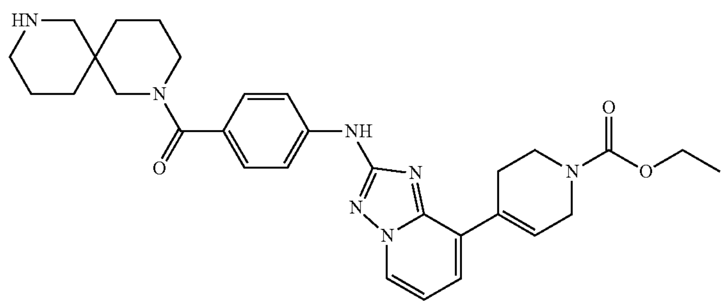 [SMILES: CCOC(=O)N1CC=C(c2cccn3nc(Nc4ccc(C(=O)N5CCCC6(CCCNC6)C5)cc4)nc23)CC1] | ethyl 4-[2-[4-(2,8-diazaspiro[5.5]undecane-2-carbonyl)anilino]-[1,2,4]triazolo[1,5-a]pyridin-8-yl]-3,6-dihydro-2H-pyridine-1-carboxylate |
| 2-133 | 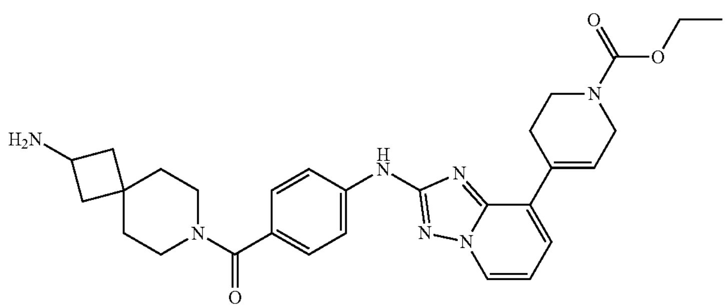 [SMILES: CCOC(=O)N1CC=C(c2cccn3nc(Nc4ccc(C(=O)N5CCC6(CC5)CC(N)C6)cc4)nc23)CC1] | ethyl 4-[2-[4-(2-amino-7-azaspiro[3.5]nonane-7-carbonyl)anilino]-[1,2,4]triazolo[1,5-a]pyridin-8-yl]-3,6-dihydro-2H-pyridine-1-carboxylate |
| 2-134 | 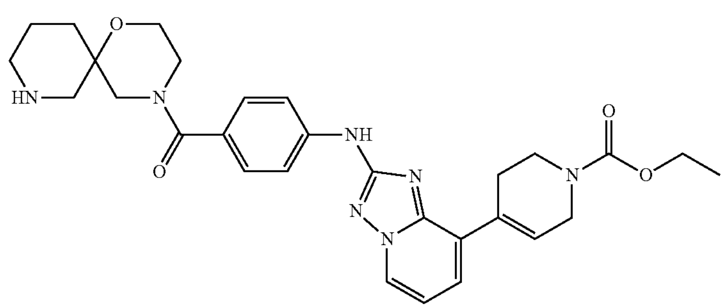 [SMILES: CCOC(=O)N1CC=C(c2cccn3nc(Nc4ccc(C(=O)N5CCOC6(CCCNC6)C5)cc4)nc23)CC1] | ethyl 4-[2-[4-(1-oxa-4,8-diazaspiro[5.5]undecane-4-carbonyl)anilino]-[1,2,4]triazolo[1,5-a]pyridin-8-yl]-3,6-dihydro-2H-pyridine-1-carboxylate |
| 2-135 | 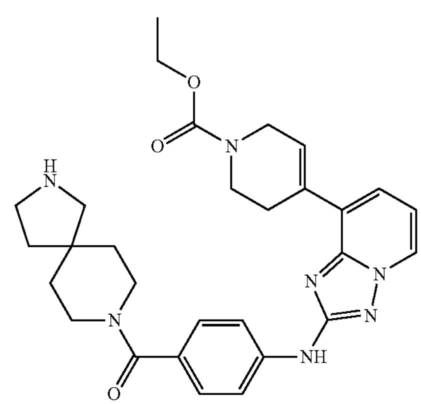 [SMILES: CCOC(=O)N1CC=C(c2cccn3nc(Nc4ccc(C(=O)N5CCC6(CCNC6)CC5)cc4)nc23)CC1] | ethyl 4-[2-[4-(2,8-diazaspiro[4.5]decane-8-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-136 | 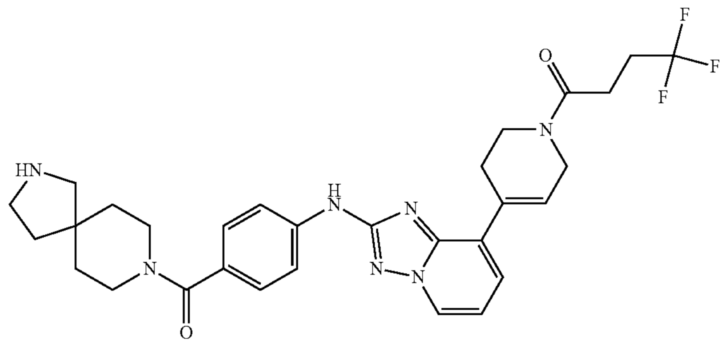 [SMILES: O=C(CCC(F)(F)F)N1CC=C(c2cccn3nc(Nc4ccc(C(=O)N5CCC6(CCNC6)CC5)cc4)nc23)CC1] | 1-[4-[2-[4-(2,8-diazaspiro[4.5]decane-8-carbonyl)anilino]-[1,2,4]triazolo[1,5-a]pyridin-8-yl]-3,6-dihydro-2H-pyridin-1-yl]-4,4,4-trifluoro-butan-1-one |
| 2-137 | 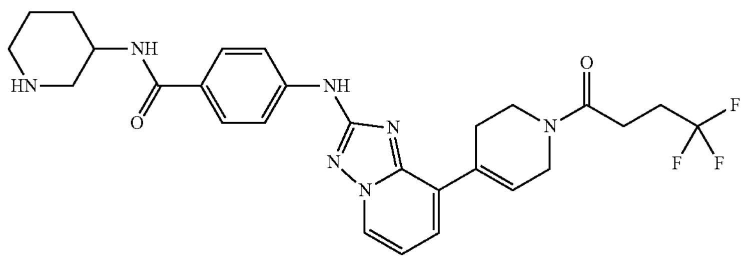 [SMILES: O=C(NC1CCCNC1)c1ccc(Nc2nc3c(C4=CCN(C(=O)CCC(F)(F)F)CC4)cccn3n2)cc1] | N-(3-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-138 | 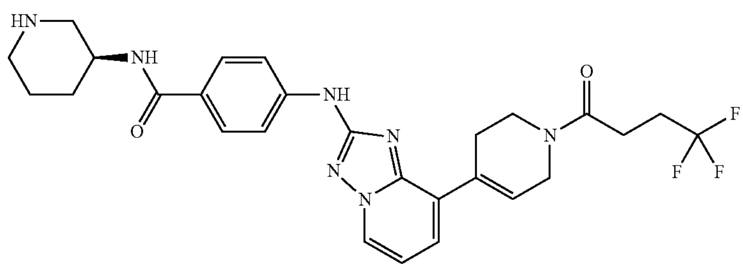 [SMILES: O=C(N[C@H]1CCCNC1)c1ccc(Nc2nc3c(C4=CCN(C(=O)CCC(F)(F)F)CC4)cccn3n2)cc1] | N-[(3S)-3-piperidyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-139 | 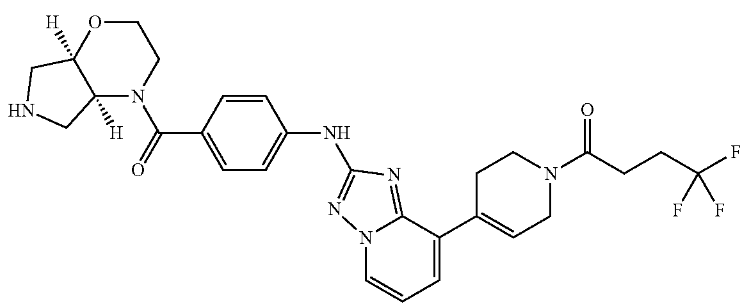 [SMILES: O=C(CCC(F)(F)F)N1CC=C(c2cccn3nc(Nc4ccc(C(=O)N5CCO[C@@H]6CNC[C@@H]65)cc4)nc23)CC1] | 1-[4-[2-[4-[(4aS,7aR)-3,4a,5,6,7,7a-hexahydro-2H-pyrrolo[3,4-b][1,4]oxazine-4-carbonyl]anilino]-[1,2,4]triazolo[1,5-a]pyridin-8-yl]-3,6-dihydro-2H-pyridin-1-yl]-4,4,4-trifluoro-butane-1-one |
| 2-140 | 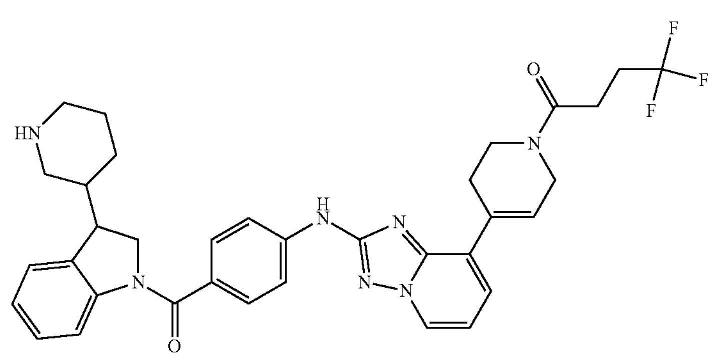 [SMILES: O=C(CCC(F)(F)F)N1CC=C(c2cccn3nc(Nc4ccc(C(=O)N5CC(C6CCCNC6)c6ccccc65)cc4)nc23)CC1] | 4,4,4-trifluoro-1-[4-[2-[4-[3-(3-piperidyl)indoline-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-141 | 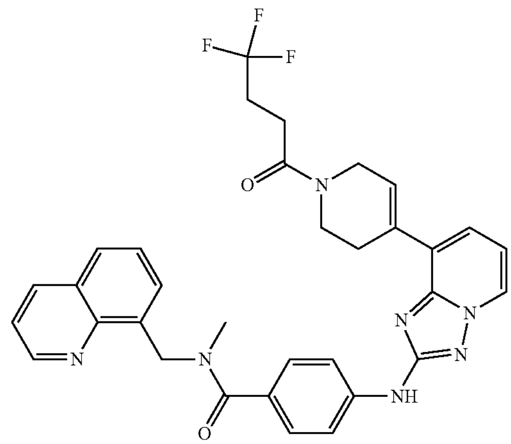 [SMILES: CN(Cc1cccc2cccnc12)C(=O)c1ccc(Nc2nc3c(C4=CCN(C(=O)CCC(F)(F)F)CC4)cccn3n2)cc1] | N-methyl-N-(8-quinolylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-142 | 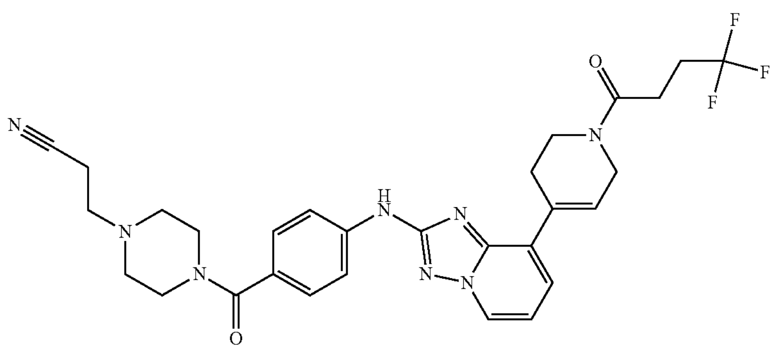 [SMILES: N#CCCN1CCN(C(=O)c2ccc(Nc3nc4c(C5=CCN(C(=O)CCC(F)(F)F)CC5)cccn4n3)cc2)CC1] | 3-[4-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazin-1-yl]propanenitrile |
| 2-143 | 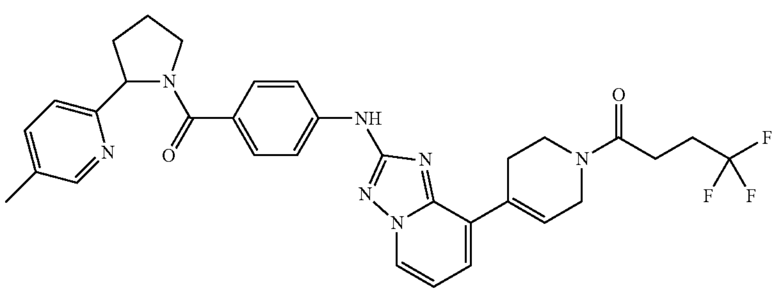 [SMILES: Cc1ccc(C2CCCN2C(=O)c2ccc(Nc3nc4c(C5=CCN(C(=O)CCC(F)(F)F)CC5)cccn4n3)cc2)nc1] | 4,4,4-trifluoro-1-[4-[2-[4-[2-(5-methyl-2-pyridyl)pyrrolidine-1-carbonyl]anilino]-[1,2,4]triazolo[1,5-a]pyridin-8-yl]-3,6-dihydro-2H-pyridin-1-yl]butan-1-one |
| 2-144 | 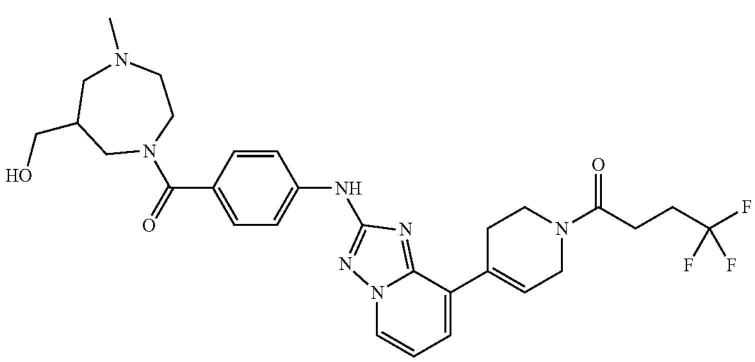 [SMILES: CN1CCN(C(=O)c2ccc(Nc3nc4c(C5=CCN(C(=O)CCC(F)(F)F)CC5)cccn4n3)cc2)CC(CO)C1] | 4,4,4-trifluoro-1-[4-[2-[4-[6-(hydroxymethyl)-4-methyl-1,4-diazepane-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-145 | 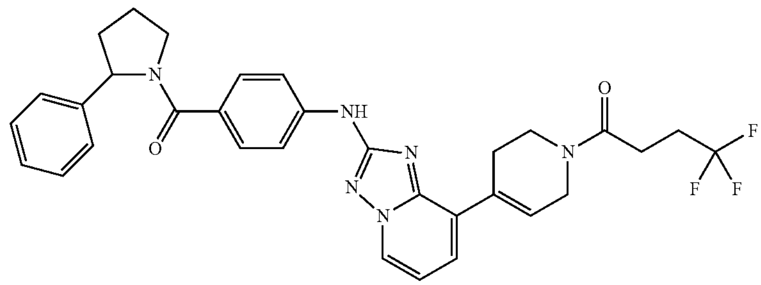 [SMILES: O=C(CCC(F)(F)F)N1CC=C(c2cccn3nc(Nc4ccc(C(=O)N5CCCC5c5ccccc5)cc4)nc23)CC1] | 4,4,4-trifluoro-1-[4-[2-[4-[2-(3-pyridyl)pyrrolidine-1-carbonyl]anilino]-[1,2,4]triazolo[1,5-a]pyridin-8-yl]-3,6-dihydro-2H-pyridin-1-yl]butan-1-one |
| 2-146 | 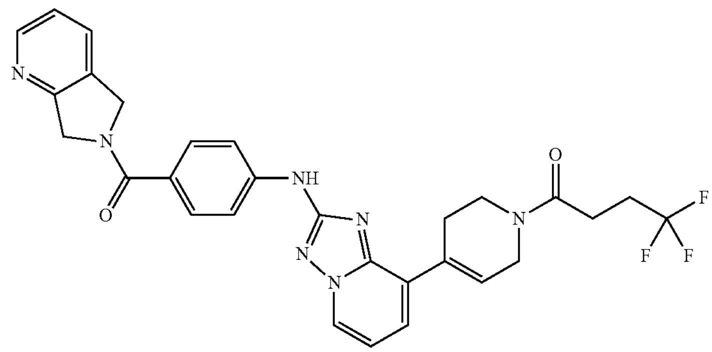 [SMILES: O=C(CCC(F)(F)F)N1CC=C(c2cccn3nc(Nc4ccc(C(=O)N5Cc6cccnc6C5)cc4)nc23)CC1] | 1-[4-[2-[4-(5,7-dihydropyrrolo[3,4-b]pyridine-6-carbonyl)anilino]-[1,2,4]triazolo[1,5-a]pyridin-8-yl]-3,6-dihydro-2H-pyridin-1-yl]-4,4,4-trifluoro-butan-1-one |
| 2-147 | 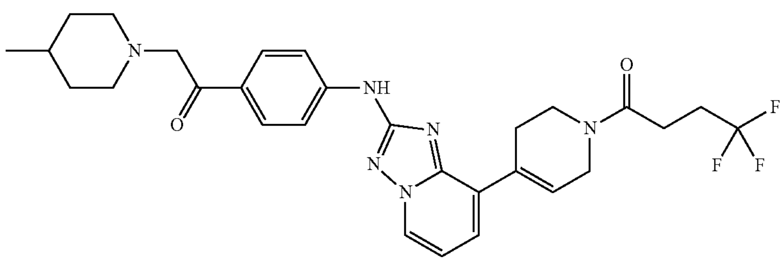 [SMILES: CC1CCN(CC(=O)c2ccc(Nc3nc4c(C5=CCN(C(=O)CCC(F)(F)F)CC5)cccn4n3)cc2)CC1] | N-[2-(4-methyl-1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-148 | 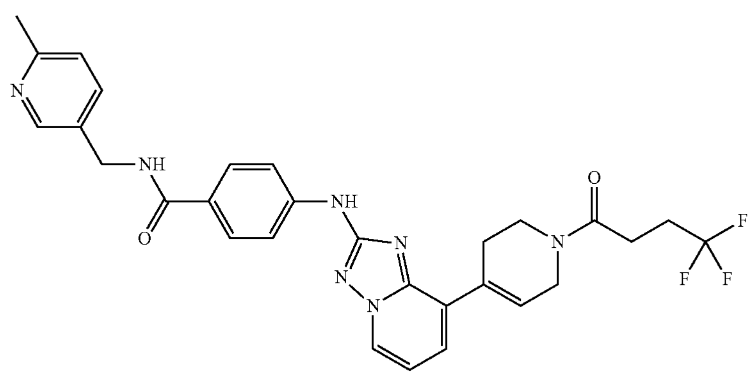 [SMILES: Cc1ccc(CNC(=O)c2ccc(Nc3nc4c(C5=CCN(C(=O)CCC(F)(F)F)CC5)cccn4n3)cc2)cn1] | N-[(6-methyl-3-pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-149 | 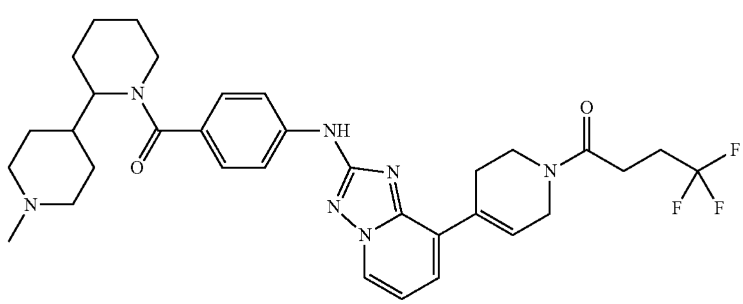 [SMILES: CN1CCC(C2CCCCN2C(=O)c2ccc(Nc3nc4c(C5=CCN(C(=O)CCC(F)(F)F)CC5)cccn4n3)cc2)CC1] | 4,4,4-trifluoro-1-[4-[2-[4-[2-(1-methyl-4-piperidyl)piperidine-1-carbonyl]anilino]-[1,2,4]triazolo[1,5-a]pyridin-8-yl]-3,6-dihydro-2H-pyridin-1-yl]butane-1-one |

TABLE A-continued

Exemplary Compounds of the Present Invention

| Ex. | Structure | Name |
| --- | --- | --- |
| 2-150 | 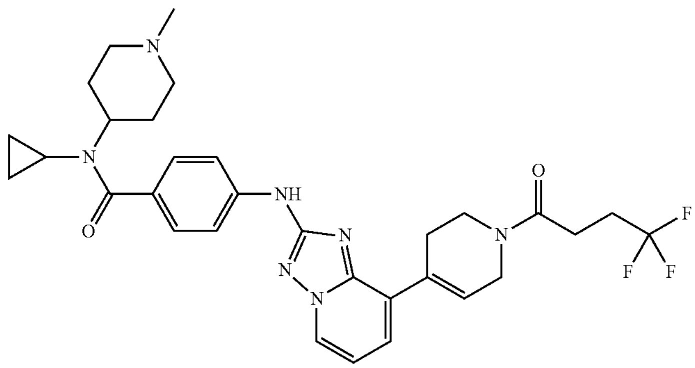 [SMILES: CN1CCC(N(C(=O)c2ccc(Nc3nc4c(C5=CCN(C(=O)CCC(F)(F)F)CC5)cccn4n3)cc2)C2CC2)CC1] | N-cyclopropyl-N-(1-methyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-151 | 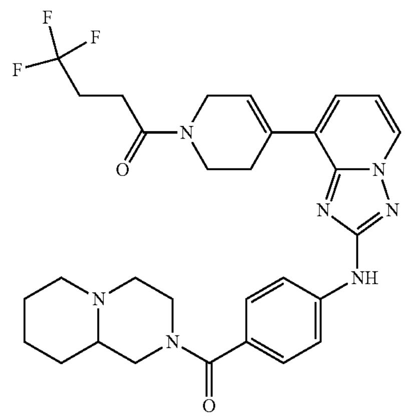 [SMILES: O=C(CCC(F)(F)F)N1CC=C(c2cccn3nc(Nc4ccc(C(=O)N5CCN6CCCCC6C5)cc4)nc23)CC1] | 1-[4-[2-[4-(1,3,4,6,7,8,9,9a-octahydropyrido[1,2-a]pyrazine-2-carbonyl)anilino]-[1,2,4]triazolo[1,5-a]pyridin-8-yl]-3,6-dihydro-2H-pyridin-1-yl]-4,4,4-trifluoro-butan-1-one |
| 2-152 | 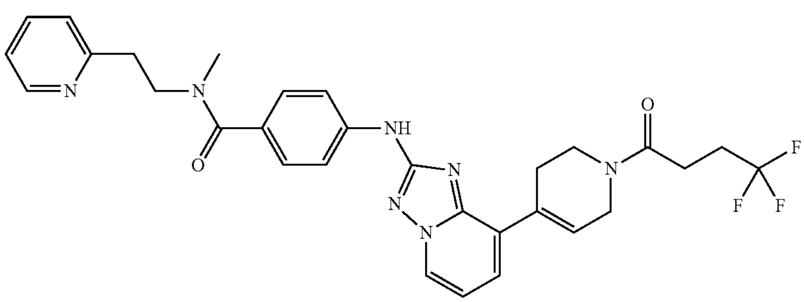 [SMILES: CN(CCc1ccccn1)C(=O)c1ccc(Nc2nc3c(C4=CCN(C(=O)CCC(F)(F)F)CC4)cccn3n2)cc1] | N-methyl-N-[2-(2-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-153 | 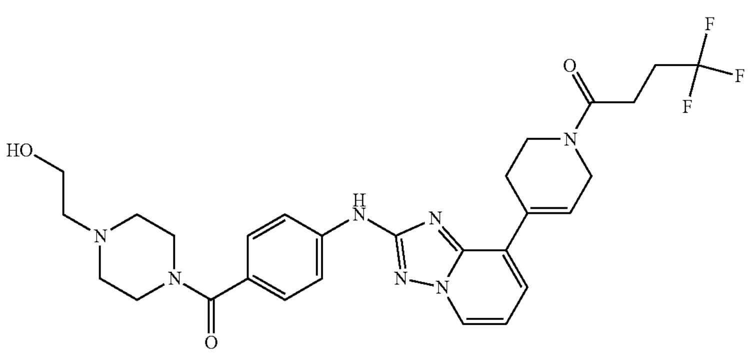 [SMILES: O=C(CCC(F)(F)F)N1CC=C(c2cccn3nc(Nc4ccc(C(=O)N5CCN(CCO)CC5)cc4)nc23)CC1] | 4,4,4-trifluoro-1-[4-[2-[4-[4-(2-hydroxyethyl)piperazine-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-154 | 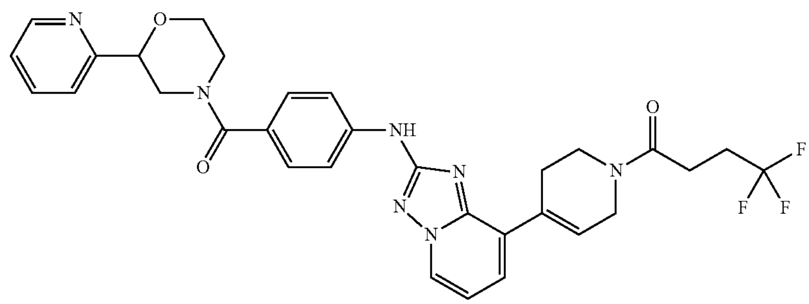 [SMILES: O=C(CCC(F)(F)F)N1CC=C(c2cccn3nc(Nc4ccc(C(=O)N5CCOC(c6ccccn6)C5)cc4)nc23)CC1] | 4,4,4-trifluoro-1-[4-[2-[4-[2-(2-pyridyl)morpholine-4-carbonyl]anilino]-[1,2,4]triazolo[1,5-a]pyridin-8-yl]-3,6-dihydro-2H-pyridin-1-yl]butan-1-one |
| 2-155 | 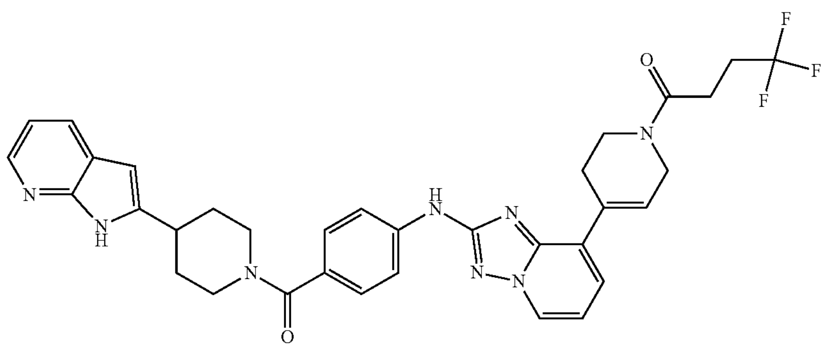 [SMILES: O=C(CCC(F)(F)F)N1CC=C(c2cccn3nc(Nc4ccc(C(=O)N5CCC(c6cc7cccnc7[nH]6)CC5)cc4)nc23)CC1] | 4,4,4-trifluoro-1-[4-[2-[4-[4-(1H-pyrrolo[2,3-b]pyridin-2-yl)piperidine-1-carbonyl]anilino]-[1,2,4]triazolo[1,5-a]pyridin-8-yl]-3,6-dihydro-2H-pyridin-1-yl]butan-1-one |
| 2-156 | 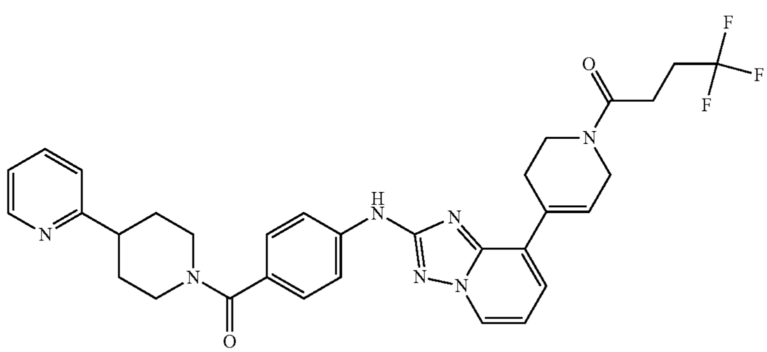 [SMILES: O=C(CCC(F)(F)F)N1CC=C(c2cccn3nc(Nc4ccc(C(=O)N5CCC(c6ccccn6)CC5)cc4)nc23)CC1] | 4,4,4-trifluoro-1-[4-[2-[4-[4-(2-pyridyl)piperidine-1-carbonyl]anilino]-[1,2,4]triazolo[1,5-a]pyridin-8-yl]-3,6-dihydro-2H-pyridin-1-yl]butan-1-one |
| 2-157 | 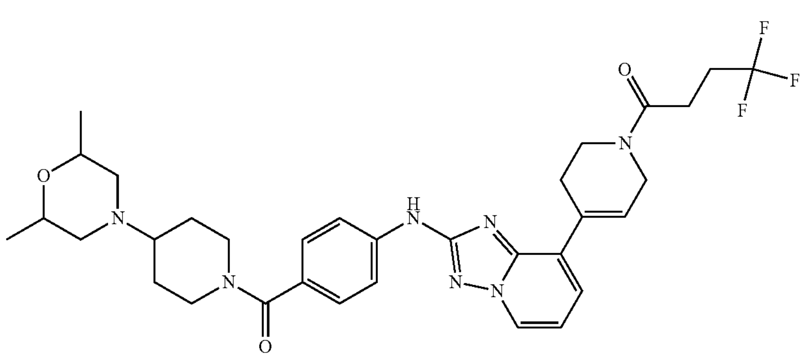 | 1-[4-[2-[4-[4-(2,6-dimethylmorpholin-4-yl)piperidine-1-carbonyl]anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-158 | 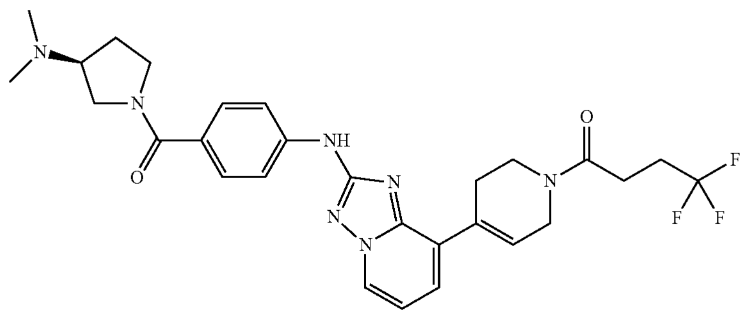 [SMILES: CN(C)[C@H]1CCN(C(=O)c2ccc(Nc3nc4c(C5=CCN(C(=O)CCC(F)(F)F)CC5)cccn4n3)cc2)C1] | 1-[4-[2-[4-[(3S)-3-(dimethylamino)pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-159 | 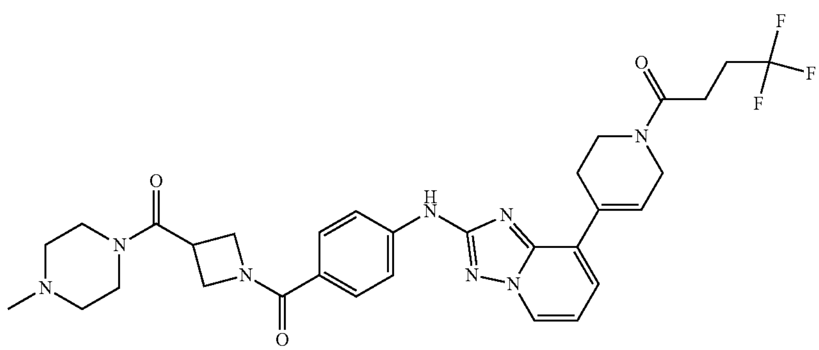 [SMILES: CN1CCN(C(=O)C2CN(C(=O)c3ccc(Nc4nc5c(C6=CCN(C(=O)CCC(F)(F)F)CC6)cccn5n4)cc3)C2)CC1] | 4,4,4-trifluoro-1-[4-[2-[4-[3-(4-methylpiperazine-1-carbonyl)azetidine-1-carbonyl]anilino]-[1,2,4]triazolo[1,5-a]pyridin-8-yl]-3,6-dihydro-2H-pyridin-1-yl]butan-1-one |
| 2-160 | 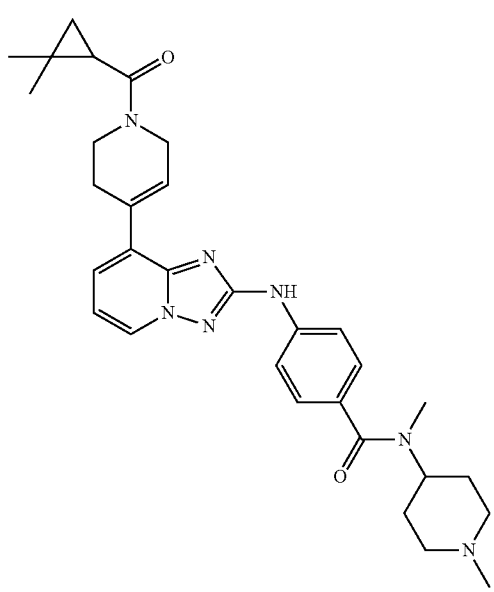 | 4-[[8-[1-(2,2-dimethylcyclopropanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 2-161 | 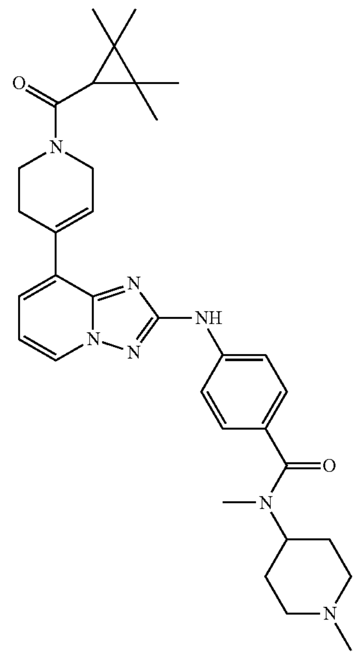 [SMILES: CN1CCC(N(C)C(=O)c2ccc(Nc3nc4c(C5=CCN(C(=O)C6C(C)(C)C6(C)C)CC5)cccn4n3)cc2)CC1] | N-methyl-N-(1-methyl-4-piperidyl)-4-[[8-[1-(2,2,3,3-tetramethylcyclopropanecarbonyl)-3,6-dihydro-2H-pyridin-4-yl]-[1,2,4]triazolo[1,5-a]pyridin-2-yl]amino]benzamide |
| 2-162 | 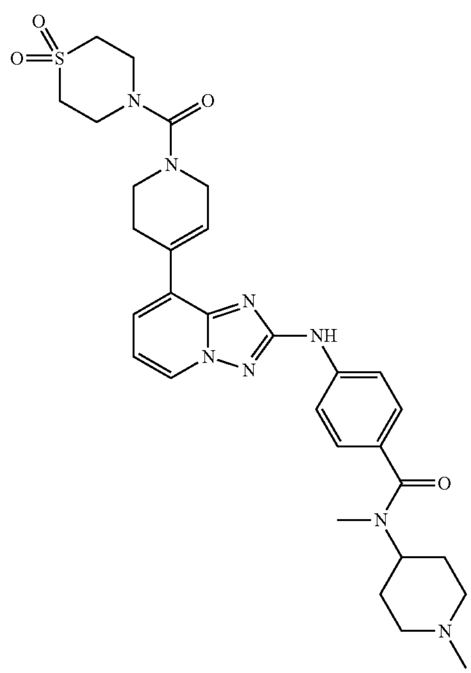 [SMILES: CN1CCC(N(C)C(=O)c2ccc(Nc3nc4c(C5=CCN(C(=O)N6CCS(=O)(=O)CC6)CC5)cccn4n3)cc2)CC1] | 4-[[8-[1-(1,1-dioxo-1,4-thiazinane-4-carbonyl)-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 2-163 | 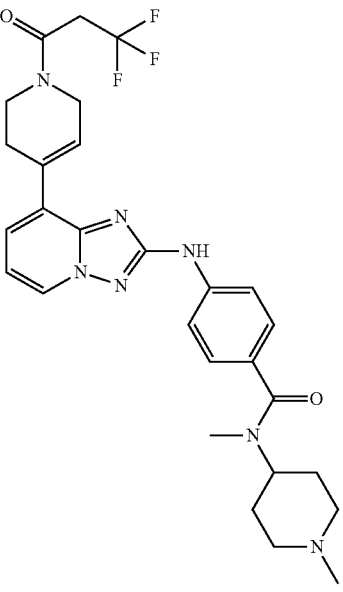 [SMILES: CN1CCC(N(C)C(=O)c2ccc(Nc3nc4c(C5=CCN(C(=O)CC(F)(F)F)CC5)cccn4n3)cc2)CC1] | N-methyl-N-(1-methyl-4-piperidyl)-4-[[8-[1-(3,3,3-trifluoropropanoyl)-3,6-dihydro-2H-pyridin-4-yl]-[1,2,4]triazolo[1,5-a]pyridin-2-yl]amino]benzamide |
| 2-164 | 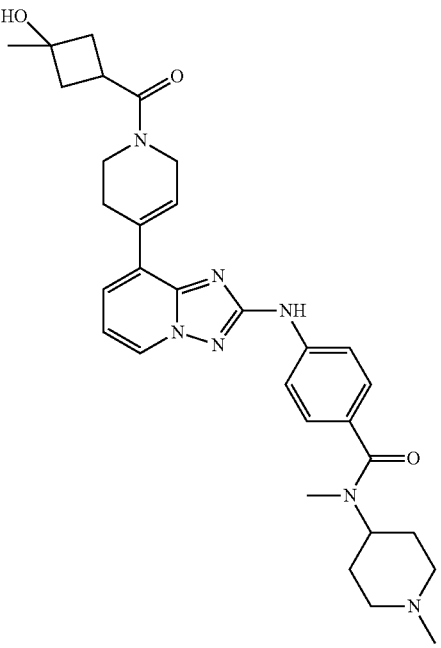 | 4-[[8-[1-(3-hydroxy-3-methyl-cyclobutanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 2-165 | 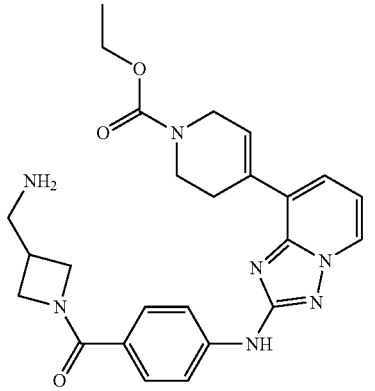 [SMILES: CCOC(=O)N1CC=C(c2cccn3nc(Nc4ccc(C(=O)N5CC(CN)C5)cc4)nc23)CC1] | ethyl 4-[2-[4-[3-(aminomethyl)azetidine-1-carbonyl]anilino]-[1,2,4]triazolo[1,5-a]pyridin-8-yl]-3,6-dihydro-2H-pyridine-1-carboxylate |
| 2-166 | 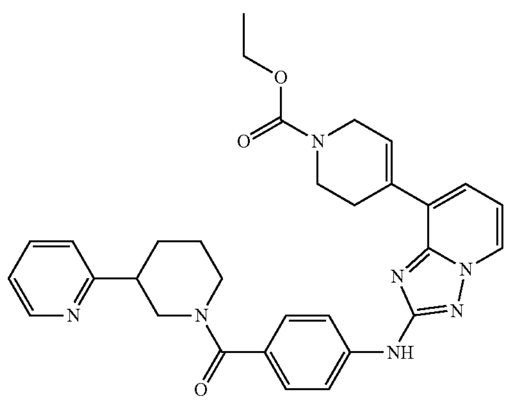 [SMILES: CCOC(=O)N1CC=C(c2cccn3nc(Nc4ccc(C(=O)N5CCCC(c6ccccn6)C5)cc4)nc23)CC1] | ethyl 4-[2-[4-[3-(2-pyridyl)piperidine-1-carbonyl]anilino]-[1,2,4]triazolo[1,5-a]pyridin-8-yl]-3,6-dihydro-2H-pyridine-1-carboxylate |
| 2-167 | 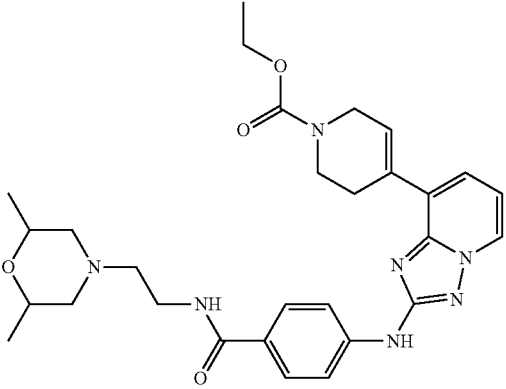 [SMILES: CCOC(=O)N1CC=C(c2cccn3nc(Nc4ccc(C(=O)NCCN5CC(C)OC(C)C5)cc4)nc23)CC1] | ethyl 4-[2-[4-[2-(2,6-dimethylmorpholin-4-yl)ethylcarbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-168 | 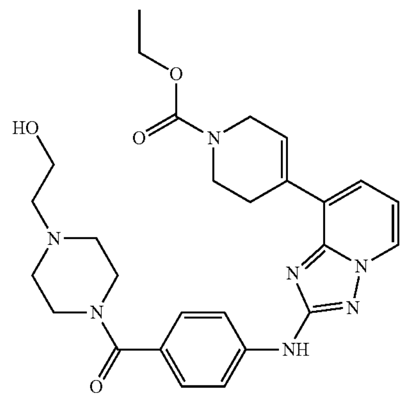 [SMILES: CCOC(=O)N1CC=C(c2cccn3nc(Nc4ccc(C(=O)N5CCN(CCO)CC5)cc4)nc23)CC1] | ethyl 4-[2-[4-[4-(2-hydroxyethyl)piperazine-1-carbonyl]anilino]-[1,2,4]triazolo[1,5-a]pyridin-8-yl]-3,6-dihydro-2H-pyridine-1-carboxylate |
| 2-169 | 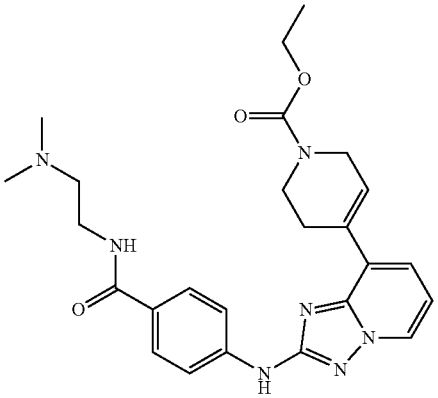 [SMILES: CCOC(=O)N1CC=C(c2cccn3nc(Nc4ccc(C(=O)NCCN(C)C)cc4)nc23)CC1] | ethyl 4-[2-[4-[2-(dimethylamino)ethylcarbamoyl]anilino]-[1,2,4]triazolo[1,5-a]pyridin-8-yl]-3,6-dihydro-2H-pyridine-1-carboxylate |
| 2-170 | 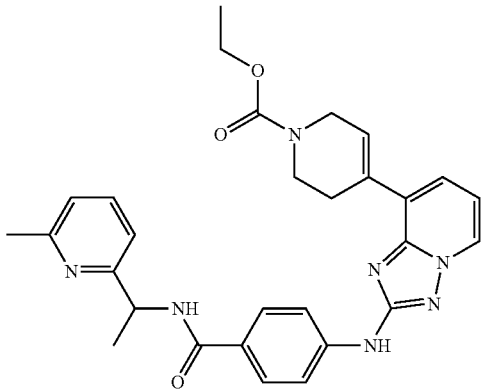 [SMILES: CCOC(=O)N1CC=C(c2cccn3nc(Nc4ccc(C(=O)NC(C)c5cccc(C)n5)cc4)nc23)CC1] | ethyl 4-[2-[4-[1-(6-methyl-2-pyridyl)ethylcarbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-171 | 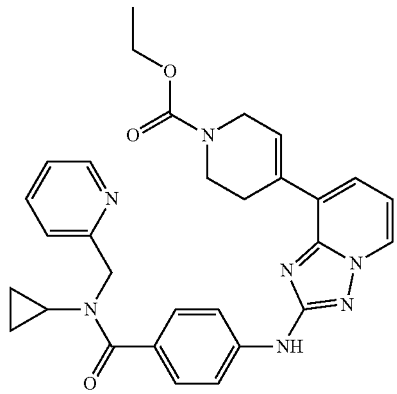 [SMILES: CCOC(=O)N1CC=C(c2cccn3nc(Nc4ccc(C(=O)N(Cc5ccccn5)C5CC5)cc4)nc23)CC1] | ethyl 4-[2-[4-[cyclopropyl(2-pyridylmethyl)carbamoyl]anilino]-[1,2,4]triazolo[1,5-a]pyridin-8-yl]-3,6-dihydro-2H-pyridine-1-carboxylate |
| 2-172 | 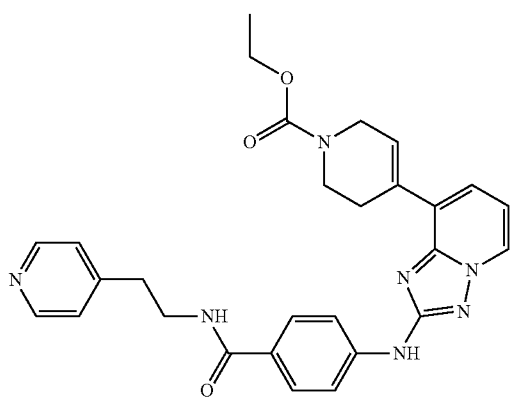 [SMILES: CCOC(=O)N1CC=C(c2cccn3nc(Nc4ccc(C(=O)NCCc5ccncc5)cc4)nc23)CC1] | ethyl 4-[2-[4-[2-(4-pyridyl)ethylcarbamoyl]anilino]-[1,2,4]triazolo[1,5-a]pyridin-8-yl]-3,6-dihydro-2H-pyridine-1-carboxylate |
| 2-173 | 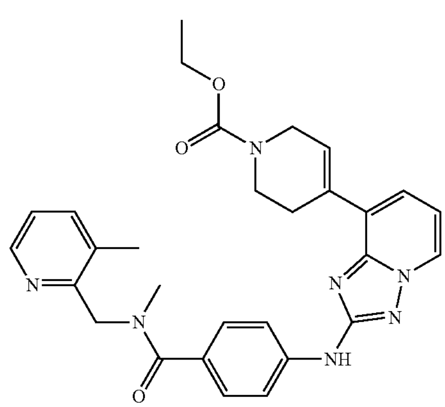 [SMILES: CCOC(=O)N1CC=C(c2cccn3nc(Nc4ccc(C(=O)N(C)Cc5ncccc5C)cc4)nc23)CC1] | ethyl 4-[2-[4-[methyl-[(3-methyl-2-pyridyl)methyl]carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-174 | 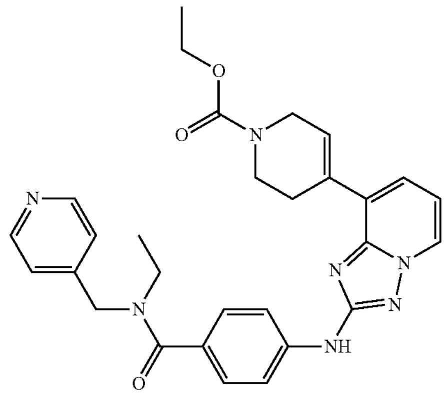 [SMILES: CCOC(=O)N1CC=C(c2cccn3nc(Nc4ccc(C(=O)N(CC)Cc5ccncc5)cc4)nc23)CC1] | ethyl 4-[2-[4-[ethyl(4-pyridylmethyl)carbamoyl]anilino]-[1,2,4]triazolo[1,5-a]pyridin-8-yl]-3,6-dihydro-2H-pyridine-1-carboxylate |
| 2-175 | 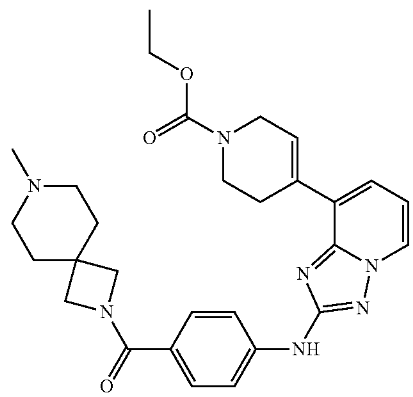 [SMILES: CCOC(=O)N1CC=C(c2cccn3nc(Nc4ccc(C(=O)N5CC6(CCN(C)CC6)C5)cc4)nc23)CC1] | ethyl 4-[2-[4-(7-methyl-2,7-diazaspiro[3.5]nonane-2-carbonyl)anilino]-[1,2,4]triazolo[1,5-a]pyridin-8-yl]-3,6-dihydro-2H-pyridine-1-carboxylate |
| 2-176 | 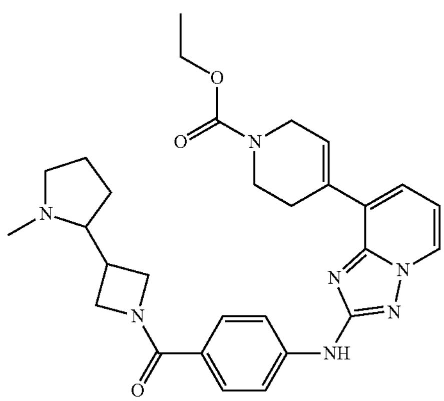 [SMILES: CCOC(=O)N1CC=C(c2cccn3nc(Nc4ccc(C(=O)N5CC(C6CCCN6C)C5)cc4)nc23)CC1] | ethyl 4-[2-[4-(5-methyl-2,5-diazaspiro[3.4]octane-2-carbonyl)anilino]-[1,2,4]triazolo[1,5-a]pyridin-8-yl]-3,6-dihydro-2H-pyridine-1-carboxylate |
| 2-177 | 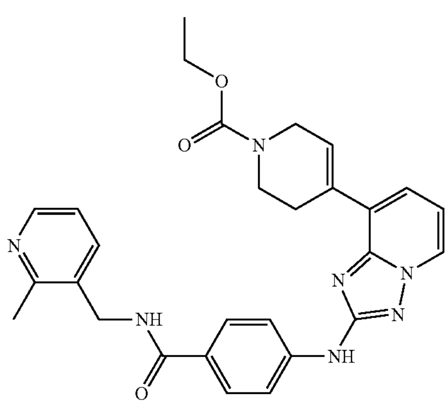 [SMILES: CCOC(=O)N1CC=C(c2cccn3nc(Nc4ccc(C(=O)NCc5cccnc5C)cc4)nc23)CC1] | ethyl 4-[2-[4-[(2-methyl-3-pyridyl)methylcarbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-178 | 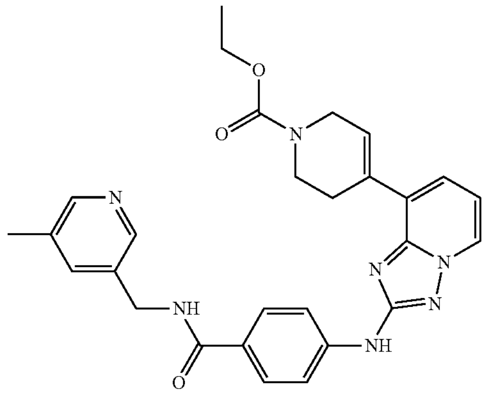 [SMILES: CCOC(=O)N1CC=C(c2cccn3nc(Nc4ccc(C(=O)NCc5cncc(C)c5)cc4)nc23)CC1] | ethyl 4-[2-[4-[(5-methyl-3-pyridyl)methylcarbamoyl]anilino]-[1,2,4]triazolo[1,5-a]pyridin-8-yl]-3,6-dihydro-2H-pyridine-1-carboxylate |
| 2-179 | 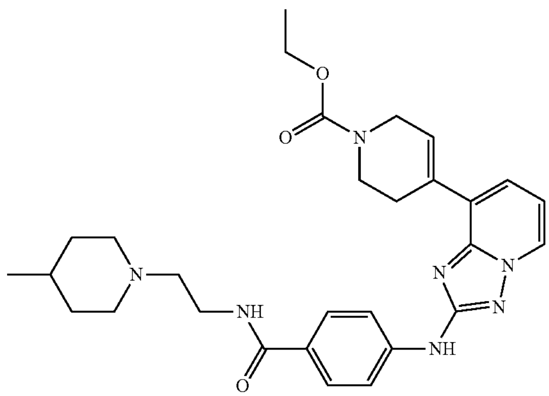 | ethyl 4-[2-[4-[2-(4-methyl-1-piperidyl)ethylcarbamoyl]anilino]-[1,2,4]triazolo[1,5-a]pyridin-8-yl]-3,6-dihydro-2H-pyridine-1-carboxylate |
| 2-180 | 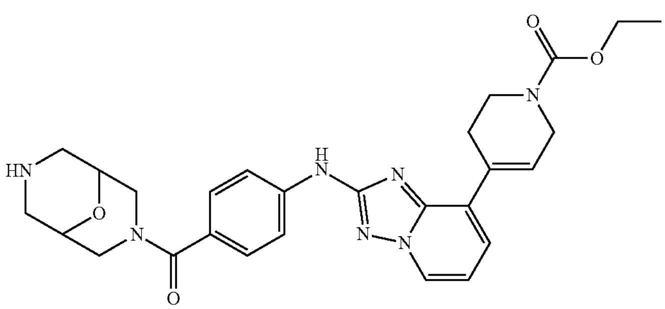 [SMILES: CCOC(=O)N1CC=C(c2cccn3nc(Nc4ccc(C(=O)N5CC6CNCC(C5)O6)cc4)nc23)CC1] | ethyl 4-[2-[4-(9-oxa-3,7-diazabicyclo[3.3.1]nonane-3-carbonyl)anilino]-[1,2,4]triazolo[1,5-a]pyridin-8-yl]-3,6-dihydro-2H-pyridine-1-carboxylate |
| 2-181 | 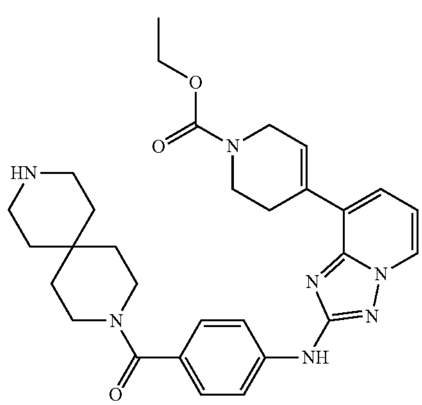 [SMILES: CCOC(=O)N1CC=C(c2cccn3nc(Nc4ccc(C(=O)N5CCC6(CCNCC6)CC5)cc4)nc23)CC1] | ethyl 4-[2-[4-(3,9-diazaspiro[5.5]undecane-3-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-182 | 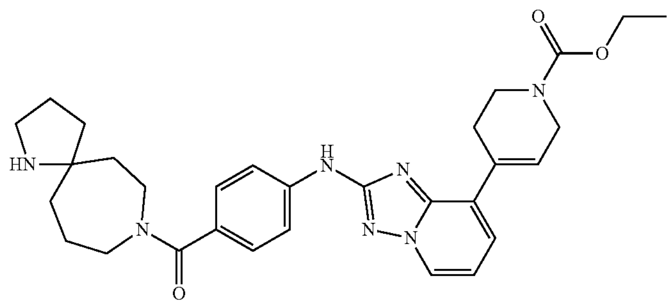 [SMILES: CCOC(=O)N1CC=C(c2cccn3nc(Nc4ccc(C(=O)N5CCCC6(CCCN6)CC5)cc4)nc23)CC1] | ethyl 4-[2-[4-(1,9-diazaspiro[4.6]undecane-9-carbonyl)anilino]-[1,2,4]triazolo[1,5-a]pyridin-8-yl]-3,6-dihydro-2H-pyridine-1-carboxylate |
| 2-183 | 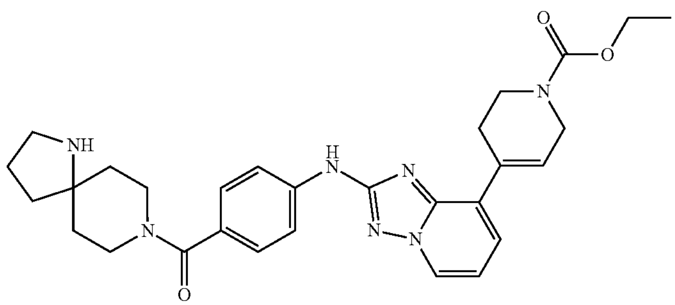 [SMILES: CCOC(=O)N1CC=C(c2cccn3nc(Nc4ccc(C(=O)N5CCC6(CCCN6)CC5)cc4)nc23)CC1] | ethyl 4-[2-[4-(1,8-diazaspiro[4,5]decane-8-carbonyl)anilino]-[1,2,4]triazolo[1,5-a]pyridin-8-yl]-3,6-dihydro-2H-pyridine-1-carboxylate |
| 2-184 | 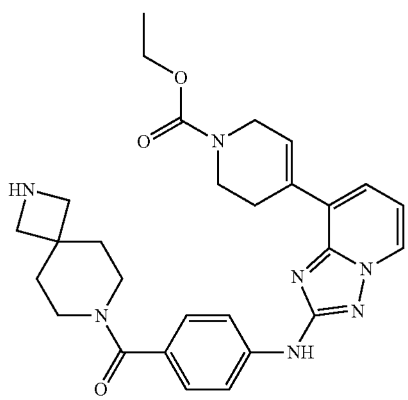 [SMILES: CCOC(=O)N1CC=C(c2cccn3nc(Nc4ccc(C(=O)N5CCC6(CC5)CNC6)cc4)nc23)CC1] | ethyl 4-[2-[4-(2,7-diazaspiro[3.5]nonane-7-carbonyl)anilino]-[1,2,4]triazolo[1,5-a]pyridin-8-yl]-3,6-dihydro-2H-pyridine-1-carboxylate |
| 2-185 | 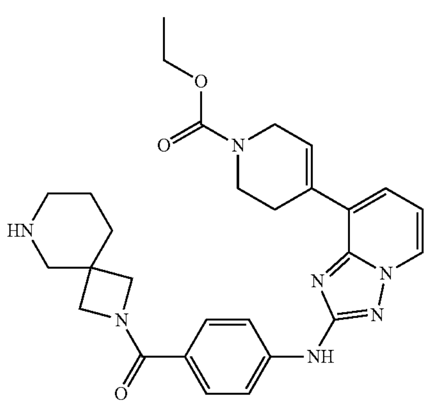 [SMILES: CCOC(=O)N1CC=C(c2cccn3nc(Nc4ccc(C(=O)N5CC6(CCCNC6)C5)cc4)nc23)CC1] | ethyl 4-[2-[4-(2,8-diazaspiro[3,5]nonane-2-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-186 | 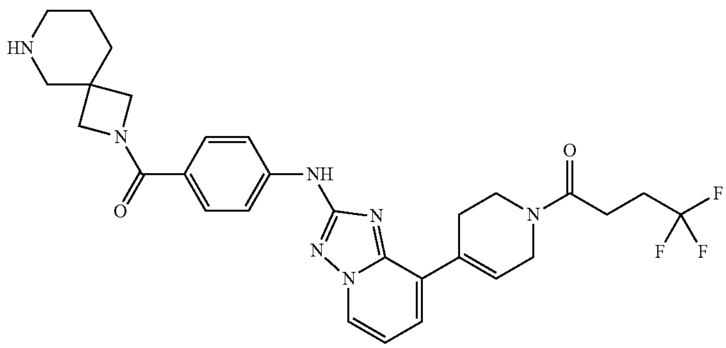 [SMILES: O=C(CCC(F)(F)F)N1CC=C(c2cccn3nc(Nc4ccc(C(=O)N5CC6(CCCNC6)C5)cc4)nc23)CC1] | 1-[4-[2-[4-(2,8-diazaspiro[3.5]nonane-2-carbonyl)anilino]-[1,2,4]triazolo[1,5-a]pyridin-8-yl]-3,6-dihydro-2H-pyridin-1-yl]-4,4,4-trifluoro-butan-1-one |
| 2-187 | 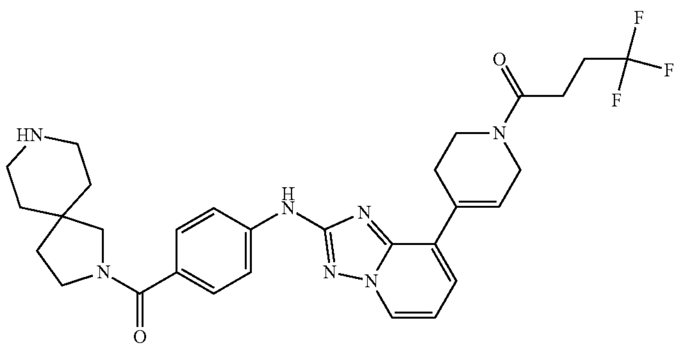 [SMILES: O=C(CCC(F)(F)F)N1CC=C(c2cccn3nc(Nc4ccc(C(=O)N5CCC6(CCNCC6)C5)cc4)nc23)CC1] | 1-[4-[2-[4-(2,8-diazaspiro[4.5]decane-2-carbonyl)anilino]-[1,2,4]triazolo[1,5-a]pyridin-8-yl]-3,6-dihydro-2H-pyridin-1-yl]-4,4,4-trifluoro-butan-1-one |
| 2-188 | 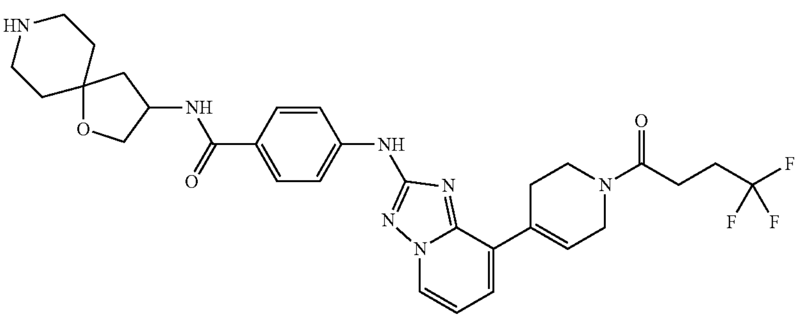 [SMILES: O=C(NC1COC2(CCNCC2)C1)c1ccc(Nc2nc3c(C4=CCN(C(=O)CCC(F)(F)F)CC4)cccn3n2)cc1] | N-(1-oxa-8-azaspiro[4.5]decan-3-yl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-189 | 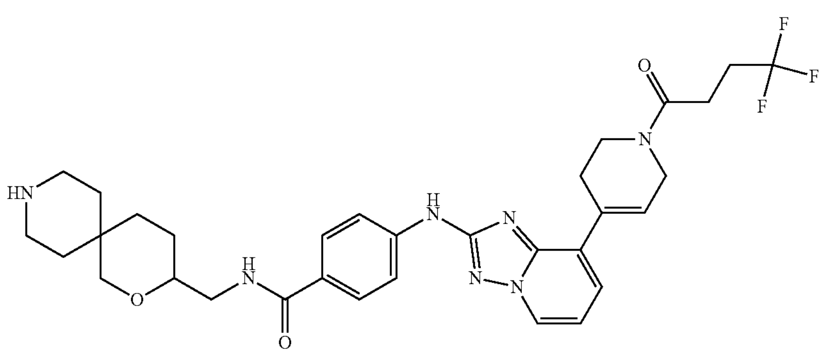 [SMILES: O=C(NCC1CCC2(CCNCC2)CO1)c1ccc(Nc2nc3c(C4=CCN(C(=O)CCC(F)(F)F)CC4)cccn3n2)cc1] | N-(2-oxa-9-azaspiro[5.5]undecan-3-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-190 | 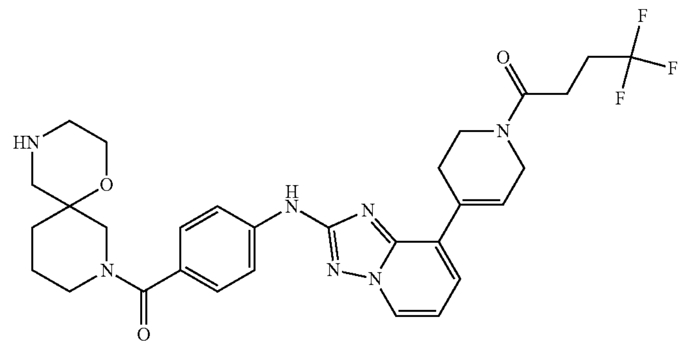 [SMILES: O=C(CCC(F)(F)F)N1CC=C(c2cccn3nc(Nc4ccc(C(=O)N5CCCC6(CNCCO6)C5)cc4)nc23)CC1] | 4,4,4-trifluoro-1-[4-[2-[4-[4-(1-oxa-4,8-diazaspiro[5.5]undecane-8-carbonyl)anilino]-[1,2,4]triazolo[1,5-a]pyridin-8-yl]-3,6-dihydro-2H-pyridin-1-yl]butan-1-one |
| 2-191 | 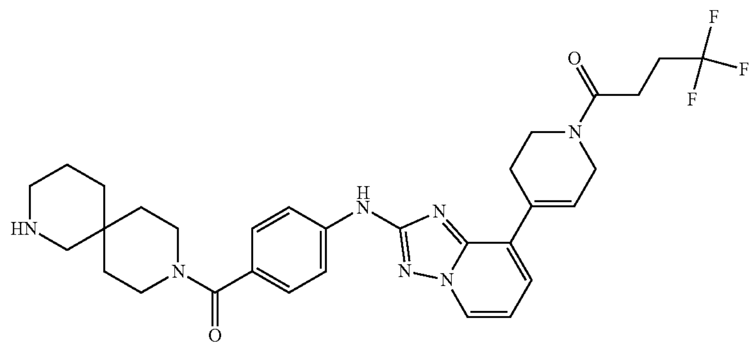 [SMILES: O=C(CCC(F)(F)F)N1CC=C(c2cccn3nc(Nc4ccc(C(=O)N5CCC6(CCCNC6)CC5)cc4)nc23)CC1] | 1-[4-[2-[4-(2,9-diazaspiro[5.5]undecane-9-carbonyl)anilino]-[1,2,4]triazolo[1,5-a]pyridin-8-yl]-3,6-dihydro-2H-pyridin-1-yl]-4,4,4-trifluoro-butan-1-one |
| 2-192 | 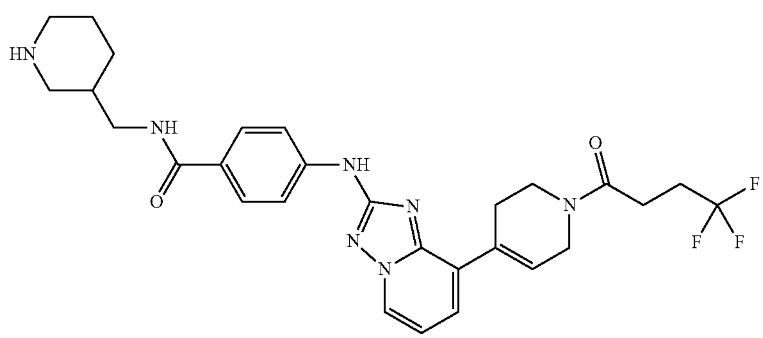 [SMILES: O=C(NCC1CCCNC1)c1ccc(Nc2nc3c(C4=CCN(C(=O)CCC(F)(F)F)CC4)cccn3n2)cc1] | N-(3-piperidylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-193 | 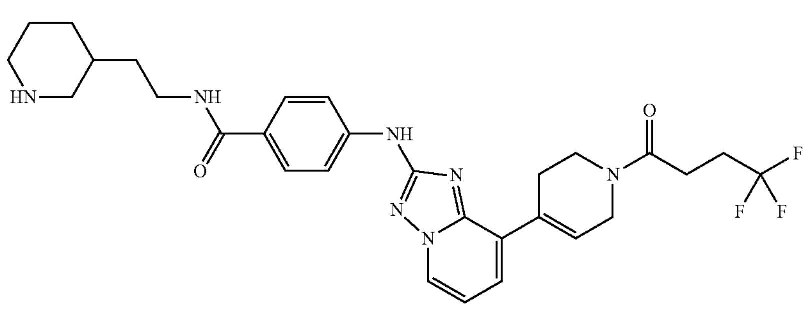 [SMILES: O=C(NCCC1CCCNC1)c1ccc(Nc2nc3c(C4=CCN(C(=O)CCC(F)(F)F)CC4)cccn3n2)cc1] | N-[2-(3-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-194 | 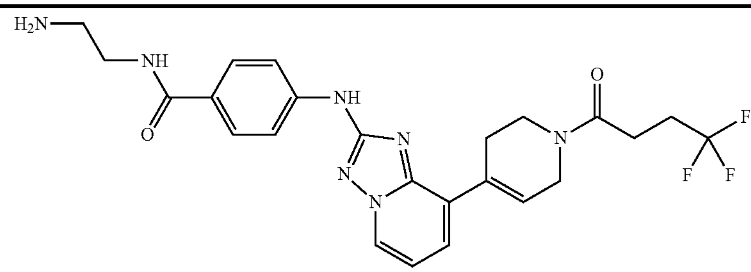 | N-(2-aminoethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-195 | 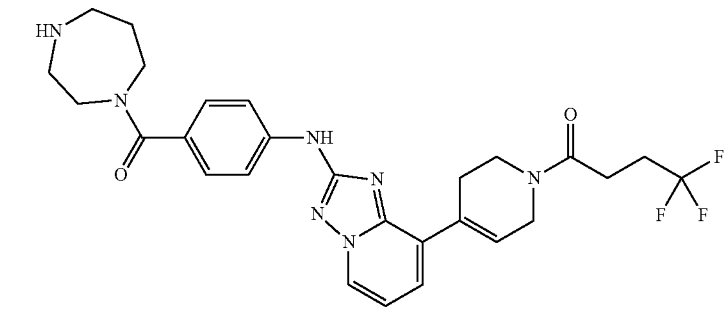 [SMILES: O=C(CCC(F)(F)F)N1CC=C(c2cccn3nc(Nc4ccc(C(=O)N5CCCNCC5)cc4)nc23)CC1] | 1-[4-[2-[4-(1,4-diazepane-1-carbonyl)anilino]-[1,2,4]triazolo[1,5-a]pyridin-8-yl]-3,6-dihydro-2H-pyridin-1-yl]-4,4,4-trifluoro-butan-1-one |
| 2-196 | 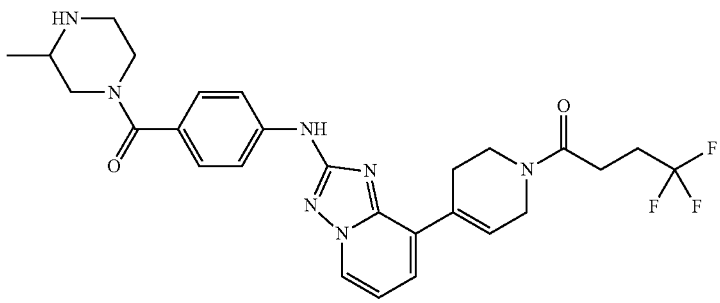 [SMILES: CC1CN(C(=O)c2ccc(Nc3nc4c(C5=CCN(C(=O)CCC(F)(F)F)CC5)cccn4n3)cc2)CCN1] | 4,4,4-trifluoro-1-[4-[2-[4-(3-methylpiperazine-1-carbonyl)anilino]-[1,2,4]triazolo[1,5-a]pyridin-8-yl]-3,6-dihydro-2H-pyridin-1-yl]butan-1-one |
| 2-197 | 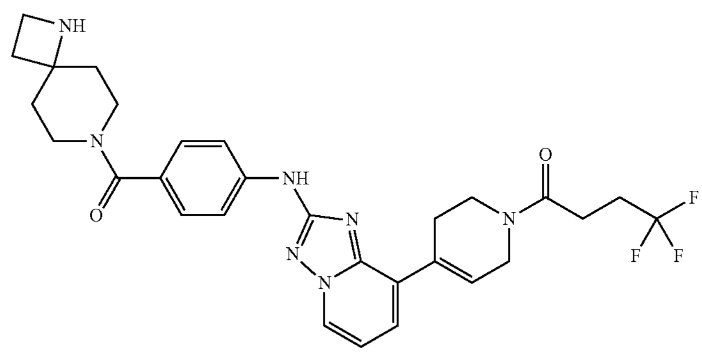 [SMILES: O=C(CCC(F)(F)F)N1CC=C(c2cccn3nc(Nc4ccc(C(=O)N5CCC6(CCN6)CC5)cc4)nc23)CC1] | 1-[4-[2-[4-(1,7-diazaspiro[3.5]nonane-7-carbonyl)anilino]-[1,2,4]triazolo[1,5-a]pyridin-8-yl]-3,6-dihydro-2H-pyridin-1-yl]-4,4,4-trifluoro-butan-1-one |
| 2-198 | 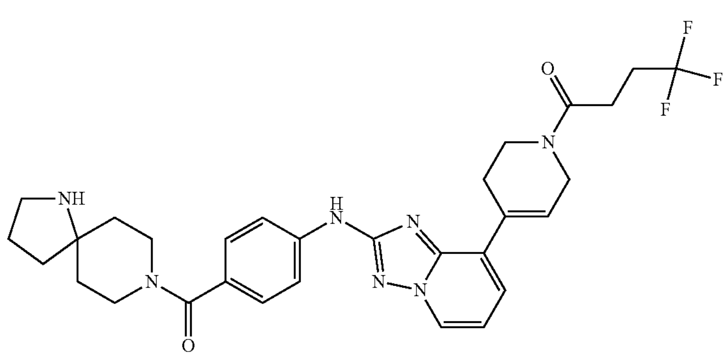 [SMILES: O=C(CCC(F)(F)F)N1CC=C(c2cccn3nc(Nc4ccc(C(=O)N5CCC6(CCCN6)CC5)cc4)nc23)CC1] | 1-[4-[2-[4-(1,8-diazaspiro[4.5]decane-8-carbonyl)anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-199 | 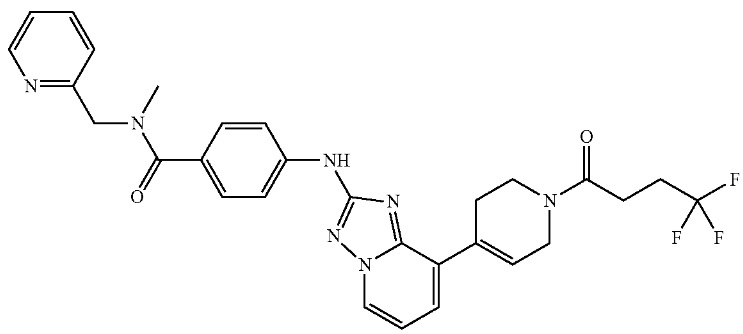 [SMILES: CN(Cc1ccccn1)C(=O)c1ccc(Nc2nc3c(C4=CCN(C(=O)CCC(F)(F)F)CC4)cccn3n2)cc1] | N-methyl-N-(2-pyridylmethyl)-4-[[8-[1-(4,4,4-trifluorobulanoyl)-3,6-dihydro-2H-pyridin-4-yl]-[1,2,4]triazolo[1,5-a]pyridin-2-yl]amino]benzamide |
| 2-200 | 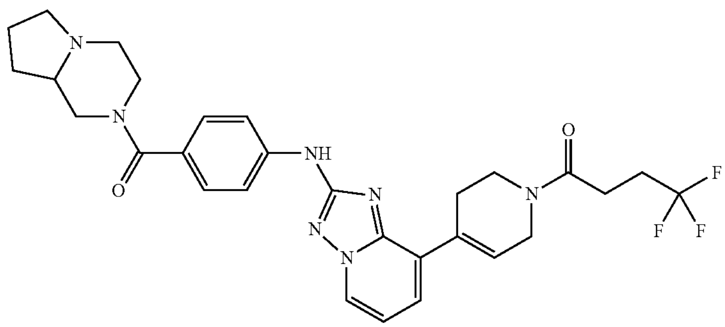 [SMILES: O=C(CCC(F)(F)F)N1CC=C(c2cccn3nc(Nc4ccc(C(=O)N5CCN6CCCC6C5)cc4)nc23)CC1] | 1-[4-[2-[4-(3,4,6,7,8,8a-hexahydro-1H-pyrrolo[1,2-a]pyrazine-2-carbonyl)anilino]-[1,2,4]triazolo[1,5-a]pyridin-8-yl]-3,6-dihydro-2H-pyridin-1-yl]-4,4,4-trifluoro-butan-1-one |
| 2-201 | 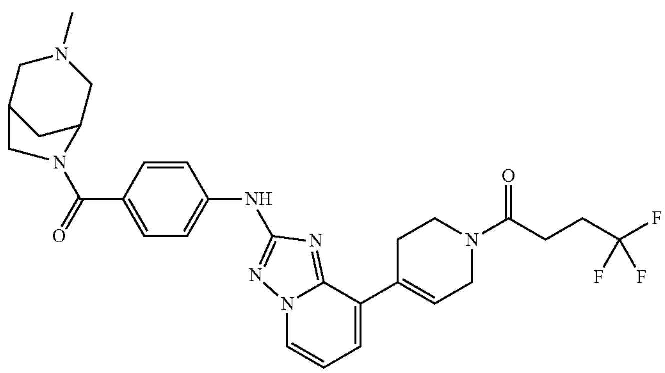 [SMILES: CN1CC2CC(C1)N(C(=O)c1ccc(Nc3nc4c(C5=CCN(C(=O)CCC(F)(F)F)CC5)cccn4n3)cc1)C2] | 4,4,4-trifluoro-1-[4-[2-[4-(3-methyl-3,6-diazabicyclo[3.2.1]octane-6-carbonyl)anilino]-[1,2,4]triazolo[1,5-a]pyridin-8-yl]-3,6-dihydro-2H-pyridin-1-yl]butan-1-one |
| 2-202 | 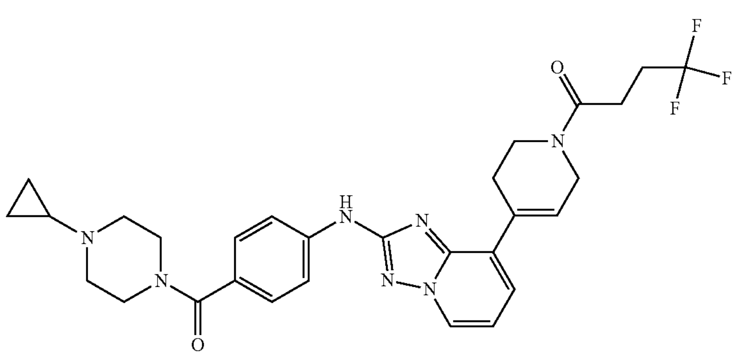 [SMILES: O=C(CCC(F)(F)F)N1CC=C(c2cccn3nc(Nc4ccc(C(=O)N5CCN(C6CC6)CC5)cc4)nc23)CC1] | 1-[4-[2-[4-(4-cyclopropylpiperazine-1-carbonyl)anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-203 | 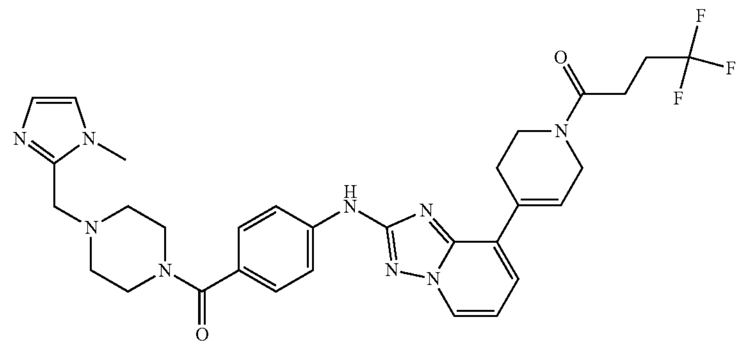 [SMILES: Cn1ccnc1CN1CCN(C(=O)c2ccc(Nc3nc4c(C5=CCN(C(=O)CCC(F)(F)F)CC5)cccn4n3)cc2)CC1] | 4,4,4-trifluoro-1-[4-[2-[4-[4-[(1-methylimidazol-2-yl)methyl]piperazine-1-carbonyl]anilino]-[1,2,4]triazolo[1,5-a]pyridin-8-yl]-3,6-dihydro-2H-pyridin-1-yl]butan-1-one |
| 2-204 | 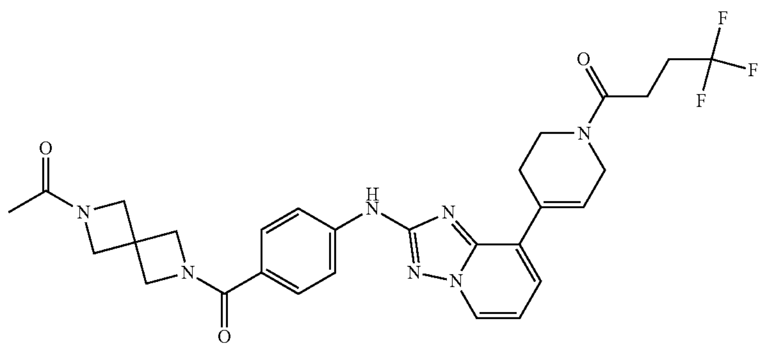 [SMILES: CC(=O)N1CC2(C1)CN(C(=O)c1ccc(Nc3nc4c(C5=CCN(C(=O)CCC(F)(F)F)CC5)cccn4n3)cc1)C2] | 1-[4-[2-[4-(6-acetyl-2,6-diazaspiro[3.3]heptane-2-carbonyl)anilino]-[1,2,4]triazolo[1,5-a]pyridin-8-yl]-3,6-dihydro-2H-pyridin-1-yl]-4,4,4-trifluoro-butan-1-one |
| 2-205 | 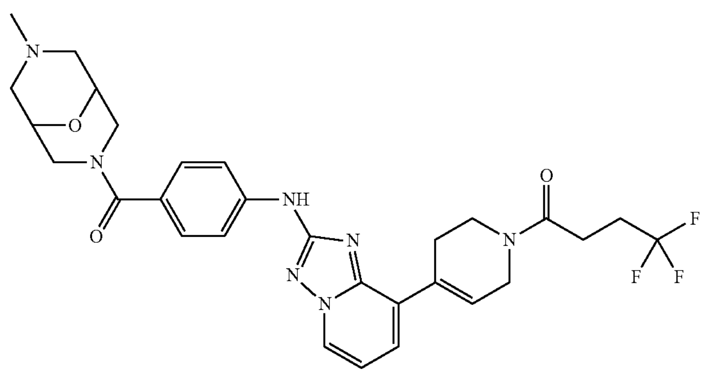 [SMILES: CN1CC2CN(C(=O)c3ccc(Nc4nc5c(C6=CCN(C(=O)CCC(F)(F)F)CC6)cccn5n4)cc3)CC(C1)O2] | 4,4,4-trifluoro-1-[4-[2-[4-(7-methyl-9-oxa-3,7-diazabicyclo[3.3.1]nonane-3-carbonyl)anilino]-[1,2,4]triazolo[1,5-a]pyridin-8-yl]-3,6-dihydro-2H-pyridin-1-yl]butan-1-one |
| 2-206 | 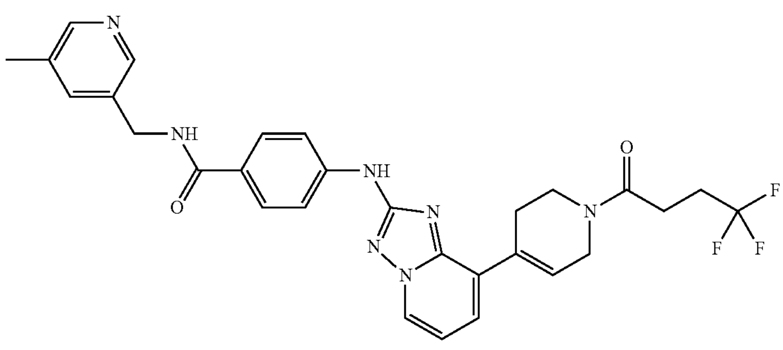 [SMILES: Cc1cncc(CNC(=O)c2ccc(Nc3nc4c(C5=CCN(C(=O)CCC(F)(F)F)CC5)cccn4n3)cc2)c1] | N-[(5-methyl-3-pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-207 | 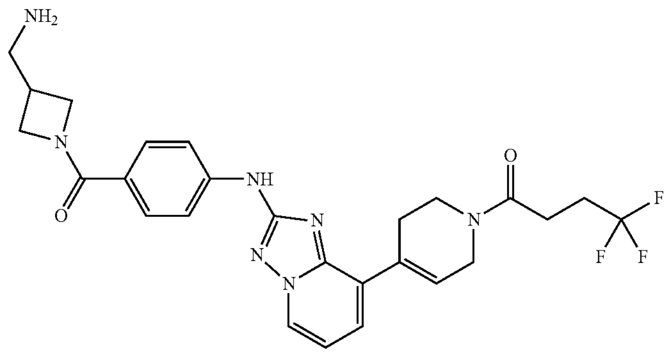 [SMILES: NCC1CN(C(=O)c2ccc(Nc3nc4c(C5=CCN(C(=O)CCC(F)(F)F)CC5)cccn4n3)cc2)C1] | 1-[4-[2-[4-[3-(aminomethyl)azetidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-208 | 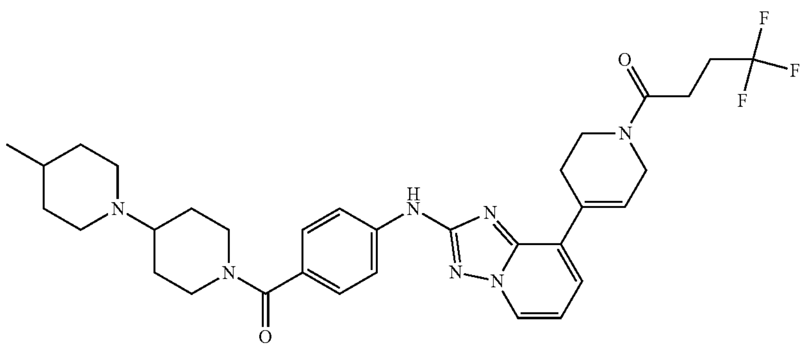 | 4,4,4-trifluoro-1-[4-[2-[4-[4-(4-methyl-1-piperidyl)piperidine-1-carbonyl]anilino]-[1,2,4]triazolo[1,5-a]pyridin-8-yl]-3,6-dihydro-2H-pyridin-1-yl]butan-1-one |
| 2-209 | 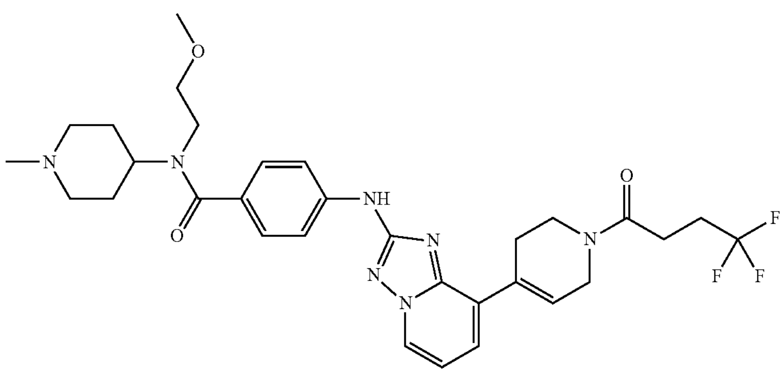 [SMILES: COCCN(C(=O)c1ccc(Nc2nc3c(C4=CCN(C(=O)CCC(F)(F)F)CC4)cccn3n2)cc1)C1CCN(C)CC1] | N-(2-methoxyethyl)-N-(1-methyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-210 | 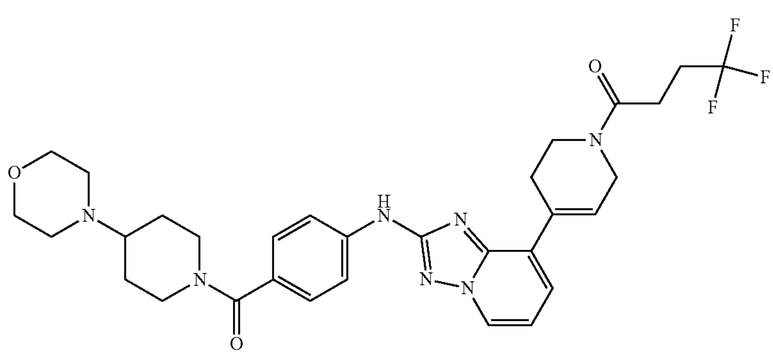 [SMILES: O=C(CCC(F)(F)F)N1CC=C(c2cccn3nc(Nc4ccc(C(=O)N5CCC(N6CCOCC6)CC5)cc4)nc23)CC1] | 4,4,4-trifluoro-1-[4-[2-[4-(4-morpholinopiperidine-1-carbonyl)anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-211 | 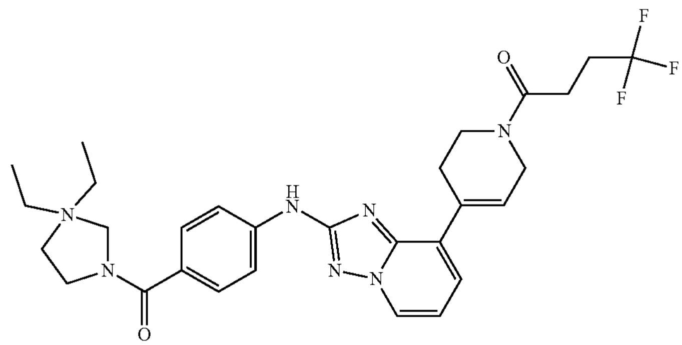 | 1-[4-[2-[4-[3-(diethylamino)pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-212 | 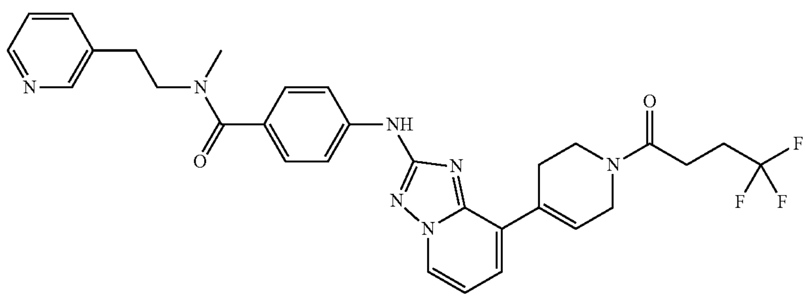 [SMILES: CN(CCc1cccnc1)C(=O)c1ccc(Nc2nc3c(C4=CCN(C(=O)CCC(F)(F)F)CC4)cccn3n2)cc1] | N-methyl-N-[2-(3-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-213 | 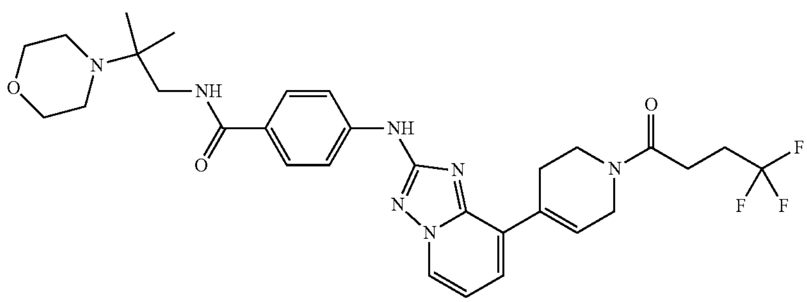 [SMILES: CC(C)(CNC(=O)c1ccc(Nc2nc3c(C4=CCN(C(=O)CCC(F)(F)F)CC4)cccn3n2)cc1)N1CCOCC1] | N-(2-methyl-2-morpholino-propyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-214 | 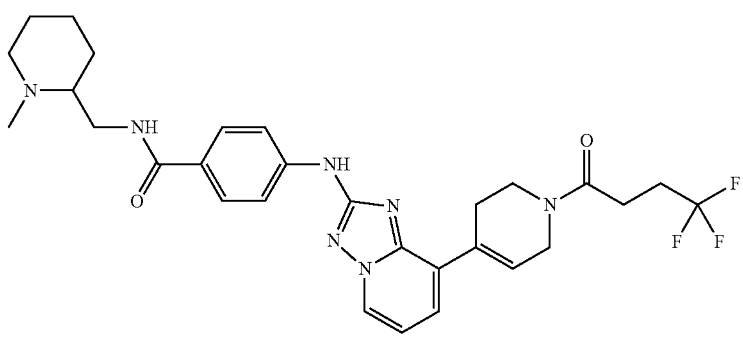 [SMILES: CN1CCCCC1CNC(=O)c1ccc(Nc2nc3c(C4=CCN(C(=O)CCC(F)(F)F)CC4)cccn3n2)cc1] | N-[(1-methyl-2-piperidyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-215 | 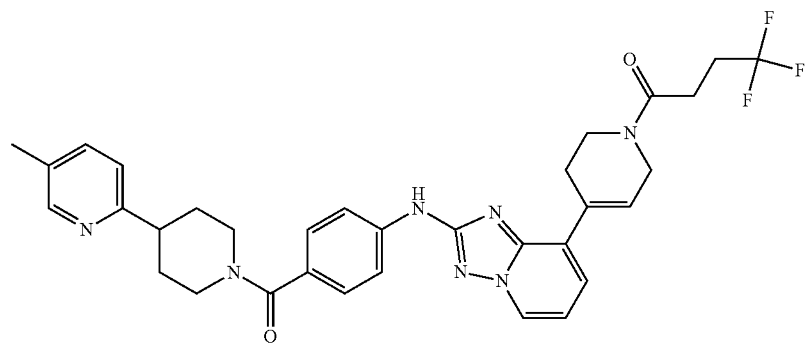 [SMILES: Cc1ccc(C2CCN(C(=O)c3ccc(Nc4nc5c(C6=CCN(C(=O)CCC(F)(F)F)CC6)cccn5n4)cc3)CC2)nc1] | 4,4,4-trifluoro-1-[4-[2-[4-[4-(5-methyl-2-pyridyl)piperidine-1-carbonyl]anilino]-[1,2,4]triazolo[1,5-a]pyridin-8-yl]-3,6-dihydro-2H-pyridin-1-yl]butan-1-one |
| 2-216 | 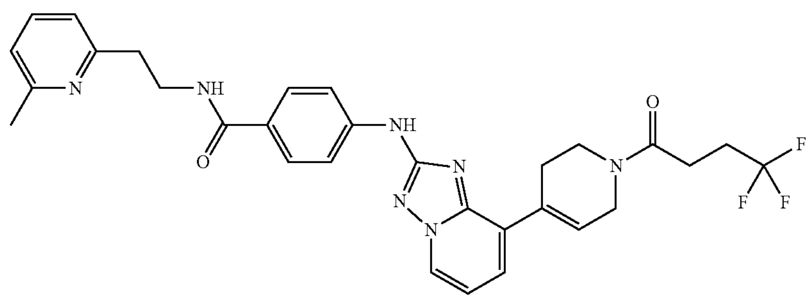 [SMILES: Cc1cccc(CCNC(=O)c2ccc(Nc3nc4c(C5=CCN(C(=O)CCC(F)(F)F)CC5)cccn4n3)cc2)n1] | N-[2-(6-methyl-2-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-217 | 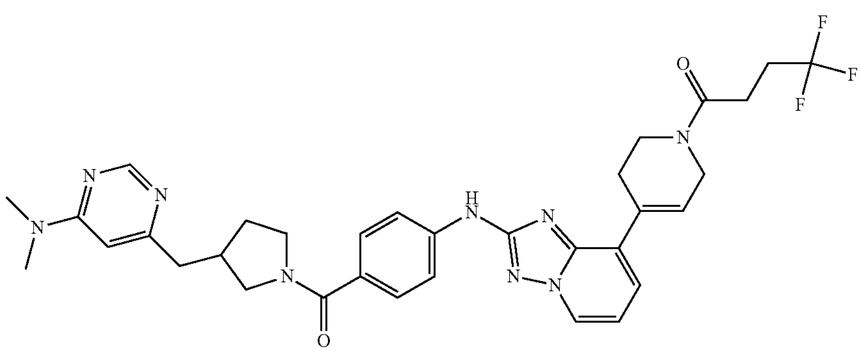 [SMILES: CN(C)c1cc(CC2CCN(C(=O)c3ccc(Nc4nc5c(C6=CCN(C(=O)CCC(F)(F)F)CC6)cccn5n4)cc3)C2)ncn1] | 1-[4-[2-[4-[3-[[6-(dimethylamino)pyrimidin-4-yl]methyl]pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-218 | 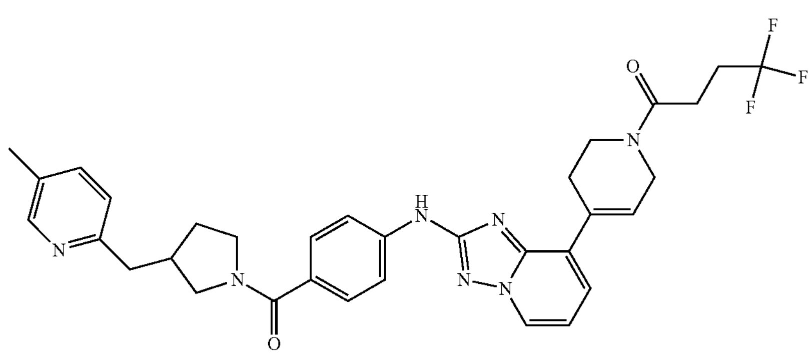 [SMILES: Cc1ccc(CC2CCN(C(=O)c3ccc(Nc4nc5c(C6=CCN(C(=O)CCC(F)(F)F)CC6)cccn5n4)cc3)C2)nc1] | 4,4,4-trifluoro-1-[4-[2-[4-[3-[(5-methyl-2-pyridyl)methyl]pyrrolidine-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-219 | 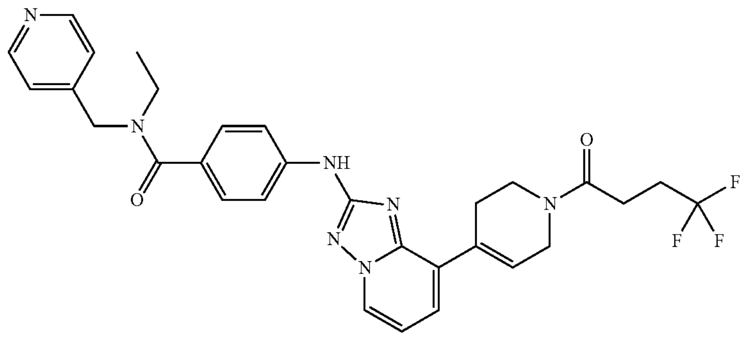 [SMILES: CCN(Cc1ccncc1)C(=O)c1ccc(Nc2nc3c(C4=CCN(C(=O)CCC(F)(F)F)CC4)cccn3n2)cc1] | N-ethyl-N-(4-pyridylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-220 | 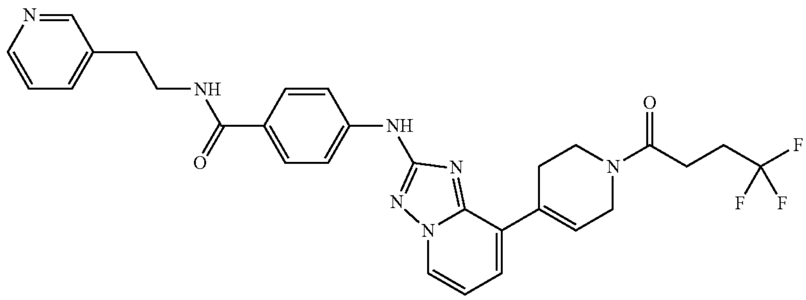 [SMILES: O=C(NCCc1cccnc1)c1ccc(Nc2nc3c(C4=CCN(C(=O)CCC(F)(F)F)CC4)cccn3n2)cc1] | N-[2-(3-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-221 | 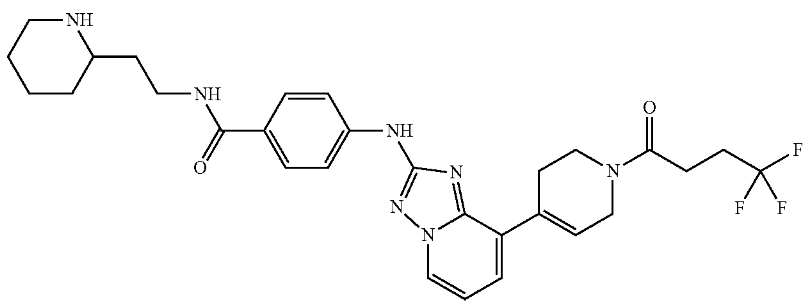 [SMILES: O=C(NCCC1CCCCN1)c1ccc(Nc2nc3c(C4=CCN(C(=O)CCC(F)(F)F)CC4)cccn3n2)cc1] | N-[2-(2-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-222 | 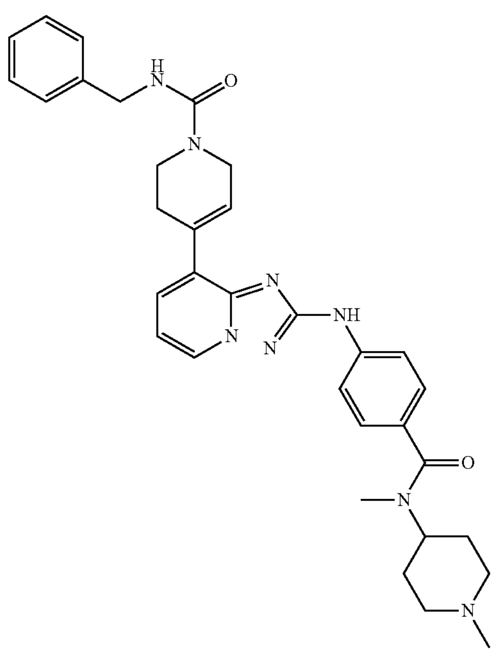 [SMILES: CN1CCC(N(C)C(=O)c2ccc(NC(=N)/N=c3\[nH]cccc3C3=CCN(C(=O)NCc4ccccc4)CC3)cc2)CC1] | N-benzyl-4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxamide |

TABLE A-continued
Exemplary Compounds of the Present Invention
| Ex. | Structure | Name |
|---|---|---|
| 2-223 | 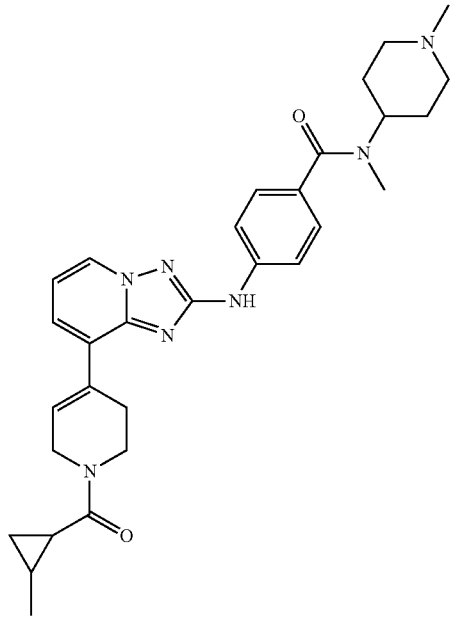 [SMILES: CC1CC1C(=O)N1CC=C(c2cccn3nc(Nc4ccc(C(=O)N(C)C5CCN(C)CC5)cc4)nc23)CC1] | N-methyl-4-[[8-[1-(2-methylcyclopropane carbonyl)-3,6-dihydro-2H-pyridin-4-yl]-[1,2,4]triazolo[1,5-a]pyridin-2-yl]amino]-N-(1-methyl-4-piperidyl)benzamide |
| 2-224 | 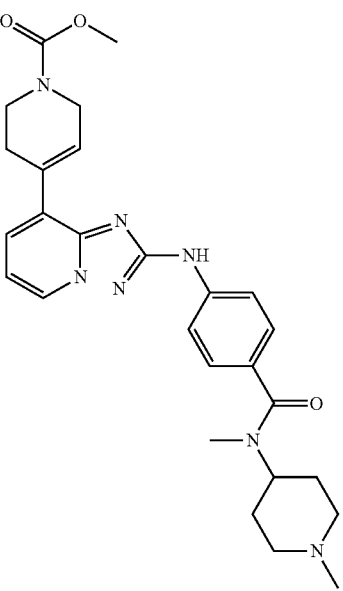 [SMILES: COC(=O)N1CC=C(c2ccc[nH]/c2=N\C(=N)Nc2ccc(C(=O)N(C)C3CCN(C)CC3)cc2)CC1] | methyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-225 | 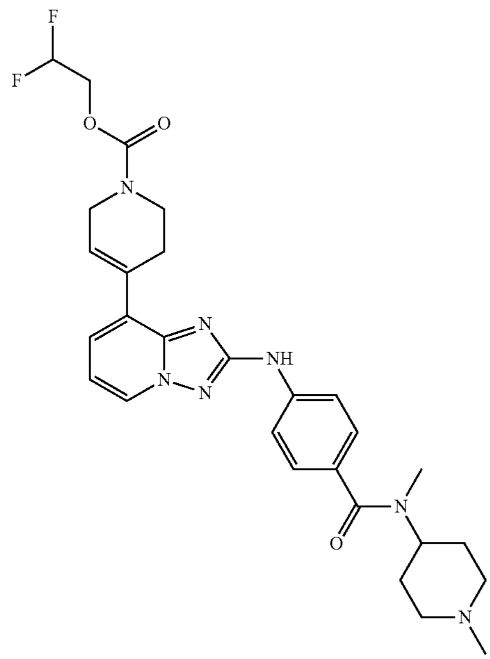 [SMILES: CN1CCC(N(C)C(=O)c2ccc(Nc3nc4c(C5=CCN(C(=O)OCC(F)F)CC5)cccn4n3)cc2)CC1] | 2,2-difluoroethyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |
| 2-226 | 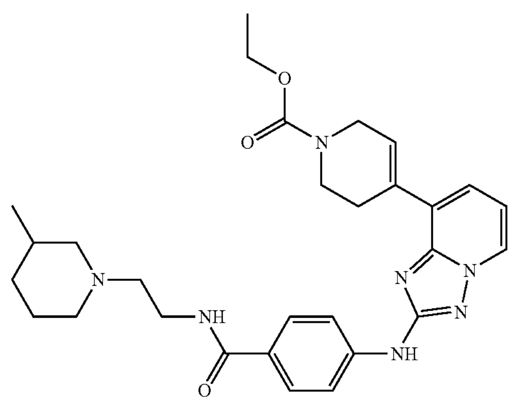 [SMILES: CCOC(=O)N1CC=C(c2cccn3nc(Nc4ccc(C(=O)NCCN5CCCC(C)C5)cc4)nc23)CC1] | ethyl 4-[2-[4-[2-(3-methyl-1-piperidyl)ethylcarbamoyl]anilino]-[1,2,4]triazolo[1,5-a]pyridin-8-yl]-3,6-dihydro-2H-pyridine-1-carboxylate |
| 2-227 | 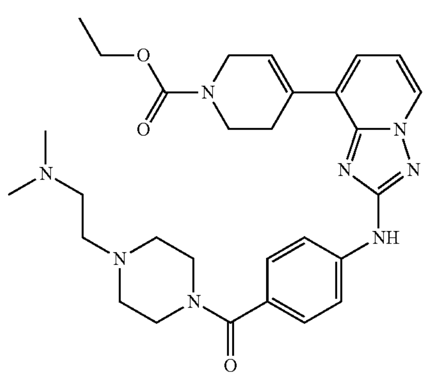 [SMILES: CCOC(=O)N1CC=C(c2cccn3nc(Nc4ccc(C(=O)N5CCN(CCN(C)C)CC5)cc4)nc23)CC1] | ethyl 4-[2-[4-[4-[2-(dimethylamino)ethyl]piperazine-1-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-228 | 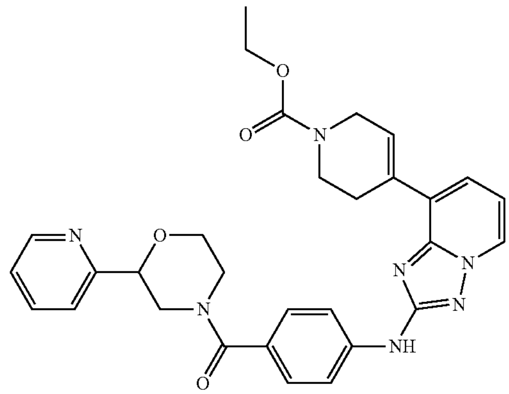 [SMILES: CCOC(=O)N1CC=C(c2cccn3nc(Nc4ccc(C(=O)N5CCOC(c6ccccn6)C5)cc4)nc23)CC1] | ethyl 4-[2-[4-[2-(2-pyridyl)morpholine-4-carbonyl]anilino]-[1,2,4]triazolo[1,5-a]pyridin-8-yl]-3,6-dihydro-2H-pyridine-1-carboxylate |
| 2-229 | 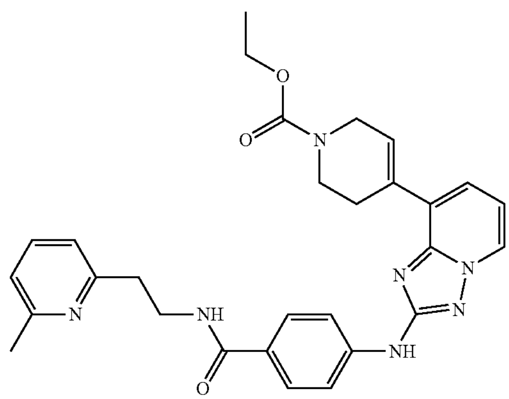 [SMILES: CCOC(=O)N1CC=C(c2cccn3nc(Nc4ccc(C(=O)NCCc5cccc(C)n5)cc4)nc23)CC1] | ethyl 4-[2-[4-[2-(6-methyl-2-pyridyl)ethylcarbamoyl]anilino]-[1,2,4]triazolo[1,5-a]pyridin-8-yl]-3,6-dihydro-2H-pyridine-1-carboxylate |
| 2-230 | 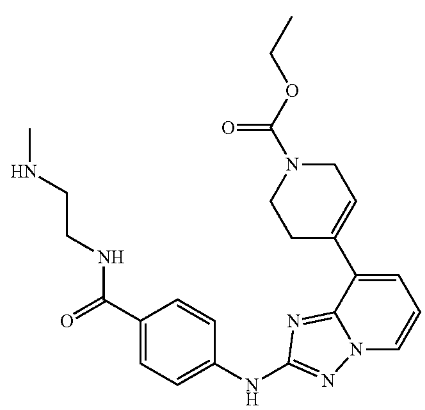 [SMILES: CCOC(=O)N1CC=C(c2cccn3nc(Nc4ccc(C(=O)NCCNC)cc4)nc23)CC1] | ethyl 4-[2-[4-[2-(methylamino)ethylcarbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-231 | 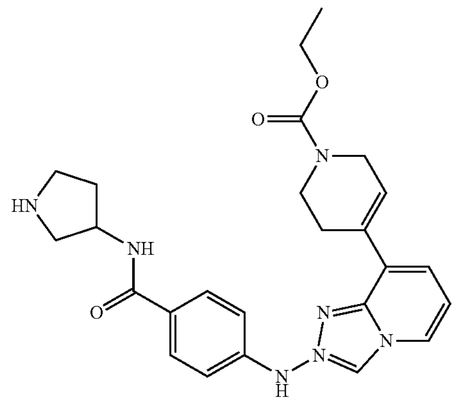 | ethyl 4-[2-[4-(pyrrolidin-3-ylcarbamoyl)anilino]-[1,2,4]triazolo[1,5-a]pyridin-8-yl]-3,6-dihydro-2H-pyridine-1-carboxylate |
| 2-232 | 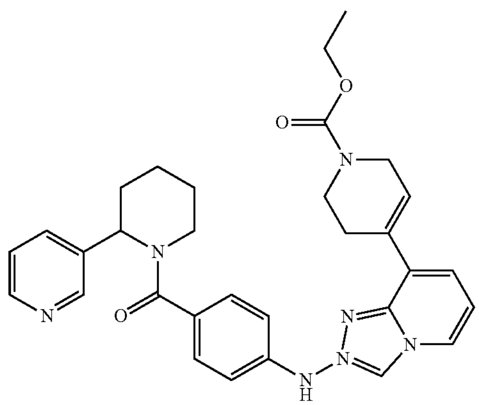 | ethyl 4-[2-[4-[2-(3-pyridyl)piperidine-1-carbonyl]anilino]-[1,2,4]triazolo[1,5-a]pyridin-8-yl]-3,6-dihydro-2H-pyridine-1-carboxylate |
| 2-233 | 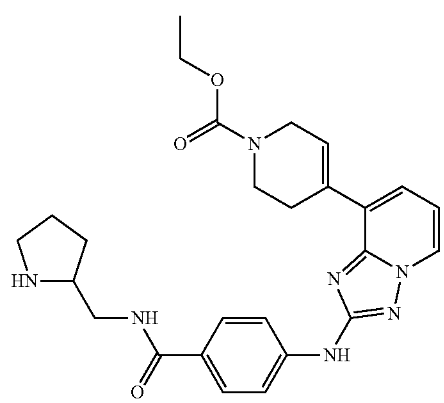 [SMILES: CCOC(=O)N1CC=C(c2cccn3nc(Nc4ccc(C(=O)NCC5CCCN5)cc4)nc23)CC1] | ethyl 4-[2-[4-(pyrrolidin-2-ylmethylcarbamoyl)anilino]-[1,2,4]triazolo[1,5-a]pyridin-8-yl]-3,6-dihydro-2H-pyridine-1-carboxylate |
| 2-234 | 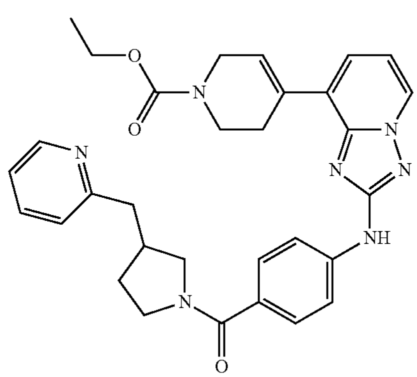 [SMILES: CCOC(=O)N1CC=C(c2cccn3nc(Nc4ccc(C(=O)N5CCC(Cc6ccccn6)C5)cc4)nc23)CC1] | ethyl 4-[2-[4-[3-(2-pyridylmethyl)pyrrolidine-1-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-235 | 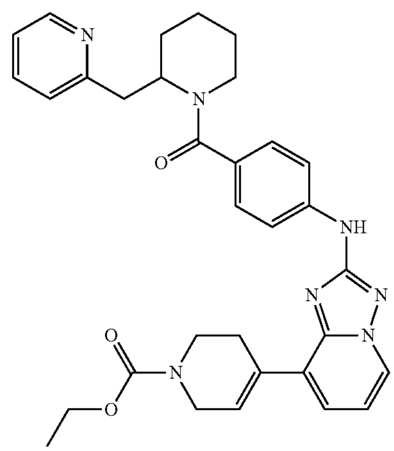 [SMILES: CCOC(=O)N1CC=C(c2cccn3nc(Nc4ccc(C(=O)N5CCCCC5Cc5ccccn5)cc4)nc23)CC1] | ethyl 4-[2-[4-[2-(2-pyridylmethyl)piperidine-1-carbonyl]anilino]-[1,2,4]triazolo[1,5-a]pyridin-8-yl]-3,6-dihydro-2H-pyridine-1-carboxylate |
| 2-236 | 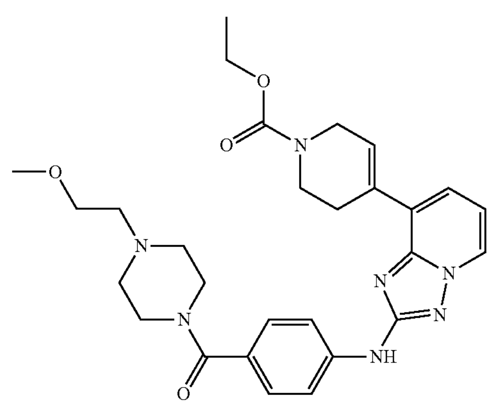 [SMILES: CCOC(=O)N1CC=C(c2cccn3nc(Nc4ccc(C(=O)N5CCN(CCOC)CC5)cc4)nc23)CC1] | ethyl 4-[2-[4-[4-(2-methoxyethyl)piperazine-1-carbonyl]anilino]-[1,2,4]triazolo[1,5-a]pyridin-8-yl]-3,6-dihydro-2H-pyridine-1-carboxylate |
| 2-237 | 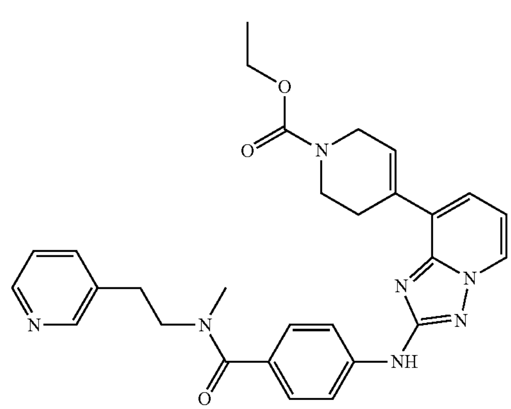 [SMILES: CCOC(=O)N1CC=C(c2cccn3nc(Nc4ccc(C(=O)N(C)CCc5cccnc5)cc4)nc23)CC1] | ethyl 4-[2-[4-[methyl-[2-(3-pyridyl)ethyl]carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-238 | 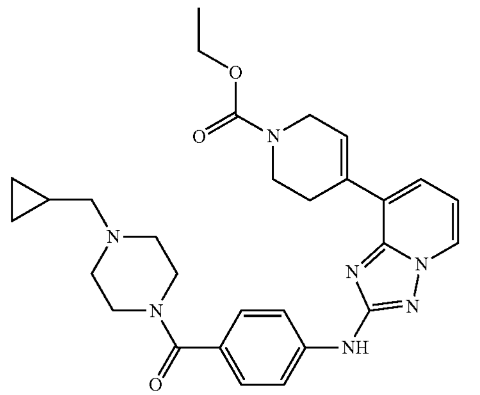 [SMILES: CCOC(=O)N1CC=C(c2cccn3nc(Nc4ccc(C(=O)N5CCN(CC6CC6)CC5)cc4)nc23)CC1] | ethyl 4-[2-[4-[4-(cyclopropylmethyl)piperazine-1-carbonyl]anilino]-[1,2,4]triazolo[1,5-a]pyridin-8-yl]-3,6-dihydro-2H-pyridine-1-carboxylate |
| 2-239 | 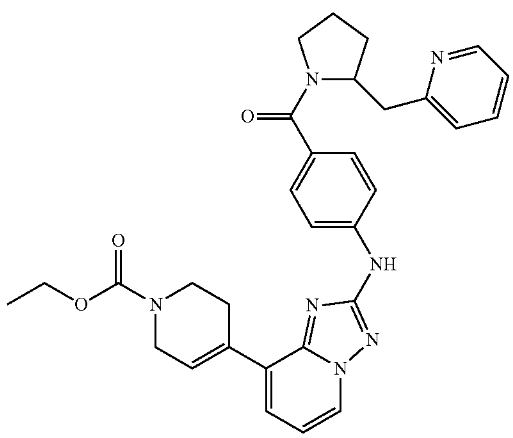 [SMILES: CCOC(=O)N1CC=C(c2cccn3nc(Nc4ccc(C(=O)N5CCCC5Cc5ccccn5)cc4)nc23)CC1] | ethyl 4-[2-[4-[2-(2-pyridylmethyl)pyrrolidine-1-carbonyl]anilino]-[1,2,4]triazolo[1,5-a]pyridin-8-yl]-3,6-dihydro-2H-pyridine-1-carboxylate |
| 2-240 | 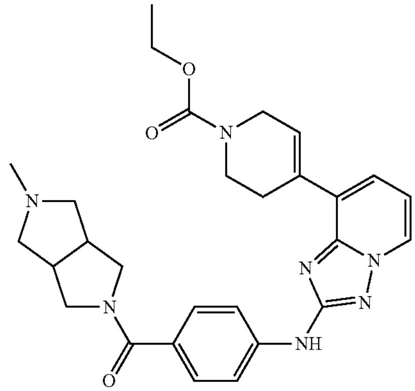 [SMILES: CCOC(=O)N1CC=C(c2cccn3nc(Nc4ccc(C(=O)N5CC6CN(C)CC6C5)cc4)nc23)CC1] | ethyl 4-[2-[4-(2-methyl-1,3,3a,4,6,6a-hexahydropyrrolo[3,4-c]pyrrole-5-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-241 | 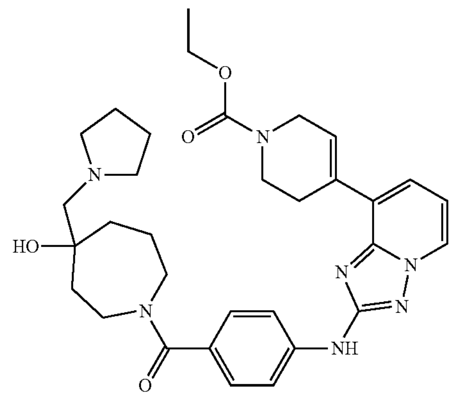 [SMILES: CCOC(=O)N1CC=C(c2cccn3nc(Nc4ccc(C(=O)N5CCCC(O)(CN6CCCC6)CC5)cc4)nc23)CC1] | ethyl 4-[2-[4-[4-hydroxy-4-(pyrrolidin-1-ylmethyl)azepane-1-carbonyl]anilino]-[1,2,4]triazolo[1,5-a]pyridin-8-yl]-3,6-dihydro-2H-pyridine-1-carboxylate |
| 2-242 | 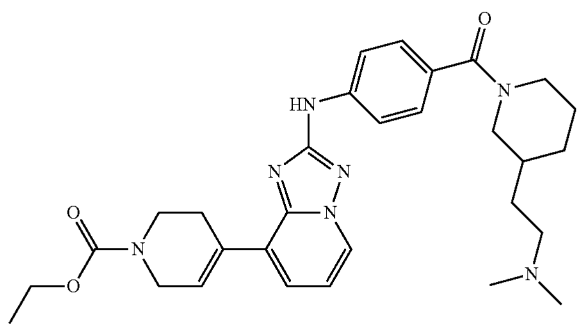 [SMILES: CCOC(=O)N1CC=C(c2cccn3nc(Nc4ccc(C(=O)N5CCCC(CCN(C)C)C5)cc4)nc23)CC1] | ethyl 4-[2-[4-[3-[2-(dimethylamino)ethyl]piperidine-1-carbonyl]anilino]-[1,2,4]triazolo[1,5-a]pyridin-8-yl]-3,6-dihydro-2H-pyridine-1-carboxylate |
| 2-243 | 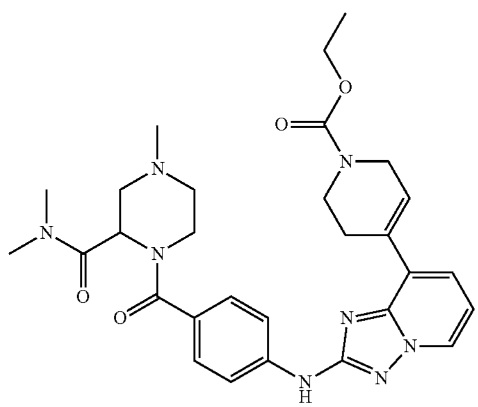 [SMILES: CCOC(=O)N1CC=C(c2cccn3nc(Nc4ccc(C(=O)N5CCN(C)CC5C(=O)N(C)C)cc4)nc23)CC1] | ethyl 4-[2-[4-[2-(dimethylcarbamoyl)-4-methyl-piperazine-1-carbonyl]anilino]-[1,2,4]triazolo[1,5-a]pyridin-8-yl]-3,6-dihydro-2H-pyridine-1-carboxylate |
| 2-244 | 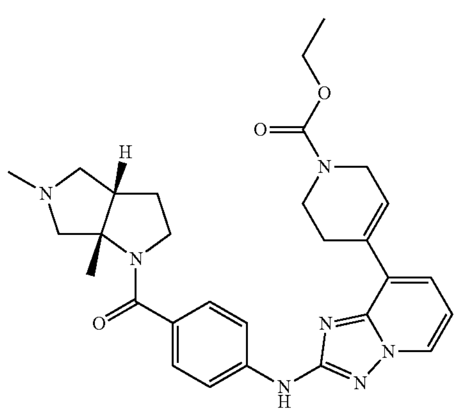 [SMILES: CCOC(=O)N1CC=C(c2cccn3nc(Nc4ccc(C(=O)N5CC[C@H]6CN(C)C[C@]65C)cc4)nc23)CC1] | ethyl 4-[2-[4-[(3aS,6aS)-5-methyl-2,3,3a,4,6,6a-hexahydropyrrolo[2,3-c]pyrrole-1-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-245 | 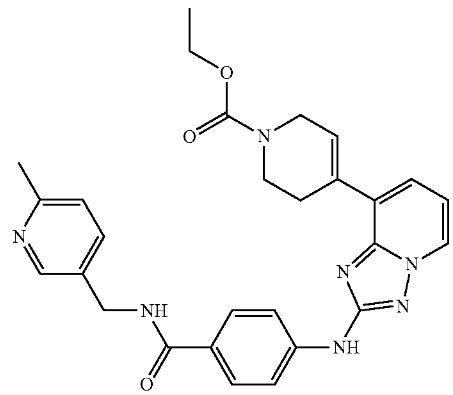 [SMILES: CCOC(=O)N1CC=C(c2cccn3nc(Nc4ccc(C(=O)NCc5ccc(C)nc5)cc4)nc23)CC1] | ethyl 4-[2-[4-[(6-methyl-3-pyridyl)methylcarbamoyl]anilino]-[1,2,4]triazolo[1,5-a]pyridin-8-yl]-3,6-dihydro-2H-pyridine-1-carboxylate |
| 2-246 | 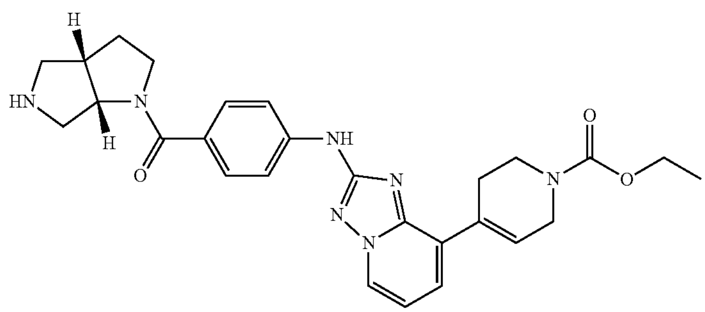 [SMILES: CCOC(=O)N1CC=C(c2cccn3nc(Nc4ccc(C(=O)N5CC[C@H]6CNC[C@H]65)cc4)nc23)CC1] | ethyl 4-[2-[4-[(3aS,6aS)-3,3a,4,5,6,6a-hexahydro-2H-pyrrolo[2,3-c]pyrrole-1-carbonyl]anilino]-[1,2,4]triazolo[1,5-a]pyridin-8-yl]-3,6-dihydro-2H-pyridine-1-carboxylate |
| 2-247 | 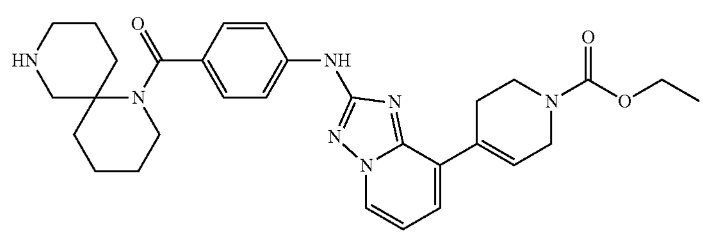 [SMILES: CCOC(=O)N1CC=C(c2cccn3nc(Nc4ccc(C(=O)N5CCCCC56CCCNC6)cc4)nc23)CC1] | ethyl 4-[2-[4-(1,8-diazaspiro[5.5]undecane-1-carbonyl)anilino]-[1,2,4]triazolo[1,5-a]pyridin-8-yl]-3,6-dihydro-2H-pyridine-1-carboxylate |
| 2-248 | 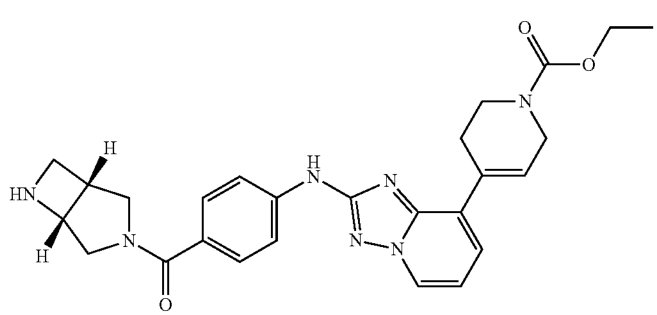 [SMILES: CCOC(=O)N1CC=C(c2cccn3nc(Nc4ccc(C(=O)N5C[C@H]6CN[C@H]6C5)cc4)nc23)CC1] | ethyl 4-[2-[4-[(1R,5R)-3,6-diazabicyclo[3.2.0]heptane-3-carbonyl]anilino]-[1,2,4]triazolo[1,5-a]pyridin-8-yl]-3,6-dihyro-2H-pyridine-1-carboxylate |

TABLE A-continued

Exemplary Compounds of the Present Invention

| Ex. | Structure | Name |
|---|---|---|
| 2-249 | 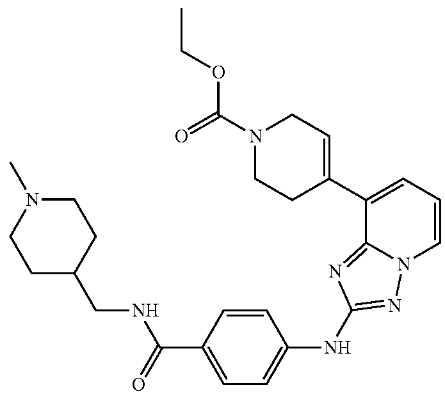 [SMILES: CCOC(=O)N1CC=C(c2cccn3nc(Nc4ccc(C(=O)NCC5CCN(C)CC5)cc4)nc23)CC1] | ethyl 4-[2-[4-[(1-methyl-4-piperidyl)methylcarbamoyl]anilino]-[1,2,4]triazolo[1,5-a]pyridin-8-yl]-3,6-dihydro-2H-pyridine-1-carboxylate |
| 2-250 | 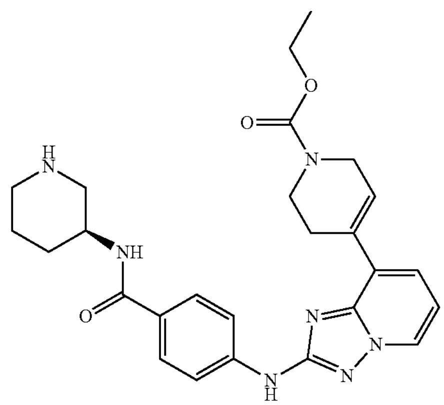 [SMILES: CCOC(=O)N1CC=C(c2cccn3nc(Nc4ccc(C(=O)N[C@H]5CCCNC5)cc4)nc23)CC1] | ethyl 4-[2-[4-[[(3S)-3-piperidyl]carbamoyl]anilino]-[1,2,4]triazolo[1,5-a]pyridin-8-yl]-3,6-dihydro-2H-pyridine-1-carboxylate |
| 2-251 | 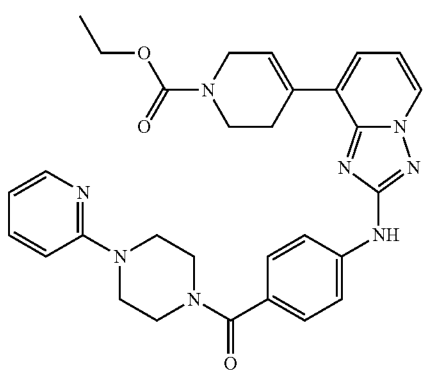 [SMILES: CCOC(=O)N1CC=C(c2cccn3nc(Nc4ccc(C(=O)N5CCN(c6ccccn6)CC5)cc4)nc23)CC1] | ethyl 4-[2-[4-[4-(2-pyridyl)piperazine-1-carbonyl]anilino]-[1,2,4]triazolo[1,5-a]pyridin-8-yl]-3,6-dihydro-2H-pyridine-1-carboxylate |
| 2-252 | 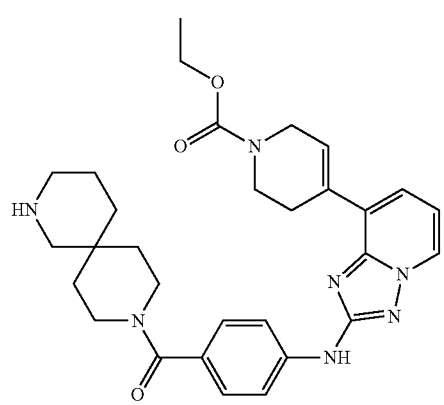 [SMILES: CCOC(=O)N1CC=C(c2cccn3nc(Nc4ccc(C(=O)N5CCC6(CCCNC6)CC5)cc4)nc23)CC1] | ethyl 4-[2-[4-(2,9-diazaspiro[5.5]undecane-9-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-253 | 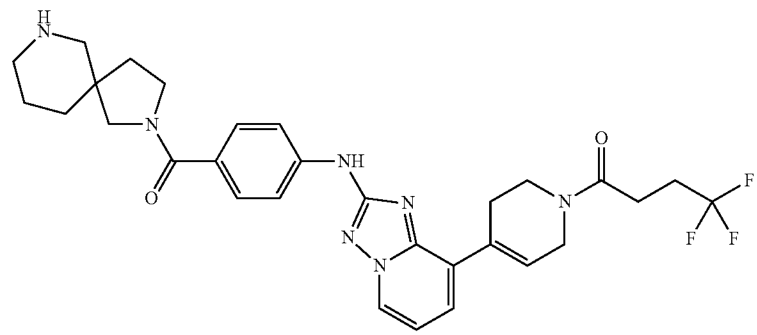 [SMILES: O=C(CCC(F)(F)F)N1CC=C(c2cccn3nc(Nc4ccc(C(=O)N5CCC6(CCCNC6)C5)cc4)nc23)CC1] | 1-[4-[2-[4-(2,9-diazaspiro[4.5]decane-2-carbonyl)anilino]-[1,2,4]triazolo[1,5-a]pyridin-8-yl]-3,6-dihydro-2H-pyridin-1-yl]-4,4,4-trifluoro-butan-1-one |
| 2-254 | 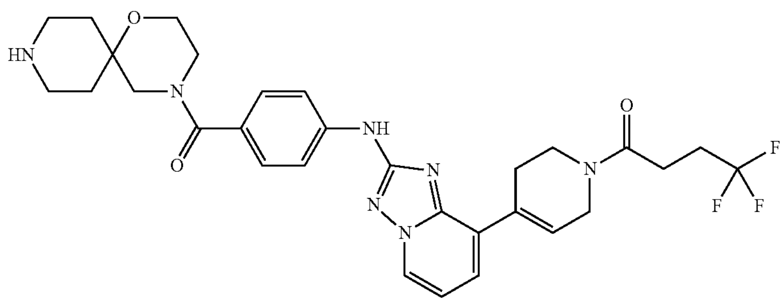 [SMILES: O=C(CCC(F)(F)F)N1CC=C(c2cccn3nc(Nc4ccc(C(=O)N5CCOC6(CCNCC6)C5)cc4)nc23)CC1] | 4,4,4-trifluoro-1-[4-[2-[4-(1-oxa-4,9-diazaspiro[5.5]undecane-4-carbonyl)anilino]-[1,2,4]triazolo[1,5-a]pyridin-8-yl]-3,6-dihydro-2H-pyridin-1-yl]butan-1-one |
| 2-255 | 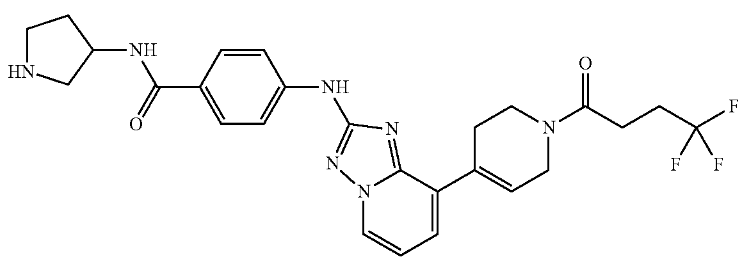 [SMILES: O=C(NC1CCNC1)c1ccc(Nc2nc3c(C4=CCN(C(=O)CCC(F)(F)F)CC4)cccn3n2)cc1] | N-pyrrolidin-3-yl-4-[[8-[1-(4,4,4-trifluorobutanoyl)-3,6-dihydro-2H-pyridin-4-yl][1,2,4]triazolo[1,5-a]pyridin-2-yl]amino]benzamide |
| 2-256 | 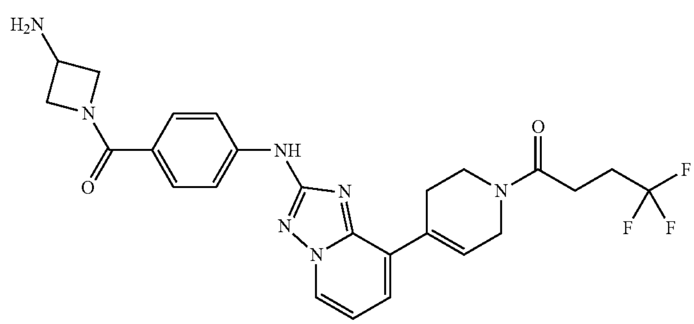 [SMILES: NC1CN(C(=O)c2ccc(Nc3nc4c(C5=CCN(C(=O)CCC(F)(F)F)CC5)cccn4n3)cc2)C1] | 1-[4-[2-[4-(3-aminoazetidine-1-carbonyl)anilino]-[1,2,4]triazolo[1,5-a]pyridin-8-yl]-3,6-dihydro-2H-pyridin-1-yl]-4,4,4-trifluoro-butan-1-one |
| 2-257 | 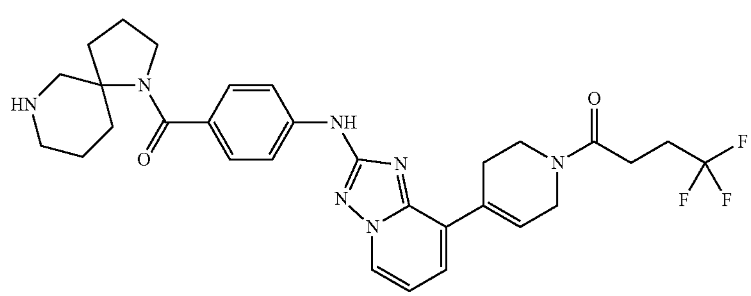 [SMILES: O=C(CCC(F)(F)F)N1CC=C(c2cccn3nc(Nc4ccc(C(=O)N5CCCC56CCCNC6)cc4)nc23)CC1] | 1-[4-[2-[4-(1,9-diazaspiro[4.5]decane-1-carbonyl)anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-258 | 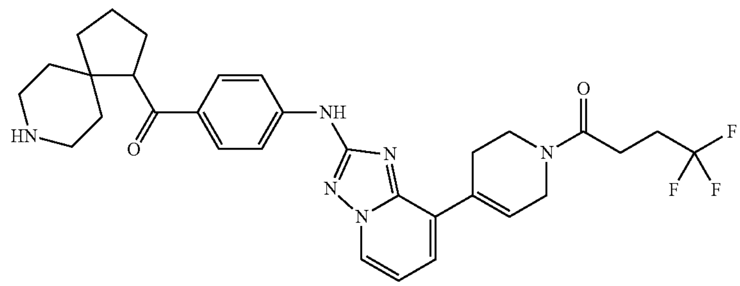 [SMILES: O=C(c1ccc(Nc2nc3c(C4=CCN(C(=O)CCC(F)(F)F)CC4)cccn3n2)cc1)C1CCCC12CCNCC2] | 1-[4-[2-[4-(1,8-diazaspiro[4.5]decane-1-carbonyl)anilino]-[1,2,4]triazolo[1,5-a]pyridin-8-yl]-3,6-dihydro-2H-pyridin-1-yl]-4,4,4-trifluoro-butan-1-one |
| 2-259 | 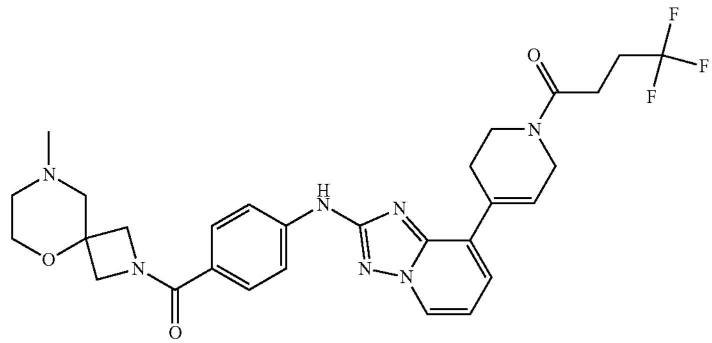 [SMILES: CN1CCOC2(C1)CN(C(=O)c1ccc(Nc3nc4c(C5=CCN(C(=O)CCC(F)(F)F)CC5)cccn4n3)cc1)C2] | 4,4,4-trifluoro-1-[4-[2-[4-(8-methyl-5-oxa-2,8-diazaspiro[3.5]nonane-2-carbonyl)anilino]-[1,2,4]triazolo[1,5-a]pyridin-8-yl]-3,6-dihydro-2H-pyridin-1-yl]butan-1-one |
| 2-260 | 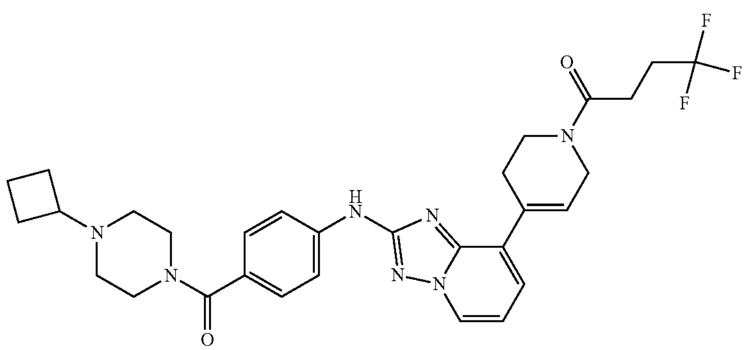 [SMILES: O=C(CCC(F)(F)F)N1CC=C(c2cccn3nc(Nc4ccc(C(=O)N5CCN(C6CCC6)CC5)cc4)nc23)CC1] | 1-[4-[2-[4-(4-cyclobutylpiperazine-1-carbonyl)anilino]-[1,2,4]triazolo[1,5-a]pyridin-8-yl]-3,6-dihydro-2H-pyridin-1-yl]-4,4,4-trifluoro-butan-1-one |
| 2-261 | 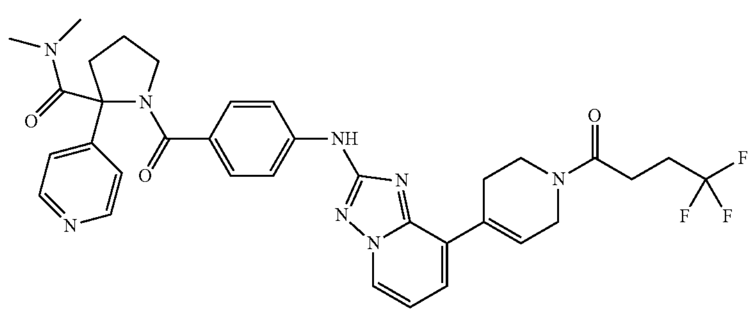 [SMILES: CN(C)C(=O)C1(c2ccncc2)CCCN1C(=O)c1ccc(Nc2nc3c(C4=CCN(C(=O)CCC(F)(F)F)CC4)cccn3n2)cc1] | N,N-dimethyl-2-(4-pyridyl)-1-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]pyrrolidine-2-carboxamide |

TABLE A-continued

Exemplary Compounds of the Present Invention

| Ex. | Structure | Name |
|---|---|---|
| 2-262 | 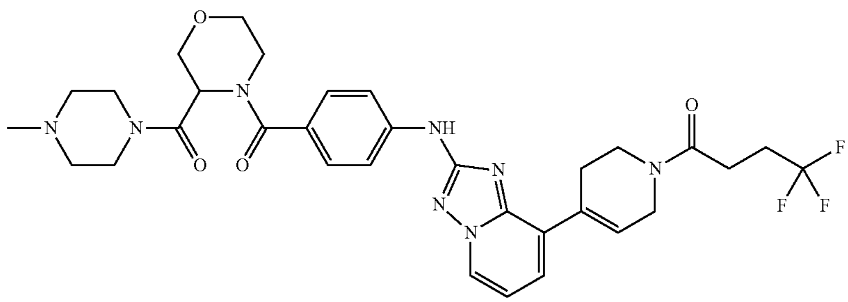 [SMILES: CN1CCN(C(=O)C2COCCN2C(=O)c2ccc(Nc3nc4c(C5=CCN(C(=O)CCC(F)(F)F)CC5)cccn4n3)cc2)CC1] | 4,4,4-trifluoro-1-[4-[2-[4-[3-(4-methylpiperazine-1-carbonyl)morpholine-4-carbonyl]anilino]-[1,2,4]triazolo[1,5-a]pyridin-8-yl]-3,6-dihydro-2H-pyridin-1-yl]butane-1-one |
| 2-263 | 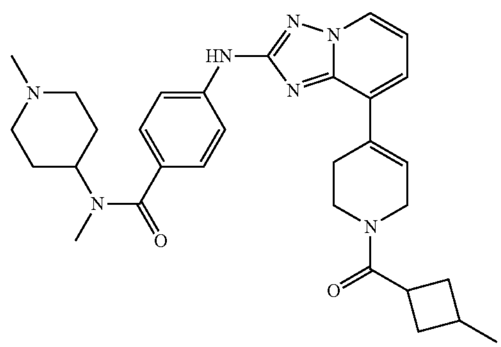 [SMILES: CC1CC(C(=O)N2CC=C(c3cccn4nc(Nc5ccc(C(=O)N(C)C6CCN(C)CC6)cc5)nc34)CC2)C1] | N-methyl-4-[[8-[1-(3-methylcyclobutane carbonyl)-3,6-dihydro-2H-pyridin-4-yl]-[1,2,4]triazolo[1,5-a]pyridin-2-yl]amino]-N-(1-methyl-4-piperidyl)benzamide |
| 2-264 | 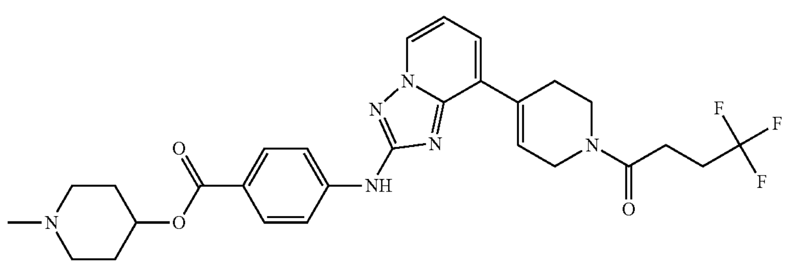 [SMILES: CN1CCC(OC(=O)c2ccc(Nc3nc4c(C5=CCN(C(=O)CCC(F)(F)F)CC5)cccn4n3)cc2)CC1] | (1-methyl-4-piperidyl) 4-[[8-[1-(4,4,4-trifluorobutanoyl)-3,6-dihydro-2H-pyridin-4-yl]-[1,2,4]triazolo[1,5-a]pyridin-2-yl]amino]benzoate |
| 2-265 | 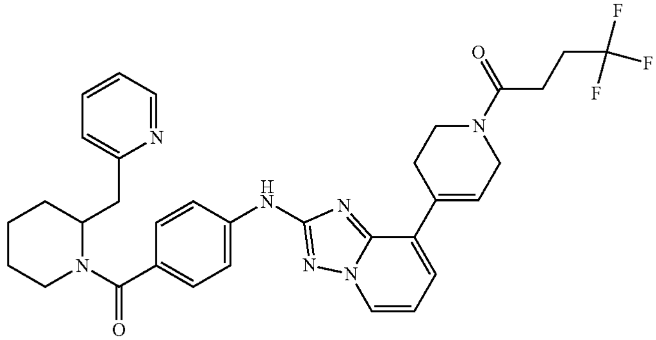 [SMILES: O=C(CCC(F)(F)F)N1CC=C(c2cccn3nc(Nc4ccc(C(=O)N5CCCCC5Cc5ccccn5)cc4)nc23)CC1] | 4,4,4-trifluoro-1-[4-[2-[4-[2-(2-pyridylmethyl)piperidine-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-266 | 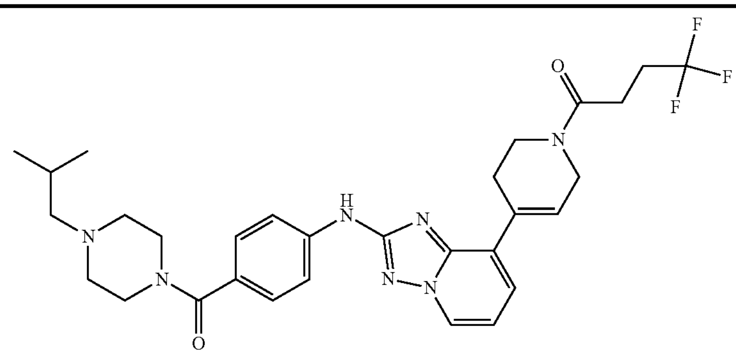 | 4,4,4-trifluoro-1-[4-[2-[4-(4-isobutylpiperazine-1-carbonyl)anilino]-[1,2,4]triazolo[1,5-a]pyridin-8-yl]-3,6-dihydro-2H-pyridin-1-yl]butan-1-one |
| 2-267 | 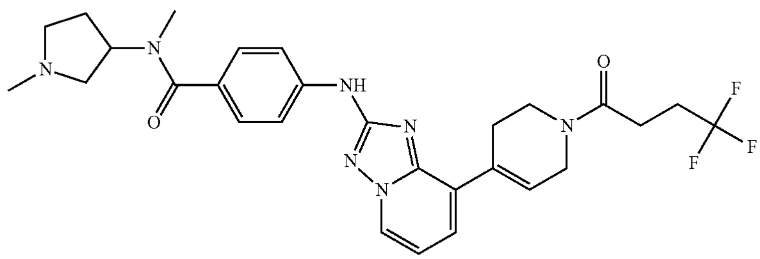 [SMILES: CN1CCC(N(C)C(=O)c2ccc(Nc3nc4c(C5=CCN(C(=O)CCC(F)(F)F)CC5)cccn4n3)cc2)C1] | N-methyl-N-(1-methylpyrrolidin-3-yl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-268 | 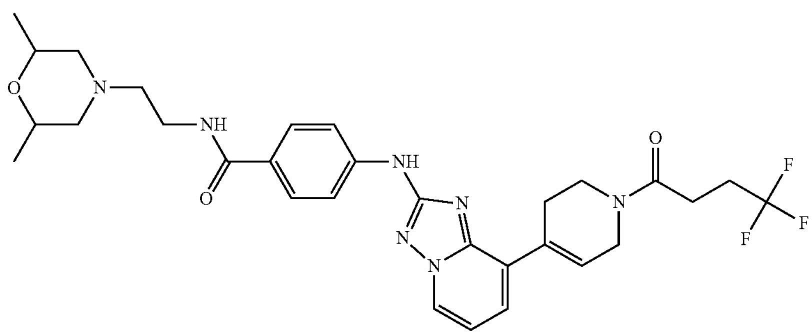 [SMILES: CC1CN(CCNC(=O)c2ccc(Nc3nc4c(C5=CCN(C(=O)CCC(F)(F)F)CC5)cccn4n3)cc2)CC(C)O1] | N-[2-(2,6-dimethylmorpholin-4-yl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-269 | 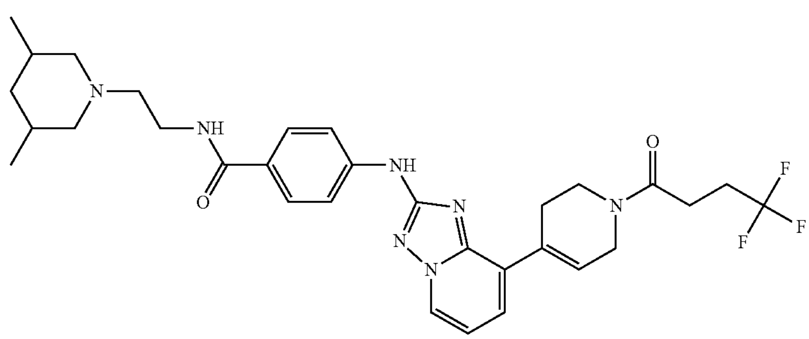 [SMILES: CC1CC(C)CN(CCNC(=O)c2ccc(Nc3nc4c(C5=CCN(C(=O)CCC(F)(F)F)CC5)cccn4n3)cc2)C1] | N-[2-(3,5-dimethyl-1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-270 | 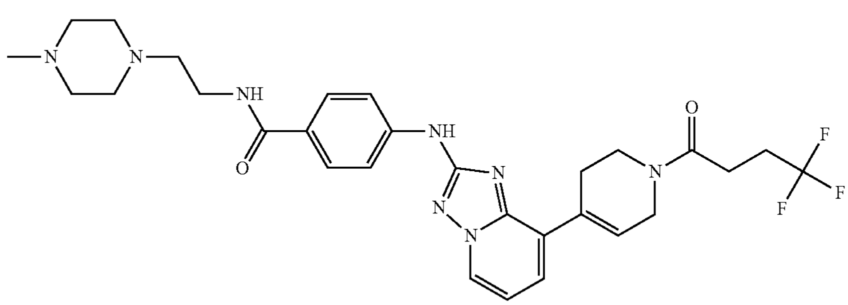 [SMILES: CN1CCN(CCNC(=O)c2ccc(Nc3nc4c(C5=CCN(C(=O)CCC(F)(F)F)CC5)cccn4n3)cc2)CC1] | N-[2-(4-methylpiperazin-1-yl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-271 | 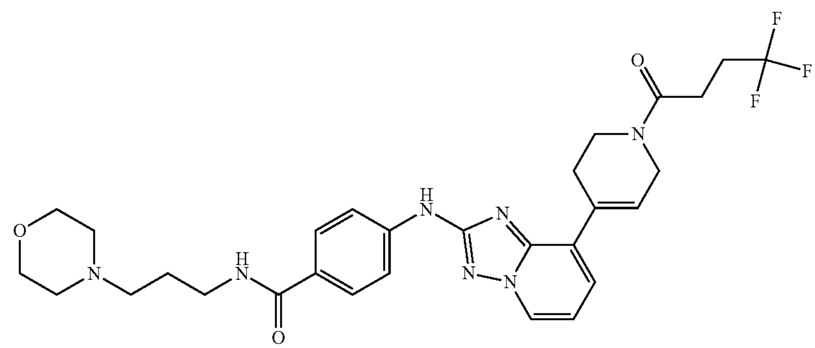 [SMILES: O=C(NCCCN1CCOCC1)c1ccc(Nc2nc3c(C4=CCN(C(=O)CCC(F)(F)F)CC4)cccn3n2)cc1] | N-(3-morpholinopropyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-272 | 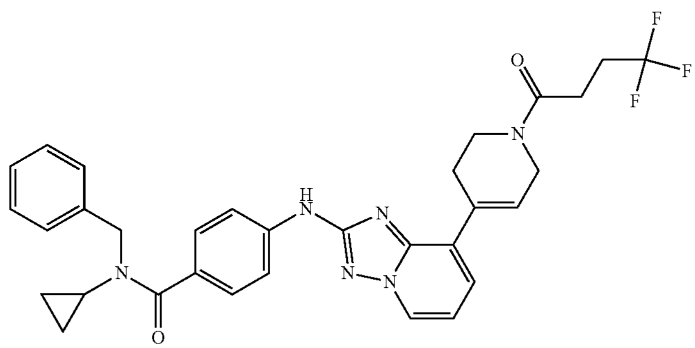 [SMILES: O=C(CCC(F)(F)F)N1CC=C(c2cccn3nc(Nc4ccc(C(=O)N(Cc5ccccc5)C5CC5)cc4)nc23)CC1] | N-cyclopropyl-N-(2-pyridylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-273 | 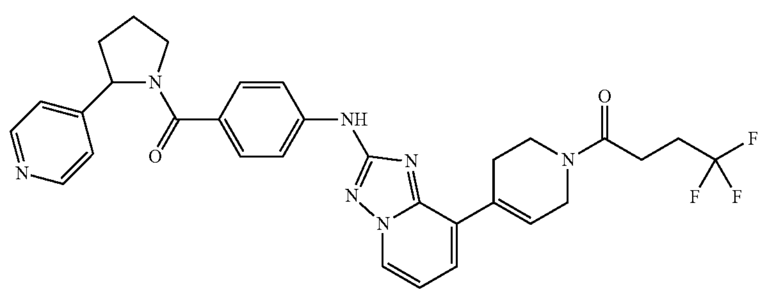 [SMILES: O=C(CCC(F)(F)F)N1CC=C(c2cccn3nc(Nc4ccc(C(=O)N5CCCC5c5ccncc5)cc4)nc23)CC1] | 4,4,4-trifluoro-1-[4-[2-[4-[2-(4-pyridyl)pyrrolidine-1-carbonyl]anilino]-[1,2,4]triazolo[1,5-a]pyridin-8-yl]-3,6-dihydro-2H-pyridin-1-yl]butan-1-one |
| 2-274 | 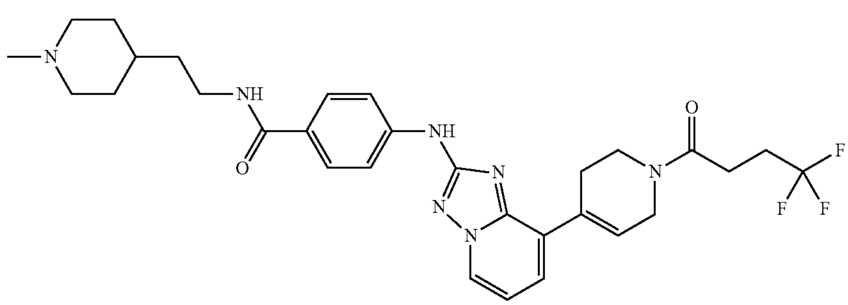 [SMILES: CN1CCC(CCNC(=O)c2ccc(Nc3nc4c(C5=CCN(C(=O)CCC(F)(F)F)CC5)cccn4n3)cc2)CC1] | N-[2-(1-methyl-4-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-275 | 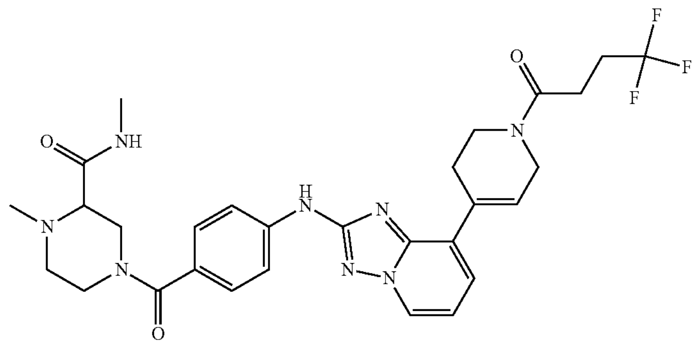 | N,1-dimethyl-4-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide |
| 2-276 | 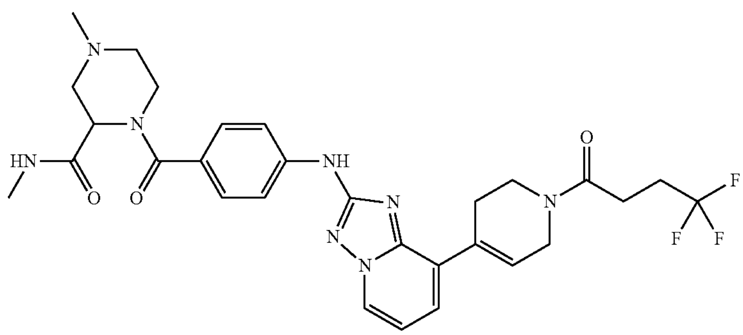 [SMILES: CNC(=O)C1CN(C)CCN1C(=O)c1ccc(Nc2nc3c(C4=CCN(C(=O)CCC(F)(F)F)CC4)cccn3n2)cc1] | N,4-dimethyl-1-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide |
| 2-277 | 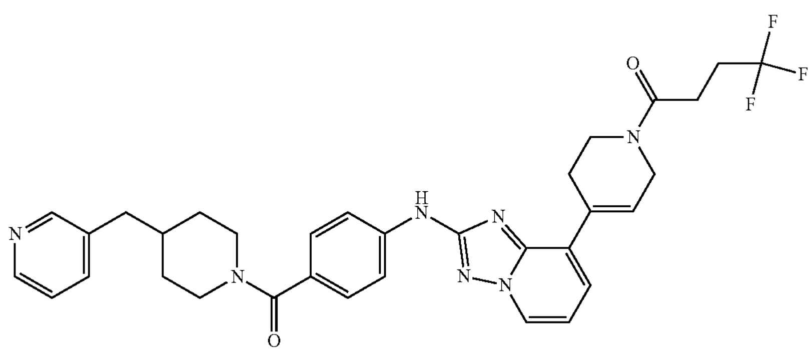 [SMILES: O=C(CCC(F)(F)F)N1CC=C(c2cccn3nc(Nc4ccc(C(=O)N5CCC(Cc6cccnc6)CC5)cc4)nc23)CC1] | 4,4,4-trifluoro-1-[4-[2-[4-[4-(3-pyridylmethyl)piperidine-1-carbonyl]anilino]-[1,2,4]triazolo[1,5-a]pyridin-8-yl]-3,6-dihydro-2H-pyridin-1-yl]butan-1-one |
| 2-278 | 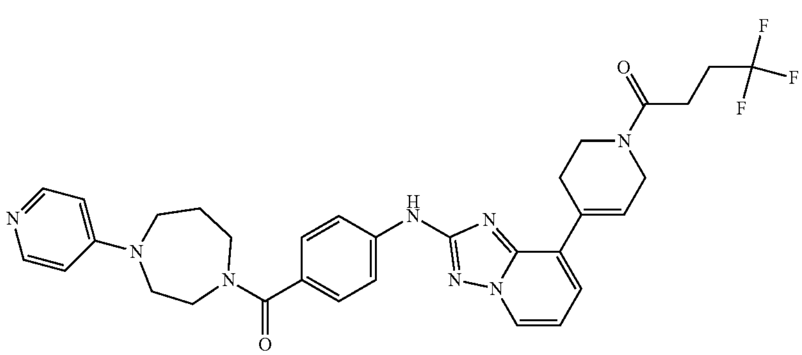 [SMILES: O=C(CCC(F)(F)F)N1CC=C(c2cccn3nc(Nc4ccc(C(=O)N5CCCN(c6ccncc6)CC5)cc4)nc23)CC1] | 4,4,4-trifluoro-1-[4-[2-[4-[4-(4-pyridyl)-1,4-diazepane-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-279 | 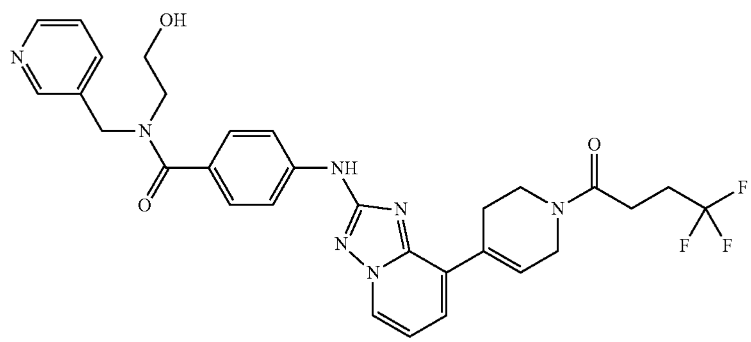 [SMILES: O=C(CCC(F)(F)F)N1CC=C(c2cccn3nc(Nc4ccc(C(=O)N(CCO)Cc5cccnc5)cc4)nc23)CC1] | N-(2-hydroxyethyl)-N-(3-pyridylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-280 | 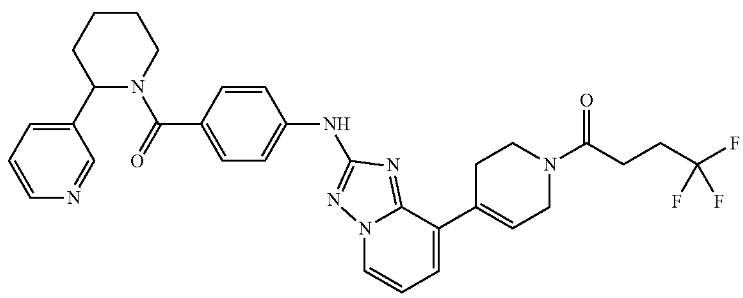 [SMILES: O=C(CCC(F)(F)F)N1CC=C(c2cccn3nc(Nc4ccc(C(=O)N5CCCCC5c5cccnc5)cc4)nc23)CC1] | 4,4,4-trifluoro-1-[4-[2-[4-[2-(3-pyridyl)piperidine-1-carbonyl]anilino]-[1,2,4]triazolo[1,5-a]pyridin-8-yl]-3,6-dihydro-2H-pyridin-1-yl]butan-1-one |
| 2-281 | 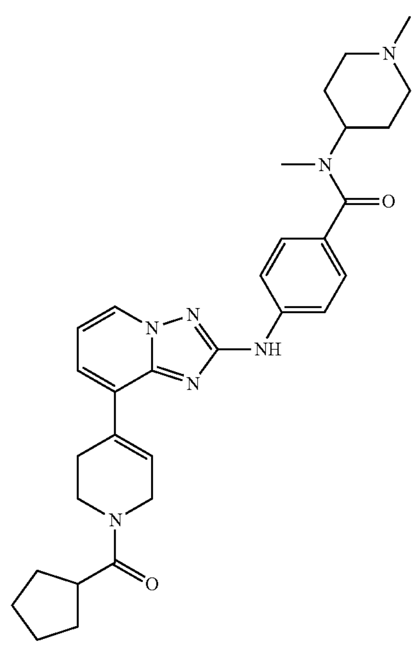 [SMILES: CN1CCC(N(C)C(=O)c2ccc(Nc3nc4c(C5=CCN(C(=O)C6CCCC6)CC5)cccn4n3)cc2)CC1] | 4-[[8-[1-(cyclopentanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 2-282 | 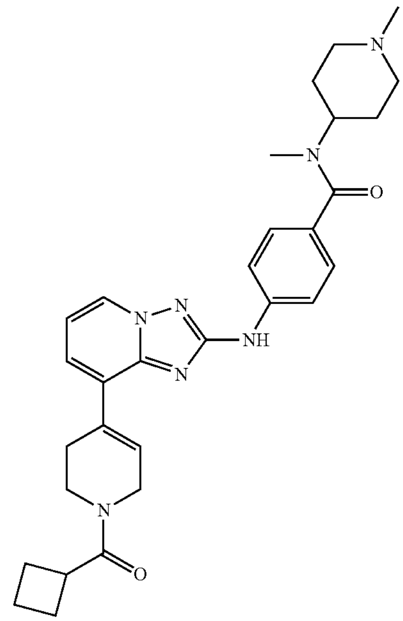 [SMILES: CN1CCC(N(C)C(=O)c2ccc(Nc3nc4c(C5=CCN(C(=O)C6CCC6)CC5)cccn4n3)cc2)CC1] | 4-[[8-[1-(cyclobutanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide |
| 2-283 | 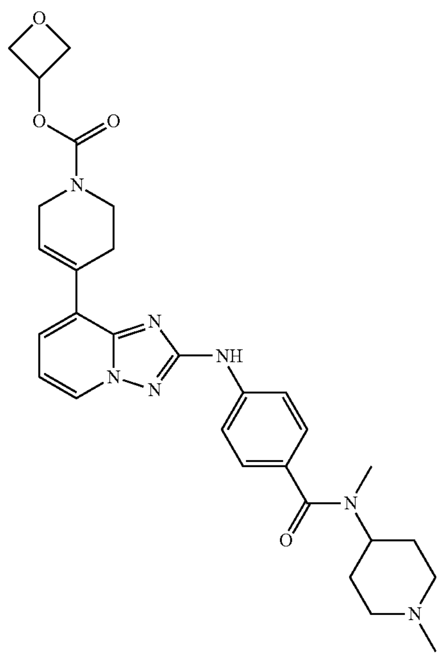 [SMILES: CN1CCC(N(C)C(=O)c2ccc(Nc3nc4c(C5=CCN(C(=O)OC6COC6)CC5)cccn4n3)cc2)CC1] | oxetan-3-yl-4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |
| 2-284 | 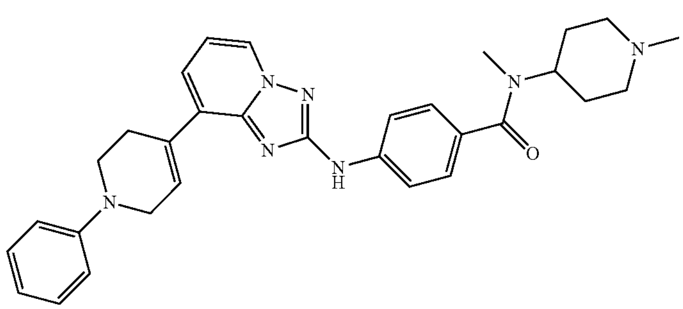 [SMILES: CN1CCC(N(C)C(=O)c2ccc(Nc3nc4c(C5=CCN(c6ccccc6)CC5)cccn4n3)cc2)CC1] | N-methyl-N-(1-methyl-4-piperidyl)-4-[[8-(1-phenyl-3,6-dihydro-2H-pyridin-4-yl)-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-285 | 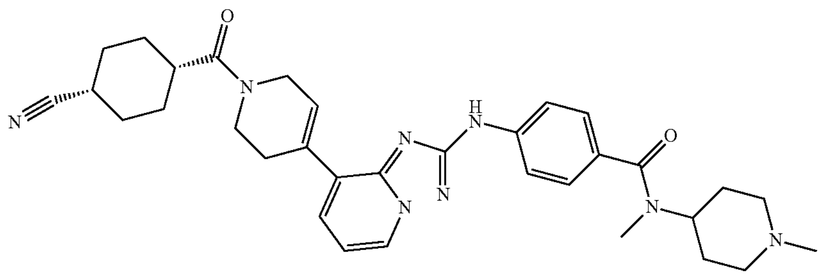 [SMILES: CN1CCC(N(C)C(=O)c2ccc(NC(=N)/N=c3\[nH]cccc3C3=CCN(C(=O)[C@H]4CC[C@@H](C#N)CC4)CC3)cc2)CC1] | 4-[[8-[1-(4-cyanocyclohexane carbonyl)-3,6-dihydro-2H-pyridin-4-yl]-[1,2,4]triazolo[1,5-a]pyridin-2-yl]amino]-N-methyl-N-(1-methyl-4-piperidyl)benzamide |
| 2-286 | 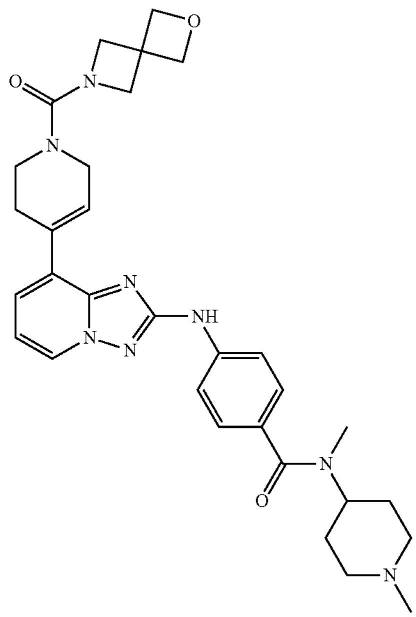 [SMILES: CN1CCC(N(C)C(=O)c2ccc(Nc3nc4c(C5=CCN(C(=O)N6CC7(COC7)C6)CC5)cccn4n3)cc2)CC1] | N-methyl-N-(1-methyl-4-piperidyl)-4-[[8-[1-(2-oxa-6-azaspiro[3.3]heptane-6-carbonyl)-3,6-dihydro-2H-pyridin-4-yl]-[1,2,4]triazolo[1,5-a]pyridin-2-yl]amino]benzamide |
| 2-287 | 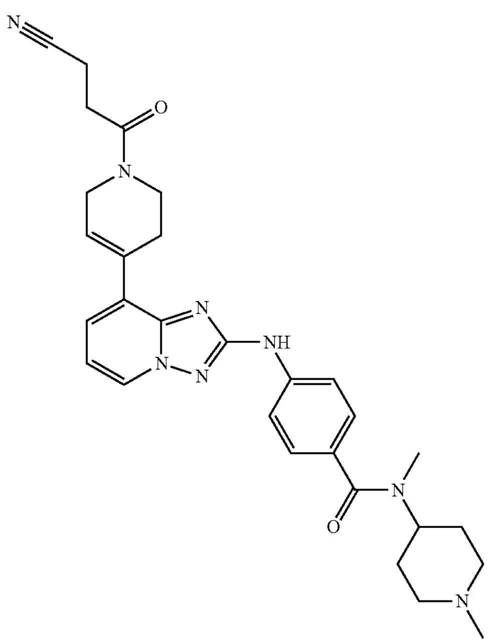 [SMILES: CN1CCC(N(C)C(=O)c2ccc(Nc3nc4c(C5=CCN(C(=O)CCC#N)CC5)cccn4n3)cc2)CC1] | 4-[[8-[1-(3-cyanopropanoyl)-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 2-288 | 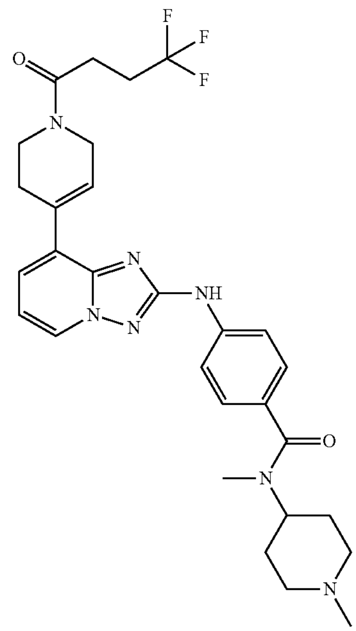 [SMILES: CN1CCC(N(C)C(=O)c2ccc(Nc3nc4c(C5=CCN(C(=O)CCC(F)(F)F)CC5)cccn4n3)cc2)CC1] | N-methyl-N-(1-methyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-289 | 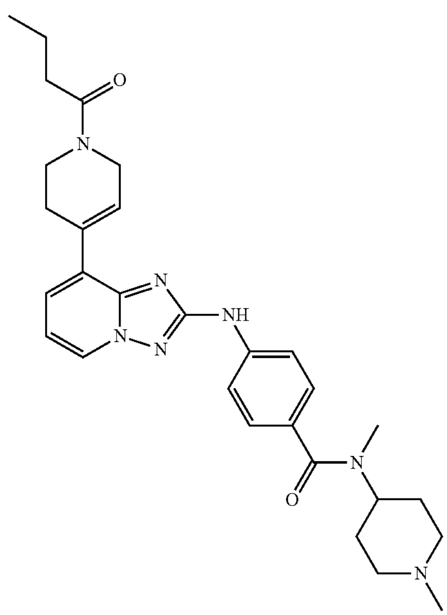 [SMILES: CCCC(=O)N1CC=C(c2cccn3nc(Nc4ccc(C(=O)N(C)C5CCN(C)CC5)cc4)nc23)CC1] | 4-[[8-(1-butanoyl-3,6-dihydro-2H-pyridin-4-yl)-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 2-290 | 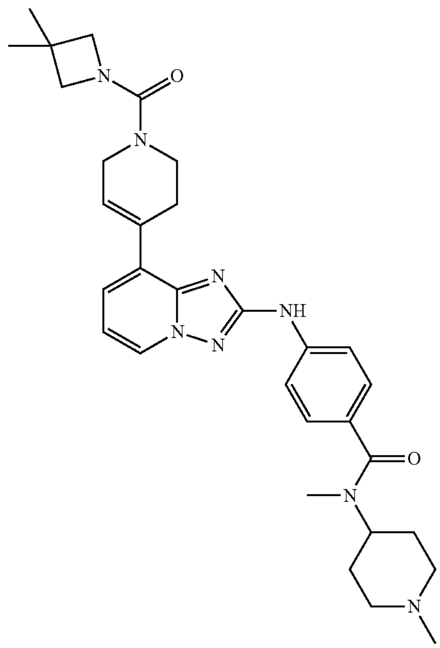 | 4-[[8-[1-(3,3-dimethylazetidine-1-carbonyl)-3,6-dihydro-2H-pyridin-4-yl]-[1,2,4]triazolo[1,5-a]pyridin-2-yl]amino]-N-methyl-N-(1-methyl-4-piperidyl)benzamide |
| 2-291 | 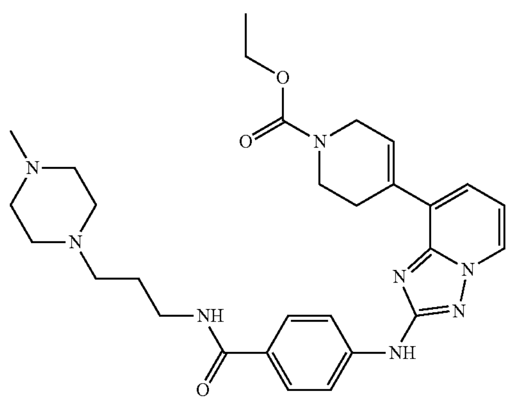 [SMILES: CCOC(=O)N1CC=C(c2cccn3nc(Nc4ccc(C(=O)NCCCN5CCN(C)CC5)cc4)nc23)CC1] | ethyl 4-[2-[4-[3-(4-methylpiperazin-1-yl)propylcarbamoyl]anilino]-[1,2,4]triazolo[1,5-a]pyridin-8-yl]-3,6-dihydro-2H-pyridine-1-carboxylate |
| 2-292 | 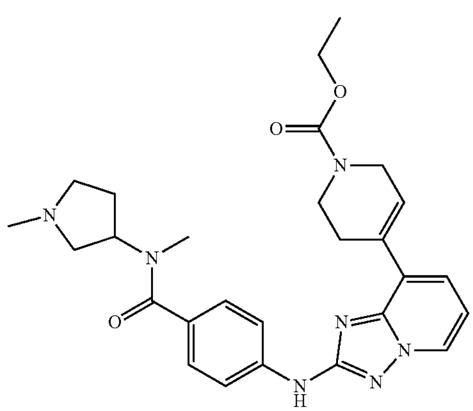 [SMILES: CCOC(=O)N1CC=C(c2cccn3nc(Nc4ccc(C(=O)N(C)C5CCN(C)C5)cc4)nc23)CC1] | ethyl 4-[2-[4-[methyl-(1-methylpyrrolidin-3-yl)carbamoyl]anilino]-[1,2,4]triazolo[1,5-a]pyridin-8-yl]-3,6-dihydro-2H-pyridine-1-carboxylate |

| Ex. | Structure | Name |
|---|---|---|
| 2-293 | 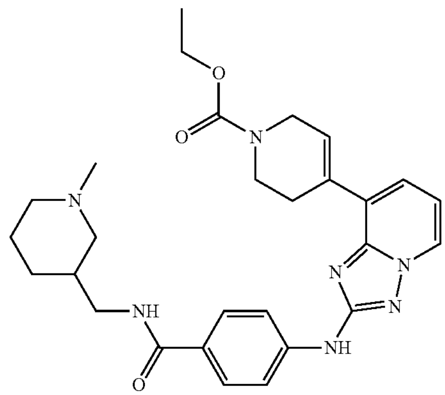 [SMILES: CCOC(=O)N1CC=C(c2cccn3nc(Nc4ccc(C(=O)NCC5CCCN(C)C5)cc4)nc23)CC1] | ethyl 4-[2-[4-[(1-methyl-3-piperidyl)methylcarbamoyl]anilino]-[1,2,4]triazolo[1,5-a]pyridin-8-yl]-3,6-dihydro-2H-pyridine-1-carboxylate |
| 2-294 | 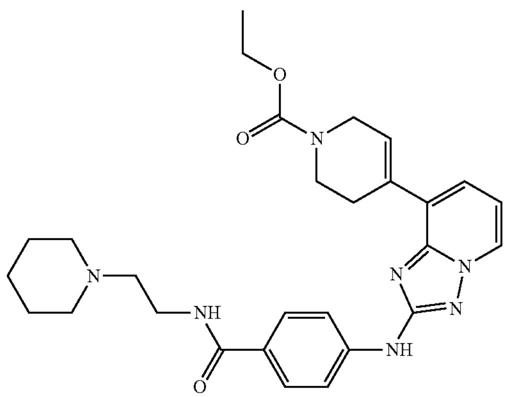 [SMILES: CCOC(=O)N1CC=C(c2cccn3nc(Nc4ccc(C(=O)NCCN5CCCCC5)cc4)nc23)CC1] | ethyl 4-[2-[4-[2-(1-piperidyl)ethylcarbamoyl]anilino]-[1,2,4]triazolo[1,5-a]pyridin-8-yl]-3,6-dihydro-2H-pyridine-1-carboxylate |
| 2-295 | 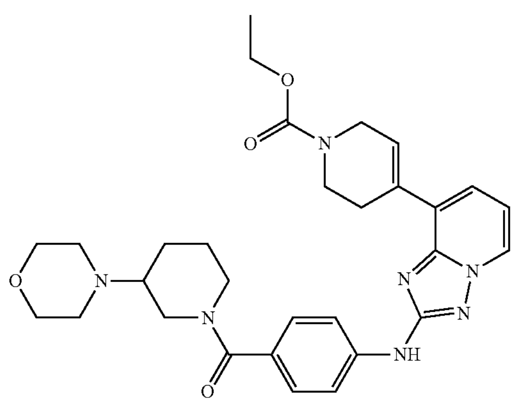 [SMILES: CCOC(=O)N1CC=C(c2cccn3nc(Nc4ccc(C(=O)N5CCCC(N6CCOCC6)C5)cc4)nc23)CC1] | ethyl 4-[2-[4-(3-morpholinopiperidine-1-carbonyl)anilino]-[1,2,4]triazolo[1,5-a]pyridin-8-yl]-3,6-dihydro-2H-pyridine-1-carboxylate |
| 2-296 | 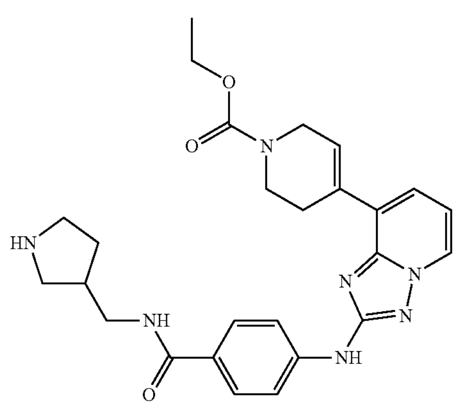 [SMILES: CCOC(=O)N1CC=C(c2cccn3nc(Nc4ccc(C(=O)NCC5CCNC5)cc4)nc23)CC1] | ethyl 4-[2-[4-(pyrrolidin-3-ylmethylcarbamoyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-297 | 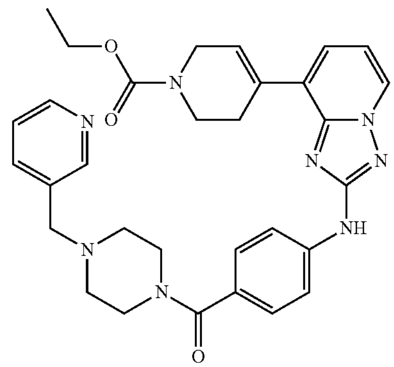 [SMILES: CCOC(=O)N1CC=C(c2cccn3nc(Nc4ccc(C(=O)N5CCN(Cc6cccnc6)CC5)cc4)nc23)CC1] | ethyl 4-[2-[4-[4-(3-pyridylmethyl)piperazine-1-carbonyl]anilino]-[1,2,4]triazolo[1,5-a]pyridin-8-yl]-3,6-dihydro-2H-pyridine-1-carboxylate |
| 2-298 | 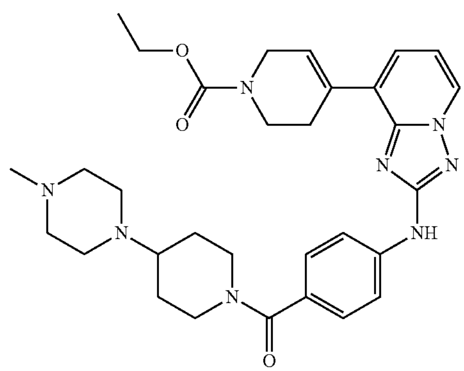 [SMILES: CCOC(=O)N1CC=C(c2cccn3nc(Nc4ccc(C(=O)N5CCC(N6CCN(C)CC6)CC5)cc4)nc23)CC1] | ethyl 4-[2-[4-[4-(4-methylpiperazin-1-yl)piperidine-1-carbonyl]anilino]-[1,2,4]triazolo[1,5-a]pyridin-8-yl]-3,6-dihydro-2H-pyridine-1-carboxylate |
| 2-299 | 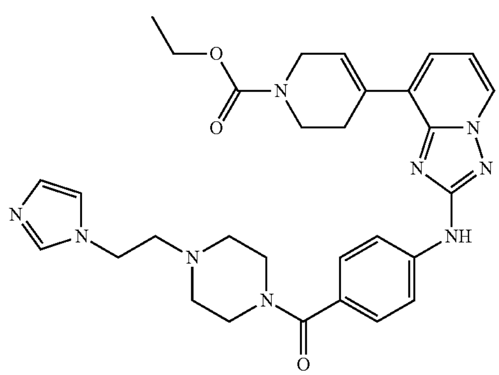 [SMILES: CCOC(=O)N1CC=C(c2cccn3nc(Nc4ccc(C(=O)N5CCN(CCn6ccnc6)CC5)cc4)nc23)CC1] | ethyl 4-[2-[4-[4-(2-imidazol-1-ylethyl)piperazine-1-carbonyl]anilino]-[1,2,4]triazolo[1,5-a]pyridin-8-yl]-3,6-dihydro-2H-pyridine-1-carboxylate |
| 2-300 | 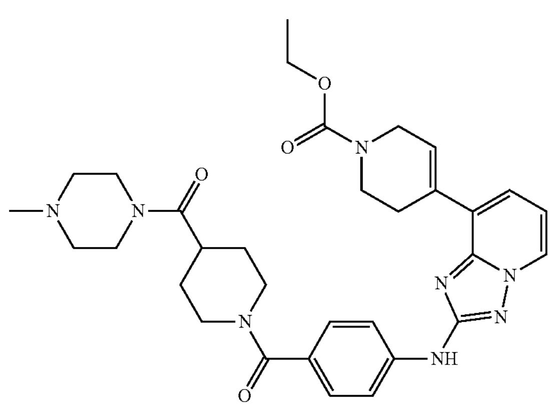 [SMILES: CCOC(=O)N1CC=C(c2cccn3nc(Nc4ccc(C(=O)N5CCC(C(=O)N6CCN(C)CC6)CC5)cc4)nc23)CC1] | ethyl 4-[2-[4-[4-(4-methylpiperazine-1-carbonyl)piperidine-1-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-301 | 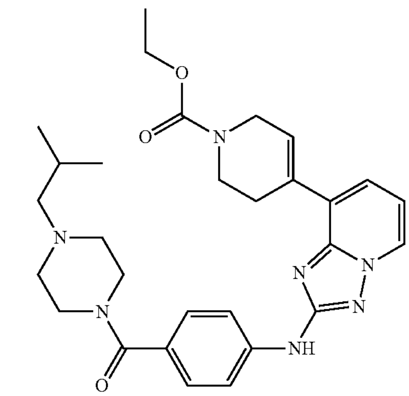 [SMILES: CCOC(=O)N1CC=C(c2cccn3nc(Nc4ccc(C(=O)N5CCN(CC(C)C)CC5)cc4)nc23)CC1] | ethyl 4-[2-[4-(4-isobutylpiperazine-1-carbonyl)anilino]-[1,2,4]triazolo[1,5-a]pyridin-8-yl]-3,6-dihydro-2H-pyridine-1-carboxylate |
| 2-302 | 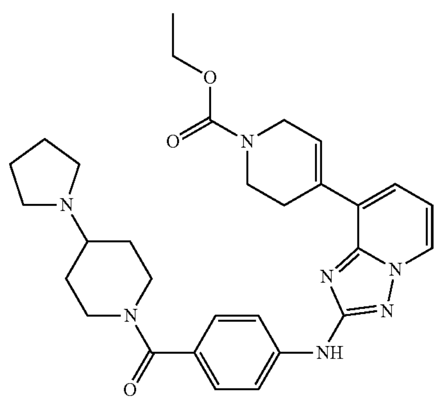 [SMILES: CCOC(=O)N1CC=C(c2cccn3nc(Nc4ccc(C(=O)N5CCC(N6CCCC6)CC5)cc4)nc23)CC1] | ethyl 4-[2-[4-(4-pyrrolidin-1-ylpiperidine-1-carbonyl)anilino]-[1,2,4]triazolo[1,5-a]pyridin-8-yl]-3,6-dihydro-2H-pyridine-1-carboxylate |
| 2-303 | 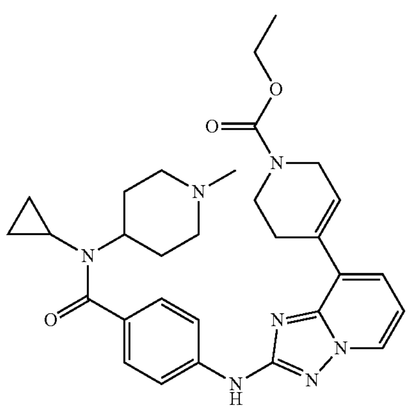 [SMILES: CCOC(=O)N1CC=C(c2cccn3nc(Nc4ccc(C(=O)N(C5CC5)C5CCN(C)CC5)cc4)nc23)CC1] | ethyl 4-[2-[4-[cyclopropyl-(1-methyl-4-piperidyl)carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-304 | 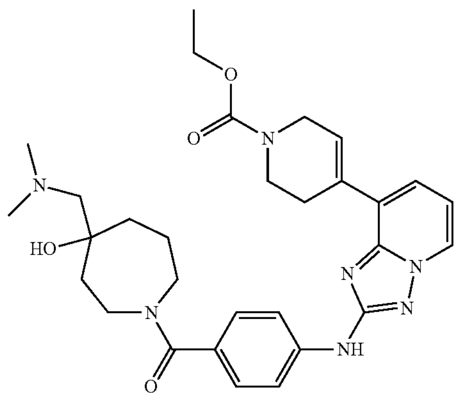 [SMILES: CCOC(=O)N1CC=C(c2cccn3nc(Nc4ccc(C(=O)N5CCCC(O)(CN(C)C)CC5)cc4)nc23)CC1] | ethyl 4-[2-[4-[4-[(dimethylamino)methyl]-4-hydroxy-azepane-1-carbonyl]anilino]-[1,2,4]triazolo[1,5-a]pyridin-8-yl]-3,6-dihydro-2H-pyridine-1-carboxylate |
| 2-305 | 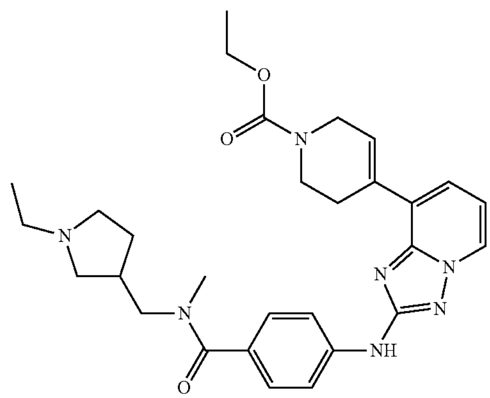 [SMILES: CCOC(=O)N1CC=C(c2cccn3nc(Nc4ccc(C(=O)N(C)CC5CCN(CC)C5)cc4)nc23)CC1] | ethyl 4-[2-[4-[(1-ethylpyrrolidin-3-yl)methyl-methyl-carbamoyl]anilino]-[1,2,4]triazolo[1,5-a]pyridin-8-yl]-3,6-dihydro-2H-pyridine-1-carboxylate |
| 2-306 | 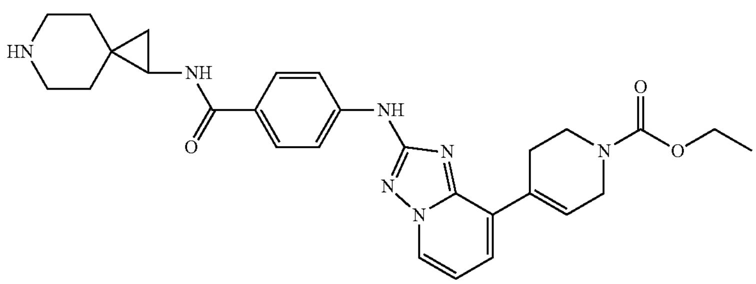 [SMILES: CCOC(=O)N1CC=C(c2cccn3nc(Nc4ccc(C(=O)NC5CC56CCNCC6)cc4)nc23)CC1] | ethyl 4-[2-[4-(6-azaspiro[2.5]octan-2-ylmethylcarbamoyl)anilino]-[1,2,4]triazolo[1,5-a]pyridin-8-yl]-3,6-dihydro-2H-pyridine-1-carboxylate |
| 2-307 | 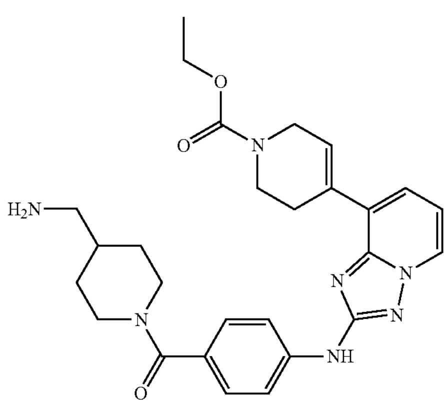 [SMILES: CCOC(=O)N1CC=C(c2cccn3nc(Nc4ccc(C(=O)N5CCC(CN)CC5)cc4)nc23)CC1] | ethyl 4-[2-[4-[4-(aminomethyl)piperidine-1-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-308 | 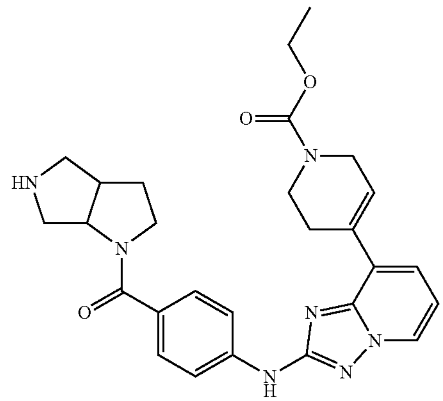 [SMILES: CCOC(=O)N1CC=C(c2cccn3nc(Nc4ccc(C(=O)N5CCC6CNCC65)cc4)nc23)CC1] | ethyl 4-[2-[4-(3,3a,4,5,6,6a-hexahydro-2H-pyrrolo[2,3-c]pyrrole-1-carbonyl)anilino]-[1,2,4]triazolo[1,5-a]pyridin-8-yl]-3,6-dihydro-2H-pyridine-1-carboxylate |
| 2-309 | 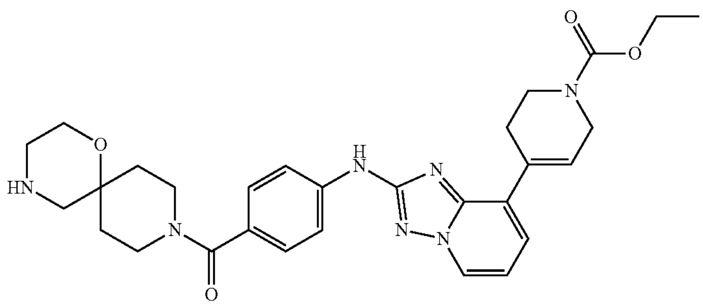 [SMILES: CCOC(=O)N1CC=C(c2cccn3nc(Nc4ccc(C(=O)N5CCC6(CC5)CNCCO6)cc4)nc23)CC1] | ethyl 4-[2-[4-(1-oxa-4,9-diazaspiro[5.5]undecane-9-carbonyl)anilino]-[1,2,4]triazolo[1,5-a]pyridin-8-yl]-3,6-dihydro-2H-pyridine-1-carboxylate |
| 2-310 | 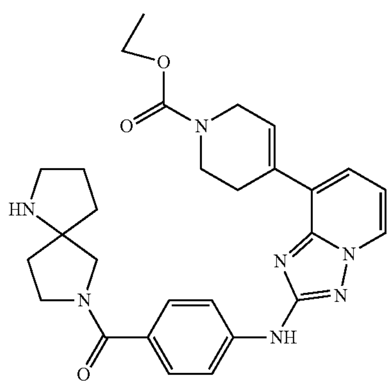 [SMILES: CCOC(=O)N1CC=C(c2cccn3nc(Nc4ccc(C(=O)N5CCC6(CCCN6)C5)cc4)nc23)CC1] | ethyl 4-[2-[4-(1,7-diazaspiro[4.4]nonane-7-carbonyl)anilino]-[1,2,4]triazolo[1,5-a]pyridin-8-yl]-3,6-dihydro-2H-pyridine-1-carboxylate |
| 2-311 | 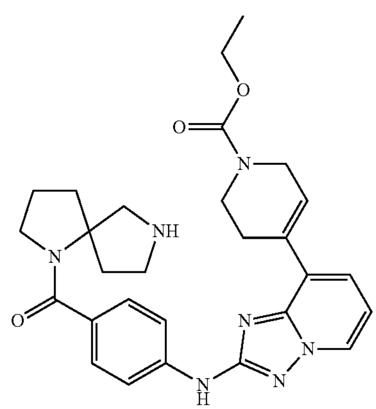 [SMILES: CCOC(=O)N1CC=C(c2cccn3nc(Nc4ccc(C(=O)N5CCCC56CCNC6)cc4)nc23)CC1] | ethyl 4-[2-[4-(1,7-diazaspiro[4.4]nonane-1-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-312 | 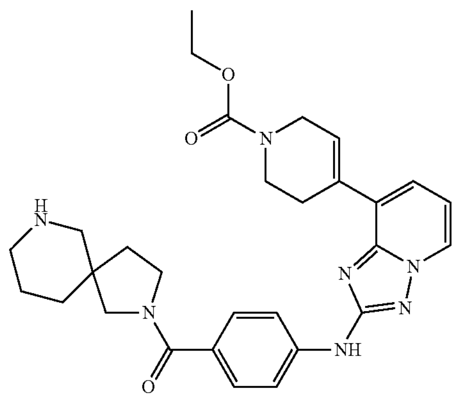 [SMILES: CCOC(=O)N1CC=C(c2cccn3nc(Nc4ccc(C(=O)N5CCC6(CCCNC6)C5)cc4)nc23)CC1] | ethyl 4-[2-[4-(2,9-diazaspiro[4.5]decane-2-carbonyl)anilino]-[1,2,4]triazolo[1,5-a]pyridin-8-yl]-3,6-dihydro-2H-pyridine-1-carboxylate |
| 2-313 | 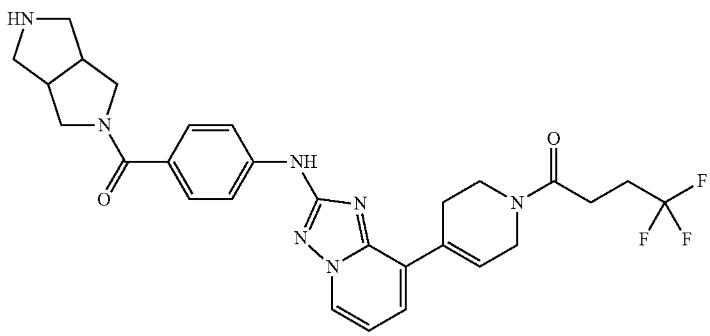 [SMILES: O=C(CCC(F)(F)F)N1CC=C(c2cccn3nc(Nc4ccc(C(=O)N5CC6CNCC6C5)cc4)nc23)CC1] | 1-[4-[2-[4-(2,3,3a,4,6,6a-hexahydro-1H-pyrrolo[3,4-c]pyrrole-5-carbonyl)anilino]-[1,2,4]triazolo[1,5-a]pyridin-8-yl]-3,6-dihydro-2H-pyridin-1-yl]-4,4,4-trifluoro-butan-1-one |
| 2-314 | 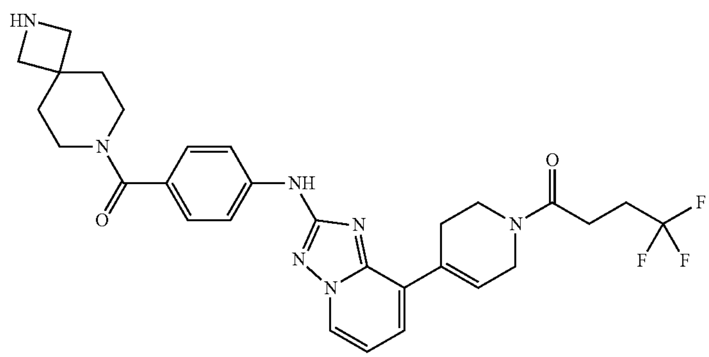 [SMILES: O=C(CCC(F)(F)F)N1CC=C(c2cccn3nc(Nc4ccc(C(=O)N5CCC6(CC5)CNC6)cc4)nc23)CC1] | 1-[4-[2-[4-(2,7-diazaspiro[3.5]nonane-7-carbonyl)anilino]-[1,2,4]triazolo[1,5-a]pyridin-8-yl]-3,6-dihydro-2H-pyridin-1-yl]-4,4,4-trifluoro-butan-1-one |
| 2-315 | 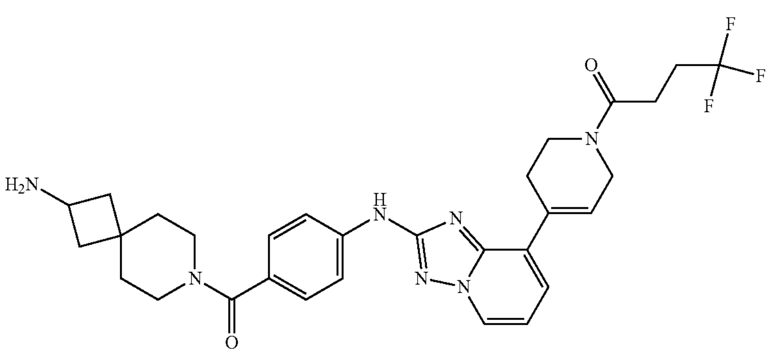 [SMILES: NC1CC2(CCN(C(=O)c3ccc(Nc4nc5c(C6=CCN(C(=O)CCC(F)(F)F)CC6)cccn5n4)cc3)CC2)C1] | 1-[4-[2-[4-(2-amino-7-azaspiro[3.5]nonane-7-carbonyl)anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-316 | 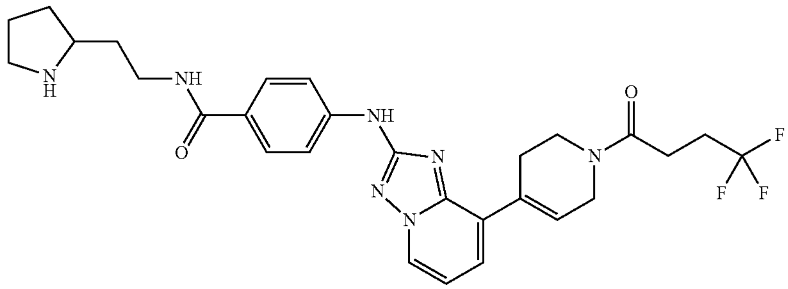 [SMILES: O=C(NCCC1CCCN1)c1ccc(Nc2nc3c(C4=CCN(C(=O)CCC(F)(F)F)CC4)cccn3n2)cc1] | N-(2-pyrrolidin-2-ylethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-317 | 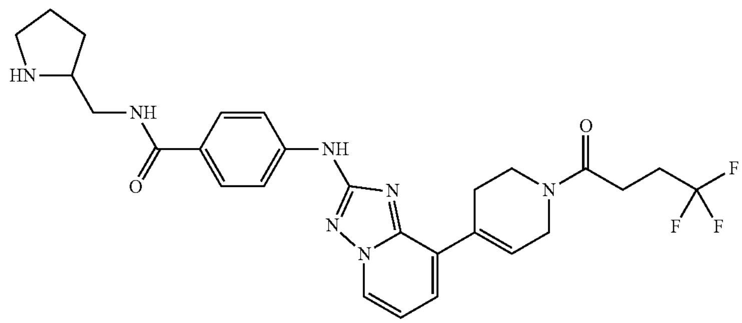 [SMILES: O=C(NCC1CCCN1)c1ccc(Nc2nc3c(C4=CCN(C(=O)CCC(F)(F)F)CC4)cccn3n2)cc1] | N-(pyrrolidin-2-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-318 | 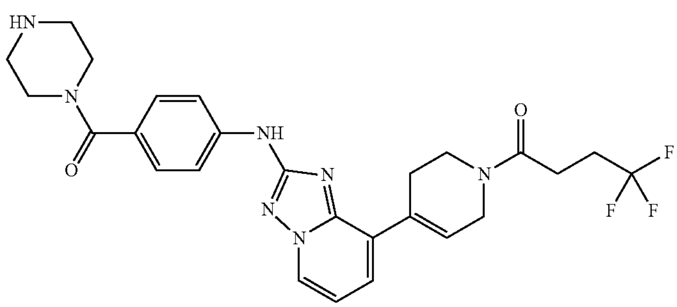 [SMILES: O=C(CCC(F)(F)F)N1CC=C(c2cccn3nc(Nc4ccc(C(=O)N5CCNCC5)cc4)nc23)CC1] | 4,4,4-trifluoro-1-[4-[2-[4-(piperazine-1-carbonyl)anilino]-[1,2,4]triazolo[1,5-a]pyridin-8-yl]-3,6-dihydro-2H-pyridin-1-yl]butan-1-one |
| 2-319 | 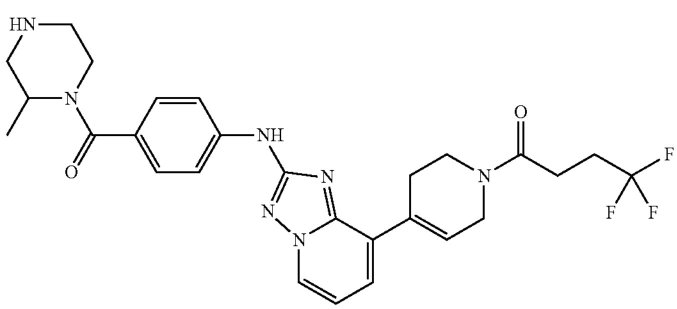 [SMILES: CC1CNCCN1C(=O)c1ccc(Nc2nc3c(C4=CCN(C(=O)CCC(F)(F)F)CC4)cccn3n2)cc1] | 4,4,4-trifluoro-1-[4-[2-[4-(2-methylpiperazine-1-carbonyl)anilino]-[1,2,4]triazolo[1,5-a]pyridin-8-yl]-3,6-dihydro-2H-pyridin-1-yl]butan-1-one |
| 2-320 | 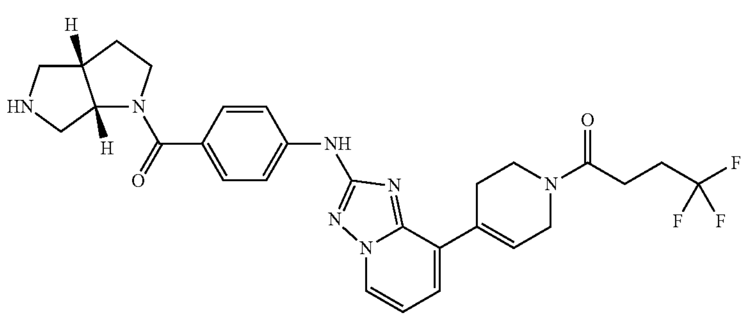 [SMILES: O=C(CCC(F)(F)F)N1CC=C(c2cccn3nc(Nc4ccc(C(=O)N5CC[C@H]6CNC[C@H]65)cc4)nc23)CC1] | 1-[4-[2-[4-[(3aS,6aS)-3,3a,4,5,6,6a-hexahydro-2H-pyrrolo[2,3-c]pyrrole-1-carbonyl]anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-321 | 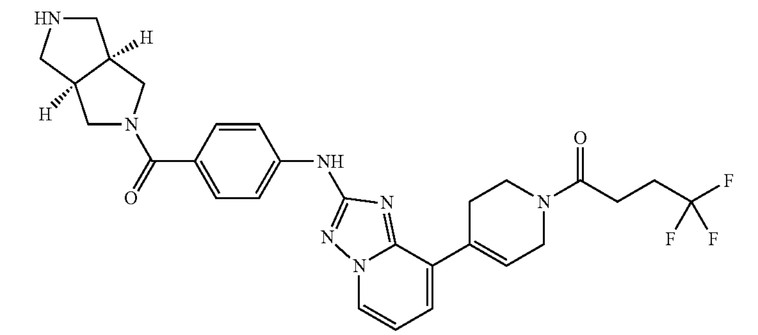 [SMILES: O=C(CCC(F)(F)F)N1CC=C(c2cccn3nc(Nc4ccc(C(=O)N5C[C@H]6CNC[C@H]6C5)cc4)nc23)CC1] | 1-[4-[2-[4-[(3aR,6aS)-2,3,3a,4,6,6a-hexahydro-1H-pyrrolo[3,4-c]pyrrole-5-carbonyl]anilino]-[1,2,4]triazolo[1,5-a]pyridin-8-yl]-3,6-dihydro-2H-pyridin-yl]-4,4,4-trifluoro-butan-1-one |
| 2-322 | 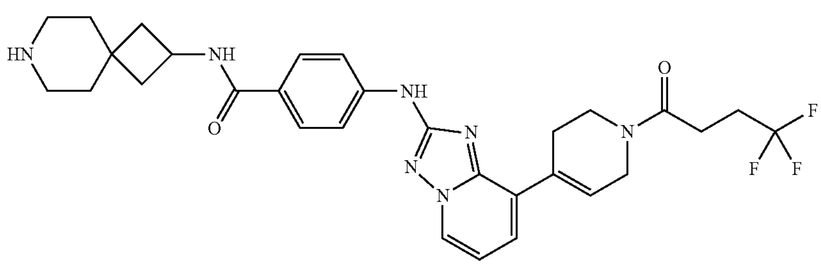 [SMILES: O=C(NC1CC2(CCNCC2)C1)c1ccc(Nc2nc3c(C4=CCN(C(=O)CCC(F)(F)F)CC4)cccn3n2)cc1] | N-(7-azaspiro[3.5]nonan-2-yl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-323 | 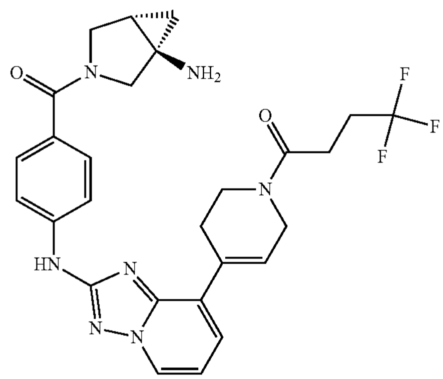 [SMILES: N[C@]12C[C@H]1CN(C(=O)c1ccc(Nc3nc4c(C5=CCN(C(=O)CCC(F)(F)F)CC5)cccn4n3)cc1)C2] | 1-[4-[2-[4-[(1S,5R)-5-amino-3-azabicyclo[3.1.0]hexne-3-carbonyl[anilino]-[1,2,4]triazolo[1,5-a]pyridin-8-yl]-3,6-dihydro-2H-pyridin-yl]-4,4,4-trifluoro-butan-1-one |
| 2-324 | 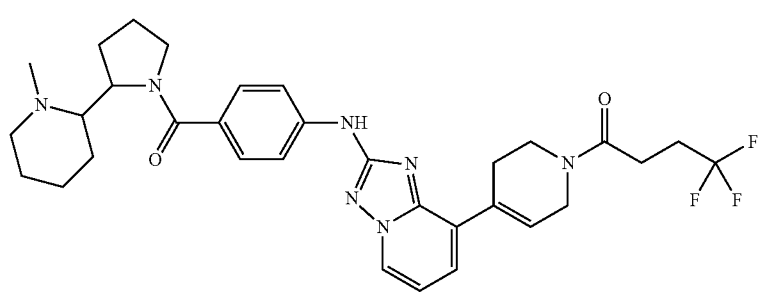 [SMILES: CN1CCCCC1C1CCCN1C(=O)c1ccc(Nc2nc3c(C4=CCN(C(=O)CCC(F)(F)F)CC4)cccn3n2)cc1] | 4,4,4-trifluoro-1-[4-[2-[4-[2-(1-methyl-2-piperidyl)pyrrolidine-1-carbonyl]anilino]-[1,2,4]triazolo[1,5-a]pyridin-8-yl]-3,6-dihydro-2H-pyridin-yl]butan-1-one |

TABLE A-continued

Exemplary Compounds of the Present Invention

| Ex. | Structure | Name |
|---|---|---|
| 2-325 | 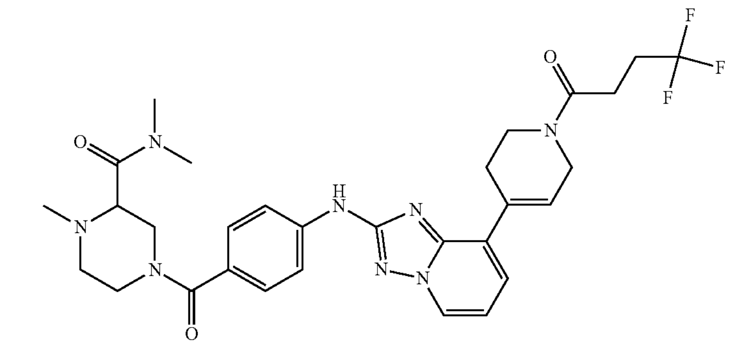 [SMILES: CN(C)C(=O)C1CN(C(=O)c2ccc(Nc3nc4c(C5=CCN(C(=O)CCC(F)(F)F)CC5)cccn4n3)cc2)CCN1C] | N,N,1-trimethyl-4-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide |
| 2-326 | 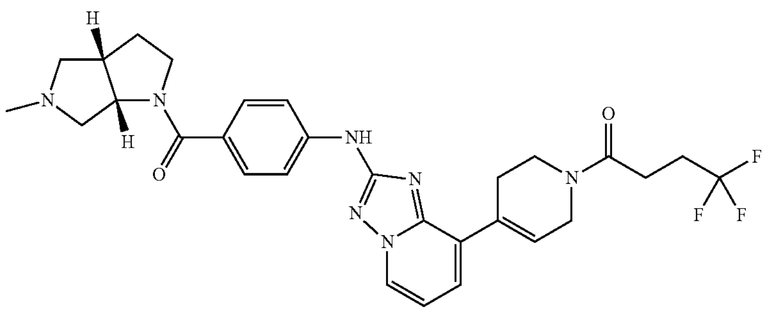 [SMILES: CN1C[C@@H]2CCN(C(=O)c3ccc(Nc4nc5c(C6=CCN(C(=O)CCC(F)(F)F)CC6)cccn5n4)cc3)[C@@H]2C1] | 1-[4-[2-[4-[(3aS,6aS)-5-methyl-2,3,3a,4,6,6a-hexahydropyrrolo[2,3-c]pyrrole-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-327 | 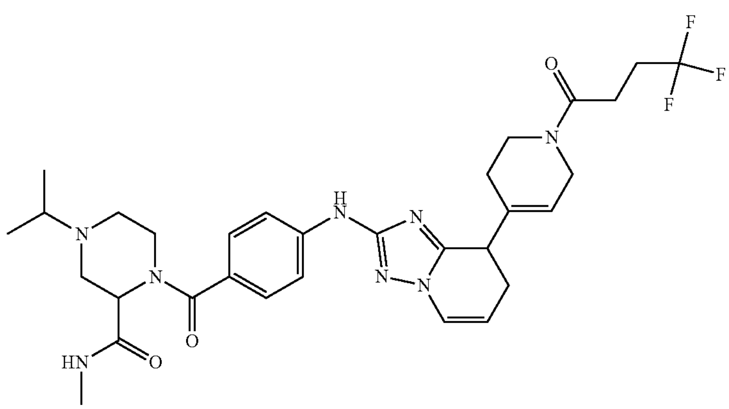 [SMILES: CNC(=O)C1CN(C(C)C)CCN1C(=O)c1ccc(Nc2nc3n(n2)C=CCC3C2=CCN(C(=O)CCC(F)(F)F)CC2)cc1] | 4-isopropyl-N-methyl-1-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide |
| 2-328 | 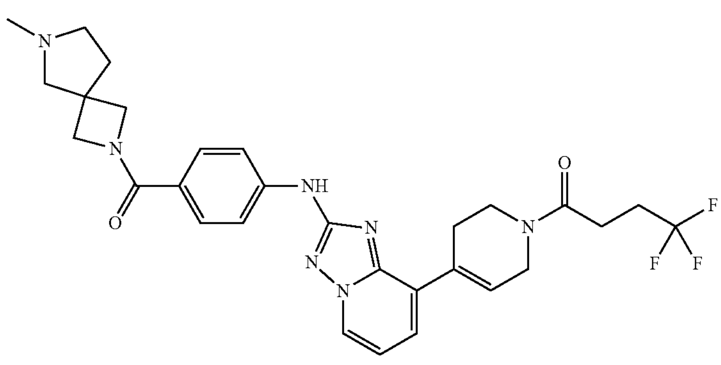 [SMILES: CN1CCC2(C1)CN(C(=O)c1ccc(Nc3nc4c(C5=CCN(C(=O)CCC(F)(F)F)CC5)cccn4n3)cc1)C2] | 4,4,4-trifluoro-1-[4-[2-[4-(7-methyl-2,7-diazaspiro[3.4]octane-2-carbonyl)anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-329 | 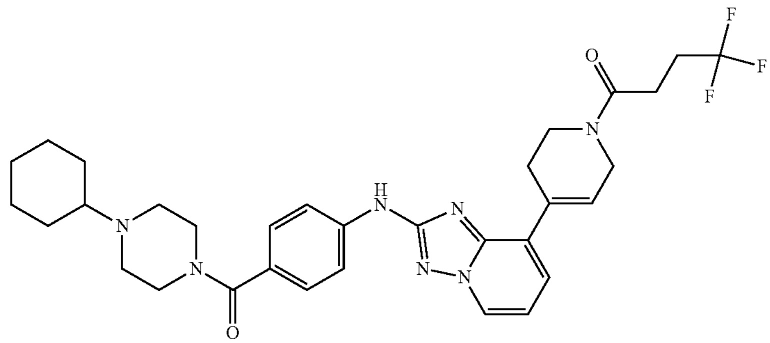 [SMILES: O=C(CCC(F)(F)F)N1CC=C(c2cccn3nc(Nc4ccc(C(=O)N5CCN(C6CCCCC6)CC5)cc4)nc23)CC1] | 1-[4-[2-[4-(4-cyclohexylpiperazine-1-carbonyl)anilino]-[1,2,4]triazolo[1,5-a]pyridin-8-yl]-3,6-dihydro-2H-pyridin-1-yl]-4,4,4-trifluoro-butan-1-one |
| 2-330 | 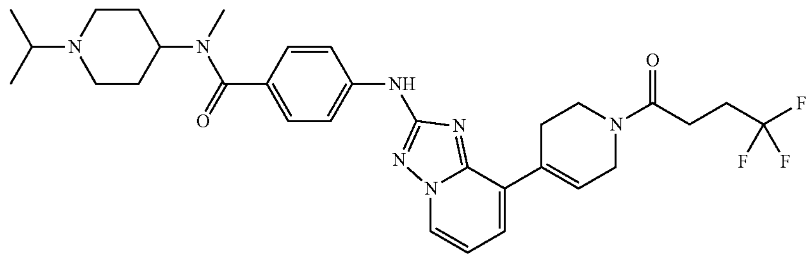 [SMILES: CC(C)N1CCC(N(C)C(=O)c2ccc(Nc3nc4c(C5=CCN(C(=O)CCC(F)(F)F)CC5)cccn4n3)cc2)CC1] | N-(1-isopropyl-4-piperidyl)-N-methyl-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-331 | 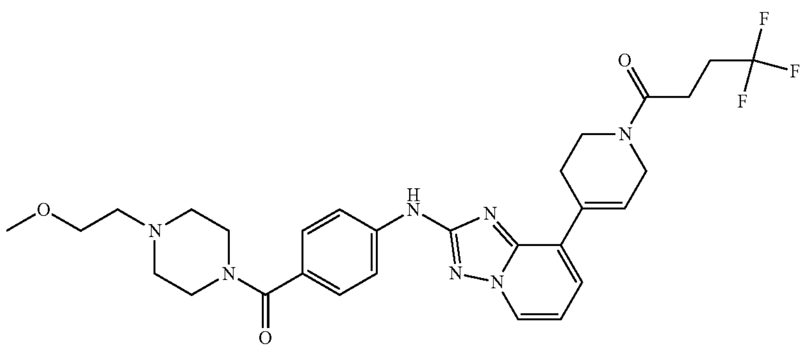 [SMILES: COCCN1CCN(C(=O)c2ccc(Nc3nc4c(C5=CCN(C(=O)CCC(F)(F)F)CC5)cccn4n3)cc2)CC1] | 4,4,4-trifluoro-1-[4-[2-[4-[4-(2-methoxyethyl)piperazine-1-carbonyl]anilino]-[1,2,4]triazolo[1,5-a]pyridin-8-yl]-3,6-dihydro-2H-pyridin-1-yl]butan-1-one |
| 2-332 | 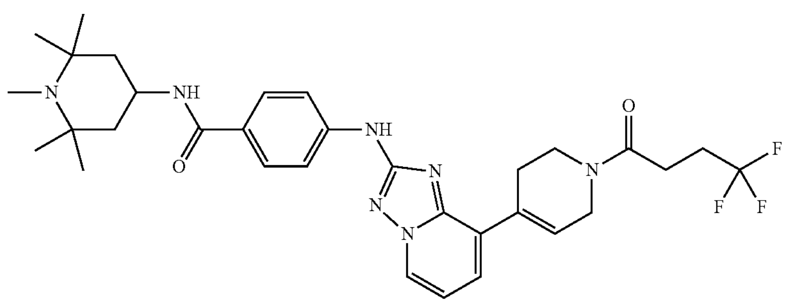 [SMILES: CN1C(C)(C)CC(NC(=O)c2ccc(Nc3nc4c(C5=CCN(C(=O)CCC(F)(F)F)CC5)cccn4n3)cc2)CC1(C)C] | N-(1,2,2,6,6-pentamethyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-333 | 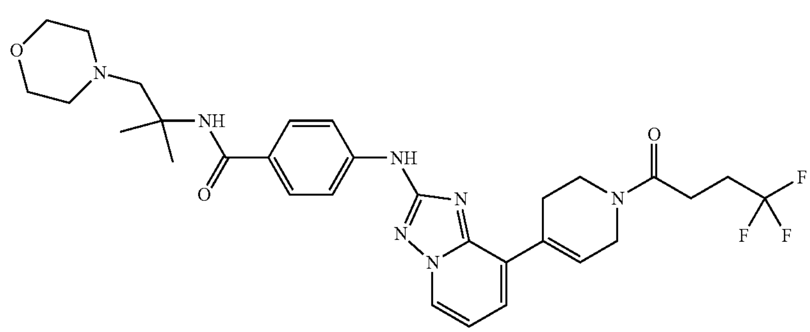 [SMILES: CC(C)(CN1CCOCC1)NC(=O)c1ccc(Nc2nc3c(C4=CCN(C(=O)CCC(F)(F)F)CC4)cccn3n2)cc1] | N-(1,1-dimethyl-2-morpholino-ethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-334 | 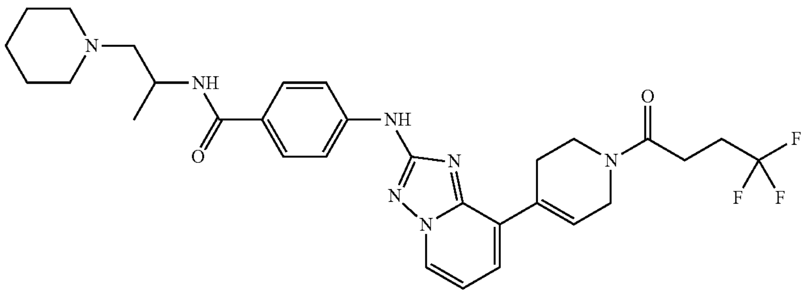 [SMILES: CC(CN1CCCCC1)NC(=O)c1ccc(Nc2nc3c(C4=CCN(C(=O)CCC(F)(F)F)CC4)cccn3n2)cc1] | N-[1-methyl-2-(1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-335 | 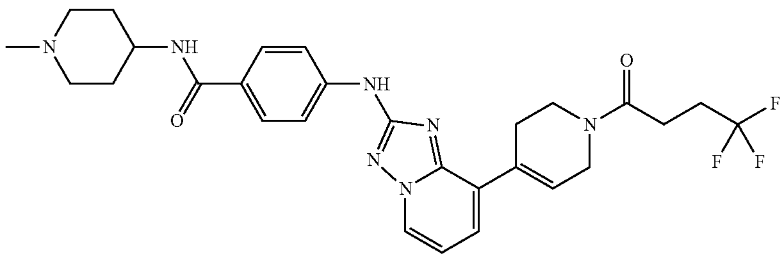 [SMILES: CN1CCC(NC(=O)c2ccc(Nc3nc4c(C5=CCN(C(=O)CCC(F)(F)F)CC5)cccn4n3)cc2)CC1] | N-(1-methyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-336 | 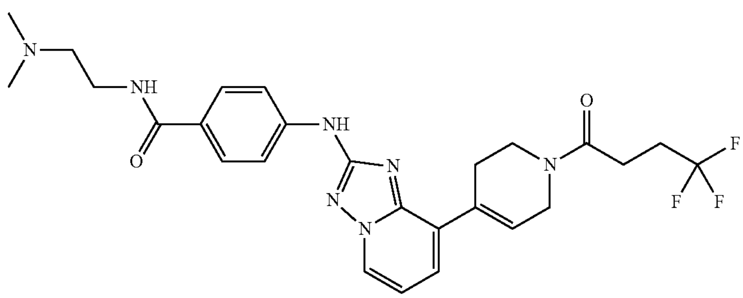 [SMILES: CN(C)CCNC(=O)c1ccc(Nc2nc3c(C4=CCN(C(=O)CCC(F)(F)F)CC4)cccn3n2)cc1] | N-[2-(dimethylamino)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-337 | 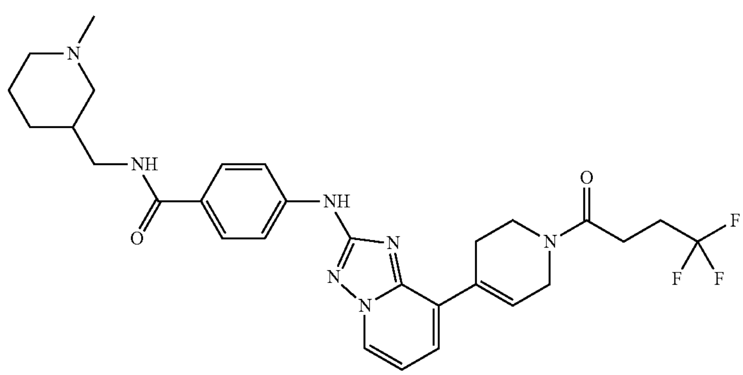 [SMILES: CN1CCCC(CNC(=O)c2ccc(Nc3nc4c(C5=CCN(C(=O)CCC(F)(F)F)CC5)cccn4n3)cc2)C1] | N-[(1-methyl-3-piperidyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-338 | 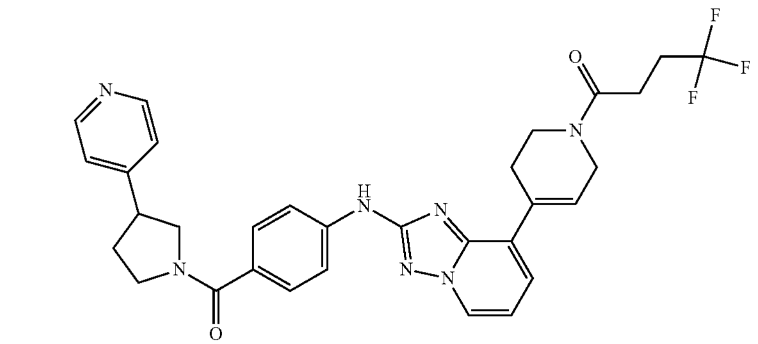 [SMILES: O=C(CCC(F)(F)F)N1CC=C(c2cccn3nc(Nc4ccc(C(=O)N5CCC(c6ccncc6)C5)cc4)nc23)CC1] | 4,4,4-trifluoro-1-[4-[2-[4-[3-(4-pyridyl)pyrrolidine-1-carbonyl]anilino]-[1,2,4]triazolo[1,5-a]pyridin-8-yl]-3,6-dihydro-2H-pyridin-1-yl]butan-1-one |
| 2-339 | 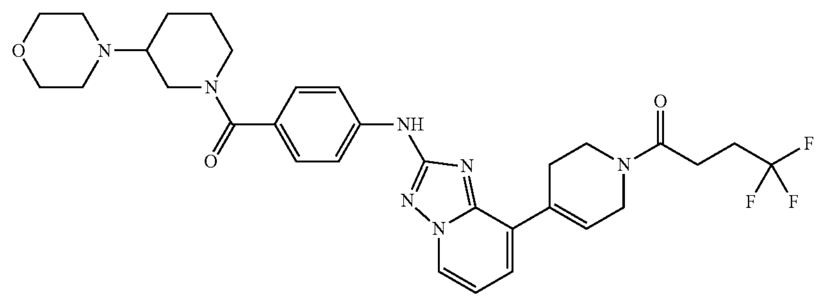 [SMILES: O=C(CCC(F)(F)F)N1CC=C(c2cccn3nc(Nc4ccc(C(=O)N5CCCC(N6CCOCC6)C5)cc4)nc23)CC1] | 4,4,4-trifluoro-1-[4-[2-[4-(3-morpholinopiperidine-1-carbonyl)anilino]-[1,2,4]triazolo[1,5-a]pyridin-8-yl]-3,6-dihydro-2H-pyridin-1-yl]butan-1-one |
| 2-340 | 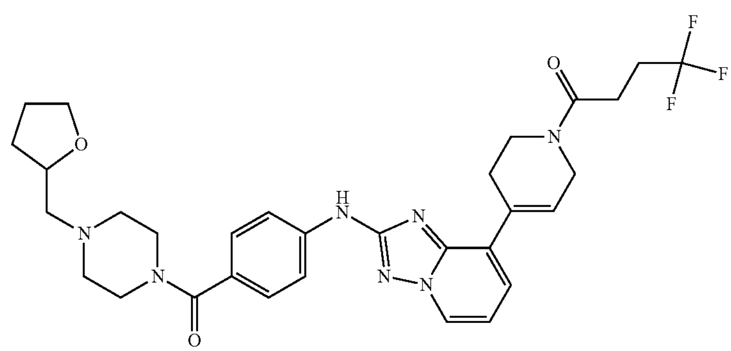 [SMILES: O=C(CCC(F)(F)F)N1CC=C(c2cccn3nc(Nc4ccc(C(=O)N5CCN(CC6CCCO6)CC5)cc4)nc23)CC1] | 4,4,4-trifluoro-1-[4-[2-[4-[4-(tetrahydrofuran-2-ylmethyl)piperazine-1-carbonyl]anilino]-[1,2,4]triazolo[1,5-a]pyridin-8-yl]-3,6-dihydro-2H-pyridin-1-yl]butan-1-one |
| 2-341 | 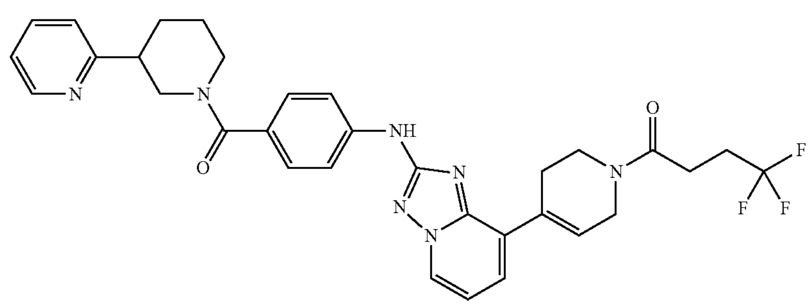 [SMILES: O=C(CCC(F)(F)F)N1CC=C(c2cccn3nc(Nc4ccc(C(=O)N5CCCC(c6ccccn6)C5)cc4)nc23)CC1] | 4,4,4-trifluoro-1-[4-[2-[4-[3-(2-pyridyl)piperidine-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-342 | 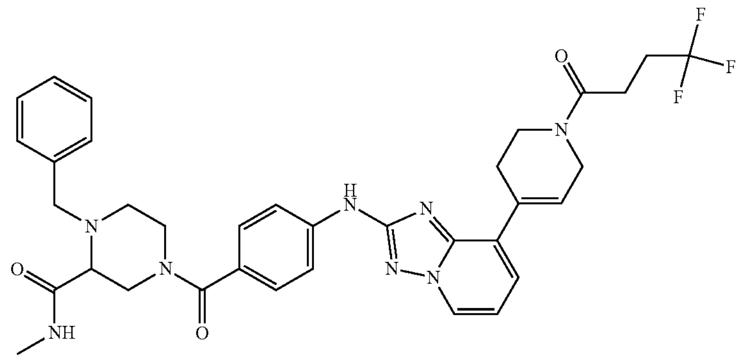 [SMILES: CNC(=O)C1CN(C(=O)c2ccc(Nc3nc4c(C5=CCN(C(=O)CCC(F)(F)F)CC5)cccn4n3)cc2)CCN1Cc1ccccc1] | 1-benzyl-N-methyl-4-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide |
| 2-343 | 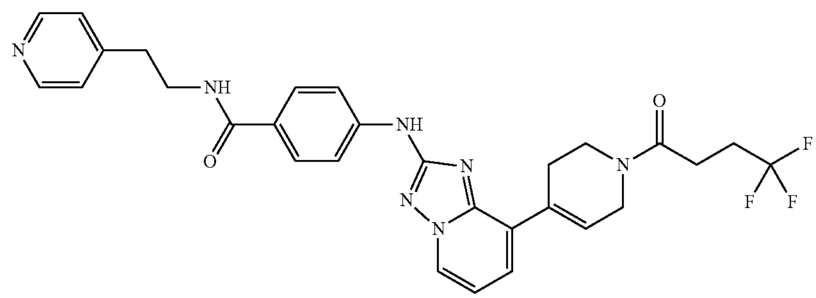 [SMILES: O=C(NCCc1ccncc1)c1ccc(Nc2nc3c(C4=CCN(C(=O)CCC(F)(F)F)CC4)cccn3n2)cc1] | N-[2-(4-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-344 | 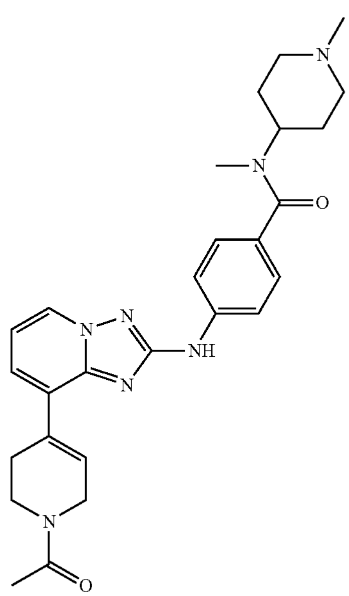 [SMILES: CC(=O)N1CC=C(c2cccn3nc(Nc4ccc(C(=O)N(C)C5CCN(C)CC5)cc4)nc23)CC1] | 4-[[8-(1-acetyl-3,6-dihydro-2H-pyridin-4-yl)-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 2-345 | 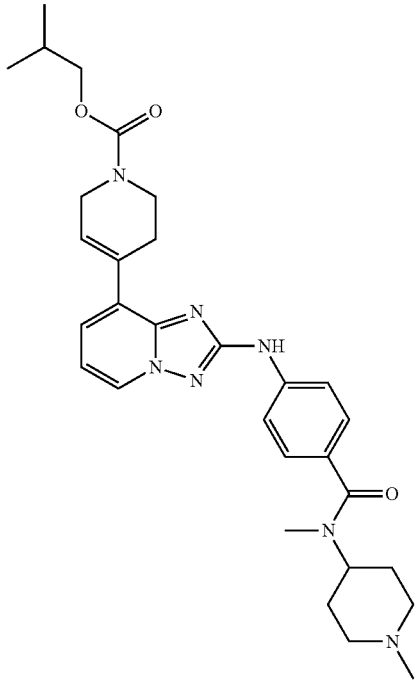 [SMILES: CC(C)COC(=O)N1CC=C(c2cccn3nc(Nc4ccc(C(=O)N(C)C5CCN(C)CC5)cc4)nc23)CC1] | isobutyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |
| 2-346 | 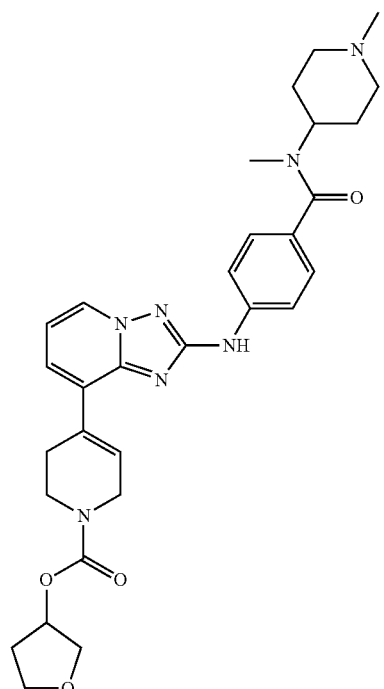 [SMILES: CN1CCC(N(C)C(=O)c2ccc(Nc3nc4c(C5=CCN(C(=O)OC6CCOC6)CC5)cccn4n3)cc2)CC1] | tetrahydrofuran-3-yl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-347 | 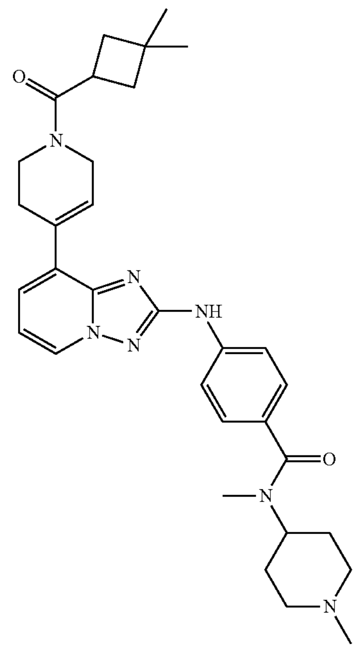 [SMILES: CN1CCC(N(C)C(=O)c2ccc(Nc3nc4c(C5=CCN(C(=O)C6CC(C)(C)C6)CC5)cccn4n3)cc2)CC1] | 4-[[8-[1-(3,3-dimethylcyclobutanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide |
| 2-348 | 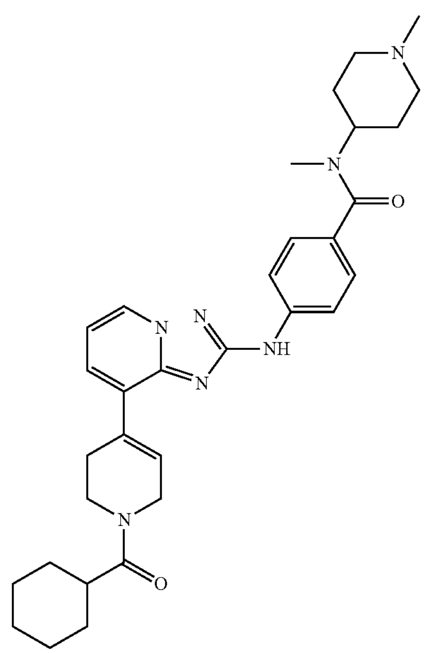 [SMILES: CN1CCC(N(C)C(=O)c2ccc(NC(=N)/N=c3\[nH]cccc3C3=CCN(C(=O)C4CCCCC4)CC3)cc2)CC1] | 4-[[8-[1-(cyclohexanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 2-349 | 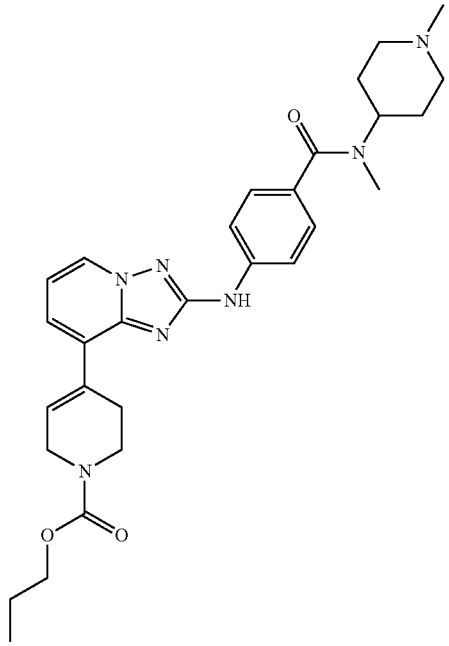 [SMILES: CCCOC(=O)N1CC=C(c2cccn3nc(Nc4ccc(C(=O)N(C)C5CCN(C)CC5)cc4)nc23)CC1] | propyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |
| 2-350 | 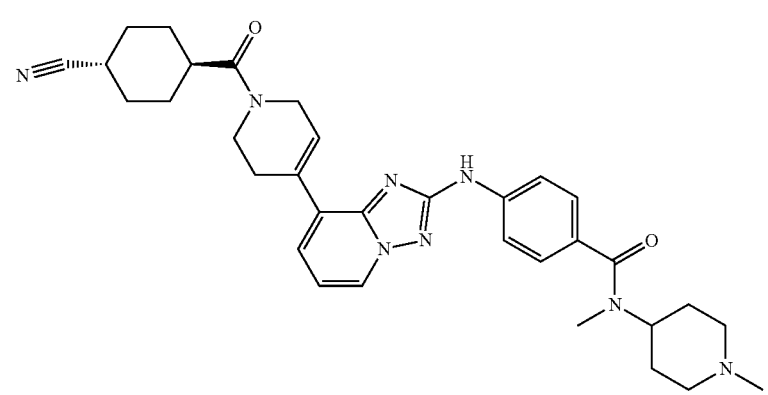 [SMILES: CN1CCC(N(C)C(=O)c2ccc(Nc3nc4c(C5=CCN(C(=O)[C@H]6CC[C@H](C#N)CC6)CC5)cccn4n3)cc2)CC1] | 4-[[8-[1-(4-cyanocyclohexanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 2-351 | 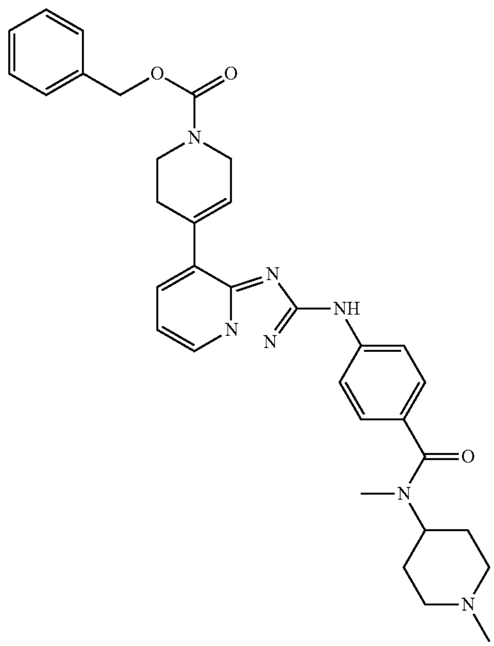 [SMILES: CN1CCC(N(C)C(=O)c2ccc(NC(=N)/N=c3\[nH]cccc3C3=CCN(C(=O)OCc4ccccc4)CC3)cc2)CC1] | benzyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |
| 2-352 | 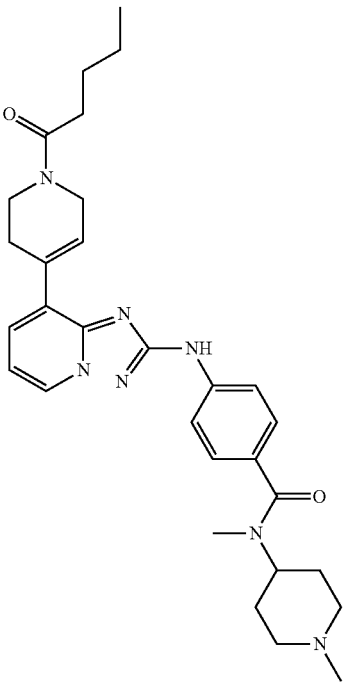 [SMILES: CCCCC(=O)N1CC=C(c2ccc[nH]/c2=N\C(=N)Nc2ccc(C(=O)N(C)C3CCN(C)CC3)cc2)CC1] | N-methyl-N-(1-methyl-4-piperidyl)-4-[[8-(1-pentanoyl-3,6-dihydro-2H-pyridin-4-yl)-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-353 | 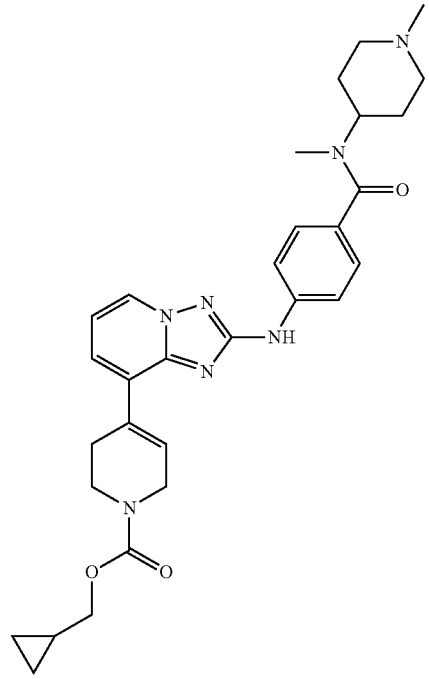 [SMILES: CN1CCC(N(C)C(=O)c2ccc(Nc3nc4c(C5=CCN(C(=O)OCC6CC6)CC5)cccn4n3)cc2)CC1] | cyclopropylmethyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate |
| 2-354 | 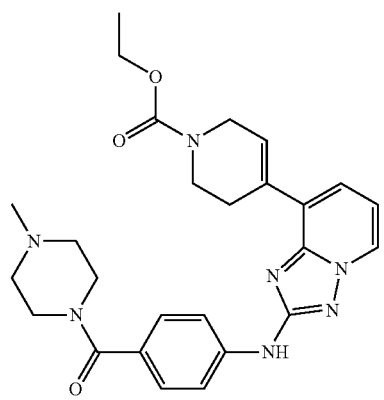 [SMILES: CCOC(=O)N1CC=C(c2cccn3nc(Nc4ccc(C(=O)N5CCN(C)CC5)cc4)nc23)CC1] | ethyl 4-[2-[4-(4-methylpiperazine-1-carbonyl)anilino]-[1,2,4]triazolo[1,5-a]pyridin-8-yl]-3,6-dihydro-2H-pyridine-1-carboxylate |
| 2-355 | 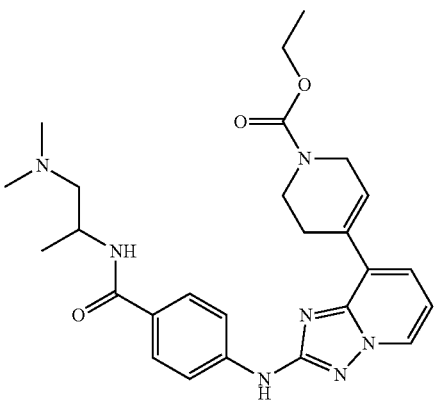 [SMILES: CCOC(=O)N1CC=C(c2cccn3nc(Nc4ccc(C(=O)NC(C)CN(C)C)cc4)nc23)CC1] | ethyl 4-[2-[4-[[2-(dimethylamino)-1-methyl-ethyl]carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-356 | 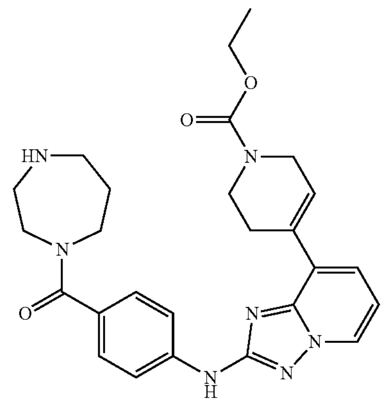 [SMILES: CCOC(=O)N1CC=C(c2cccn3nc(Nc4ccc(C(=O)N5CCCNCC5)cc4)nc23)CC1] | ethyl 4-[2-[4-(1,4-diazepane-1-carbonyl)anilino]-[1,2,4]triazolo[1,5-a]pyridin-8-yl]-3,6-dihydro-2H-pyridine-1-carboxylate |
| 2-357 | 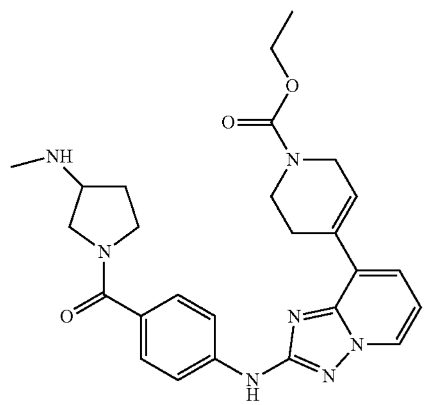 [SMILES: CCOC(=O)N1CC=C(c2cccn3nc(Nc4ccc(C(=O)N5CCC(NC)C5)cc4)nc23)CC1] | ethyl 4-[2-[4-[3-(methylamino)pyrrolidine-1-carbonyl]anilino]-[1,2,4]triazolo[1,5-a]pyridin-8-yl]-3,6-dihydro-2H-pyridine-1-carboxylate |
| 2-358 | 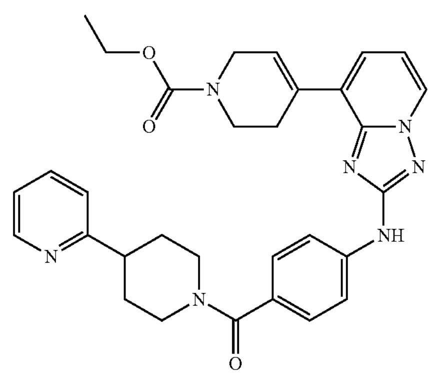 [SMILES: CCOC(=O)N1CC=C(c2cccn3nc(Nc4ccc(C(=O)N5CCC(c6ccccn6)CC5)cc4)nc23)CC1] | ethyl 4-[2-[4-[4-(2-pyridyl)piperidine-1-carbonyl]anilino]-[1,2,4]triazolo[1,5-a]pyridin-8-yl]-3,6-dihydro-2H-pyridine-1-carboxylate |
| 2-359 | 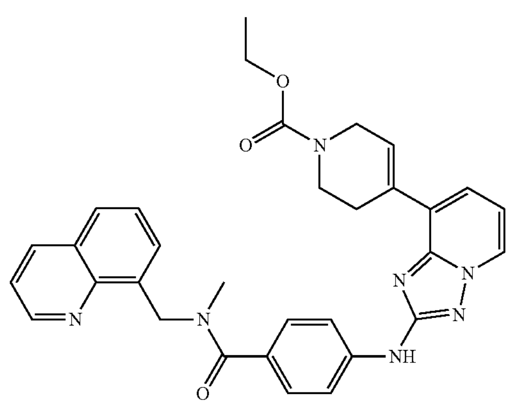 [SMILES: CCOC(=O)N1CC=C(c2cccn3nc(Nc4ccc(C(=O)N(C)Cc5cccc6cccnc56)cc4)nc23)CC1] | ethyl 4-[2-[4-[methyl(8-quinolylmethyl)carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-360 | 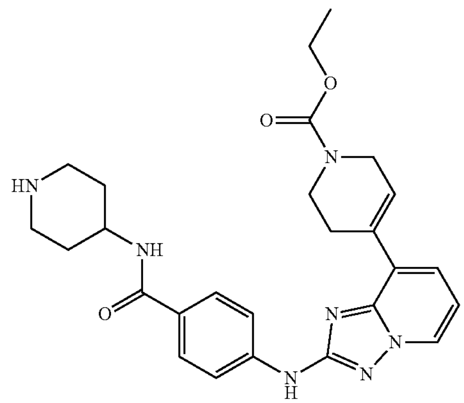 [SMILES: CCOC(=O)N1CC=C(c2cccn3nc(Nc4ccc(C(=O)NC5CCNCC5)cc4)nc23)CC1] | ethyl 4-[2-[4-(4-piperidylcarbamoyl)anilino]-[1,2,4]triazolo[1,5-a]pyridin-8-yl]-3,6-dihydro-2H-pyridine-1-carboxylate |
| 2-361 | 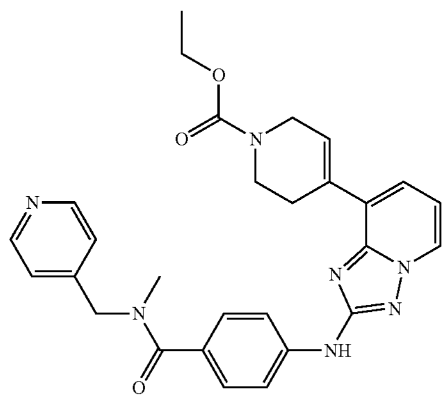 [SMILES: CCOC(=O)N1CC=C(c2cccn3nc(Nc4ccc(C(=O)N(C)Cc5ccncc5)cc4)nc23)CC1] | ethyl 4-[2-[4-[methyl(4-pyridylmethyl)carbamoyl]anilino]-[1,2,4]triazolo[1,5-a]pyridin-8-yl]-3,6-dihydro-2H-pyridine-1-carboxylate |
| 2-362 | 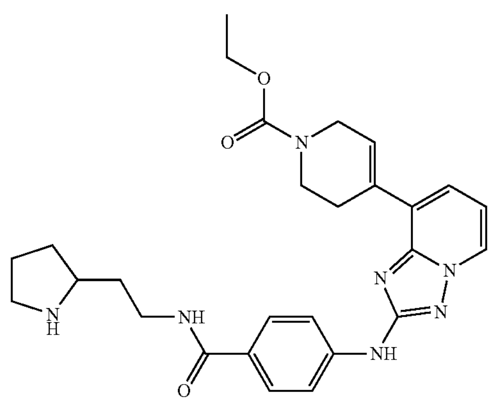 [SMILES: CCOC(=O)N1CC=C(c2cccn3nc(Nc4ccc(C(=O)NCCC5CCCN5)cc4)nc23)CC1] | ethyl 4-[2-[4-(2-pyrrolidin-2-ylethylcarbamoyl)anilino]-[1,2,4]triazolo[1,5-a]pyridin-8-yl]-3,6-dihydro-2H-pyridine-1-carboxylate |
| 2-363 | 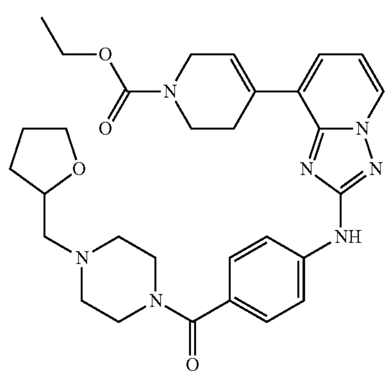 [SMILES: CCOC(=O)N1CC=C(c2cccn3nc(Nc4ccc(C(=O)N5CCN(CC6CCCO6)CC5)cc4)nc23)CC1] | ethyl 4-[2-[4-[4-(tetrahydrofuran-2-ylmethyl)piperazine-1-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-364 | 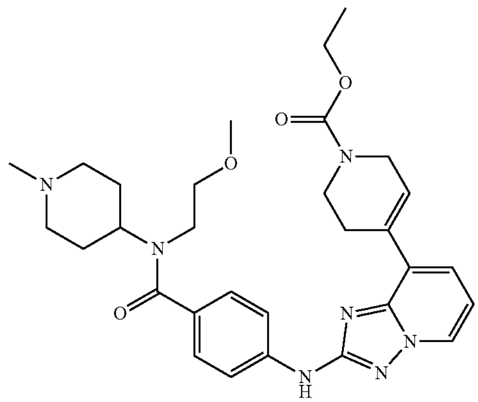 [SMILES: CCOC(=O)N1CC=C(c2cccn3nc(Nc4ccc(C(=O)N(CCOC)C5CCN(C)CC5)cc4)nc23)CC1] | ethyl 4-[2-[4-[2-methoxyethyl-(1-methyl-4-piperidyl)carbamoyl]anilino]-[1,2,4]triazolo[1,5-a]pyridin-8-yl]-3,6-dihydro-2H-pyridine-1-carboxylate |
| 2-365 | 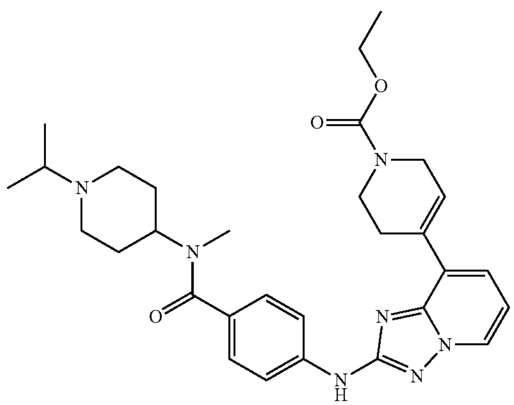 [SMILES: CCOC(=O)N1CC=C(c2cccn3nc(Nc4ccc(C(=O)N(C)C5CCN(C(C)C)CC5)cc4)nc23)CC1] | ethyl 4-[2-[4-[(1-isopropyl-4-piperidyl)-methyl-carbamoyl]anilino]-[1,2,4]triazolo[1,5-a]pyridin-8-yl]-3,6-dihydro-2H-pyridine-1-carboxylate |
| 2-366 | 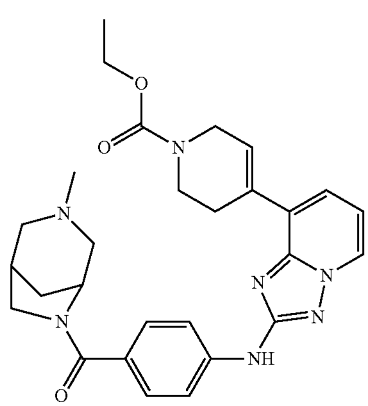 [SMILES: CCOC(=O)N1CC=C(c2cccn3nc(Nc4ccc(C(=O)N5CC6CC5CN(C)C6)cc4)nc23)CC1] | ethyl 4-[2-[4-(3-methyl-3,6-diazabicyclo[3.2.1]octane-6-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-367 | 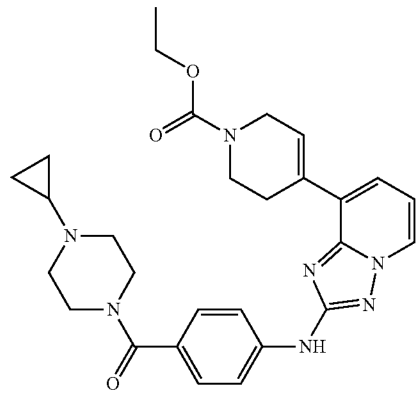 [SMILES: CCOC(=O)N1CC=C(c2cccn3nc(Nc4ccc(C(=O)N5CCN(C6CC6)CC5)cc4)nc23)CC1] | ethyl 4-[2-[4-(4-cyclopropylpiperazine-1-carbonyl)anilino]-[1,2,4]triazolo[1,5-a]pyridin-8-yl]-3,6-dihydro-2H-pyridine-1-carboxylate |
| 2-368 | 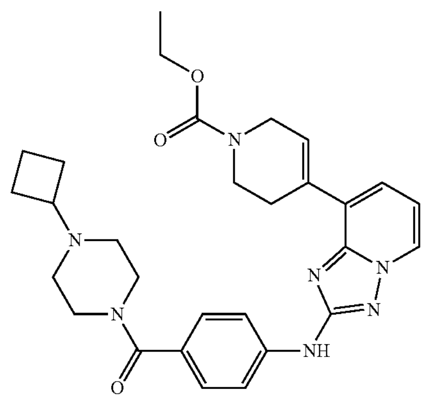 [SMILES: CCOC(=O)N1CC=C(c2cccn3nc(Nc4ccc(C(=O)N5CCN(C6CCC6)CC5)cc4)nc23)CC1] | ethyl 4-[2-[4-(4-cyclobutylpiperazine-1-carbonyl)anilino]-[1,2,4]triazolo[1,5-a]pyridin-8-yl]-3,6-dihydro-2H-pyridine-1-carboxylate |
| 2-369 | 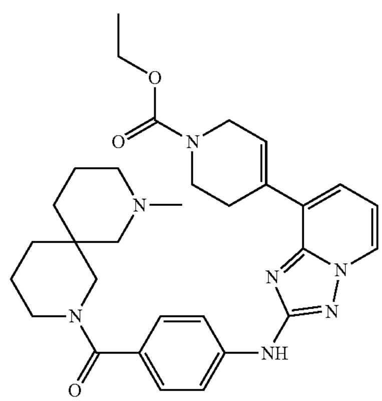 [SMILES: CCOC(=O)N1CC=C(c2cccn3nc(Nc4ccc(C(=O)N5CCCC6(CCCN(C)C6)C5)cc4)nc23)CC1] | ethyl 4-[2-[4-(8-methyl-2,8-diazaspiro[5.5]undecane-2-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-370 | 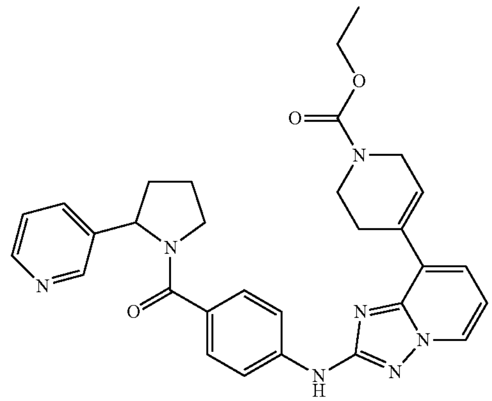 [SMILES: CCOC(=O)N1CC=C(c2cccn3nc(Nc4ccc(C(=O)N5CCCC5c5cccnc5)cc4)nc23)CC1] | ethyl 4-[2-[4-[2-(3-pyridyl)pyrrolidine-1-carbonyl]anilino]-[1,2,4]triazolo[1,5-a]pyridin-8-yl]-3,6-dihydro-2H-pyridine-1-carboxylate |
| 2-371 | 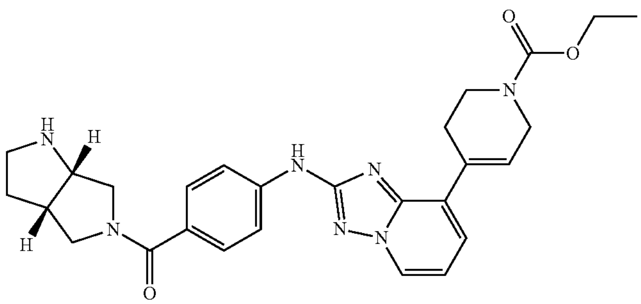 [SMILES: CCOC(=O)N1CC=C(c2cccn3nc(Nc4ccc(C(=O)N5C[C@@H]6CCN[C@@H]6C5)cc4)nc23)CC1] | ethyl 4-[2-[4-[(3aS,6aS)-2,3,3a,4,6,6a-hexahydro-1H-pyrrolo[2,3-c]pyrrole-5-carbonyl]anilino]-[1,2,4]triazolo[1,5-a]pyridin-8-yl]-3,6-dihydro-2H-pyridine-1-carboxylate |
| 2-372 | 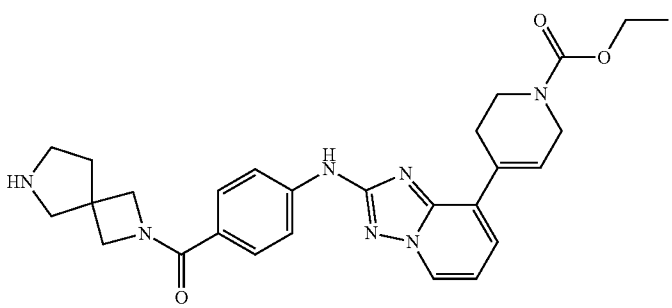 [SMILES: CCOC(=O)N1CC=C(c2cccn3nc(Nc4ccc(C(=O)N5CC6(CCNC6)C5)cc4)nc23)CC1] | ethyl 4-[2-[4-(2,7-diazaspiro[3.4]octane-2-carbonyl)anilino]-[1,2,4]triazolo[1,5-a]pyridin-8-yl]-3,6-dihydro-2H-pyridine-1-carboxylate |
| 2-373 | 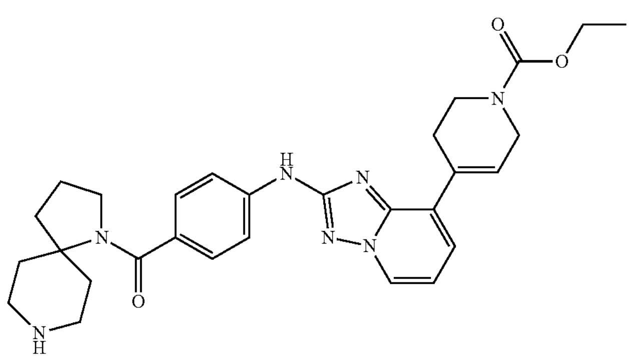 [SMILES: CCOC(=O)N1CC=C(c2cccn3nc(Nc4ccc(C(=O)N5CCCC56CCNCC6)cc4)nc23)CC1] | ethyl 4-[2-[4-(1,8-diazaspiro[4.5]decane-1-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-374 | 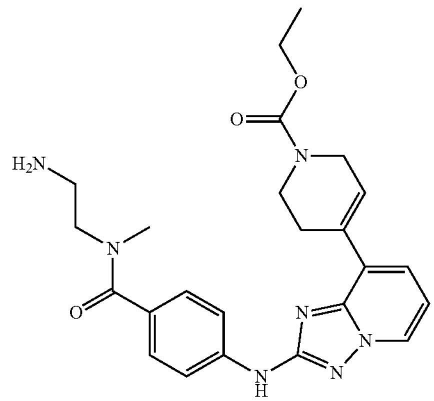 [SMILES: CCOC(=O)N1CC=C(c2cccn3nc(Nc4ccc(C(=O)N(C)CCN)cc4)nc23)CC1] | ethyl 4-[2-[4-[2-aminoethyl(methyl)carbamoyl]anilino]-[1,2,4]triazolo[1,5-a]pyridin-8-yl]-3,6-dihydro-2H-pyridine-1-carboxylate |
| 2-375 | 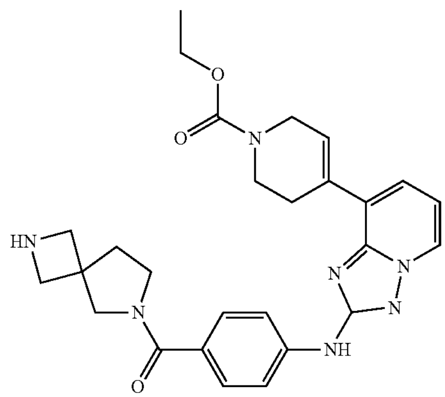 [SMILES: CCOC(=O)N1CC=C(C2=CC=CN3NC(Nc4ccc(C(=O)N5CCC6(CNC6)C5)cc4)N=C23)CC1] | ethyl 4-[2-[4-(2,6-diazaspiro[3.4]octane-6-carbonyl)anilino]-[1,2,4]triazolo[1,5-a]pyridin-8-yl]-3,6-dihydro-2H-pyridine-1-carboxylate |
| 2-376 | 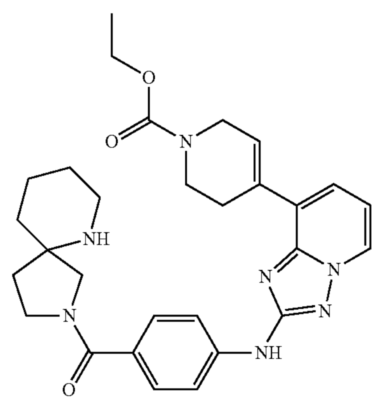 [SMILES: CCOC(=O)N1CC=C(c2cccn3nc(Nc4ccc(C(=O)N5CCC6(CCCCN6)C5)cc4)nc23)CC1] | ethyl 4-[2-[4-(2,6-diazaspiro[4.5]decane-2-carbonyl)anilino]-[1,2,4]triazolo[1,5-a]pyridin-8-yl]-3,6-dihydro-2H-pyridine-1-carboxylate |
| 2-377 | 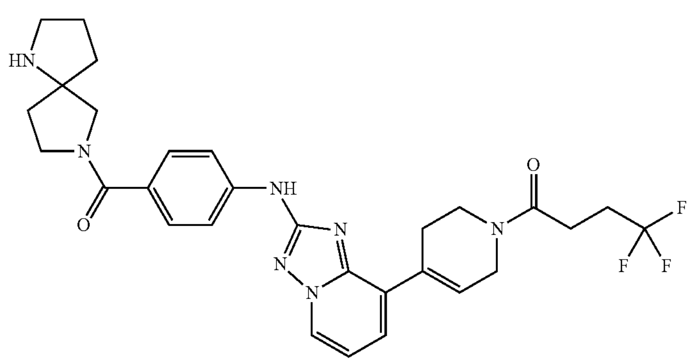 [SMILES: O=C(CCC(F)(F)F)N1CC=C(c2cccn3nc(Nc4ccc(C(=O)N5CCC6(CCCN6)C5)cc4)nc23)CC1] | 1-[4-[2-[4-(1,7-diazaspiro[4.4]nonane-7-carbonyl)anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-378 | 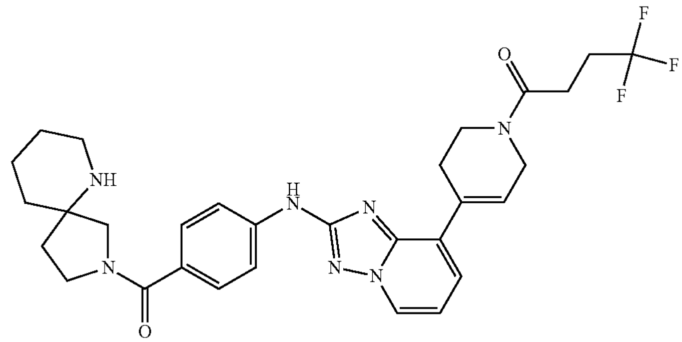 [SMILES: O=C(CCC(F)(F)F)N1CC=C(c2cccn3nc(Nc4ccc(C(=O)N5CCC6(CCCCN6)C5)cc4)nc23)CC1] | 1-[4-[2-[4-(2,6-diazaspiro[4.5]decane-2-carbonyl)anilino]-[1,2,4]triazolo[1,5-a]pyridin-8-yl]-3,6-dihydro-2H-pyridin-1-yl]-4,4,4-trifluoro-butan-1-one |
| 2-379 | 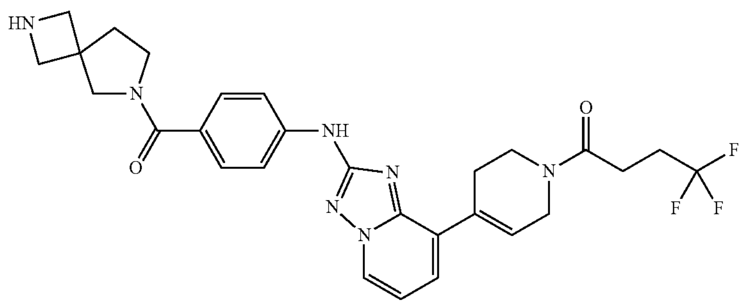 [SMILES: O=C(CCC(F)(F)F)N1CC=C(c2cccn3nc(Nc4ccc(C(=O)N5CCC6(CNC6)C5)cc4)nc23)CC1] | 1-[4-[2-[4-(2,6-diazaspiro[3,4]octane-6-carbonyl)anilino]-[1,2,4]triazolo[1,5-a]pyridin-8-yl]-3,6-dihydro-2H-pyridin-1-yl]-4,4,4-trifluoro-butan-1-one |
| 2-380 | 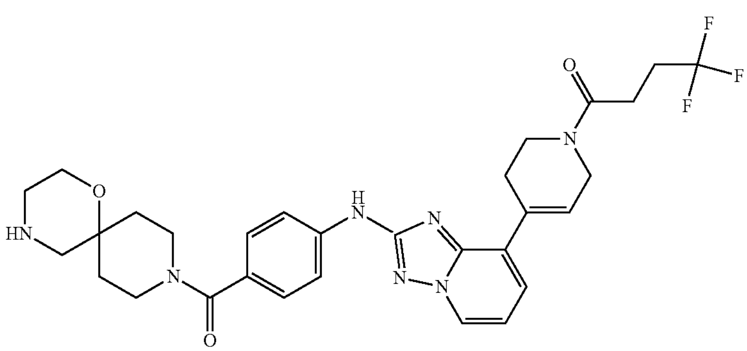 | 4,4,4-trifluoro-1-[4-[2-[4-(1-oxa-4,9-diazaspiro[5.5]undecane-9-carbonyl)anilino]-[1,2,4]triazolo[1,5-a]pyridin-8-yl]-3,6-dihydro-2H-pyridin-1-yl]butan-1-one |
| 2-381 | 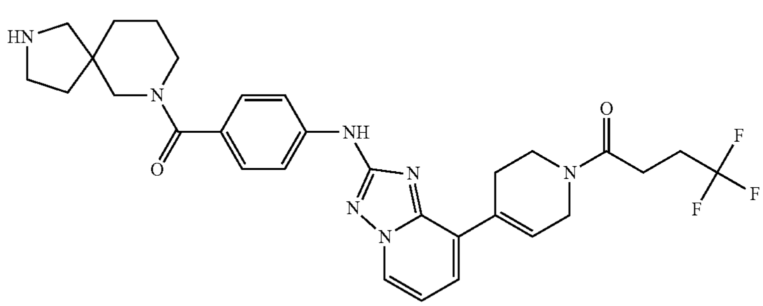 [SMILES: O=C(CCC(F)(F)F)N1CC=C(c2cccn3nc(Nc4ccc(C(=O)N5CCCC6(CCNC6)C5)cc4)nc23)CC1] | 1-[4-[2-[4-(2,7-diazaspiro[4.5]decane-7-carbonyl)anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-382 | 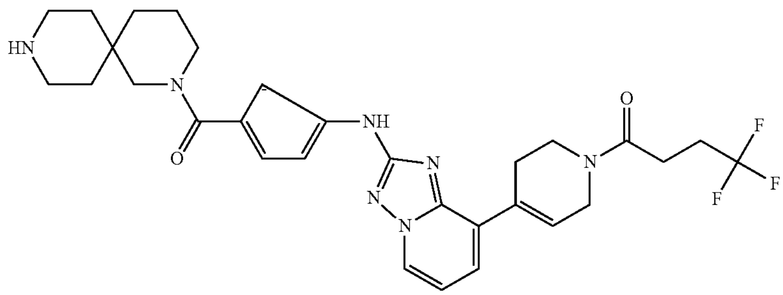 | 1-[4-[2-[4-(2,9-diazaspiro[5.5]undecane-2-carbonyl)anilino]-[1,2,4]triazolo[1,5-a]pyridin-8-yl]-3,6-dihydro-2H-pyridin-1-yl]-4,4,4-trifluoro-butan-1-one |
| 2-383 | 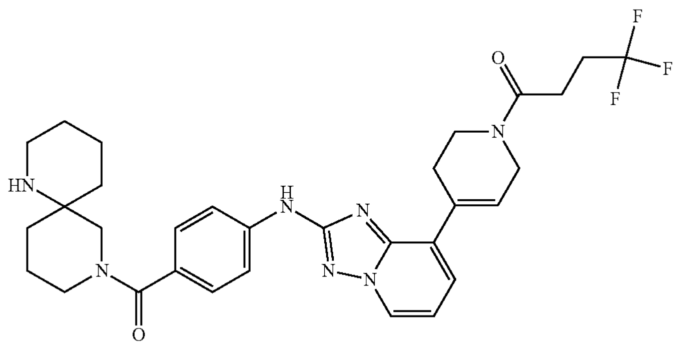 [SMILES: O=C(CCC(F)(F)F)N1CC=C(c2cccn3nc(Nc4ccc(C(=O)N5CCCC6(CCCCN6)C5)cc4)nc23)CC1] | 1-[4-[2-[4-(1,8-diazaspiro[5.5]undecane-8-carbonyl)anilino]-[1,2,4]triazolo[1,5-a]pyridin-8-yl]-3,6-dihydro-2H-pyridin-1-yl]-4,4,4-trifluoro-butan-1-one |
| 2-384 | 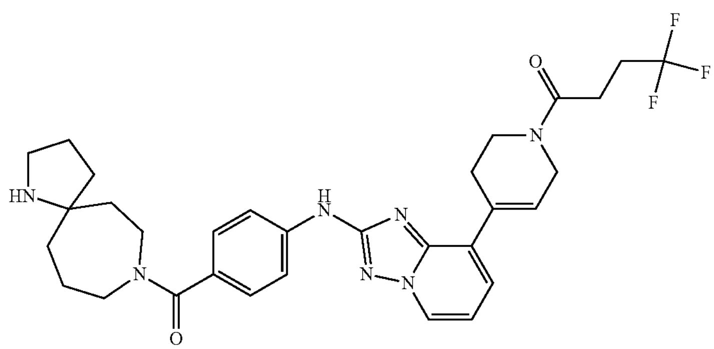 [SMILES: O=C(CCC(F)(F)F)N1CC=C(c2cccn3nc(Nc4ccc(C(=O)N5CCCC6(CCCN6)CC5)cc4)nc23)CC1] | 1-[4-[2-[4-(1,9-diazaspiro[4.6]undecane-9-carbonyl)anilino]-[1,2,4]triazolo[1,5-a]pyridin-8-yl]-3,6-dihydro-2H-pyridin-1-yl]-4,4,4-trifluoro-butan-1-one |
| 2-385 | 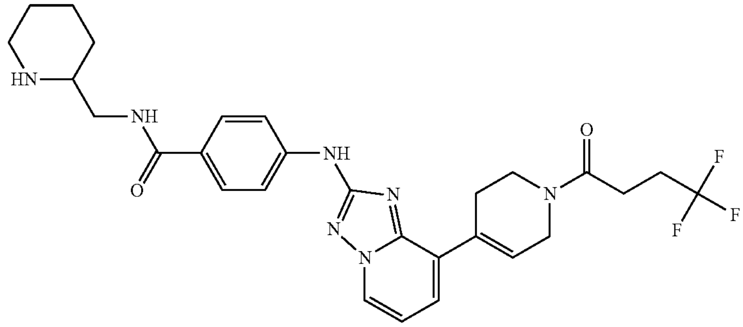 [SMILES: O=C(NCC1CCCCN1)c1ccc(Nc2nc3c(C4=CCN(C(=O)CCC(F)(F)F)CC4)cccn3n2)cc1] | N-(2-piperidylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-386 | 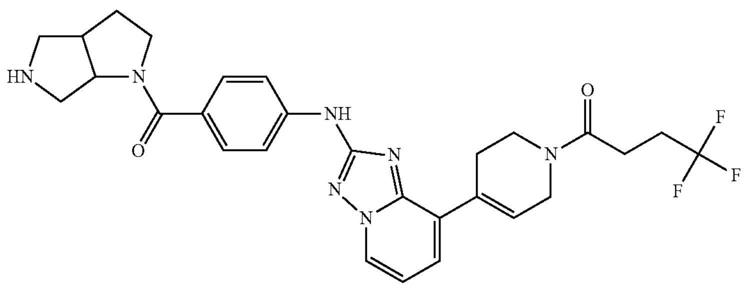 [SMILES: O=C(CCC(F)(F)F)N1CC=C(c2cccn3nc(Nc4ccc(C(=O)N5CCC6CNCC65)cc4)nc23)CC1] | 1-[4-[2-[4-(3,3a,4,5,6,6a-hexahydro-2H-pyrrolo[2,3-c]pyrrole-1-carbonyl)anilino]-[1,2,4]triazolo[1,5-a]pyridin-8-yl]-3,6-dihydro-2H-pyridin-1-yl]-4,4,4-trifluoro-butan-1-one |
| 2-387 | 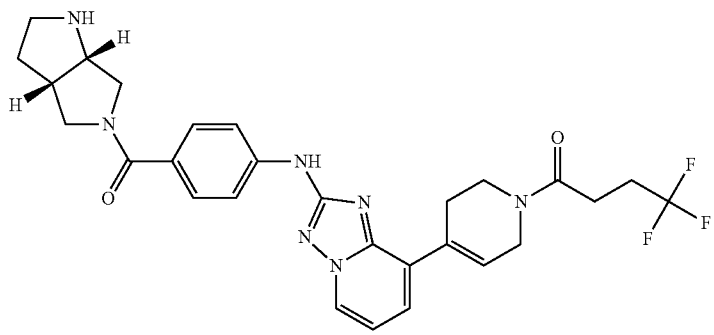 [SMILES: O=C(CCC(F)(F)F)N1CC=C(c2cccn3nc(Nc4ccc(C(=O)N5C[C@@H]6CCN[C@@H]6C5)cc4)nc23)CC1] | 1-[4-[2-[4-[(3aS,6aS)-2,3,3a,4,6,6a-hexahydro-1H-pyrrolo[2,3-c]pyrrole-5-carbonyl]anilino]-[1,2,4]triazolo[1,5-a]pyridin-8-yl]-3,6-dihydro-2H-pyridin-1-yl]-4,4,4-trifluoro-butan-1-one |
| 2-388 | 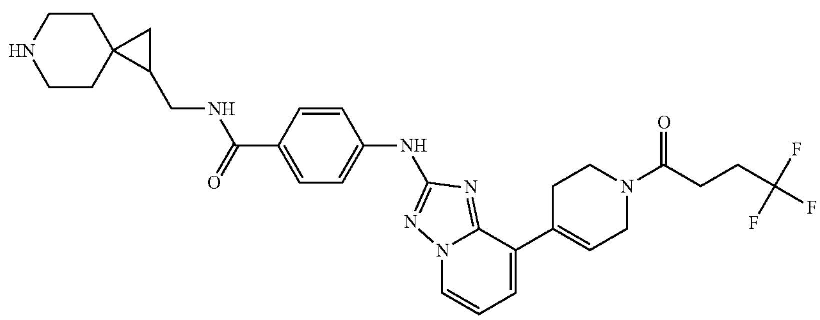 [SMILES: O=C(NCC1CC12CCNCC2)c1ccc(Nc2nc3c(C4=CCN(C(=O)CCC(F)(F)F)CC4)cccn3n2)cc1] | N-(6-azaspiro[2.5]octan-2-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-389 | 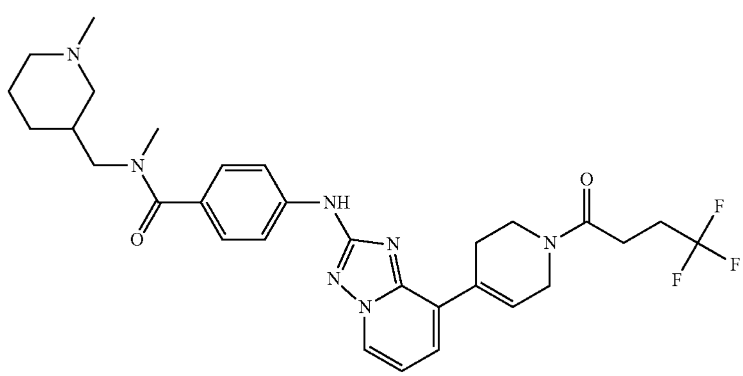 [SMILES: CN1CCCC(CN(C)C(=O)c2ccc(Nc3nc4c(C5=CCN(C(=O)CCC(F)(F)F)CC5)cccn4n3)cc2)C1] | N-methyl-N-[(1-methyl-3-piperidyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-390 | 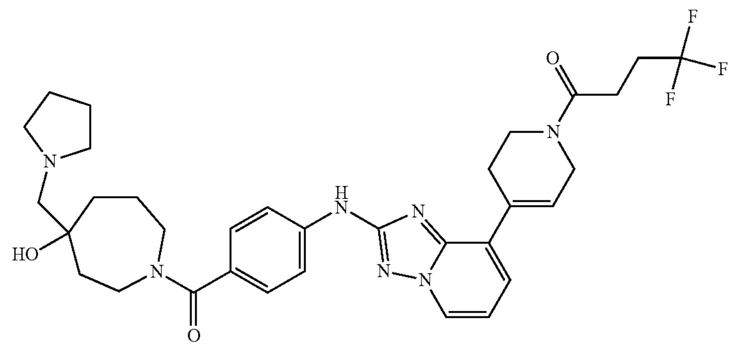 [SMILES: O=C(CCC(F)(F)F)N1CC=C(c2cccn3nc(Nc4ccc(C(=O)N5CCCC(O)(CN6CCCC6)CC5)cc4)nc23)CC1] | 4,4,4-trifluoro-1-[4-[2-[4-[4-hydroxy-4-(pyrrolidin-1-ylmethyl)azepane-1-carbonyl]anilino]-[1,2,4]triazolo[1,5-a]pyridin-8-yl]-3,6-dihydro-2H-pyridin-1-yl]butan-1-one |
| 2-391 | 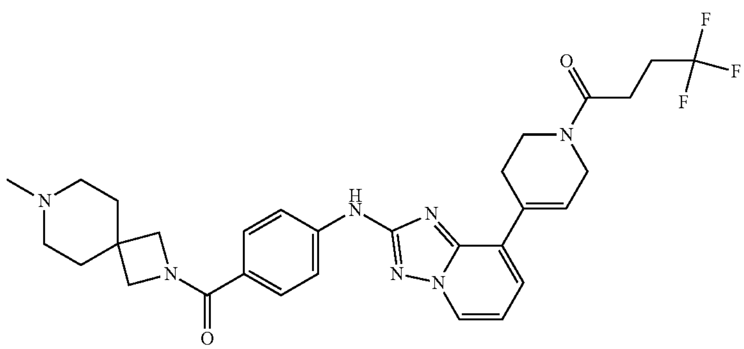 [SMILES: CN1CCC2(CC1)CN(C(=O)c1ccc(Nc3nc4c(C5=CCN(C(=O)CCC(F)(F)F)CC5)cccn4n3)cc1)C2] | 4,4,4-trifluoro-1-[4-[2-[4-(7-methyl-2,7-diazaspiro[3.5]nonane-2-carbonyl)anilino]-[1,2,4]triazolo[1,5-a]pyridin-8-yl]-3,6-dihydro-2H-pyridin-1-yl]butan-1-one |
| 2-392 | 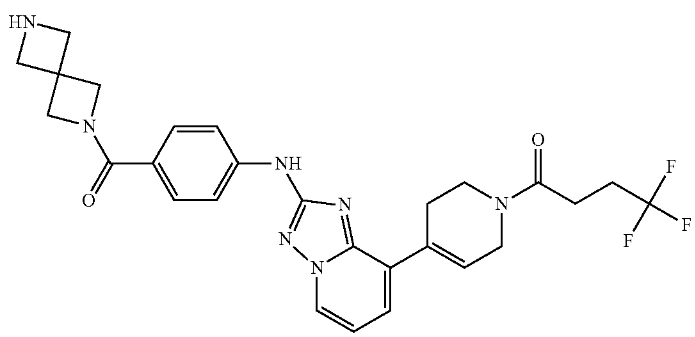 [SMILES: O=C(CCC(F)(F)F)N1CC=C(c2cccn3nc(Nc4ccc(C(=O)N5CC6(CNC6)C5)cc4)nc23)CC1] | 1-[4-[2-[4-(2,6-diazaspiro[3.3]heptane-2-carbonyl)anilino]-[1,2,4]triazolo[1,5-a]pyridin-8-yl]-3,6-dihydro-2H-pyridin-1-yl]-4,4,4-trifluoro-butan-1-one |
| 2-393 | 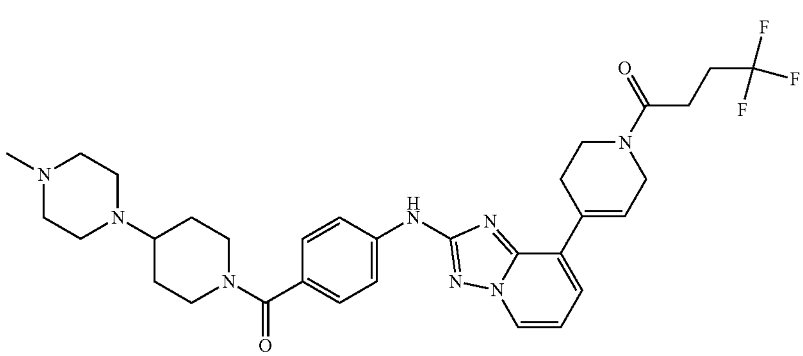 [SMILES: CN1CCN(C2CCN(C(=O)c3ccc(Nc4nc5c(C6=CCN(C(=O)CCC(F)(F)F)CC6)cccn5n4)cc3)CC2)CC1] | 4,4,4-trifluoro-1-[4-[2-[4-[4-(4-methylpiperazin-1-yl)piperidine-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
| --- | --- | --- |
| 2-394 | 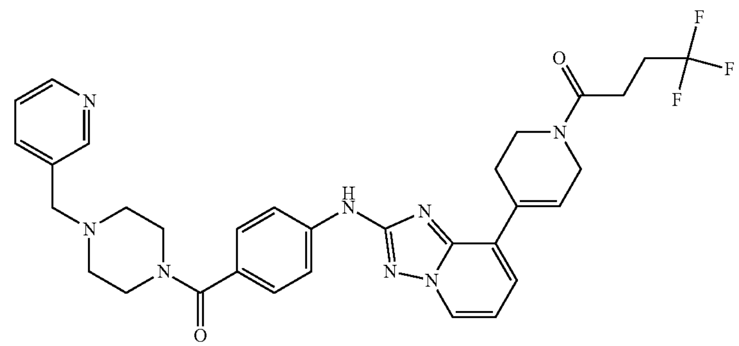 | 4,4,4-trifluoro-1-[4-[2-[4-[4-(3-pyridylmethyl)piperazine-1-carbonyl]anilino]-[1,2,4]triazolo[1,5-a]pyridin-8-yl]-3,6-dihydro-2H-pyridin-1-yl]butan-1-one |
| 2-395 | 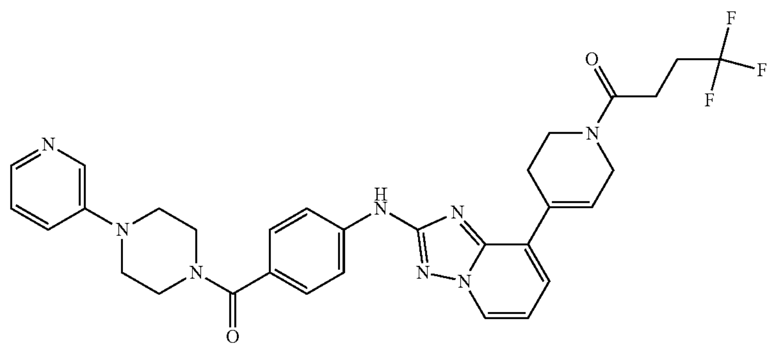 [SMILES: O=C(CCC(F)(F)F)N1CC=C(c2cccn3nc(Nc4ccc(C(=O)N5CCN(c6cccnc6)CC5)cc4)nc23)CC1] | 4,4,4-trifluoro-1-[4-[2-[4-[4-(3-pyridyl)piperazine-1-carbonyl]anilino]-[1,2,4]triazolo[1,5-a]pyridin-8-yl]-3,6-dihydro-2H-pyridin-1-yl]butan-1-one |
| 2-396 | 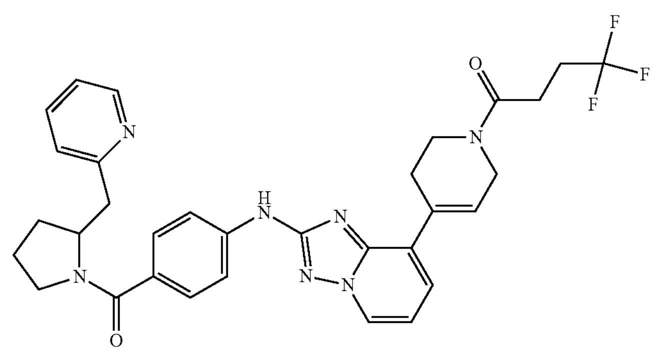 [SMILES: O=C(CCC(F)(F)F)N1CC=C(c2cccn3nc(Nc4ccc(C(=O)N5CCCC5Cc5ccccn5)cc4)nc23)CC1] | 4,4,4-trifluoro-1-[4-[2-[4-[2-(2-pyridylmethyl)pyrrolidine-1-carbonyl]anilino]-[1,2,4]triazolo[1,5-a]pyridin-8-yl]-3,6-dihydro-2H-pyridin-1-yl]butan-1-one |
| 2-397 | 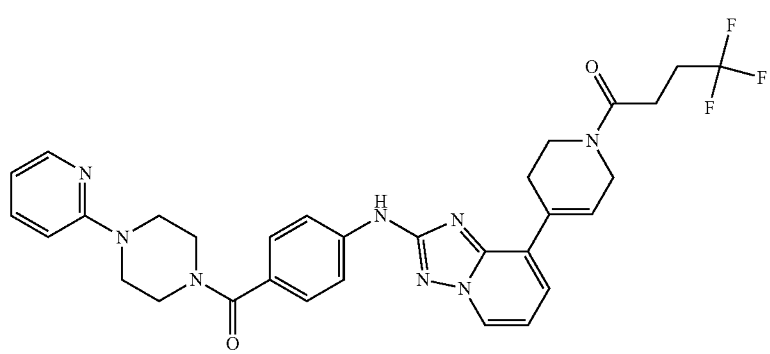 [SMILES: O=C(CCC(F)(F)F)N1CC=C(c2cccn3nc(Nc4ccc(C(=O)N5CCN(c6ccccn6)CC5)cc4)nc23)CC1] | 4,4,4-trifluoro-1-[4-[2-[4-[4-(2-pyridyl)piperazine-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-398 | 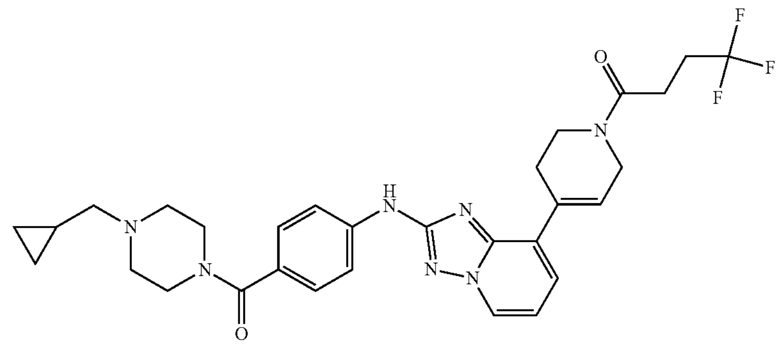 [SMILES: O=C(CCC(F)(F)F)N1CC=C(c2cccn3nc(Nc4ccc(C(=O)N5CCN(CC6CC6)CC5)cc4)nc23)CC1] | 1-[4-[2-[4-[4-(cyclopropylmethyl)piperazine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-399 | 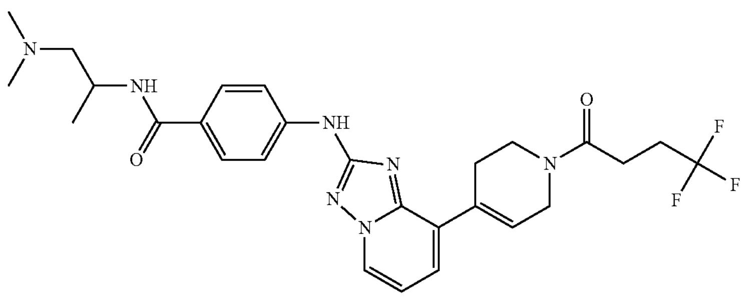 [SMILES: CC(CN(C)C)NC(=O)c1ccc(Nc2nc3c(C4=CCN(C(=O)CCC(F)(F)F)CC4)cccn3n2)cc1] | N-[2-(dimethylamino)-1-methyl-ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-400 | 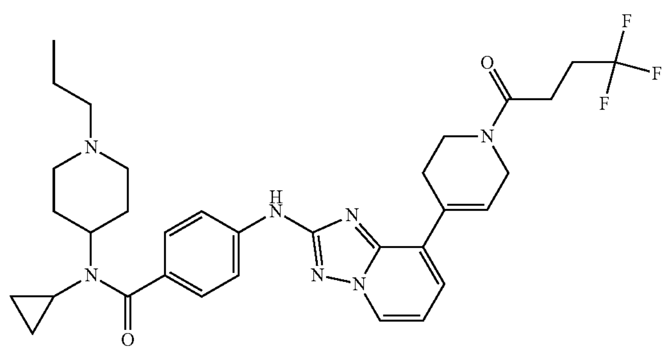 [SMILES: CCCN1CCC(N(C(=O)c2ccc(Nc3nc4c(C5=CCN(C(=O)CCC(F)(F)F)CC5)cccn4n3)cc2)C2CC2)CC1] | N-cyclopropyl-N-(1-propyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-401 | 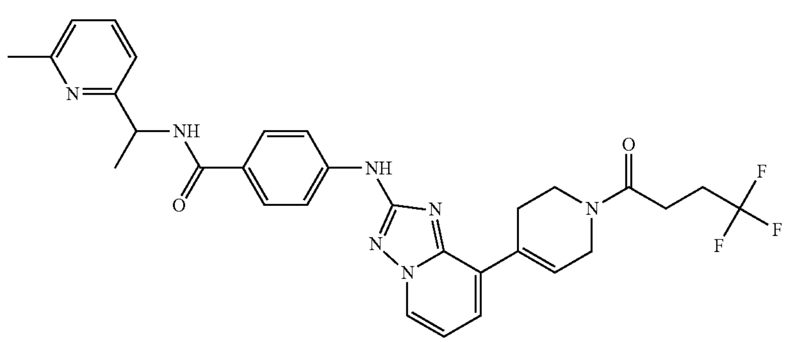 [SMILES: Cc1cccc(C(C)NC(=O)c2ccc(Nc3nc4c(C5=CCN(C(=O)CCC(F)(F)F)CC5)cccn4n3)cc2)n1] | N-[1-(6-methyl-2-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-402 | 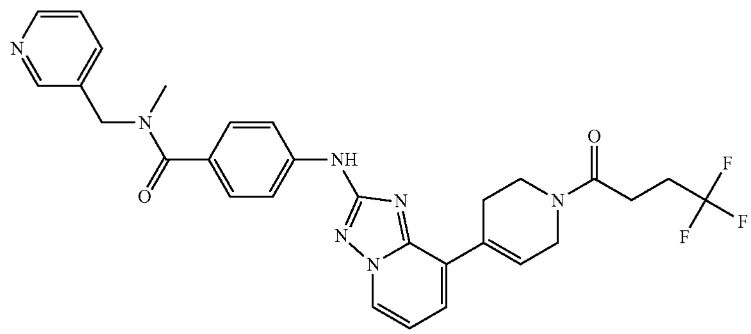 [SMILES: CN(Cc1cccnc1)C(=O)c1ccc(Nc2nc3c(C4=CCN(C(=O)CCC(F)(F)F)CC4)cccn3n2)cc1] | N-methyl-N-(3-pyridylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-403 | 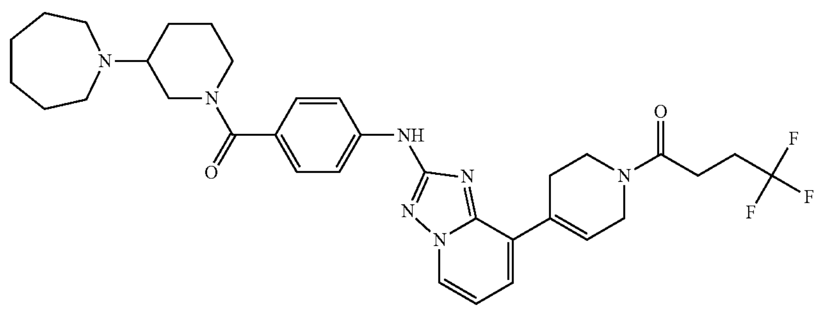 [SMILES: O=C(CCC(F)(F)F)N1CC=C(c2cccn3nc(Nc4ccc(C(=O)N5CCCC(N6CCCCCC6)C5)cc4)nc23)CC1] | 1-[4-[2-[4-[3-(azepan-1-yl)piperidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-404 | 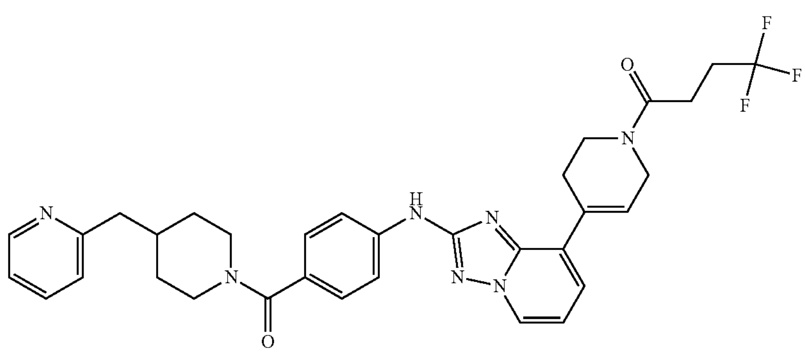 [SMILES: O=C(CCC(F)(F)F)N1CC=C(c2cccn3nc(Nc4ccc(C(=O)N5CCC(Cc6ccccn6)CC5)cc4)nc23)CC1] | 4,4,4-trifluoro-1-[4-[2-[4-[4-(2-pyridylmethyl)piperidine-1-carbonyl]anilino]-[1,2,4]triazolo[1,5-a]pyridin-8-yl]-3,6-dihydro-2H-pyridin-1-yl]butan-1-one |
| 2-405 | 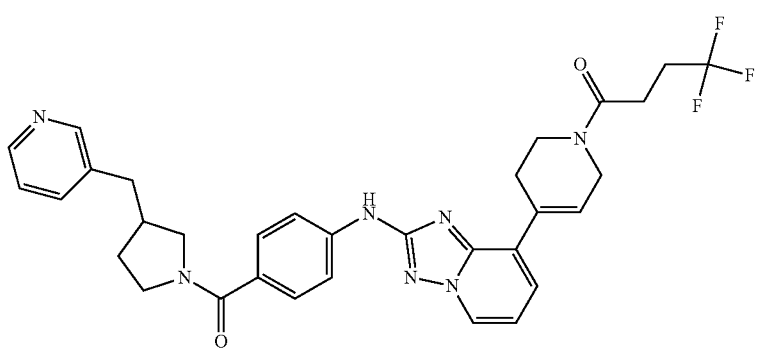 [SMILES: O=C(CCC(F)(F)F)N1CC=C(c2cccn3nc(Nc4ccc(C(=O)N5CCC(Cc6cccnc6)C5)cc4)nc23)CC1] | 4,4,4-trifluoro-1-[4-[2-[4-[3-(3-pyridylmethyl)pyrrolidine-1-carbonyl]anilino]-[1,2,4]triazolo[1,5-a]pyridin-8-yl]-3,6-dihydro-2H-pyridin-1-yl]butan-one |

TABLE A-continued

Exemplary Compounds of the Present Invention

| Ex. | Structure | Name |
|---|---|---|
| 2-406 | 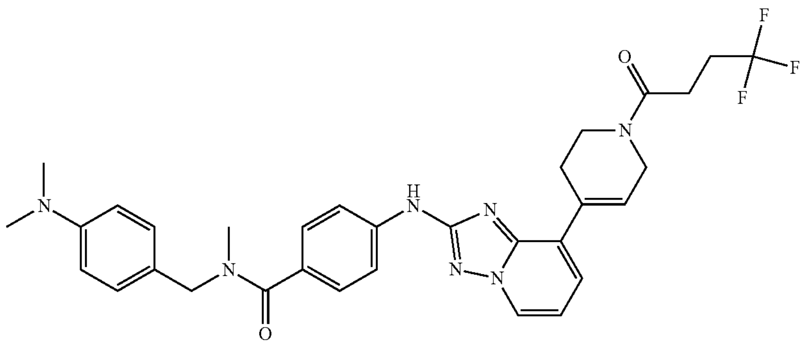 [SMILES: CN(Cc1ccc(N(C)C)cc1)C(=O)c1ccc(Nc2nc3c(C4=CCN(C(=O)CCC(F)(F)F)CC4)cccn3n2)cc1] | N-[[4-(dimethylamino)phenyl]-methyl]-N-methyl-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-407 | 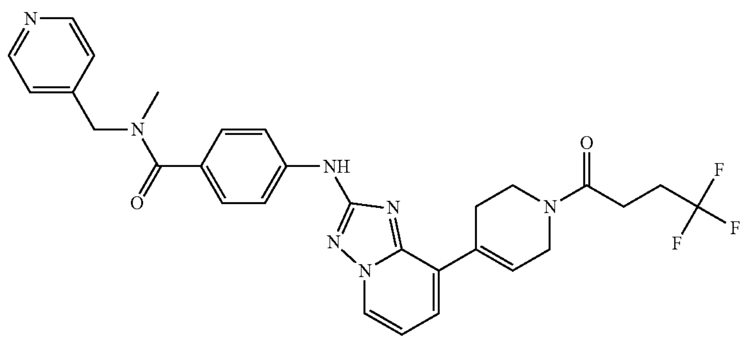 [SMILES: CN(Cc1ccncc1)C(=O)c1ccc(Nc2nc3c(C4=CCN(C(=O)CCC(F)(F)F)CC4)cccn3n2)cc1] | N-methyl-N-(4-pyridylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-408 | 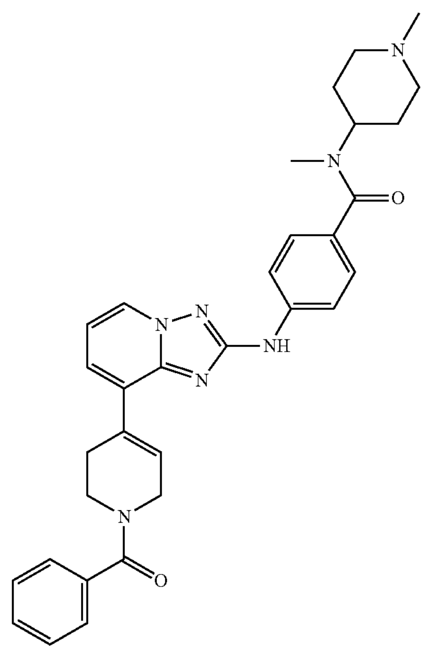 [SMILES: CN1CCC(N(C)C(=O)c2ccc(Nc3nc4c(C5=CCN(C(=O)c6ccccc6)CC5)cccn4n3)cc2)CC1] | 4-[[8-(1-benzoyl-3,6-dihydro-2H-pyridin-4-yl)-[1,2,4]triazolo[1,5-a]pyridin-2-yl]amino]-N-methyl-N-(1-methyl-4-piperidyl)benzamide |

TABLE A-continued
Exemplary Compounds of the Present Invention
| Ex. | Structure | Name |
|---|---|---|
| 2-409 | 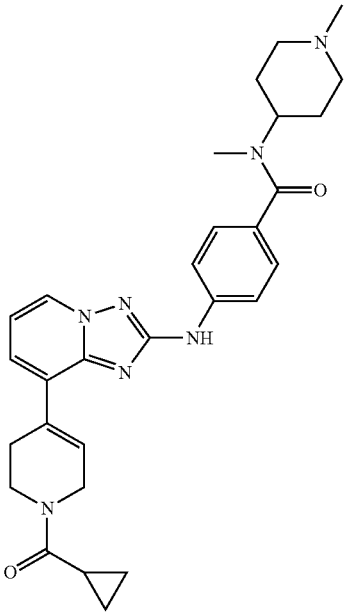 [SMILES: CN1CCC(N(C)C(=O)c2ccc(Nc3nc4c(C5=CCN(C(=O)C6CC6)CC5)cccn4n3)cc2)CC1] | 4-[[8-[1-(cyclopropanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide |
| 2-410 | 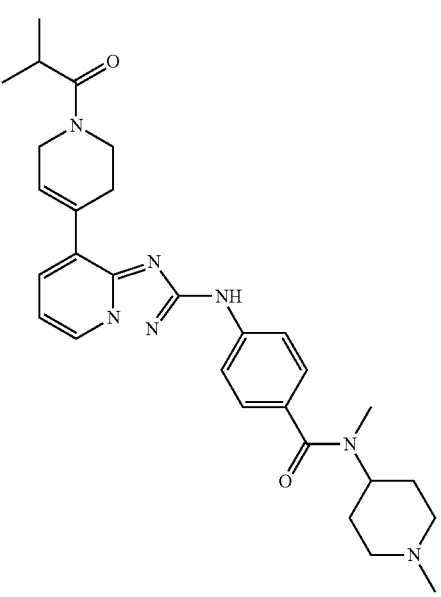 [SMILES: CC(C)C(=O)N1CC=C(c2ccc[nH]/c2=N\C(=N)Nc2ccc(C(=O)N(C)C3CCN(C)CC3)cc2)CC1] | N-methyl-N-(1-methyl-4-piperidyl)-4-[[8-[1-(2-methylpropanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-411 | 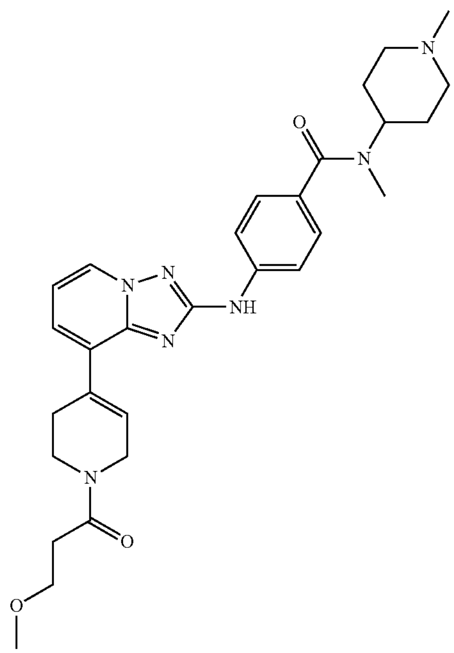 [SMILES: COCCC(=O)N1CC=C(c2cccn3nc(Nc4ccc(C(=O)N(C)C5CCN(C)CC5)cc4)nc23)CC1] | 4-[[8-[1-(3-methoxypropanoyl)-3,6-dihydro-2H-pyridin-4-yl]-[1,2,4]triazolo[1,5-a]pyridin-2-yl]amino]-N-methyl-N-(1-methyl-4-piperidyl)benzamide |
| 2-412 | 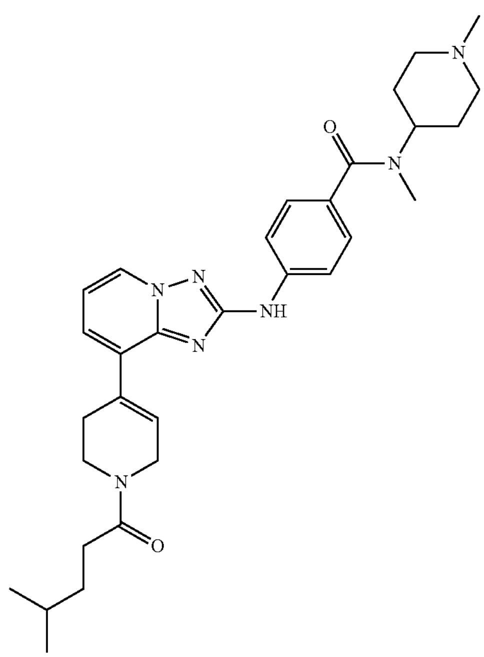 [SMILES: CC(C)CCC(=O)N1CC=C(c2cccn3nc(Nc4ccc(C(=O)N(C)C5CCN(C)CC5)cc4)nc23)CC1] | N-methyl-4-[[8-[1-(4-methylpentanoyl)-3,6-dihydro-2H-pyridin-4-yl]-[1,2,4]triazolo[1,5-a]pyridin-2-yl]amino]-N-(1-methyl-4-piperidyl)benzamide |

TABLE A-continued

Exemplary Compounds of the Present Invention

| Ex. | Structure | Name |
|---|---|---|
| 2-413 | 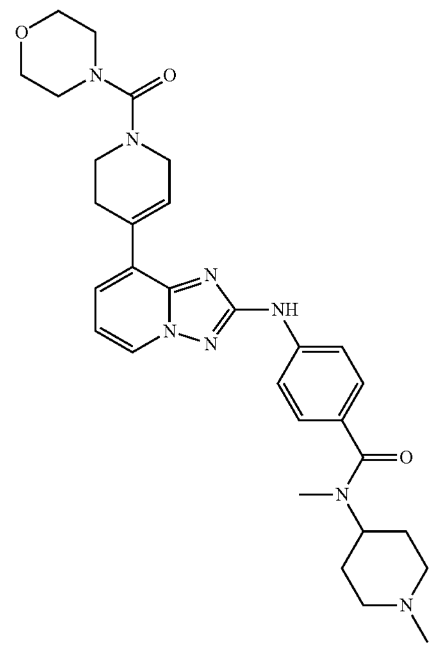 [SMILES: CN1CCC(N(C)C(=O)c2ccc(Nc3nc4c(C5=CCN(C(=O)N6CCOCC6)CC5)cccn4n3)cc2)CC1] | N-methyl-N-(1-methyl-4-piperidyl)-4-[[8-[1-(morpholine-4-carbonyl)-3,6-dihydro-2H-pyridin-4-yl]-[1,2,4]triazolo[1,5-a]pyridin-2-yl]amino]benzamide |
| 2-414 | 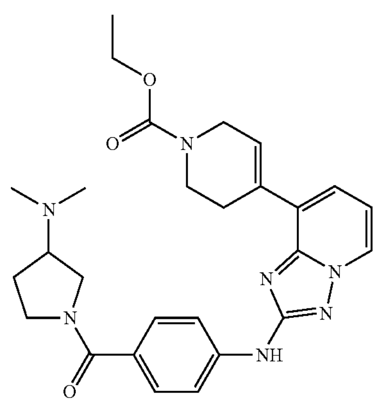 [SMILES: CCOC(=O)N1CC=C(c2cccn3nc(Nc4ccc(C(=O)N5CCC(N(C)C)C5)cc4)nc23)CC1] | ethyl 4-[2-[4-[3-(dimethylamino)pyrrolidine-1-carbonyl]anilino]-[1,2,4]triazolo[1,5-a]pyridin-8-yl]-3,6-dihydro-2H-pyridine-1-carboxylate |
| 2-415 | 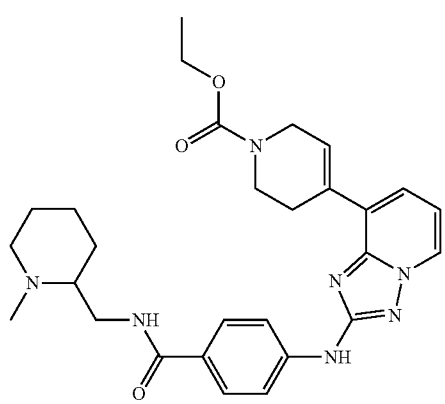 [SMILES: CCOC(=O)N1CC=C(c2cccn3nc(Nc4ccc(C(=O)NCC5CCCCN5C)cc4)nc23)CC1] | ethyl 4-[2-[4-[(1-methyl-2-piperidyl)methylcarbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-416 | 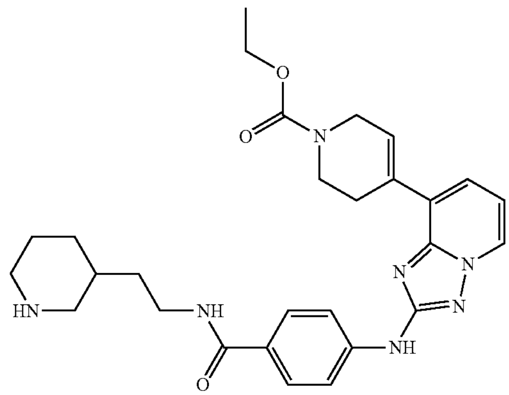 [SMILES: CCOC(=O)N1CC=C(c2cccn3nc(Nc4ccc(C(=O)NCCC5CCCNC5)cc4)nc23)CC1] | ethyl 4-[2-[4-[2-(3-piperidyl)ethylcarbamoyl]anilino]-[1,2,4]triazolo[1,5-a]pyridin-8-yl]-3,6-dihydro-2H-pyridine-1-carboxylate |
| 2-417 | 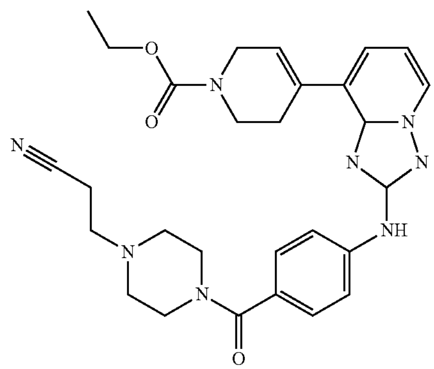 [SMILES: CCOC(=O)N1CC=C(C2=CC=CN3NC(Nc4ccc(C(=O)N5CCN(CCC#N)CC5)cc4)NC23)CC1] | ethyl 4-[2-[4-[4-(2-cyanoethyl)piperazine-1-carbonyl]anilino]-[1,2,4]triazolo[1,5-a]pyridin-8-yl]-3,6-dihydro-2H-pyridine-1-carboxylate |
| 2-418 | 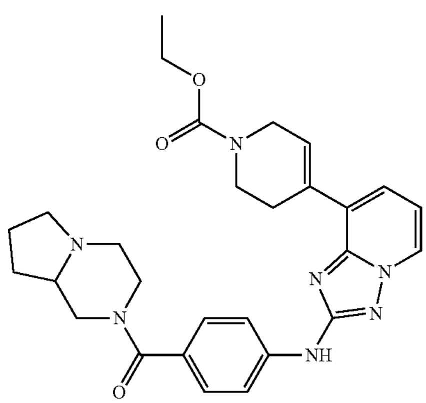 [SMILES: CCOC(=O)N1CC=C(c2cccn3nc(Nc4ccc(C(=O)N5CCN6CCCC6C5)cc4)nc23)CC1] | ethyl 4-[2-[4-(3,4,6,7,8,8a-hexahydro-1H-pyrrolo[1,2-a]pyrazine-2-carbonyl)anilino]-[1,2,4]triazolo[1,5-a]pyridin-8-yl]-3,6-dihydro-2H-pyridine-1-carboxylate |
| 2-419 | 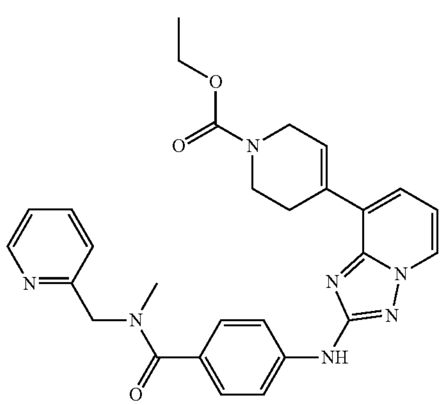 [SMILES: CCOC(=O)N1CC=C(c2cccn3nc(Nc4ccc(C(=O)N(C)Cc5ccccn5)cc4)nc23)CC1] | ethyl 4-[2-[4-[methyl(2-pyridylmethyl)carbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-420 | 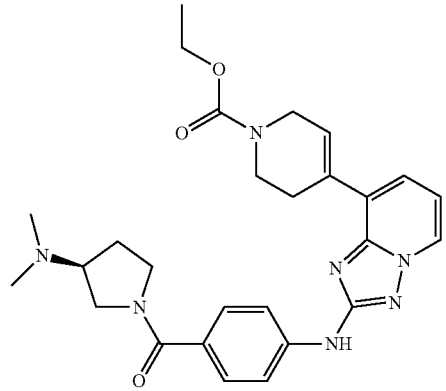 [SMILES: CCOC(=O)N1CC=C(c2cccn3nc(Nc4ccc(C(=O)N5CC[C@H](N(C)C)C5)cc4)nc23)CC1] | ethyl 4-[2-[4-[(3S)-3-(dimethylamino)pyrrolidine-1-carbonyl]anilino]-[1,2,4]triazolo[1,5-a]pyridin-8-yl]-3,6-dihydro-2H-pyridine-1-carboxylate |
| 2-421 | 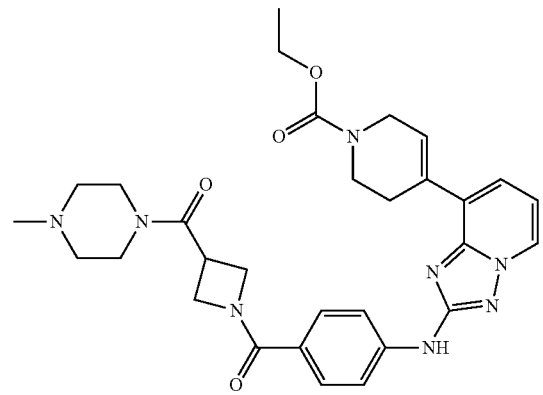 [SMILES: CCOC(=O)N1CC=C(c2cccn3nc(Nc4ccc(C(=O)N5CC(C(=O)N6CCN(C)CC6)C5)cc4)nc23)CC1] | ethyl 4-[2-[4-[3-(4-methylpiperazine-1-carbonyl)azetidine-1-carbonyl]anilino]-[1,2,4]triazolo[1,5-a]pyridin-8-yl]-3,6-dihydro-2H-pyridine-1-carboxylate |
| 2-422 | 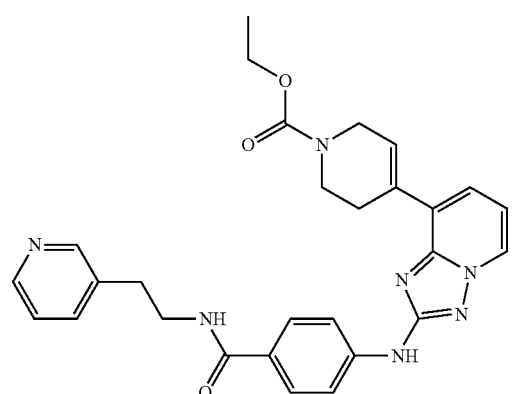 | ethyl 4-[2-[4-[2-(3-pyridyl)ethylcarbamoyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-423 | 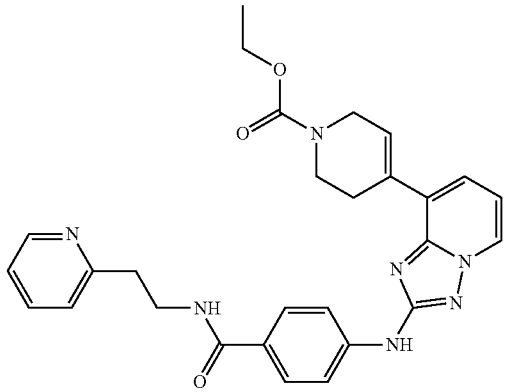 [SMILES: CCOC(=O)N1CC=C(c2cccn3nc(Nc4ccc(C(=O)NCCc5ccccn5)cc4)nc23)CC1] | ethyl 4-[2-[4-[2-(2-pyridyl)ethylcarbamoyl]anilino]-[1,2,4]triazolo[1,5-a]pyridin-8-yl]-3,6-dihydro-2H-pyridine-1-carboxylate |
| 2-424 | 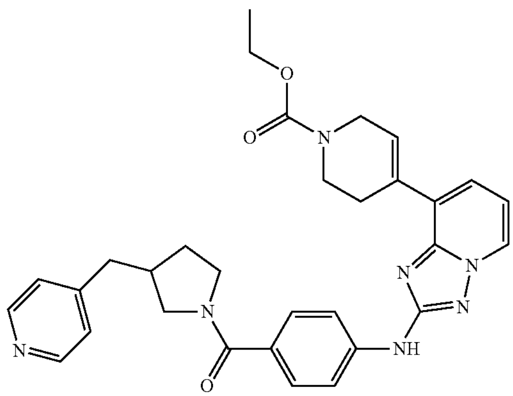 [SMILES: CCOC(=O)N1CC=C(c2cccn3nc(Nc4ccc(C(=O)N5CCC(Cc6ccncc6)C5)cc4)nc23)CC1] | ethyl 4-[2-[4-[3-(4-pyridylmethyl)pyrrolidine-1-carbonyl]anilino]-[1,2,4]triazolo[1,5-a]pyridin-8-yl]-3,6-dihydro-2H-pyridine-1-carboxylate |
| 2-425 | 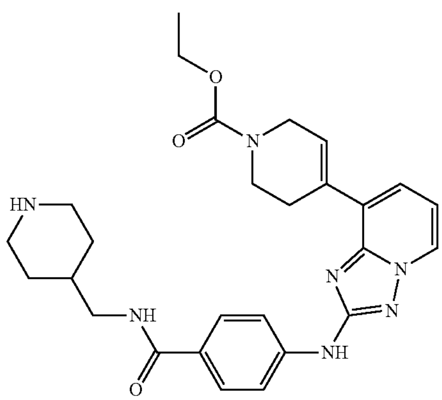 [SMILES: CCOC(=O)N1CC=C(c2cccn3nc(Nc4ccc(C(=O)NCC5CCNCC5)cc4)nc23)CC1] | ethyl 4-[2-[4-(4-piperidylmethylcarbamoyl)anilino]-[1,2,4]triazolo[1,5-a]pyridin-8-yl]-3,6-dihydro-2H-pyridine-1-carboxylate |
| 2-426 | 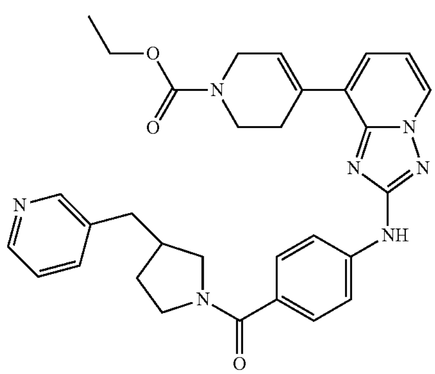 [SMILES: CCOC(=O)N1CC=C(c2cccn3nc(Nc4ccc(C(=O)N5CCC(Cc6cccnc6)C5)cc4)nc23)CC1] | ethyl 4-[2-[4-[3-(3-pyridylmethyl)pyrrolidine-1-carbonyl]anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-427 | 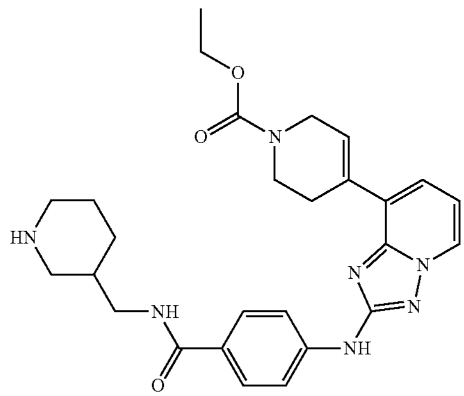 [SMILES: CCOC(=O)N1CC=C(c2cccn3nc(Nc4ccc(C(=O)NCC5CCCNC5)cc4)nc23)CC1] | ethyl 4-[2-[4-(3-piperidylmethylcarbamoyl)anilino]-[1,2,4]triazolo[1,5-a]pyridin-8-yl]-3,6-dihydro-2H-pyridine-1-carboxylate |
| 2-428 | 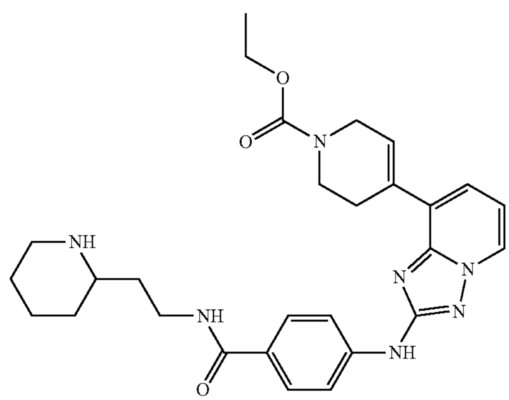 [SMILES: CCOC(=O)N1CC=C(c2cccn3nc(Nc4ccc(C(=O)NCCC5CCCCN5)cc4)nc23)CC1] | ethyl 4-[2-[4-[2-(2-piperidyl)ethylcarbamoyl]anilino]-[1,2,4]triazolo[1,5-a]pyridin-8-yl]-3,6-dihydro-2H-pyridine-1-carboxylate |
| 2-429 | 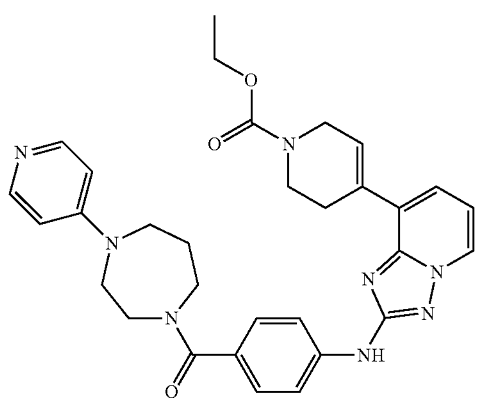 [SMILES: CCOC(=O)N1CC=C(c2cccn3nc(Nc4ccc(C(=O)N5CCCN(c6ccncc6)CC5)cc4)nc23)CC1] | ethyl 4-[2-[4-[4-(4-pyridyl)-1,4-diazepane-1-carbonyl]anilino]-[1,2,4]triazolo[1,5-a]pyridin-8-yl]-3,6-dihydro-2H-pyridine-1-carboxylate |

| Ex. | Structure | Name |
|---|---|---|
| 2-430 | 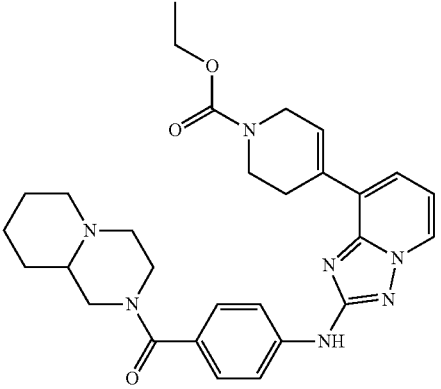 [SMILES: CCOC(=O)N1CC=C(c2cccn3nc(Nc4ccc(C(=O)N5CCN6CCCCC6C5)cc4)nc23)CC1] | ethyl 4-[2-[4-(1,3,4,6,7,8,9,9a-octahydropyrido[1,2-a]pyrazine-2-carbonyl)anilino]-[1,2,4]triazolo[1,5-a]pyridin-8-yl]-3,6-dihydro-2H-pyridine-1-carboxylate |
| 2-431 | 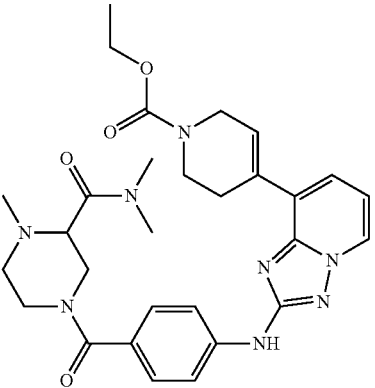 [SMILES: CCOC(=O)N1CC=C(c2cccn3nc(Nc4ccc(C(=O)N5CCN(C)C(C(=O)N(C)C)C5)cc4)nc23)CC1] | ethyl 4-[2-[4-[3-(dimethylcarbamoyl)-4-methyl-piperazine-1-carbonyl]anilino]-[1,2,4]triazolo[1,5-a]pyridin-8-yl]-3,6-dihydro-2H-pyridine-1-carboxylate |
| 2-432 | 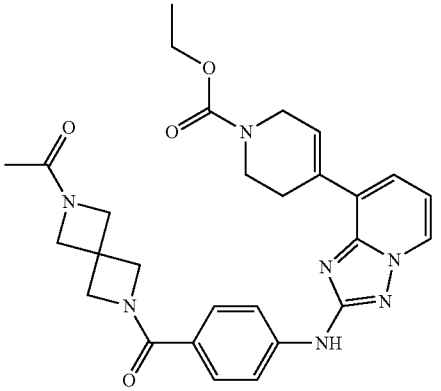 [SMILES: CCOC(=O)N1CC=C(c2cccn3nc(Nc4ccc(C(=O)N5CC6(CN(C(C)=O)C6)C5)cc4)nc23)CC1] | ethyl 4-[2-[4-(6-acetyl-2,6-diazaspiro[3.3]heptane-2-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-433 | 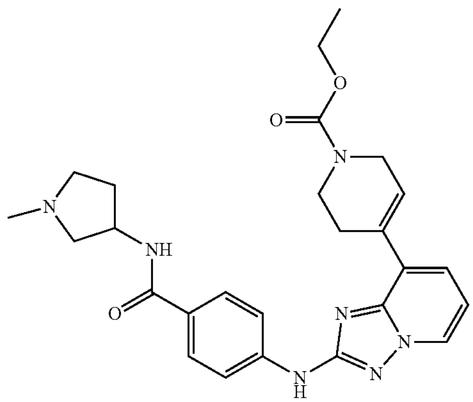 [SMILES: CCOC(=O)N1CC=C(c2cccn3nc(Nc4ccc(C(=O)NC5CCN(C)C5)cc4)nc23)CC1] | ethyl 4-[2-[4-[(1-methylpyrrolidin-3-yl)carbamoyl]anilino]-[1,2,4]triazolo[1,5-a]pyridin-8-yl]-3,6-dihydro-2H-pyridine-1-carboxylate |
| 2-434 | 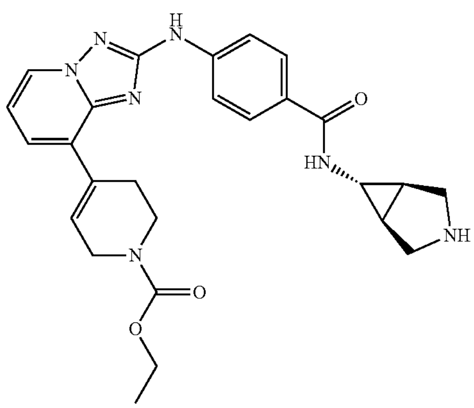 [SMILES: CCOC(=O)N1CC=C(c2cccn3nc(Nc4ccc(C(=O)N[C@H]5[C@@H]6CNC[C@@H]65)cc4)nc23)CC1] | ethyl 4-[2-[4-[[(1S,5R)-3-azabicyclo[3.10]hexan-6-yl]carbamoyl]anilino]-[1,2,4]triazolo[1,5-a]pyridin-8-yl]-3,6-dihydro-2H-pyridine-1-carboxylate |
| 2-435 | 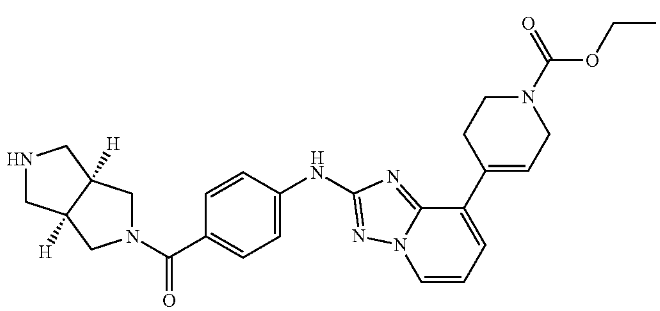 [SMILES: CCOC(=O)N1CC=C(c2cccn3nc(Nc4ccc(C(=O)N5C[C@H]6CNC[C@H]6C5)cc4)nc23)CC1] | ethyl 4-[2-[4-[(3aR,6aS)-2,3,3a,4,6,6a-hexahydro-1H-pyrrolo[3,4-c]pyrrole-5-carbonyl]anilino]-[1,2,4]triazolo[1,5-a]pyridin-8-yl]-3,6-dihydro-2H-pyridine-1-carboxylate |
| 2-436 | 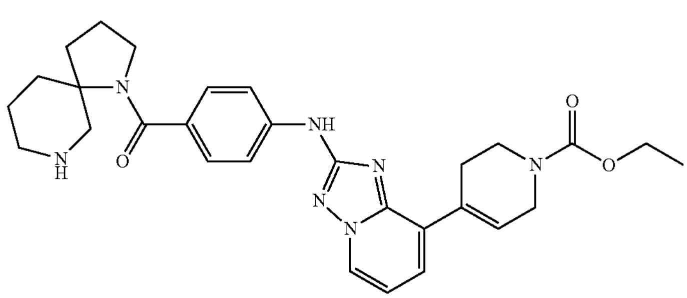 [SMILES: CCOC(=O)N1CC=C(c2cccn3nc(Nc4ccc(C(=O)N5CCCC56CCCNC6)cc4)nc23)CC1] | ethyl 4-[2-[4-(1,9-diazaspiro[4.5]decane-1-carbonyl)anilino]-[1,2,4]triazolo[1,5-a]pyridin-8-yl]-3,6-dihydro-2H-pyridine-1-carboxylate |

TABLE A-continued

Exemplary Compounds of the Present Invention

| Ex. | Structure | Name |
|---|---|---|
| 2-437 | 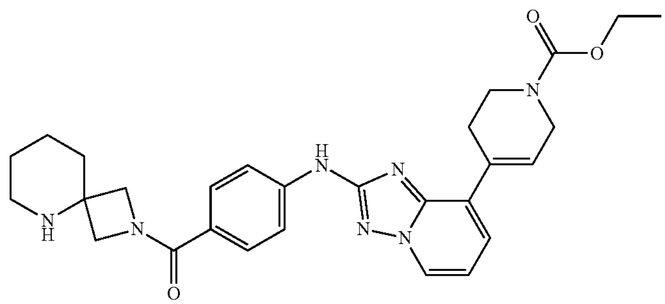 [SMILES: CCOC(=O)N1CC=C(c2cccn3nc(Nc4ccc(C(=O)N5CC6(CCCCN6)C5)cc4)nc23)CC1] | ethyl 4-[2-[4-(2,5-diazaspiro[3.5]nonane-2-carbonyl)anilino]-[1,2,4]triazolo[1,5-a]pyridin-8-yl]-3,6-dihydro-2H-pyridine-1-carboxylate |
| 2-438 | 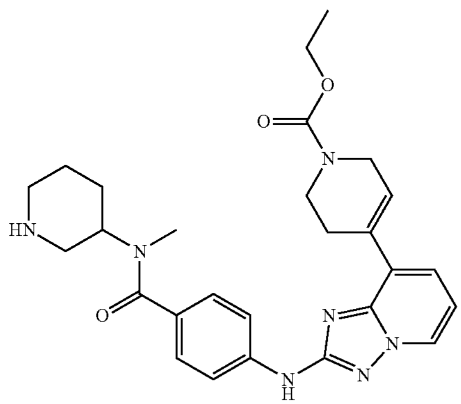 [SMILES: CCOC(=O)N1CC=C(c2cccn3nc(Nc4ccc(C(=O)N(C)C5CCCNC5)cc4)nc23)CC1] | ethyl 4-[2-[4-[methyl(3-piperidyl)carbamoyl]anilino]-[1,2,4]triazolo[1,5-a]pyridin-8-yl]-3,6-dihydro-2H-pyridine-1-carboxylate |
| 2-439 | 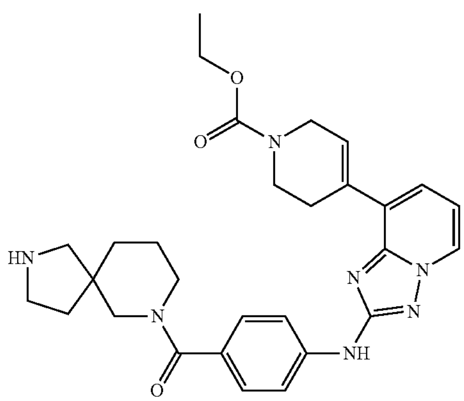 [SMILES: CCOC(=O)N1CC=C(c2cccn3nc(Nc4ccc(C(=O)N5CCCC6(CCNC6)C5)cc4)nc23)CC1] | ethyl 4-[2-[4-(2,7-diazaspiro[4.5]decane-7-carbonyl)anilino]-[1,2,4]triazolo[1,5-a]pyridin-8-yl]-3,6-dihydro-2H-pyridine-1-carboxylate |
| 2-440 | 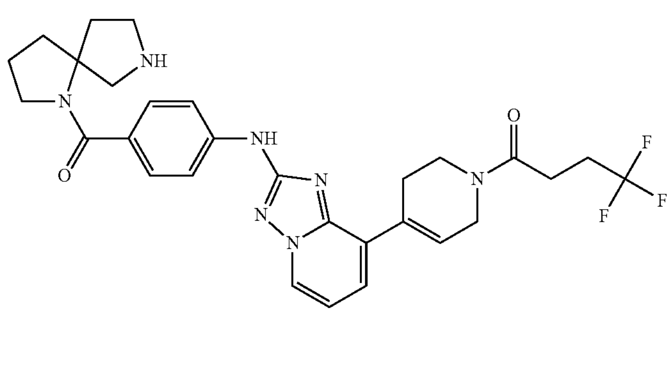 [SMILES: O=C(CCC(F)(F)F)N1CC=C(c2cccn3nc(Nc4ccc(C(=O)N5CCCC56CCNC6)cc4)nc23)CC1] | 1-[4-[2-[4-(1,7-diazaspiro[4.4]nonane-1-carbonyl)anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-441 | 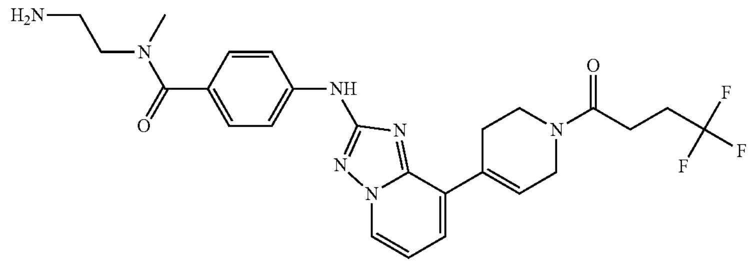 [SMILES: CN(CCN)C(=O)c1ccc(Nc2nc3c(C4=CCN(C(=O)CCC(F)(F)F)CC4)cccn3n2)cc1] | N-(2-aminoethyl)-N-methyl-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-442 | 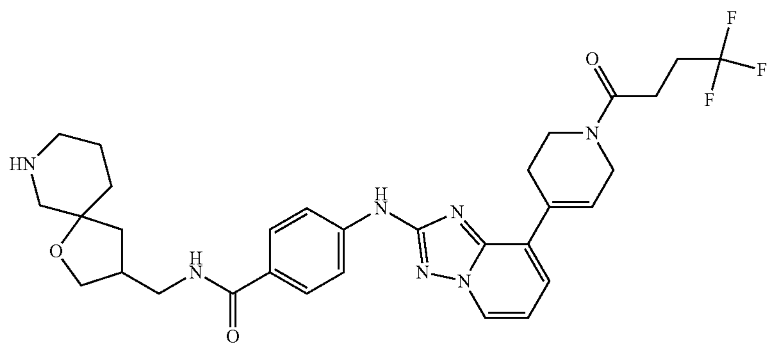 [SMILES: O=C(NCC1COC2(CCCNC2)C1)c1ccc(Nc2nc3c(C4=CCN(C(=O)CCC(F)(F)F)CC4)cccn3n2)cc1] | N-(1-oxa-8-azaspiro[4.5]decan-3-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-443 | 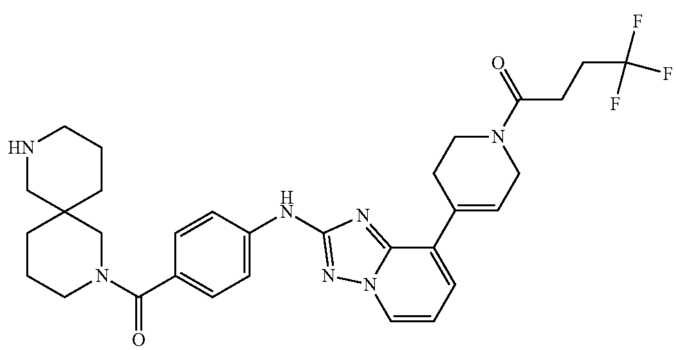 [SMILES: O=C(CCC(F)(F)F)N1CC=C(c2cccn3nc(Nc4ccc(C(=O)N5CCCC6(CCCNC6)C5)cc4)nc23)CC1] | 1-[4-[2-[4-(2,8-diazaspiro[5.5]undecane-2-carbonyl)anilino]-[1,2,4]triazolo[1,5-a]pyridin-8-yl]-3,6-dihydro-2H-pyridin-1-yl]-4,4,4-trifluoro-butan-1-one |
| 2-444 | 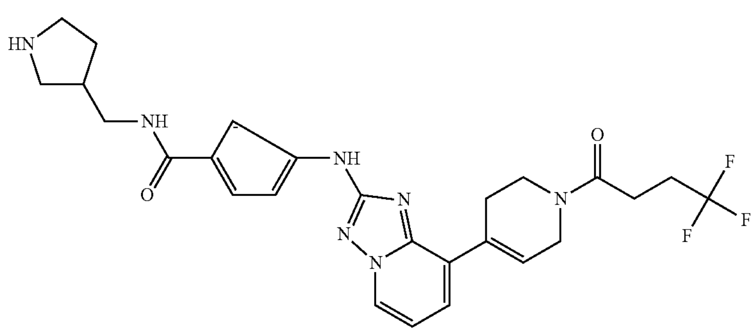 | N-(pyrrolidin-3-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-445 | 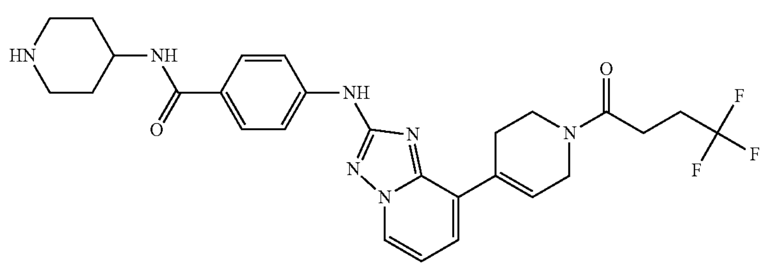 [SMILES: O=C(NC1CCNCC1)c1ccc(Nc2nc3c(C4=CCN(C(=O)CCC(F)(F)F)CC4)cccn3n2)cc1] | N-(4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-446 | 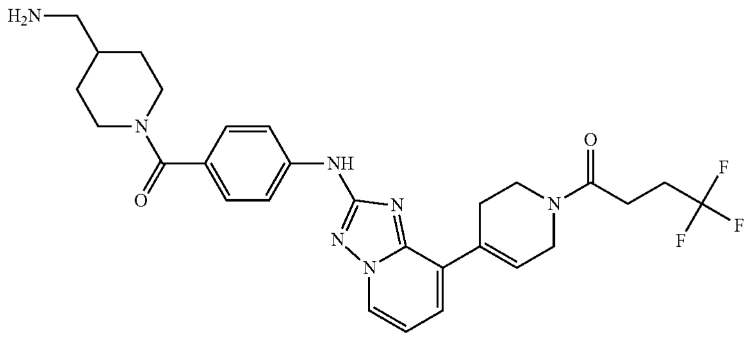 [SMILES: NCC1CCN(C(=O)c2ccc(Nc3nc4c(C5=CCN(C(=O)CCC(F)(F)F)CC5)cccn4n3)cc2)CC1] | 1-[4-[2-[4-[4-(aminomethyl)piperidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-447 | 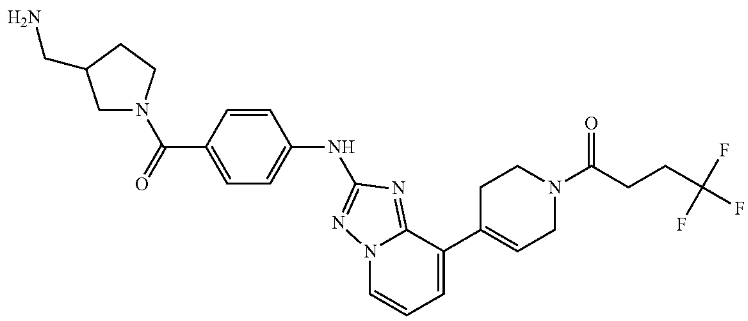 [SMILES: NCC1CCN(C(=O)c2ccc(Nc3nc4c(C5=CCN(C(=O)CCC(F)(F)F)CC5)cccn4n3)cc2)C1] | 1-[4-[2-[4-[3-(aminomethyl)pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-448 | 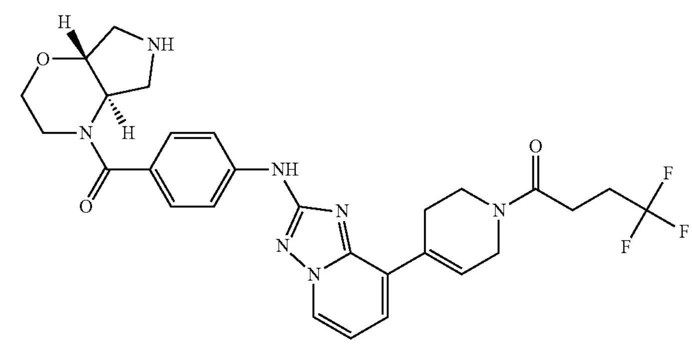 [SMILES: O=C(CCC(F)(F)F)N1CC=C(c2cccn3nc(Nc4ccc(C(=O)N5CCO[C@@H]6CNC[C@H]65)cc4)nc23)CC1] | 1-[4-[2-[4-[(4aR,7aR)-3,4a,5,6,7,7a-hexahydro-2H-pyrrolo[3,4-b][1,4]oxazine-4-carbonyl]anilino]-[1,2,4]triazolo[1,5-a]pyridin-8-yl]-3,6-dihydro-2H-pyridin-1-yl]-4,4,4-trifluoro-butan-1-one |
| 2-449 | 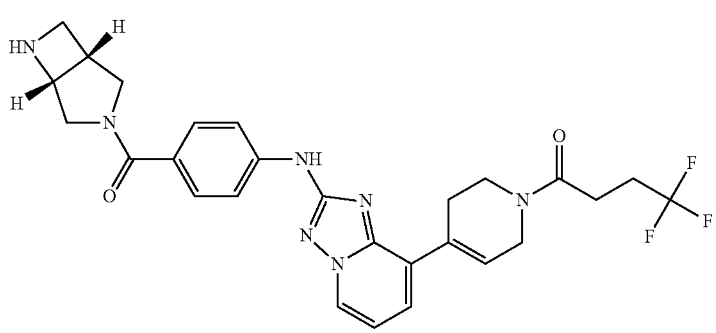 [SMILES: O=C(CCC(F)(F)F)N1CC=C(c2cccn3nc(Nc4ccc(C(=O)N5C[C@H]6CN[C@H]6C5)cc4)nc23)CC1] | 1-[4-[2-[4-[(1R,5R)-3,6-diazabicyclo[3.2.0]heptane-3-carbonyl]anilino]-[1,2,4]triazolo[1,5-a]pyridin-8-yl]-3,6-dihydro-2H-pyridin-1-yl]-4,4,4-trifluoro-butan-1-one |
| 2-450 | 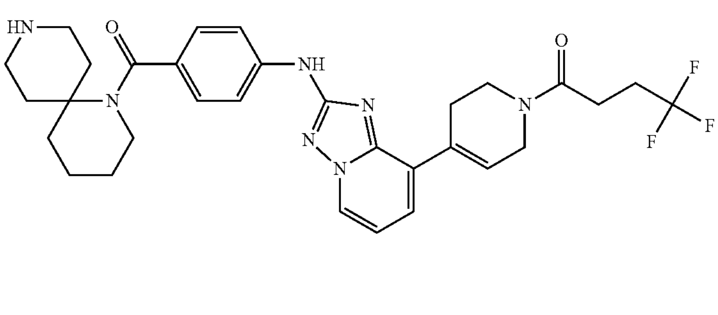 [SMILES: O=C(CCC(F)(F)F)N1CC=C(c2cccn3nc(Nc4ccc(C(=O)N5CCCCC56CCNCC6)cc4)nc23)CC1] | 1-[4-[2-[4-(1,9-diazaspiro[5.5]undecane-1-carbonyl)anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 2-451 | 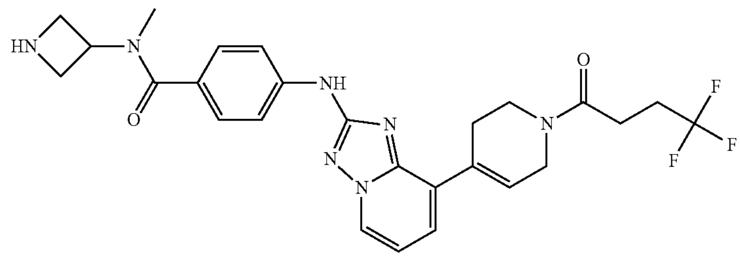 [SMILES: CN(C(=O)c1ccc(Nc2nc3c(C4=CCN(C(=O)CCC(F)(F)F)CC4)cccn3n2)cc1)C1CNC1] | N-(azetidin-3-yl)-N-methyl-4-[[8-[1-(4,4,4-trifluorobutanoyl)-3,6-dihydro-2H-pyridin-4-yl]-[1,2,4]triazolo[1,5-a]pyridin-2-y)]amino]benzamide |
| 2-452 | 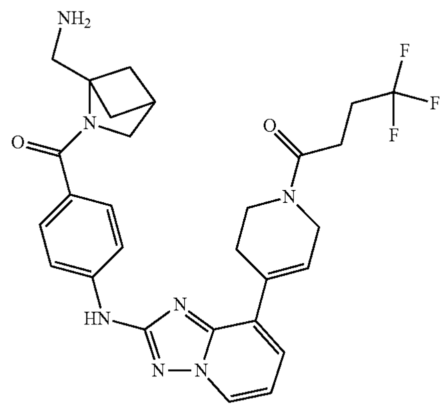 [SMILES: NCC12CC(CN1C(=O)c1ccc(Nc3nc4c(C5=CCN(C(=O)CCC(F)(F)F)CC5)cccn4n3)cc1)C2] | 1-[4-[2-[4-[4-(aminomethyl)-3-azabicyclo[2.1.1]hexane-3-carbonyl]anilino]-[1,2,4]triazolo[1,5-a]pyridin-8-yl]-3,6-dihydro-2H-pyridin-1-yl]-4,4,4-trifluoro-butan-1-one |
| 2-453 | 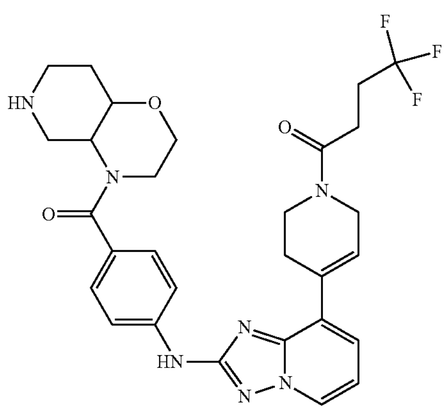 [SMILES: O=C(CCC(F)(F)F)N1CC=C(c2cccn3nc(Nc4ccc(C(=O)N5CCOC6CCNCC65)cc4)nc23)CC1] | 1-[4-[2-[4-(2,3,4a,5,6,7,8,8a-octahydropyrido[4,3-b][1,4]oxazine-4-carbonyl)anilino]-[1,2,4]triazolo[1,5-a]pyridin-8-yl]-3,6-dihydro-2H-pyridin-1-yl]-4,4,4-trifluoro-butan-1one |
| 2-454 | 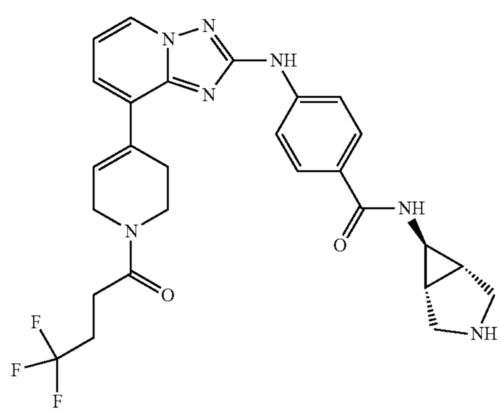 [SMILES: O=C(N[C@H]1[C@@H]2CNC[C@@H]21)c1ccc(Nc2nc3c(C4=CCN(C(=O)CCC(F)(F)F)CC4)cccn3n2)cc1] | N-[(1R,5S)-3-azabicyclo[3.1.0]hexan-6-yl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-455 | 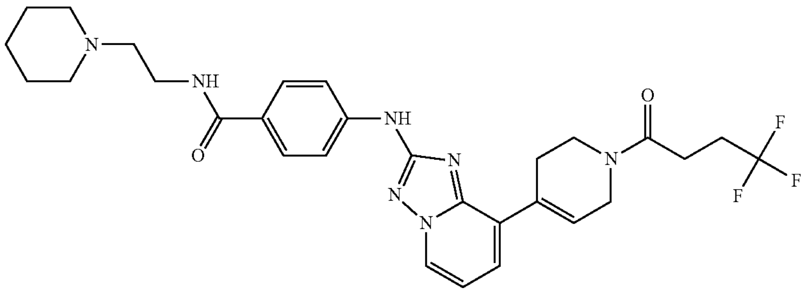 [SMILES: O=C(NCCN1CCCCC1)c1ccc(Nc2nc3c(C4=CCN(C(=O)CCC(F)(F)F)CC4)cccn3n2)cc1] | N-[2-(1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-456 | 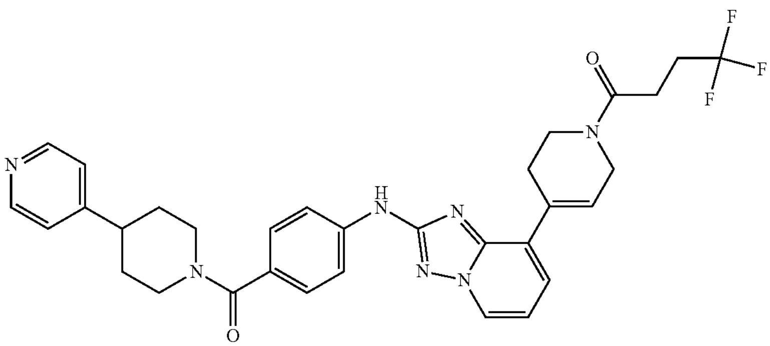 [SMILES: O=C(CCC(F)(F)F)N1CC=C(c2cccn3nc(Nc4ccc(C(=O)N5CCC(c6ccncc6)CC5)cc4)nc23)CC1] | 4,4,4-trifluoro-1-[4-[2-[4-[4-(4-pyridyl)piperidine-1-carbonyl]anilino]-[1,2,4]triazolo[1,5-a]pyridin-8-yl]-3,6-dihydro-2H-pyridin-1-yl]butan-1-one |
| 2-457 | 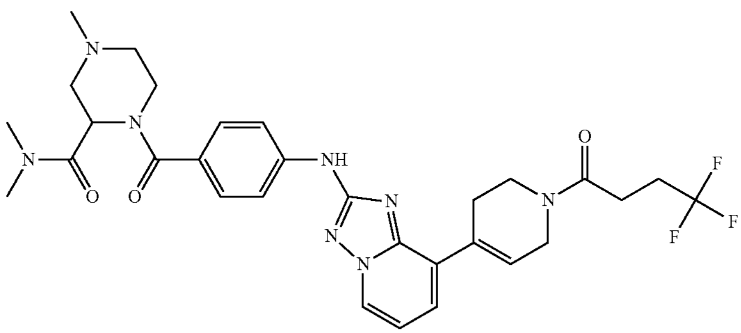 [SMILES: CN1CCN(C(=O)c2ccc(Nc3nc4c(C5=CCN(C(=O)CCC(F)(F)F)CC5)cccn4n3)cc2)C(C(=O)N(C)C)C1] | N,N,4-trimethyl-1-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide |
| 2-458 | 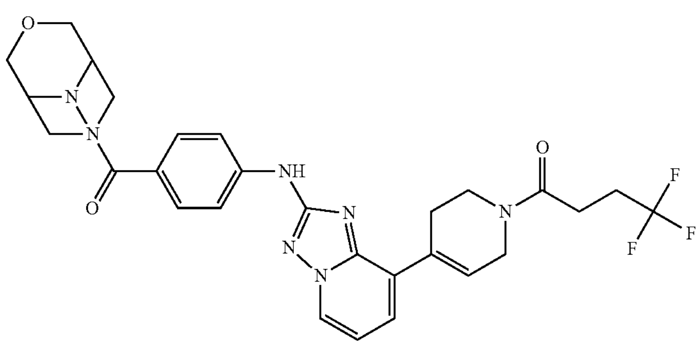 | 4,4,4-trifluoro-1-[4-[2-[4-(9-methyl-3-oxa-7,9-diazabicyclo[3.3.1]nonane-7-carbonyl)anilino]-[1,2,4]triazolo[1,5-a]pyridin-8-yl]-3,6-dihydro-2H-pyridin-1-yl]butan-1-one |
| 2-459 | 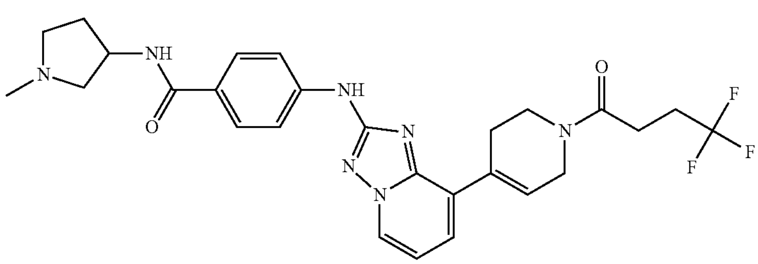 [SMILES: CN1CCC(NC(=O)c2ccc(Nc3nc4c(C5=CCN(C(=O)CCC(F)(F)F)CC5)cccn4n3)cc2)C1] | N-(1-methylpyrrolidin-3-yl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-460 | 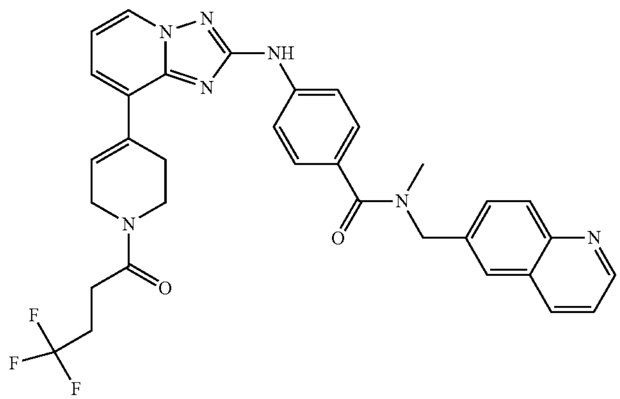 [SMILES: CN(Cc1ccc2ncccc2c1)C(=O)c1ccc(Nc2nc3c(C4=CCN(C(=O)CCC(F)(F)F)CC4)cccn3n2)cc1] | N-methyl-N-(6-quinolylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-461 | 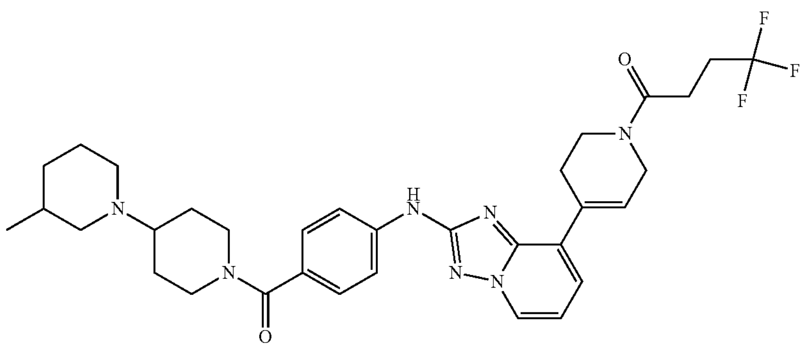 [SMILES: CC1CCCN(C2CCN(C(=O)c3ccc(Nc4nc5c(C6=CCN(C(=O)CCC(F)(F)F)CC6)cccn5n4)cc3)CC2)C1] | 4,4,4-trifluoro-1-[4-[2-[4-[4-(3-methyl-1-piperidyl)piperidine-1-carbonyl]anilino]-[1,2,4]triazolo[1,5-a]pyridin-8-yl]-3,6-dihydro-2H-pyridin-1-yl]butan-1-one |
| 2-462 | 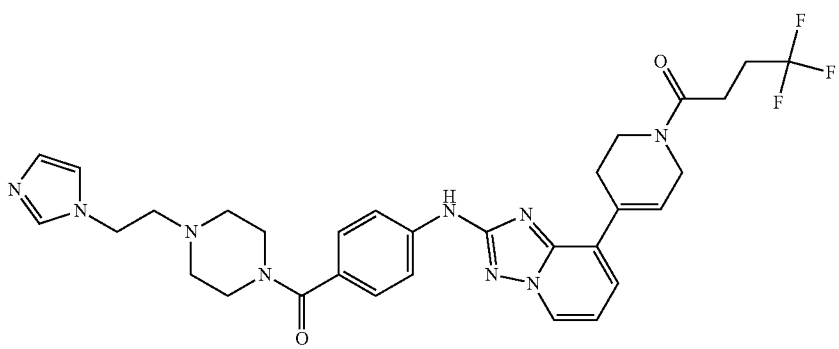 [SMILES: O=C(CCC(F)(F)F)N1CC=C(c2cccn3nc(Nc4ccc(C(=O)N5CCN(CCn6ccnc6)CC5)cc4)nc23)CC1] | 4,4,4-trifluoro-1-[4-[2-[4-[4-(2-imidazol-1-ylethyl)piperazine-1-carbonyl]anilino]-[1,2,4]triazolo[1,5-a]pyridin-8-yl]-3,6-dihydro-2H-pyridin-1-yl]butan-1-one |
| 2-463 | 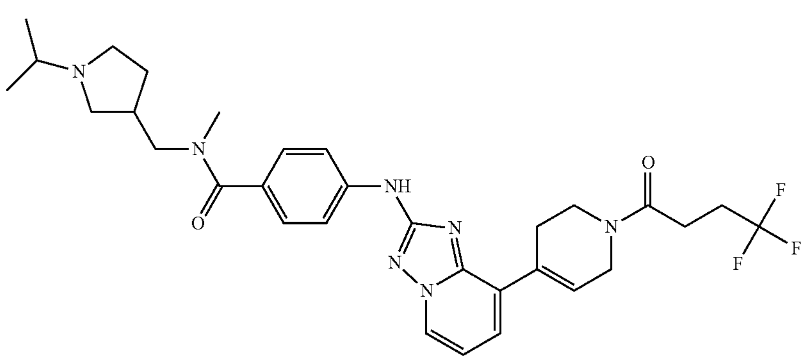 [SMILES: CC(C)N1CCC(CN(C)C(=O)c2ccc(Nc3nc4c(C5=CCN(C(=O)CCC(F)(F)F)CC5)cccn4n3)cc2)C1] | N-[(1-isopropylpyrrolidin-3-yl)methyl]-N-methyl-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-464 | 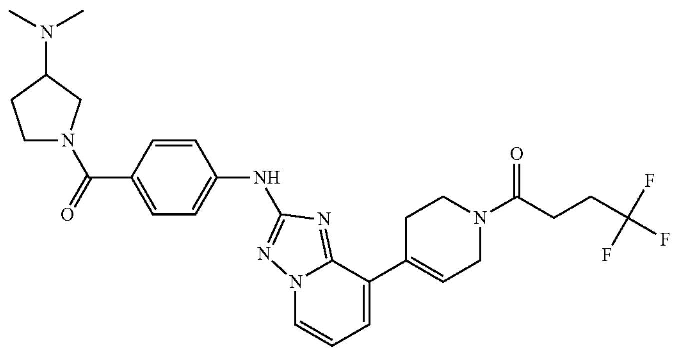 [SMILES: CN(C)C1CCN(C(=O)c2ccc(Nc3nc4c(C5=CCN(C(=O)CCC(F)(F)F)CC5)cccn4n3)cc2)C1] | 1-[4-[2-[4-[3-(dimethylamino)pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-465 | 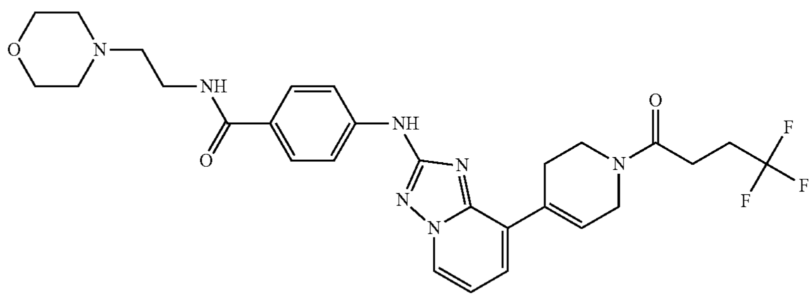 [SMILES: O=C(NCCN1CCOCC1)c1ccc(Nc2nc3c(C4=CCN(C(=O)CCC(F)(F)F)CC4)cccn3n2)cc1] | N-(2-morpholinoethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-466 | 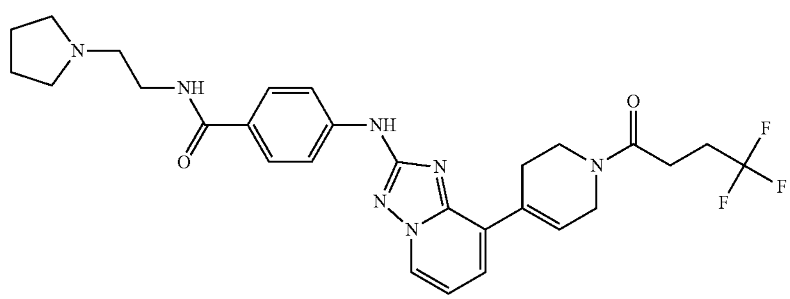 [SMILES: O=C(NCCN1CCCC1)c1ccc(Nc2nc3c(C4=CCN(C(=O)CCC(F)(F)F)CC4)cccn3n2)cc1] | N-(2-pyrrolidin-1-ylethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-467 | 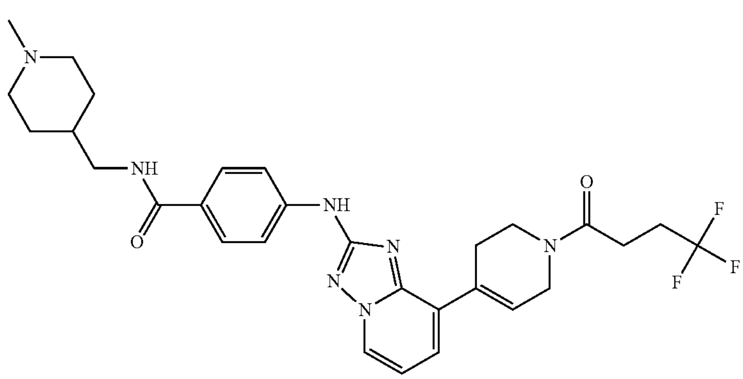 [SMILES: CN1CCC(CNC(=O)c2ccc(Nc3nc4c(C5=CCN(C(=O)CCC(F)(F)F)CC5)cccn4n3)cc2)CC1] | N-[(1-methyl-4-piperidyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |

TABLE A-continued

Exemplary Compounds of the Present Invention

| Ex. | Structure | Name |
|---|---|---|
| 2-468 | 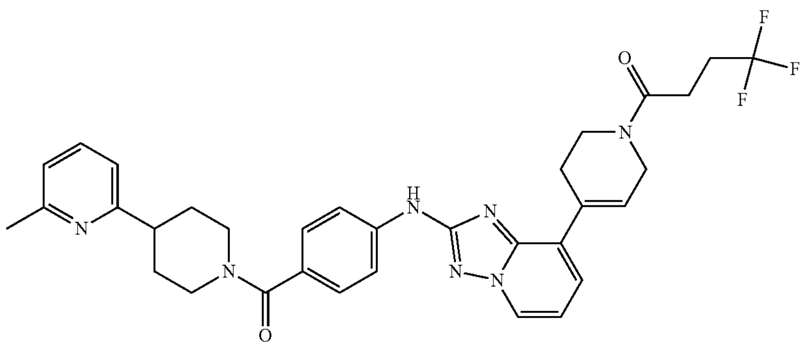 [SMILES: Cc1cccc(C2CCN(C(=O)c3ccc(Nc4nc5c(C6=CCN(C(=O)CCC(F)(F)F)CC6)cccn5n4)cc3)CC2)n1] | 4,4,4-trifluoro-1-[4-[2-[4-[4-(6-methyl-2-pyridyl)piperidine-1-carbonyl]anilino]-[1,2,4]triazolo[1,5-a]pyridin-8-yl]-3,6-dihydro-2H-pyridin-1-yl]butan-1-one |
| 2-469 | 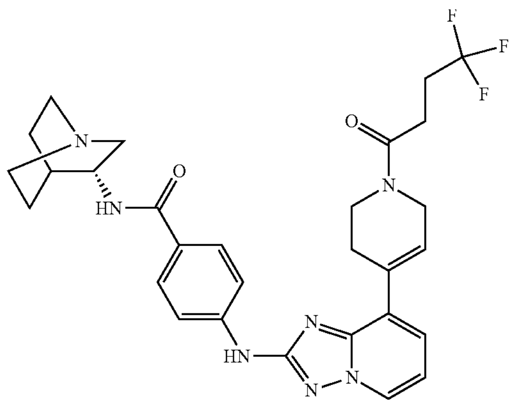 [SMILES: O=C(N[C@H]1CN2CCC1CC2)c1ccc(Nc2nc3c(C4=CCN(C(=O)CCC(F)(F)F)CC4)cccn3n2)cc1] | N-[(3R)-quinuclidin-3-yl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-470 | 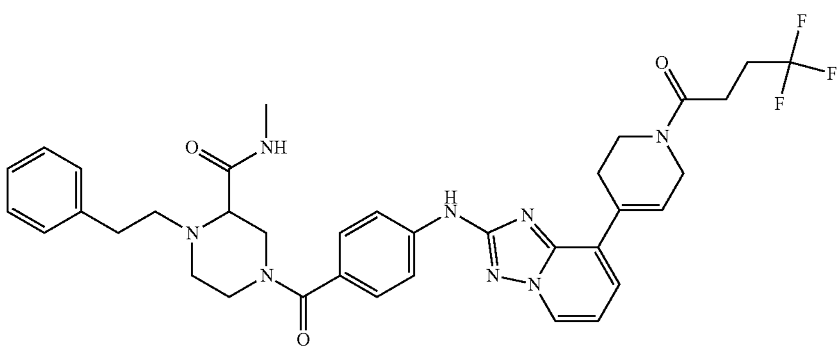 [SMILES: CNC(=O)C1CN(C(=O)c2ccc(Nc3nc4c(C5=CCN(C(=O)CCC(F)(F)F)CC5)cccn4n3)cc2)CCN1CCc1ccccc1] | N-methyl-1-(2-phenylethyl)-4-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide |
| 2-471 | 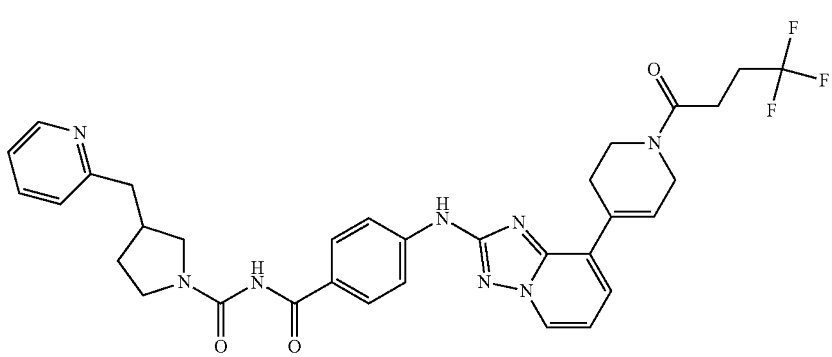 [SMILES: O=C(NC(=O)N1CCC(Cc2ccccn2)C1)c1ccc(Nc2nc3c(C4=CCN(C(=O)CCC(F)(F)F)CC4)cccn3n2)cc1] | 4,4,4-trifluoro-1-[4-[2-[4-[3-(2-pyridylmethyl)pyrrolidine-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-472 | 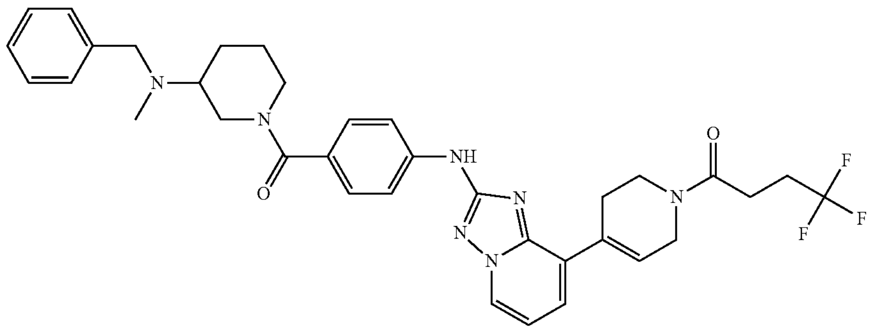 [SMILES: CN(Cc1ccccc1)C1CCCN(C(=O)c2ccc(Nc3nc4c(C5=CCN(C(=O)CCC(F)(F)F)CC5)cccn4n3)cc2)C1] | 1-[4-[2-[4-[3-[benzyl(methyl)amino]piperidine-1-carbonyl]anilino]-[1,2,4]triazolo[1,5-a]pyridin-8-yl]-3,6-dihydro-2H-pyridin-1-yl]-4,4,4-trifluoro-butan-1-one |
| 2-473 | 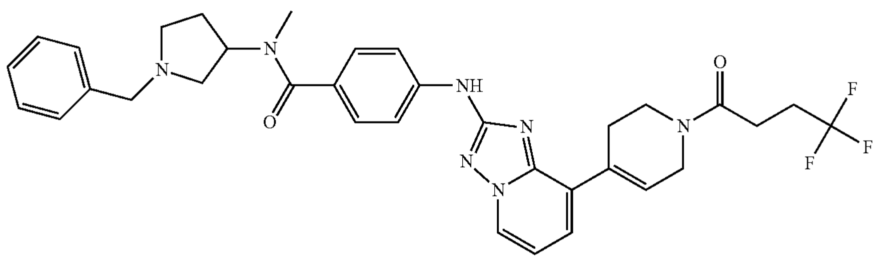 [SMILES: CN(C(=O)c1ccc(Nc2nc3c(C4=CCN(C(=O)CCC(F)(F)F)CC4)cccn3n2)cc1)C1CCN(Cc2ccccc2)C1] | N-(1-benzylpyrrolidin-3-yl)-N-methyl-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-474 | 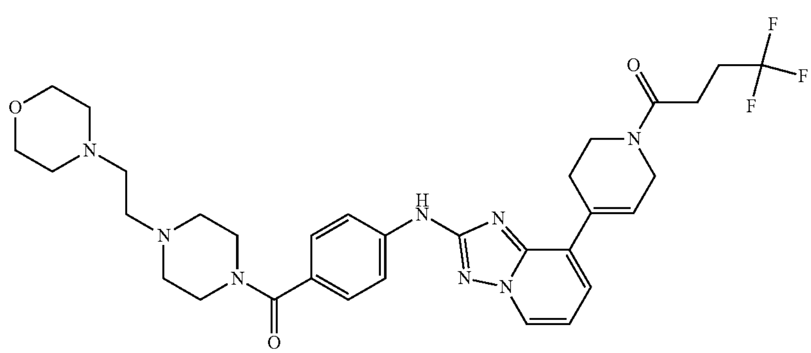 [SMILES: O=C(CCC(F)(F)F)N1CC=C(c2cccn3nc(Nc4ccc(C(=O)N5CCN(CCN6CCOCC6)CC5)cc4)nc23)CC1] | 4,4,4-trifluoro-1-[4-[2-[4-[4-(2-morpholinoethyl)piperazine-1-carbonyl]anilino]-[1,2,4]triazolo[1,5-a]pyridin-8-yl]-3,6-dihydro-2H-pyridin-1-yl]butan-1-one |
| 2-475 | 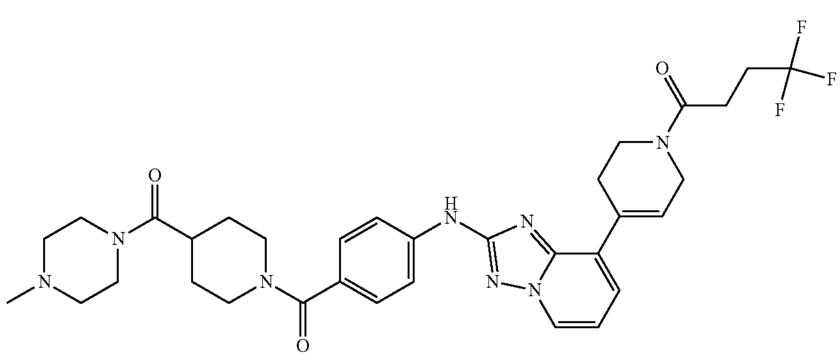 [SMILES: CN1CCN(C(=O)C2CCN(C(=O)c3ccc(Nc4nc5c(C6=CCN(C(=O)CCC(F)(F)F)CC6)cccn5n4)cc3)CC2)CC1] | 4,4,4-trifluoro-1-[4-[2-[4-[4-(4-methylpiperazine-1-carbonyl)piperidine-1-carbonyl]anilino]-[1,2,4]triazolo[1,5-a]pyridin-8-yl]-3,6-dihydro-2H-pyridin-1-yl]butan-1-one |

TABLE A-continued

Exemplary Compounds of the Present Invention

| Ex. | Structure | Name |
|---|---|---|
| 2-476 | 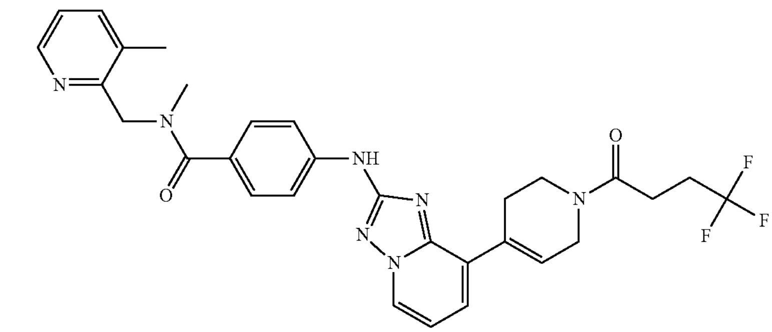 [SMILES: Cc1cccnc1CN(C)C(=O)c1ccc(Nc2nc3c(C4=CCN(C(=O)CCC(F)(F)F)CC4)cccn3n2)cc1] | N-methyl-N-[(3-methyl-2-pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-477 | 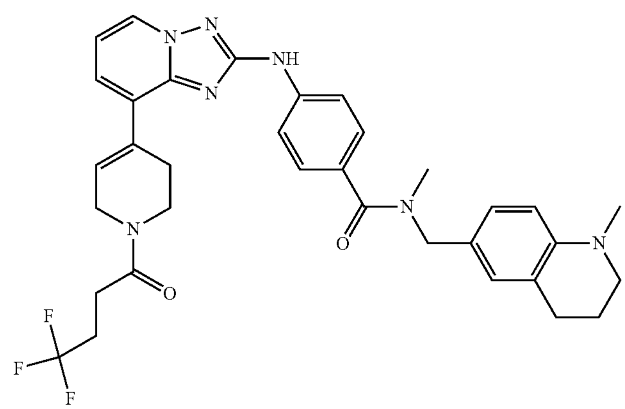 [SMILES: CN(Cc1ccc2c(c1)CCCN2C)C(=O)c1ccc(Nc2nc3c(C4=CCN(C(=O)CCC(F)(F)F)CC4)cccn3n2)cc1] | N-methyl-N-[(1-methyl-3,4-dihydro-2H-quinolin-6-yl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-478 | 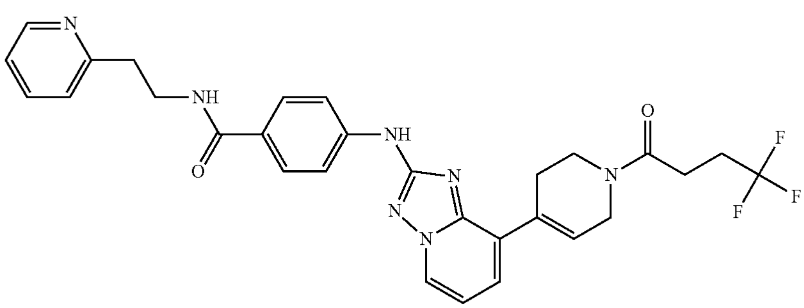 [SMILES: O=C(NCCc1ccccn1)c1ccc(Nc2nc3c(C4=CCN(C(=O)CCC(F)(F)F)CC4)cccn3n2)cc1] | N-[2-(2-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-479 | 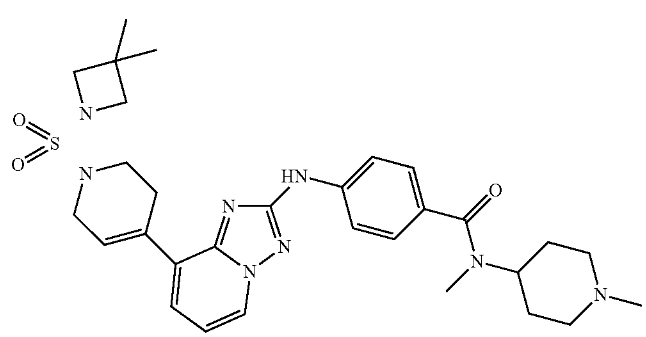 | 4-[[8-[1-(3,3-dimethylazetidin-1-yl)sulfonyl-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 2-480 | 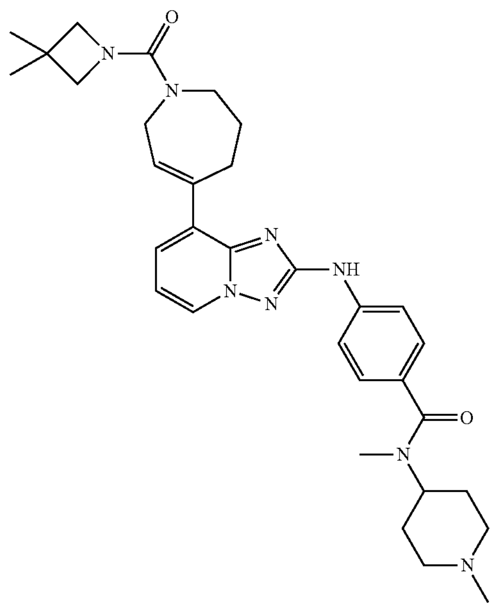 | 4-[[8-[1-(3,3-dimethylazetidine-1-carbonyl)-2,3,4,7-tetrahydroazepin-5-yl]-[1,2,4]triazolo[1,5-a]pyridin-2-yl]amino]-N-methyl-N-(1-methyl-4-piperidyl)benzamide |
| 2-481 | 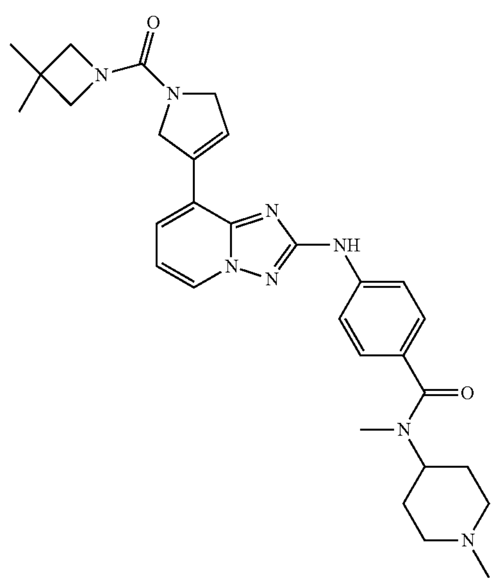 | 4-[[8-[1-(3,3-dimethylazetidine-1-carbonyl)-2,5-dihydropyrrol-3-yl]-[1,2,4]triazolo[1,5-a]pyridin-2-yl]amino]-N-methyl-N-(1-methyl-4-piperidyl)benzamide |
| 2-482 | 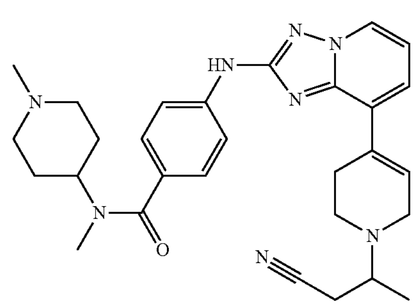 [SMILES: CC(CC#N)N1CC=C(c2cccn3nc(Nc4ccc(C(=O)N(C)C5CCN(C)CC5)cc4)nc23)CC1] | 4-[[8-[1-(2-cyano-1-methyl-ethyl)-3,6-dihydro-2H-pyridin-4-yl]-[1,2,4]triazolo[1,5-a]pyridin-2-yl]amino]-N-methyl-N-(1-methyl-4-piperidyl)benzamide |

TABLE A-continued

Exemplary Compounds of the Present Invention

| Ex. | Structure | Name |
|---|---|---|
| 2-483 | 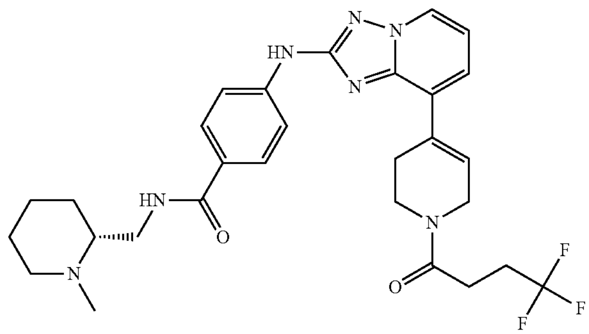 [SMILES: CN1CCCC[C@@H]1CNC(=O)c1ccc(Nc2nc3c(C4=CCN(C(=O)CCC(F)(F)F)CC4)cccn3n2)cc1] | N-[[(2R)-1-methyl-2-piperidyl]methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-484 | 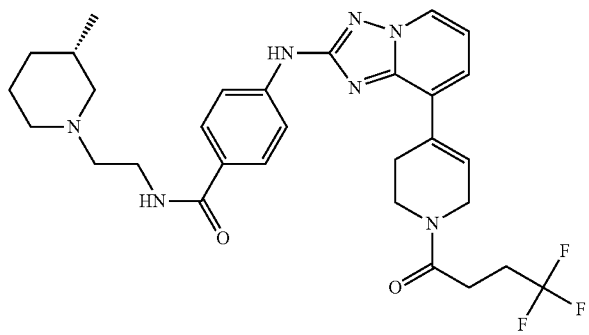 [SMILES: C[C@H]1CCCN(CCNC(=O)c2ccc(Nc3nc4c(C5=CCN(C(=O)CCC(F)(F)F)CC5)cccn4n3)cc2)C1] | N-[2-[(3S)-3-methyl-1-piperidyl]ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-485 | 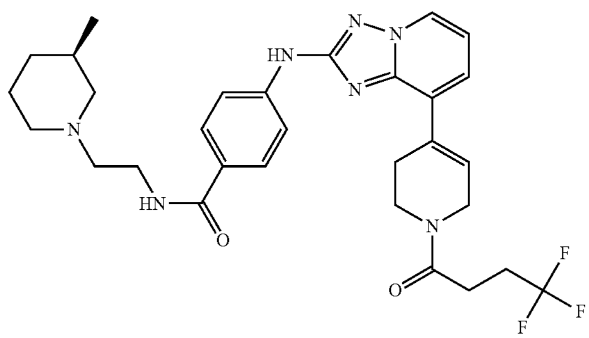 [SMILES: C[C@@H]1CCCN(CCNC(=O)c2ccc(Nc3nc4c(C5=CCN(C(=O)CCC(F)(F)F)CC5)cccn4n3)cc2)C1] | N-[2-[(3R)-3-methyl-1-piperidyl]ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide |
| 2-486 | 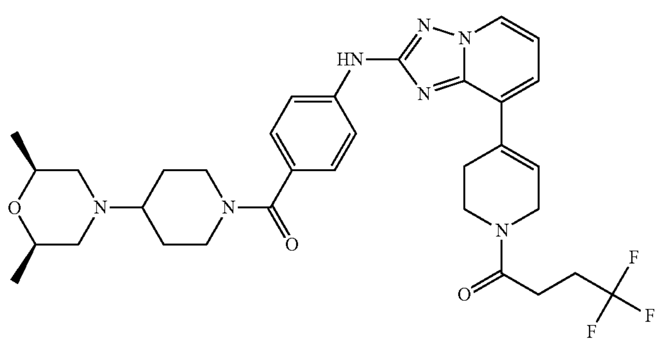 [SMILES: C[C@@H]1CN(C2CCN(C(=O)c3ccc(Nc4nc5c(C6=CCN(C(=O)CCC(F)(F)F)CC6)cccn5n4)cc3)CC2)C[C@H](C)O1] | 1-[4-[2-[4-[4-[(2R,6S)-2,6-dimethylmorpholin-4-yl]piperidine-1-carbonyl]anilino]-[1,2,4]triazolo[1,5-a]pyridin-8-yl]-3,6-dihydro-2H-pyridin-1-yl]-4,4,4-trifluoro-butan-1-one |

TABLE A-continued

Exemplary Compounds of the Present Invention

| Ex. | Structure | Name |
|---|---|---|
| 3-1 | 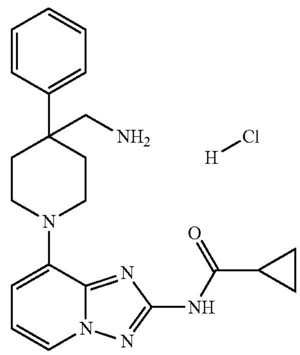 [SMILES: NCC1(c2ccccc2)CCN(c2cccn3nc(NC(=O)C4CC4)nc23)CC1 ; Cl] | N-[8-[4-(aminomethyl)-4-phenyl-1-piperidyl]-[1,2,4]triazolo[1,5-a]pyridin-2-yl]cyclopropane carboxamide; hydrochloride |

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the present invention, such as a compound of Formula 0, I, Ia, Ib, Ic, Id, Ie, If, Ig or II, or a compound of any of Examples 1-1 to 1-303, 2-1 to 2-486 or 3-1, including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—O—R—O—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of Formula 0, Formula I or Formula II. Prodrugs may be prepared by reacting a compound of the present invention, such as a compound of Formula 0, I, Ia, Ib, Ic, Id, Ie, If, Ig or II, or a compound of any of Examples 1-1 to 1-303, 2-1 to 2-486 or 3-1, with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention, such as a compound of Formula 0, I, Ia, Ib, Ic, Id, Ie, If, Ig or II, or suitable free carboxyl-containing compound of any of Examples 1-1 to 1-303, 2-1 to 2-486 or 3-1, can be derivatized as an amide or alkyl ester. As another example, compounds of the present invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_1$-$C_6$)alkanoyl oxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, alpha-amino($C_1$-$C_4$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

Synthesis of Janus Kinase Inhibitor Compounds

Compounds of the present invention may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or Comprehensive Heterocyclic Chemistry, Editors Katrizky and Rees, Pergamon Press, 1984.

Compounds may be prepared singly or as compound libraries comprising at least 2, for example 5 to 1,000 compounds, or 10 to 100 compounds. Libraries of compounds may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of the present invention, such as a compound of Formula 0, I, Ia, Ib, Ic, Id, Ie, If, Ig or II, or a compound of any of Examples 1-1 to 1-303, 2-1 to 2-486 or 3-1.

For illustrative purposes, reaction Schemes 1-24 depicted below provide routes for synthesizing the compounds of the present invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, benzyl, phenylsulfonyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Other conversions commonly used in the synthesis of compounds of the present invention, and which can be carried out using a variety of reagents and conditions, include the following:

(1) Reaction of a carboxylic acid with an amine to form an amide. Such a transformation can be achieved using various reagents known to those skilled in the art but a comprehensive review can be found in *Tetrahedron*, 2005, 61, 10827-10852.

(2) Reaction of a primary or secondary amine with an aryl halide or pseudo halide, e.g., a triflate, commonly known as a "Buchwald-Hartwig cross-coupling," can be achieved using a variety of catalysts, ligands and bases. A review of these methods is provided in *Comprehensive Organic Name Reactions and Reagents*, 2010, 575-581.

(3) A palladium cross-coupling reaction between an aryl halide and a vinyl boronic acid or boronate ester. This transformation is a type of "Suzuki-Miyaura cross-coupling," a class of reaction that has been thoroughly reviewed in *Chemical Reviews*, 1995, 95(7), 2457-2483.

(4) The hydrolysis of an ester to give the corresponding carboxylic acid is well known to those skilled in the art and conditions include: for methyl and ethyl esters, the use of a strong aqueous base such as lithium, sodium or potassium hydroxide or a strong aqueous mineral acid such as HCl; for a tert-butyl ester, hydrolysis would be carried out using acid, for example, HCl in dioxane or trifluoroacetic acid (TFA) in dichloromethane (DCM).

Scheme 1 provides details of the reactions available for the preparation of compounds of the invention wherein $R^2$ of Formula 0 is of type (a). Compound (1-3) can be prepared from 3-bromo-2-aminopyridine (1-1) according to WO2009/155551, incorporated herein by reference, and may undergo a Buchwald-Hartwig cross-coupling reaction with an aryl halide, an example of which would be ethyl 4-iodobenzoate, using a catalyst such as tris(dibenzylideneacetone)dipalladium (0) ($Pd_2(dba)_3$) or palladium (II) acetate ($Pd(OAc)_2$), a phosphine ligand such as 4,5-bis(diphenylphosphino)-9,9-dimethylxanthene (Xantphos) and a base such as caesium carbonate. Where (1-1) has additional substituents in the pyridine ring, a compound (1-3) having additional substitution in the 6-membered ring can be prepared. A wide range of substituted 3-bromo-2-aminopyridines are known in the literature and are commercially available and the preparations of compounds (i), (ii) and (iii) from the corresponding substituted 3-bromo-2-aminopyridine, using analogous chemistry to that shown for (1-3) in Scheme 1, are described in WO2011/092272, WO2010/141796 and WO2010/141796, respectively, each incorporated herein by reference.

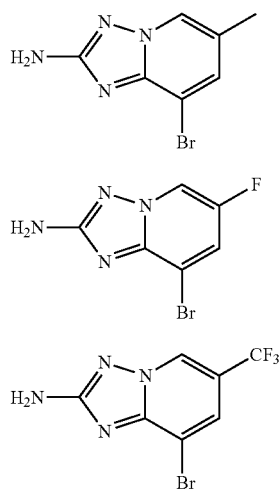

An ester (1-4) can be hydrolysed to the corresponding carboxylic acid (1-5) using standard conditions which would be dependent upon the particular ester group present. An amide (1-6) may be formed from (1-5) using an amine $R^1R^2NH$ under standard coupling conditions, for example using (O-(7-azabenzotriazol-1-yl)-N,N,N',N'-tetramethyluronium hexafluorophosphate) (HATU) in the presence of a base such as N,N-diisopropylethylamine (DIPEA). Intermediate (1-6) may also be prepared directly from (1-3) and amide (1-7) using the same chemistries in an alternative sequence. Compound (1-6) may then be converted into (1-9) by reaction with a cyclic secondary amine (1-8) via a Buchwald-Hartwig cross-coupling using a palladium catalyst such as $Pd_2(dba)_3$ and a suitable ligand such as Xantphos in the presence of a base providing structures of Formula 0 with $R^2$ being of type (a). Alternatively, ester (1-4) may undergo a palladium catalysed amination with (1-8) to give (1-10). The ester moiety in (1-10) may then be hydrolysed under standard conditions to give an acid (1-11) which then may be reacted with an amine $R^1R^2NH$ to give a compound (1-9).

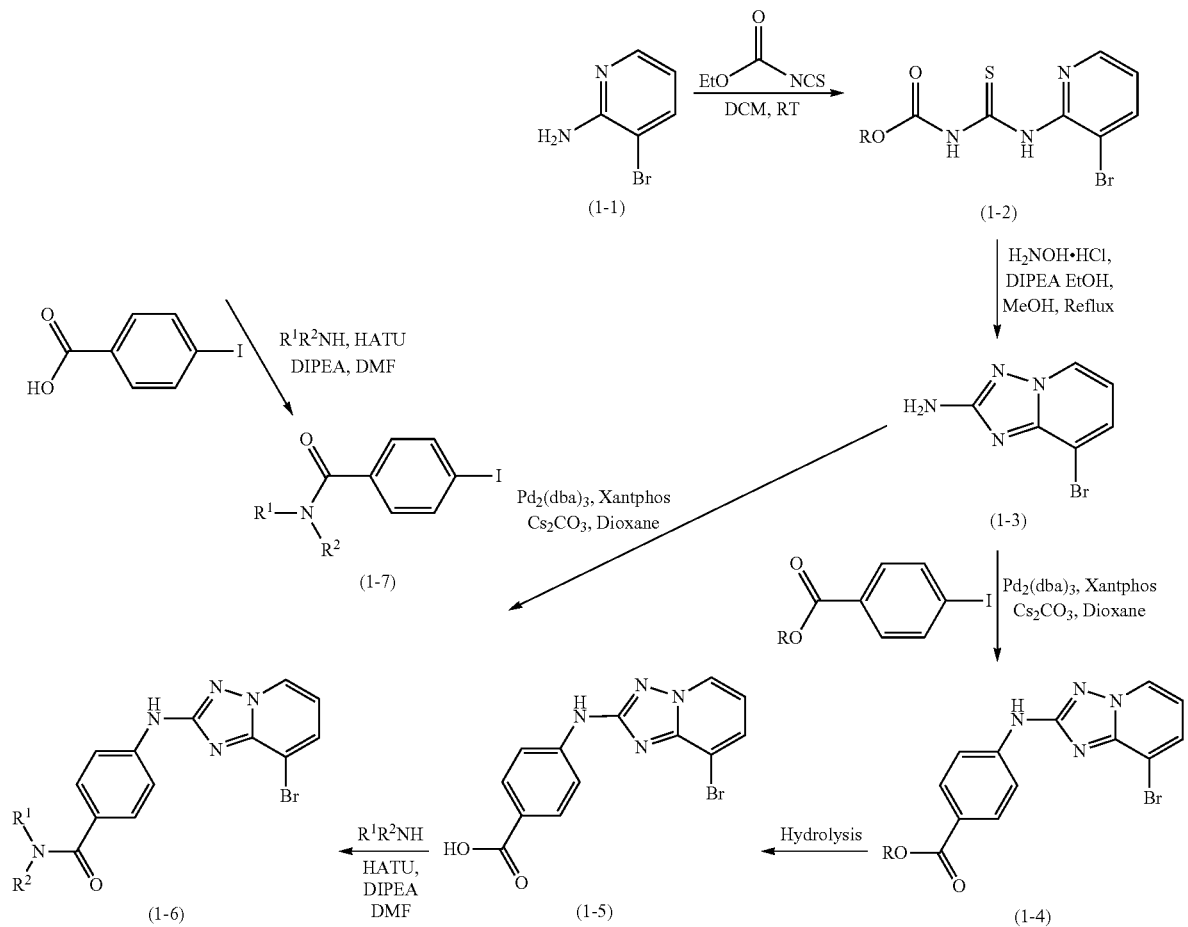

Scheme 1

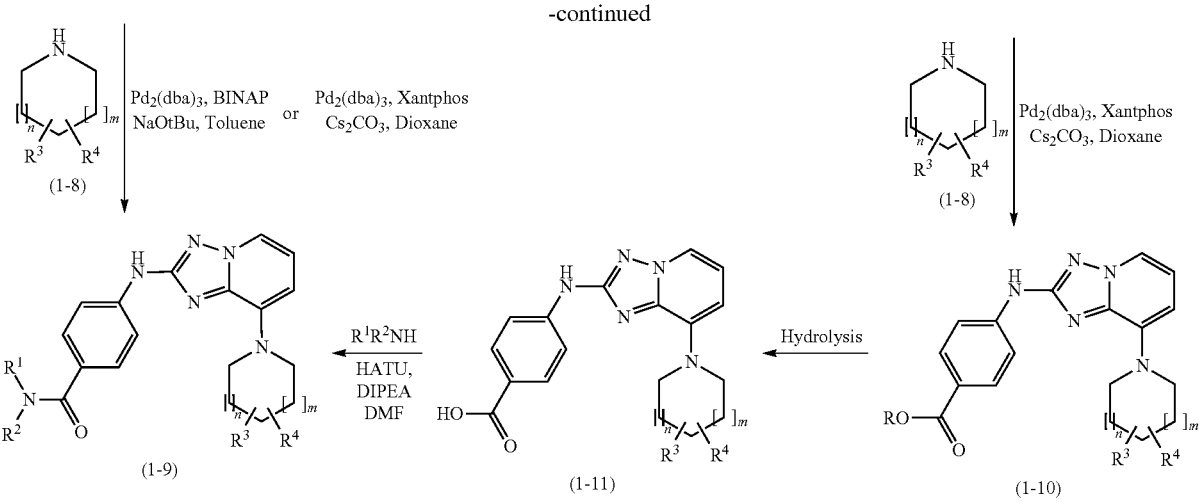

In Scheme 1, $R^3$ or $R^4$ may be further elaborated. For example, in Scheme 2, where $R^4$ is $CH_2CN$ (2-1), the nitrile group may be converted into the corresponding primary amide (2-2). Reagents suitable for this conversion include acetaldoxime in the presence of palladium (II) acetate and triphenylphosphine. The nitrile group in (2-1) may also be hydrolysed to the corresponding carboxylic acid (2-3) which in turn can be treated with an amine $R^4R^5NH$ under standard amidation conditions to provide compounds of type (2-4).

Scheme 2

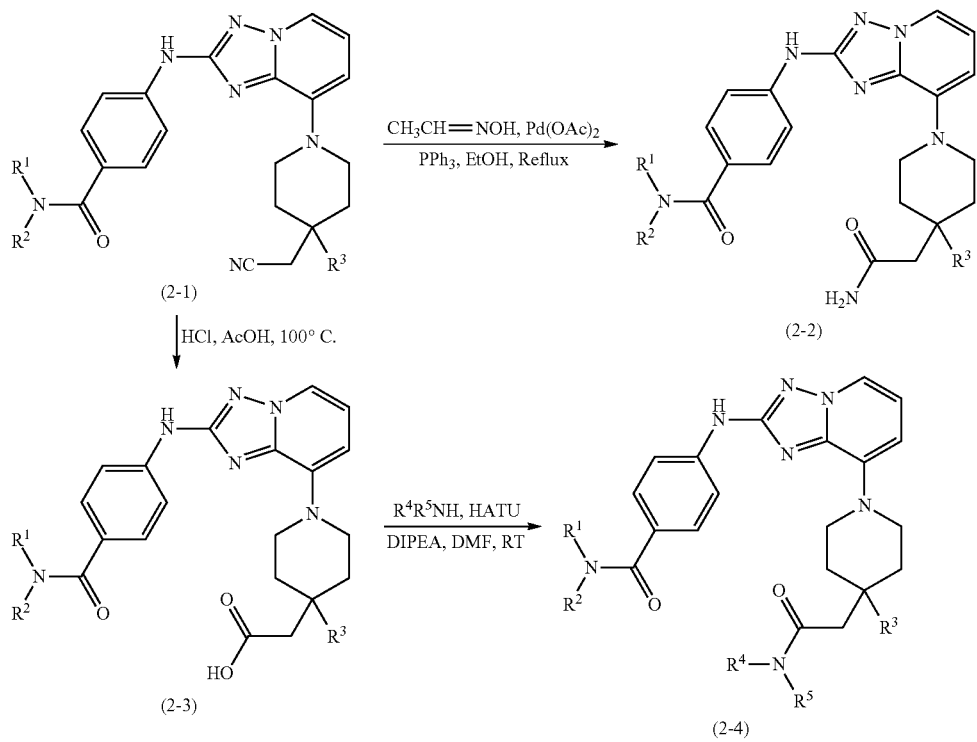

Where $R^4$ in the compounds of Scheme 1 is an ester, exemplified by structure (3-1) of Scheme 3, this group may be hydrolysed under standard conditions to give an acid of type (3-2). Common amidation conditions may then be used to prepare an amide (3-3) from (3-2) and a suitable amine $R^3R^4NH$.

Scheme 3

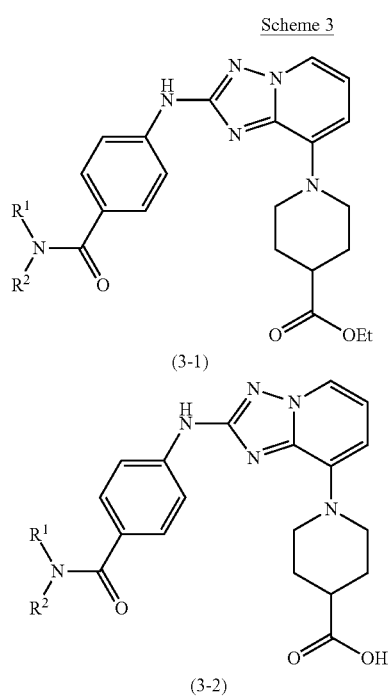

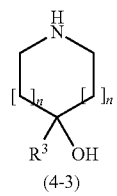

(4-3)

Pg = e.g. CBz, Bn, Boc

Schemes 5 to 8 and 18 to 24 describe the methods that can be used to prepare other cyclic secondary amines (1-8), of Scheme 1, which are required for preparation of examples where the required amine (1-8) is hitherto unknown in the scientific literature. The methods use standard reactions known to those skilled in the art.

Scheme 5 provides a preparation of 1-oxa-3,7-diazaspiro[4.4]nonan-2-one (5-4). Starting with the commercially available aminoalcohol (5-1), reaction with triphosgene, or one of its equivalents, followed by removal of the benzyl group by catalytic hydrogenation can provide (5-3).

Scheme 5

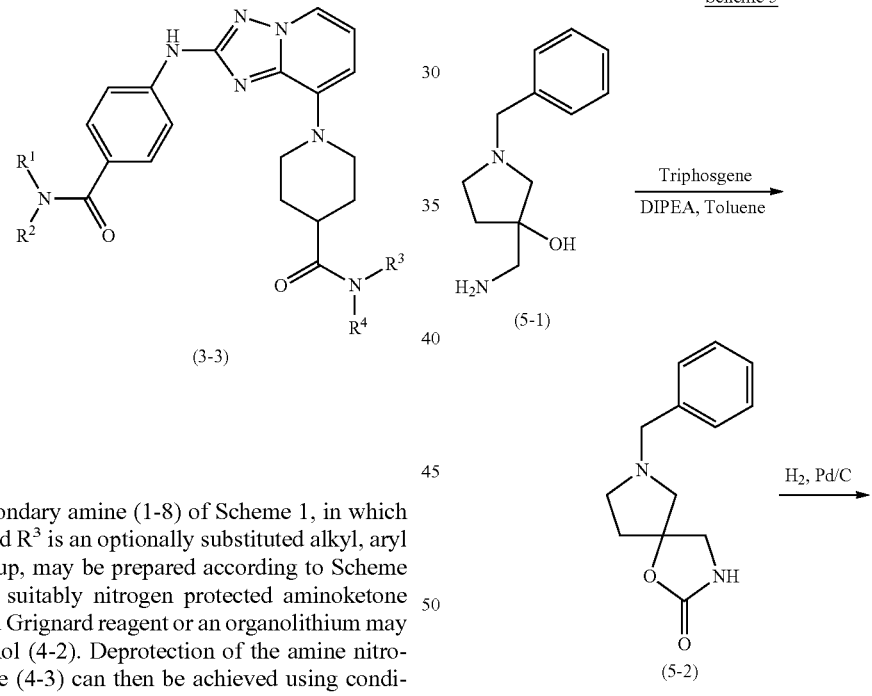

The cyclic secondary amine (1-8) of Scheme 1, in which $R^4$ is hydroxyl and $R^3$ is an optionally substituted alkyl, aryl or heteroaryl group, may be prepared according to Scheme 4. Reaction of a suitably nitrogen protected aminoketone (4-1) with either a Grignard reagent or an organolithium may provide the alcohol (4-2). Deprotection of the amine nitrogen to give amine (4-3) can then be achieved using conditions designed to remove the protecting group of choice.

Scheme 6 describes routes to secondary amines (1-8) of Scheme 1 in which $R^3$ is phenyl or substituted phenyl and $R^4$ is either cyano (6-6) or hydroxymethyl (6-5). Treatment of a cyanomethylbenzene with a base such as sodium hydride and subsequent reaction of the resultant anion with commercially available (6-1) may provide (6-2). The deprotection of (6-2) under acidic conditions gives amine (6-6). Reduction of the nitrile in intermediate (6-2), using diisobutylaluminium hydride for example, affords the aldehyde (6-3) which may be further reduced to the alcohol (6-4) by treatment with sodium borohydride. Boc deprotection will give the amine (6-5).

Scheme 4

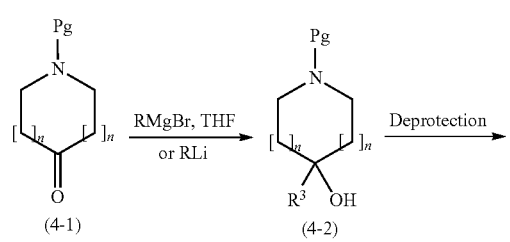

Scheme 6

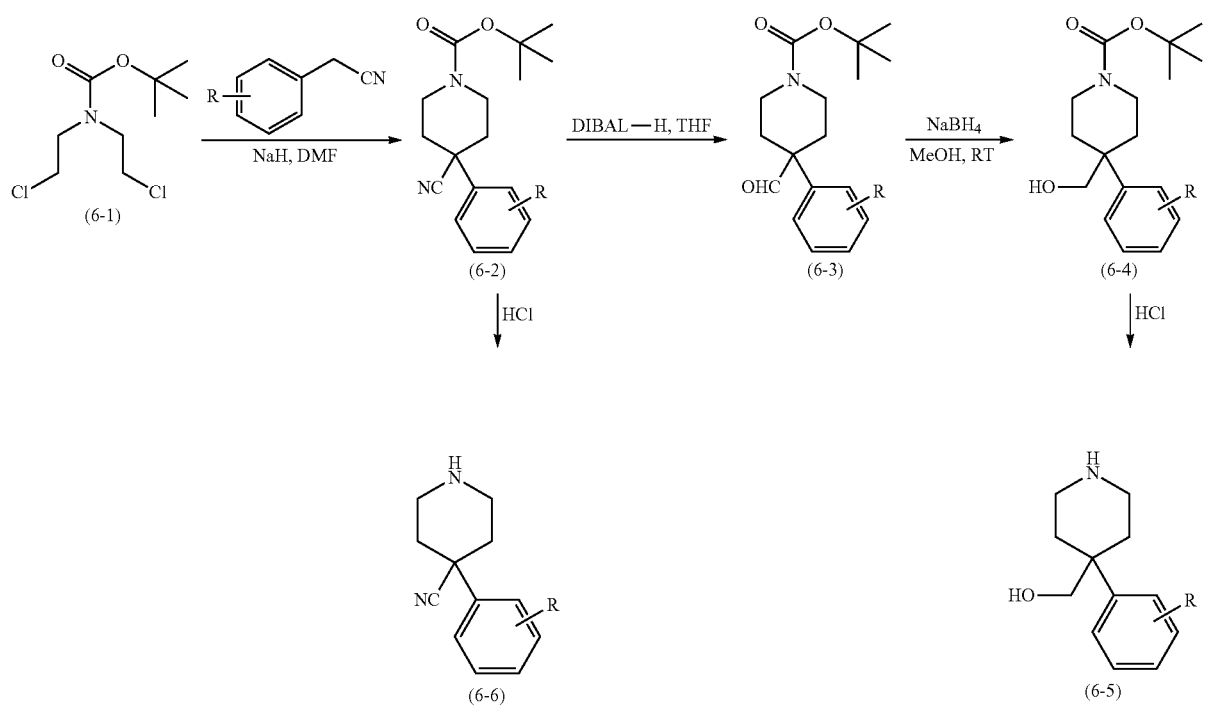

Scheme 7 shows methods that can be used to prepare a secondary amine (1-8) of Scheme 1 in which R³ is hydrogen and R⁴ is 2-(2-methoxyethoxy)pyridin-4-ylmethoxy (7-4). Treatment of Boc-protected 4-piperidinol (7-2) with a base such as potassium tert-butoxide, and reaction with commercially available 4-(chloromethyl)-2-(2-methoxyethoxy)pyridine (7-1) in the presence of an iodide source such as terabutylammonium iodide gives (7-3). Treatment of the latter with acid leads to Boc deprotection and provides amine (7-4)

-continued

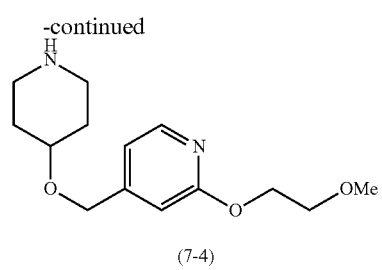

Scheme 7

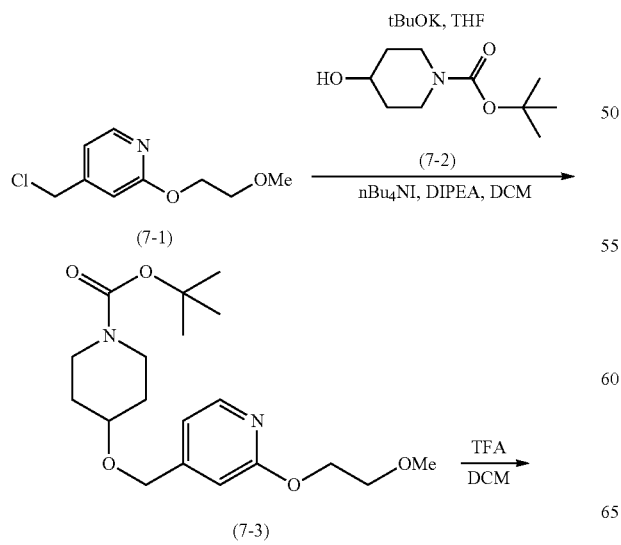

Scheme 8 describes routes to amines 1-8 from Scheme 1 in which R³ is a phenyl or substituted phenyl and R⁴ is either cyanomethyl (8-6), hydroxyethyl (8-9) or cyanoethyl (8-12). The synthesis of intermediates of type (8-5) is described in Journal of Medicinal Chemistry, 2011, 54 (11), 3756-3767 and Boc deprotection can be achieved by treatment with acid. Reduction of the nitrile in (8-5) firstly to the aldehyde (8-7) using diisobutylaluminium hydride and then to the alcohol (8-8) with sodium borohydride provides (8-8) which can be Boc-deprotected in acid to give (8-9). Conversion of the alcohol (8-8) into the corresponding methanesulfonate ester (8-10) and subsequent reaction with a cyanide source such as sodium cyanide provides (8-11). Boc-deprotection of (8-11) results in the formation of amine (8-12).

Scheme 8
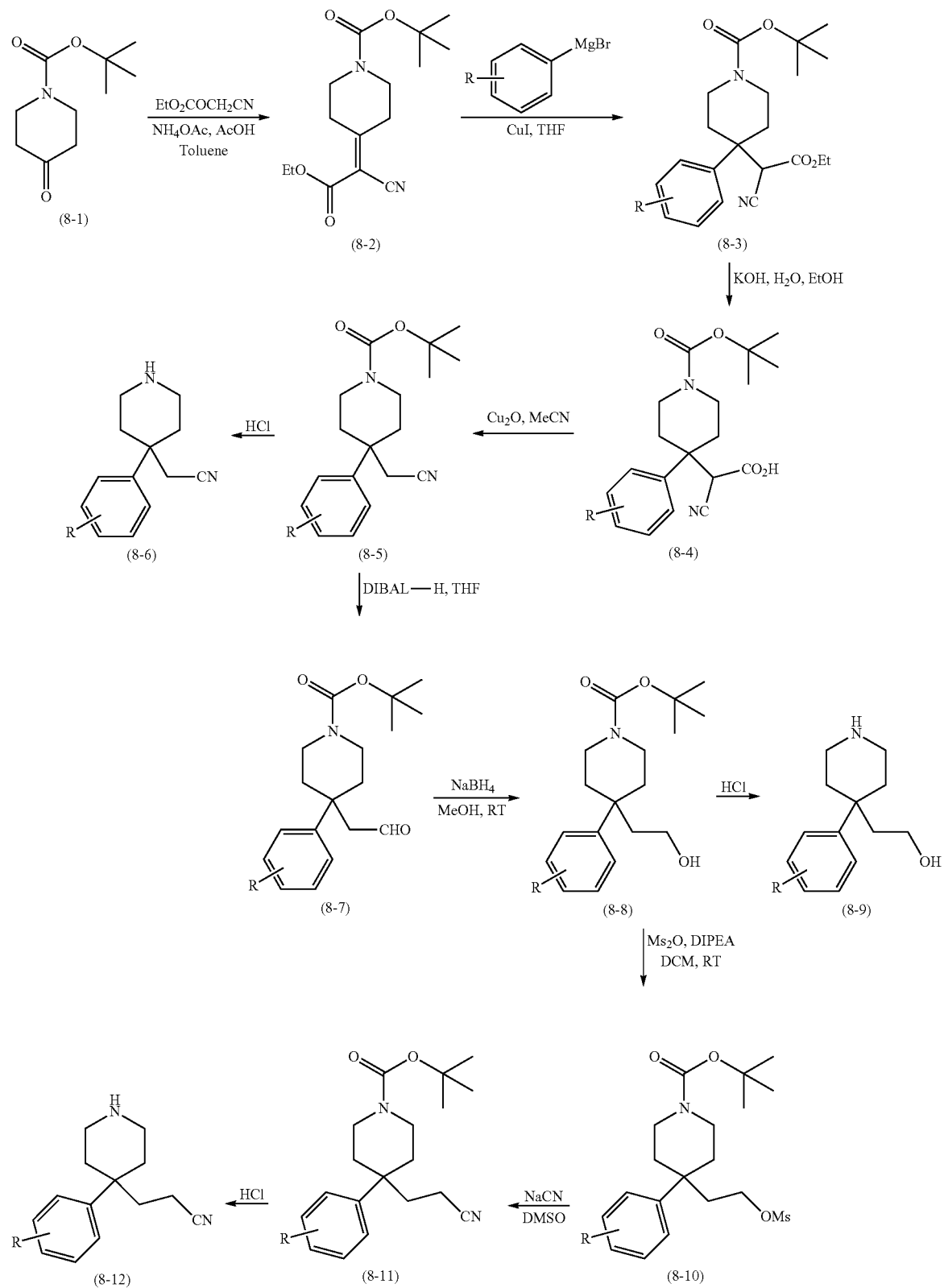

Analogous chemistries to those described in Scheme 1 may be used prepare compounds of the invention wherein $R^2$ of Formula 0 is of type (b) by replacing the cyclic secondary amine (1-8) with an amine of type (iv). Here, $R^3/R^4$ may be modified further using standard chemistries.

protecting group, it may be removed under standard conditions and the resulting amine (9-6) may be further modified through alkylation, arylation, acylation, sulfonylation etc.

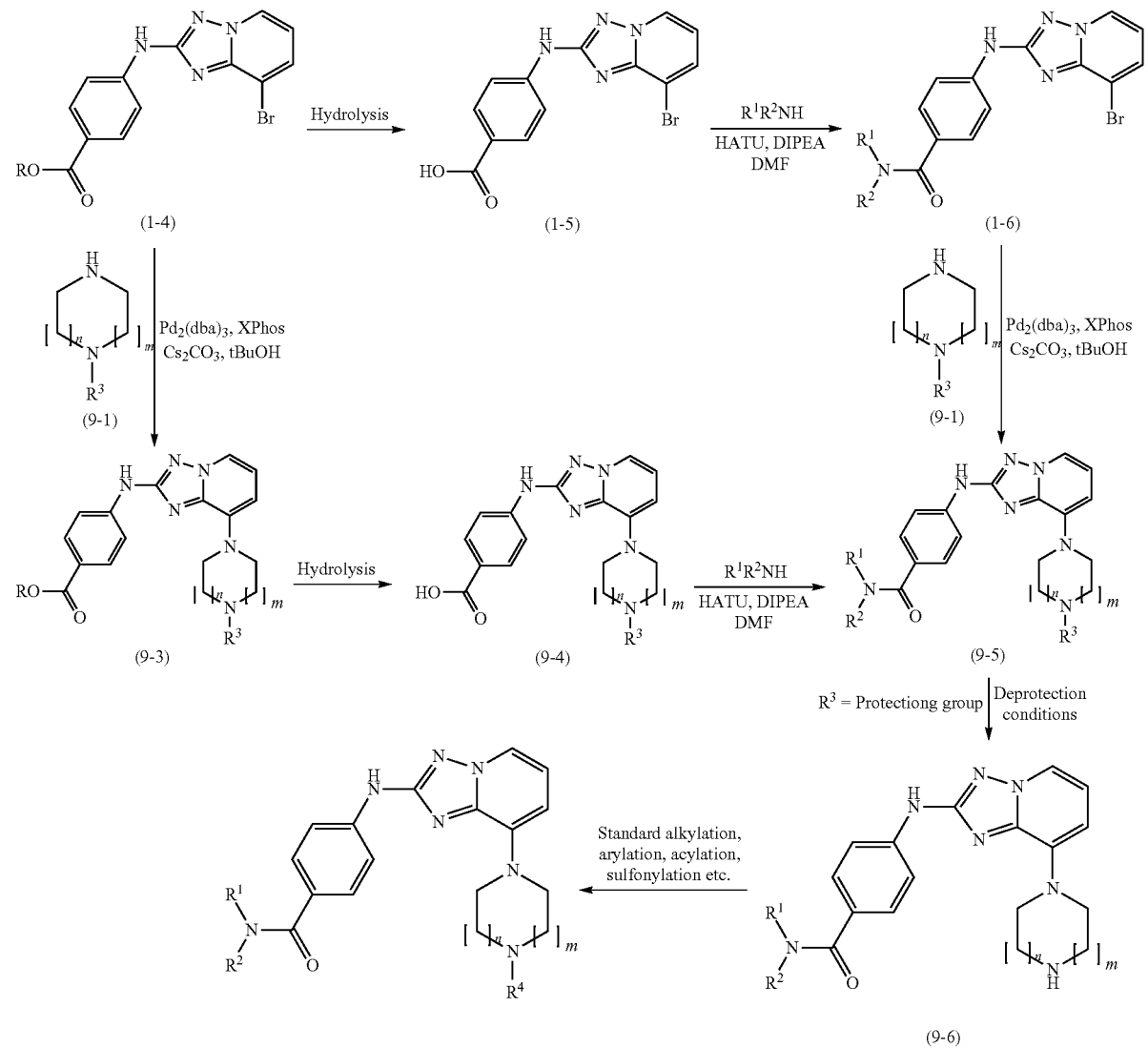

Scheme 9

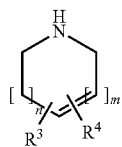

(iv)

Scheme 9 indicates how other compounds of the invention may be prepared wherein $R^2$ of Formula 0 is of type (d). Ester (1-4) or amide (1-6) from Scheme 1 may undergo a palladium catalysed Buchwald-Hartwig cross-coupling with a diamine (9-1). Where $R^3$ in (9-5), or indeed (9-3), is a Scheme 10 indicates how other compounds of the invention may be prepared wherein $R^2$ of Formula 0 is of type (c). Either ester (1-4) or amide (1-6) from Scheme 1 may be reacted with a suitable boronate ester or boronic acid in a Suzuki-Miyaura cross-coupling reaction. An example of a palladium catalyst that may be useful in such a transformation would be bis(triphenylphosphine)palladium (II) dichloride ($Pd(PPh_3)_2Cl_2$). Where $R^3$ in intermediate (10-2) or (10-5) is a protecting group, it may be removed under standard conditions to give amines (10-3) and (10-6), respectively. The latter may be further modified using standard chemistries, examples of which are given in Scheme 11. The ester may later be converted into an amide if required.

Scheme 10

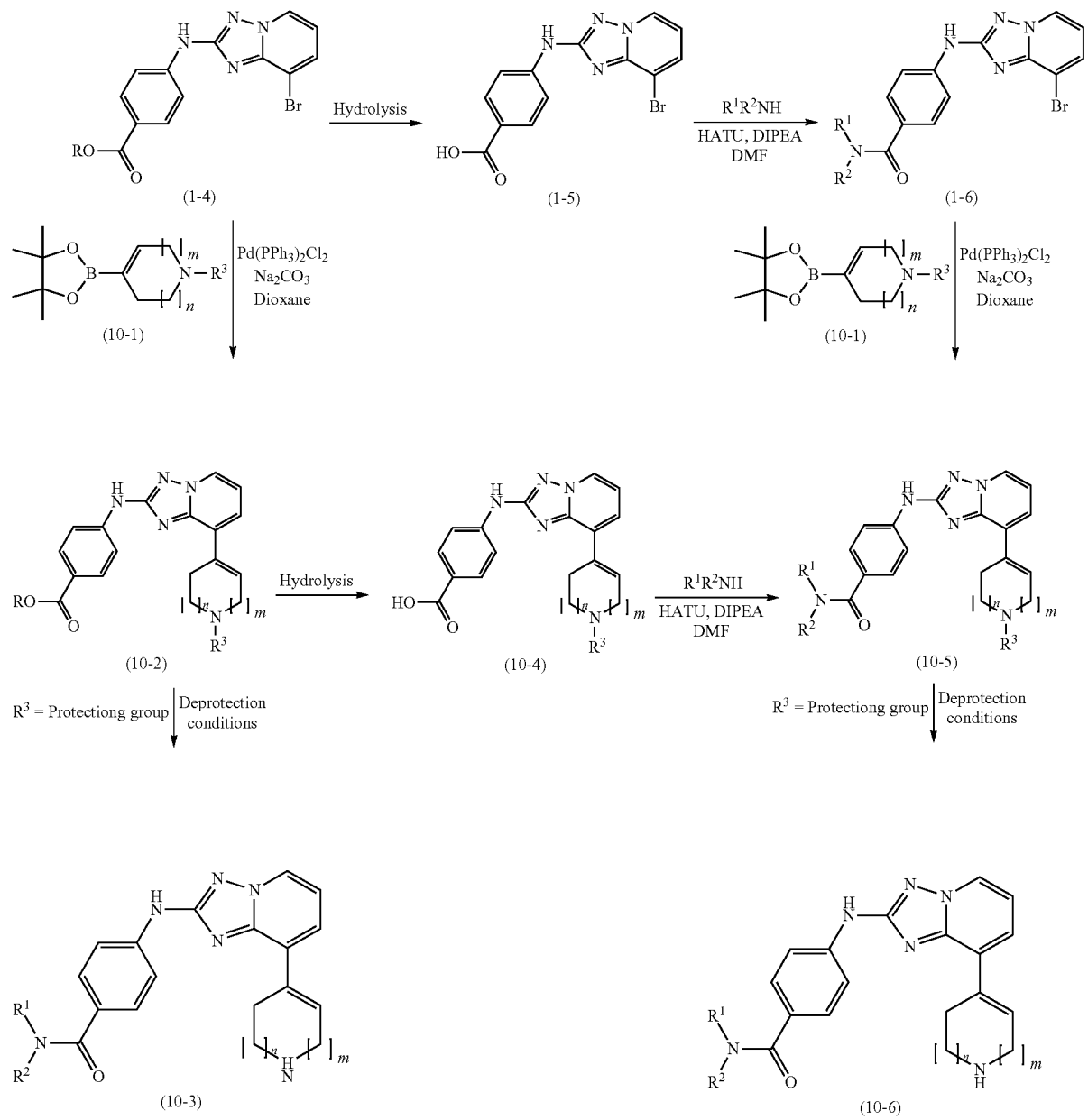

By hydrogenation of the double bond in either compound (10-3) or (10-6), or in the preceding intermediates (10-2), (10-4) and (10-5) of Scheme 10, other compounds of the invention may be prepared wherein $R^2$ of Formula 0 is of type (e). The amine (11-1) in Scheme 11 may be further modified using standard acylation, alkylation, arylation and sulfonylation chemistries. These specifically include: (i) Reaction with a chloroformate in the presence of a base such as triethylamine to give the corresponding carbamate; (ii) Alkylation with an alkyl halide in the presence of a base or reductive alkylation using an aldehyde or ketone and a reducing agent such as sodium triacetoxyborohydride; (iii) Acylation by reaction with a carboxylic acid and an amide coupling agent such as HATU or by reaction with an acid chloride in the presence of a base; (iv) Hydrogenation using hydrogen gas over a palladium catalyst; (v) Formation of an activated carbamate by reaction with 4-nitrophenyl chloroformate and then further reaction with an amine to form a urea; (vi) Arylation using an arylboronic acid or boronate ester in the presence of copper (II) acetate; (vii) Formation of a sulphonamide by reaction with a sulfonyl chloride in the presence of a base. The product of hydrogenation (11-2) can be subjected to reactions (i), (ii), (iii), (v), (vi) and (vii) in order to form compounds (11-3) wherein $R^2$ of is of type (e).

Scheme 11

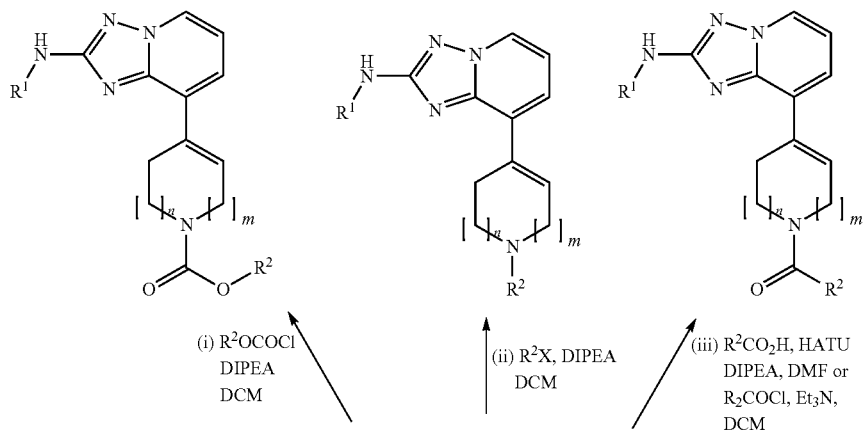

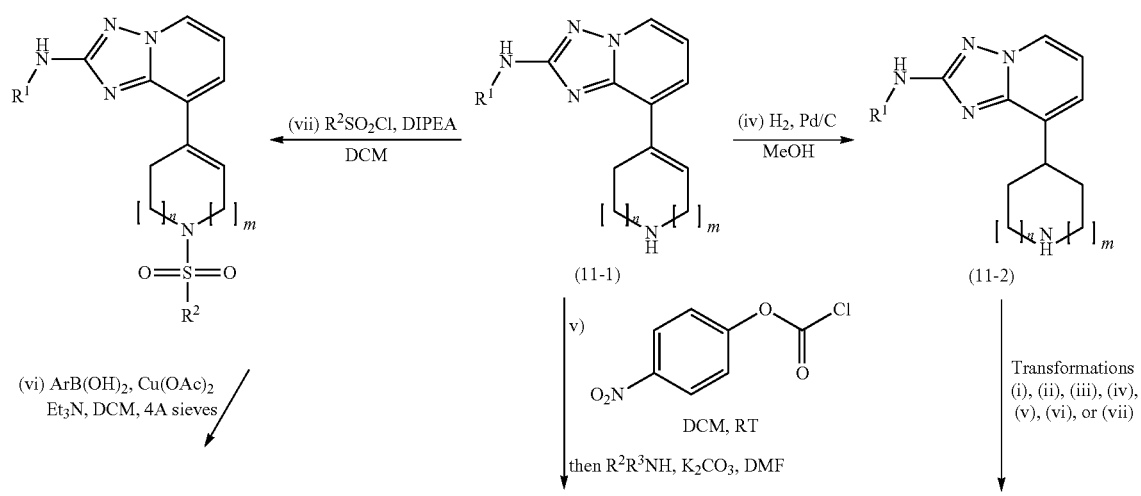

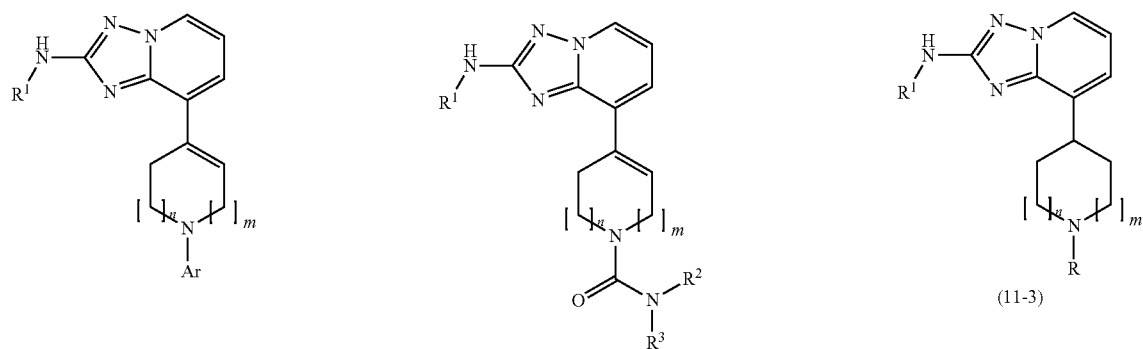

Scheme 12 indicates how other compounds of the invention may be prepared wherein $R^2$ of Formula 0 is of type (f). Either ester (1-4) or amide (1-6) from Scheme 1 may be reacted with a suitable boronate ester (12-1) or boronic acid in a Suzuki-Miyaura cross-coupling to give (12-2) and (12-4), respectively. The palladium catalyst may be for example $Pd(PPh_3)_2Cl_2$ or $Pd_2(dba)_3$ and the base may be sodium or cesium carbonate or sodium tert-butoxide. Groups $R^3$ and $R^4$ may be further modified using standard chemistries.

Scheme 12

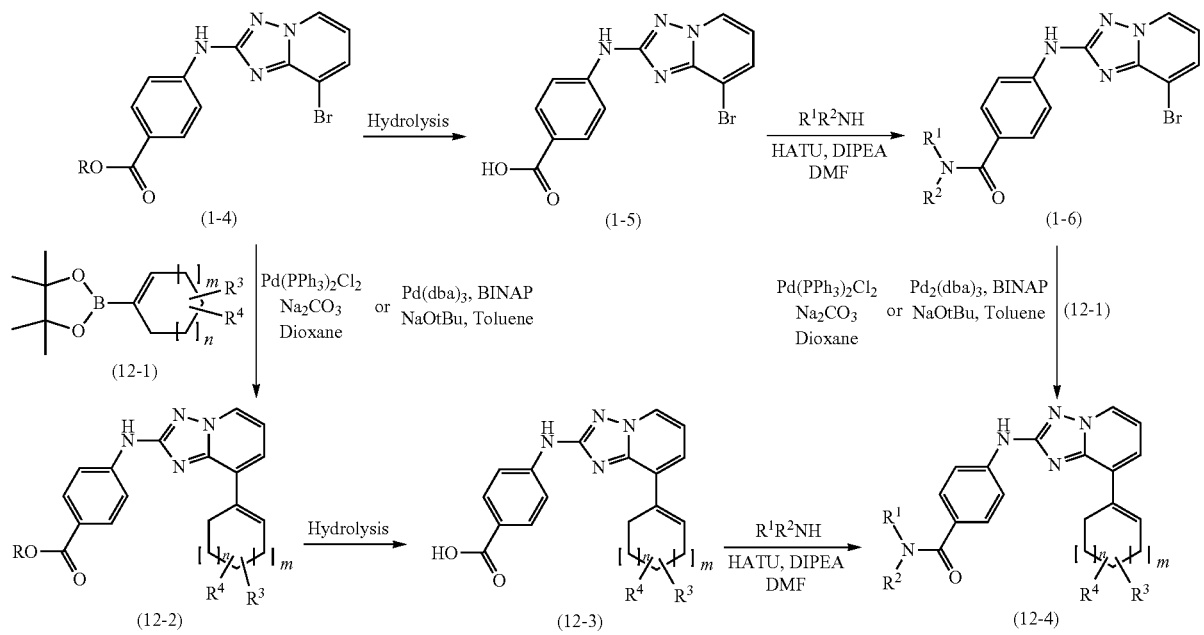

Scheme 13 shows an alternative approach available for the preparation of compounds of the invention. The Group $R^1$ may be incorporated into a 2-aminopyridine (13-1) prior to formation of the bicycle (13-3) which may then be further modified using the methodologies described herein. This method is of particular use in the synthesis of compounds of Formula 0 wherein $R^2$ is of type (g). A method for preparing compounds (13-1) from 3-bromo-2-aminopyridine is available in WO2012/020848, incorporated herein by reference.

Scheme 13

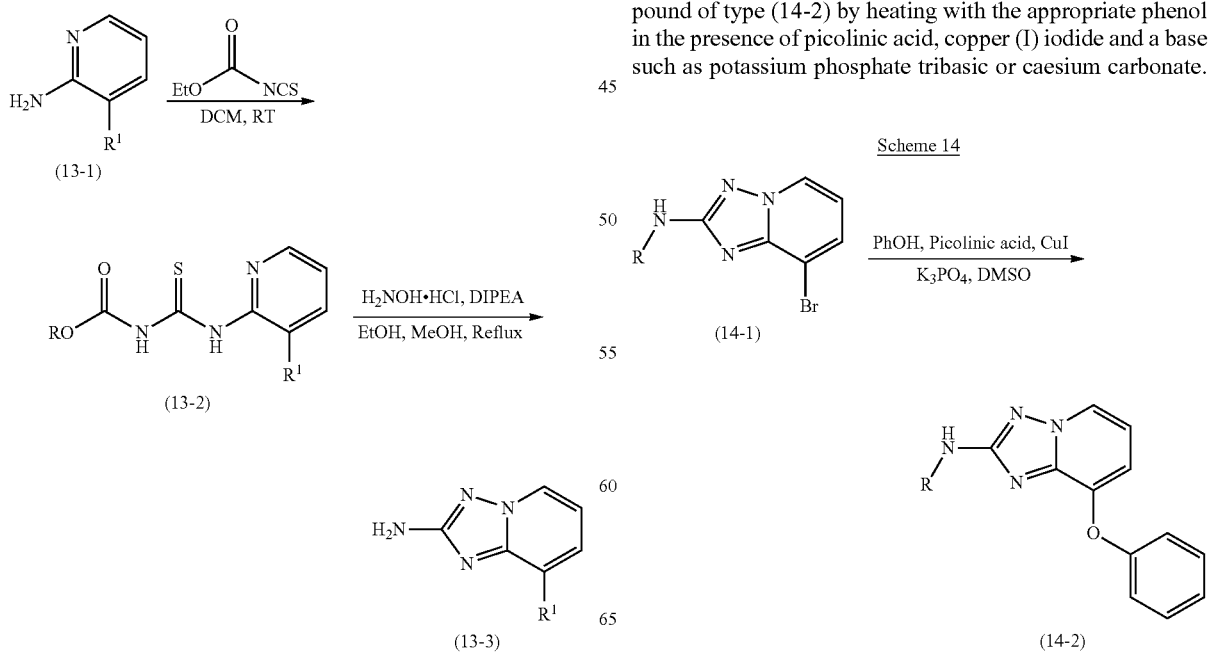

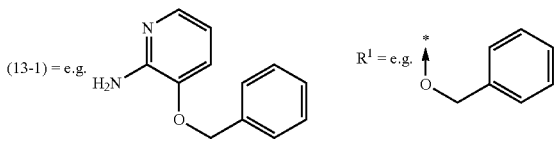

An alternative route to compounds of structure (g) wherein $R^2$ is OAr is described in Scheme 14. An intermediate (14-1) can be reacted with a phenol using a copper catalyst. Specifically, (14-1) can be converted into a compound of type (14-2) by heating with the appropriate phenol in the presence of picolinic acid, copper (I) iodide and a base such as potassium phosphate tribasic or caesium carbonate.

Scheme 14

-continued

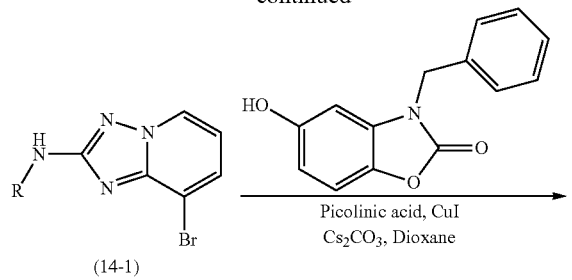

(14-1)

Picolinic acid, CuI
Cs₂CO₃, Dioxane (14-3)

During the synthesis of compounds of the invention it may be convenient to convert an intermediate carboxylic acid, exemplified by structure (15-1) in Scheme 15, into an ester (15-2) wherein $R^2$ is different to that present in the original intermediate (1-5) of Scheme 1. This can be achieved using standard esterification protocols such as the use of EDC in combination with HOBt as shown in Scheme 15.

Scheme 15

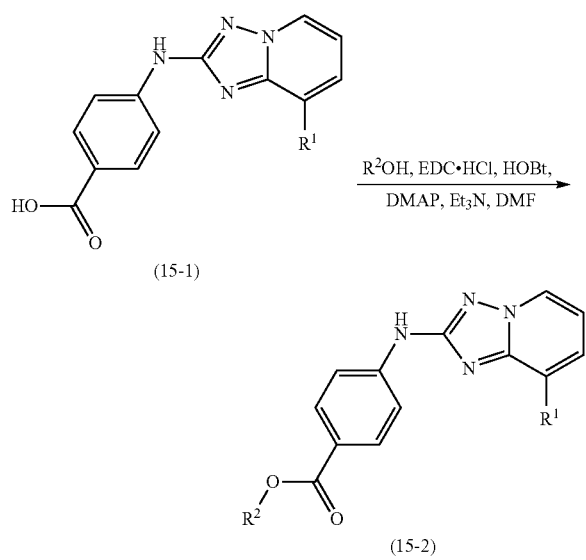

(15-1)

$R^2$OH, EDC·HCl, HOBt,
DMAP, Et₃N, DMF (15-2)

Analogous chemistries to those described in Scheme 1 to 15 may be used prepare compounds of the invention wherein $R^2$ of Formula 0 is of type (b) by replacing the cyclic analogues where $Ar^1$ present in Formula 0 is replaced by a 1,3 or 1,2-disubstituted phenyl or a di-substituted heteroaryl group.

An alternative method for the introduction of an aryl or heteroaryl ring $Ar^1$ in structure (I) is given in Scheme 16. In this case, the 8-substituted [1,2,4]triazolo[1,5-a]pyridin-2-ylamine (1-3) from Scheme 1 may be converted into the 2-iodo analogue (16-1) via the diazonium salt which is formed in situ by the action of sodium nitrite and p-toluenesulfonic acid and which is converted into (16-1) by potassium iodide. Intermediate (16-1) can then undergo a Buchwald-Hartwig cross-coupling with an aryl or heteroaryl amine. One such example of the latter would be aminopyrazole (16-2).

Scheme 16

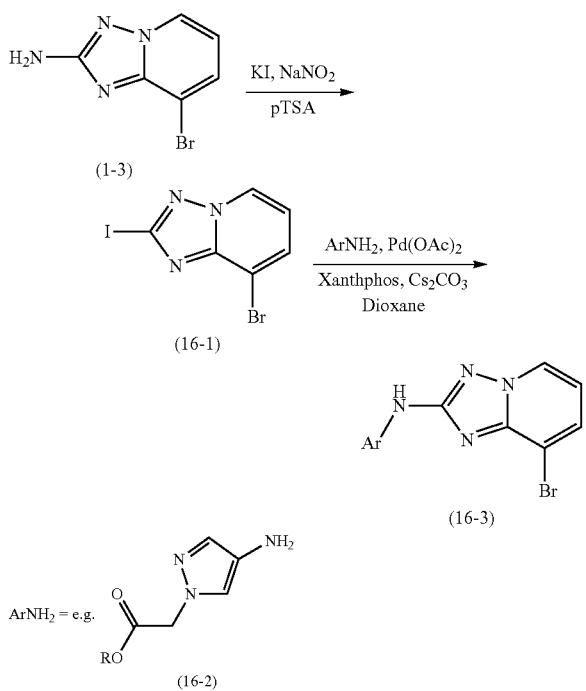

Reaction of Intermediate (1-3) from Scheme 1 with an acid chloride such as cyclopropanecarbonyl chloride in the presence of pyridine may give rise to key intermediate (17-1) for the preparation of compounds of Formula (II) as described in Scheme 17. Analogous chemistries to those described in Schemes 1 to 15 may be used to further elaborate the bromo substituent into groups $Q^1$ of Formula (II).

Scheme 17

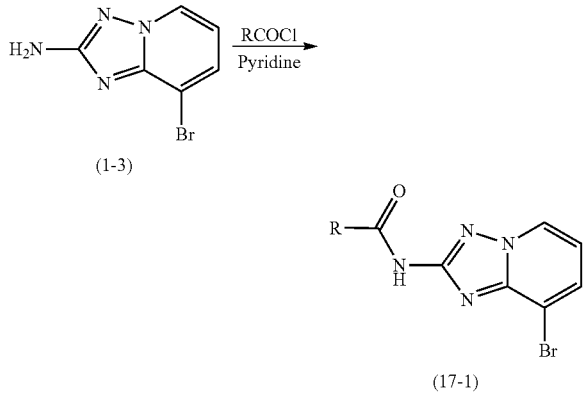

Scheme 18 describes routes to amines 1-8 from Scheme 1 in which $R^3$ is a phenyl or substituted phenyl and $R^4$ is methyl acetamido. Reduction of the nitrile (6-2) using a metal catalyzed reduction under an atmosphere of hydrogen with a reagent such as Raney Nickel may be used to afford the methylamino intermediate (18-1) which may be protected as the acetamide using acetic anhydride and a base to afford acetamide intermediate (18-2). Boc deprotection under standard acidic conditions may be used to afford the amine (18-3).

Scheme 18

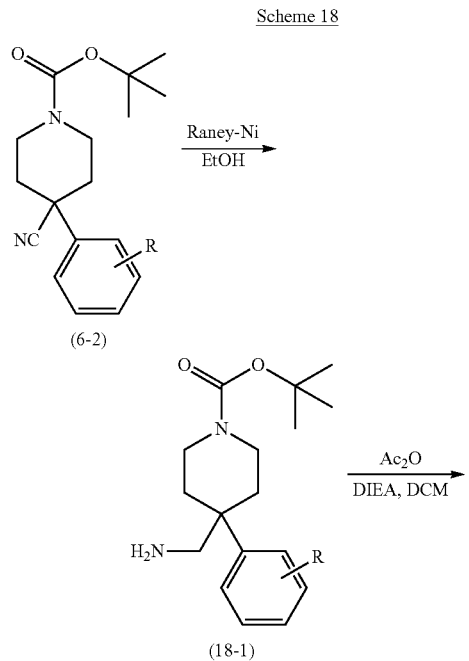

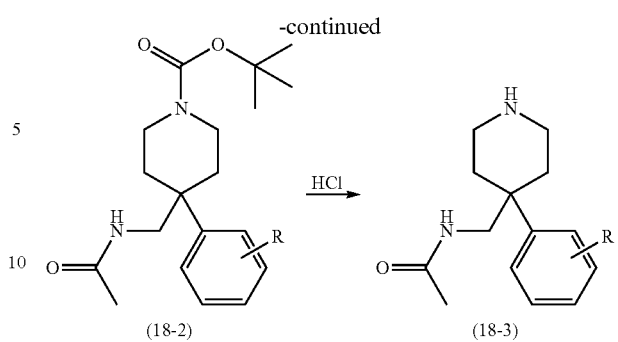

Scheme 19 describes routes to amines 1-8 from Scheme 1 in which $R^3$ is ethyl-(2,2,2-trifluoroethyl)amine and $R^4$ is hydroxymethyl. Deprotonation adjacent to the nitrile of commercially available (19-1), using a base such as LDA, followed by treatment with BOM-Cl affords the benzyloxy intermediate (19-2). The nitrile of intermediate (18-2) may be reduced to the aldehyde (18-3) using a suitable reducing agent such as DIBAl-H. The aldehyde may then be converted to the amine (18-4) using trifluoroethylamine and a reducing agent such as sodium cyanoborohydride. Hydrogenation of the benzyloxy intermediate (19-4) using palladium catalysis under an atmosphere of hydrogen may be used to prepare the hydroxymethyl intermediate (19-5). Removal of the Boc protecting group under standard conditions may be used to give the amine (19-6).

Scheme 19

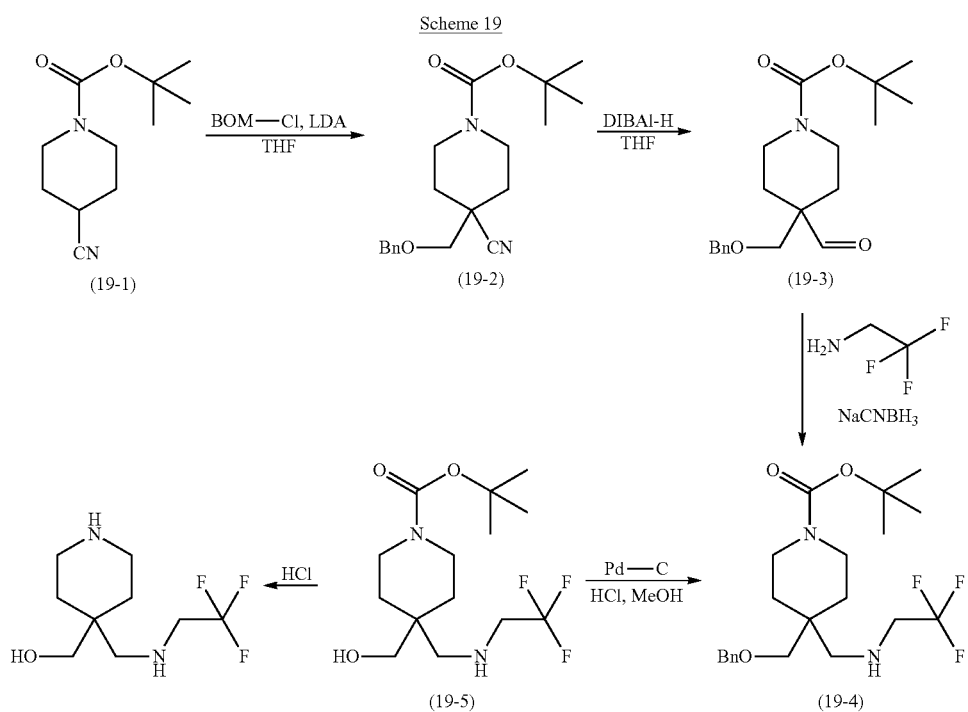

Scheme 20 describes routes to amines 1-8 from Scheme 1 in which $R^3$ is a 4-difluoromethyl substituted phenyl and $R^4$ is hydroxymethyl. Treatment of commercially available 4-bromobenzylcyanide with a base such as sodium hydride and reaction of the resultant anion with the commercially available alkylating agent (6-1) may be used to prepare intermediate (20-1). The ester (20-2) may be prepared from Intermediate (20-1) using a carbonylation reaction with a palladium catalyst such as Pd(dppf)Cl$_2$ under an atmosphere of carbon monoxide. Reduction of the ester in intermediate (20-2) using, for example, DIBAl-H affords the alcohol (20-3) which may then be oxidized to the aldehyde (20-4) using an oxidant such as DMP. The aldehyde of (20-4) may be converted to the difluoromethyl intermediate (20-5) using a reagent such as DAST. Reduction of the nitrile in Intermediate (20-5), using DIBAl-H for example, may afford the aldehyde (20-6) which may be further reduced to the alcohol (20-7) by treatment with sodium borohydride. Boc deprotection under standard conditions may be used to prepare the amine (20-8).

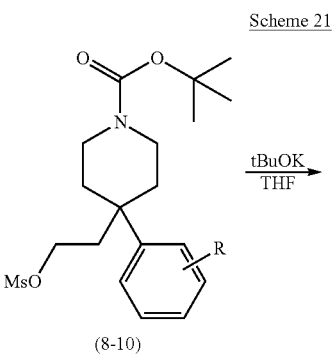

Scheme 21

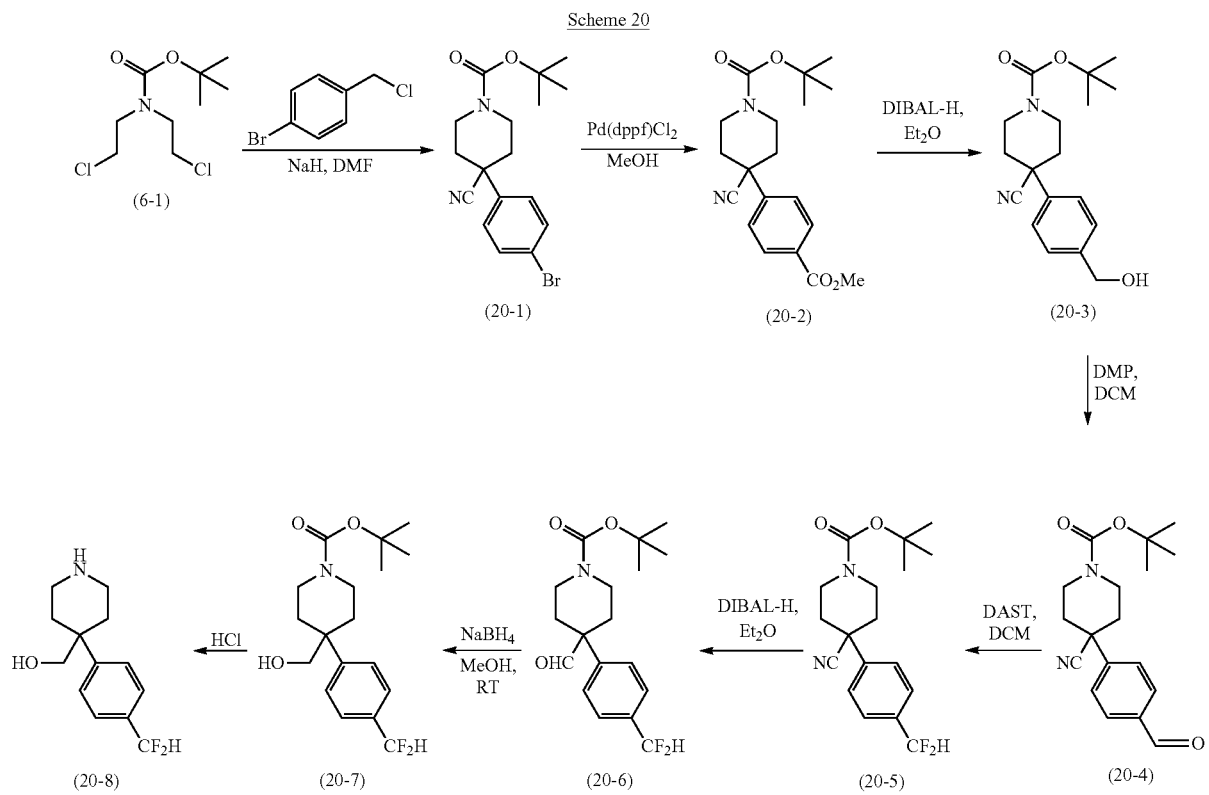

Scheme 20

Scheme 21 describes routes to amines 1-8 from Scheme 1 in which $R^3$ is a phenyl or substituted phenyl and $R^4$ is a propane-1,2-diol. Treatment of methanesulfonate ester (8-10) with a base such as potassium tert-butoxide may provide the alkene (21-1). Intermediate (21-1) may be treated with an oxidant such as osmium tetroxide to afford diol (21-2). Boc deprotection under standard conditions may be used to give the amine (21-3).

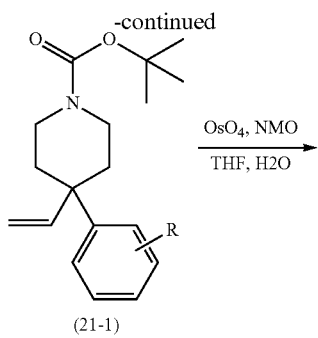

-continued

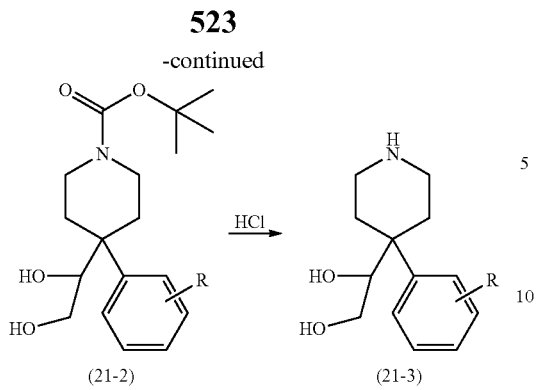

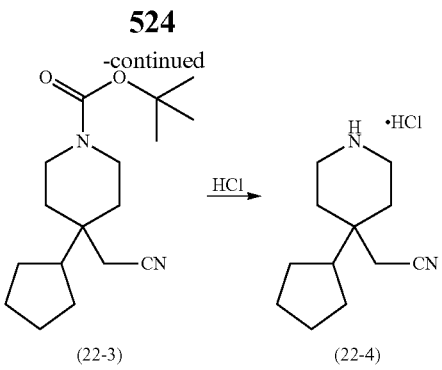

Scheme 22 describes a route to the amine (22-4) in which $R^3$ is a cycloalkyl and $R^4$ is either cyanomethyl. Conjugate addition to Intermediate (8-2) using reagents such as a Grignard and copper(I) iodide may be used to prepare intermediate (22-1). Hydrolysis of the ester in Intermediate (22-1) with a base such as potassium hydroxide followed by decarboxylation using a reagent such as copper (I) oxide may be used to give Intermediate (22-3). Boc deprotection under standard conditions may be used to give the amine (22-4)

Scheme 23 describes routes to amines 1-8 from Scheme 1 in which $R^3$ is a phenyl or substituted phenyl and $R^4$ is a propionic acid ethyl ester. Hydrolysis of the nitrile (8-6) under acidic conditions with a reagent such as HCl in acetic acid gives the acid (23-1). Esterification of the acid with an alcohol such as ethanol under acidic conditions gives the ester (23-2). Boc deprotection under standard conditions may be used to give the amine (23-3).

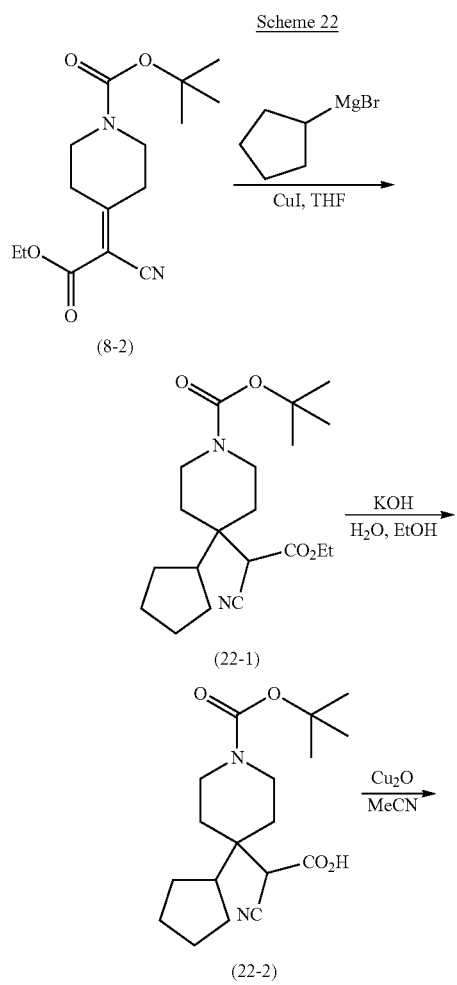

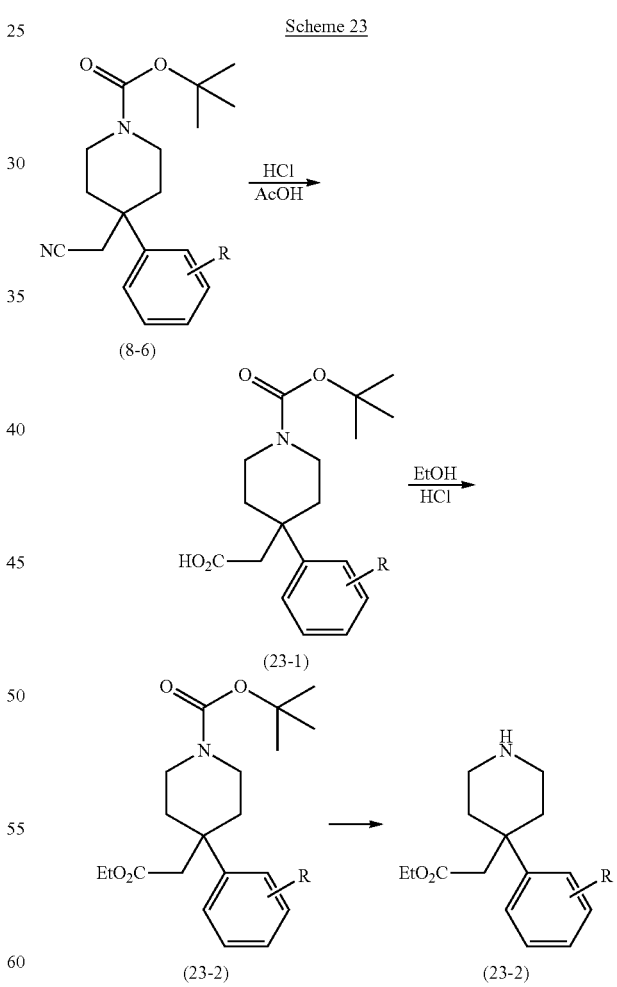

Scheme 24 describes routes to amines 1-8 from Scheme 1 in which $R^3$ is a phenyl or substituted phenyl and $R^4$ is either carboxylic acid (24-6), difluoroethyl (24-7), 2-hydroxyethyl (24-8), 2-hydroxytrifluoroethyl (24-9), or methoxymethyl (24-10). Hydrolysis of the nitrile (6-2)

under acidic conditions with a reagent such as HCl in acetic acid may be used to afford the acid (24-1). Treatment of the aldehyde (8-7) with a reagent such as DAST may be used to afford the difluoroethyl intermediate (24-2). Addition of a methyl Grignard such as methyl magnesium bromide to the aldehyde (6-3) may be used to afford the 2-hydroxyethyl intermediate (24-3). Treatment of the aldehyde (6-3) with a reagent such as CF3-TMS in the presence of a base such as potassium carbonate may be used to give the trifluorohydroxy intermediate (24-4). Treatment of the alcohol (6-4) with a base such as sodium hydride in the presence of methyl iodide may be used to afford the methyl ether (24-5). Standard conditions may be used to deprotect Intermediates (24-1) to (24-5) to afford the amines (24-6) to (24-10).

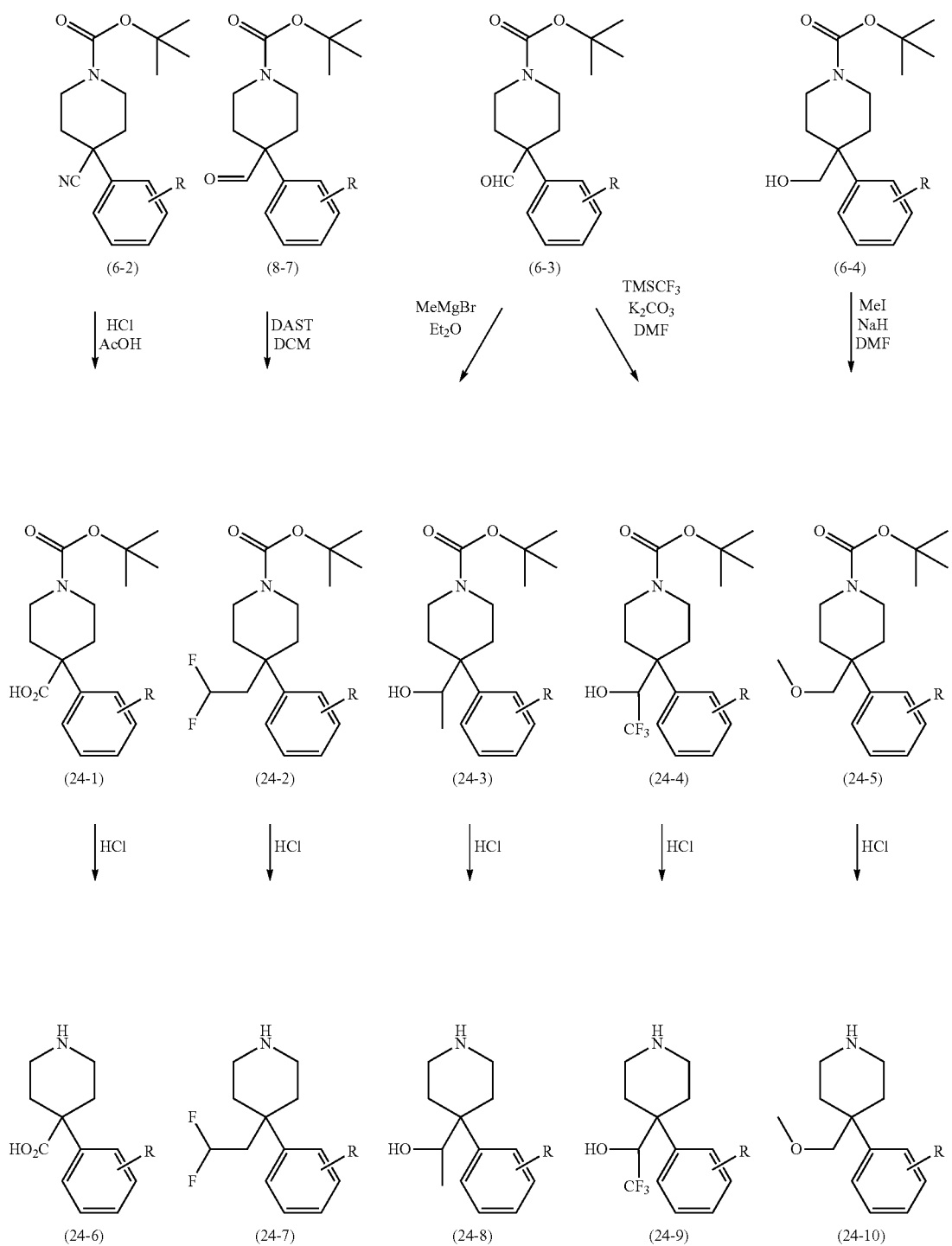

Scheme 24

Scheme 25 describes a route to compounds of the invention wherein Ar¹ is a pyrazole. Ester (16.2) from Scheme 16 may undergo a palladium catalysed Buchwald-Hartwig cross-coupling with an amine (1-8). Where R¹ in (25-1) is a protecting group, it may be removed under standard conditions and the resulting acid (25-2) may be further modified through an amide coupling to afford amides of the Formula 25-3.

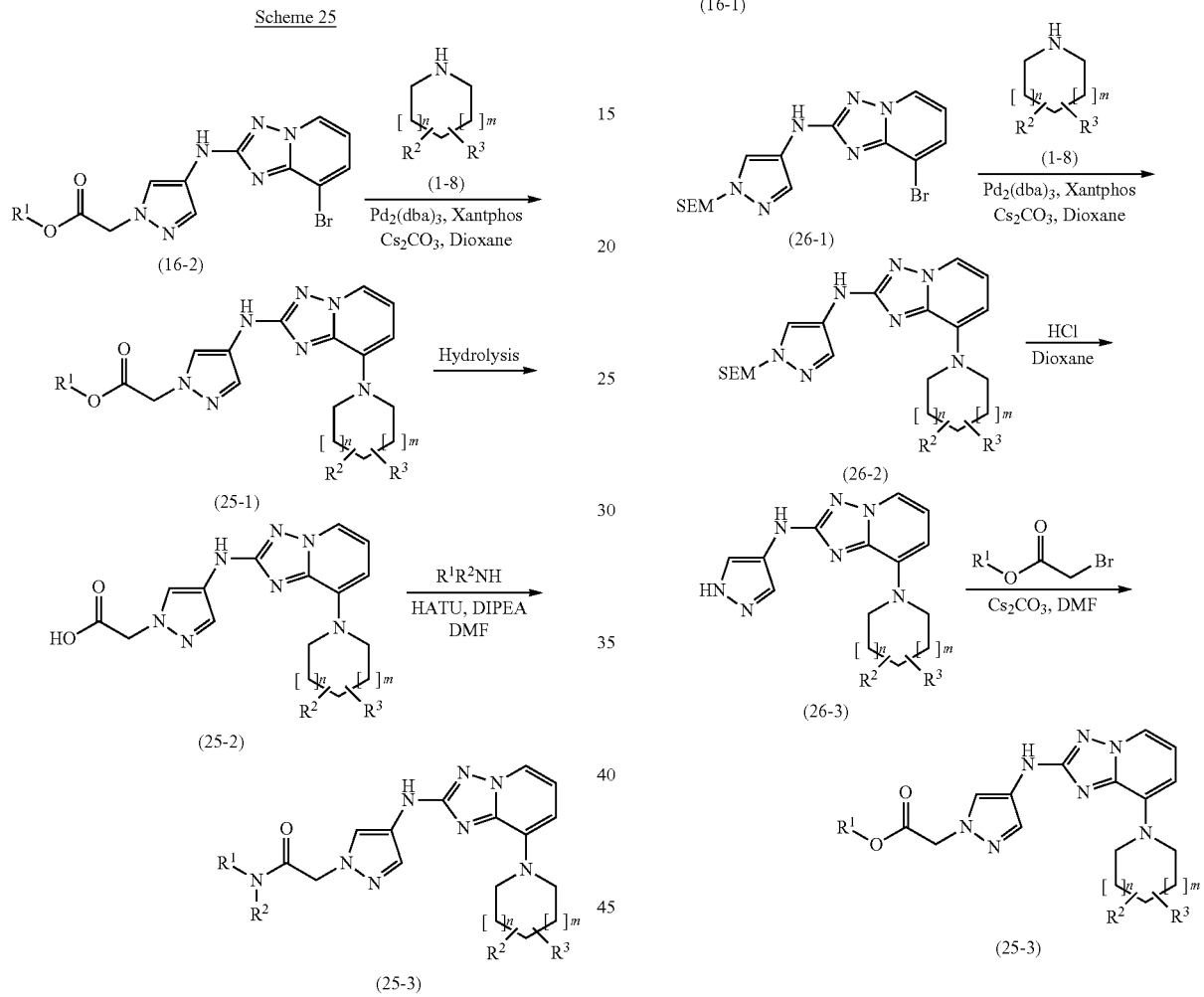

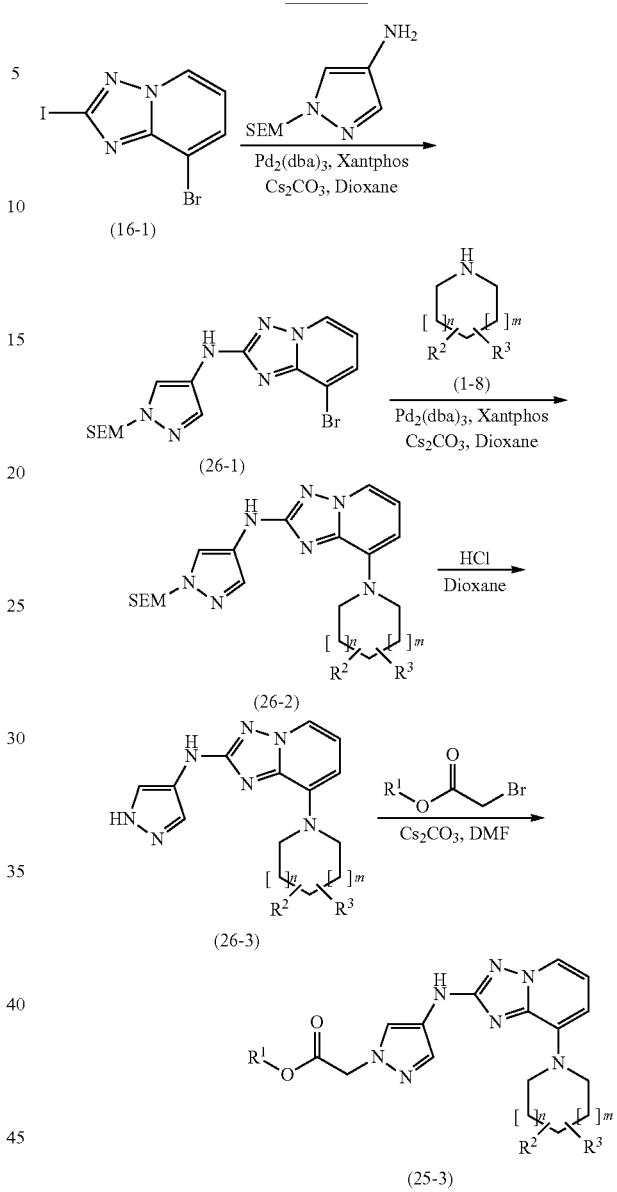

Scheme 26 describes an alternative route towards compounds where Ar¹ is a pyrazole. The 2-iodo analogue (16-1) may undergo a palladium catalysed Buchwald-Hartwig cross-coupling with a protected aminopyrazole, such as the SEM amino pyrazole, to afford compounds of Formula (26-1). Compounds of Formula (26-1) may then undergo a further palladium catalysed Buchwald-Hartwig cross-coupling with an amine (1-8) to afford compounds of Formula (26-2). The pyrazole protecting group in (26-2) may then be removed under standard conditions to afford compounds of Formula (26-3) which may be subsequently alkylated with a suitable alkylating agent and base to afford compounds of formula (25-1). Compounds of Formula (25-1) may be further modified as in Scheme 25 to afford amides of Formula (25-3).

Methods of Separation

In each of the exemplary Schemes it may be advantageous to separate reaction products from one another or from starting materials. The desired products of each step or series of steps is separated or purified (hereinafter separated) to the desired degree of homogeneity by the techniques common in the art. Typically such separations involve multiphase extraction, crystallization or trituration from a solvent or solvent mixture, distillation, sublimation, or chromatography. Chromatography can involve any number of methods including, for example: reverse-phase and normal phase; size exclusion; ion exchange; supercritical fluid; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. Example separation methods include boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column or supercritical fluid chromatography.

A single stereoisomer, e.g., an enantiomer, substantially free of its stereoisomer may be obtained by resolution of the racemic mixture using a method such as formation of diastereomers using optically active resolving agents (Eliel, E. and Wilen, S., Stereochemistry of Organic Compounds, John Wiley & Sons, Inc., New York, 1994; Lochmuller, C. H., J. Chromatogr., 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Drug Stereochemistry, Analytical Methods and Pharmacology, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., Stereochemistry of Organic Compounds, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob, J. Org. Chem. 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111, incorporated herein by reference). By method (3), a racemic mixture of two enantiomers can be separated by chromatography using a chiral stationary phase (Chiral Liquid Chromatography W. J. Lough, Ed., Chapman and Hall, New York, (1989); Okamoto, J. of Chromatogr. 513:375-378 (1990)). Enriched or purified enantiomers can be distinguished by methods used to distinguish other chiral molecules with asymmetric carbon atoms, such as optical rotation and circular dichroism. The absolute stereochemistry of chiral centers and enatiomers can be determined by x-ray crystallography.

Positional isomers, for example E and Z forms, of compounds of Formula 0, Formula I or Formula II, and intermediates for their synthesis, may be observed by characterization methods such as NMR and analytical HPLC. For certain compounds where the energy barrier for interconversion is sufficiently high, the E and Z isomers may be separated, for example by preparatory HPLC.

Pharmaceutical Compositions and Administration

The compounds with which the invention is concerned are JAK kinase inhibitors, such as JAK1 inhibitors, and are useful in the treatment of several diseases, for example, inflammatory diseases, such as asthma.

Accordingly, another embodiment provides pharmaceutical compositions or medicaments containing a compound of the invention, such as a compound of Formula 0, I, Ia, Ib, Ic, Id, Ie, If, Ig or II, or a compound of any of Examples 1-1 to 1-303, 2-1 to 2-486 or 3-1, and a pharmaceutically acceptable carrier, diluent or excipient, as well as methods of using the compounds of the invention to prepare such compositions and medicaments.

In one example, a compound of Formula 0, I, Ia, Ib, Ic, Id, Ie, If, Ig or II, or a compound of any of Examples 1-1 to 1-303, 2-1 to 2-486 or 3-1, may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but typically ranges anywhere from about 3 to about 8. In one example, a compound of Formula 0, I, Ia, Ib, Ic, Id, Ie, If, Ig or II, or a compound of any of Examples 1-1 to 1-303, 2-1 to 2-486 or 3-1, is formulated in an acetate buffer, at pH 5. In another embodiment, the compounds of the present invention, such as a compound of Formula 0, I, Ia, Ib, Ic, Id, Ie, If, Ig or II, or a compound of any of Examples 1-1 to 1-303, 2-1 to 2-486 or 3-1, are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 μg to about 1 mg per kg body weight of a human, preferably 0.1 μg to 50 μg per kg, in single or divided doses. On the other hand, it may be necessary to use dosages outside these limits in some cases.

The compounds of the invention, such as a compound of Formula 0, I, Ia, Ib, Ic, Id, Ie, If, Ig or II, or a compound of any of Examples 1-1 to 1-303, 2-1 to 2-486 or 3-1, may be administered by any suitable means, including oral, topical (including buccal and sublingual), rectal, vaginal, transdermal, parenteral, subcutaneous, intraperitoneal, intrapulmonary, intradermal, intrathecal, inhaled and epidural and intranasal, and, if desired for local treatment, intralesional administration. Parenteral infusions include intramuscular, intravenous, intraarterial, intraperitoneal, or subcutaneous administration. In some embodiments, inhaled administration is employed.

The compounds of the present invention, such as a compound of Formula 0, I, Ia, Ib, Ic, Id, Ie, If, Ig or II, or a compound of any of Examples 1-1 to 1-303, 2-1 to 2-486 or 3-1, may be administered in any convenient administrative form, e.g., tablets, powders, capsules, lozenges, granules, solutions, dispersions, suspensions, syrups, sprays, vapors, suppositories, gels, emulsions, patches, etc. Such compositions may contain components conventional in pharmaceutical preparations, e.g., diluents (e.g., glucose, lactose or mannitol), carriers, pH modifiers, buffers, sweeteners, bulking agents, stabilizing agents, surfactants, wetting agents, lubricating agents, emulsifiers, suspending agents, preservatives, antioxidants, opaquing agents, glidants, processing aids, colorants, perfuming agents, flavoring agents, other known additives as well as further active agents.

Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. For example, carriers include solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated. Exemplary excipients include dicalcium phosphate, mannitol, lactose, starch, magnesium stearate, sodium saccharine, cellulose, magnesium carbonate or combinations thereof. A pharmaceutical composition may comprise different types of carriers or excipients depending on whether it is to be administered in solid, liquid or aerosol form, and whether it need to be sterile for such routes of administration.

For example, tablets and capsules for oral administration may be in unit dose presentation form, and may contain conventional excipients such as binding agents, for example syrup, acacia, gelatin, sorbitol, tragacanth, or polyvinylpyrrolidone; fillers, for example, lactose, sugar, maize-starch, calcium phosphate, sorbitol or glycine; tabletting lubricant, for example, magnesium stearate, talc, polyethylene glycol or silica; disintegrants, for example, potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example, sorbitol, syrup, methyl cellulose, glucose syrup, gelatin hydrogenated edible fats; emulsifying agents, for example, lecithin, sorbitan monooleate, or acacia; non-aqueous vehicles (which may include edible oils), for example, almond oil, fractionated coconut oil, oily esters such as glycerine, propylene glycol, or ethyl alcohol; preservatives, for example, methyl or propyl p-hydroxybenzoate or sorbic acid, and if desired conventional flavoring or coloring agents.

For topical application to the skin, a compound may be made up into a cream, lotion or ointment. Cream or ointment formulations which may be used for the drug are conventional formulations well known in the art, for example as described in standard textbooks of pharmaceutics such as the British Pharmacopoeia.

Compounds of the invention, such as a compound of Formula 0, I, Ia, Ib, Ic, Id, Ie, If, Ig or II, or a compound of any of Examples 1-1 to 1-303, 2-1 to 2-486 or 3-1, may also be formulated for inhalation, for example, as a nasal spray, or dry powder or aerosol inhalers. For delivery by inhalation, the compound is typically in the form of microparticles, which can be prepared by a variety of techniques, including spray-drying, freeze-drying and micronisation. Aerosol generation can be carried out using, for example, pressure-driven jet atomizers or ultrasonic atomizers, such as by using propellant-driven metered aerosols or propellant-free administration of micronized compounds from, for example, inhalation capsules or other "dry powder" delivery systems.

By way of example, a composition of the invention may be prepared as a suspension for delivery from a nebulizer or as an aerosol in a liquid propellant, for example, for use in a pressurized metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In some embodiments, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of, for example, greater than 90 µm.

In the case of an aerosol-based formulation, an example is:

Compound of the invention*24 mg/canister
Lecithin, NF Liq. Conc. 1.2 mg/canister
Trichlorofluoromethane, NF 4.025 g/canister
Dichlorodifluoromethane, NF 12.15 g/canister.
*Such as a compound of Formula 0, I, Ia, Ib, Ic, Id, Ie, If, Ig or II, or a compound of any of Examples 1-1 to 1-303, 2-1 to 2-486 or 3-1.

A compound, such as a compound of Formula 0, I, Ia, Ib, Ic, Id, Ie, If, Ig or II, or a compound of any of Examples 1-1 to 1-303, 2-1 to 2-4816 or 3-1, may be dosed as described depending on the inhaler system used. In addition to the compound, the administration forms may additionally contain excipients as described above, or, for example, propellants (e.g., Frigen in the case of metered aerosols), surface-active substances, emulsifiers, stabilizers, preservatives, flavorings, fillers (e.g., lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g., Nebulator®, Volumatic®), and automatic devices emitting a puffer spray (Autohaler®), for metered aerosols, in the case of powder inhalers in particular, a number of technical solutions are available (e.g., Diskhaler®, Rotadisk®, Turbohaler® or the inhalers, for example, as described in U.S. Pat. No. 5,263,475, incorporated herein by reference). Additionally, compounds of the invention, such as a compound of Formula 0, I, Ia, Ib, Ic, Id, Ie, If, Ig or II, or a compound of any of Examples 1-1 to 1-303, 2-1 to 2-486 or 3-1, may be delivered in multi-chamber devices thus allowing for delivery of combination agents.

The compound, such as a compound of Formula 0, I, Ia, Ib, Ic, Id, Ie, If, Ig or II, or a compound of any of Examples 1-1 to 1-303, 2-1 to 2-486 or 3-1, may also be administered parenterally in a sterile medium. Depending on the vehicle and concentration used, the compound can either be suspended or dissolved in the vehicle. Advantageously, adjuvants such as a local anaesthetic, preservative or buffering agents can be dissolved in the vehicle.

Methods of Treatment with and Uses of Janus Kinase Inhibitors

The compounds of the present invention, such as a compound of Formula 0, I, Ia, Ib, Ic, Id, Ie, If, Ig or II, or a compound of any of Examples 1-1 to 1-303, 2-1 to 2-486 or 3-1, inhibit the activity of a Janus kinase, such as JAK1 kinase. For example, a compound of the present invention, such as a compound of Formula 0, I, Ia, Ib, Ic, Id, Ie, If, Ig or II, or a compound of any of Examples 1-1 to 1-303, 2-1 to 2-486 or 3-1, inhibits the phosphorylation of signal transducers and activators of transcription (STATs) by JAK1 kinase as well as STAT mediated cytokine production. Compounds of the present invention, such as a compound of Formula 0, I, Ia, Ib, Ic, Id, Ie, If, Ig or II, or a compound of any of Examples 1-1 to 1-303, 2-1 to 2-486 or 3-1, are useful for inhibiting JAK1 kinase activity in cells through cytokine pathways, such as IL-6, IL-15, IL-7, IL-2, IL-4, IL-9, IL-10, IL-13, IL-21, G-CSF, IFNalpha, IFNbeta or IFNgamma pathways. Accordingly, in one embodiment is provided a method of contacting a cell with a compound of the present invention, such as a compound of Formula 0, I, Ia, Ib, Ic, Id, Ie, If, Ig or II, or a compound of any of Examples 1-1 to 1-303, 2-1 to 2-486 or 3-1, to inhibit a Janus kinase activity in the cell (e.g., JAK1 activity).

The compounds of the present invention, such as compounds of Formula 0, I, Ia, Ib, Ic, Id, Ie, If, Ig or II, or a compound of any of Examples 1-1 to 1-303, 2-1 to 2-486 or 3-1, can be used for the treatment of immunological disorders driven by aberrant IL-6, IL-15, IL-7, IL-2, IL-4, IL9, IL-10, IL-13, IL-21, G-CSF, IFNalpha, IFNbeta or IFNgamma cytokine signaling.

Accordingly, one embodiment includes compounds of the present invention, such as a compound of Formula 0, I, Ia, Ib, Ic, Id, Ie, If, Ig or II, or a compound of any of Examples 1-1 to 1-303, 2-1 to 2-486 or 3-1, for use in therapy.

In some embodiments, there is provided use a compound of the present invention, such as a compound of Formula 0, I, Ia, Ib, Ic, Id, Ie, If, Ig or II, or a compound of any of Examples 1-1 to 1-303, 2-1 to 2-486 or 3-1, in the treatment of an inflammatory disease. Further provided is use of a compound of the present invention, such as a compound of Formula 0, I, Ia, Ib, Ic, Id, Ie, If, Ig or II, or a compound of any of Examples 1-1 to 1-303, 2-1 to 2-486 or 3-1, for the preparation of a medicament for the treatment of an inflammatory disease, such as asthma. Also provided is a compound of the present invention, such as a compound of Formula 0, I, Ia, Ib, Ic, Id, Ie, If, Ig or II, or a compound of any of Examples 1-1 to 1-303, 2-1 to 2-486 or 3-1, for use in the treatment of an inflammatory disease, such as asthma.

Another embodiment includes a method of preventing, treating or lessening the severity of a disease or condition, such as asthma, responsive to the inhibition of a Janus kinase activity, such as JAK1 kinase activity, in a patient. The method can include the step of administering to a patient a therapeutically effective amount of a compound of the present invention, such as a compound of Formula 0, I, Ia, Ib, Ic, Id, Ie, If, Ig or II, or a compound of any of Examples 1-1 to 1-303, 2-1 to 2-486 or 3-1. In one embodiment, the disease or condition responsive to the inhibition of a Janus kinase, such as JAK1 kinase, is asthma.

In one embodiment, the disease or condition is cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation (e.g., transplant rejection), immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the inflammatory disease is rheumatoid arthritis, psoriasis, asthma, inflammatory bowel disease, contact dermatitis or delayed hypersensitivity reactions. In one embodiment, the autoimmune disease is rheumatoid arthritis, lupus or multiple sclerosis.

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the disease is a myeloproliferative disorder. In one embodiment, the myeloproliferative disorder is polycythemia vera, essential thrombocytosis, myelofibrosis or chronic myelogenous leukemia (CML).

Another embodiment includes the use of a compound of the present invention, such as a compound of Formula 0, I, Ia, Ib, Ic, Id, Ie, If, Ig or II, or a compound of any of Examples 1-1 to 1-303, 2-1 to 2-486 or 3-1, for the manufacture of a medicament for the treatment of a disease described herein (e.g., an inflammatory disorder, an immunological disorder or cancer).

Combination Therapy

The compounds of the present invention, such as a compound of Formula 0, I, Ia, Ib, Ic, Id, Ie, If, Ig or II, or a compound of any of Examples 1-1 to 1-303, 2-1 to 2-486 or 3-1, may be employed alone or in combination with other agents for treatment. The second compound of a pharmaceutical composition or dosing regimen typically has complementary activities to the compound of this invention such that they do not adversely affect each other. Such agents are suitably present in combination in amounts that are effective for the purpose intended. The compounds may be administered together in a unitary pharmaceutical composition or separately and, when administered separately this may occur simultaneously or sequentially. Such sequential administration may be close or remote in time.

For example, other compounds may be combined with compounds with which the invention is concerned for the prevention and treatment of inflammatory diseases, such as asthma. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: an adenosine A2A receptor antagonist; an anti-infective; a non-steroidal Glucocorticoid Receptor (GR Receptor) agonist; an antioxidant; a 132 adrenoceptor agonist; a CCR1 antagonist; a chemokine antagonist (not CCR1); a corticosteroid; a CRTh2 antagonist; a DPI antagonist; a formyl peptide receptor antagonist; a histone deacetylase activator; a chloride channel hCLCA1 blocker; an epithelial sodium channel blocker (ENAC blocker; an inter-cellular adhesion molecule 1 blocker (ICAM blocker); an IKK2 inhibitor; a JNK inhibitor; a cyclooxygenase inhibitor (COX inhibitor); a lipoxygenase inhibitor; a leukotriene receptor antagonist; a dual 132 adrenoceptor agonist/M3 receptor antagonist (MABA compound); a MEK-1 inhibitor; a myeloperoxidase inhibitor (MPO inhibitor); a muscarinic antagonist; a p38 MAPK inhibitor; a phosphodiesterase PDE4 inhibitor; a phosphatidylinositol 3-kinase γ inhibitor (PI3-kinase γ inhibitor); a peroxisome proliferator activated receptor agonist (PPARγ agonist); a protease inhibitor; a retinoic acid receptor modulator (RAR γ modulator); a statin; a thromboxane antagonist; or a vasodilator.

In addition, compounds of the invention, such as a compound of Formula 0, I, Ia, Ib, Ic, Id, Ie, If, Ig or II, or a compound of any of Examples 1-1 to 1-303, 2-1 to 2-486 or 3-1, may be combined with: (1) corticosteroids, such as alclometasone dipropionate, amelometasone, beclomethasone dipropionate, budesonide, butixocort propionate, biclesonide, blobetasol propionate, desisobutyrylciclesonide, dexamethasone, dtiprednol dicloacetate, fluocinolone acetonide, fluticasone furoate, fluticasone propionate, loteprednol etabonate (topical) or mometasone furoate; (2) β2-adrenoreceptor agonists such as salbutamol, albuterol, terbutaline, fenoterol, and long acting β2-adrenoreceptor agonists such as metaproterenol, isoproterenol, isoprenaline, salmeterol, indacaterol, formoterol (including formoterol fumarate), arformoterol, carmoterol, GSK 642444, GSK 159797, GSK 159802, GSK 597501, GSK 678007, or AZD3199; (3) corticosteroid/long acting β2 agonist combination products such as salmeterol/fluticasone propionate (Advair®, also sold as Seretide®), formoterol/budesonide (Symbicort®), formoterol/fluticasone propionate (Flutiform®), form oterol/ciclesonide, formoterol/mometasone furoate, indacaterol/mometasone furoate, indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, or arformoterol/ciclesonide; (4) anticholinergic agents, for example, muscarinic-3 (M3) receptor antagonists such as ipratropium bromide, tiotropium bromide, aclidinium (LAS-34273), NVA-237, GSK 233705, darotropium, GSK 573719, GSK 961081, QAT 370, or QAX 028; (5) dual pharmacology M3-anticholinergic/β2-adrenoreceptor agonists such as GSK961081; (6) leukotriene modulators, for example, leukotriene antagonists such as montelukast, zafirulast or pranlukast or leukotriene biosynthesis inhibitors such as zileuton or BAY-1005, or LTB4 antagonists such as amelubant, or FLAP inhibitors such as GSK 2190914, AM-103; (7) phosphodiesterase-IV (PDE-IV) inhibitors (oral or inhaled), such as roflumilast, cilomilast, oglemilast, ONO-6126, tetomilast, tofimilast, UK 500,001, or GSK 256066; (8) antihistamines, for example, selective histamine-1 (H1) receptor antagonists such as fexofenadine, citirizine, loratidine or astemizole or dual H1/H3 receptor antagonists such as GSK 835726, or GSK 1004723; (9) antitussive agents, such as codeine or dextramorphan; (10) a mucolytic, for example, N-acetyl cysteine or fudostein; (11) a expectorant/mucokinetic modulator, for example, ambroxol, hypertonic solutions (e.g., saline or mannitol) or surfactant; (12) a peptide mucolytic, for example, recombinant human deoxyribonuclease I (dornase-alpha and rhDNase) or helicidin; (13) antibiotics, for example azithromycin, tobramycin or aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO97/03094 and WO97/02289, each incorporated herein by reference; (17) TACE inhibitors and TNF-α inhibitors, for example anti-TNF monoclonal antibodies, such as Remicade® and CDP-870 and TNF receptor immunoglobulin molecules, such as Enbrel®; (18) inhibitors of matrix metalloprotease, for example MMP-12; (19) human neutrophil elastase inhibitors, such as ONO-6818 or those described in WO2005/026124, WO2003/053930 and WO06/082412, each incorporated herein by reference; (20) A2b antagonists such as those described in WO2002/42298, incorporated herein by reference; (21) modulators of chemokine receptor function, for example antagonists of CCR3 and CCR8; (22) compounds which modulate the action of other prostanoid receptors, for example, a thromboxane $A_2$ antagonist; DP1 antagonists such as MK-0524, CRTH2 antagonists such as ODC9101 and AZD1981 and mixed DP1/CRTH2 antagonists such as AMG 009; (23) PPAR agonists including PPAR alpha agonists (such as fenofibrate), PPAR delta agonists, PPAR gamma agonists such as pioglitazone, rosiglitazone and balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) A2a agonists such as those described in EP1052264 and EP1241176; (26) CXCR2 or IL-8 antagonists such as SCH 527123 or GSK 656933; (27) IL-R signalling modulators such as kineret and ACZ 885; and (28) MCP-1 antagonists such as ABN-912.

In some embodiments, the compounds of the present invention, such as a compound of Formula 0, I, Ia, Ib, Ic, Id, Ie, If, Ig or II, or a compound of any of Examples 1-1 to 1-303, 2-1 to 2-486 or 3-1, can be used in combination with one or more additional drugs, for example anti-hyperproliferative, anti-cancer, cytostatic, cytotoxic, anti-inflammatory or chemotherapeutic agents, such as those agents disclosed in U.S. Publ. Appl. No. 2010/0048557, incorporated herein by reference. A compound of the present invention, such as a compound of Formula 0, I, Ia, Ib, Ic, Id, Ie, If, Ig or II, or a compound of any of Examples 1-1 to 1-303, 2-1 to 2-486 or 3-1, can be also used in combination with radiation therapy or surgery, as is known in the art.

Articles of Manufacture

Another embodiment includes an article of manufacture (e.g., a kit) for treating a disease or disorder responsive to the inhibition of a Janus kinase, such as a JAK1 kinase. The kit can comprise:

(a) a first pharmaceutical composition comprising a compound of the present invention, such as a compound of Formula 0, I, Ia, Ib, Ic, Id, Ie, If, Ig or II, or a compound of any of Examples 1-1 to 1-303, 2-1 to 2-486 or 3-1; and (b) instructions for use.

In another embodiment, the kit further comprises:

(c) a second pharmaceutical composition, such as a pharmaceutical composition comprising an agent for treatment as described above, such as an agent for treatment of an inflammatory disorder, or a chemotherapeutic agent.

In one embodiment, the instructions describe the simultaneous, sequential or separate administration of said first and second pharmaceutical compositions to a patient in need thereof.

In one embodiment, the first and second compositions are contained in separate containers. In another embodiment, the first and second compositions are contained in the same container.

Containers for use include, for example, bottles, vials, syringes, blister pack, etc. The containers may be formed from a variety of materials such as glass or plastic. The container includes a compound of the present invention, such as a compound of Formula 0, I, Ia, Ib, Ic, Id, Ie, If, Ig or II, or a compound of any of Examples 1-1 to 1-303, 2-1 to 2-486 or 3-1, or composition thereof, which is effective for treating the condition and may have a sterile access port (for example the container may be an intravenous solution bag or a vial having a stopper pierceable by a hypodermic injection needle). The label or package insert indicates that the compound or composition is used for treating the condition of choice, such as asthma or cancer. In one embodiment, the label or package inserts indicates that the compound or composition can be used to treat a disorder. In addition, the label or package insert may indicate that the patient to be treated is one having a disorder characterized by overactive or irregular Janus kinase activity, such as overactive or irregular JAK1 activity. The label or package insert may also indicate that the compound or composition can be used to treat other disorders.

Alternatively, or additionally, the kit may further comprise a second (or third) container comprising a pharmaceutically acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of the present invention, and alternative methods for preparing the compounds are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

Abbreviations
AcOH Acetic acid
BINAP 2,2'-Bis(diphenylphosphino)-1,1'-binaphthalene
n-BuLi n-Butyllithium solution
t-BuOH tert-butanol
t-BuOK Potassium tert-butoxide
t-BuONa Sodium tert-butoxide
$CDCl_3$ Deuterated chloroform
$CD_3OD$ Deuterated methanol
CO Carbon monoxide
$Cs_2CO_3$ Cesium carbonate
CuI Copper (I) iodide
$Cu_2O$ Copper (I) oxide
DIBAl-H Diisobutylaluminum hydride
DIPEA Diisopropylethylamine
DMF Dimethylformamide
DMSO Dimethylsulfoxide
DMSO-d6 Deuterated dimethylsulfoxide
EtOAc Ethyl acetate
EtOH Ethanol
g Gram
HATU (O-(7-azabenzotriazol-1-yl)-N,N,N',N'-tetramethyluronium hexafluorophosphate)
HCl Hydrochloric acid
HCOOH Formic acid
HM-N Isolute HM-N is a modified form of diatomaceous earth
KOAc Potassium acetate
KOH Potassium hydroxide K$_3$PO$_4$ Potassium phosphate tribasic
L Litre
MeOH Methanol
mg Milligram
mL Millilitre
mmol Millimoles
Ms$_2$O Methanesulfonic anhydride
NaBH$_3$CN Sodium cyanoborohydride
NaBH$_4$ Sodium borohydride
NaCN Sodium cyanide
NaHCO$_3$ Sodium hydrogen carbonate
NaOH Sodium hydroxide
Na$_2$SO$_4$ Sodium sulfate
NH$_3$.H$_2$O 0.880 ammonia solution
NH$_2$OH.HCl Hydroxylamine hydrochloride
NH$_4$HCO$_3$ Ammonium bicarbonate
NH$_4$OAc Ammonium acetate
Pd/C Palladium on carbon
Pd$_2$(dba)$_3$ Tris(dibenzylidineacetone)palladium(0)
Pd(dppf)Cl$_2$ [1,1'-Bis(diphenylphosphino)ferrocene]-dichloropalladium-(II), complex with dichloromethane
Pd(OAc)$_2$ Palladium (II) acetate
Pd(PPh$_3$)$_4$ Tetrakis(triphenylphosphine)palladium(0)
PTSA p-Toluene sulfonic acid
r,t or rt or r t Room temperature
SCX-2 ISOLUTE® Si-Propylsulfonic acid
THF Tetrahydrofuran
TFA Trifluoroacetic acid
TLC Thin layer chromatography
XantPhos 4,5-Bis(diphenylphosphino)-9,9-dimethylxanthene
X-phos 2-Dicyclohexylphosphino-2',4',6'-triisopropylbiphenyl NMR Analytical Methods $^1$H NMR spectra were recorded at ambient temperature using a Varian Unity Inova (400 MHz) spectrometer with a 400 4NUC 5 mm probe, a Bruker Avance DRX400 (400 MHz) spectrometer with a PABBO 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

LCMS Analytical Methods High Pressure Liquid Chromatography—Mass Spectrometry (LCMS) experiments to determine retention times (RT) and associated mass ions were performed using one of the following methods with either UV detector monitoring at 220 nm and 254 nm or evaporative light scattering detection, and mass spectrometry scanning 110-800 amu in ESI+ ionization mode.

Method 1

Experiments were performed on a Waters ZMD single quadrupole mass spectrometer with an electrospray source operating in positive and negative ion mode linked to a Waters 1525 LC system. Detection was achieved using a UV diode array detector and a Sedex 85 evaporative light scattering detector. The LC column was a Phenomenex Luna 3 micron C18(2) 30×4.6 mm. The flow rate was 2 mL/minute. The initial solvent system was 95% water containing 0.1% formic acid (solvent A) and 5% acetonitrile containing 0.1% formic acid (solvent B) for 0.5 minute followed by a gradient up to 5% solvent A and 95% solvent B over the next 4 minutes. The final solvent system was held constant for a further 1 minute.

Method 2

Experiments were performed on a Waters Micromass ZQ2000 single quadrupole mass spectrometer with an electrospray source operating in positive and negative ion mode linked to a Waters Acquity UPLC system. Detection was achieved using a UV PDA detector. The flow rate was 2 mL/minute. The initial solvent system was 95% water containing 0.1% formic acid (solvent A) and 5% acetonitrile containing 0.1% formic acid (solvent B) for 0.4 minute followed by a gradient up to 5% solvent A and 95% solvent B over the next 5.6 minutes. The final solvent system was held constant for a further 0.8 minute.

Method 3

Experiments were performed on a Waters Acquity UPLC with a Shim-pack XR-ODS column (50×3.0 mm Acquity BEH C18, 2.2 µm particle size), elution with solvent A: Water/0.05% TFA; solvent B: Acetonitrile/0.05% TFA at 40° C. Gradient:

| Gradient - Time | flow ml/min | % A | % B |
| --- | --- | --- | --- |
| 0.00 | 1.0 | 95 | 5 |
| 2.00 | 1.0 | 0 | 100 |
| 3.20 | 1.0 | 0 | 100 |
| 3.30 | 1.0 | 95 | 5 |

Detection—UV (220 and 254 nm) and ELSD
MS ionisation method—ESI+

Method 4

Experiments were performed on a SHIMADZU 20A HPLC with a C18-reverse-phase column (30×2.1 mm Xtimate™—C18, 3 µm particle size), elution with solvent A: water+0.038% trifluoroacetic acid; solvent B: acetonitrile+0.02% trifluoroacetic acid. Gradient:

| Gradient - Time | flow ml/min | % A | % B |
| --- | --- | --- | --- |
| 0.01 | 1.5 | 95 | 5 |
| 0.70 | 1.5 | 5 | 95 |
| 1.1 | 1.5 | 5 | 95 |
| 1.11 | 1.5 | 95 | 5 |

Method 5

Experiments were performed on a HPLC Agilent 1200 with an Agilent SB C18 column (30×2.1mm Agilent SB C18, 1.8 µm particle size), elution with solvent A: Water/0.05% TFA; solvent B: Acetonitrile/0.05% TFA at 25° C. Gradient:

| Gradient - Time | flow ml/min | % A | % B |
| --- | --- | --- | --- |
| 0.00 | 0.4 | 97 | 3 |
| 0.3 | 0.4 | 95 | 3 |
| 6.8 | 0.4 | 5 | 95 |
| 10 | 0.4 | 97 | 3 |

Detection—UV 254 nm
MS ionisation method—ESI+

Method 6

Experiments were performed on a SHIMADZU 20A HPLC with a C18-reverse-phase column (50×3 mm Xtimate™—C18, 2.2 µm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 2.00 | 1.0 | 0 | 100 |

541 -continued

| Gradient - Time | flow ml/min | % A | % B |
|---|---|---|---|
| 3.10 | 1.0 | 0 | 100 |
| 3.30 | 1.0 | 95 | 5 |

Detection—UV (220 and 254 nm) and ELSD

Method 7

Experiments were performed on a SHIMADZU 20A HPLC with a C18-reverse-phase column (50×3 mm Xtimate™—C18, 2.2 μm particle size), elution with solvent A: water+0.05% trifluoroacetic acid; solvent B: acetonitrile+ 0.05% trifluoroacetic acid. Gradient:

| Gradient - Time | flow ml/min | % A | % B |
|---|---|---|---|
| 0.00 | 1.0 | 95 | 5 |
| 2.00 | 1.0 | 0 | 100 |
| 3.20 | 1.0 | 0 | 100 |
| 3.30 | 1.0 | 95 | 5 |

Detection—UV (220 and 254 nm) and ELSD

Method 8

Experiments were performed on a SHIMADZU 20A HPLC with a C18-reverse-phase column (50×3 mm Xtimate™—C18, 2.2 μm particle size), elution with solvent A: water+0.05% trifluoroacetic acid; solvent B: acetonitrile+ 0.05% trifluoroacetic acid. Gradient:

| Gradient - Time | flow ml/min | % A | % B |
|---|---|---|---|
| 0.00 | 1.0 | 95 | 5 |
| 2.00 | 1.0 | 0 | 100 |
| 3.20 | 1.0 | 0 | 100 |
| 3.30 | 1.0 | 95 | 5 |

Detection—UV (220 and 254 nm) and ELSD

Method 9

Experiments were performed on a SHIMADZU 20A HPLC with a C18-reverse-phase column (50×3 mm Xtimate™—C18, 2.2 μm particle size), elution with solvent A: water+0.05% formic acid; solvent B: acetonitrile+0.05% formic acid. Gradient:

| Gradient - Time | flow ml/min | % A | % B |
|---|---|---|---|
| 0.00 | 1.0 | 95 | 5 |
| 1.20 | 1.0 | 0 | 100 |
| 2.20 | 1.0 | 0 | 100 |
| 2.30 | 1.0 | 95 | 5 |

Detection—UV (220 and 254 nm) and ELSD

Method 10

Experiments were performed on a SHIMADZU 20A HPLC with a C18-reverse-phase column (50×3 mm Xtimate™—C18, 2.2 μm particle size), elution with solvent A: water+0.1% formic acid; solvent B: acetonitrile+0.05% formic acid. Gradient:

| Gradient - Time | flow ml/min | % A | % B |
|---|---|---|---|
| 0.00 | 1.0 | 95 | 5 |
| 2.00 | 1.0 | 0 | 100 |

542 -continued

| Gradient - Time | flow ml/min | % A | % B |
|---|---|---|---|
| 3.10 | 1.0 | 0 | 100 |
| 3.20 | 1.0 | 95 | 5 |

Detection—UV (220 and 254 nm) and ELSD

Method 11

Experiments were performed on a SHIMADZU 20A HPLC with a C18-reverse-phase column (50×3 mm Xtimate™—C18, 2.2 μm particle size), elution with solvent A: water+0.04% Ammonia; solvent B: acetonitrile. Gradient:

| Gradient - Time | flow ml/min | % A | % B |
|---|---|---|---|
| 0.00 | 1.2 | 95 | 5 |
| 1.20 | 1.2 | 0 | 100 |
| 2.20 | 1.2 | 0 | 100 |
| 2.30 | 1.2 | 95 | 5 |

Detection—UV (220 and 254 nm) and ELSD

Method 12

Experiments were performed on a SHIMADZU 20A HPLC with a C18-reverse-phase column (30×2.1 mm Xtimate™—C18, 3 μm particle size), elution with solvent A: water+0.05% trifluoroacetic acid; solvent B: acetonitrile+ 0.05% trifluoroacetic acid. Gradient:

| Gradient - Time | flow ml/min | % A | % B |
|---|---|---|---|
| 0.00 | 1.0 | 95 | 5 |
| 1.10 | 1.0 | 0 | 100 |
| 1.60 | 1.0 | 0 | 100 |
| 1.70 | 1.0 | 95 | 5 |

Detection—UV (220 and 254 nm) and ELSD

Example 1a

N-methyl-4-(8-(4-methyl-4-phenylpiperidin-1-yl)-[1,2,4]triazolo[1,5-a]pyridin-2-ylamino)-N-(1-methyl-piperidin-4-yl)benzamide (Example 1-1 of Table I)

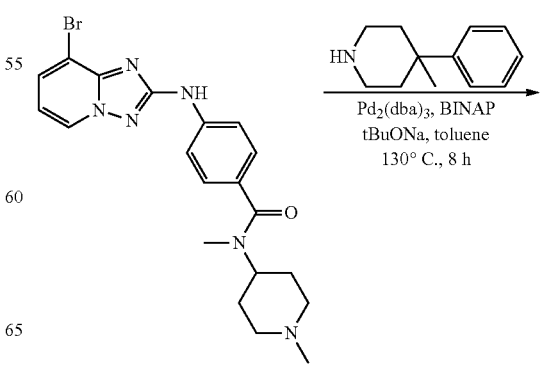

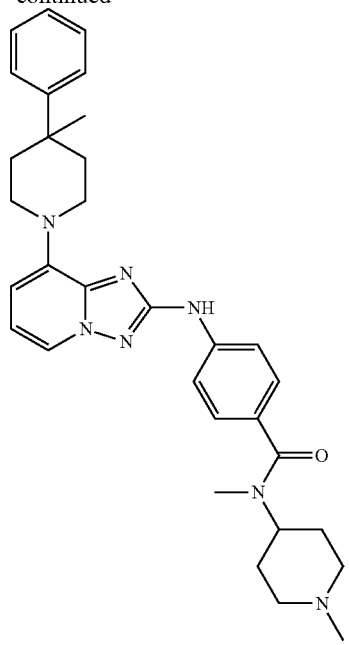

A degassed mixture of 4-((8-bromo-[1,2,4]triazolo[1,5-a]pyridin-2-yl)amino)-N-methyl-N-(1-methylpiperidin-4-yl)benzamide (200 mg, 0.45 mmol), 4-methyl-4-phenylpiperidine (158.2 mg, 0.90 mmol), tBuONa (130.2 mg, 1.36 mmol), BINAP (56.4 mg, 0.09 mmol) and tris(dibenzylideneacetone)palladium (0) (41.4 mg, 0.045 mmol) in toluene (8 mL) was heated at 130° C. under nitrogen for 8 h. When the starting material was consumed, the reaction mixture was added to water (10 mL) and extracted with dichloromethane (50 mL×3). The organic layers were dried over $Na_2SO_4$ and concentrated to give the residue which was purified by prep-HPLC to give Example 1-1 (see Table I) (120 mg, 56.1%).

$^1$H NMR (400 MHz, $CD_3OD$) δ 8.74 (d, J=6.8 Hz, 1H), 7.95 (d, J=8.0 Hz, 1H), 7.77 (d, J=8.4 Hz, 2H), 7.52 (d, J=0.8 Hz, 2H), 7.50-7.38 (m, 4H), 7.28-7.24 (m, 1H), 7.21-7.18 (m, 1H), 4.6-4.46 (m, 1H), 4.26-4.21 (m, 2H), 3.76-3.70 (m, 2H), 3.61 (d, J=10.8 Hz, 2H), 3.16 (s, 2H), 2.99 (s, 3H), 2.86 (s, 3H), 2.66-2.59 (s, 2H), 2.31-2.21 (m, 4H), 2.07-2.02 (m, 2H), 1.15 (s, 3H).

Example 1b

4-{8-[4-(4-Chloro-phenyl)-4-hydroxy-piperidin-1-yl]-[1,2,4]triazolo[1,5-a]pyridin-2-ylamino}-benzoic acid

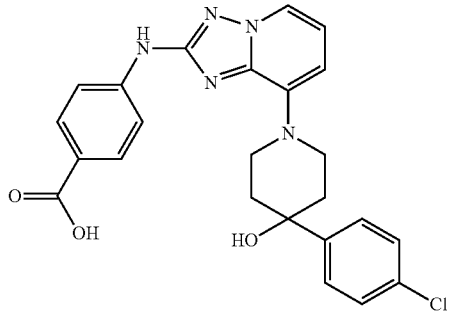 [SMILES: O=C(O)c1ccc(Nc2nc3c(N4CCC(O)(c5ccc(Cl)cc5)CC4)cccn3n2)cc1]

Step 1. A microwave vial was charged with 4-(8-bromo-[1,2,4]triazolo[1,5-a]pyridin-2-ylamino)-benzoic acid ethyl ester (1.00 g, 2.77 mmol), 4-(4-chloro-phenyl)-piperidin-4-ol (879 mg, 4.15 mmol), tris(dibenzylideneacetone)dipalladium(0) (256 mg, 0.28 mmol), cesium carbonate (1.81 g, 5.54 mmol), 4,5-bis(diphenylphosphino)-9,9-dimethylxanthene (321 mg, 0.55 mmol) and dioxane (12 mL). The vessel was sealed, evacuated and refilled with argon three times before being purged with argon whilst being sonicated for 5 minutes. The reaction mixture was stirred at 110° C. for 18 hours then cooled to room temperature before being filtered through a pad of Celite, eluting with ethyl acetate. The filtrate was concentrated in vacuo before being purified by flash chromatography on silica eluting with 0-4% MeOH in dichloromethane. 4-{8-[4-(4-chloro-phenyl)-4-hydroxy-piperidin-1-yl]-[1,2,4]triazolo[1,5-a]pyridin-2-ylamino}-benzoic acid ethyl ester was obtained as a pale yellow solid (1.13 g, 83%). LCMS (Method 1) [M+H]$^+$ 492.4, $R_T$=4.07 min. $^1$H NMR (400 MHz, DMSO-$d_6$) δ 10.14 (s, 1H), 8.35 (dd, J=6.0, 1.5 Hz, 1H), 7.92-7.86 (m, 2H), 7.82-7.76 (m, 2H), 7.60-7.53 (m, 2H), 7.43-7.34 (m, 2H), 6.99-6.88 (m, 2H), 5.21 (s, 1H), 4.27 (q, J=7.1 Hz, 2H), 4.12 (d, J=11.8 Hz, 2H), 3.22 (t, J=11.4 Hz, 2H), 2.13 (td, J=12.9, 4.3 Hz, 2H), 1.76 (d, J=12.7 Hz, 2H), 1.30 (t, J=7.1 Hz, 3H).

Step 2. A mixture of 4-{8-[4-(4-chloro-phenyl)-4-hydroxy-piperidin-1-yl]-[1,2,4]triazolo[1,5-a]pyridin-2-ylamino}-benzoic acid ethyl ester (5.12 g, 10.41 mmol), 2M LiOH aqueous solution (10.41 mL, 20.82 mmol), methanol (25 mL), THF (150 mL) and water (15 mL) was stirred at 55° C. for 18 hours then at room temperature for 24 hours. The methanol and THF were removed in vacuo before the solution was adjusted to pH 4 with 1M HCl. The resultant precipitate was collected by filtration then washed with water, diethyl ether and acetonitrile sequentially. The solid was dried under reduced pressure giving the target compound Example 1b as a pale yellow solid (4.38 g, 91%). LCMS (Method 2) [M+H]$^+$ 464.1/466.1, $R_T$=4.32 min. $^1$H NMR (400 MHz, DMSO-$d_6$) δ 12.45 (s, 1H), 10.10 (s, 1H), 8.36 (dd, J=5.9, 1.6 Hz, 1H), 7.95-7.84 (m, 2H), 7.78 (d, J=2.1 Hz, 1H), 7.76 (d, J=1.8 Hz, 1H), 7.62-7.51 (m, 2H), 7.44-7.35 (m, 2H), 6.99-6.88 (m, 2H), 5.22 (s, 1H), 4.12 (d, J=11.7 Hz, 2H), 3.21 (dd, J=13.3, 10.9 Hz, 2H), 2.12 (dp, J=20.8, 9.0, 6.6 Hz, 2H), 1.76 (d, J=12.8 Hz, 2H).

Example 1c

General Methods for Preparation of Amides

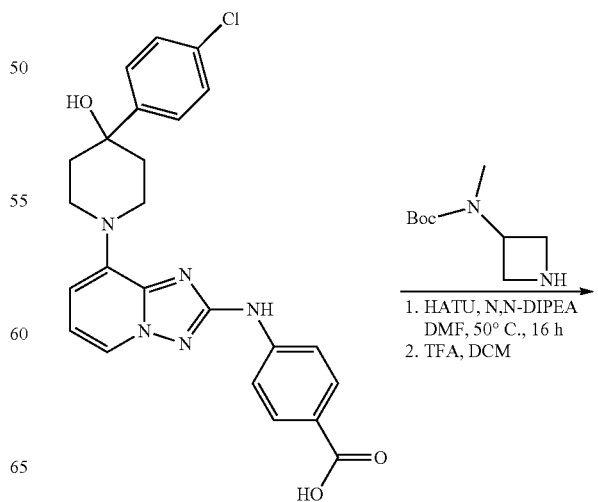

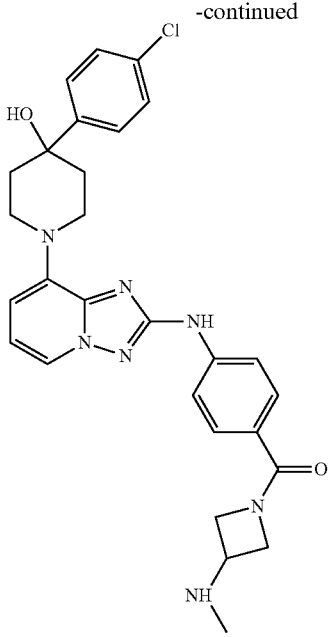

[4-[[8-[4-(4-chlorophenyl)-4-hydroxy-1-piperidyl]-[1,2,4]triazolo[1,5-a]pyridin-2-yl]amino]phenyl]-[3-(methylamino)azetidin-1-yl]methanone (Example 1-47 in Table I)

A solution of 4-[[8-[4-(4-chlorophenyl)-4-hydroxy-1-piperidyl]-[1,2,4]triazolo[1,5-a]pyridin-2-yl]amino]benzoic acid (25 mg, 0.054 mmol, 1.0 equiv), tert-butyl azetidine-3-ylmethylcarbamate HCl (25 mg, 0.11 mmol, 2.0 equiv), HATU (30 mg, 0.08 mmol, 1.5 equiv) and N,N-diisopropylethylamine (47 μL, 0.27 mmol, 5.0 equiv) in DMF (1.0 mL) was stirred at 50° C. overnight. The reaction mixture was concentrated under vacuum. A solution of crude product in dichloromethane (1 mL) was mixed with trifluoroacetic acid (60 μL, 0.8 mmol, 15 equiv) and stirred at room temperature for 72 hours. The reaction was concentrated under vacuum and the crude product was purified by Prep-HPLC (Column, Gemini C18 100×30 mm; mobile phase, CH$_3$CN:NH$_4$OH/ H$_2$O (10 mmol/L)=5%-85%, 10 min; flow rate, 70 mL/min; Detector, UV 254 nm) to give 7.4 mg (26%) of [4-[[8-[4-(4-chlorophenyl)-4-hydroxy-1-piperidyl]-[1,2,4]triazolo[1, 5-a]pyridin-2-yl]amino]phenyl]-[3-(methylamino)azetidin-1-yl]methanone as an off white solid, Example 1-47. $^1$H NMR (400 MHz, DMSO-d$_6$) δ 9.92 (s, 1H), 8.33 (dd, J=5.8, 1.7 Hz, 1H), 7.81-7.70 (m, 2H), 7.63-7.52 (m, 4H), 7.46-7.35 (m, 2H), 6.97-6.86 (m, 2H), 5.19 (s, 1H), 4.43 (s, 1H), 4.16-4.08 (m, 3H), 3.98 (s, 1H), 3.71 (s, 1H), 3.54-3.43 (m, 1H), 3.30-3.16 (m, 2H), 2.22 (s, 3H), 2.19-2.05 (m, 2H), 1.80-1.72 (m, 2H). LCMS (Method 5): Observed MW=532.3; Rt 4.0 min.

Example 1d

4-{8-[4-(4-chloro-phenyl)-4-hydroxymethyl-piperidin-1-yl]-1,8a-dihydro-[1,2,4]triazolo[1,5-a]pyridine-2-ylamino}-N-methyl-N-(1-methyl-piperidin-4-yl)-benzamide (Example 1-246 in Table I)

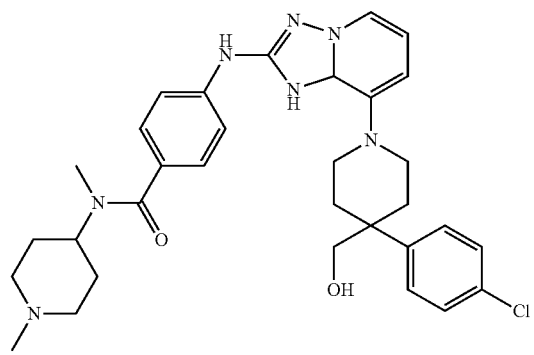

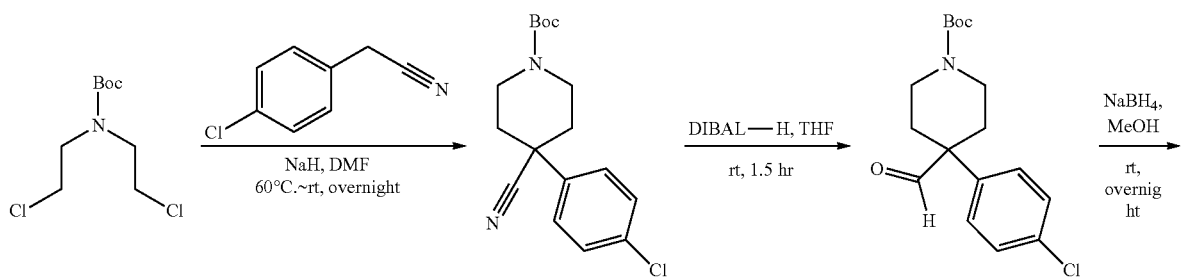

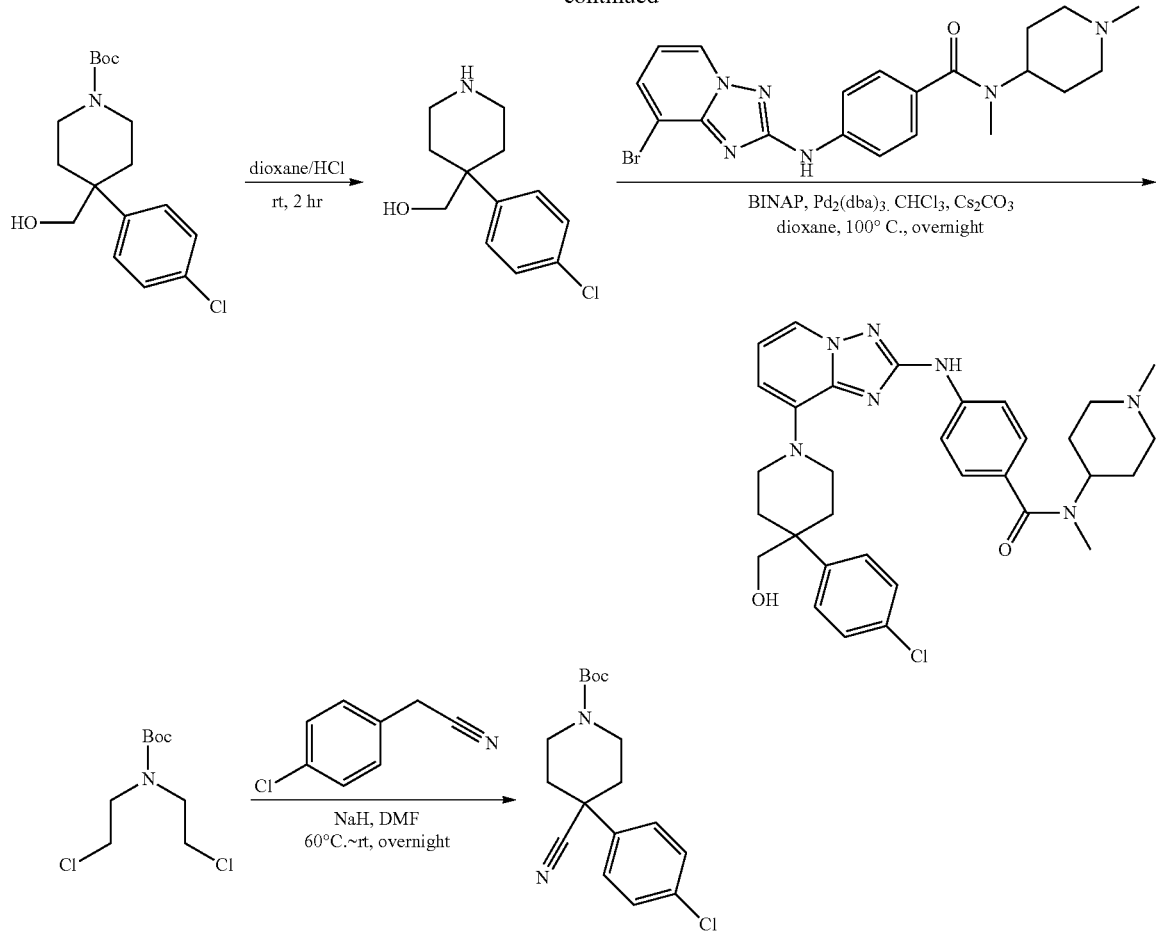

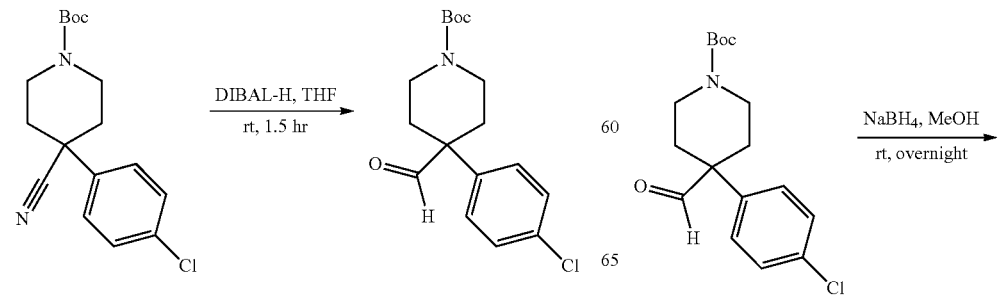

Step 1. To the solution of 2-(4-chlorophenyl)acetonitrile (20.1 g, 132.59 mmol, 1.00 equiv) and tert-butyl N,N-bis(2-chloroethyl)carbamate (35.4 g, 146.19 mmol, 1.10 equiv) in anhydrous DMF (200 mL) was added sodium hydride (27 g, 60% in mineral oil, 666.73 mmol, 3.00 equiv) portionwise at 0° C. under N₂ over 2 hr. The resulting solution was stirred at 60° C. for 1.5 hr, and then stirred overnight at room temperature. The reaction was quenched by the careful addition of 250 mL of sat. aq. NH₄Cl. The resulting solution was extracted with 3×200 mL of dichloromethane. The combined extracts were washed with 2×300 mL of brine, then dried over anhydrous sodium sulfate and concentrated under vacuum. The residue was purified on a silica gel column with dichloromethane/petroleum ether (1:1). 30 g (71%) of tert-butyl 4-(4-chlorophenyl)-4-cyanopiperidine-1-carboxylate was obtained as a yellow solid. TLC: Rf=0.15; ethyl acetate/petroleum ether=1/5.

Step 2. The solution of tert-butyl 4-(4-chlorophenyl)-4-cyanopiperidine-1-carboxylate (1 g, 3.12 mmol, 1.00 equiv) in anhydrous tetrahydrofuran (5 mL, 61.71 mmol) was placed in a 100-mL round-bottom flask purged and maintained under an inert atmosphere of nitrogen, then diisobutyl aluminium hydride (1 M in hexane, 7.8 mL, 7.81 mmol) was added dropwise with cooling in an ice/water bath. The resulting solution was stirred for 1.5 hr at ambient temperature. The reaction mixture was poured into 100 mL water/ice. The resulting solution was extracted with 200 mL of ethyl acetate. The extracts were washed with 2×50 mL of 2M hydrogen chloride solution, then 3×50 mL of sat.aq. sodium bicarbonate and 1×50 mL of brine. The mixture was dried over anhydrous sodium sulfate and concentrated under vacuum to give 610 mg crude tert-butyl 4-(4-chlorophenyl)-4-formylpiperidine-1-carboxylate as a yellow solid, which was used in the next step without further purification. TLC: R$_f$=0.15; ethyl acetate/petroleum ether=1/5.

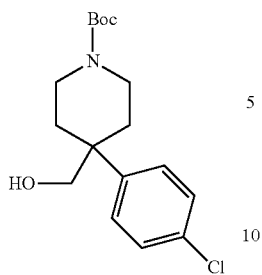

Step 3. The solution of tert-butyl 4-(4-chlorophenyl)-4-formylpiperidine-1-carboxylate (610 mg, 1.88 mmol, 1.00 equiv) in methanol (5 mL, 123.49 mmol) was placed in a 100-mL round-bottom flask, then NaBH$_4$ (144 mg, 3.81 mmol, 2.00 equiv) was added in ice/water bath. The resulting solution was stirred at room temperature overnight. The reaction was quenched by the addition of three drops of water. The resulting mixture was concentrated under vacuum. The residue was purified on a silica gel column with ethyl acetate/petroleum ether (1:10) to give 320 mg (52%) of tert-butyl 4-(4-chlorophenyl)-4-(hydroxymethyl)piperidine-1-carboxylate as a white solid. TLC: R$_f$=0.4; ethyl acetate/petroleum ether=1/1.

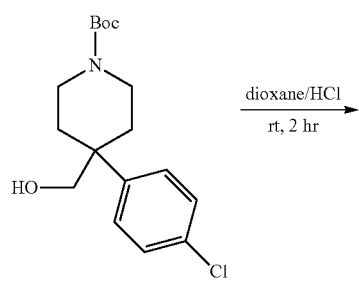

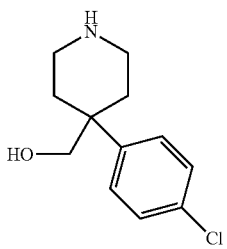

Step 4. The solution of tert-butyl 4-(4-chlorophenyl)-4-(hydroxymethyl)piperidine-1-carboxylate (300 mg, 0.92 mmol, 1.00 equiv) in HCl/dioxane (1M, 10 mL) was stirred for 2 h at room temperature. The resulting mixture was concentrated under vacuum, and sat.aq.NaHCO$_3$ was added to the residue to make pH>10. The resulting mixture was concentrated to dryness under vacuum. The residue was purified on a silica gel column eluting with dichloromethane/methanol (10:1) to give 180 mg (86%) of [4-(4-chlorophenyl)piperidin-4-yl]methanol as a yellow solid. LCMS (method 3): RT=1.03 min, m/z=226.0 [M+H]+

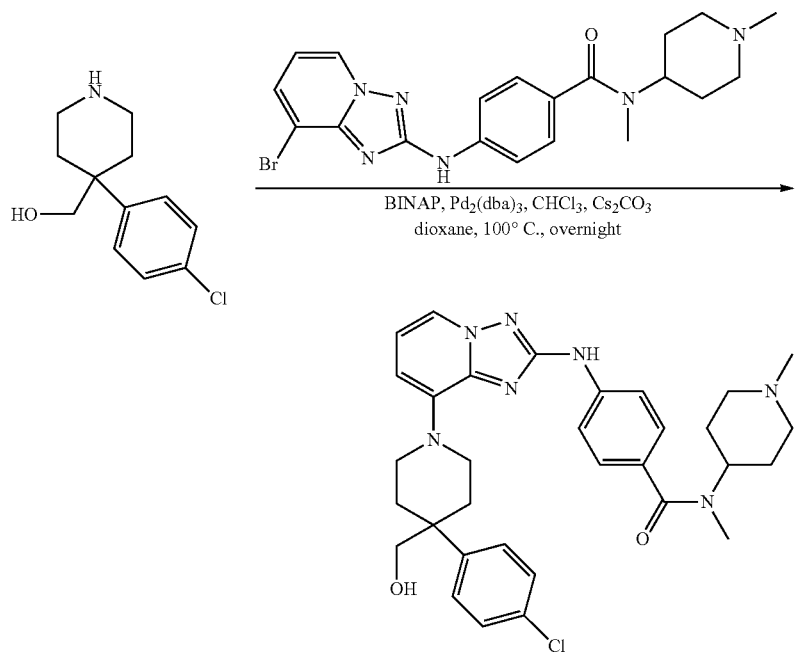

Step 5. The solution of 4-([8-bromo-[1,2,4]triazolo[1,5-a]pyridin-2-yl]amino)-N-methyl-N-(1-methylpiperidin-4-yl)benzamide (242 mg, 0.55 mmol, 1.50 equiv) in 1,4-dioxane (20 mL) was placed in a 100-mL round-bottom flask purged and maintained with an inert atmosphere of nitrogen, then [4-(4-chlorophenyl)piperidin-4-yl]methanol (160 mg, 0.71 mmol, 1.00 equiv), Cs$_2$CO$_3$ (357 mg, 1.10 mmol, 2.00 equiv), Pd$_2$(dba)$_3$.CHCl$_3$ (314.6 mg, 0.30 mmol, 0.45 equiv), BINAP (377.7 mg, 0.61 mmol, 0.90 equiv) was added. The resulting solution was stirred for 48 hours at 100° C. in an oil bath. The solids were filtered off. The filtrate was concentrated under vacuum. The residue was applied onto a silica gel column eluting with dichloromethane/methanol (5:1) to give a crude product. The crude product was purified again by Prep-HPLC under the following conditions Column, XBridge™ Prep C18 OBD Column, 5 um, 19×150 mm,; mobile phase, water with 10 mmol NH$_4$HCO$_3$ and MeCN (30.0% MeCN up to 45.0% in 10 min, up to 95.0% in 1 min, hold 95.0% in 1 min, down to 30.0% in 2 min); Detector, UV 254/220 nm to give 20.8 mg (5%) of 4-([8-[4-(4-chlorophenyl)-4-(hydroxymethyl)piperidin-1-yl]-[1,2,4]triazolo[1,5-a]pyridin-2-yl ]amino)-N-methyl-N-(1-methylpiperidin-4-yl)benzamide, Example 1-246 as an off-white solid. LCMS (Method 3): RT=2.09 min, m/z=588.2 [M+H]$^+$, $^1$H NMR (300 MHz, DMSO-d$_6$, ppm): δ 9.87 (s, 1H), 8.29-8.28 (m, 1H), 7.71 (d, J=8.8 Hz, 2H), 7.45 (d, J=8.4 Hz, 2H), 7.38 (d, J=8.8 Hz, 2H), 7.31 (d, J=8.8 Hz, 2H), 6.29-8.28 (m, 1H), 6.27-6.26 (m, 1H), 4.71 (t, J=5.6 Hz, 1H), 3.88-3.78 (m, 2H), 3.41 (d, J=5.6 Hz, 2H), 3.30 (s, 3H), 3.06-2.92 (m, 2H), 2.90-2.78 (m, 4H), 2.26-2.18 (m, 5H), 2.17-2.02 (m, 2H), 1.73-1.85 (m, 3H), 1.57-1.51 (m, 2H).

Example 1e

4-{8-[4-(4-Chloro-phenyl)-4-(2-cyano-ethyl)-piperidin-1-yl]-1,8a-dihydro[1,2,4]triazolo[1,5-a]pyridine-2-ylamino}-N-methyl-N-(1-methyl-piperidin-4-yl)-benzamide (Example 1-247 in Table I)

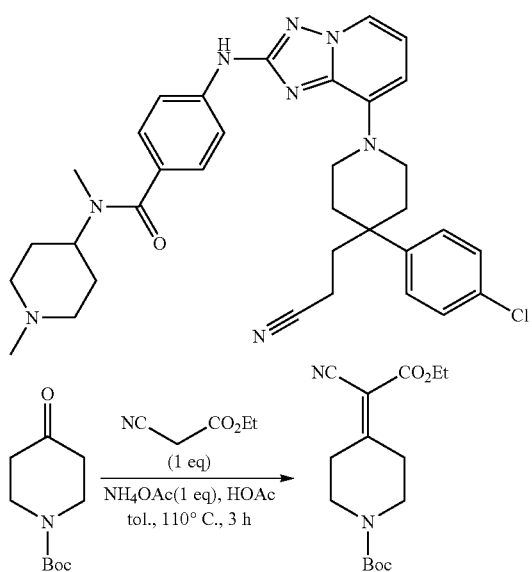

Step 1. Into a 2-L 3-necked round-bottom flask purged and maintained with an inert atmosphere of nitrogen, was placed tert-butyl 4-oxopiperidine-1-carboxylate (100 g, 501.89 mmol, 1.00 equiv), toluene (800 mL), ethyl 2-cyanoacetate (56.8 g, 502.15 mmol, 1.00 equiv), NH$_4$OAc (38.5 g, 1.00 equiv), acetic acid (80 mL). The resulting solution was stirred for 3 h at 110° C. The reaction mixture was cooled to room temperature and concentrated under vacuum. The resulting solution was diluted with 300 mL of H$_2$O and extracted with 2×1 L of ethyl acetate and the organic layers combined and dried over anhydrous sodium sulfate. The solids were filtered off, and the filtrate was concentrated under vacuum. The residue was purified on a silica gel column with ethyl acetate/petroleum ether (1:10). 110 g (74%) of tert-butyl 4-(1-cyano-2-ethoxy-2-oxoethylidene)piperidine-1-carboxylate was obtained as a white solid. TLC: R$_f$=0.4; ethyl acetate/petroleum ether=1/4.

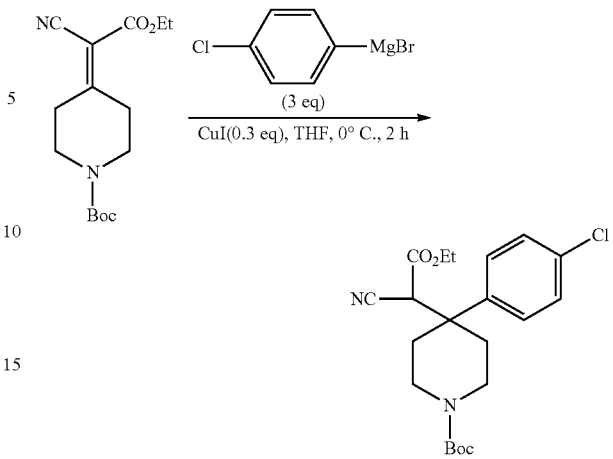

Step 2. Into a 3-L 3-necked round-bottom flask purged and maintained with an inert atmosphere of nitrogen, was placed tert-butyl 4-(1-cyano-2-ethoxy-2-oxoethylidene)piperidine-1-carboxylate (100 g, 339.74 mmol, 1.00 equiv), tetrahydrofuran (500 mL), CuI (19.4 g, 101.86 mmol, 0.30 equiv). The bromo(4-chlorophenyl)magnesium (1M in THF, 1.02 L, 3.00 equiv) was added dropwise at 0° C. The resulting solution was stirred for 2 h at 0° C. The resulting mixture was warmed to room temperature and concentrated under vacuum. The residue was suspended in 1 L of EtOAc and the solids were filtered off. The filtrate was concentrated under vacuum. The residue was purified on a silica gel column eluting with ethyl acetate/petroleum ether (1:15~1:10). 100 g (72%) of tert-butyl 4-(4-chlorophenyl)-4-(1-cyano-2-ethoxy-2-oxoethyl)piperidine-1-carboxylate was obtained as a light yellow solid. TLC: R$_f$=0.3; ethyl acetate/petroleum ether=1/4.

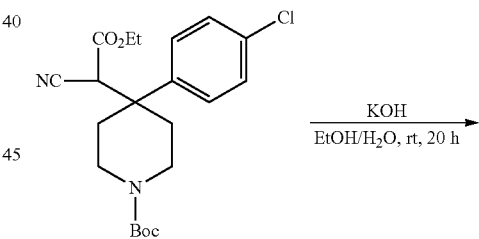

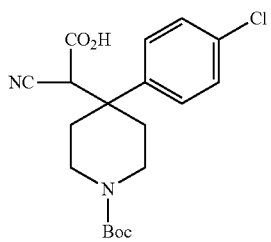

Step 3. Into a 3-L 3-necked round-bottom flask, was placed tert-butyl 4-(4-chlorophenyl)-4-(1-cyano-2-ethoxy-2-oxoethyl)piperidine-1-carboxylate (100 g, 245.76 mmol, 1.00 equiv), ethanol (500 mL), water (500 mL), potassium hydroxide (30 g, 534.71 mmol, 2.18 equiv). The resulting solution was stirred for 20 h at room temperature. EtOH was removed under vacuum. The resulting aqueous solution was extracted with 1×200 mL of ether, and the pH value of the aqueous phase was adjusted to 6 with 6N hydrogen chloride solution at 0° C., and then concentrated to dryness under vacuum. The resulting solid was suspended in 500 mL of a mixture of dichloromethane/MeOH (5:1, v/v), and the solid was filtered off. The filtrate was concentrated under vacuum to give 76 g of crude 2-[1-[(tert-butoxy)carbonyl]-4-(4-chlorophenyl)piperidin-4-yl]-2-cyanoacetic acid as a light yellow solid, which was used in next step without further purification. TLC: $R_f$=0.3; dichloromethane/methanol=5/1.

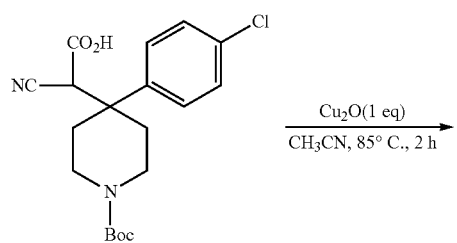

Step 4. Into a 2-L 3-necked round-bottom flask purged and maintained with an inert atmosphere of nitrogen, was placed 2-[1-[(tert-butoxy)carbonyl]-4-(4-chlorophenyl)piperidin-4-yl]-2-cyanoacetic acid (76 g, 200.61 mmol, 1.00 equiv), acetonitrile (800 mL), Cu$_2$O (28 g, 195.68 mmol, 1.00 equiv). The resulting solution was stirred for 2 h at 85° C. The reaction mixture was cooled to room temperature and concentrated under vacuum. The residual solid was suspended in 500 mL of EA and the solid was filtered off. The filtrate was concentrated under vacuum, and the residue was purified on a silica gel column eluting with ethyl acetate/petroleum ether (1:10~1:2) to yield 50 g (74%) of tert-butyl 4-(4-chlorophenyl)-4-(cyanomethyl)piperidine-1-carboxylate as a light yellow solid. TLC: $R_f$=0.3; ethyl acetate/petroleum ether=1/2. $^1$H NMR (300 MHz, DMSO-d$_6$, ppm): δ 7.42-7.38 (m, 2H), 7.34-7.30 (m, 2H), 3.79-3.72 (m, 2H), 3.13-3.04 (m, 2H), 2.54 (s, 2H), 2.32-2.27 (m, 2H), 1.91-1.82 (m, 2H), 1.45 (s, 9H).

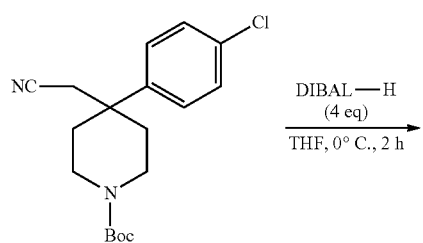

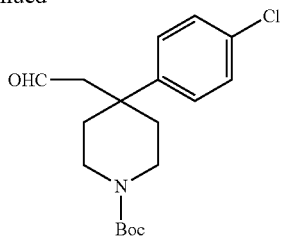

Step 5. Into a 250-mL round-bottom flask purged and maintained with an inert atmosphere of nitrogen, was placed tert-butyl 4-(4-chlorophenyl)-4-(cyanomethyl)piperidine-1-carboxylate (5 g, 14.93 mmol, 1.00 equiv) and anhydrous tetrahydrofuran (80 mL). DIBAL-H solution (1 M in hexane, 30 mL, 2.00 equiv) was added dropwise at 0° C. The resulting solution was stirred for 2 h at 0° C. The reaction was then quenched by addition of 40 mL of water/ice. The resulting solution was extracted with 2×200 mL of ethyl acetate. The organic layers were combined, washed with 1×20 mL of 1 M hydrogen chloride and 1×20 mL of sodium bicarbonate saturated solution, and dried over anhydrous sodium sulfate. The solid was filtered off and the filtrate was concentrated under vacuum to yield 3 g of crude tert-butyl 4-(4-chlorophenyl)-4-(2-oxoethyl)piperidine-1-carboxylate as colorless oil. TLC: $R_f$=0.4; ethyl acetate/petroleum ether=1/2.

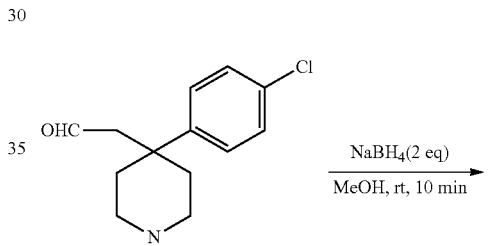

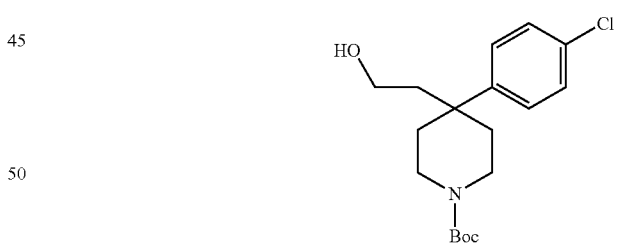

Step 6. Into a 250-mL round-bottom flask purged and maintained with an inert atmosphere of nitrogen, was placed a solution of tert-butyl 4-(4-chlorophenyl)-4-(2-oxoethyl)piperidine-1-carboxylate (3 g, 8.88 mmol, 1.00 equiv) in methanol (80 mL), NaBH$_4$ (680 mg, 17.89 mmol, 1.00 equiv) was added portionwise. The resulting solution was stirred for 10 min at 25° C. The reaction was then quenched by the addition of 5 mL of water. The resulting mixture was concentrated under vacuum. The residue was purified on a silica gel column with ethyl acetate/petroleum ether (1:2~1:1) to yield 1.4 g (46%) of tert-butyl 4-(4-chlorophenyl)-4-(2-hydroxyethyl)piperidine-1-carboxylate as a white solid. TLC: $R_f$=0.3; ethyl acetate/petroleum ether=1/1.

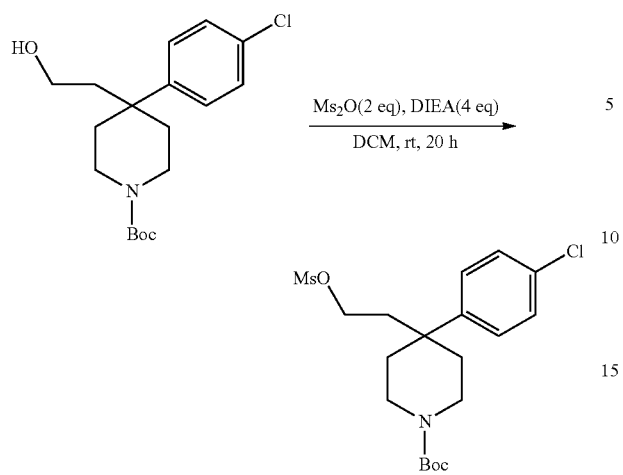

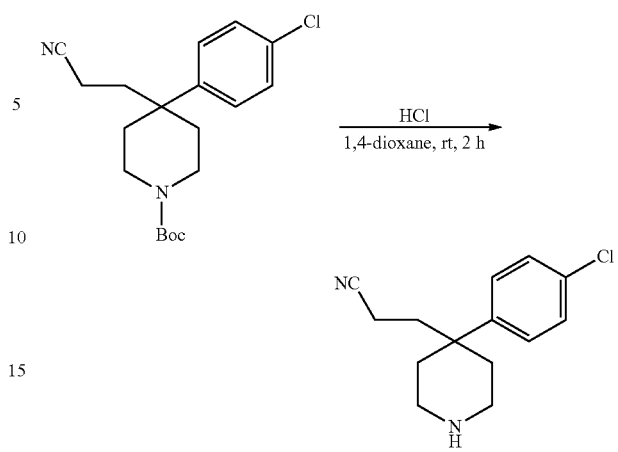

Step 7. To a mixture of tert-butyl 4-(4-chlorophenyl)-4-(2-hydroxyethyl)piperidine-1-carboxylate (600.00 mg, 1.77 mmol, 1.00 equiv) and DIPEA (930 mg, 7.06 mmol, 4.00 equiv) in dry dichloromethane (20.00 mL, 314.60 mmol, 178.20 equiv) was added Ms$_2$O (630 mg, 3.53 mmol, 2.00 equiv) dropwise under N$_2$. The resulting solution was stirred for 4 h at ambient temperature. The resulting mixture was concentrated under vacuum. The residue was purified on a silica gel column with ethyl acetate/petroleum ether (1/4) to give 550 mg (67%) of tert-butyl 4-(4-chlorophenyl)-4-[2-(methanesulfonyloxy)ethyl]piperidine-1-carboxylate as colorless oil. TLC: R$_f$=0.4; ethyl acetate/petroleum ether=1/2.

Step 9. A mixture of tert-butyl 4-(4-chlorophenyl)-4-(2-cyanoethyl)piperidine-1-carboxylate (360 mg, 1.03 mmol, 1.00 equiv) in 1M HCl/1,4-dioxane (30 mL) was stirred for 2 h at 25° C. The reaction mixture was concentrated under vacuum. The residue was dissolved in 5 mL of H$_2$O. The pH value of the solution was adjusted to 8 with potassium carbonate. The resulting mixture was concentrated to dryness under vacuum. The residue was purified on a silica gel column with dichloromethane/methanol (5/1). The collected fractions were combined and concentrated under vacuum. This resulted in 180 mg of 3-[4-(4-chlorophenyl)piperidin-4-yl]propanenitrile as light yellow oil. TLC: R$_f$=0.3; dichloromethane/methanol=5/1. LCMS (Method 3): RT=1.05 min, m/z=249.0 [M+H]$^+$;

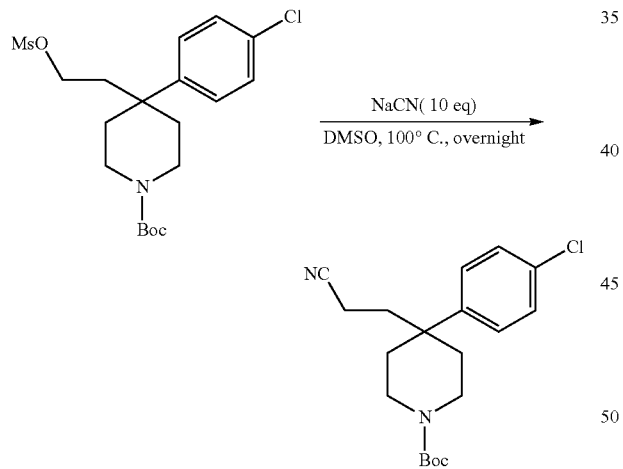

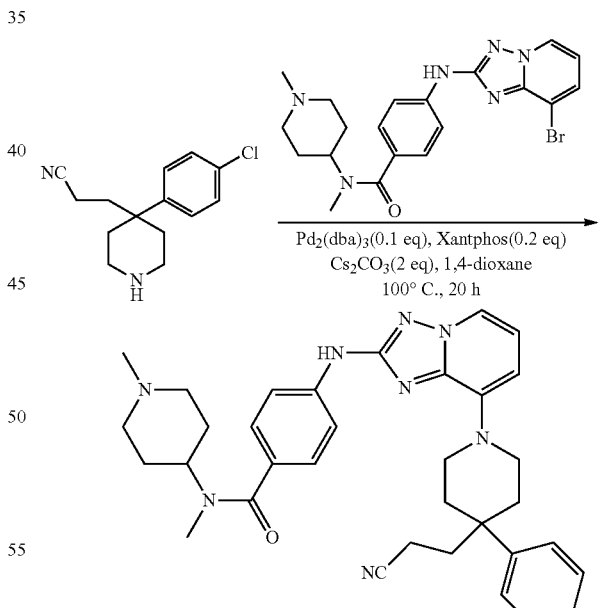

Step 8. A mixture of tert-butyl 4-(4-chlorophenyl)-4-[2-(methanesulfonyloxy)ethyl]piperidine-1-carboxylate (550.00 mg, 1.32 mmol, 1.00 equiv) and NaCN (650 mg, 13.16 mmol, 10.00 equiv) in DMSO (20.00 mL) was stirred overnight at 100° C. The reaction mixture was cooled, and diluted with 100 mL of ethyl acetate. The resulting mixture was washed with 3×20 mL of H$_2$O. The organic phase was dried over Na$_2$SO$_4$, and concentrated under vacuum. The residue was purified on a silica gel column with ethyl acetate/petroleum ether (1:4). The collected fractions were combined and concentrated under vacuum to give 360 mg (71%) of tert-butyl 4-(4-chlorophenyl)-4-(2-cyanoethyl)piperidine-1-carboxylate as colorless oil. TLC: R$_f$=0.5; ethyl acetate/petroleum ether =1/2.

Step 10. Into a 100-mL round-bottom flask purged and maintained under an inert atmosphere of nitrogen, was placed 3-[4-(4-chlorophenyl)piperidin-4-yl]propanenitrile (180 mg, 0.72 mmol, 1.00 equiv), 4-(8-bromo-[1,2,4]triazolo[1,5-a]pyridin-2-ylamino)-N-methyl-N-(1-methylpiperidin-4-yl)benzamide (320 mg, 0.72 mmol, 1.00 equiv), 1,4-dioxane (20 mL, 335.12 mmol, 463.10 equiv), Cs$_2$CO$_3$ (473 mg, 1.45 mmol, 2.00 equiv), XantPhos (84 mg, 0.15 mmol, 0.20 equiv), Pd$_2$(dba)$_3$ (70 mg, 0.08 mmol, 0.10 equiv). The resulting mixture was stirred for 20 h at 100° C. in an oil bath. The reaction mixture was cooled and concentrated under vacuum. The residue was applied onto a silica gel column eluting with dichloromethane/methanol (10:1 and 5:1). The obtained crude product (200 mg) was purified again by Prep-HPLC with the following conditions (IntelFlash-1): Column, silica gel; mobile phase, CH$_3$CN/H$_2$O=20% increasing to CH$_3$CN/H$_2$O=60% within 17 min; Detector, UV 254 nm to give 27.2 mg (6%) of 4-([8-[4-(4-chlorophenyl)-4-(2-cyanoethyl)piperidin-1-yl]-[1,2,4]triazolo[1,5-a]pyridin-2-yl]amino)-N-methyl-N-(1-methylpiperidin-4-yl)benzamide as an off-white solid. LCMS (Method 3): RT=1.78 min, m/z=611.1 [M+H]$^+$; $^1$H NMR (400 MHz, DMSO-d$_6$, ppm): δ 9.88 (s, 1H), 8.30 (d, J=6.0 Hz, 1H), 7.71 (d, J=8.8 Hz, 2H), 7.48-7.43 (m, 4H), 7.33-7.31 (d, J=8.4 Hz, 2H), 6.86 (t, J=7.2 Hz, 1H), 6.76 (d, J=8.0 Hz, 1H), 3.80-3.77 (m, 2H), 3.32-3.30 (m, 1H), 3.08-3.03 (m, 2H), 2.83-2.81 (m, 5H), 2.33-2.30 (m, 2H), 2.15-2.00 (m, 5H), 1.99-1.96 (m, 4H), 1.95-1.65 (m, 4H), 1.58-1.55 (m, 2H).

Example 1f

4-{8-[4-(3,3-Dimethyl-azetidine-1-carbonyl)-piperidin-1-yl]-1,8a-dihydro [1,2,4]triazolo[1,5a]pyridine-2-ylamino}-N-methyl-N-(1-methyl-piperidin-4-yl)-benzamide (Example 1-42 in Table I)

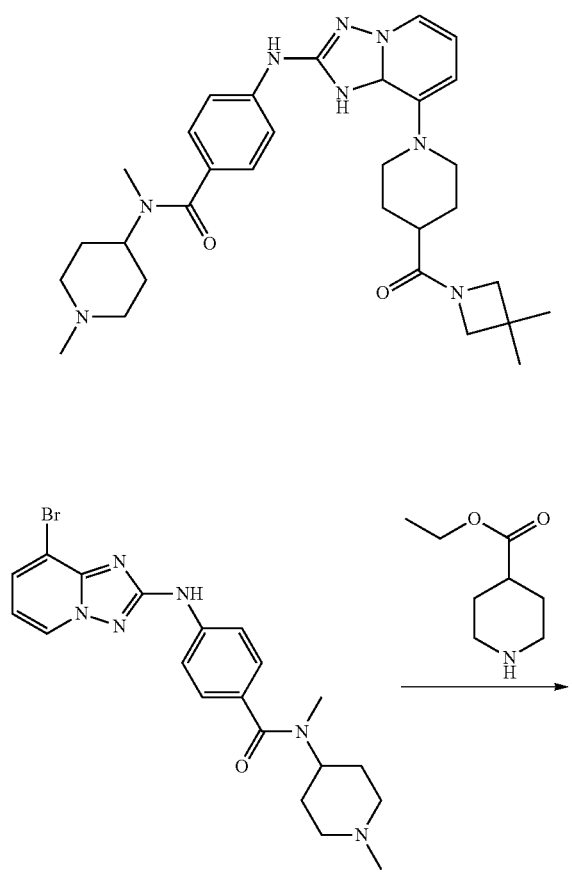
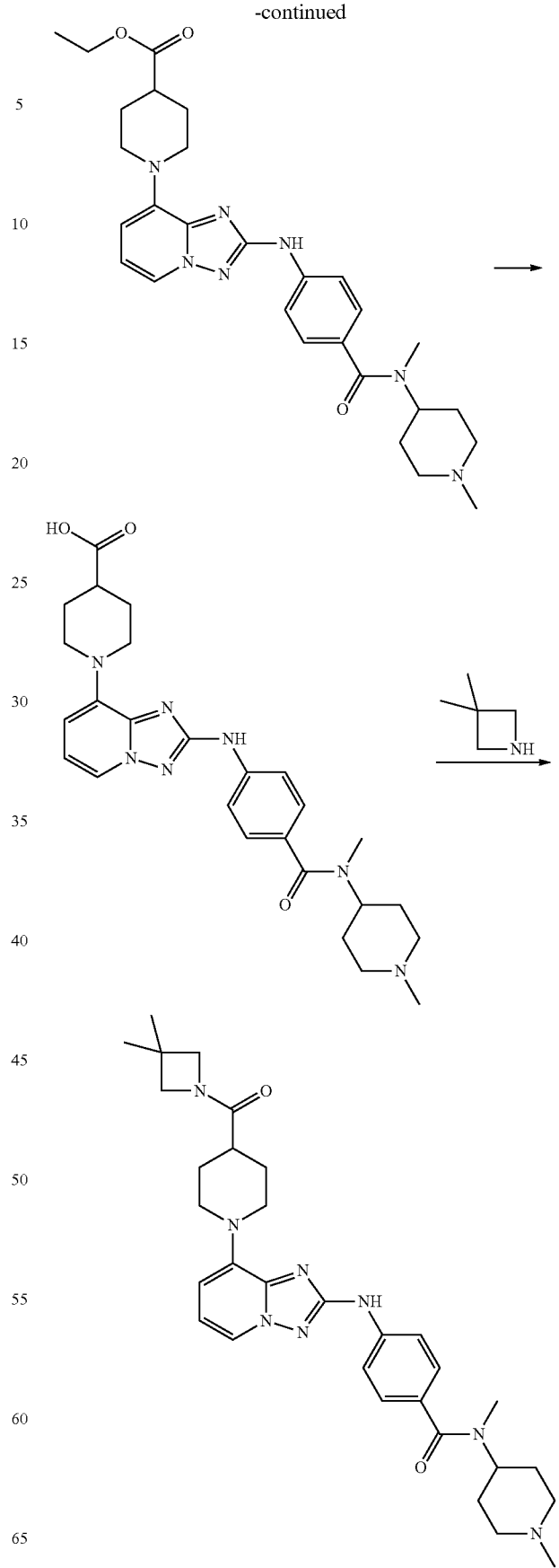

559

-continued

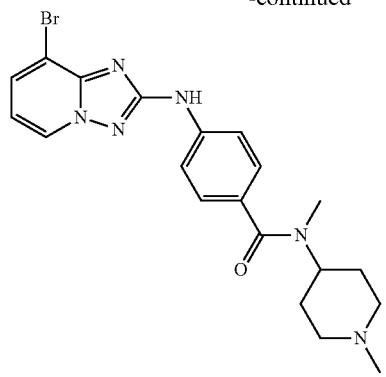
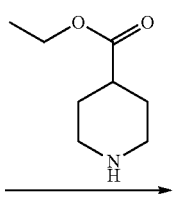

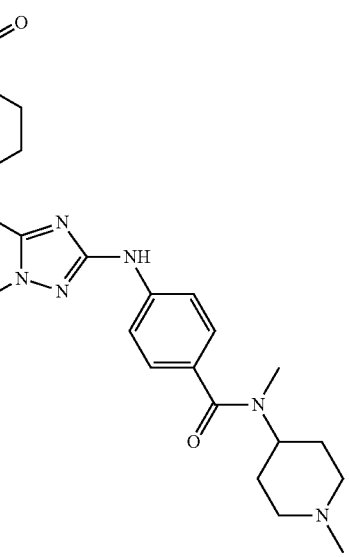

560

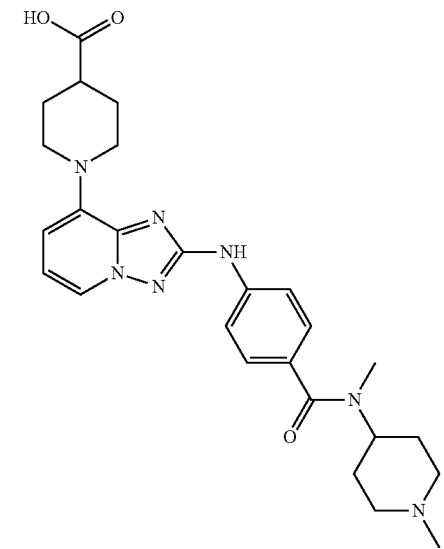

Step 1. The mixture of 4-(8-bromo-[1,2,4]triazolo[1,5-a]pyridin-2-ylamino)-N-methyl-N-(1-methylpiperidin-4-yl)benzamide (150 mg, 0.338mmol) piperidine-4-carboxylic acid ethyl ester (159.4 mg, 1.01mmol) X-phos (39 mg, 0.067 mmol) Pd$_2$(dba)$_3$ (47 mg, 0.067 mmol) Cs$_2$CO$_3$ (329 mg, 1.01 mmol) in t-BuOH (3 mL) was heated to 100° C. and stirred for 1 h on microwave. The mixture was evaporated and water was added, extracted with EtOAc three times, the combined organic layer was washed with water and brine and dried (Na$_2$SO$_4$). The solvent was concentrated and the residue was purified by column (dichloromethane:MeOH=10:1) to give 1-(2-{4-[methyl-(1-methyl-piperidin-4-yl)-carbamoyl]-phenylamino}8 1,2,4]triazolo[1,5-a]pyridine-8-yl)-piperidin-4-carboxylic acid ethyl ester (40 mg, 22% yield).

Step 2. To a solution of 1-(2-{4-[methyl-(1-methyl-piperidin-4-yl)-carbamoyl]-phenylamino}-[1,2,4]triazolo[1,5-a]pyridine-8-yl)-piperidin-4-carboxylic acid ethyl ester (100 mg, 0.192 mmol) in dioxane (2 mL) was added 1M NaOH aq (0.2 mL) and the mixture was heated to 80° C. and stirred for 2 h. The solvent was evaporated and EtOAc was added, the mixture was extracted with 1M NaOH aq, the combined aqueous layer was adjusted to pH7 with 4M HCl, extracted with dichloromethane three times, the combined organic layer was washed with water and brine, dried (Na$_2$SO$_4$), and the solvent was evaporated in vacuo to give 1-(2-{4-[methyl-(1-methyl-piperidin-4-yl)-carbamoyl]-phenylamino-[1,2,4]triazolo[1,5-a]pyridine-8-yl)-piperidin-4-carboxylic acid (70 mg, 98% of yield).

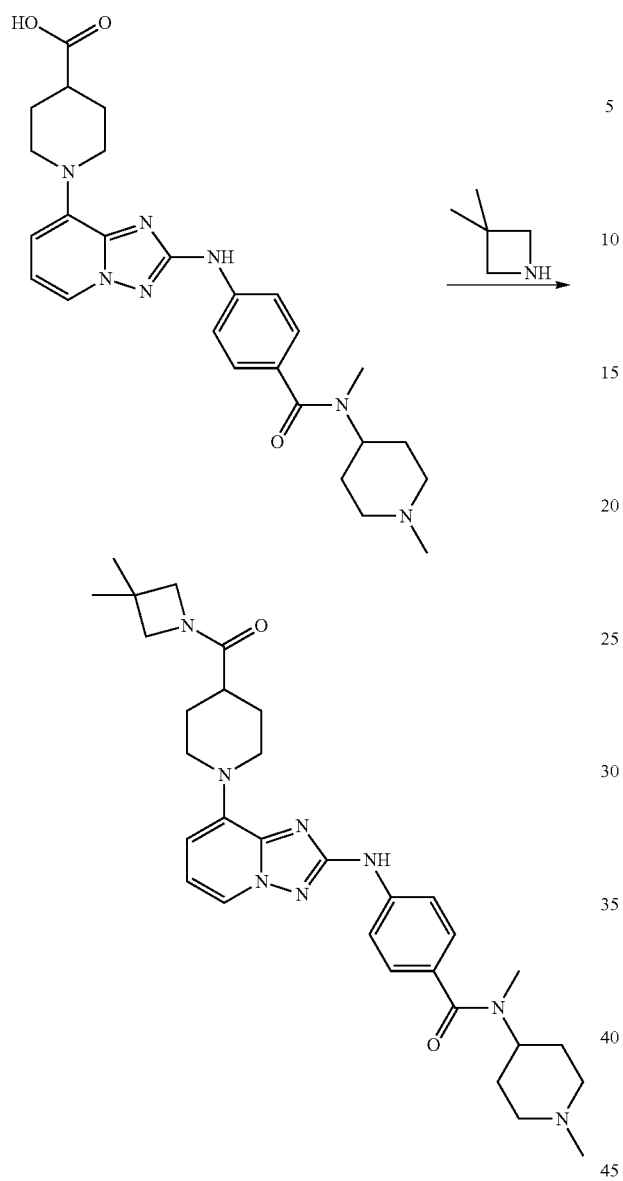

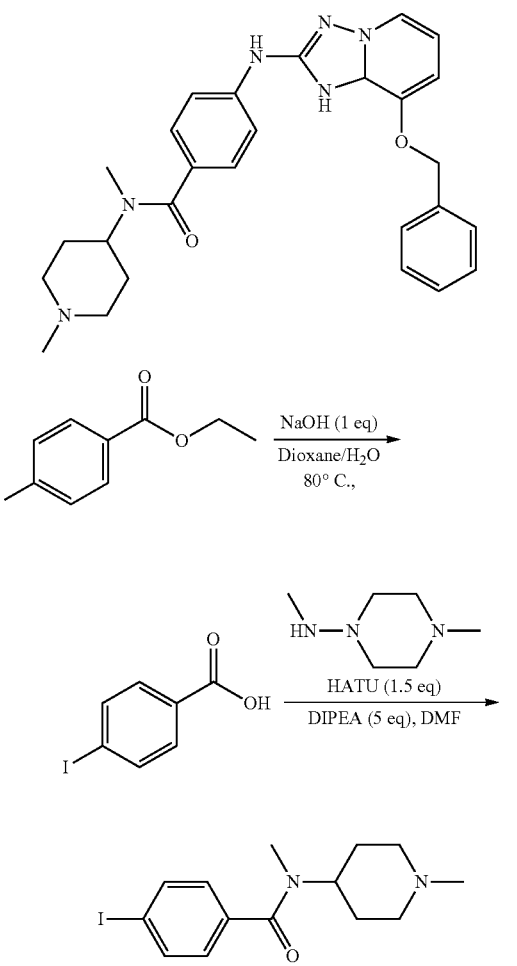

The mixture of 1-(2-{4-[methyl-(1-methyl-piperidin-4-yl)-carbamoyl]-phenylamino}-[1,2,4]triazolo[1,5-a]pyridine-8-yl)-piperidin-4-carboxylic acid (70 mg, 0.142 mmol) HATU (64.7 mg, 0.17 mmol) DIPEA (55 mg, 0.426 mmol) in DMF was stirred for 10 min at r,t. then 3,3-dimethyl azetidine (49.5 mg, 0.284 mmol) was added and the mixture was stirred for 2 h at r.t. The reaction mixture was poured into water and extracted three times with dichloromethane, the combined organic layer was washed with water and brine, dried ($Na_2SO_4$) the solvent was evaporated and the residue was purified by preparative scale-TLC to give 4-{8-[4-(3,3-dimethyl-azetidine-1-carbonyl)-piperidin-1-yl]-1,8a-dihydro[1,2,4]triazolo-[1,5a]pyridine-2-ylamino-N-methyl-N-(1-methyl-piperidin-4-yl)-benzamide (30 mg, 38% yield).

$^1$H NMR (400 MHz, methanol-$d_4$) δ 8.15 (d, J=5.51 Hz, 1H), 7.74 (d, J=8.60 Hz, 2H), 7.39 (d, J=8.38 Hz, 2H), 6.83-6.91 (m, 2H), 4.24 (d, J=12.13 Hz, 2H), 3.96 (s, 2H), 3.66 (s, 2H), 3.47 (br. s., 2H), 2.97 (s, 4H), 2.72-2.87 (m, 5H), 2.48-2.56 (m, 1H), 2.10-2.19 (m, 2H), 1.90-2.04 (m, 4H), 1.82 (d, J=11.25 Hz, 2H), 1.24-1.41 (m, 8H).

Example 1g 4-(8-Benzyloxy-1,8a-dihydro-[1,2,4]triazolo[1,5-a]pyridine-2-ylamino)-N-methyl-N-(1-methyl-piperidin-4-yl)-benzamide (Example 1-249 in Table I)

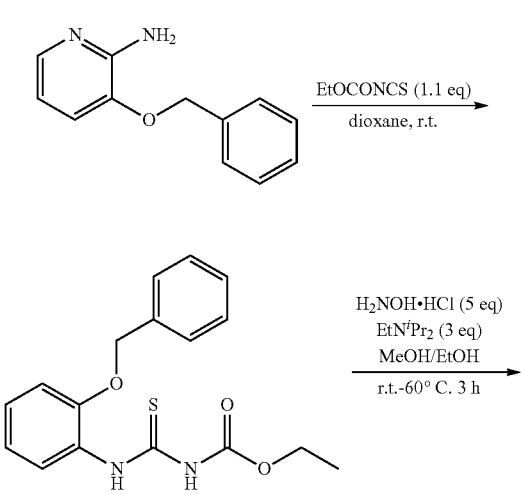

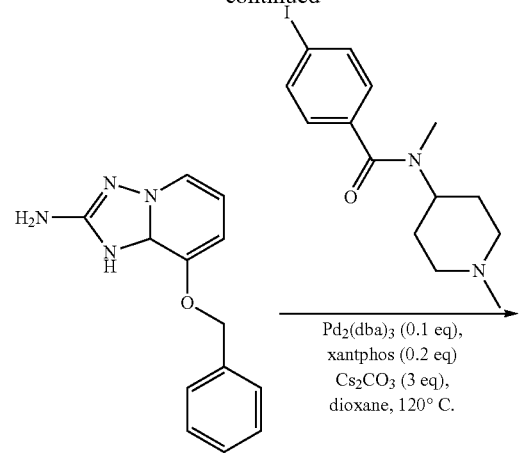

Step 2. To a mixture of 4-iodobenzoic acid (1.0 g, 4 mmol) HATU (1.8 g, 4.8 mmol) in DMF was added DIPEA (1.5 g, 12 mmol) at 0° C. and the mixture was stirred for 10 min, then methyl-(1-methyl-piperidin-4-yl)-amine (1.02 g, 8 mmol) was added, and the reaction mixture was stirred for 2 h at r.t. The reaction mixture was poured into water and the mixture was extracted with EtOAc three times. The combined organic layer was washed with water and brine, dried ($Na_2SO_4$), the solvent was evaporated in vacuo to give 4-iodo-N-methyl-N-(1-methyl-piperidin-4-yl)-benzamide (1.2 g, 83% of yield).

Step 3. The mixture of 3-benzyloxy-pyridin-2-ylamine (400 mg, 2 mmol) EtOCONCS (282 uL) in dioxane was stirred overnight at rt the solvent was evaporated and the residue (600 mg) was used for the next step without purification.

Step 1. To a solution of 4-iodobenzoic acid ethyl ester (5.0 g, 18.1 mmol) was added 1M NaOH aq (18.1 mL, 18.1 mmol) and the mixture was heated to 100° C. and stirred for 1.5 h. The solvent was evaporated, the residue was adjusted to pH6, and the precipitated solid was filtered off and washed with water to give 4-iodobenzoic acid (4.0 g, 89% yield).

-continued

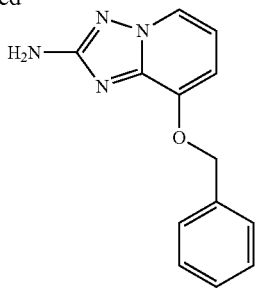

Step 4. To a solution of NH₂OH-HCl (704 mg, 10.6 mmol) DIPEA (1 mL, 6.6 mmol) in MeOH (4 mL) and EtOH (4 mL) was added a solution of the thiourea prepared in step 3 (600 mg, 2.12 mmol) in MeOH (4 mL) and EtOH (4 mL) at rt the mixture was stirred at r,t for 1 h and then at 60° C. for 2 h. The solvent was evaporated and saturated NaHCO₃ solution was added to the residue. The aqueous layer was extracted three times with dichloromethane, the combined organic layer was washed with water and brine, dried (Na₂SO₄), the solvent was evaporated and solid was washed with petroleum ether to give 8-benzyloxy-[1,2,4]triazolo[1,5-a]pyridine-2-ylamine (430 mg, 86% of yield).

¹-H NMR (400 MHz, DMSO-d₆) δ 8.13 (d, J=6.39 Hz, 1H), 7.42-7.50 (m, 2H), 7.38 (t, J=7.39 Hz, 2H), 7.29-7.35 (m, 1H), 6.96 (d, J=7.72 Hz, 1H), 6.73 (dd, J=6.84, 7.72 Hz, 1H), 5.89 (s, 2H), 5.25 (s, 2H).

Step 5. The mixture of 8-benzyloxy-[1,2,4]triazolo[1,5-a]pyridine-2-ylamine (150 mg, 0.625 mmol), 4-iodo-N-methyl-N-(1-methyl-piperidin-4-yl)-benzamide (268.5 mg, 0.75 mmol) Pd₂(dba)₃ (57 mg, 0.0625 mmol) Cs₂CO₃ (610 mg,1.87 mmol) Xantphos (72 mg, 0.125 mmol) in dioxane was stirred for 2 h at 120° C. The solvent was concentrated, water was added and the mixture was extracted three times with EtOAc. The combined organic layer was washed with water and brine, dried (Na₂SO₄), the solvent was evaporated and the residue was purified by prep TLC (dichloromethane:MeOH=7:1) to give 4-(8-benzyloxy-1,8a-dihydro-[1,2,4]triazolo[1,5-a]pyridine-2-ylamino)-N-methyl-N-(1-methyl-piperidin-4-yl)-benzamide (55 mg, 18% yield).

¹H NMR (400 MHz, methanol-d₄) δ 8.23 (d, J=6.39 Hz, 1H), 7.74 (d, J=8.60 Hz, 2H), 7.53 (d, J=7.06 Hz, 2H), 7.29-7.43 (m, 5H), 7.09 (d, J=7.72 Hz, 1H), 6.90-6.94 (m, 1H), 5.34 (s, 2H), 4.58 (s, 1H), 2.96 (s, 3H), 2.63 (br. s., 7H), 2.07 (d, J=11.25 Hz, 2H), 1.93 (br. s., 2H)

Example 1h

N-Methyl-N-(1-methyl-piperidin-4-yl)-4-(8-phenoxy-[1,2,4]triazolo[1,5-a]pyridine-2-ylamino)-benzamide (Example 1-248 in Table I)

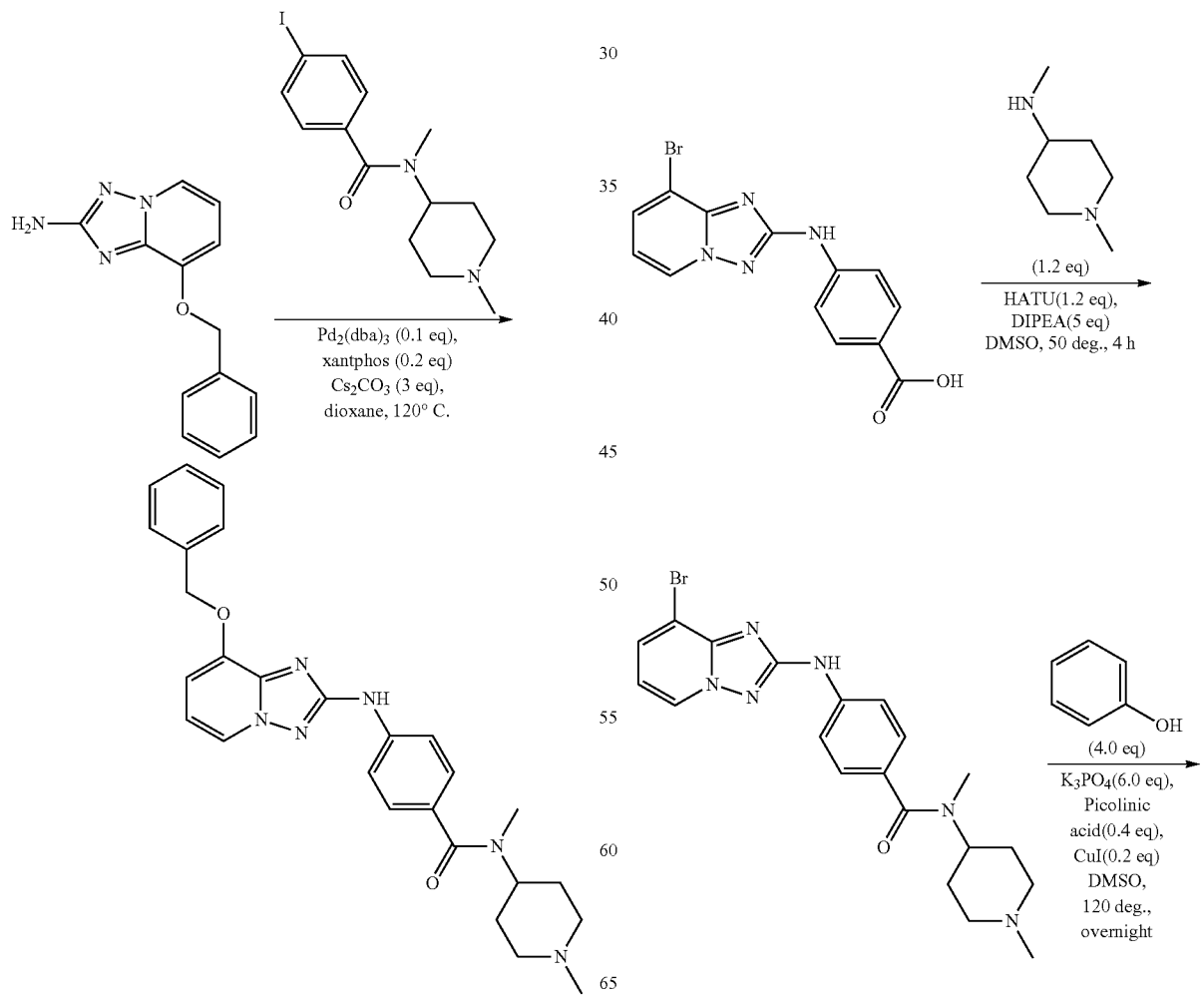

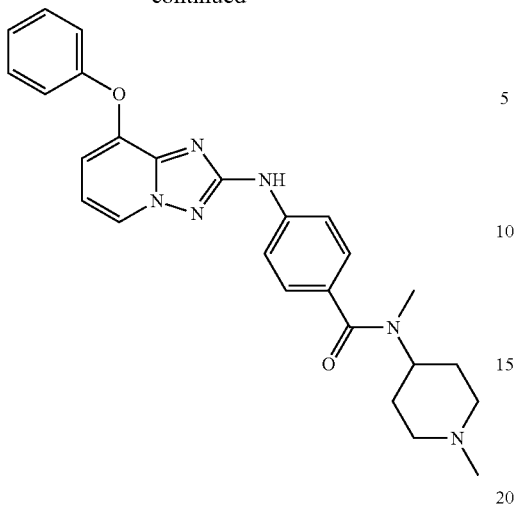

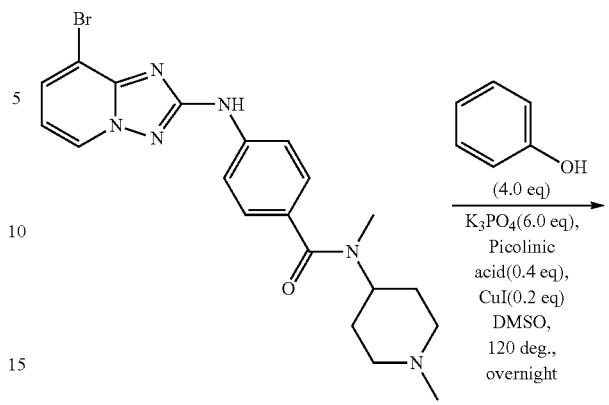

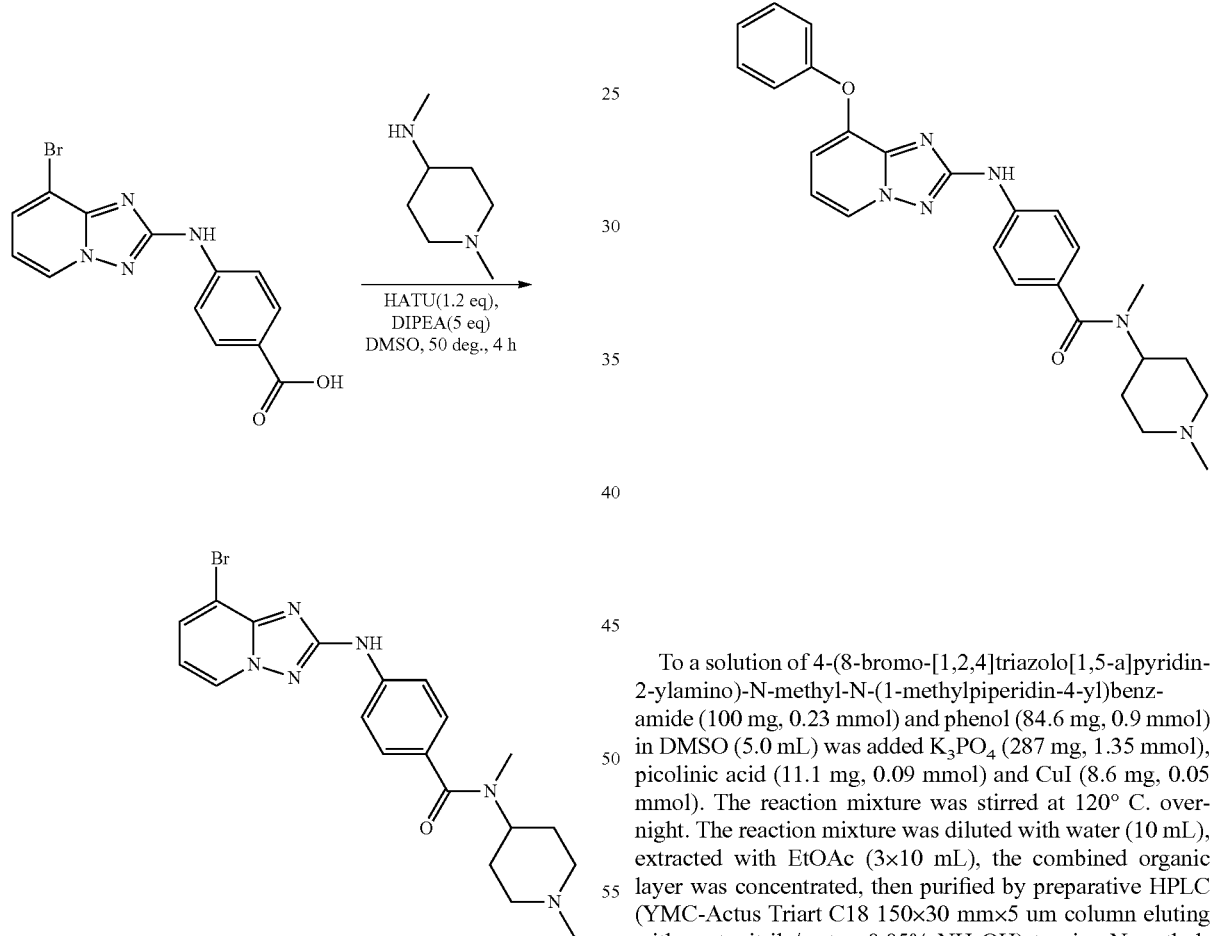

Step 1. To a solution of 4-(8-bromo-[1,2,4]triazolo[1,5-a]pyridine-2-ylamino)-benzoic acid (1 g, 3.0 mmol), methyl-(1-methyl-piperidin-4-yl)-amine (460 mg, 3.6 mmol) and DIPEA (2.65 ml, 15 mmol) in DMSO (10.0 mL) was added HATU (1.37 g, 3.6 mmol). The reaction mixture was stirred at 50° C. for 4 hours. The reaction mixture was filtered, the filter cake was dried to give 4-(8-bromo-[1,2,4]triazolo[1,5-a]pyridin-2-ylamino)-N-methyl-N-(1-methyl-piperidin-4-yl)benzamide (1.1 g, 82.7%).

To a solution of 4-(8-bromo-[1,2,4]triazolo[1,5-a]pyridin-2-ylamino)-N-methyl-N-(1-methylpiperidin-4-yl)benzamide (100 mg, 0.23 mmol) and phenol (84.6 mg, 0.9 mmol) in DMSO (5.0 mL) was added K$_3$PO$_4$ (287 mg, 1.35 mmol), picolinic acid (11.1 mg, 0.09 mmol) and CuI (8.6 mg, 0.05 mmol). The reaction mixture was stirred at 120° C. overnight. The reaction mixture was diluted with water (10 mL), extracted with EtOAc (3×10 mL), the combined organic layer was concentrated, then purified by preparative HPLC (YMC-Actus Triart C18 150×30 mm×5 um column eluting with acetonitrile/water+0.05% NH$_4$OH) to give N-methyl-N-(1-methyl-piperidin-4-yl)-4-(8-phenoxy-[1,2,4]triazolo[1,5-a]pyridine-2-ylamino)-benzamide (20.0 mg, 19.6%).

$^1$H NMR (400 MHz, methanol-d$_4$) δ 8.41 (d, J=6.17 Hz, 1H), 7.73 (d, J=8.38 Hz, 2H), 7.43 (d, J=7.94 Hz, 2H), 7.38 (d, J=7.28 Hz, 2H), 7.21-7.25 (m, 1H), 7.16 (d, J=7.94 Hz, 2H), 6.92-7.00 (m, 2H), 2.96 (s, 5H), 2.24-2.37 (m, 3H), 1.93-2.01 (m, 2H), 1.73-1.83 (m, 2H), 1.31 (d, J=18.52 Hz, 3H).

LCMS(Method 4):R$_T$=0.740 min, m/z: 457.0(M+H$^+$).

Example 1i

4-([8-[1-(1-cyanopropan-2-yl)-1,2,3,6-tetrahydro-pyridin-4-yl]-[1,2,4]triazolo[1,5-a]pyridin-2-yl]amino)-N-methyl-N-(1-methylpiperidin-4-yl)benzamide (Example 1-264 in Table I)

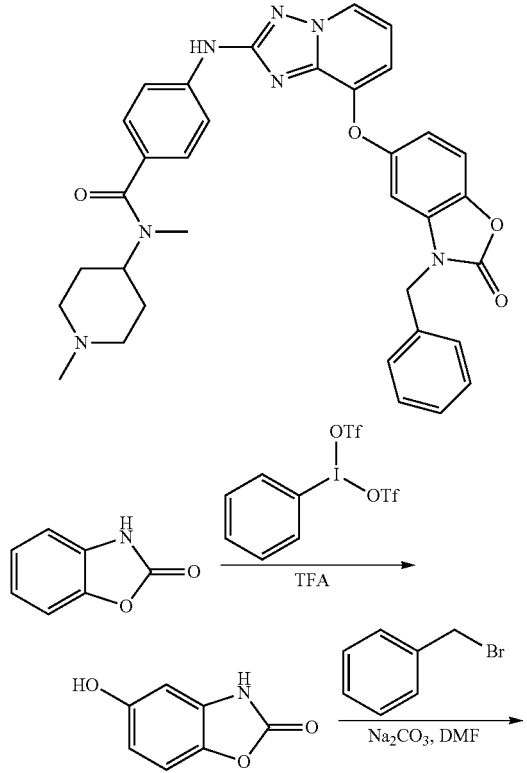

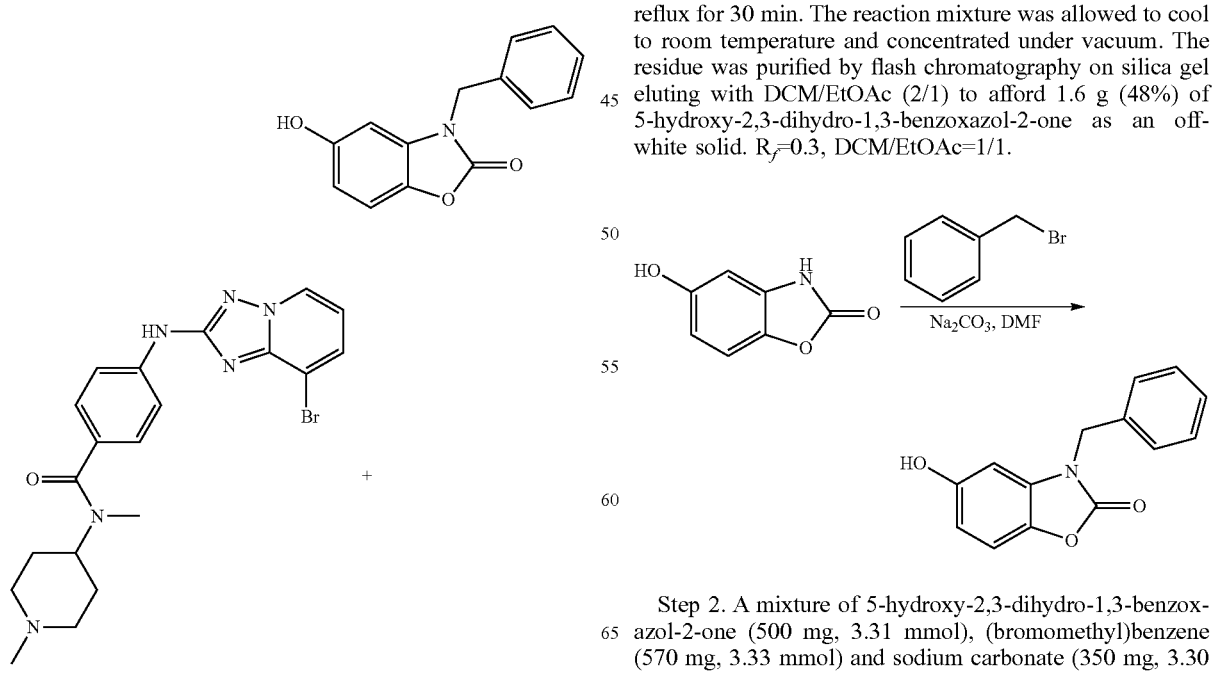

Step 1. A mixture of 2,3-dihydro-1,3-benzoxazol-2-one (3 g, 22.2 mmol) and phenyl[(trifluoromethane)sulfonyloxy]-lambda-3-iodanyl trifluoromethanesulfonate (11.6 g, 23.1 mmol) in in trifluoroacetic acid (50 mL) was heated under reflux for 30 min. The reaction mixture was allowed to cool to room temperature and concentrated under vacuum. The residue was purified by flash chromatography on silica gel eluting with DCM/EtOAc (2/1) to afford 1.6 g (48%) of 5-hydroxy-2,3-dihydro-1,3-benzoxazol-2-one as an off-white solid. $R_f$=0.3, DCM/EtOAc=1/1.

Step 2. A mixture of 5-hydroxy-2,3-dihydro-1,3-benzoxazol-2-one (500 mg, 3.31 mmol), (bromomethyl)benzene (570 mg, 3.33 mmol) and sodium carbonate (350 mg, 3.30 mmol) in N,N-dimethylformamide (10 mL) was heated at 40° C. for 3 h then allowed to cool to room temperature. The pH of the reaction mixture was adjusted to ~6 by the addition of 3 N HCl. EtOAc (100 mL) was added and the resulting mixture was washed with water (3×30 mL) and brine (2×30 mL). The organic phase was dried over anhydrous sodium sulfate and concentrated under vacuum. The residue was purified by flash chromatography on silica gel eluting with DCM/EtOAc (5/1) to afford 0.65 g (81%) of 3-benzyl-5-hydroxy-2,3-dihydro-1,3-benzoxazol-2-one as a white solid. $R_f$=0.3, DCM/EtOAc=2/1.

N-methyl-N-(1-methylpiperidin-4-yl)benzamide as a white solid. $^1$H NMR (300 MHz, DMSO-d6): δ 9.55 (s, 1H), 8.69 (d, J=6.0 Hz, 1H), 7.69 (d, J=7.2 Hz, 2H), 7.37-7.16 (m, 9H), 7.08 (d, J=3.6 Hz, 1H), 7.02-6.97 (m, 1H), 6.86-6.82 (m, 1H), 5.00 (s, 2H), 2.81-2.75 (m, 5H), 2.50 (m, 1H), 2.12 (brs, 3H), 1.80 (m, 4H), 1.59 (m, 2H); LCMS (Method 7) $R_T$=1.79 min, m/z=604.2 [M+H]$^+$.

Example 1j 4-([8-[4-(4-chlorophenyl)-4-(1,2-dihydroxyethyl) piperidin-1-yl]-[1,2,4]triazolo[1,5-a]pyridin-2-yl] amino)-N-methyl-N-(1-methylpiperidin-4-yl)benzamide (Example 1-253 in Table I)

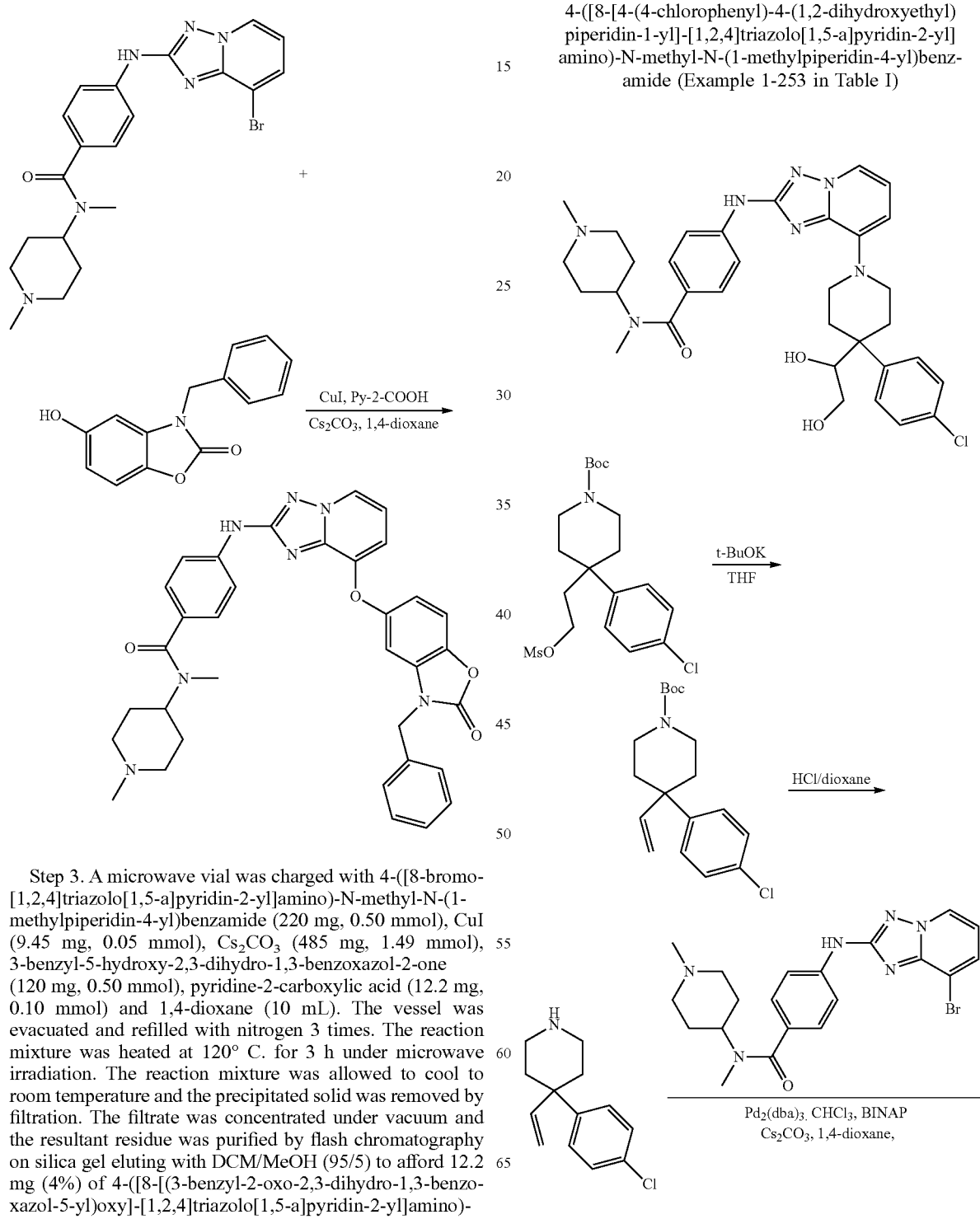

Step 3. A microwave vial was charged with 4-([8-bromo-[1,2,4]triazolo[1,5-a]pyridin-2-yl]amino)-N-methyl-N-(1-methylpiperidin-4-yl)benzamide (220 mg, 0.50 mmol), CuI (9.45 mg, 0.05 mmol), Cs$_2$CO$_3$ (485 mg, 1.49 mmol), 3-benzyl-5-hydroxy-2,3-dihydro-1,3-benzoxazol-2-one (120 mg, 0.50 mmol), pyridine-2-carboxylic acid (12.2 mg, 0.10 mmol) and 1,4-dioxane (10 mL). The vessel was evacuated and refilled with nitrogen 3 times. The reaction mixture was heated at 120° C. for 3 h under microwave irradiation. The reaction mixture was allowed to cool to room temperature and the precipitated solid was removed by filtration. The filtrate was concentrated under vacuum and the resultant residue was purified by flash chromatography on silica gel eluting with DCM/MeOH (95/5) to afford 12.2 mg (4%) of 4-([8-[(3-benzyl-2-oxo-2,3-dihydro-1,3-benzoxazol-5-yl)oxy]-[1,2,4]triazolo[1,5-a]pyridin-2-yl]amino)-

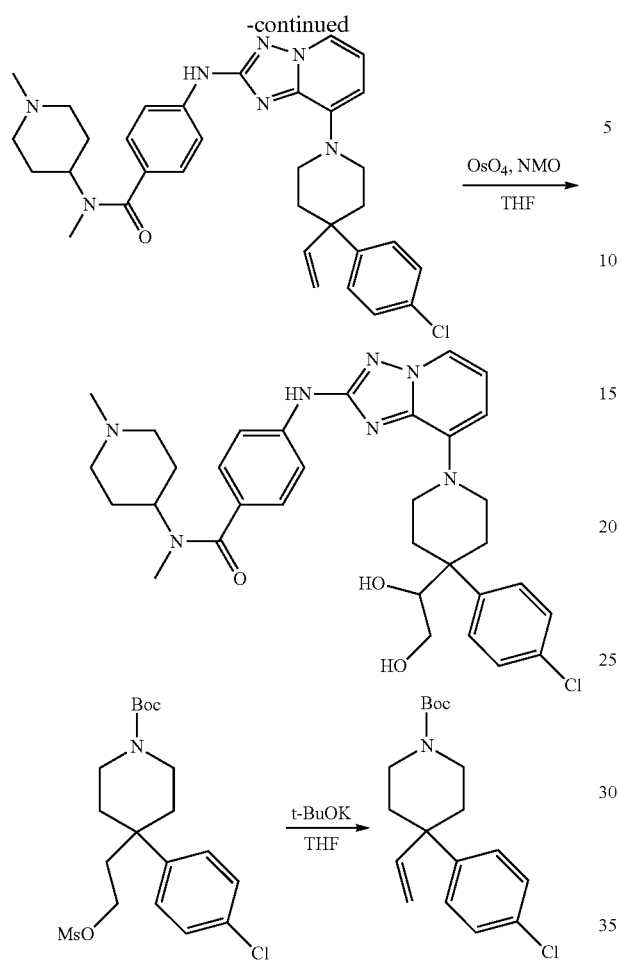

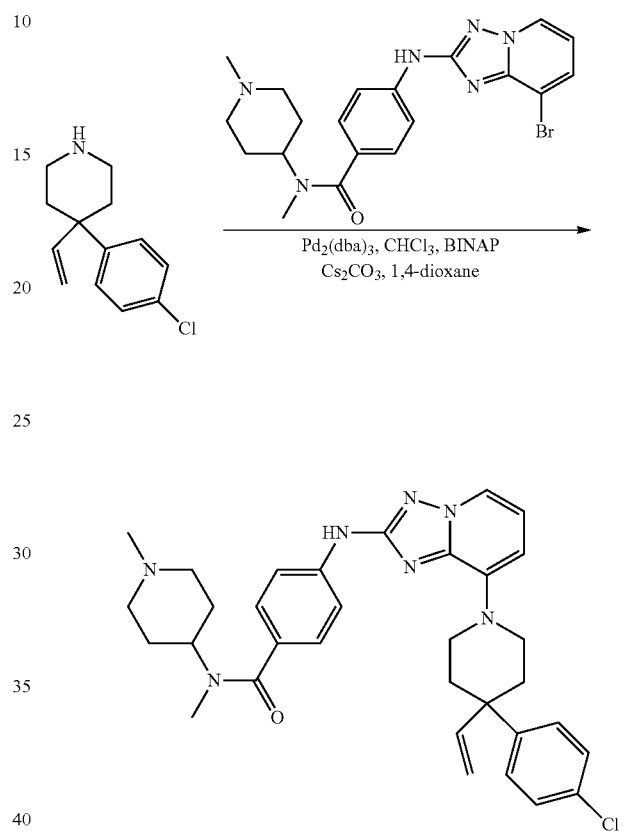

$K_2CO_3$ (2 g) was added. The resulting mixture was concentrated under vacuum and the residue was triturated with a mixture of DCM/MeOH (3/1(v/v), 40 mL). The remaining solid was removed by filtration and the filtrate was concentrated under vacuum to afford 4-(4-chlorophenyl)-4-ethenylpiperidine as a yellow oil (200 mg). TLC: $R_f$=0.3; DCM/MeOH=5/1.

Step 1. A mixture of tert-butyl 4-(4-chlorophenyl)-4-[2-(methanesulfonyloxy)-ethyl]piperidine-1-carboxylate (Example 1e, step 7, 1.1 g, 2.63 mmol) and t-BuOK (580 mg, 5.17 mmol) in THF (50 mL) was heated under nitrogen at 60° C. for 4 h then cooled to room temperature. The resulting mixture was concentrated under vacuum and the residue was purified by flash chromatography on silica gel eluting with EtOAc/petroleum ether (1/4) to afford tert-butyl-4-(4-chlorophenyl)-4-ethenylpiperidine-1-carboxylate as colourless oil (400 mg, 47%). TLC: $R_f$=0.5; EtOAc/petroleum ether=1/4.

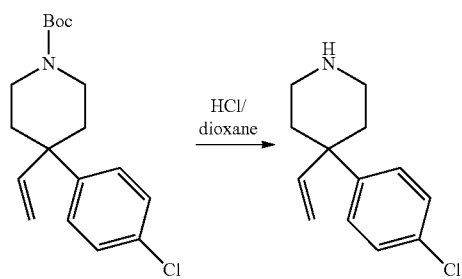 [SMILES: C=CC1(c2ccc(Cl)cc2)CCN(C(=O)OC(C)(C)C)CC1 ; C=CC1(c2ccc(Cl)cc2)CCNCC1]

Step 2. A mixture of tert-butyl-4-(4-chlorophenyl)-4-ethenylpiperidine-1-carboxylate (400 mg, 1.24 mmol) and a solution of saturated HCl in 1,4-dioxane (10 mL) was stirred for 1 h at room temperature then concentrated under vacuum. The residue was dissolved in $H_2O$ (5 mL) and solid Step 3. A microwave vial was charged with 4-(4-chlorophenyl)-4-ethenylpiperidine (130 mg, 0.59 mmol), 4-(8-bromo-[1,2,4]triazolo[1,5-a]pyridin-2-ylamino)-N-methyl-N-(1-methylpiperidin-4-yl)benzamide (250 mg, 0.56 mmol), $Pd_2(dba)_3 \cdot CHCl_3$ (30 mg, 0.03 mmol), BINAP (36 mg, 0.06 mmol), $Cs_2CO_3$ (390 mg, 1.20 mmol) and 1,4-dioxane (10 mL). The sealed vial was evacuated and refilled with nitrogen 3 times. The resulting mixture was heated at 100° C. for 20 h, allowed to cool to room temperature and concentrated under vacuum. The residue was purified by flash chromatography on silica gel eluting with a gradient of MeOH in DCM (1/10 to 1/3). Appropriate fractions were collected and evaporated to afford 200 mg (58%) of 4-([8-[4-(4-chlorophenyl)-4-ethenylpiperidin-1-yl]-[1,2,4]triazolo[1,5-a]pyridin-2-yl]amino)-N-methyl-N-(1-methylpiperidin-4-yl)benzamide as a yellow solid. LCMS (Method 11) $R_T$=1.65 min, m/z=584.2 $[M+H]^+$.

575

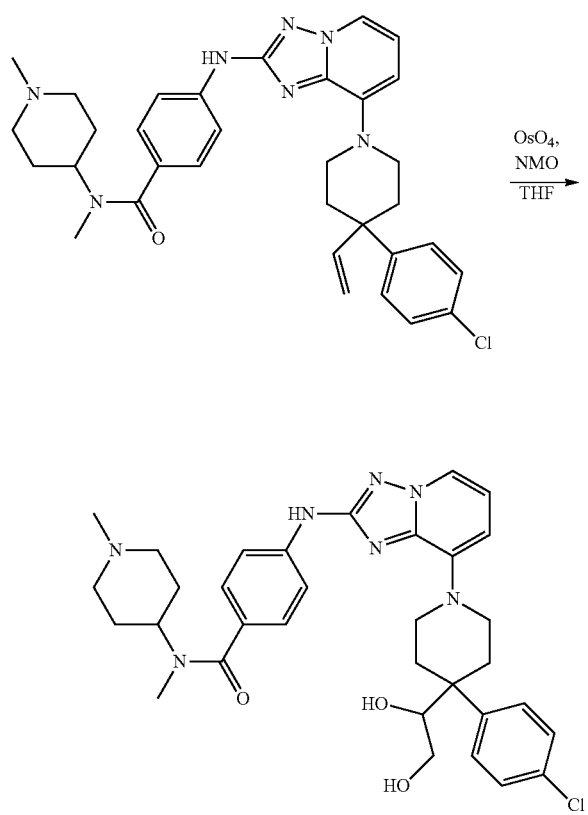

Step 4: A mixture of 4-([8-[4-(4-chlorophenyl)-4-ethenylpiperidin-1-yl]-[1,2,4]triazolo[1,5-a]pyridin-2-yl]amino)-N-methyl-N-(1-methylpiperidin-4-yl)-benzamide (200 mg, 0.34 mmol), 4-methylmorpholin-4-ium-4-olate (80 mg, 0.68 mmol) and osmium tetraoxide (174 mg, 0.68 mmol) in THF (30 mL) was stirred at room temperature for 20 h. The reaction mixture was concentrated under vacuum and the residue was purified using a short pad of silica gel eluting with DCM on a gradient of MeOH (1/20 to 1/3). Appropriate fractions were collected and evaporated and the residue was purified by Flash-Prep-HPLC using the following conditions: Column, silica gel; mobile phase, MeCN/H₂O=15% increasing to MeCN/H₂O=50% over 20 min; Detection, UV 254 nm to afford 26.2 mg (12%) of 4-([8-[4-(4-chlorophenyl)-4-(1,2-dihydroxyethyl)piperidin-1-yl]-[1,2,4]triazo[1,5-a]pyridin-2-yl]amino)-N-methyl-N-(1-methylpiperidin-4-yl)benzamide as an off white solid. $^1$H NMR (300 MHz, DMSO-d$_6$): δ 9.88 (s, 1H), 8.28 (d, J=6.0 Hz, 1H), 7.71 (d, J=8.7 Hz, 2H), 7.47-7.30 (m, 6H), 6.82 (t, J=3.3 Hz, 1H), 6.71 (d, J=8.1 Hz, 1H), 4.88 (d, J=4.8 Hz, 1H), 4.33 (t, J=2.7 Hz, 1H), 4.05-3.91 (m, 2H), 3.50-3.41 (m, 1H), 3.28-3.19 (m, 1H), 2.91-2.64 (m, 8H), 2.46-2.30 (m, 3H), 2.21-2.03 (m, 5H), 1.93-1.69 (m, 4H), 1.63-1.49 (m, 2H); LCMS (Method 7) R$_T$=2.01 min, m/z=618.2 [M+H]$^+$.

576

Example 1k 4-([8-[4-(4-chlorophenyl)-4-(1-hydroxyethyl)piperidin-1-yl]-[1,2,4]triazolo[1,5-a]pyridin-2-yl]amino)-N-methyl-N-(1-methylpiperidin-4-yl)benzamide
(Example 1-253 in Table I)

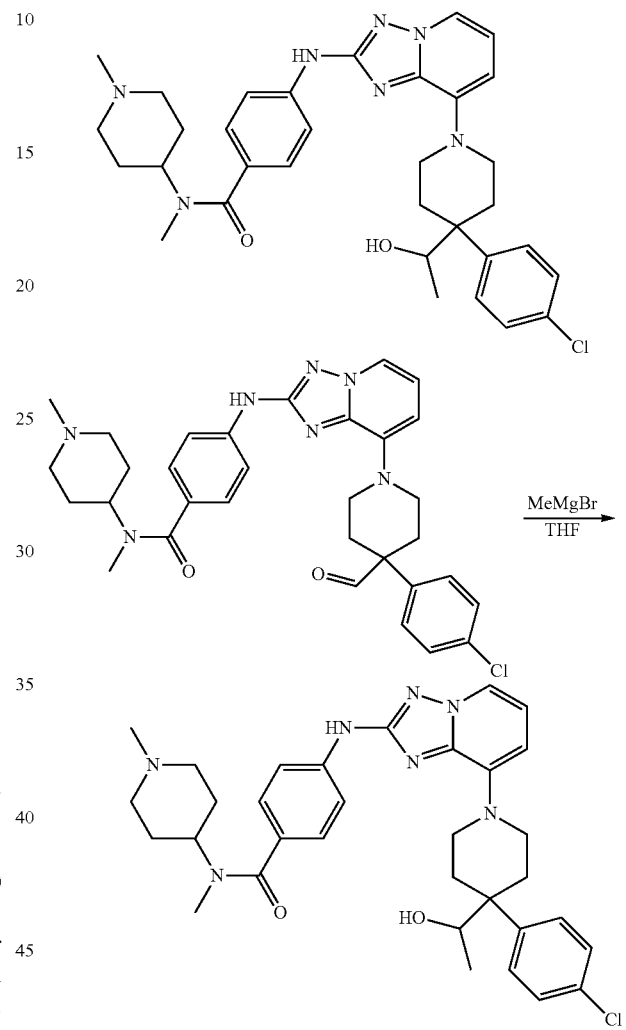

Methyl magnesium bromide (3 M in Et₂O, 0.28 mL, 0.9 mmol) was added to a solution of 4-([8-[4-(4-chlorophenyl)-4-formylpiperidin-1-yl]-[1,2,4]triazolo[1,5-a]pyridin-2-yl]amino)-N-methyl-N-(1-methylpiperidin-4-yl)benzamide (50 mg, 0.09 mmol) in THF (10 mL) at 0° C. The resulting solution was stirred at 0° C. for 1 h then quenched by the addition of MeOH (2 mL). The resulting mixture was concentrated under vacuum and the residue was purified using a short pad of silica gel eluting with MeOH/DCM (1/3). Appropriate fractions were combined and concentrated under vacuum and the crude residue was purified by Flash-Prep-HPLC with the following conditions: Column: X Bridge C18, 19*150 mm, 5 um; Mobile Phase A:Water/10 mmol NH₄HCO₃, Mobile Phase B: MeCN; Flow rate: 20 mL/min; Gradient: 30% B to 70% B over 10 min; Detection, UV 254 nm to afford 13.1 mg (26%) of 4-([8-[4-(4-chlorophenyl)-4-(1-hydroxyethyl)piperidin-1-yl]-[1,2,4]triazolo[1,5-a]pyridin-2-yl]amino)-N-methyl-N-(1-methylpiperidin-4-yl)benzamide as an off-white solid. $^1$H NMR (300 MHz, DMSO-d$_6$): δ 9.84 (s, 1H), 8.27 (d, J=6.3 Hz, 1H), 7.71 (d, J=8.7 Hz, 2H), 7.46-7.37 (m, 4H), 7.32 (d, J=8.7 Hz, 2H), 6.83 (t, J=7.2 Hz, 1H), 6.71 (d, J=8.1 Hz, 1H), 4.65 (d, J=4.8 Hz, 1H), 4.05-3.95 (m, 2H), 3.60 (t, J=5.7 Hz, 1H), 2.82-2.75 (m, 5H), 2.73-2.63 (m, 4H), 2.28-2.26 (m, 1H), 2.12-1.85 (m, 5H), 1.85-1.75 (m, 4H), 1.58-1.56 (m, 2H), 0.76 (d, J=6.3 Hz, 3H); LCMS (Method 10) R$_T$=1.64 min, m/z=602.2 [M+H]$^+$.

Example 11

4-(8-(4-(4-chlorophenyl)-4-(2,2,2-trifluoro-1-hydroxyethyl)piperidin-1-yl)-[1,2,4]triazolo[1,5-a]pyridin-2-ylamino)-N-methyl-N-(1-methylpiperidin-4-yl)benzamide (Example 1-253 in Table I)

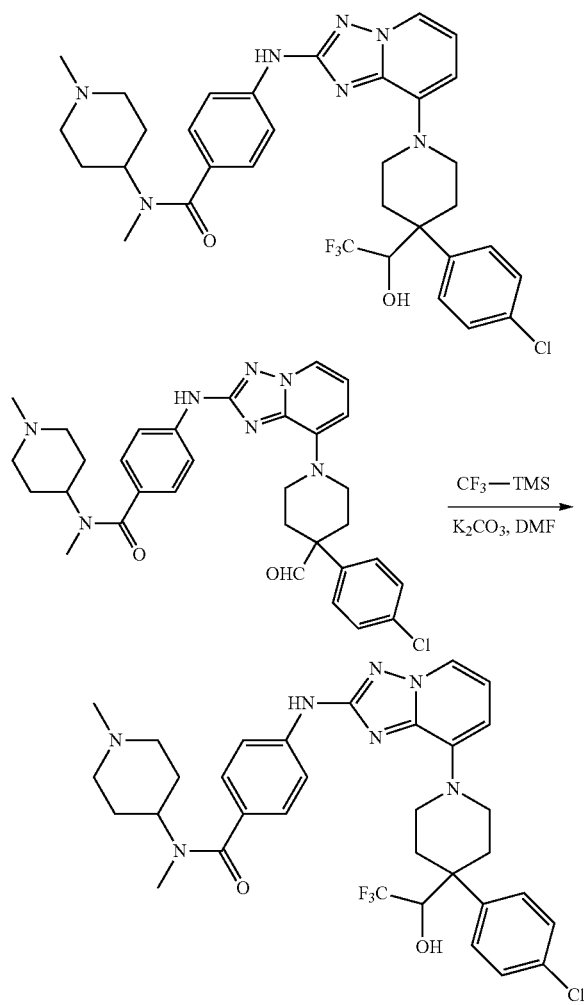

A mixture of trimethyl(trifluoromethyl)silane (242 mg, 1.70 mmol), 4-([8-[4-(4-chlorophenyl)-4-formylpiperidin-1-yl[-]1,2,4]triazolo[1,5-a]pyridin-2-yl]amino)-N-methyl-N-(1-methylpiperidin-4-yl)benzamide (100 mg, 0.17 mmol) and potassium carbonate (23 mg, 0.17 mmol) in N,N-dimethylformamide (10 mL) was heated under nitrogen at 80° C. for 5 h. The reaction mixture was allowed to cool to room temperature and concentrated under vacuum. The residue purified using a short pad of silica gel eluting with DCM/MeOH (3/1). Appropriate fractions were collected and concentrated under vacuum and the crude residue was purified by Flash-Prep-HPLC using the following conditions: Column, silica gel; mobile phase, MeCN/H$_2$O=15% increasing to MeCN/H$_2$O=50% over 20 min; Detection, UV 254 nm to afford 13.1 mg (12%) of 4-(8-(4-(4-chlorophenyl)-4-(2,2,2-trifluoro-1-hydroxyethyl)piperidin-1-yl)-[1,2,4]triazo[1,5-a]pyridin-2-ylamino)-N-methyl-N-(1-methylpiperidin-4-yl)benzamide as an off white solid. $^1$H NMR (300 MHz, DMSO-d$_6$): δ 9.85 (s, 1H), 8.28 (d, J=6.0 Hz, 1H), 7.71 (d, J=8.7 Hz, 2H), 7.53 (d, J=9.0 Hz, 2H), 7.40 (d, J=8.7 Hz, 2H), 7.32 (d, J=8.7 Hz, 2H), 6.84 (t, J=7.2 Hz, 1H), 6.72-6.66 (m, 2H), 4.10-4.04 (m, 3H), 2.87-2.76 (m, 5H), 2.75-2.62 (m, 2H), 2.49-2.40 (m, 3H), 2.35-2.06 (m, 5H), 1.92-1.70 (m, 4H), 1.65-1.51 (m, 2H); LCMS (Method 7) R$_T$=2.20 min, m/z=656.4 [M+H]$^+$.

Example 1m

Ethyl 2-[4-(4-chlorophenyl)-1-[2-([4-[methyl(1-methylpiperidin-4-yl)carbamoyl]phenyl]amino)-]1,2,4]triazolo[1,5-a]pyridin-8-yl]piperidin-4-yl]acetate (Example 1-254 in Table I)

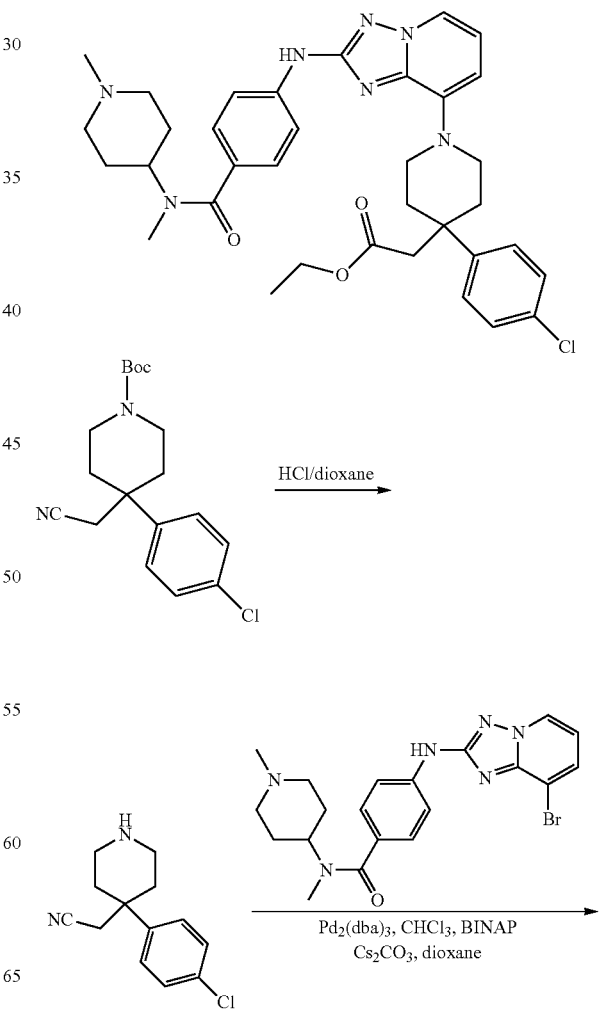

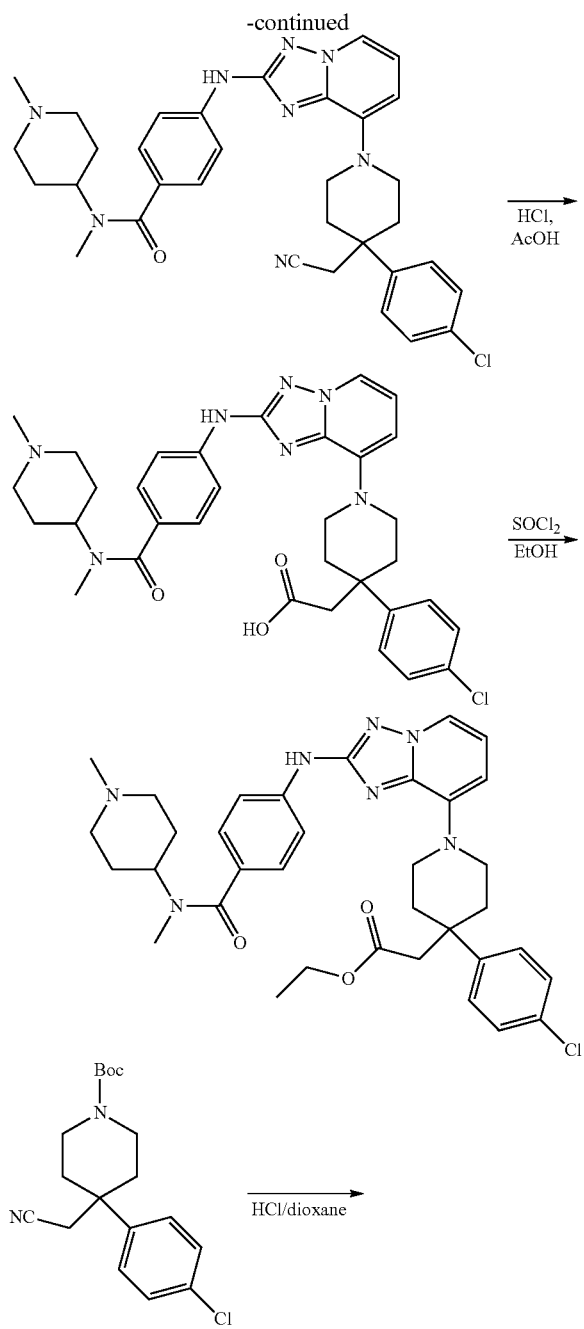
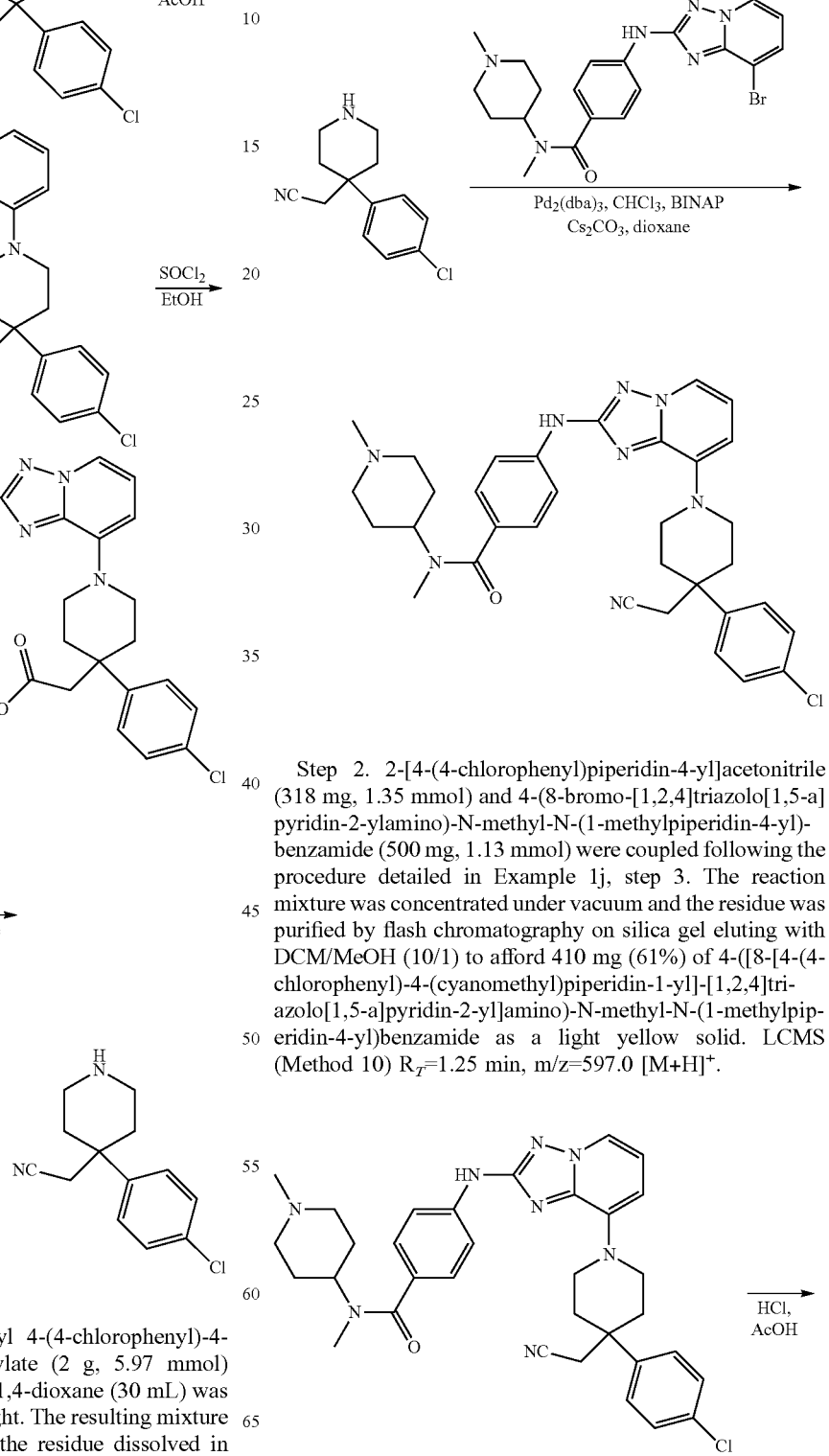

Step 1. A mixture of tert-butyl 4-(4-chlorophenyl)-4-(cyanomethyl)piperidine-1-carboxylate (2 g, 5.97 mmol) and a solution of saturated HCl in 1,4-dioxane (30 mL) was stirred at room temperature overnight. The resulting mixture was concentrated under vacuum, the residue dissolved in H$_2$O (20 mL) and the pH of the solution was adjusted to 9 by the addition of solid potassium carbonate. The resulting mixture was concentrated under vacuum and the residue was purified by flash chromatography on silica gel eluting with DCM/MeOH (3/1) to afford 1.3 g (93%) of 2-[4-(4-chlorophenyl)piperidin-4-yl]acetonitrile as light yellow oil. TLC: R$_f$=0.2; DCM/MeOH=5/1.

Step 2. 2-[4-(4-chlorophenyl)piperidin-4-yl]acetonitrile (318 mg, 1.35 mmol) and 4-(8-bromo-[1,2,4]triazolo[1,5-a]pyridin-2-ylamino)-N-methyl-N-(1-methylpiperidin-4-yl)-benzamide (500 mg, 1.13 mmol) were coupled following the procedure detailed in Example 1j, step 3. The reaction mixture was concentrated under vacuum and the residue was purified by flash chromatography on silica gel eluting with DCM/MeOH (10/1) to afford 410 mg (61%) of 4-([8-[4-(4-chlorophenyl)-4-(cyanomethyl)piperidin-1-yl]-[1,2,4]triazolo[1,5-a]pyridin-2-yl]amino)-N-methyl-N-(1-methylpiperidin-4-yl)benzamide as a light yellow solid. LCMS (Method 10) R$_T$=1.25 min, m/z=597.0 [M+H]$^+$.

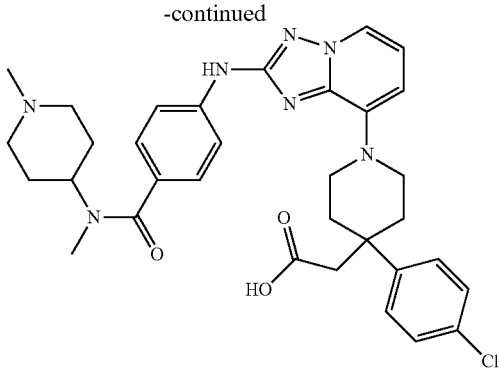

Step 3. A mixture of 4-([8-[4-(4-chlorophenyl)-4-(cyanomethyl)piperidin-1-yl]-[1,2,4]triazolo[1,5-a]pyridin-2-yl]amino)-N-methyl-N-(1-methylpiperidin-4-yl)-benzamide (400 mg, 0.67 mmol) in concentrated HCl (4 mL) and AcOH (1 mL) was heated at 100° C. for 20 h then allowed to cool to room temperature. The resulting mixture was concentrated under vacuum to afford 450 mg of 2-[4-(4-chlorophenyl)-1-[2-([4-[methyl(1-methylpiperidin-4-yl)carbamoyl]phenyl]amino)-[1,2,4]triazolo[1,5-a]pyridin-8-yl]piperidin-4-yl]acetic acid; hydrochloride salt as yellow crude oil. TLC: $R_f$=0.3; DCM/MeOH=4/1.

with DCM on a gradient of MeOH (1/10 to 1/5). Appropriate fractions were combined and concentrated under vacuum and the crude residue was purified by Prep-HPLC with the following conditions: Column, XBridge Shield RP18 OBD Column, 19*150 mm Sum 13 nm; mobile phase, Water with 10 mmol $NH_4HCO_3$ and MeCN (12% MeCN up to 55% over 9 min); Detection, UV 254 nm to afford 52.9 mg (11%) of ethyl 2-[4-(4-chlorophenyl)-1-[2-([4-[methyl(1-methylpiperidin-4-yl)carbamoyl]phenyl]amino)-[1,2,4]triazolo[1,5-a]pyridin-8-yl]piperidin-4-yl]acetate as an off-white solid. $^1$H NMR (400 MHz, DMSO-$d_6$): δ 9.87 (s, 1H), 8.31 (d, J=6.4 Hz, 1H), 7.71 (d, J=8.8 Hz, 2H), 7.47 (d, J=8.8 Hz, 2H), 7.40 (d, J=8.8 Hz, 2H), 7.32 (d, J=8.0 Hz, 2H), 6.87 (t, J=7.2 Hz, 1H), 6.79 (d, J=8.0 Hz, 1H), 3.83 (t, J=7.0 Hz, 2H), 3.79-3.68 (m, 2H), 3.27-3.22 (m, 2H), 2.82-2.73 (m, 5H), 2.70-2.67 (m, 2H), 2.51-2.50 (m, 2H), 2.37-2.33 (m, 2H), 2.20-2.12 (m, 5H), 1.86-1.79 (m, 3H), 1.65-1.56 (m, 2H), 0.95 (t, J=7.5 Hz, 3H); LCMS (Method 7) $R_T$=2.88 min, m/z=644.3 [M+H]$^+$.

Example 1n 4-([8-[4-(carbamoylmethyl)-4-(4-chlorophenyl)piperidin-1-yl]-[1,2,4]triazolo[1,5-b]pyridazin-2-yl]amino)-N-methyl-N-(1-methylpiperidin-4-yl)benzamide (Example 1-298 in Table I)

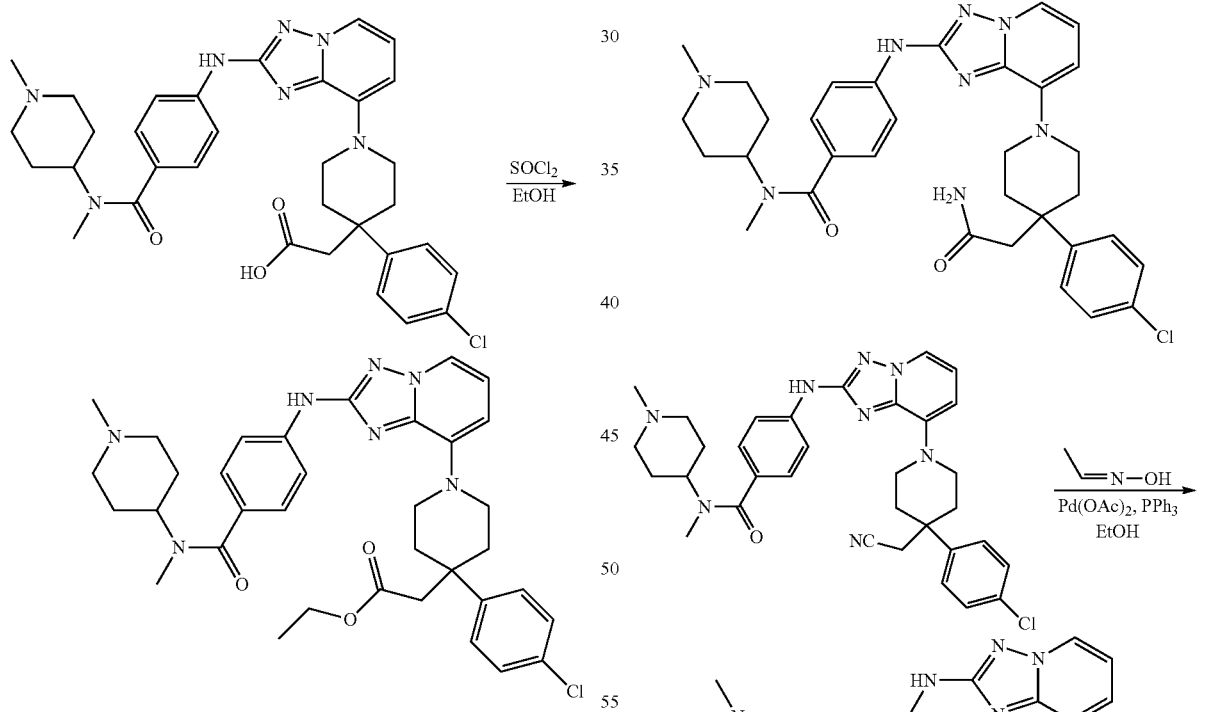

Step 4. Thionyl chloride (4 mL, 55 mmol) was added dropwise to a solution of 2-[4-(4-chlorophenyl)-1-[2-([4-[methyl(1-methylpiperidin-4-yl)carbamoyl]phenyl]amino)-[1,2,4]triazolo[1,5-a]pyridin-8-yl]piperidin-4-yl]acetic acid (450 mg, 0.73 mmol) in ethanol (20 mL) at room temperature. The resulting solution was heated at 80° C. for 3 h then allowed to cool to room temperature. The resulting mixture was concentrated under vacuum and the resultant residue treated with saturated aqueous $NaHCO_3$ solution (4 mL). The resulting mixture was concentrated under vacuum and the residue was purified using a short pad of silica gel eluting A mixture of 4-([8-[4-(4-chlorophenyl)-4-(cyanomethyl)piperidin-1-yl]-[1,2,4]triazolo[1,5-a]pyridin-2-yl]amino)-N-methyl-N-(1-methylpiperidin-4-yl)-benzamide (200 mg, 0.33 mmol), (E)-N-ethylidenehydroxylamine (110 mg, 1.67 mmol), PPh₃ (89 mg, 0.33 mmol) and Pd(OAc)₂ (38 mg, 0.17 mmol) in ethanol (20 mL) was heated under nitrogen at 85° C. for 20 h. The reaction mixture was allowed to cool to room temperature and concentrated under vacuum. The residue was purified using a short pad of silica gel eluting with DCM/MeOH (5/1). Appropriate fractions were combined and concentrated under vacuum and the crude residue was purified by Flash-Prep-HPLC using the following conditions: Column, silica gel; mobile phase, MeCN/H₂O=15% increasing to MeCN/H₂O=55% over 13 min; Detection, UV 254 nm to afford 55.3 mg (27%) of 4-([8-[4-(carbamoylmethyl)-4-(4-chlorophenyl)piperidin-1-yl]-[1,2,4]-triazol[1,5-b]pyridazin-2-yl]amino)-N-methyl-N-(1-methylpiperidin-4-yl)-benzamide as an off-white solid. $^1$H NMR (400 MHz, DMSO-d₆): δ 9.85 (s, 1H), 8.29 (d, J=6.0 Hz, 1H), 7.71 (d, J=8.4 Hz, 2H), 7.45 (d, J=8.8 Hz, 2H), 7.38 (d, J=8.8 Hz, 2H), 7.32 (d, J=8.8 Hz, 2H), 7.01 (s, 1H), 6.86 (t, J=7.2 Hz, 1H), 6.76 (d, J=7.6 Hz, 1H), 6.58 (s, 1H), 3.75-3.72 (m, 2H), 3.31-3.29 (m, 1H), 3.17-3.12 (m, 2H), 2.85-2.75 (m, 5H), 2.42-2.38 (m, 2H), 2.33-2.19 (m, 5H), 2.12 (s, 3H), 1.79-1.56 (m, 5H); LCMS (Method 8) $R_T$=1.76 min, m/z=615.1 [M+H]⁺.

Example 1o 4-([8-[4-(4-chlorophenyl)-4-[(dimethylcarbamoyl)methyl]piperidin-1-yl]-[1,2,4]triazolo[1,5-a]pyridin-2-yl]amino)-N-methyl-N-(1-methylpiperidin-4-yl) benzamide (Example 1-300 in Table I)

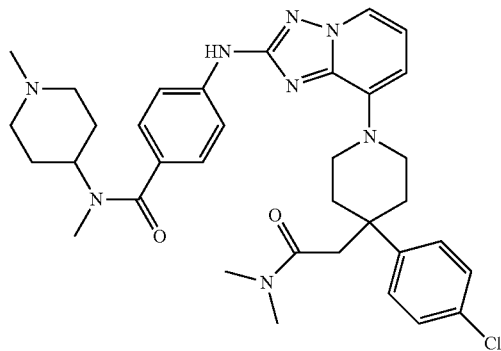

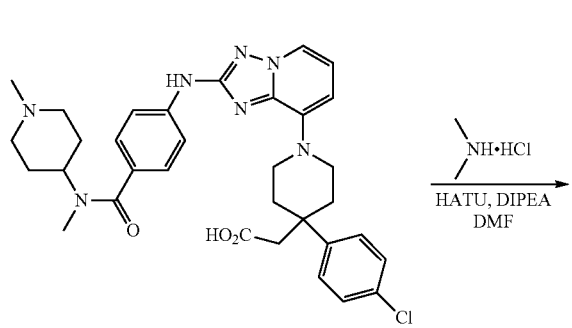

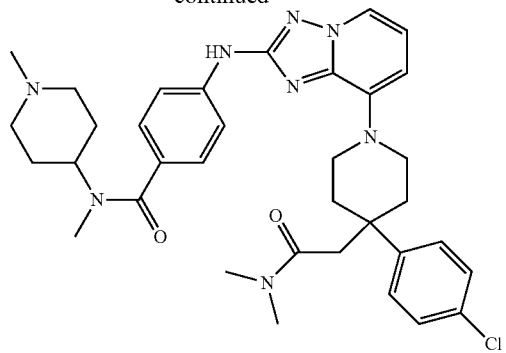

A mixture of crude 2-[4-(4-chlorophenyl)-1-[2-([4-[methyl(1-methylpiperidin-4-yl)carbamoyl]phenyl]amino)-[1,2,4]triazolo[1,5-a]pyridin-8-yl]piperidin-4-yl]acetic acid (200 mg), dimethylamine hydrochloride (132 mg, 1.62 mmol), DIPEA (260 mg, 2.01 mmol) and HATU (190 mg, 0.50 mmol) in DMF (10 mL) was stirred at room temperature for 20 h. The reaction mixture was concentrated under vacuum and the residue was purified using a short pad of silica gel eluting with DCM/MeOH (10/1). The filtrate was concentrated under vacuum and the crude product was purified by Flash-Prep-HPLC using the following conditions: Column, silica gel; mobile phase, MeCN/H₂O (containing NH₃.H₂O)=13% increasing to MeCN/H₂O (containing NH₃.H₂O)=45% over 13 min; Detection, UV 254 nm to afford 19.9 mg of 4-([8-[4-(4-chlorophenyl)-4-[(dimethylcarbamoyl)-methyl]piperidin-1-yl]-[1,2,4]triazol-[1,5-a]pyridin-2-yl]amino)-N-methyl-N-(1-methylpiperidin-4-yl) benzamide as an off-white solid. $^1$H NMR (300 MHz, DMSO-d₆): δ 9.85 (s, 1H), 8.29 (d, J=6.0 Hz, 1H), 7.71 (d, J=8.7 Hz, 2H), 7.46 (d, J=9.0 Hz, 2H), 7.38 (d, J=8.7 Hz, 2H), 7.32 (d, J=8.7 Hz, 2H), 6.86 (t, J=6.6 Hz, 1H), 6.77 (d, J=8.4 Hz, 1H), 3.80-3.70 (m, 2H), 3.29-3.19 (m, 2H), 2.85-2.75 (m, 4H), 2.69-2.51 (m, 8H), 2.49-2.37 (m, 3H), 2.36-2.23 (m, 3H), 2.20-2.10 (m, 3H), 1.90-1.70 (m, 4H), 1.65-1.50 (m, 2H); LCMS (Method 7) $R_T$=2.15 min, m/z=643.3 [M+H]⁺.

Example 1p 4-([8-[4-(4-chlorophenyl)-4-(2,2-difluoroethyl)piperidin-1-yl]-[1,2,4]triazolo[1,5-a]pyridin-2-yl]amino)-N-methyl-N-(1-methylpiperidin-4-yl)benzamide (Example 1-256 in Table I)

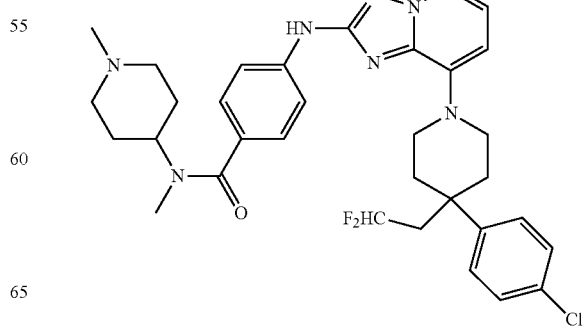

585
-continued

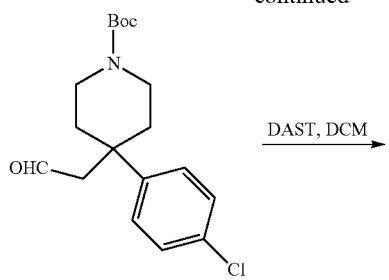

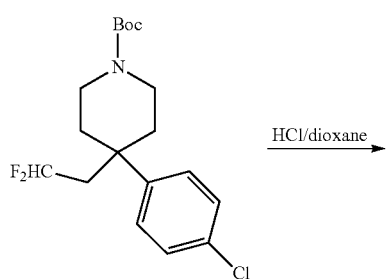

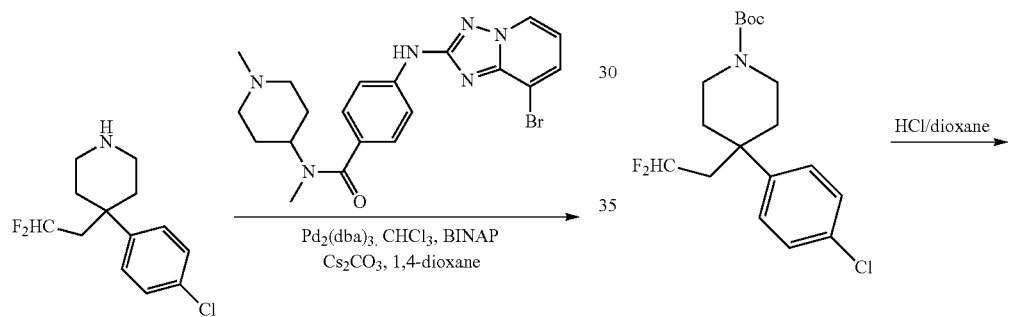

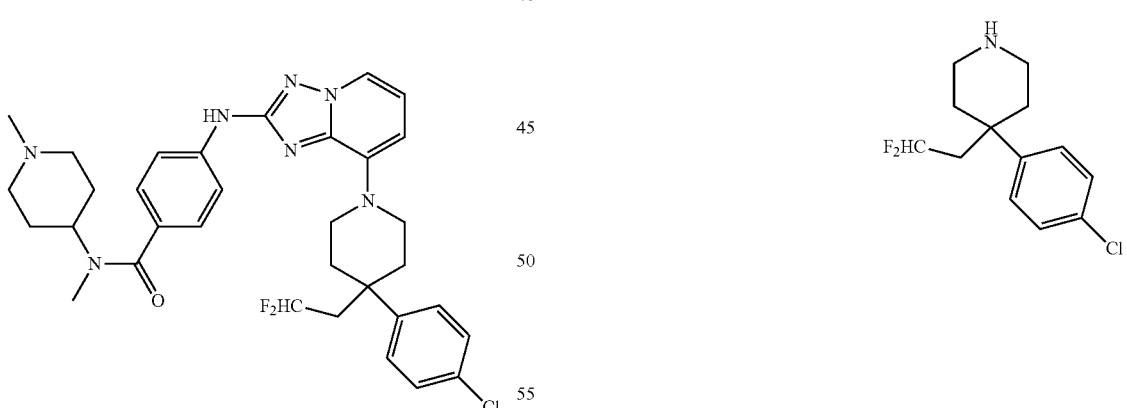

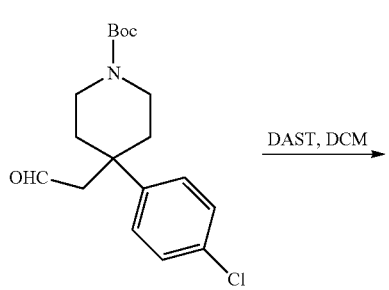

586
-continued

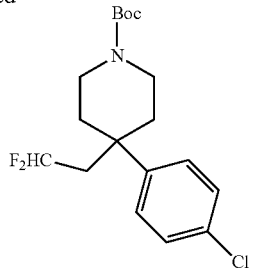

Step 1. DAST (0.5 mL, 2.87 mmol) was added dropwise to a solution of tert-butyl 4-(4-chlorophenyl)-4-(2-oxoethyl)piperidine-1-carboxylate (1.6 g, 4.74 mmol) in DCM (100 mL) at 0° C. The resulting solution was stirred at 0° C. for 10 min then quenched by the addition of water (30 mL). The resulting solution was extracted with DCM (2×100 mL) and the combined organic layer was concentrated under vacuum. The residue was purified by flash chromatography on silica gel eluting with EtOAc/hexane (1/10) to afford 500 mg (29%) of tert-butyl 4-(4-chlorophenyl)-4-(2,2-difluoroethyl)piperidine-1-carboxylate as light yellow oil. TLC: $R_f$=0.5; EtOAc/petroleum ether=1/4.

Step 2. A mixture of tert-butyl-4-(4-chlorophenyl)-4-(2,2-difluoroethyl)-piperidine-1-carboxylate (500 mg, 1.39 mmol) in saturated HCl solution of 1,4-dioxane (30 mL) was stirred at room temperature for 2 h. The reaction mixture was concentrated under vacuum, the residue dissolved in $H_2O$ (5 mL) and solid $K_2CO_3$ (1 g) was added. The resulting mixture was concentrated under vacuum and the residue was triturated with DCM (100 mL). The remaining solid was removed by filtration and the filtrate was concentrated under vacuum to afford 300 mg (crude) of 4-(4-chlorophenyl)-4-(2,2-difluoroethyl)piperidine as a off white solid. LCMS (Method 7) $R_T$=1.16 min, m/z=260.1 [M+H]$^+$.

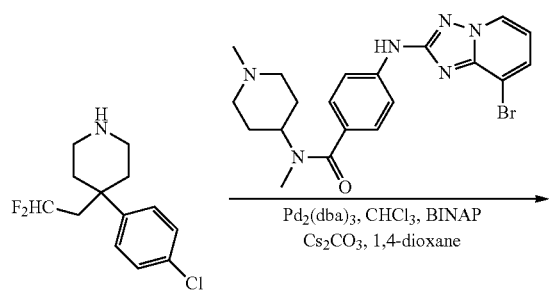

Step 3. 4-([8-bromo-[1,2,4]triazolo[1,5-a]pyridin-2-yl]amino)-N-methyl-N-(1-methylpiperidin-4-yl)benzamide (300 mg, 0.68 mmol) and 4-(4-chlorophenyl)-4-(2,2-difluoroethyl)piperidine (260 mg, 1.00 mmol) were coupled following the procedure detailed in Example 1j, step 3. The reaction mixture was concentrated under vacuum and the residue was purified by flash chromatography on silica eluting with DCM/MeOH (5/1). Appropriate fractions were combined and concentrated under vacuum. The crude product was purified by Flash-Prep-HPLC using the following conditions: Column, silica gel; mobile phase, MeCN/H$_2$O=15% increasing to MeCN/H$_2$O=40% over 13 min; Detection, UV 254 nm to afford 38.8 mg (8%) of 4-([8-[4-(4-chlorophenyl)-4-(2,2-difluoroethyl)piperidin-1-yl]-[1,2,4]triazolo-[1,5-a]pyridin-2-yl]amino)-N-methyl-N-(1-methylpiperidin-4-yl)benzamide; formic acid salt as a light yellow solid. $^1$H NMR (400 MHz, DMSO-d$_6$): δ 9.85 (s, 1H), 8.30 (d, J=6.0 Hz, 1H), 8.19 (s, 1H), 7.71 (d, J=8.8 Hz, 2H), 7.53 (d, J=8.8 Hz, 2H), 7.44 (d, J=8.8 Hz, 2H), 7.32 (d, J=8.4 Hz, 2H), 6.86 (t, J=7.2 Hz, 1H), 6.77 (d, J=7.6 Hz, 1H), 5.82-5.53 (m, 1H), 3.79-3.76 (m, 2H), 3.14-3.09 (m, 2H), 2.83-2.81 (m, 4H), 2.50-2.06 (m, 10H), 1.91-1.57 (m, 6H); LCMS (Method 10) R$_T$=1.85 min, m/z=622.2 [M+H]$^+$.

Example 1q 4-([8-[4-(4-chlorophenyl)-4-[(1E)-(methoxyimino)methyl]piperidin-1-yl]-[1,2,4]triazolo[1,5-a]pyridin-2-yl]amino)-N-methyl-N-(1-methylpiperidin-4-yl)benzamide (Example 1-250 in Table I)

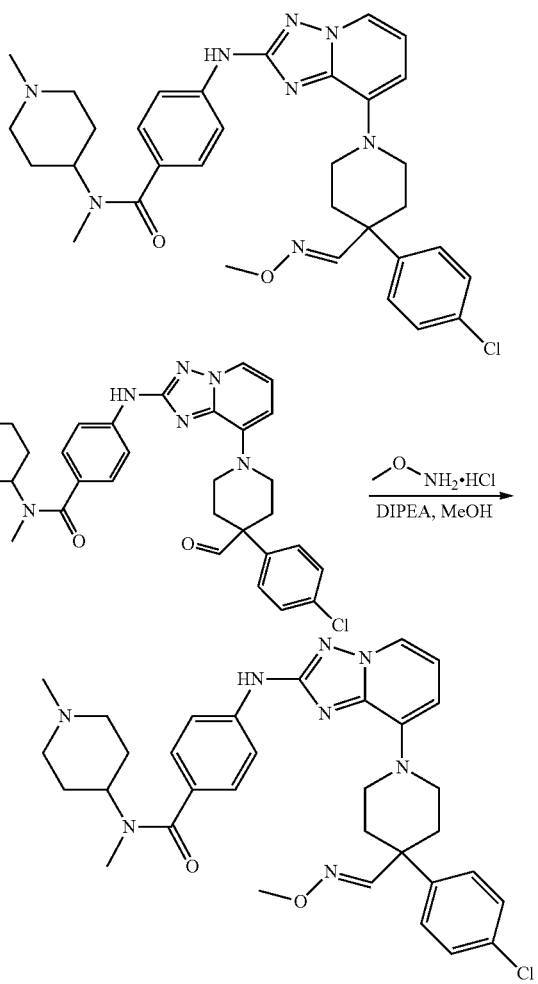

A mixture of 4-([8-[4-(4-chlorophenyl)-4-formylpiperidin-1-yl]-[1,2,4]triazolo[1,5-a]pyridin-10yl]amino)-N-methyl -N-(1-methylpiperidin-4-yl)benzamide (50 mg, 0.09 mmol), DIPEA (2 mL, 12.10 mmol) and N-methylhydroxylamine hydrochloride (630 mg, 7.54 mmol) in MeOH (10 mL) was stirred at room temperature for 20 h. The resulting mixture was concentrated under vacuum and the residue purified using a short pad of silica gel eluting with DCM on a gradient of MeOH (1/5 to 1/3). Appropriate fractions were combined and concentrated and the resultant residue was purified by Flash-Prep-HPLC using the following conditions: Column, silica gel; mobile phase, MeCN/H$_2$O=20% increasing to MeCN/H$_2$O=40% over 20 min; Detection, UV 254 nm to afford 3.2 mg (6%) of 4-([8-[4-(4-chlorophenyl)-4-[(1E)-(methoxyimino)methyl]piperidin-1-yl]-[1,2,4]triazolo[1,5-a]pyridin-2-yl]amino)-N-methyl-N-(1-methylpiperidin-4-yl)benzamide as an off white solid. $^1$H NMR (400 MHz, CD$_3$OD): δ 8.07-8.06 (m, 1H), 7.64 (d, J=8.8 Hz, 2H), 7.34-7.23 (m, 7H), 6.80-6.77 (d, J=6.4, 10.0 Hz, 2H), 3.80-3.76 (m, 2H), 3.75 (s, 3H), 3.21-3.20 (m, 3H), 2.90-2.80 (m, 5H), 2.30-1.95 (m, 8H), 1.90-1.75 (m, 3H), 1.65-1.55 (m, 2H); LCMS (Method 6) $R_T$=1.76 min, m/z=615.2 [M+H]$^+$.

Example 1r 4-([8-[4-(4-chlorophenyl)-4-(acetamidomethyl)piperidin-1-yl]-[1,2,4]triazolo[1,5-a]pyridin-2-yl]amino)-N-methyl-N-(1-methylpiperidin-4-yl)benzamide (Example 1-268 in Table I)

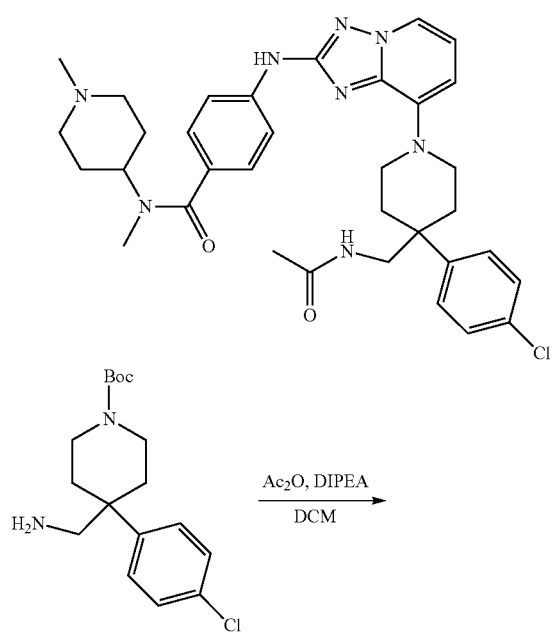

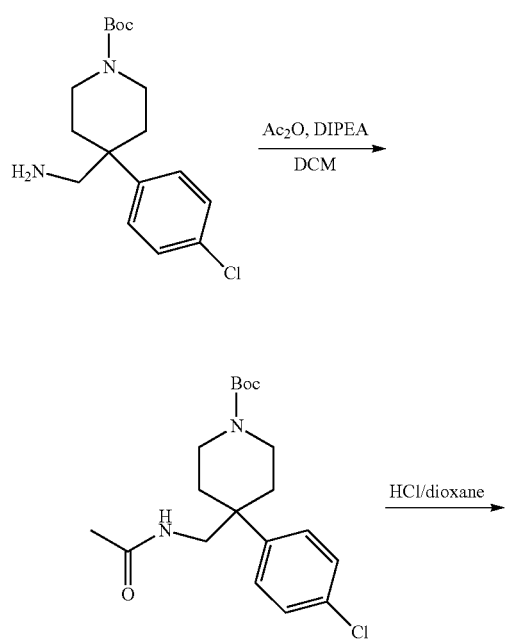

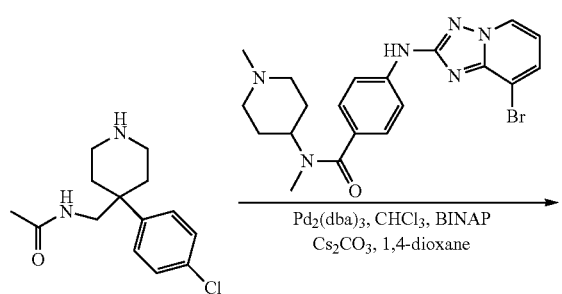

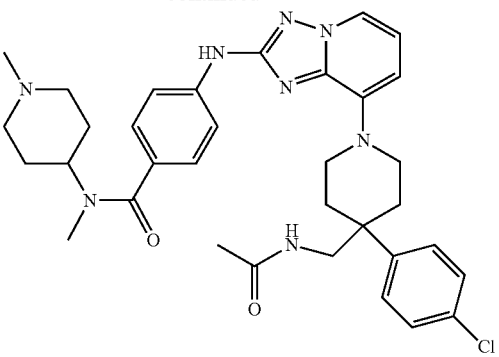

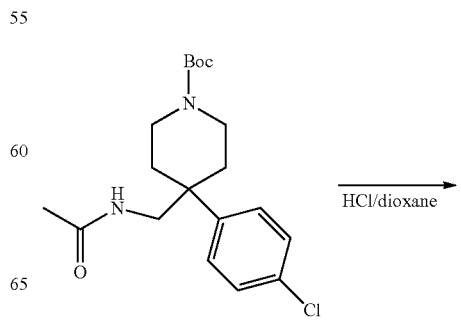

Step 1. Acetic anhydride (2.5 g, 24.49 mmol) was added to a solution of tert-butyl 4-(aminomethyl)-4-(4-chlorophenyl)piperidine-1-carboxylate (800 mg, 2.46 mmol) (prepared according to the procedure contained in Journal of Medicinal Chemistry, 2008, 51(7), 2147-2157) and DIPEA (3.2 g, 24.8 mmol) in DCM (50 mL). On complete addition the reaction mixture was stirred at room temperature for 20 h then concentrated under vacuum. The residue was purified by flash chromatography on silica gel eluting with EtOAc/petroleum ether (1/4) to afford tert-butyl 4-(4-chlorophenyl)-4-(acetamidomethyl)piperidine-1-carboxylate as an off-white solid (900 mg, 99%). TLC: $R_f$=0.4; EtOAc/petroleum ether=1/4.

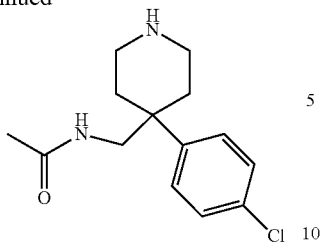

Step 2. A mixture of tert-butyl 4-(4-chlorophenyl)-4-(acetamidomethyl)piperidine-1-carboxylate (900 mg, 2.45 mmol) in a saturated solution of HCl in 1,4-dioxane (20 mL) was stirred at room temperature for 2 h. The resulting mixture was concentrated under vacuum and the residue was dissolved in $H_2O$ (5 mL) and treated with solid $K_2CO_3$ (1 g). The resulting mixture was concentrated under vacuum and the residue triturated with a mixture of DCM/MeOH (3/1 (v/v), 50 mL). The remaining solid was removed by filtration and the filtrate was evaporated to afford N-[[4-(4-chlorophenyl)piperidin-4-yl]methyl]acetamide as a white solid (400 mg). TLC: $R_f$=0.3; DCM/MeOH=5/1.

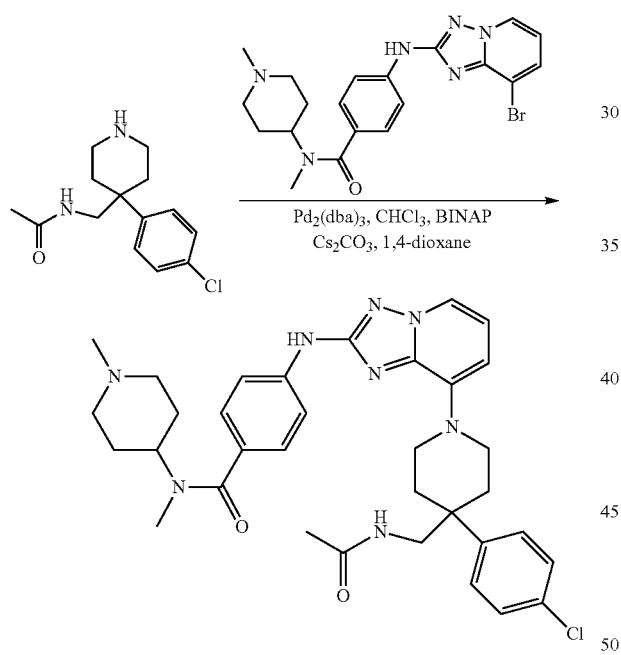

Step 3. 4-([8-bromo-[1,2,4]triazolo[1,5-a]pyridin-2-yl]amino)-N-methyl-N-(1-methylpiperidin-4-yl)benzamide (420 mg, 0.95 mmol) and N-[4-(4-chlorophenyl)piperidin-4-yl]methylacetamide (266 mg, 1.00 mmol) were coupled following the procedure detailed in Example 1j, step 3. The resulting mixture was concentrated under vacuum and the residue was purified using a short pad of silica gel eluting with DCM/MeOH (3/1). Appropriate fractions were combined and concentrated to afford crude 4-([8-[4-(4-chlorophenyl)-4-(acetamidomethyl)piperidin-1-yl]-[1,2,4]triazolo[1,5-a]pyridin-2-yl]amino)-N-methyl-N-(1-methylpiperidin-4-yl)benzamide as a light-yellow solid (450 mg). A third of the above crude product (150 mg) was purified by Flash-Prep-HPLC using the following conditions: Column, silica gel; mobile phase, MeCN/$H_2O$=15% increasing to MeCN/$H_2O$=40% over 20 min; Detection, UV 254 nm to afford 4-([8-[4-(4-chlorophenyl)-4-(acetamidomethyl)-piperidin-1-yl]-[1,2,4]triazolo[1,5-a]pyridin-2-yl]amino)-N-methyl -N-(1-methyl-piperidin-4-yl)benzamide as a off white solid (37.4 mg). $^1$H NMR (400 MHz, $CD_3OD$): δ 8.17 (d, J=6.4 Hz, 1H), 7.76 (d, J=8.4 Hz, 2H), 7.47 (d, J=8.8 Hz, 2H), 7.40 (d, J=8.8 Hz, 4H), 6.88 (t, J=7.0 Hz, 1H), 6.81 (d, J=8.0 Hz, 1H), 3.87-3.84 (m, 2H), 3.43 (s, 2H), 3.12 (t, J=10 Hz, 2H), 3.03-3.00 (br, 2H), 2.98 (s, 3H), 2.42-2.10 (m, 8H), 2.06-1.90 (m, 3H), 1.88 (s, 3H), 1.79 (br, 2H); LCMS (Method 6) $R_T$=2.51 min, m/z=629.4 $[M+H]^+$.

Example 1s 4-([8-[4-(4-chlorophenyl)-4-(acetamidomethyl)piperidin-1-yl]-[1,2,4]triazolo[1,5-a]pyridin-2-yl]amino)-N-methyl-N-(1-methylpiperidin-4-yl)benzamide (Example 1-265 in Table I)

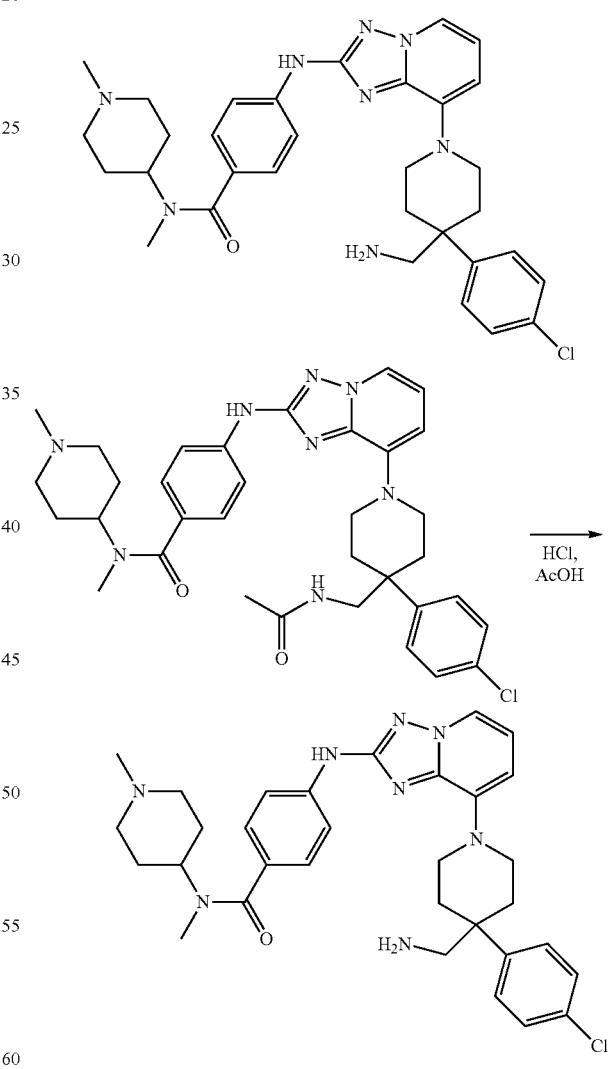

A solution of 4-([8-[4-(4-chlorophenyl)-4-(acetamidomethyl)piperidin-1-yl]-[1,2,4]triazolo[1,5-a]pyridin-2-yl]amino)-N-methyl-N-(1-methylpiperidin-4-yl)-benzamide (200 mg, 0.32 mmol) in 12 N HCl aqueous solution (8 mL) and AcOH (2 mL) was heated at 100° C. for 20 h. The reaction mixture was allowed to cool to room temperature and concentrated under vacuum. DIPEA (1 mL) was added and the mixture was concentrated under vacuum. The residue was purified by Prep-HPLC using the following conditions: Column,)(Bridge Shield RP18 OBD Column, 19*150 mm 5 um 13 nm; mobile phase, Water with 10 mmol HCOOH and MeCN (10% MeCN to 55% over 9 min); Detection, UV 254 nm to afford 4.1 mg of 4-([8-[4-(aminomethyl)-4-(4-chlorophenyl)piperidin-1-yl]-[1,2,4]triazolo[1,5-a]-pyridin-2-yl]amino)-N-methyl-N-(1-methylpiperidin-4-yl)benzamide; formic acid salt as a light yellow solid. $^1$H NMR (400 MHz, CD$_3$OD): δ 8.60-8.50 (m, 1H), 8.19 (d, J=6.4 Hz, 1H), 7.77 (d, J=8.8 Hz, 2H), 7.56-7.52 (m, 4H), 7.42 (d, J=8.4 Hz, 2H), 6.90-6.85 (m, 2H), 3.95-3.85 (m, 2H), 3.33-3.30 (m, 2H), 3.22 (s, 2H), 3.11-3.05 (m, 2H), 3.00 (s, 3H), 2.90-2.35 (m, 7H), 2.30-1.80 (m, 7H); LCMS (Method 6): R$_T$=1.75 min, m/z=587.2 [M+H]$^+$.

Example 1t

4-[(8-[4-[4-(difluoromethyl)phenyl]-4-(hydroxymethyl)piperidin-1-yl]-[1,2,4]triazolo[1,5-a]pyridin-2-yl)amino]-N-methyl-N-(1-methylpiperidin-4-yl)benzamide (Example 1-267 in Table I)

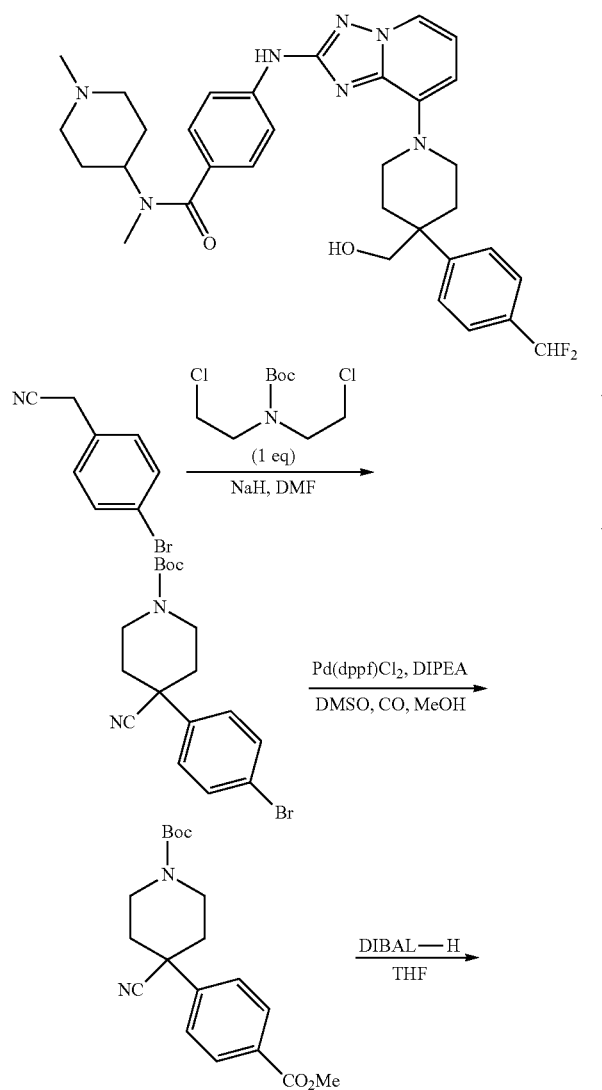

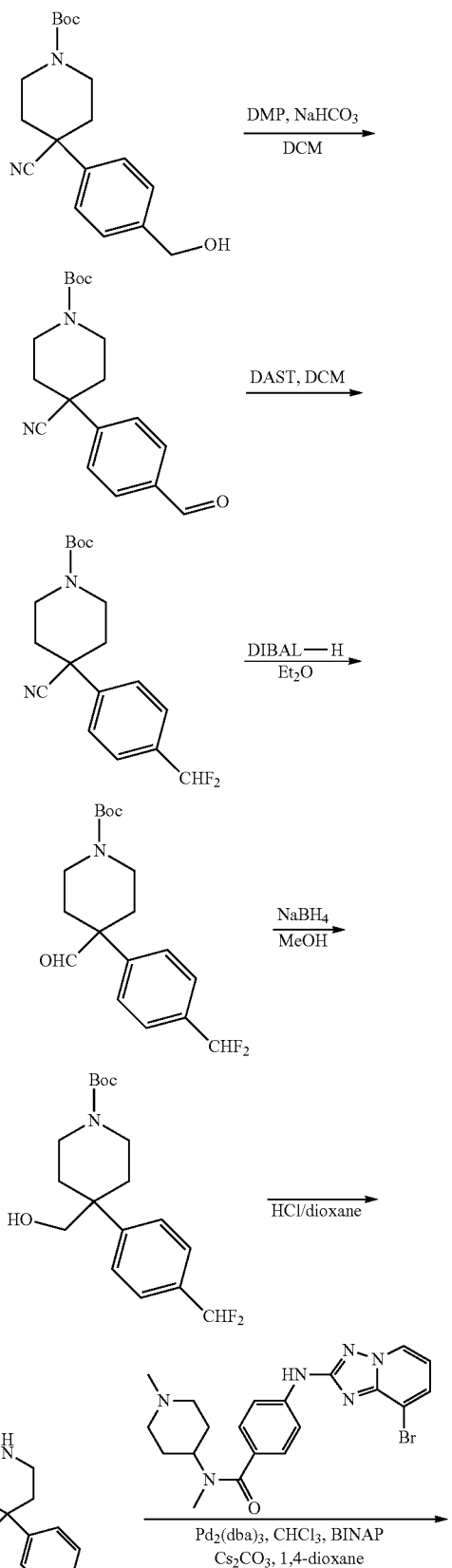

-continued

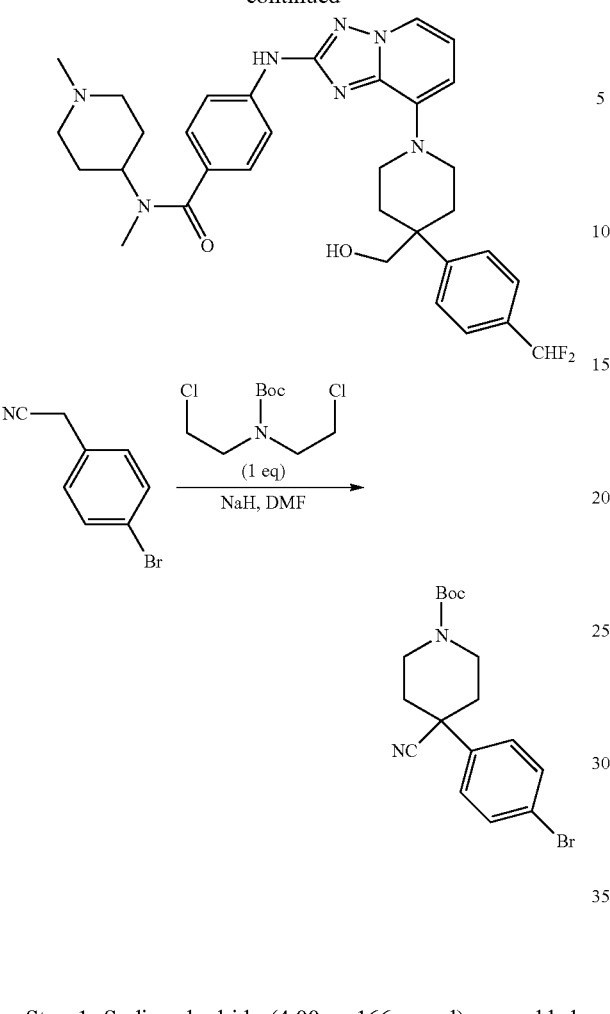

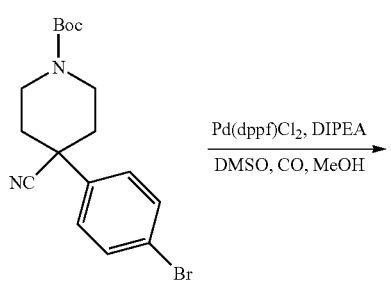

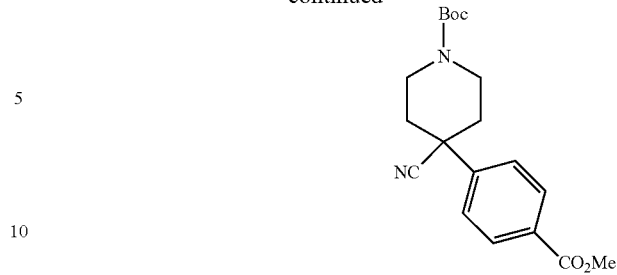

Step 2. Into a 250-mL pressure tank reactor purged and maintained with an inert atmosphere of nitrogen, were placed tert-butyl-4-(4-bromophenyl)-4-cyanopiperidine-1-carboxylate (5 g, 13.69 mmol), DIPEA (5 g, 38.69 mmol), Pd(dppf)Cl$_2$ (1.00 g, 1.37 mmol), DMSO (2.2 g, 28.16 mmol) and MeOH (150 mL) and the resulting solution was heated at 100° C. for 20 h under a pressure of 10 atm of CO. The reaction mixture was allowed to cool to room temperature and the solvent evaporated. The residue was purified by flash chromatography on silica gel eluting with EtOAc/petroleum ether (1/10 to 1/4) to afford tert-butyl-4-cyano-4-[4-(methoxycarbonyl)phenyl]piperidine-1-carboxylate as a off white solid (3.5 g, 74%). TLC: R$_f$=0.3; EtOAc/petroleum ether=1/4.

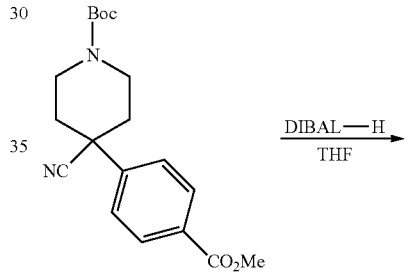

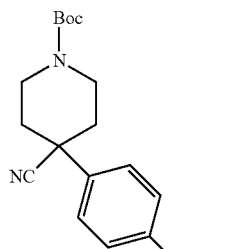

Step 1. Sodium hydride (4.00 g, 166 mmol) was added portionwise to a solution of 2-(4-bromophenyl)acetonitrile (8 g, 40.8 mmol) and tert-butyl-N,N-bis(2-chloroethyl)carbamate (10.0 g, 41.3 mmol) in DMF (100 mL). On complete addition the resulting solution was stirred at room temperature for 1 h and at 65° C. for an additional 2 h. The reaction mixture was allowed to cool to room temperature, poured into crushed ice (200 g) and extracted with DCM (3×500 mL). The combined organic layer was concentrated under vacuum and the residue was purified by flash chromatography on silica gel eluting with EtOAc/hexane (1/4) to give tert-butyl-4-(4-bromophenyl)-4-cyanopiperidine-1-carboxylate as an off white solid (6.00 g, 40%). TLC: R$_f$=0.3; ethyl acetate/petroleum ether=1/4.

Step 3. DIBAl-H (1 M in hexanes, 20 mL, 20 mmol) was added dropwise to a solution of tert-butyl-4-cyano-4-[4-(methoxycarbonyl)phenyl]piperidine-1-carboxylate (3.5 g, 10.2 mmol) and THF (100 mL) at 0° C. The resulting solution was stirred at 0° C. for 0.5 h, quenched by the addition of water (3 mL) and concentrated under vacuum. The resultant residue was purified by column chromatography on silica eluting with petroleum ether on a gradient of EtOAc (1/4 to 4/1). Appropriate fractions were combined and evaporated to afford tert-butyl 4-cyano-4-[4-(hydroxymethyl)-phenyl]piperidine-1-carboxylate as a white solid (3.00 g, 93%). TLC: R$_f$=0.3; EtOAc/petroleum ether=1/1.

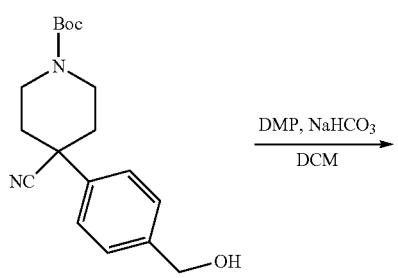

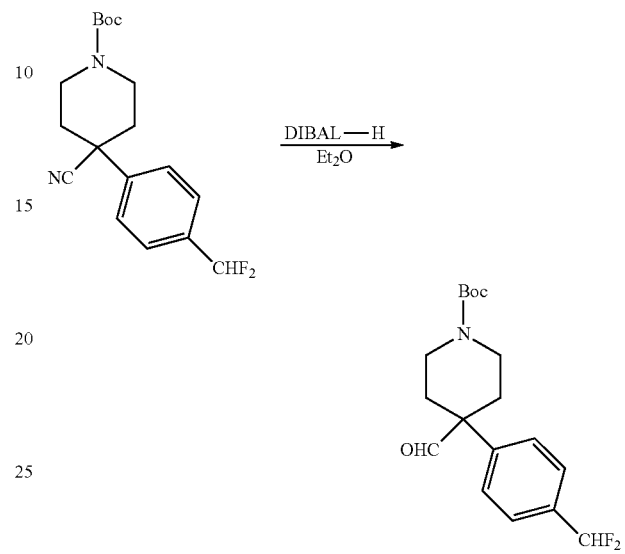

centrated. The residue was purified by flash chromatography on silica gel eluting with EtOAc/hexane (1/10) to afford tert-butyl 4-cyano-4-[4-(difluoromethyl)phenyl]piperidine-1-carboxylate as colourless oil (1.20 g, 45%). TLC: $R_f$=0.3; EtOAc/petroleum ether=1/4.

Step 4. A mixture of tert-butyl 4-cyano-4-[4-(hydroxymethyl)phenyl]piperidine-1-carboxylate (3.00 g, 9.48 mmol), sodium bicarbonate (800 mg, 9.52 mmol) and DMP (4 g, 9.43 mmol) in DCM (100 mL) was stirred at room temperature for 20 h. The resulting mixture was evaporated and the resultant residue was purified by flash chromatography on silica gel eluting with EtOAc/petroleum ether (1/4). Appropriate fractions were combined and evaporated to afford tert-butyl-4-cyano-4-(4-formylphenyl)piperidine-1-carboxylate as colourless oil (2.3 g, 77%). $^1$H NMR (400 MHz, CDCl$_3$): δ 10.04 (s, 1H), 7.94 (d, J=8.4 Hz, 2H), 7.67 (d, J=8.4 Hz, 2H), 4.48-4.19 (m, 2H), 3.34-3.10 (m, 2H), 2.16-2.07 (m, 2H), 2.04-1.91 (m, 2H), 1.49 (s, 9H).

Step 6. DIBAl-H (1 M in hexanes, 3 mL, 3 mmol) was added dropwise to a solution of tert-butyl-4-cyano-4-[4-(difluoromethyl)phenyl]piperidine-1-carboxylate (500 mg, 1.49 mmol) in diethyl ether (50 mL) under nitrogen at 0° C. The resulting solution was stirred at 0° C. for 1 h then quenched by the addition of water (1 mL). The precipitated solid was removed by filtration and the filtrate was concentrated under vacuum to afford crude tert-butyl-4-[4-(difluoromethyl)phenyl]-4-formylpiperidine-1-carboxylate as colourless oil (340 mg). The product was used in the next step without purification. TLC: $R_f$=0.5; EtOAc/petroleum ether=1/4.

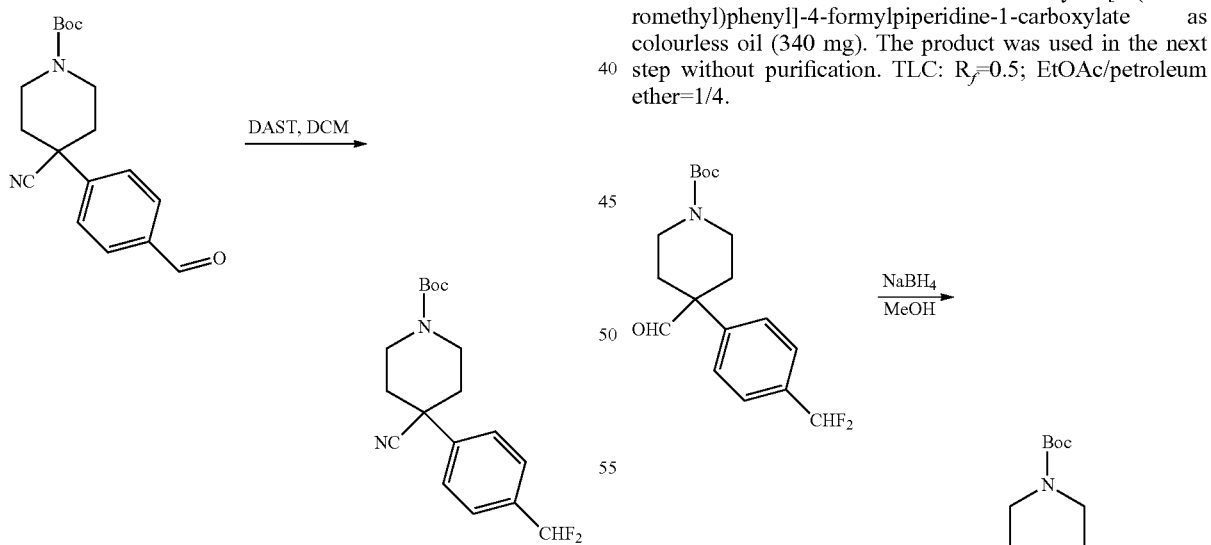

Step 5. DAST (2.0 mL, 12.4 mmol) was added to a solution of tert-butyl 4-cyano-4-(4-formylphenyl)piperidine-1-carboxylate (2.50 g, 7.95 mmol) in DCM (100 mL) under nitrogen. The resulting solution was stirred at room temperature for 20 h and quenched by the addition of saturated aqueous NaHCO$_3$ solution (50 mL). The resulting solution was extracted with DCM (3×100 mL) and the combined organic layer was dried over Na$_2$SO$_4$ and con- Step 7. NaBH$_4$ (38 mg, 1.00 mmol) was added to a solution of crude tert-butyl-4-[4-(difluoromethyl)phenyl]-4- formylpiperidine-1-carboxylate (340 mg, 1.00 mmol) in MeOH (10 mL). The resulting solution was stirred at room temperature for 10 min then quenched by the addition of water (2 mL). The reaction mixture was concentrated under vacuum and the resultant residue was purified by flash chromatography on silica gel eluting with hexane on a gradient of EtOAc (1/4 to 4/1). Appropriate fractions were collected and evaporated to afford tert-butyl-4-[4-(difluoromethyl)phenyl]-4-(hydroxymethyl)piperidine-1-carboxylate as colourless oil (150 mg, 44%). TLC: $R_f$=0.3; EtOAc/petroleum ether=1/2.

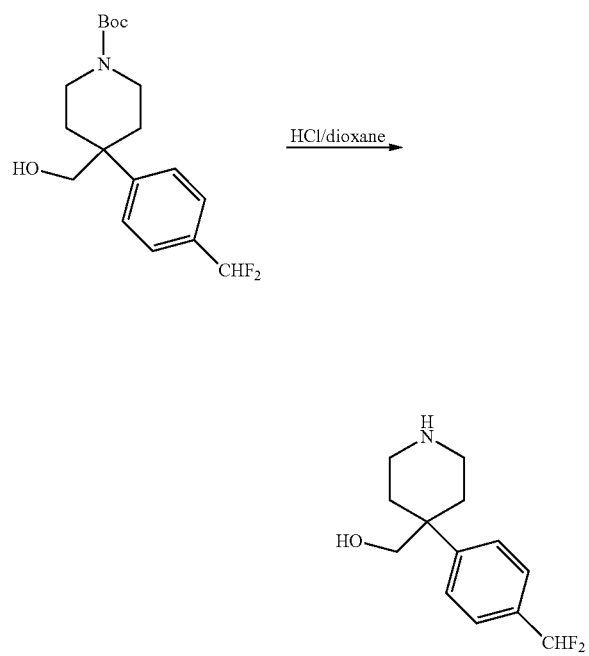

Step 8. A mixture of tert-butyl 4-[4-(difluoromethyl)phenyl]-4-(hydroxymethyl)piperidine-1-carboxylate (150 mg, 0.44 mmol) in a saturated solution of HCl in 1,4-dioxane (10 mL) was stirred at room temperature for 2 h. The resulting mixture was concentrated under vacuum to afford crude [4-[4-(difluoromethyl)phenyl]piperidin-4-yl]methanol as a light yellow solid (90 mg) as the hydrochloride salt. TLC: $R_f$=0.4; DCM/MeOH=5/1.

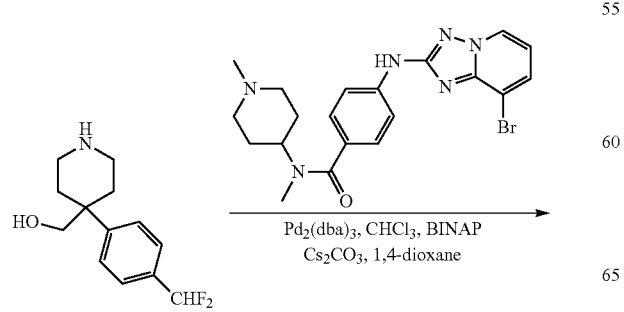

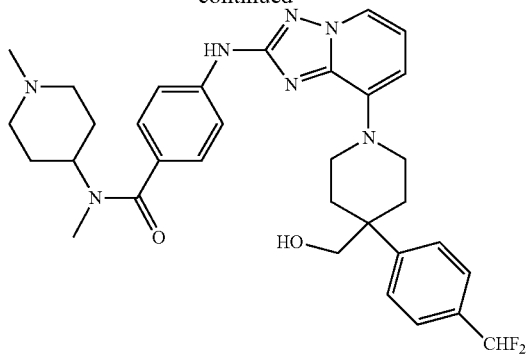

Step 9. 4-([8-bromo-[1,2,4]triazolo[1,5-a]pyridin-2-yl]amino)-N-methyl-N-(1-methylpiperidin-4-yl)benzamide; hydrochloride salt (200 mg, 0.45 mmol) and 4-[4-(difluoromethyl)phenyl]piperidin-4-ylmethanol (110 mg, 0.46 mmol) were coupled following the procedure detailed in Example 1j, step 3. The resulting mixture was concentrated under vacuum and the residue was purified using a short pad of silica gel eluting with DCM/MeOH (3/1). Appropriate fractions were combined and evaporated to afford a residue that was purified by Flash-Prep-HPLC using the following conditions: Column, silica gel; mobile phase, MeCN/$H_2O$=15% increasing to MeCN/$H_2O$=40% over 20 min; Detection, UV 254 nm to afford 4-[(8-[4-[4-(difluoromethyl)phenyl]-4-(hydroxymethyl)piperidin-1-yl]-[1,2,4]triazolo[1,5-a]pyridin-2-yl)amino]-N-methyl-N-(1-methylpiperidin-4-yl)benzamide as a off white solid (37 mg, 14%). $^1$H NMR (400 MHz, DMSO-$d_6$): δ 9.87 (s, 1H), 8.29 (d, J=6.0 Hz, 1H), 7.72 (d, J=8.8 Hz, 2H), 7.60-7.53 (m, 4H), 7.32 (d, J=8.4 Hz, 2H), 7.16-6.83 (m, 2H), 6.75 (d, J=8.0 Hz, 1H), 4.74 (t, J=5.4 Hz, 1H), 3.87-3.83 (m, 2H), 3.45 (d, J=5.6 Hz, 2H), 3.03-2.97 (m, 2H), 2.88-2.72 (m, 5H), 2.31-2.21 (m, 2H), 2.16-2.05 (m, 5H), 1.81-1.50 (m, 7H); LCMS (Method 10) $R_T$=1.52 min, m/z=604.3 [M+H]$^+$.

Example 1u 4-([8-[4-(hydroxymethyl)-4-[4-(methylsulfanyl)phenyl]piperidin-1-yl]-[1,2,4]triazolo[1,5-a]pyridin-2-yl]amino)-N-methyl-N-(1-methylpiperidin-4-yl)benzamide (Example 1-251 in Table I)

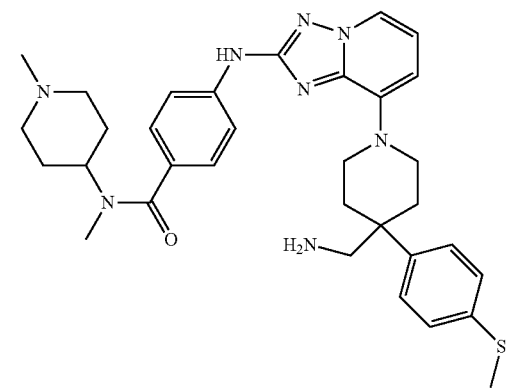

601

-continued

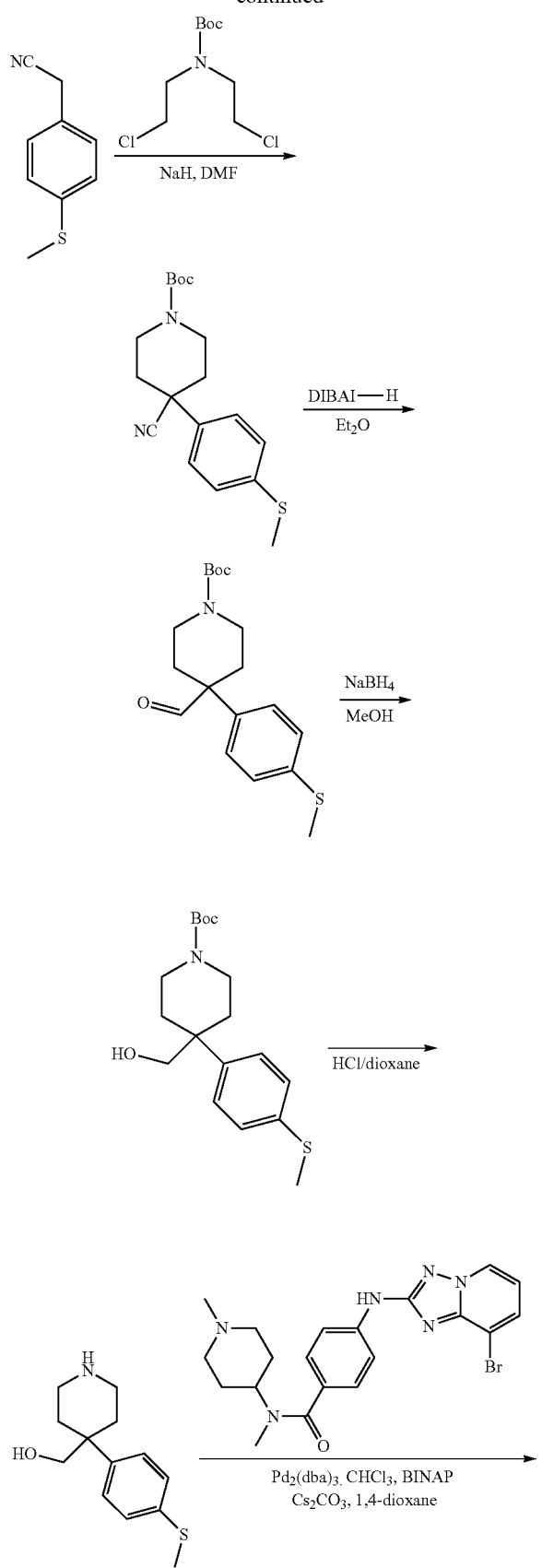

602

-continued

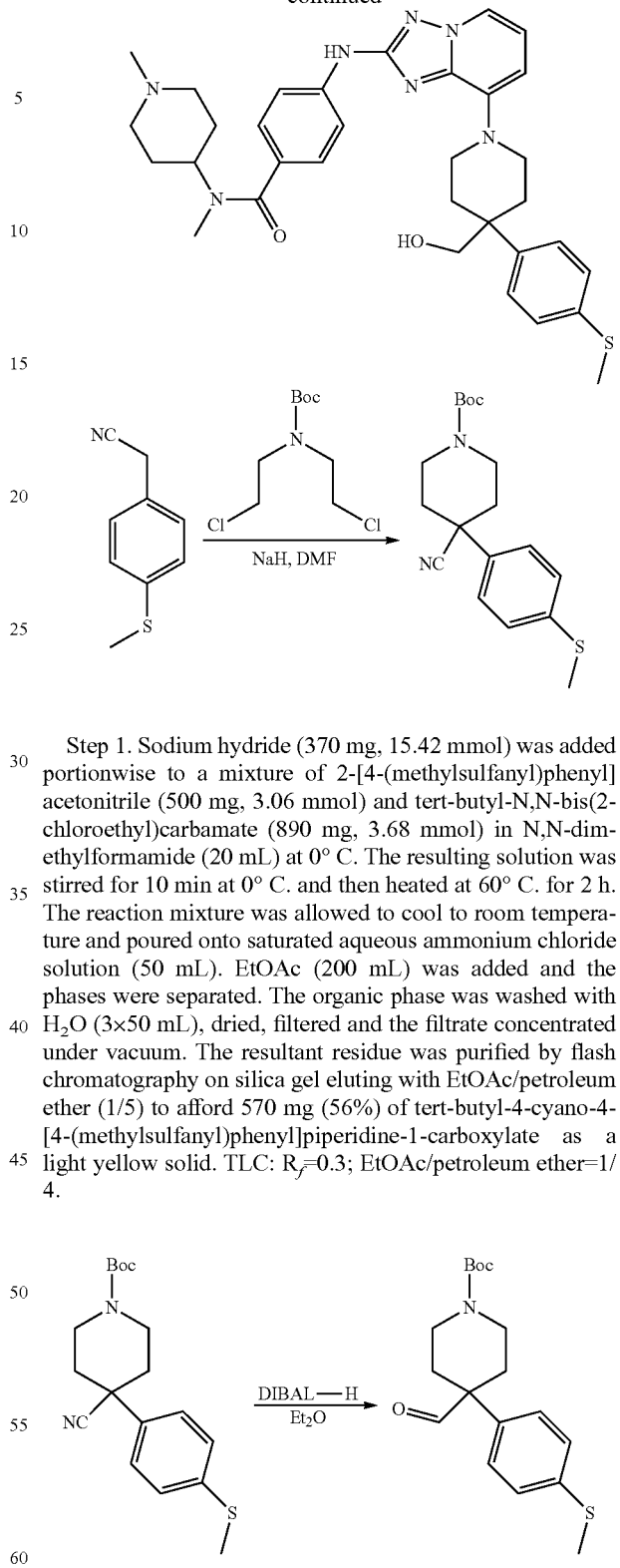

Step 1. Sodium hydride (370 mg, 15.42 mmol) was added portionwise to a mixture of 2-[4-(methylsulfanyl)phenyl]acetonitrile (500 mg, 3.06 mmol) and tert-butyl-N,N-bis(2-chloroethyl)carbamate (890 mg, 3.68 mmol) in N,N-dimethylformamide (20 mL) at 0° C. The resulting solution was stirred for 10 min at 0° C. and then heated at 60° C. for 2 h. The reaction mixture was allowed to cool to room temperature and poured onto saturated aqueous ammonium chloride solution (50 mL). EtOAc (200 mL) was added and the phases were separated. The organic phase was washed with $H_2O$ (3×50 mL), dried, filtered and the filtrate concentrated under vacuum. The resultant residue was purified by flash chromatography on silica gel eluting with EtOAc/petroleum ether (1/5) to afford 570 mg (56%) of tert-butyl-4-cyano-4-[4-(methylsulfanyl)phenyl]piperidine-1-carboxylate as a light yellow solid. TLC: $R_f$=0.3; EtOAc/petroleum ether=1/4.

Step 2. DIBAl-H (1 M in hexanes, 3.4 mL, 3.4 mmol) was added dropwise to a solution of tert-butyl-4-cyano-4-[4-(methylsulfanyl)phenyl]piperidine-1-carboxylate (570 mg, 1.71 mmol) in diethyl ether (20 mL) at 0° C. The resulting solution was stirred at 0° C. for 10 min and quenched by the addition of water (1 mL), citric (0.5 g) and celite (5 g). The precipitated solid was removed by filtration. The filtrate was concentrated under vacuum to afford 300 mg of crude tert-butyl-4-formyl-4-[4-(methylsulfanyl)-phenyl]piperidine-1-carboxylate as a light yellow solid. TLC: $R_f$=0.2; EtOAc/petroleum ether=1/4.

was concentrated under vacuum to afford 200 mg (crude) of [4-[4-(methylsulfanyl)phenyl]piperidin-4-yl]methanol as a light yellow solid. LCMS (Method 7) $R_T$=1.08 min, m/z=238.1 [M+H]$^+$.

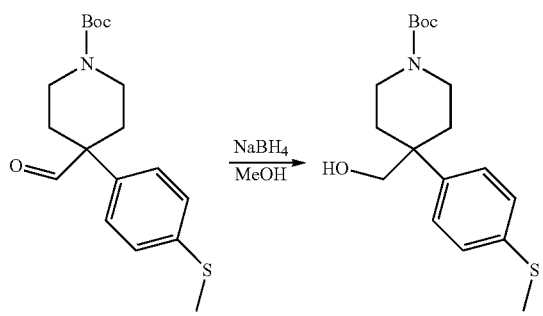 [SMILES: "MeOH" ; CSc1ccc(C2(C=O)CCN(C(=O)OC(C)(C)C)CC2)cc1 ; "NaBH4" ; CSc1ccc(C2(CO)CCN(C(=O)OC(C)(C)C)CC2)cc1]

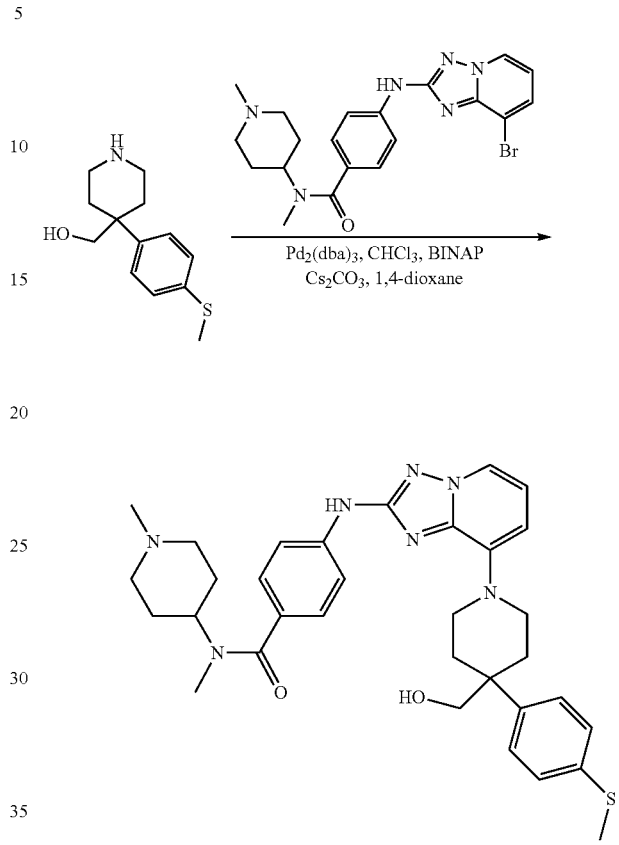

Step 3. NaBH$_4$ (68 mg, 1.80 mmol) was added to a solution of tert-butyl-4-formyl-4-[4-(methylsulfanyl)phenyl]piperidine-1-carboxylate (300 mg, 0.89 mmol) in MeOH (10 mL). The resulting solution was stirred for 30 min at room temperature then quenched by the addition of water (2 mL). The resulting mixture was concentrated under vacuum and the residue purified by flash chromatography on silica gel eluting with petroleum ether on a gradient of EtOAc (1/4 to 1/1) to afford 150 mg (50%) of tert-butyl-4-(hydroxymethyl)-4-[4-(methylsulfanyl)phenyl]piperidine-1-carboxylate as light yellow oil. TLC: $R_f$=0.3; EtOAc/petroleum ether=1/1.

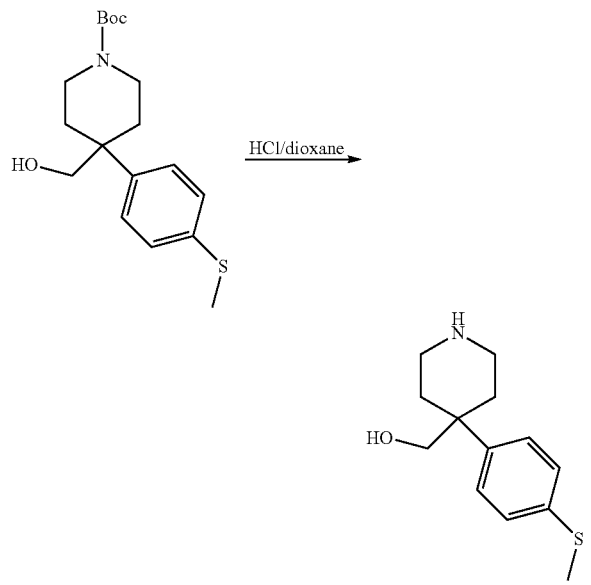

Step 4. A mixture of tert-butyl-4-(hydroxymethyl)-4-[4-(methylsulfanyl)-phenyl]piperidine-1-carboxylate (150 mg, 0.44 mmol) in a saturated solution of HCl in 1,4-dioxane (10 mL) was stirred at room temperature for 2 h. The resulting mixture was concentrated under vacuum, H$_2$O (10 mL) was added and the pH of the solution was adjusted to 9 by the addition of solid potassium carbonate. The resulting mixture was concentrated under vacuum and the residue was triturated with a mixture of DCM/MeOH (5/1(v/v), 30 mL). The remaining solid was removed by filtration and the filtrate Step 5. 4-[4-(methylsulfanyl)-phenyl]piperidin-4-ylmethanol (170 mg, 0.72 mmol) and 4-([8-bromo-[1,2,4]triazolo[1,5-a]pyridin-2-yl]amino)-N-methyl-N-(1-methylpiperidin-4-yl)benzamide (317 mg, 0.72 mmol) were coupled following the procedure detailed in Example 1j, step 3. The reaction mixture was concentrated and the residue was purified using a short pad of silica gel eluting with DCM on a gradient of MeOH (1/10 to 1/2). The filtrate was concentrated under vacuum and the resultant residue was purified by Prep-HPLC using the following conditions: Column,)(Bridge Shield RP18 OBD Column, 19*150 mm 5 um 13 nm; mobile phase, Water with 10 mmol NH$_4$HCO$_3$ and MeCN (15% MeCN up to 55% over 11 min); Detection, UV 254 nm to afford 31.8 mg (7%) of 4-([8-[4-(hydroxymethyl)-4-[4-(methylsulfanyl)phenyl]piperidin-1-yl]-[1,2,4]triazolo[1,5-a]pyridin-2-yl]amino)-N-methyl-N-(1-methylpiperidin-4-yl)benzamide as an off-white solid. $^1$H NMR (400 MHz, DMSO-d$_6$): δ 9.86 (s, 1H), 8.29 (d, J=6.4 Hz, 1H), 7.72 (d, J=8.8 Hz, 2H), 7.38 (d, J=8.4 Hz, 2H), 7.32 (d, J=8.8 Hz, 2H), 7.24 (d, J=8.8 Hz, 2H), 6.85 (t, J=7.2 Hz, 1H), 6.74 (d, J=7.6 Hz, 1H), 4.67 (t, J=5.4 Hz, 1H), 3.88-3.85 (m, 2H), 3.40-3.36 (m, 2H), 2.96 (t, J=10.2 Hz, 2H), 2.86-2.72 (m, 5H), 2.46 (s, 3H), 2.25-2.01 (m, 7H), 1.91-1.70 (m, 4H), 1.62-1.49 (m, 3H). LCMS (Method 10) $R_T$=1.85 min, m/z=600.3 [M+H]$^+$.

Example 1v
4-([8-[4-(4-chlorophenyl)-4-(cyanomethyl)cyclohex-1-en-1-yl]-[1,2,4]triazolo[1,5-a]pyridin-2-yl]amino)-N-methyl-N-(1-methylpiperidin-4-yl)benzamide (Example 1-294 in Table I)
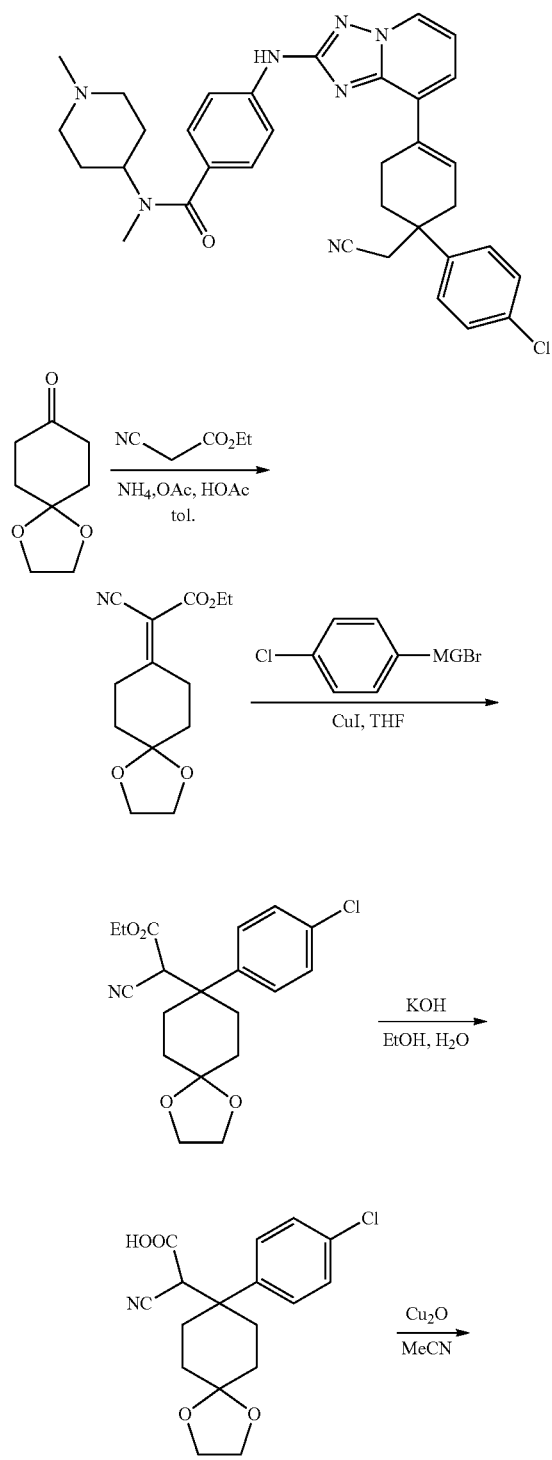
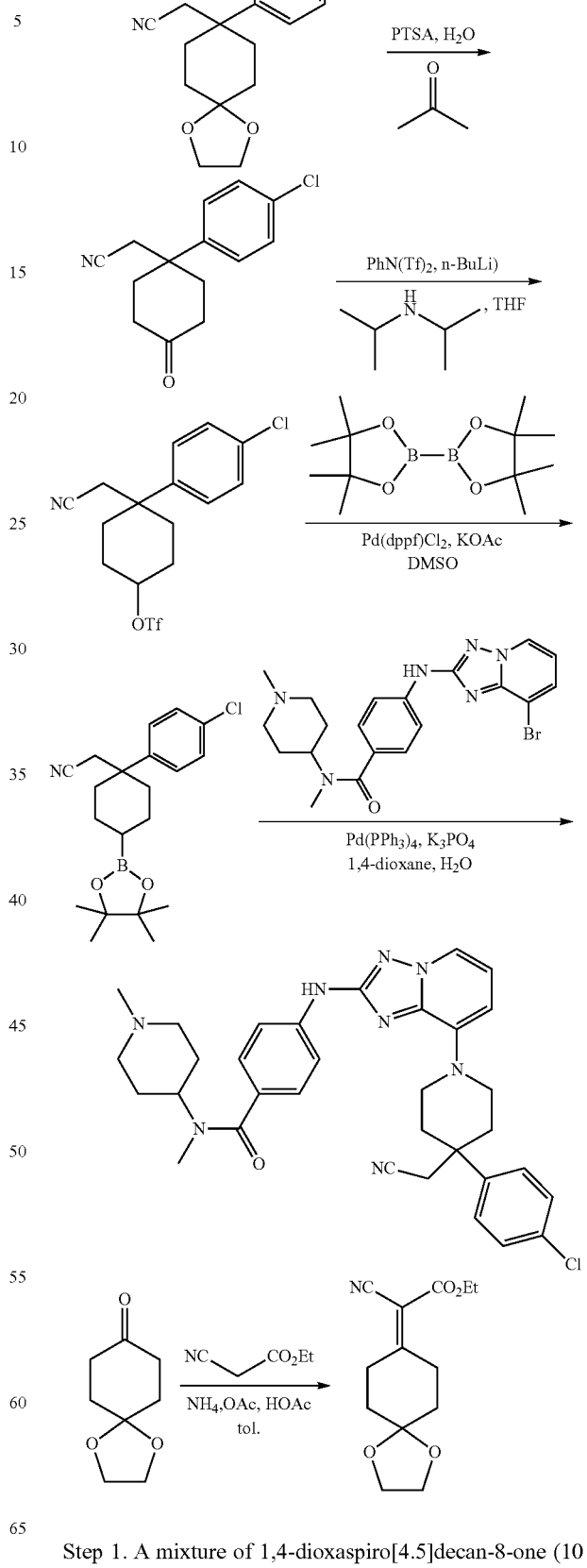
Step 1. A mixture of 1,4-dioxaspiro[4.5]decan-8-one (10 g, 64.0 mmol), ethyl 2-cyanoacetate (7.24 g, 64.0 mmol), NH₄OAc (4.94 g, 64.1 mmol) and acetic acid (20 mL, 349 mmol) in toluene (200 mL) was heated under nitrogen at 110° C. for 3 h. The reaction mixture was allowed to cool to room temperature and concentrated under vacuum, diluted with EtOAc (200 mL), washed with H₂O (50 mL) and concentrated under vacuum. The residue was purified by flash chromatography on silica gel eluting with petroleum ether on a gradient of EtOAc (1/10 to 1/5) to afford 10 g (57%) of ethyl 2-cyano-2-[1,4-dioxaspiro[4.5]decan-8-ylidene]acetate as a white solid. TLC: R_f=0.4; EtOAc/petroleum ether=1/2.

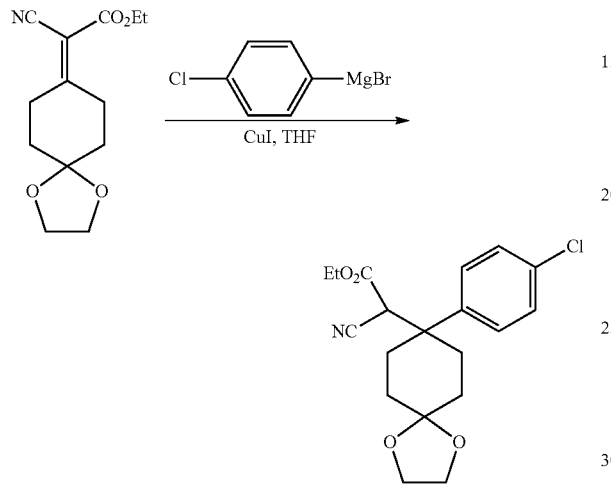

Step 2. A solution of bromo(4-chlorophenyl)magnesium (1 M in THF, 12 mL, 12 mmol) was added dropwise to a mixture of ethyl 2-cyano-2-[1,4-dioxaspiro[4.5]decan-8-ylidene]acetate (1.00 g, 3.98 mmol) and CuI (230 mg, 1.21 mmol) in THF (20 mL) under nitrogen at 0° C. The resulting solution was stirred for 2 h at 0° C., quenched by the addition of 10 mL of ethanol and concentrated under vacuum. The resultant residue was purified by flash chromatography on silica gel eluting with petroleum ether on a gradient of EtOAc (1/10 to 1/5) to afford 1.2 g (70%) of ethyl 2-[8-(4-chlorophenyl)-1,4-dioxaspiro-[4.5]decan-8-yl]-2-cyanoacetate as light yellow oil. TLC: R_f=0.3; EtOAc/petroleum ether=1/2.

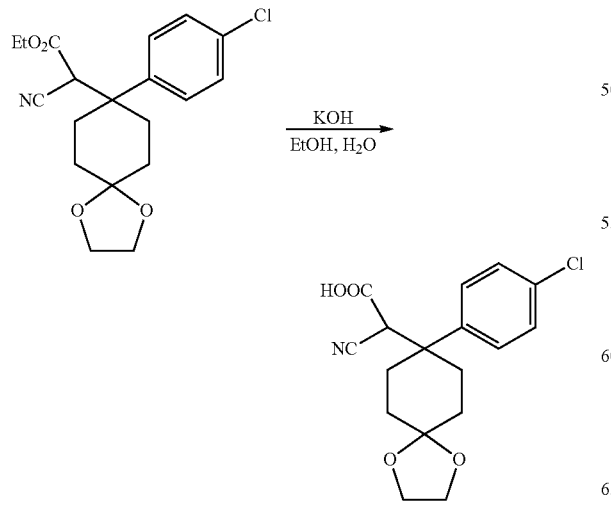

Step 3. A solution of KOH (1.2 g, 21.39 mmol) in water (10 mL) was added dropwise to a solution of ethyl 2-[8-(4-chlorophenyl)-1,4-dioxaspiro[4.5]decan-8-yl]-2-cyanoacetate (1.2 g, 3.30 mmol) in ethanol (10 mL). On complete addition the mixture was stirred at room temperature for 20 h then concentrated under vacuum. The resultant residue was dissolved in H₂O (20 mL) and washed with diethylether (2×50 mL). The pH of the aqueous phase was adjusted to 6 by the addition of 6N HCl and the resulting mixture was concentrated under vacuum. The residue was triturated with DCM and the remaining solid removed by filtration. The filtrate was concentrated under vacuum to afford 1 g of 2-[8-(4-chlorophenyl)-1,4-dioxaspiro[4.5]decan-8-yl]-2-cyanoacetic acid as a light yellow solid. TLC: R_f=0.3; DCM/MeOH=5/1.

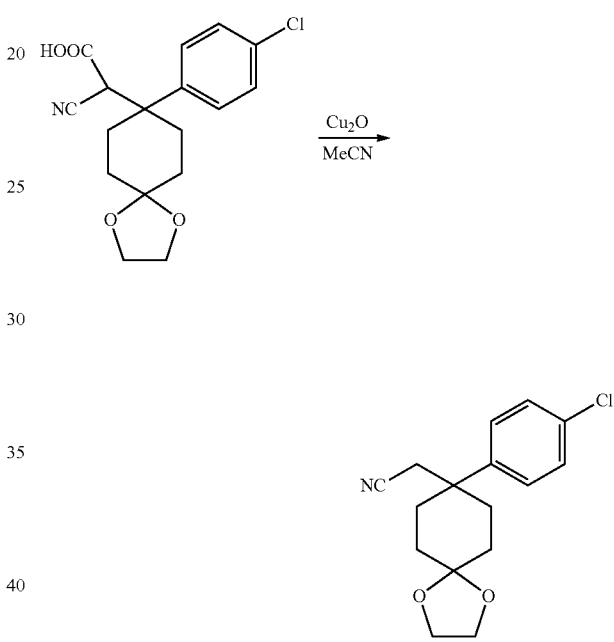

Step 4. A mixture of 2-[8-(4-chlorophenyl)-1,4-dioxaspiro[4.5]decan-8-yl]-2-cyanoacetic acid (1 g, 2.98 mmol) and Cu₂O (480 mg, 3.35 mmol) in MeCN (30 mL) was heated under nitrogen at 85° C. for 2 h. The reaction mixture was allowed to cool to room temperature and concentrated under vacuum. The resultant residue was purified by flash chromatography on silica gel eluting with EtOAc/petroleum ether (1/3) to afford 600 mg (62%) of 2-[8-(4-chlorophenyl)-1,4-dioxaspiro[4.5]decan-8-yl]acetonitrile as light yellow oil. TLC: R_f=0.3; EtOAc/petroleum ether=1/2.

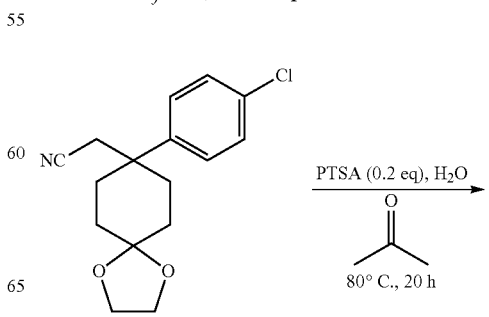

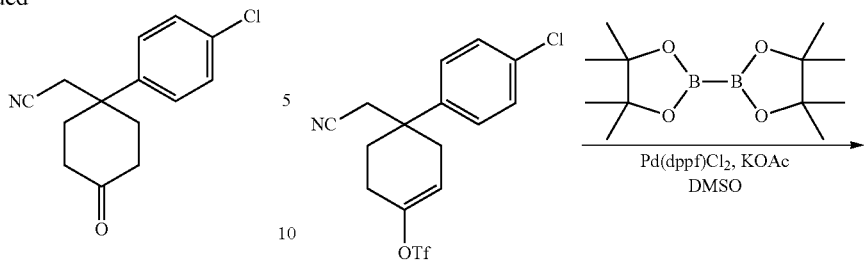

Step 5. A mixture of 2-[8-(4-chlorophenyl)-1,4-dioxaspiro[4.5]decan-8-yl]acetonitrile (600 mg, 2.06 mmol) and PTSA (71 mg, 0.41 mmol) in propan-2-one (20 mL) and water (5 mL) was heated at 80° C. for 20 h. The reaction mixture was allowed to cool to room temperature and concentrated under vacuum. Water (20 mL) was added and the aqueous phase extracted with EtOAc (2×100 mL). The combined organic phase was evaporated and the resultant residue purified by silica gel eluting with petroleum ether on a gradient of EtOAc (1/5 to 1/2) to give 400 mg (72%) of 2-[1-(4-chlorophenyl)-4-oxocyclohexyl]acetonitrile as a white solid. TLC: $R_f$=0.2; EtOAc/petroleum ether=1/2.

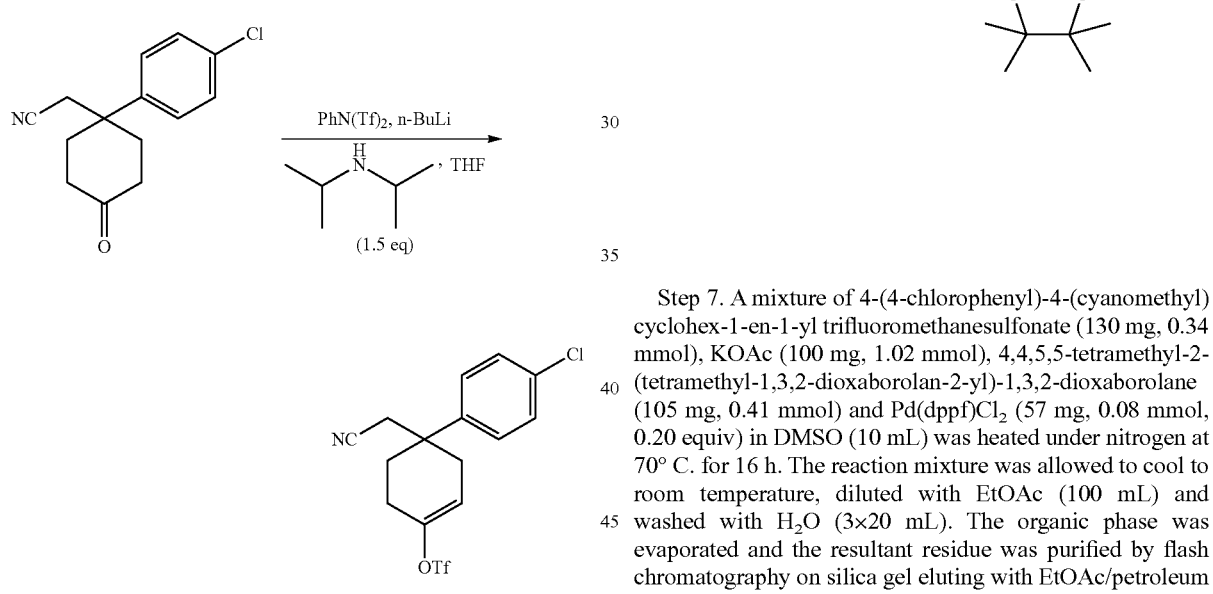

Step 6. A solution of n-BuLi (2.5 M in hexanes, 0.6 mL, 1.5 mmol) was added dropwise to a solution of diisopropylamine (190 mg, 1.88 mmol) in THF (20 mL) under nitrogen at −70° C. The resulting solution was stirred at −70° C. for 0.5 h then a solution of 2-[1-(4-chlorophenyl)-4-oxocyclohexyl]acetonitrile (300 mg, 1.21 mmol) in a minimum amount of THF was added. The resulting solution was stirred at −70° C. for 0.5 h before the addition of 1,1,1-trifluoro-N-phenyl-N-(trifluoromethane)sulfonylmethanesulfonamide (520 mg, 1.46 mmol). The resulting solution was stirred for 0.5 h at −70° C. then allowed to warm to room temperature. The reaction mixture was concentrated under vacuum and the resultant residue purified by flash chromatography on silica gel eluting with petroleum ether on a gradient of EtOAc (1/10 to 1/5) to afford 130 mg (20%) of 4-(4-chlorophenyl)-4-(cyanomethyl)cyclohex-1-en-1-yl trifluoromethanesulfonate as light yellow oil. TLC: $R_f$=0.4; EtOAc/petroleum ether=1/2.

Step 7. A mixture of 4-(4-chlorophenyl)-4-(cyanomethyl)cyclohex-1-en-1-yl trifluoromethanesulfonate (130 mg, 0.34 mmol), KOAc (100 mg, 1.02 mmol), 4,4,5,5-tetramethyl-2-(tetramethyl-1,3,2-dioxaborolan-2-yl)-1,3,2-dioxaborolane (105 mg, 0.41 mmol) and Pd(dppf)Cl$_2$ (57 mg, 0.08 mmol, 0.20 equiv) in DMSO (10 mL) was heated under nitrogen at 70° C. for 16 h. The reaction mixture was allowed to cool to room temperature, diluted with EtOAc (100 mL) and washed with H$_2$O (3×20 mL). The organic phase was evaporated and the resultant residue was purified by flash chromatography on silica gel eluting with EtOAc/petroleum ether (1/10) to afford 2-[1-(4-chlorophenyl)-4-(tetramethyl-1,3 ,2-dioxaborolan-2-yl)cyclohex-3-en-1-yl]acetonitrile (100 mg, 49%) as light yellow oil. TLC: $R_f$=0.6; EtOAc/petroleum ether=1/2.

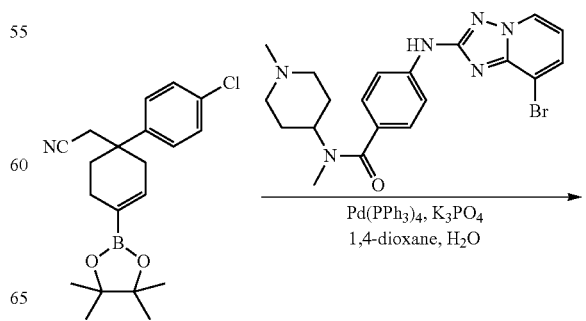

611
-continued

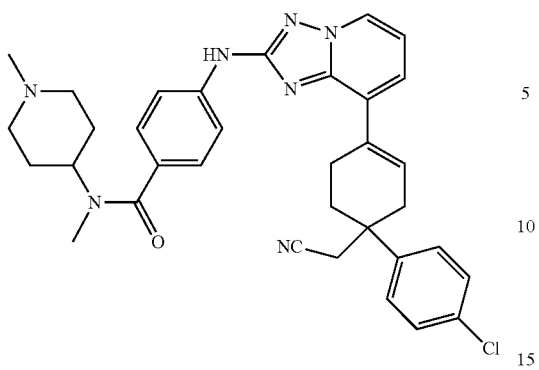

Step 8. A mixture of 2-[1-(4-chlorophenyl)-4-(tetramethyl-1,3,2-dioxaborolan-2-yl)cyclohex-3-en-1-yl]acetonitrile (150 mg, 0.42 mmol), 4-(8-bromo-[1,2,4]triazolo[1,5-a]pyridin-2-ylamino)-N-methyl-N-(1-methylpiperidin-4-yl)benzamide (190 mg, 0.43 mmol), $K_3PO_4$ (270 mg, 1.27 mmol) and $Pd(PPh_3)_4$ (100 mg, 0.09 mmol) in 1,4-dioxane (30 mL) and water (3 mL) was degassed and refilled with nitrogen 3 times. The reaction mixture was heated at 100° C. for 20 h, allowed to cool to room temperature and concentrated under vacuum. The residue was purified using a short pad of silica gel eluting with DCM/MeOH (10/1). Appropriate fractions were combined and concentrated under vacuum. The resultant residue was purified by Flash-Prep-HPLC using the following conditions: Column, silica gel; mobile phase, $MeCN/H_2O$=13% increasing to $MeCN/H_2O$=45% over 11 min; Detection, UV 254 nm to afford 61.4 mg (24%) of 4-([8-[4-(4-chlorophenyl)-4-(cyanomethyl)cyclohex-1-en-1-yl]-[1,2,4]-triazolo[1,5-a]pyridin-2-yl]amino)-N-methyl-N-(1-methylpiperidin-4-yl)benzamide as a white solid.

$^1$H NMR (300 MHz, DMSO-$d_6$): δ 9.93 (s, 1H), 8.66 (d, J=5.7 Hz, 1H), 7.74 (d, J=8.7 Hz, 2H), 7.55 (d, J=8.7 Hz, 2H), 7.44 (t, J=9.0 Hz, 4H), 7.33 (d, J=8.4 Hz, 2H), 6.98 (t, J=7.0 Hz, 1H), 3.29 (s, 1H), 3.07-2.82 (m, 8H), 2.74-2.56 (m, 2H), 2.27-2.12 (m, 6H), 1.80 (s, 4H), 1.59-1.56 (m, 2H); LCMS (Method 8) $R_T$=1.78 min, m/z=594.1 [M+H]$^+$.

Example 1w 4-([8-[4-(hydroxymethyl)-4-[[(2,2,2-trifluoroethyl)amino]methyl]piperidin-1-yl]-[1,2,4]triazolo[1,5-a]pyridin-2-yl]amino)-N-methyl-N-(1-methylpiperidin-4-yl)benzamide (Example 1-266 in Table I)

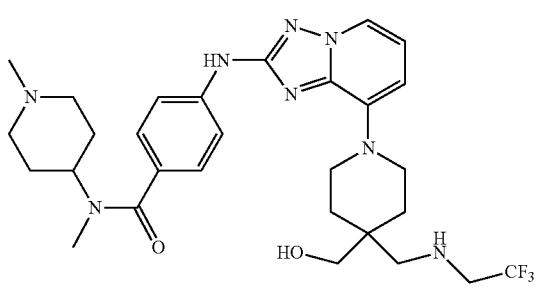

612
-continued

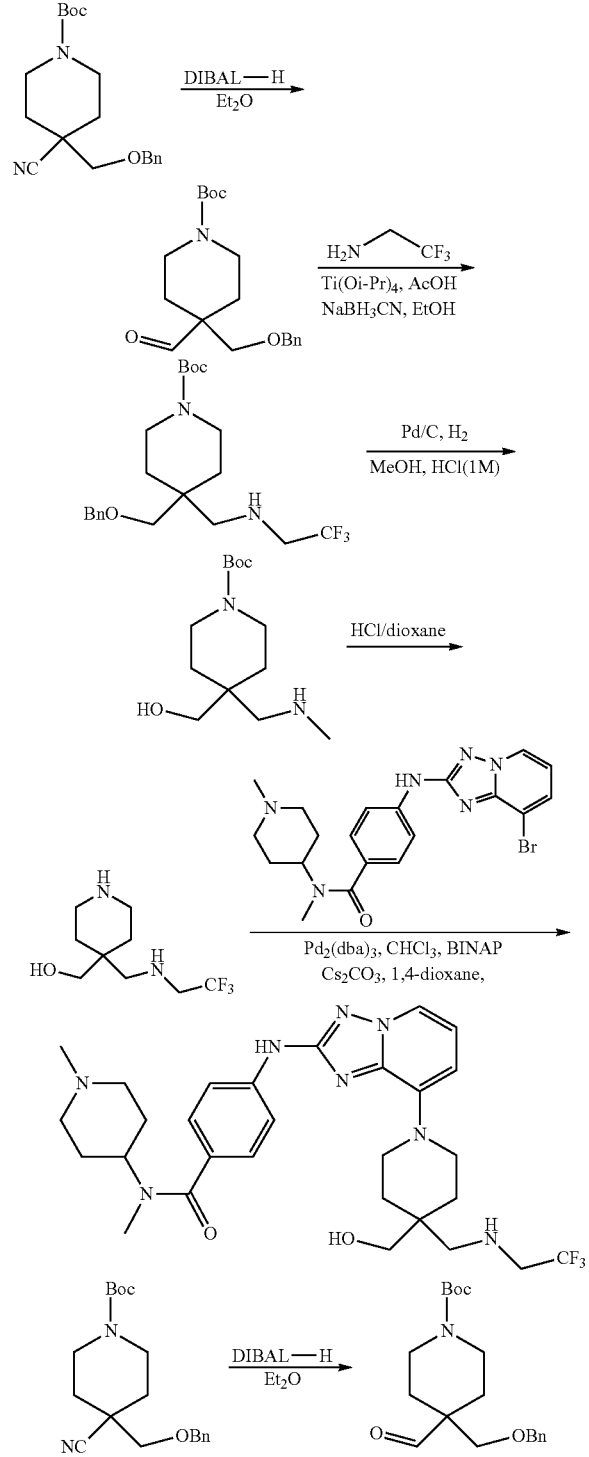

Step 1. DIBAl-H (1 M in hexane, 30 mL, 30 mmol) was added dropwise to a solution of tert-butyl -4-[(benzyloxy)methyl]-4-cyanopiperidine-1-carboxylate (4 g, 12.11 mmol) in diethyl ether (100 mL) under nitrogen at 0° C. The resulting solution was stirred at 0° C. for 1 h then quenched by the addition of water (2 mL). The precipitated solid was removed by filtration and the filtrate was concentrated under vacuum. The resultant residue was purified by chromatography on silica gel eluting with EtOAc/hexane (1/2) to afford tert-butyl-4-[(benzyloxy)methyl]-4-formylpiperidine-1-carboxylate as yellow oil (1.3 g, 32%). TLC: $R_f$=0.4; EtOAc/petroleum ether=1/2.

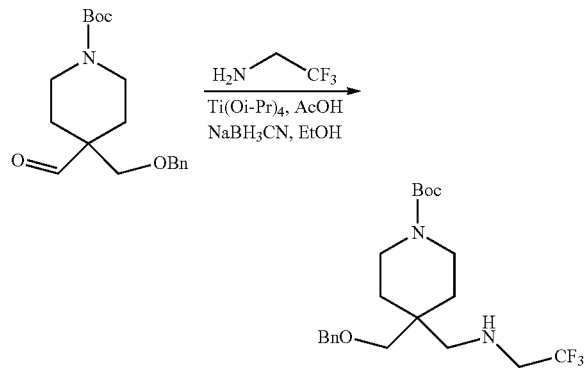

Step 2. A mixture of tert-butyl-4-[(benzyloxy)methyl]-4-formylpiperidine-1-carboxylate (1 g, 3.00 mmol), 2,2,2-trifluoroethan-1-amine (1.5 g, 15.14 mmol), and tetrakis(propan-2-yloxy)titanium (850 mg, 2.99 mmol) in ethanol (30 mL) was heated under nitrogen at 60° C. for 2 h. AcOH (0.1 mL, 1.75 mmol) was added, followed by NaBH$_3$CN (370 mg, 5.89 mmol). The resulting solution was heated at 60° C. for an additional 2 h then allowed to cool to room temperature. The mixture was concentrated under vacuum and the resultant residue was purified by flash chromatography on silica gel eluting with EtOAc/hexane (1/10) to afford tert-butyl-4-[(benzyloxy)methyl]-4-[[(2,2,2-trifluoroethyl)amino]methyl]piperidine-1-carboxylate as colourless oil (310 mg, 25%). TLC: $R_f$=0.5; EtOAc/petroleum ether=1/4.

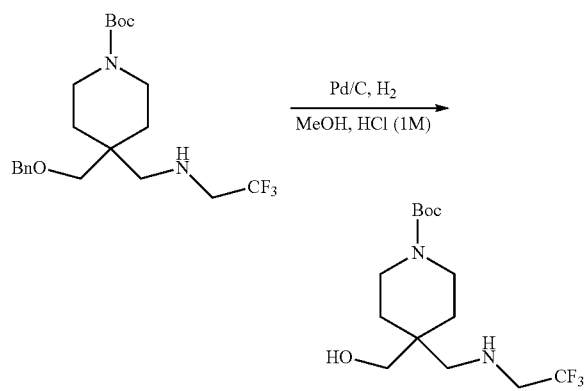

Step 3. A mixture of tert-butyl-4-[(benzyloxy)methyl]-4-[[(2,2,2-trifluoroethyl)amino]methyl]piperidine-1-carboxylate (300 mg, 0.72 mmol) and 10% Pd/C (50 mg) in MeOH (20 mL) and aqueous 6 N HCl solution (1 mL) was stirred under H$_2$ at room temperature for 20 h. The catalyst was removed by filtration and the filtrate was concentrated under vacuum. The residue was purified by flash chromatography on silica gel eluting with DCM/MeOH (1/3) to afford tert-butyl-4-(hydroxymethyl)-4-[[(2,2,2-trifluoroethyl)amino]methyl]piperidine-1-carboxylate as colourless oil (120 mg, 51%). LCMS (Method 12) $R_T$=0.66 min, m/z=327.0 [M+H]$^+$.

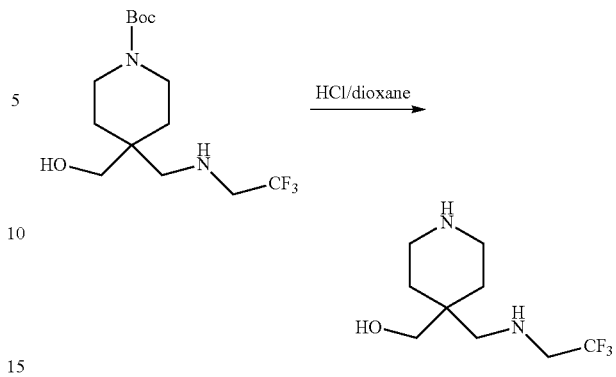

Step 4. A solution of tert-butyl-4-(hydroxymethyl)-4-[[(2,2,2-trifluoroethyl)amino]-methyl]piperidine-1-carboxylate (120 mg, 0.37 mmol) in a saturated solution of HCl in 1,4-dioxane (6 mL) was stirred at room temperature for 1 h. The resulting mixture was evaporated, H$_2$O (1mL) was added, followed by solid K$_2$CO$_3$ (0.5 g). The resulting mixture was concentrated under vacuum and the residue was triturated with a mixture of DCM/MeOH (3/1(v/v), 30 mL) and the remaining solid was removed by filtration. The filtrate was concentrated under vacuum to afford (4-[[(2,2,2-trifluoroethyl)-amino]methyl]piperidin-4-yl)methanol as colourless oil (65 mg). TLC: $R_f$=0.2; DCM/MeOH=4/1.

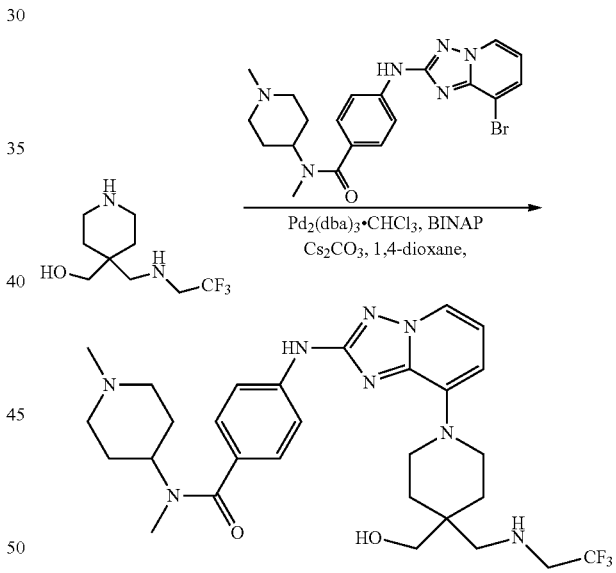

Step 5. (4-[[(2,2,2-trifluoroethyl)amino]-methyl]piperidin-4-yl)methanol (55 mg, 0.24 mmol) and 4-(8-bromo-[1,2,4]triazolo[1,5-a]pyridin-2-ylamino)-N-methyl-N-(1-methylpiperidin-4-yl)benzamide (100 mg, 0.23 mmol) were coupled following the procedure detailed in Example 1j, step 3. The reaction mixture was concentrated under vacuum and the residue purified using a short pad of silica gel eluting with DCM/MeOH (10/1). Appropriate fractions were combined and evaporated and the resultant residue was purified by Flash-Prep-HPLC using the following conditions: Column, silica gel; mobile phase, MeCN/H$_2$O=15% increasing to MeCN/H$_2$O=40% over 20 min; Detection, UV 254 nm to afford 4-([8-[4-(hydroxymethyl)-4-[[(2,2,2-trifluoroethyl)amino]methyl]piperidin-1-yl]-[1,2,4]triazolo[1,5-a]pyridin-2-yl]amino)-N-methyl-N-(1-methylpiperidin-4-yl)benzamide as a off white solid (12.2 mg, 9%). $^1$H NMR (400 MHz, DMSO-$d_6$): δ 9.86 (s, 1H), 8.31 (d, J=6.4 Hz, 1H), 7.71 (d, J=8.4 Hz, 2H), 7.32 (d, J=8.4 Hz, 2H), 6.88 (t, J=3.4 Hz, 1H), 6.82 (d, J=3.6Hz, 1H), 4.61 (t, J=3.2 Hz, 1H), 3.51-3.36 (m, 6H), 3.31-3.23 (m, 3H), 2.85-2.76 (m, 5H), 2.70-2.65 (m, 2H), 2.33-2.24 (m, 1H), 2.18-2.04 (m, 3H), 1.91-1.70 (m, 4H), 1.64-1.50 (m, 6H); LCMS (Method 7) $R_T$=1.21 min, m/z=589.4 [M+H]$^+$.

Example 1x 4-([8-[4-(cyanomethyl)-4-cyclopentylpiperidin-1-yl]-[1,2,4]triazolo[1,5-a]pyridin-2-yl]amino)-N-methyl-N-(1-methylpiperidin-4-yl)benzamide (Example 1-257 in Table I)

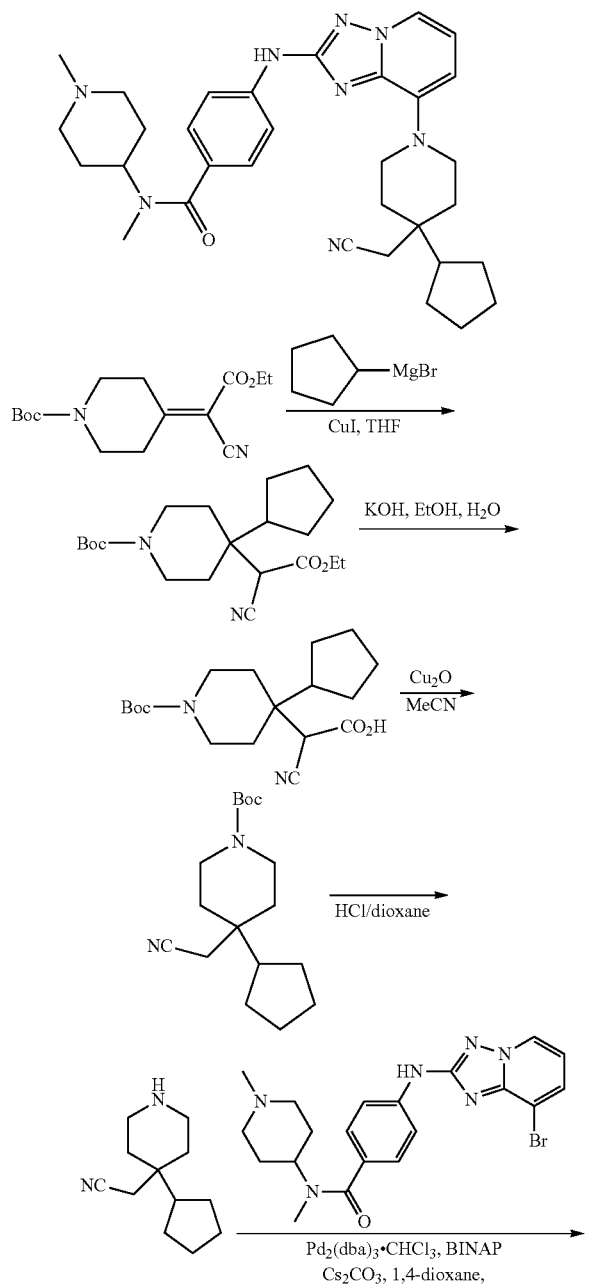

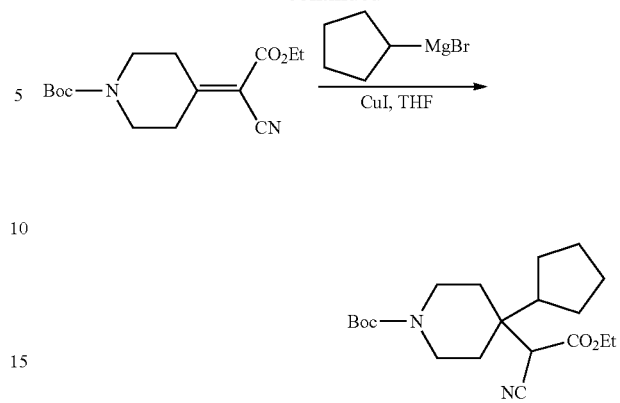

Step 1. A solution of bromo(cyclopentyl)magnesium (1 M in THF, 20 mL, 115.4 mmol) was added dropwise to a mixture of tert-butyl-4-(1-cyano-2-ethoxy-2-oxoethylidene) piperidine-1-carboxylate (Example 1e, step 2, 2 g, 6.79 mmol) and CuI (380 mg, 2.00 mmol) in THF (20 mL) under nitrogen at 0° C. The resulting solution was stirred 0° C. for 2 h at then quenched by the addition of ethanol (10 mL). The mixture was concentrated under vacuum and the residue was purified by flash chromatography on silica gel eluting with EtOAc/petroleum ether (1/10) to afford 1.7 g (69%) of tert-butyl-4-(1-cyano-2-ethoxy-2-oxoethyl)-4-cyclopentylpiperidine-1-carboxylate as light yellow oil. TLC: $R_f$=0.4; EtOAc/petroleum ether=1/4.

Step 2. A mixture of potassium hydroxide (2.0 g, 35.65 mmol) and tert-butyl-4-(1-cyano-2-ethoxy-2-oxoethyl)-4-cyclopentylpiperidine-1-carboxylate (1.7 g, 4.66 mmol) in ethanol (20 mL) and water (20 mL) was stirred at room temperature overnight. The reaction mixture was evaporated to half original volume and washed with ether (3×30 mL). The pH of the aqueous phase was adjusted to 6 by the addition of 6N HCl aqueous solution and the resulting mixture was concentrated under vacuum. The residue was triturated with a mixture of DCM and MeOH (5/1(v/v), 50 mL) and the remaining solid was removed by filtration. The filtrate evaporated to afford 1.3 g (83%) of 2-[1-[(tert-butoxy)carbonyl]-4-cyclopentylpiperidin-4-yl]-2-cyanoacetic acid as a light yellow solid. TLC: $R_f$=0.5; DCM/MeOH=5/1.

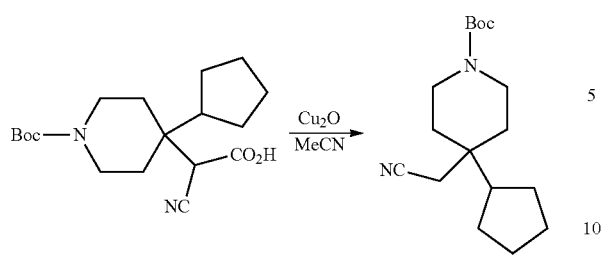

Step 3. A mixture of 2-[1-[(tert-butoxy)carbonyl]-4-cyclopentylpiperidin-4-yl]-2-cyanoacetic acid (1.3 g, 3.86 mmol) and Cu$_2$O (550 mg, 3.84 mmol) in MeCN (30 mL) was heated at 85° C. for 2 h under nitrogen then allowed to cool to room temperature. The reaction mixture was concentrated under vacuum and the residue purified by flash chromatography on silica gel eluting with EtOAc/petroleum ether (1/4) to afford 830 mg (73%) of tert-butyl-4-(cyanomethyl)-4-cyclopentylpiperidine-1-carboxylate as colourless oil. TLC: R$_f$=0.4; EtOAc/petroleum ether=1/2.

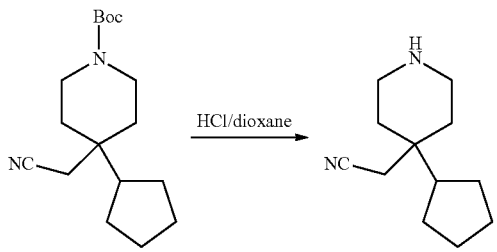 [SMILES: CC(C)(C)OC(=O)N1CCC(CC#N)(C2CCCC2)CC1 ; N#CCC1(C2CCCC2)CCNCC1]

Step 4. A mixture of tert-butyl-4-(cyanomethyl)-4-cyclopentylpiperidine-1-carboxylate (830 mg, 2.84 mmol) in saturated HCl in 1,4-dioxane (30 mL) was stirred at room temperature for 2 h. The resulting mixture was concentrated under vacuum and the residue was dissolved in H$_2$O (10 mL). The pH of the aqueous phase was adjusted to 9 by the addition of solid potassium carbonate. The resultant mixture was concentrated under vacuum and the residue triturated with a mixture of DCM and MeOH (5/1(v/v), 10 mL). The precipitated solid was removed by filtration and the filtrate evaporated to afford 580 mg (crude) of 2-(4-cyclopentylpiperidin-4-yl)acetonitrile as light yellow oil. TLC: R$_f$=0.3; DCM/MeOH=5/1.

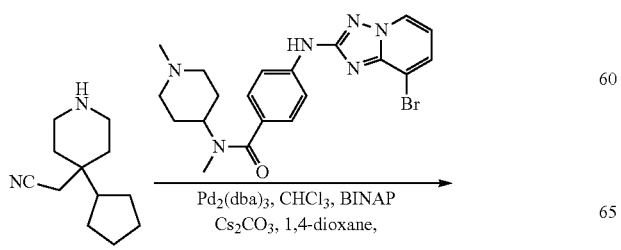

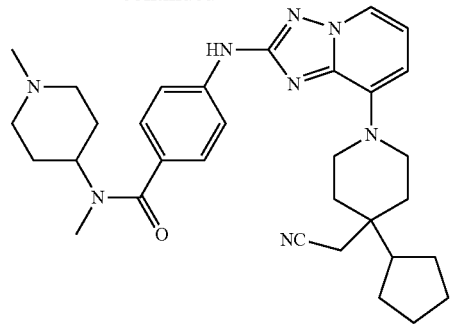

Step 5. 4-([8-bromo-[1,2,4]triazolo[1,5-a]pyridin-2-yl]amino)-N-methyl-N-(1-methylpiperidin-4-yl)benzamide (200 mg, 0.45 mmol) and 2-(4-cyclopentylpiperidin-4-yl)acetonitrile (173 mg, 0.90 mmol) were coupled following the procedure detailed in Example 1j, step 3. The resulting mixture was concentrated under vacuum and the residue purified using a short pad of silica gel eluting with DCM/MeOH (10/1). Appropriate fractions were combined and concentrated under vacuum and the crude product was purified by Prep-HPLC using the following conditions: Column, XBridge Shield RP18 OBD Column, 19*150 mm Sum 13 nm; mobile phase, Water with 10 mmol NH$_4$HCO$_3$ and MeCN (13% MeCN up to 55% over 12 min); Detection, UV 254 nm to afford 55.6 mg (22%) of 4-([8-[4-(cyanomethyl)-4-cyclopentylpiperidin-1-yl]-[1,2,4]triazolo[1,5-a]pyridin-2-yl]amino)-N-methyl-N-(1-methylpiperidin-4-yl)benzamide as a white solid. $^1$H NMR (300 MHz, DMSO-d$_6$): δ 9.85 (s, 1H), 8.34 (t, J=3.1 Hz, 1H), 7.71 (d, J=8.7 Hz, 2H), 7.32 (d, J=8.7 Hz, 2H), 6.93-6.84 (m, 2H), 3.84-3.82 (m, 2H), 3.18 (t, J=10.2 Hz, 2H), 2.82-2.73 (m, 7H), 2.12 (s, 4H), 1.90-1.35 (m, 19H); LCMS (Method 10) R$_T$=1.69 min, m/z=555.3 [M+H]$^+$.

Example 1y

N-methyl-N-[1-(2-methylpropyl)piperidin-4-yl]-2-[4-([8-[1-(4,4,4-trifluorobutanoyl)-1,2,3,6-tetrahydropyridin-4-yl]-[1,2,4]triazolo[1,5-a]pyridin-2-yl]amino)-1H-pyrazol-1-yl]acetamide (Example 1-297 in Table I)

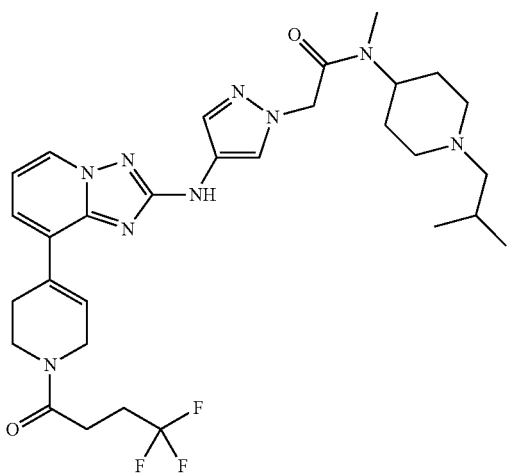

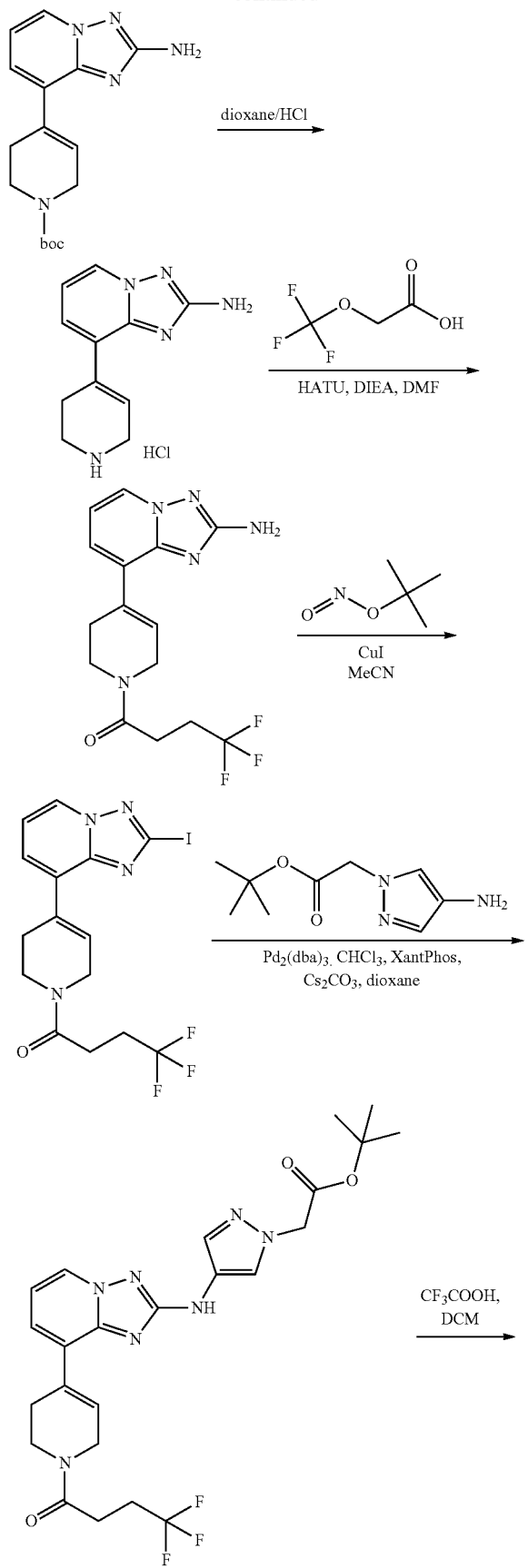

Step 1. A mixture of tert-butyl 4-[2-amino-[1,2,4]triazolo[1,5-a]pyridin-8-yl]-1,2,3,6-tetrahydropyridine-1-carboxylate (13 g, 41.22 mmol) in a saturated solution of HCl in 1,4-dioxane (150 mL) was stirred at room temperature overnight. The precipitated solid was collected by filtration to afford 10 g of (crude) of the hydrochloride salt of 8-(1,2,3,6-tetrahydropyridin-4-yl)-[1,2,4]triazolo[1,5-a]pyridin-2-amine as a yellow solid. LCMS (Method 7) $R_T$=0.49 min, m/z=216.0 [M+H]$^+$.

-continued

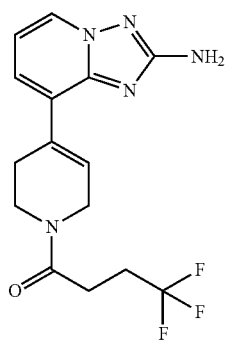

Step 2. A mixture of 8-(1,2,3,6-tetrahydropyridin-4-yl)-[1,2,4]triazolo[1,5-a]pyridin-2-amine hydrochloride (10 g, 39.73 mmol), DIPEA (14 g, 108.32 mmol), 4,4,4-trifluorobutanoic acid (6 g, 42.23 mmol) and HATU (16 g, 42.08 mmol) in N,N-dimethylformamide (100 mL) was stirred at room temperature overnight. The reaction mixture was evaporated; water (250 mL) and EtOAc (200 mL) were added. The phases were separated, and the aqueous phase was extracted with EtOAc (200 mL). The combined organic phase was washed with brine, dried over sodium sulfate and concentrated under vacuum. The residue was purified by flash chromatography on silica gel eluting with 65% EtOAc/petroleum ether. Appropriate fractions were combined and evaporated to afford 1-(4-[2-amino-[1,2,4]triazolo[1,5-a]pyridin-8-yl]-1,2,3,6-tetrahydropyridin-1-yl)-4,4,4-trifluorobutan-1-one (10 g, 74%) as a yellow solid. LCMS (Method 8) $R_T$=1.18 min, m/z=340.0 [M+H]$^+$.

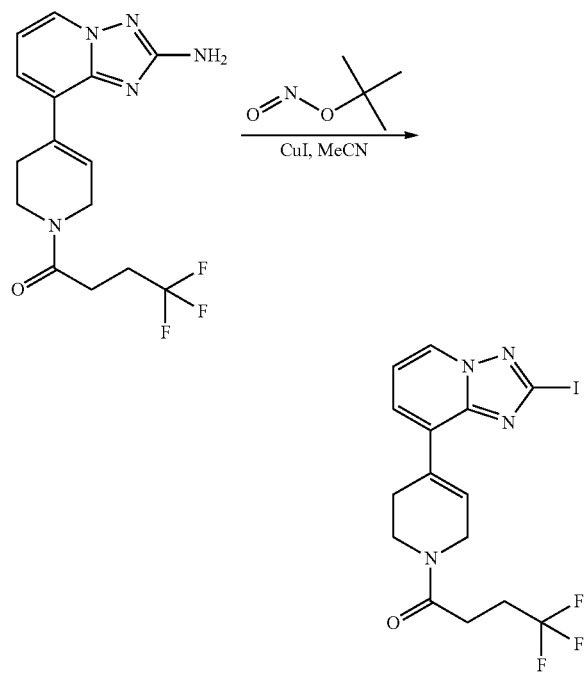

Step 3. tert-butyl nitrite (15.20 g, 147.4 mmol) was added to a solution of 1-(4-[2-amino-[1,2,4]triazolo[1,5-a]pyridin-8-yl]-1,2,3,6-tetrahydropyridin-1-yl)-4,4,4-trifluorobutan-1-one (10.0 g, 29.5 mmol) and CuI (11.23 g, 59.0 mmol) in MeCN (150 mL) under nitrogen. The mixture was stirred for 20 min at room temperature then heated at 55° C. for 30 min. The reaction mixture was allowed to cool to room temperature and the precipitated solid removed by filtration. The filtrate was concentrated under vacuum and the residue was dissolved in water (500 mL). The pH of the aqueous phase was adjusted to 7 by the addition of 2M aqueous sodium hydroxide solution then extracted with DCM (3×200 mL). The combined organic layer was washed with brine (500 mL), dried over anhydrous sodium sulfate and concentrated. The residue was purified by column chromatography eluting with DCM/EtOAc (3/1). Appropriate fractions were combined and evaporated to afford 4,4,4-trifluoro-1-(4-[2-iodo-[1,2,4]triazolo[1,5-a]pyridin-8-yl]-1,2,3,6-tetrahydropyridin-1-yl)butan-1-one (5.3 g, 40%) as a light yellow solid. LCMS (Method 7) $R_T$=1.48 min, m/z=450.9 [M+H]$^+$.

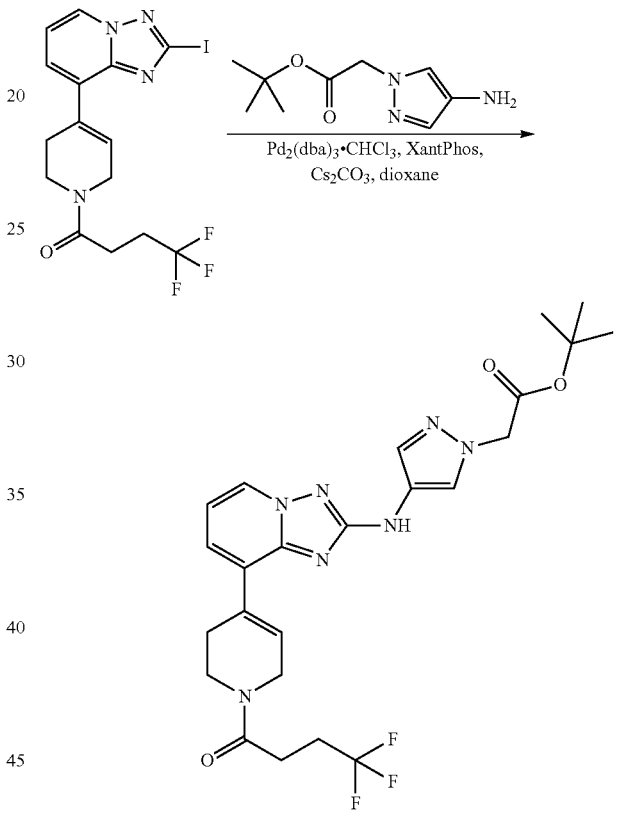

Step 4. A degassed mixture of tert-butyl-2-(4-amino-1H-pyrazol-1-yl)acetate (796 mg, 4.04 mmol), Cs$_2$CO$_3$ (2.63 g, 8.07 mmol), 4,4,4-trifluoro-1-(4-2-iodo-[1,2,4]triazolo[1,5-a]pyridin-8-yl-1,2,3 ,6-tetrahydropyridin-1-yl)butan-1 -one (2 g, 4.44 mmol), Pd$_2$(dba)$_3$.CHCl$_3$ (418 mg, 0.40 mmol) and XantPhos (468 mg, 0.81 mmol) in 1,4-dioxane (100 mL) was heated at 100° C. overnight. The reaction mixture was allowed to cool to room temperature and the precipitated solid was removed by filtration. The filtrate was concentrated under vacuum and the residue purified by flash chromatography on silica gel eluting with 70% EtOAc/petroleum ether to afford 1.2 g (57%) of tert-butyl 2-[4-([8-[1-(4,4,4-trifluorobutanoyl)-1,2,3,6-tetrahydropyridin-4-yl]-[1,2,4]-triazolo[1,5-a]pyridin-2-yl]amino)-1H-pyrazol-1-yl]acetate as a yellow solid. LCMS (Method 7) $R_T$=1.46 min, m/z=520.0 [M+H]$^+$.

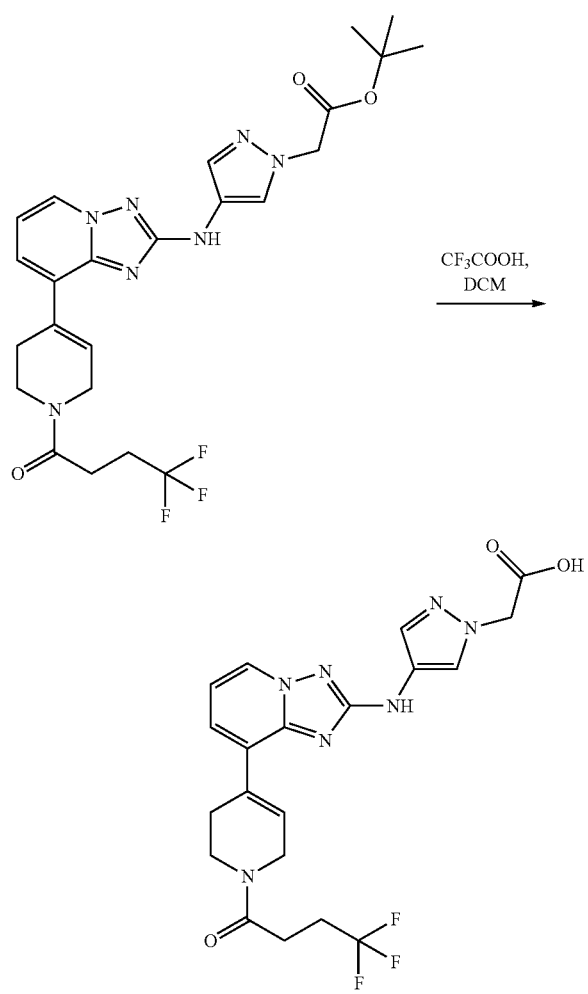

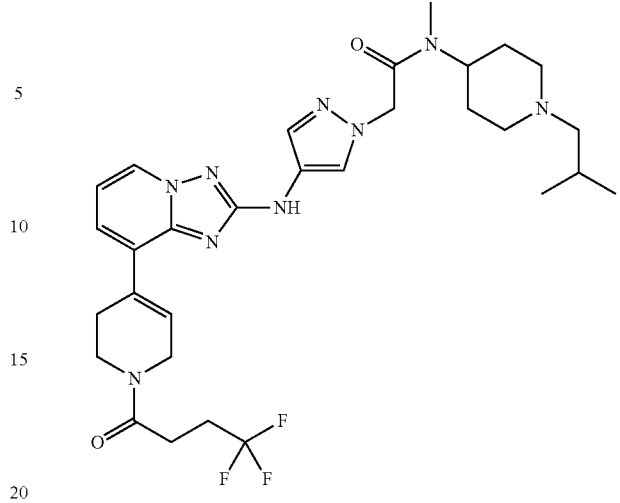

Step 5. A mixture of tert-butyl-2-[4-([8-[1-(4,4,4-trifluorobutanoyl)-1,2,3,6-tetrahydropyridin-4-yl]-[1,2,4]triazolo[1,5-a]pyridin-2-yl]amino)-1H-pyrazol-1-yl]acetate (1.2 g, 2.31 mmol) in DCM (15 mL) and TFA (20 mL) was stirred at room temperature overnight. The resulting mixture was concentrated under vacuum to afford 2-[4-([8-[1-(4,4,4-trifluorobutanoyl)-1,2,3,6-tetrahydropyridin-4-yl]-[1,2,4]triazolo[1,5-a]pyridin-2-yl]amino)-1H-pyrazol-1-yl]acetic acid (900 mg, 84%) as a yellow solid.

Step 6. A mixture of 2-[4-([8-[1-(4,4,4-trifluorobutanoyl)-1,2,3,6-tetrahydropyridin-4-yl]-[1,2,4]triazolo[1,5-a]pyridin-2-yl]amino)-1H-pyrazol-1-yl]acetic acid hydrochloride (200 mg, 0.40 mmol), DIPEA (104 mg, 0.80 mmol), N-methyl-1-(2-methylpropyl)piperidin-4-amine (88 mg, 0.52 mmol) and HATU (198 mg, 0.52 mmol) in DMF (5 mL) was stirred at room temperature for 3 h. The mixture was concentrated under vacuum and the residue diluted with water (60 mL). The aqueous phase was extracted with DCM (3×50 mL) and the combined organic layer was washed with brine, dried over anhydrous sodium sulfate and concentrated under vacuum. The residue was purified by flash chromatography on silica eluting with DCM/MeOH (20/1). The crude product was purified by Prep-HPLC using the following conditions: Column, XBridge Prep C18 OBD Column, 5 um, 19*150 mm,; mobile phase, water with 10 mmol NH$_3$.H$_2$O and MeCN (40% MeCN up to 55% over 10 min, up to 95% over 1 min, hold 95.0% for 1 min, down to 40% over 2 min); Detection, UV 254/220 nm to afford 94.3 mg (38%) of N-methyl-N-[1-(2-methylpropyl)piperidin-4-yl]-2-[4-([8-[1-(4,4,4-trifluorobutanoyl)-1,2,3,6-tetrahydropyridin-4-yl]-[1,2,4]triazolo[1,5-a]pyridin-2-yl]amino)-1H-pyrazol-1-yl]acetamide as a yellow solid. $^1$H NMR (400 MHz, DMSO-d$_6$): δ 9.31 (s, 1H), 8.59-8.58 (m, 1H), 7.80-7.77 (m, 1H), 7.48-7.37 (m, 3H), 6.99-6.95 (m, 1H), 5.11-5.04 (m, 2H), 4.33-4.24 (m, 3H), 3.76-3.62 (m, 2H), 2.86-2.52 (m, 11H), 2.01-1.43 (m, 9H), 0.89-0.77 (m, 6H); LCMS (Method 7) R$_T$=1.10 min, m/z=616.3 [M+H]$^+$.

Example 1z

Methyl 3-(4-[2-[4-([8-[4-(4-chlorophenyl)-4-(hydroxymethyl)piperidin-1-yl]-[1,2,4]triazolo[1,5-a]pyridin-2-yl]amino)-1H-pyrazol-1-yl]acetyl]piperazin-1-yl)propanoate (Example 1-290 in Table I)

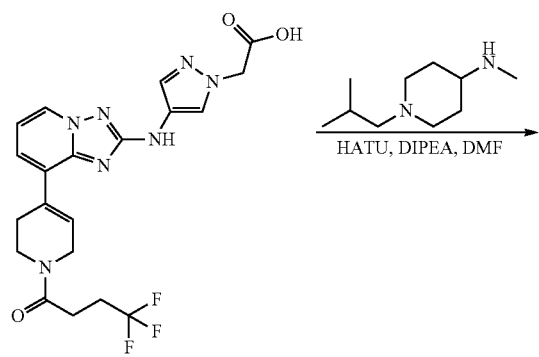

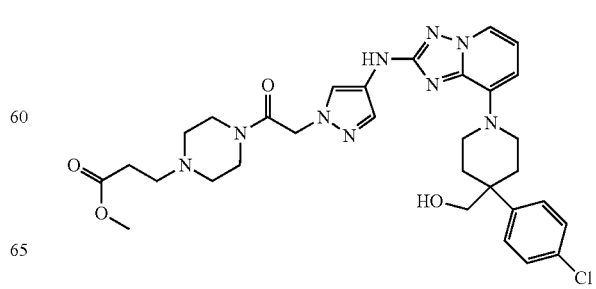

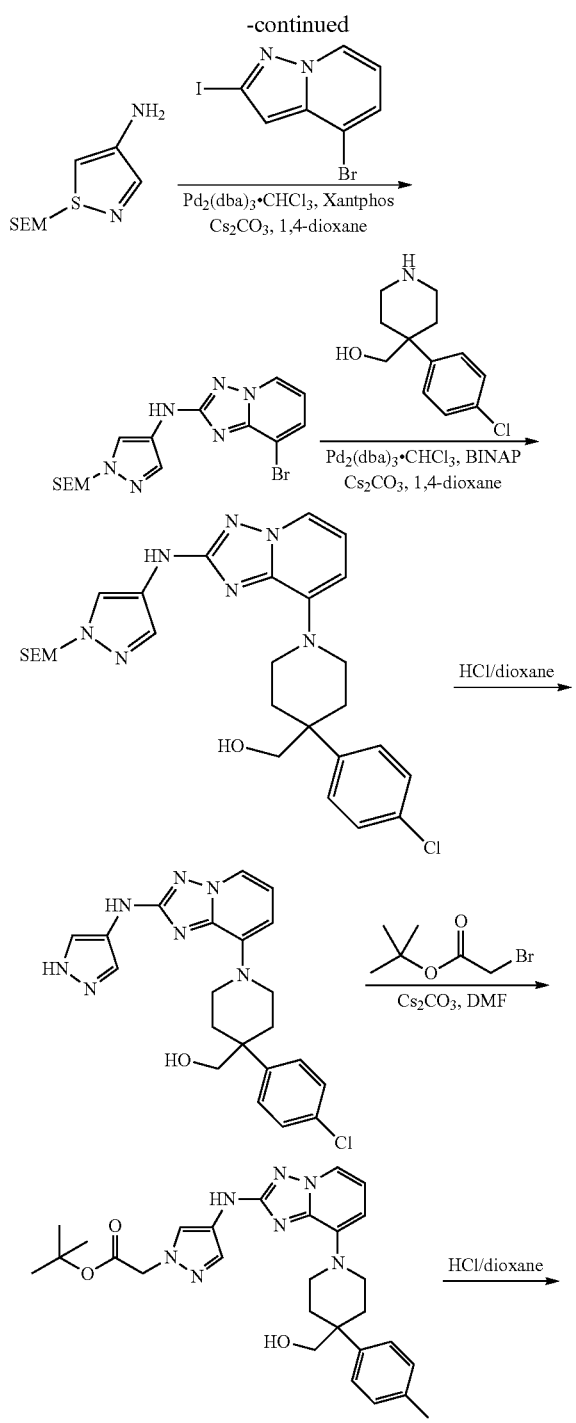

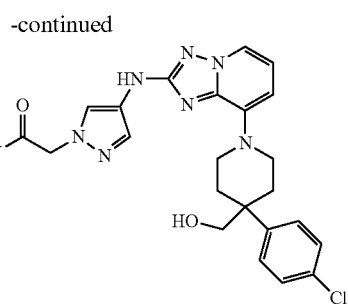

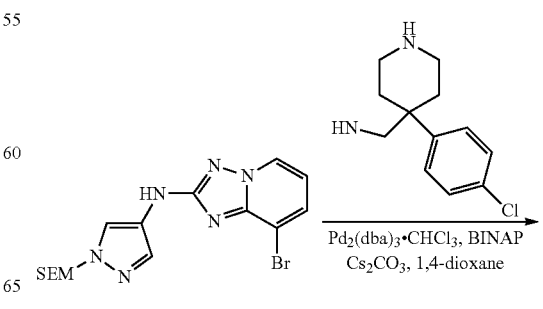

Step 1. A microwave vial was charged with 1-[[2-(trimethylsilyl)ethoxy]methyl]-1H-pyrazol-4-amine (630 mg, 2.95 mmol), 8-bromo-2-iodo-[1,2,4]triazolo[1,5-a]pyridine (960 mg, 2.96 mmol), Pd$_2$(dba)$_3$ (150 mg, 0.16 mmol), XantPhos (170 mg, 0.29 mmol), Cs$_2$CO$_3$ (1.9 g, 5.83 mmol) and 1,4-dioxane (15 mL). The vessel was evacuated and refilled with nitrogen 3 times. The reaction mixture was heated at 60° C. for 20 h then allowed to cool to room temperature. The resulting mixture was concentrated under vacuum and the residue was purified by flash chromatography on silica gel eluting with EtOAc/petroleum ether (1/1) to afford 800 mg (66%) of N-[-8-bromo-[1,2,4]triazolo[1,5-a]pyridin-2-yl]-1-[[2-(trimethylsilyl)ethoxy]methyl]-1H-pyrazol-4-amine as a red solid. TLC: R$_f$=0.5; EtOAc/petroleum ether=1/1.

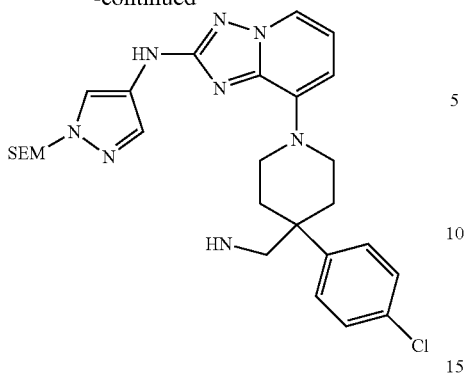

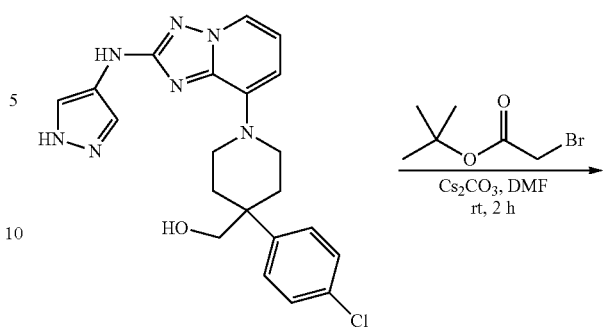

Step 2. N-[8-bromo-[1,2,4]triazolo[1,5-a]pyridin-2-yl]-1-[[2-(trimethylsilyl)-ethoxy]methyl]-1H-pyrazol-4-amine (400 mg, 0.98 mmol) and [4-(4-chlorophenyl)piperidin-4-yl]methanol (270 mg, 1.20 mmol) were coupled following the procedure detailed in Example 1j, step 3. The reaction mixture was concentrated under vacuum and the residue was purified by flash chromatography on silica gel eluting with EtOAc/petroleum ether (1:1) to give 350 mg (65%) of [4-(4-chlorophenyl)-1-[2-[(1-[[2-(trimethylsilyl)ethoxy]methyl]-1H-pyrazol-4-yl)amino]-[1,2,4]triazolo[1,5-a]pyridin-8-yl]piperidin-4-yl]methanol as a yellow solid. LCMS (Method 12) $R_T$=1.12 min, m/z=554.2 [M+H]$^+$.

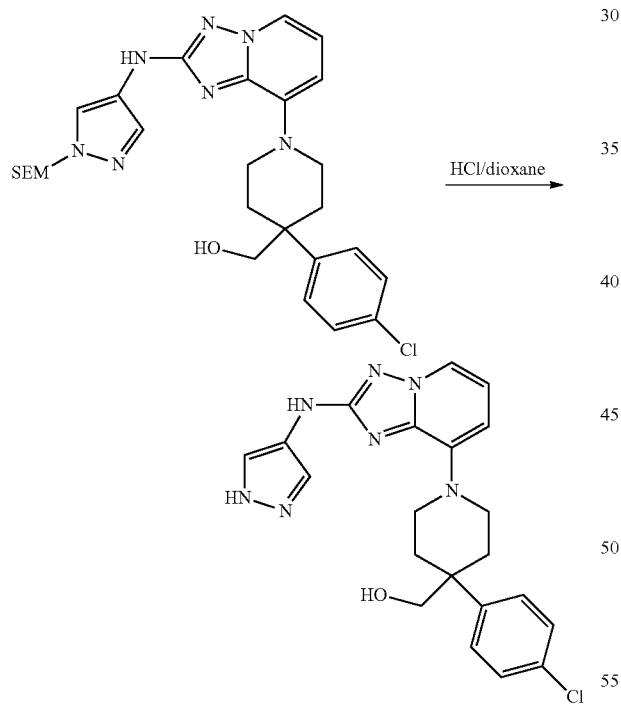

Step 3. A mixture of [4-(4-chlorophenyl)-1-[2-[(1-[[2-(trimethylsilyl)ethoxy]methyl]-1H-pyrazol-4-yl)amino]-[1,2,4]triazolo[1,5-a]pyridin-8-yl]piperidin-4-yl]methanol (650 mg, 1.17 mmol) in a saturated solution of HCl in 1,4-dioxane (20 mL) was stirred at room temperature for 20 h. The mixture was concentrated under vacuum to afford 500 mg of [4-(4-chlorophenyl)-1-[2-[(1H-pyrazol-4-yl)amino]-[1,2,4]triazolo[1,5-a]pyridine-8-yl]piperidin-4-yl]methanol as a light yellow solid. LCMS (Method 12) $R_T$=0.61 min, m/z=424.0 [M+H]$^+$.

Step 4. A mixture of [4-(4-chlorophenyl)-1-[2-[(1H-pyrazol-4-yl)amino]-[1,2,4]triazolo[1,5-a]pyridin-8-yl]piperidin-4-yl]methanol (400 mg, 0.94 mmol), Cs$_2$CO$_3$ (1.00 g, 3.07 mmol) and tert-butyl-2-bromoacetate (190 mg, 0.97 mmol) in N,N-dimethylformamide (20 mL) was stirred at room temperature for 2 h. The reaction mixture was diluted with EtOAc (100 mL) and washed with H$_2$O (3×30 mL). The organic phase was concentrated under vacuum and the residue was purified by flash chromatography on silica gel eluting with EtOAc to afford 500 mg (98%) of tert-butyl-2-[4-([8-[4-(4-chlorophenyl)-4-(hydroxymethyl)piperidin-1-yl]-[1,2,4]triazolo[1,5-a]pyridin-2-yl]amino)-1H-pyrazol-1-yl]acetate as yellow oil. LCMS (Method 12) $R_T$=0.98 min, m/z=538.3 [M+H]$^+$.

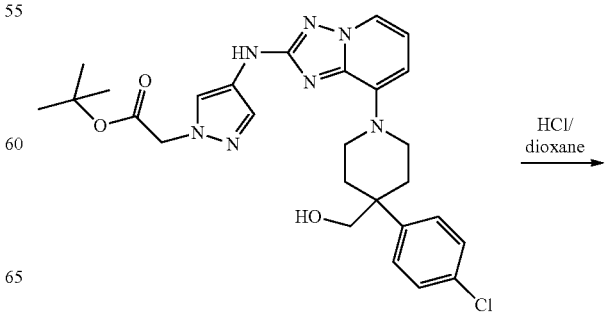

629
-continued

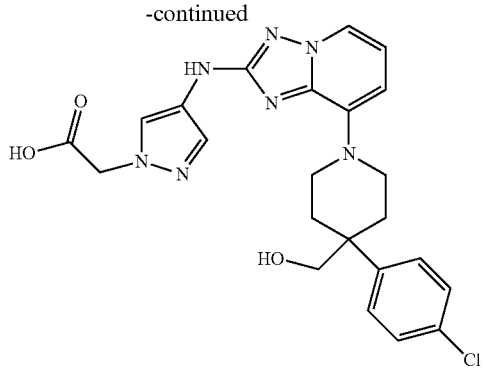

Step 5. A mixture of tert-butyl-2-[4-([8-[4-(4-chlorophenyl)-4-(hydroxymethyl)-piperidin-1-yl]-[1,2,4]triazolo[1,5-a]pyridin-2-yl]amino)-1H-pyrazol-1-yl]acetate (500 mg, 0.93 mmol) in a saturated solution of HCl in 1,4-dioxane (20 mL) was stirred at room temperature for 20 h then concentrated under vacuum to afford 400 mg of 2-[4-([8-[4-(4-chlorophenyl)-4-(hydroxymethyl)piperidin-1-yl]-[1,2,4]triazolo[1,5-a]pyridin-2-yl]amino)-1H-pyrazol-1-yl]acetic acid as a light yellow crude solid. LCMS (Method 12) $R_T$=0.44 min, m/z=482.0 [M+H]$^+$.

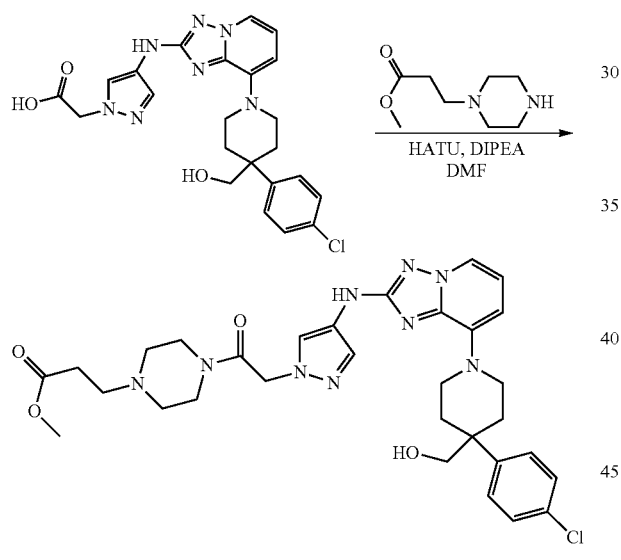

630

Step 6. A mixture of 2-[4-([8-[4-(4-chlorophenyl)-4-(hydroxymethyl)piperidin-1-yl]-[1,2,4]triazolo[1,5-a]pyridin-2-yl]amino)-1H-pyrazol-1-yl]acetic acid (100 mg, 0.207 mmol), HATU (95 mg, 0.250 mmol), DIPEA (108 mg, 0.836 mmol) and methyl 3-(piperazin-1-yl)propanoate (72 mg, 0.418 mmol) in N,N-dimethylformamide (10 mL) was stirred at room temperature overnight then concentrated under vacuum. The residue was purified using a short pad of silica gel eluting with DCM on a gradient of MeOH (1/10 to 1/4). Appropriate fractions were combined and evaporated and the crude product was purified by Prep-HPLC using the following conditions: Column,)(Bridge Shield RP18 OBD Column, 19*150 mm 5 um 13 nm; mobile phase, Water with 10 mmol HCOOH and MeCN (10% MeCN up to 55% over 11 min); Detection, UV 254 nm to afford 10.8 mg (8%) of methyl 3-(4-[2-[4-([8-[4-(4-chlorophenyl)-4-(hydroxymethyl)piperidin-1-yl]-[1,2,4]triazolo[1,5-a]pyridin-2-yl]amino)-1H-pyrazol-1-yl]acetyl]piperazin-1-yl)propanoate; formic acid salt as an off-white solid. $^1$H NMR (400 MHz, DMSO-d$_6$): δ 9.21 (s, 1H), 8.26 (s, 1H), 8.17 (d, J=6.4 Hz, 1H), 7.72 (s, 1H), 7.47-7.37 (m, 5H), 6.77 (t, J=7.2 Hz, 1H), 6.69 (d, J=8.0 Hz, 1H), 5.06 (s, 2H), 4.69 (s, 1H), 3.86-3.78 (m, 2H), 3.59 (s, 3H), 3.50-3.35 (m, 8H), 3.05-2.91 (m, 2H), 2.61-2.57 (m, 2H), 2.44-2.32 (m, 4H), 2.25-2.14 (m, 2H), 2.09-1.97 (m, 2H); LCMS (Method 6) $R_T$=2.59 min, m/z=636.4 [M+H]$^+$.

Example 1aa 4-([8-[(3aR,5R,6aS)-5-hydroxy-5-phenyl-octahydrocyclopenta[c]pyrrol-2-yl]-[1,2,4]-triazolo[1,5-a]pyridin-2-yl]amino)-N-methyl-N-(1-methylpiperidin-4-yl)benzamide (Example 1-292 in Table I)

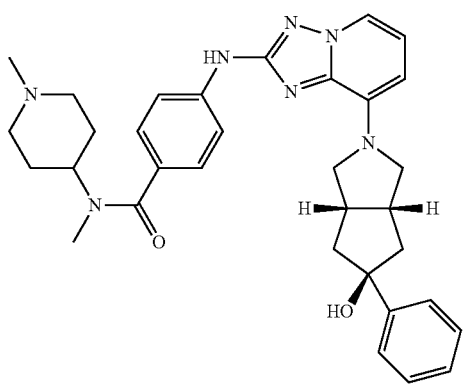

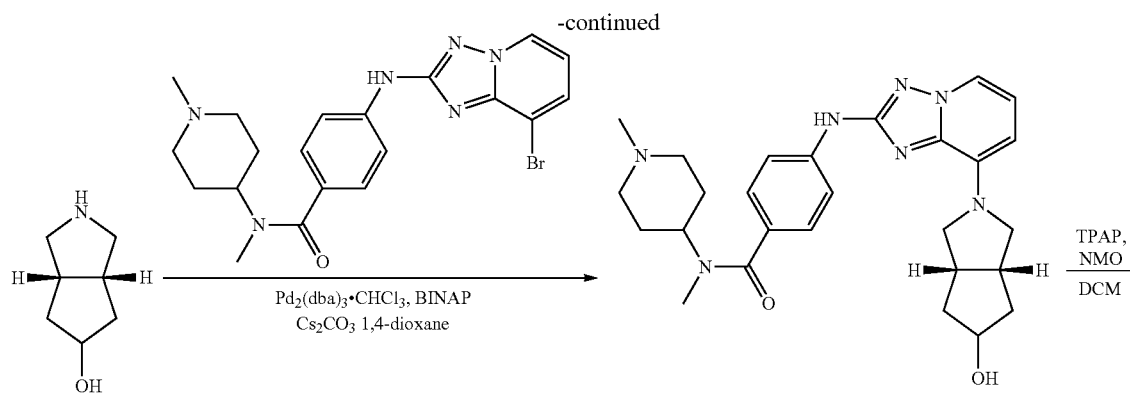

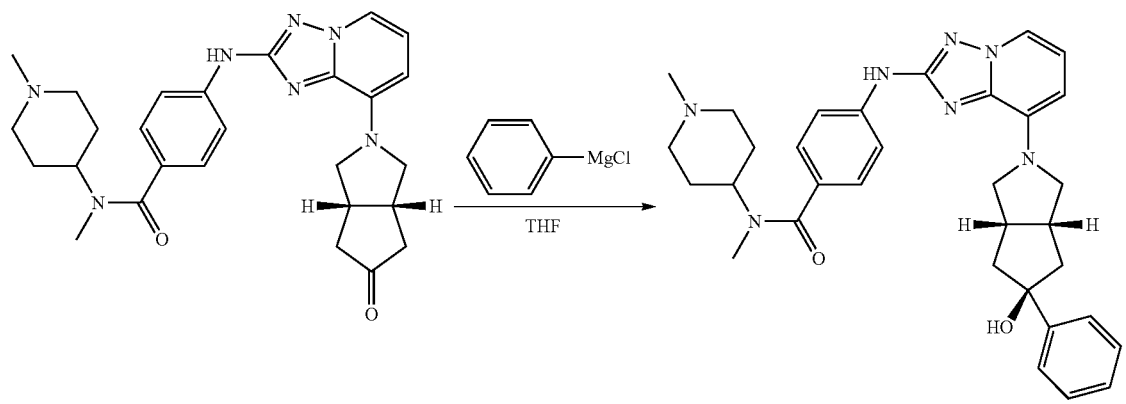

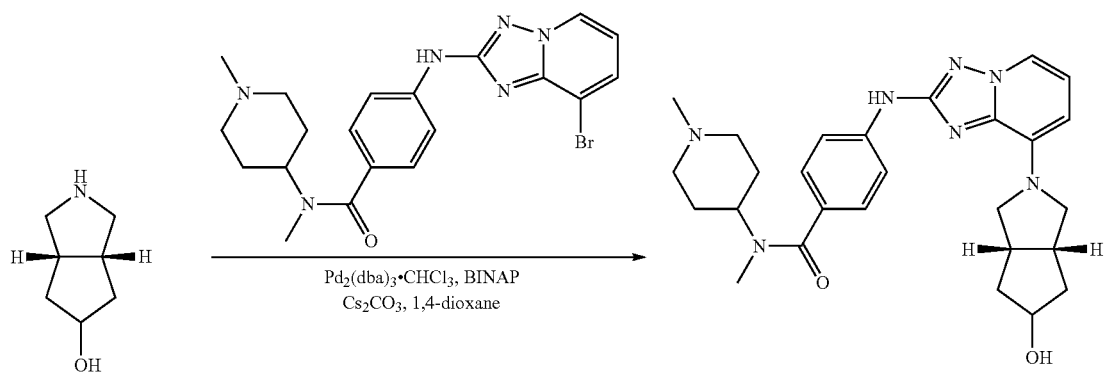

Step 1. 4-([8-bromo-[1,2,4]triazolo[1,5-a]pyridin-2-yl]amino)-N-methyl-N-(1-methylpiperidin-4-yl)benzamide (200 mg, 0.45 mmol) and octahydrocyclopenta[c]pyrrol-5-ol (86 mg, 0.68 mmol) were coupled following the procedure detailed in Example 1j, step 3. The reaction mixture was concentrated and the residue was purified by flash chromatography on silica eluting with DCM on a gradient of MeOH (1/10 to 1/5). Appropriate fractions were combined and concentrated under vacuum to afford 300 mg of 4-[(8-[5-hydroxy-octahydrocyclopenta[c]pyrrol-2-yl]-[1,2,4]triazolo[1,5-a]pyridin-2-yl)amino]-N-methyl-N-(1-methylpiperidin-4-yl)benzamide as a light yellow solid. LCMS (Method 8) $R_T$=1.04 min, m/z=490.1 [M+H]$^+$.

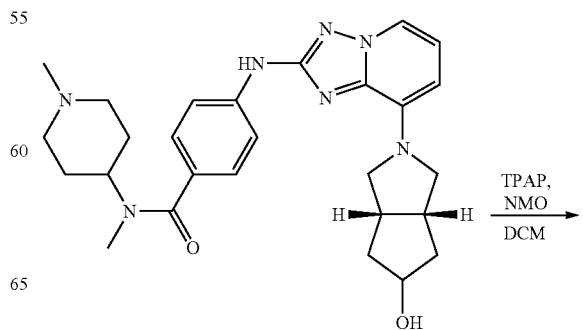

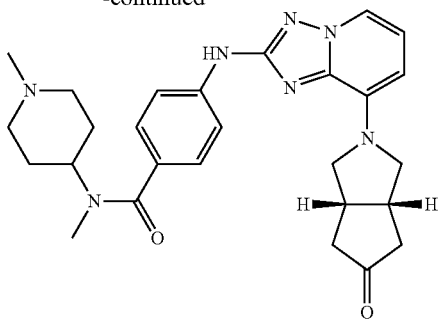

Step 2. A mixture of 4-[(8-[5-hydroxy-octahydrocyclopenta[c]pyrrol-2-yl]-[1,2,4]triazolo[1,5-a]pyridin-2-yl)amino]-N-methyl-N-(1-methylpiperidin-4-yl)benzamide (280 mg, 0.57 mmol), 4-methylmorpholin-4-ium-4-olate (340 mg, 2.90 mmol) and rutheniumoylolate; tetrapropylazanium (200 mg, 0.57 mmol) in DCM (20 mL) was stirred at room temperature for 0.5 h. The resulting mixture was concentrated under vacuum and the residue purified by flash chromatography on silica gel eluting with DCM on a gradient of MeOH (1/10 to 1/3) to afford 130 mg (47%) of N-methyl-N-(1-methylpiperidin-4-yl)-4-[(8-[5-oxo-octahydrocyclopenta[c]pyrrol-2-yl]-[1,2,4]triazolo-[1,5-a]pyridin-2-yl)amino]benzamide as a light yellow solid. TLC: $R_f$=0.3; DCM/MeOH=5/1.

Step 3. Phenyl magnesium chloride (2 M solution in THF, 0.45 mL, 0.9 mmol) was added dropwise to a solution of N-methyl-N-(1-methylpiperidin-4-yl)-4-[(8-[5-oxo-octahydrocyclopenta[c]pyrrol-2-yl]-[1,2,4]triazolo[1,5-a]pyridin-2-yl)amino]benzamide (110 mg, 0.23 mmol) in THF (10 mL) under nitrogen at 0° C. On complete addition, the reaction mixture was stirred at 0° C. for 0.5 h, quenched by the addition of MeOH (2 mL) and concentrated under vacuum. The residue was purified using a short pad of silica gel eluting with DCM on a gradient of MeOH (1/10 to 1/2). Appropriate fractions were combined and concentrated under vacuum. The crude product was purified by Prep-HPLC using the following conditions: Column, XBridge Shield RP18 OBD Column, 19*150 mm 5 um 13 nm; mobile phase, Water with 10 mmol NH$_4$HCO$_3$ and MeCN (12% MeCN up to 56% over 13 min); Detection, UV 254 nm to afford 4.4 mg (3%) of 4-([8-[(3aR,5R,6aS)-5-hydroxy-5-phenyl-octahydrocyclopenta[c]pyrrol-2-yl]-[1,2,4]triazolo[1,5-a]pyridin-2-yl]amino)-N-methyl-N-(1-methylpiperidin-4-yl)benzamide as an off white solid. $^1$H NMR (400 MHz, DMSO-d$_6$): δ 9.76 (s, 1H), 8.20 (d, J=6.4 Hz, 1H), 7.72 (d, J=8.8 Hz, 2H), 7.50 (d, J=8.4 Hz, 2H), 7.34-7.30 (m, 4H), 7.22 (t, J=7.2 Hz, 1H), 6.89-6.86 (m, 1H), 6.54 (d, J=7.6 Hz, 1H), 5.09 (s, 1H), 3.89-3.84 (m, 2H), 3.73-3.69 (m, 2H), 3.01-2.89 (m, 2H), 2.88-2.72 (m, 5H), 2.35-2.24 (m, 3H), 2.15-2.08 (m, 3H), 2.00-1.94 (m, 2H), 1.89-1.66 (m, 4H), 1.62-1.54 (m, 2H); LCMS (Method 8) R$_T$=2.22 min, m/z=566.1 [M+H]$^+$.

Example 1ab 4-(4-chlorophenyl)-1-[2-([4-[methyl(1-methylpiperidin-4-yl)carbamoyl]phenyl]amino)-[1,2,4]-triazolo[1,5-a]pyridin-8-yl]piperidine-4-carboxylic acid (Example 1-269 in Table I)

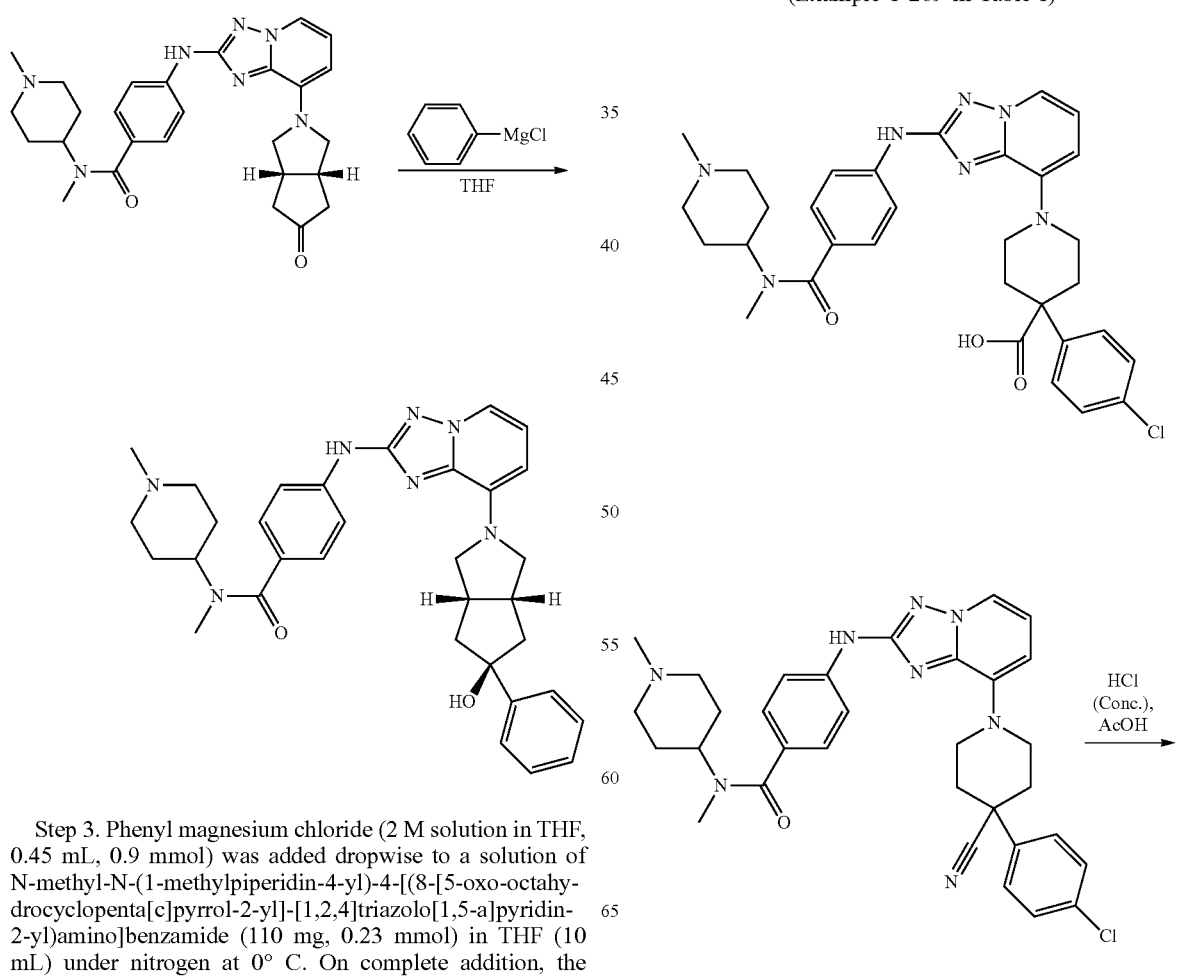

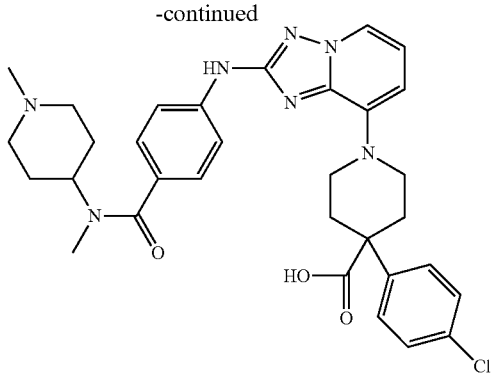

A mixture of 4-([8-[4-(4-chlorophenyl)-4-cyanopiperidin-1-yl]-[1,2,4]triazolo[1,5-a]pyridin-2-yl]amino)-N-methyl-N-(1-methylpiperidin-4-yl)benzamide (100 mg, 0.17 mmol) in 12 N aqueous HCl (4 mL) and acetic (1 mL) was heated at 100° C. for 8 h then allowed to cool to room temperature. The reaction mixture was evaporated; MeOH (10 mL) and DIPEA (1 mL) were added. The resulting mixture was concentrated under vacuum and the residue was purified by Prep-HPLC using the following conditions: Column, XBridge Shield RP18 OBD Column, 19*150 mm 5 um 13 nm; mobile phase, Water with 10 mmol HCOOH and MeCN (10% MeCN up to 55% over 11 min); Detection, UV 254 nm to afford 4-(4-chlorophenyl)-1-[2-([4-[methyl(1-methylpiperidin-4-yl)carbamoyl]phenyl]amino)-[1,2,4]triazolo[1,5-a]pyridin-8-yl]piperidine-4-carboxylic acid; formic acid salt as an off white solid (11.9 mg, 10%). $^1$H NMR (400 MHz, DMSO-$d_6$): δ 9.90 (s, 1H), 8.33 (t, J=3.6 Hz, 1H), 8.20 (s, 1H), 7.73 (d, J=8.8 Hz, 2H), 7.50 (d, J=8.8 Hz, 2H), 7.44 (d, J=8.4 Hz, 2H), 7.33 (d, J=8.4 Hz, 2H), 6.92-6.86 (m, 2H), 4.08-4.04 (m, 2H), 3.04 (t, J=11.2 Hz, 2H), 2.82 (s, 3H), 2.81 (br, 2H), 2.60-2.51 (m, 3H), 2.13 (s, 3H), 2.00 (t, J=10.2 Hz, 2H), 1.91-1.70 (m, 4H), 1.60-1.57 (m, 2H); LCMS (Method 6) $R_T$=1.61 min, m/z=602.4 [M+H]$^+$.

Example 1ac

N-methyl-4-([8-[4-methyl-4-(N-methylbenzenesulfonamido)cyclohexyl]-[1,2,4]triazolo[1,5-a]pyridin-2-yl]amino)-N-(1-methylpiperidin-4-yl)benzamide
(Example 1-261 in Table I)

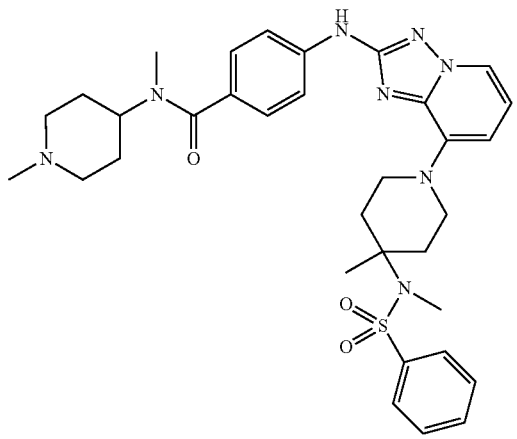

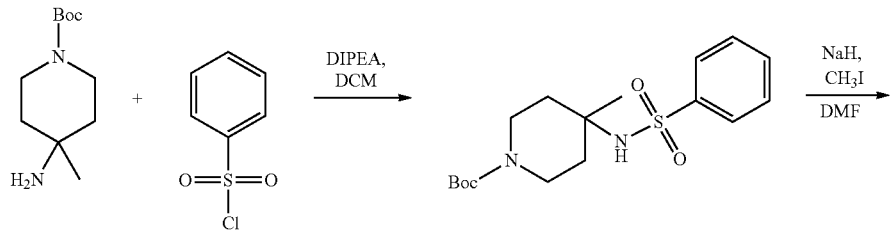

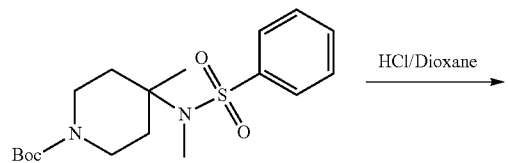

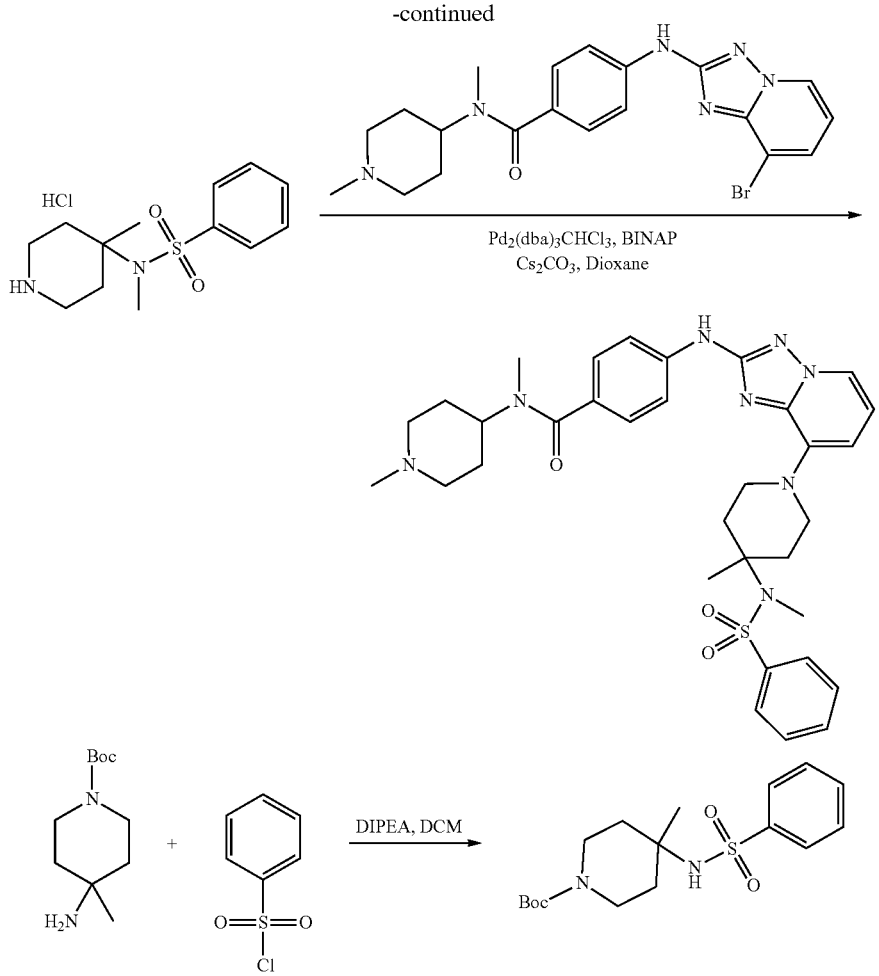

Step 1: Benzenesulfonyl chloride (329 mg, 1.86 mmol) was added dropwise to a solution of tert-butyl-4-amino-4-methylpiperidine-1-carboxylate (400 mg, 1.87 mmol) and DIPEA (1 mL, 6.05 mmol) in DCM (50 mL) at room temperature. The resulting solution was stirred for 2 h then concentrated under vacuum. The residue was purified by flash chromatography on silica gel eluting with EtOAc/petroleum ether (1:5) to afford 540 mg (82%) of tert-butyl-4-benzene-sulfonamido-4-methylpiperidine-1-carboxylate as a white solid. LCMS (Method 12) $R_T$=1.19 min, m/z=355.0 $[M+H]^+$.

before addition of iodomethane (560 mg, 3.95 mmol). The resulting solution was stirred for 2 h at room temperature and then quenched by the addition of $H_2O$ (50 mL). The resulting solution was extracted with EtOAc (100 mL) and the layers separated. The organic phase was dried over sodium sulfate and concentrated under vacuum to afford 350 mg (96%) of tert-butyl-4-methyl-4-(N-methylbenzenesulfonamido)piperidine-1-carboxylate as a white solid. LCMS (Method 7) $R_T$=1.57 min, m/z=369.0 $[M+H]^+$.

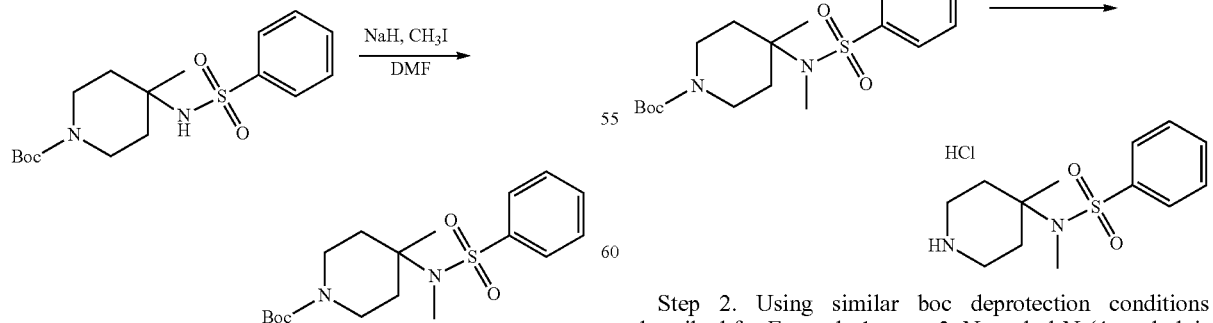

Step 1. A mixture of tert-butyl 4-benzenesulfonamido-4-methylpiperidine-1-carboxylate (350 mg, 0.99 mmol) and sodium hydride (80 mg, 3.33 mmol) in N,N-dimethylformamide (20 mL) was stirred at room temperature for 20 min Step 2. Using similar boc deprotection conditions described for Example 1r, step 2, N-methyl-N-(4-methylpiperidin-4-yl)benzenesulfonamide hydrochloride (230 mg, 79%) was prepared from tert-butyl-4-methyl-4-(N-methylbenzene-sulfonamido)piperidine-1-carboxylate (350 mg). LCMS (Method 9) $R_T$=1.05 min, m/z=269.0 $[M+H]^+$.

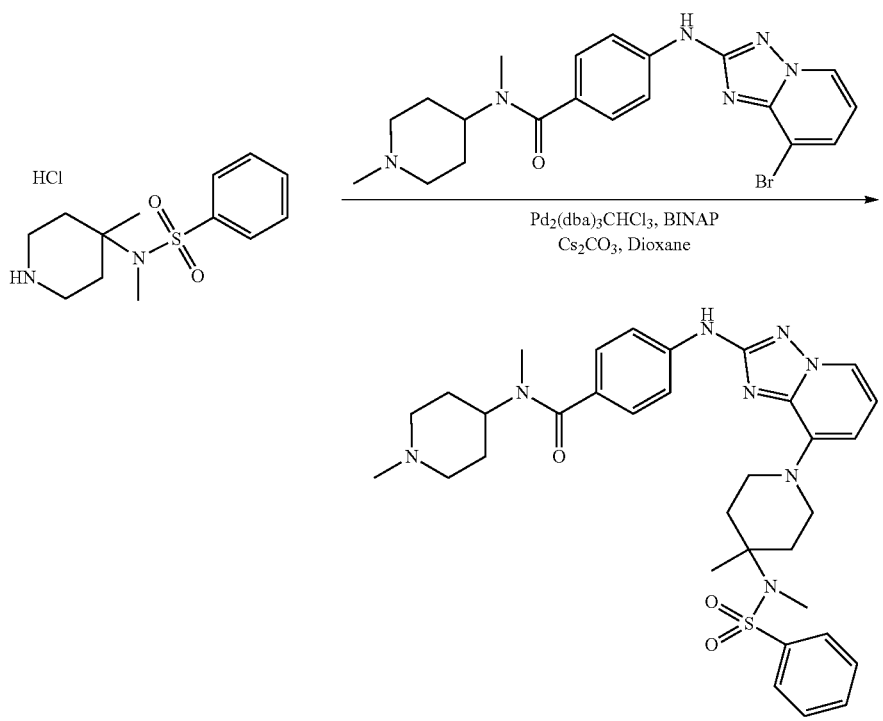

Step 3. 4-([8-bromo-[1,2,4]triazolo[1,5-a]pyridin-2-yl]amino)-N-methyl-N-(1-methylpiperidin-4-yl)benzamide (150 mg, 0.34 mmol) and N-methyl-N-(4-methylpiperidin-4-yl)benzenesulfonamide hydrochloride (150 mg, 0.49 mmol) were coupled following the procedure detailed in Example 1j, step 3. The reaction mixture was allowed to cool to room temperature and the precipitated solid was removed by filtration. The filtrate was concentrated under vacuum and the residue was purified by flash chromatography on silica gel eluting with DCM/MeOH (100/6) to afford 85 mg (40%) of N-methyl-4-([8-[4-methyl-4-(N-methylbenzenesulfonamido)-cyclohexyl]-[1,2,4]triazolo-[1,5-a]pyridin-2-yl]amino)-N-(1-methylpiperidin-4-yl)benzamide as a white solid. $^1$H NMR (300MHz, DMSO-$d_6$): δ 9.85 (s, 1H), 8.33 (d, J=6.0 Hz, 1H), 7.87 (dd, J=1.2, 7.8, Hz, 1H), 7.72-7.57 (m, 5H), 7.33(d, J=8.7 Hz, 2H), 6.89 (t, J=7.2 Hz, 1H), 6.77 (d, J=7.2 Hz, 1H), 3.57-3.54 (m, 2H), 3.40-3.28 (m, 3H), 2.88 (s, 3H), 2.82-2.71 (m,5H), 2.28-2.49 (m, 2H), 2.11 (s, 3H), 1.97-1.70 (m,6H), 1.62-1.51 (m, 2H), 1.23 (s, 3H); LCMS (Method 11) $R_T$=1.59 min, m/z=631.2 [M+H]$^+$.

Example 1ad

4-[[8-(4-acetamido-4-methylpiperidin-1-yl)-[1,2,4]-triazolo[1,5-a]pyridin-2-yl]amino]-N-methyl-N-(1-methylpiperidin-4-yl)benzamide (Example 1-260 in Table I)

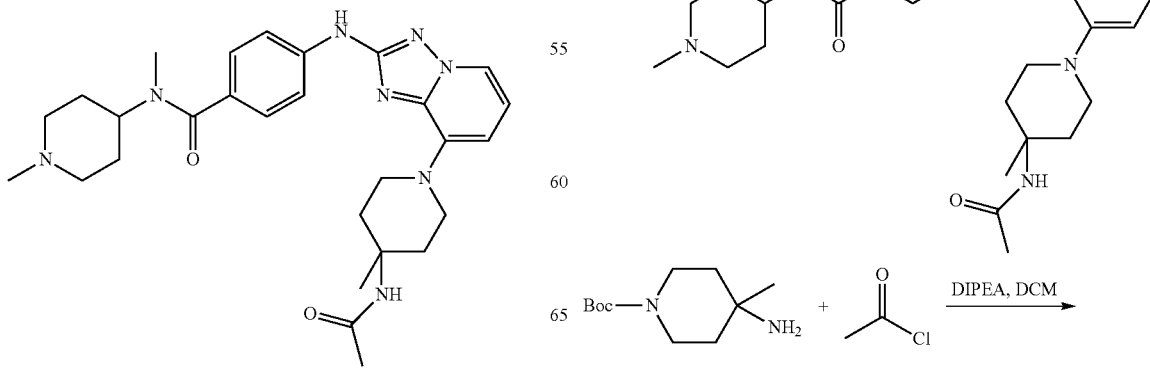

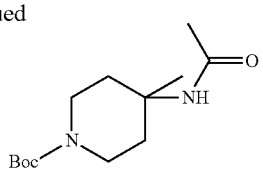

Step 1. Acetyl chloride (350 mg, 4.46 mmol) was added dropwise to a solution of tert-butyl 4-amino-4-methylpiperidine-1-carboxylate (600 mg, 2.80 mmol) and DIPEA (2 mL, 12.10 mmol) in DCM (50 mL). The reaction mixture was stirred at room temperature for 2 h then washed with H$_2$O (50 mL). The organic layer was dried over anhydrous sodium sulfate, filtered and concentrated under vacuum to afford 850 mg of tert-butyl-4-acetamido-4-methylpiperidine-1-carboxylate as brown oil. LCMS (Method 7) R$_T$=1.26 min, m/z=257.0 [M+H]$^+$.

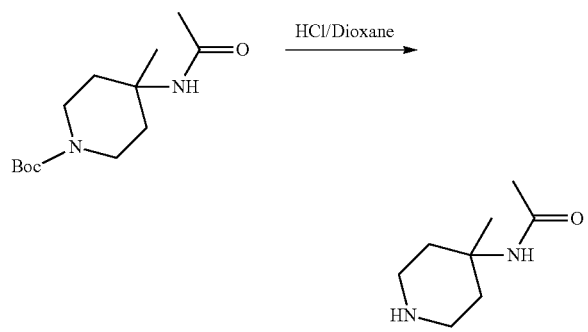

Step 2. Using the boc deprotection method described in Example 1r, step 2, N-(4-methylpiperidin-4-yl)acetamide as a brown oil (350 mg) was prepared from tert-butyl-4-acetamido-4-methylpiperidine-1-carboxylate (850 mg). LCMS (Method 6) R$_T$=0.69 min, m/z=157.0 [M+H]$^+$.

Step 3. 4-([8-bromo-[1,2,4]triazolo[1,5-a]pyridin-2-yl]amino)-N-methyl-N-(1-methylpiperidin-4-yl)benzamide (200 mg, 0.45 mmol) and N-(4-methylpiperidin-4-yl)acetamide (106 mg, 0.68 mmol) were coupled following the procedure detailed in Example 1j, step 3. The reaction mixture was allowed to cool to room temperature and the precipitated solid removed by filtration. The filtrate was concentrated under vacuum and the residue was purified by flash chromatography on silica gel eluting with DCM/MeOH (100/7) to afford 45 mg (19%) of 4-[[8-(4-acetamido-4-methylpiperidin-1-yl)-[1,2,4]triazolo[1,5-a]pyridin-2-yl]amino]-N-methyl-N-(1-methylpiperidin-4-yl)benzamide as a white solid. $^1$H NMR (400 MHz, DMSO-d$_6$): δ 9.85 (s, 1H), 8.32 (d, J=5.6 Hz, 1H), 7.73 (d, J=8.8 Hz, 2H), 7.73 (s, 1H), 6.89 (t, J=7.2 Hz, 1H), 6.83 (d, J=7.6 Hz, 1H), 3.78-3.75 (m, 2H), 3.33 (s, 1H), 3.12 (t, J=10.2 Hz, 2H), 2.82-2.75 (m, 5H), 2.26 (d, J=13.6 Hz, 2H), 2.11 (s, 3H), 1.83-1.72 (m,6H), 1.57-1.56 (m,4H), 1.34 (s, 3H); LCMS (Method 8) R$_T$=1.69 min, m/z=519.2 [M+H]$^+$.

The immediately preceding Examples may be modified via conventionally known chemistries to provide access to other compounds that fall within the scope of the present invention, such as compounds of Formula 0, non-limiting examples of which are seen in Table I.

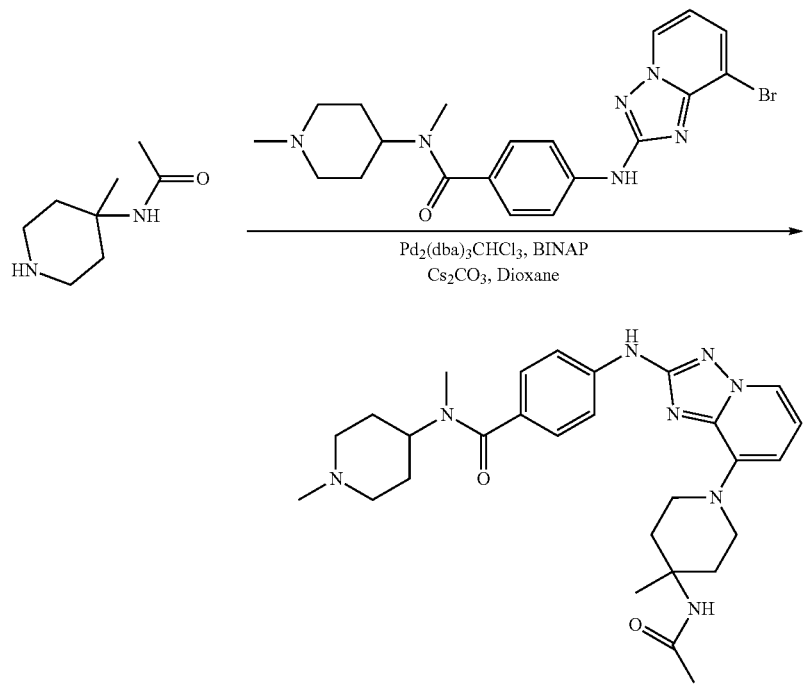

TABLE I

| Ex | R² | [second structure] | LCMS(ESI) m/z [M + H⁺] |
|---|---|---|---|
| 1-1 | 1-methyl-4-phenylpiperidin-4-yl (N-attached) | N-methyl-N-(1-methylpiperidin-4-yl)benzamide linker | 538 |
| 1-2 | 4-cyclohexyl-4-hydroxypiperidin-1-yl | " | 546 |
| 1-3 | 4-hydroxypiperidin-1-yl | " | 464 |
| 1-4 | 4-phenyl-1,2,3,6-tetrahydropyridin-1-yl | " | 522 |
| 1-5 | 4-methoxy-4-phenylpiperidin-1-yl | " | 554 |

TABLE I-continued
| Ex | R² | | LCMS(ESI) m/z [M + H⁺] |
|---|---|---|---|
| 1-6 | 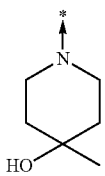 | " | 478 |
| 1-7 | 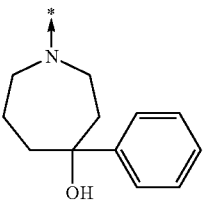 | " | 554 |
| 1-8 | 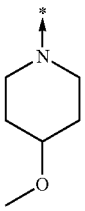 | " | 478 |
| 1-9 | 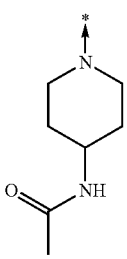 | " | 505 |
| 1-10 | 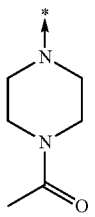 | " | 491 |

TABLE I-continued
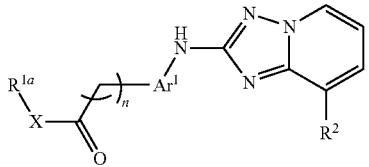
| Ex | R² | | LCMS(ESI) m/z [M + H⁺] |
|---|---|---|---|
| 1-11 | 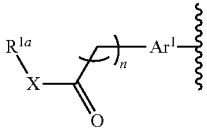 | " | 473 |
| 1-12 | 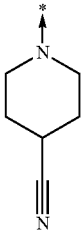 | " | 448 |
| 1-13 | 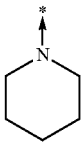 | " | 525 |
| 1-14 | 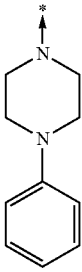 | " | 536 |
| 1-15 | 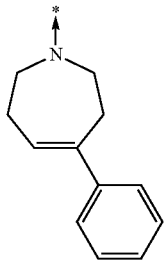 | " | 536 |

TABLE I-continued
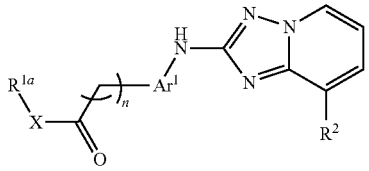
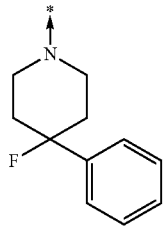
| Ex | R² | | LCMS(ESI) m/z [M + H⁺] |
|---|---|---|---|
| 1-16 | 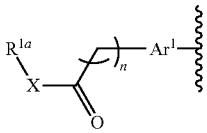 | " | 542 |
| 1-17 | 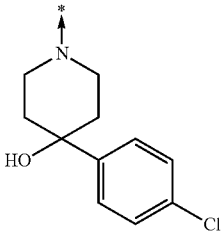 | " | 574 |
| 1-18 | 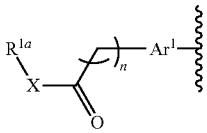 | " | 574 |
| 1-19 | 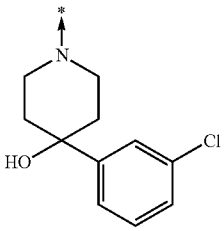 | " | 541 |
| 1-20 | 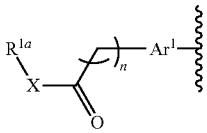 | " | 541 |

TABLE I-continued

| Ex | R² | | LCMS(ESI) m/z [M + H⁺] |
|---|---|---|---|
| 1-21 | 4-(4-cyanophenyl)-4-hydroxypiperidin-1-yl | " | 565 |
| 1-22 | 4-(3-cyanophenyl)-4-hydroxypiperidin-1-yl | " | 565 |
| 1-23 | 4-(cyanomethoxy)piperidin-1-yl | " | 503 |
| 1-24 | 2-oxo-1-oxa-3,8-diazaspiro[4.4]nonan-8-yl | " | 505 |
| 1-25 | (8aS)-hexahydropyrazino[2,1-c][1,4]oxazin-2-yl | " | 505 |

TABLE I-continued
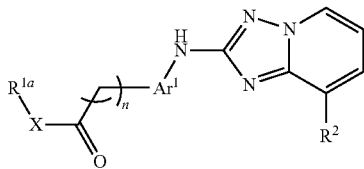
| Ex | R² | | LCMS(ESI) m/z [M + H⁺] |
|---|---|---|---|
| 1-26 | 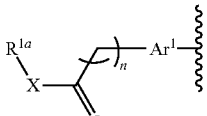 | " | 594 |
| 1-27 | 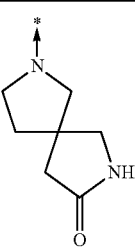 | " | 517 |
| 1-28 |  | " | 519 |
| 1-29 |  | " | 506 |
| 1-30 | 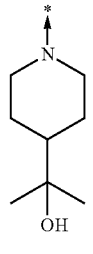 | " | 581 |

TABLE I-continued
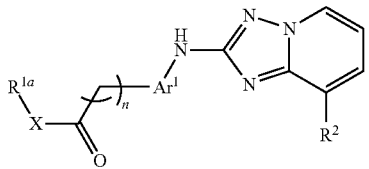
| Ex | R² | | LCMS(ESI) m/z [M + H⁺] |
|---|---|---|---|
| 1-31 | 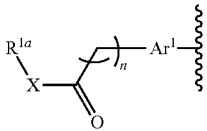 | " | 518 |
| 1-32 | 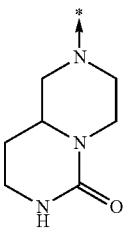 | " | 519 |
| 1-33 | 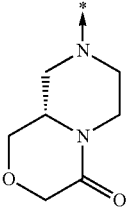 | " | 519 |
| 1-34 | 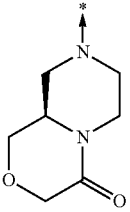 | " | 560 |
| 1-35 | 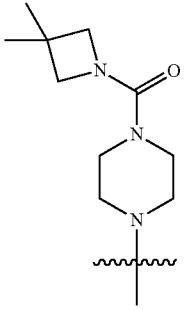 [SMILES: *N1CCN(C(=O)N2CC(C)(C)C2)CC1] | " | 574 |

TABLE I-continued
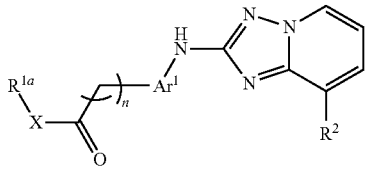
| Ex | R² | | LCMS(ESI) m/z [M + H⁺] |
|---|---|---|---|
| 1-36 | 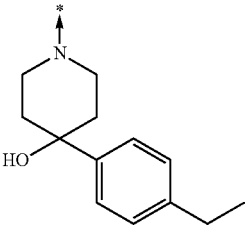 | " | 568 |
| 1-37 | 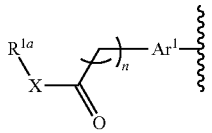 | " | 558 |
| 1-38 | 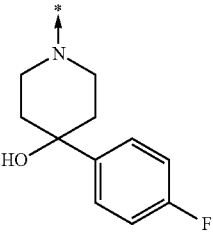 | " | 582 |
| 1-39 | 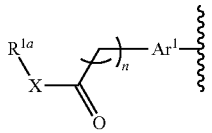 | " | 554 |
| 1-40 | 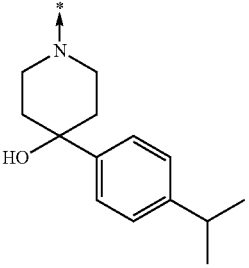 | " | 570 |

TABLE I-continued
| Ex | R² | | LCMS(ESI) m/z [M + H⁺] |
|---|---|---|---|
| 1-41 | 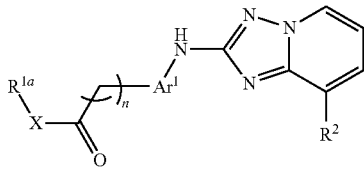 | " | 563 |
| 1-42 | 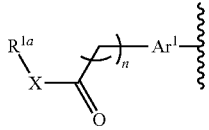 | " | 559 |
| 1-43 | 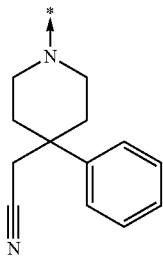 | " | 540 |
| 1-44 | 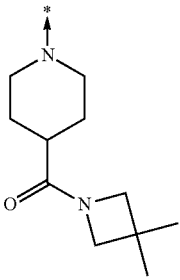 | " | 629 |
| 1-45 | 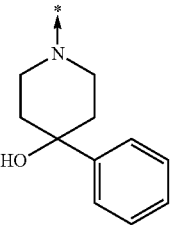 | " | 549 |

TABLE I-continued
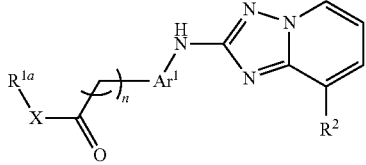

TABLE I-continued
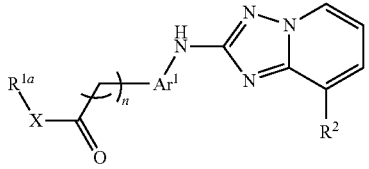
| Ex | R² | | LCMS(ESI) m/z [M + H⁺] |
|---|---|---|---|
| 1-52 | " | 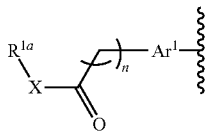 | 614 |
| 1-53 | " | 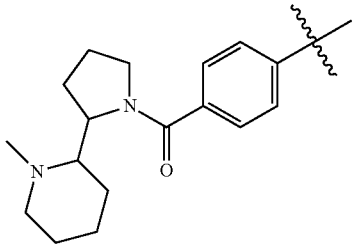 [SMILES: *c1ccc(C(=O)N2CCCC2C2CCCCN2C)cc1] | 586 |
| 1-54 | " | 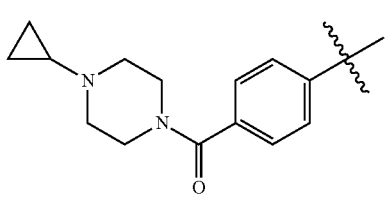 [SMILES: *c1ccc(C(=O)N2CCN(C3CC3)CC2)cc1] | 572 |
| 1-55 | " | 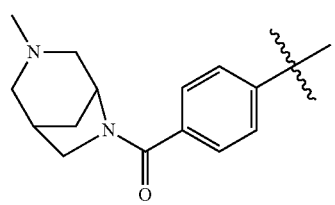 [SMILES: *c1ccc(C(=O)N2CC3CC2CN(C)C3)cc1] | 572 |
| 1-56 | " | 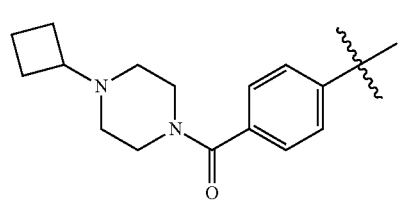 [SMILES: *c1ccc(C(=O)N2CCN(C3CCC3)CC2)cc1] | 586 |
| 1-57 | " | 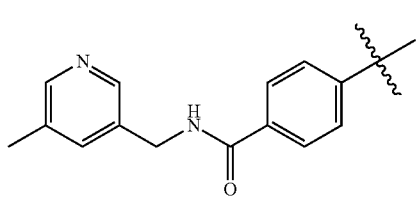 [SMILES: *c1ccc(C(=O)NCc2cncc(C)c2)cc1] | 568 |

TABLE I-continued
| Ex | R² | | LCMS(ESI) m/z [M + H⁺] |
|---|---|---|---|
| 1-58 | " | 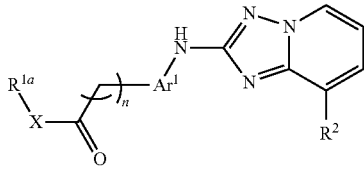 | 568 |
| 1-59 | " | 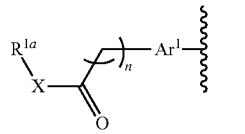 | 572 |
| 1-60 | " | 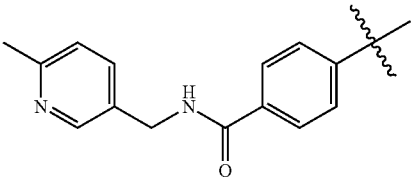 [SMILES: *c1ccc(C(=O)NCc2ccc(C)nc2)cc1] | 572 |
| 1-61 | " | 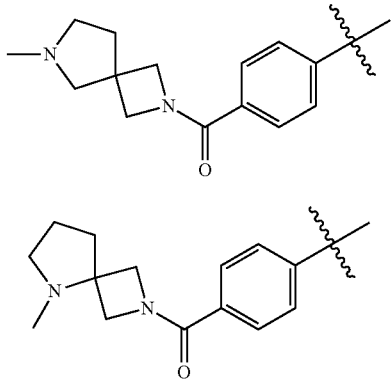 | 588 |
| 1-62 | " | 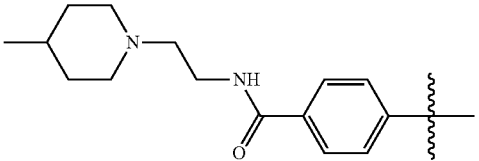 | 546 |
| 1-63 | " | 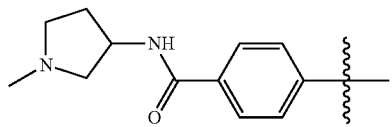 | 568 |
| 1-64 | " | 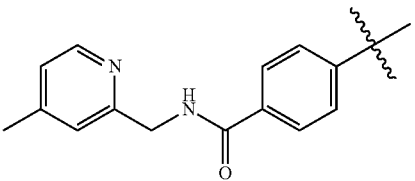 [SMILES: *c1ccc(C(=O)NCc2cc(C)ccn2)cc1] | 568 |

TABLE I-continued
| Ex | R² | | LCMS(ESI) m/z [M + H⁺] |
|---|---|---|---|
| 1-65 | " | 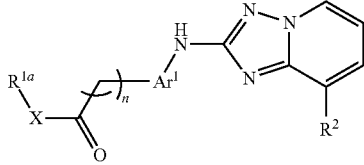 | 588 |
| 1-66 | " | 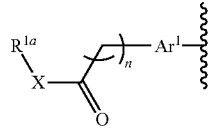 | 614 |
| 1-67 | " | 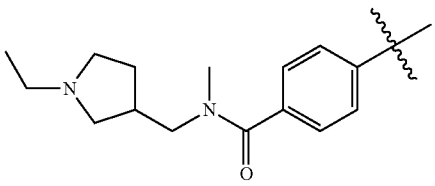 [SMILES: *c1ccc(C(=O)N(C)CC2CCN(CC)C2)cc1] | 626 |
| 1-68 | " | 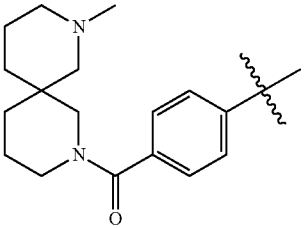 [SMILES: *c1ccc(C(=O)N2CCCC3(CCCN(C)C3)C2)cc1] | 594 |
| 1-69 | " | 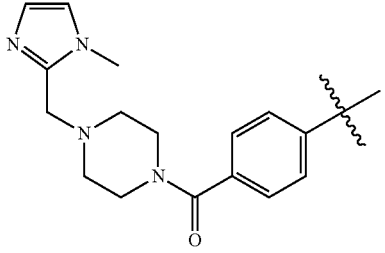 [SMILES: *c1ccc(C(=O)N2CCN(Cc3nccn3C)CC2)cc1] | 590 |

TABLE I-continued
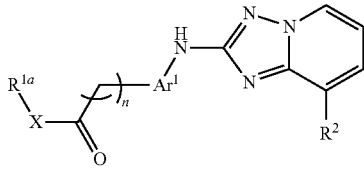
| Ex | R² | | LCMS(ESI) m/z [M + H⁺] |
|---|---|---|---|
| 1-70 | " | 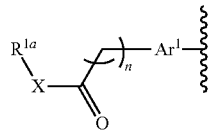 | 588 |
| 1-71 | " | 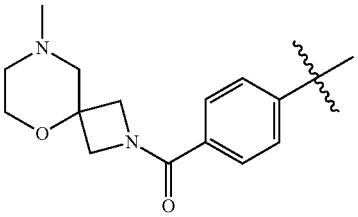 [SMILES: *c1ccc(C(=O)N2CC3(CN(C)CCO3)C2)cc1] | 617 |
| 1-72 | " | 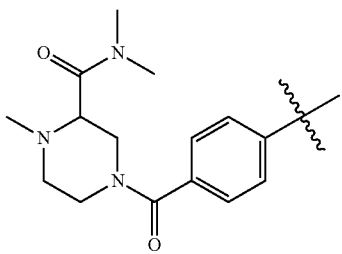 [SMILES: *c1ccc(C(=O)N2CCN(C)C(C(=O)N(C)C)C2)cc1] | 608 |
| 1-73 | " | 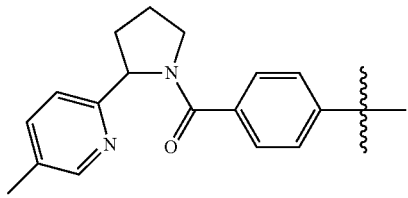 [SMILES: *c1ccc(C(=O)N2CCCC2c2ccc(C)cn2)cc1] | 666 |
| 1-74 | " | 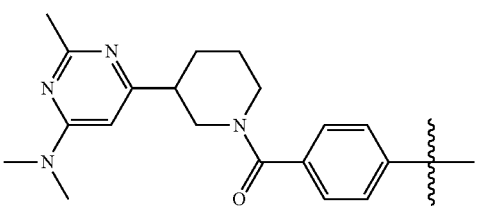 [SMILES: *c1ccc(C(=O)N2CCCC(c3cc(N(C)C)nc(C)n3)C2)cc1] | 665 |
| 1-75 | " | 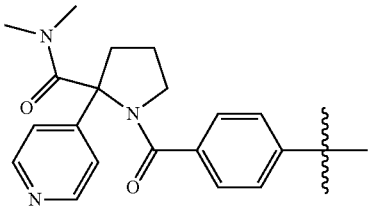 [SMILES: *c1ccc(C(=O)N2CCCC2(C(=O)N(C)C)c2ccncc2)cc1] | 572 |

TABLE I-continued

| Ex | R² | | LCMS(ESI) m/z [M + H⁺] |
|---|---|---|---|
| 1-76 | " | | 572 |
| 1-77 | " | | 618 |
| 1-78 | " | | 659 |
| 1-79 | " | | 651 |
| 1-80 | " | | 602 |

TABLE I-continued
| Ex | R² | | LCMS(ESI) m/z [M + H⁺] |
|---|---|---|---|
| 1-81 | " | 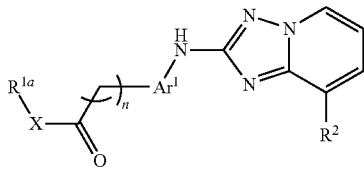 | 586 |
| 1-82 | " |  | 617 |
| 1-83 | " |  | 608 |
| 1-84 | " |  | 576 |
| 1-85 | " |  | 582 |
| 1-86 | " | 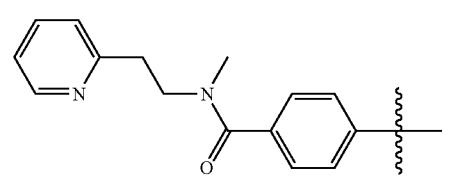 [SMILES: *c1ccc(C(=O)N(C)CCc2ccccn2)cc1] | 574 |

TABLE I-continued
| Ex | R² | | LCMS(ESI) m/z [M + H⁺] |
|---|---|---|---|
| 1-87 | " | 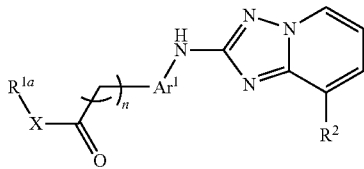 | 560 |
| 1-88 | " | 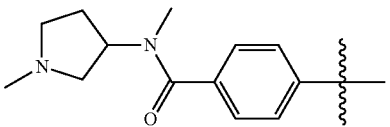 [SMILES: *c1ccc(C(=O)N(C)C2CCN(C)C2)cc1] | 560 |
| 1-89 | " | 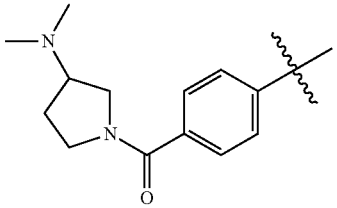 [SMILES: *c1ccc(C(=O)N2CCC(N(C)C)C2)cc1] | 572 |
| 1-90 | " | 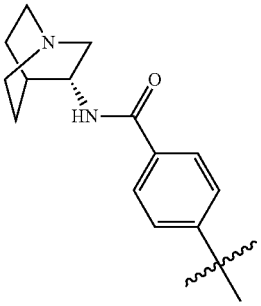 [SMILES: *c1ccc(C(=O)N[C@H]2CN3CCC2CC3)cc1] | 528 (M + H − H2O) |
| 1-91 | " | 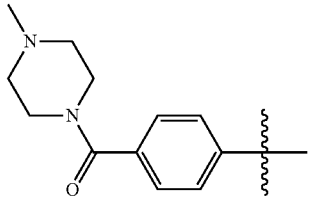 [SMILES: *c1ccc(C(=O)N2CCN(C)CC2)cc1] | 604 |
| 1-92 | " | 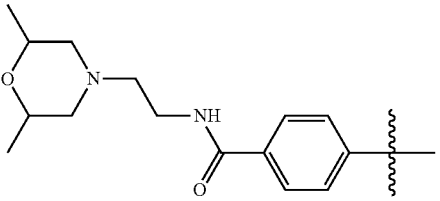 [SMILES: *c1ccc(C(=O)NCCN2CC(C)OC(C)C2)cc1] | 532 |

TABLE I-continued
| Ex | R² | | LCMS(ESI) m/z [M + H⁺] |
|---|---|---|---|
| 1-93 | " | 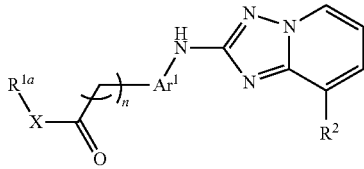 | 604 |
| 1-94 | " | 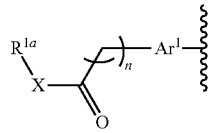 | 604 |
| 1-95 | " | 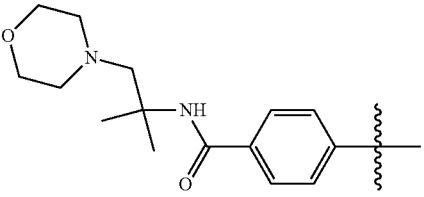 [SMILES: *c1ccc(C(=O)NC(C)(C)CN2CCOCC2)cc1] | 590 |
| 1-96 | " | 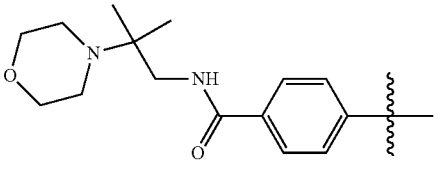 [SMILES: *c1ccc(C(=O)NCC(C)(C)N2CCOCC2)cc1] | 603 |
| 1-97 | " | 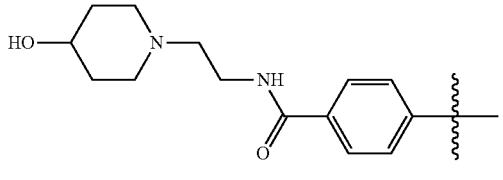 [SMILES: *c1ccc(C(=O)NCCN2CCC(O)CC2)cc1] | 589 |
| 1-98 | " | 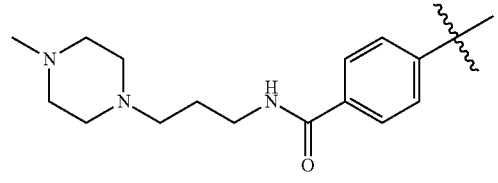 [SMILES: *c1ccc(C(=O)NCCCN2CCN(C)CC2)cc1] | 590 |
| 1-99 | " | 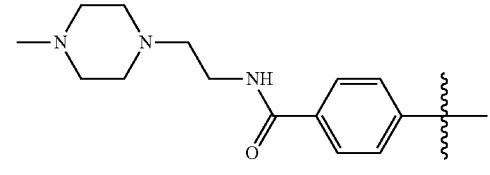 [SMILES: *c1ccc(C(=O)NCCN2CCN(C)CC2)cc1] | 588 |

TABLE I-continued
| Ex | R² | | LCMS(ESI) m/z [M + H⁺] |
|---|---|---|---|
| 1-100 | " | 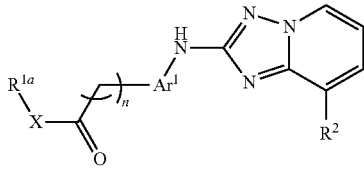 | 588 |
| 1-101 | " | 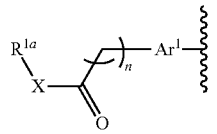 | 576 |
| 1-102 | " |  | 574 |
| 1-103 | " |  | 574 |
| 1-104 | " | 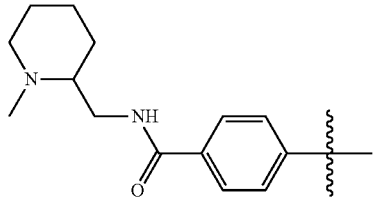 [SMILES: *c1ccc(C(=O)NCC2CCCCN2C)cc1] | 574 |
| 1-105 | " |  | 560 |
| 1-106 | " |  | 560 |

TABLE I-continued
| Ex | R² | | LCMS(ESI) m/z [M + H⁺] |
|---|---|---|---|
| 1-107 | " | 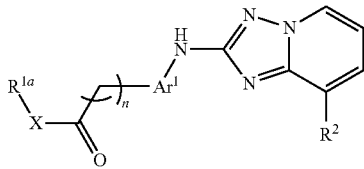 | 548 |
| 1-108 | " | 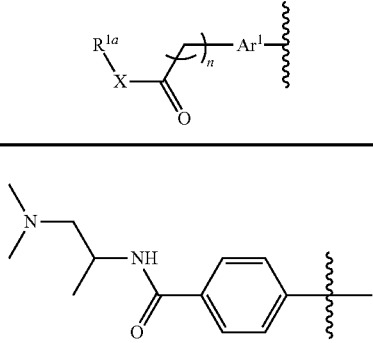 | 534 |
| 1-109 | " |  | 582 |
| 1-110 | " |  | 608 |
| 1-111 | " | 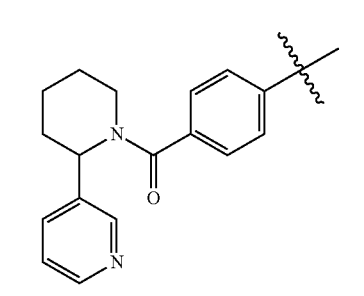 [SMILES: *c1ccc(C(=O)N2CCCCC2c2cccnc2)cc1] | 568 |
| 1-112 | " | 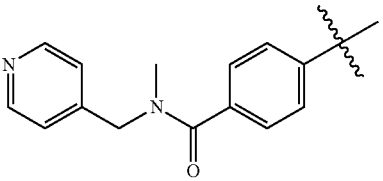 [SMILES: *c1ccc(C(=O)N(C)Cc2ccncc2)cc1] | 609 |

TABLE I-continued

| Ex | R² | | LCMS(ESI) m/z [M + H⁺] |
|---|---|---|---|
| 1-113 | " | (4-methylpiperazine-carbonyl-piperidine-carbonyl-phenyl) | 639 (M + H − H2O) |
| 1-114 | " | (4-(pyridin-4-yl)-1,4-diazepane-carbonyl-phenyl) | 623 |
| 1-115 | " | (N-ethyl-N-(pyridin-4-ylmethyl)benzamide) | 582 |
| 1-116 | " | (4-(2-(1H-imidazol-1-yl)ethyl)piperazine-carbonyl-phenyl) | 626 |
| 1-117 | " | (4-(4-methylpiperazin-1-yl)piperidine-carbonyl-phenyl) | 629 |
| 1-118 | " | (4-(2,6-dimethylmorpholino)piperidine-carbonyl-phenyl) | 644 |

TABLE I-continued
| Ex | R² | | LCMS(ESI) m/z [M + H⁺] |
|---|---|---|---|
| 1-119 | " |  | 645 |
| 1-120 | " |  | 618 |
| 1-121 | " | 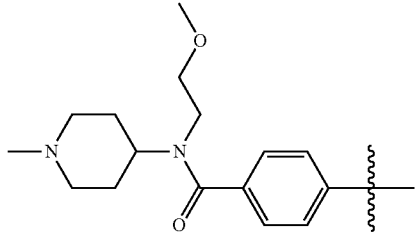 | 622 |
| 1-122 | " |  | 623 |

TABLE I-continued
| Ex | R² | | LCMS(ESI) m/z [M + H⁺] |
|---|---|---|---|
| 1-123 | " | 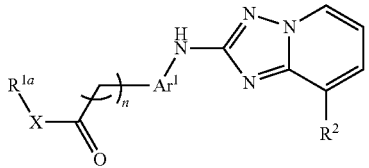 | 623 |
| 1-124 | " | 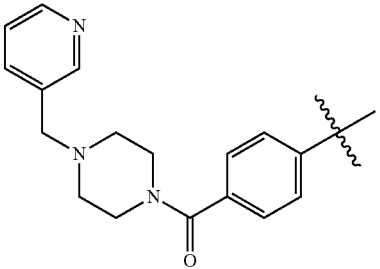 [SMILES: *c1ccc(C(=O)N2CCN(Cc3cccnc3)CC2)cc1] | 608 |
| 1-125 | " | 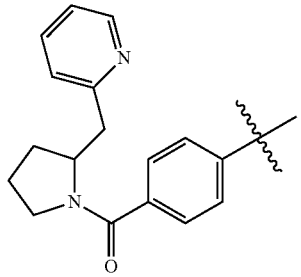 [SMILES: *c1ccc(C(=O)N2CCCC2Cc2ccccn2)cc1] | 616 |
| 1-126 | " | 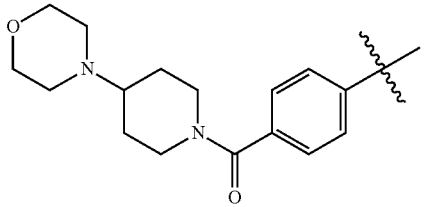 [SMILES: *c1ccc(C(=O)N2CCC(N3CCOCC3)CC2)cc1] | 609 |
| 1-127 | " | 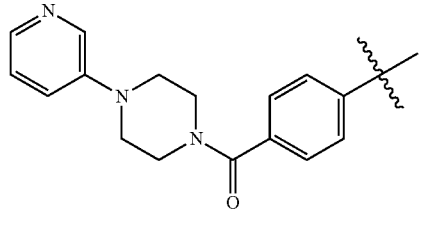 [SMILES: *c1ccc(C(=O)N2CCN(c3cccnc3)CC2)cc1] | 602 |

US 9,873,709 B2
TABLE I-continued
| Ex | R² | | LCMS(ESI) m/z [M + H⁺] |
|---|---|---|---|
| 1-128 | " | 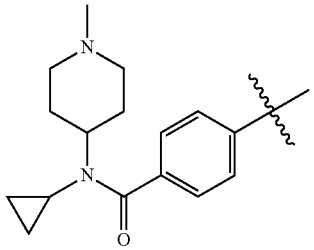 [SMILES: *c1ccc(C(=O)N(C2CC2)C2CCN(C)CC2)cc1] | 600 |
| 1-129 | " | 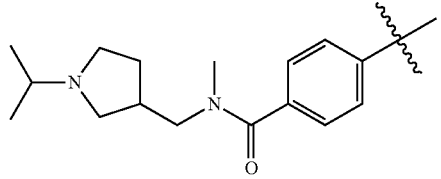 [SMILES: *c1ccc(C(=O)N(C)CC2CCN(C(C)C)C2)cc1] | 602 |
| 1-130 | " | 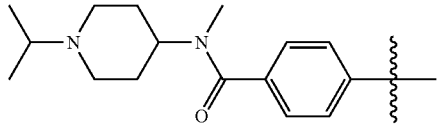 | 602 |
| 1-131 | " | 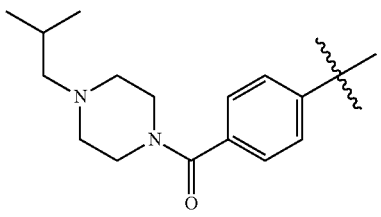 [SMILES: *c1ccc(C(=O)N2CCN(CC(C)C)CC2)cc1] | 588 |
| 1-132 | " | 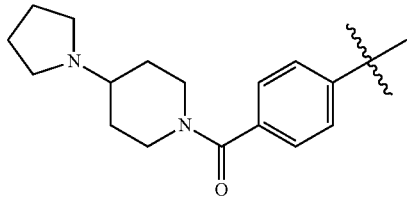 [SMILES: *c1ccc(C(=O)N2CCC(N3CCCC3)CC2)cc1] | 600 |
| 1-133 | " | 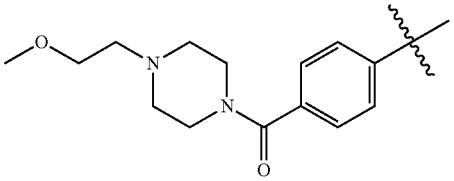 [SMILES: *c1ccc(C(=O)N2CCN(CCOC)CC2)cc1] | 590 |

TABLE I-continued
| Ex | R² | | LCMS(ESI) m/z [M + H⁺] |
|---|---|---|---|
| 1-134 | " | 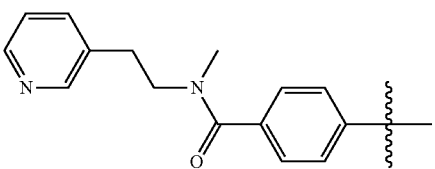 [SMILES: *c1ccc(C(=O)N(C)CCc2cccnc2)cc1] | 582 |
| 1-135 | " |  | 582 |
| 1-136 | " | 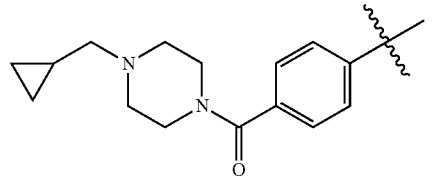 [SMILES: *c1ccc(C(=O)N2CCN(CC3CC3)CC2)cc1] | 586 |
| 1-137 | " |  | 586 |
| 1-138 | " | 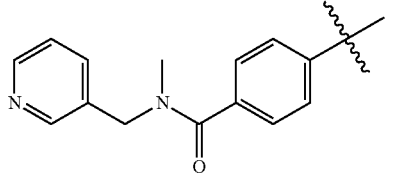 [SMILES: *c1ccc(C(=O)N(C)Cc2cccnc2)cc1] | 568 |

TABLE I-continued
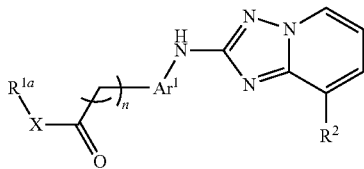
| Ex | R² | | LCMS(ESI) m/z [M + H⁺] |
|---|---|---|---|
| 1-139 | " | 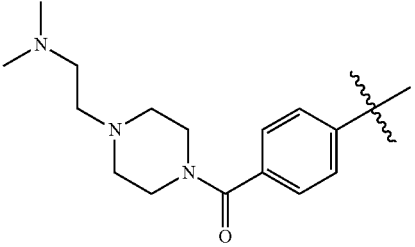 [SMILES: *c1ccc(C(=O)N2CCN(CCN(C)C)CC2)cc1] | 603 |
| 1-140 | " | 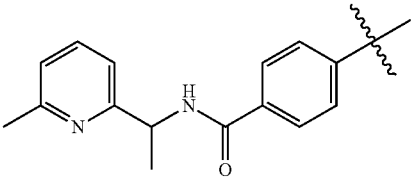 [SMILES: *c1ccc(C(=O)NC(C)c2cccc(C)n2)cc1] | 582 |
| 1-141 | " | 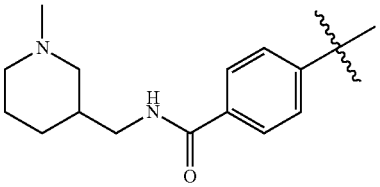 [SMILES: *c1ccc(C(=O)NCC2CCCN(C)C2)cc1] | 574 |
| 1-142 | " | 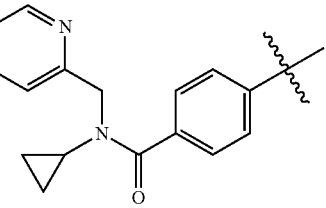 | 594 |
| 1-143 | " | 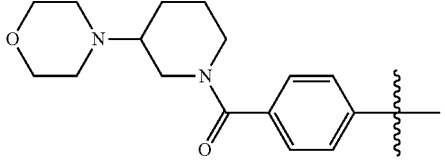 [SMILES: *c1ccc(C(=O)N2CCCC(N3CCOCC3)C2)cc1] | 616 |
| 1-144 | " | 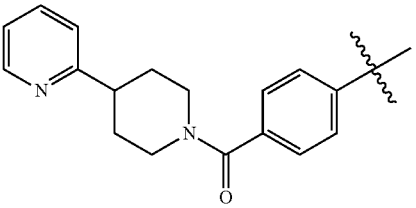 [SMILES: *c1ccc(C(=O)N2CCC(c3ccccn3)CC2)cc1] | 608 |

TABLE I-continued

| Ex | R² | | LCMS(ESI) m/z [M + H⁺] |
|---|---|---|---|
| 1-145 | " | | 622 |
| 1-146 | " | | 608 |
| 1-147 | " | | 594 |
| 1-148 | " | | 610 |
| 1-149 | " | | 608 |
| 1-150 | " | | 693 |

TABLE I-continued
| Ex | R² | | LCMS(ESI) m/z [M + H⁺] |
|---|---|---|---|
| 1-151 | " | 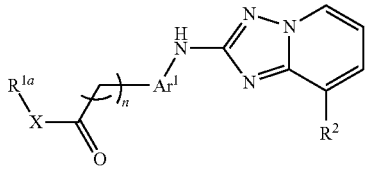 | 652 |
| 1-152 | " | 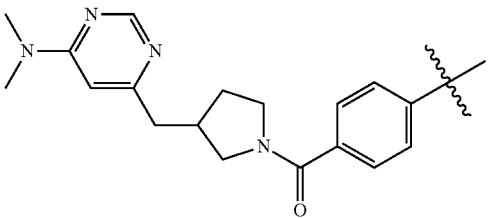 [SMILES: *c1ccc(C(=O)N2CCC(Cc3cc(N(C)C)ncn3)C2)cc1] | 603 |
| 1-153 | " | 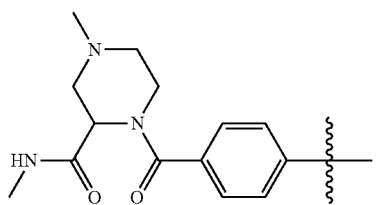 [SMILES: *c1ccc(C(=O)N2CCN(C)CC2C(=O)NC)cc1] | 679 |
| 1-154 | " | 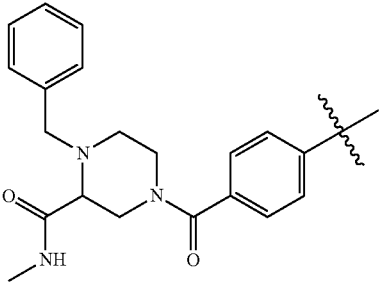 [SMILES: *c1ccc(C(=O)N2CCN(Cc3ccccc3)C(C(=O)NC)C2)cc1] | 588 |
| 1-155 | " | 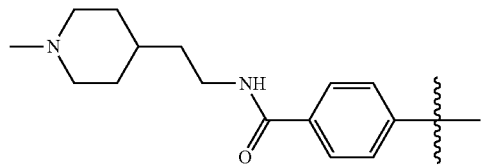 | 608 |

TABLE I-continued
| Ex | R² | | LCMS(ESI) m/z [M + H⁺] |
|---|---|---|---|
| 1-156 | " | 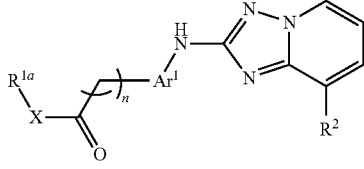 | 622 |
| 1-157 | " | 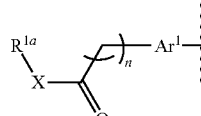 | 608 |
| 1-158 | " | 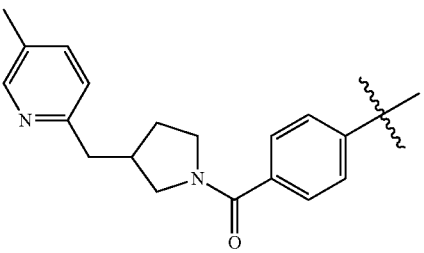 [SMILES: *c1ccc(C(=O)N2CCC(Cc3ccc(C)cn3)C2)cc1] | 622 |
| 1-159 | " | 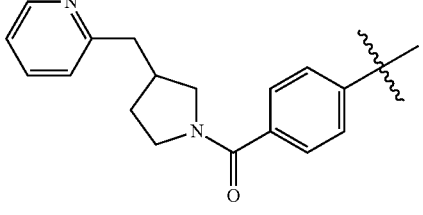 | 582 |
| 1-160 | " |  | 568 |
| 1-161 | " |  | 568 |

TABLE I-continued
| Ex | R² | | LCMS(ESI) m/z [M + H⁺] |
|---|---|---|---|
| 1-162 | " |  | 568 |
| 1-163 | " | 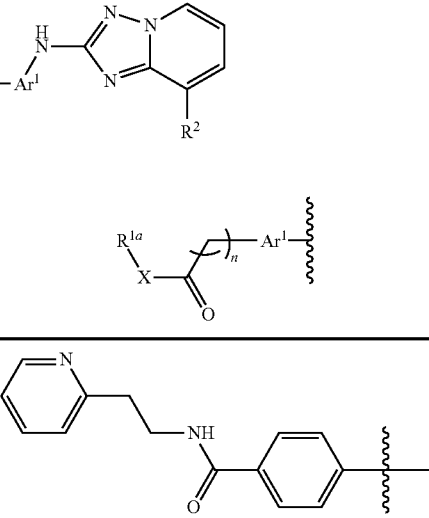 | 603 |
| 1-164 | " |  | 574 |
| 1-165 | " | 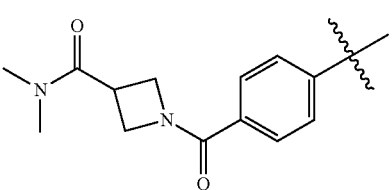 [SMILES: *c1ccc(C(=O)N2CC(C(=O)N(C)C)C2)cc1] | 629 |
| 1-166 | " |  | 560 |
| 1-167 | " | 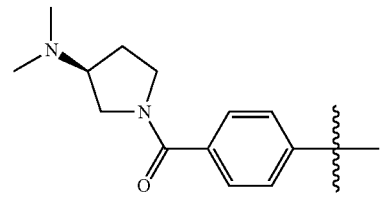 [SMILES: *c1ccc(C(=O)N2CC[C@H](N(C)C)C2)cc1] | 585 |

TABLE I-continued
| Ex | R² | | LCMS(ESI) m/z [M + H⁺] |
|---|---|---|---|
| 1-168 | " | 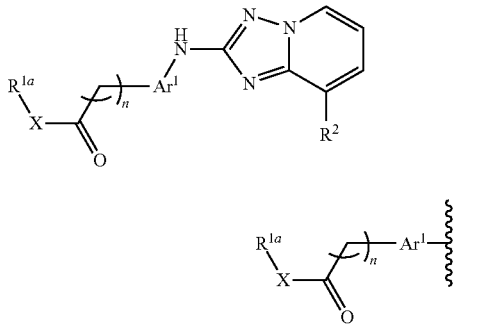 | 572 |
| 1-169 | " | 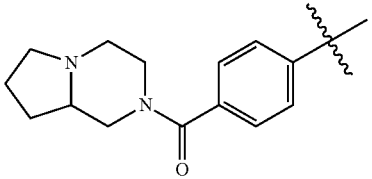 [SMILES: *c1ccc(C(=O)N2CCN3CCCC3C2)cc1] | 618 |
| 1-170 | " | 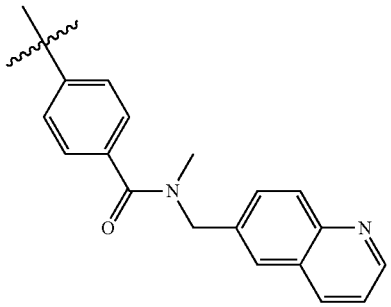 [SMILES: *c1ccc(C(=O)N(C)Cc2ccc3ncccc3c2)cc1] | 588 |
| 1-171 | " | 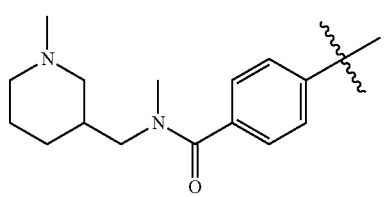 [SMILES: *c1ccc(C(=O)N(C)CC2CCCN(C)C2)cc1] | 636 |
| 1-172 | " | 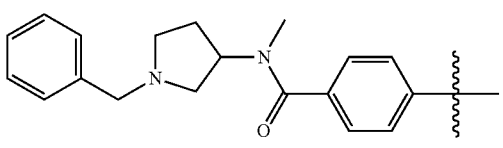 [SMILES: *c1ccc(C(=O)N(C)C2CCN(Cc3ccccc3)C2)cc1] | 616 |
| 1-173 | " | 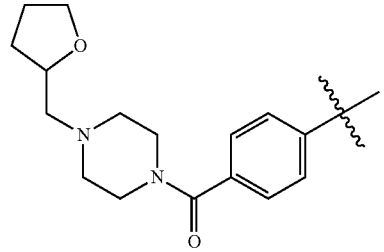 [SMILES: *c1ccc(C(=O)N2CCN(CC3CCCO3)CC2)cc1] | 574 |

TABLE I-continued
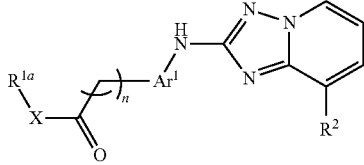
| Ex | R² | | LCMS(ESI) m/z [M + H⁺] |
|---|---|---|---|
| 1-174 | " | 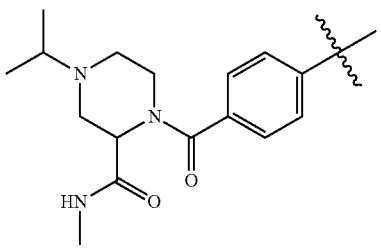 [SMILES: *c1ccc(C(=O)N2CCN(C(C)C)CC2C(=O)NC)cc1] | 631 |
| 1-175 | " | 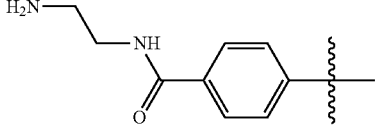 [SMILES: *c1ccc(C(=O)NCCN)cc1] | 506 |
| 1-176 | " | 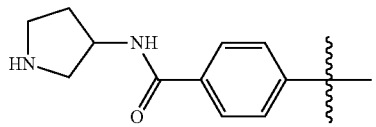 | 532 |
| 1-177 | " | 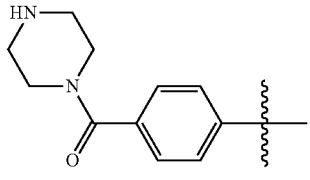 [SMILES: *c1ccc(C(=O)N2CCNCC2)cc1] | 532 |
| 1-178 | " | 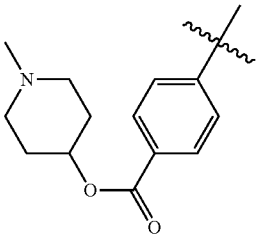 [SMILES: *c1ccc(C(=O)OC2CCN(C)CC2)cc1] | 561 |
| 1-179 | " | 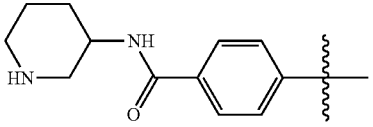 | 546 |
| 1-180 | " | 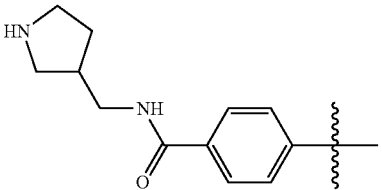 [SMILES: *c1ccc(C(=O)NCC2CCNC2)cc1] | 546 |

TABLE I-continued
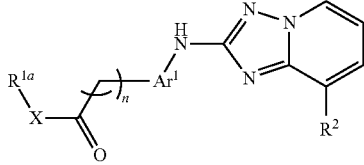
| Ex | R² | 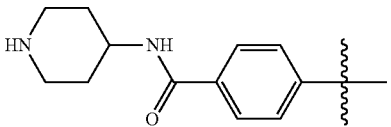 [SMILES: *c1ccc(C(=O)NC2CCNCC2)cc1] | LCMS(ESI) m/z [M + H⁺] |
|---|---|---|---|
| 1-181 | " | 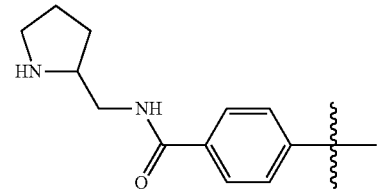 [SMILES: *c1ccc(C(=O)NCC2CCCN2)cc1] | 546 |
| 1-182 | " |  | 546 |
| 1-183 | " | 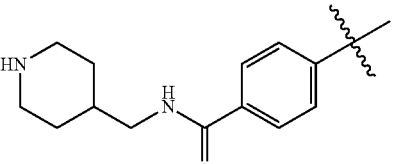 | 560 |
| 1-184 | " | 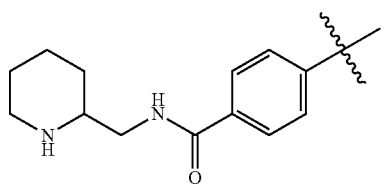 [SMILES: *c1ccc(C(=O)NCC2CCCCN2)cc1] | 560 |
| 1-185 | " | 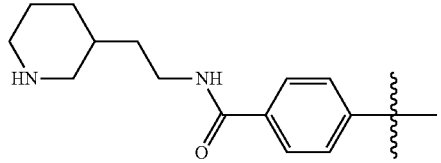 | 560 |
| 1-186 | " | 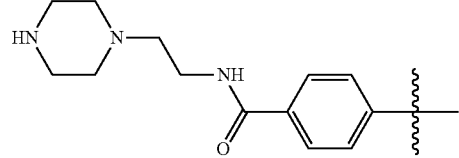 [SMILES: *c1ccc(C(=O)NCCN2CCNCC2)cc1] | 574 |
| 1-187 | " | | 575 |

US 9,873,709 B2
TABLE I-continued
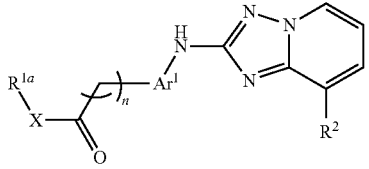
| Ex | R² | | LCMS(ESI) m/z [M + H⁺] |
|---|---|---|---|
| 1-188 | " | 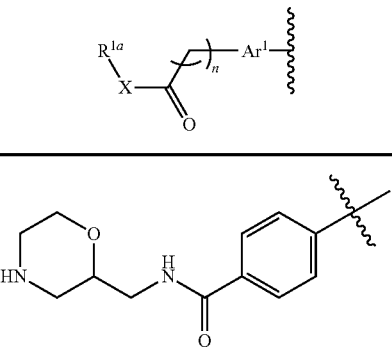 | 562 |
| 1-189 | " | 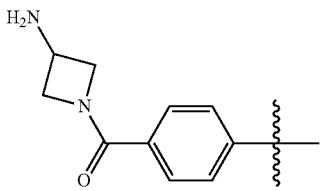 [SMILES: *c1ccc(C(=O)N2CC(N)C2)cc1] | 518 |
| 1-190 | " | 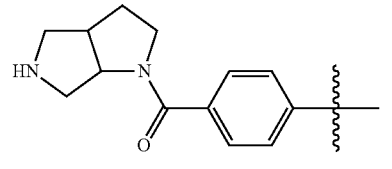 [SMILES: *c1ccc(C(=O)N2CCC3CNCC32)cc1] | 558 |
| 1-191 | " | 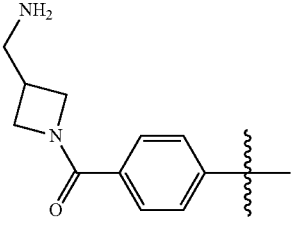 [SMILES: *c1ccc(C(=O)N2CC(CN)C2)cc1] | 532 |
| 1-192 | " | 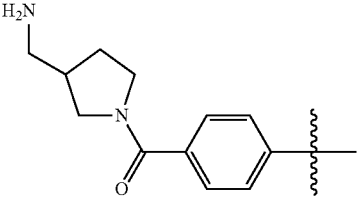 [SMILES: *c1ccc(C(=O)N2CCC(CN)C2)cc1] | 546 |
| 1-193 | " | 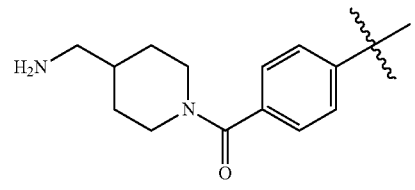 [SMILES: *c1ccc(C(=O)N2CCC(CN)CC2)cc1] | 560 |

TABLE I-continued
| Ex | R² | | LCMS(ESI) m/z [M + H⁺] |
|---|---|---|---|
| 1-194 | " | 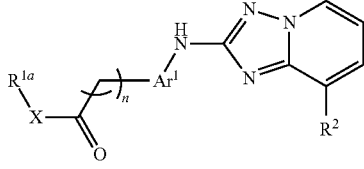 | 520 |
| 1-195 | " | 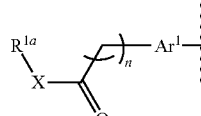 | 546 |
| 1-196 | " | 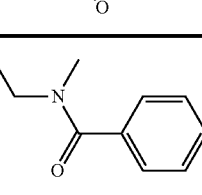 | 562 |
| 1-197 | " | 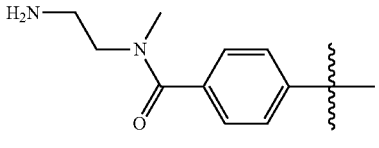 | 558 |
| 1-198 | " | 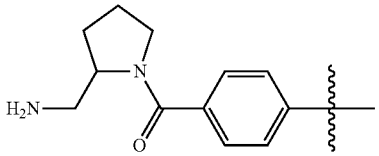 [SMILES: *c1ccc(C(=O)N2CCCC2CN)cc1] | 546 |
| 1-199 | " |  | 572 |
| 1-200 | " |  | 546 |

TABLE I-continued
| Ex | R² | | LCMS(ESI) m/z [M + H⁺] |
|---|---|---|---|
| 1-201 | " | 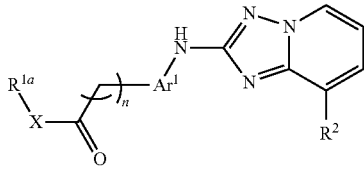 | 572 |
| 1-202 | " | 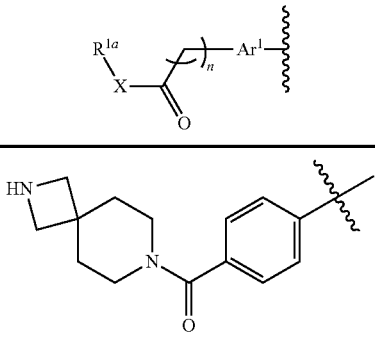 | 560 |
| 1-203 | " | 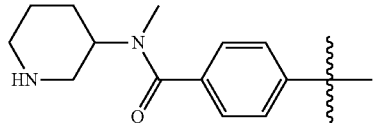 | 544 |
| 1-204 | " | 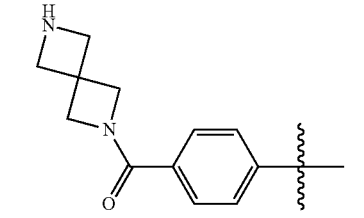 [SMILES: *c1ccc(C(=O)N2CC3(CNC3)C2)cc1] | 546 |
| 1-205 | " | 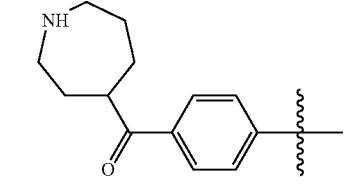 [SMILES: *c1ccc(C(=O)C2CCCNCC2)cc1] | 558 |
| 1-206 | " | 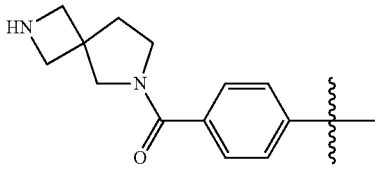 [SMILES: *c1ccc(C(=O)N2CCC3(CNC3)C2)cc1] | 546 |
| 1-207 | " | 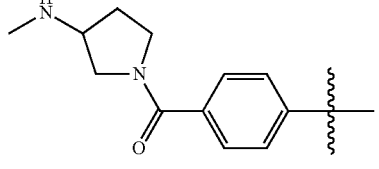 | 572 |

TABLE I-continued
| Ex | R² | | LCMS(ESI) m/z [M + H⁺] |
|---|---|---|---|
| 1-208 | " |  | 572 |
| 1-209 | " | 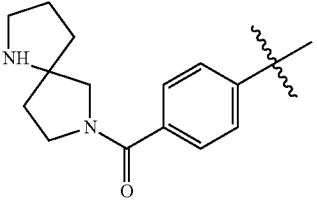 [SMILES: *c1ccc(C(=O)N2CCC3(CCCN3)C2)cc1] | 572 |
| 1-210 | " |  | 572 |
| 1-211 | " | 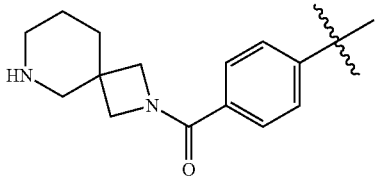 [SMILES: *c1ccc(C(=O)N2CC3(CCCNC3)C2)cc1] | 586 |
| 1-212 | " |  | 586 |
| 1-213 | " | 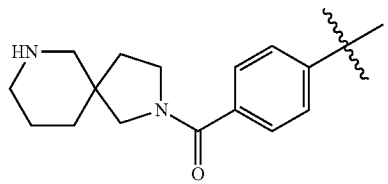 [SMILES: *c1ccc(C(=O)N2CCC3(CCCNC3)C2)cc1] | 586 |

TABLE I-continued
| Ex | R² | | LCMS(ESI) m/z [M + H⁺] |
|---|---|---|---|
| 1-214 | " | 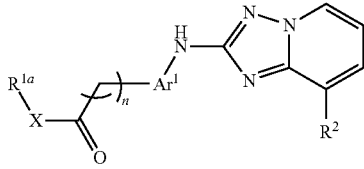 | 586 |
| 1-215 | " | 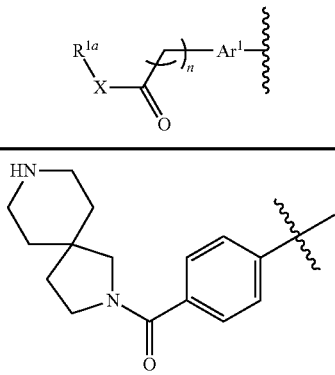 | 600 |
| 1-216 | " | 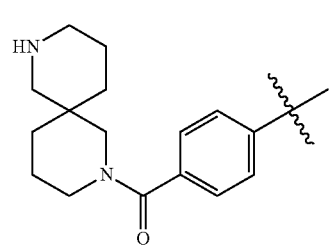 [SMILES: *c1ccc(C(=O)N2CCCC3(CCCNC3)C2)cc1] | 600 |
| 1-217 | " | 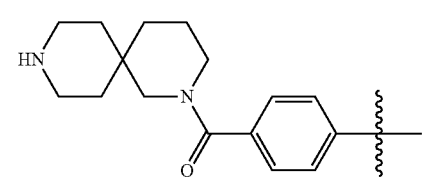 [SMILES: *c1ccc(C(=O)N2CCCC3(CCNCC3)C2)cc1] | 600 |
| 1-218 | " | 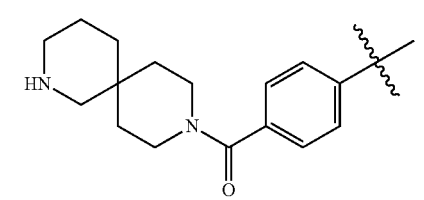 | 600 |
| 1-219 | " | 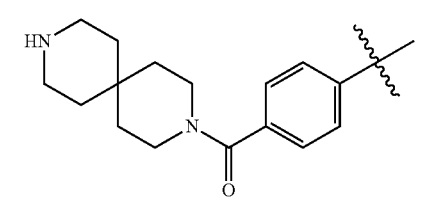 [SMILES: *c1ccc(C(=O)N2CCC3(CCNCC3)CC2)cc1] | 600 |

TABLE I-continued

| Ex | R² | (structure) | LCMS(ESI) m/z [M + H⁺] |
|---|---|---|---|
| 1-220 | " | | 616 |
| 1-221 | " | | 602 |
| 1-222 | " | | 616 |
| 1-223 | " | | 600 |
| 1-224 | " | | 558 |
| 1-225 | " | | 602 |

TABLE I-continued
| Ex | R² | | LCMS(ESI) m/z [M + H⁺] |
|---|---|---|---|
| 1-226 | " |  | 586 |
| 1-227 | " | 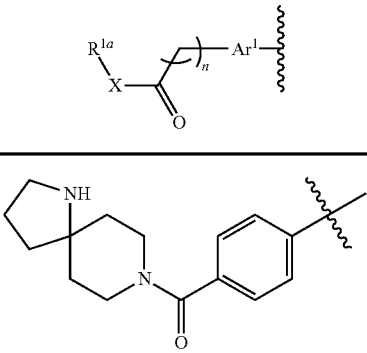 | 586 |
| 1-228 | " | 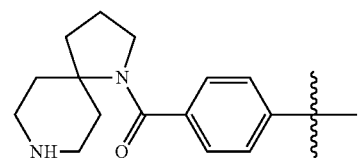 [SMILES: *c1ccc(C(=O)N2CCCC23CCNCC3)cc1] | 586 |
| 1-229 | " | 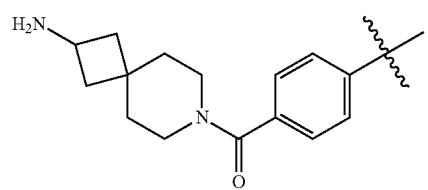 [SMILES: *c1ccc(C(=O)N2CCC3(CC2)CC(N)C3)cc1] | 602 |
| 1-230 | " | 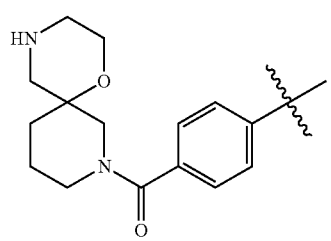 [SMILES: *c1ccc(C(=O)N2CCCC3(CNCCO3)C2)cc1] | 602 |
| 1-231 | " | 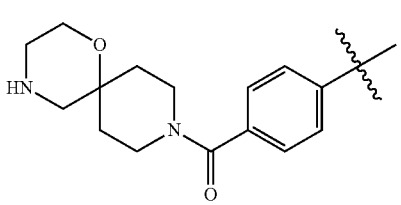 [SMILES: *c1ccc(C(=O)N2CCC3(CC2)CNCCO3)cc1] | 602 |

TABLE I-continued

| Ex | R² | | LCMS(ESI) m/z [M + H⁺] |
|---|---|---|---|
| 1-232 | " | | 544 |
| 1-233 | " | | 586 |
| 1-234 | " | | 558 |
| 1-235 | " | | 558 |
| 1-236 | " | | 572 |

TABLE I-continued

| Ex | R² | | LCMS(ESI) m/z [M + H⁺] |
|---|---|---|---|
| 1-237 | " | | 544 |
| 1-238 | " | | 544 |
| 1-239 | " | | 574 |
| 1-240 | " | | 558 |

TABLE I-continued
| Ex | R² | | LCMS(ESI) m/z [M + H⁺] |
|---|---|---|---|
| 1-241 | " | 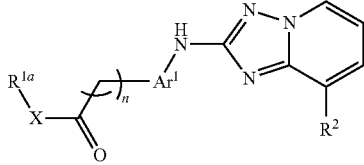 | 558 |
| 1-242 | " | 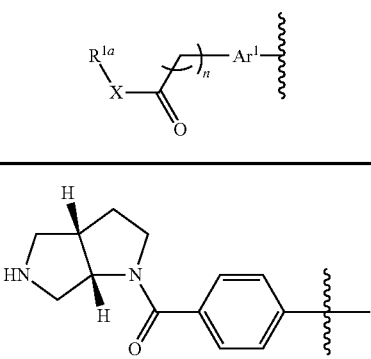 | 574 |
| 1-243 | " | 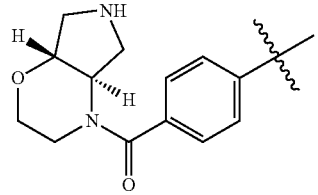 [SMILES: *c1ccc(C(=O)N2CCO[C@@H]3CNC[C@H]32)cc1] | 574 |
| 1-244 | " | 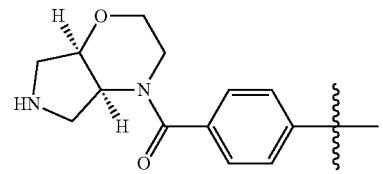 [SMILES: *c1ccc(C(=O)N2CCO[C@@H]3CNC[C@@H]32)cc1] | 588 |
| 1-245 | " | 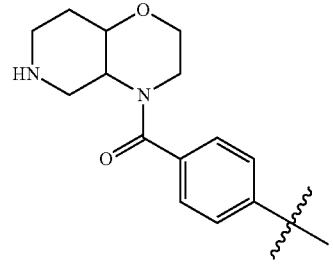 [SMILES: *c1ccc(C(=O)N2CCOC3CCNCC32)cc1] | 630 |

TABLE I-continued
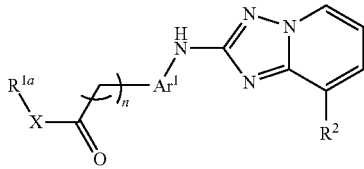
| Ex | R² | 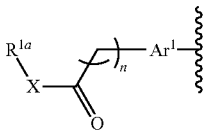 | LCMS(ESI) m/z [M + H⁺] |
|---|---|---|---|
| 1-246 | 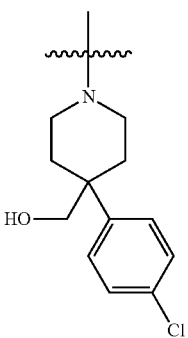 [SMILES: *N1CCC(CO)(c2ccc(Cl)cc2)CC1] | 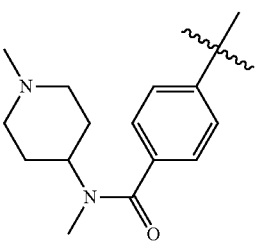 [SMILES: *c1ccc(C(=O)N(C)C2CCN(C)CC2)cc1] | 589 |
| 1-247 | 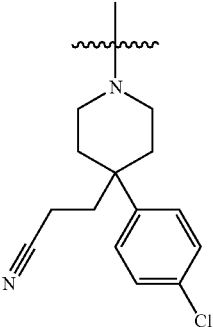 [SMILES: *N1CCC(CCC#N)(c2ccc(Cl)cc2)CC1] | " | 611 |
| 1-248 | 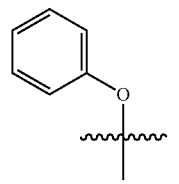 [SMILES: *Oc1ccccc1] | " | 457 |
| 1-249 | 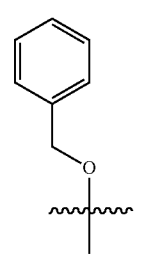 [SMILES: *OCc1ccccc1] | " | 471 |

TABLE I-continued
| Ex | R² | | LCMS(ESI) m/z [M + H⁺] |
|---|---|---|---|
| 1-250 | 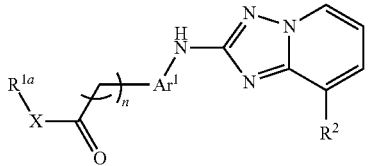 | " | 615 |
| 1-251 | 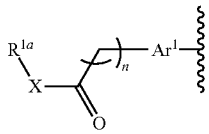 | " | 600 |
| 1-252 | 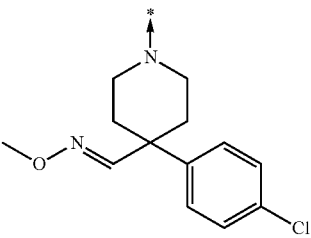 | " | 602 |
| 1-253 | 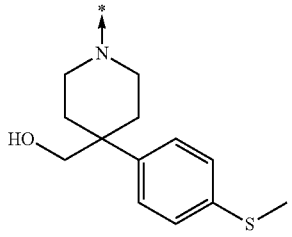 | " | 656 |
| 1-254 | 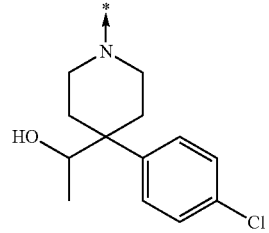 | " | 644 |

TABLE I-continued
| Ex | R² | | LCMS(ESI) m/z [M + H⁺] |
|---|---|---|---|
| 1-255 | 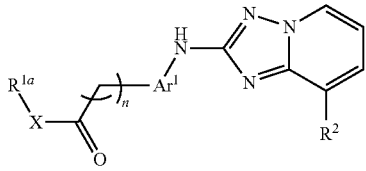 | " | 603 |
| 1-256 | 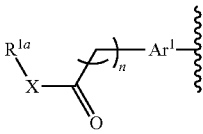 | " | 623 |
| 1-257 | 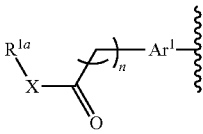 | " | 555 |
| 1-258 | 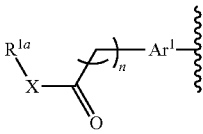 | " | 603 |
| 1-259 | 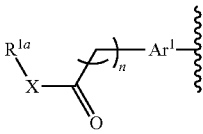 | " | 595 |

TABLE I-continued
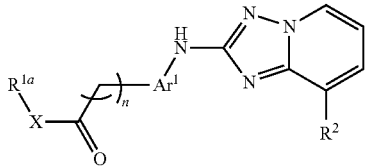
| Ex | R² | | LCMS(ESI) m/z [M + H⁺] |
|---|---|---|---|
| 1-260 | 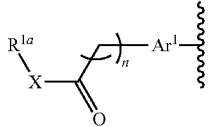 | " | 519 |
| 1-261 | 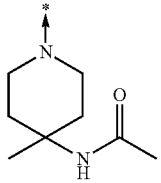 | " | 631 |
| 1-262 | 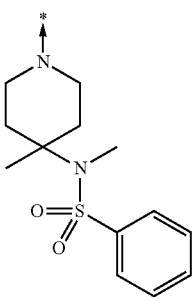 | " | 573 |
| 1-263 | 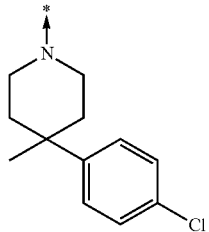 | " | 616 |
| 1-264 | 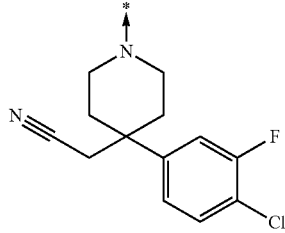 | " | 604 |

US 9,873,709 B2
737                                                                                         738
TABLE I-continued
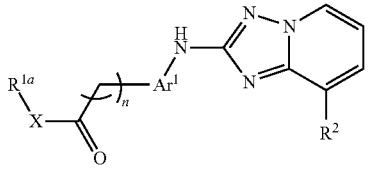
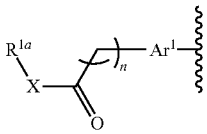
| Ex | R² | | LCMS(ESI) m/z [M + H⁺] |
|---|---|---|---|
| 1-265 | 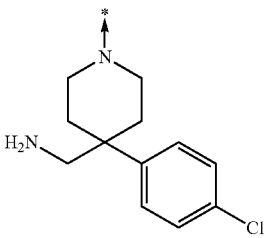 | " | 588 |
| 1-266 | 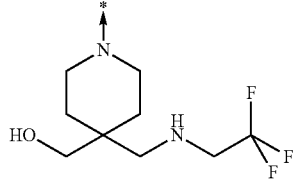 | " | 589 |
| 1-267 | 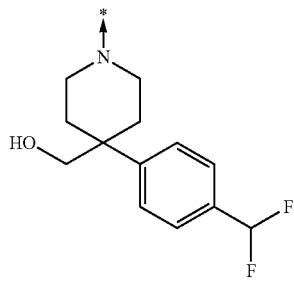 | " | 604 |
| 1-268 | 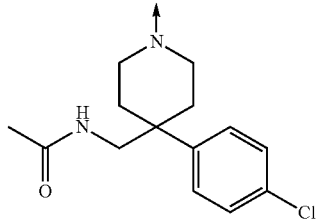 | " | 630 |
| 1-269 | 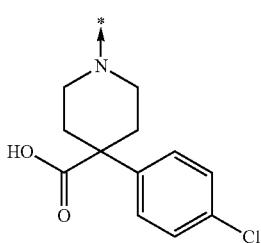 | " | 603 |

TABLE I-continued
| Ex | R² | | LCMS(ESI) m/z [M + H⁺] |
|---|---|---|---|
| 1-270 | 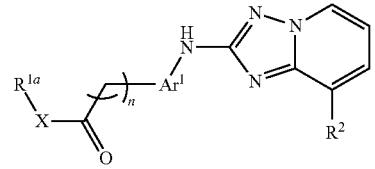 | " | 619 |
| 1-271 | 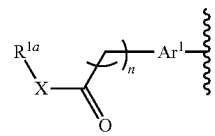 | 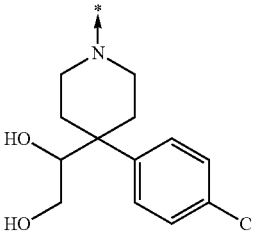 | 657 |
| 1-272 | " | 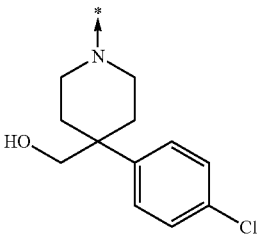 | 603 |
| 1-273 | " | 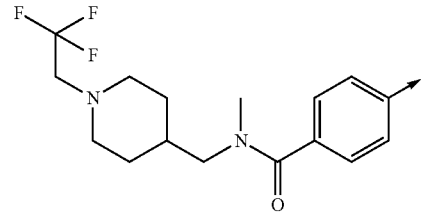 | 617 |
| 1-274 | " | 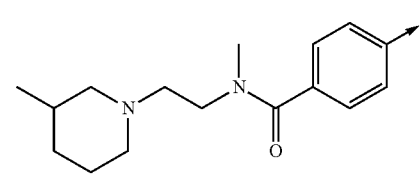 | 587 |
| 1-275 | " | 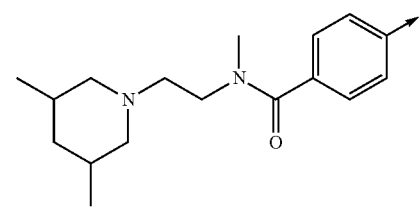 | 587 |

TABLE I-continued
| Ex | R² | | LCMS(ESI) m/z [M + H⁺] |
|---|---|---|---|
| 1-276 | " | 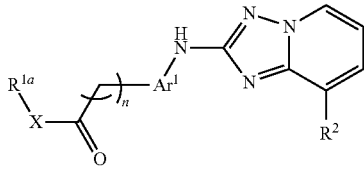 | 623 |
| 1-277 | " | 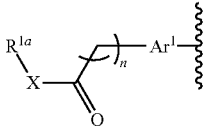 | 619 |
| 1-278 | " | 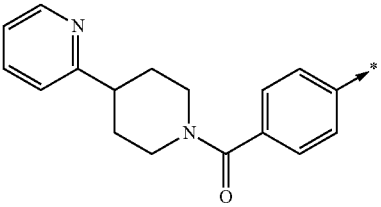 | 619 |
| 1-279 | " | 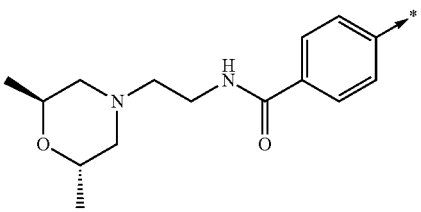 | 609 |
| 1-280 | " | 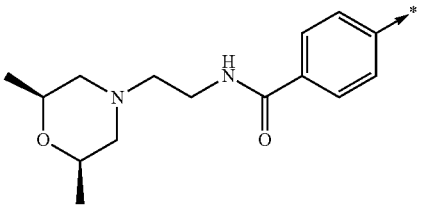 | 629 |
| 1-281 | " | 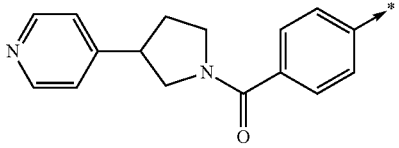 | 659 |

TABLE I-continued

| Ex | R² | | LCMS(ESI) m/z [M + H⁺] |
|---|---|---|---|
| 1-282 | " | (2,6-dimethylmorpholin-4-yl-piperidinyl benzoyl group) | 659 |
| 1-283 | " | (3-methylamino-azetidinyl benzoyl group) | 547 |
| 1-284 | " | (6-methylpyridin-3-yl-methylaminocarbonyl benzoyl group) | 583 |
| 1-285 | " | (morpholinyl-dimethyl-methylaminocarbonyl benzoyl group) | 619 |
| 1-286 | " | (morpholinyl-propyl-aminocarbonyl benzoyl group) | 605 |
| 1-287 | " | (pyridin-4-yl-methyl-ethyl-aminocarbonyl benzoyl group) | 597 |

TABLE I-continued

| Ex | R² | | LCMS(ESI) m/z [M + H⁺] |
|---|---|---|---|
| 1-288 | " | (pyrrolidine-pyridine-benzoyl structure) | 609 |
| 1-289 | " | (morpholine-methyl-piperidine-acetyl-pyrazole structure) | 649 |
| 1-290 | " | (methoxy-oxobutyl-piperazine-acetyl-pyrazole structure) | 637 |
| 1-291 | " | (methylamino-piperidine-acetyl-pyrazole structure) | 579 |
| 1-292 | (hydroxy-phenyl-octahydrocyclopenta[c]pyrrole structure) | (methylpiperidine-N-methyl-benzamide structure) | 566 |

TABLE I-continued
| Ex | R² | | LCMS(ESI) m/z [M + H⁺] |
|---|---|---|---|
| 1-293 | 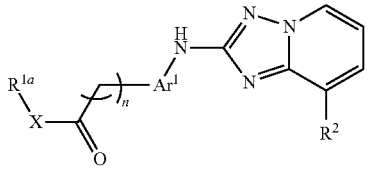 | " | 551 |
| 1-294 | 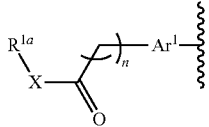 | 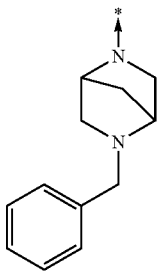 | 595 |
| 1-295 | 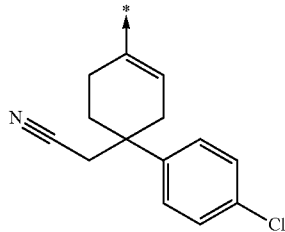 | 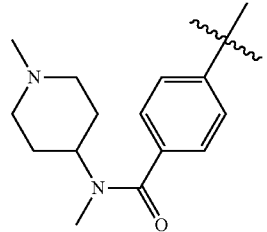 [SMILES: *c1ccc(C(=O)N(C)C2CCN(C)CC2)cc1] | 586 |
| 1-296 | 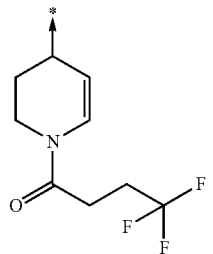 | 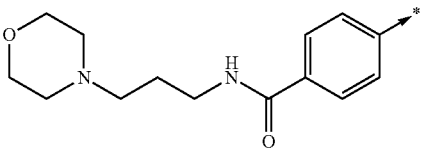 | 632 |
| 1-297 | 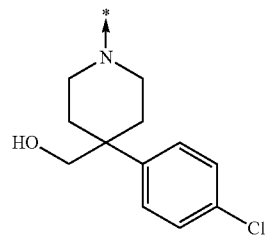 | 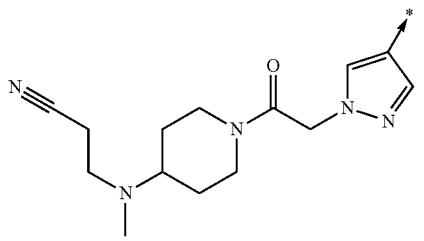 | 616 |

TABLE I-continued
| Ex | R² | | LCMS(ESI) m/z [M + H⁺] |
|---|---|---|---|
| 1-298 | 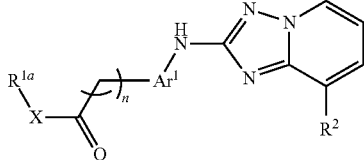 | 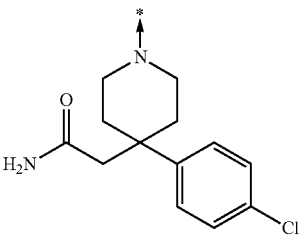 | 616 |
| 1-299 | 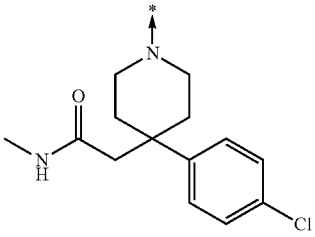 | " | 630 |
| 1-300 | 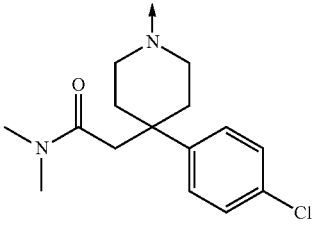 | " | 644 |
| 1-301 | 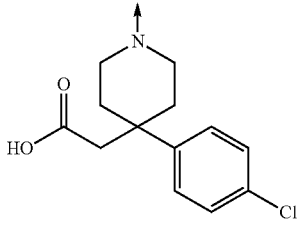 | " | 617 |
| 1-302 | 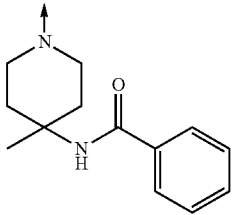 | " | 581 |

TABLE I-continued

| Ex | R² | R¹ᵃ-X group | LCMS(ESI) m/z [M + H⁺] |
|---|---|---|---|
| 1-303 | *4-methyl-4-(phenylsulfonamido)piperidin-1-yl* | " | 617 |

Example 2a

Tert-butyl 4-(2-((4-(methyl(1-methylpiperidin-4-yl)carbamoyl)-phenyl)-amino)-[1,2,4]triazolo[1,5-a]pyridin-8-yl)-5,6-dihydropyridine-1(2H)-carboxylate

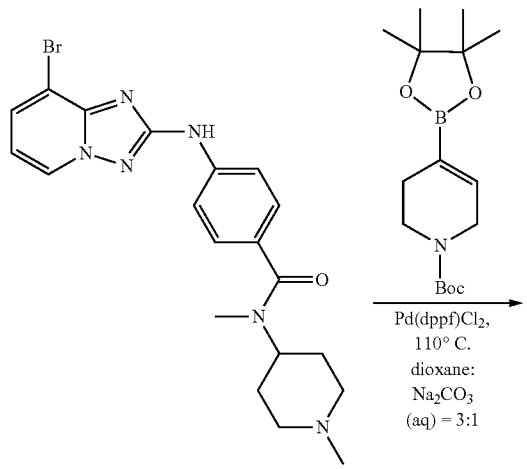

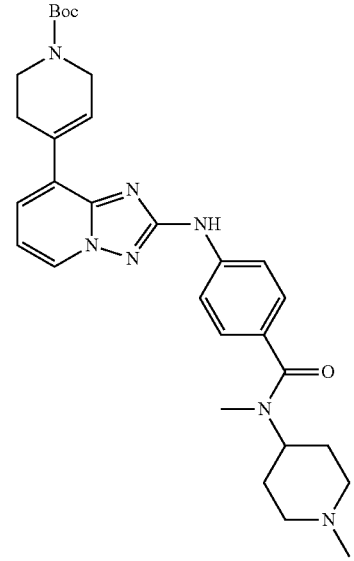

Step 1. To a solution of 4-((8-bromo-[1,2,4]triazolo[1,5-a]pyridin-2-yl)amino)-N-methyl-N-(1-methylpiperidin-4-yl)benzamide (2.5g, 5.1mmol), tert-butyl 4-(4,4,5,5-tetramethyl-1,3,2-dioxaborolan-2-yl)-5,6-dihydropyridine-1(2H)-carboxylate (1.8, 6.12 mmol), [1,1'-bis(diphenylphosphino)ferrocene]dichloropalladium(II) (360 mg, 0.5 mmol) in dioxane (60 mL) was added saturated sodium carbonate (20 mL); then the reaction mixture was degassed and heated at 110° C. under nitrogen for 4 h. The reaction mixture was poured into water (50 mL) and the mixture was extracted with ethyl acetate (150 mL×3). The combined organic layers were dried over anhydrous sodium sulfate, filtered and the filtrate was evaporated. The residue was purified on silica gel column (eluting with 2% to 5% methanol in dichloromethane) to give tert-butyl 4-(2-((4-(methyl(1-methylpiperidin-4-yl)carbamoyl)phenyl)amino)-[1,2,4]triazolo[1,5-a]pyridin-8-yl)-5,6-dihydropyridine-1(2H)-carboxylate (2 g, 72%) as a solid. ¹H NMR (400 MHz, DMSO-d₆) 9.92 (s, 1H), 8.68 (d, J=6.6 Hz, 1H), 7.71 (d, J=8.6 Hz, 2H), 7.50 (d, J=7.5 Hz, 1H), 7.31 (d, J=8.2 Hz, 2H), 7.02 (t, J=7.1 Hz, 1H), 4.17-4.00 (m, 3H), 3.65-3.49 (m, 2H), 3.14 (d, J=5.3 Hz, 2H), 2.79 (s, 5H), 2.61 (brs, 2H), 2.11 (brs, 2H), 1.78 (d, J=8.6 Hz, 1H), 1.56 (d, J=10.4 Hz, 2H), 1.42 (s, 9H), MS (Method 4): m/z 546.1 [M+1]⁺.

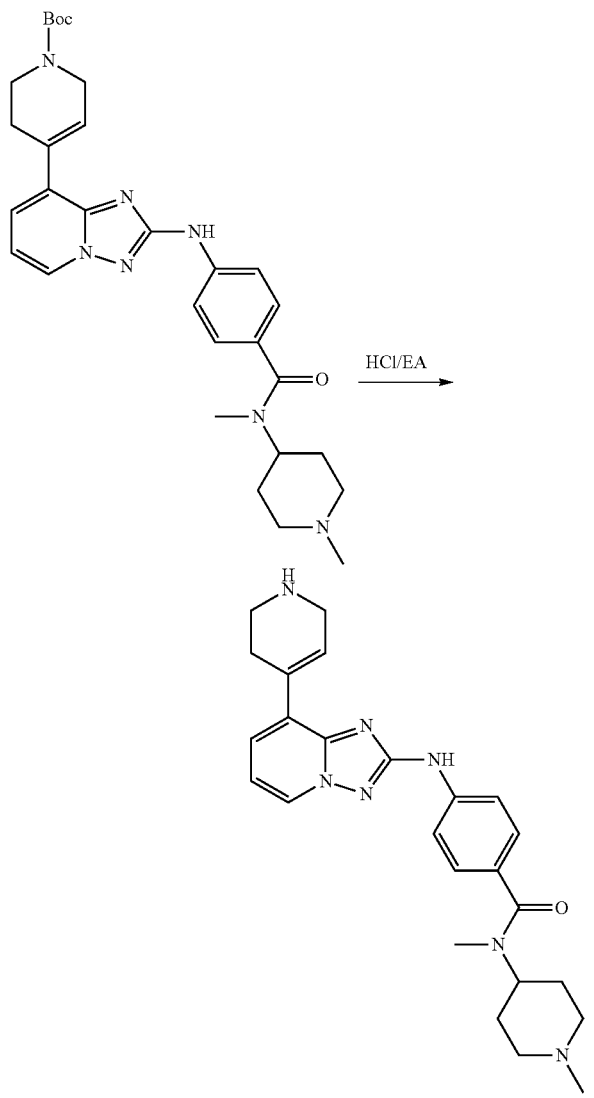

Step 2. A mixture of tert-butyl 4-(2-((4-(methyl(1-methylpiperidin-4-yl)carbamoyl)phenyl)amino)-[1,2,4]triazolo[1,5-a]pyridin-8-yl)-5,6-dihydropyridine-1(2H)-carboxylate (1.7 g, 3.1 mmol) in methanolic hydrochloride solution (4 M, 10 mL) was stirred at room temperature for 1.5 h. The solvent was evaporated to afford 2.3 g of the hydrochloride salt of N-methyl-N-(1-methylpiperidin-4-yl)-4-((8-(1,2,3,6-tetrahydropyridin-4-yl)-[1,2,4]triazolo[1,5-a]pyridin-2-yl)amino)benzamide; bis-hydrochloride salt. ¹H NMR (400 MHz, DMSO-d₆): 10.00 (s, 1H), 9.47 (brs, 1H), 8.74 (d, J=6.6 Hz, 1H), 7.74 (d, J=8.6 Hz, 2H), 7.59 (d, J=7.5 Hz, 1H), 7.46 (brs, 1H), 7.37 (d, J=8.4 Hz, 2H), 7.07 (t, J=7.2 Hz, 1H), 3.49-3.28 (m, 4H), 2.86-2.80 (m, 5H), 2.65 (brs, 2H), 2.21 (d, J=11.9 Hz, 2H), 1.89 (s, 5H), 1.81 (d, J=12.6 Hz, 2H); LCMS (Method 4) m/z 446.1 [M+H]⁺.

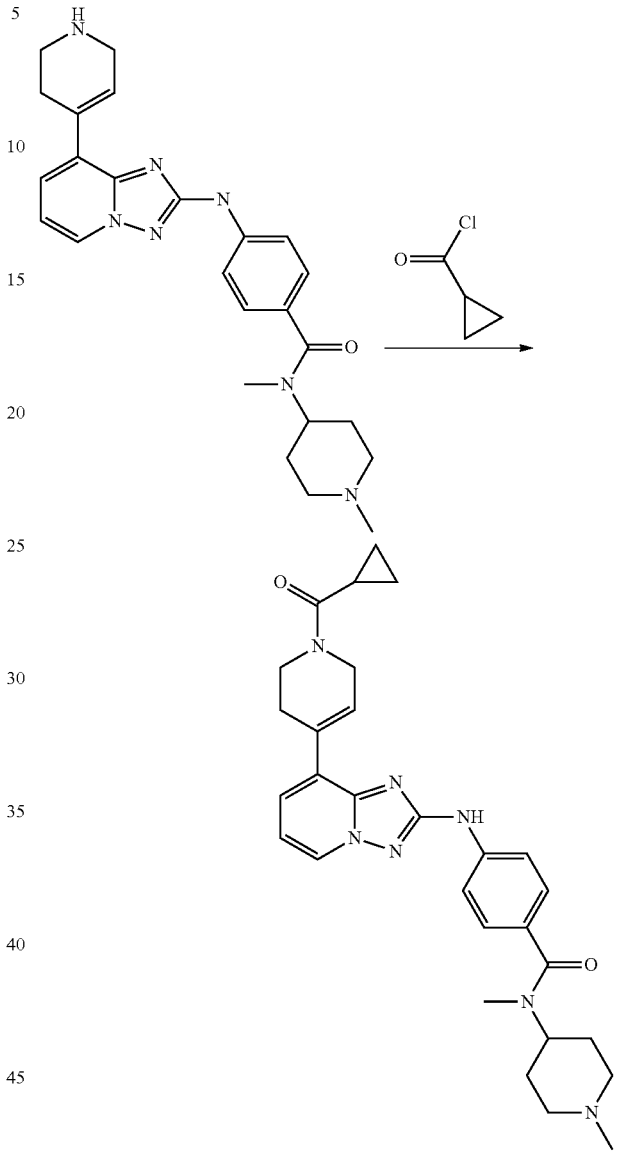

Step 3. [To a mixture of N-methyl-N-(1-methylpiperidin-4-yl)-4-((8-(1,2,3,6-tetrahydropyridin-4-yl)-[1,2,4]triazolo[1,5-a]pyridin-2-yl)amino)benzamide; bis-hydrochloride salt (100 mg, 0.224 mmol) and Et₃N (75 mg, 0.448 mmol) in dichloromethane (5 mL) was added dropwise cyclopropanecarbonyl chloride (26 mg, 0.248 mmol) at 0° C. The reaction mixture was allowed to warm to room temperature and stirred 0.5 h. MeOH (1 ml) was added and the reaction mixture was concentrated. The residue was purified by prep-HPLC to give the final compound (Example 2-409, Table II) (40 mg, 36.4% yield). ¹H NMR (400 MHz, DMSO-d₆) δ 9.95 (s,1H), 8.72-8.71 (m,1H), 7.75 (d, J=8.4 Hz,2H), 7.55 (d, J=7.2 Hz,1H),7.44-7.33 (m,3H), 7.06 (t, J=6.8 Hz, 1H), 4.52 (s, 1H), 4.24 (s, 2H), 3.95 (s, 2H), 3.75 (s, 1H), 2.82-2.75 (m, 6H), 2.62 (s, 1H), 2.12-2.02 (m, 5H), 1.81 (d, J=7.2Hz, 4H), 1.59 (d, J=8.8 Hz, 2H) 0.78-0.73 (m, 4H). LCMS (Method 4): R_T=0.711 min, m/z:514.1(M+H⁺).

Example 2b

4-{8-[1-(4,4,4-Trifluoro-butyryl)-1,2,3,6-tetrahydro-pyridin-4-yl]-[1,2,4]triazolo[1,5a]pyridin-2-ylamino}-benzoic acid

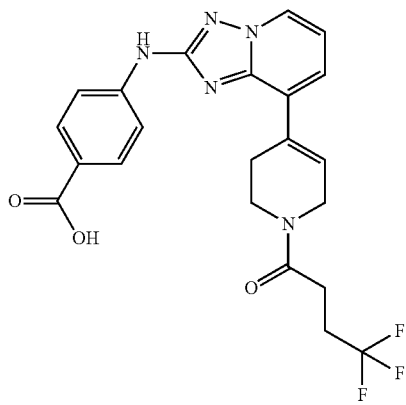 [SMILES: O=C(O)c1ccc(Nc2nc3c(C4=CCN(C(=O)CCC(F)(F)F)CC4)cccn3n2)cc1]

To a suspension of 4-[8-(1,2,3,6-tetrahydro-pyridin-4-yl)-[1,2,4]triazolo[1,5-a]pyridin-2-ylamino]-benzoic acid trifluoroacetic acid salt (5.00 g, 11.15 mmol) in dichloromethane (80 mL) was added triethylamine (5.13 mL, 36.80 mmol) and the reaction cooled to 0° C. To the reaction mixture was added a solution of 4,4,4-trifluoro-butyric acid (1.88 g, 11.71 mmol) in dichloromethane (20 mL). The resultant reaction mixture was warmed to room temperature and stirred for 18 hours before the further addition of a solution of 4,4,4-trifluoro-butyric acid (1.88 g, 11.71 mmol) in dichloromethane (5 mL) and stirred for 5 hours at room temperature. The reaction was quenched with water then diluted with a mixture of dichloromethane/water/acetonitrile. The suspension was loaded onto a SCX-2 cartridge and eluted with a mixture of dichloromethane/methanol/water/acetonitrile. The solution was concentrated in vacuo giving the title compound as a triethylamine salt. The salt was suspended in dioxane (160 mL) and water (40 mL) before being treated with SCX-2 resin (50 g). The mixture was stirred for 20 minutes before the suspension was filtered and the filtrate concentrated in vacuo. The resultant residue was taken up into 1M NaOH and washed with ethyl acetate (×3) then diethyl ether. The yellow aqueous phase was acidified with 1M HCl to pH 5, forming a precipitate. The precipitate was collected by filtration and washed with water then diethyl ether before being dried under reduced pressure. This gave the title compound as an off white solid (3.73 g, 73%). LCMS (Method 1) [M+H]$^+$ 460.3, R$_T$=3.14 min. $^1$H NMR (400 MHz, DMSO-d$_6$) δ 10.21 (s, 1H), 8.75 (dd, J=6.5, 1.1 Hz, 1H), 7.90 (d, J=8.6 Hz, 2H), 7.79 (dd, J=8.9, 2.3 Hz, 2H), 7.55 (t, J=7.6 Hz, 1H), 7.44-7.35 (m, 1H), 7.08 (t, J=7.1 Hz, 1H), 4.29 (dd, J=26.4, 3.5 Hz, 2H), 3.74 (dt, J=11.1, 5.7 Hz, 2H), 2.78-2.50 (m, 6H).

Example 2c

4-[2-(4-Carboxy-phenylamino)-[1,2,4]triazolo[1,5-a]pyridin-8-yl]-3,6-dihydro-2H-pyridine-1-carboxylic acid ethyl ester

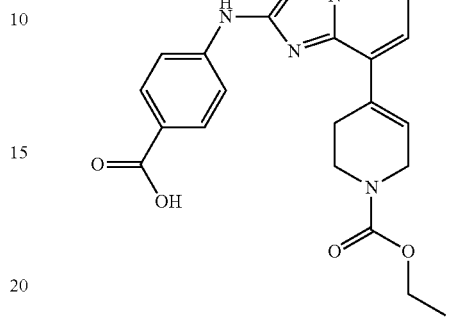

To a suspension of 4-[8-(1,2,3,6-tetrahydro-pyridin-4-yl)-[1,2,4]triazolo[1,5-a]pyridin-2-ylamino]-benzoic acid trifluoroacetic acid salt (10.00 g, 22.3 mmol) in dichloromethane (100 mL) was added N,N-diisopropylethylamine (19 mL, 111.5 mmol) and the reaction cooled to 0° C. To the reaction mixture was added a solution of ethyl chloroformate (2.4 g, 22.3 mmol) dropwise over 5 minutes. The resultant mixture was stirred at 0° C. for 1 h then evaporated under reduced pressure. The resultant residue was quenched with water and the resultant solid collected by filtration. The solid was washed with water, methanol and diethyl ether and left to air dry. The solid was purified by flash column chromatography on silica eluting with toluene on a gradient of acetic acid (10-20%). Appropriate fractions were collected and evaporated to afford a solid. The solid was triturated with methanol then diethyl ether to afford a white solid (6.2 g, 68%). $^1$H NMR (400 MHz, DMSO-d$_6$) δ 12.45 (s, 1H), 10.17 (s, 1H), 8.73 (dd, J=6.5, 1.1 Hz, 1H), 7.92-7.87 (m, 2H), 7.81-7.76 (m, 2H), 7.54 (t, dd =7.4, 1.0 Hz, 1H), 7.34 (brs, 1H), 7.07 (dd, J=7.5, 7.5 Hz, 1H), 4.18 (brs, 2H), 4.10 (dt, J=7.0, 7.0 Hz, 2H), 3.65 (t, J=5.6 Hz, 2H), 2.68-2.62 (m, 2H), 1.23 (t, J=7.1 Hz, 3H).

General Method for Preparation of Amides

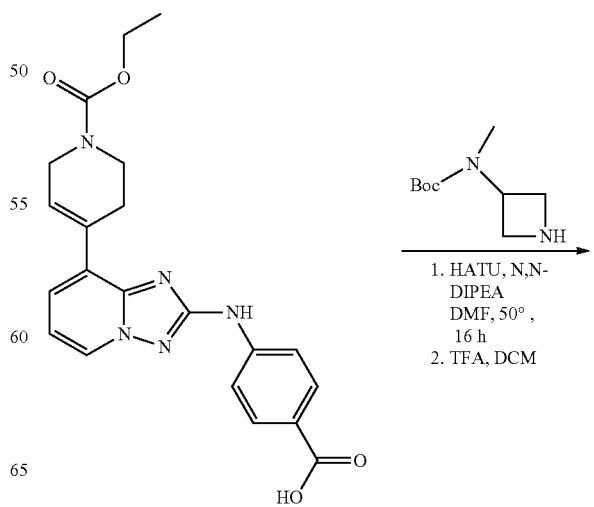

Example 2d

Ethyl 4-[2-[4-[3-(methylamino)azetidine-1-carbonyl]anilino]-[1,2,4]triazolo[1,5-a]pyridin-8-yl]-3,6-dihydro-2H-pyridine-1-carboxylate

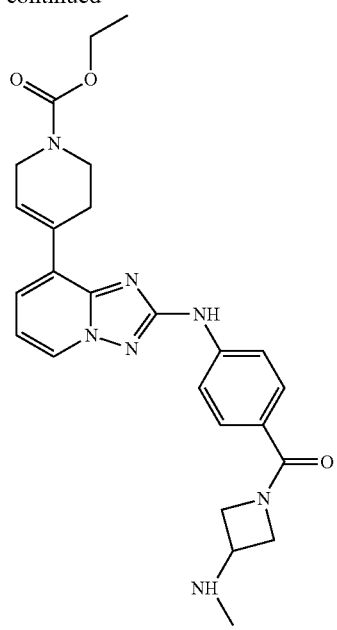

A solution of 4-[[8-(1-ethoxycarbonyl-3,6-dihydro-2H-pyridin-4-yl)-[1,2,4]triazolo[1,5-a]pyridin-2-yl]amino]benzoic acid (30 mg, 0.074 mmol, 1.0 equiv), tert-butyl azetidine-3-ylmethylcarbamate HCl (33 mg, 0.15 mmol, 2.0 equiv), HATU (42 mg, 0.11 mmol, 1.5 equiv) and N,N-diisopropylethylamine (65 uL, 0.37 mmol, 5.0 equiv) in DMF (1.0 mL) was stirred at 50° C. overnight. The reaction mixture was concentrated under vacuum. A solution of crude product in dichloromethane (1 mL) was mixed with trifluoroacetic acid (56 uL, 0.74 mmol, 10 equiv) and stirred at 50° C. overnight. The reaction was concentrated under vacuum and the crude product was purified by Prep-HPLC (Column, Gemini C18 100×30 mm; mobile phase, $CH_3CN:NH_4OH/H_2O$ (10 mmol/L)=5%-85%, 10 min; flow rate, 70 mL/min; Detector, UV 254 nm) to give 5.7 mg (16%) of Ethyl 4-[2-[4-[3 -(methylamino)azetidine-1-carbonyl]anilino]-[1,2,4]triazolo[1,5-a]pyridin-8-yl]-3,6-dihydro-2H-pyridine-1-carboxylate as an off white solid, (Example 2-55, Table II). $^1$H NMR (400 MHz, DMSO-$d_6$) δ 10.01 (s, 1H), 8.71 (dd, J=6.5, 1.1 Hz, 1H), 7.78-7.71 (m, 2H), 7.65-7.57 (m, 2H), 7.53 (d, J=7.4 Hz, 1H), 7.32 (s, 1H), 7.06 (t, J=7.0 Hz, 1H), 4.43 (s, 1H), 4.18 (s, 2H), 4.10 (q, J=7.0 Hz, 2H), 3.98 (s, 1H), 3.65 (t, J=5.7 Hz, 2H), 3.48 (s, 1H), 3.40-3.23 (m, 1H), 3.20-3.14 (m, 1H), 2.68-2.62 (m, 2H), 2.21 (s, 3H), 1.22 (t, J=7.1 Hz, 3H). LCMS (method 5): Found 476.3 [M+H]$^+$ Rt 3.8 min).

Example 2e 4-([8-[1-(1-cyanopropan-2-yl)-1,2,3,6-tetrahydropyridin-4-yl]-[1,2,4]triazolo [1,5-a]pyridin-2-yl] amino)-N-methyl-N-(1-methylpiperidin-4-yl)benzamide (Example 2-482 in Table II)

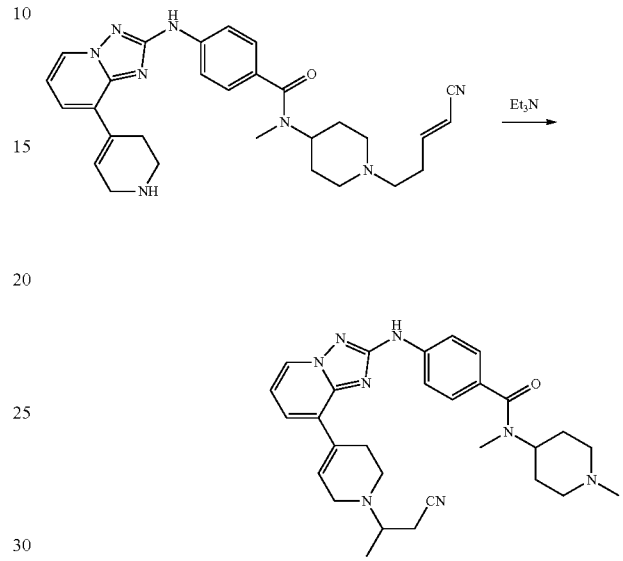

A mixture of triethylamine (49.96 mg, 0.494 mmol), N-methyl-N-(1-methylpiperidin-4-yl)-4-[[8-(1,2,3,6-tetrahydropyridin-4-yl)-[1,2,4]-triazolo[1,5-a]pyridin-2-yl]amino]benzamide (110 mg, 0.247 mmol), (2E)-but-2-enenitrile (33 mg, 0.494 mmol) in propane-1,2,3-triol (5 mL) was heated at 80° C. for 14 h. The resulting mixture was concentrated under vacuum and the residue was purified by flash chromatography on silica gel eluting with DCM/MeOH (10/1) to afford 15.6 mg (12%) of 4-([8-[1-(1-cyanopropan-2-yl)-1,2,3,6-tetrahydropyridin-4-yl]-[1,2,4]triazolo[1,5-a]pyridin-2-yl]-amino)-N-methyl-N-(1-methylpiperidin-4-yl)benzamide as a light yellow solid. $^1$H NMR (300 MHz, DMSO-$d_6$): δ 9.94 (s, 1H), 8.68 (d, J=6.0 Hz, 1H), 7.72 (d, J=8.7 Hz, 2H), 7.49 (d, J=7.2 Hz, 1H), 7.42 (s, 1H), 7.32 (d, J=8.7 Hz, 2H), 7.06-7.01 (m, 1H), 3.32-3.09 (m, 2H), 2.82-2.76 (m, 1H), 2.74-2.68 (m, 9H), 2.66-2.62 (m, 2H), 2.54-2.51 (m, 1H), 2.28-2.27 (m, 3H), 1.80-1.59 (m, 4H), 1.56-1.53 (m, 2H), 1.16-1.14 (m, 3H). LCMS (Method 7) $R_T$=2.48 min, m/z=513.0 [M+H]$^+$.

The immediately preceding Examples may be modified via conventionally known chemistries to provide access to other compounds that fall within the scope of the present invention, such as compounds of Formula 0, non-limiting examples of which are seen in Table II.

TABLE II

| Ex | R¹ᵃ—X ↘* | R⁸ | n | LCMS(ESI) m/z [M + H⁺] |
|---|---|---|---|---|
| 2-1 | N-methylpiperidin-4-yl(methyl)amino | ethyl 2-methylpropanoate-yl | 1 | 518 |
| 2-2 | " | cyclopropyl 2-methylpropanoate-yl | 1 | 530 |
| 2-3 | " | 4-hydroxy-4-methyl-2-oxopentan-2-yl | 1 | 546 |
| 2-4 | " | 1-cyclopropyl-3-oxobutan-2-yl | 1 | 528 |
| 2-5 | " | 1-(3-cyanoazetidin-1-yl)-2-methyl-1-oxopropan-2-yl | 1 | 554 |
| 2-6 | " | 4-cyano-2-methyl-3-oxobutan-2-yl | 1 | 485 |

TABLE II-continued
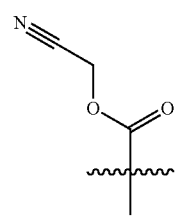 [SMILES: *C(=O)OCC#N]
| Ex | R$^{1a}$—X <br> ↘* | R$^8$ | n | LCMS(ESI) m/z [M + H$^+$] |
|---|---|---|---|---|
| 2-7 | " | 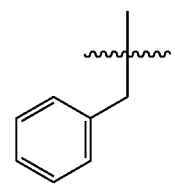 [SMILES: *Cc1ccccc1] | 1 | 529 |
| 2-8 | " | 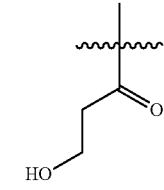 [SMILES: *C(=O)CCO] | 1 | 536 |
| 2-9 | " | 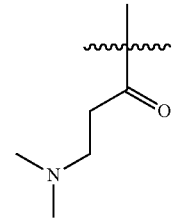 [SMILES: *C(=O)CCN(C)C] | 1 | 518 |
| 2-10 | " | 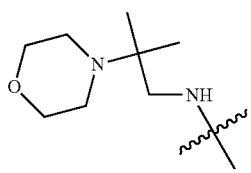 [SMILES: *NCC(C)(C)N1CCOCC1] | 1 | 545 |
| 2-11 | 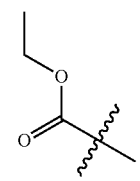 [SMILES: *C(=O)OCC] | 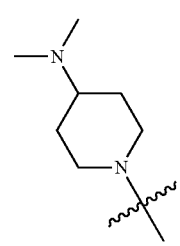 [SMILES: *N1CCC(N(C)C)CC1] | 1 | 548 |
| 2-12 |  | " | 1 | 518 |

TABLE II-continued
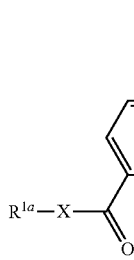
| Ex | R<sup>1a</sup>—X | R<sup>8</sup> | n | LCMS(ESI) m/z [M + H<sup>+</sup>] |
|---|---|---|---|---|
| 2-13 | 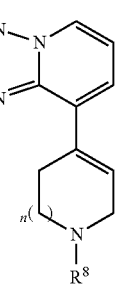 | " | 1 | 518 |
| 2-14 |  | " | 1 | 512 |
| 2-15 | 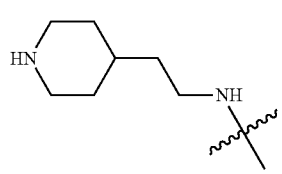 [SMILES: *NCCC1CCNCC1] | " | 1 | 538 |
| 2-16 | 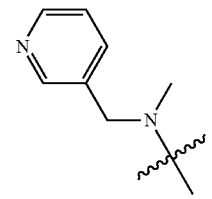 [SMILES: *N(C)Cc1cccnc1] | " | 1 | 566 |
| 2-17 | 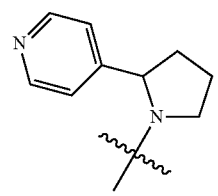 [SMILES: *N1CCCC1c1ccncc1] | " | 1 | 567 |

TABLE II-continued

| Ex | R¹ᵃ—X *→ | R⁸ | n | LCMS(ESI) m/z [M + H⁺] |
|---|---|---|---|---|
| 2-18 | (morpholin-4-yl-piperidin-1-yl) | " | 1 | 560 |
| 2-19 | (3-(pyridin-3-yl)piperazin-1-yl) | " | 1 | 553 |
| 2-20 | (6-(hydroxymethyl)-4-methyl-1,4-diazepan-1-yl) | " | 1 | 534 |
| 2-21 | (2-(1-methylpiperidin-2-yl)pyrrolidin-1-yl) | " | 1 | 558 |
| 2-22 | (2-(4-(dimethylamino)-6-methylpyridin-2-yl)pyrrolidin-1-yl) | " | 1 | 595 |
| 2-23 | (3-oxa-7,9-diazabicyclo) | " | 1 | 532 |

TABLE II-continued
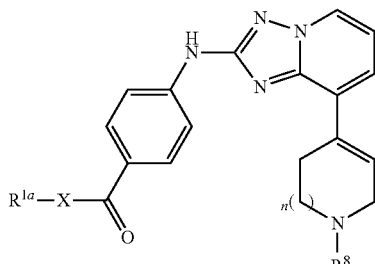
| Ex | R^{1a}—X—* | R^8 | n | LCMS(ESI) m/z [M + H^+] |
|---|---|---|---|---|
| 2-24 | 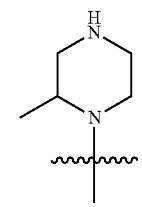 | " | 1 | 490 |
| 2-25 | 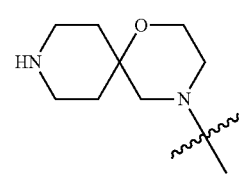 [SMILES: *N1CCOC2(CCNCC2)C1] | " | 1 | 546 |
| 2-26 | 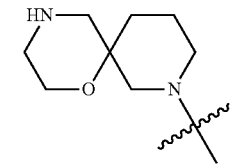 [SMILES: *N1CCCC2(CNCCO2)C1] | " | 1 | 546 |
| 2-27 | 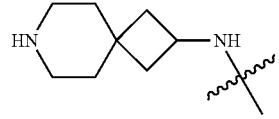 [SMILES: *NC1CC2(CCNCC2)C1] | " | 1 | 530 |
| 2-28 | 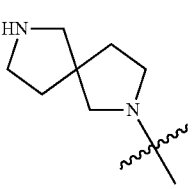 | 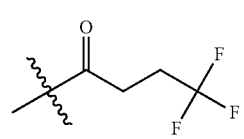 [SMILES: *C(=O)CCC(F)(F)F] | 1 | 568 |
| 2-29 | 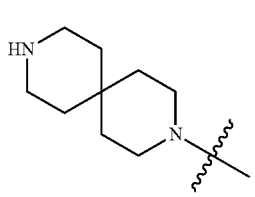 | " | 1 | 596 |
| 2-30 | 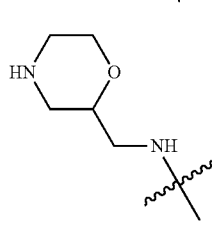 | " | 1 | 558 |

TABLE II-continued
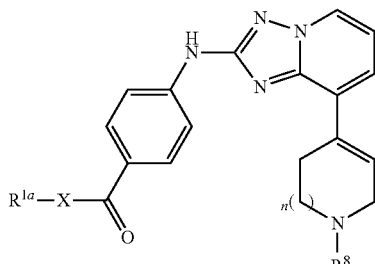
| Ex | R¹ᵃ—X ↘ * | R⁸ | n | LCMS(ESI) m/z [M + H⁺] |
|---|---|---|---|---|
| 2-31 | 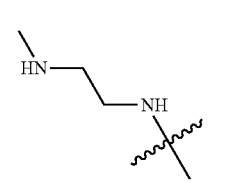 [SMILES: *NCCNC] | " | 1 | 516 |
| 2-32 | 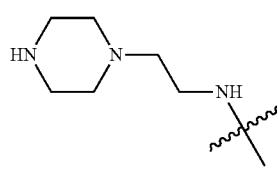 | " | 1 | 571 |
| 2-33 | 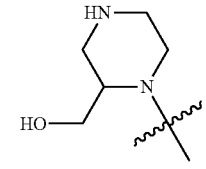 | " | 1 | 558 |
| 2-34 | 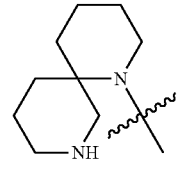 [SMILES: *N1CCCCC12CCCNC2] | " | 1 | 596 |
| 2-35 | 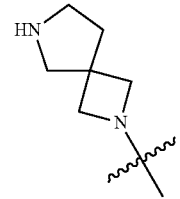 | " | 1 | 554 |
| 2-36 | 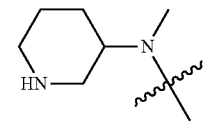 [SMILES: *N(C)C1CCCNC1] | " | 1 | 556 |
| 2-37 | 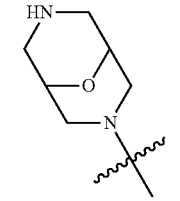 [SMILES: *N1CC2CNCC(C1)O2] | " | 1 | 570 |

TABLE II-continued

| Ex | R¹ᵃ—X ↘ * | R⁸ | n | LCMS(ESI) m/z [M + H⁺] |
|---|---|---|---|---|
| 2-38 | (octahydropyrrolo[3,4-b]pyrrole, N-methyl) | " | 1 | 568 |
| 2-39 | (1-ethylpyrrolidin-3-yl)methyl-N-methyl | " | 1 | 584 |
| 2-40 | (2-methyl-2,6-diazaspiro[3.4]octane) | " | 1 | 568 |
| 2-41 | (4-methylpyridin-2-yl)methyl-NH | " | 1 | 564 |
| 2-42 | (2-methylpyridin-3-yl)methyl-NH | " | 1 | 564 |
| 2-43 | 1-methyl-N-methyl-piperidin-4-amine | CH₃-C(O)-CH₂-CH(CF₃)- | 1 | 584 |

TABLE II-continued

| Ex | R¹ᵃ—X ↘ * | R⁸ | n | LCMS(ESI) m/z [M + H⁺] |
|---|---|---|---|---|
| 2-44 | | | 1 | 543 |
| 2-45 | | | 1 | 598 |
| 2-46 | | " | 1 | 596 |
| 2-47 | | " | 1 | 598 |
| 2-48 | | " | 1 | 570 |
| 2-49 | | " | 1 | 610 |
| 2-50 | | " | 1 | 618 |

TABLE II-continued
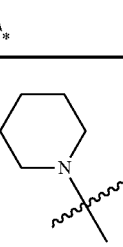
| Ex | R¹ᵃ—X ↘* | R⁸ | n | LCMS(ESI) m/z [M + H⁺] |
|---|---|---|---|---|
| 2-51 | 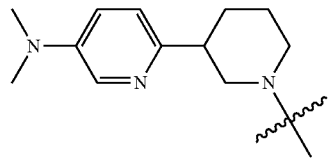 [SMILES: *N1CCCC(c2ccc(N(C)C)cn2)C1] | " | 1 | 647 |
| 2-52 | 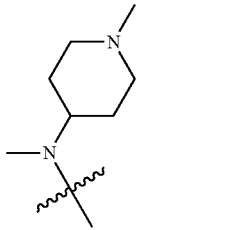 | 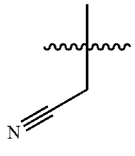 | 1 | 485 |
| 2-53 | " | 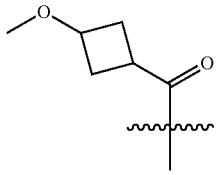 [SMILES: *C(=O)C1CC(OC)C1] | 1 | 558 |
| 2-54 | " | 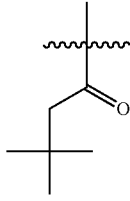 | 1 | 544 |
| 2-55 | 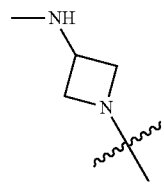 [SMILES: *N1CC(NC)C1] | 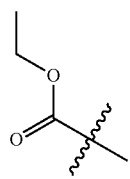 [SMILES: *C(=O)OCC] | 1 | 476 |
| 2-56 | 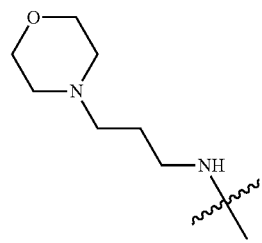 [SMILES: *NCCCN1CCOCC1] | " | 1 | 534 |

TABLE II-continued
| Ex | R^1a—X ↘ * | R^8 | n | LCMS(ESI) m/z [M + H^+] |
|---|---|---|---|---|
| 2-57 | 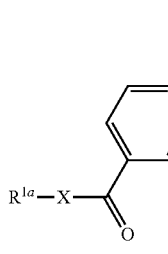 | " | 1 | 533 |
| 2-58 | 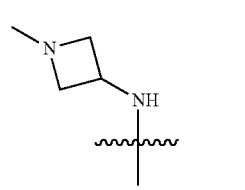 [SMILES: *NC1CN(C)C1] | " | 1 | 476 |
| 2-59 | 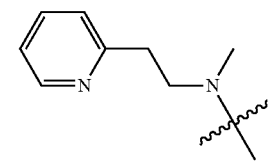 [SMILES: *N(C)CCc1ccccn1] | " | 1 | 526 |
| 2-60 | 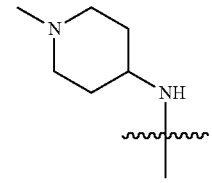 [SMILES: *NC1CCN(C)CC1] | " | 1 | 504 |
| 2-61 | 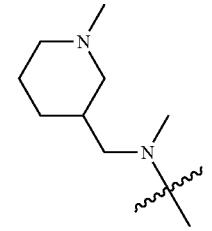 [SMILES: *N(C)CC1CCCN(C)C1] | " | 1 | 532 |
| 2-62 | 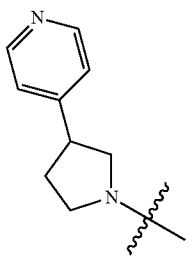 [SMILES: *N1CCC(c2ccncc2)C1] | " | 1 | 538 |

TABLE II-continued
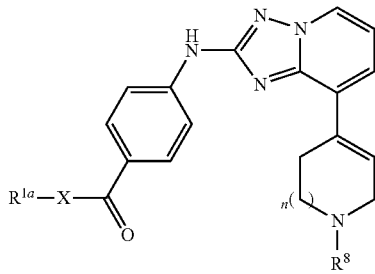
| Ex | R{1a}—X—* | R{8} | n | LCMS(ESI) m/z [M + H{+}] |
|---|---|---|---|---|
| 2-63 | 2,6-dimethylmorpholin-4-yl-piperidin-1-yl | " | 1 | 588 |
| 2-64 | 4-(2-morpholinoethyl)piperazin-1-yl | " | 1 | 589 |
| 2-65 | (1-isopropylpyrrolidin-3-yl)methyl(methyl)amino | " | 1 | 546 |
| 2-66 | 3-morpholinopyrrolidin-1-yl | " | 1 | 546 |
| 2-67 | 2-(5-methylpyridin-2-yl)pyrrolidin-1-yl | " | 1 | 552 |

TABLE II-continued

| Ex | R1a—X→* | R8 | n | LCMS(ESI) m/z [M + H+] |
|---|---|---|---|---|
| 2-68 | (1-methyl-2,6-diazaspiro[3.3]heptan-2-yl) | " | 1 | 516 |
| 2-69 | (quinuclidin-3-ylamino) | " | 1 | 516 |
| 2-70 | (6,7-dihydro-5H-pyrrolo[3,4-b]pyridin-6-yl) | " | 1 | 510 |
| 2-71 | (2-(aminomethyl)-2-methylpyrrolidin-1-yl) | " | 1 | 502 |
| 2-72 | (octahydropyrrolo[3,4-b][1,4]oxazin-4-yl) | " | 1 | 518 |
| 2-73 | (3-amino-3-methyl-bicyclic pyrrolidinyl) | " | 1 | 488 |

TABLE II-continued
| Ex | R¹ᵃ—X ↘* | R⁸ | n | LCMS(ESI) m/z [M + H⁺] |
|---|---|---|---|---|
| 2-74 |  | " | 1 | 462 |
| 2-75 | 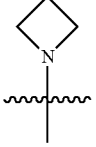 | " | 1 | 544 |
| 2-76 | 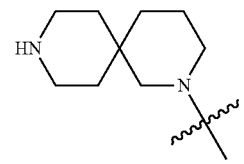 | " | 1 | 490 |
| 2-77 |  | " | 1 | 488 |
| 2-78 | 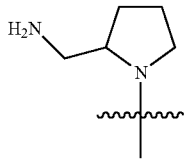 [SMILES: *N1CCCC1CN] | " | 1 | 516 |
| 2-79 |  | " | 1 | 530 |

TABLE II-continued
| Ex | R¹ᵃ—X ↓ * | R⁸ | n | LCMS(ESI) m/z [M + H⁺] |
|---|---|---|---|---|
| 2-80 | 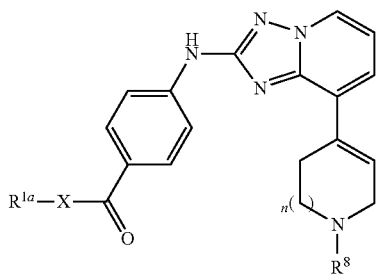 | 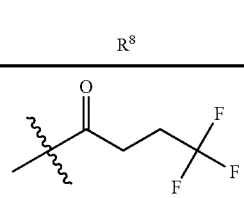 | 1 | 542 |
| 2-81 | 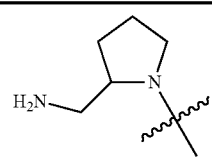 | " | 1 | 568 |
| 2-82 | 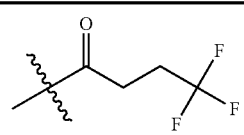 | " | 1 | 598 |
| 2-83 | 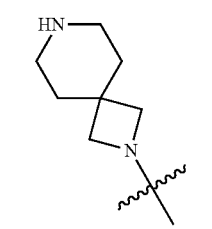 [SMILES: *N1CC2(CCNCC2)C1] | " | 1 | 612 |
| 2-84 | 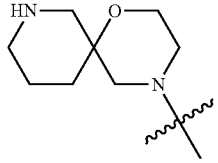 [SMILES: *N1CCOC2(CCCNC2)C1] | " | 1 | 556 |
| 2-85 | 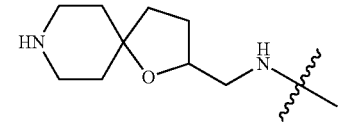 | " | 1 | 542 |
| 2-86 | 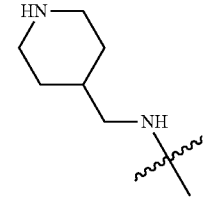 [SMILES: *NCC1CCNCC1] | " | 1 | 570 |

TABLE II-continued

| Ex | R¹ᵃ—X—* | R⁸ | n | LCMS(ESI) m/z [M + H⁺] |
|---|---|---|---|---|
| 2-87 | | " | 1 | 568 |
| 2-88 | | " | 1 | 598 |
| 2-89 | | " | 1 | 614 |
| 2-90 | | " | 1 | 662 |
| 2-91 | | " | 1 | 647 |
| 2-92 | | " | 1 | 647 |

TABLE II-continued
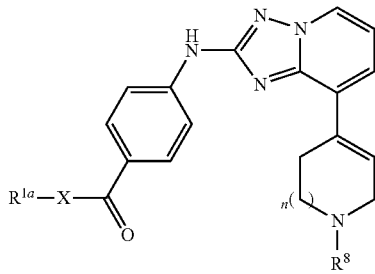
| Ex | R$^{1a}$—X<br>*  | R$^8$ | n | LCMS(ESI) m/z<br>[M + H$^+$] |
|---|---|---|---|---|
| 2-93 | 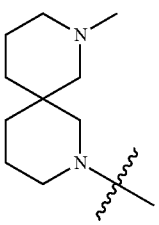 [SMILES: *N1CCCC2(CCCN(C)C2)C1] | " | 1 | 610 |
| 2-94 | 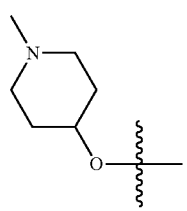 [SMILES: *OC1CCN(C)CC1] | 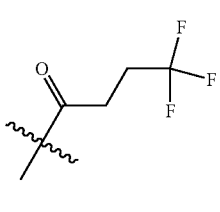 [SMILES: *C(=O)CCC(F)(F)F] | 1 | 505 |
| 2-95 | 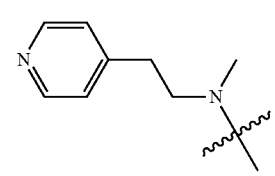 [SMILES: *N(C)CCc1ccncc1] | 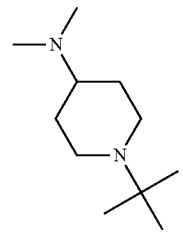 | 1 | 619 |
| 2-96 |  | " | 1 | 578 |
| 2-97 |  | " | 1 | 570 |

TABLE II-continued
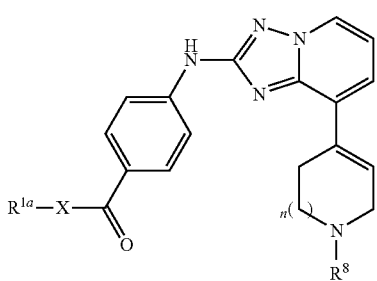
| Ex | R^1a—X ↘ * | R^8 | n | LCMS(ESI) m/z [M + H^+] |
|---|---|---|---|---|
| 2-98 | (4-methylpiperazin-1-yl)methyl | " | 1 | 542 |
| 2-99 | 3-(4-methylpiperazin-1-yl)propylamino | " | 1 | 599 |
| 2-100 | 2-(4-hydroxypiperidin-1-yl)ethylamino | " | 1 | 586 |
| 2-101 | 2-(3-methylpiperidin-1-yl)ethylamino | " | 1 | 584 |
| 2-102 | 4-(2-(dimethylamino)ethyl)piperazin-1-yl | " | 1 | 599 |
| 2-103 | 3-(1H-pyrrolo[2,3-b]pyridin-2-yl)piperidin-1-yl | " | 1 | 643 |

TABLE II-continued
| Ex | R¹ᵃ—X | R⁸ | n | LCMS(ESI) m/z [M + H⁺] |
|---|---|---|---|---|
| 2-104 |  | " | 1 | 640 |
| 2-105 | 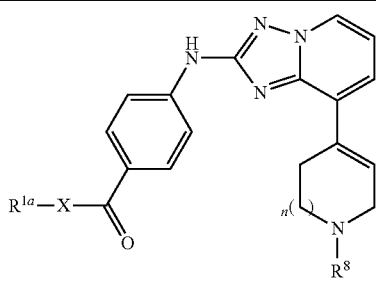 |  | 1 | 558 |
| 2-106 | " | 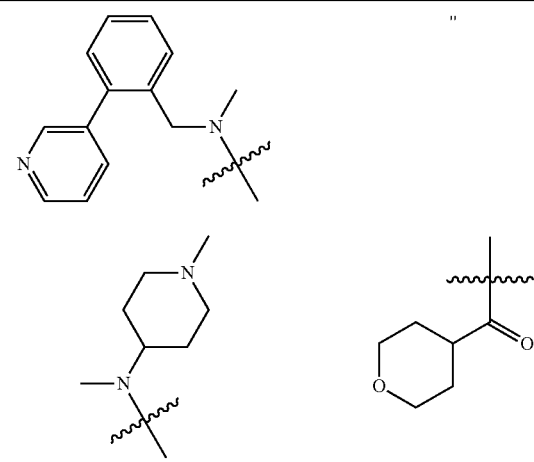 | 1 | 503 |
| 2-107 | " |  | 1 | 544 |
| 2-108 | " | 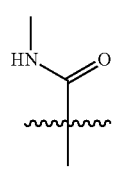 [SMILES: *C(=O)NC] | 1 | 572 |
| 2-109 | " | 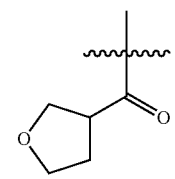 [SMILES: *C(=O)C1CCOC1] | 1 | 530 |

TABLE II-continued

| Ex | R1a—X ↓ * | R8 | n | LCMS(ESI) m/z [M + H+] |
|---|---|---|---|---|
| 2-110 | morpholine-CH2-C(CH3)2-NH- | ethyl 2-methylpropanoate | 1 | 548 |
| 2-111 | (1-methylpyrrolidin-2-yl)-CH2CH2-NH- | " | 1 | 518 |
| 2-112 | (piperazin-1-yl)-CH2CH2-NH- | " | 1 | 519 |
| 2-113 | (piperidin-3-yl)-NH- | " | 1 | 490 |
| 2-114 | (piperidin-2-yl)-CH2-NH- | " | 1 | 504 |
| 2-115 | N,N-dimethyl-azetidine-3-carboxamide | " | 1 | 518 |

TABLE II-continued
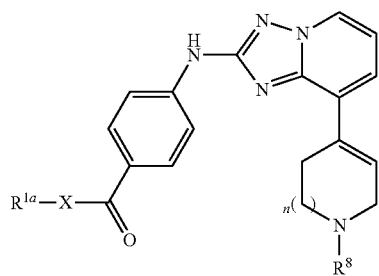
| Ex | R$^{1a}$—X $\overset{\downarrow}{*}$ | R$^8$ | n | LCMS(ESI) m/z [M + H$^+$] |
|---|---|---|---|---|
| 2-116 | [N-methylpiperidin-4-yl-ethyl-N(Me)-] | " | 1 | 532 |
| 2-117 | [1-benzylpyrrolidin-3-yl-N(Me)-] | " | 1 | 580 |
| 2-118 | [1-ethylpyrrolidin-3-yl-N(Et)-] | " | 1 | 532 |
| 2-119 | [pyridin-4-yl-ethyl-N(Me)-] | " | 1 | 526 |
| 2-120 | [2-oxa-5,8-diazaspiro group] | " | 1 | 532 |

TABLE II-continued
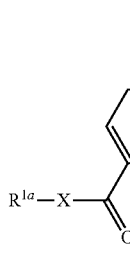
| Ex | R<sup>1a</sup>—X \*→ | R<sup>8</sup> | n | LCMS(ESI) m/z [M + H<sup>+</sup>] |
|---|---|---|---|---|
| 2-121 | 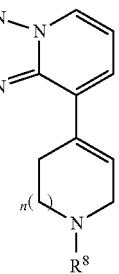 | " | 1 | 552 |
| 2-122 | 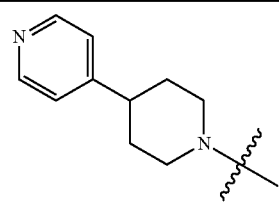 | " | 1 | 516 |
| 2-123 | 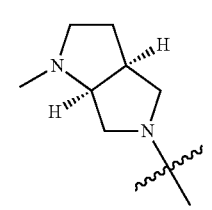 [SMILES: *N1C[C@@H]2CCN(C)[C@@H]2C1] | " | 1 | 532 |
| 2-124 | 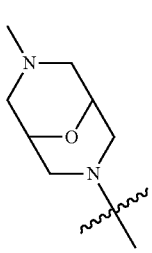 [SMILES: *N1CC2CN(C)CC(C1)O2] | " | 1 | 512 |
| 2-125 | 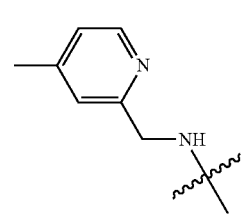 [SMILES: *NCc1cc(C)ccn1] | " | 1 | 532 |
| 2-126 | 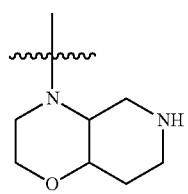 [SMILES: *N1CCOC2CCNCC21] | " | 1 | 502 |

TABLE II-continued
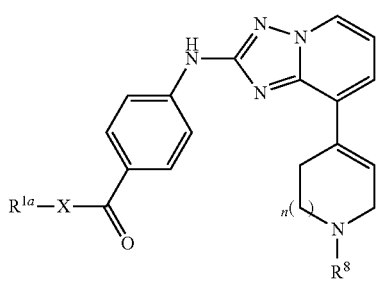
| Ex | $R^{1a}$—X (*) | $R^8$ | n | LCMS(ESI) m/z [M + H$^+$] |
|---|---|---|---|---|
| 2-127 | (octahydropyrrolo[3,4-b][1,4]oxazine) | " | 1 | 518 |
| 2-128 | (1-azaspiro[3.5]nonane with azetidine NH) | " | 1 | 516 |
| 2-129 | (piperazine) | " | 1 | 476 |
| 2-130 | (3-(aminomethyl)pyrrolidine) | " | 1 | 490 |
| 2-131 | (2,9-diazaspiro[5.5]undecane) | " | 1 | 544 |
| 2-132 | (2,9-diazaspiro[5.5]undecane isomer) | " | 1 | 544 |

TABLE II-continued
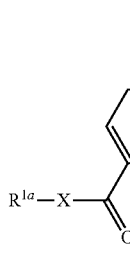
| Ex | R¹ᵃ—X | R⁸ | n | LCMS(ESI) m/z [M + H⁺] |
|---|---|---|---|---|
| 2-133 | 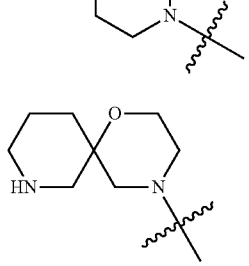 | " | 1 | 530 |
| 2-134 | 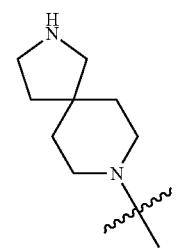 [SMILES: *N1CCC2(CCNC2)CC1] | " | 1 | 546 |
| 2-135 | 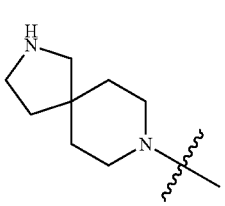 [SMILES: *N1CCC2(CCNC2)CC1] | " | 1 | 530 |
| 2-136 | 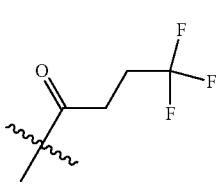 [SMILES: *C(=O)CCC(F)(F)F] | 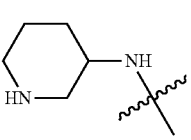 [SMILES: *NC1CCCNC1] | 1 | 582 |
| 2-137 | 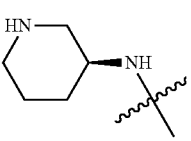 [SMILES: *N[C@H]1CCCNC1] | " | 1 | 542 |
| 2-138 | 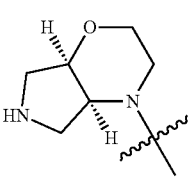 | " | 1 | 542 |
| 2-139 |  | " | 1 | 570 |

TABLE II-continued
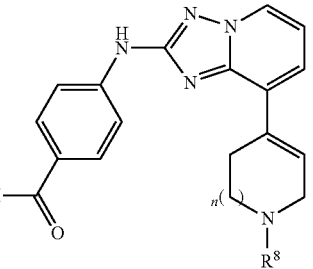
| Ex | R1a—X → * | R8 | n | LCMS(ESI) m/z [M + H+] |
|---|---|---|---|---|
| 2-140 | 3-(piperidin-3-yl)indolin-1-yl | " | 1 | 644 |
| 2-141 | (quinolin-8-ylmethyl)(methyl)amino | " | 1 | 614 |
| 2-142 | 4-(2-cyanoethyl)piperazin-1-yl | " | 1 | 581 |
| 2-143 | 2-(5-methylpyridin-2-yl)pyrrolidin-1-yl | " | 1 | 604 |
| 2-144 | 6-(hydroxymethyl)-4-methyl-1,4-diazepan-1-yl | " | 1 | 586 |

TABLE II-continued

| Ex | R¹ᵃ—X (*) | R⁸ | n | LCMS(ESI) m/z [M + H⁺] |
|---|---|---|---|---|
| 2-145 | pyrrolidine-pyridine group | " | 1 | 590 |
| 2-146 | pyrrolo-pyridine group | " | 1 | 562 |
| 2-147 | 4-methylpiperidine-ethyl-NH group | " | 1 | 584 |
| 2-148 | 6-methylpyridine-methyl-NH group | " | 1 | 564 |
| 2-149 | piperidine-N-methylpiperidine group | " | 1 | 624 |

TABLE II-continued
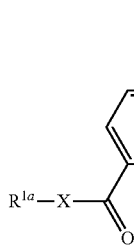
| Ex | R1a—X—* | R8 | n | LCMS(ESI) m/z [M + H+] |
|---|---|---|---|---|
| 2-150 | 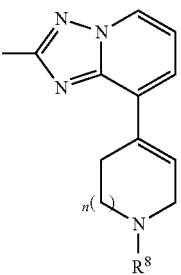 | " | 1 | 596 |
| 2-151 |  | " | 1 | 582 |
| 2-152 | 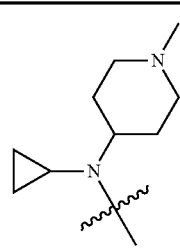 | " | 1 | 578 |
| 2-153 | 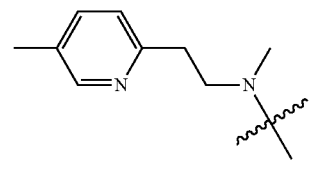 | " | 1 | 572 |
| 2-154 | 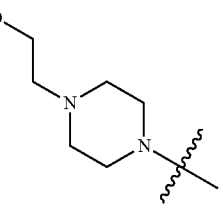 | " | 1 | 606 |
| 2-155 | 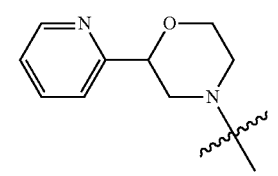 [SMILES: *N1CCOC(c2ccccn2)C1] | " | 1 | 643 |

TABLE II-continued
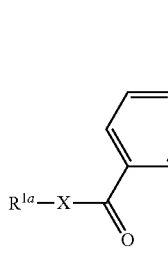
| Ex | R¹ᵃ—X—* | R⁸ | n | LCMS(ESI) m/z [M + H⁺] |
|---|---|---|---|---|
| 2-156 | 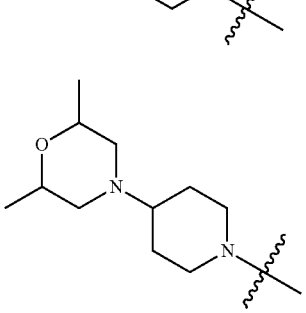 | " | 1 | 604 |
| 2-157 | 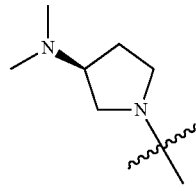 [SMILES: *N1CC[C@H](N(C)C)C1] | " | 1 | 640 |
| 2-158 | 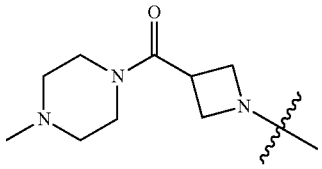 [SMILES: *N1CC(C(=O)N2CCN(C)CC2)C1] | " | 1 | 556 |
| 2-159 | 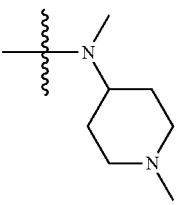 [SMILES: *N(C)C1CCN(C)CC1] | " | 1 | 625 |
| 2-160 | 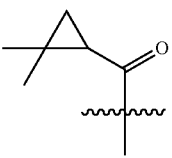 [SMILES: *C(=O)C1CC1(C)C] | 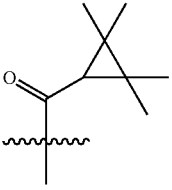 [SMILES: *C(=O)C1C(C)(C)C1(C)C] | 1 | 542 |
| 2-161 | " |  | 1 | 570 |

TABLE II-continued
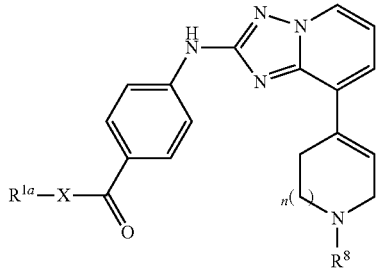
| Ex | R¹ᵃ—X ↘ * | R⁸ | n | LCMS(ESI) m/z [M + H⁺] |
|---|---|---|---|---|
| 2-162 | " | 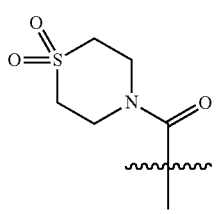 [SMILES: *C(=O)N1CCS(=O)(=O)CC1] | 1 | 607 |
| 2-163 | " | 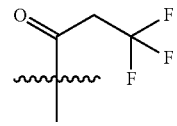 | 1 | 556 |
| 2-164 | " | 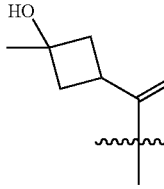 | 1 | 558 |
| 2-165 | 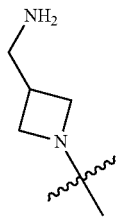 | 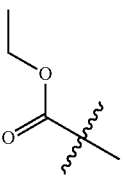 [SMILES: *C(=O)OCC] | 1 | 476 |
| 2-166 | 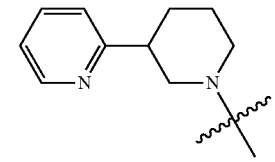 [SMILES: *N1CCCC(c2ccccn2)C1] | " | 1 | 552 |
| 2-167 | 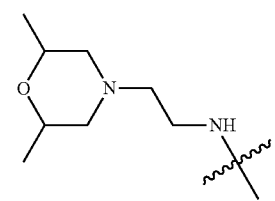 [SMILES: *NCCN1CC(C)OC(C)C1] | " | 1 | 548 |

TABLE II-continued
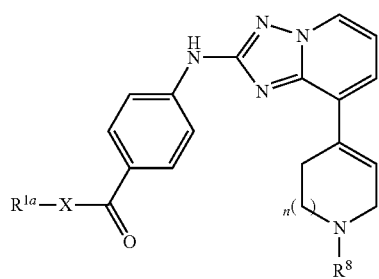
| Ex | R¹ᵃ—X—* | R⁸ | n | LCMS(ESI) m/z [M + H⁺] |
|---|---|---|---|---|
| 2-168 | HO-CH₂CH₂-piperazinyl- | " | 1 | 520 |
| 2-169 | (CH₃)₂N-CH₂CH₂-NH- | " | 1 | 478 |
| 2-170 | 6-methylpyridin-2-yl-CH(CH₃)-NH- | " | 1 | 526 |
| 2-171 | (pyridin-2-yl-CH₂)(cyclopropyl)N- | " | 1 | 538 |
| 2-172 | pyridin-4-yl-CH₂CH₂-NH- | " | 1 | 512 |

TABLE II-continued
| Ex | R¹ᵃ—X⸺* | R⁸ | n | LCMS(ESI) m/z [M + H⁺] |
|---|---|---|---|---|
| 2-173 | 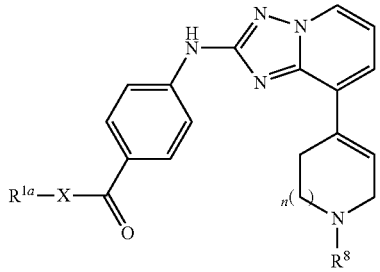 | " | 1 | 526 |
| 2-174 | 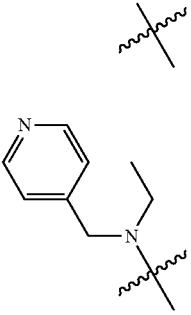 | " | 1 | 526 |
| 2-175 | 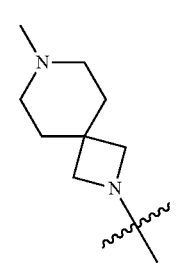 [SMILES: *N1CC2(CCN(C)CC2)C1] | " | 1 | 530 |
| 2-176 | 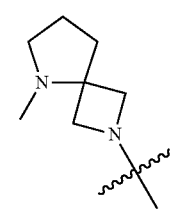 [SMILES: *N1CC2(CCCN2C)C1] | " | 1 | 516 |
| 2-177 | 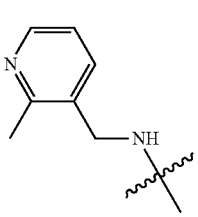 [SMILES: *NCc1cccnc1C] | " | 1 | 512 |

TABLE II-continued

| Ex | R¹ᵃ—X ↘ * | R⁸ | n | LCMS(ESI) m/z [M + H⁺] |
|---|---|---|---|---|
| 2-178 | (5-methylpyridin-3-yl)methyl-NH- | " | 1 | 512 |
| 2-179 | (4-methylpiperidin-1-yl)ethyl-NH- | " | 1 | 532 |
| 2-180 | 3-oxa-7,9-diazabicyclo[3.3.1]nonan-7-yl | " | 1 | 518 |
| 2-181 | 3,9-diazaspiro[5.5]undecan-3-yl | " | 1 | 544 |
| 2-182 | 1,8-diazaspiro[4.6]undecan-8-yl | " | 1 | 544 |
| 2-183 | 2,8-diazaspiro[4.5]decan-8-yl | " | 1 | 530 |

TABLE II-continued
| Ex | R¹ᵃ—X ↘* | R⁸ | n | LCMS(ESI) m/z [M + H⁺] |
|---|---|---|---|---|
| 2-184 | 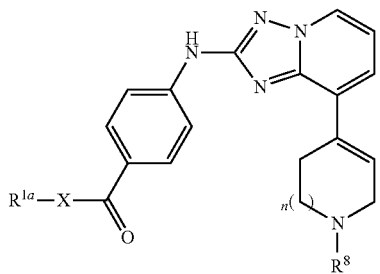 | " | 1 | 516 |
| 2-185 |  | " | 1 | 516 |
| 2-186 | 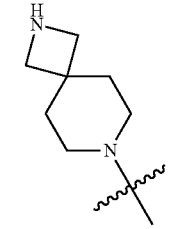 [SMILES: *N1CCC2(CC1)CNC2] |  | 1 | 568 |
| 2-187 | 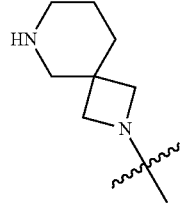 | " | 1 | 582 |
| 2-188 |  | " | 1 | 598 |
| 2-189 | 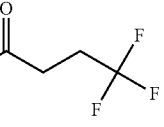 | " | 1 | 626 |

TABLE II-continued
| Ex | R$^{1a}$—X $\rightarrow$ * | R$^8$ | n | LCMS(ESI) m/z [M + H$^+$] |
|---|---|---|---|---|
| 2-190 | 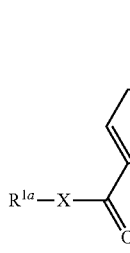 | " | 1 | 598 |
| 2-191 | 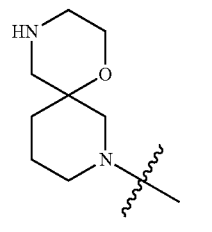 [SMILES: *N1CCCC2(CNCCO2)C1] | " | 1 | 596 |
| 2-192 | 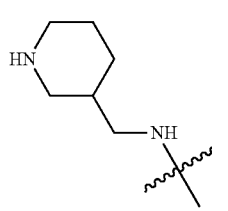 [SMILES: *NCC1CCCNC1] | " | 1 | 556 |
| 2-193 | 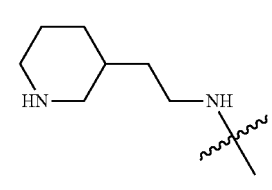 [SMILES: *NCCC1CCCNC1] | " | 1 | 570 |
| 2-194 | 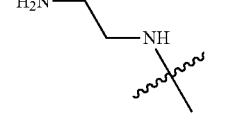 | " | 1 | 502 |
| 2-195 | 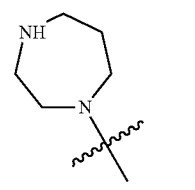 [SMILES: *N1CCCNCC1] | " | 1 | 542 |
| 2-196 | 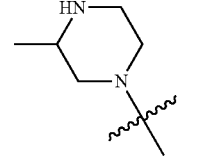 [SMILES: *N1CCNC(C)C1] | " | 1 | 542 |

TABLE II-continued
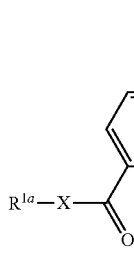
| Ex | R$^{1a}$—X $\overset{}{\underset{*}{\searrow}}$ | R$^8$ | n | LCMS(ESI) m/z [M + H$^+$] |
|---|---|---|---|---|
| 2-197 | 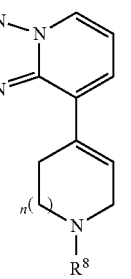 | " | 1 | 568 |
| 2-198 | 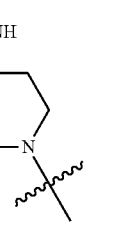 | " | 1 | 582 |
| 2-199 | 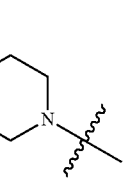 | " | 1 | 564 |
| 2-200 | 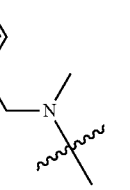 | " | 1 | 568 |
| 2-201 | 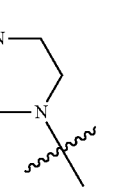 | " | 1 | 568 |
| 2-202 | 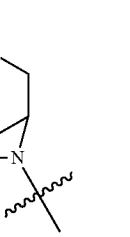 | " | 1 | 568 |

TABLE II-continued
| Ex | R1a—X * | R8 | n | LCMS(ESI) m/z [M + H+] |
|---|---|---|---|---|
| 2-203 | 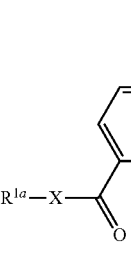 | " | 1 | 622 |
| 2-204 |  | " | 1 | 582 |
| 2-205 | 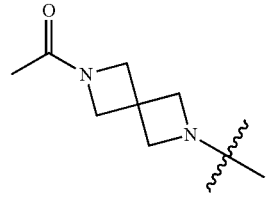 [SMILES: *N1CC2(C1)CN(C(C)=O)C2] | " | 1 | 584 |
| 2-206 |  | " | 1 | 564 |
| 2-207 | 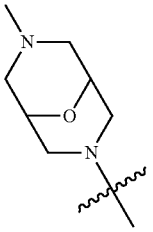 [SMILES: *N1CC2CN(C)CC(C1)O2] | " | 1 | 528 |

TABLE II-continued

| Ex | R¹ᵃ—X—* | R⁸ | n | LCMS(ESI) m/z [M + H⁺] |
|---|---|---|---|---|
| 2-208 | 4-methylpiperidinyl-piperidinyl | " | 1 | 624 |
| 2-209 | (2-methoxyethyl)(1-methylpiperidin-4-yl)amino | " | 1 | 614 |
| 2-210 | morpholinyl-piperidinyl | " | 1 | 612 |
| 2-211 | 3-(diethylamino)pyrrolidinyl | " | 1 | 584 |
| 2-212 | methyl(2-(pyridin-3-yl)ethyl)amino | " | 1 | 578 |
| 2-213 | (2-morpholino-2-methylpropyl)amino | " | 1 | 600 |

TABLE II-continued

| Ex | R¹ᵃ—X ↘* | R⁸ | n | LCMS(ESI) m/z [M + H⁺] |
|---|---|---|---|---|
| 2-214 | | " | 1 | 570 |
| 2-215 | | " | 1 | 618 |
| 2-216 | | " | 1 | 578 |
| 2-217 | | " | 1 | 648 |
| 2-218 | | " | 1 | 618 |
| 2-219 | | " | 1 | 578 |

TABLE II-continued

| Ex | R¹ᵃ—X↘* | R⁸ | n | LCMS(ESI) m/z [M + H⁺] |
|---|---|---|---|---|
| 2-220 | 3-pyridyl-CH₂CH₂-NH- | " | 1 | 564 |
| 2-221 | piperidin-2-yl-CH₂CH₂-NH- | " | 1 | 570 |
| 2-222 | 1-methylpiperidin-4-yl(methyl)amino- | benzyl-NH-C(O)- | 1 | 579 |
| 2-223 | " | 2-methylcyclopropane-1-carbonyl | 1 | 528 |
| 2-224 | " | methoxycarbonyl | 1 | 504 |
| 2-225 | " | 2,2-difluoroethoxycarbonyl | 1 | 554 |

TABLE II-continued
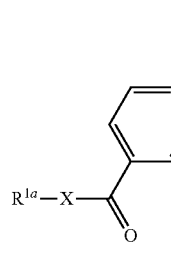
| Ex | R<sup>1a</sup>—X | R<sup>8</sup> | n | LCMS(ESI) m/z [M + H<sup>+</sup>] |
|---|---|---|---|---|
| 2-226 | 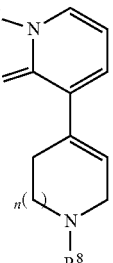 | 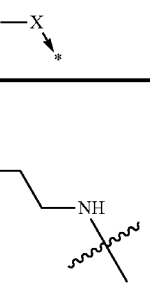 | 1 | 532 |
| 2-227 | 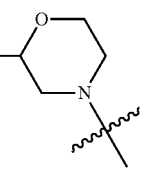 | " | 1 | 547 |
| 2-228 | 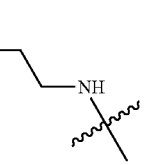 | " | 1 | 554 |
| 2-229 | 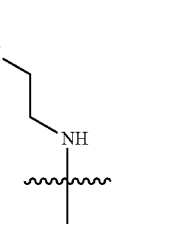 | " | 1 | 526 |
| 2-230 | 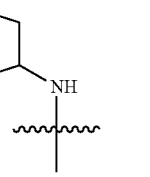 | " | 1 | 464 |
| 2-231 |  | " | 1 | 476 |

TABLE II-continued
| Ex | R1a—X—* | R8 | n | LCMS(ESI) m/z [M + H+] |
|---|---|---|---|---|
| 2-232 |  | " | 1 | 552 |
| 2-233 | 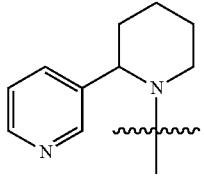 [SMILES: *N1CCCCC1c1cccnc1] | " | 1 | 490 |
| 2-234 | 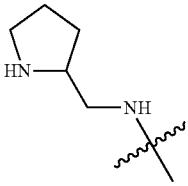 | " | 1 | 552 |
| 2-235 | 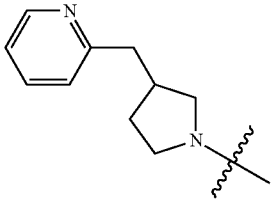 [SMILES: *N1CCC(Cc2ccccn2)C1] | " | 1 | 566 |
| 2-236 | 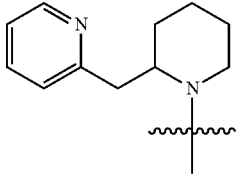 [SMILES: *N1CCCCC1Cc1ccccn1] | " | 1 | 534 |
| 2-237 | 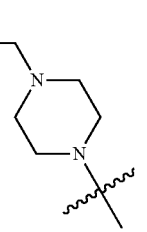 | " | 1 | 526 |

TABLE II-continued
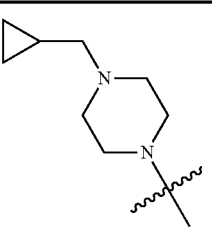
| Ex | R¹ᵃ—X ⤡ * | R⁸ | n | LCMS(ESI) m/z [M + H⁺] |
|---|---|---|---|---|
| 2-238 | 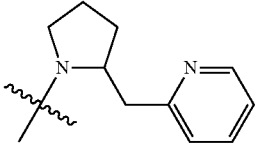 [SMILES: *N1CCCC1Cc1ccccn1] | " | 1 | 530 |
| 2-239 | 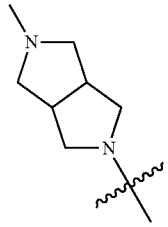 [SMILES: *N1CC2CN(C)CC2C1] | " | 1 | 552 |
| 2-240 | 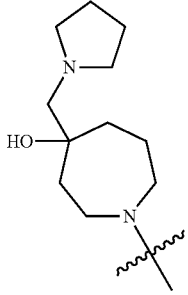 | " | 1 | 516 |
| 2-241 | 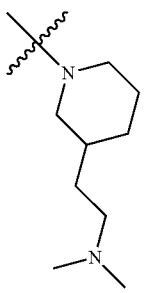 [SMILES: *N1CCCC(CCN(C)C)C1] | " | 1 | 588 |
| 2-242 |  | " | 1 | 546 |

TABLE II-continued
| Ex | R¹ᵃ—X ↘ * | R⁸ | n | LCMS(ESI) m/z [M + H⁺] |
|---|---|---|---|---|
| 2-243 |  | " | 1 | 561 |
| 2-244 | 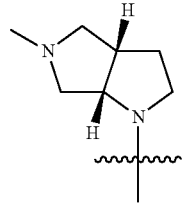 [SMILES: *N1CC[C@H]2CN(C)C[C@H]21] | " | 1 | 516 |
| 2-245 | 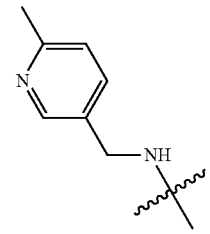 [SMILES: *NCc1ccc(C)nc1] | " | 1 | 512 |
| 2-246 | 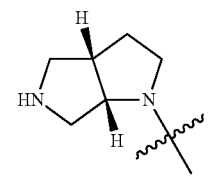 | " | 1 | 502 |
| 2-247 | 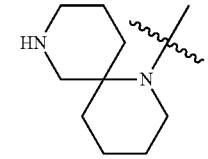 | " | 1 | 544 |
| 2-248 | 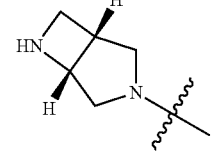 | " | 1 | 488 |

TABLE II-continued
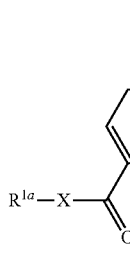
| Ex | R1a—X→* | R8 | n | LCMS(ESI) m/z [M + H+] |
|---|---|---|---|---|
| 2-249 | 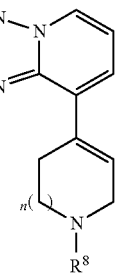 | " | 1 | 518 |
| 2-250 | 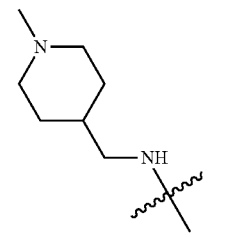 [SMILES: *NCC1CCN(C)CC1] | " | 1 | 490 |
| 2-251 |  | " | 1 | 553 |
| 2-252 | 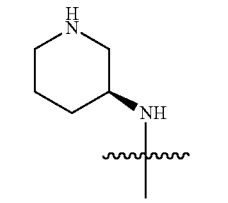 [SMILES: *N[C@H]1CCCNC1] | " | 1 | 544 |
| 2-253 |  | 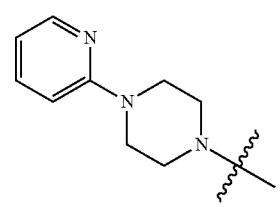 [SMILES: *N1CCN(c2ccccn2)CC1] | 1 | 582 |
| 2-254 |  | " | 1 | 598 |

TABLE II-continued
| Ex | R¹ᵃ—X ↘ * | R⁸ | n | LCMS(ESI) m/z [M + H⁺] |
|---|---|---|---|---|
| 2-255 | 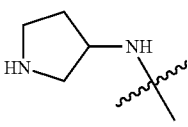 | " | 1 | 528 |
| 2-256 | 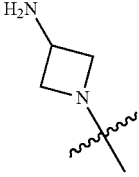 [SMILES: *N1CC(N)C1] | " | 1 | 514 |
| 2-257 | 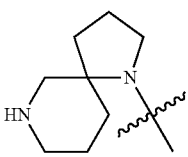 | " | 1 | 582 |
| 2-258 | 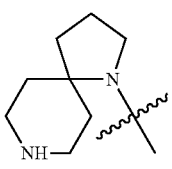 [SMILES: *N1CCCC12CCNCC2] | " | 1 | 582 |
| 2-259 | 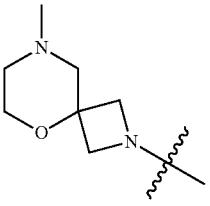 [SMILES: *N1CC2(C1)CN(C)CCO2] | " | 1 | 584 |
| 2-260 | 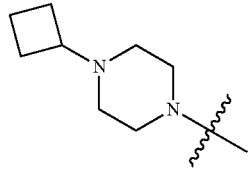 [SMILES: *N1CCN(C2CCC2)CC1] | " | 1 | 582 |

TABLE II-continued

| Ex | R¹ᵃ—X—* | R⁸ | n | LCMS(ESI) m/z [M + H⁺] |
|---|---|---|---|---|
| 2-261 | | " | 1 | 661 |
| 2-262 | | " | 1 | 655 |
| 2-263 | | | 1 | 542 |
| 2-264 | | | 1 | 557 |
| 2-265 | | " | 1 | 618 |
| 2-266 | | " | 1 | 584 |

TABLE II-continued

| Ex | R¹ᵃ—X ↓ * | R⁸ | n | LCMS(ESI) m/z [M + H⁺] |
|---|---|---|---|---|
| 2-267 | | " | 1 | 556 |
| 2-268 | | " | 1 | 600 |
| 2-269 | | " | 1 | 598 |
| 2-270 | | " | 1 | 585 |
| 2-271 | | " | 1 | 586 |
| 2-272 | | " | 1 | 590 |
| 2-273 | | " | 1 | 590 |

TABLE II-continued
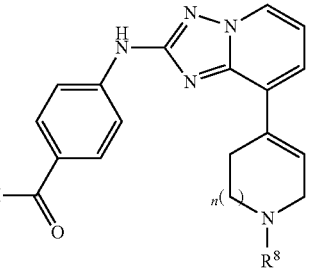
| Ex | R¹ᵃ—X—* | R⁸ | n | LCMS(ESI) m/z [M + H⁺] |
|---|---|---|---|---|
| 2-274 |  | " | 1 | 584 |
| 2-275 | 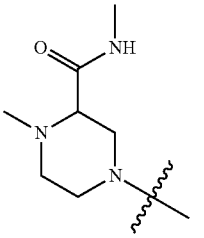 [SMILES: *N1CCN(C)C(C(=O)NC)C1] | " | 1 | 599 |
| 2-276 | 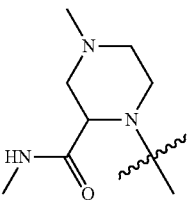 [SMILES: *N1CCN(C)CC1C(=O)NC] | " | 1 | 599 |
| 2-277 | 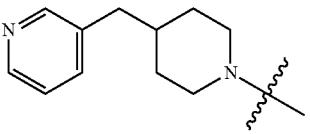 [SMILES: *N1CCC(Cc2cccnc2)CC1] | " | 1 | 618 |
| 2-278 | 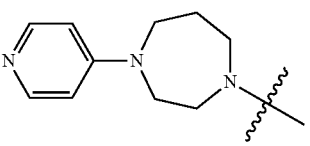 [SMILES: *N1CCCN(c2ccncc2)CC1] | " | 1 | 619 |
| 2-279 | 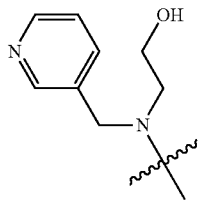 [SMILES: *N(CCO)Cc1cccnc1] | " | 1 | 594 |

TABLE II-continued
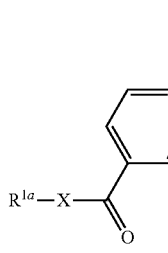
| Ex | R¹ᵃ—X ↘ * | R⁸ | n | LCMS(ESI) m/z [M + H⁺] |
|---|---|---|---|---|
| 2-280 | 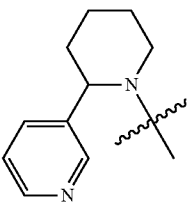 [SMILES: *N1CCCCC1c1cccnc1] | " | 1 | 604 |
| 2-281 | 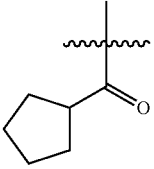 [SMILES: *C(=O)C1CCCC1] | 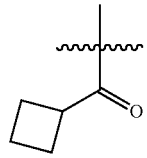 [SMILES: *C(=O)C1CCC1] | 1 | 542 |
| 2-282 | " | 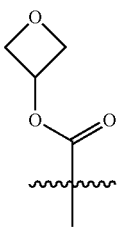 [SMILES: *C(=O)OC1COC1] | 1 | 528 |
| 2-283 | " | 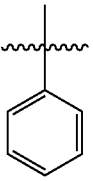 [SMILES: *c1ccccc1] | 1 | 546 |
| 2-284 | " | 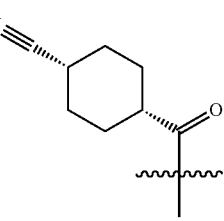 | 1 | 522 |
| 2-285 | " |  | 1 | 581 |

TABLE II-continued

| Ex | R¹ᵃ—X | R⁸ | n | LCMS(ESI) m/z [M + H⁺] |
|---|---|---|---|---|
| 2-286 | " | (2-oxa-6-azaspiro[3.3]heptane carbonyl group) | 1 | 571 |
| 2-287 | " | (3-cyanopropanoyl group) | 1 | 527 |
| 2-288 | " | (4,4,4-trifluorobutanoyl group) | 1 | 570 |
| 2-289 | " | (butanoyl group) | 1 | 516 |
| 2-290 | " | (3,3-dimethylazetidine-1-carbonyl group) | 1 | 556 |
| 2-291 | (3-(4-methylpiperazin-1-yl)propylamino group) | (ethyl 2-methylpropanoate group) | 1 | 547 |

TABLE II-continued

| Ex | R¹ᵃ—X ⌇* | R⁸ | n | LCMS(ESI) m/z [M + H⁺] |
|---|---|---|---|---|
| 2-292 | | " | 1 | 504 |
| 2-293 | | " | 1 | 518 |
| 2-294 | | " | 1 | 518 |
| 2-295 | | " | 1 | 560 |
| 2-296 | | " | 1 | 490 |
| 2-297 | | " | 1 | 567 |

TABLE II-continued
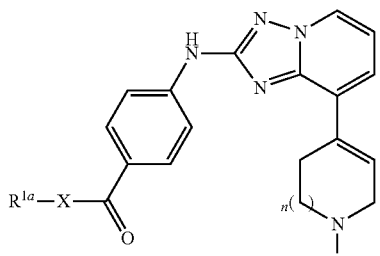
| Ex | R$^{1a}$—X $\overset{}{\underset{*}{\searrow}}$ | R$^8$ | n | LCMS(ESI) m/z [M + H$^+$] |
|---|---|---|---|---|
| 2-298 | 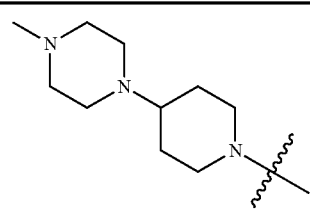 | " | 1 | 573 |
| 2-299 | 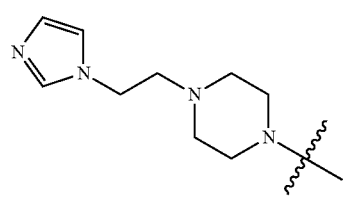 [SMILES: *N1CCN(CCn2ccnc2)CC1] | " | 1 | 570 |
| 2-300 | 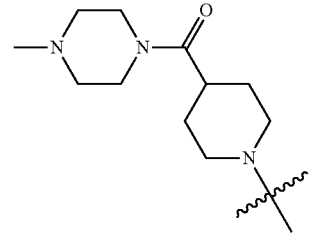 [SMILES: *N1CCC(C(=O)N2CCN(C)CC2)CC1] | " | 1 | 601 |
| 2-301 | 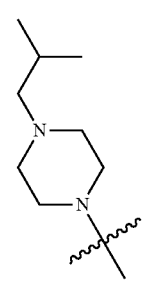 [SMILES: *N1CCN(CC(C)C)CC1] | " | 1 | 532 |
| 2-302 | 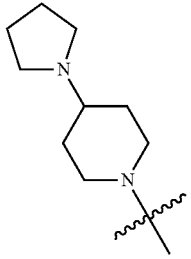 [SMILES: *N1CCC(N2CCCC2)CC1] | " | 1 | 544 |

TABLE II-continued

| Ex | R¹ᵃ—X ↓ * | R⁸ | n | LCMS(ESI) m/z [M + H⁺] |
|---|---|---|---|---|
| 2-303 | (cyclopropyl-N-(1-methylpiperidin-4-yl) group) | " | 1 | 544 |
| 2-304 | (dimethylaminomethyl-hydroxy-azepane group) | " | 1 | 562 |
| 2-305 | (1-ethylpyrrolidin-3-yl)methyl-N-methyl group | " | 1 | 532 |
| 2-306 | (6-azaspiro[2.5]octane-methylamino group) | " | 1 | 530 |
| 2-307 | (4-aminomethylpiperidin-1-yl group) | " | 1 | 504 |
| 2-308 | (octahydropyrrolo[3,4-b]pyrrole group) | " | 1 | 502 |

TABLE II-continued

| Ex | R¹ᵃ—X ↘ * | R⁸ | n | LCMS(ESI) m/z [M + H⁺] |
|---|---|---|---|---|
| 2-309 | (oxa-diazaspiro with HN and N-*) | " | 1 | 546 |
| 2-310 | (diazaspiro[4.4] with HN and N-*) | " | 1 | 516 |
| 2-311 | (diazaspiro[4.4] with NH and N-*) | " | 1 | 516 |
| 2-312 | (diazaspiro with NH-piperidine and N-*) | " | 1 | 530 |
| 2-313 | (octahydropyrrolo[3,4-c]pyrrole with HN and N-*) | —C(O)CH₂CH₂CF₃ | 1 | 554 |
| 2-314 | (azaspiro azetidine-piperidine with HN and N-*) | " | 1 | 568 |

TABLE II-continued
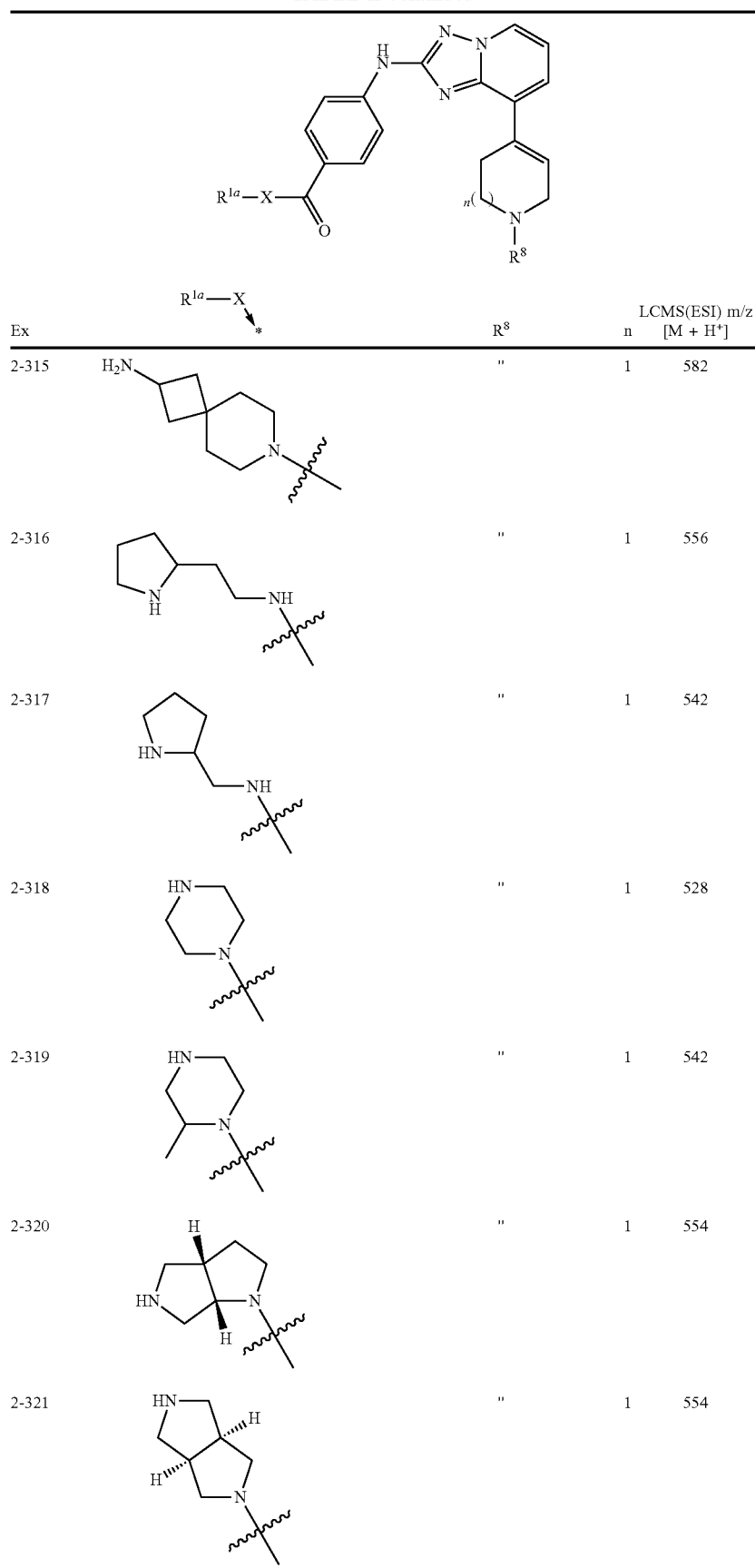
| Ex | R¹ᵃ—X ⟶ * | R⁸ | n | LCMS(ESI) m/z [M + H⁺] |
|---|---|---|---|---|
| 2-315 | H₂N–[spiro] | " | 1 | 582 |
| 2-316 | pyrrolidine-CH₂CH₂-NH- | " | 1 | 556 |
| 2-317 | pyrrolidine-CH₂-NH- | " | 1 | 542 |
| 2-318 | piperazine | " | 1 | 528 |
| 2-319 | 2-methylpiperazine | " | 1 | 542 |
| 2-320 | octahydropyrrolo[3,2-b]pyrrole | " | 1 | 554 |
| 2-321 | octahydropyrrolo[3,4-b]pyrrole | " | 1 | 554 |

TABLE II-continued
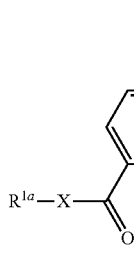
| Ex | R¹ᵃ—X<br>↘* | R⁸ | n | LCMS(ESI) m/z<br>[M + H⁺] |
|---|---|---|---|---|
| 2-322 | 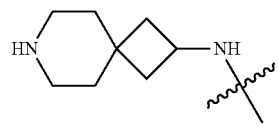 | " | 1 | 582 |
| 2-323 | 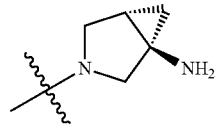 [SMILES: *N1C[C@@H]2C[C@]2(N)C1] | " | 1 | 540 |
| 2-324 | 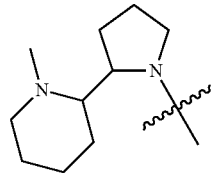 [SMILES: *N1CCCC1C1CCCCN1C] | " | 1 | 610 |
| 2-325 | 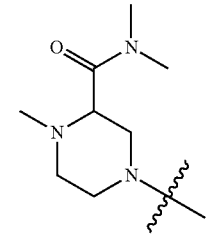 | " | 1 | 613 |
| 2-326 | 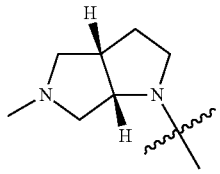 [SMILES: *N1CC[C@H]2CN(C)C[C@H]21] | " | 1 | 568 |
| 2-327 | 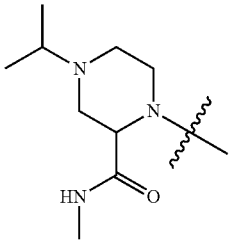 [SMILES: *N1CCN(C(C)C)CC1C(=O)NC] | " | 1 | 627 |

TABLE II-continued

| Ex | R¹ᵃ—X ↘* | R⁸ | n | LCMS(ESI) m/z [M + H⁺] |
|---|---|---|---|---|
| 2-328 | | " | 1 | 568 |
| 2-329 | | " | 1 | 610 |
| 2-330 | | " | 1 | 598 |
| 2-331 | | " | 1 | 586 |
| 2-332 | | " | 1 | 612 |
| 2-333 | | " | 1 | 600 |
| 2-334 | | " | 1 | 584 |

TABLE II-continued
| Ex | R1a—X ↘ * | R8 | n | LCMS(ESI) m/z [M + H+] |
|---|---|---|---|---|
| 2-335 | 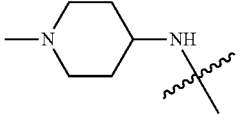 [SMILES: *NC1CCN(C)CC1] | " | 1 | 556 |
| 2-336 |  | " | 1 | 530 |
| 2-337 | 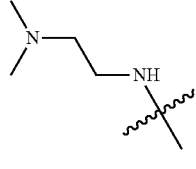 [SMILES: *NCCN(C)C] | " | 1 | 570 |
| 2-338 |  | " | 1 | 590 |
| 2-339 | 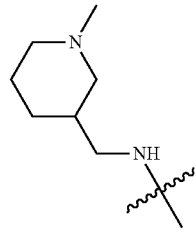 [SMILES: *NCC1CCCN(C)C1] | " | 1 | 612 |
| 2-340 |  | " | 1 | 612 |

TABLE II-continued
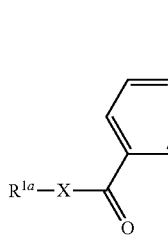
| Ex | R1a—X ↘ * | R8 | n | LCMS(ESI) m/z [M + H+] |
|---|---|---|---|---|
| 2-341 | 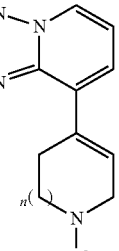 | " | 1 | 604 |
| 2-342 | 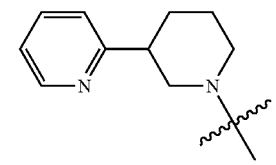 [SMILES: *N1CCCC(c2ccccn2)C1] | " | 1 | 675 |
| 2-343 | 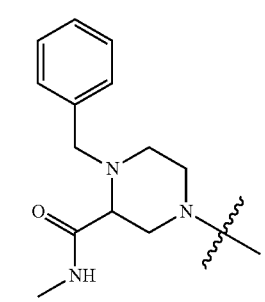 [SMILES: *N1CCN(Cc2ccccc2)C(C(=O)NC)C1] | " | 1 | 564 |
| 2-344 | 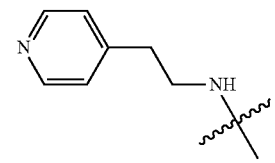 [SMILES: *NCCc1ccncc1] | 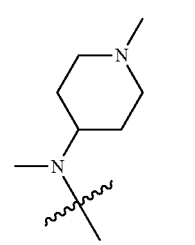 | 1 | 488 |
| 2-345 | " | 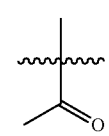 [SMILES: *C(C)=O] | 1 | 530 |

TABLE II-continued

| Ex | R¹ᵃ—X ↘ * | R⁸ | n | LCMS(ESI) m/z [M + H⁺] |
|---|---|---|---|---|
| 2-346 | " | (tetrahydrofuran-3-yl ester group) | 1 | 560 |
| 2-347 | " | (3,3-dimethylcyclobutyl ketone group) | 1 | 556 |
| 2-348 | " | (cyclohexyl ketone group) | 1 | 556 |
| 2-349 | " | (propyl ester group) | 1 | 532 |
| 2-350 | " | (4-cyanocyclohexyl ketone group) | 1 | 581 |
| 2-351 | " | (benzyl ester group) | 1 | 580 |

TABLE II-continued
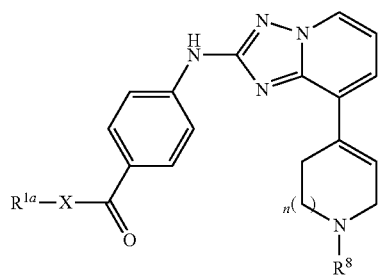
| Ex | R$^{1a}$—X $\overset{}{*}$ | R$^8$ | n | LCMS(ESI) m/z [M + H$^+$] |
|---|---|---|---|---|
| 2-352 | " | (pentan-1-oyl, methyl) | 1 | 530 |
| 2-353 | " | (cyclopropylmethyl ester, methyl) | 1 | 544 |
| 2-354 | 4-methylpiperazin-1-yl | (ethyl ester, dimethyl) | 1 | 490 |
| 2-355 | 2-(dimethylamino)-1-methylethylamino | " | 1 | 492 |
| 2-356 | 1,4-diazepan-1-yl | " | 1 | 490 |

TABLE II-continued
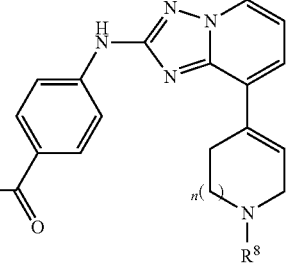
| Ex | R¹ᵃ—X ↘ * | R⁸ | n | LCMS(ESI) m/z [M + H⁺] |
|---|---|---|---|---|
| 2-357 | 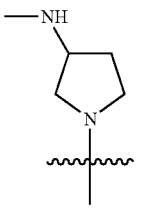 [SMILES: *N1CCC(NC)C1] | " | 1 | 490 |
| 2-358 | 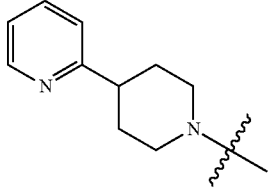 [SMILES: *N1CCC(c2ccccn2)CC1] | " | 1 | 552 |
| 2-359 | 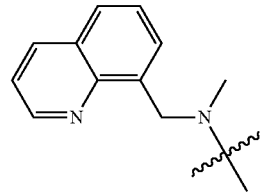 [SMILES: *N(C)Cc1cccc2cccnc12] | " | 1 | 562 |
| 2-360 | 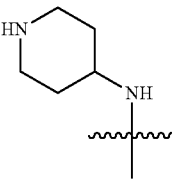 | " | 1 | 490 |
| 2-361 | 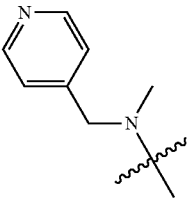 [SMILES: *N(C)Cc1ccncc1] | " | 1 | 512 |
| 2-362 | 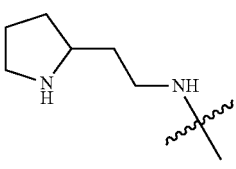 [SMILES: *NCCC1CCCN1] | " | 1 | 504 |

TABLE II-continued
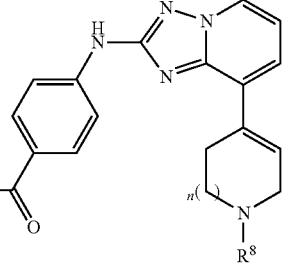
| Ex | R<sup>1a</sup>—X | R<sup>8</sup> | n | LCMS(ESI) m/z [M + H<sup>+</sup>] |
|---|---|---|---|---|
| 2-363 | 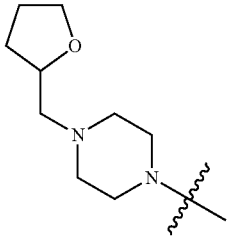 [SMILES: *N1CCN(CC2CCCO2)CC1] | " | 1 | 560 |
| 2-364 | 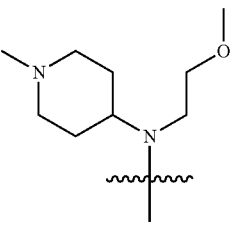 | " | 1 | 562 |
| 2-365 | 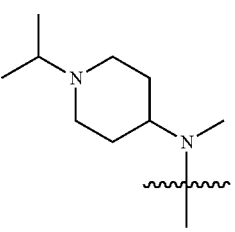 [SMILES: *N(C)C1CCN(C(C)C)CC1] | " | 1 | 546 |
| 2-366 | 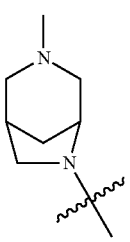 [SMILES: *N1CC2CC1CN(C)C2] | " | 1 | 516 |
| 2-367 | 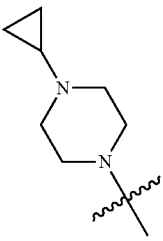 [SMILES: *N1CCN(C2CC2)CC1] | " | 1 | 516 |

TABLE II-continued

| Ex | R¹ᵃ—X ↘* | R⁸ | n | LCMS(ESI) m/z [M + H⁺] |
|---|---|---|---|---|
| 2-368 | | " | 1 | 530 |
| 2-369 | | " | 1 | 558 |
| 2-370 | | " | 1 | 538 |
| 2-371 | | " | 1 | 502 |
| 2-372 | | " | 1 | 502 |
| 2-373 | | " | 1 | 530 |

TABLE II-continued
| Ex | R¹ᵃ—X—* | R⁸ | n | LCMS(ESI) m/z [M + H⁺] |
|---|---|---|---|---|
| 2-374 |  | " | 1 | 464 |
| 2-375 |  | " | 1 | 502 |
| 2-376 | 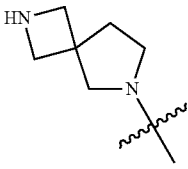 [SMILES: *N1CCC2(CNC2)C1] | " | 1 | 530 |
| 2-377 |  | 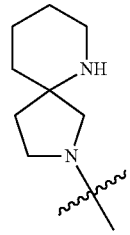 | 1 | 568 |
| 2-378 |  | " | 1 | 582 |
| 2-379 | 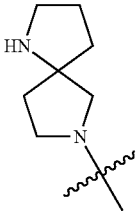 | " | 1 | 554 |

TABLE II-continued
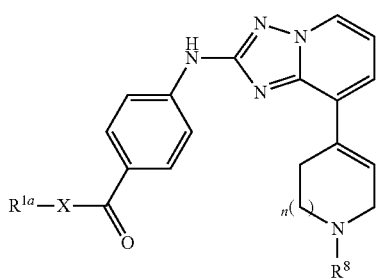
| Ex | R$^{1a}$—X $\overset{\searrow}{*}$ | R$^8$ | n | LCMS(ESI) m/z [M + H$^+$] |
|---|---|---|---|---|
| 2-380 | | " | 1 | 598 |
| 2-381 | | " | 1 | 582 |
| 2-382 | | " | 1 | 596 |
| 2-383 | | " | 1 | 596 |
| 2-384 | | " | 1 | 596 |
| 2-385 | | " | 1 | 556 |

TABLE II-continued
| Ex | R1a—X ↓ * | R8 | n | LCMS(ESI) m/z [M + H+] |
|---|---|---|---|---|
| 2-386 | 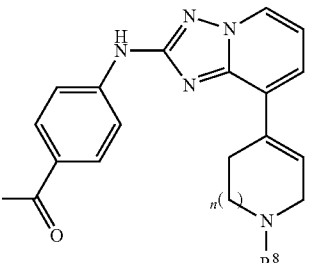 | " | 1 | 554 |
| 2-387 | 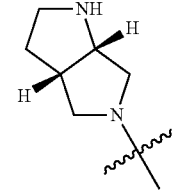 | " | 1 | 554 |
| 2-388 | 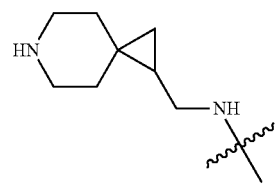 [SMILES: *NCC1CC12CCNCC2] | " | 1 | 582 |
| 2-389 | 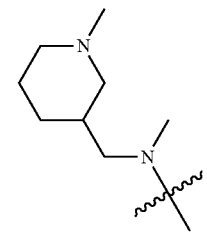 [SMILES: *N(C)CC1CCCN(C)C1] | " | 1 | 584 |
| 2-390 | 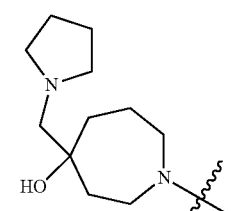 | " | 1 | 640 |
| 2-391 | 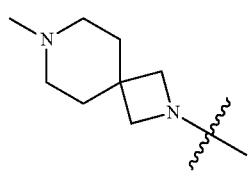 [SMILES: *N1CC2(CCN(C)CC2)C1] | " | 1 | 582 |

TABLE II-continued
| Ex | R<sup>1a</sup>—X<sub>*</sub> | R<sup>8</sup> | n | LCMS(ESI) m/z [M + H<sup>+</sup>] |
|---|---|---|---|---|
| 2-392 | 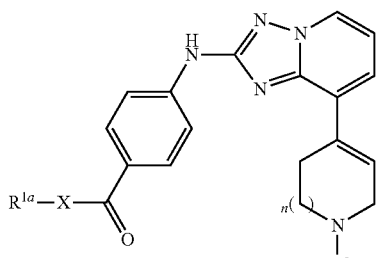 | " | 1 | 540 |
| 2-393 |  | " | 1 | 625 |
| 2-394 | 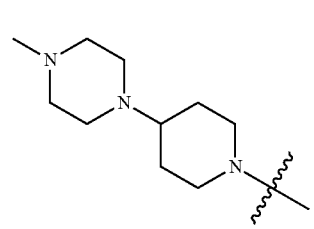 [SMILES: *N1CCC(N2CCN(C)CC2)CC1] | " | 1 | 619 |
| 2-395 |  | " | 1 | 605 |
| 2-396 | 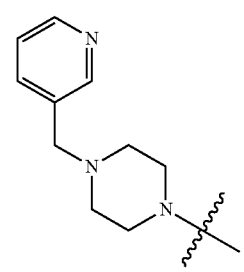 [SMILES: *N1CCN(Cc2cccnc2)CC1] | " | 1 | 604 |

TABLE II-continued

| Ex | R¹ᵃ—X—* | R⁸ | n | LCMS(ESI) m/z [M + H⁺] |
|---|---|---|---|---|
| 2-397 | 2-pyridyl-piperazinyl | " | 1 | 605 |
| 2-398 | cyclopropylmethyl-piperazinyl | " | 1 | 582 |
| 2-399 | (dimethylamino)propan-2-ylamino | " | 1 | 544 |
| 2-400 | (1-propylpiperidin-4-yl)(cyclopropyl)amino | " | 1 | 624 |
| 2-401 | 1-(6-methylpyridin-2-yl)ethylamino | " | 1 | 578 |
| 2-402 | N-methyl-N-(pyridin-3-ylmethyl)amino | " | 1 | 564 |

TABLE II-continued
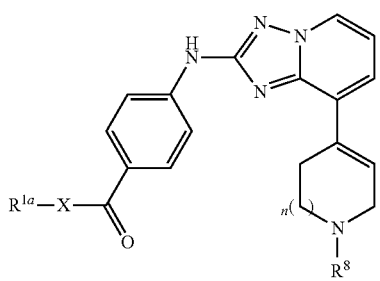
| Ex | R1a—X ↘ * | R8 | n | LCMS(ESI) m/z [M + H+] |
|---|---|---|---|---|
| 2-403 | ![azepan-piperidine] | " | 1 | 624 |
| 2-404 | ![pyridin-2-ylmethyl-piperidine] | " | 1 | 618 |
| 2-405 | ![pyridin-3-ylmethyl-pyrrolidine] | " | 1 | 604 |
| 2-406 | ![dimethylamino-phenyl-N-methyl] | " | 1 | 606 |
| 2-407 | ![pyridin-4-ylmethyl-N-methyl] | " | 1 | 564 |
| 2-408 | ![1-methylpiperidin-4-yl-N-methyl] | ![phenyl ketone] | 1 | 488 |

TABLE II-continued
| Ex | R$^{1a}$—X $\rightarrow$ * | R$^8$ | n | LCMS(ESI) m/z [M + H$^+$] |
|---|---|---|---|---|
| 2-409 | " | 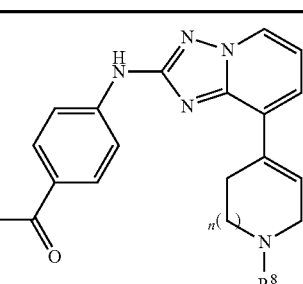 | 1 | 514 |
| 2-410 | " | 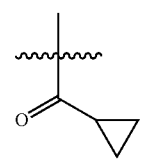 [SMILES: *C(=O)C1CC1] | 1 | 516 |
| 2-411 | " | 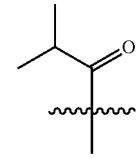 [SMILES: *C(=O)C(C)C] | 1 | 532 |
| 2-412 | " | 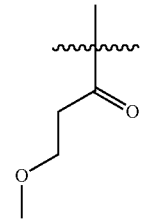 | 1 | 544 |
| 2-413 | " | 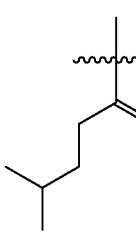 | 1 | 559 |
| 2-414 | 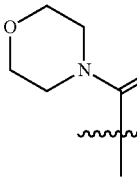 | 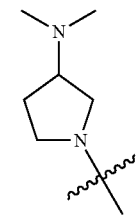 [SMILES: *N1CCC(N(C)C)C1] | 1 | 504 |

TABLE II-continued
| Ex | R1a—X 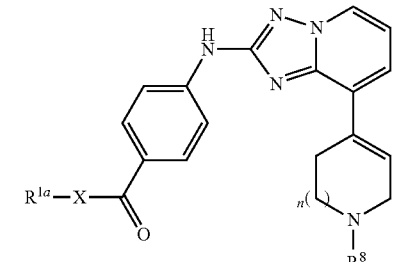 | R8 | n | LCMS(ESI) m/z [M + H+] |
|---|---|---|---|---|
| 2-415 | 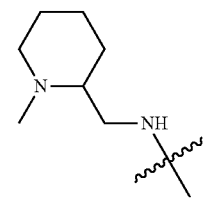 [SMILES: *NCC1CCCCN1C] | " | 1 | 518 |
| 2-416 | 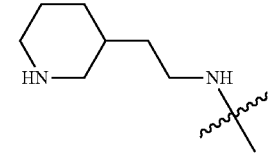 [SMILES: *NCCC1CCCNC1] | " | 1 | 518 |
| 2-417 | 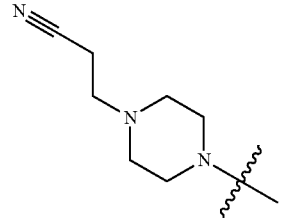 [SMILES: *N1CCN(CCC#N)CC1] | " | 1 | 529 |
| 2-418 | 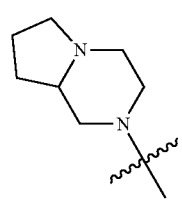 [SMILES: *N1CCN2CCCC2C1] | " | 1 | 516 |
| 2-419 | 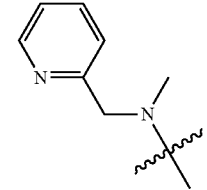 [SMILES: *N(C)Cc1ccccn1] | " | 1 | 512 |
| 2-420 | 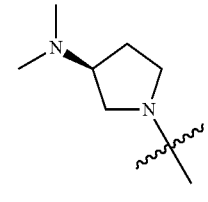 [SMILES: *N1CC[C@H](N(C)C)C1] | " | 1 | 504 |

TABLE II-continued
| Ex | R1a—X—* | R8 | n | LCMS(ESI) m/z [M + H+] |
|---|---|---|---|---|
| 2-421 | 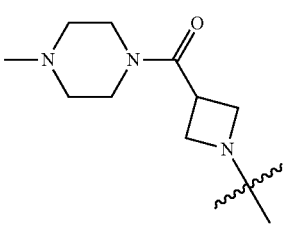 [SMILES: *N1CC(C(=O)N2CCN(C)CC2)C1] | " | 1 | 573 |
| 2-422 |  | " | 1 | 512 |
| 2-423 | 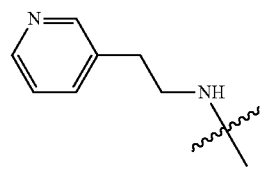 [SMILES: *NCCc1cccnc1] | " | 1 | 512 |
| 2-424 |  | " | 1 | 552 |
| 2-425 | 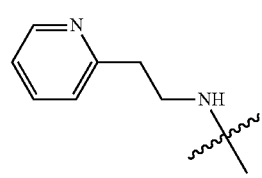 | " | 1 | 504 |
| 2-426 |  | " | 1 | 552 |

TABLE II-continued

| Ex | R¹ᵃ—X ↘ * | R⁸ | n | LCMS(ESI) m/z [M + H⁺] |
|---|---|---|---|---|
| 2-427 | piperidin-3-ylmethylamino | " | 1 | 504 |
| 2-428 | 2-(piperidin-2-yl)ethylamino | " | 1 | 518 |
| 2-429 | 4-(pyridin-4-yl)-1,4-diazepan-1-yl | " | 1 | 567 |
| 2-430 | octahydro-2H-pyrido[1,2-a]pyrazin-2-yl | " | 1 | 530 |
| 2-431 | 4-methyl-N,N-dimethyl-piperazine-2-carboxamide | " | 1 | 561 |

TABLE II-continued
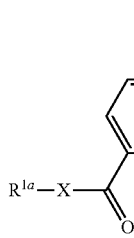
| Ex | R¹ª—X ↗ * | R⁸ | n | LCMS(ESI) m/z [M + H⁺] |
|---|---|---|---|---|
| 2-432 | 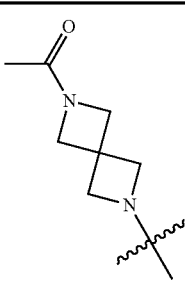 | " | 1 | 530 |
| 2-433 | 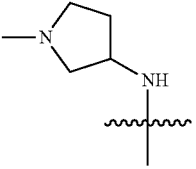 [SMILES: *NC1CCN(C)C1] | " | 1 | 490 |
| 2-434 | 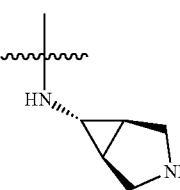 | " | 1 | 488 |
| 2-435 | 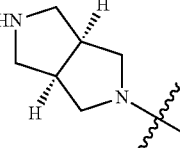 | " | 1 | 502 |
| 2-436 | 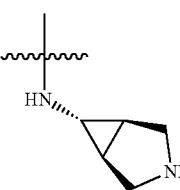 | " | 1 | 530 |
| 2-437 | 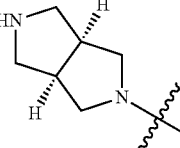 | " | 1 | 516 |

TABLE II-continued
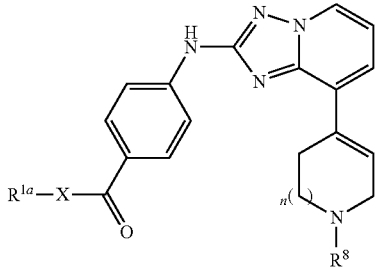
| Ex | R<sup>1a</sup>—X ⤷ * | R<sup>8</sup> | n | LCMS(ESI) m/z [M + H<sup>+</sup>] |
|---|---|---|---|---|
| 2-438 | | " | 1 | 504 |
| 2-439 | | " | 1 | 530 |
| 2-440 | | | 1 | 568 |
| 2-441 | | " | 1 | 516 |
| 2-442 | | " | 1 | 612 |
| 2-443 | | " | 1 | 596 |

TABLE II-continued
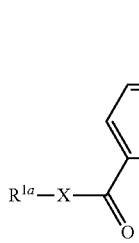
| Ex | R¹ᵃ—X ↘* | R⁸ | n | LCMS(ESI) m/z [M + H⁺] |
|---|---|---|---|---|
| 2-444 | 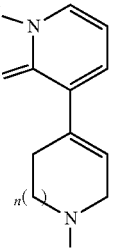 | " | 1 | 542 |
| 2-445 | 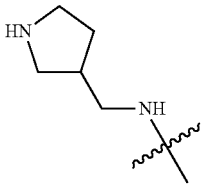 [SMILES: *NCC1CCNC1] | " | 1 | 542 |
| 2-446 | 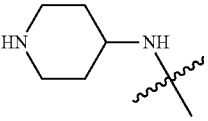 | " | 1 | 556 |
| 2-447 | 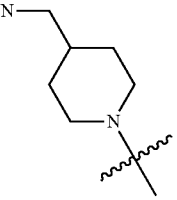 | " | 1 | 542 |
| 2-448 | 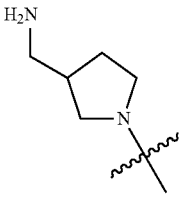 | " | 1 | 570 |
| 2-449 | 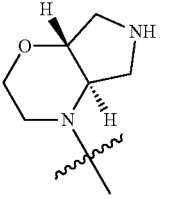 [SMILES: *N1CCO[C@@H]2CNC[C@H]21] | " | 1 | 540 |

TABLE II-continued
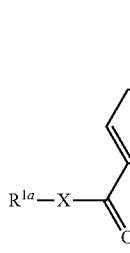
| Ex | R<sup>1a</sup>—X | R<sup>8</sup> | n | LCMS(ESI) m/z [M + H<sup>+</sup>] |
|---|---|---|---|---|
| 2-450 | 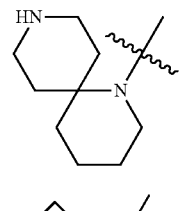 | " | 1 | 596 |
| 2-451 | 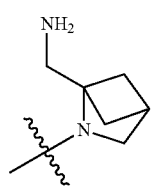 [SMILES: *N1CC2CC1(CN)C2] | " | 1 | 528 |
| 2-452 | 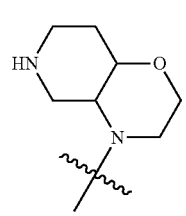 [SMILES: *N1CCOC2CCNCC21] | " | 1 | 554 |
| 2-453 | 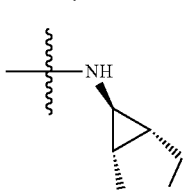 | " | 1 | 584 |
| 2-454 | 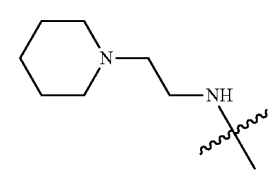 | " | 1 | 540 |
| 2-455 | 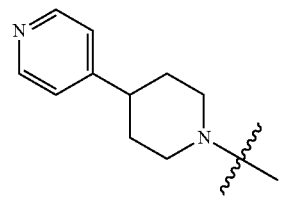 [SMILES: *N1CCC(c2ccncc2)CC1] | " | 1 | 570 |
| 2-456 |  | " | 1 | 604 |

TABLE II-continued
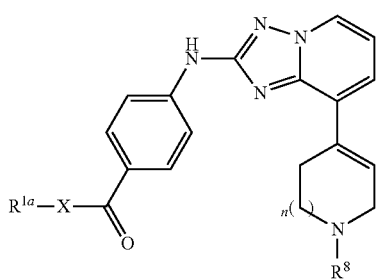
| Ex | R¹ᵃ—X ↘* | R⁸ | n | LCMS(ESI) m/z [M + H⁺] |
|---|---|---|---|---|
| 2-457 | | " | 1 | 613 |
| 2-458 | | " | 1 | 584 |
| 2-459 | | " | 1 | 542 |
| 2-460 | | " | 1 | 614 |
| 2-461 | | " | 1 | 624 |
| 2-462 | | " | 1 | 622 |

TABLE II-continued
| Ex | R¹ᵃ—X ↘* | R⁸ | n | LCMS(ESI) m/z [M + H⁺] |
|---|---|---|---|---|
| 2-463 | 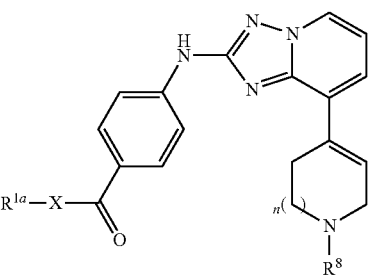 | " | 1 | 598 |
| 2-464 |  | " | 1 | 556 |
| 2-465 | 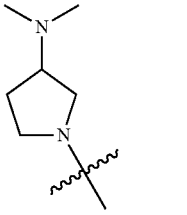 [SMILES: *N1CCC(N(C)C)C1] | " | 1 | 572 |
| 2-466 |  | " | 1 | 556 |
| 2-467 | 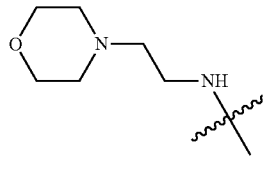 [SMILES: *NCCN1CCOCC1] | " | 1 | 570 |
| 2-468 | 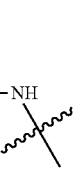 | " | 1 | 618 |

TABLE II-continued

| Ex | R¹ᵃ—X \* | R⁸ | n | LCMS(ESI) m/z [M + H⁺] |
|---|---|---|---|---|
| 2-469 | (3-aminoquinuclidinyl) | " | 1 | 568 |
| 2-470 | (1-phenethyl-piperazine-2-carboxamide N-methyl) | " | 1 | 689 |
| 2-471 | (3-(pyridin-2-ylmethyl)pyrrolidinyl) | " | 1 | 604 |
| 2-472 | (3-(N-benzyl-N-methylamino)piperidinyl) | " | 1 | 646 |
| 2-473 | (1-benzyl-3-(N-methylamino)pyrrolidinyl) | " | 1 | 632 |
| 2-474 | (4-(2-morpholinoethyl)piperazinyl) | " | 1 | 641 |

TABLE II-continued

| Ex | R¹ᵃ—X—* | R⁸ | n | LCMS(ESI) m/z [M + H⁺] |
|---|---|---|---|---|
| 2-475 | | " | 1 | 653 |
| 2-476 | | " | 1 | 578 |
| 2-477 | | " | 1 | 632 |
| 2-478 | | " | 1 | 564 |
| 2-479 | | | 1 | 593 |
| 2-480 | | | 2 | 571 |

TABLE II-continued
| Ex | R¹ᵃ—X ↘* | R⁸ | n | LCMS(ESI) m/z [M + H⁺] |
|---|---|---|---|---|
| 2-481 | 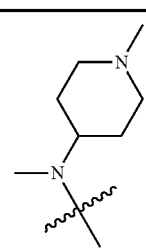 | " | 0 | 543 |
| 2-482 | 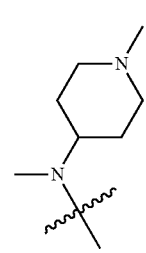 | 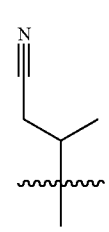 [SMILES: *C(C)CC#N] | 1 | 513 |
| 2-483 | 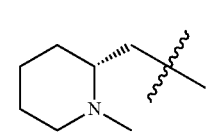 [SMILES: *C[C@H]1CCCCN1C] | 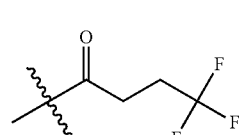 | 1 | 570 |
| 2-484 | 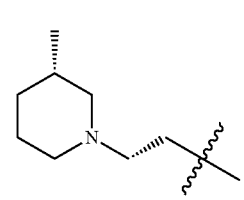 | " | 1 | 584 |
| 2-485 | 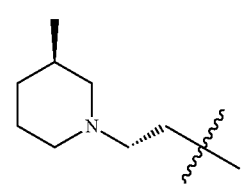 | " | 1 | 584 |
| 2-486 | 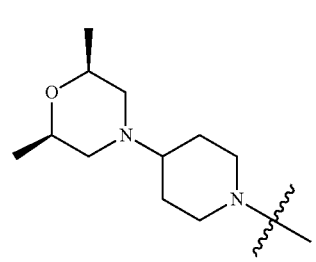 [SMILES: *N1CCC(N2C[C@@H](C)O[C@@H](C)C2)CC1] | " | 1 | 640 |

Example 3a

Cyclopropanecarboxylic acid (8-Bromo-1,8a-di-hydro-[1,2,4]triazolo[1,5-a]pyridin-2-yl)-amide

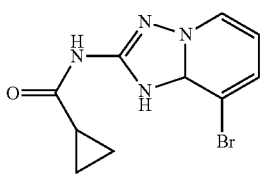 [SMILES: O=C(NC1=NN2C=CC=C(Br)C2N1)C1CC1]

Cyclopropanecarboxylic acid (8-bromo-[1,2,4]triazolo[1,5-a]pyridin-2-yl)-amide may be prepared according to WO 2010/010186, incorporated herein by reference, and functionalised using the methods described above in Examples 1 and 2.

TABLE III

| Ex | Q¹ | Q² | LCMS (ESI) m/z [M + H⁺] |
|---|---|---|---|
| 3-1 | (piperidine with phenyl and CH₂NH₂) | cyclopropyl | 391 |

Enzymatic Assays

JAK Enzyme Assays were Carried Out as Follows:

The activity of the isolated recombinant JAK1 and JAK2 kinase domain was measured by monitoring phosphorylation of a peptide derived from JAK3 (Val-Ala-Leu-Val-Asp-Gly-Tyr-Phe-Arg-Leu-Thr-Thr, fluorescently labeled on the N-terminus with 5-carboxyfluorescein) using the Caliper LabChip® technology (Caliper Life Sciences, Hopkinton, Mass.). To determine inhibition constants ($K_i$), compounds were diluted serially in DMSO and added to 50 µL kinase reactions containing purified enzyme (1.5 nM JAK1, or 0.2 nM JAK2), 100 mM HEPES buffer (pH 7.2), 0.015% Brij-35, 1.5 µM peptide substrate, ATP (25 µM), 10 mM MgCl$_2$, 4 mM DTT at a final DMSO concentration of 2%. Reactions were incubated at 22° C. in 384-well polypropylene microtiter plates for 30 minutes and then stopped by addition of 25 µL of an EDTA containing solution (100 mM HEPES buffer (pH 7.2), 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip® 3000 according to the manufacturer's specifications. $K_i$ values were then determined using the Morrison tight binding model (Morrison, J. F., Biochim. Biophys. Acta. 185:269-296 (1969); William, J. W. and Morrison, J. F., Meth. Enzymol., 63:437-467 (1979)) modified for ATP-competitive inhibition $[K_i = K_{i,app}/(1+[ATP]/K_{m,app})]$.

JAK1 Pathway Assay in Cell Lines was Carried Out as Follows:

Inhibitor potency (EC$_{50}$) was determined in cell-based assays designed to measure JAK1 dependent STAT phosphorylation. As noted above, inhibition of IL-4, IL-13, and IL-9 signaling by blocking the Jak/Stat signaling pathway can alleviate asthmatic symptoms in pre-clinical lung inflammation models (Mathew et al., 2001, J Exp Med 193(9): 1087-1096; Kudlacz et. al., 2008, Eur J. Pharmacol 582(1-3): 154-161).

In one assay approach, TF-1 human erythroleukemia cells obtained from the American Type Culture Collection (ATCC; Manassas, Va.) were used to measure JAK1-dependent STATE phosphorylation downstream of IL-13 stimulation. Prior to use in the assays, TF-1 cells were starved of GM-CSF overnight in OptiMEM medium (Life Technologies, Grand Island, N.Y.) supplemented with 0.5% charcoal/dextran stripped fetal bovine serum (FBS), 0.1 mM non-essential amino acids (NEAA), and 1 mM sodium pyruvate. The assays were run in 384-well plates in serum-free OptiMEM medium using 300,000 cells per well. In a second assay approach, BEAS-2B human bronchial epithelial cells obtained from ATCC were plated at 100,000 cells per well of a 96-well plate one day prior to the experiment. The BEAS-2B assay was run in complete growth medium (bronchial epithelial basal medium plus bulletkit; Lonza; Basel, Switzerland).

Test compounds were serially diluted 1:2 in DMSO and then diluted 1:50 in medium just before use. Diluted compounds were added to the cells, for a final DMSO concentration of 0.2%, and incubated for 30 min (for the TF-1 assay) or 1 hr (for the BEAS-2B assay) at 37° C. Then, cells were stimulated with human recombinant cytokine at their respective EC$_{90}$ concentrations, as previously determined for each individual lot. Cells were stimulated with IL-13 (R&D Systems, Minneapolis, Minn.) for 15 min at 37° C. The TF-1 cell reactions were stopped by the direct addition of 10× lysis buffer (Cell Signaling Technologies, Danvers, Mass.), whereas the BEAS-2B cell incubations were halted by the removal of medium and addition of 1× lysis buffer. The resultant samples were frozen in the plates at −80° C. Compound mediated inhibition of STAT6 phosphorylation was measured in the cell lysates using MesoScale Discovery (MSD) technology (Gaithersburg, Md.). EC$_{50}$ values were determined as the concentration of compound required for 50% inhibition of STAT phosphorylation relative to that measured for the DMSO control.

Table 4 provides JAK1 $K_i$, JAK2 $K_i$ and IL-13-pSTAT6 IC$_{50}$ information for the noted Examples of the indicated Tables.

TABLE 4

| Table number | Example number | JAK1 Ki (µM) | JAK2 Ki (µM) | IL-13-pSTAT6 IC50 (µM) | IL13-pSTAT6 BEASB2B IC50 (µM) |
|---|---|---|---|---|---|
| 1 | 1-1 | 0.01672 | 0.00085 | | |
| 1 | 1-2 | 0.07402 | 0.01425 | | |
| 1 | 1-3 | 0.45468 | 0.09239 | >10 | |
| 1 | 1-4 | 0.08151 | 0.01240 | 6.5881 | |
| 1 | 1-5 | 0.04475 | 0.00515 | 0.7669 | |

TABLE 4-continued

| Table number | Example number | JAK1 Ki (μM) | JAK2 Ki (μM) | IL-13-pSTAT6 IC50 (μM) | IL13-pSTAT6 BEASB2B IC50 (μM) |
|---|---|---|---|---|---|
| 1 | 1-6 | 0.26472 | 0.03993 | 3.0729 | |
| 1 | 1-7 | 0.06210 | 0.00651 | | |
| 1 | 1-8 | 0.14044 | 0.02309 | 0.7563 | |
| 1 | 1-9 | 0.48874 | 0.06321 | >10 | |
| 1 | 1-10 | 0.32136 | 0.07465 | >10 | |
| 1 | 1-11 | 0.02593 | 0.00628 | 0.2352 | |
| 1 | 1-12 | 0.40601 | 0.07747 | 3.4017 | |
| 1 | 1-13 | 0.05838 | 0.01312 | 0.4936 | |
| 1 | 1-14 | 0.05240 | 0.00753 | | |
| 1 | 1-15 | 0.18745 | 0.01220 | | |
| 1 | 1-16 | 0.18468 | 0.02552 | | |
| 1 | 1-17 | 0.00291 | 0.00112 | 0.0339 | 0.1530 |
| 1 | 1-18 | 0.08788 | 0.01733 | | |
| 1 | 1-19 | 0.17775 | 0.03197 | | |
| 1 | 1-20 | 0.19653 | 0.03681 | | |
| 1 | 1-21 | 0.01461 | 0.00649 | 0.3330 | |
| 1 | 1-22 | 0.17116 | 0.03212 | | |
| 1 | 1-23 | 0.01108 | 0.00250 | 0.0737 | |
| 1 | 1-24 | 0.15679 | 0.01914 | | |
| 1 | 1-25 | 0.39046 | 0.04911 | | |
| 1 | 1-26 | 0.03691 | 0.00408 | | |
| 1 | 1-27 | 0.22126 | 0.01721 | | |
| 1 | 1-28 | 0.07039 | 0.00821 | | |
| 1 | 1-29 | 0.40172 | 0.04742 | | |
| 1 | 1-30 | 0.00170 | 0.00027 | 0.2523 | |
| 1 | 1-31 | 0.45295 | 0.05243 | | |
| 1 | 1-32 | 0.10910 | 0.02875 | | |
| 1 | 1-33 | 0.21856 | 0.03866 | | |
| 1 | 1-34 | 0.01874 | 0.00861 | 0.9155 | |
| 1 | 1-35 | 0.18364 | 0.02768 | | |
| 1 | 1-36 | 0.00735 | 0.00432 | 0.1422 | |
| 1 | 1-37 | 0.02357 | 0.00670 | 0.0763 | |
| 1 | 1-38 | 0.00686 | 0.00559 | 0.1517 | |
| 1 | 1-39 | 0.00773 | 0.00352 | | |
| 1 | 1-40 | 0.01146 | 0.00458 | | |
| 1 | 1-41 | 0.00205 | 0.00020 | 0.0159 | 0.0420 |
| 1 | 1-42 | 0.91987 | 1.09362 | | |
| 1 | 1-43 | 0.03101 | 0.00784 | | 0.9680 |
| 1 | 1-44 | 0.05244 | 0.00703 | 0.1679 | |
| 1 | 1-45 | 0.19352 | 0.02040 | | |
| 1 | 1-46 | 0.10061 | 0.01013 | | |
| 1 | 1-47 | 0.00135 | | 0.0103 | 0.0581 |
| 1 | 1-48 | 0.00230 | | | |
| 1 | 1-49 | 0.00321 | | | |
| 1 | 1-50 | 0.00311 | | | |
| 1 | 1-51 | 0.00374 | | | |
| 1 | 1-52 | 0.00188 | | 0.0211 | |
| 1 | 1-53 | 0.00103 | | 0.0274 | |
| 1 | 1-54 | 0.00115 | | 0.1004 | |
| 1 | 1-55 | 0.00319 | | | |
| 1 | 1-56 | 0.00430 | | | |
| 1 | 1-57 | 0.00336 | | | |
| 1 | 1-58 | 0.00318 | | | |
| 1 | 1-59 | 0.00127 | | 0.0155 | |
| 1 | 1-60 | 0.00106 | | 0.0122 | |
| 1 | 1-61 | 0.00253 | | | |
| 1 | 1-62 | 0.00142 | | 0.0228 | |
| 1 | 1-63 | 0.00413 | | | |
| 1 | 1-64 | 0.00227 | | | |
| 1 | 1-65 | 0.00234 | | | |
| 1 | 1-66 | 0.00222 | | | |
| 1 | 1-67 | 0.00341 | | | |
| 1 | 1-68 | 0.00216 | | | |
| 1 | 1-69 | 0.00612 | | | |
| 1 | 1-70 | 0.00257 | | | |
| 1 | 1-71 | 0.00450 | | | |
| 1 | 1-72 | 0.00353 | | | |
| 1 | 1-73 | 0.01098 | | | |
| 1 | 1-74 | 0.00134 | | 0.0335 | |
| 1 | 1-75 | 0.00248 | | | |
| 1 | 1-76 | 0.00151 | | 0.0127 | |
| 1 | 1-77 | 0.00329 | | | |
| 1 | 1-78 | 0.00326 | | | |
| 1 | 1-79 | 0.00479 | | | |
| 1 | 1-80 | 0.00347 | | | |
| 1 | 1-81 | 0.00082 | | 0.0109 | |
| 1 | 1-82 | 0.00309 | | | |
| 1 | 1-83 | 0.00324 | | | |
| 1 | 1-84 | 0.00237 | | | |
| 1 | 1-85 | 0.00249 | | | |
| 1 | 1-86 | 0.00201 | | 0.0213 | |
| 1 | 1-87 | 0.00474 | | | |
| 1 | 1-88 | 0.00270 | | | |
| 1 | 1-89 | 0.00190 | | 0.1266 | |
| 1 | 1-90 | 0.00297 | | | |
| 1 | 1-91 | 0.00255 | | | |
| 1 | 1-92 | 0.00168 | | 0.0593 | |
| 1 | 1-93 | 0.00613 | | | |
| 1 | 1-94 | 0.00258 | | | |
| 1 | 1-95 | 0.00193 | | 0.1148 | |
| 1 | 1-96 | 0.00172 | | 0.0646 | |
| 1 | 1-97 | 0.00198 | | 0.0250 | |
| 1 | 1-98 | 0.00144 | | 0.0119 | 0.0424 |
| 1 | 1-99 | 0.00332 | | | |
| 1 | 1-100 | 0.00281 | | | |
| 1 | 1-101 | 0.00194 | | 0.0140 | |
| 1 | 1-102 | 0.00173 | | 0.0450 | 0.0547 |
| 1 | 1-103 | 0.00154 | | 0.0238 | |
| 1 | 1-104 | 0.00326 | | | |
| 1 | 1-105 | 0.00114 | | 0.0141 | |
| 1 | 1-106 | 0.00227 | | | |
| 1 | 1-107 | 0.00277 | | | |
| 1 | 1-108 | 0.00277 | | | |
| 1 | 1-109 | 0.00408 | | | |
| 1 | 1-110 | 0.00458 | | | |
| 1 | 1-111 | 0.00149 | | 0.0156 | |
| 1 | 1-112 | 0.01145 | 0.00380 | | |
| 1 | 1-113 | 0.00164 | | 0.0267 | |
| 1 | 1-114 | 0.00186 | | 0.0297 | |
| 1 | 1-115 | 0.00302 | | | |
| 1 | 1-116 | 0.00295 | | 0.0340 | |
| 1 | 1-117 | 0.00252 | 0.00085 | 0.0292 | |
| 1 | 1-118 | 0.00269 | | | 0.1120 |
| 1 | 1-119 | 0.00266 | | | |
| 1 | 1-120 | 0.00510 | | | |
| 1 | 1-121 | 0.00297 | | 0.1311 | |
| 1 | 1-122 | 0.00271 | | | |
| 1 | 1-123 | 0.00257 | 0.00070 | 0.0258 | |
| 1 | 1-124 | 0.00542 | | | |
| 1 | 1-125 | 0.00225 | 0.00063 | 0.0164 | 0.0428 |
| 1 | 1-126 | 0.00322 | | | |
| 1 | 1-127 | 0.00199 | | 0.0147 | 0.0245 |
| 1 | 1-128 | 0.00448 | | | |
| 1 | 1-129 | 0.00187 | 0.00174 | 0.0377 | |
| 1 | 1-130 | 0.00371 | | | |
| 1 | 1-131 | 0.00720 | | | |
| 1 | 1-132 | 0.00279 | | | |
| 1 | 1-133 | 0.00278 | | | |
| 1 | 1-134 | 0.00207 | | | |
| 1 | 1-135 | 0.00148 | | | |
| 1 | 1-136 | 0.00342 | | | |
| 1 | 1-137 | 0.00388 | | | |
| 1 | 1-138 | 0.00153 | 0.00356 | 0.1351 | |
| 1 | 1-139 | 0.00248 | 0.00195 | 0.0206 | |
| 1 | 1-140 | 0.00488 | | | |
| 1 | 1-141 | 0.00171 | | 0.0579 | |
| 1 | 1-142 | 0.00311 | | | |
| 1 | 1-143 | 0.00349 | | | |
| 1 | 1-144 | 0.00424 | | | |
| 1 | 1-145 | 0.00576 | | | |
| 1 | 1-146 | 0.00305 | | | |
| 1 | 1-147 | 0.00210 | 0.00141 | 0.0665 | |
| 1 | 1-148 | 0.00565 | | | |
| 1 | 1-149 | 0.00896 | | | |
| 1 | 1-150 | 0.00559 | | | |
| 1 | 1-151 | 0.00280 | | 0.1073 | 0.1670 |
| 1 | 1-152 | 0.00279 | | 0.0650 | |
| 1 | 1-153 | 0.00243 | 0.00114 | 0.0260 | |
| 1 | 1-154 | 0.00198 | 0.00064 | 0.0373 | |
| 1 | 1-155 | 0.00320 | | | |

TABLE 4-continued

| Table number | Example number | JAK1 Ki (μM) | JAK2 Ki (μM) | IL-13-pSTAT6 IC50 (μM) | IL13-pSTAT6 BEASB2B IC50 (μM) |
|---|---|---|---|---|---|
| 1 | 1-156 | 0.00651 | | | |
| 1 | 1-157 | 0.00370 | | | |
| 1 | 1-158 | 0.00401 | | | |
| 1 | 1-159 | 0.00482 | | | |
| 1 | 1-160 | 0.00285 | | | |
| 1 | 1-161 | 0.00199 | | 0.0234 | 0.0485 |
| 1 | 1-162 | 0.00291 | | | |
| 1 | 1-163 | 0.00257 | | | |
| 1 | 1-164 | 0.00080 | | 0.0108 | |
| 1 | 1-165 | 0.00088 | | 0.0251 | |
| 1 | 1-166 | 0.00213 | | | |
| 1 | 1-167 | 0.00179 | 0.00286 | 0.0121 | |
| 1 | 1-168 | 0.00275 | | 0.0226 | |
| 1 | 1-169 | 0.00670 | | | |
| 1 | 1-170 | 0.00151 | 0.00098 | 0.0155 | |
| 1 | 1-171 | 0.01426 | | | |
| 1 | 1-172 | 0.00303 | | | |
| 1 | 1-173 | 0.00195 | 0.00245 | 0.0231 | |
| 1 | 1-174 | 0.00241 | 0.00231 | 0.0311 | |
| 1 | 1-175 | 0.00174 | 0.00092 | 0.1889 | |
| 1 | 1-176 | 0.00192 | 0.00207 | 0.2792 | |
| 1 | 1-177 | 0.00208 | 0.00151 | 0.0232 | |
| 1 | 1-178 | 0.00115 | 0.00107 | 0.0983 | |
| 1 | 1-179 | 0.00169 | | 0.0843 | |
| 1 | 1-180 | 0.00164 | | 0.3219 | |
| 1 | 1-181 | 0.00140 | | 0.1812 | |
| 1 | 1-182 | 0.00259 | | | |
| 1 | 1-183 | 0.00177 | | 0.5361 | |
| 1 | 1-184 | 0.00115 | | 0.1273 | |
| 1 | 1-185 | 0.00218 | | | |
| 1 | 1-186 | 0.00203 | | 1.0299 | |
| 1 | 1-187 | 0.00147 | | 0.4620 | |
| 1 | 1-188 | 0.00135 | | 0.0347 | |
| 1 | 1-189 | | | | |
| 1 | 1-190 | | | | |
| 1 | 1-191 | | | | |
| 1 | 1-192 | | | | |
| 1 | 1-193 | 0.00195 | | 0.2487 | |
| 1 | 1-194 | 0.00352 | | | |
| 1 | 1-195 | 0.00374 | | | |
| 1 | 1-196 | 0.00164 | | 0.0531 | |
| 1 | 1-197 | 0.00163 | | 0.1575 | |
| 1 | 1-198 | 0.00157 | | 0.0685 | |
| 1 | 1-199 | 0.00066 | | 0.1061 | |
| 1 | 1-200 | 0.00360 | | | |
| 1 | 1-201 | 0.00254 | | | |
| 1 | 1-202 | 0.00335 | | | |
| 1 | 1-203 | 0.00148 | | 0.3424 | |
| 1 | 1-204 | 0.00408 | | | |
| 1 | 1-205 | 0.00189 | | 0.5215 | |
| 1 | 1-206 | 0.00234 | | | |
| 1 | 1-207 | 0.00197 | | 0.1915 | |
| 1 | 1-208 | 0.00231 | | | |
| 1 | 1-209 | 0.00563 | | | |
| 1 | 1-210 | 0.00091 | | 0.0435 | |
| 1 | 1-211 | 0.00219 | | | |
| 1 | 1-212 | 0.00188 | | 0.1962 | |
| 1 | 1-213 | 0.00280 | | | |
| 1 | 1-214 | 0.00253 | | | |
| 1 | 1-215 | 0.00228 | | | |
| 1 | 1-216 | 0.00234 | | | |
| 1 | 1-217 | 0.00230 | | | |
| 1 | 1-218 | 0.00192 | | 0.1647 | |
| 1 | 1-219 | 0.00260 | | | |
| 1 | 1-220 | 0.00131 | | 0.6369 | |
| 1 | 1-221 | 0.00117 | | 0.8665 | |
| 1 | 1-222 | 0.00212 | | | |
| 1 | 1-223 | 0.00354 | | | |
| 1 | 1-224 | 0.00095 | | 0.1109 | |
| 1 | 1-225 | 0.00179 | | 0.0308 | |
| 1 | 1-226 | 0.00181 | | 0.0794 | |
| 1 | 1-227 | 0.00285 | | | |
| 1 | 1-228 | 0.00216 | | | |
| 1 | 1-229 | 0.00294 | | | |
| 1 | 1-230 | 0.00263 | | 0.0581 | |
| 1 | 1-231 | 0.00178 | | 0.9157 | |
| 1 | 1-232 | 0.00283 | | | |
| 1 | 1-233 | 0.00258 | | 0.1645 | |
| 1 | 1-234 | 0.00193 | | 0.0361 | |
| 1 | 1-235 | 0.00186 | | 0.3105 | |
| 1 | 1-236 | 0.00256 | | | |
| 1 | 1-237 | 0.00147 | | 0.0107 | |
| 1 | 1-238 | 0.00173 | | 0.1805 | |
| 1 | 1-239 | 0.00355 | | | |
| 1 | 1-240 | 0.00372 | | | |
| 1 | 1-241 | 0.00163 | | 0.1154 | |
| 1 | 1-242 | 0.00251 | | | |
| 1 | 1-243 | 0.00252 | | | |
| 1 | 1-244 | 0.00270 | | | |
| 1 | 1-245 | 0.00261 | | | |
| 1 | 1-246 | 0.00036 | 0.00033 | 0.0054 | 0.0892 |
| 1 | 1-247 | 0.00050 | 0.00033 | 0.0184 | 0.1150 |
| 1 | 1-248 | 0.10335 | 0.02210 | | |
| 1 | 1-249 | 0.37191 | 0.05267 | | |
| 1 | 1-250 | 0.00393 | 0.00129 | | 0.732 |
| 1 | 1-251 | 0.00061 | 0.00041 | | 0.0566 |
| 1 | 1-252 | 0.00048 | 0.00050 | | 0.0902 |
| 1 | 1-253 | 0.00116 | 0.00092 | | 0.4177 |
| 1 | 1-254 | 0.00064 | 0.00039 | 0.0899 | 0.661 |
| 1 | 1-255 | 0.00085 | 0.00035 | 0.0271 | 0.159 |
| 1 | 1-256 | 0.00117 | 0.00069 | 0.0563 | 0.426 |
| 1 | 1-257 | 0.02663 | 0.00234 | | |
| 1 | 1-258 | 0.00181 | 0.00052 | 0.0934 | 1.44 |
| 1 | 1-259 | 0.02629 | 0.01070 | | |
| 1 | 1-260 | 0.10551 | 0.01633 | | |
| 1 | 1-261 | 0.04149 | 0.00356 | | |
| 1 | 1-262 | 0.00222 | 0.00064 | 0.1201 | |
| 1 | 1-263 | 0.00082 | 0.00096 | 0.0182 | |
| 1 | 1-264 | 0.13357 | 0.12124 | | |
| 1 | 1-265 | 0.00084 | 0.00057 | | 0.0948 |
| 1 | 1-266 | 0.00880 | 0.00254 | | |
| 1 | 1-267 | 0.00042 | 0.00025 | | 0.0324 |
| 1 | 1-268 | 0.00071 | 0.00038 | | 0.0562 |
| 1 | 1-269 | 0.02853 | 0.01321 | | |
| 1 | 1-270 | 0.00064 | 0.00045 | | 0.114 |
| 1 | 1-271 | 0.00088 | 0.00094 | 0.1125 | 0.533 |
| 1 | 1-272 | 0.00048 | 0.00039 | 0.0487 | 0.172 |
| 1 | 1-273 | 0.00059 | 0.00044 | 0.1525 | 0.259 |
| 1 | 1-274 | 0.00020 | 0.00017 | 0.0079 | 0.0289 |
| 1 | 1-275 | 0.00021 | 0.00014 | 0.003 | 0.0555 |
| 1 | 1-276 | 0.00085 | 0.00048 | 0.0957 | 0.082 |
| 1 | 1-277 | 0.00039 | 0.00024 | 0.0231 | 0.0733 |
| 1 | 1-278 | 0.00033 | 0.00023 | 0.0163 | 0.0376 |
| 1 | 1-279 | 0.00041 | 0.00025 | 0.0281 | 0.0346 |
| 1 | 1-280 | 0.00030 | 0.00023 | 0.1245 | 0.0528 |
| 1 | 1-281 | 0.00063 | 0.00039 | 0.0702 | 0.134 |
| 1 | 1-282 | 0.00037 | 0.00021 | 0.0426 | 0.0556 |
| 1 | 1-283 | 0.00018 | 0.00015 | 0.0155 | 0.0313 |
| 1 | 1-284 | 0.00057 | 0.00049 | 0.0177 | 0.031 |
| 1 | 1-285 | 0.00056 | 0.00055 | 0.0221 | 0.0576 |
| 1 | 1-286 | 0.00027 | 0.00026 | 0.0067 | 0.0762 |
| 1 | 1-287 | 0.00054 | 0.00039 | 0.0225 | 0.0364 |
| 1 | 1-288 | 0.00051 | 0.00040 | 0.028 | 0.0677 |
| 1 | 1-289 | 0.00026 | 0.00042 | | 0.0081 |
| 1 | 1-290 | 0.00018 | 0.00030 | | 0.0059 |
| 1 | 1-291 | 0.00018 | 0.00036 | | 0.525 |
| 1 | 1-292 | 0.14231 | 0.01850 | | |
| 1 | 1-293 | 0.17252 | 0.11010 | | |
| 1 | 1-294 | 0.00068 | 0.00040 | 0.0627 | |
| 1 | 1-295 | 0.00738 | 0.01611 | | 0.729 |
| 1 | 1-296 | 0.00013 | 0.00020 | | 0.0126 |
| 1 | 1-297 | 0.00170 | 0.00944 | 0.0367 | |
| 1 | 1-298 | 0.00063 | 0.00045 | 0.1252 | |
| 1 | 1-299 | 0.00103 | 0.00057 | 0.0557 | |
| 1 | 1-300 | 0.00123 | 0.00055 | 0.0263 | |
| 1 | 1-301 | 0.00123 | 0.00032 | 0.1792 | |
| 1 | 1-302 | 0.0222 | 0.00637 | | |
| 1 | 1-303 | 0.046 | 0.00498 | | |
| 2 | 2-1 | 0.00525 | 0.00107 | 0.0237 | |
| 2 | 2-2 | 0.00499 | 0.00081 | 0.0340 | |

TABLE 4-continued

| Table number | Example number | JAK1 Ki (μM) | JAK2 Ki (μM) | IL-13-pSTAT6 IC50 (μM) | IL13-pSTAT6 BEASB2B IC50 (μM) |
|---|---|---|---|---|---|
| 2 | 2-3 | 0.00226 | 0.00074 | 0.1630 | |
| 2 | 2-4 | 0.00327 | 0.00062 | 0.0466 | |
| 2 | 2-5 | 0.00223 | 0.00044 | 1.0911 | |
| 2 | 2-6 | 0.00223 | 0.00038 | 0.5846 | |
| 2 | 2-7 | 0.00114 | 0.00025 | 0.0429 | |
| 2 | 2-8 | 0.04210 | 0.01367 | 0.8488 | |
| 2 | 2-9 | 0.00876 | 0.00148 | 0.6195 | |
| 2 | 2-10 | 0.05312 | 0.01562 | | |
| 2 | 2-11 | 0.00194 | | 0.0067 | |
| 2 | 2-12 | 0.00271 | | | |
| 2 | 2-13 | 0.00154 | 0.00244 | 0.3382 | |
| 2 | 2-14 | 0.00251 | | | |
| 2 | 2-15 | 0.00128 | 0.00066 | 0.0171 | |
| 2 | 2-16 | 0.00267 | | | |
| 2 | 2-17 | 0.00267 | | | |
| 2 | 2-18 | 0.00219 | | | 0.1340 |
| 2 | 2-19 | 0.00190 | 0.00033 | 0.0557 | |
| 2 | 2-20 | 0.00162 | 0.00145 | 0.2562 | |
| 2 | 2-21 | 0.00285 | | | |
| 2 | 2-22 | 0.00760 | | | |
| 2 | 2-23 | 0.00379 | | | |
| 2 | 2-24 | 0.00156 | 0.00098 | 0.0216 | |
| 2 | 2-25 | 0.00285 | | | |
| 2 | 2-26 | 0.00305 | | | |
| 2 | 2-27 | 0.00163 | 0.00116 | 0.2568 | |
| 2 | 2-28 | 0.00142 | | 0.2074 | |
| 2 | 2-29 | 0.00149 | | 0.0803 | |
| 2 | 2-30 | 0.00143 | | 0.0403 | |
| 2 | 2-31 | 0.00151 | | 0.1811 | |
| 2 | 2-32 | 0.00138 | | 0.5361 | |
| 2 | 2-33 | 0.00063 | | 0.0233 | |
| 2 | 2-34 | 0.00193 | | 0.3523 | |
| 2 | 2-35 | 0.00082 | | 0.0950 | |
| 2 | 2-36 | 0.00229 | | | |
| 2 | 2-37 | 0.00116 | | 0.0854 | |
| 2 | 2-38 | 0.00121 | 0.00056 | 0.0029 | 0.0286 |
| 2 | 2-39 | 0.00179 | | 0.0347 | |
| 2 | 2-40 | 0.00051 | 0.00046 | 0.0035 | 0.0187 |
| 2 | 2-41 | 0.00058 | | 0.0052 | |
| 2 | 2-42 | 0.00056 | 0.00040 | 0.0047 | |
| 2 | 2-43 | 0.00258 | 0.00136 | 0.0278 | |
| 2 | 2-44 | 0.00070 | 0.00050 | 0.0482 | |
| 2 | 2-45 | 0.00113 | 0.00038 | 0.0090 | |
| 2 | 2-46 | 0.00140 | 0.00043 | 0.0205 | |
| 2 | 2-47 | 0.00073 | 0.00060 | 0.0157 | |
| 2 | 2-48 | 0.00071 | 0.00067 | 0.0335 | |
| 2 | 2-49 | 0.00061 | 0.00058 | 0.0038 | 0.0102 |
| 2 | 2-50 | 0.00121 | 0.00058 | 0.0651 | |
| 2 | 2-51 | 0.00140 | 0.00060 | 0.0702 | |
| 2 | 2-52 | 0.00619 | 0.00183 | 0.0600 | |
| 2 | 2-53 | 0.01531 | 0.00271 | | |
| 2 | 2-54 | 0.00329 | 0.00076 | 0.0163 | |
| 2 | 2-55 | 0.00175 | 0.00117 | 0.0100 | |
| 2 | 2-56 | 0.00142 | 0.00086 | 0.0067 | 0.0594 |
| 2 | 2-57 | 0.00275 | | | |
| 2 | 2-58 | 0.00269 | | | |
| 2 | 2-59 | 0.00239 | | | |
| 2 | 2-60 | 0.00129 | 0.00096 | 0.0204 | |
| 2 | 2-61 | 0.00364 | | | |
| 2 | 2-62 | 0.00109 | 0.00041 | 0.0300 | |
| 2 | 2-63 | 0.00284 | | | 0.1510 |
| 2 | 2-64 | 0.00277 | | | |
| 2 | 2-65 | 0.00257 | | | |
| 2 | 2-66 | 0.00241 | | | 0.2240 |
| 2 | 2-67 | 0.00294 | | 0.0409 | |
| 2 | 2-68 | 0.00112 | 0.00092 | 0.0119 | |
| 2 | 2-69 | 0.00410 | | | |
| 2 | 2-70 | 0.00194 | 0.00080 | 0.0298 | |
| 2 | 2-71 | 0.00604 | | | |
| 2 | 2-72 | 0.00501 | | | |
| 2 | 2-73 | 0.00258 | | | |
| 2 | 2-74 | 0.00082 | 0.00101 | 0.0189 | |
| 2 | 2-75 | 0.00893 | | | |
| 2 | 2-76 | 0.00508 | | | |
| 2 | 2-77 | 0.00072 | 0.00109 | 0.1340 | |
| 2 | 2-78 | 0.00136 | 0.00099 | 0.3603 | |
| 2 | 2-79 | 0.00280 | | | |
| 2 | 2-80 | 0.00067 | | 0.0794 | |
| 2 | 2-81 | 0.00157 | | 0.0600 | |
| 2 | 2-82 | 0.00141 | | 0.2235 | |
| 2 | 2-83 | 0.00126 | | 0.1971 | |
| 2 | 2-84 | 0.00093 | | 0.0714 | |
| 2 | 2-85 | 0.00051 | | 0.0626 | |
| 2 | 2-86 | 0.00159 | | 0.2155 | |
| 2 | 2-87 | 0.00149 | | 0.0086 | |
| 2 | 2-88 | 0.00225 | | | |
| 2 | 2-89 | 0.00218 | | | |
| 2 | 2-90 | 0.00299 | | | |
| 2 | 2-91 | 0.00367 | | | |
| 2 | 2-92 | 0.00044 | | 0.0209 | |
| 2 | 2-93 | 0.00127 | 0.00093 | 0.0047 | |
| 2 | 2-94 | 0.00168 | 0.00105 | 0.0236 | |
| 2 | 2-95 | 0.00075 | 0.00034 | 0.0043 | |
| 2 | 2-96 | 0.00068 | 0.00034 | 0.0052 | |
| 2 | 2-97 | 0.00107 | 0.00021 | 0.0137 | |
| 2 | 2-98 | 0.00111 | 0.00034 | 0.0115 | |
| 2 | 2-99 | 0.00058 | 0.00050 | 0.0294 | |
| 2 | 2-100 | 0.00065 | 0.00064 | 0.0847 | |
| 2 | 2-101 | 0.00081 | 0.00074 | 0.0035 | 0.0318 |
| 2 | 2-102 | 0.00084 | 0.00035 | 0.0337 | |
| 2 | 2-103 | 0.00269 | 0.00132 | 0.1453 | |
| 2 | 2-104 | 0.00194 | 0.00044 | 0.0597 | |
| 2 | 2-105 | 0.00757 | 0.00144 | 0.3728 | |
| 2 | 2-106 | 0.03856 | 0.00729 | 8.5694 | |
| 2 | 2-107 | 0.00550 | 0.00104 | 0.4219 | |
| 2 | 2-108 | 0.00137 | 0.00050 | 0.0098 | |
| 2 | 2-109 | 0.00502 | 0.00098 | 0.0343 | |
| 2 | 2-110 | 0.00327 | | | |
| 2 | 2-111 | 0.00159 | 0.00106 | 0.0226 | |
| 2 | 2-112 | 0.00170 | 0.00147 | 0.2326 | |
| 2 | 2-113 | 0.00142 | 0.00109 | 0.0968 | |
| 2 | 2-114 | 0.00173 | 0.00140 | 0.0692 | |
| 2 | 2-115 | 0.00129 | 0.00092 | 0.0190 | |
| 2 | 2-116 | 0.00214 | | | |
| 2 | 2-117 | 0.00457 | | | |
| 2 | 2-118 | 0.00348 | | | |
| 2 | 2-119 | 0.00168 | 0.00067 | 0.0239 | |
| 2 | 2-120 | 0.00878 | | | |
| 2 | 2-121 | 0.00223 | | | |
| 2 | 2-122 | 0.00474 | | | |
| 2 | 2-123 | 0.00194 | 0.00067 | 0.0488 | |
| 2 | 2-124 | 0.00134 | 0.00085 | 0.0385 | |
| 2 | 2-125 | 0.00382 | | | |
| 2 | 2-126 | 0.00233 | | | |
| 2 | 2-127 | 0.00313 | | | |
| 2 | 2-128 | 0.00273 | | | |
| 2 | 2-129 | 0.00402 | | | |
| 2 | 2-130 | 0.00128 | 0.00109 | 0.2256 | |
| 2 | 2-131 | 0.00287 | | | |
| 2 | 2-132 | 0.00239 | | | |
| 2 | 2-133 | 0.00265 | | | |
| 2 | 2-134 | 0.00235 | | | |
| 2 | 2-135 | 0.00299 | | | |
| 2 | 2-136 | 0.00170 | | 0.1631 | |
| 2 | 2-137 | 0.00083 | 0.00079 | 0.0788 | |
| 2 | 2-138 | 0.00047 | | 0.0619 | |
| 2 | 2-139 | 0.00118 | | 0.3584 | |
| 2 | 2-140 | 0.00429 | | | |
| 2 | 2-141 | 0.00299 | | | |
| 2 | 2-142 | 0.00118 | | 0.0066 | |
| 2 | 2-143 | 0.00091 | | 0.0079 | |
| 2 | 2-144 | 0.00098 | | 0.1870 | |
| 2 | 2-145 | 0.00066 | | 0.0064 | |
| 2 | 2-146 | 0.00163 | | 0.0065 | |
| 2 | 2-147 | 0.00681 | | 0.0066 | |
| 2 | 2-148 | 0.00044 | 0.00051 | 0.0032 | 0.0150 |
| 2 | 2-149 | 0.00087 | 0.00040 | 0.0107 | |
| 2 | 2-150 | 0.00125 | 0.00087 | 0.0083 | |
| 2 | 2-151 | 0.00149 | 0.00036 | 0.0057 | |
| 2 | 2-152 | 0.00167 | 0.00049 | 0.0093 | |

TABLE 4-continued

| Table number | Example number | JAK1 Ki (µM) | JAK2 Ki (µM) | IL-13-pSTAT6 IC50 (µM) | IL13-pSTAT6 BEASB2B IC50 (µM) |
|---|---|---|---|---|---|
| 2 | 2-153 | 0.00103 | 0.00030 | 0.0286 | |
| 2 | 2-154 | 0.00091 | 0.00055 | 0.0045 | 0.0806 |
| 2 | 2-155 | 0.00151 | 0.00060 | 0.1317 | |
| 2 | 2-156 | 0.00056 | 0.00020 | 0.0083 | |
| 2 | 2-157 | 0.00071 | 0.00027 | 0.0047 | |
| 2 | 2-158 | 0.00105 | | 0.0073 | |
| 2 | 2-159 | 0.00041 | 0.00044 | 0.0351 | |
| 2 | 2-160 | 0.01113 | 0.00151 | 0.0470 | |
| 2 | 2-161 | 0.00838 | 0.00172 | 0.0442 | |
| 2 | 2-162 | 0.03732 | 0.00652 | | |
| 2 | 2-163 | 0.00135 | 0.00029 | 0.0284 | |
| 2 | 2-164 | 0.01502 | 0.00217 | | |
| 2 | 2-165 | 0.00161 | 0.00121 | 0.1874 | |
| 2 | 2-166 | 0.00357 | | | |
| 2 | 2-167 | 0.00198 | | 0.0158 | |
| 2 | 2-168 | 0.00253 | | | |
| 2 | 2-169 | 0.00274 | | | |
| 2 | 2-170 | 0.00139 | 0.00086 | 0.0148 | |
| 2 | 2-171 | 0.00351 | | | |
| 2 | 2-172 | 0.00153 | 0.00082 | 0.0120 | |
| 2 | 2-173 | 0.00496 | | | |
| 2 | 2-174 | 0.00251 | | | |
| 2 | 2-175 | 0.00119 | 0.00077 | 0.0122 | |
| 2 | 2-176 | 0.00141 | 0.00078 | 0.0081 | |
| 2 | 2-177 | 0.00087 | 0.00054 | 0.0154 | |
| 2 | 2-178 | 0.00097 | 0.00057 | 0.0326 | |
| 2 | 2-179 | 0.00234 | | | |
| 2 | 2-180 | 0.00556 | | | |
| 2 | 2-181 | 0.00274 | | | |
| 2 | 2-182 | 0.00320 | | | |
| 2 | 2-183 | 0.00335 | | | |
| 2 | 2-184 | 0.00351 | | | |
| 2 | 2-185 | 0.00093 | 0.00095 | 0.0299 | |
| 2 | 2-186 | 0.00135 | | 0.0233 | |
| 2 | 2-187 | 0.00160 | | 0.6517 | |
| 2 | 2-188 | 0.00068 | | 0.2390 | |
| 2 | 2-189 | 0.00088 | | 0.1096 | |
| 2 | 2-190 | 0.00176 | | 0.0409 | |
| 2 | 2-191 | 0.00133 | | 0.0637 | |
| 2 | 2-192 | 0.00058 | | 0.2133 | |
| 2 | 2-193 | 0.00150 | | 0.2781 | |
| 2 | 2-194 | 0.00154 | | 0.0942 | |
| 2 | 2-195 | 0.00066 | | 0.1629 | |
| 2 | 2-196 | 0.00111 | | 0.0299 | |
| 2 | 2-197 | 0.00171 | | 0.2953 | |
| 2 | 2-198 | 0.00145 | | 0.0539 | |
| 2 | 2-199 | 0.00104 | 0.00050 | 0.0042 | |
| 2 | 2-200 | 0.00185 | 0.00058 | 0.0041 | |
| 2 | 2-201 | 0.00186 | | 0.0060 | |
| 2 | 2-202 | 0.00104 | | 0.0115 | |
| 2 | 2-203 | 0.00152 | | 0.0301 | |
| 2 | 2-204 | 0.00056 | | 0.0897 | |
| 2 | 2-205 | 0.00122 | | 0.0100 | |
| 2 | 2-206 | 0.00458 | 0.00734 | 0.0034 | |
| 2 | 2-207 | 0.00223 | | 0.1412 | |
| 2 | 2-208 | 0.00095 | 0.00036 | 0.0044 | |
| 2 | 2-209 | 0.00199 | 0.00095 | 0.0299 | |
| 2 | 2-210 | 0.00081 | 0.00029 | 0.0069 | 0.0456 |
| 2 | 2-211 | 0.00132 | 0.00056 | 0.0071 | |
| 2 | 2-212 | 0.00091 | 0.00023 | 0.0080 | |
| 2 | 2-213 | 0.00075 | 0.00058 | 0.0056 | 0.0206 |
| 2 | 2-214 | 0.00061 | 0.00070 | 0.0055 | |
| 2 | 2-215 | 0.00055 | 0.00021 | 0.0135 | |
| 2 | 2-216 | 0.00078 | 0.00043 | 0.0074 | |
| 2 | 2-217 | 0.00076 | 0.00033 | 0.0095 | |
| 2 | 2-218 | 0.00099 | 0.00044 | 0.0154 | |
| 2 | 2-219 | 0.00066 | 0.00028 | 0.0033 | 0.0372 |
| 2 | 2-220 | 0.00057 | 0.00039 | 0.0058 | |
| 2 | 2-221 | | | | |
| 2 | 2-222 | 0.00413 | 0.00156 | 0.4679 | |
| 2 | 2-223 | 0.00136 | 0.00035 | 0.0173 | |
| 2 | 2-224 | 0.01502 | 0.00279 | 0.2044 | |
| 2 | 2-225 | 0.00129 | 0.00035 | 0.0113 | |
| 2 | 2-226 | 0.00337 | | | |
| 2 | 2-227 | 0.00371 | | | |
| 2 | 2-228 | 0.00320 | | | |
| 2 | 2-229 | 0.00339 | | | |
| 2 | 2-230 | 0.00240 | 0.00096 | 0.1574 | |
| 2 | 2-231 | 0.00139 | 0.00114 | 0.2677 | |
| 2 | 2-232 | 0.00210 | 0.00115 | 0.2879 | |
| 2 | 2-233 | 0.00280 | | | |
| 2 | 2-234 | 0.00372 | | | |
| 2 | 2-235 | 0.00168 | 0.00047 | 0.0231 | |
| 2 | 2-236 | 0.00294 | | | |
| 2 | 2-237 | 0.00237 | | | |
| 2 | 2-238 | 0.00288 | | | |
| 2 | 2-239 | 0.00321 | | | |
| 2 | 2-240 | | | | |
| 2 | 2-241 | 0.00108 | 0.00061 | 0.0637 | |
| 2 | 2-242 | 0.00640 | | | |
| 2 | 2-243 | 0.00547 | | | |
| 2 | 2-244 | 0.00328 | | | |
| 2 | 2-245 | 0.00304 | 0.00074 | 0.0122 | |
| 2 | 2-246 | 0.00209 | 0.00074 | | |
| 2 | 2-247 | 0.00437 | | | |
| 2 | 2-248 | 0.00413 | | | |
| 2 | 2-249 | 0.01960 | | | |
| 2 | 2-250 | 0.00134 | 0.00103 | 0.0767 | |
| 2 | 2-251 | 0.00369 | | | |
| 2 | 2-252 | 0.00234 | | | |
| 2 | 2-253 | 0.00143 | | 0.1513 | |
| 2 | 2-254 | 0.00137 | | 0.5875 | |
| 2 | 2-255 | 0.00286 | | 0.2970 | |
| 2 | 2-256 | 0.00067 | | 0.0684 | |
| 2 | 2-257 | 0.00187 | | 0.0605 | |
| 2 | 2-258 | 0.00194 | | 0.2379 | |
| 2 | 2-259 | 0.00097 | | 0.0058 | |
| 2 | 2-260 | 0.00183 | | 0.0053 | |
| 2 | 2-261 | 0.00167 | | 0.0465 | |
| 2 | 2-262 | 0.00091 | | 0.0971 | |
| 2 | 2-263 | 0.00143 | 0.00065 | 0.0296 | |
| 2 | 2-264 | 0.00081 | 0.00071 | 0.0117 | |
| 2 | 2-265 | 0.00056 | 0.00026 | 0.0042 | |
| 2 | 2-266 | 0.00134 | 0.00039 | 0.0097 | |
| 2 | 2-267 | 0.00161 | 0.00075 | 0.0087 | |
| 2 | 2-268 | 0.00060 | 0.00048 | 0.0030 | 0.0266 |
| 2 | 2-269 | 0.00088 | 0.00071 | 0.0051 | |
| 2 | 2-270 | 0.00062 | 0.00079 | 0.0164 | |
| 2 | 2-271 | 0.00048 | 0.00045 | 0.0053 | 0.0159 |
| 2 | 2-272 | 0.00076 | 0.00046 | 0.0039 | 0.1065 |
| 2 | 2-273 | 0.00049 | 0.00035 | 0.0055 | |
| 2 | 2-274 | 0.00062 | 0.00076 | 0.0450 | |
| 2 | 2-275 | 0.00115 | 0.00053 | 0.0372 | |
| 2 | 2-276 | 0.00129 | 0.00066 | 0.1290 | |
| 2 | 2-277 | 0.00068 | 0.00023 | 0.0198 | |
| 2 | 2-278 | 0.00121 | 0.00008 | 0.0393 | |
| 2 | 2-279 | 0.00076 | 0.00039 | 0.0388 | |
| 2 | 2-280 | 0.00067 | 0.00026 | 0.0095 | |
| 2 | 2-281 | 0.00253 | 0.00066 | 0.0394 | |
| 2 | 2-282 | 0.00261 | 0.00045 | 0.0464 | |
| 2 | 2-283 | 0.00465 | 0.00085 | 0.0540 | |
| 2 | 2-284 | 0.01229 | 0.00135 | 0.1629 | |
| 2 | 2-285 | 0.00643 | 0.00187 | 0.7389 | |
| 2 | 2-286 | 0.00899 | 0.00172 | 1.7549 | |
| 2 | 2-287 | 0.00110 | 0.00022 | 0.2475 | |
| 2 | 2-288 | 0.00132 | 0.00044 | 0.0127 | 0.0777 |
| 2 | 2-289 | 0.00578 | 0.00101 | 0.0429 | |
| 2 | 2-290 | 0.00164 | 0.00044 | 0.0377 | |
| 2 | 2-291 | 0.00190 | 0.00135 | 0.0223 | |
| 2 | 2-292 | 0.00527 | | | |
| 2 | 2-293 | 0.00126 | 0.00121 | 0.0295 | |
| 2 | 2-294 | 0.00315 | | | |
| 2 | 2-295 | 0.00327 | | | |
| 2 | 2-296 | 0.00173 | 0.00128 | 0.3831 | |
| 2 | 2-297 | 0.00205 | 0.00033 | | |
| 2 | 2-298 | 0.00308 | | | |
| 2 | 2-299 | 0.00305 | | | |
| 2 | 2-300 | | | | |
| 2 | 2-301 | 0.00371 | | | |
| 2 | 2-302 | 0.00348 | | | |

TABLE 4-continued

| Table number | Example number | JAK1 Ki (µM) | JAK2 Ki (µM) | IL-13-pSTAT6 IC50 (µM) | IL13-pSTAT6 BEASB2B IC50 (µM) |
|---|---|---|---|---|---|
| 2 | 2-303 | 0.00361 | | | |
| 2 | 2-304 | 0.00624 | | | |
| 2 | 2-305 | 0.00384 | | | |
| 2 | 2-306 | 0.00144 | 0.00116 | 0.4378 | |
| 2 | 2-307 | 0.00265 | | | |
| 2 | 2-308 | 0.00198 | 0.00089 | 0.0761 | |
| 2 | 2-309 | 0.00209 | | | |
| 2 | 2-310 | 0.00387 | | | |
| 2 | 2-311 | 0.00686 | 0.00093 | | |
| 2 | 2-312 | 0.00206 | 0.00087 | | |
| 2 | 2-313 | 0.00157 | | 0.1836 | |
| 2 | 2-314 | 0.00063 | | 0.1939 | |
| 2 | 2-315 | 0.00173 | | 0.1089 | |
| 2 | 2-316 | 0.00069 | | 0.1448 | |
| 2 | 2-317 | 0.00303 | 0.00399 | 0.2284 | |
| 2 | 2-318 | 0.00065 | | 0.0377 | |
| 2 | 2-319 | 0.00057 | | 0.0243 | |
| 2 | 2-320 | 0.00076 | | 0.1199 | |
| 2 | 2-321 | 0.00078 | | 0.2500 | |
| 2 | 2-322 | 0.00086 | | 0.1040 | |
| 2 | 2-323 | 0.00144 | | 0.0175 | |
| 2 | 2-324 | 0.00105 | | 0.0082 | |
| 2 | 2-325 | 0.00159 | | 0.1910 | |
| 2 | 2-326 | 0.00098 | 0.00066 | 0.0042 | |
| 2 | 2-327 | 0.00180 | | 0.0199 | |
| 2 | 2-328 | 0.00050 | | 0.0123 | |
| 2 | 2-329 | 0.00091 | 0.00042 | 0.0083 | |
| 2 | 2-330 | 0.00162 | 0.00073 | 0.0134 | |
| 2 | 2-331 | 0.00118 | 0.00032 | 0.0089 | |
| 2 | 2-332 | 0.00051 | 0.00062 | 0.0092 | |
| 2 | 2-333 | 0.00101 | 0.00039 | 0.0055 | |
| 2 | 2-334 | 0.00105 | 0.00062 | 0.0043 | 0.0307 |
| 2 | 2-335 | 0.00061 | 0.00064 | 0.0143 | |
| 2 | 2-336 | 0.00085 | 0.00085 | 0.0086 | |
| 2 | 2-337 | 0.00057 | 0.00061 | 0.0289 | |
| 2 | 2-338 | 0.00040 | 0.00022 | 0.0033 | 0.0234 |
| 2 | 2-339 | 0.00116 | 0.00037 | 0.0098 | |
| 2 | 2-340 | 0.00095 | 0.00031 | 0.0039 | |
| 2 | 2-341 | 0.00084 | 0.00038 | 0.0114 | |
| 2 | 2-342 | 0.00074 | 0.00032 | 0.0162 | |
| 2 | 2-343 | 0.00061 | 0.00037 | 0.0046 | 0.0383 |
| 2 | 2-344 | 0.01982 | 0.00369 | 1.7992 | |
| 2 | 2-345 | 0.00531 | 0.00153 | 0.0237 | |
| 2 | 2-346 | 0.00452 | 0.00099 | 0.0891 | |
| 2 | 2-347 | 0.00110 | 0.00033 | 0.0175 | 0.0411 |
| 2 | 2-348 | 0.00493 | 0.00154 | 0.0347 | |
| 2 | 2-349 | 0.00346 | 0.00087 | 0.0216 | |
| 2 | 2-350 | 0.01759 | 0.00481 | 0.7190 | |
| 2 | 2-351 | 0.00195 | 0.00077 | 0.0526 | |
| 2 | 2-352 | 0.00557 | 0.00077 | 0.0342 | |
| 2 | 2-353 | 0.00262 | 0.00079 | 0.0327 | |
| 2 | 2-354 | 0.00385 | | | |
| 2 | 2-355 | 0.00302 | | | |
| 2 | 2-356 | 0.00613 | | | |
| 2 | 2-357 | 0.00393 | | | |
| 2 | 2-358 | 0.00199 | | 0.0413 | |
| 2 | 2-359 | 0.00611 | | | |
| 2 | 2-360 | 0.00132 | 0.00108 | 0.4112 | |
| 2 | 2-361 | 0.00170 | 0.00061 | 0.0089 | |
| 2 | 2-362 | 0.00175 | 0.00133 | 0.2286 | |
| 2 | 2-363 | 0.00267 | | | |
| 2 | 2-364 | 0.00569 | | | |
| 2 | 2-365 | 0.00434 | | | |
| 2 | 2-366 | 0.00366 | | | |
| 2 | 2-367 | 0.00462 | | | |
| 2 | 2-368 | 0.00357 | | | |
| 2 | 2-369 | 0.00262 | | | |
| 2 | 2-370 | | | | |
| 2 | 2-371 | 0.00268 | | | |
| 2 | 2-372 | 0.00137 | 0.00100 | 0.2962 | |
| 2 | 2-373 | 0.00276 | | | |
| 2 | 2-374 | 0.00252 | 0.00158 | 0.0625 | |
| 2 | 2-375 | 0.00318 | | | |
| 2 | 2-376 | 0.00254 | | | |
| 2 | 2-377 | 0.00110 | | 0.0555 | |
| 2 | 2-378 | 0.00153 | | 0.2376 | |
| 2 | 2-379 | 0.00146 | | 0.2821 | |
| 2 | 2-380 | 0.00141 | | 0.0384 | |
| 2 | 2-381 | | | | |
| 2 | 2-382 | 0.00115 | | 0.3755 | |
| 2 | 2-383 | 0.00155 | | 0.0090 | |
| 2 | 2-384 | 0.00173 | | 0.0930 | |
| 2 | 2-385 | 0.00106 | | 0.1738 | |
| 2 | 2-386 | 0.00121 | | 0.1548 | |
| 2 | 2-387 | 0.00088 | | 0.1472 | |
| 2 | 2-388 | 0.00114 | | 0.1413 | |
| 2 | 2-389 | 0.00134 | | 0.0126 | |
| 2 | 2-390 | 0.00202 | | 0.1779 | |
| 2 | 2-391 | 0.00071 | | 0.0057 | |
| 2 | 2-392 | 0.00118 | | 0.2170 | |
| 2 | 2-393 | 0.00096 | 0.00039 | 0.0234 | |
| 2 | 2-394 | 0.00063 | 0.00024 | 0.0040 | |
| 2 | 2-395 | 0.00065 | 0.00018 | 0.0046 | |
| 2 | 2-396 | 0.00097 | 0.00044 | 0.0054 | |
| 2 | 2-397 | 0.00118 | 0.00034 | 0.0202 | |
| 2 | 2-398 | 0.00239 | 0.00068 | 0.0086 | |
| 2 | 2-399 | 0.00128 | 0.00079 | 0.0121 | |
| 2 | 2-400 | 0.00135 | 0.00095 | 0.0068 | |
| 2 | 2-401 | 0.00058 | 0.00034 | 0.0060 | |
| 2 | 2-402 | 0.00060 | 0.00029 | 0.0056 | |
| 2 | 2-403 | 0.00085 | 0.00037 | 0.0074 | |
| 2 | 2-404 | 0.00060 | 0.00024 | 0.0132 | |
| 2 | 2-405 | 0.00060 | 0.00027 | 0.0075 | |
| 2 | 2-406 | 0.00112 | 0.00062 | 0.0404 | |
| 2 | 2-407 | 0.00063 | 0.00028 | 0.0047 | |
| 2 | 2-408 | 0.02337 | 0.00422 | 0.1878 | |
| 2 | 2-409 | 0.00400 | 0.00112 | 0.1243 | |
| 2 | 2-410 | 0.00912 | 0.00155 | 0.1299 | |
| 2 | 2-411 | 0.00667 | 0.00197 | 0.3481 | |
| 2 | 2-412 | 0.00435 | 0.00070 | 0.0265 | |
| 2 | 2-413 | 0.01955 | 0.00359 | 1.2609 | |
| 2 | 2-414 | 0.00320 | | | |
| 2 | 2-415 | 0.00171 | 0.00132 | 0.0130 | |
| 2 | 2-416 | 0.00164 | 0.00125 | 0.5977 | |
| 2 | 2-417 | 0.00123 | 0.00045 | 0.0143 | |
| 2 | 2-418 | 0.00329 | | | |
| 2 | 2-419 | 0.00510 | | | |
| 2 | 2-420 | 0.00289 | | | |
| 2 | 2-421 | 0.00131 | 0.00082 | 0.0241 | |
| 2 | 2-422 | 0.00180 | | 0.0140 | |
| 2 | 2-423 | 0.00190 | 0.00088 | 0.0173 | |
| 2 | 2-424 | 0.00225 | | | |
| 2 | 2-425 | 0.00085 | 0.00100 | 0.2262 | |
| 2 | 2-426 | 0.00189 | 0.00055 | 0.0510 | |
| 2 | 2-427 | 0.00101 | 0.00098 | 0.2152 | |
| 2 | 2-428 | 0.00168 | 0.00115 | 0.4627 | |
| 2 | 2-429 | 0.00126 | 0.00068 | 0.0274 | |
| 2 | 2-430 | 0.00479 | | | |
| 2 | 2-431 | 0.00679 | | | |
| 2 | 2-432 | 0.00164 | 0.00062 | 0.0430 | |
| 2 | 2-433 | 0.00121 | 0.00112 | 0.0132 | |
| 2 | 2-434 | 0.00155 | 0.00114 | 0.2315 | |
| 2 | 2-435 | 0.00233 | | | |
| 2 | 2-436 | 0.00299 | | | |
| 2 | 2-437 | 0.00179 | 0.00114 | 0.0337 | |
| 2 | 2-438 | 0.00403 | | | |
| 2 | 2-439 | 0.00289 | | | |
| 2 | 2-440 | 0.00047 | | 0.1555 | |
| 2 | 2-441 | 0.00053 | | 0.0824 | |
| 2 | 2-442 | 0.00088 | | 0.3050 | |
| 2 | 2-443 | 0.00120 | | 0.0723 | |
| 2 | 2-444 | 0.00092 | 0.00090 | 0.1538 | |
| 2 | 2-445 | 0.00127 | 0.06143 | 0.4557 | |
| 2 | 2-446 | 0.00040 | | 0.2085 | |
| 2 | 2-447 | 0.00090 | | 0.2752 | |
| 2 | 2-448 | 0.00103 | | 0.1198 | |
| 2 | 2-449 | 0.00117 | | 0.3546 | |
| 2 | 2-450 | 0.00177 | | 0.1152 | |
| 2 | 2-451 | 0.00146 | | 0.2871 | |
| 2 | 2-452 | 0.00097 | | 0.1343 | |

TABLE 4-continued

| Table number | Example number | JAK1 Ki (μM) | JAK2 Ki (μM) | IL-13-pSTAT6 IC50 (μM) | IL13-pSTAT6 BEASB2B IC50 (μM) |
|---|---|---|---|---|---|
| 2 | 2-453 | 0.00123 | | | 0.1713 |
| 2 | 2-454 | 0.00057 | | | 0.0879 |
| 2 | 2-455 | 0.00123 | | | 0.0055 |
| 2 | 2-456 | 0.00092 | | | 0.0075 |
| 2 | 2-457 | 0.00259 | | | |
| 2 | 2-458 | 0.00115 | | | 0.0459 |
| 2 | 2-459 | 0.00061 | | | 0.0205 |
| 2 | 2-460 | 0.00093 | | | 0.0276 |
| 2 | 2-461 | 0.00084 | 0.00030 | | 0.0061 |
| 2 | 2-462 | 0.00087 | 0.00029 | | 0.0444 |
| 2 | 2-463 | 0.00116 | 0.00065 | | 0.0260 |
| 2 | 2-464 | 0.00108 | 0.00044 | | 0.0091 |
| 2 | 2-465 | 0.00052 | 0.00073 | | 0.0094 |
| 2 | 2-466 | 0.00097 | 0.00079 | | 0.0179 |
| 2 | 2-467 | 0.00164 | 0.00068 | | 0.0209 |
| 2 | 2-468 | 0.00069 | 0.00026 | | 0.0128 |
| 2 | 2-469 | 0.00068 | 0.00076 | | 0.0838 |
| 2 | 2-470 | 0.00075 | 0.00033 | | 0.0130 |
| 2 | 2-471 | 0.00083 | 0.00040 | | 0.0064 |
| 2 | 2-472 | 0.00182 | 0.00062 | | 0.0679 |
| 2 | 2-473 | 0.00261 | 0.00139 | | 0.0481 |
| 2 | 2-474 | 0.00100 | 0.00029 | | 0.0141 |
| 2 | 2-475 | 0.00075 | 0.00038 | | 0.0429 |
| 2 | 2-476 | 0.00092 | 0.00042 | | 0.0105 |
| 2 | 2-477 | 0.00157 | 0.00080 | | 0.1128 |
| 2 | 2-478 | 0.00076 | 0.00043 | | 0.0048 |
| 2 | 2-479 | 0.01796 | 0.00310 | | 0.2390 |
| 2 | 2-480 | 0.00446 | 0.00085 | | 0.1779 |
| 2 | 2-481 | 0.26562 | 0.05267 | | |
| 3 | 3-1 | 0.10799 | 0.14510 | | |

Blank: not determined

What is claimed is:

1. A compound selected from the group consisting of
N-methyl-4-[[8-(4-methyl-4-phenyl-1-piperidyl)-[1,2,4]triazolo[1,5-a]pyridin-2-yl]amino]-N-(1-methyl-4-piperidyl)benzamide;hydrochloride
4-[[8-(4-cyclohexyl-4-hydroxy-1-piperidyl)-[1,2,4]triazolo[1,5-a]pyridin-2-yl]amino]-N-methyl-N-(1-methyl-4-piperidyl)benzamide
4-[[8-(4-hydroxy-1-piperidyl)-[1,2,4]triazolo[1,5-a]pyridin-2-yl]amino]-N-methyl-N-(1-methyl-4-piperidyl)benzamide;hydrochloride
N-methyl-N-(1-methyl-4-piperidyl)-4-[[8-(4-phenyl-3,6-dihydro-2H-pyridin-1-yl)-[1,2,4]triazolo[1,5-a]pyridin-2-yl]amino]bhenzamide
4-[[8-(4-methoxy-4-phenyl-1-piperidyl)-[1,2,4]triazolo[1,5-a]pyridin-2-yl]amino]-N-methyl-N-(1-methyl-4-piperidyl)benzamide;hydrochloride
4-[[8-(4-hydroxy-4-methyl-1-piperidyl)-[1,2,4]triazolo[1,5-a]pyridin-2-yl]amino]-N-methyl-N-(1-methyl-4-piperidyl)benzamide;hydrochloride
4-[[8-(4-hydroxy-4-phenyl-azepan-1-yl)-[1,2,4]triazolo[1,5-a]pyridin-2-yl]amino]-N-methyl-N-(1-methyl-4-piperidyl)benzamide
4-[[8-(4-methoxy-1-piperidyl)-[1,2,4]triazolo[1,5-a]pyridin-2-yl]amino]-N-methyl-N-(1-methyl-4-piperidyl)benzamide
4-[[8-(4-acetamido-1-piperidyl)-[1,2,4]triazolo[1,5-a]pyridin-2-yl]amino]-N-methyl-N-(1-methyl-4-piperidyl)benzamide;hydrochloride
4-[[8-(4-acetylpiperazin-1-yl)-[1,2,4]triazolo[1,5-a]pyridin-2-yl]amino]-N-methyl-N-(1-methyl-4-piperidyl)benzamide
4-[[8-(4-cyano-1-piperidyl)-[1,2,4]triazolo[1,5-a]pyridin-2-yl]amino]-N-methyl-N-(1-methyl-4-piperidyl)benzamide
N-methyl-N-(1-methyl-4-piperidyl)-4-[[8-(1-piperidyl)-[1,2,4]triazolo[1,5-a]pyridin-2-yl]amino]benzamide; dihydrochloride
N-methyl-N-(1-methyl-4-piperidyl)-4-[[8-(4-phenylpiperazin-1-yl)-[1,2,4]triazolo[1,5-a]pyridin-2-yl]amino]benzamide
N-methyl-N-(1-methyl-4-piperidyl)-4-[[8-(4-phenyl-2,3,6,7-tetrahydroazepin-1-yl)-[1,2,4]triazolo[1,5-a]pyridin-2-yl]amino]benzamide
N-methyl-N-(1-methyl-4-piperidyl)-4-[[8-(5-phenyl-2,3,4,7-tetrahydroazepin-1-yl)-[1,2,4]triazolo[1,5-a]pyridin-2-yl]amino]benzamide
4-[[8-(4-fluoro-4-phenyl-1-piperidyl)-[1,2,4]triazolo[1,5-a]pyridin-2-yl]amino]-N-methyl-N-(1-methyl-4-piperidyl)benzamide
4-[[8-[4-(4-chlorophenyl)-4-hydroxy-1-piperidyl]-[1,2,4]triazolo[1,5-a]pyridin-2-yl]amino]-N-methyl-N-(1-methyl-4-piperidyl)benzamide
4-[[8-[4-(3-chlorophenyl)-4-hydroxy-1-piperidyl]-[1,2,4]triazolo[1,5-a]pyridin-2-yl]amino]-N-methyl-N-(1-methyl-4-piperidyl)benzamide
4-[[8-[4-hydroxy-4-(3-pyridyl)-1-piperidyl]-[1,2,4]triazolo[1,5-a]pyridin-2-yl]amino]-N-methyl-N-(1-methyl-4-piperidyl)benzamide
4-[[8-[4-hydroxy-4-(4-pyridyl)-1-piperidyl]-[1,2,4]triazolo[1,5-a]pyridin-2-yl]amino]-N-methyl-N-(1-methyl-4-piperidyl)benzamide
4-[[8-[4-(4-cyanophenyl)-4-hydroxy-1-piperidyl]-[1,2,4]triazolo[1,5-a]pyridin-2-yl]amino]-N-methyl-N-(1-methyl-4-piperidyl)benzamide
4-[[8-[4-(3-cyanophenyl)-4-hydroxy-1-piperidyl]-[1,2,4]triazolo[1,5-a]pyridin-2-yl]amino]-N-methyl-N-(1-methyl-4-piperidyl)benzamide
4-[[8-[4-(cyanomethoxy)-1-piperidyl]-[1,2,4]triazolo[1,5-a]pyridin-2-yl]amino]-N-methyl-N-(1-methyl-4-piperidyl)benzamide
N-methyl-N-(1-methyl-4-piperidyl)-4-[[8-(2-oxo-1-oxa-3,7-diazaspiro[4.4]nonan-7-yl)-[1,2,4]triazolo[1,5-a]pyridin-2-yl]amino]benzamide
4-[[8-[(9aS)-3,4,6,7,9,9a-hexahydro-1H-pyrazino[2,1-c][1,4]oxazin-8-yl]-[1,2,4]triazolo[1,5-a]pyridin-2-yl]amino]-N-methyl-N-(1-methyl-4-piperidyl)benzamide
N-methyl-N-(1-methyl-4-piperidyl)-4-[[8-(8-oxo-2,7-diazaspiro[4.4]nonan-2-yl)-[1,2,4]triazolo[1,5-a]pyridin-2-yl]amino]benzamide
N-methyl-N-(1-methyl-4-piperidyl)-4-[[8-(3-oxo-2,8-diazaspiro[4.5]decan-8-yl)-[1,2,4]triazolo[1,5-a]pyridin-2-yl]amino]benzamide
N-methyl-N-(1-methyl-4-piperidyl)-4-][8-(2-oxo-1-oxa-3,8-diazaspiro[4.5]decan-8-yl)-[1,2,4]triazolo[1,5-a]pyridin-2-yl]amino]benzamide
4-[[8-[4-(1-hydroxy-1-methyl-ethyl)-1-piperidyl]-[1,2,4]triazolo[1,5-a]pyridin-2-yl]amino]-N-methyl-N-(1-methyl-4-piperidyl)benzamide
4-[[8-[4-(2-amino-2-oxo-ethyl)-4-phenyl-1-piperidyl]-[1,2,4]triazolo[1,5-a]pyridin-2-yl]amino]-N-methyl-N-(1-methyl-4-piperidyl)benzamide
N-methyl-N-(1-methyl-4-piperidyl)-4-[[8-(6-oxo-3,4,7,8,9,9a-hexahydro-1H-pyrazino[1,2-c]pyrimidin-2-yl)-[1,2,4]triazolo[1,5-a]pyridin-2-yl]amino]benzamide
4-[[8-[(9aS)-4-oxo-6,7,9,9a-tetrahydro-1H-pyrazino[2,1-c][1,4]oxazin-8-yl]-[1,2,4]triazolo[1,5-a]pyridin-2-yl]amino]-N-methyl-N-(1-methyl-4-piperidyl)benzamide
4-[[8-[(9aR)-4-oxo-6,7,9,9a-tetrahydro-1H-pyrazino[2,1-c][1,4]oxazin-8-yl]-[1,2,4]triazolo[1,5-a]pyridin-2-yl]amino]-N-methyl-N-(1-methyl-4-piperidyl)benzamide 4-[[8-[4-(3,3-dimethylazetidine-1-carbonyl)piperazin-1-yl]-[1,2,4]triazolo[1,5-a]pyridin-2-yl]amino]-N-methyl-N-(1-methyl-4-piperidyl)benzamide
4-[[8-[4-(2-chlorophenyl)-4-hydroxy-1-piperidyl]-[1,2,4]triazolo[1,5-a]pyridin-2-yl]amino]-N-methyl-N-(1-methyl-4-piperidyl)benzamide
4-[[8-[4-(4-ethylphenyl)-4-hydroxy-1-piperidyl]-[1,2,4]triazolo[1,5-a]pyridin-2-yl]amino]-N-methyl-N-(1-methyl-4-piperidyl)benzamide
4-[[8-[4-(4-fluorophenyl)-4-hydroxy-1-piperidyl]-[1,2,4]triazolo[1,5-a]pyridin-2-yl]amino]-N-methyl-N-(1-methyl-4-piperidyl)benzamide
4-[[8-[4-hydroxy-4-(4-isopropylphenyl)-1-piperidyl]-[1,2,4]triazolo[1,5-a]pyridin-2-yl]amino]-N-methyl-N-(1-methyl-4-piperidyl)benzamide
4-[[8-[4-hydroxy-4-(p-tolyl)-1-piperidyl]-[1,2,4]triazolo[1,5-a]pyridin-2-yl]amino]-N-methyl-N-(1-methyl-4-piperidyl)benzamide
4-[[8-[4-hydroxy-4-(4-methoxyphenyl)-1-piperidyl]-[1,2,4]triazolo[1,5-a]pyridin-2-yl]amino]-N-methyl-N-(1-methyl-4-piperidyl)benzamide
4-[[8-[4-(cyanomethyl)-4-phenyl-1-piperidyl]-[1,2,4]triazolo[1,5-a]pyridin-2-yl]amino]-N-methyl-N-(1-methyl-4-piperidyl)benzamide
4-[[8-[4-(3,3-dimethylazetidine-1-carbonyl)-1-piperidyl]-[1,2,4]triazolo[1,5-a]pyridin-2-yl]amino]-N-methyl-N-(1-methyl-4-piperidyl)benzamide
4-[[8-(4-hydroxy-4-phenyl-1-piperidyl)-[1,2,4]triazolo[1,5-a]pyridin-2-yl]amino]-N-methyl-N-(1-methyl-4-piperidyl)benzamide
4-[[8-[4-[[2-(2-methoxyethoxy)-4-pyridyl]methoxy]-1-piperidyl]-[1,2,4]triazolo[1,5-a]pyridin-2-yl]amino]-N-methyl-N-(1-methyl-4-piperidyl)benzamide
4-][8-(4-cyano-4-phenyl-1-piperidyl)-[1,2,4]triazolo[1,5-a]pyridin-2-yl]amino]-N-methyl-N-(1-methyl-4-piperidyl)benzamide
4-[[8-(3,4-dihydro-1H-isoquinolin-2-yl)-[1,2,4]triazolo[1,5-a]pyridin-2-yl]amino]-N-methyl-N-(1-methyl-4-piperidyl)benzamide
[4-[[8-[4-(4-chlorophenyl)-4-hydroxy-1-piperidyl]-[1,2,4]triazolo[1,5-a]pyridin-2-yl]amino]phenyl]-[3-(methylamino)azetidin-1-yl]methanone
[4-[[8-[4-(4-chlorophenyl)-4-hydroxy-1-piperidyl]-[1,2,4]triazolo[1,5-a]pyridin-2-yl]amino]phenyl]-(2-methyl-1,3,3a,4,6,6a-hexahydropyrrolo[3,4-c]pyrrol-5-yl)methanone
[4-[[8-[4-(4-chlorophenyl)-4-hydroxy-1-piperidyl]-[1,2,4]triazolo[1,5-a]pyridin-2-yl]amino]phenyl]-(7-methyl-9-oxa-3,7-diazabicyclo[3.3.1]nonan-3-yl)methanone
[4-[[8-[4-(4-chlorophenyl)-4-hydroxy-1-piperidyl]-[1,2,4]triazolo[1,5-a]pyridin-2-yl]amino]phenyl]-(9-methyl-3-oxa-7,9-diazabicyclo[3.3.1]nonan-7-yl)methanone
[4-[[8-[4-(4-chlorophenyl)-4-hydroxy-1-piperidyl]-[1,2,4]triazolo[1,5-a]pyridin-2-yl]amino]phenyl]-[4-hydroxy-4-(pyrrolidin-1-ylmethyl)azepan-1-yl]methanone
[4-[[8-[4-(4-chlorophenyl)-4-hydroxy-1-piperidyl]-[1,2,4]triazolo[1,5-a]pyridin-2-yl]amino]phenyl]-[2-(1-methyl-2-piperidyl)pyrrolidin-1-yl]methanone
1-[2-[4-[[8-[4-(4-chlorophenyl)-4-hydroxy-1-piperidyl]-[1,2,4]triazolo[1,5-a]pyridin-2-yl]amino]benzoyl]-2,6-diazaspiro[3.3]heptan-6-yl]ethanone
[4-[[8-[4-(4-chlorophenyl)-4-hydroxy-1-piperidyl]-[1,2,4]triazolo[1,5-a]pyridin-2-yl]amino]phenyl]-(4-cyclopropylpiperazin-1-yl)methanone
[4-[[8-[4-(4-chlorophenyl)-4-hydroxy-1-piperidyl]-[1,2,4]triazolo[1,5-a]pyridin-2-yl]amino]phenyl]-(3-methyl-3,6-diazabicyclo[3.2.1]octan-6-yl)methanone
[4-[[8-[4-(4-chlorophenyl)-4-hydroxy-1-piperidyl]-[1,2,4]triazolo[1,5-a]pyridin-2-yl]amino]phenyl]-(4-cyclobutylpiperazin-1-yl)methanone
4-[[8-[4-(4-chlorophenyl)-4-hydroxy-1-piperidyl]-[1,2,4]triazolo[1,5-a]pyridin-2-yl]amino]-N-[(5-methyl-3-pyridyl)methyl]benzamide
4-[[8-[4-(4-chlorophenyl)-4-hydroxy-1-piperidyl]-[1,2,4]triazolo[1,5a]pyridin-2-yl]amino]-N-[(6-methyl-3-pyridyl)methyl]benzamide
[4-[[8-[4-(4-chlorophenyl)-4-hydroxy-1-piperidyl]-[1,2,4]triazolo[1,5a]pyridin-2-yl]amino]phenyl]-(7-methyl-2,7-diazaspiro[3.4]octan-2-yl)methanone
[4-[[8-[4-(4-chlorophenyl)-4-hydroxy-1-piperidyl]-[1,2,4]triazolo[1,5a]pyridin-2-yl]amino]phenyl]-(5-methyl-2,5-diazaspiro[3.4]octan-2-yl)methanone
4-[[8-[4-(4-chlorophenyl)-4-hydroxy-1-piperidyl]-[1,2,4]triazolo[1,5-a]pyridin-2-yl]amino]-N-[2-(4-methyl-1-piperidyl)ethyl]benzamide
4-[[8-[4-(4-chlorophenyl)-4-hydroxy-1-piperidyl]-[1,2,4]triazolo[1,5-a]pyridin-2-yl]amino]-N-(1-methylpyrrolidin-3-yl)benzamide
4-[[8-[4-(4-chlorophenyl)-4-hydroxy-1-piperidyl]-[1,2,4]triazolo[1,5-a]pyridin-2-yl]amino]-N-[(4-methyl-2-pyridyl)methyl]benzamide
4-[[8-[4-(4-chlorophenyl)-4-hydroxy-1-piperidyl]-[1,2,4]triazolo[1,5-a]pyridin-2-yl]amino]-N-[(2-methyl-3-pyridyl)methyl]benzamide
4-[[8-[4-(4-chlorophenyl)-4-hydroxy-1-piperidyl]-[1,2,4]triazolo[1,5-a]pyridin-2-yl]amino]-N-[(1-ethylpyrrolidin-3-yl)methyl]-N-methyl-benzamide
[4-[[8-[4-(4-chlorophenyl)-4-hydroxy-1-piperidyl]-[1,2,4]triazolo[1,5a]pyridin-2-yl]amino]phenyl]-(8-methyl-2,8-diazaspiro[5.5]undecan-2-yl)methanone
[4-[[8-[4-(4-chlorophenyl)-4-hydroxy-1-piperidyl]-[1,2,4]triazolo[1,5a]pyridin-2-yl]amino]phenyl]-[4-[(1-methylimidazol-2-yl)methyl]piperazin-1-yl]methanone
[4-[[8-[4-(4-chlorophenyl)-4-hydroxy-1-piperidyl]-[1,2,4]triazolo[1,5a]pyridin-2-yl]amino]phenyl]-[2-(3-pyridyl)pyrrolidin-1-yl]methanone
[4-[[8-[4-(4-chlorophenyl)-4-hydroxy-1-piperidyl]-[1,2,4]triazolo[1,5a]pyridin-2-yl]amino]phenyl]-[6-(hydroxymethyl)-4-methyl-1,4-diazepan-1-yl]methanone
[4-[[8-[4-(4-chlorophenyl)-4-hydroxy-1-piperidyl]-[1,2,4]triazolo[1,5-a]pyridin-2-yl]amino]phenyl]-(8-methyl-5-oxa-2,8-diazaspiro[3.5]nonan-2-yl)methanone
4-[4-[[8-[4-(4-chlorophenyl)-4-hydroxy-1-piperidyl]-[1,2,4]triazolo[1,5-a]pyridin-2-yl]amino]benzoyl]-N,N,1-trimethyl-piperazine-2-carboxamide
[4-[[8-[4-(4-chlorophenyl)-4-hydroxy-1-piperidyl]-[1,2,4]triazolo[1,5a]pyridin-2-yl]amino]phenyl]-[2-(5-methyl-2-pyridyl)pyrrolidin-1-yl]methanone
[4-[[8-[4-(4-chlorophenyl)-4-hydroxy-1-piperidyl]-[1,2,4]triazolo[1,5-a]pyridin-2-yl]amino]phenyl]-[3-[6-(dimethylamino)-2-methyl-pyrimidin-4-yl]-1-piperidyl]methanone
1-[4-[[8-[4-(4-chlorophenyl)-4-hydroxy-1-piperidyl]-[1,2,4]triazolo[1,5-a]pyridin-2-yl]amino[benzoyl]-N,N-dimethyl-2-(4-pyridyl)pyrrolidine-2-carboxamide
[(3aS,6aS)-1-methyl-2,3,3a,4,6,6a-hexahydropyrrolo[3,4-b]pyrrol-5-yl]-[4-[[8-[4-(4-chlorophenyl)-4-hydroxy-1-piperidyl]-[1,2,4]triazolo[1,5-a]pyridin-2-yl]amino]phenyl]methanone

[(3aS,6aS)-5-methyl-2,3,3a,4,6,6a-hexahydropyrrolo[2,3-c]pyrrol-1-yl]-[4-[[8-[4-(4-chlorophenyl)-4-hydroxy-1-piperidyl]-[1,2,4]triazolo[1,5-a]pyridin-2-yl]amino]phenyl]methanone

[4-[[8-[4-(4-chlorophenyl)-4-hydroxy-1-piperidyl]-[1,2,4]triazolo[1,5-a]pyridin-2-yl]amino]phenyl]-[4-[(dimethylamino)methyl]-4-hydroxy-azepan-1-yl]methanone

[4-[[8-[4-(4-chlorophenyl)-4-hydroxy-1-piperidyl]-[1,2,4]triazolo[1,5-a]pyridin-2-yl]amino]phenyl]-[3-(4-methylpiperazine-1-carbonyl)morpholin-4-yl]methanone

[4-[[8-[4-(4-chlorophenyl)-4-hydroxy-1-piperidyl]-[1,2,4]triazolo[1,5-a]pyridin-2-yl]amino]phenyl]-[2-[4-(dimethylamino)-6-methyl-2-pyridyl]pyrrolidin-1-yl]methanone

[4-[[8-[4-(4-chlorophenyl)-4-hydroxy-1-piperidyl]-[1,2,4]triazolo[1,5-a]pyridin-2-yl]amino]phenyl]-[3-[2-(dimethylamino)ethyl]-1-piperidyl]methanone

[4-[[8-[4-(4-chlorophenyl)-4-hydroxy-1-piperidyl]-[1,2,4]triazolo[1,5-a]pyridin-2-yl]amino]phenyl]-(7-methyl-2,7-diazaspiro[3.5]nonan-2-yl)methanone 1-[4-[[8-[4-(4-chlorophenyl)-4-hydroxy-1-piperidyl]-[1,2,4]triazolo[1,5-a]pyridin-2-yl]amino]benzoyl]-N,N,4-trimethyl-piperazine-2-carboxamide

[4-[[8-[4-(4-chlorophenyl)-4-hydroxy-1-piperidyl]-[1,2,4]triazolo[1,5-a]pyridin-2-yl]amino]phenyl]-[4-(4-pyridyl)-1-piperidyl]methanone

[4-[[8-[4-(4-chlorophenyl)-4-hydroxy-1-piperidyl]-[1,2,4]triazolo[1,5-a]pyridin-2-yl]amino]phenyl]-[4-(2-hydroxyethyl)piperazin-1-yl]methanone 4-[[8-[4-(4-chlorophenyl)-4-hydroxy-1-piperidyl]-[1,2,4]triazolo[1,5-a]pyridin-2-yl]amino]-N-methyl-N-[2-(2-pyridyl)ethyl]benzamide

[4-[[8-[4-(4-chlorophenyl)-4-hydroxy-1-piperidyl]-[1,2,4]triazolo[1,5-a]pyridin-2-yl]amino]phenyl]-[4-(dimethylamino)-1-piperidyl]methanone 4-[[8-[4-(4-chlorophenyl)-4-hydroxy-1-piperidyl]-[1,2,4]triazolo[1,5-a]pyridin-2-yl]amino]-N-methyl-N-(1-methylpyrrolidin-3-yl)benzamide

[4-[[8-[4-(4-chlorophenyl)-4-hydroxy-1-piperidyl]-[1,2,4]triazolo[1,5-a]pyridin-2-yl]amino]phenyl]-[3-(dimethylamino)pyrrolidin-1-yl]methanone 4-[[8-[4-(4-chlorophenyl)-4-hydroxy-1-piperidyl]-[1,2,4]triazolo[1,5-a]pyridin-2-yl]amino]-N-[(3R)-quinuclidin-3-yl]benzamide

[4-[[8-[4-(4-chlorophenyl)-4-hydroxy-1-piperidyl]-[1,2,4]triazolo[1,5-a]pyridin-2-yl]amino]phenyl]-(4-methylpiperazin-1-yl)methanone 4-[[8-[4-(4-chlorophenyl)-4-hydroxy-1-piperidyl]-[1,2,4]triazolo[1,5-a]pyridin-2-yl]amino]-N-[2-(2,6-dimethylmorpholin-4-yl)ethyl]benzamide 4-[[8-[4-(4-chlorophenyl)-4-hydroxy-1-piperidyl]-[1,2,4]triazolo[1,5-a]pyridin-2-yl]amino]-N-(1-methylazetidin-3-yl)benzamide 4-[[8-[4-(4-chlorophenyl)-4-hydroxy-1-piperidyl]-[1,2,4]triazolo[1,5-a]pyridin-2-yl]amino]-N-(1,1-dimethyl-2-morpholino-ethyl)benzamide 4-[[8-[4-(4-chlorophenyl)-4-hydroxy-1-piperidyl]-[1,2,4]triazolo[1,5-a]pyridin-2-yl]amino]-N-(2-methyl-2-morpholino-propyl)benzamide 4-[[8-[4-(4-chlorophenyl)-4-hydroxy-1-piperidyl]-[1,2,4]triazolo[1,5-a]pyridin-2-yl]amino]-N-[2-(4-hydroxy-1-piperidyl)ethyl]benzamide 4-[[8-[4-(4-chlorophenyl)-4-hydroxy-1-piperidyl]-[1,2,4]triazolo[1,5-a]pyridin-2-yl]amino]-N-[3-(4-methylpiperazin-1-yl)propyl]benzamide 4-[[8-[4-(4-chlorophenyl)-4-hydroxy-1-piperidyl]-[1,2,4]triazolo[1,5-a]pyridin-2-yl]amino]-N-[2-(4-methylpiperazin-1-yl)ethyl]benzamide 4-[[8-[4-(4-chlorophenyl)-4-hydroxy-1-piperidyl]-[1,2,4]triazolo[1,5-a]pyridin-2-yl]amino]-N-(3-morpholino-propyl)benzamide 4-[[8-[4-(4-chlorophenyl)-4-hydroxy-1-piperidyl]-[1,2,4]triazolo[1,5-a]pyridin-2-yl]amino]-N-[1-methyl-2-(1-piperidyl)ethyl]benzamide 4-[[8-[4-(4-chlorophenyl)-4-hydroxy-1-piperidyl]-[1,2,4]triazolo[1,5-a]pyridin-2-yl]amino]-N-[2-(3-methyl-1-piperidyl)ethyl]benzamide 4-[[8-[4-(4-chlorophenyl)-4-hydroxy-1-piperidyl]-[1,2,4]triazolo[1,5-a]pyridin-2-yl]amino]-N-(2-morpholino-ethyl)benzamide 4-[[8-[4-(4-chlorophenyl)-4-hydroxy-1-piperidyl]-[1,2,4]triazolo[1,5-a]pyridin-2-yl]amino]-N-[2-(1-methylpyrrolidin-2-yl)ethyl]benzamide 4-[[8-[4-(4-chlorophenyl)-4-hydroxy-1-piperidyl]-[1,2,4]triazolo[1,5-a]pyridin-2-yl]amino]-N-[(1-methyl-2-piperidyl)methyl]benzamide 4-[[8-[4-(4-chlorophenyl)-4-hydroxy-1-piperidyl]-[1,2,4]triazolo[1,5-a]pyridin-2-yl]amino]-N-[(1-methyl-4-piperidyl)methyl]benzamide 4-[[8-[4-(4-chlorophenyl)-4-hydroxy-1-piperidyl]-[1,2,4]triazolo[1,5-a]pyridin-2-yl]amino]-N-(1-methyl-4-piperidyl)benzamide 4-[[8-[4-(4-chlorophenyl)-4-hydroxy-1-piperidyl]-[1,2,4]triazolo[1,5-a]pyridin-2-yl]amino]-N-(2-pyrrolidin-1-ylethyl)benzamide 4-[[8-[4-(4-chlorophenyl)-4-hydroxy-1-piperidyl]-[1,2,4]triazolo[1,5-a]pyridin-2-yl]amino]-N-[2-(dimethylamino)-1-methyl-ethyl]benzamide 4-[[8-[4-(4-chlorophenyl)-4-hydroxy-1-piperidyl]-[1,2,4]triazolo[1,5-a]pyridin-2-yl]amino]-N-[2-(dimethylamino)ethyl]benzamide 4-[[8-[4-(4-chlorophenyl)-4-hydroxy-1-piperidyl]-[1,2,4]triazolo[1,5-a]pyridin-2-yl]amino]-N-methyl-N-[(3-methyl-2-pyridyl)methyl]benzamide

[4-[[8-[4-(4-chlorophenyl)-4-hydroxy-1-piperidyl]-[1,2,4]triazolo[1,5-a]pyridin-2-yl]amino]phenyl]-[2-(3-pyridyl)-1-piperidyl]methanone 4-[[8-[4-(4-chlorophenyl)-4-hydroxy-1-piperidyl]-[1,2,4]triazolo[1,5-a]pyridin-2-yl]amino]-N-methyl-N-(4-pyridylmethyl)benzamide

[4-[[8-[4-(4-chlorophenyl)-4-hydroxy-1-piperidyl]-[1,2,4]triazolo[1,5-a]pyridin-2-yl]amino]phenyl]-[4-(2-pyridyl)piperazin-1-yl]methanone

[4-[[8-[4-(4-chlorophenyl)-4-hydroxy-1-piperidyl]-[1,2,4]triazolo[1,5-a]pyridin-2-yl]amino]phenyl]-[4-(4-methylpiperazine-1-carbonyl)-1-piperidyl]methanone

[4-[[8-[4-(4-chlorophenyl)-4-hydroxy-1-piperidyl]-[1,2,4]triazolo[1,5-a]pyridin-2-yl]amino]phenyl]-[4-(4-pyridyl)-1,4-diazepan-1-yl]methanone 4-[[8-[4-(4-chlorophenyl)-4-hydroxy-1-piperidyl]-[1,2,4]triazolo[1,5-a]pyridin-2-yl]amino]-N-ethyl-N-(4-pyridylmethyl)benzamide

[4-[[8-[4-(4-chlorophenyl)-4-hydroxy-1-piperidyl]-[1,2,4]triazolo[1,5-a]pyridin-2-yl]amino]phenyl]-[4-(2-imidazol-1-ylethyl)piperazin-1-yl]methanone

[4-[[8-[4-(4-chlorophenyl)-4-hydroxy-1-piperidyl]-[1,2,4]triazolo[1,5-a]pyridin-2-yl]amino]phenyl]-[4-(4-methylpiperazin-1-yl)-1-piperidyl]methanone

[4-[[8-[4-(4-chlorophenyl)-4-hydroxy-1-piperidyl]-[1,2,4]triazolo[1,5-a]pyridin-2-yl]amino]phenyl]-[4-(2,6-dimethylmorpholin-4-yl)-1-piperidyl]methanone

[4-[[8-[4-(4-chlorophenyl)-4-hydroxy-1-piperidyl]-[1,2,4]triazolo[1,5-a]pyridin-2-yl]amino]phenyl]-[4-(2-morpholinoethyl)piperazin-1-yl]methanone 4-[[8-[4-(4-chlorophenyl)-4-hydroxy-1-piperidyl]-[1,2,4]triazolo[1,5-a]pyridin-2-yl]amino]-N-(2-methoxyethyl)-N-(1-methyl-4-piperidyl)benzamide

[4-[[8-[4-(4-chlorophenyl)-4-hydroxy-1-piperidyl]-[1,2,4]triazolo[1,5-a]pyridin-2-yl]amino]phenyl]-[2-(2-pyridylmethyl)-1-piperidyl]methanone

[4-[[8-[4-(4-chlorophenyl)-4-hydroxy-1-piperidyl]-[1,2,4]triazolo[1,5-a]pyridin-2-yl]amino]phenyl]-[4-(2-pyridylmethyl)piperazin-1-yl]methanone

[4-[[8-[4-(4-chlorophenyl)-4-hydroxy-1-piperidyl]-[1,2,4]triazolo[1,5-a]pyridin-2-yl]amino]phenyl]-[4-(3-pyridylmethyl)piperazin-1-yl]methanone

[4-[[8-[4-(4-chlorophenyl)-4-hydroxy-1-piperidyl]-[1,2,4]triazolo[1,5-a]pyridin-2-yl]amino]phenyl]-[2-(2-pyridylmethyl)pyrrolidin-1-yl]methanone

[4-[[8-[4-(4-chlorophenyl)-4-hydroxy-1-piperidyl]-[1,2,4]triazolo[1,5-a]pyridin-2-yl]amino]phenyl]-(4-morpholino-1-piperidyl)methanone

[4-[[8-[4-(4-chlorophenyl)-4-hydroxy-1-piperidyl]-[1,2,4]triazolo[1,5-a]pyridin-2-yl]amino]phenyl]-[4-(3-pyridyl)piperazin-1-yl]methanone

[4-[[8-[4-(4-chlorophenyl)-4-hydroxy-1-piperidyl]-[1,2,4]triazolo[1,5-a]pyridin-2-yl]amino]phenyl]-(3-morpholinopyrrolidin-1-yl)methanone 4-[[8-[4-(4-chlorophenyl)-4-hydroxy-1-piperidyl]-[1,2,4]triazolo[1,5-a]pyridin-2-yl]amino]-N-cyclopropyl-N-(1-methyl-4-piperidyl)benzamide 4-[[8-[4-(4-chlorophenyl)-4-hydroxy-1-piperidyl]-[1,2,4]triazolo[1,5-a]pyridin-2-yl]amino]-N-[(1-isopropylpyrrolidin-3 -yl)methyl]-N-methyl-benzamide 4-[[8-[4-(4-chlorophenyl)-4-hydroxy-1-piperidyl]-[1,2,4]triazolo[1,5-a]pyridin-2-yl]amino]-N-(1-isopropyl-4-piperidyl)-N-methyl-benzamide

[4-[[8-[4-(4-chlorophenyl)-4-hydroxy-1-piperidyl]-[1,2,4]triazolo[1,5-a]pyridin-2-yl]amino]phenyl]-(4-isobutylpiperazin-1-yl)methanone

[4-[[8-[4-(4-chlorophenyl)-4-hydroxy-1-piperidyl]-[1,2,4]triazolo[1,5-a]pyridin-2-yl]amino]phenyl]-(4-pyrrolidin-1-yl-1-piperidyl)methanone

[4-[[8-[4-(4-chlorophenyl)-4-hydroxy-1-piperidyl]-[1,2,4]triazolo[1,5-a]pyridin-2-yl]amino]phenyl]-[4-(2-methoxyethyl)piperazin-1-yl]methanone 4-[[8-[4-(4-chlorophenyl)-4-hydroxy-1-piperidyl]-[1,2,4]triazolo[1,5-a]pyridin-2-yl]amino]-N-methyl-N-[2-(3 -pyridyl)ethyl]benzamide 4-[[8-[4-(4-chlorophenyl)-4-hydroxy-1-piperidyl]-[1,2,4]triazolo[1,5-a]pyridin-2-yl]amino]-N-methyl-N-[2-(4-pyridyl)ethyl]benzamide

[4-[[8-[4-(4-chlorophenyl)-4-hydroxy-1-piperidyl]-[1,2,4]triazolo[1,5-a]pyridin-2-yl]amino]phenyl]-[4-(cyclopropylmethyl)piperazin-1-yl]methanone 1,3,4,6,7,8,9,9a-octahydropyrido[1,2-a]pyrazin-2-yl-[4-[[8-[4-(4-chlorophenyl)-4-hydroxy-1-piperidyl]-[1,2,4]triazolo[1,5-a]pyridin-2-yl]amino]phenyl]methanone 4-[[8-[4-(4-chlorophenyl)-4-hydroxy-1-piperidyl]-[1,2,4]triazolo[1,5-a]pyridin-2-yl]amino]-N-methyl-N-(3-pyridylmethyl)benzamide

[4-[[8-[4-(4-chlorophenyl)-4-hydroxy-1-piperidyl]-[1,2,4]triazolo[1,5-a]pyridin-2-yl]amino]phenyl]-[4-[2-(dimethylamino)ethyl]piperazin-1-yl]methanone 4-[[8-[4-(4-chlorophenyl)-4-hydroxy-1-piperidyl]-[1,2,4]triazolo[1,5-a]pyridin-2-yl]amino]-N-1-(6-methyl-2-pyridypethyl]benzamide 4-[[8-[4-(4-chlorophenyl)-4-hydroxy-1-piperidyl]-[1,2,4]triazolo[1,5-a]pyridin-2-yl]amino]-N-[(1-methyl-3-piperidyl)methyl]benzamide 4-[[8-[4-(4-chlorophenyl)-4-hydroxy-1-piperidyl]-[1,2,4]triazolo[1,5-a]pyridin-2-yl]amino]-N-cyclopropyl-N-(2-pyridylmethyl)benzamide

[4-[[8-[4-(4-chlorophenyl)-4-hydroxy-1-piperidyl]-[1,2,4]triazolo[1,5-a]pyridin-2-yl]amino]phenyl]-(3-morpholino-1-piperidyl)methanone

[4-[[8-[4-(4-chlorophenyl)-4-hydroxy-1-piperidyl]-[1,2,4]triazolo[1,5-a]pyridin-2-yl]amino]phenyl]-[4-(2-pyridyl)-1-piperidyl]methanone

[4-[[8-[4-(4-chlorophenyl)-4-hydroxy-1-piperidyl]-[1,2,4]triazolo[1,5-a]pyridin-2-yl]amino]phenyl]-[4-(3-pyridylmethyl)-1-piperidyl]methanone

[4-[[8-[4-(4-chlorophenyl)-4-hydroxy-1-piperidyl]-[1,2,4]triazolo[1,5-a]pyridin-2-yl]amino]phenyl]-[3-(4-pyridylmethyl)pyrrolidin-1-yl]methanone

[4-[[8-[4-(4-chlorophenyl)-4-hydroxy-1-piperidyl]-[1,2,4]triazolo[1,5-a]pyridin-2-yl]amino]phenyl]-[2-(4-pyridyl)pyrrolidin-1-yl]methanone

[4-[[8-[4-(4-chlorophenyl)-4-hydroxy-1-piperidyl]-[1,2,4]triazolo[1,5-a]pyridin-2-yl]amino]phenyl]-[2-(2-pyridyl)morpholin-4-yl]methanone

[4-[[8-[4-(4-chlorophenyl)-4-hydroxy-1-piperidyl]-[1,2,4]triazolo[1,5-a]pyridin-2-yl]amino]phenyl]-[3-(2-pyridyl)-1-piperidyl]methanone 4-[4-[[8-[4-(4-chlorophenyl)-4-hydroxy-1-piperidyl]-[1,2,4]triazolo[1,5-a]pyridin-2-yl]amino]benzoyl]-N-methyl-1-(2-phenylethyl)piperazine-2-carboxamide

[4-[[8-[4-(4-chlorophenyl)-4-hydroxy-1-piperidyl]-[1,2,4]triazolo[1,5-a]pyridin-2-yl]amino]phenyl]-[3-[[6-(dimethylamino)pyrimidin-4-yl]methyl]pyrrolidin-1-yl]methanone 1-[4-[[8-[4-(4-chlorophenyl)-4-hydroxy-1-piperidyl]-[1,2,4]triazolo[1,5-a]pyridin-2-yl]amino]benzoyl]-N,4-dimethyl-piperazine-2-carboxamide 1-benzyl-4-[4-[[4-(4-chlorophenyl)-4-hydroxy-1-piperidyl]-[1,2,4]triazolo[1,5-a]pyridin-2-yl]amino]benzoyl]-N-methyl-piperazine-2-carboxamide 4-[[8-[4-(4-chlorophenyl)-4-hydroxy-1-piperidyl]-[1,2,4]triazolo[1,5-a]pyridin-2-yl]amino]-N-[2-(1-methyl-4-piperidyl)ethyl]benzamide

[4-[[8-[4-(4-chlorophenyl)-4-hydroxy-1-piperidyl]-[1,2,4]triazolo[1,5-a]pyridin-2-yl]amino]phenyl]-[3-(3-pyridylmethyl)pyrrolidin-1-yl]methanone

[4-[[8-[4-(4-chlorophenyl)-4-hydroxy-1-piperidyl]-[1,2,4]triazolo[1,5-a]pyridin-2-yl]amino]phenyl]-[3-[(5-methyl-2-pyridyl)methyl]pyrrolidin-1-yl]methanone

[4-[[8-[4-(4-chlorophenyl)-4-hydroxy-1-piperidyl]-[1,2,4]triazolo[1,5-a]pyridin-2-yl]amino]phenyl]-[3-(2-pyridylmethyl)pyrrolidin-1-yl]methanone

[4-[[8-[4-(4-chlorophenyl)-4-hydroxy-1-piperidyl]-[1,2,4]triazolo[1,5-a]pyridin-2-yl]amino]phenyl]-[4-(2-pyridylmethyl)-1-piperidyl]methanone 4-[[8-[4-(4-chlorophenyl)-4-hydroxy-1-piperidyl]-[1,2,4]triazolo[1,5-a]pyridin-2-yl]amino]-N-[2-(6-methyl-2-pyridyl)ethyl]benzamide 4-[[8-[4-(4-chlorophenyl)-4-hydroxy-1-piperidyl]-[1,2,4]triazolo[1,5-a]pyridin-2-yl]amino]-N-[2-(3-pyridyl)ethyl]benzamide 4-[[8-[4-(4-chlorophenyl)-4-hydroxy-1-piperidyl]-[1,2,4]triazolo[1,5-a]pyridin-2-y]amino]-N-[2-(4-pyridyl)ethyl]benzamide 4-[[8-[4-(4-chlorophenyl)-4-hydroxy-1-piperidyl]-[1,2,4]triazolo[1,5-a]pyridin-2-yl]amino]-N-[2-(2-pyridyl)ethyl]benzamide 4-[4-[[8-[4-(4-chlorophenyl)-4-hydroxy-1-piperidyl]-[1,2,4]triazolo[1,5-a]pyridin-2-yl]amino]benzoyl]-N,1-dimethyl-piperazine-2-carboxamide
1-[4-[[8-[4-(4-chlorophenyl)-4-hydroxy-1-piperidyl]-[1,2,4]triazolo[1,5-a]pyridin-2-yl]amino]benzoyl]-N,N-dimethyl-azetidine-3-carboxamide
[4-[[8-[4-(4-chlorophenyl)-4-hydroxy-1-piperidyl]-[1,2,4]triazolo[1,5-a]pyridin-2-yl]amino]phenyl]-[3-(4-methylpiperazine-1-carbonyl)azetidin-1-yl]methanone
[4-[[8-[4-(4-chlorophenyl)-4-hydroxy-1-piperidyl]-[1,2,4]triazolo[1,5-a]pyridin-2-yl]amino]phenyl]-[(3S)-3-(dimethylamino)pyrrolidin-1-yl]methanone
3-[4-[4-[[8-[4-(4-chlorophenyl)-4-hydroxy-1-piperidyl]-[1,2,4]triazolo[1,5-a]pyridin-2-yl]amino]benzoyl]piperazin-1-yl]propanenitrile
3,4,6,7,8,8a-hexahydro-1H-pyrrolo[1,2-a]pyrazin-2-yl-[4-[[8-[4-(4-chlorophenyl)-4-hydroxy-1-piperidyl]-[1,2,4]triazolo[1,5-a]pyridin-2-yl]amino]phenyl]methanone
4-[[8-[4-(4-chlorophenyl)-4-hydroxy-1-piperidyl]-[1,2,4]triazolo[1,5-a]pyridin-2-yl]amino]-N-methyl-N-(6-quinolylmethyl)benzamide
4-[[8-[4-(4-chlorophenyl)-4-hydroxy-1-piperidyl]-[1,2,4]triazolo[1,5-a]pyridin-2-yl]amino]-N-methyl-N-[(1-methyl-3-piperidyl)methyl]benzamide
N-(1-benzylpyrrolidin-3-yl)-4-[[8-[4-(4-chlorophenyl)-4-hydroxy-1-piperidyl]-[1,2,4]triazolo[1,5-a]pyridin-2-yl]amino]-N-methyl-benzamide
[4-[[8-[4-(4-chlorophenyl)-4-hydroxy-1-piperidyl]-[1,2,4]triazolo[1,5-a]pyridin-2-yl]amino]phenyl]-[4-(tetrahydrofuran-2-ylmethyl)piperazin-1-yl]methanone
4-[[8-[4-(4-chlorophenyl)-4-hydroxy-1-piperidyl]-[1,2,4]triazolo[1,5-a]pyridin-2-yl]amino]-N-[2-(1-piperidyl)ethyl]benzamide
1-[4-[[8-[4-(4-chlorophenyl)-4-hydroxy-1-piperidyl]-[1,2,4]triazolo[1,5-a]pyridin-2-yl]amino]benzoyl]-4-isopropyl-N-methyl-piperazine-2-carboxamide
N-(2-aminoethyl)-4-[[8-[4-(4-chlorophenyl)-4-hydroxy-1-piperidyl]-[1,2,4]triazolo[1,5-a]pyridin-2-yl]amino]benzamide
4-[[8-[4-(4-chlorophenyl)-4-hydroxy-1-piperidyl]-[1,2,4]triazolo[1,5-a]pyridin-2-yl]amino]-N-pyrrolidin-3-yl-benzamide
[4-[[8-[4-(4-chlorophenyl)-4-hydroxy-1-piperidyl]-[1,2,4]triazolo[1,5-a]pyridin-2-yl]amino]phenyl]-piperazin-1-yl-methanone
(1-methyl-4-piperidyl) 4-[[8-[4-(4-chlorophenyl)-4-hydroxy-1-piperidyl]-[1,2,4]triazolo[1,5-a]pyridin-2-yl]amino]benzoate
4-[[8-[4-(4-chlorophenyl)-4-hydroxy-1-piperidyl]-[1,2,4]triazolo[1,5-a]pyridin-2-yl]amino]-N-(3-piperidyl)benzamide
4-[[8-[4-(4-chlorophenyl)-4-hydroxy-1-piperidyl]-[1,2,4]triazolo[1,5-a]pyridin-2-yl]amino]-N-(pyrrolidin-3-ylmethyl)benzamide
4-[[8-[4-(4-chlorophenyl)-4-hydroxy-1-piperidyl]-[1,2,4]triazolo[1,5-a]pyridin-2-yl]amino]-N-(4-piperidyl)benzamide
4-[[8-[4-(4-chlorophenyl)-4-hydroxy-1-piperidyl]-[1,2,4]triazolo[1,5-a]pyridin-2-yl]amino]-N-(pyrrolidin-2-ylmethyl)benzamide
4-[[8-[4-(4-chlorophenyl)-4-hydroxy-1-piperidyl]-[1,2,4]triazolo[1,5-a]pyridin-2-yl]amino]-N-(3-piperidylmethyl)benzamide
4-[[8-[4-(4-chlorophenyl)-4-hydroxy-1-piperidyl]-[1,2,4]triazolo[1,5-a]pyridin-2-yl]amino]-N-(4-piperidylmethyl)benzamide
4-[[8-[4-(4-chlorophenyl)-4-hydroxy-1-piperidyl]-[1,2,4]triazolo[1,5-a]pyridin-2-yl]amino]-N-(2-piperidylmethyl)benzamide
4-[[8-[4-(4-chlorophenyl)-4-hydroxy-1-piperidyl]-[1,2,4]triazolo[1,5-a]pyridin-2-yl]amino]-N-[2-(3-piperidyl)ethyl]benzamide
4-[[8-[4-(4-chlorophenyl)-4-hydroxy-1-piperidyl]-[1,2,4]triazolo[1,5-a]pyridin-2-yl]amino]-N-(2-piperazin-1-ylethyl)benzamide
4-[[8-[4-(4-chlorophenyl)-4-hydroxy-1-piperidyl]-[1,2,4]triazolo[1,5-a]pyridin-2-yl]amino]-N-(morpholin-2-ylmethyl)benzamide
(3-aminoazetidin-1-yl)-[4-[[8-[4-(4-chlorophenyl)-4-hydroxy-1-piperidyl]-[1,2,4]triazolo[1,5-a]pyridin-2-yl]amino]phenyl]methanone
3,3a,4,5,6,6a-hexahydro-2H-pyrrolo[2,3-c]pyrrol-1-yl-[4-[[8-[4-(4-chlorophenyl)-4-hydroxy-1-piperidyl]-[1,2,4]triazolo[1,5-a]pyridin-2-yl]amino]phenyl]methanone
[3-(aminomethyl)azetidin-1-yl]-[4-[[8-[4-(4-chlorophenyl)-4-hydroxy-1-piperidyl]-[1,2,4]triazolo[1,5-a]pyridin-2-yl]amino]phenyl]methanone
[3-(aminomethyl)pyrrolidin-1-yl]-[4-[[8-[4-(4-chlorophenyl)-4-hydroxy-1-piperidyl]-[1,2,4]triazolo[1,5-a]pyridin-2-yl]amino]phenyl]methanone
[4-(aminomethyl)-1-piperidyl]-[4-[[8-[4-(4-chlorophenyl)-4-hydroxy-1-piperidyl]-[1,2,4]triazolo[1,5-a]pyridin-2-yl]amino]phenyl]methanone
N-(2-aminoethyl)-4-[[8-[4-(4-chlorophenyl)-4-hydroxy-1-piperidyl]-[1,2,4]triazolo[1,5-a]pyridin-2-yl]amino]-N-methyl-benzamide
[2-(aminomethyl)pyrrolidin-1-yl]-[4-[[8-[4-(4-chlorophenyl)-4-hydroxy-1-piperidyl]-[1,2,4]triazolo[1,5-a]pyridin-2-yl]amino]phenyl]methanone
[4-[[8-[4-(4-chlorophenyl)-4-hydroxy-1-piperidyl]-[1,2,4]triazolo[1,5-a]pyridin-2-yl]amino]phenyl]-[2-(hydroxymethyl)piperazin-1-yl]methanone
2,3,3a,4,6,6a-hexahydro-1H-pyrrolo[3,4-c]pyrrol-5-yl-[4-[[8-[4-(4-chlorophenyl)-4-hydroxy-1-piperidyl]-[1,2,4]triazolo[1,5-a]pyridin-2-yl]amino]phenyl]methanone
4-[[8-[4-(4-chlorophenyl)-4-hydroxy-1-piperidyl]-[1,2,4]triazolo[1,5-a]pyridin-2-yl]amino]-N-[(3S)-3-piperidyl]benzamide
[4-[[8-[4-(4-chlorophenyl)-4-hydroxy-1-piperidyl]-[1,2,4]triazolo[1,5-a]pyridin-2-yl]amino]phenyl]-(2,7-diazaspiro[3.5]nonan-2-yl)methanone
[4-[[8-[4-(4-chlorophenyl)-4-hydroxy-1-piperidyl]-[1,2,4]triazolo[1,5-a]pyridin-2-yl]amino]phenyl]-(3-methylpiperazin-1-yl)methanone
[4-[[8-[4-(4-chlorophenyl)-4-hydroxy-1-piperidyl]-[1,2,4]triazolo[1,5-a]pyridin-2-yl]amino]phenyl]-(2,7-diazaspiro[3.5]nonan-7-yl)methanone
4-[[8-[4-(4-chlorophenyl)-4-hydroxy-1-piperidyl]-[1,2,4]triazolo[1,5-a]pyridin-2-yl]amino]-N-methyl-N-(3-piperidyl)benzamide
[4-[[8-[4-(4-chlorophenyl)-4-hydroxy-1-piperidyl]-[1,2,4]triazolo[1,5-a]pyridin-2-yl]amino]phenyl]-(2,6-diazaspiro[3.3]heptan-2-yl)methanone
[4-[[8-[4-(4-chlorophenyl)-4-hydroxy-1-piperidyl]-[1,2,4]triazolo[1,5-a]pyridin-2-yl]amino]phenyl]-(1,4-diazepan-1-yl)methanone
[4-[[8-[4-(4-chlorophenyl)-4-hydroxy-1-piperidyl]-[1,2,4]triazolo[1,5-a]pyridin-2-yl]amino]phenyl]-(2,6-diazaspiro[3.4]octan-6-yl)methanone

[4-[[8-[4-(4-chlorophenyl)-4-hydroxy-1-piperidyl]-[1,2,
    4]triazolo[1,5-a]pyridin-2-yl]amino]phenyl]-[3-(meth-
    ylamino)pyrrolidin-1-yl]methanone
[4-[[8-[4-(4-chlorophenyl)-4-hydroxy-1-piperidyl]-[1,2,
    4]triazolo[1,5-a]pyridin-2-yl]amino]phenyl]-(2,7-diaz-
    aspiro[4.4]nonan-2-yl)methanone
[4-[[8-[4-(4-chlorophenyl)-4-hydroxy-1-piperidyl]-[1,2,
    4]triazolo[1,5-a]pyridin-2-yl]amino]phenyl]-(1,7-diaz-
    aspiro[4.4]nonan-7-yl)methanone
[4-[[8-[4-(4-chlorophenyl)-4-hydroxy-1-piperidyl]-[1,2,
    4]triazolo[1,5-a]pyridin-2-yl]amino]phenyl]-(1,7-diaz-
    aspiro[4.4]nonan-1-yl)methanone
[4-[[8-[4-(4-chlorophenyl)-4-hydroxy-1-piperidyl]-[1,2,
    4]triazolo[1,5-a]pyridin-2-yl]amino]phenyl]-(2,8-diaz-
    aspiro[3.5]nonan-2-yl)methanone
[4-[[8-[4-(4-chlorophenyl)-4-hydroxy-1-piperidyl]-[1,2,
    4]triazolo[1,5-a]pyridin-2-yl]amino]phenyl]-(2,6-diaz-
    aspiro[4.5]decan-2-yl)methanone
[4-[[8-[4-(4-chlorophenyl)-4-hydroxy-1-piperidyl]-[1,2,
    4]triazolo[1,5-a]pyridin-2-yl]amino]phenyl]-(2,9-diaz-
    aspiro[4.5]decan-2-yl)methanone
[4-[[8-[4-(4-chlorophenyl)-4-hydroxy-1-piperidyl]-[1,2,
    4]triazolo[1,5-a]pyridin-2-yl]amino]phenyl]-(2,8-diaz-
    aspiro[4.5]decan-8-yl)methanone
[4-[[8-[4-(4-chlorophenyl)-4-hydroxy-1-piperidyl]-[1,2,
    4]triazolo[1,5-a]pyridin-2-yl]amino]phenyl]-(2,8-diaz-
    aspiro[4.5]decan-2-yl)methanone
[4-[[8-[4-(4-chlorophenyl)-4-hydroxy-1-piperidyl]-[1,2,
    4]triazolo[1,5-a]pyridin-2-yl]amino]phenyl]-(2,8-diaz-
    aspiro[5.5]undecan-2-yl)methanone
[4-[[8-[4-(4-chlorophenyl)-4-hydroxy-1-piperidyl]-[1,2,
    4]triazolo[1,5-a]pyridin-2-yl]amino]phenyl]-(2,9-diaz-
    aspiro[5.5]undecan-2-yl)methanone
[4-[[8-[4-(4-chlorophenyl)-4-hydroxy-1-piperidyl]-[1,2,
    4]triazolo[1,5-a]pyridin-2-yl]amino]phenyl]-(2,9-diaz-
    aspiro[5.5]undecan-9-yl)methanone
[4-[[8-[4-(4-chlorophenyl)-4-hydroxy-1-piperidyl]-[1,2,
    4]triazolo[1,5-a]pyridin-2-yl]amino]phenyl]-(3,9-diaz-
    aspiro[5.5]undecan-3-yl)methanone
[4-[[8-[4-(4-chlorophenyl)-4-hydroxy-1-piperidyl]-[1,2,
    4]triazolo[1,5-a]pyridin-2-yl]amino]phenyl]-(1,8-diaz-
    aspiro[5.5]undecan-8-yl)methanone
4-[[8-[4-(4-chlorophenyl)-4-hydroxy-1-piperidyl]-[1,2,4]
    triazolo[1,5-a]pyridin-2-yl]amino]-N-(1-oxa-8-
    azaspiro[4.5]decan-3-ylmethyl)benzamide
4-[[8-[4-(4-chlorophenyl)-4-hydroxy-1-piperidyl]-[1,2,4]
    triazolo[1,5-a]pyridin-2-yl]amino]-N-(1-oxa-8-
    azaspiro[4.5]decan-3-yl)benzamide
4-[[8-[4-(4-chlorophenyl)-4-hydroxy-1-piperidyl]-[1,2,4]
    triazolo[1,5-a]pyridin-2-yl]amino]-N-(1-oxa-8-
    azaspiro[4.5]decan-2-ylmethyl)benzamide
[4-[[8-[4-(4-chlorophenyl)-4-hydroxy-1-piperidyl]-[1,2,
    4]triazolo[1,5-a]pyridin-2-yl]amino]phenyl]-(1,9-diaz-
    aspiro[4.6]undecan-9-yl)methanone
[4-[[8-[4-(4-chlorophenyl)-4-hydroxy-1-piperidyl]-[1,2,
    4]triazolo[1,5-a]pyridin-2-yl]amino]phenyl]-(2,7-diaz-
    aspiro[3.4]octan-2-yl)methanone
[4-[[8-[4-(4-chlorophenyl)-4-hydroxy-1-piperidyl]-[1,2,
    4]triazolo[1,5-a]pyridin-2-yl]amino]phenyl]-(1-oxa-4,
    8-diazaspiro[5.5]undecan-4-yl)methanone
[4-[[8-[4-(4-chlorophenyl)-4-hydroxy-1-piperidyl]-[1,2,
    4]triazolo[1,5-a]pyridin-2-yl]amino]phenyl]-(1,8-diaz-
    aspiro[4.5]decan-8-yl)methanone
[4-[[8-[4-(4-chlorophenyl)-4-hydroxy-1-piperidyl]-[1,2,
    4]triazolo[1,5-a]pyridin-2-yl]amino]phenyl]-(1,8-diaz-
    aspiro[4.5]decan-1-yl)methanone
(2-amino-7-azaspiro[3.5]nonan-7-yl)-[4-[[8-[4-(4-chlo-
    rophenyl)-4-hydroxy-1-piperidyl]-[1,2,4]triazolo[1,5-
    a]pyridin-2-yl]amino]phenyl]methanone
[4-[[8-[4-(4-chlorophenyl)-4-hydroxy-1-piperidyl]-[1,2,
    4]triazolo[1,5-a]pyridin-2-yl]amino]phenyl]-(1-oxa-4,
    8-diazaspiro[5.5]undecan-8-yl)methanone
[4-[[8-[4-(4-chlorophenyl)-4-hydroxy-1-piperidyl]-[1,2,
    4]triazolo[1,5-a]pyridin-2-yl]amino]phenyl]-(1-oxa-4,
    9-diazaspiro[5.5]undecan-9-yl)methanone
[4-[[8-[4-(4-chlorophenyl)-4-hydroxy-1-piperidyl]-[1,2,
    4]triazolo[1,5-a]pyridin-2-yl]amino]phenyl]-(1-oxa-4,
    9-diazaspiro[5.5]undecan-4-yl)methanone
[4-[[8-[4-(4-chlorophenyl)-4-hydroxy-1-piperidyl]-[1,2,
    4]triazolo[1,5-a]pyridin-2-yl]amino]phenyl]-[(1R,5R)-
    3,6-diazabicyclo[3.2.0]heptan-3-yl]methanone
[4-[[8-[4-(4-chlorophenyl)-4-hydroxy-1-piperidyl]-[1,2,
    4]triazolo[1,5-a]pyridin-2-yl]amino]phenyl]-(1,9-diaz-
    aspiro[4.5]decan-1-yl)methanone
[(3aS,6aS)-2,3,3a,4,6,6a-hexahydro-1H-pyrrolo[2,3
    -c]pyrrol-5-yl]-[4-[[8-[4-(4-chlorophenyl)-4-hydroxy-
    1-piperidyl]-[1,2,4]triazolo[1,5-a]pyridin-2-yl]amino]
    phenyl]methanone
[(3aR,6aS)-2,3,3a,4,6,6a-hexahydro-1H-pyrrolo[3,4-c]
    pyrrol-5-yl]-[4-[[8-[4-(4-chlorophenyl)-4-hydroxy-1-
    piperidyl]-[1,2,4]triazolo[1,5-a]pyridin-2-yl]amino]
    phenyl]methanone
[4-[[8-[4-(4-chlorophenyl)-4-hydroxy-1-piperidyl]-[1,2,
    4]triazolo[1,5-a]pyridin-2-yl]amino]phenyl]-(1,7-diaz-
    aspiro[3.5]nonan-7-yl)methanone
[(1S,5R)-5-amino-3 -azabicyclo[3.1.0]hexan-3-yl]-[4-
    [[8-[4-(4-chlorophenyl)-4-hydroxy-1-piperidyl]-[1,2,
    4]triazolo[1,5-a]pyridin-2-yl]amino]phenyl]metha-
    none
N-[1R,5S)-3-azabicyclo[3.1.0]hexan-6-yl]-4-[[8-[4-(4-
    chlorophenyl)-4-hydroxy-1-piperidyl]-[1,2,4]triazolo
    [1,5-a]pyridin-2-yl]amino]benzamide
[4-[[8-[4-(4-chlorophenyl)-4-hydroxy-1-piperidyl]-[1,2,
    4]triazolo[1,5-a]pyridin-2-yl]amino]phenyl]-(9-oxa-3,
    7-diazabicyclo[3.3.1]nonan-3-yl)methanone
[4-(aminomethyl)-3-azabicyclo[2.1.1]hexan-3-yl]-[4-[[8-
    [4-(4-chlorophenyl)-4-hydroxy-1-piperidyl]-[1,2,4]tri-
    azolo[1,5-a]pyridin-2-yl]amino]phenyl]methanone
[(3aS,6aS)-3,3a,4,5,6,6a-hexahydro-2H-pyrrolo[2,3
    -c]pyrrol-1-yl]-[4-[[8-[4-(4-chlorophenyl)-4-hydroxy-
    1-piperidyl]-[1,2,4]triazolo[1,5-a]pyridin-2-yl]amino]
    phenyl]methanone
[(4aR,7aR)-3,4a,5,6,7,7a-hexahydro-2H-pyrrolo[3,4-b]
    [1,4]oxazin-4-yl]-[4-[[8-[4-(4-chlorophenyl)-4-hy-
    droxy-1 -piperidyl]-[1,2,4]triazolo[1,5-a]pyridin-2-yl]
    amino]phenyl]methanone
[(4aS,7aR)-3,4a,5,6,7,7a-hexahydro-2H-pyrrolo[3,4-b]
    [1,4]oxazin-4-yl]-[4-[[8-[4-(4-chlorophenyl)-4-hy-
    droxy-1-piperidyl]-[1,2,4]triazolo[1,5-a]pyridin-2-yl]
    amino]phenyl]methanone
2,3,4a,5,6,7,8,8a-octahydropyrido[4,3-b][1,4]oxazin-4-
    yl]-[4-[[8-[4-(4-chlorophenyl)-4-hydroxy-1-piperidyl]-
    [1,2,4]triazolo[1,5-a]pyridin-2-yl]amino]phenyl]
    methanone
4-[[8-[4-(4-chlorophenyl)-4-hydroxy-1-piperidyl]-[1,2,4]
    triazolo[1,5-a]pyridin-2-yl]amino]-N-(2-oxa-9-
    azaspiro[5.5]undecan-3-ylmethyl)benzamide
4-[[8-[4-(4-chlorophenyl)-4-(hydroxymethyl)-1-piper-
    idyl]-[1,2,4]triazolo[1,5-a]pyridin-2-yl]amino]-N-
    methyl-N-(1-methyl-4-piperidyl)benzamide
4-[[8-[4-(4-chlorophenyl)-4-(2-cyanoethyl)-1-piperidyl]-
    [1,2,4]triazolo[1,5-a]pyridin-2-yl]amino]-N-methyl-N-
    (1-methyl-4-piperidyl)benzamide N-methyl-N-(1-methyl-4-piperidyl)-4-[(8-phenoxy-[1,2,4]triazolo[1,5-a]pyridin-2-yl)amino]benzamide
4-[(8-benzyloxy-[1,2,4]triazolo[1,5-a]pyridin-2-yl)amino]-N-methyl-N-(1-methyl-4-piperidyl)benzamide
4-[[8-[4-(4-chlorophenyl)-4-[(E)-methoxyiminomethyl]-1-piperidyl]-[1,2,4]triazolo[1,5-a]pyridin-2-yl]amino]-N-methyl-N-(1-methyl-4-piperidyl)benzamide
4-[[8-[4-(hydroxymethyl)-4-(4-methylsulfanylphenyl)-1-piperidyl]-[1,2,4]triazolo[1,5-a]pyridin-2-yl]amino]-N-methyl-N-(1-methyl-4-piperidyl)benzamide
4-[[8-[4-(4-chlorophenyl)-4-(1-hydroxyethyl)-1-piperidyl]-[1,2,4]triazolo[1,5-a]pyridin-2-yl]amino]-N-methyl-N-(1-methyl-4-piperidyl)benzamide
4-[[8-[4-(4-chlorophenyl)-4-(2,2,2-trifluoro-1-hydroxyethyl)-1-piperidyl]-[1,2,4]triazolo[1,5-a]pyridin-2-yl]amino]-N-methyl-N-(1-methyl-4-piperidyl)benzamide
ethyl 2-[4-(4-chlorophenyl)-1-[2-[4-[methyl-(1-methyl-4-piperidyl)carbamoyl]anilino]-[1,2,4]triazolo[1,5-a]pyridin-8-yl]-4-piperidyl]acetate
4-[[8-[4-(4-chlorophenyl)-4-(2-hydroxyethyl)-1-piperidyl]-[1,2,4]triazolo[1,5-a]pyridin-2-yl]amino]-N-methyl-N-(1-methyl-4-piperidyl)benzamide;formic acid
4-[[8-[4-(4-chlorophenyl)-4-(2,2-difluoroethyl)-1-piperidyl]-[1,2,4]triazolo[1,5-a]pyridin-2-yl]amino]-N-methyl-N-(1-methyl-4-piperidyl)benzamide;formic acid
4-[[8-[4-(cyanomethyl)-4-cyclopentyl-1-piperidyl]-[1,2,4]triazolo[1,5-a]pyridin-2-yl]amino]-N-methyl-N-(1-methyl-4-piperidyl)benzamide
4-[[8-[4-(4-chlorophenyl)-4-(methoxymethyl)-1-piperidyl]-[1,2,4]triazolo[1,5-a]pyridin-2-yl]amino]-N-methyl-N-(1-methyl-4-piperidyl)benzamide;formic acid
N-benzyl-4-methyl-1-[2-[4-[methyl-(1-methyl-4-piperidyl)carbamoyl]anilino]-[1,2,4]triazolo[1,5-a]pyridin-8-yl]piperidine-4-carboxamide
4-[[8-(4-acetamido-4-methyl-1-piperidyl)-[1,2,4]triazolo[1,5-a]pyridin-2-yl]amino]-N-methyl-N-(1-methyl-4-piperidyl)benzamide
4-[[8-[4-[benzenesulfonyl(methyl)amino]-4-methyl-1-piperidyl]-[1,2,4]triazolo[1,5-a]pyridin-2-yl]amino]-N-methyl-N-(1-methyl-4-piperidyl)benzamide
4-[[8-[4-(4-chlorophenyl)-4-methyl-1-piperidyl]-[1,2,4]triazolo[1,5-a]pyridin-2-yl]amino]-N-methyl-N-(1-methyl-4-piperidyl)benzamide
4-[[8-[4-(4-chloro-3-fluoro-phenyl)-4-(cyanomethyl)-1-piperidyl]-[1,2,4]triazolo[1,5-a]pyridin-2-yl]amino]-N-methyl-N-(1-methyl-4-piperidyl)benzamide
4-[[8-[(3-benzyl-2-oxo-1,3-benzoxazol-5-yl)oxy]-[1,2,4]triazolo[1,5-a]pyridin-2-yl]amino]-N-methyl-N-(1-methyl-4-piperidyl)benzamide
4-[[8-[4-(aminomethyl)-4-(4-chlorophenyl)-1-piperidyl]-[1,2,4]triazolo[1,5-a]pyridin-2-yl]amino]-N-methyl-N-(1-methyl-4-piperidyl)benzamide;formic acid
4-[[8-[4-(hydroxymethyl)-4-[(2,2,2-trifluoroethylamino)methyl]-1-piperidyl]-[1,2,4]triazolo[1,5-a]pyridin-2-yl]amino]-N-methyl-N-(1-methyl-4-piperidyl)benzamide
4-[[8-[4-[4-(difluoromethyl)phenyl]-4-(hydroxymethyl)-1-piperidyl]-[1,2,4]triazolo[1,5-a]pyridin-2-yl]amino]-N-methyl-N-(1-methyl-4-piperidyl)benzamide
4-[[8-[4-(acetamidomethyl)-4-(4-chlorophenyl)-1-piperidyl]-[1,2,4]triazolo[1,5-a]pyridin-2-yl]amino]-N-methyl-N-(1-methyl-4-piperidyl)benzamide
4-(4-chlorophenyl)-1-[2-[4-[methyl-(1-methyl-4-piperidyl)carbamoyl]anilino]-[1,2,4]triazolo[1,5-a]pyridin-8-yl]piperidine-4-carboxylic acid;formic acid
4-[[8-[4-(4-chlorophenyl)-4-(1,2-dihydroxyethyl)-1-piperidyl]-[1,2,4]triazolo[1,5-a]pyridin-2-yl]amino]-N-methyl-N-(1-methyl-4-piperidyl)benzamide
4-[[8-[4-(4-chlorophenyl)-4-(hydroxymethyl)-1-piperidyl]-[1,2,4]triazolo[1,5-a]pyridin-2-yl]amino]-N-[[1-(2,2,2-trifluoroethyl)-4-piperidyl]methyl]benzamide
4-[[8-[4-(4-chlorophenyl)-4-(hydroxymethyl)-1-piperidyl]-[1,2,4]triazolo[1,5-a]pyridin-2-yl]amino]-N-[2-(3-methyl-1-piperidyl)ethyl]benzamide
4-[[8-[4-(4-chlorophenyl)-4-(hydroxymethyl)-1-piperidyl]-[1,2,4]triazolo[1,5-a]pyridin-2-yl]amino]-N-[2-(3,5-dimethyl-1-piperidyl)ethyl]benzamide
[4-[[844-(4-chlorophenyl)-4-(hydroxymethyl)-1-piperidyl]-[1,2,4]triazolo[1,5-a]pyridin-2-yl]amino]phenyl]-(5-methyl-2,5-diazaspiro[3.4]octan-2-yl)methanone
[4-[[8-[4-(4-chlorophenyl)-4-(hydroxymethyl)-1-piperidyl]-[1,2,4]triazolo[1,5-a]pyridin-2-yl]amino]phenyl]-(1-methyl-2,3,3a,4,6,6a-hexahydropyrrolo[2,3-c]pyrrol-5-yl)methanone
[4-[[8-[4-(4-chlorophenyl)-4-(hydroxymethyl)-1-piperidyl]-[1,2,4]triazolo[1,5-a]pyridin-2-yl]amino]phenyl]-[4-(2-pyridyl)-1-piperidyl]methanone
4-[[8-[4-(4-chlorophenyl)-4-(hydroxymethyl)-1-piperidyl]-[1,2,4]triazolo[1,5-a]pyridin-2-yl]amino]-N-[2-[(2S,6S)-2,6-dimethylmorpholin-4-yl]ethyl]benzamide
4-[[8-[4-(4-chlorophenyl)-4-(hydroxymethyl)-1-piperidyl]-[1,2,4]triazolo[1,5-a]pyridin-2-yl]amino]-N-[2-[(2R,6S)-2,6-dimethylmorpholin-4-yl]ethyl]benzamide
[4-[[8-[4-(4-chlorophenyl)-4-(hydroxymethyl)-1-piperidyl]-[1,2,4]triazolo[1,5-a]pyridin-2-yl]amino]phenyl]-[3-(4-pyridyl)pyrrolidin-1-yl]methanone
4-[[8-[4-(4-chlorophenyl)-4-(hydroxymethyl)-1-piperidyl]-[1,2,4]triazolo[1,5-a]pyridin-2-yl]amino]-N-(1-cyclopentyl-4-piperidyl)benzamide
[4-[[8-[4-(4-chlorophenyl)-4-(hydroxymethyl)-1-piperidyl]-[1,2,4]triazolo[1,5-a]pyridin-2-yl]amino]phenyl]-[4-[(2S,6S)-2,6-dimethylmorpholin-4-yl]-1-piperidyl]methanone
[4-[[8-[4-(4-chlorophenyl)-4-(hydroxymethyl)-1-piperidyl]-[1,2,4]triazolo[1,5-a]pyridin-2-yl]amino]phenyl]-[4-[(2R,6S)-2,6-dimethylmorpholin-4-yl]-1-piperidyl]methanone
[4-[[8-[4-(4-chlorophenyl)-4-(hydroxymethyl)-1-piperidyl]-[1,2,4]triazolo[1,5-a]pyridin-2-yl]amino]phenyl]-[3-(methylamino)azetidin-1-yl]methanone
4-[[8-[4-(4-chlorophenyl)-4-(hydroxymethyl)-1-piperidyl]-[1,2,4]triazolo[1,5-a]pyridin-2-yl]amino]-N-[(6-methyl-3-pyridyl)methyl]benzamide
4-[[8-[4-(4-chlorophenyl)-4-(hydroxymethyl)-1-piperidyl]-[1,2,4]triazolo[1,5-a]pyridin-2-yl]amino]-N-(2-methyl-2-morpholino-propyl)benzamide
4-[[8-[4-(4-chlorophenyl)-4-(hydroxymethyl)-1-piperidyl]-[1,2,4]triazolo[1,5-a]pyridin-2-yl]amino]-N-(3-morpholinopropyl)benzamide
4-[[8-[4-(4-chlorophenyl)-4-(hydroxymethyl)-1-piperidyl]-[1,2,4]triazolo[1,5-a]pyridin-2-yl]amino]-N-ethyl-N-(4-pyridylmethyl)benzamide
[4-[[8-[4-(4-chlorophenyl)-4-(hydroxymethyl)-1-piperidyl]-[1,2,4]triazolo[1,5-a]pyridin-2-yl]amino]phenyl]-[2-(4-pyridyl)pyrrolidin-1-yl]methanone 2-[4-[[8-[4-(4-chlorophenyl)-4-(hydroxymethyl)-1-piperidyl]-[1,2,4]triazolo[1,5-a]pyridin-2-yl]amino]pyrazol-1-yl]-1-[4-(morpholinomethyl)-1-piperidyl]ethanone
formic acid; methyl 3-[4-[2-[4-[[8-[4-(4-chlorophenyl)-4-(hydroxymethyl)-1-piperidyl]-[1,2,4]triazolo[1,5-a]pyridin-2-yl]amino]pyrazol -1-yl]acetyl]piperazin-1-yl]propanoate
2-[4-[[8-[4-(4-chlorophenyl)-4-(hydroxymethyl)-1-piperidyl]-[1,2,4]triazolo[1,5-a]pyridin-2-yl]amino]pyrazol-1-yl]-1-[4-(methylamino)-1-piperidyl]ethanone
4-[[8-[(3aR,6aS)-5-hydroxy-5-phenyl-1,3,3a,4,6,6a-hexahydrocyclopenta[c]pyrrol-2-yl]-[1,2,4]triazolo[1,5-a]pyridin-2-yl]amino]-N-methyl-N-(1-methyl-4-piperidyl)benzamide
4-[[8-(5-benzyl-2,5-diazabicyclo[2.2.1]heptan-2-yl)-[1,2,4]triazolo[1,5-a]pyridin-2-yl]amino]-N-methyl-N-(1-methyl-4-piperidyl)benzamide
4-[[8-[4-(4-chlorophenyl)-4-(cyanomethyl)cyclohexen-1-yl]-[1,2,4]triazolo[1,5-a]pyridin-2-yl]amino]-N-methyl-N-(1-methyl-4-piperidyl)benzamide
N-(3 -morpholinopropyl)-4-[[8-[1-(4,4,4-trifluorobutanoyl)-3,4-dihydro-2H-pyridin-4-yl]-[1,2,4]triazolo[1,5-a]pyridin-2-yl]amino]benzamide
3-[[1-[2-[4-[[8-[4-(4-chlorophenyl)-4-(hydroxymethyl)-1-piperidyl]-[1,2,4]triazolo[1,5-a]pyridin-2-yl]amino]pyrazol-1-yl]acetyl]-4-piperidyl]-methyl-amino]propanenitrile
N-(1-isobutyl-4-piperidyl)-N-methyl-2-[4-[[8-[1-(4,4,4-trifluorobutanoyl)-3,6-dihydro-2H-pyridin-4-yl]-[1,2,4]triazolo[1,5-a]pyridin-2-yl]amino]pyrazol-1-yl]acetamide
4-[[8-[4-(2-amino-2-oxo-ethyl)-4-(4-chlorophenyl)-1-piperidyl]-[1,2,4]triazolo[1,5-a]pyridin-2-yl]amino]-N-methyl-N-(1-methyl-4-piperidyl)benzamide
4-[[8-[4-(4-chlorophenyl)-4-[2-(methylamino)-2-oxo-ethyl]-1-piperidyl]-[1,2,4]triazolo[1,5-a]pyridin-2-yl]amino]-N-methyl-N-(1-methyl-4-piperidyl)benzamide
4-[[8-[4-(4-chlorophenyl)-4-[2-(dimethylamino)-2-oxo-ethyl]-1-piperidyl]-[1,2,4]triazolo[1,5-a]pyridin-2-yl]amino]-N-methyl-N-(1-methyl-4-piperidyl)benzamide
2-[4-(4-chlorophenyl)-1-[2-[4-[methyl-(1-methyl-4-piperidyl)carbamoyl]anilino]-[1,2,4]triazolo[1,5-a]pyridin-8-yl]-4-piperidyl]acetic acid
4-[[8-(4-benzamido-4-methyl-1-piperidyl)-[1,2,4]triazolo[1,5-a]pyridin-2-yl]amino]-N-methyl-N-(1-methyl-4-piperidyl)benzamide
4-[[8-[4-(benzenesulfonamido)-4-methyl-1-piperidyl]-[1,2,4]triazolo[1,5-a]pyridin-2-yl]amino]-N-methyl-N-(1-methyl-4-piperidyl)benzamide
ethyl 4-[4-[4-[methyl-(1-methyl-4-piperidyl)carbamoyl]anilino]-[1,2,4]triazolo[1,5-a]pyridin-8-yl]-3,6-dihydro-2H-pyridine-1-carboxylate
cyclopropyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate
4-[[8-[1-(3-hydroxy-3-methyl-butanoyl)-3,6-dihydro-2H-pyridin-4-yl]-[1,2,4]triazolo[1,5-a]pyridin-2-yl]amino]-N-methyl-N-(1-methyl-4-piperidyl)benzamide
4-[[8-[1-(2-cyclopropylacetyl)-3,6-dihydro-2H-pyridin-4-yl]-[1,2,4]triazolo[1,5-a]pyridin-2-yl]amino]-N-methyl-N-(1-methyl-4-piperidyl)benzamide
4-[[8-[1-(3-cyanoazetidine-1-carbonyl)-3,6-dihydro-2H-pyridin-4-yl]-[1,2,4]triazolo[1,5-a]pyridin-2-yl]amino]-N-methyl-N-(1-methyl-4-piperidyl)benzamide
4-[[8-[1-(2-cyanoacetyl)-3,6-dihydro-2H-pyridin-4-yl]-[1,2,4]triazolo[1,5-a]pyridin-2-yl]amino]-N-methyl-N-(1-methyl-4-piperidyl)benzamide
cyanomethyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate
4-[[8-(1-benzyl-3,6-dihydro-2H-pyridin-4-yl)[1,2,4]triazolo[1,5-a]pyridin-2-yl]amino]-N-methyl-N-(1-methyl-4-piperidyl)benzamide;hydrochloride
4-[[8-[1-(3-hydroxypropanoyl)-3,6-dihydro-2H-pyridin-4-yl]-[1,2,4]triazolo[1,5-a]pyridin-2-yl]amino]-N-methyl-N-(1-methyl-4-piperidyl)benzamide
4-[[8-[1-[3-(dimethylamino)propanoyl]-3,6-dihydro-2H-pyridin-4-yl]-[1,2,4]triazolo[1,5-a]pyridin-2-yl]amino]-N-methyl-N-(1-methyl-4-piperidyl)benzamide;dihydrochloride
ethyl 4-[2-[4-[(2-methyl-2-morpholino-propyl)carbamoyl]anilino]-[1,2,4]triazolo[1,5-a]pyridin-8-yl]-3,6-dihydro-2H-pyridine-1-carboxylate
ethyl 4-[2-[4-[4-(dimethylamino)piperidine-1-carbonyl]anilino]-[1,2,4]triazolo[1,5-a]pyridin-8-yl]-3,6-dihydro-2H-pyridine-1-carboxylate
ethyl 4-[2-[4-[2-(4-piperidyl)ethylcarbamoyl]anilino]-[1,2,4]triazolo[1,5-a]pyridin-8-yl]-3,6-dihydro-2H-pyridine-1-carboxylate
ethyl 4-[2-[4-[methyl(3-pyridylmethyl)carbamoyl]anilino]-[1,2,4]triazolo[1,5-a]pyridin-8-yl]-3,6-dihydro-2H-pyridine-1-carboxylate
ethyl 4-[2-[4-[2-(4-pyridyl)pyrrolidine-1-carbonyl]anilino]-[1,2,4]triazolo[1,5-a]pyridin-8-yl]-3,6-dihydro-2H-pyridine-1-carboxylate
ethyl 4-[2-[4-[4-(2-pyridylmethyl)piperidine-1-carbonyl]anilino]-[1,2,4]triazolo[1,5-a]pyridin-8-yl]-3,6-dihydro-2H-pyridine-1-carboxylate
ethyl 4-[2-[4-[4-(2-pyridylmethyl)piperazine-1-carbonyl]anilino]-[1,2,4]triazolo[1,5-a]pyridin-8-yl]-3,6-dihydro-2H-pyridine-1-carboxylate
ethyl 4-[2-[4-(4-morpholinopiperidine-1-carbonyl)anilino]-[1,2,4]triazolo[1,5-a]pyridin-8-yl]-3,6-dihydro-2H-pyridine-1-carboxylate
ethyl 4-[2-[4-[4-(3-pyridyl)piperazine-1-carbonyl]anilino]-[1,2,4]triazolo[1,5-a]pyridin-8-yl]-3,6-dihydro-2H-pyridine-1-carboxylate
ethyl 4-[2-[4-[6-(hydroxymethyl)-4-methyl-1,4-diazepane-1-carbonyl]anilino]-[1,2,4]triazolo[1,5-a]pyridin-8-yl]-3,6-dihydro-2H-pyridine-1-carboxylate
ethyl 4-[2-[4-[2-(1-methyl-2-piperidyl)pyrrolidine-1-carbonyl]anilino]-[1,2,4]triazolo[1,5-a]pyridin-8-yl]-3,6-dihydro-2H-pyridine-1-carboxylate
ethyl 4-[2-[4-[2-[4-(dimethylamino)-6-methyl-2-pyridyl]pyrrolidine-1-carbonyl]anilino]-[1,2,4]triazolo[1,5-a]pyridin-8-yl]-3,6-dihydro-2H-pyridine-1-carboxylate
ethyl 4-[2-[4-(9-methyl-3-oxa-7,9-diazabicyclo[3.3.1]nonane-7-carbonyl)anilino]-[1,2,4]triazolo[1,5-a]pyridin-8-yl]-3,6-dihydro-2H-pyridine-1-carboxylate
ethyl 4-[2-[4-(2-methylpiperazine-1-carbonyl)anilino]-[1,2,4]triazolo[1,5-a]pyridin-8-yl]-3,6-dihydro-2H-pyridine-1-carboxylate
ethyl 4-[2-[4-(1-oxa-4,9-diazaspiro[5.5]undecane-4-carbonyl)anilino]-[1,2,4]triazolo[1,5-a]pyridin-8-yl]-3,6-dihydro-2H-pyridine-1-carboxylate
ethyl 4-[2-[4-(1-oxa-4,8-diazaspiro[5.5]undecane-8-carbonyl)anilino]-[1,2,4]triazolo[1,5-a]pyridin-8-yl]-3,6-dihydro-2H-pyridine-1-carboxylate
ethyl 4-[2-[4-(7-azaspiro[3.5]nonan-2-ylcarbamoyl)anilino]-[1,2,4]triazolo[1,5-a]pyridin-8-yl]-3,6-dihydro-2H-pyridine-1-carboxylate
1-[4-[2-[4-(2,7-diazaspiro[4.4]nonane-2-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(3,9-diazaspiro[5.5]undecane-3-carbonyl)anilino]-[1,2,4]triazolo[1,5-a]pyridin-8-yl]-3,6-dihydro-2H-pyridin-1-yl]-4,4,4-trifluoro-butan-1-one N-(morpholin-2-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(methylamino)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(2-piperazin-1-ylethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[2-(hydroxymethyl)piperazine-1-carbonyl]anilino]-[1,2,4]triazolo[1,5-a]pyridin-8-yl]-3,6-dihydro-2H-pyridin-1-yl]butan-1-one 1-[4-[2-[4-(1,8-diazaspiro[5.5]undecane-1-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(2,7-diazaspiro[3.4]octane-2-carbonyl)anilino]-[1,2,4]triazolo[1,5-a]pyridin-8-yl]-3,6-dihydro-2H-pyridin-1-yl]-4,4,4-trifluoro-butan-1-one N-methyl -N-(3 -piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-(9-oxa-3,7-diazabicyclo[3.3.1]nonane-3-carbonyl)anilino]-[1,2,4]triazolo[1,5-a]pyridin-8-yl]-3,6-dihydro-2H-pyridin-1-yl]butan-1-one 1-[4-[2-[4-[(3aS,6aS)-1-methyl-2,3,3 a,4,6,6a-hexahydropyrrolo[3,4-b]pyrrole-5-carbonyl]anilino]-[1,2,4]triazolo[1,5-a]pyridin-8-yl]-3,6-dihydro-2H-pyridin-1-yl]-4,4,4-trifluoro-butan-1-one N-[(1-ethylpyrrolidin-3-yl)methyl]-N-methyl-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-(5-methyl-2,5-diazaspiro[3.4]octane-2-carbonyl)anilino]-[1,2,4]triazolo[1,5-a]pyridin-8-yl]-3,6-dihydro-2H-pyridin-1-yl]butan-1-one N-[(4-methyl-2-pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[(2-methyl-3 -pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-methyl -N-(1-methyl -4-piperidyl)-4-[[8-[1-(4,4,4-trifluoro-3 -methyl-butanoyl)-3,6-dihydro-2H-pyridin-4-yl]-[1,2,4]triazolo[1,5-a]pyridin-2-yl]amino]benzamide (1-methyl-4-piperidyl) 4-[[8-[1-(3,3-dimethylcyclobutanecarbonyl)-3,6-dihydro-2H-pyridin-4-yl]-[1,2,4]triazolo[1,5-a]pyridin-2-yl]amino]benzoate 4,4,4-trifluoro-1-[4-[2-[4-(3-morpholinopyrrolidine-1-carbonyl)anilino]-[1,2,4]triazolo[1,5-a]pyridin-8-yl]-3,6-dihydro-2H-pyridin-1-yl]butan-1-one 4,4,4-trifluoro-1-[4-[2-[4-(4-pyrrolidin-1-ylpiperidine-1-carbonyl)anilino]-[1,2,4]triazolo[1,5-a]pyridin-8-yl]-3,6-dihydro-2H-pyridin-1-yl]butan-1-one N-[3-(2-methyl-1-piperidyl)propyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(1-methylpyrrolidin-2-yl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(1-cyclopentyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[3 -(5-methyl-2-pyridyl)piperidine-1-carbonyl]anilino]-[1,2,4]triazolo[1,5-a]pyridin-8-yl]-3,6-dihydro-2H-pyridin-1-yl]butan-1-one 1-[4-[2-[4-[3-[5-(dimethylamino)-2-pyridyl]piperidine-1-carbonyl]anilino]-[1,2,4]triazolo[1,5-a]pyridin-8-yl]-3,6-dihydro-2H-pyridin-1-yl]-4,4,4-trifluoro-butan-1-one 4-[[8-[1-(cyanomethyl)-3,6-dihydro-2H-pyridin-4-yl]-[1,2,4]triazolo[1,5-a]pyridin-2-yl]amino]-N-methyl-N-(1-methyl-4-piperidyl)benzamide 4-[[8-[1-(3-methoxycyclobutanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide 4-[[8-[1-(3,3-dimethylbutanoyl)-3,6-dihydro-2H-pyridin-4-yl]-[1,2,4]triazolo[1,5-a]pyridin-2-yl]amino]-N-methyl-N-(1-methyl-4-piperidyl)benzamide ethyl 4-[2-[4-[3-(methylamino)azetidine-1-carbonyl]anilino]-[1,2,4]triazolo[1,5-a]pyridin-8-yl]-3,6-dihydro-2H-pyridine-1-carboxylate ethyl 4-[2-[4-(3-morpholinopropylcarbamoyl)anilino]-[1,2,4]triazolo[1,5-a]pyridin-8-yl]-3,6-dihydro-2H-pyridine-1-carboxylate ethyl 4-[2-[4-[2-(4-methylpiperazin-1-yl)ethylcarbamoyl]anilino]-[1,2,4]triazolo[1,5-a]pyridin-8-yl]-3,6-dihydro-2H-pyridine-1-carboxylate ethyl 4-[2-[4-[(1-methylazetidin-3-yl)carbamoyl]anilino]-[1,2,4]triazolo[1,5-a]pyridin-8-yl]-3,6-dihydro-2H-pyridine-1-carboxylate ethyl 4-[2-[4-[methyl-[2-(2-pyridypethyl]carbamoyl]anilino]-[1,2,4]triazolo[1,5-a]pyridin-8-yl]-3,6-dihydro-2H-pyridine-1-carboxylate ethyl 4-[2-[4-[(1-methyl-4-piperidyl)carbamoyl]anilino]-[1,2,4]triazolo[1,5-a]pyridin-8-yl]-3,6-dihydro-2H-pyridine-1-carboxylate ethyl 4-[2-[4-[methyl-[(1-methyl-3-piperidyl)methyl]carbamoyl]anilino]-[1,2,4]triazolo[1,5-a]pyridin-8-yl]-3,6-dihydro-2H-pyridine-1-carboxylate ethyl 4-[2-[4-[3-(4-pyridyl)pyrrolidine-1-carbonyl]anilino]-[1,2,4]triazolo[1,5-a]pyridin-8-yl]-3,6-dihydro-2H-pyridine-1-carboxylate ethyl 4-[2-[4-[4-(2,6-dimethylmorpholin-4-yl)piperidine-1-carbonyl]anilino]-[1,2,4]triazolo[1,5-a]pyridin-8-yl]-3,6-dihydro-2H-pyridine-1-carboxylate ethyl 4-[2-[4-[4-(2-morpholinoethyl)piperazine-1-carbonyl]anilino]-[1,2,4]triazolo[1,5-a]pyridin-8-yl]-3,6-dihydro-2H-pyridine-1-carboxylate ethyl 4-[2-[4-[(1-isopropylpyrrolidin-3-yl)methyl-methyl-carbamoyl]anilino]-[1,2,4]triazolo[1,5-a]pyridin-8-yl]-3,6-dihydro-2H-pyridine-1-carboxylate ethyl 4-[2-[4-(3-morpholinopyrrolidine-1-carbonyl)anilino]-[1,2,4]triazolo[1,5-a]pyridin-8-yl]-3,6-dihydro-2H-pyridine-1-carboxylate ethyl 4-[2-[4-[2-(5-methyl-2-pyridyl)pyrrolidine-1-carbonyl]anilino]-[1,2,4]triazolo[1,5-a]pyridin-8-yl]-3,6-dihydro-2H-pyridine-1-carboxylate ethyl 4-[2-[4-(7-methyl-2,7-diazaspiro[3.4]octane-2-carbonyl)anilino]-[1,2,4]triazolo[1,5-a]pyridin-8-yl]-3,6-dihydro-2H-pyridine-1-carboxylate ethyl 4-[2-[4-[[(3R)-quinuclidin-3-yl]carbamoyl]anilino]-[1,2,4]triazolo[1,5-a]pyridin-8-yl]-3,6-dihydro-2H-pyridine-1-carboxylate ethyl 4-[2-[4-(5,7-dihydropyrrolo[3,4-b]pyridine-6-carbonyl)anilino]-[1,2,4]triazolo[1,5-a]pyridin-8-yl]-3,6-dihydro-2H-pyridine-1-carboxylate ethyl 4-[2-[4-[4-(aminomethyl)-3-azabicyclo[2.1.1]hexane-3-carbonyl]anilino]-[1,2,4]triazolo[1,5-a]pyridin-8-yl]-3,6-dihydro-2H-pyridine-1-carboxylate ethyl 4-[2-[4-[(4aS,7aR)-3,4a,5,6,7,7a-hexahydro-2H-pyrrolo[3,4-b][1,4]oxazine-4-carbonyl]anilino]-[1,2,4]triazolo[1,5-a]pyridin-8-yl]-3,6-dihydro-2H-pyridine-1-carboxylate ethyl 4-[2-[4-[(1S,5R)-5-amino-3-azabicyclo[3.1.0]hexane-3-carbonyl]anilino]-[1,2,4]triazolo[1,5-a]pyridin-8-yl]-3,6-dihydro-2H-pyridine-1-carboxylate ethyl 4-[2-[4-(3-aminoazetidine-1-carbonyl)anilino]-[1,2,4]triazolo[1,5-a]pyridin-8-yl]-3,6-dihydro-2H-pyridine-1-carboxylate ethyl 4-[2-[4-(2,9-diazaspiro[5.5]undecane-2-carbonyl)anilino]-[1,2,4]triazolo[1,5-a]pyridin-8-yl]-3,6-dihydro-2H-pyridine-1-carboxylate ethyl 4-[2-[4-[2-(aminomethyl)pyrrolidine-1-carbonyl]anilino]-[1,2,4]triazolo[1,5-a]pyridin-8-yl]-3,6-dihydro-2H-pyridine-1-carboxylate ethyl 4-[2-[4-(2,6-diazaspiro[3.3]heptane-2-carbonyl)anilino]-[1,2,4]triazolo[1,5-a]pyridin-8-yl]-3,6-dihydro-2H-pyridine-1-carboxylate ethyl 4-[2-[4-(2,7-diazaspiro[4.4]nonane-2-carbonyl)anilino]-[1,2,4]triazolo[1,5-a]pyridin-8-yl]-3,6-dihydro-2H-pyridine-1-carboxylate ethyl 4-[2-[4-(2,8-diazaspiro[4.5]decane-2-carbonyl)anilino]-[1,2,4]triazolo[1,5-a]pyridin-8-yl]-3,6-dihydro-2H-pyridine-1-carboxylate 1-[4-[2-[4-[2-(aminomethyl)pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-(2,7-diazaspiro[3.5]nonane-2-carbonyl)anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-(1-oxa-4,8-diazaspiro[5.5]undecane-4-carbonyl)anilino]-[1,2,4]triazolo[1,5-a]pyridin-8-yl]-3,6-dihydro-2H-pyridin-1-yl]butan-1-one N-(1-oxa-8-azaspiro[4.5]decan-2-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(4-piperidylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[3-(methylamino)pyrrolidine-1-carbonyl]anilino]-[1,2,4]triazolo[1,5-a]pyridin-8-yl]-3,6-dihydro-2H-pyridin-1-yl]butan-1-one N-[2-(4-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-(2-methyl-1,3,3a,4,6,6a-hexahydropyrrolo[3,4-c]pyrrole-5-carbonyl)anilino]-[1,2,4]triazolo[1,5-a]pyridin-8-yl]-3,6-dihydro-2H-pyridin-1-yl]butan-1-one 1-[4-[2-[4-[3-[2-(dimethylamino)ethyl]piperidine-1-carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-[4-[(dimethyl amino)methyl]-4-hydroxy-azepane-1-carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-[3-[6-(dimethylamino)-2-methyl-pyrimidin-4-yl]piperidine-1-carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-[4-[6-(dimethylamino)-2-pyridyl]piperidine-1-carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-[2-[4-(dimethylamino)-6-methyl-2-pyridyl]pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-(8-methyl-2,8-diazaspiro[5.5]undecane-2-carbonyl)anilino]-[1,2,4]triazolo[1,5-a]pyridin-8-yl]-3,6-dihydro-2H-pyridin-1-yl]butan-1-one ethyl 4-[2-[4-[(1-methyl-4-piperidyl)oxycarbonyl]anilino]-[1,2,4]triazolo[1,5-a]pyridin-8-yl]-3,6-dihydro-2H-pyridine-1-carboxylate 4,4,4-trifluoro-1-[4-[2-[4-[4-(2-pyridylmethyl)piperazine-1-carbonyl]anilino]-[1,2,4]triazolo[1,5-a]pyridin-8-yl]-3,6-dihydro-2H-pyridin-1-yl]butan-1-one N-methyl-N-[2-(4-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-[4-(dimethylamino)piperidine-1-carbonyl]anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-(4-methylpiperazine-1-carbonyl)anilino]-[1,2,4]triazolo[1,5-a]pyridin-8-yl]-3,6-dihydro-2H-pyridin-1-yl]butan-1-one N-[3-(4-methylpiperazin-1-yl)propyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(4-hydroxy-1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(3-methyl-1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-[4-[2-(dimethylamino)ethyl]piperazine-1-carbonyl]anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-[3-(1H-pyrrolo[2,3-b]pyridin-2-yl)piperidine-1-carbonyl]anilino]-[1,2,4]triazolo[1,5-a]pyridin-8-yl]-3,6-dihydro-2H-pyridin-1-yl]butan-1-one N-methyl-N-[[2-(3-pyridyl)phenyl]methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-methyl-N-(1-methyl-4-piperidyl)-4-[[8-[1-(tetrahydropyran-4-carbonyl)-3,6-dihydro-2H-pyridin-4-yl]-[1,2,4]triazolo[1,5-a]pyridin-2-yl]amino]benzamide N-methyl-4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxamide;hydrochloride N-methyl-N-(1-methyl-4-piperidyl)-4-[[8-[1-(tetrahydrofuran-3-carbonyl)-3,6-dihydro-2H-pyridin-4-yl]-[1,2,4]triazolo[1,5-a]pyridin-2-yl]amino]benzamide;hydrochloride 2,2,2-trifluoroethyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate N-methyl-4-[[8-[1-(3-methylbutanoyl)-3,6-dihydro-2H-pyridin-4-yl]-[1,2,4]triazolo[1,5-a]pyridin-2-yl]amino]-N-(1-methyl-4-piperidyl)benzamide ethyl 4-[2-[4-[(1,1-dimethyl-2-morpholino-ethyl)carbamoyl]anilino]-[1,2,4]triazolo[1,5-a]pyridin-8-yl]-3,6-dihydro-2H-pyridine-1-carboxylate ethyl 4-[2-[4-[2-(1-methylpyrrolidin-2-yl)ethylcarbamoyl]anilino]-[1,2,4]triazolo[1,5-a]pyridin-8-yl]-3,6-dihydro-2H-pyridine-1-carboxylate ethyl 4-[2-[4-(2-piperazin-1-ylethylcarbamoyl)anilino]-[1,2,4]triazolo[1,5-a]pyridin-8-yl]-3,6-dihydro-2H-pyridine-1-carboxylate ethyl 4-[2-[4-(3-piperidylcarbamoyl)anilino]-[1,2,4]triazolo[1,5-a]pyridin-8-yl]-3,6-dihydro-2H-pyridine-1-carboxylate ethyl 4-[2-[4-(2-piperidylmethylcarbamoyl)anilino]-[1,2,4]triazolo[1,5-a]pyridin-8-yl]-3,6-dihydro-2H-pyridine-1-carboxylate ethyl 4-[2-[4-[3-(dimethylcarbamoyl)azetidine-1-carbonyl]anilino]-[1,2,4]triazolo[1,5-a]pyridin-8-yl]-3,6-dihydro-2H-pyridine-1-carboxylate ethyl 4-[2-[4-[2-(1-methyl-4-piperidyl)ethylcarbamoyl]anilino]-[1,2,4]triazolo[1,5-a]pyridin-8-yl]-3,6-dihydro-2H-pyridine-1-carboxylate ethyl 4-[2-[4-[[(1-benzylpyrrolidin-3-yl)-methyl-carbamoyl]anilino]-[1,2,4]triazolo[1,5-a]pyridin-8-yl]-3,6-dihydro-2H-pyridine-1-carboxylate ethyl 4-[2-[4-[3-(diethylamino)pyrrolidine-1-carbonyl]anilino]-[1,2,4]triazolo[1,5-a]pyridin-8-yl]-3,6-dihydro-2H-pyridine-1-carboxylate ethyl 4-[2-[4-[methyl-[2-(4-pyridyl)ethyl]carbamoyl]anilino]-[1,2,4]triazolo[1,5-a]pyridin-8-yl]-3,6-dihydro-2H-pyridine-1-carboxylate ethyl 4-[2-[4-(8-methyl-5-oxa-2,8-diazaspiro[3.5]nonane-2-carbonyl)anilino]-[1,2,4]triazolo[1,5-a]pyridin-8-yl]-3,6-dihydro-2H-pyridine-1-carboxylate ethyl 4-[2-[4-[4-(4-pyridyl)piperidine-1-carbonyl]anilino]-[1,2,4]triazolo[1,5-a]pyridin-8-yl]-3,6-dihydro-2H-pyridine-1-carboxylate ethyl 4-[2-[4-[(3aS,6aS)-1-methyl-2,3,3a,4,6,6a-hexahydropyrrolo[3,4-b]pyrrole-5-carbonyl]anilino]-[1,2,4]triazolo[1,5-a]pyridin-8-yl]-3,6-dihydro-2H-pyridine-1-carboxylate ethyl 4-[2-[4-(7-methyl-9-oxa-3,7-diazabicyclo[3.3.1]nonane-3-carbonyl)anilino]-[1,2,4]triazolo[1,5-a]pyridin-8-yl]-3,6-dihydro-2H-pyridine-1-carboxylate ethyl 4-[2-[4-[(4-methyl-2-pyridyl)methylcarbamoyl]anilino]-[1,2,4]triazolo[1,5-a]pyridin-8-yl]-3,6-dihydro-2H-pyridine-1-carboxylate ethyl 4-[2-[4-(2,3,4a,5,6,7,8,8a-octahydropyrido[4,3-b][1,4]oxazine-4-carbonyl)anilino]-[1,2,4]triazolo[1,5-a]pyridin-8-yl]-3,6-dihydro-2H-pyridine-1-carboxylate ethyl 4-[2-[4-(2,3,3a,4,6,6a-hexahydro-1H-pyrrolo[3,4-c]pyrrole-5-carbonyl]anilino]-[1,2,4]triazolo[1,5-a]pyridin-8-yl]-3,6-dihydro-2H-pyridine-1-carboxylate ethyl 4-[2-[4-[(4aR,7aR)-3,4a,5,6,7,7a-hexahydro-2H-pyrrolo[3,4-b][1,4]oxazine-4-carbonyl]anilino]-[1,2,4]triazolo[1,5-a]pyridin-8-yl]-3,6-dihydro-2H-pyridine-1-carboxylate ethyl 4-[2-[4-(1,7-diazaspiro[3.5]nonane-7-carbonyl)anilino]-[1,2,4]triazolo[1,5-a]pyridin-8-yl]-3,6-dihydro-2H-pyridine-1-carboxylate ethyl 4-[2-[4-(piperazine-1-carbonyl)anilino]-[1,2,4]triazolo[1,5-a]pyridin-8-yl]-3,6-dihydro-2H-pyridine-1-carboxylate ethyl 4-[2-[4-[3-(aminomethyl)pyrrolidine-1-carbonyl]anilino]-[1,2,4]triazolo[1,5-a]pyridin-8-yl]-3,6-dihydro-2H-pyridine-1-carboxylate ethyl 4-[2-[4-(1,8-diazaspiro[5.5]undecane-8-carbonyl)anilino]-[1,2,4]triazolo[1,5-a]pyridin-8-yl]-3,6-dihydro-2H-pyridine-1-carboxylate ethyl 4-[2-[4-(2,8-diazaspiro[5.5]undecane-2-carbonyl)anilino]-[1,2,4]triazolo[1,5-a]pyridin-8-yl]-3,6-dihydro-2H-pyridine-1-carboxylate ethyl 4-[2-[4-(2-amino-7-azaspiro[3.5]nonane-7-carbonyl)anilino]-[1,2,4]triazolo[1,5-a]pyridin-8-yl]-3,6-dihydro-2H-pyridine-1-carboxylate ethyl 4-[2-[4-(1-oxa-4,8-diazaspiro[5.5]undecane-4-carbonyl)anilino]-[1,2,4]triazolo[1,5-a]pyridin-8-yl]-3,6-dihydro-2H-pyridine-1-carboxylate ethyl 4-[2-[4-(2,8-diazaspiro[4.5]decane-8-carbonyl)anilino]-[1,2,4]triazolo[1,5-a]pyridin-8-yl]-3,6-dihydro-2H-pyridine-1-carboxylate 1-[4-[2-[4-(2,8-diazaspiro[4.5]decane-8-carbonyl)anilino]-[1,2,4]triazolo[1,5-a]pyridin-8-yl]-3,6-dihydro-2H-pyridin-1-yl]-4,4,4-trifluoro-butan-1-one N-(3-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[(3S)-3-piperidyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-[(4aS,7aR)-3,4a,5,6,7,7a-hexahydro-2H-pyrrolo[3,4-b][1,4]oxazine-4-carbonyl]anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-[3-(3-piperidyl)indoline-1-carbonyl]anilino]-[1,2,4]triazolo[1,5-a]pyridin-8-yl]-3,6-dihydro-2H-pyridin-1-yl]butan-1-one N-methyl-N-(8-quinolylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 3-[4-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazin-1-yl]propanenitrile 4,4,4-trifluoro-1-[4-[2-[4-[2-(5-methyl-2-pyridyl)pyrrolidine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[6-(hydroxymethyl)-4-methyl-1,4-diazepane-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[2-(3-pyridyl)pyrrolidine-1-carbonyl]anilino]-[1,2,4]triazolo[1,5-a]pyridin-8-yl]-3,6-dihydro-2H-pyridin-1-yl]butan-1-one 1-[4-[2-[4-(5,7-dihydropyrrolo[3,4-b]pyridine-6-carbonyl)anilino]-[1,2,4]triazolo[1,5-a]pyridin-8-yl]-3,6-dihydro-2H-pyridin-1-yl]-4,4,4-trifluoro-butan-1-one N-[2-(4-methyl-1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[(6-methyl-3-pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[2-(1-methyl-4-piperidyl)piperidine-1-carbonyl]anilino]-[1,2,4]triazolo[1,5-a]pyridin-8-yl]-3,6-dihydro-2H-pyridin-1-yl]butan-1-one N-cyclopropyl-N-(1-methyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-(1,3,4,6,7,8,9,9a-octahydropyrido[1,2-a]pyrazine-2-carbonyl)anilino]-[1,2,4]triazolo[1,5-a]pyridin-8-yl]-3,6-dihydro-2H-pyridin-1-yl]-4,4,4-trifluoro-butan-1-one N-methyl-N-[2-(2-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[4-(2-hydroxyethyl)piperazine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[2-(2-pyridyl)morpholine-4-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[4-(1H-pyrrolo[2,3-b]pyridin-2-yl)piperidine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[4-(2-pyridyl)piperidine-1-carbonyl]anilino]-[1,2,4]triazolo[1,5-a]pyridin-8-yl]-3,6-dihydro-2H-pyridin-1-yl]butan-1-one 1-[4-[2-[4-[4-(2,6-dimethylmorpholin-4-yl)piperidine-1-carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-[(3S)-3-(dimethylamino)pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-[3-(4-methylpiperazine-1-carbonyl)azetidine-1-carbonyl]anilino]-[1,2,4]triazolo[1,5-a]pyridin-8-yl]-3,6-dihydro-2H-pyridin-1-yl]butan-1-one 4-[[8-[1-(2,2-dimethylcyclopropanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide N-methyl-N-(1-methyl-4-piperidyl)-4-[[8-[1-(2,2,3,3-tetramethylcyclopropanecarbonyl)-3,6-dihydro-2H-pyridin-4-yl]-[1,2,4]triazolo[1,5-a]pyridin-2-yl]amino]benzamide 4-[[8-[1-(1,1-dioxo-1,4-thiazinane-4-carbonyl)-3,6-dihydro-2H-pyridin-4-yl]-[1,2,4]triazolo[1,5-a]pyridin-2-yl]amino]-N-methyl-N-(1-methyl-4-piperidyl)benzamide N-methyl-N-(1-methyl-4-piperidyl)-4-[[8-[1-(3,3,3-trifluoropropanoyl)-3,6-dihydro-2H-pyridin-4-yl]-[1,2,4]triazolo[1,5-a]pyridin-2-yl]amino]benzamide 4-[[8-[1-(3-hydroxy-3-methyl-cyclobutanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide ethyl 4-[2-[4-[3-(aminomethyl)azetidine-1-carbonyl]anilino]-[1,2,4]triazolo[1,5-a]pyridin-8-yl]-3,6-dihydro-2H-pyridine-1-carboxylate ethyl 4-[2-[4-[3-(2-pyridyl)piperidine-1-carbonyl]anilino]-[1,2,4]triazolo[1,5-a]pyridin-8-yl]-3,6-dihydro-2H-pyridine-1-carboxylate ethyl 4-[2-[4-[2-(2,6-dimethylmorpholin-4-yl)ethylcarbamoyl]anilino]-[1,2,4]triazolo[1,5-a]pyridin-8-yl]-3,6-dihydro-2H-pyridine-1-carboxylate ethyl 4-[2-[4-[4-(2-hydroxyethyl)piperazine-1-carbonyl]anilino]-[1,2,4]triazolo[1,5-a]pyridin-8-yl]-3,6-dihydro-2H-pyridine-1-carboxylate ethyl 4-[2-[4-[2-(dimethylamino)ethylcarbamoyl]anilino]-[1,2,4]triazolo[1,5-a]pyridin-8-yl]-3,6-dihydro-2H-pyridine-1-carboxylate ethyl 4-[2-[4-[1-(6-methyl-2-pyridyl)ethylcarbamoyl]anilino]-[1,2,4]triazolo[1,5-a]pyridin-8-yl]-3,6-dihydro-2H-pyridine-1-carboxylate ethyl 4-[2-[4-[cyclopropyl(2-pyridylmethyl)carbamoyl]anilino]-[1,2,4]triazolo[1,5-a]pyridin-8-yl]-3,6-dihydro-2H-pyridine-1-carboxylate ethyl 4-[2-[4-[2-(4-pyridyl)ethylcarbamoyl]anilino]-[1,2,4]triazolo[1,5-a]pyridin-8-yl]-3,6-dihydro-2H-pyridine-1-carboxylate ethyl 4-[2-[4-[methyl-[(3-methyl-2-pyridyl)methyl]carbamoyl]anilino]-[1,2,4]triazolo[1,5-a]pyridin-8-yl]-3,6-dihydro-2H-pyridine-1-carboxylate ethyl 4-[2-[4-[ethyl(4-pyridylmethyl)carbamoyl]anilino]-[1,2,4]triazolo[1,5-a]pyridin-8-yl]-3,6-dihydro-2H-pyridine-1-carboxylate ethyl 4-[2-[4-(7-methyl-2,7-diazaspiro[3.5]nonane-2-carbonyl)anilino]-[1,2,4]triazolo[1,5-a]pyridin-8-yl]-3,6-dihydro-2H-pyridine-1-carboxylate ethyl 4-[2-[4-(5-methyl-2,5-diazaspiro[3.4]octane-2-carbonyl)anilino]-[1,2,4]triazolo[1,5-a]pyridin-8-yl]-3,6-dihydro-2H-pyridine-1-carboxylate ethyl 4-[2-[4-[(2-methyl-3-pyridyl)methylcarbamoyl]anilino]-[1,2,4]triazolo[1,5-a]pyridin-8-yl]-3,6-dihydro-2H-pyridine-1-carboxylate ethyl 4-[2-[4-[(5-methyl-3-pyridyl)methylcarbamoyl]anilino]-[1,2,4]triazolo[1,5-a]pyridin-8-yl]-3,6-dihydro-2H-pyridine-1-carboxylate ethyl 4-[2-[4-[2-(4-methyl-1-piperidyl)ethylcarbamoyl]anilino]-[1,2,4]triazolo[1,5-a]pyridin-8-yl]-3,6-dihydro-2H-pyridine-1-carboxylate ethyl 4-[2-[4-(9-oxa-3,7-diazabicyclo[3.3.1]nonane-3-carbonyl)anilino]-[1,2,4]triazolo[1,5-a]pyridin-8-yl]-3,6-dihydro-2H-pyridine-1-carboxylate ethyl 4-[2-[4-(3,9-diazaspiro[5.5]undecane-3-carbonyl)anilino]-[1,2,4]triazolo[1,5-a]pyridin-8-yl]-3,6-dihydro-2H-pyridine-1-carboxylate ethyl 4-[2-[4-(1,9-diazaspiro[4.6]undecane-9-carbonyl)anilino]-[1,2,4]triazolo[1,5-a]pyridin-8-yl]-3,6-dihydro-2H-pyridine-1-carboxylate ethyl 4-[2-[4-(1,8-diazaspiro[4.5]decane-8-carbonyl)anilino]-[1,2,4]triazolo[1,5-a]pyridin-8-yl]-3,6-dihydro-2H-pyridine-1-carboxylate ethyl 4-[2-[4-(2,7-diazaspiro[3.5]nonane-7-carbonyl)anilino]-[1,2,4]triazolo[1,5-a]pyridin-8-yl]-3,6-dihydro-2H-pyridine-1-carboxylate ethyl 4-[2-[4-(2,8-diazaspiro[3.5]nonane-2-carbonyl)anilino]-[1,2,4]triazolo[1,5-a]pyridin-8-yl]-3,6-dihydro-2H-pyridine-1-carboxylate 1-[4-[2-[4-(2,8-diazaspiro[3.5]nonane-2-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(2,8-diazaspiro[4.5]decane-2-carbonyl)anilino]-[1,2,4]triazolo[1,5-a]pyridin-8-yl]-3,6-dihydro-2H-pyridin-1-yl]-4,4,4-trifluoro-butan-1-one N-(1-oxa-8-azaspiro[4.5]decan-3-yl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(2-oxa-9-azaspiro[5.5]undecan-3-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-(1-oxa-4,8-diazaspiro[5.5]undecane-8-carbonyl)anilino]-[1,2,4]triazolo[1,5-a]pyridin-8-yl]-3,6-dihydro-2H-pyridin-1-yl]butan-1-one 1-[4-[2-[4-(2,9-diazaspiro[5.5]undecane-9-carbonyl)anilino]-[1,2,4]triazolo[1,5-a]pyridin-8-yl]-3,6-dihydro-2H-pyridin-1-yl]-4,4,4-trifluoro-butan-1-one N-(3-piperidylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(3-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(2-aminoethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-(1,4-diazepane-1-carbonyl)anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-(3-methylpiperazine-1-carbonyl)anilino]-[1,2,4]triazolo[1,5-a]pyridin-8-yl]-3,6-dihydro-2H-pyridin-1-yl]butan-1-one 1-[4-[2-[4-(1,7-diazaspiro[3.5]nonane-7-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(1,8-diazaspiro[4.5]decane-8-carbonyl)anilino]-[1,2,4]triazolo[1,5-a]pyridin-8-yl]-3,6-dihydro-2H-pyridin-1-yl]-4,4,4-trifluoro-butan-1-one N-methyl-N-(2-pyridylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-(3,4,6,7,8,8a-hexahydro-1H-pyrrolo[1,2-a]pyrazine-2-carbonyl)anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-(3-methyl-3,6-diazabicyclo[3.2.1]octane-6-carbonyl)anilino]-[1,2,4]triazolo[1,5-a]pyridin-8-yl]-3,6-dihydro-2H-pyridin-1-yl]butan-1-one 1-[4-[2-[4-(4-cyclopropylpiperazine-1-carbonyl)anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-[4-[(1-methylimidazol-2-yl)methyl]piperazine-1-carbonyl]anilino]-[1,2,4]triazolo[1,5-a]pyridin-8-yl]-3,6-dihydro-2H-pyridin-1-yl]butan-1-one 1-[4-[2-[4-(6-acetyl-2,6-diazaspiro[3.3]heptane-2-carbonyl)anilino]-[1,2,4]triazolo[1,5-a]pyridin-8-yl]-3,6-dihydro-2H-pyridin-1-yl]-4,4,4-trifluoro-butan-1-one 4,4,4-trifluoro-4-[4-[2-[4-(7-methyl-9-oxa-3,7-diazabicyclo[3.3.1]nonane-3-carbonyl)anilino]-[1,2,4]triazolo[1,5-a]pyridin-8-yl]-3,6-dihydro-2H-pyridin-1-yl]butan-1-one N-[(5-methyl-3-pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-[3-(aminomethyl)azetidine-1-carbonyl]anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-[4-(4-methyl-1-piperidyl)piperidine-1-carbonyl]anilino]-[1,2,4]triazolo[1,5-a]pyridin-8-yl]-3,6-dihydro-2H-pyridin-1-yl]butan-1-one N-(2-methoxyethyl)-N-(1-methyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-(4-morpholinopiperidine-1-carbonyl)anilino]-[1,2,4]triazolo[1,5-a]pyridin-8-yl]-3,6-dihydro-2H-pyridin-1-yl]butan-1-one 1-[4-[2-[4-[3-(diethylamino)pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one N-methyl-N-[2-(3-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(2-methyl-2-morpholino-propyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[(1-methyl-2-piperidyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[4-(5-methyl-2-pyridyl)piperidine-1-carbonyl]anilino]-[1,2,4]triazolo[1,5-a]pyridin-8-yl]-3,6-dihydro-2H-pyridin-1-yl]butan-1-one N-[2-(6-methyl-2-pyridyl)ethyl]-4-[[8-1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-[3-[[6-(dimethylamino)pyrimidin-4-yl]methyl]pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-[3-[(5-methyl-2-pyridyl)methyl]pyrrolidine-1-carbonyl]anilino]-[1,2,4]triazolo[1,5-a]pyridin-8-yl]-3,6-dihydro-2H-pyridin-1-yl]butan-1-one N-ethyl-N-(4-pyridylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(3-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(2-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-benzyl-4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxamide N-methyl-4-[[8-[1-(2-methylcyclopropanecarbonyl)-3,6-dihydro-2H-pyridin-4-yl]-[1,2,4]triazolo[1,5-a]pyridin-2-yl]amino]-N-(1-methyl-4-piperidyl)benzamide methyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate 2,2-difluoroethyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate ethyl 4-[2-[4-[2-(3-methyl-1-piperidyl)ethylcarbamoyl]anilino]-[1,2,4]triazolo[1,5-a]pyridin-8-yl]-3,6-dihydro-2H-pyridine-1-carboxylate ethyl 4-[2-[4-[4-[2-(dimethylamino)ethyl]piperazine-1-carbonyl]anilino]-[1,2,4]triazolo[1,5-a]pyridin-8-yl]-3,6-dihydro-2H-pyridine-1-carboxylate ethyl 4-[2-[4-[2-(2-pyridyl)morpholine-4-carbonyl]anilino]-[1,2,4]triazolo[1,5-a]pyridin-8-yl]-3,6-dihydro-2H-pyridine-1-carboxylate ethyl 4-[2-[4-[2-(6-methyl-2-pyridyl)ethylcarbamoyl]anilino]-[1,2,4]triazolo[1,5-a]pyridin-8-yl]-3,6-dihydro-2H-pyridine-1-carboxylate ethyl 4-[2-[4-[2-(methylamino)ethylcarbamoyl]anilino]-[1,2,4]triazolo[1,5-a]pyridin-8-yl]-3,6-dihydro-2H-pyridine-1-carboxylate ethyl 4-[2-[4-(pyrrolidin-3-ylcarbamoyl)anilino]-[1,2,4]triazolo[1,5-a]pyridin-8-yl]-3,6-dihydro-2H-pyridine-1-carboxylate ethyl 4-[2-[4-[2-(3-pyridyl)piperidine-1-carbonyl]anilino]-[1,2,4]triazolo[1,5-a]pyridin-8-yl]-3,6-dihydro-2H-pyridine-1-carboxylate ethyl 4-[2-[4-(pyrrolidin-2-ylmethylcarbamoyl)anilino]-[1,2,4]triazolo[1,5-a]pyridin-8-yl]-3,6-dihydro-2H-pyridine-1-carboxylate ethyl 4-[2-[4-[3-(2-pyridylmethyl)pyrrolidine-1-carbonyl]anilino]-[1,2,4]triazolo[1,5-a]pyridin-8-yl]-3,6-dihydro-2H-pyridine-1-carboxylate ethyl 4-[2-[4-[2-(2-pyridylmethyl)piperidine-1-carbonyl]anilino]-[1,2,4]triazolo[1,5-a]pyridin-8-yl]-3,6-dihydro-2H-pyridine-1-carboxylate ethyl 4-[2-[4-[4-(2-methoxyethyl)piperazine-1-carbonyl]anilino]-[1,2,4]triazolo[1,5-a]pyridin-8-yl]-3,6-dihydro-2H-pyridine-1-carboxylate ethyl 4-[2-[4-[methyl42-(3-pyridyl)ethyl]carbamoyl]anilino]-[1,2,4]triazolo[1,5-a]pyridin-8-yl]-3,6-dihydro-2H-pyridine-1-carboxylate ethyl 4-[2-[4-[4-(cyclopropylmethyl)piperazine-1-carbonyl]anilino]-[1,2,4]triazolo[1,5-a]pyridin-8-yl]-3,6-dihydro-2H-pyridine-1-carboxylate ethyl 4-[2-[4-[2-(2-pyridylmethyl)pyrrolidine-1-carbonyl]anilino]-[1,2,4]triazolo[1,5-a]pyridin-8-yl]-3,6-dihydro-2H-pyridine-1-carboxylate ethyl 4-[2-[4-(2-methyl-1,3,3a,4,6,6a-hexahydropyrrolo[3,4-c]pyrrole-5-carbonyl)anilino]-[1,2,4]triazolo[1,5-a]pyridin-8-yl]-3,6-dihydro-2H-pyridine-1-carboxylate ethyl 4-[2-[4-[4-hydroxy-4-(pyrrolidin-1-ylmethyl)azepane-1-carbonyl]anilino]-[1,2,4]triazolo[1,5-a]pyridin-8-yl]-3,6-dihydro-2H-pyridine-1-carboxylate ethyl 4-[2-[4-[3-[2-(dimethylamino)ethyl]piperidine-1-carbonyl]anilino]-[1,2,4]triazolo[1,5-a]pyridin-8-yl]-3,6-dihydro-2H-pyridine-1-carboxylate ethyl 4-[2-[4-[2-(dimethylcarbamoyl)-4-methyl-piperazine-1-carbonyl]anilino]-[1,2,4]triazolo[1,5-a]pyridin-8-yl]-3,6-dihydro-2H-pyridine-1-carboxylate ethyl 4-[2-[4-[(3aS,6aS)-5-methyl-2,3,3a,4,6,6a-hexahydropyrrolo[2,3-c]pyrrole-1-carbonyl]anilino]-[1,2,4]triazolo[1,5-a]pyridin-8-yl]-3,6-dihydro-2H-pyridine-1-carboxylate ethyl 4-[2-[4-[(6-methyl-3-pyridyl)methylcarbamoyl]anilino]-[1,2,4]triazolo[1,5-a]pyridin-8-yl]-3,6-dihydro-2H-pyridine-1-carboxylate ethyl 4-[2-[4-[(3aS,6aS)-3,3a,4,5,6,6a-hexahydro-2H-pyrrolo[2,3-c]pyrrole-1-carbonyl]anilino]-[1,2,4]triazolo[1,5-a]pyridin-8-yl]-3,6-dihydro-2H-pyridine-1-carboxylate ethyl 4-[2-[4-(1,8-diazaspiro[5.5]undecane-1-carbonyl)anilino]-[1,2,4]triazolo[1,5-a]pyridin-8-yl]-3,6-dihydro-2H-pyridine-1-carboxylate ethyl 4-[2-[4-[(1R,5R)-3,6-diazabicyclo[3.2.0]heptane-3-carbonyl]anilino]-[1,2,4]triazolo[1,5-a]pyridin-8-yl]-3,6-dihydro-2H-pyridine-1-carboxylate ethyl 4-[2-[4-[(1-methyl-4-piperidyl)methylcarbamoyl]anilino]-[1,2,4]triazolo[1,5-a]pyridin-8-yl]-3,6-dihydro-2H-pyridine-1-carboxylate ethyl 4-[2-[4-[[(3S)-3-piperidyl]carbamoyl]anilino]-[1,2,4]triazolo[1,5-a]pyridin-8-yl]-3,6-dihydro-2H-pyridine-1-carboxylate ethyl 4-[2-[4-[4-(2-pyridyl)piperazine-1-carbonyl]anilino]-[1,2,4]triazolo[1,5-a]pyridin-8-yl]-3,6-dihydro-2H-pyridine-1-carboxylate ethyl 4-[2-[4-(2,9-diazaspiro[5.5]undecane-9-carbonyl)anilino]-[1,2,4]triazolo[1,5-a]pyridin-8-yl]-3,6-dihydro-2H-pyridine-1-carboxylate 1-[4-[2-[4-(2,9-diazaspiro[4.5]decane-2-carbonyl)anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-(1-oxa-4,9-diazaspiro[5.5]undecane-4-carbonyl)anilino]-[1,2,4]triazolo[1,5-a]pyridin-8-yl]-3,6-dihydro-2H-pyridin-1-yl]butan-1-one N-pyrrolidin-3-yl-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-(3-aminoazetidine-1-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(1,9-diazaspiro[4.5]decane-1-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(1,8-diazaspiro[4.5]decane-1-carbonyl)anilino]-[1,2,4]triazolo[1,5-a]pyridin-8-yl]-3,6-dihydro-2H-pyridin-1-yl]-4,4,4-trifluoro-butan-1-one 4,4,4-trifluoro-4-[4-[2-[4-(8-methyl-5-oxa-2,8-diazaspiro[3.5]nonane-2-carbonyl)anilino]-[1,2,4]triazolo[1,5-a]pyridin-8-yl]-3,6-dihydro-2H-pyridin-1-yl]butan-1-one 1-[4-[2-[4-(4-cyclobutylpiperazine-1-carbonyl)anilino]-[1,2,4]triazolo[1,5-a]pyridin-8-yl]-3,6-dihydro-2H-pyridin-1-yl]-4,4,4-trifluoro-butan-1-one N,N-dimethyl-2-(4-pyridyl)-1-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]pyrrolidine-2-carboxamide 4,4,4-trifluoro-1-[4-[2-[4-[3-(4-methylpiperazine-1-carbonyl)morpholine-4-carbonyl]anilino]-[1,2,4]triazolo[1,5-a]pyridin-8-yl]-3,6-dihydro-2H-pyridin-1-yl]butan-1-one N-methyl-4-[[8-[1-(3-methylcyclobutanecarbonyl)-3,6-dihydro-2H-pyridin-4-yl]-[1,2,4]triazolo[1,5-a]pyridin-2-yl]amino]-N-(1-methyl-4-piperidyl)benzamide (1-methyl-4-piperidyl) 4-[[8-[1-(4,4,4-trifluorobutanoyl)-3,6-dihydro-2H-pyridin-4-yl]-[1,2,4]triazolo[1,5-a]pyridin-2-yl]amino]benzoate 4,4,4-trifluoro-1-[4-[2-[4-[2-(2-pyridylmethyl)piperidine-1-carbonyl]anilino]-[1,2,4]triazolo[1,5-a]pyridin-8-yl]-3,6-dihydro-2H-pyridin-1-yl]butan-1-one 4,4,4-trifluoro-4-[4-[2-[4-(4--isobutylpiperazine-1-carbonyl)anilino]-[1,2,4]triazolo[1,5-a]pyridin-8-yl]-3,6-dihydro-2H-pyridin-1-yl]butan-1-one N-methyl-N-(1-methylpyrrolidin-3-yl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(2,6-dimethylmorpholin-4-yl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(3,5-dimethyl-1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(4-methylpiperazin-1-yl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(3-morpholinopropyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-cyclopropyl-N-(2-pyridylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[2-(4-pyridyl)pyrrolidine-1-carbonyl]anilino]-[1,2,4]triazolo[1,5-a]pyridin-8-yl]-3,6-dihydro-2H-pyridin-1-yl]butan-1-one N-[2-(1-methyl-4-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N,1-dimethyl-4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide N,4-dimethyl-1-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide 4,4,4-trifluoro-1-[4-[2-[4-[4-(3-pyridylmethyl)piperidine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[4-(4-pyridyl)-1,4-diazepane-1-carbonyl]anilino]-[1,2,4]triazolo[1,5-a]pyridin-8-yl]-3,6-dihydro-2H-pyridin-1-yl]butan-1-one N-(2-hydroxyethyl)-N-(3-pyridylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[2-(3-pyridyl)piperidine-1-carbonyl]anilino]-[1,2,4]triazolo[1,5-a]pyridin-8-yl]-3,6-dihydro-2H-pyridin-1-yl]butan-1-one 4-[[8-[1-(cyclopentanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide 4-[[8-[1-(cyclobutanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide oxetan-3-yl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate N-methyl-N-(1-methyl-4-piperidyl)-4-[[8-(1-phenyl-3,6-dihydro-2H-pyridin-4-yl)-[1,2,4]triazolo[1,5-a]pyridin-2-yl]amino]benzamide 4-[8-[1-(4-cyanocyclohexanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide N-methyl-N-(1-methyl-4-piperidyl)-4-[[8-[1-(2-oxa-6-azaspiro[3.3]heptane-6-carbonyl)-3,6-dihydro-2H-pyridin-4-yl]-[1,2,4]triazolo[1,5-a]pyridin-2-yl]amino]benzamide 4-[[8-[1-(3-cyanopropanoyl)-3,6-dihydro-2H-pyridin-4-yl]-[1,2,4]triazolo[1,5-a]pyridin-2-yl]amino]-N-methyl-N-(1-methyl-4-piperidyl)benzamide N-methyl-N-(1-methyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4-[[8-(1-butanoyl-3,6-dihydro-2H-pyridin-4-yl)-[1,2,4]triazolo[1,5-a]pyridin-2-yl]amino]-N-methyl-N-(1-methyl-4-piperidyl)benzamide 4-[[8-[1-(3,3-dimethylazetidine-1-carbonyl)-3,6-dihydro-2H-pyridin-4-yl]-[1,2,4]triazolo[1,5-a]pyridin-2-yl]amino]-N-methyl-N-(1-methyl-4-piperidyl)benzamide ethyl 4-[2-[4-[3-(4-methylpiperazin-1-yl)propylcarbamoyl]anilino]-[1,2,4]triazolo[1,5-a]pyridin-8-yl]-3,6-dihydro-2H-pyridine-1-carboxylate ethyl 4-[2-[4-[methyl-(1-methylpyrrolidin-3-yl)carbamoyl]anilino]-[1,2,4]triazolo[1,5-a]pyridin-8-yl]-3,6-dihydro-2H-pyridine-1-carboxylate ethyl 4-[2-[4-[(1-methyl-3-piperidyl)methylcarbamoyl]anilino]-[1,2,4]triazolo[1,5-a]pyridin-8-yl]-3,6-dihydro-2H-pyridine-1-carboxylate ethyl 4-[2-[4-[2-(1-piperidyl)ethylcarbamoyl]anilino]-[1,2,4]triazolo[1,5-a]pyridin-8-yl]-3,6-dihydro-2H-pyridine-1-carboxylate ethyl 4-[2-[4-(3-morpholinopiperidine-1-carbonyl)anilino]-[1,2,4]triazolo[1,5-a]pyridin-8-yl]-3,6-dihydro-2H-pyridine-1-carboxylate ethyl 4-[2-[4-(pyrrolidin-3-ylmethylcarbamoyl)anilino]-[1,2,4]triazolo[1,5-a]pyridin-8-yl]-3,6-dihydro-2H-pyridine-1-carboxylate ethyl 4-[2-[4-[4-(3-pyridylmethyl)piperazine-1-carbonyl]anilino]-[1,2,4]triazolo[1,5-a]pyridin-8-yl]-3,6-dihydro-2H-pyridine-1-carboxylate ethyl 4-[2-[4-[4-(4-methylpiperazin-1-yl)piperidine-1-carbonyl]anilino]-[1,2,4]triazolo[1,5-a]pyridin-8-yl]-3,6-dihydro-2H-pyridine-1-carboxylate ethyl 4-[2-[4-[4-(2-imidazol-1-ylethyl)piperazine-1-carbonyl]anilino]-[1,2,4]triazolo[1,5-a]pyridin-8-yl]-3,6-dihydro-2H-pyridine-1-carboxylate ethyl 4-[2-[4-[4-(4-methylpiperazine-1-carbonyl)piperidine-1-carbonyl]anilino]-[1,2,4]triazolo[1,5-a]pyridin-8-yl]-3,6-dihydro-2H-pyridine-1-carboxylate ethyl 4-[2-[4-(4-isobutylpiperazine-1-carbonyl)anilino]-[1,2,4]triazolo[1,5-a]pyridin-8-yl]-3,6-dihydro-2H-pyridine-1-carboxylate ethyl 4-[2-[4-(4-pyrrolidin-1-ylpiperidine-1-carbonyl)anilino]-[1,2,4]triazolo[1,5-a]pyridin-8-yl]-3,6-dihydro-2H-pyridine-1-carboxylate ethyl 4-[2-[4-[cyclopropyl-(1-methyl-4-piperidyl)carbamoyl]anilino]-[1,2,4]triazolo[1,5-a]pyridin-8-yl]-3,6-dihydro-2H-pyridine-1-carboxylate ethyl 4-[2-[4-[4-[(dimethylamino)methyl]-4-hydroxyazepane-1-carbonyl]anilino]-[1,2,4]triazolo[1,5-a]pyridin-8-yl]-3,6-dihydro-2H-pyridine-1-carboxylate ethyl 4-[2-[4-[(1-ethylpyrrolidin-3-yl)methyl-methyl-carbamoyl]anilino]-[1,2,4]triazolo[1,5-a]pyridin-8-yl]-3,6-dihydro-2H-pyridine-1-carboxylate ethyl 4-[2-[4-(6-azaspiro[2.5]octan-2-ylmethylcarbamoyl)anilino]-[1,2,4]triazolo[1,5-a]pyridin-8-yl]-3,6-dihydro-2H-pyridine-1-carboxylate ethyl 4-[2-[4-[4-(aminomethyl)piperidine-1-carbonyl]anilino]-[1,2,4]triazolo[1,5-a]pyridin-8-yl]-3,6-dihydro-2H-pyridine-1-carboxylate ethyl 4-[2-[4-(3,3a,4,5,6,6a-hexahydro-2H-pyrrolo[2,3-c]pyrrole-1-carbonyl)anilino]-[1,2,4]triazolo[1,5-a]pyridin-8-yl]-3,6-dihydro-2H-pyridine-1-carboxylate ethyl 4-[2-[4-(1-oxa-4,9-diazaspiro[5.5]undecane-9-carbonyl)anilino]-[1,2,4]triazolo[1,5-a]pyridin-8-yl]-3,6-dihydro-2H-pyridine-1-carboxylate ethyl 4-[2-[4-(1,7-diazaspiro[4.4]nonane-7-carbonyl)anilino]-[1,2,4]triazolo[1,5-a]pyridin-8-yl]-3,6-dihydro-2H-pyridine-1-carboxylate ethyl 4-[2-[4-(1,7-diazaspiro[4.4]nonane-1-carbonyl)anilino]-[1,2,4]triazolo[1,5-a]pyridin-8-yl]-3,6-dihydro-2H-pyridine-1-carboxylate ethyl 4-[2-[4-(2,9-diazaspiro[4.5]decane-2-carbonyl)anilino]-[1,2,4]triazolo[1,5-a]pyridin-8-yl]-3,6-dihydro-2H-pyridine-1-carboxylate 1-[4-[2-[4-(2,3,3a,4,6,6a-hexahydro-1H-pyrrolo[3,4-c]pyrrole-5-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(2,7-diazaspiro[3.5]nonane-7-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(2-amino-7-azaspiro[3.5]nonane-7-carbonyl)anilino]-[1,2,4]triazolo[1,5-a]pyridin-8-yl]-3,6-dihydro-2H-pyridin-1-yl]-4,4,4-trifluoro-butan-1-one N-(2-pyrrolidin-2-ylethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(pyrrolidin-2-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-(piperazine-1 -carbonyl)anilino]-[1,2,4]triazolo[1,5-a]pyridin-8-yl]-3,6-dihydro-2H-pyridin-1 -yl]butan-1-one 4,4,4-trifluoro-1-[4-[2-[4-(2-methylpiperazine-1-carbonyl)anilino]-[1,2,4]triazolo[1,5-a]pyridin-8-yl]-3,6-dihydro-2H-pyridin-1-yl]butan-1-one 1-[4-[2-[4-[(3aS,6aS)-3,3 a,4,5,6,6a-hexahydro-2H-pyrrolo[2,3 -c]pyrrole-1-carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-[(3aR,6aS)-2,3,3a,4,6,6a-hexahydro-1H-pyrrolo[3,4-c]pyrrole-5-carbonyl]anilino]-[1,2,4]triazolo[1,5-a]pyridin-8-yl]-3,6-dihydro-2H-pyridin-1-yl]-4,4,4-trifluoro-butan-1-one N-(7-azaspiro[3.5]nonan-2-yl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-[(1S,5R)-5-amino-3-azabicyclo[3.1.9]hexane-3-carbonyl]anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-[2-(1-methyl-2-piperidyl)pyrrolidine-1-carbonyl]anilino]-[1,2,4]triazolo[1,5-a]pyridin-8-yl]-3,6-dihydro-2H-pyridin-1-yl]butan-1-one N,N,1-trimethyl-4-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide 1-[4-[2-[4-[(3aS,6aS)-5-methyl-2,3,3a,4,6,6a-hexahydropyrrolo[2,3-c]pyrrole-1-carbonyl]anilino]-[1,2,4]triazolo[1,5-a]pyridin-8-yl]-3,6-dihydro-2H-pyridin-1-yl]-4,4,4-trifluoro-butan-1-one 4-isopropyl-N-methyl-1-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide 4,4,4-trifluoro-1-[4-[2-[4-(7-methyl-2,7-diazaspiro[3.4]octane-2-carbonyl)anilino]-[1,2,4]triazolo[1,5-a]pyridin-8-yl]-3,6-dihydro-2H-pyridin-1-yl]butan-1-one 1-[4-[2-[4-(4-cyclohexylpiperazine-1-carbonyl)anilino]-[1,2,4]triazolo[1,5-a]pyridin-8-yl]-3,6-dihydro-2H-pyridin-1-yl]-4,4,4-trifluoro-butan-1-one N-(1-isopropyl-4-piperidyl)-N-methyl-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[4-(2-methoxyethyl)piperazine-1-carbonyl]anilino]-[1,2,4]triazolo[1,5-a]pyridin-8-yl]-3,6-dihydro-2H-pyridin-1-yl]butan-1-one N-(1,2,2,6,6-pentamethyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(1,1-dimethyl-2-morpholino-ethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[1-methyl-2-(1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(1-methyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(dimethylamino)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[(1-methyl-3-piperidyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[3-(4-pyridyl)pyrrolidine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-(3-morpholinopiperidine-1-carbonyl)anilino]-[1,2,4]triazolo[1,5-a]pyridin-8-yl]-3,6-dihydro-2H-pyridin-1-yl]butan-1-one 4,4,4-trifluoro-1-[4-[2-[4-[4-(tetrahydrofuran-2-ylmethyl)piperazine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[3-(2-pyridyl)piperidine-1-carbonyl]anilino]-[1,2,4]triazolo[1,5-a]pyridin-8-yl]-3,6-dihydro-2H-pyridin-1-yl]butan-1-one 1-benzyl-N-methyl-4-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide N-[2-(4-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 4-[[8-(1-acetyl-3,6-dihydro-2H-pyridin-4-yl)-[1,2,4]triazolo[1,5-a]pyridin-2-yl]amino]-N-methyl-N-(1-methyl-4-piperidyl)benzamide isobutyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate tetrahydrofuran-3-yl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate 4-[[8-[1-(3,3-dimethylcyclobutanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide 4-[[8-[1-(cyclohexanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide propyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate 4-[[8-[1-(4-cyanocyclohexanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide benzyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate N-methyl-N-(1-methyl-4-piperidyl)-4-[[8-(1-pentanoyl-3,6-dihydro-2H-pyridin-4-yl)[1,2,4]triazolo[1,5-a]pyridin-2-yl]amino]benzamide cyclopropylmethyl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate ethyl 4-[2-[4-(4-methylpiperazine-1-carbonyl)anilino]-[1,2,4]triazolo[1,5-a]pyridin-8-yl]-3,6-dihydro-2H-pyridine-1-carboxylate ethyl 4-[2-[4-[[2-(dimethylamino)-1-methyl-ethyl]carbamoyl]anilino]-[1,2,4]triazolo[1,5-a]pyridin-8-yl]-3,6-dihydro-2H-pyridine-1-carboxylate ethyl 4-[2-[4-(1,4-diazepane-1-carbonyl)anilino]-[1,2,4]triazolo[1,5-a]pyridin-8-yl]-3,6-dihydro-2H-pyridine-1-carboxylate ethyl 4-[2-[4-[3-(methylamino)pyrrolidine-1-carbonyl]anilino]-[1,2,4]triazolo[1,5-a]pyridin-8-yl]-3,6-dihydro-2H-pyridine-1-carboxylate ethyl 4-[2-[4-[4-(2-pyridyl)piperidine-1-carbonyl]anilino]-[1,2,4]triazolo[1,5-a]pyridin-8-yl]-3,6-dihydro-2H-pyridine-1-carboxylate ethyl 4-[2-[4-[methyl(8-quinolylmethyl)carbamoyl]anilino]-[1,2,4]triazolo[1,5-a]pyridin-8-yl]-3,6-dihydro-2H-pyridine-1-carboxylate ethyl 4-[2-[4-(4-piperidylcarbamoyl)anilino]-[1,2,4]triazolo[1,5-a]pyridin-8-yl]-3,6-dihydro-2H-pyridine-1-carboxylate ethyl 4-[2-[4-[methyl(4-pyridylmethyl)carbamoyl]anilino]-[1,2,4]triazolo[1,5-a]pyridin-8-yl]-3,6-dihydro-2H-pyridine-1-carboxylate ethyl 4-[2-[4-(2-pyrrolidin-2-ylethylcarbamoyl)anilino]-[1,2,4]triazolo[1,5-a]pyridin-8-yl]-3,6-dihydro-2H-pyridine-1-carboxylate ethyl 4-[2-[4-[4-(tetrahydrofuran-2-ylmethyl)piperazine-1-carbonyl]anilino]-[1,2,4]triazolo[1,5-a]pyridin-8-yl]-3,6-dihydro-2H-pyridine-1-carboxylate ethyl 4-[2-[4-[2-methoxyethyl-(1-methyl-4-piperidyl)carbamoyl]anilino]-[1,2,4]triazolo[1,5-a]pyridin-8-yl]-3,6-dihydro-2H-pyridine-1-carboxylate ethyl 4-[2-[4-[(1-isopropyl-4-piperidyl)-methyl-carbamoyl]anilino]-[1,2,4]triazolo[1,5-a]pyridin-8-yl]-3,6-dihydro-2H-pyridine-1-carboxylate ethyl 4-[2-[4-(3-methyl-3,6-diazabicyclo[3.2.1]octane-6-carbonyl)anilino]-[1,2,4]triazolo[1,5-a]pyridin-8-yl]-3,6-dihydro-2H-pyridine-1-carboxylate ethyl 4-[2-[4-(4-cyclopropylpiperazine-1-carbonyl)anilino]-[1,2,4]triazolo[1,5-a]pyridin-8-yl]-3,6-dihydro-2H-pyridine-1-carboxylate ethyl 4-[2-[4-(4-cyclobutylpiperazine-1-carbonyl)anilino]-[1,2,4]triazolo[1,5-a]pyridin-8-yl]-3,6-dihydro-2H-pyridine-1-carboxylate ethyl 4-[2-[4-(8-methyl-2,8-diazaspiro[5.5]undecane-2-carbonyl)anilino]-[1,2,4]triazolo[1,5-a]pyridin-8-yl]-3,6-dihydro-2H-pyridine-1-carboxylate ethyl 4-[2-[4-[2-(3-pyridyl)pyrrolidine-1-carbonyl]anilino]-[1,2,4]triazolo[1,5-a]pyridin-8-yl]-3,6-dihydro-2H-pyridine-1-carboxylate ethyl 4-[2-[4-[(3aS,6aS)-2,3,3a,4,6,6a-hexahydro-1H-pyrrolo[2,3-c]pyrrole-5-carbonyl]anilino]-[1,2,4]triazolo[1,5-a]pyridin-8-yl]-3,6-dihydro-2H-pyridine-1-carboxylate ethyl 4-[2-[4-(2,7-diazaspiro[3.4]octane-2-carbonyl)anilino]-[1,2,4]triazolo[1,5-a]pyridin-8-yl]-3,6-dihydro-2H-pyridine-1-carboxylate ethyl 4-[2-[4-(1,8-diazaspiro[4.5]decane-1-carbonyl)anilino]-[1,2,4]triazolo[1,5-a]pyridin-8-yl]-3,6-dihydro-2H-pyridine-1-carboxylate ethyl 4-[2-[4-[2-aminoethyl(methyl)carbamoyl]anilino]-[1,2,4]triazolo[1,5-a]pyridin-8-yl]-3,6-dihydro-2H-pyridine-1-carboxylate ethyl 4-[2-[4-(2,6-diazaspiro[3.4]octane-6-carbonyl)anilino]-[1,2,4]triazolo[1,5-a]pyridin-8-yl]-3,6-dihydro-2H-pyridine-1-carboxylate ethyl 4-[2-[4-(2,6-diazaspiro[4.5]decane-2-carbonyl)anilino]-[1,2,4]triazolo[1,5-a]pyridin-8-yl]-3,6-dihydro-2H-pyridine-1-carboxylate 1-[4-[2-[4-(1,7-diazaspiro[4.4]nonane-7-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(2,6-diazaspiro[4.5]decane-2-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(2,6-diazaspiro[3.4]octane-6-carbonyl)anilino]-[1,2,4]triazolo[1,5-a]pyridin-8-yl]-3,6-dihydro-2H-pyridin-1-yl]-4,4,4-trifluoro-butan-1-one 4,4,4-trifluoro-4-[4-[2-[4-(1-oxa-4,9-diazaspiro[5.5]undecane-9-carbonyl)anilino]-[1,2,4]triazolo[1,5-a]pyridin-8-yl]-3,6-dihydro-2H-pyridin-1-yl]butan-1-one 1-[4-[2-[4-(2,7-diazaspiro[4.5]decane-7-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(2,9-diazaspiro[5.5]undecane-2-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(1,8-diazaspiro[5.5]undecane-8-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-(1,9-diazaspiro[4.6]undecane-9-carbonyl)anilino]-[1,2,4]triazolo[1,5-a]pyridin-8-yl]-3,6-dihydro-2H-pyridin-1-yl]-4,4,4-trifluoro-butan-1-one N-(2-piperidylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-(3,3a,4,5,6,6a-hexahydro-2H-pyrrolo[2,3-c]pyrrole-1-carbonyl)anilino]-[1,2,4]triazolo[1,5-a]pyridin-8-yl]-3,6-dihydro-2H-pyridin-1-yl]-4,4,4-trifluoro-butan-1-one 1-[4-[2-[4-[(3aS,6aS)-2,3,3a,4,6,6a-hexahydro-1H-pyrrolo[2,3-c]pyrrole-5-carbonyl]anilino]-[1,2,4]triazolo[1,5-a]pyridin-8-yl]-3,6-dihydro-2H-pyridin-1-yl]-4,4,4-trifluoro-butan-1-one N-(6-azaspiro[2.5]octan-2-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-methyl-N-[(1-methyl-3-piperidyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[4-hydroxy-4-(pyrrolidin-1-ylmethyl)azepane-1-carbonyl]anilino]-[1,2,4]triazolo[1,5-a]pyridin-8-yl]-3,6-dihydro-2H-pyridin-1-yl]butan-1-one 4,4,4-trifluoro-4-[4-[2-[4-(7-methyl-2,7-diazaspiro[3.5]nonane-2-carbonyl)anilino]-[1,2,4]triazolo[1,5-a]pyridin-8-yl]-3,6-dihydro-2H-pyridin-1-yl]butan-1-one 1-[4-[2-[4-(2,6-diazaspiro[3.3]heptane-2-carbonyl)anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-[4-(4-methylpiperazin-1-yl)piperidine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[4-(3-pyridylmethyl)piperazine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[4-(3-pyridyl)piperazine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[2-(2-pyridylmethyl)pyrrolidine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[4-(2-pyridyl)piperazine-1-carbonyl]anilino]-[1,2,4]triazolo[1,5-a]pyridin-8-yl]-3,6-dihydro-2H-pyridin-1-yl]butan-1-one 1-[4-[2-[4-[4-(cyclopropylmethyl)piperazine-1-carbonyl]anilino]-[1,2,4]triazolo[1,5-a]pyridin-8-yl]-3,6-dihydro-2H-pyridin-1-yl]-4,4,4-trifluoro-butan-1-one N-[2-(dimethylamino)-1-methyl-ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-cyclopropyl-N-(1-propyl-4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[1-(6-methyl-2-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-methyl-N-(3-pyridylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-[3-(azepan-1-yl)piperidine-1-carbonyl]anilino]-[1,2,4]triazolo[1,5-a]pyridin-8-yl]-3,6-dihydro-2H-pyridin-1-yl]-4,4,4-trifluoro-butan-1-one 4,4,4-trifluoro-1-[4-[2-[4-[4-(2-pyridylmethyl)piperidine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[3-(3-pyridylmethyl)pyrrolidine-1-carbonyl]anilino]-[1,2,4]triazolo[1,5-a]pyridin-8-yl]-3,6-dihydro-2H-pyridin-1-yl]butan-1-one N-[[4-(dimethyl amino)phenyl]methyl]-N-methyl-4-[[8-]1-(4,4,4-trifluorobutanoyl)-3,6-dihydro-2H-pyridin-4-yl]-[1,2,4]triazolo[1,5-a]pyridin-2-yl]amino]benzamide N-methyl-N-(4-pyridylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4-[[8-(1-benzoyl-3,6-dihydro-2H-pyridin-4-yl)-[1,2,4]triazolo[1,5-a]pyridin-2-yl]amino]-N-methyl-N-(1-methyl-4-piperidyl)benzamide 4-[[8-[1-(cyclopropanecarbonyl)-3,6-dihydro-2H-pyridin-4-yl]-[1,2,4]triazolo[1,5-a]pyridin-2-yl]amino]-N-methyl-N-(1-methyl-4-piperidyl)benzamide N-methyl -N-(1-methyl-4-piperidyl)-4-[[8-[1-(2-methylpropanoyl)-3,6-dihydro-2H-pyridin-4-yl]-[1,2,4]triazolo[1,5-a]pyridin-2-yl]amino]benzamide 4-[[8-[1-(3-methoxypropanoyl)-3,6-dihydro-2H-pyridin-4-yl]-[1,2,4]triazolo[1,5-a]pyridin-2-yl]amino]-N-methyl-N-(1-methyl-4-piperidyl)benzamide N-methyl -4-[[8-[1-(4-methylpentanoyl)-3,6-dihydro-2H-pyridin-4-yl]-[1,2,4]triazolo[1,5-a]pyridin-2-yl]amino]-N-(1-methyl-4-piperidyl)benzamide N-methyl-N-(1-methyl-4-piperidyl)-4-[[[8-[1-(morpholine-4-carbonyl)-3,6-dihydro-2H-pyridin-4-yl]-[1,2,4]triazolo[1,5-a]pyridin-2-yl]amino]benzamide ethyl 4-[2-[4-[3 -(dimethylamino)pyrrolidine-1-carbonyl]anilino]-[1,2,4]triazolo[1,5-a]pyridin-8-yl]-3,6-dihydro-2H-pyridine-1-carboxylate ethyl 4-[2-[4-[(1-methyl-2-piperidyl)methylcarbamoyl]anilino]-[1,2,4]triazolo[1,5-a]pyridin-8-yl]-3,6-dihydro-2H-pyridine-1-carboxylate ethyl 4-[2-[4-[2-(3-piperidyl)ethylcarbamoyl]anilino]-[1,2,4]triazolo[1,5-a]pyridin-8-yl]-3,6-dihydro-2H-pyridine-1-carboxylate ethyl 4-[2[4-[4-(2-cyanoethyl)piperazine-1-carbonyl]anilino]-[1,2,4]triazolo[1,5-a]pyridin-8-yl]-3,6-dihydro-2H-pyridine-1-carboxylate ethyl 4-[2-[4-(3,4,6,7,8,8a-hexahydro-1H-pyrrolo[1,2-a]pyrazine-2-carbonyl)anilino]-[1,2,4]triazolo[1,5-a]pyridin-8-yl]-3,6-dihydro-2H-pyridine-1-carboxylate ethyl 4-[2-[4-[methyl(2-pyridylmethyl)carbamoyl]anilino]-[1,2,4]triazolo[1,5-a]pyridin-8-yl]-3,6-dihydro-2H-pyridine-1-carboxylate ethyl 4-[2-[4-[(3S)-3-(dimethylamino)pyrrolidine-1-carbonyl]anilino]-[1,2,4]triazolo[1,5-a]pyridin-8-yl]-3,6-dihydro-2H-pyridine-1-carboxylate ethyl 4-[2-[4-[3 -(4-methylpiperazine-1-carbonyl)azetidine-1-carbonyl]anilino]-[1,2,4]triazolo[1,5-a]pyridin-8-yl]-3,6-dihydro-2H-pyridine-1-carboxylate ethyl 4-[2-[4-[2-(3-pyridyl)ethylcarbamoyl]anilino]-[1,2,4]triazolo[1,5-a]pyridin-8-yl]-3,6-dihydro-2H-pyridine-1-carboxylate ethyl 4-[2-[4-[2-(2-pyridyl)ethylcarbamoyl]anilino]-[1,2,4]triazolo[1,5-a]pyridin-8-yl]-3,6-dihydro-2H-pyridine-1-carboxylate ethyl 4-[2-[4-[3-(4-pyridylmethyl)pyrrolidine-1-carbonyl]anilino]-[1,2,4]triazolo[1,5-a]pyridin-8-yl]-3,6-dihydro-2H-pyridine-1-carboxylate ethyl 4-[2-[4-(4-piperidylmethylcarbamoyl)anilino]-[1,2,4]triazolo[1,5-a]pyridin-8-yl]-3,6-dihydro-2H-pyridine-1-carboxylate ethyl 4-[2-[4-[3-(3-pyridylmethyl)pyrrolidine-1-carbonyl]anilino]-[1,2,4]triazolo[1,5-a]pyridin-8-yl]-3,6-dihydro-2H-pyridine-1-carboxylate ethyl 4-[2-[4-(3-piperidylmethylcarbamoyl)anilino]-[1,2,4]triazolo[1,5-a]pyridin-8-yl]-3,6-dihydro-2H-pyridine-1-carboxylate ethyl 4-[2-[4-[2-(2-piperidyl)ethylcarbamoyl]anilino]-[1,2,4]triazolo[1,5-a]pyridin-8-yl]-3,6-dihydro-2H-pyridine-1-carboxylate ethyl 4-[2-[4-[4-(4-pyridyl)-1,4-diazepane-1-carbonyl]anilino]-[1,2,4]-triazolo[1,5-a]pyridin-8-yl]-3,6-dihydro-2H-pyridine-1-carboxylate ethyl 4-[2-[4-(1,3,4,6,7,8,9,9a-octahydropyrido[1,2-a]pyrazine-2-carbonyl)anilino]-[1,2,4]triazolo[1,5-a]pyridin-8-yl]-3,6-dihydro-2H-pyridine-1-carboxylate ethyl 4-[2-[4-[3-(dimethylcarbamoyl)-4-methyl-piperazine-1-carbonyl]anilino]-[1,2,4]-triazolo[1,5-a]pyridin-8-yl]-3,6-dihydro-2H-pyridine-1-carboxlate ethyl 4-[2-[4-(6-acetyl-2,6-diazaspiro[3.3]heptane-2-carbonyl)anilino]-[1,2,4]triazolo[1,5-a]pyridin-8-yl]-3,6-dihydro-2H-pyridine-1-carboxylate ethyl 4-[2-[4-[(1-methylpyrrolidin-3-yl)carbamoyl]anilino]-[1,2,4]triazolo[1,5-a]pyridin-8-yl]-3,6-dihydro-2H-pyridine-1-carboxylate ethyl 4-[2-[4-[[(1S,5R)-3-azabicyclo[3.1.0]hexan-6-yl]carbamoyl]anilino]-[1,2,4]triazolo[1,5-a]pyridin-8-yl]-3,6-dihydro-2H-pyridine-1-carboxylate ethyl 4-[2-[4-[(3aR,6aS)-2,3,3a,4,6,6a-hexahydro-1H-pyrrolo[3,4-c]pyrrole-5-carbonyl]anilino]-[1,2,4]triazolo[1,5-a]pyridin-8-yl]-3,6-dihydro-2H-pyridine-1-carboxylate ethyl 4-[2-[4-(1,9-diazaspiro[4.5]decane-1-carbonyl)anilino]-[1,2,4]triazolo[1,5-a]pyridin-8-yl]-3,6-dihydro-2H-pyridine-1-carboxylate ethyl 4-[2-[4-(2,5-diazaspiro[3.5]nonane-2-carbonyl)anilino]-[1,2,4]triazolo[1,5-a]pyridin-8-yl]-3,6-dihydro-2H-pyridine-1-carboxylate ethyl 4-[2-[4-[methyl(3-piperidyl)carbamoyl]anilino]-[1,2,4]triazolo[1,5-a]pyridin-8-yl]-3,6-dihydro-2H-pyridine-1-carboxylate ethyl 4-[2-[4-(2,7-diazaspiro[4.5]decane-7-carbonyl)anilino]-[1,2,4]triazolo[1,5-a]pyridin-8-yl]-3,6-dihydro-2H-pyridine-1-carboxylate 1-[4-[2-[4-(1,7-diazaspiro[4.4]nonane-1-carbonyl)anilino]-[1,2,4]triazolo[1,5-a]pyridin-8-yl]-3,6-dihydro-2H-pyridin-1-yl]-4,4,4-trifluoro-butan-1-one N-(2-aminoethyl)-N-methyl-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(1-oxa-8-azaspiro[4.5]decan-3-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-(2,8-diazaspiro[5.5]undecane-2-carbonyl)anilino]-[1,2,4]triazolo[1,5-a]pyridin-8-yl]-3,6-dihydro-2H-pyridin-1-yl]-4,4,4-trifluoro-butan-1-one N-(pyrrolidin-3-ylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(4-piperidyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-[4-(aminomethyl)piperidine-1-carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-[3-(aminomethyl)pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-[(4aR,7aR)-3,4a,5,6,7,7a-hexahydro-2H-pyrrolo[3,4-b][1,4]oxazine-4-carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-[(1R,5R)-3,6-diazabicyclo[3.2.0]heptane-3-carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-(1,9-diazaspiro[5.5]undecane-1-carbonyl)anilino]-[1,2,4]triazolo[1,5-a]pyridin-8-yl]-3,6-dihydro-2H-pyridin-1-yl]-4,4,4-trifluoro-butan-1-one N-(azetidin-3-yl)-N-methyl -4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-[4-(aminomethyl)-3-azabicyclo[2.1.1]hexane-3 -carbonyl]anilino]-[1,2,4]triazolo[1,5-a]pyridin-8-yl]-3,6-dihydro-2H-pyridin-1-yl]-4,4,4-trifluoro-butan-1-one 1-[4-[2-[4-(2,3,4a,5,6,7,8,8a-octahydropyrido[4,3 -b][1,4]oxazine-4-carbonyl)anilino]-[1,2,4]triazolo[1,5-a]pyridin-8-yl]-3,6-dihydro-2H-pyridin-1-yl]-4,4,4-trifluoro-butan-1-one N-[(1R,5S)-3-azabicyclo[3.1.0]hexan-6-yl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(1-piperidyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[4-(4-pyridyl)piperidine-1-carbonyl]anilino]-[1,2,4]triazolo[1,5-a]pyridin-8-yl]-3,6-dihydro-2H-pyridin-1-yl]butan-1-one N,N,4-trimethyl -1-[4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide 4,4,4-trifluoro-4-[4-[2-[4-(9-methyl-3-oxa-7,9-diazabicyclo[3.3.1]nonane-7-carbonyl)anilino]-[1,2,4]triazolo[1,5-a]pyridin-8-yl]-3,6-dihydro-2H-pyridin-1-yl]butan-1-one N-(1-methylpyrrolidin-3-yl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-methyl-N-(6-quinolylmethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[4-(3-methyl-1-piperidyl)piperidine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[4-(2-imidazol-1-ylethyl)piperazine-1-carbonyl]anilino]-[1,2,4]triazolo[1,5-a]pyridin-8-yl]-3,6-dihydro-2H-pyridin-1-yl]butan-1-one N-[(1-isopropylpyrrolidin-3-yl)methyl]-N-methyl-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-[3-(dimethylamino)pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one N-(2-morpholinoethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-(2-pyrrolidin-1-ylethyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[(1-methyl-4-piperidyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[4-(6-methyl -2-pyridyl)piperidine-1-carbonyl]anilino]-[1,2,4]triazolo[1,5-a]pyridin-8-yl]-3,6-dihydro-2H-pyridin-1-yl]butan-1-one N-[(3R)-quinuclidin-3-yl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-methyl-1-(2-phenyl ethyl)-4-[[8-[1-(4,4,4-trifluorobutanoyl)-3,6-dihydro-2H-pyridin-4-yl]-[1,2,4]triazolo[1,5-a]pyridin-2-yl]amino]benzoyl]piperazine-2-carboxamide 4,4,4-trifluoro-1-[4-[2-[4-[3-(2-pyridylmethyl)pyrrolidine-1-carbonyl]anilino]-[1,2,4]triazolo[1,5-a]pyridin-8-yl]-3,6-dihydro-2H-pyridin-1-yl]butan-1-one 1-[4-[2-[4-[3 -[benzyl(methyl)amino]piperidine-1-carbonyl]anilino]-[1,2,4]triazolo[1,5-a]pyridin-8-yl]-3,6-dihydro-2H-pyridin-1-yl]-4,4,4-trifluoro-butan-1-one N-(1-benzylpyrrolidin-3-yl)-N-methyl-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[4-(2-morpholinoethyl)piperazine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[4-(4-methylpiperazine-1-carbonyl)piperidine-1-carbonyl]anilino]-[1,2,4]triazolo[1,5-a]pyridin-8-yl]-3,6-dihydro-2H-pyridin-1-yl]butan-1-one N-methyl -N-[(3-methyl-2-pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-methyl -N-[(1-methyl -3,4-dihydro-2H-quinolin-6-yl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-(2-pyridyl)ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 4-[[8-[1-(3,3-dimethylazetidin-1-yl)sulfonyl-3,6-dihydro-2H-pyridin-4-yl]-[1,2,4]triazolo[1,5-a]pyridin-2-yl]amino]-N-methyl-N-(1-methyl-4-piperidyl)benzamide 4-[[8-[1-(3,3-dimethylazetidine-1-carbonyl)-2,3,4,7-tetrahydroazepin-5-yl]-[1,2,4]triazolo[1,5-a]pyridin-2-yl]amino]-N-methyl-N-(1-methyl-4-piperidyl)benzamide 4-[[8-[1-(3,3-dimethylazetidine-1-carbonyl)-2,5-dihydropyrrol-3-yl]-[1,2,4]triazolo[1,5-a]pyridin-2-yl]amino]-N-methyl-N-(1-methyl-4-piperidyl)benzamide 4-[[8-[1-(2-cyano-1-methyl-ethyl)-3,6-dihydro-2H-pyridin-4-yl]-[1,2,4]triazolo[1,5-a]pyridin-2-yl]amino]-N-methyl-N-(1-methyl-4-piperidyl)benzamide N-[[(2R)-1-methyl-2-piperidyl]methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-[(3S)-3-methyl-1-piperidyl]ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[2-[(3R)-3-methyl-1-piperidyl]ethyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 1-[4-[2-[4-[4-[(2R,6S)-2,6-dimethylmorpholin-4-yl]piperidine-1-carbonyl]anilino]-[1,2,4]triazolo[1,5-a]pyridin-8-yl]-3,6-dihydro-2H-pyridin-1-yl]-4,4,4-trifluoro-butan-1-one and N-[8-[4-(aminomethyl)-4-phenyl-1-piperidyl]-[1,2,4]triazolo[1,5-a]pyridin-2-yl]cyclopropanecarboxamide; hydrochloride, or a salt thereof.

2. A pharmaceutical composition comprising a compound of claim 1, or a salt thereof, and a pharmaceutically acceptable carrier, diluent or excipient.

3. A method of treating or lessening the severity of a disease or condition responsive to the inhibition of a Janus kinase activity in a patient, comprising administering to the patient a therapeutically effective amount of a compound of claim 1, or a salt thereof.

4. The method of claim 3, wherein the disease or condition is asthma.

5. The method of claim 3, wherein the Janus kinase is JAK1.

6. A compound selected from the group consisting of
4-[[8-[4-(4-chlorophenyl)-4-(hydroxymethyl)-1-piperidyl]-[1,2,4]triazolo[1,5-a]pyridin-2-yl]amino]-N-methyl-N-(1-methyl-4-piperidyl)benzamide 4-[[8-[4-(4-chlorophenyl)-4-(1-hydroxyethyl)-1-piperidyl]-[1,2,4]triazolo[1,5-a]pyridin-2-yl]amino]-N-methyl-N-(1-methyl-4-piperidyl)benzamide 4-[[8-[4-[4-(difluoromethyl)phenyl]-4-(hydroxymethyl)-1-piperidyl]-[1,2,4]triazolo[1,5-a]pyridin-2-yl]amino]-N-methyl-N-(1-methyl-4-piperidyl)benzamide 4-[[8-[4-(4-chlorophenyl)-4-(hydroxymethyl)-1-piperidyl]-[1,2,4]triazolo[1,5-a]pyridin-2-yl]amino]-N-[2-(3-methyl-1-piperidyl)ethyl]benzamide

[4-[[8-[4-(4-chlorophenyl)-4-(hydroxymethyl)-1-piperidyl]-[1,2,4]triazolo[1,5-a]pyridin-2-yl]amino]phenyl]-(5-methyl-2,5-diazaspiro[3.4]octan-2-yl)methanone

[4-[[8-[4-(4-chlorophenyl)-4-(hydroxymethyl)-1-piperidyl]-[1,2,4]triazolo [1,5 -a]pyridin-2-yl]amino]phenyl]-(1-methyl-2,3,3a,4,6,6a-hexahydropyrrolo[2,3-c]pyrrol-5-yl)methanone 4-[[8-[4-(4-chlorophenyl)-4-(hydroxymethyl)-1-piperidyl]-[1,2,4]triazolo[1,5-a]pyridin-2-yl]amino]-N-[2-[(2S,6S)-2,6-dimethylmorpholin-4-yl]ethyl]benzamide 4-[[8-[4-(4-chlorophenyl)-4-(hydroxymethyl)-1-piperidyl]-[1,2,4]triazolo[1,5-a]pyridin-2-yl]amino]-N-[2-[(2R,6S)-2,6-dimethylmorpholin-4-yl ]ethyl]benzamide

[4-[[8-[4-(4-chlorophenyl)-4-(hydroxymethyl)-1-piperidyl]-[1,2,4]triazolo[1,5-a]pyridin-2-yl]amino]phenyl]-[3-(4-pyridyl)pyrrolidin-1-yl]methanone 4-[[8-[4-(4-chlorophenyl)-4-(hydroxymethyl)-1-piperidyl]-[1,2,4]triazolo[1,5-a]pyridin-2-yl]amino]-N-(1-cyclopentyl-4-piperidyl)benzamide

[4-[[8-[4-(4-chlorophenyl)-4-(hydroxymethyl)-1-piperidyl]-[1,2,4]triazolo[1,5-a]pyridin-2-yl]amino]phenyl]-[4-[(2R,6S)-2,6-dimethylmorpholin-4-yl]-1-piperidyl]methanone

[4-[[8-[4-(4-chlorophenyl)-4-(hydroxymethyl)-1-piperidyl]-[1,2,4]triazolo[1,5-a]pyridin-2-yl]amino]phenyl]-[3-(methylamino)azetidin-1-yl]methanone 4-[[8-[4-(4-chlorophenyl)-4-(hydroxymethyl)-1-piperidyl]-[1,2,4]triazolo[1,5-a]pyridin-2-yl]amino]-N-(3-morpholinopropyl)benzamide 2-[4-[[8-[4-(4-chlorophenyl)-4-(hydroxymethyl)-1-piperidyl]-[1,2,4]triazolo[1,5-a]pyridin-2-yl]amino]pyrazol-1-yl]-1-[4-(morpholinomethyl)-1-piperidyl]ethanone formic acid;methyl 3-[4-[2-[4-[[8-[4-(4-chlorophenyl)-4-(hydroxymethyl)-1-piperidyl]-[1,2,4]triazolo[1,5-a]pyridin-2-yl]amino]pyrazol-1-yl]acetyl]piperazin-1-yl]propanoate 2-[4-[[8-[4-(4-chlorophenyl)-4-(hydroxymethyl)-1-piperidyl]-[1,2,4]triazolo[1,5-a]pyridin-2-yl]amino]pyrazol-1-yl]-1-[4-(methylamino)-1-piperidyl]ethanone 3-[[1-[2-[4-[[8-[4-(4-chlorophenyl)-4-(hydroxymethyl)-1-piperidyl]-[1,2,4]triazolo[1,5-a]pyridin-2-yl]amino]pyrazol-1-yl]acetyl]-4-piperidyl]-methyl-amino]propanenitrile 1-[4-[2-[4-[2-[4-(dimethylamino)-6-methyl-2-pyridyl]pyrrolidine-1-carbonyl]anilino]-[1,2,4]triazolo[1,5-a]pyridin-8-yl]-3,6-dihydro-2H-pyridin-1-yl]-4,4,4-trifluoro-butan-1-one N-[(3S)-3-piperidyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide N-[(6-methyl-3-pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[3-(4-methylpiperazine-1-carbonyl)azetidine-1-carbonyl]anilino]-[1,2,4]triazolo[1,5-a]pyridin-8-yl]-3,6-dihydro-2H-pyridin-1-yl]butan-1-one N-(3-morpholinopropyl)-4-[[8-[1-(4,4,4-trifluorobutanoyl)-3,6-dihydro-2H-pyridin-4-yl]-[1,2,4]triazolo[1,5-a]pyridin-2-yl]amino]benzamide 4,4,4-trifluoro-1-[4-[2-[4-[2-(4-pyridyl)pyrrolidine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[3-(4-pyridyl)pyrrolidine-1-carbonyl]anilino]-[1,2,4]triazolo[1,5-a]pyridin-8-yl]-3,6-dihydro-2H-pyridin-1-yl]butan-1-one 4,4,4-trifluoro-1-[4-[2-[4-[4-(tetrahydrofuran-2-ylmethyl)piperazine-1-carbonyl]anilino]-[1,2,4]triazolo[1,5-a]pyridin-8-yl]-3 ,6-dihydro-2H-pyridin-1-yl]butan-1-one and tetrahydrofuran-3-yl 4-[2-[4-[methyl-(1-methyl-4-piperidyl)carbamoyl]anilino]-[1,2,4]triazolo[1,5-a]pyridin-8-yl]-3,6-dihydro-2H-pyridine-1-carboxylate, or a salt thereof.

7. A compound, which is 4-[[8-[4-[4-(difluoromethyl)phenyl]-4-(hydroxymethyl)-1-piperidyl]-[1,2,4]triazolo[1,5-a]pyridin-2-yl]amino]-N-methyl-N-(1-methyl-4-piperidyl)benzamide, or a salt thereof.

8. A compound, which is 4-[[8-[4-(4-chlorophenyl)-4-(hydroxymethyl)-1-piperidyl]-[1,2,4]triazolo[1,5-a]pyridin-2-yl]amino]-N-[2-[(2R,6S)-2,6-dimethylmorpholin-4-yl]ethyl]benzamide, or a salt thereof.

9. A compound, which is 4-[[8-[4-(4-chlorophenyl)-4-(hydroxymethyl)-1-piperidyl]-[1,2,4]triazolo[1,5-a]pyridin-2-yl]amino]-N-(1-cyclopentyl-4-piperidyl)benzamide, or a salt thereof.

10. A compound, which is [4-[[8-[4-(4-chlorophenyl)-4-(hydroxymethyl)-1-piperidyl]-[1,2,4]triazolo[1,5-a]pyridin-2-yl]amino]phenyl]-[3-(methylamino)azetidin-1-yl]methanone, or a salt thereof.

11. A compound, which is 4-[[8-[4-(4-chlorophenyl)-4-(hydroxymethyl)-1-piperidyl]-[1,2,4]triazolo[1,5-a]pyridin-2-yl]amino]-N-(3-morpholinopropyl)benzamide, or a salt thereof.

12. A compound, which is 2-[4-[[8-[4-(4-chlorophenyl)-4-(hydroxymethyl)-1-piperidyl]-[1,2,4]triazolo[1,5-a]pyridin-2-yl]amino]pyrazol-1-yl]-1-[4-(methylamino)-1-piperidyl]ethanone, or a salt thereof.

13. A compound, which is 3-[[1-[2-[4-[[8-[4-(4-chlorophenyl)-4-(hydroxymethyl)-1-piperidyl]-[1,2,4]triazolo[1,5-a]pyridin-2-yl]amino]pyrazol-1-yl]acetyl]-4-piperidyl]-methyl-amino]propanenitrile, or a salt thereof.

14. A compound, which is N-[(6-methyl-3-pyridyl)methyl]-4-[[8-[1-(4,4,4-trifluorobutanoyl)-3,6-dihydro-2H-pyridin-4-yl]-[1,2,4]triazolo[1,5-a]pyridin-2-yl]amino]benzamide, or a salt thereof.

* * * * *